United States Patent
Bannen et al.

(10) Patent No.: US 12,371,428 B2
(45) Date of Patent: Jul. 29, 2025

(54) PYRIDONE COMPOUNDS AND METHODS OF USE

(71) Applicant: Exelixis, Inc., Alameda, CA (US)

(72) Inventors: Lynne Bannen, Novato, CA (US); Minna Bui, Oakland, CA (US); Faming Jiang, Castro Valley, CA (US); Jack Maung, Daly City, CA (US); Andrew Raub, Redwood City, CA (US); Justin Salvant, Alameda, CA (US); Benjamin Spangler, Richmond, CA (US); Kin Tso, San Francisco, CA (US); Yong Wang, Belmont, CA (US); Wei Xu, Danville, CA (US)

(73) Assignee: Exelixis, Inc., Alameda, CA (US)

( * ) Notice: Subject to any disclaimer, the term of this patent is extended or adjusted under 35 U.S.C. 154(b) by 667 days.

(21) Appl. No.: 17/033,475

(22) Filed: Sep. 25, 2020

(65) Prior Publication Data
US 2022/0315579 A1 Oct. 6, 2022

Related U.S. Application Data

(60) Provisional application No. 63/053,530, filed on Jul. 17, 2020, provisional application No. 62/906,647, filed on Sep. 26, 2019.

(51) Int. Cl.
*C07D 471/04* (2006.01)

(52) U.S. Cl.
CPC .................. *C07D 471/04* (2013.01)

(58) Field of Classification Search
None
See application file for complete search history.

(56) References Cited

U.S. PATENT DOCUMENTS

| | | | |
|---|---|---|---|
| 7,732,613 B2 | 6/2010 | Kim | |
| 9,522,902 B2 | 12/2016 | Dandu et al. | |
| 2021/0355107 A1* | 11/2021 | Duan | C07D 401/12 |
| 2022/0324869 A1* | 10/2022 | Duan | C07D 471/04 |

FOREIGN PATENT DOCUMENTS

| | | |
|---|---|---|
| CN | 101528702 A | 9/2009 |
| CN | 102643268 A | 8/2012 |
| CN | 104072480 A | 10/2014 |
| CN | 108530426 A | 9/2018 |
| CN | 109896997 A | 6/2019 |
| EP | 3026045 A1 | 6/2016 |
| EP | 3239147 A1 | 11/2017 |
| EP | 3741752 | 11/2020 |
| WO | WO2006116713 A1 | 11/2006 |
| WO | WO 2007/033196 A1 | 3/2007 |
| WO | WO 2008/048375 A1 | 4/2008 |
| WO | WO2012167600 A1 | 12/2012 |
| WO | WO 2013/074633 A1 | 5/2013 |
| WO | 2013/180949 A1 | 12/2013 |
| WO | WO2019080723 A1 | 5/2019 |
| WO | WO 2020/038460 | 2/2020 |
| WO | WO 2020/042618 | 3/2020 |
| WO | WO 2020/047184 A1 | 3/2020 |
| WO | WO2021012717 * | 1/2021 |
| WO | 2021/062245 A1 | 4/2021 |
| WO | 2021/173591 A1 | 9/2021 |

OTHER PUBLICATIONS

Machine-generated English translation of Foreign Patent Application Publication No. WO2021012717, published on Jan. 28, 2021.*
Clark et al., "A flexible high content imaging assay for profiling macrophage efferocytosis", Journal Of Immunological Methods, Elsevier Science Publishers B.V.,Amsterdam, NL, vol. 473, Jul. 29, 2019, XP085783040.
International Search Report & Written Opinion dated Nov. 20, 2020 for PCT/US2020/052850, 18 pages.
Li et al., "Design, synthesis and antitumour activity of bisquinoline derivatives connected by 4-oxy-3-fluoroaniline moiety", European Journal of Medicinal Chemistry, Elsevier, Amsterdam, NL, vol. 64, Apr. 15, 2013, pp. 62-73, XP028566334.
Liu et al., "Design, synthesis and biological evaluation of novel 4-phenoxyquinoline derivatives containing 3-oxo-3,4-dihydroquinoxaline moiety as c-Met kinase inhibitors", Bioorganic & Medicinal Chemistry, Elsevier, NL, vol. 25, No. 16, Jun. 27, 2017, pp. 4475-4486, XP085133591.
Tang et al., "Design, synthesis, and structure-activity relationships of novel 6,7-disubstituted-4-phenoxyquinoline derivatives as potential antitumor agents", European Journal of Medicinal Chemistry, Elsevier, Amsterdam, NL, vol. 69, Aug. 19, 2013, pp. 77-89, XP028762794.
Tang, et al, "Synthesis and antiproliferative activity of 6,7-disubstituted-4-phenoxyquinoline derivatives bearing the 1,8-naphthyridin-2-one moiety", European Journal Of Medicinal Chemistry, vol. 158, Oct. 2018, pp. 201-213, XP055748184.
Zhang et al., "Discovery of Novel c-Met Inhibitors Bearing a 3-Carboxyl Piperidin-2-one Scaffold", Molecules, vol. 19, No. 2, Feb. 24, 2014, pp. 2655-2673, XP055460997.
Zhang et al., "Discovery of novel type II c-Met inhibitors based on BMS-777607", European Journal of Medicinal Chemistry, vol. 80, Apr. 21, 2014, pp. 254-266, XP055394473.
International Search Report & Written Opinion dated Apr. 23, 2021 for PCT/US2021/019294, 10 pages.
International Search Report & Written Opinion dated Apr. 8, 2022 for PCT/US2022/016915, 21 pages.

* cited by examiner

*Primary Examiner* — Po-Chih Chen
(74) *Attorney, Agent, or Firm* — Sheppard Mullin Richter & Hampton LLP

(57) ABSTRACT

The present disclosure relates generally to compounds and pharmaceutical compositions suitable as modulators of protein kinases, and methods for their use in treating disorders mediated, at least in part by, protein kinases.

27 Claims, No Drawings

PYRIDONE COMPOUNDS AND METHODS OF USE

CROSS-REFERENCE TO RELATED APPLICATIONS

This application claims the benefit under 35 U.S.C. § 119(e) of U.S. Provisional Application No. 62/906,647, filed Sep. 26, 2019, and U.S. Provisional Application No. 63/053,530, filed Jul. 17, 2020, each of which is hereby incorporated by reference in its entirety.

FIELD

Provided herein are compounds and pharmaceutical compositions suitable as modulators of protein kinases, and methods for their use in treating disorders mediated, at least in part, by protein kinases.

BACKGROUND

Human Axl belongs to the TAM subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers including, but not limiting to lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis, most likely by generation of soluble Mer extracellular domain protein as a decoy receptor. Tumor cells secrete a soluble form of the extracellular Mer receptor which reduces the ability of soluble Gas-6 ligand to activate Mer on endothelial cells, leading to cancer progression.

c-Met, is the prototypic member of a subfamily of heterodimeric receptor tyrosine kinases (RTKs) which include Met, Ron and Sea. Expression of c-Met occurs in a wide variety of cell types including epithelial, endothelial and mesenchymal cells where activation of the receptor induces cell migration, invasion, proliferation and other biological activities associated with invasive cell growth. Signal transduction through c-Met receptor activation is responsible for many of the characteristics of tumor cells.

KDR is a tyrosine kinase receptor that binds vascular endothelial growth factor (VEGF). The binding of VEGF to the KDR receptor leads to angiogenesis. High levels of VEGF are found in various cancers causing tumor angiogenesis and permitting the rapid growth of cancerous cells.

Therefore, a need exists for new compounds that modulate Axl, Mer, c-Met, and/or KDR kinases for the treatment of cancers.

SUMMARY

Provided herein are compounds that inhibit c-Met, Axl, Mer and/or KDR. In certain embodiments, the compounds are of formula (I'''):

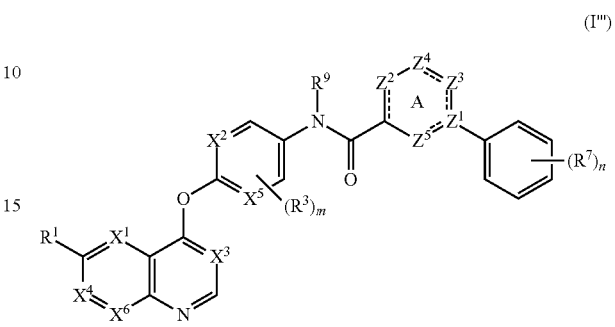

or a pharmaceutically acceptable salt, a stereoisomer, tautomer or a mixture of stereoisomers thereof.

Some embodiments provide for a compound, or a pharmaceutically acceptable salt, stereoisomer, or a mixture of stereoisomers thereof, selected from Table 1, Table 2, or Table 3.

Also provided herein are pharmaceutical compositions comprising a compound as described herein, or a pharmaceutically acceptable salt, stereoisomer, tautomer, or mixture of stereoisomers thereof, and a pharmaceutically acceptable carrier or excipient.

Some embodiments provide for methods of modulating in vivo activity of a protein kinase in a subject, the method comprising administering to the subject a therapeutically effective amount of a compound as described herein, or a pharmaceutically acceptable salt, stereoisomer, tautomer, or mixture of stereoisomers thereof, or a pharmaceutical composition as described herein.

Some embodiments provide for methods of treating a disease, disorder, or syndrome in a subject, the method comprising administering to the subject in need thereof a therapeutically effective amount of a compound as described herein, or a pharmaceutically acceptable salt, stereoisomer, tautomer, or mixture of stereoisomers thereof, or a pharmaceutical composition as described herein, wherein the disease, disorder, or syndrome is mediated at least in part by modulating in vivo activity of a protein kinase.

Some embodiments provide for methods of treating a disease, disorder, or syndrome in a subject, the method comprising: administering to the subject in need thereof a therapeutically effective amount of a compound as described herein, or a pharmaceutically acceptable salt, stereoisomer, tautomer, or mixture of stereoisomers thereof, or a pharmaceutical composition as described herein, in combination with a therapeutic agent or therapy.

The disclosure also provides compositions, including pharmaceutical compositions, kits that include the compounds, and method of using (or administering) and making the compounds. The disclosure further provides compounds or compositions for use in a method of treating a disease, disorder, or condition that is mediated, at least in part, by c-Met, Axl, Mer and/or KDR activity. Moreover, the disclosure provides uses of the compounds or compositions thereof in the manufacture of a medicament for the treatment of a disease, disorder, or condition that is mediated, at least in part, by c-Met, Axl, Mer and/or KDR.

DETAILED DESCRIPTION

Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through or perpendicular across the end of a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount 5%. In certain other embodiments, the term "about" includes the indicated amount 1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{24}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{24}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocycloalkyl, aryl, heteroalkyl or heteroaryl; each of which may be optionally substituted, as defined herein. Examples of acyl include, e.g., formyl, acetyl, cyclohexylcarbonyl, cyclohexylmethyl-carbonyl and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocycloalkyl, aryl, heteroalkyl or heteroaryl; each of which may be optionally substituted, as defined herein, or R$^y$ and R$^z$ are taken together to form a cycloalkyl or heterocycloalkyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocycloalkyl, aryl, heteroalkyl or heteroaryl; each of which may be optionally substituted, as defined herein.

"Amidino" refers to —C(NR$^y$)(NR$^z{}_2$), wherein R$^y$ and R$^z$ are independently hydrogen, alkyl, alkenyl, alkynyl, cycloalkyl, heterocycloalkyl, aryl, heteroalkyl or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl and anthryl. Aryl, however, does not encompass or overlap in any way with heteroaryl defined below. If one or more aryl groups are fused with a heteroaryl, the resulting ring system is heteroaryl. If one or more aryl groups are fused with a heterocycloalkyl, the resulting ring system is heterocycloalkyl.

"Arylalkyl" or "Aralkyl" refers to the group "aryl-alkyl-".

"Carbamoyl" refers to —C(O)NR$^y$R$^z$. "O-carbamoyl" refers to —O—C(O)NR$^y$R$^z$ and "N-carbamoyl" refers to —NR$^y$C(O)OR$^z$, wherein R$^y$ and R$^z$ are independently hydrogen, alkyl, alkenyl, alkynyl, cycloalkyl, heterocycloalkyl, aryl, heteroalkyl or heteroaryl; each of which may be optionally substituted, as defined herein.

"Carboxyl ester" or "ester" refer to both —OC(O)R$^y$ and —C(O)OR$^x$, wherein Rx is alkyl, alkenyl, alkynyl, cycloalkyl, heterocycloalkyl, aryl, heteroalkyl or heteroaryl; each of which may be optionally substituted, as defined herein.

"Cycloalkyl" refers to a saturated or partially unsaturated cyclic alkyl group having a single ring or multiple rings including fused, bridged and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl and the like. In some embodiments, one or more ring carbons of "cycloalkyl" can be optionally replaced by a carbonyl group. Examples of such cycloalkyl include cyclohexanone-4-yl, and the like. Further, the term cycloalkyl is intended to encompass moieties that have one or more aromatic ring fused (i.e., having a bond in common with) to the cycloalkyl ring, e.g., benzo or thienyl derivatives of cyclopentane, cyclohexane, and the like. A cycloalkyl group containing a fused aromatic ring can be attached through any ring-forming atom including a ring-forming atom of the fused aromatic ring. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkylalkyl" refers to the group "cycloalkyl-alkyl-".

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocycloalkyl, aryl, heteroalkyl or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocycloalkyl, aryl, heteroalkyl or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocycloalkyl, aryl, heteroalkyl or heteroaryl; each of which may be optionally substituted, as defined herein.

"Halogen" or "halo" refers to atoms occupying group VIIA of the periodic table, such as fluoro, chloro, bromo or iodo.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocycloalkyl, aryl, heteroalkyl or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.) and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocycloalkyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, boron, phosphorus and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen and sulfur. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-14, or 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl and triazinyl. In some embodiments, any ring-forming N in a heteroaryl moiety can be an N-oxide.

In certain instances, a fused heteroaryl refers to a heteroaryl ring fused to another heteroaryl ring. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocycloalkyl" or "heterocyclyl" refers to a saturated or partially unsaturated cyclic alkyl group, with one or more ring heteroatoms independently selected from boron, phosphorus, nitrogen, oxygen and sulfur. The term "heterocycloalkyl" includes heterocycloalkenyl groups (i.e., the heterocycloalkyl group having at least one double bond), bridged-heterocycloalkyl groups, fused-heterocycloalkyl groups and spiro-heterocycloalkyl groups. A heterocycloalkyl may be a single ring or multiple rings wherein the multiple rings may be fused, bridged or spiro. One or more ring carbon atoms and ring heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring carbon atom or a ring heteroatom. Any non-aromatic ring containing at least one heteroatom is considered a heterocycloalkyl, regardless of the attachment (i.e., can be bound through a carbon atom or a heteroatom). As used herein, heterocycloalkyl has 2 to 20 ring carbon atoms (i.e., $C_{2-20}$ heterocycloalkyl), 2 to 12 ring carbon atoms (i.e., $C_{2-12}$ heterocycloalkyl), 2 to 10 ring carbon atoms (i.e., $C_{2-10}$ heterocycloalkyl), 2 to 8 ring carbon atoms (i.e., $C_{2-8}$ heterocycloalkyl), 3 to 12 ring carbon atoms (i.e., $C_{3-12}$ heterocycloalkyl), 3 to 8 ring carbon atoms (i.e., $C_{3-8}$ heterocyclyl), or 3 to 6 ring carbon atoms (i.e., $C_{3-6}$ heterocycloalkyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocycloalkyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), tetrahydropyranyl, thiomorpholinyl, thiamorpholinyl, 1-oxo-thiomorpholinyl and 1,1-dioxo-thiomorpholinyl. The term "heterocycloalkyl" also includes "spiroheterocycloalkyl" when there are two positions for substitution on the same carbon atom. Examples of the spiro-heterocycloalkyl rings include, e.g., bicyclic and tricyclic ring systems, such as 2-oxa-7-azaspiro[3.5]nonanyl, 2-oxa-6-azaspiro[3.4]octanyl and 6-oxa-1-azaspiro[3.3]heptanyl.

Further, the term heterocycloalkyl is intended to encompass any non-aromatic ring containing at least one heteroatom, which ring is fused to one or more aryl or heteroaryl rings, regardless of the attachment to the remainder of the molecule (i.e., a heterocycloalkyl group containing a fused aromatic ring can be attached through any ring atom including a ring atom of the fused aromatic ring). Examples of the fused-heterocycloalkyl rings include, but are not limited to, 1,2,3,4-tetrahydroisoquinolinyl, 4,5,6,7-tetrahydrothieno[2,3-c]pyridinyl, indolinyl and isoindolinyl, where the heterocycloalkyl can be bound via either ring of the fused system.

"Heterocycloalkylalkyl" refers to the group "heterocycloalkyl-alkyl-."

"Oxime" refers to the group —CR$^y$(=NOH) wherein R$^y$ is hydrogen, alkyl, alkenyl, alkynyl, cycloalkyl, heterocycloalkyl, aryl, heteroalkyl or heteroaryl; each of which may be optionally substituted, as defined herein.

"Sulfonyl" refers to the group —S(O)$_2$R$^y$, where R$^y$ is hydrogen, alkyl, alkenyl, alkynyl, cycloalkyl, heterocycloalkyl, aryl, heteroalkyl or heteroaryl; each of which may be optionally substituted, as defined herein. Examples of sulfonyl are methylsulfonyl, ethylsulfonyl, phenylsulfonyl and toluenesulfonyl.

"Sulfinyl" refers to the group —S(O)R$^y$, where R$^y$ is hydrogen, alkyl, alkenyl, alkynyl, cycloalkyl, heterocycloalkyl, aryl, heteroalkyl or heteroaryl; each of which may be optionally substituted, as defined herein. Examples of sulfinyl are methylsulfinyl, ethylsulfinyl, phenylsulfinyl and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, cycloalkyl, heterocycloalkyl, aryl, heteroalkyl or heteroaryl; each of which may be optionally substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocycloalkyl, heteroaryl, and/or heteroalkyl) wherein at least one (e.g., 1 to 5 or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanidino, halo, haloalkyl, haloalkoxy, hydroxyalkyl, heteroalkyl, heteroaryl, heteroarylalkyl, heterocycloalkyl, heterocycloalkylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide or —Si(R$^y$)$_3$, wherein each R$^y$ is independently hydrogen, alkyl, alkenyl, alkynyl, heteroalkyl, cycloalkyl, aryl, heteroaryl or heterocycloalkyl.

In certain embodiments, "substituted" includes any of the above alkyl, alkenyl, alkynyl, cycloalkyl, heterocycloalkyl, aryl or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocycloalkyl, aryl, heteroaryl, —NR$^q$R$^h$, —NR$^q$C(=O)R$^h$, —NR$^q$C(=O)NR$^q$R$^h$, —NR$^q$C(=O)OR$^h$, —NR$^q$S(=O)$_{1-2}$R$^h$, —C(=O)R$^q$, —C(=O)OR$^q$, —OC(=O)OR$^q$, —OC(=O)R$^q$, —C(=O) NR$^q$R$^h$, —OC(=O)NR$^q$R$^h$, —OR$^q$, —SR$^q$, —S(=O)R$^q$, —S(=O)$_2$R$^q$, —OS(=O)$_{1-2}$R$^q$, —S(=O)$_{1-2}$OR$^q$, —NR$^q$S (=O)$_{1-2}$NR$^q$R$^h$, —NSO$_2$R$^q$, =NOR$^q$, —S(=O)$_{1-2}$NR$^q$R$^h$, —SF$_5$, —SCF$_3$ or —OCF$_3$. In certain embodiments, "substituted" also means any of the above groups in which one or more (e.g., 1 to 5 or 1 to 3) hydrogen atoms are replaced with —C(=O)R$^q$, —C(=O)NR$^q$R$^q$, —CH$_2$SO$_2$R$^q$, or —CH$_2$SO$_2$NR$^q$R$^h$. In the foregoing, R$^q$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocycloalkyl, heterocycloalkylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocycloalkyl, N-heterocycloalkyl, heterocycloalkylalkyl, heteroaryl, and/or heteroarylalkyl, or two of R$^q$ and R$^h$ and R$^i$ are taken together with the atoms to which they are attached to form a heterocycloalkyl ring optionally substituted with oxo, halo or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is intended to represent unlabeled forms as well as isotopically labeled forms (isotopologues) of the compounds. These forms of compounds may also be referred to as and include "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index (see e.g., A. Kerekes et. al. J. Med. Chem. 2011, 54, 201-210; R. Xu et. al. J. Label Compd. Radiopharm. 2015, 58, 308-312). An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a C$_{1-6}$ alkyl group can be replaced by deuterium atoms, such as —CH$_3$ being replaced for —CD$_3$). In some embodiments, the compound includes two or more deuterium atoms. In some embodiments, the compound includes 1, 2, 3, 4, 5, 6, 7, 8, 9, 10, 11, or 12 deuterium atoms. In some embodiments, all of the hydrogen atoms in a compound can be replaced or substituted by deuterium atoms. Synthetic methods for including isotopes into organic compounds are known in the art (Deuterium Labeling in Organic Chemistry by Alan F. Thomas (New York, New York, Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium. Further, in some embodiments, the corresponding deuterated analog is provided.

In many cases, the compounds of this disclosure are capable of forming acid and/or base salts by virtue of the presence of amino and/or carboxyl groups or groups similar thereto.

Provided also are a pharmaceutically acceptable salt, isotopically enriched analog, deuterated analog, isomer (such as a stereoisomer), mixture of isomers (such as a mixture of stereoisomers), and prodrug of the compounds described herein.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from non-toxic inorganic and organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in Remington's Pharmaceutical Sciences, 17$^{th}$ Ed., (Mack Publishing Company, Easton, 1985), p. 1418, Berge et al., J. Pharm. Sci., 1977, 66(1), 1-19 and in Stahl et al., Handbook of Pharmaceutical Salts: Properties, Selection, and Use, (Wiley, 2002).

The term "tautomer" means compounds produced by the phenomenon wherein a proton of one atom of a molecule shifts to another atom of the molecule. The tautomers also refer to one of two or more structural isomers that exist in equilibrium and are readily converted from one isomeric form to another. Non-limiting examples include enol-keto, imine-enamine, amide-imidic acid tautomers, the tautomeric forms of heteroaryl groups containing a —N=C(H)—NH— ring atom arrangement, such as pyrazoles, imidazoles, benzimidazoles, triazoles, and tetrazoles, and the tautomeric forms of hydroxy substituted 6-membered heteroaryl groups (e.g., hydroxy substituted pyridine, pyrimidine, pyrazine or pyridazine) such as 4-hydroxypyridine and puridin-4(1H)-one, and the like. The compounds described herein may have one or more tautomers and therefore include various isomers. A person of ordinary skill in the art would recognize that other tautomeric ring atom arrangements are possible. All such isomeric forms of these compounds are expressly included in the present disclosure.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L) for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present invention contemplates various stereoisomers and mixtures thereof and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate and benzoate derivatives), amides, guanidines, carbamates (e.g., N,N-dimethylaminocarbonyl) of hydroxy functional groups in compounds described herein and the like. Preparation, selection and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromobenzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene)sulfonyloxy, and the like.

The term "amide coupling conditions" refers to the reaction conditions under which an amine and a carboxylic acid couple to form an amide using a coupling reagent in presence of a base. The non-limiting examples of coupling reagents include 1-Ethyl-3-(3-dimethylaminopropyl) carbodiimide (EDC) with hydroxybenzotriazole monohydrate (HOBt), 0-(7-Azabenzotriazole-1-yl)-N,N,N',N'-tetramethyluronium hexafluorophosphate (HATU), 1-hydroxy-7-azabenzotriazole, and the like. The non-limiting examples of the base include N-methylmorpholine, pyridine, morpholine, imidazole, and the like.

The term "protecting group" refers to a moiety of a compound that masks or alters the properties of a functional group or the properties of the compound as a whole. The chemical substructure of a protective group varies widely. One function of a protective group is to serve as an intermediate in the synthesis of the parental drug substance. Chemical protective groups and strategies for protection/deprotection are well known in the art. See: "Protective Groups in Organic Chemistry", Theodora W. Greene (John Wiley & Sons, Inc., New York, 1991. Protective groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

The non-limiting examples of protecting groups for a hydroxy (i.e. a "hydroxy protecting group") include methoxymethyl ether, tetrahydropyranyl ether, t-butyl ether, allyl ether, benzyl ether, t-butyldiphenylsilyl ether, acetate ester, pivalate ester, benzoate ester, benzylidene acetal, acetonide, silyl ether, and the like.

List of Abbreviations and Acronyms

| Abbreviation | Meaning |
| --- | --- |
| ACN | acetonitrile |
| Amphos$_2$PdCl$_2$ | bis(di-tert-butyl(4-dimethylaminophenyl)phosphine)dichloropalladium(II) |
| anhyd. | anhydrous |
| aq. | aqueous |

-continued

| Abbreviation | Meaning |
| --- | --- |
| δ | Chemical shift (ppm) |
| DCC | dicyclohexylcarbodiimide |
| DCE | dicholoroethane |
| DCM | dichloromethane |
| DIEA | diisopropylethylamine |
| DMAP | dimethylaminopyridine |
| DMSO | dimethylsulfoxide |
| eq. or equiv. | Equivalent(s) |
| Et | Ethyl |
| EtOAc | ethyl acetate |
| EtOH | ethanol |
| HATU | N-[(dimethylamino)-1H-1,2,3-triazolo-[4,5-b]pyridin-1-ylmethylene]-N-methylmethanaminium hexafluorophosphate N-oxide |
| HPLC | High performance liquid chromatography |
| LC-MS | Liquid chromatography - mass spectrometry |
| Meldrum's acid | 2,2-dimethyl-1,3-dioxane-4,6-dione |
| MeOH | methanol |
| MS | Mass spectrometry |
| m/z | Mass to charge ratio |
| NBS | N-bromosuccinimide |
| NMP | N-methyl-2-pyrrolidone |
| NMR | Nuclear magnetic resonance spectroscopy |
| Ph | phenyl |
| Pd(PPh$_3$)$_4$ or tetrakis | tetrakis(triphenylphosphine)palladium(0) |
| Prep | preparatory |
| THF | tetrahydrofuran |
| TLC | Thin layer chromatography |
| XPhos Pd G2 | chloro(2-dicyclohexylphosphino-2',4',6'-triisopropyl-1,1'-biphenyl)[2-(2'-amino-1,1'-biphenyl)]palladium(II) |

Compounds

Provided herein is a compound of Formula (I'''):

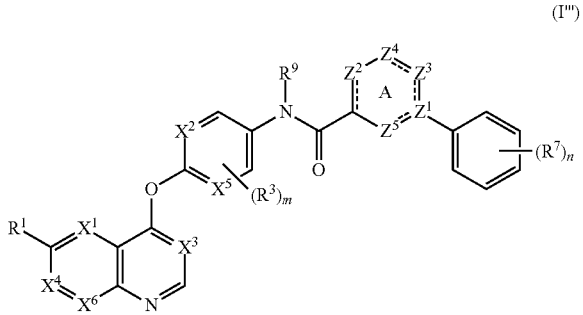

(I''')

or a pharmaceutically acceptable salt, a stereoisomer, tautomer or a mixture of stereoisomers thereof, wherein:

$X^1$ is N or $CR^{11}$;

$X^2$ is N, $CR^3$, or CH;

$X^3$ is N or CH;

$X^4$ is N or $CR^2$;

$X^5$ is N, $CR^3$, or CH;

$X^6$ is N or $CR^{10}$;

$Z^1$ is N, CH or C;

$Z^2$ is N, $NR^{40}$, —C(=O)—, or $CR^{45}$;

$Z^3$ is N, $NR^{41}$, $CR^{42}$, —C(=O)—, —C(=S)—;

$Z^4$ is N, $NR^{43}$, $CR^{44}$, —C(=O)— or a bond;

$Z^5$ is N, $COR^{46}$, —C(=O)— or $CR^{18}$;

==== is a single bond or a double bond;

one or two of $Z^1$, $Z^2$, $Z^3$, $Z^4$, and $Z^5$ are independently selected from N, $NR^{40}$, $NR^{41}$, and $NR^{43}$;

no more than two of $Z^2$, $Z^3$, $Z^4$ and $Z^5$ are —C(=O)—;

when ring A is

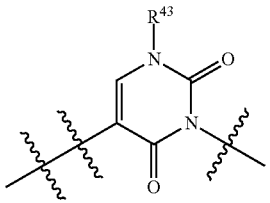

then $X^1$ is N, wherein the single wavy line indicates the point of attachment to the phenyl ring and the double wavy line indicates the point of attachment to the carbonyl of the amide linkage;

$R^1$ and $R^2$ and $R^{10}$ are each independently selected from H, halo, $C_{1-6}$ alkyl, $C_{2-6}$ alkenyl, $C_{2-6}$ alkynyl, $C_{1-6}$ haloalkyl, $C_{1-6}$haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$, $R^2$ and $R^{10}$ are each optionally substituted with 1, 2, 3, 4 or 5 independently selected R substituents;

each $R^3$ is independently selected from halo, OH, CN, —COOH, —CONH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^{40}$, $R^{41}$ and $R^{43}$ are each independently selected from H, halo, $C_{1-6}$ alkyl, $C_{2-6}$ alkenyl, $C_{2-6}$ alkynyl, $C_{1-6}$haloalkyl, $C_{1-6}$haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N=C(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_4$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^{40}$, $R^{41}$ and $R^{43}$ are each optionally substituted with 1, 2, 3, 4 or 5 independently selected $R^b$ substituents;

$R^{45}$, $R^{42}$ and $R^{44}$ are each independently H, halo, $C_{1-6}$ alkyl optionally substituted with 1 or 2 independently selected $R^g$ substituents, $C_{2-6}$ alkenyl, $C_{3-14}$ cycloalkyl, $C_{1-6}$ alkoxy, CN, $C_{1-4}$ haloalkyl, $C_{1-4}$ haloalkoxy, OH, —S—$C_{1-6}$ alkyl, —COOH, —COC$_{1-4}$alkyl, —COOC$_{1-4}$alkyl, —CONH$_2$, —CONHC$_{1-4}$ alkyl, —NHC(O)OC$_{1-4}$alkyl, $NH_2$, —NHC$_{1-4}$alkyl, or —N($C_{1-4}$ alkyl)$_2$;

each $R^7$ is independently selected from halo, OH, $COOR^a$, $CONR^aR^a$, CN, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ haloalkoxy, $C_1$-$C_6$ haloalkoxy, $CONR^aR^a$, $NR^aCOR^a$, $NR^aCONR^aR^a$, $SO_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_{1-4}$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^{46}$ is H, $C_{1-6}$ alkyl or a hydroxy protecting group;

$R^9$ is H or $C_{1-6}$ alkyl optionally substituted with 1, 2, or 3 independently selected $R^g$ substituents;

$R^{11}$ is selected from H, $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^{11}$ are each optionally substituted with 1, 2, or 3 independently selected $R^f$ substituents;

$R^{18}$ is H, halo, CN, $C_{1-6}$ alkyl, $NH_2$, —NHC$_{1-4}$alkyl, —N($C_{1-4}$ alkyl)$_2$, or —S—$C_{1-6}$ alkyl;

or $R^{40}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{43}$ and $R^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{44}$ and $R^{45}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents and wherein one or two ring carbon atoms of the fused $C_{3-7}$ cycloalkyl are optionally replaced by a carbonyl;

or when $Z^4$ is a bond, $R^{40}$ and $R^{42}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{41}$ and $R^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{42}$ and $R^{45}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents and wherein one or two ring carbon atoms of the fused $C_{3-7}$ cycloalkyl are optionally replaced by a carbonyl;

or $R^{41}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{42}$ and $R^{43}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{42}$ and $R^{44}$ taken together with the atoms to which they are attached form fused $C_{3-7}$ cycloalkyl, fused phenyl, or fused heteroaryl, wherein the fused $C_{3-7}$ cycloalkyl, fused phenyl, and fused heteroaryl are each optionally substituted with 1 or 2 independently selected $R^g$ substituents and wherein one or two ring carbon atoms of the fused $C_{3-7}$ cycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)NR^cR^c$, $C(=NR)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)R^cR^c$, $P(O)(OR^c)(OR^c)$, $B(OH)_2$, $B(OR^c)_2$, and $S(O)_2NR^cR^c$; wherein the $C_1$-$C_6$ alkyl, $C_1$-$C_6$ haloalkyl, $C_1$-$C_6$ haloalkoxy, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene- of $R^c$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$alkylene-, (5-10 membered heteroaryl)-$C_1$-$C_4$alkylene-, (4-10 membered heterocycloalkyl)-C$_1$-C$_4$ alkylene-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$; wherein the C$_1$-C$_6$ alkyl, C$_1$-C$_6$haloalkyl, C$_6$-C$_{10}$ aryl, 5-10 membered heteroaryl, C$_3$-C$_{10}$ cycloalkyl, 4-10 membered heterocycloalkyl, C$_6$-C$_{10}$ aryl-C$_1$-C$_4$ alkylene-, C$_3$-C$_{10}$ cycloalkyl-C$_1$-C$_4$ alkylene-, (5-10 membered heteroaryl)-C$_1$-C$_4$ alkylene-, and (4-10 membered heterocycloalkyl)-C$_1$-C$_4$ alkylene- of R$^d$ are each optionally substituted with 1, 2, or 3 independently selected R$^f$ substituents;

each R$^e$ is independently selected from the group consisting of H, C$_1$-C$_6$ alkyl, C$_3$-C$_6$ cycloalkyl, C$_3$-C$_6$ cycloalkyl-C$_1$-C$_4$ alkylene-, C$_6$-C$_{10}$ aryl, C$_6$-C$_{10}$ aryl-C$_1$-C$_4$ alkylene-, 5- or 6-membered heteroaryl, (5- or 6-membered heteroaryl)-C$_1$-C$_4$ alkylene-, 4-7-membered heterocycloalkyl, (4-7-membered heterocycloalkyl)-C$_1$-C$_4$ alkylene-, C$_1$-C$_6$ haloalkyl, C$_1$-C$_6$ haloalkoxy, C$_2$-C$_4$ alkenyl, and C$_2$-C$_4$ alkynyl, wherein the C$_1$-C$_6$ alkyl, C$_3$-C$_6$ cycloalkyl, C$_6$-C$_{10}$ aryl, 5 or 6-membered heteroaryl, 4-7-membered heterocycloalkyl, C$_6$-C$_{10}$ aryl-C$_1$-C$_4$ alkylene-, (5- or 6-membered heteroaryl)-C$_1$-C$_4$ alkylene-, (4-7-membered heterocycloalkyl)-C$_1$-C$_4$ alkylene-, C$_2$-C$_4$ alkenyl, and C$_2$-C$_4$ alkynyl of R$^e$ are each optionally substituted with 1, 2, or 3 R$^f$ substituents;

or any two R$^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected R$^f$ substituents;

each R$^f$ is independently selected from the group consisting of halo, OH, CN, COOH, NH$_2$, —NH(C$_1$-C$_6$ alkyl), —N(C$_1$-C$_6$ alkyl)$_2$, C$_1$-C$_6$ alkyl, C$_1$-C$_6$ alkoxy, C$_1$-C$_6$ alkylthio, C$_1$-C$_6$haloalkyl, C$_1$-C$_6$haloalkoxy, phenyl, 5-6 membered heteroaryl, 4-6 membered heterocycloalkyl, and C$_3$-C$_6$ cycloalkyl, wherein the C$_1$-C$_6$ alkyl, phenyl, C$_3$-C$_6$ cycloalkyl, 4-6 membered heterocycloalkyl, and 5-6 membered heteroaryl of R$^f$ are each optionally substituted with 1, 2, or 3 substituents selected from halo, OH, CN, —COOH, —NH$_2$, C$_1$-C$_4$alkyl, C$_1$-C$_4$ alkoxy, C$_1$-C$_4$ haloalkyl, C$_1$-C$_4$ haloalkoxy, phenyl, C$_3$-C$_{10}$ cycloalkyl, 5-6 membered heteroaryl, and 4-6 membered heterocycloalkyl;

each R$^g$ is independently selected from the group consisting of halo, OH, CN, COOH, —COO—C$_1$-C$_4$ alkyl, —OC(O)C$_1$-C$_4$ alkyl, NH$_2$, NH(C$_1$-C$_6$ alkyl), —N(C$_1$-C$_6$ alkyl)$_2$, C$_1$-C$_6$ alkyl, C$_1$-C$_6$ alkoxy, C$_1$-C$_6$ alkylthio, C$_1$-C$_6$haloalkyl, C$_1$-C$_6$haloalkoxy, phenyl, 5-6 membered heteroaryl, 4-6 membered heterocycloalkyl, and C$_3$-C$_6$ cycloalkyl;

the ring nitrogen atom in Formula (I′″) is optionally oxidized;

the subscript m is 0, 1, 2, or 3; and the subscript n is 0, 1, 2, 3, 4 or 5.

In some embodiments, provided is a compound of Formula (I′″) with the proviso that the compound is not

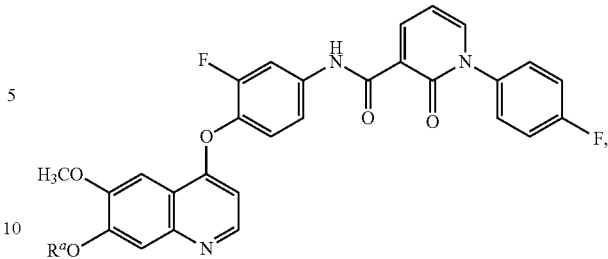

wherein R$^a$ is H, methyl, benzyl, piperidin-4-yl, (piperidin-4-yl)methyl, (1-methylpiperidin-4-yl)methyl, or (1-t-butoxypiperidin-4-yl)methyl.

In some embodiments, provided is a compound of Formula (I′″) with the proviso that when X$^1$ is CH, X$^2$ is CF, X$^3$ is CH, X$^4$ is CR$^2$, X$^5$ is CH, m is 0, R$^g$ is H, R$^{10}$ is H, n is 1, R$^1$ is OCH$_3$ or CN, R$^2$ is OCH$_3$, R$^7$ is fluoro and is para to ring A, and Z$^3$ is CR$^{42}$, then R$^{42}$ cannot be CN, —CH$_2$NH$_2$, —CH$_2$NHCH$_3$, —CH$_2$OCH$_3$, or OH.

In some embodiments, provided is a compound of Formula (I′″) with the proviso that when X$^1$ is CH, X$^3$ is CH, X$^4$ is CR$^2$, R$^1$ is OCH$_3$, R$^2$ is OCH$_3$, R$^g$ is H, n is 1, R$^7$ is fluoro and is para to ring A, one of X$^2$ and X$^5$ is N, or X$^2$ and X$^5$ are each N, then R$^{43}$ is not cyclopropyl or isopropyl.

In some embodiments, provided is a compound of Formula (I′″) with the proviso that the compound is not:

6-cyano-N-(4-((6,7-dimethoxyquinolin-4-yl)oxy)-3-fluorophenyl)-5-(4-fluorophenyl)-1-methyl-4-oxo-1,4-dihydropyridine-3-carboxamide;

6-cyano-1-cyclopropyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-1-cyclobutyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-N-(4-((6,7-dimethoxyquinolin-4-yl)oxy)-3-fluorophenyl)-5-(4-fluorophenyl)-1-isopropyl-4-oxo-1,4-dihydropyridine-3-carboxamide;

6-cyano-N-(4-((6-cyano-7-methoxyquinolin-4-yl)oxy)-3-fluorophenyl)-5-(4-fluorophenyl)-1-isopropyl-4-oxo-1,4-dihydropyridine-3-carboxamide;

6-(aminomethyl)-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

N-(4-((6,7-dimethoxyquinolin-4-yl)oxy)-3-fluorophenyl)-1-(4-fluorophenyl)-5-methyl-6-((methylamino)methyl)-2-oxo-1,2-dihydropyridine-3-carboxamide;

N-(4-((6,7-dimethoxyquinolin-4-yl)oxy)-3-fluorophenyl)-1-(4-fluorophenyl)-6-(methoxymethyl)-5-methyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

5-bromo-N-(4-((6,7-dimethoxyquinolin-4-yl)oxy)-3-fluorophenyl)-1-(4-fluorophenyl)-6-hydroxy-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-isopropyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-2-oxo-5-(prop-1-en-2-yl)-1,2-dihydropyridine-3-carboxamide;

N-(6-((6,7-dimethoxyquinolin-4-yl)oxy)pyridin-3-yl)-5-(4-fluorophenyl)-1-isopropyl-4-oxo-1,4-dihydropyridazine-3-carboxamide;

N-(2-((6,7-dimethoxyquinolin-4-yl)oxy)pyrimidin-5-yl)-5-(4-fluorophenyl)-1-isopropyl-4-oxo-1,4-dihydropyridazine-3-carboxamide;

1-cyclopropyl-N-(6-((6,7-dimethoxyquinolin-4-yl)oxy)pyridin-3-yl)-5-(4-fluorophenyl)-4-oxo-1,4-dihydropyridazine-3-carboxamide;

1-cyclopropyl-N-(2-((6,7-dimethoxyquinolin-4-yl)oxy)pyrimidin-5-yl)-5-(4-fluorophenyl)-4-oxo-1,4-dihydropyridazine-3-carboxamide;

N-(2-((6,7-dimethoxyquinolin-4-yl)oxy)pyrimidin-5-yl)-6-(4-fluorophenyl)-2-isopropyl-5-oxo-2,5-dihydropyridazine-4-carboxamide;

2-cyclopropyl-N-(6-((6,7-dimethoxyquinolin-4-yl)oxy)pyridin-3-yl)-6-(4-fluorophenyl)-5-oxo-2,5-dihydropyridazine-4-carboxamide; or 2-cyclopropyl-N-(2-((6,7-dimethoxyquinolin-4-yl)oxy)pyrimidin-5-yl)-6-(4-fluorophenyl)-5-oxo-2,5-dihydropyridazine-4-carboxamide.

Provided herein is a compound of Formula (I'):

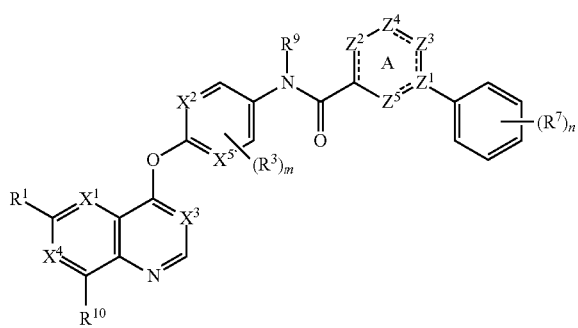

(I')

or a pharmaceutically acceptable salt, a stereoisomer, tautomer or a mixture of stereoisomers thereof, wherein:

$X^1$ is N or $CR^{11}$;
$X^2$ is N, $CR^3$, or CH;
$X^3$ is N or CH;
$X^4$ is N or $CR^2$;
$X^5$ is N, $CR^3$, or CH;
$Z^1$ is N, CH or C;
$Z^2$ is N, $NR^{40}$, —C(=O)—, or $CR^{45}$;
$Z^3$ is N, $NR^{41}$, $CR^{42}$, —C(=O)—, —C(=S)—;
$Z^4$ is N, $NR^{43}$, $CR^{44}$, —C(=O)— or a bond;
$Z^5$ is $COR^{46}$, —C(=O)— or $CR^{18}$;
==== is a single bond or a double bond;
one or two of $Z^1$, $Z^2$, $Z^3$ and $Z^4$ are independently selected from N, $NR^{40}$, $NR^{41}$, and $NR^{43}$;
no more than two of $Z^2$, $Z^3$, $Z^4$ and $Z^5$ are —C(=O)—;
when ring A is

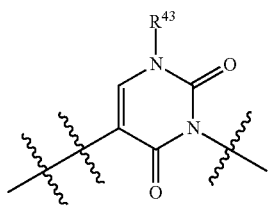

then $X^1$ is N, wherein the single wavy line indicates the point of attachment to the phenyl ring and the double wavy line indicates the point of attachment to the carbonyl of the amide linkage;

$R^1$ and $R^2$ and $R^{10}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$ and $R^2$ are each optionally substituted with 1, 2, 3, 4 or 5 independently selected $R^b$ substituents;

each $R^3$ is independently selected from halo, OH, CN, —COOH, —CONH($C_{1-6}$ alkyl), —$SO_2$($C_{1-6}$ alkyl), —$SO_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^{40}$, $R^{41}$ and $R^{43}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_1$-4 alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $N=C(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^{40}$, $R^{41}$ and $R^{43}$ are each optionally substituted with 1, 2, 3, 4 or 5 independently selected $R^b$ substituents;

$R^{45}$, $R^{42}$ and $R^{44}$ are each independently H, halo, $C_{1-6}$ alkyl optionally substituted with 1 or 2 independently selected $R^g$ substituents, $C_{2-6}$ alkenyl, $C_{1-6}$ alkoxy, CN, $C_{1-4}$ haloalkyl, $C_{1-6}$ haloalkoxy, OH, —S—$C_{1-6}$ alkyl, —COOH, —COC$_{1-4}$alkyl, —COOC$_{1-4}$alkyl, —CONH$_2$, —CONHC$_{1-4}$alkyl, —NHC(O)OC$_{1-4}$alkyl, $NH_2$, —NHC$_{1-4}$alkyl, or —N(C$_{1-4}$ alkyl)$_2$;

each $R^7$ is independently selected from halo, OH, COOR$^a$, CONR$^a$R$^a$, CN, NH$_2$, —NH(C$_1$-C$_6$ alkyl), —N(C$_1$-C$_6$ alkyl)$_2$, C$_1$-C$_6$ alkyl, C$_1$-C$_6$ alkoxy, C$_1$-C$_6$ haloalkyl, C$_1$-C$_6$ haloalkoxy, CONR$^a$R$^a$, NR$^a$COR$^a$, NR$^a$CONR$^a$R$^a$, SO$_2$R$^a$, NR$^a$S(O)$_2$R$^a$, NR$^a$S(O)$_2$NR$^a$R$^a$, C$_3$-C$_6$ cycloalkyl, 4- to 6-membered heterocycloalkyl, phenyl, 5- or 6-membered heteroaryl, C$_3$-C$_6$ cycloalkyl-C$_1$-C$_4$ alkylene-, (4- to 6-membered heterocycloalkyl)-C$_1$-C$_4$ alkylene-, phenyl-C$_1$-C$_2$ alkylene, and (5- or 6-membered heteroaryl)-C$_1$-C$_4$ alkylene-; wherein the C$_1$-C$_6$ alkyl, C$_3$-C$_6$ cycloalkyl, 4- to 6-membered heterocycloalkyl, phenyl, 5- or 6-membered heteroaryl, C$_3$-C$_6$ cycloalkyl-C$_1$-C$_4$ alkylene-, (4- to 6-membered heterocycloalkyl)-C$_1$-C$_4$ alkylene-, phenyl-C$_1$-C$_2$ alkylene, and (5- or 6-membered heteroaryl)-C$_1$-C$_4$ alkylene- of R$^7$ are each optionally substituted with 1, 2, or 3 independently selected R$^f$ substituents;

$R^{46}$ is H, C$_{1-6}$ alkyl or a hydroxy protecting group;

$R^9$ is H or C$_{1-6}$ alkyl optionally substituted with 1, 2, or 3 independently selected R$^g$ substituents;

$R^{11}$ is selected from H, C$_1$-C$_6$ alkyl, C$_1$-C$_6$ haloalkyl, halo, C$_6$-C$_{10}$ aryl, 5-10 membered heteroaryl, C$_3$-C$_{10}$ cycloalkyl, 4-10 membered heterocycloalkyl, C$_6$-C$_{10}$ aryl-C$_1$-C$_4$ alkylene-, C$_3$-C$_{10}$ cycloalkyl-C$_1$-C$_4$ alkylene-, (5-10 membered heteroaryl)-C$_1$-C$_4$ alkylene-, (4-10 membered heterocycloalkyl)-C$_1$-C$_4$ alkylene-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$; wherein the C$_1$-C$_6$ alkyl, C$_1$-C$_6$ haloalkyl, C$_6$-C$_{10}$ aryl, 5-10 membered heteroaryl, C$_3$-C$_{10}$ cycloalkyl, 4-10 membered heterocycloalkyl, C$_6$-C$_{10}$ aryl-C$_1$-C$_4$ alkylene-, C$_3$-C$_{10}$ cycloalkyl-C$_1$-C$_4$ alkylene-, (5-10 membered heteroaryl)-C$_1$-C$_4$ alkylene-, and (4-10 membered heterocycloalkyl)-C$_1$-C$_4$ alkylene- of R$^{11}$ are each optionally substituted with 1, 2, or 3 independently selected R$^f$ substituents;

$R^{18}$ is H, halo, CN, C$_{1-6}$ alkyl, NH$_2$, —NHC$_{1-4}$alkyl, —N(C$_{1-4}$ alkyl)$_2$, or —S—C$_{1-6}$ alkyl;

or $R^{40}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or $R^{43}$ and $R^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or $R^{44}$ and $R^{45}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents and wherein one or two ring carbon atoms of the fused C$_{3-7}$ cycloalkyl are optionally replaced by a carbonyl;

or when Z$^4$ is a bond, R$^{40}$ and R$^{42}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or when Z$^4$ is a bond, R$^{41}$ and R$^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or when Z$^4$ is a bond, R$^{42}$ and R$^{45}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents and wherein one or two ring carbon atoms of the fused C$_{3-7}$ cycloalkyl are optionally replaced by a carbonyl;

or $R^{41}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or $R^{42}$ and $R^{43}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or $R^{42}$ and $R^{44}$ taken together with the atoms to which they are attached form fused C$_{3-7}$ cycloalkyl, fused phenyl, or fused heteroaryl, wherein the fused C$_{3-7}$ cycloalkyl, fused phenyl, and fused heteroaryl are each optionally substituted with 1 or 2 independently selected R$^g$ substituents and wherein one or two ring carbon atoms of the fused C$_{3-7}$ cycloalkyl are optionally replaced by a carbonyl;

each R$^a$ is independently selected from the group consisting of H, CN, C$_1$-C$_6$ alkyl, C$_1$-C$_6$ haloalkyl, C$_2$-C$_6$ alkenyl, C$_2$-C$_6$ alkynyl, C$_6$-C$_{10}$ aryl, C$_3$-C$_{10}$ cycloalkyl, 5-14 membered heteroaryl, 4-14 membered heterocycloalkyl, C$_6$-C$_{10}$ aryl-C$_1$-C$_4$ alkylene-, C$_3$-C$_{10}$ cycloalkyl-C$_1$-C$_4$ alkylene-, (5-14 membered heteroaryl)-C$_1$-C$_4$ alkylene-, and (4-14 membered heterocycloalkyl)-C$_1$-C$_4$ alkylene-; wherein the C$_1$-C$_6$ alkyl, C$_1$-C$_6$ haloalkyl, C$_2$-C$_6$ alkenyl, C$_2$-C$_6$ alkynyl, C$_6$-C$_{10}$ aryl, C$_3$-C$_{10}$ cycloalkyl, 5-14 membered heteroaryl, 4-14 membered heterocycloalkyl, C$_6$-C$_{10}$ aryl-C$_1$-C$_4$ alkylene-, C$_3$-C$_{10}$ cycloalkyl-C$_1$-C$_4$ alkylene-, (5-14 membered heteroaryl)-C$_1$-C$_4$ alkylene-, and (4-14 membered heterocycloalkyl)-C$_1$-C$_4$ alkylene- of R$^a$ are each optionally substituted with 1, 2, 3, 4, or 5 independently selected R$^d$ substituents;

or any two R$^a$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

each R$^b$ is independently selected from the group consisting of halo, C$_1$-C$_6$ alkyl, C$_2$-C$_6$ alkenyl, C$_2$-C$_6$ alkynyl, C$_1$-C$_6$ haloalkyl, C$_1$-C$_6$ haloalkoxy, C$_6$-C$_{10}$ aryl, C$_3$-C$_{10}$ cycloalkyl, 5-10 membered heteroaryl, 4-10 membered heterocycloalkyl, C$_6$-C$_{10}$ aryl-C$_1$-C$_4$ alkylene-, C₃-C₁₀ cycloalkyl-C₁-C₄ alkylene-, (5-10 membered heteroaryl)-C₁-C₄ alkylene-, (4-10 membered heterocycloalkyl)-C₁-C₄ alkylene-, CN, OH, NH₂, NO₂, NHOR$^e$, OR$^e$, SR$^e$, C(O)R$^e$, C(O)NR$^e$R$^e$, C(O)OR$^e$, C(O)NR$^e$S(O)₂R$^e$, OC(O)R$^e$, OC(O)NR$^e$R$^e$, C(=NOH)R$^e$, C(=NOH)NR$^e$, C(=NCN)NR$^e$R$^e$, NR$^e$C(=NCN)NR$^e$R$^e$, C(=NR$^e$)NR$^e$R$^e$, NR$^e$C (=NR$^e$)NR$^e$R$^e$, NHR$^e$, NR$^e$R$^e$, NR$^e$C(O)R$^e$, NR$^e$C (=NR$^e$)R$^e$, NR$^e$C(O)OR$^e$, NR$^e$C(O)NR$^e$R$^e$, NR$^e$S(O) R$^e$, NR$^e$S(O)₂R$^e$, NR$^e$S(O)₂NR$^e$R$^e$, S(O)R$^e$, S(O) NR$^e$R$^e$, S(O)₂R$^e$, S(O)₂NR$^e$C(O)R$^e$, Si(R$^e$)₃, P(O) R$^e$R$^e$, P(O)(OR$^e$)(OR$^e$), B(OH)₂, B(OR$^e$)₂, and S(O)₂ NR$^e$R$^e$; wherein the C₁-C₆ alkyl, C₁-C₆ haloalkyl, C₁-C₆ haloalkoxy, C₂-C₆ alkenyl, C₂-C₆ alkynyl, C₆-C₁₀ aryl, C₃-C₁₀ cycloalkyl, 5-10 membered heteroaryl, 4-10 membered heterocycloalkyl, C₆-C₁₀ aryl-C₁-C₄ alkylene-, C₃-C₁₀ cycloalkyl-C₁-C₄ alkylene-, (5-10 membered heteroaryl)-C₁-C₄ alkylene-, and (4-10 membered heterocycloalkyl)-C₁-C₄ alkylene- of R$^b$ are each further optionally substituted with 1, 2, or 3 independently selected R$^d$ substituents;

each R$^c$ is independently selected from the group consisting of H, C₁-C₆ alkyl, C₁-C₆ haloalkyl, C₂-C₆ alkenyl, C₂-C₆ alkynyl, C₆-C₁₀ aryl, C₃-C₁₀ cycloalkyl, 5-10 membered heteroaryl, 4-10 membered heterocycloalkyl, C₆-C₁₀ aryl-C₁-C₄ alkylene-, C₃-C₁₀ cycloalkyl-C₁-C₄ alkylene-, (5-10 membered heteroaryl)-C₁-C₄ alkylene-, and (4-10 membered heterocycloalkyl)-C₁-C₄ alkylene-; wherein the C₁-C₆ alkyl, C₂-C₆ alkenyl, C₂-C₆ alkynyl, C₆-C₁₀ aryl, C₃-C₁₀ cycloalkyl, 5-10 membered heteroaryl, 4-10 membered heterocycloalkyl, C₆-C₁₀ aryl-C₁-C₄ alkylene-, C₃-C₁₀ cycloalkyl-C₁-C₄ alkylene-, (5-10 membered heteroaryl)-C₁-C₄ alkylene-, and (4-10 membered heterocycloalkyl)-C₁-C₄ alkylene- of R$^c$ are each optionally substituted with 1, 2, 3, 4, or 5 independently selected R$^f$ substituents;

or any two R$^C$ substituents together with the nitrogen atom to which they are attached form 4-, 5-, 6-, 7-, 8-, 9-, or 10-membered heterocycloalkyl, each of which is optionally substituted with 1, 2, or 3 independently selected R$^f$ substituents;

each R$^d$ is independently selected from the group consisting of C₁-C₆ alkyl, C₁-C₆ haloalkyl, halo, C₆-C₁₀ aryl, 5-10 membered heteroaryl, C₃-C₁₀ cycloalkyl, 4-10 membered heterocycloalkyl, C₆-C₁₀ aryl-C₁-C₄ alkylene-, C₃-C₁₀ cycloalkyl-C₁-C₄ alkylene-, (5-10 membered heteroaryl)-C₁-C₄ alkylene-, (4-10 membered heterocycloalkyl)-C₁-C₄ alkylene-, CN, NH₂, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C (=NCN)NR$^e$R$^e$, S(O)R$^e$, S(O)NR$^e$R$^e$, S(O)₂R$^e$, NR$^e$S (O)₂R$^e$, NR$^e$S(O)₂NR$^e$R$^e$, and S(O)₂NR$^e$R$^e$; wherein the C₁-C₆ alkyl, C₁-C₆ haloalkyl, C₆-C₁₀ aryl, 5-10 membered heteroaryl, C₃-C₁₀ cycloalkyl, 4-10 membered heterocycloalkyl, C₆-C₁₀ aryl-C₁-C₄ alkylene-, C₃-C₁₀ cycloalkyl-C₁-C₄ alkylene-, (5-10 membered heteroaryl)-C₁-C₄ alkylene-, and (4-10 membered heterocycloalkyl)-C₁-C₄ alkylene- of R$^d$ are each optionally substituted with 1, 2, or 3 independently selected R$^f$ substituents;

each R$^e$ is independently selected from the group consisting of H, C₁-C₆ alkyl, C₃-C₆ cycloalkyl, C₃-C₆ cycloalkyl-C₁-C₄ alkylene-, C₆-C₁₀ aryl, C₆-C₁₀ aryl-C₁-C₄ alkylene-, 5- or 6-membered heteroaryl, (5- or 6-membered heteroaryl)-C₁-C₄ alkylene-, 4-7-membered heterocycloalkyl, (4-7-membered heterocycloalkyl)-C₁-C₄ alkylene-, C₁-C₆ haloalkyl, C₁-C₆ haloalkoxy, C₂-C₄ alkenyl, and C₂-C₄ alkynyl, wherein the C₁-C₆ alkyl, C₃-C₆ cycloalkyl, C₆-C₁₀ aryl, 5 or 6-membered heteroaryl, 4-7-membered heterocycloalkyl, C₆-C₁₀ aryl-C₁-C₄ alkylene-, (5- or 6-membered heteroaryl)-C₁-C₄ alkylene-, (4-7-membered heterocycloalkyl)-C₁-C₄ alkylene-, C₂-C₄ alkenyl, and C₂-C₄ alkynyl of R$^e$ are each optionally substituted with 1, 2, or 3 R$^f$ substituents;

or any two R$^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected R$^f$ substituents;

each R$^f$ is independently selected from the group consisting of halo, OH, CN, COOH, NH₂, —NH(C₁-C₆ alkyl), —N(C₁-C₆ alkyl)₂, C₁-C₆ alkyl, C₁-C₆ alkoxy, C₁-C₆ alkylthio, C₁-C₆ haloalkyl, C₁-C₆ haloalkoxy, phenyl, 5-6 membered heteroaryl, 4-6 membered heterocycloalkyl, and C₃-C₆ cycloalkyl, wherein the C₁-C₆ alkyl, phenyl, C₃-C₆ cycloalkyl, 4-6 membered heterocycloalkyl, and 5-6 membered heteroaryl of R$^f$ are each optionally substituted with 1, 2, or 3 substituents selected from halo, OH, CN, —COOH, —NH₂, C₁-C₄ alkyl, C₁-C₄ alkoxy, C₁-C₄ haloalkyl, C₁-C₄ haloalkoxy, phenyl, C₃-C₁₀ cycloalkyl, 5-6 membered heteroaryl, and 4-6 membered heterocycloalkyl;

each R$^g$ is independently selected from the group consisting of halo, OH, CN, COOH, —COO—C₁-C₄ alkyl, —OC(O)C₁-C₄ alkyl, NH₂, NH(C₁-C₆ alkyl), —N(C₁-C₆ alkyl)₂, C₁-C₆ alkyl, C₁-C₆ alkoxy, C₁-C₆ alkylthio, C₁-C₆ haloalkyl, C₁-C₆ haloalkoxy, phenyl, 5-6 membered heteroaryl, 4-6 membered heterocycloalkyl, and C₃-C₆ cycloalkyl;

the ring nitrogen atom in Formula (I') is optionally oxidized;

the subscript m is 0, 1, 2, or 3; and the subscript n is 0, 1, 2, 3, 4 or 5.

In some embodiments, provided is a compound of Formula (I') with the proviso that the compound is not

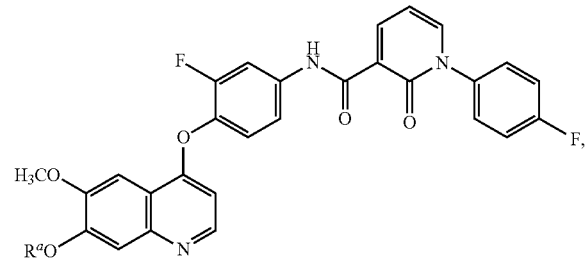

wherein R$^a$ is H, methyl, benzyl, piperidin-4-yl, (piperidin-4-yl)methyl, (1-methylpiperidin-4-yl)methyl, or (1-t-butoxypiperidin-4-yl)methyl.

In some embodiments, provided is a compound of Formula (I') with the proviso that when X¹ is CH, X² is CF, X³ is CH, X⁴ is CR², X⁵ is CH, m is 0, R⁹ is H, R¹⁰ is H, n is 1, R¹ is OCH₃ or CN, R² is OCH₃, R⁷ is fluoro and is para to ring A, and Z³ is CR⁴², then R⁴² cannot be CN, —CH₂NH₂, —CH₂NHCH₃, —CH₂OCH₃, or OH.

In some embodiments, provided is a compound of Formula (I') with the proviso that when X¹ is CH, X³ is CH, X⁴ is CR², R¹ is OCH₃, R² is OCH₃, R⁹ is H, n is 1, R⁷ is fluoro and is para to ring A, one of $X^2$ and $X^5$ is N, or $X^2$ and $X^5$ are each N, then $R^{43}$ is not cyclopropyl or isopropyl.

In some embodiments, provided is a compound of Formula (I') with the proviso that the compound is not:

6-cyano-N-(4-((6,7-dimethoxyquinolin-4-yl)oxy)-3-fluorophenyl)-5-(4-fluorophenyl)-1-methyl-4-oxo-1,4-dihydropyridine-3-carboxamide;

6-cyano-1-cyclopropyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-1-cyclobutyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-N-(4-((6,7-dimethoxyquinolin-4-yl)oxy)-3-fluorophenyl)-5-(4-fluorophenyl)-1-isopropyl-4-oxo-1,4-dihydropyridine-3-carboxamide;

6-cyano-N-(4-((6-cyano-7-methoxyquinolin-4-yl)oxy)-3-fluorophenyl)-5-(4-fluorophenyl)-1-isopropyl-4-oxo-1,4-dihydropyridine-3-carboxamide;

6-(aminomethyl)-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

N-(4-((6,7-dimethoxyquinolin-4-yl)oxy)-3-fluorophenyl)-1-(4-fluorophenyl)-5-methyl-6-((methylamino)methyl)-2-oxo-1,2-dihydropyridine-3-carboxamide;

N-(4-((6,7-dimethoxyquinolin-4-yl)oxy)-3-fluorophenyl)-1-(4-fluorophenyl)-6-(methoxymethyl)-5-methyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

5-bromo-N-(4-((6,7-dimethoxyquinolin-4-yl)oxy)-3-fluorophenyl)-1-(4-fluorophenyl)-6-hydroxy-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-isopropyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-2-oxo-5-(prop-1-en-2-yl)-1,2-dihydropyridine-3-carboxamide;

N-(6-((6,7-dimethoxyquinolin-4-yl)oxy)pyridin-3-yl)-5-(4-fluorophenyl)-1-isopropyl-4-oxo-1,4-dihydropyridazine-3-carboxamide;

N-(2-((6,7-dimethoxyquinolin-4-yl)oxy)pyrimidin-5-yl)-5-(4-fluorophenyl)-1-isopropyl-4-oxo-1,4-dihydropyridazine-3-carboxamide;

1-cyclopropyl-N-(6-((6,7-dimethoxyquinolin-4-yl)oxy)pyridin-3-yl)-5-(4-fluorophenyl)-4-oxo-1,4-dihydropyridazine-3-carboxamide;

1-cyclopropyl-N-(2-((6,7-dimethoxyquinolin-4-yl)oxy)pyrimidin-5-yl)-5-(4-fluorophenyl)-4-oxo-1,4-dihydropyridazine-3-carboxamide;

N-(2-((6,7-dimethoxyquinolin-4-yl)oxy)pyrimidin-5-yl)-6-(4-fluorophenyl)-2-isopropyl-5-oxo-2,5-dihydropyridazine-4-carboxamide;

2-cyclopropyl-N-(6-((6,7-dimethoxyquinolin-4-yl)oxy)pyridin-3-yl)-6-(4-fluorophenyl)-5-oxo-2,5-dihydropyridazine-4-carboxamide; or 2-cyclopropyl-N-(2-((6,7-dimethoxyquinolin-4-yl)oxy)pyrimidin-5-yl)-6-(4-fluorophenyl)-5-oxo-2,5-dihydropyridazine-4-carboxamide.

Provided herein is a compound of formula (I):

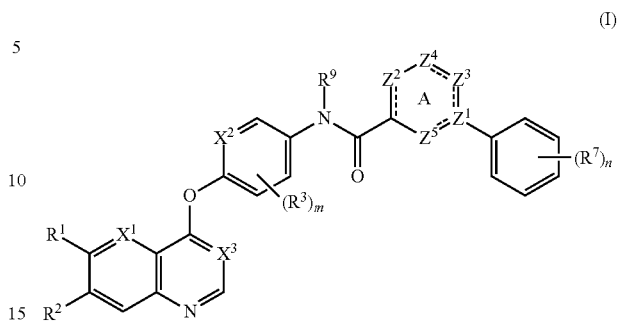

or a pharmaceutically acceptable salt, stereoisomer, or mixture of stereoisomers thereof, wherein:
$X^1$ is N or $CR^{11}$;
$X^2$ is N, $CR^3$, or CH;
$X^3$ is N or CH;
$Z^1$ is N, CH or C;
$Z^2$ is N, $NR^{40}$, —C(=O)—, or $CR^{45}$;
$Z^3$ is N, $NR^{41}$, $CR^{42}$, —C(=O)—, —C(=S)—;
$Z^4$ is N, $NR^{43}$, $CR^{44}$, —C(=O)— or a bond;
$Z^5$ is $COR^{46}$, —C(=O)— or $CR^{18}$;
==== is a single bond or a double bond;
one or two of $Z^1$, $Z^2$, $Z^3$ and $Z^4$ are independently selected from N, $NR^{40}$, $NR^{41}$, and $NR^{43}$;
no more than two of $Z^2$, $Z^3$, $Z^4$ and $Z^5$ are —C(=O)—;
when ring A is

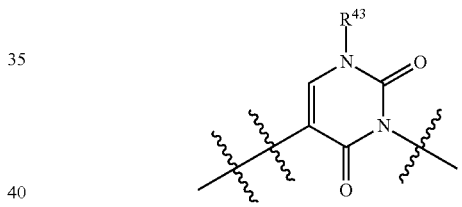

then $X^1$ is N, wherein the single wavy line indicates the point of attachment to the phenyl ring and the double wavy line indicates the point of attachment to the carbonyl of the amide linkage;

$R^1$ and $R^2$ are each independently selected from H, halo, $C_{1-6}$ alkyl, $C_{2-6}$ alkenyl, $C_{2-6}$ alkynyl, $C_{1-6}$ haloalkyl, $C_{1-6}$haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^1$ and $R^2$ are each optionally substituted with 1, 2, 3, 4 or 5 independently selected R substituents;

each $R^3$ is independently selected from halo, OH, CN, —COOH, —CONH($C_{1-6}$ alkyl), —SO$_2$($C_{1-6}$ alkyl), —SO$_2$NH($C_{1-6}$ alkyl), $C_1$-$C_6$ alkyl, $C_1$-$C_6$ alkoxy, $C_1$-$C_6$ haloalkoxy, NH$_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

$R^{40}$, $R^{41}$ and $R^{43}$ are each independently selected from H, halo, $C_{1-6}$ alkyl, $C_{2-6}$ alkenyl, $C_{2-6}$ alkynyl, $C_{1-6}$haloalkyl, $C_{1-6}$haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, NO$_2$, OR$^a$, SR$^a$, NHOR$^a$, C(O)R$^a$, C(O)NR$^a$R$^a$, C(O)OR$^a$, C(O)NR$^a$S(O)$_2$R$^a$, OC(O)R$^a$, OC(O)NR$^a$R$^a$, NHR$^a$, NR$^a$R$^a$, NR$^a$C(O)R$^a$, N=C(NR$^a$R$^a$)$_2$, NR$^a$C(=NR$^a$)R$^a$, NR$^a$C(O)OR$^a$, NR$^a$C(O)NR$^a$R$^a$, C(=NR$^a$)R$^a$, C(=NOH)R$^a$, C(=NOH)NR$^a$, C(=NCN)NR$^a$R$^a$, NR$^a$C(=NCN)NR$^a$R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, S(O)$_2$NR$^a$C(O)R$^a$, P(O)R$^a$R$^a$, P(O)(OR$^a$)(OR$^a$), B(OH)$_2$, B(OR$^a$)$_2$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^{40}$, $R^{41}$ and $R^{43}$ are each optionally substituted with 1, 2, 3, 4 or 5 independently selected $R^b$ substituents;

$R^{45}$, $R^{42}$ and $R^{44}$ are each independently H, $C_{1-6}$ alkyl optionally substituted with 1 or 2 independently selected $R^g$ substituents, $C_{1-6}$ alkoxy, CN, $C_{1-4}$ haloalkyl, $C_{1-4}$ haloalkoxy, OH, —COC$_{1-4}$alkyl, —COOC$_{1-4}$ alkyl, —CONC$_{1-4}$ alkyl, NH$_2$, —NHC$_{1-4}$alkyl, or —N(C$_{1-4}$ alkyl)$_2$;

each $R^7$ is independently selected from halo, OH, COOR$^a$, CONR$^a$R$^a$, CN, NH$_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ haloalkyl, $C_1$-$C_6$ haloalkoxy, CONR$^a$R$^a$, NR$^a$COR$^a$, NR$^a$CONR$^a$R$^a$, SO$_2$R$^a$, NR$^a$S(O)$_2$R$^a$, NR$^a$S(O)$_2$NR$^a$R$^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-; wherein the $C_1$-$C_6$ alkyl, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4- to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene- of $R^7$ are each optionally substituted with 1, 2, or 3 independently selected $R^f$ substituents;

$R^{46}$ is H, $C_{1-6}$ alkyl or a hydroxy protecting group;

$R^9$ is H or $C_{1-6}$ alkyl optionally substituted with 1, 2, or 3 independently selected $R^g$ substituents;

$R^{11}$ is selected from H, $C_1$-$C_6$ alkyl, $C_1$-$C_6$haloalkyl, halo, $C_{6-10}$ aryl, 5-10 membered heteroaryl, $C_3$-$C_{10}$ cycloalkyl, 4-10 membered heterocycloalkyl, $C_{6-10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, and S(O)$_2$NR$^e$R$^e$; wherein the $C_1$-$C_6$ alkyl, $C_1$-$C_6$haloalkyl, $C_{6-10}$ aryl, 5-10 membered heteroaryl, $C_3$-$C_{10}$ cycloalkyl, 4-10 membered heterocycloalkyl, $C_{6-10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^{11}$ are each optionally substituted with 1, 2, or 3 independently selected $R^f$ substituents;

$R^{18}$ is H, halo, CN, or $C_{1-6}$ alkyl;

or $R^{40}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{43}$ and $R^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{44}$ and $R^{45}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents and wherein one or two ring carbon atoms of the fused $C_{3-7}$ cycloalkyl are optionally replaced by a carbonyl;

or when $Z^4$ is a bond, $R^{40}$ and $R^{42}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{41}$ and $R^{45}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or when $Z^4$ is a bond, $R^{42}$ and $R^{45}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents and wherein one or two ring carbon atoms of the fused $C_{3-7}$ cycloalkyl are optionally replaced by a carbonyl;

or $R^{41}$ and $R^{44}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{42}$ and $R^{43}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{42}$ and $R^{44}$ taken together with the atoms to which they are attached form fused $C_{3-7}$ cycloalkyl, fused phenyl, or fused heteroaryl, wherein the fused $C_{3-7}$ cycloalkyl, fused phenyl, and fused heteroaryl are each optionally substituted with 1 or 2 independently selected $R^g$ substituents and wherein one or two ring carbon atoms of the fused $C_{3-7}$ cycloalkyl are optionally replaced by a carbonyl;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-14 membered heteroaryl)-$C_1$-$C_4$ alkylene-, and (4-14 membered heterocycloalkyl)-$C_1$-$C_4$ alkylene-; wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene- of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^e$, $OC(O)NR^eR^e$, $C(=NOH)R^e$, $C(=NOH)NR^e$, $C(=NCN)NR^eR^e$, $NR^eC(=NCN)NR^eR^e$, $C(=NR^e)NR^eR^e$, $NR^eC(=NR^e)NR^eR^e$, $NHR^e$, $NR^eR^e$, $NR^eC(O)R^e$, $NR^eC(=NR^e)R^e$, $NR^eC(O)OR^e$, $NR^eC(O)NR^eR^e$, $NR^eS(O)R^e$, $NR^eS(O)_2R^e$, $NR^eS(O)_2NR^eR^e$, $S(O)R^e$, $S(O)NR^eR^e$, $S(O)_2R^e$, $S(O)_2NR^eC(O)R^e$, $Si(R^e)_3$, $P(O)R^eR^e$, $P(O)(OR^e)(OR^e)$, $B(OH)_2$, $B(OR^e)_2$, and $S(O)_2NR^eR^e$; wherein the $C_1$-$C_6$ alkyl, $C_1$-$C_6$ haloalkyl, $C_1$-$C_6$ haloalkoxy, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene- of $R^b$ are each further optionally substituted with 1, 2, or 3 independently selected $R^d$ substituents;

each $R^e$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene-; wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$alkylene-, $C_3$-$C_{10}$ cycloalkyl-$C_1$-$C_4$alkylene-, (5-10 membered heteroaryl)-$C_1$-$C_4$ alkylene-, and (4-10 membered heterocycloalkyl)-$C_1$-$C_4$ alkylene- of $R^e$ are each optionally substituted with 1, 2, 3, 4, or 5 independently selected $R^f$ substituents;

or any two $R^e$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$haloalkyl, halo, $C_6$-$C_{10}$ aryl, 5–10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR$; wherein the $C_1$-$C_6$ alkyl, $C_1$-$C_6$haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene- of $R^d$ are each optionally substituted with 1, 2, or 3 independently selected $R^f$ substituents;

each $R^e$ is independently selected from the group consisting of H, $C_1$-$C_6$ alkyl, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, COOH, $NH_2$, —$NH(C_1$-$C_6$ alkyl), —$N(C_1$-$C_6$ alkyl)$_2$, $C_1$-$C_6$alkyl, $C_1$-$C_6$alkoxy, $C_1$-$C_6$alkylthio, $C_1$-$C_6$haloalkyl, $C_1$-$C_6$ haloalkoxy, phenyl, 5-6 membered heteroaryl, 4-6 membered heterocycloalkyl, and $C_3$-$C_6$ cycloalkyl, wherein the $C_1$-$C_6$ alkyl, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, —$NH_2$, $C_1$-$C_4$alkyl, $C_1$-$C_4$alkoxy, $C_1$-$C_4$ haloalkyl, $C_1$-$C_4$ haloalkoxy, phenyl, C$_3$-C$_{10}$ cycloalkyl, 5-6 membered heteroaryl, and 4-6 membered heterocycloalkyl;

each R$^g$ is independently selected from the group consisting of halo, OH, CN, COOH, —COO—C$_1$-C$_4$ alkyl, NH$_2$, NH(C$_1$-C$_6$ alkyl), —N(C$_1$-C$_6$ alkyl)$_2$, C$_1$-C$_6$alkyl, C$_1$-C$_6$alkoxy, C$_1$-C$_6$alkylthio, C$_1$-C$_6$haloalkyl, C$_1$-C$_6$haloalkoxy, phenyl, 5-6 membered heteroaryl, 4-6 membered heterocycloalkyl, and C$_3$-C$_6$ cycloalkyl;

the ring nitrogen atom in Formula (I) is optionally oxidized;

the subscript m is 0, 1, 2, or 3; and the subscript n is 0, 1, 2, 3, 4 or 5;

with the proviso that the compound is not

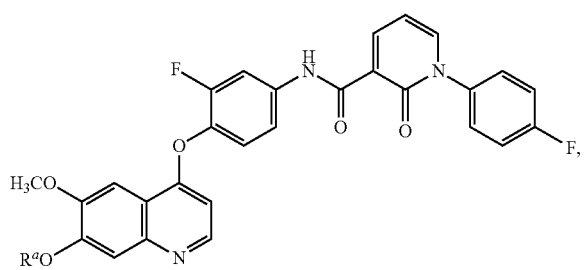

wherein R$^a$ is H, methyl, benzyl, piperidin-4-yl, (piperidin-4-yl)methyl, (1-methylpiperidin-4-yl)methyl, or (1-t-butoxypiperidin-4-yl)methyl.

In some embodiments, provided is a compound of Formula (I) with the proviso that when X$^1$ is CH, X$^2$ is CF, X$^3$ is CH, m is 0, R$^9$ is H, n is 1, R$^1$ is OCH$_3$ or CN, R$^2$ is OCH$_3$, R$^7$ is fluoro and is para to ring A, and Z$^3$ is CR$^{42}$, then R$^{42}$ cannot be CN, —CH$_2$NH$_2$, —CH$_2$NHCH$_3$, —CH$_2$OCH$_3$, or OH.

In some embodiments, provided is a compound of Formula (I) with the proviso that when X$^1$ is CH, X$^3$ is CH, R$^1$ is OCH$_3$, R$^2$ is OCH$_3$, R$^9$ is H, n is 1, R$^7$ is fluoro and is para to ring A, and X$^2$ is N, then R$^{43}$ is not cyclopropyl or isopropyl.

In some embodiments, provided is a compound of Formula (I) with the proviso that the compound is not:

6-cyano-N-(4-((6,7-dimethoxyquinolin-4-yl)oxy)-3-fluorophenyl)-5-(4-fluorophenyl)-1-methyl-4-oxo-1,4-dihydropyridine-3-carboxamide;

6-cyano-1-cyclopropyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-1-cyclobutyl-N-(4-((6,7-dimethoxyquinolin-4-yl)oxy)-3-fluorophenyl)-5-(4-fluorophenyl)-4-oxo-1,4-dihydropyridine-3-carboxamide;

6-cyano-N-(4-((6,7-dimethoxyquinolin-4-yl)oxy)-3-fluorophenyl)-5-(4-fluorophenyl)-1-isopropyl-4-oxo-1,4-dihydropyridine-3-carboxamide;

6-cyano-N-(4-((6-cyano-7-methoxyquinolin-4-yl)oxy)-3-fluorophenyl)-5-(4-fluorophenyl)-1-isopropyl-4-oxo-1,4-dihydropyridine-3-carboxamide;

6-(aminomethyl)-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

N-(4-((6,7-dimethoxyquinolin-4-yl)oxy)-3-fluorophenyl)-1-(4-fluorophenyl)-5-methyl-6-((methylamino)methyl)-2-oxo-1,2-dihydropyridine-3-carboxamide;

N-(4-((6,7-dimethoxyquinolin-4-yl)oxy)-3-fluorophenyl)-1-(4-fluorophenyl)-6-(methoxymethyl)-5-methyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-methyl-2-oxo-1,2-dihydropyridine-3-carboxamide;

5-bromo-N-(4-((6,7-dimethoxyquinolin-4-yl)oxy)-3-fluorophenyl)-1-(4-fluorophenyl)-6-hydroxy-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-5-isopropyl-2-oxo-1,2-dihydropyridine-3-carboxamide;

6-cyano-N-(4-((6,7-dimethoxyquinolin-4-yl)oxy)-3-fluorophenyl)-1-(4-fluorophenyl)-2-oxo-5-(prop-1-en-2-yl)-1,2-dihydropyridine-3-carboxamide;

N-(6-((6,7-dimethoxyquinolin-4-yl)oxy)pyridin-3-yl)-5-(4-fluorophenyl)-1-isopropyl-4-oxo-1,4-dihydropyridazine-3-carboxamide;

1-cyclopropyl-N-(6-((6,7-dimethoxyquinolin-4-yl)oxy)pyridin-3-yl)-5-(4-fluorophenyl)-4-oxo-1,4-dihydropyridazine-3-carboxamide; or 2-cyclopropyl-N-(6-((6,7-dimethoxyquinolin-4-yl)oxy)pyridin-3-yl)-6-(4-fluorophenyl)-5-oxo-2,5-dihydropyridazine-4-carboxamide.

Also provided herein is a compound of Formula (I"):

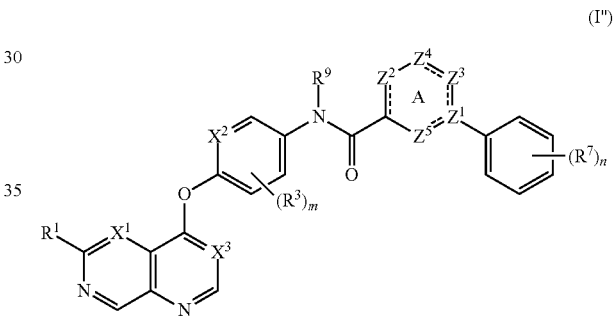

(I")

or a pharmaceutically acceptable salt, a stereoisomer, or a mixture of stereoisomers thereof.

In some embodiments, when ring A is

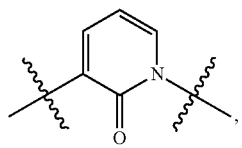 [SMILES: *c1cccn(*)c1=O]

then X$^1$ is N.

In some embodiments, ring A is

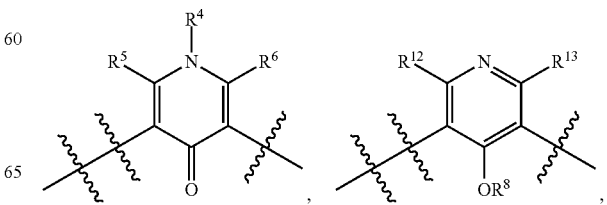

-continued

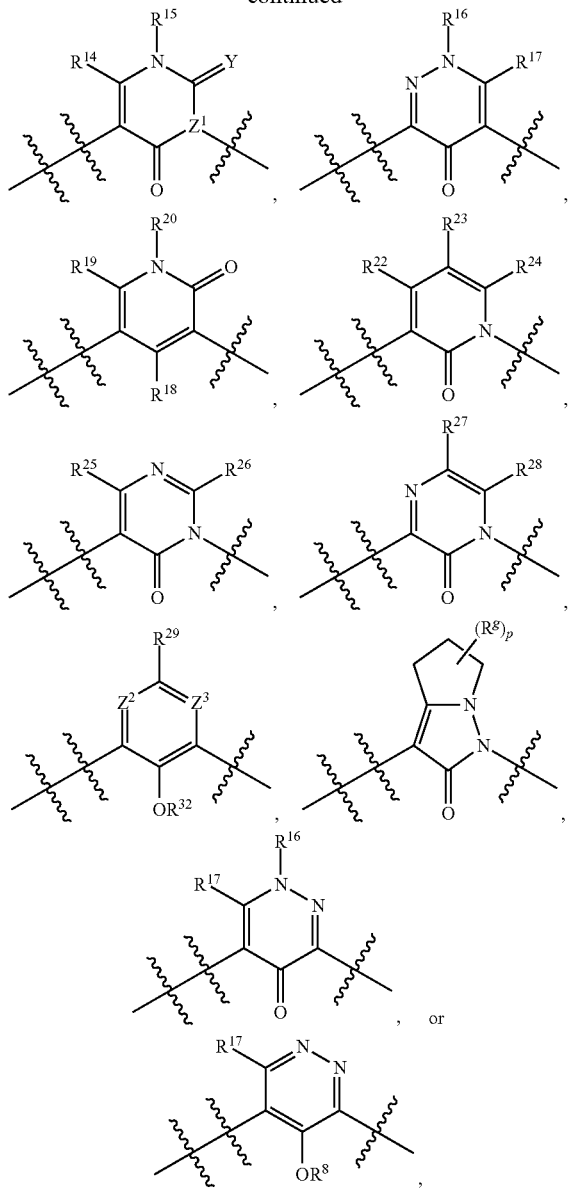

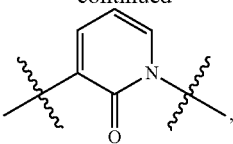

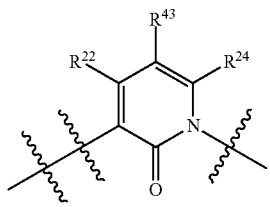

wherein the single wavy line indicates the point of attachment to the phenyl ring and the double wavy line indicates the point of attachment to the carbonyl of the amide linkage;

Y is O or S;
$Z^1$ is N or CH;
$Z^2$ is N or $CR^{45}$;
$Z^3$ is N or $CR^{42}$;
when Y is O and $Z^1$ is N, then $X^1$ is N;
alternatively, when then $X^1$ is N;

$R^4$, $R^{15}$, $R^{16}$ and $R^{20}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, N=C$(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR)(OR)$, $B(OH)_2$, $B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_1$-4 alkylene-, $C_{3-14}$ cycloalkyl-$C_{1-4}$ alkylene-, (5-14 membered heteroaryl)-$C_{1-4}$ alkylene- and (4-14 membered heterocycloalkyl)-$C_{1-4}$ alkylene- of $R^4$, $R^{15}$, $R^{16}$ and $R^{20}$ are each optionally substituted with 1, 2, 3, 4 or 5 independently selected $R^b$ substituents;

$R^5$, $R^{12}$, $R^{14}$, $R^{19}$, $R^{22}$, $R^{25}$, $R^{27}$, $R^{28}$, and $R^{45}$ are each independently H, $C_{1-6}$ alkyl optionally substituted with 1 or 2 independently selected $R^g$ substituents, CN, $C_{1-4}$ haloalkyl, $C_{1-4}$ haloalkoxy, OH, —COO$C_{1-4}$alkyl, —CON$C_{1-4}$alkyl, $NH_2$, —NH$C_{1-4}$alkyl, or —N($C_{1-4}$ alkyl)$_2$;

$R^6$, $R^{13}$, $R^{17}$, $R^{23}$, $R^{24}$, $R^{26}$, $R^{29}$ and $R^{42}$ are each independently H, $C_{1-6}$ alkyl optionally substituted with 1 or 2 independently selected $R^g$ substituents, CN, $C_{1-4}$ haloalkyl, $C_{1-4}$ haloalkoxy, OH, —COO$C_{1-4}$alkyl, —CON$C_{1-4}$alkyl, $NH_2$, —NH$C_{1-4}$alkyl, or —N($C_{1-4}$ alkyl)$_2$;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{14}$ and $R^{15}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or R$^{16}$ and R$^{17}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{19}$ and R$^{20}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{22}$ and R$^{23}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{23}$ and R$^{24}$ taken together with the atoms to which they are attached form fused C$_{3-7}$ cycloalkyl, fused phenyl, or fused heteroaryl, wherein the fused C$_{3-7}$ cycloalkyl, fused phenyl, and fused heteroaryl are each optionally substituted with 1 or 2 independently selected R$^g$ substituents;

or R$^{27}$ and R$^{28}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{29}$ and R$^{45}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{42}$ and R$^{29}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

R$^8$ and R$^{32}$ are each independently H, C$_{1-6}$ alkyl or a hydroxy protecting group;

R$^{12}$ is H or C$_{1-6}$ alkyl optionally substituted with 1 or 2 independently selected R$^g$ substituents;

R$^{13}$ is H or C$_{1-6}$ alkyl optionally substituted with 1 or 2 independently selected R$^g$ substituents; and the subscript p is 0, 1, or 2.

In some embodiments, ring A is

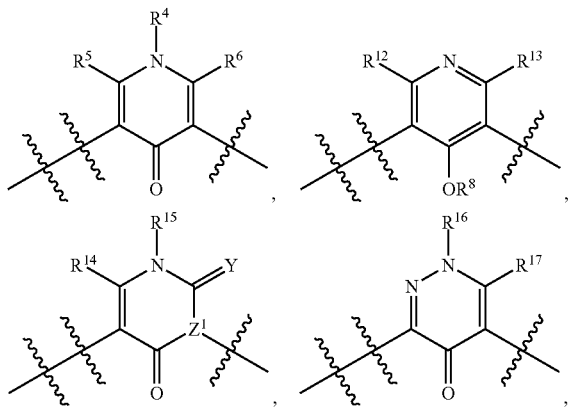

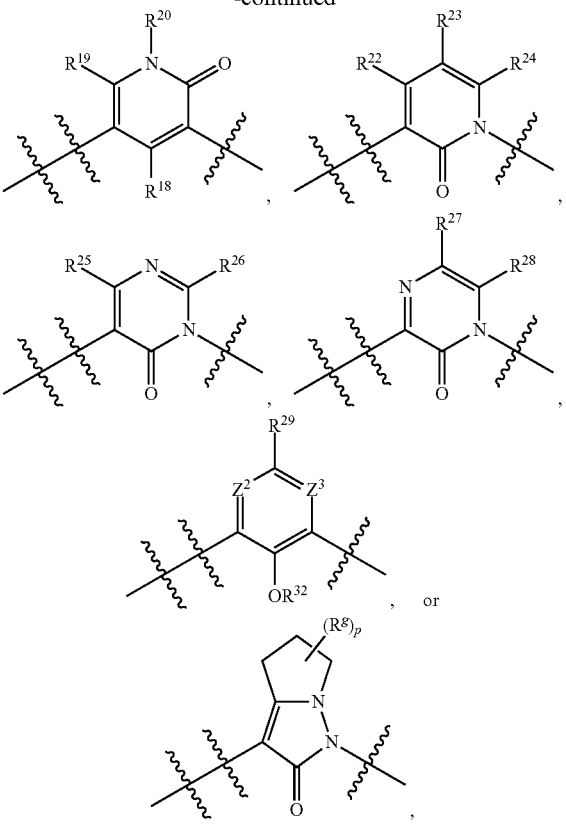

-continued wherein the single wavy line indicates the point of attachment to the phenyl ring and the double wavy line indicates the point of attachment to the carbonyl of the amide linkage;

Y is O or S;
Z$^1$ is N or CH;
Z$^2$ is N or CR$^{45}$;
Z$^3$ is N or CR$^{42}$;
when Y is O and Z$^1$ is N, then X$^1$ is N;
alternatively, when

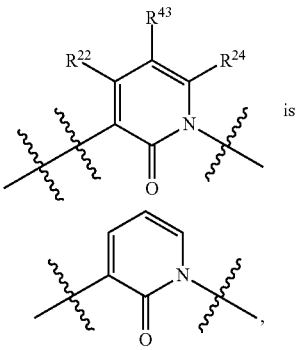

is then X$^1$ is N;

R$^4$, R$^{15}$, R$^{16}$ and R$^{20}$ are each independently selected from H, halo, C$_{1-6}$ alkyl, C$_{2-6}$ alkenyl, C$_{2-6}$ alkynyl, C$_{1-6}$ haloalkyl, C$_{1-6}$haloalkoxy, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkylene-, C$_{3-14}$ cycloalkyl-C$_{1-4}$ alkylene-, (5-14 membered heteroaryl)-C$_{1-4}$ alkylene-, (4-14 membered heterocycloalkyl)-C$_{1-4}$ alkylene-, CN, NO$_2$, OR$^a$, SR$^a$, NHOR$^a$, C(O)R$^a$, C(O)NR$^a$R$^a$, C(O)OR$^a$, C(O)NR$^a$S(O)$_2$R$^a$, OC(O)R$^a$, OC(O)NR$^a$R$^a$, NHR$^a$, NR$^a$R$^a$, NR$^a$C(O)R$^a$, N=C(NR$^a$R$^a$)$_2$, NR$^a$C(=NR$^a$)R$^a$, NR$^a$C(O)OR$^a$, NR$^a$C(O)NR$^a$R$^a$, C(=NR$^a$)R$^a$, C(=NOH)R$^a$, C(=NOH)NR$^a$R$^a$, C(=NCN)NR$^a$R$^a$, NR$^a$C(=NCN)NR$^a$R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$R$^a$, S(O)$_2$NR$^a$C(O)R$^a$, P(O)R$^a$R$^a$, P(O)(OR$^a$)(OR$^a$), B(OH)$_2$, B(OR$^a$)$_2$ and S(O)$_2$NR$^a$R$^a$, wherein the C$_{1-6}$ alkyl, C$_{2-6}$ alkenyl, C$_{2-6}$ alkynyl, C$_6$, 10 aryl, C$_{3-14}$ cycloalkyl, 5-14 membered heteroaryl, 4-14 membered heterocycloalkyl, C$_{6-10}$ aryl-C$_{1-4}$ alkylene-, C$_{3-14}$ cycloalkyl-C$_{1-4}$ alkylene-, (5-14 membered heteroaryl)-C$_{1-4}$ alkylene- and (4-14 membered heterocycloalkyl)-C$_{1-4}$ alkylene- of R$^4$, R$^{15}$, R$^{16}$ and R$^{20}$ are each optionally substituted with 1, 2, 3, 4 or 5 independently selected R$^b$ substituents;

R$^5$, R$^{12}$, R$^{14}$, R$^{19}$, R$^{22}$, R$^{25}$, R$^{27}$, R$^{28}$, and R$^{45}$ are each independently H, C$_{1-6}$ alkyl optionally substituted with 1 or 2 independently selected R$^g$ substituents, CN, C$_{1-4}$ haloalkyl, C$_{1-4}$ haloalkoxy, OH, —COOC$_{1-4}$alkyl, —CONC$_{1-4}$alkyl, NH$_2$, —NHC$_{1-4}$alkyl, or —N(C$_{1-4}$alkyl)$_2$;

R$^6$, R$^{13}$, R$^{17}$, R$^{23}$, R$^{24}$, R$^{26}$, R$^{29}$ and R$^{42}$ are each independently H, C$_{1-6}$ alkyl optionally substituted with 1 or 2 independently selected R$^g$ substituents, CN, C$_{1-4}$ haloalkyl, C$_{1-4}$ haloalkoxy, OH, —COOC$_{1-4}$ alkyl, —CONC$_{1-4}$alkyl, NH$_2$, —NHC$_{1-4}$alkyl, or —N(C$_{1-4}$alkyl)$_2$;

or R$^4$ and R$^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^4$ and R$^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{14}$ and R$^{15}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{16}$ and R$^{17}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{19}$ and R$^{20}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected R$^g$ substituents;

or R$^{22}$ and R$^{23}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{23}$ and R$^{24}$ taken together with the atoms to which they are attached form fused C$_{3-7}$ cycloalkyl, fused phenyl, or fused heteroaryl, wherein the fused C$_{3-7}$ cycloalkyl, fused phenyl, and fused heteroaryl are each optionally substituted with 1 or 2 independently selected R$^g$ substituents;

or R$^{27}$ and R$^{28}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{29}$ and R$^{45}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

or R$^{42}$ and R$^{29}$ taken together with the atoms to which they are attached form fused C$_{3-7}$ cycloalkyl or fused phenyl, wherein the fused C$_{3-7}$ cycloalkyl and fused phenyl are each optionally substituted with 1 or 2 independently selected R$^g$ substituents;

R$^8$ and R$^{32}$ are each independently H, C$_{1-6}$ alkyl or a hydroxy protecting group;

R$^{12}$ is H or C$_{1-6}$ alkyl optionally substituted with 1 or 2 independently selected R$^g$ substituents;

R$^{13}$ is H or C$_{1-6}$ alkyl optionally substituted with 1 or 2 independently selected R$^g$ substituents; and the subscript p is 1 or 2.

Some embodiments provide for a compound of Formula (II):

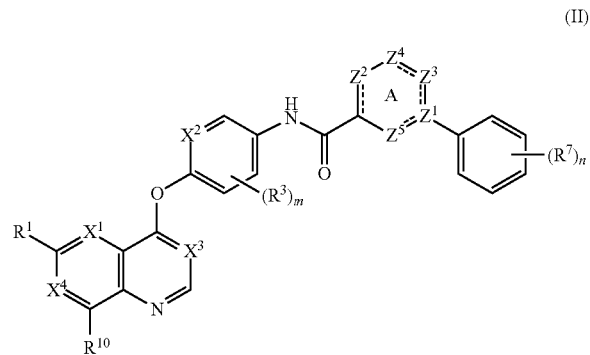

or a pharmaceutically acceptable salt, a stereoisomer, or a mixture of stereoisomers thereof, wherein:

X$^1$ is N or CR$^{11}$;

X$^2$ is CR$^3$ or CH, and R$^3$ is halo;

X$^3$ is N or CH;

X$^4$ is N or CR$^2$;

m is 0, 1, or 2;

n is 0, 1, 2, or 3;

and the remaining variables are as defined herein.

Some embodiments provide for a compound of formula (Ia):

(Ia)

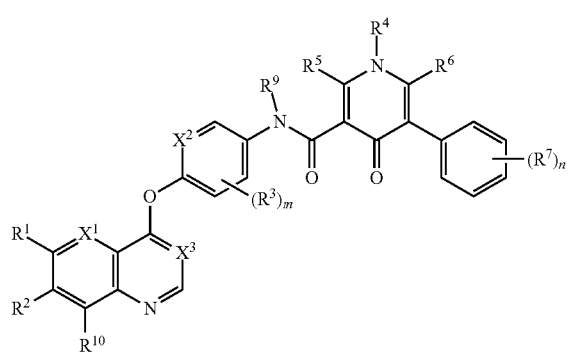

or pharmaceutically acceptable salt, stereoisomer, or mixture of stereoisomers thereof.

In some embodiments, $R^{10}$ is H.

Some embodiments provide for a compound of formula (Ib):

(Ib)

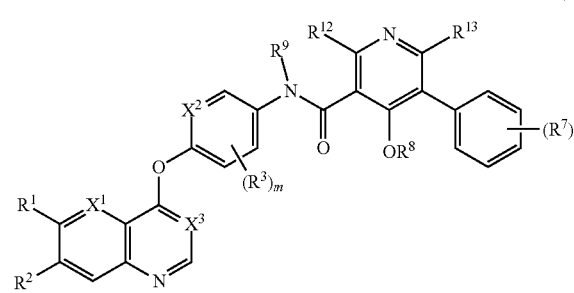

or pharmaceutically acceptable salt, stereoisomer, or mixture of stereoisomers thereof.

Some embodiments provide for a compound of formula (Ic), (Id), (Ie), (If), (Ig), (Ih), (Ij), (Ik), (Im), (In), (Io), (Ip), (Iq), (Ir), (Is), or (It):

(Ic)

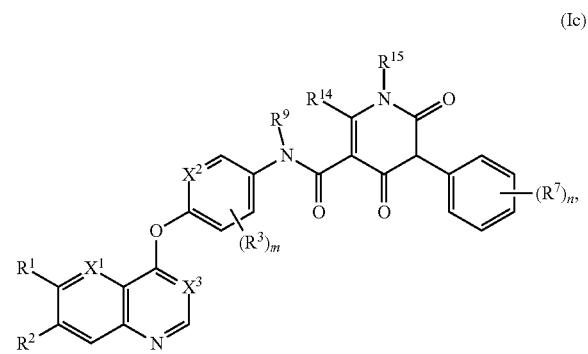

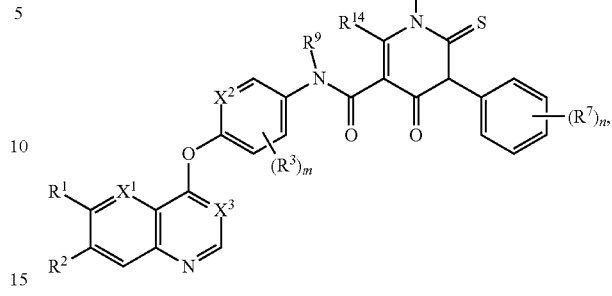

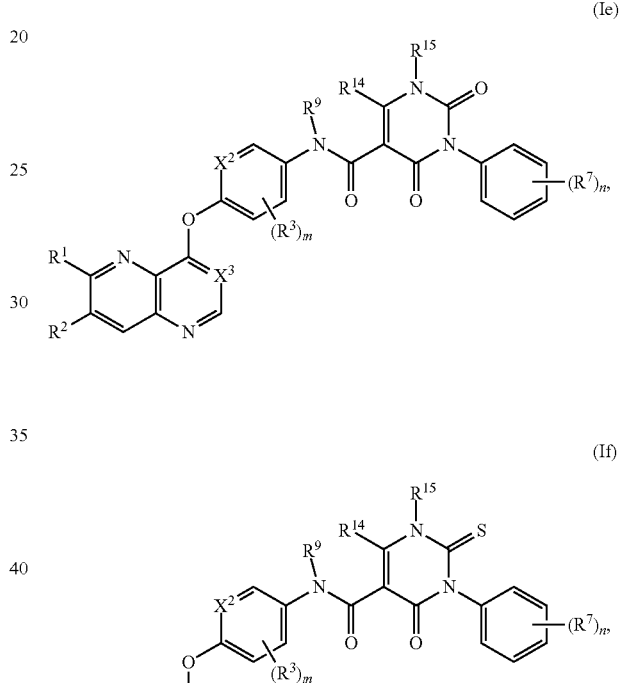

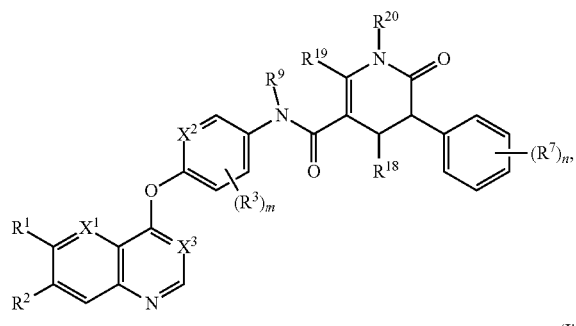 (Ih)
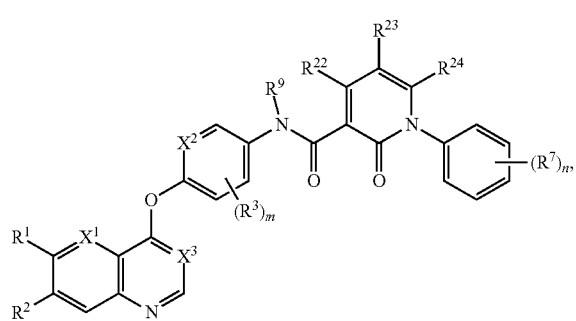 (Ij)
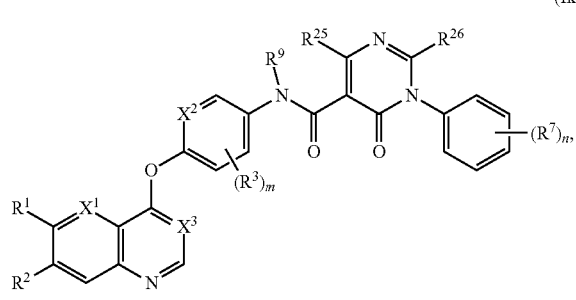 (Ik)
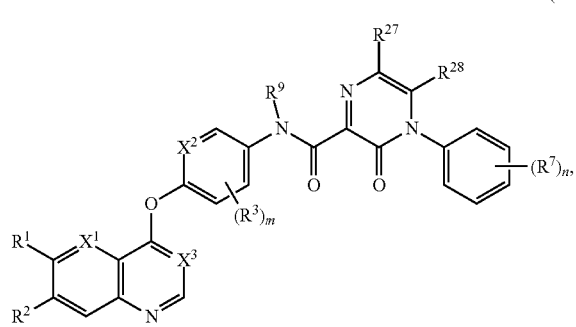 (Im)
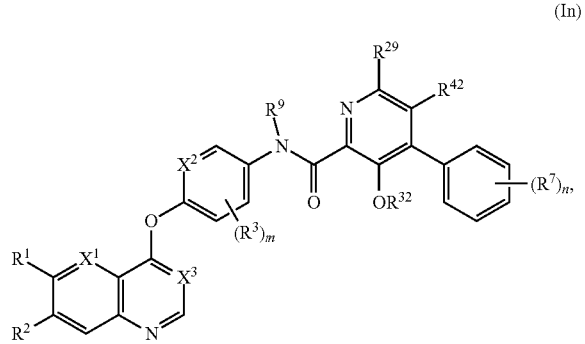 (In)
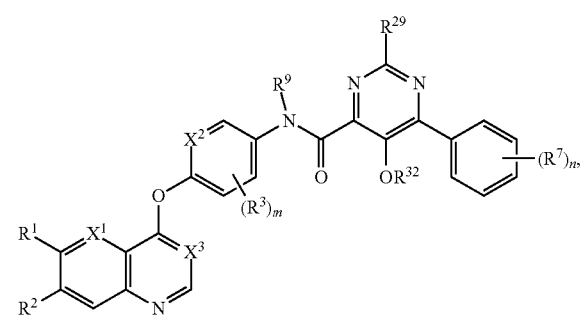 (Io)
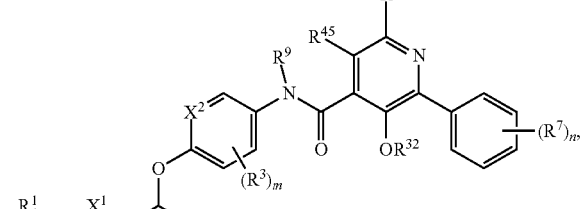 (Ip)
 (Iq)
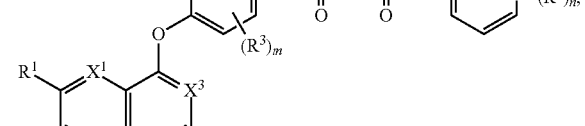 (Ir)

(Is)
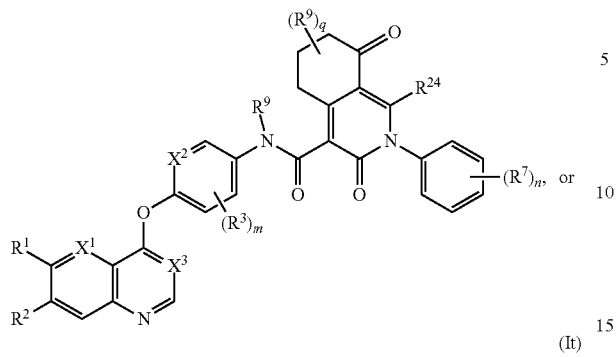
(It)
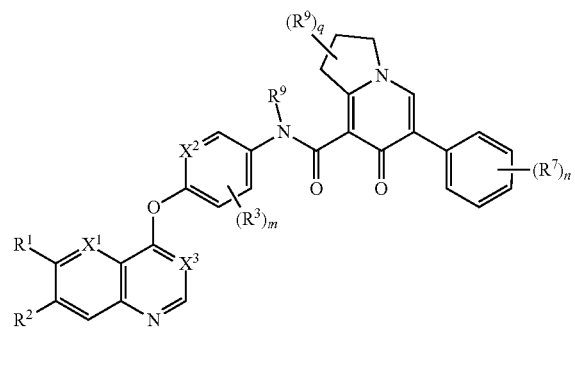
or a pharmaceutically acceptable salt, stereoisomer, or mixture of stereoisomers thereof, wherein each subscript q is independently 0, 1, or 2.
Some embodiments provide for a compound of formula (Ic), (Id), (Ie), (If), (Ig), (Ih), (Ij), (Ik), (Im), (In), (Io), (Ip), (Iq), (Ir), (Is), (It), (Iu), (Iv), (Iw), (Ix), (Iy), (Iz), (Iaa), or (Ibb):
(Ic)
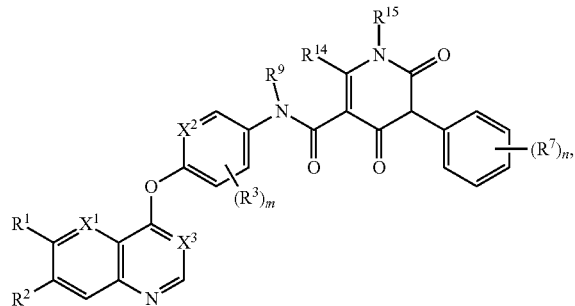
(Id)
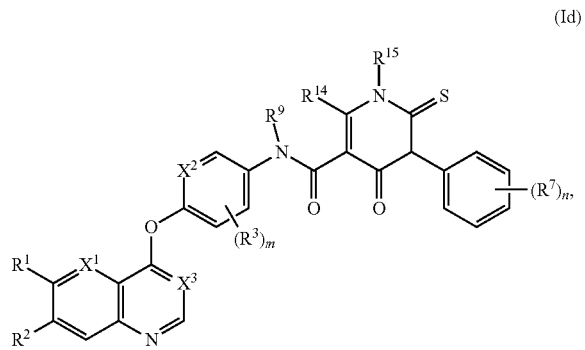
(Ie)
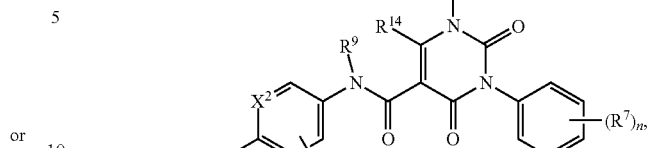
(If)
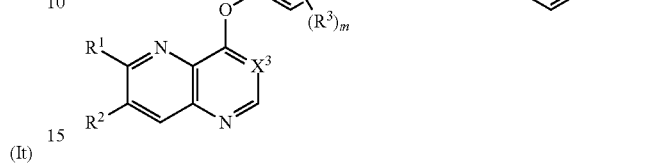
(Ig)
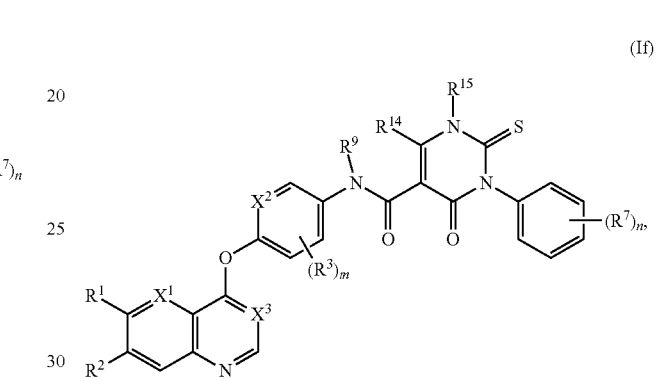
(Ih)
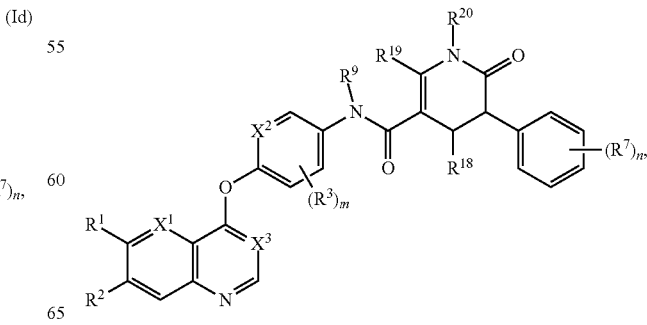

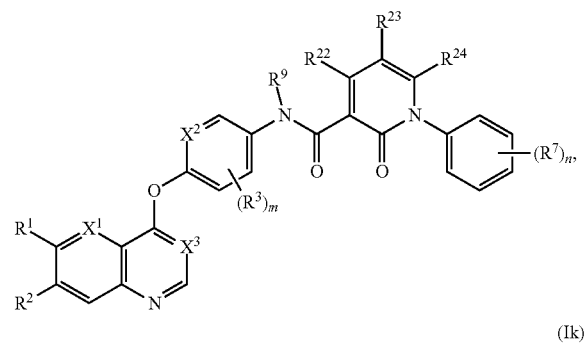
(Ij)
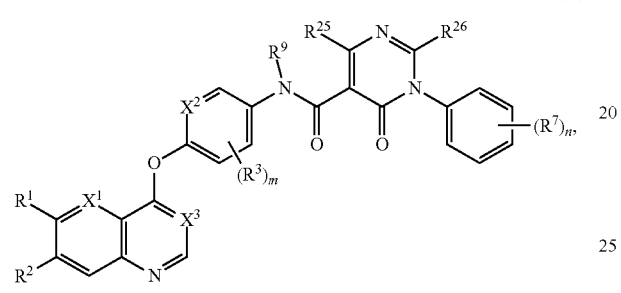
(Ik)
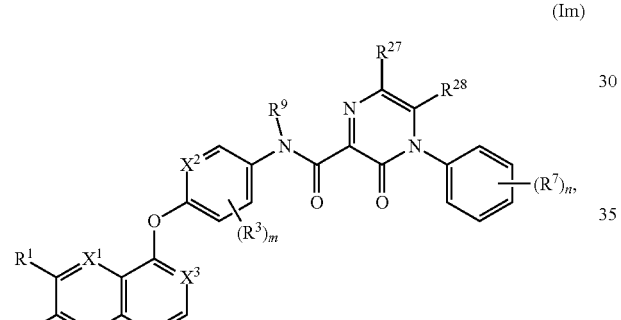
(Im)
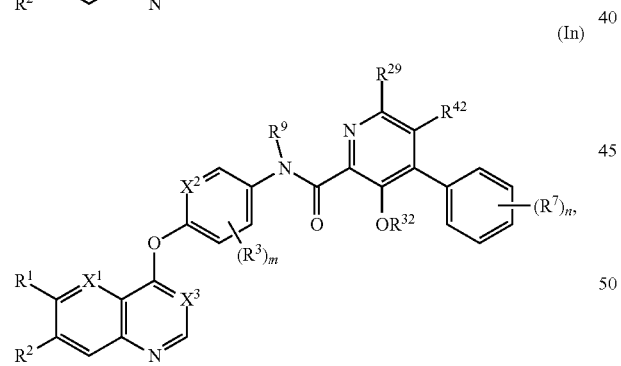
(In)
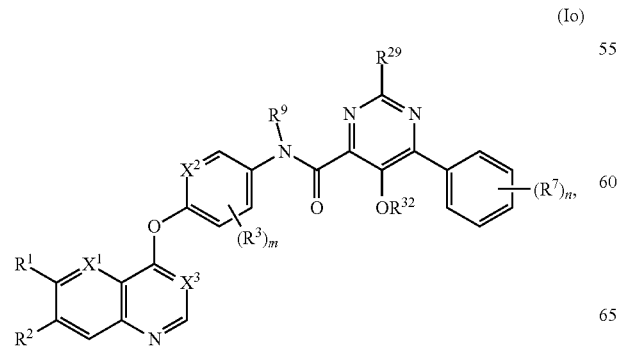
(Io)
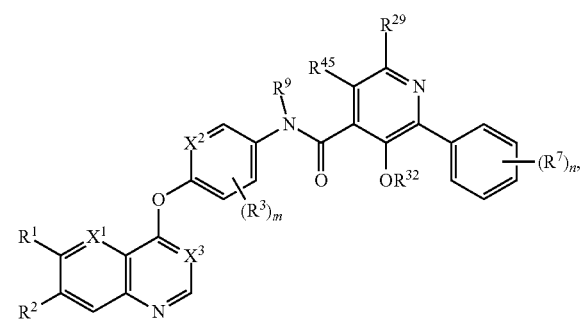
(Ip)
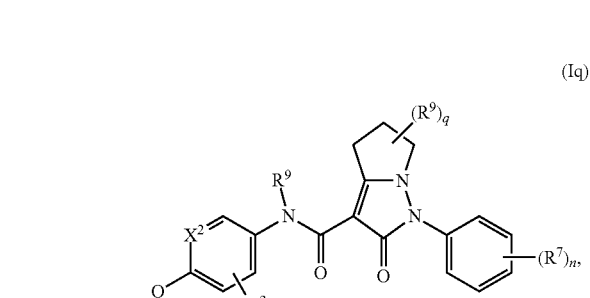
(Iq)
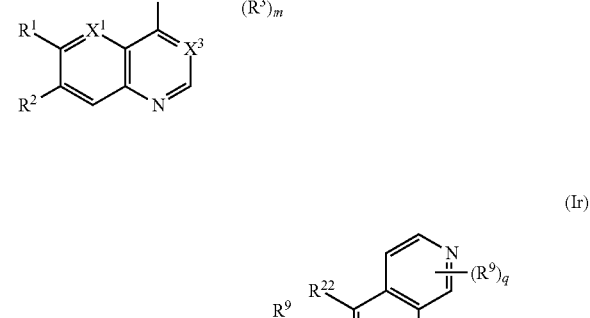
(Ir)
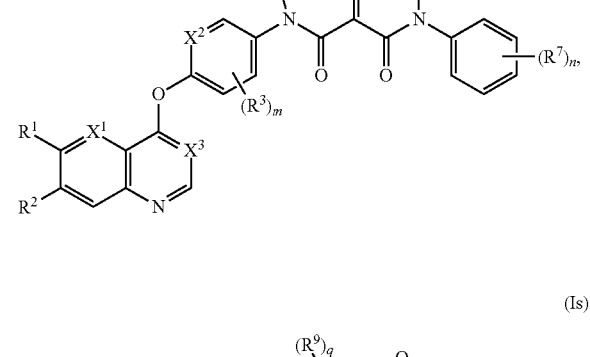
(Is)
or

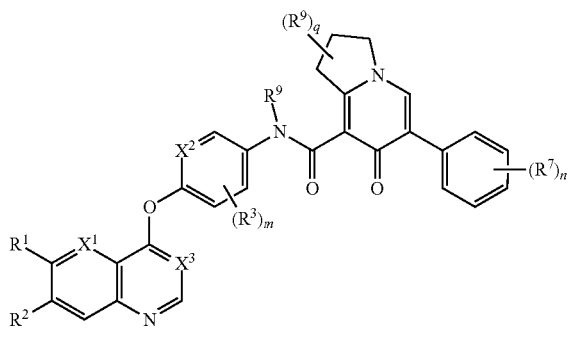
(It)
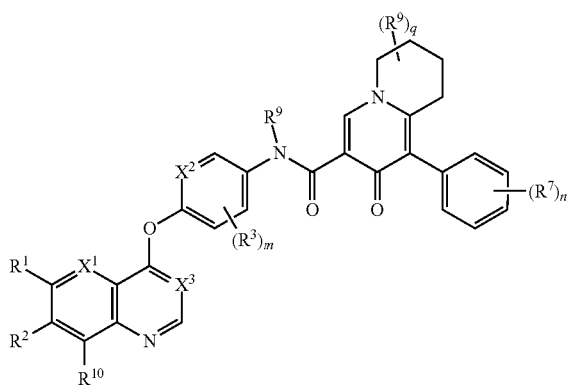
(Iu)
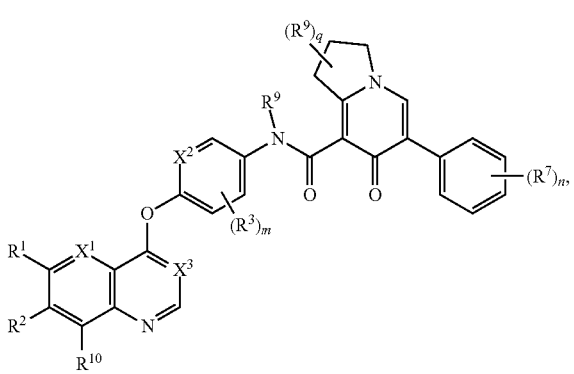
(Iv)
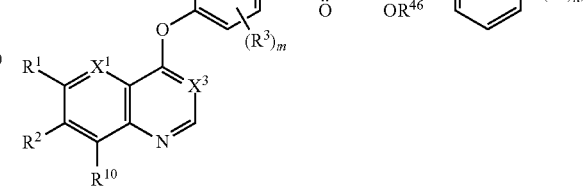
(Iw)
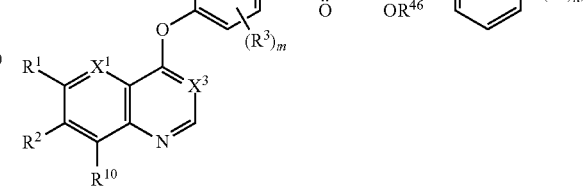
(Ix)
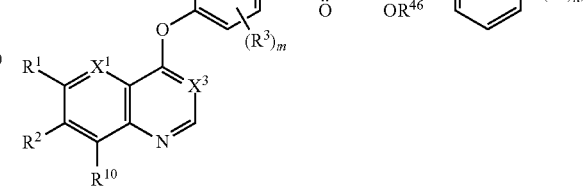
(Iy)
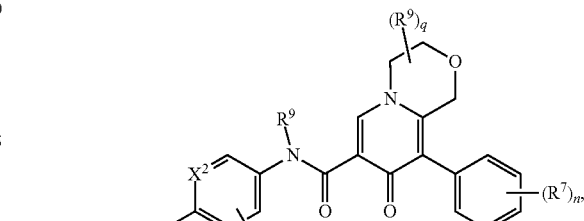
(Iz)
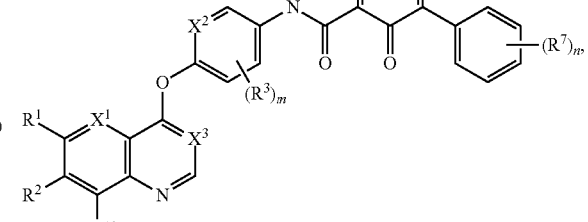
(Iaa)

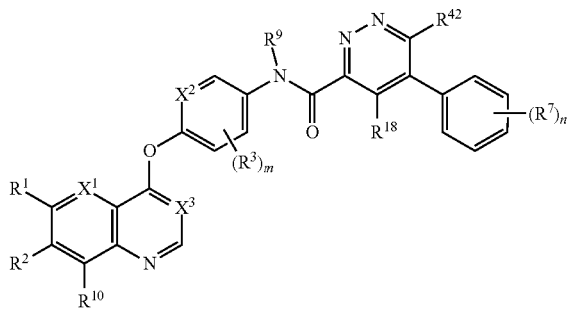

or a pharmaceutically acceptable salt, stereoisomer, or mixture of stereoisomers thereof, wherein each subscript q is independently 0, 1, or 2.

Some embodiments provide for a compound of formula (Ia-1):

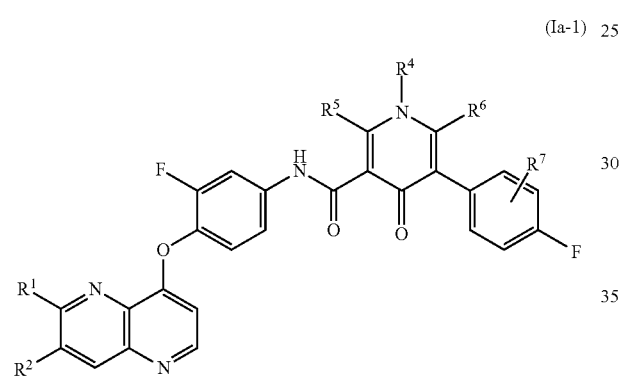

or a pharmaceutically acceptable salt, stereoisomer, or mixture of stereoisomers thereof.

Some embodiments provide for a compound of formula (Ia-2):

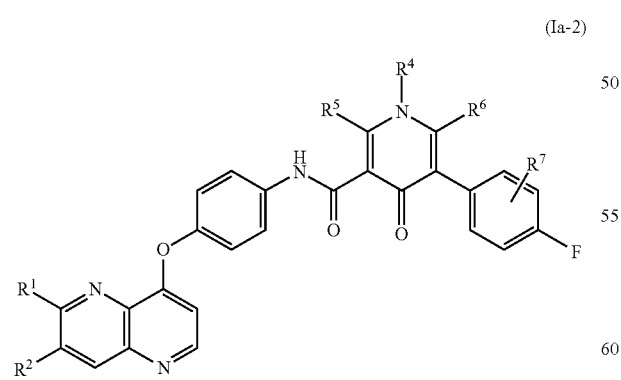

or a pharmaceutically acceptable salt, stereoisomer, or mixture of stereoisomers thereof.

Some embodiments provide for a compound of formula (III-1):

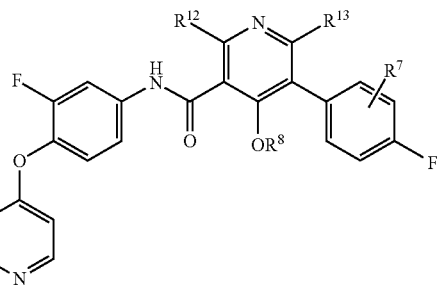

or a pharmaceutically acceptable salt, stereoisomer, or mixture of stereoisomers thereof.

Some embodiments provide for a compound of formula (III-2):

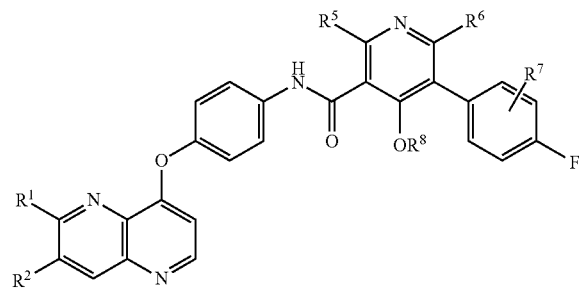

or a pharmaceutically acceptable salt, stereoisomer, or mixture of stereoisomers thereof.

Some embodiments provide for a compound of formula (IV-1):

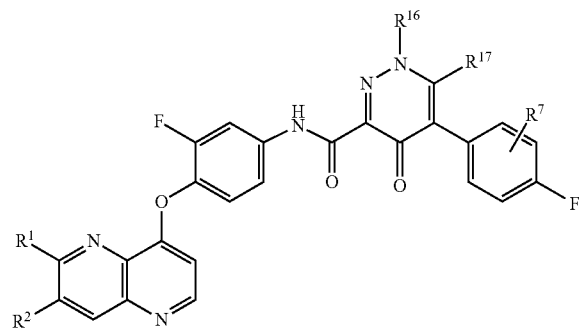

or a pharmaceutically acceptable salt, stereoisomer, or mixture of stereoisomers thereof.

Some embodiments provide for a compound of formula (IV-1), or a pharmaceutically acceptable salt, stereoisomer, or mixture of stereoisomers thereof, wherein $R^{16}$ is H, $C_{1-6}$ alkyl, or $C_{1-6}$ haloalkyl; and $R^{17}$ is H or $C_{1-6}$ alkyl.

Some embodiments provide for a compound of formula (IV-2):

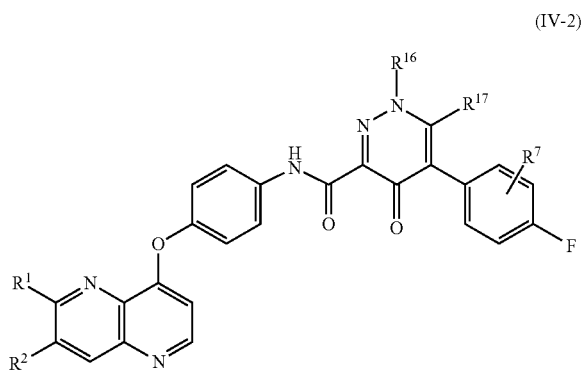

(IV-2)

or a pharmaceutically acceptable salt, stereoisomer, or mixture of stereoisomers thereof.

Some embodiments provide for a compound having formula (III-3):

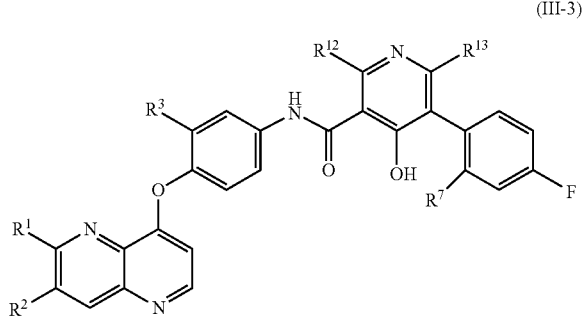

(III-3)

or a pharmaceutically acceptable salt, tautomer or stereoisomer thereof, wherein:

$R^1$ is H, halo, $C_{1-6}$ alkyl, $C_{1-6}$ alkoxy, $C_{1-6}$ alkyl-C(O)—, $NH_2C(O)$—, $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ are each optionally substituted with $C_{1-6}$ alkoxy or OH $R^2$ is $C_{1-6}$ alkoxy;

$R^3$ is H or halo;

$R^{12}$ is H or $C_{1-6}$ alkyl optionally substituted with $C_{1-6}$ alkoxy or OH;

$R^{13}$ is H or $C_{1-6}$ alkyl optionally substituted with $C_{1-6}$ alkoxy or OH; and $R^7$ is H or $C_{1-6}$ alkyl.

Some embodiments provide for a compound having formula (Ia-3):

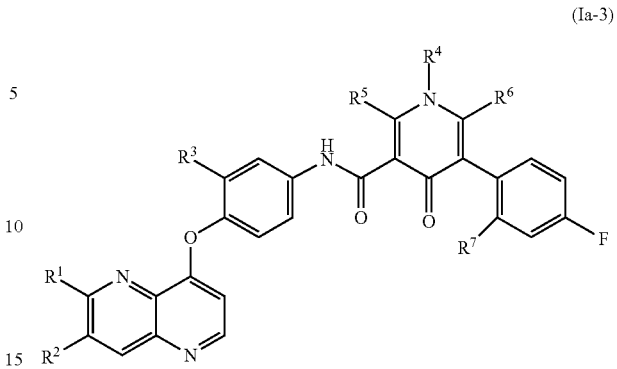

(Ia-3)

or a pharmaceutically acceptable salt, tautomer or stereoisomer thereof, wherein:

$R^1$ is $C_{1-6}$ alkyl, $C_{1-6}$ alkoxy, $C_{1-6}$ alkyl-C(O)—, $NH_2C(O)$—, $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ are each optionally substituted with $C_{1-6}$ alkoxy or OH $R^2$ is $C_{1-6}$ alkoxy;

$R^3$ is H or halo;

$R^4$ is H or $C_{1-6}$ alkyl optionally substituted with $C_{1-6}$ alkoxy or OH;

$R^5$ is H or $C_{1-6}$ alkyl optionally substituted with $C_{1-6}$ alkoxy or OH;

$R^6$ is H or $C_{1-6}$ alkyl optionally substituted with $C_{1-6}$ alkoxy or OH and $R^7$ is H or $C_{1-6}$ alkyl.

Some embodiments provide for a compound having formula (Ia-3), or a pharmaceutically acceptable salt, tautomer or stereoisomer thereof, wherein:

$R^1$ is H, $C_{1-6}$ alkyl, $C_{1-6}$ alkoxy, $C_{1-6}$ alkyl-C(O)—, $NH_2C(O)$—, $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ are each optionally substituted with $C_{1-6}$ alkoxy or OH;

$R^2$ is $C_{1-6}$ alkoxy;

$R^3$ is H or halo;

$R^4$ is H, $C_{1-6}$ haloalkyl, or $C_{1-6}$ alkyl optionally substituted with $C_{1-6}$ alkoxy or OH;

$R^5$ is H or $C_{1-6}$ alkyl optionally substituted with $C_{1-6}$ alkoxy or OH;

$R^6$ is H or $C_{1-6}$ alkyl optionally substituted with $C_{1-6}$ alkoxy or OH and $R^7$ is H or $C_{1-6}$ alkyl.

Some embodiments provide for a compound having formula (Ij-1):

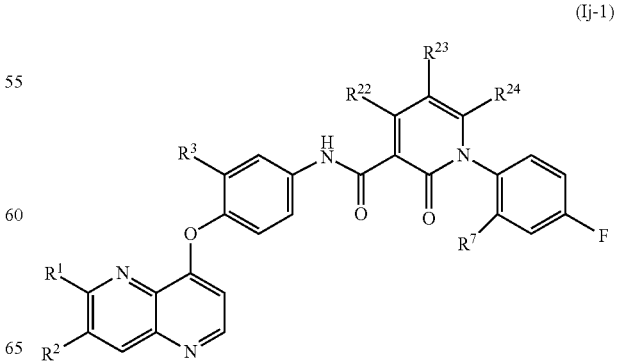

(Ij-1)

or a pharmaceutically acceptable salt, tautomer or stereoisomer thereof, wherein:
R$^1$ is C$_{1-6}$ alkyl, C$_{1-6}$ alkoxy, C$_{1-6}$ alkyl-C(O)—, NH$_2$C(O)—, C$_{1-6}$ alkyl-NHC(O)—, wherein the C$_{1-6}$ alkyl, C$_{1-6}$ alkyl-C(O)— and C$_{1-6}$ alkyl-NHC(O)— of R$^1$ is optionally substituted with C$_{1-6}$ alkoxy or OH
R$^2$ is C$_{1-6}$ alkoxy;
R$^3$ is H or halo;
R$^{22}$ is H or C$_{1-6}$ alkyl optionally substituted with C$_{1-6}$ alkoxy or OH;
R$^{23}$ is H, C$_{1-6}$ alkyl or C$_{1-6}$ alkyl-C(O)—, wherein the C$_{1-6}$ alkyl and C$_{1-6}$ alkyl-C(O)— of R$^{23}$ are each optionally substituted with C$_{1-6}$ alkoxy or OH;
R$^{24}$ is H or C$_{1-6}$ alkyl optionally substituted with C$_{1-6}$ alkoxy or OH and
R$^7$ is H or C$_{1-6}$ alkyl.

Some embodiments provide for a compound of formula (V):

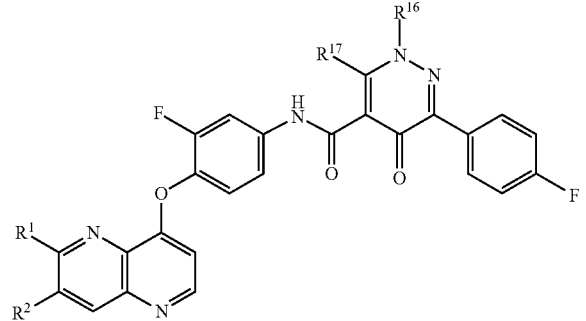

(V)

or a pharmaceutically acceptable salt, stereoisomer, or mixture of stereoisomers thereof, wherein:
R$^1$ is H, halo, C$_{1-6}$ alkyl, C$_{1-6}$ alkoxy, C$_{1-6}$ alkyl-C(O)—, NH$_2$C(O)—, C$_{1-6}$ alkyl-NHC(O)—, wherein the C$_{1-6}$ alkyl, C$_{1-6}$ alkyl-C(O)— and C$_{1-6}$ alkyl-NHC(O)— of R$^1$ are each optionally substituted with C$_{1-6}$ alkoxy or OH;
R$^2$ is C$_{1-6}$ alkoxy;
R$^{16}$ is H, C$_{1-6}$ alkyl, or C$_{1-6}$ haloalkyl; and
R$^{17}$ is H or C$_{1-6}$ alkyl.

Some embodiments provide for a compound of formula (VI):

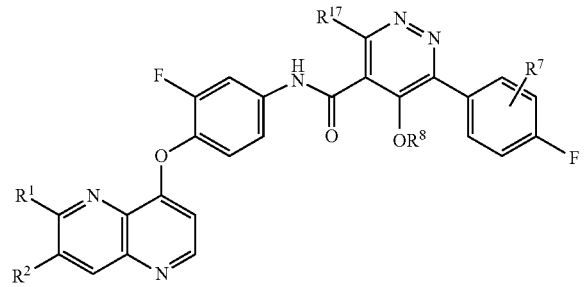

(VI)

or a pharmaceutically acceptable salt, stereoisomer, or mixture of stereoisomers thereof, wherein:
R$^1$ is H, halo, C$_{1-6}$ alkyl, C$_{1-6}$ alkoxy, C$_{1-6}$ alkyl-C(O)—, NH$_2$C(O)—, C$_{1-6}$ alkyl-NHC(O)—, wherein the C$_{1-6}$ alkyl, C$_{1-6}$ alkyl-C(O)— and C$_{1-6}$ alkyl-NHC(O)— of R$^1$ are each optionally substituted with C$_{1-6}$ alkoxy or OH;
R$^2$ is C$_{1-6}$ alkoxy;
R$^7$ is H or C$_{1-6}$ alkyl.
R$^8$ is H or C$_{1-6}$ alkyl; and
R$^{17}$ is H or C$_{1-6}$ alkyl.

Some embodiments provide for a compound of formula (VII):

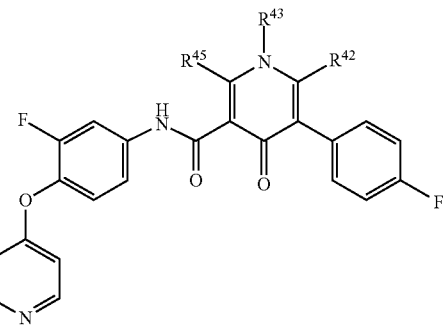

(VII)

or a pharmaceutically acceptable salt, stereoisomer, or mixture of stereoisomers thereof, wherein:
R$^1$ is H, halo, C$_{1-6}$ alkyl, C$_{1-6}$ alkoxy, C$_{1-6}$ alkyl-C(O)—, NH$_2$C(O)—, C$_{1-6}$ alkyl-NHC(O)—, wherein the C$_{1-6}$ alkyl, C$_{1-6}$ alkyl-C(O)— and C$_{1-6}$ alkyl-NHC(O)— of R$^1$ are each optionally substituted with C$_{1-6}$ alkoxy or OH;
R$^2$ is C$_{1-6}$ alkoxy;
R$^{42}$ and R$^{43}$ taken together with the atoms to which they are attached form 5- to 6-membered fused heterocycloalkyl having 0-1 additional ring heteroatoms selected from 0 and N; and
R$^{45}$ is H or C$_{1-6}$ alkyl.

Some embodiments provide for a compound of formula (VII), or a pharmaceutically acceptable salt, stereoisomer, or mixture of stereoisomers thereof, wherein:
R$^1$ is H, halo, C$_{1-6}$ alkyl, C$_{1-6}$ alkoxy, C$_{1-6}$ alkyl-C(O)—, NH$_2$C(O)—, C$_{1-6}$ alkyl-NHC(O)—, wherein the C$_{1-6}$ alkyl, C$_{1-6}$ alkyl-C(O)— and C$_{1-6}$ alkyl-NHC(O)— of R$^1$ are each optionally substituted with C$_{1-6}$ alkoxy or OH;
R$^2$ is C$_{1-6}$ alkoxy;
R$^{43}$ and R$^{45}$ taken together with the atoms to which they are attached form 5- to 6-membered fused heterocycloalkyl having 0-1 additional ring heteroatoms selected from 0 and N; and
R$^{42}$ is H or C$_{1-6}$ alkyl.

In some embodiments, R$^1$ is H, C$_{1-6}$ alkyl, C$_{1-6}$ alkoxy, halo, NH$_2$, —NH(C$_{1-6}$ alkyl), —N(C$_{1-6}$ alkyl)$_2$, C$_{1-6}$ alkylNHC(O)—, or C$_{1-6}$alkylSO$_2$NH—.

In some embodiments, R$^2$ is H, C$_{1-6}$ alkyl, C$_{1-6}$ alkoxy, halo, OH, NH$_2$, —NH(C$_{1-6}$ alkyl), —N(C$_{1-6}$ alkyl)$_2$, —C$_{1-6}$ alkylNHC(O)—, CF$_3$, C$_{1-6}$ alkylOC(O)—, pyridyl, C$_{1-6}$alkylSO$_2$NH— or 1H-pyrazol-4-yl optionally substituted with R$^g$.

In some embodiments, R$^3$ is H or halo.
In some embodiments, R$^7$ is H, halo, C$_{1-6}$ alkyl or C$_{1-6}$ alkoxy.
In some embodiments, R$^7$ is H, CH$_3$, F, Cl or OCH$_3$.
In some embodiments, R$^9$ is H.

In some embodiments, $R^{43}$, $R^4$, $R^{15}$, $R^{16}$, $R^{20}$, $R^{23}$, $R^{27}$ and $R^{29}$ are each independently selected from H, $C_{1-6}$ alkyl, $C_{1-6}$ alkoxy, OH, $NH_2$, —$NHC_{1-6}$ alkyl, —$N(C_{1-6}$ alkyl$)_2$, $C_{3-6}$ cycloalkyl, $C_{1-6}$haloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N=C[N($C_{1-6}$ alkyl)($C_{1-6}$ alkyl)]$_2$, wherein the $C_{1-6}$ alkyl, $C_{1-6}$ alkoxy, —$NHC_{1-6}$ alkyl, —$N(C_{1-6}$ alkyl$)_2$, $C_{3-6}$ cycloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N=C[N($C_{1-6}$ alkyl)($C_{1-6}$ alkyl)]$_2$ of $R^{43}$, $R^4$, $R^{15}$, $R^{16}$, $R^{20}$, $R^{23}$, $R^{27}$ and $R^{29}$ are each optionally substituted with 1 or 2 independently selected $R^b$ or $R^g$ substituents.

In some embodiments, $R^{43}$, $R^4$, $R^{15}$, $R^{16}$, $R^{20}$, $R^{23}$, $R^{27}$ and $R^{29}$ are each independently selected from H, methyl, isopropyl, t-butyl, ethyl, OH, methoxy, $NH_2$, methylamino, dimethylamino, —N=C(N($CH_3$)$_2$)$_2$, cyclopropyl, cyclobutyl, cyclopentyl, cyclohexyl, 1-methylcyclopropyl, 1-(trifluoromethyl)cyclopropyl, oxetan-3-yl, 3-methyloxetan-3-yl, 2,2,2-trifluoroethyl, azetidin-3-yl, 1-methylazetidin-3-yl, 1-t-butoxycarbonylazetidin-3-yl, morpholino, 2-morpholinoethyl, 1H-pyrazol-3-yl, 1H-pyrazol-4-yl, 1H-pyrazol-5-yl, 1-methylpyrazol-4-yl, 1-(difluoromethyl)pyrazol-4-yl, 2-hydroxyethyl, 2-pyridyl, 3-pyridyl, 4-pyridyl, 2-(imidazol-1-yl)ethyl, 2-(benzotriazol-1-yloxy)ethyl, and 2-hydroxy-1,1-dimethyl-ethyl, each of which when applicable is optionally substituted with 1 or 2 independently selected $R^g$ substituents.

In some embodiments, $R^{45}$, $R^{42}$, $R^{44}$, $R^5$, $R^{17}$ and $R^6$ are each independently selected from H, OH, halo, CN, $C_{1-6}$ alkyl, $C_{2-6}$ alkenyl, $C_{1-6}$ haloalkyl, $C_{1-6}$ alkoxy, $C_{1-6}$ alkylthio, $C_{1-6}$ alkyl-C(O)— and $C_{1-6}$ alkylamino, wherein the $C_{1-6}$ alkyl, $C_{2-6}$ alkenyl, $C_{1-6}$ alkoxy, $C_{1-6}$ alkylthio, $C_{1-6}$ alkyl-C(O)— and $C_{1-6}$ alkylamino of $R^{45}$, $R^{42}$, $R^4$, $R^5$, $R^{17}$ and $R^6$ are each optionally substituted with 1 or 2 independently selected $R^g$ substituents.

In some embodiments, $R^{45}$, $R^{42}$, $R^{44}$, $R^5$ and $R^6$ are each independently selected from H, $CH_3$, propen-2-yl, Br, Cl, CN, methoxy, 2-fluoroethyl, isopropyl, $CH_3C(O)$—, OH, t-butyl, ethyl, hydroxymethyl, isopropylthio, and methoxymethyl.

In some embodiments, $R^{45}$, $R^{42}$, and $R^{44}$ are each independently selected from H and $C_{1-6}$ alkyl optionally substituted with 1 or 2 independently selected $R^g$ substituents.

some embodiments, $R^{40}$, $R^{41}$ and $R^{43}$ are each independently selected from H, halo, and $C_{1-6}$ alkyl optionally substituted with 1, 2, 3, 4 or 5 independently selected $R^1$ substituents.

In some embodiments, $R^{46}$, $R^8$ and $R^{32}$ are each independently H or $C_{1-6}$ alkyl.

In some embodiments, $R^{18}$ is H or halo.

In some embodiments, $X^1$ is N.

In some embodiments, $X^2$ is CH. In some embodiments, $X^2$ is $CR^3$. In some embodiments, $X^2$ is $CR^3$, and $R^3$ is halo.

In some embodiments, $X^3$ is CH.

In some embodiments, $X^1$ is N and $X^3$ is CH.

In some embodiments, $X^4$ is $CR^2$. In some embodiments, $X^4$ is N.

In some embodiments, $X^1$ is N, $X^3$ is CH, and $X^4$ is $CR^2$.

In some embodiments, $X^1$ is CH, $X^3$ is CH, and $X^4$ is N.

In some embodiments, $X^5$ is CH. In some embodiments, $X^5$ is $CR^3$.

In some embodiments, $X^2$ is $CR^3$, $X^5$ is CH, and $R^3$ is halo.

In some embodiments, the subscript m is 0. In other embodiments, m is 1 and $R^3$ is F or H. In other embodiments, m is 1 and $R^3$ is F.

In some embodiments, the subscript n is 0.

In some embodiments, the subscript n is 1 and $R^7$ is F. In other embodiments, the n is 2 and $R^7$ is independently selected from $CH_3$, F, Cl and $OCH_3$.

In some embodiment, the subscript p is 1.

In some embodiment, the subscript q is 1.

Some embodiments provide for a compound selected from:

N-[4-[(6,7-dimethoxy-1,5-naphthyridin-4-yl)oxy]-3-fluorophenyl]-5-(4-fluorophenyl)-6-methyl-4-oxo-1-propan-2-ylpyridine-3-carboxamide;

N-[4-(6,7-dimethoxyquinolin-4-yl)oxy-3-fluorophenyl]-5-(4-fluorophenyl)-6-methyl-4-oxo-1-propan-2-ylpyridine-3-carboxamide;

5-(3,4-dichlorophenyl)-N-[4-(6,7-dimethoxyquinolin-4-yl)oxy-3-fluorophenyl]-6-methyl-4-oxo-1-propan-2-ylpyridine-3-carboxamide;

5-(3-chloro-4-fluorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide;

5-(3,4-dichlorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide;

1-cyclopentyl-N-[4-[(6,7-dimethoxy-1,5-naphthyridin-4-yl)oxy]-3-fluorophenyl]-5-(4-fluorophenyl)-6-methyl-4-oxopyridine-3-carboxamide;

5-(3-chloro-4-fluorophenyl)-1-cyclopentyl-N-[4-[(6,7-dimethoxy-1,5-naphthyridin-4-yl)oxy]-3-fluorophenyl]-6-methyl-4-oxopyridine-3-carboxamide;

N-[4-[(6,7-dimethoxy-1,5-naphthyridin-4-yl)oxy]-3-fluorophenyl]-5-(4-fluorophenyl)-4-hydroxy-6-methylpyridine-3-carboxamide;

N-[4-[(6,7-dimethoxy-1,5-naphthyridin-4-yl)oxy]-3-fluorophenyl]-6-methyl-4-oxo-5-phenyl-1-propan-2-ylpyridine-3-carboxamide;

N-[4-[(6,7-dimethoxy-1,5-naphthyridin-4-yl)oxy]-3-fluorophenyl]-5-(3-fluorophenyl)-6-methyl-4-oxo-1-propan-2-ylpyridine-3-carboxamide;

N-[4-[(6,7-dimethoxy-1,5-naphthyridin-4-yl)oxy]-3-fluorophenyl]-5-(4-methoxyphenyl)-6-methyl-4-oxo-1-propan-2-ylpyridine-3-carboxamide;

N-[4-[(6,7-dimethoxy-1,5-naphthyridin-4-yl)oxy]-3-fluorophenyl]-5-(4-fluoro-2-methylphenyl)-6-methyl-4-oxo-1-propan-2-ylpyridine-3-carboxamide;

N-[4-[(6,7-dimethoxy-1,5-naphthyridin-4-yl)oxy]-3-fluorophenyl]-1-methyl-4-oxo-5-phenylpyridine-3-carboxamide;

N-[4-[(6,7-dimethoxy-1,5-naphthyridin-4-yl)oxy]-3-fluorophenyl]-5-(4-methoxyphenyl)-1-methyl-4-oxopyridine-3-carboxamide;

N-[4-[(6,7-dimethoxy-1,5-naphthyridin-4-yl)oxy]-3-fluorophenyl]-5-(3-fluorophenyl)-1-methyl-4-oxopyridine-3-carboxamide;

N-[4-[(6,7-dimethoxy-1,5-naphthyridin-4-yl)oxy]-3-fluorophenyl]-1,6-dimethyl-4-oxo-5-phenylpyridine-3-carboxamide;

N-[4-[(6,7-dimethoxy-1,5-naphthyridin-4-yl)oxy]-3-fluorophenyl]-5-(3-fluorophenyl)-1,6-dimethyl-4-oxopyridine-3-carboxamide;

5-(4-chlorophenyl)-N-[4-[(6,7-dimethoxy-1,5-naphthyridin-4-yl)oxy]-3-fluorophenyl]-1-methyl-4-oxopyridine-3-carboxamide;

N-[4-[(6,7-dimethoxy-1,5-naphthyridin-4-yl)oxy]phenyl]-1-methyl-4-oxo-5-phenylpyridine-3-carboxamide;

N-[3-fluoro-4-[(7-methoxy-1,5-naphthyridin-4-yl)oxy]phenyl]-1-methyl-4-oxo-5-phenylpyridine-3-carboxamide;
1-cyclopropyl-N-[4-[(6,7-dimethoxy-1,5-naphthyridin-4-yl)oxy]-3-fluorophenyl]-5-(4-fluorophenyl)-4-oxopyridine-3-carboxamide;
N-[4-[(6,7-dimethoxy-1,5-naphthyridin-4-yl)oxy]-3-fluorophenyl]-5-(4-fluorophenyl)-4-hydroxypyridine-3-carboxamide;
N-[4-(6,7-dimethoxyquinolin-4-yl)oxy-3-fluorophenyl]-5-(4-fluorophenyl)-4-oxo-1-propan-2-ylpyridine-3-carboxamide;
N-[4-[(6,7-dimethoxy-1,5-naphthyridin-4-yl)oxy]-3-fluorophenyl]-5-(4-fluorophenyl)-4-oxo-1-propan-2-ylpyridine-3-carboxamide;
N-[4-[(6,7-dimethoxy-1,5-naphthyridin-4-yl)oxy]-3-fluorophenyl]-5-(4-fluorophenyl)-1-methyl-4-oxopyridine-3-carboxamide;
1-cyclopentyl-N-[4-[(6,7-dimethoxy-1,5-naphthyridin-4-yl)oxy]-3-fluorophenyl]-5-(4-fluorophenyl)-4-oxopyridine-3-carboxamide;
N-[4-[(6,7-dimethoxy-1,5-naphthyridin-4-yl)oxy]-3-fluorophenyl]-5-(4-fluorophenyl)-1-(oxetan-3-yl)-4-oxopyridine-3-carboxamide;
1-tert-butyl-N-[4-[(6,7-dimethoxy-1,5-naphthyridin-4-yl)oxy]-3-fluorophenyl]-5-(4-fluorophenyl)-4-oxopyridine-3-carboxamide;
N-[4-[(6,7-dimethoxy-1,5-naphthyridin-4-yl)oxy]-3-fluorophenyl]-5-(4-fluorophenyl)-4-oxo-1-(2,2,2-trifluoroethyl)pyridine-3-carboxamide;
1-cyclobutyl-N-[4-[(6,7-dimethoxy-1,5-naphthyridin-4-yl)oxy]-3-fluorophenyl]-5-(4-fluorophenyl)-4-oxopyridine-3-carboxamide;
N-[4-[(6,7-dimethoxy-1,5-naphthyridin-4-yl)oxy]-3-fluorophenyl]-5-(4-fluorophenyl)-1-(1-methylpyrazol-4-yl)-4-oxopyridine-3-carboxamide;
N-[4-[(6,7-dimethoxy-1,5-naphthyridin-4-yl)oxy]-3-fluorophenyl]-5-(4-fluorophenyl)-1-(1-methylazetidin-3-yl)-4-oxopyridine-3-carboxamide;
N-[4-[(6,7-dimethoxy-1,5-naphthyridin-4-yl)oxy]-3-fluorophenyl]-5-(4-fluorophenyl)-1-(1-methylpyrazol-3-yl)-4-oxopyridine-3-carboxamide;
N-[4-[(6,7-dimethoxy-1,5-naphthyridin-4-yl)oxy]-3-fluorophenyl]-5-(4-fluorophenyl)-1-(3-methyloxetan-3-yl)-4-oxopyridine-3-carboxamide;
N-[4-(6,7-dimethoxyquinolin-4-yl)oxy-3-fluorophenyl]-5-(4-fluorophenyl)-1-(3-methyloxetan-3-yl)-4-oxopyridine-3-carboxamide;
N-[4-[(6,7-dimethoxy-1,5-naphthyridin-4-yl)oxy]-3-fluorophenyl]-5-(4-fluorophenyl)-1-(1-hydroxy-2-methylpropan-2-yl)-4-oxopyridine-3-carboxamide;
N-[4-(6,7-dimethoxyquinolin-4-yl)oxy-3-fluorophenyl]-5-(4-fluorophenyl)-1-(1-hydroxy-2-methylpropan-2-yl)-4-oxopyridine-3-carboxamide;
N-[4-[(6,7-dimethoxy-1,5-naphthyridin-4-yl)oxy]-3-fluorophenyl]-5-(4-fluorophenyl)-1,6-dimethyl-4-oxopyridine-3-carboxamide;
N-[4-[(6,7-dimethoxy-1,5-naphthyridin-4-yl)oxy]-3-fluorophenyl]-5-(4-fluorophenyl)-4-oxo-1-[1-(trifluoromethyl)cyclopropyl]pyridine-3-carboxamide;
1-[1-(difluoromethyl)pyrazol-4-yl]-N-[4-[(6,7-dimethoxy-1,5-naphthyridin-4-yl)oxy]-3-fluorophenyl]-5-(4-fluorophenyl)-4-oxopyridine-3-carboxamide;
N-[4-[(6,7-dimethoxy-1,5-naphthyridin-4-yl)oxy]-3-fluorophenyl]-5-(4-fluorophenyl)-4-oxo-1-(1H-pyrazol-3-yl)pyridine-3-carboxamide;
N-[4-[(6,7-dimethoxy-1,5-naphthyridin-4-yl)oxy]-3-fluorophenyl]-5-(4-fluorophenyl)-4-oxo-1-(1H-pyrazol-4-yl)pyridine-3-carboxamide;
N-[4-[(6,7-dimethoxy-1,5-naphthyridin-4-yl)oxy]-3-fluorophenyl]-1-ethyl-5-(4-fluorophenyl)-6-methyl-4-oxopyridine-3-carboxamide;
N-[3-fluoro-4-[(7-methoxy-1,5-naphthyridin-4-yl)oxy]phenyl]-5-(4-fluorophenyl)-4-hydroxy-6-methylpyridine-3-carboxamide;
N-[4-[(6,7-dimethoxy-1,5-naphthyridin-4-yl)oxy]phenyl]-5-(4-fluorophenyl)-1,6-dimethyl-4-oxopyridine-3-carboxamide;
N-[3-fluoro-4-[(7-methoxy-1,5-naphthyridin-4-yl)oxy]phenyl]-5-(4-fluorophenyl)-4-hydroxy-2,6-dimethylpyridine-3-carboxamide;
N-[3-fluoro-4-[(6-methoxy-1,5-naphthyridin-4-yl)oxy]phenyl]-5-(4-fluorophenyl)-4-hydroxy-2,6-dimethylpyridine-3-carboxamide;
N-[3-fluoro-4-[[7-methoxy-6-(2-methoxyethoxy)-1,5-naphthyridin-4-yl]oxy]phenyl]-5-(4-fluorophenyl)-4-hydroxy-6-methylpyridine-3-carboxamide;
N-[4-[(6,7-dimethoxy-1,5-naphthyridin-4-yl)oxy]-3-fluorophenyl]-5-(4-fluoro-2-methylphenyl)-4-hydroxy-6-methylpyridine-3-carboxamide;
N-[3-fluoro-4-[(6-methoxy-1,5-naphthyridin-4-yl)oxy]phenyl]-5-(4-fluoro-2-methylphenyl)-4-hydroxy-2,6-dimethylpyridine-3-carboxamide;
N-[4-[(6,7-dimethoxy-1,5-naphthyridin-4-yl)oxy]-3-fluorophenyl]-5-(4-fluorophenyl)-4-hydroxy-6-(hydroxymethyl)pyridine-3-carboxamide;
N-[4-[(6,7-dimethoxy-1,5-naphthyridin-4-yl)oxy]-3-fluorophenyl]-5-(4-fluorophenyl)-6-(hydroxymethyl)-1-methyl-4-oxopyridine-3-carboxamide;
N-[4-[(6,7-dimethoxy-1,5-naphthyridin-4-yl)oxy]-3-fluorophenyl]-6-(fluoromethyl)-5-(4-fluorophenyl)-1-methyl-4-oxopyridine-3-carboxamide;
N-[4-[(6,7-dimethoxy-1,5-naphthyridin-4-yl)oxy]-3-fluorophenyl]-5-(4-fluorophenyl)-6-methyl-4-oxo-1-(2,2,2-trifluoroethyl)pyridine-3-carboxamide;
N-[4-[(6,7-dimethoxy-1,5-naphthyridin-4-yl)oxy]-3-fluorophenyl]-5-(4-fluoro-2-methylphenyl)-1,6-dimethyl-4-oxopyridine-3-carboxamide;
N-[4-[(6,7-dimethoxy-1,5-naphthyridin-4-yl)oxy]-3-fluorophenyl]-5-(4-fluorophenyl)-1-methyl-6-(methylamino)-4-oxopyridine-3-carboxamide;
6-cyano-N-[4-[(6,7-dimethoxy-1,5-naphthyridin-4-yl)oxy]-3-fluorophenyl]-5-(4-fluorophenyl)-1-methyl-4-oxopyridine-3-carboxamide;
N-[4-[(6,7-dimethoxy-1,5-naphthyridin-4-yl)oxy]-3-fluorophenyl]-5-(4-fluorophenyl)-6-methoxy-1-methyl-4-oxopyridine-3-carboxamide;
N-[4-[(6,7-dimethoxy-1,5-naphthyridin-4-yl)oxy]-3-fluorophenyl]-5-(4-fluorophenyl)-4-hydroxy-6-(trifluoromethyl)pyridine-3-carboxamide;
N-[3-fluoro-4-[(7-methoxy-1,5-naphthyridin-4-yl)oxy]phenyl]-5-(4-fluorophenyl)-4-hydroxy-2-methylpyridine-3-carboxamide;
N-[4-[(6,7-dimethoxy-1,5-naphthyridin-4-yl)oxy]-3-fluorophenyl]-5-(4-fluorophenyl)-1,2-dimethyl-4-oxopyridine-3-carboxamide;
N-[4-[(6,7-dimethoxy-1,5-naphthyridin-4-yl)oxy]-3-fluorophenyl]-1-ethyl-5-(4-fluorophenyl)-2-methyl-4-oxopyridine-3-carboxamide;
N-[3-fluoro-4-[(7-methoxy-1,5-naphthyridin-4-yl)oxy]phenyl]-1-(4-fluorophenyl)-6-methyl-2-oxopyridine-3-carboxamide;

N-[3-fluoro-4-[(6-methoxy-1,5-naphthyridin-4-yl)oxy]phenyl]-1-(4-fluorophenyl)-6-methyl-2-oxopyridine-3-carboxamide;

N-[3-fluoro-4-[(6-methoxy-1,5-naphthyridin-4-yl)oxy]phenyl]-1-(4-fluoro-2-methylphenyl)-6-methyl-2-oxopyridine-3-carboxamide;

5-acetyl-N-[4-[(6,7-dimethoxy-1,5-naphthyridin-4-yl)oxy]-3-fluorophenyl]-1-(4-fluorophenyl)-6-methyl-2-oxopyridine-3-carboxamide;

5-cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide;

N-[4-[(6,7-dimethoxy-1,5-naphthyridin-4-yl)oxy]-3-fluorophenyl]-5-(4-fluorophenyl)-6-methyl-4-oxo-1H-pyridazine-3-carboxamide;

N-[3-fluoro-4-[(6-methoxy-1,5-naphthyridin-4-yl)oxy]phenyl]-5-(4-fluorophenyl)-6-methyl-4-oxo-1H-pyridazine-3-carboxamide;

N-[4-[(6,7-dimethoxy-1,5-naphthyridin-4-yl)oxy]-3-fluorophenyl]-5-(4-fluoro-2-methylphenyl)-6-methyl-4-oxo-1H-pyridazine-3-carboxamide;

N-[4-[(6,7-dimethoxy-1,5-naphthyridin-4-yl)oxy]phenyl]-5-(4-fluorophenyl)-1,6-dimethyl-4-oxopyridazine-3-carboxamide;

N-[4-[(6,7-dimethoxy-1,5-naphthyridin-4-yl)oxy]-3-fluorophenyl]-5-(4-fluorophenyl)-1,6-dimethyl-4-oxopyridazine-3-carboxamide;

N-[4-[(6,7-dimethoxy-1,5-naphthyridin-4-yl)oxy]-3-fluorophenyl]-4-(4-fluorophenyl)-5-methyl-3-oxopyrazine-2-carboxamide;

N-[3-fluoro-4-[(7-methoxy-1,5-naphthyridin-4-yl)oxy]phenyl]-4-(4-fluorophenyl)-5-methyl-3-oxopyrazine-2-carboxamide;

N-[4-[(6,7-dimethoxy-1,5-naphthyridin-4-yl)oxy]-3-fluorophenyl]-4-(4-fluorophenyl)-5,6-dimethyl-3-oxopyrazine-2-carboxamide;

N-[4-[(6,7-dimethoxy-1,5-naphthyridin-4-yl)oxy]-3-fluorophenyl]-6-(4-fluorophenyl)-5-hydroxypyrimidine-4-carboxamide;

N-[4-[(6,7-dimethoxy-1,5-naphthyridin-4-yl)oxy]-3-fluorophenyl]-1-(4-fluorophenyl)-2-methyl-6-oxopyrimidine-5-carboxamide;

N-[4-[(6,7-dimethoxy-1,5-naphthyridin-4-yl)oxy]-3-fluorophenyl]-1-(4-fluorophenyl)-4-methyl-6-oxopyrimidine-5-carboxamide;

N-[4-[(6,7-dimethoxy-1,5-naphthyridin-4-yl)oxy]-3-fluorophenyl]-1-(4-fluorophenyl)-2-(methylamino)-6-oxopyrimidine-5-carboxamide;

N-[4-[(6,7-dimethoxy-1,5-naphthyridin-4-yl)oxy]-3-fluorophenyl]-2-(dimethylamino)-1-(4-fluorophenyl)-6-oxopyrimidine-5-carboxamide;

N-[4-[(6,7-dimethoxy-1,5-naphthyridin-4-yl)oxy]-3-fluorophenyl]-1-(4-fluorophenyl)-2,4-dimethyl-6-oxopyrimidine-5-carboxamide;

N-[4-[(6,7-dimethoxy-1,5-naphthyridin-4-yl)oxy]-3-fluorophenyl]-3-(4-fluorophenyl)-2,4-dioxo-1H-pyrimidine-5-carboxamide;

N-[3-fluoro-4-[(6-methoxy-1,5-naphthyridin-4-yl)oxy]phenyl]-3-(4-fluorophenyl)-2,4-dioxo-1H-pyrimidine-5-carboxamide; and N-[4-[(6,7-dimethoxy-1,5-naphthyridin-4-yl)oxy]-3-fluorophenyl]-3-(4-fluorophenyl)-4-oxo-2-sulfanylidene-1H-pyrimidine-5-carboxamide;

or a pharmaceutically acceptable salt or stereoisomer thereof.

In some embodiments, provided is a compound, or a pharmaceutically acceptable salt or stereoisomer thereof, selected from Table 1:

TABLE 1

| Cpd # | Structure | IUPAC Name |
|---|---|---|
| 21 | 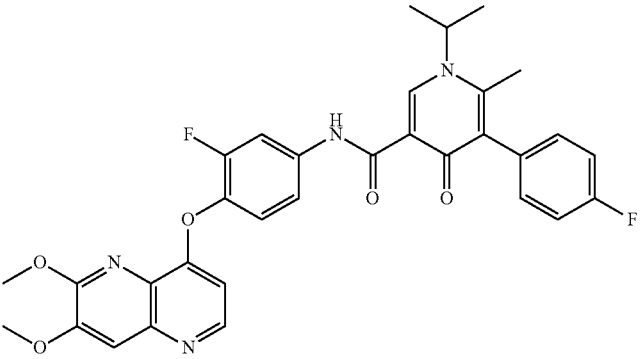 | N-[4-[(6,7-dimethoxy-1,5-naphthyridin-4-yl)oxy]-3-fluorophenyl]-5-(4-fluorophenyl)-6-methyl-4-oxo-1-propan-2-ylpyridine-3-carboxamide |
| 22 | 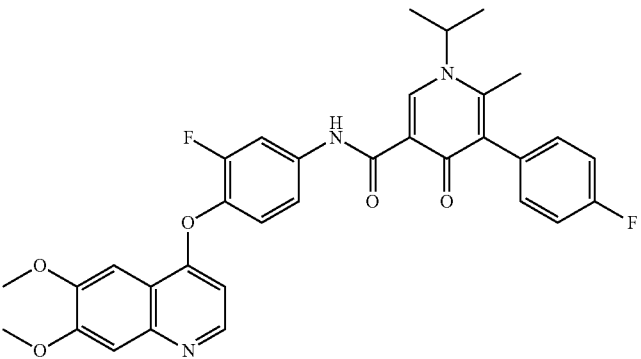 [SMILES: COc1cc2nccc(Oc3ccc(NC(=O)c4cn(C(C)C)c(C)c(-c5ccc(F)cc5)c4=O)cc3F)c2cc1OC] | N-[4-(6,7-dimethoxyquinolin-4-yl)oxy-3-fluorophenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 23 | 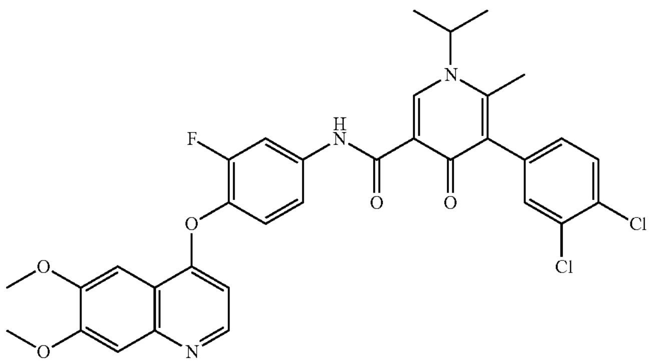 [SMILES: COc1cc2nccc(Oc3ccc(NC(=O)c4cn(C(C)C)c(C)c(-c5ccc(Cl)c(Cl)c5)c4=O)cc3F)c2cc1OC] | 5-(3,4-dichlorophenyl)-N-[4-(6,7-dimethoxyquinolin-4-yl)oxy-3-fluorophenyl]-6-methyl-4-oxo-1-propan-2-ylpyridine-3-carboxamide |
| 24 | 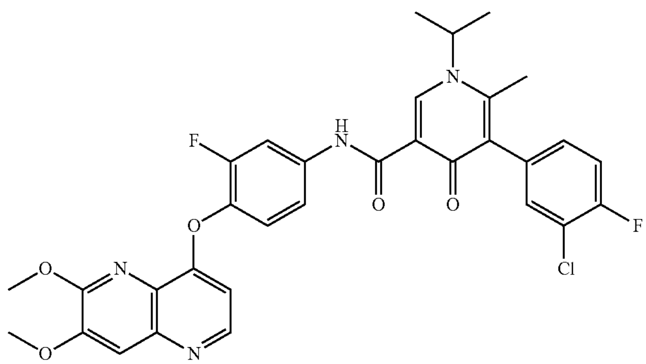 [SMILES: COc1cc2nccc(Oc3ccc(NC(=O)c4cn(C(C)C)c(C)c(-c5ccc(F)c(Cl)c5)c4=O)cc3F)c2nc1OC] | 5-(3-chloro-4-fluorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide |
| 25 | 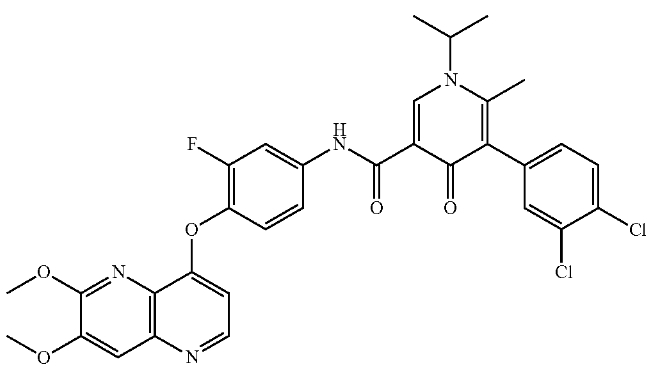 [SMILES: COc1cc2nccc(Oc3ccc(NC(=O)c4cn(C(C)C)c(C)c(-c5ccc(Cl)c(Cl)c5)c4=O)cc3F)c2nc1OC] | 5-(3,4-dichlorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide |
| 26 | 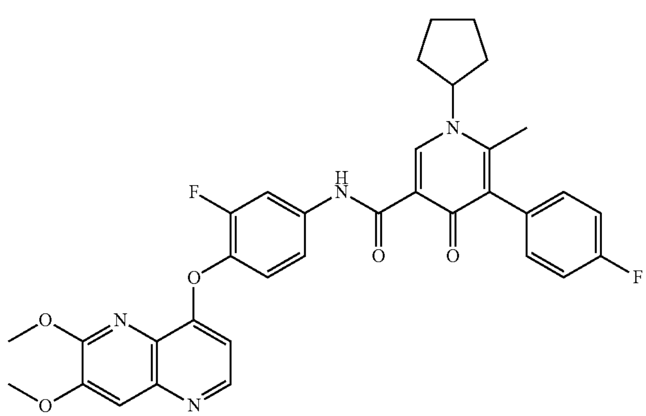 [SMILES: COc1cc2nccc(Oc3ccc(NC(=O)c4cn(C5CCCC5)c(C)c(-c5ccc(F)cc5)c4=O)cc3F)c2nc1OC] | 1-cyclopentyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |

TABLE 1-continued

| Cpd # | Structure | IUPAC Name |
|---|---|---|
| 27 | 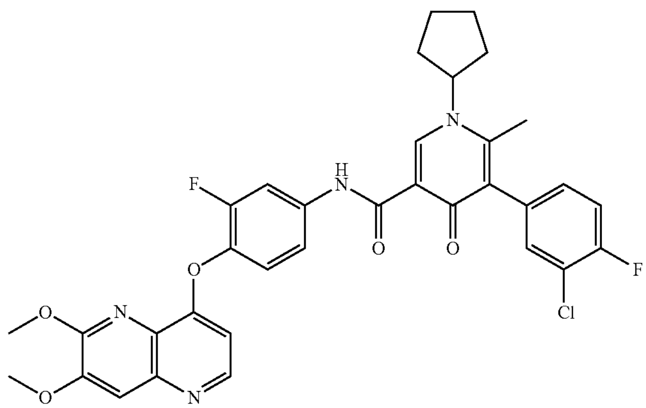 [SMILES: COc1cc2nccc(Oc3ccc(NC(=O)c4cn(C5CCCC5)c(C)c(-c5ccc(F)c(Cl)c5)c4=O)cc3F)c2nc1OC] | 5-(3-chloro-4-fluorophenyl)-1-cyclopentyl-N-[4-[(6,7-dimethoxy-1,5-naphthyridin-4-yl)oxy]-3-fluorophenyl]-6-methyl-4-oxopyridine-3-carboxamide |
| 28 | 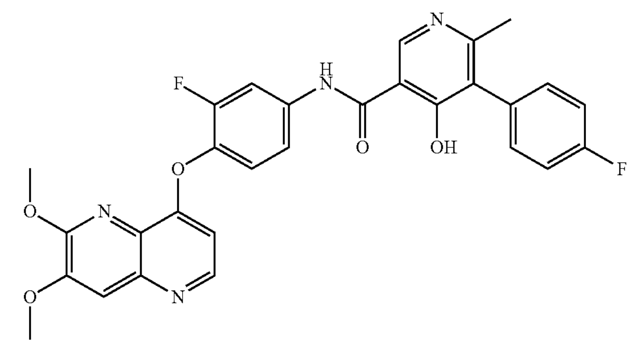 [SMILES: COc1cc2nccc(Oc3ccc(NC(=O)c4cnc(C)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-methylpyridine-3-carboxamide |
| 29 | 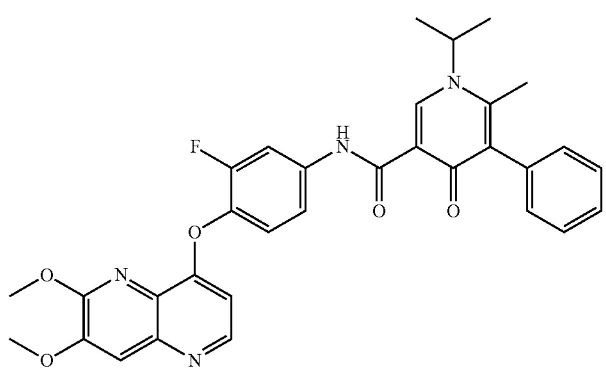 [SMILES: COc1cc2nccc(Oc3ccc(NC(=O)c4cn(C(C)C)c(C)c(-c5ccccc5)c4=O)cc3F)c2nc1OC] | N-[4-[(6,7-dimethoxy-1,5-naphthyridin-4-yl)oxy]-3-fluorophenyl]-6-methyl-4-oxo-5-phenyl-1-propan-2-ylpyridine-3-carboxamide |
| 30 | 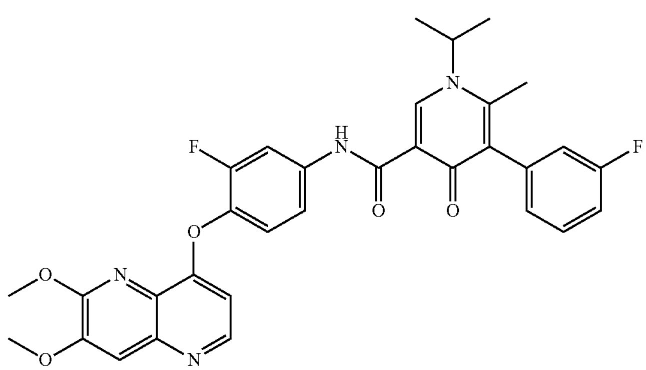 [SMILES: COc1cc2nccc(Oc3ccc(NC(=O)c4cn(C(C)C)c(C)c(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-6-methyl-4-oxo-1-propan-2-ylpyridine-3-carboxamide |

TABLE 1-continued

| Cpd # | Structure | IUPAC Name |
|---|---|---|
| 31 | 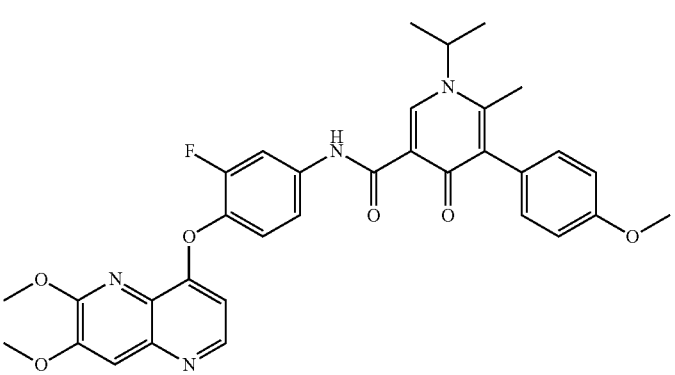 | N-[4-[(6,7-dimethoxy-1,5-naphthyridin-4-yl)oxy]-3-fluorophenyl]-5-(4-methoxyphenyl)-6-methyl-4-oxo-1-propan-2-ylpyridine-3-carboxamide |
| 32 | 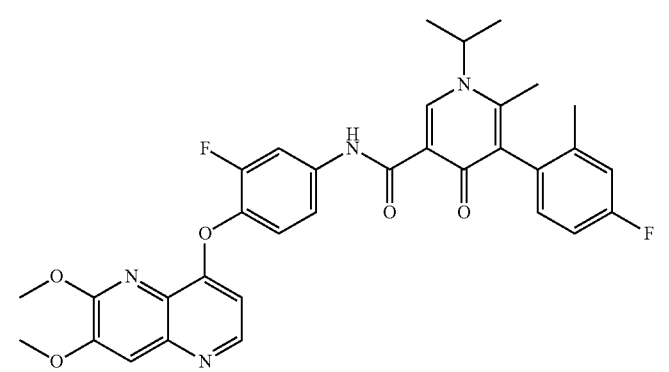 [SMILES: COc1cc2nccc(Oc3ccc(NC(=O)c4cn(C(C)C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-6-methyl-4-oxo-1-propan-2-ylpyridine-3-carboxamide |
| 33 | 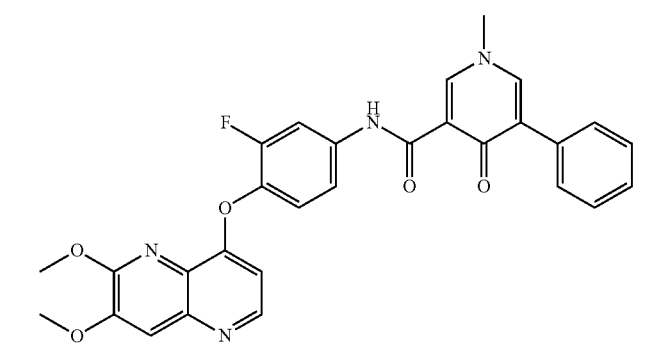 [SMILES: COc1cc2nccc(Oc3ccc(NC(=O)c4cn(C)cc(-c5ccccc5)c4=O)cc3F)c2nc1OC] | N-[4-[(6,7-dimethoxy-1,5-naphthyridin-4-yl)oxy]-3-fluorophenyl]-1-methyl-4-oxo-5-phenylpyridine-3-carboxamide |
| 34 | 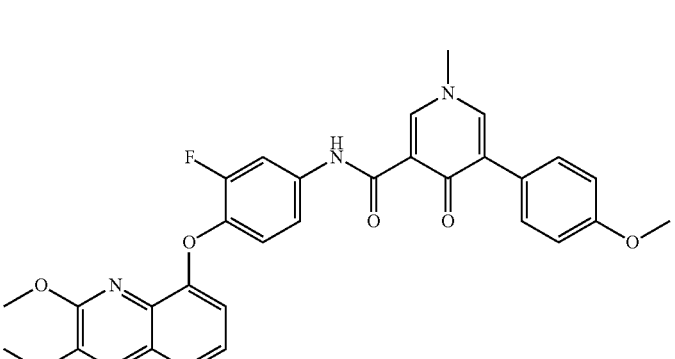 | N-[4-[(6,7-dimethoxy-1,5-naphthyridin-4-yl)oxy]-3-fluorophenyl]-5-(4-methoxyphenyl)-1-methyl-4-oxopyridine-3-carboxamide |

TABLE 1-continued

| Cpd # | Structure | IUPAC Name |
|---|---|---|
| 35 | 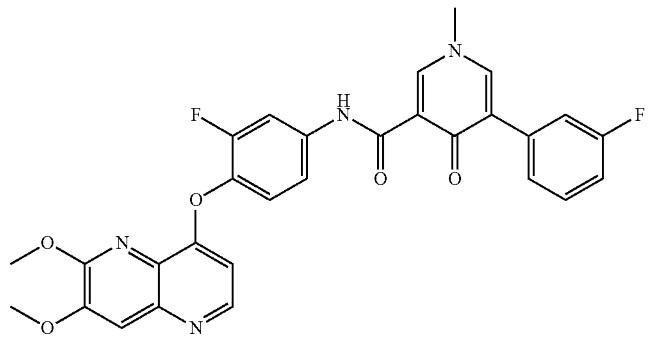 [SMILES: COc1cc2nccc(Oc3ccc(NC(=O)c4cn(C)cc(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-1-methyl-4-oxopyridine-3-carboxamide |
| 36 | 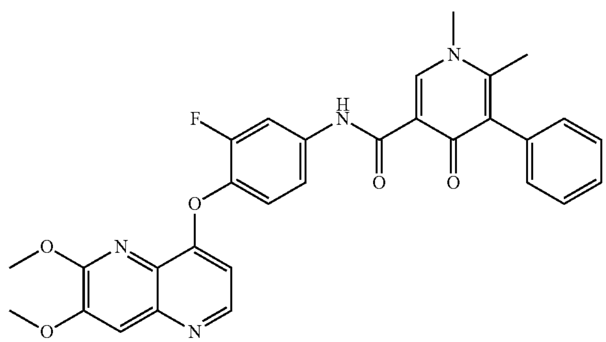 [SMILES: COc1cc2nccc(Oc3ccc(NC(=O)c4cn(C)c(C)c(-c5ccccc5)c4=O)cc3F)c2nc1OC] | N-[4-[(6,7-dimethoxy-1,5-naphthyridin-4-yl)oxy]-3-fluorophenyl]-1,6-dimethyl-4-oxo-5-phenylpyridine-3-carboxamide |
| 37 | 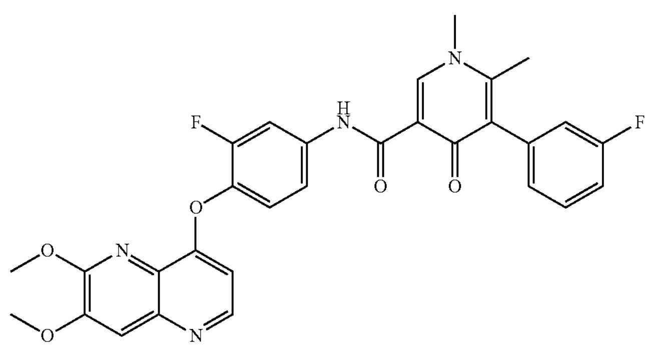 [SMILES: COc1cc2nccc(Oc3ccc(NC(=O)c4cn(C)c(C)c(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-1,6-dimethyl-4-oxopyridine-3-carboxamide |
| 38 | 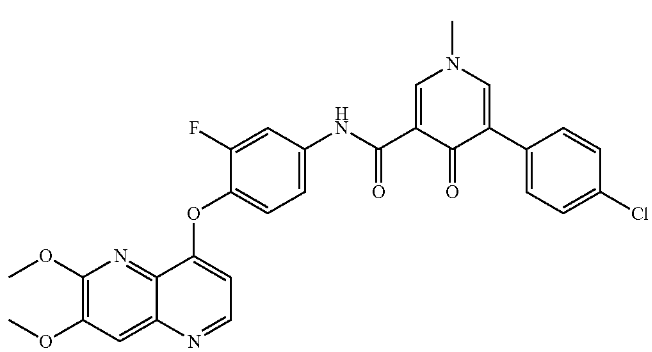 [SMILES: COc1cc2nccc(Oc3ccc(NC(=O)c4cn(C)cc(-c5ccc(Cl)cc5)c4=O)cc3F)c2nc1OC] | 5-(4-chlorophenyl)-N-[4-[(6,7-dimethoxy-1,5-naphthyridin-4-yl)oxy]-3-fluorophenyl]-1-methyl-4-oxopyridine-3-carboxamide |

TABLE 1-continued

| Cpd # | Structure | IUPAC Name |
|---|---|---|
| 39 | 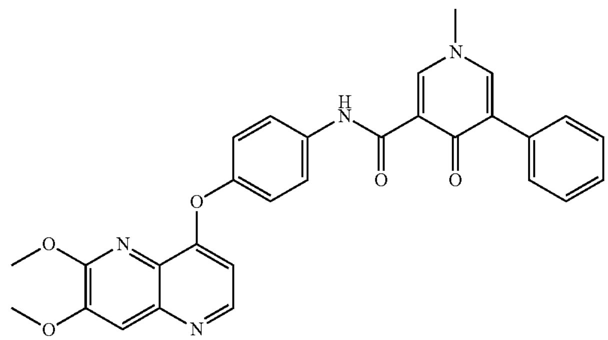 [SMILES: COc1cc2nccc(Oc3ccc(NC(=O)c4cn(C)cc(-c5ccccc5)c4=O)cc3)c2nc1OC] | N-[4-[(6,7-dimethoxy-1,5-naphthyridin-4-yl)oxy]phenyl]-1-methyl-4-oxo-5-phenylpyridine-3-carboxamide |
| 40 | 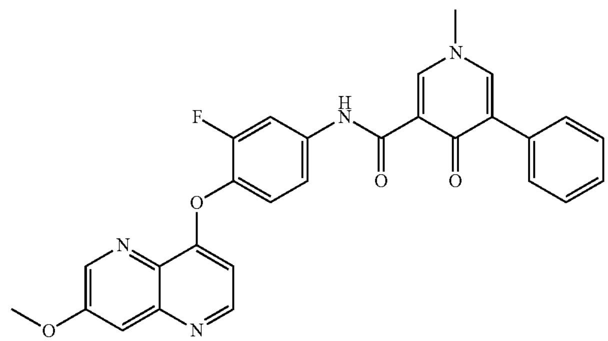 [SMILES: COc1cnc2c(Oc3ccc(NC(=O)c4cn(C)cc(-c5ccccc5)c4=O)cc3F)ccnc2c1] | N-[3-fluoro-4-[(7-methoxy-1,5-naphthyridin-4-yl)oxy]phenyl]-1-methyl-4-oxo-5-phenylpyridine-3-carboxamide |
| 41 | 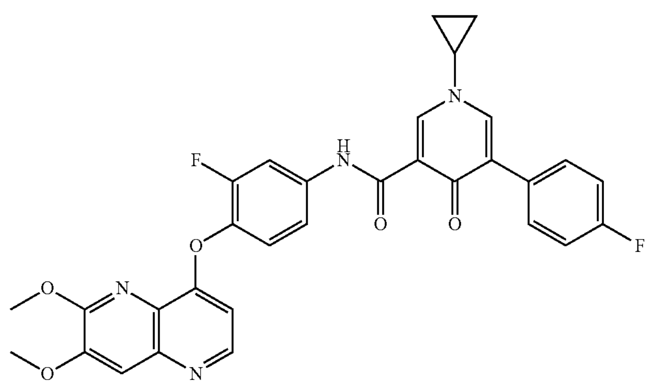 [SMILES: COc1cc2nccc(Oc3ccc(NC(=O)c4cn(C5CC5)cc(-c5ccc(F)cc5)c4=O)cc3F)c2nc1OC] | 1-cyclopropyl-N-[4-[(6,7-dimethoxy-1,5-naphthyridin-4-yl)oxy]-3-fluorophenyl]-5-(4-fluorophenyl)-4-oxopyridine-3-carboxamide |
| 42 | 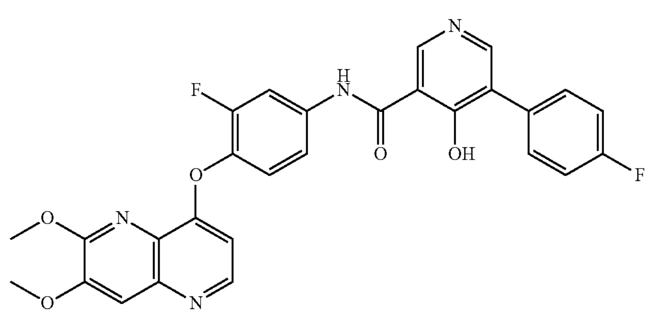 [SMILES: COc1cc2nccc(Oc3ccc(NC(=O)c4cncc(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxypyridine-3-carboxamide |

TABLE 1-continued

| Cpd # | Structure | IUPAC Name |
|---|---|---|
| 43 | 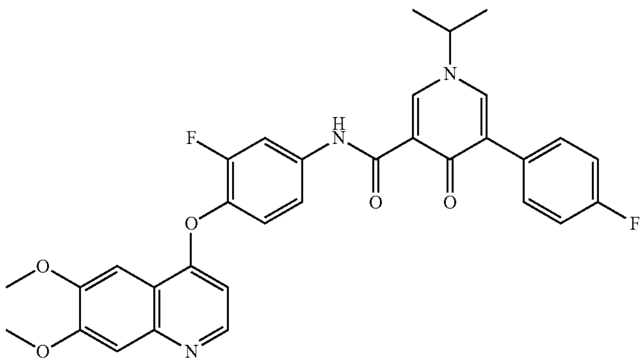 [SMILES: COc1cc2nccc(Oc3ccc(NC(=O)c4cn(C(C)C)cc(-c5ccc(F)cc5)c4=O)cc3F)c2cc1OC] | N-[4-(6,7-dimethoxyquinolin-4-yl)oxy-3-fluorophenyl]-5-(4-fluorophenyl)-4-oxo-1-propan-2-ylpyridine-3-carboxamide |
| 44 | 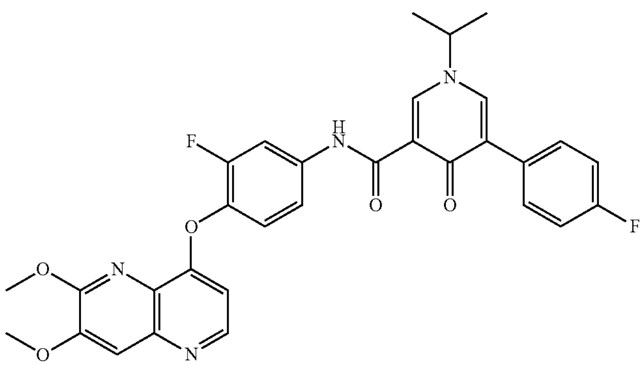 [SMILES: COc1cc2nccc(Oc3ccc(NC(=O)c4cn(C(C)C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-propan-2-ylpyridine-3-carboxamide |
| 45 | 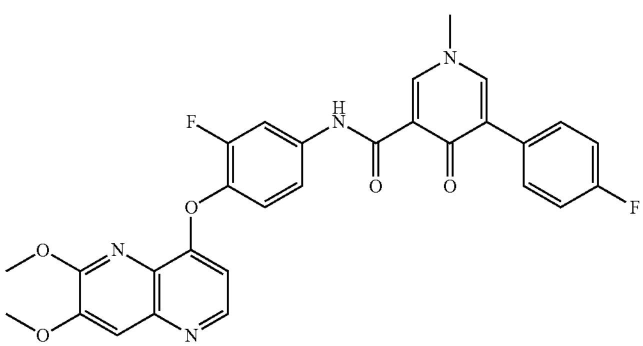 [SMILES: COc1cc2nccc(Oc3ccc(NC(=O)c4cn(C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 46 | 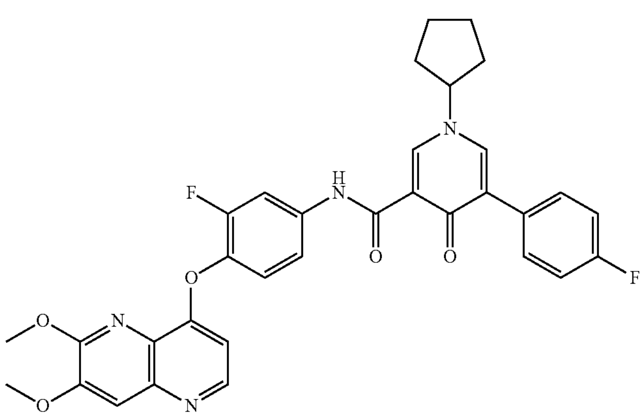 [SMILES: COc1cc2nccc(Oc3ccc(NC(=O)c4cn(C5CCCC5)cc(-c5ccc(F)cc5)c4=O)cc3F)c2nc1OC] | 1-cyclopentyl-N-[4-[(6,7-dimethoxy-1,5-naphthyridin-4-yl)oxy]-3-fluorophenyl]-5-(4-fluorophenyl)-4-oxopyridine-3-carboxamide |

TABLE 1-continued

| Cpd # | Structure | IUPAC Name |
|---|---|---|
| 47 | 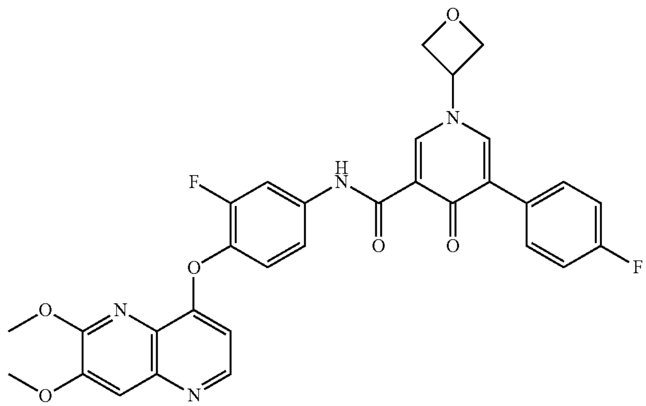 [SMILES: COc1cc2nccc(Oc3ccc(NC(=O)c4cn(C5COC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(oxetan-3-yl)-4-oxopyridine-3-carboxamide |
| 48 | 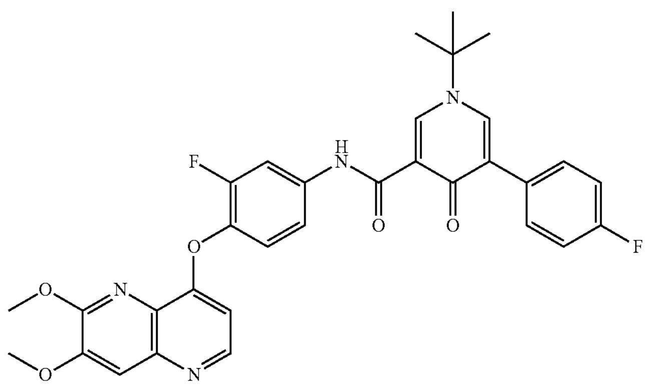 [SMILES: COc1cc2nccc(Oc3ccc(NC(=O)c4cn(C(C)(C)C)cc(-c5ccc(F)cc5)c4=O)cc3F)c2nc1OC] | 1-tert-butyl-N-[4-[(6,7-dimethoxy-1,5-naphthyridin-4-yl)oxy]-3-fluorophenyl]-5-(4-fluorophenyl)-4-oxopyridine-3-carboxamide |
| 49 | 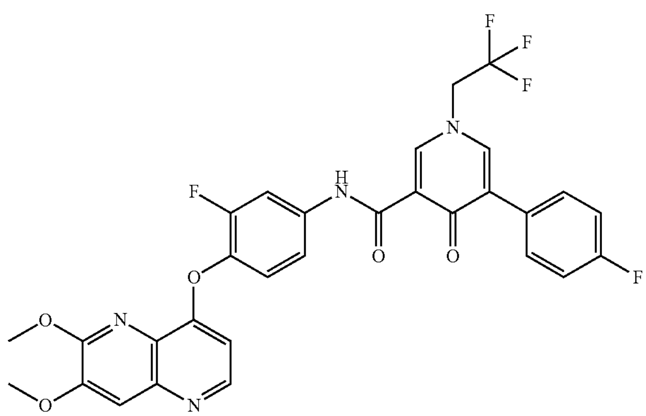 [SMILES: COc1cc2nccc(Oc3ccc(NC(=O)c4cn(CC(F)(F)F)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(2,2,2-trifluoroethyl)pyridine-3-carboxamide |
| 50 | 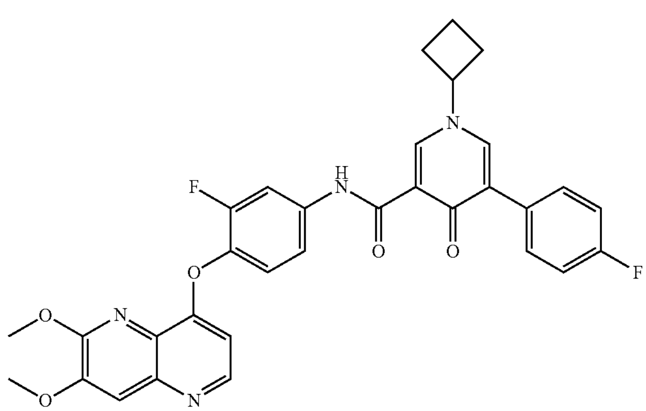 [SMILES: COc1cc2nccc(Oc3ccc(NC(=O)c4cn(C5CCC5)cc(-c5ccc(F)cc5)c4=O)cc3F)c2nc1OC] | 1-cyclobutyl-N-[4-[(6,7-dimethoxy-1,5-naphthyridin-4-yl)oxy]-3-fluorophenyl]-5-(4-fluorophenyl)-4-oxopyridine-3-carboxamide |

TABLE 1-continued

| Cpd # | Structure | IUPAC Name |
|---|---|---|
| 51 | 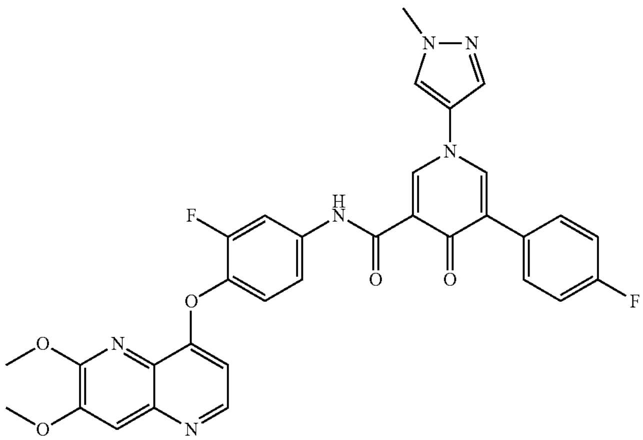 [SMILES: COc1cc2nccc(Oc3ccc(NC(=O)c4cn(-c5cnn(C)c5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-methylpyrazol-4-yl)-4-oxopyridine-3-carboxamide |
| 52 | 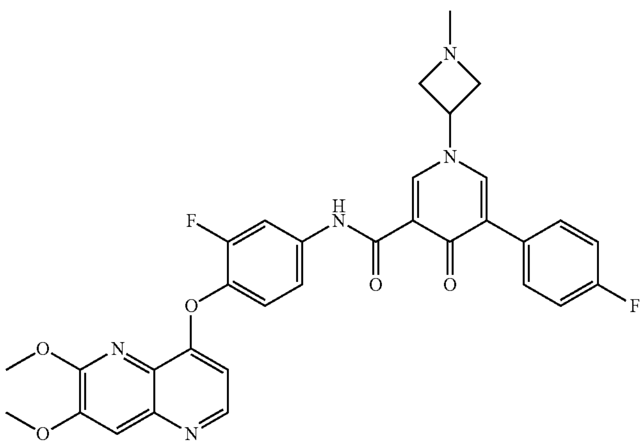 [SMILES: COc1cc2nccc(Oc3ccc(NC(=O)c4cn(C5CN(C)C5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-methylazetidin-3-yl)-4-oxopyridine-3-carboxamide |
| 53 | 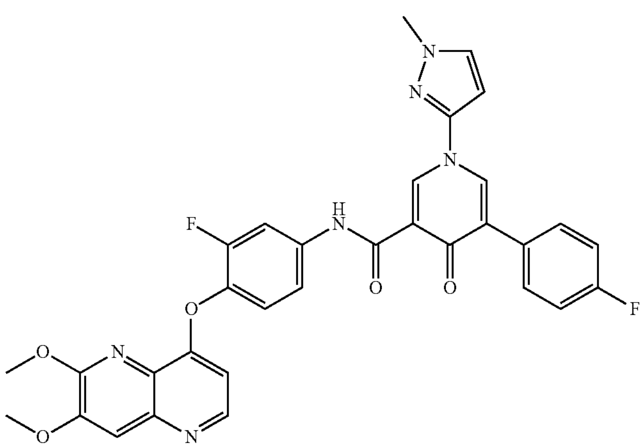 [SMILES: COc1cc2nccc(Oc3ccc(NC(=O)c4cn(-c5ccn(C)n5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-methylpyrazol-3-yl)-4-oxopyridine-3-carboxamide |

TABLE 1-continued

| Cpd # | Structure | IUPAC Name |
|---|---|---|
| 54 | 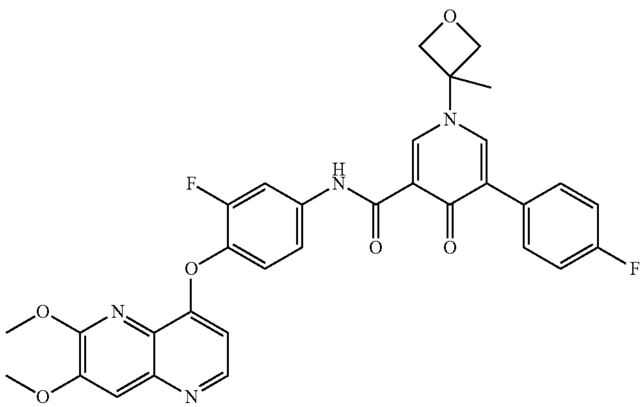 [SMILES: COc1cc2nccc(Oc3ccc(NC(=O)c4cn(C5(C)COC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(3-methyloxetan-3-yl)-4-oxopyridine-3-carboxamide |
| 55 | 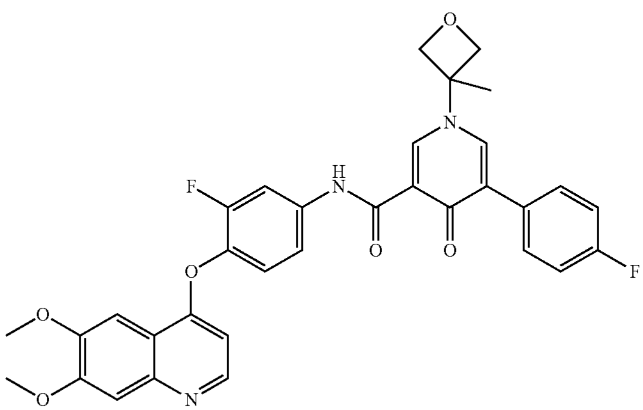 [SMILES: COc1cc2nccc(Oc3ccc(NC(=O)c4cn(C5(C)COC5)cc(-c5ccc(F)cc5)c4=O)cc3F)c2cc1OC] | N-[4-(6,7-dimethoxyquinolin-4-yl)oxy-3-fluorophenyl]-5-(4-fluorophenyl)-1-(3-methyloxetan-3-yl)-4-oxopyridine-3-carboxamide |
| 56 | 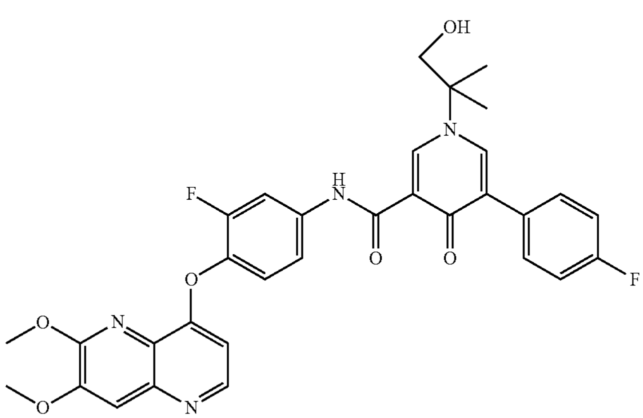 [SMILES: COc1cc2nccc(Oc3ccc(NC(=O)c4cn(C(C)(C)CO)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-hydroxy-2-methylpropan-2-yl)-4-oxopyridine-3-carboxamide |

TABLE 1-continued

| Cpd # | Structure | IUPAC Name |
|---|---|---|
| 57 | 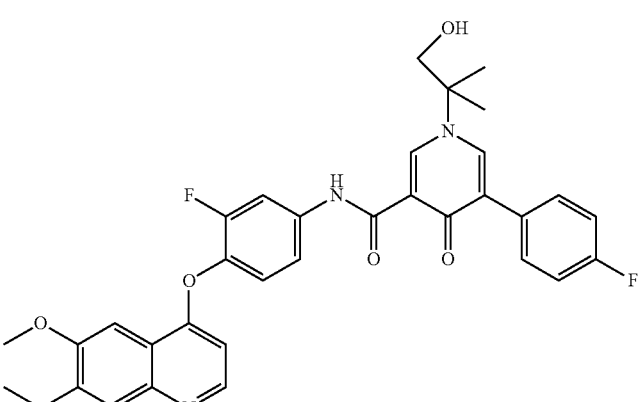 | N-[4-(6,7-dimethoxyquinolin-4-yl)oxy-3-fluorophenyl]-5-(4-fluorophenyl)-1-(1-hydroxy-2-methylpropan-2-yl)-4-oxopyridine-3-carboxamide |
| 58 | 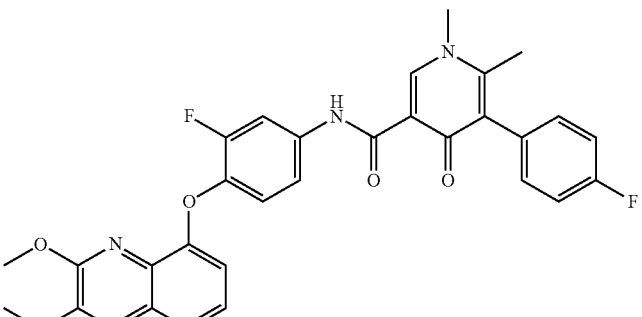 | N-[4-[(6,7-dimethoxy-1,5-naphthyridin-4-yl)oxy]-3-fluorophenyl]-5-(4-fluorophenyl)-1,6-dimethyl-4-oxopyridine-3-carboxamide |
| 59 | 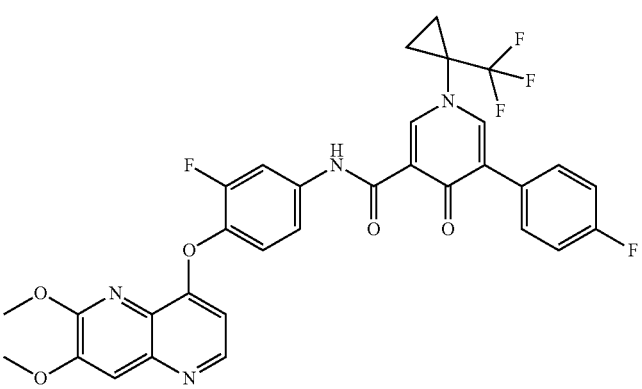 [SMILES: COc1cc2nccc(Oc3ccc(NC(=O)c4cn(C5(C(F)(F)F)CC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-[1-(trifluoromethyl)cyclopropyl]pyridine-3-carboxamide |

TABLE 1-continued
| Cpd # | Structure | IUPAC Name |
|---|---|---|
| 60 | 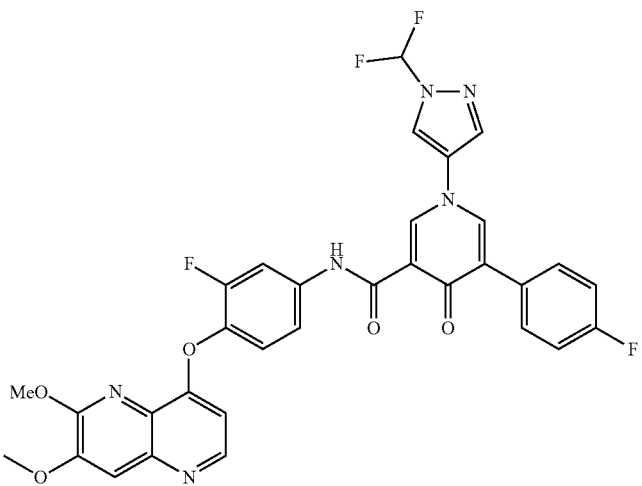 [SMILES: COc1cc2nccc(Oc3ccc(NC(=O)c4cn(-c5cnn(C(F)F)c5)cc(-c5ccc(F)cc5)c4=O)cc3F)c2nc1OC] | 1-[1-(difluoromethyl)pyrazol-4-yl]-N-[4-[(6,7-dimethoxy-1,5-naphthyridin-4-yl)oxy]-3-fluorophenyl]-5-(4-fluorophenyl)-4-oxopyridine-3-carboxamide |
| 61 | 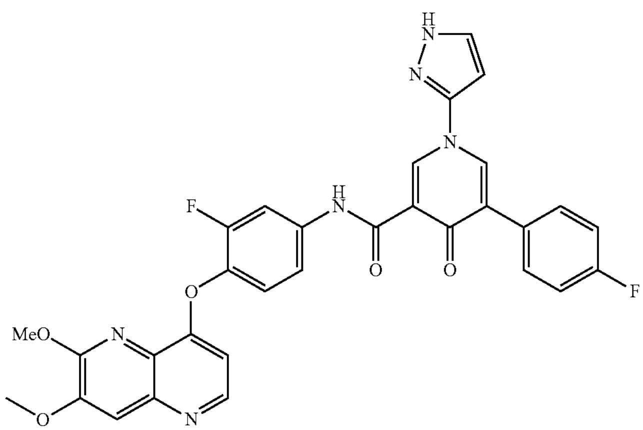 [SMILES: COc1cc2nccc(Oc3ccc(NC(=O)c4cn(-c5cc[nH]n5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(1H-pyrazol-3-yl)pyridine-3-carboxamide |
| 62 | 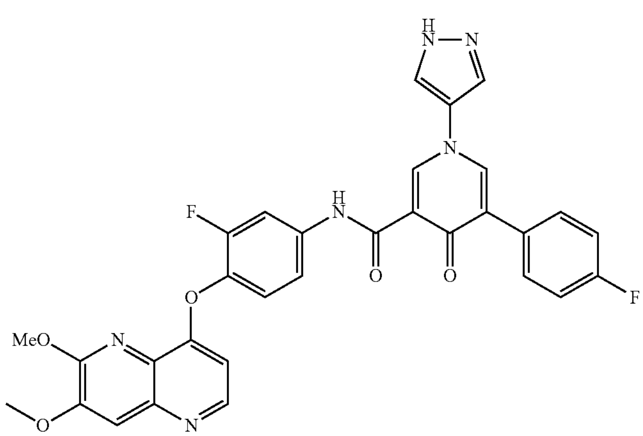 [SMILES: COc1cc2nccc(Oc3ccc(NC(=O)c4cn(-c5cn[nH]c5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(1H-pyrazol-4-yl)pyridine-3-carboxamide |

TABLE 1-continued

| Cpd # | Structure | IUPAC Name |
|---|---|---|
| 63 | 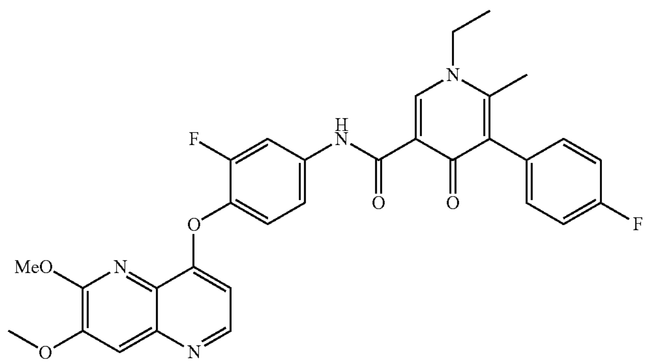 [SMILES: CCn1cc(C(=O)Nc2ccc(Oc3ccnc4cc(OC)c(OC)nc34)c(F)c2)c(=O)c(-c2ccc(F)cc2)c1C] | N-[4-[(6,7-dimethoxy-1,5-naphthyridin-4-yl)oxy]-3-fluorophenyl]-1-ethyl-5-(4-fluorophenyl)-6-methyl-4-oxopyridine-3-carboxamide |
| 64 | 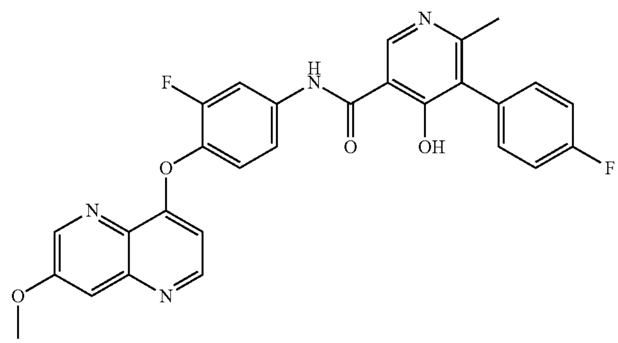 [SMILES: COc1cnc2c(Oc3ccc(NC(=O)c4cnc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-methylpyridine-3-carboxamide |
| 65 | 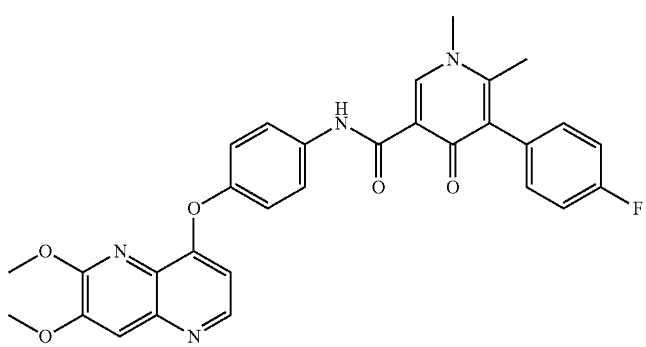 [SMILES: COc1cc2nccc(Oc3ccc(NC(=O)c4cn(C)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,6-dimethyl-4-oxopyridine-3-carboxamide |
| 66 | 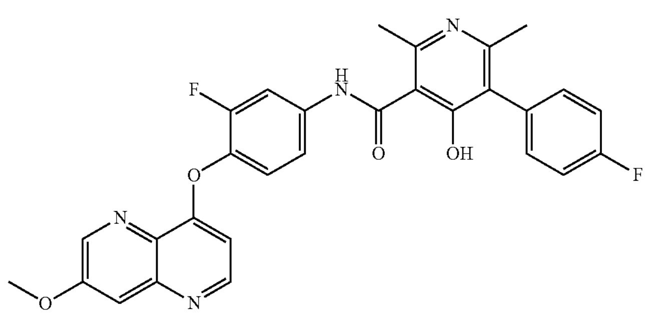 [SMILES: COc1cnc2c(Oc3ccc(NC(=O)c4c(C)nc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2,6-dimethylpyridine-3-carboxamide |

TABLE 1-continued

| Cpd # | Structure | IUPAC Name |
|---|---|---|
| 67 | 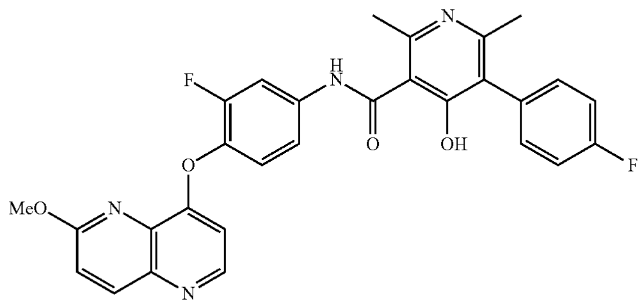 [SMILES: COc1ccc2nccc(Oc3ccc(NC(=O)c4c(C)nc(C)c(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-2,6-dimethylpyridine-3-carboxamide |
| 68 | 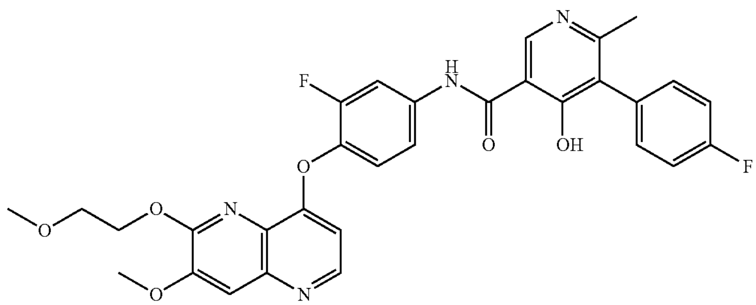 [SMILES: COCCOc1nc2c(Oc3ccc(NC(=O)c4cnc(C)c(-c5ccc(F)cc5)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-6-methylpyridine-3-carboxamide |
| 69 | 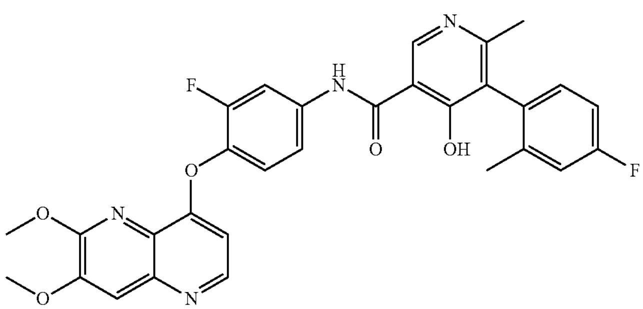 [SMILES: COc1cc2nccc(Oc3ccc(NC(=O)c4cnc(C)c(-c5ccc(F)cc5C)c4O)cc3F)c2nc1OC] | N-[4-[(6,7-dimethoxy-1,5-naphthyridin-4-yl)oxy]-3-fluorophenyl]-5-(4-fluoro-2-methylphenyl)-4-hydroxy-6-methylpyridine-3-carboxamide |
| 70 | 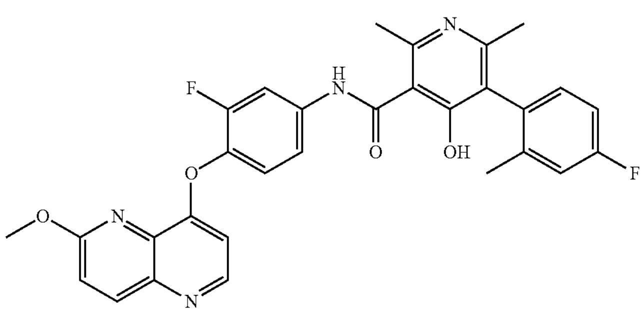 [SMILES: COc1ccc2nccc(Oc3ccc(NC(=O)c4c(C)nc(C)c(-c5ccc(F)cc5C)c4O)cc3F)c2n1] | N-[3-fluoro-4-[(6-methoxy-1,5-naphthyridin-4-yl)oxy]phenyl]-5-(4-fluoro-2-methylphenyl)-4-hydroxy-2,6-dimethylpyridine-3-carboxamide |
| 71 | 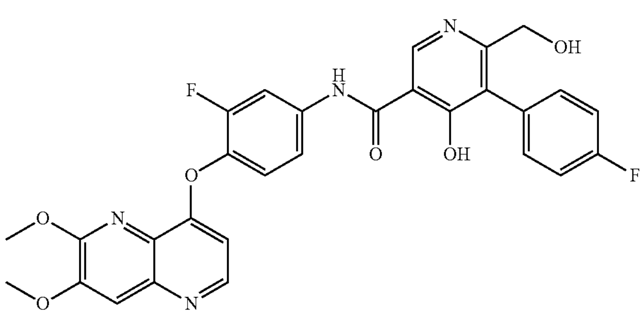 [SMILES: COc1cc2nccc(Oc3ccc(NC(=O)c4cnc(CO)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-(hydroxymethyl)pyridine-3-carboxamide |

TABLE 1-continued

| Cpd # | Structure | IUPAC Name |
|---|---|---|
| 72 | 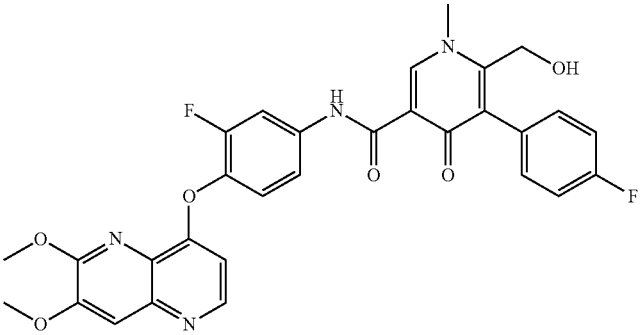 | N-[4-[(6,7-dimethoxy-1,5-naphthyridin-4-yl)oxy]-3-fluorophenyl]-5-(4-fluorophenyl)-6-(hydroxymethyl)-1-methyl-4-oxopyridine-3-carboxamide |
| 73 | 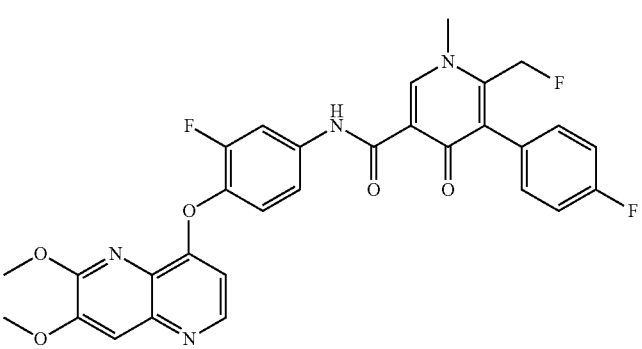 | N-[4-[(6,7-dimethoxy-1,5-naphthyridin-4-yl)oxy]-3-fluorophenyl]-6-(fluoromethyl)-5-(4-fluorophenyl)-1-methyl-4-oxopyridine-3-carboxamide |
| 74 | 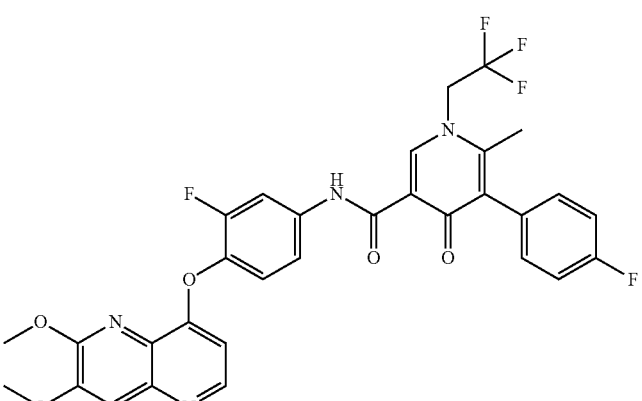 | N-[4-[(6,7-dimethoxy-1,5-naphthyridin-4-yl)oxy]-3-fluorophenyl]-5-(4-fluorophenyl)-6-methyl-4-oxo-1-(2,2,2-trifluoroethyl)pyridine-3-carboxamide |
| 75 | 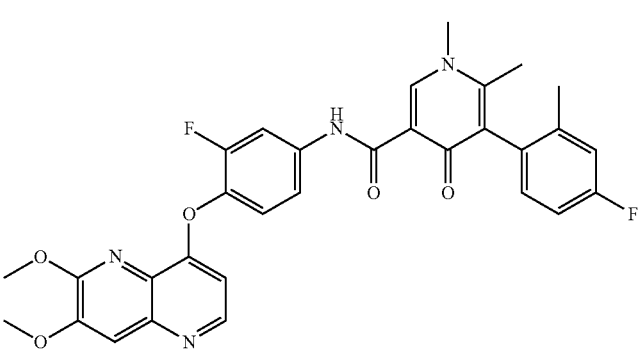 [SMILES: COc1cc2nccc(Oc3ccc(NC(=O)c4cn(C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1,6-dimethyl-4-oxopyridine-3-carboxamide |

TABLE 1-continued

| Cpd # | Structure | IUPAC Name |
|---|---|---|
| 76 | 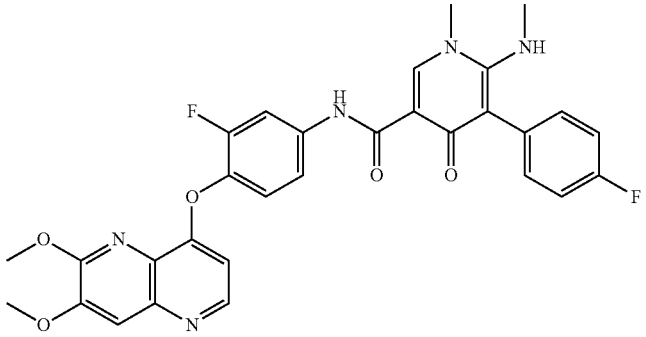 | N-[4-[(6,7-dimethoxy-1,5-naphthyridin-4-yl)oxy]-3-fluorophenyl]-5-(4-fluorophenyl)-1-methyl-6-(methylamino)-4-oxopyridine-3-carboxamide |
| 77 | 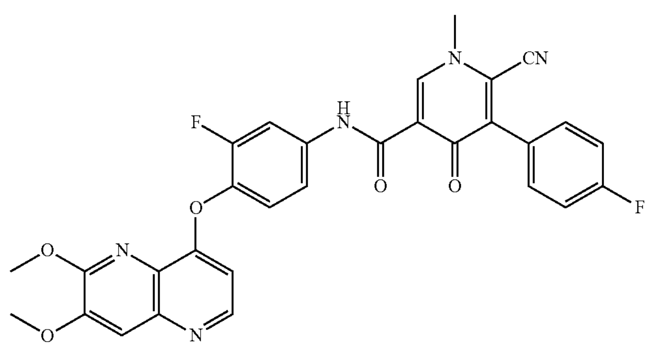 | 6-cyano-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 78 | 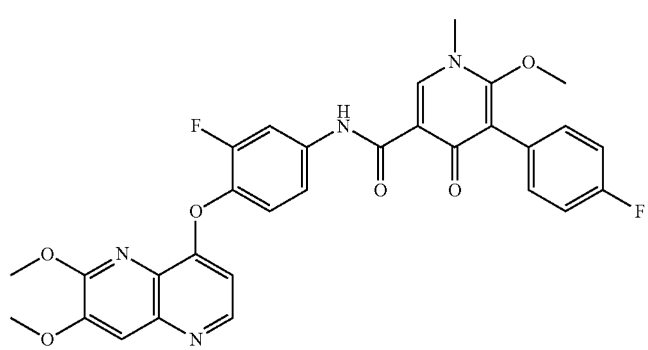 [SMILES: COc1cc2nccc(Oc3ccc(NC(=O)c4cn(C)c(OC)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methoxy-1-methyl-4-oxopyridine-3-carboxamide |
| 79 | 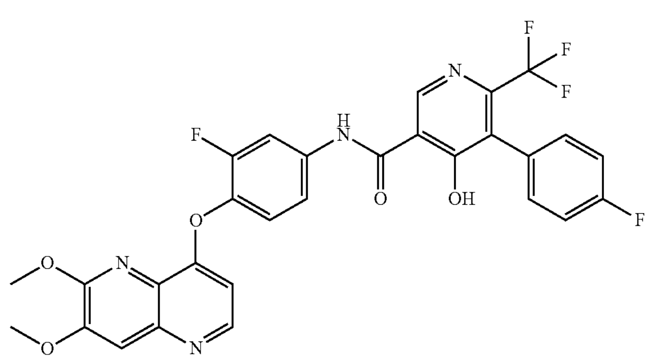 [SMILES: COc1cc2nccc(Oc3ccc(NC(=O)c4cnc(C(F)(F)F)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-(trifluoromethyl)pyridine-3-carboxamide |

TABLE 1-continued

| Cpd # | Structure | IUPAC Name |
|---|---|---|
| 80 | 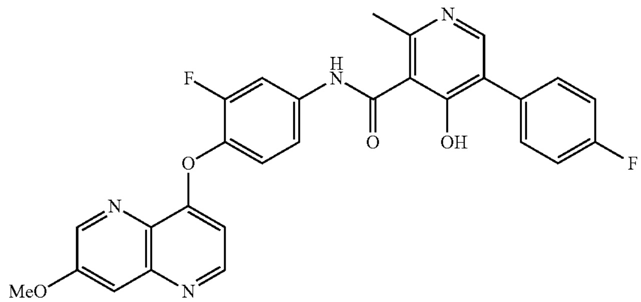 [SMILES: COc1cnc2c(Oc3ccc(NC(=O)c4c(C)ncc(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2-methylpyridine-3-carboxamide |
| 81 | 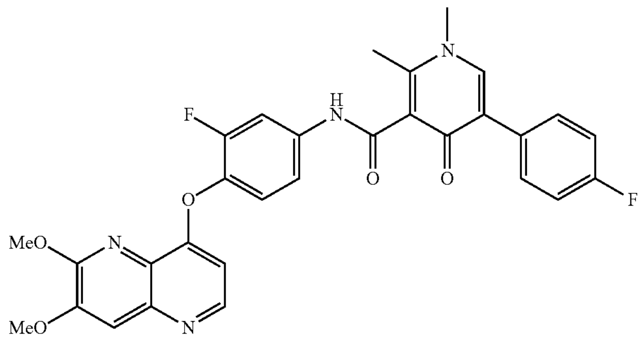 [SMILES: COc1cc2nccc(Oc3ccc(NC(=O)c4c(C)n(C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,2-dimethyl-4-oxopyridine-3-carboxamide |
| 82 | 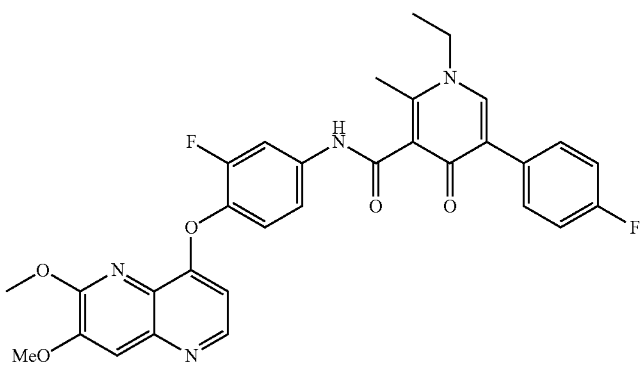 [SMILES: CCn1cc(-c2ccc(F)cc2)c(=O)c(C(=O)Nc2ccc(Oc3ccnc4cc(OC)c(OC)nc34)c(F)c2)c1C] | N-[4-[(6,7-dimethoxy-1,5-naphthyridin-4-yl)oxy]-3-fluorophenyl]-1-ethyl-5-(4-fluorophenyl)-2-methyl-4-oxopyridine-3-carboxamide |
| 83 | 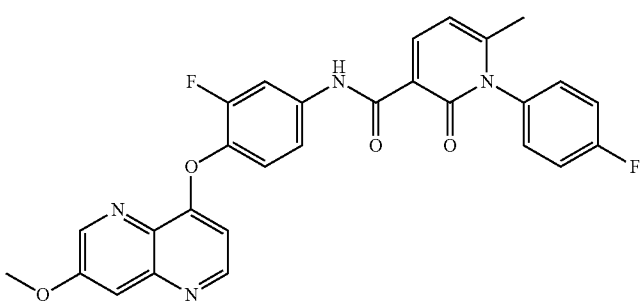 | N-[3-fluoro-4-[(7-methoxy-1,5-naphthyridin-4-yl)oxy]phenyl]-1-(4-fluorophenyl)-6-methyl-2-oxopyridine-3-carboxamide |
| 84 | 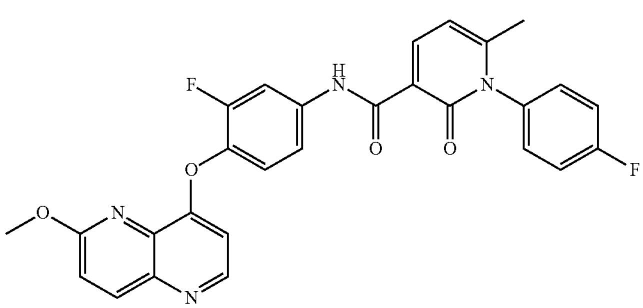 [SMILES: COc1ccc2nccc(Oc3ccc(NC(=O)c4ccc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-6-methyl-2-oxopyridine-3-carboxamide |

TABLE 1-continued

| Cpd # | Structure | IUPAC Name |
|---|---|---|
| 85 | 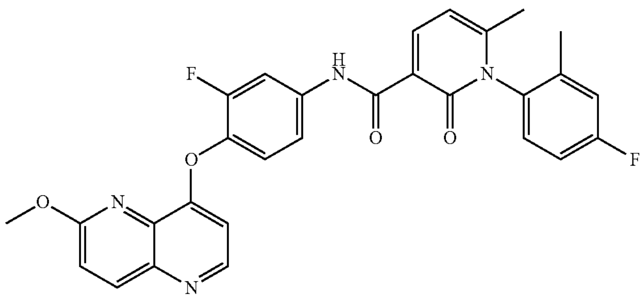 [SMILES: COc1ccc2nccc(Oc3ccc(NC(=O)c4ccc(C)n(-c5ccc(F)cc5C)c4=O)cc3F)c2n1] | N-[3-fluoro-4-[(6-methoxy-1,5-naphthyridin-4-yl)oxy]phenyl]-1-(4-fluoro-2-methylphenyl)-6-methyl-2-oxopyridine-3-carboxamide |
| 86 | 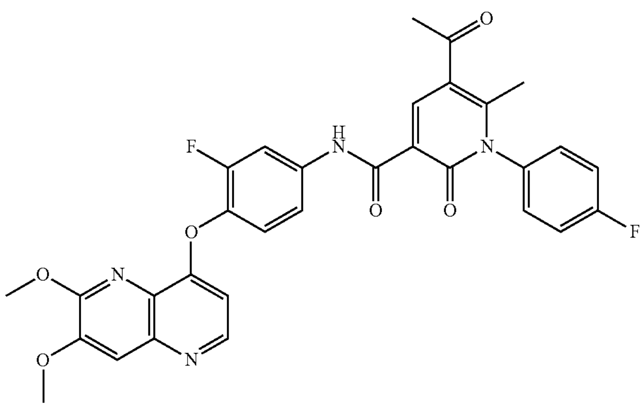 [SMILES: COc1cc2nccc(Oc3ccc(NC(=O)c4cc(C(C)=O)c(C)n(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 87 | 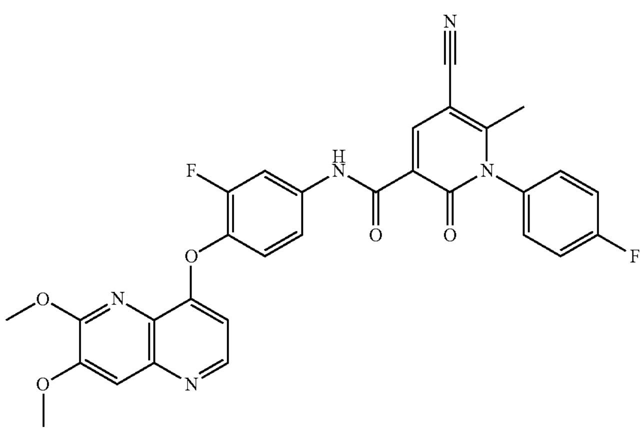 [SMILES: COc1cc2nccc(Oc3ccc(NC(=O)c4cc(C#N)c(C)n(-c5ccc(F)cc5)c4=O)cc3F)c2nc1OC] | 5-cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 88 | 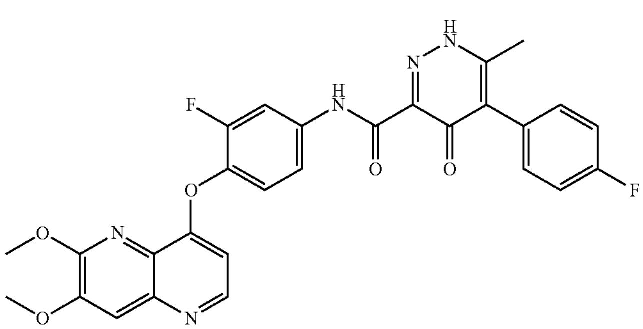 [SMILES: COc1cc2nccc(Oc3ccc(NC(=O)c4n[nH]c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-4-oxo-1H-pyridazine-3-carboxamide |

TABLE 1-continued

| Cpd # | Structure | IUPAC Name |
|---|---|---|
| 89 | 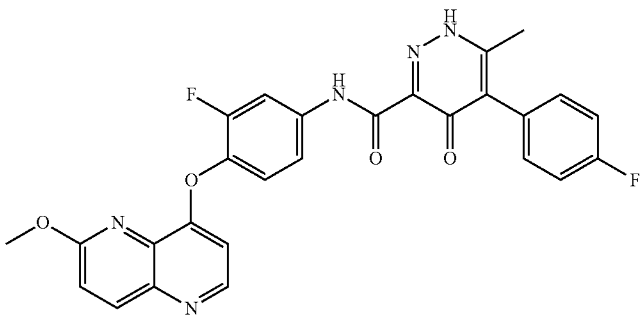 [SMILES: COc1ccc2nccc(Oc3ccc(NC(=O)c4n[nH]c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-6-methyl-4-oxo-1H-pyridazine-3-carboxamide |
| 90 | 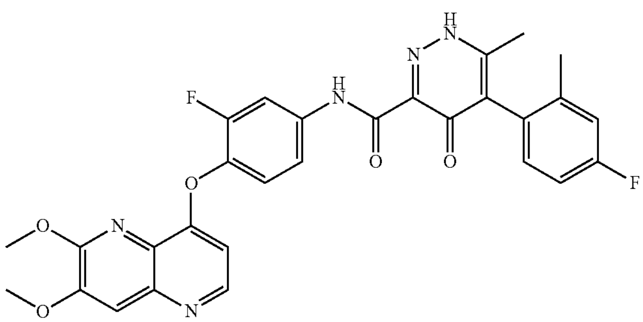 [SMILES: COc1cc2nccc(Oc3ccc(NC(=O)c4n[nH]c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-6-methyl-4-oxo-1H-pyridazine-3-carboxamide |
| 91 | 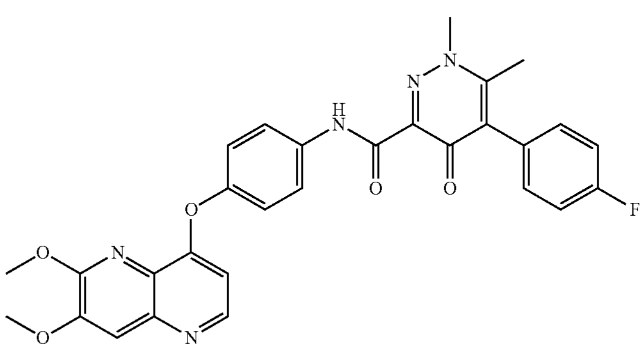 [SMILES: COc1cc2nccc(Oc3ccc(NC(=O)c4nn(C)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,6-dimethyl-4-oxopyridazine-3-carboxamide |
| 92 | 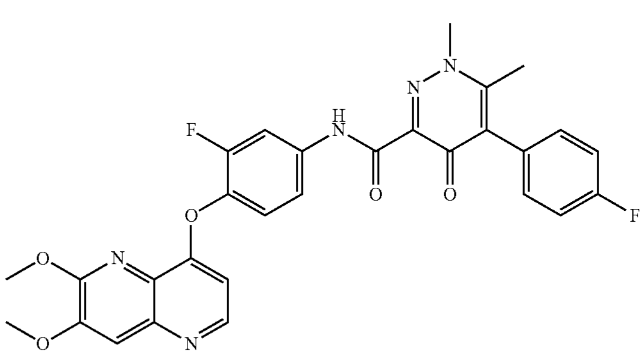 [SMILES: COc1cc2nccc(Oc3ccc(NC(=O)c4nn(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,6-dimethyl-4-oxopyridazine-3-carboxamide |

TABLE 1-continued

| Cpd # | Structure | IUPAC Name |
|---|---|---|
| 93 | 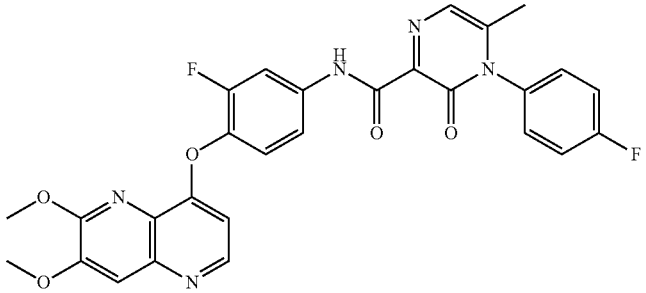 [SMILES: COc1cc2nccc(Oc3ccc(NC(=O)c4ncc(C)n(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-5-methyl-3-oxopyrazine-2-carboxamide |
| 94 | 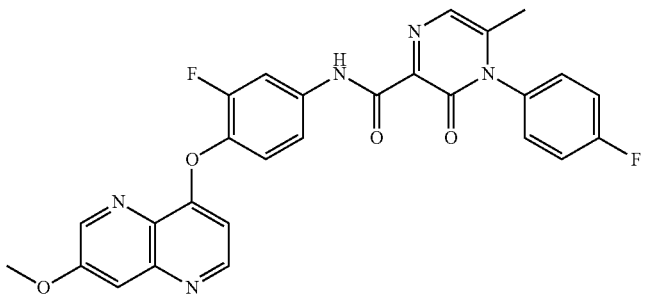 [SMILES: COc1cnc2c(Oc3ccc(NC(=O)c4ncc(C)n(-c5ccc(F)cc5)c4=O)cc3F)ccnc2c1] | N-[3-fluoro-4-[(7-methoxy-1,5-naphthyridin-4-yl)oxy]phenyl]-4-(4-fluorophenyl)-5-methyl-3-oxopyrazine-2-carboxamide |
| 95 | 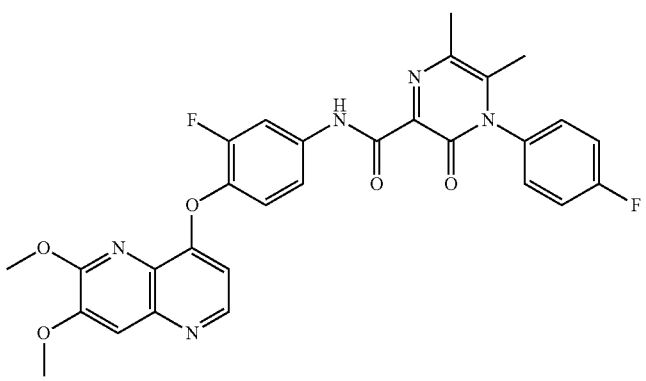 [SMILES: COc1cc2nccc(Oc3ccc(NC(=O)c4nc(C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-5,6-dimethyl-3-oxopyrazine-2-carboxamide |
| 96 | 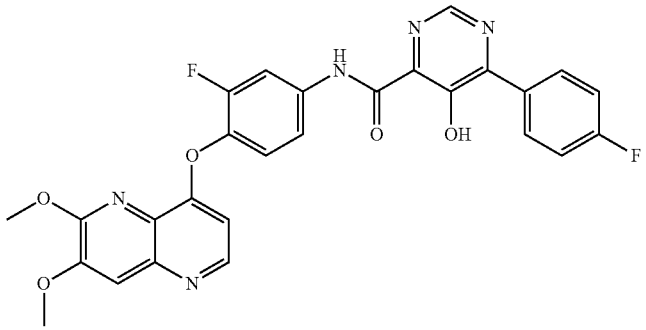 [SMILES: COc1cc2nccc(Oc3ccc(NC(=O)c4ncnc(-c5ccc(F)cc5)c4O)cc3F)c2nc1OC] | N-[4-[(6,7-dimethoxy-1,5-naphthyridin-4-yl)oxy]-3-fluorophenyl]-6-(4-fluorophenyl)-5-hydroxypyrimidine-4-carboxamide |

TABLE 1-continued

| Cpd # | Structure | IUPAC Name |
|---|---|---|
| 97 | 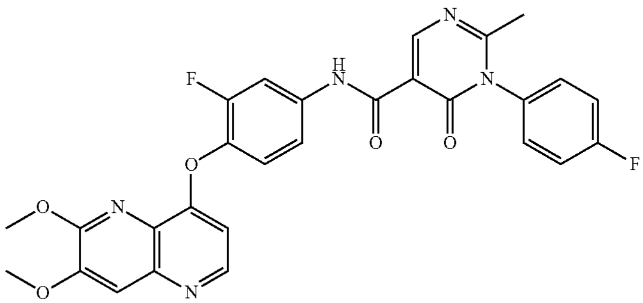 [SMILES: COc1cc2nccc(Oc3ccc(NC(=O)c4cnc(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-2-methyl-6-oxopyrimidine-5-carboxamide |
| 98 | 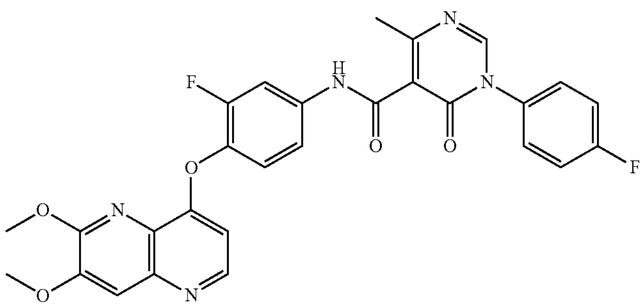 [SMILES: COc1cc2nccc(Oc3ccc(NC(=O)c4c(C)ncn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4-methyl-6-oxopyrimidine-5-carboxamide |
| 99 | 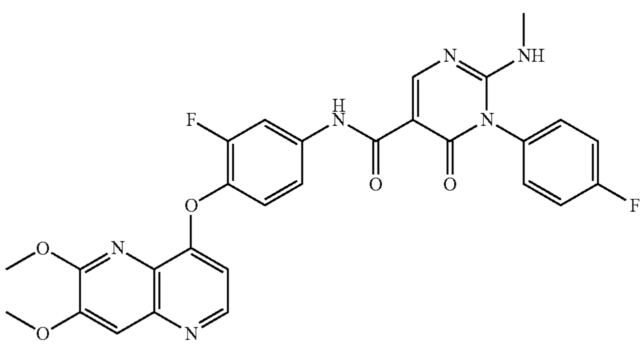 [SMILES: CNc1ncc(C(=O)Nc2ccc(Oc3ccnc4cc(OC)c(OC)nc34)c(F)c2)c(=O)n1-c1ccc(F)cc1] | N-[4-[(6,7-dimethoxy-1,5-naphthyridin-4-yl)oxy]-3-fluorophenyl]-1-(4-fluorophenyl)-2-(methylamino)-6-oxopyrimidine-5-carboxamide |
| 100 | 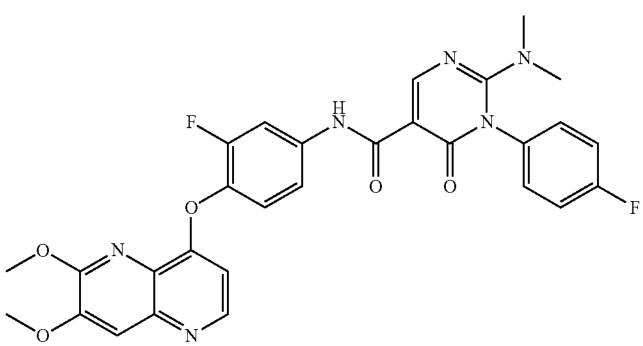 [SMILES: COc1cc2nccc(Oc3ccc(NC(=O)c4cnc(N(C)C)n(-c5ccc(F)cc5)c4=O)cc3F)c2nc1OC] | N-[4-[(6,7-dimethoxy-1,5-naphthyridin-4-yl)oxy]-3-fluorophenyl]-2-(dimethylamino)-1-(4-fluorophenyl)-6-oxopyrimidine-5-carboxamide |
| 101 | 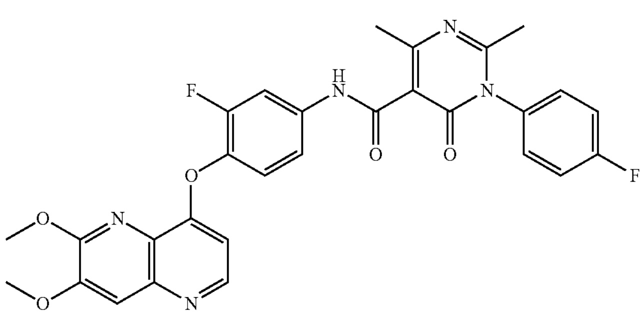 [SMILES: COc1cc2nccc(Oc3ccc(NC(=O)c4c(C)nc(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-2,4-dimethyl-6-oxopyrimidine-5-carboxamide |

TABLE 1-continued

| Cpd # | Structure | IUPAC Name |
|---|---|---|
| 102 | 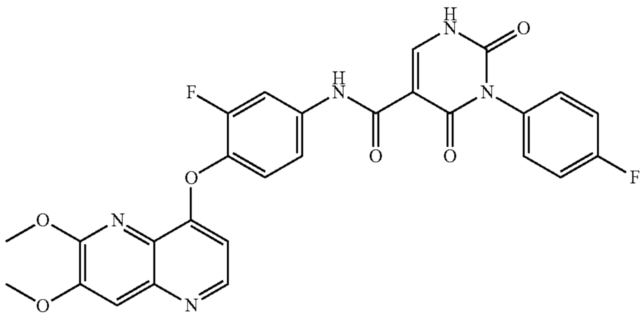 [SMILES: COc1cc2nccc(Oc3ccc(NC(=O)c4c[nH]c(=O)n(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-2,4-dioxo-1H-pyrimidine-5-carboxamide |
| 103 | 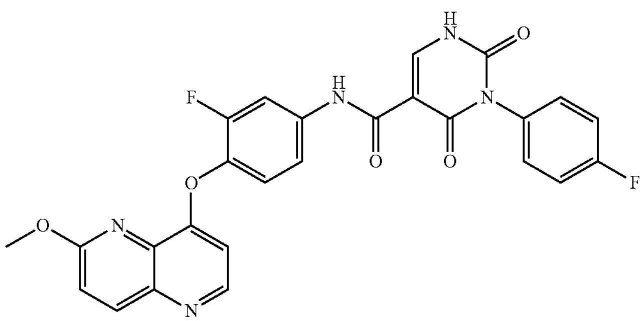 [SMILES: COc1ccc2nccc(Oc3ccc(NC(=O)c4c[nH]c(=O)n(-c5ccc(F)cc5)c4=O)cc3F)c2n1] | N-[3-fluoro-4-[(6-methoxy-1,5-naphthyridin-4-yl)oxy]phenyl]-3-(4-fluorophenyl)-2,4-dioxo-1H-pyrimidine-5-carboxamide |
| 104 | 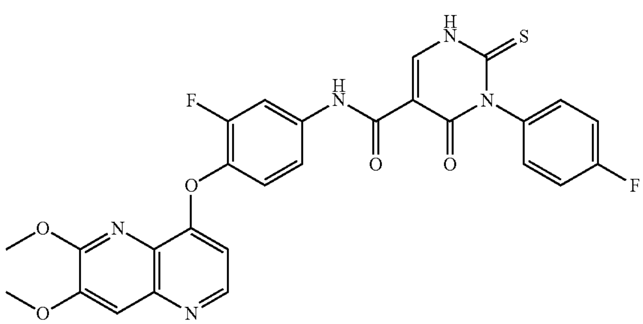 [SMILES: COc1cc2nccc(Oc3ccc(NC(=O)c4c[nH]c(=S)n(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-4-oxo-2-sulfanylidene-1H-pyrimidine-5-carboxamide |
| 105 | 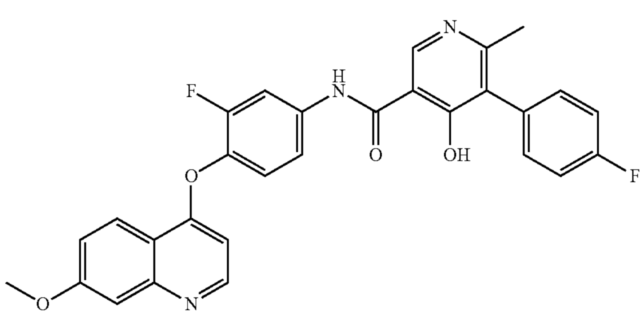 [SMILES: COc1ccc2c(Oc3ccc(NC(=O)c4cnc(C)c(-c5ccc(F)cc5)c4O)cc3F)ccnc2c1] | N-[3-fluoro-4-(7-methoxyquinolin-4-yl)oxyphenyl]-5-(4-fluorophenyl)-4-hydroxy-6-methylpyridine-3-carboxamide |

TABLE 1-continued

| Cpd # | Structure | IUPAC Name |
|---|---|---|
| 106 | 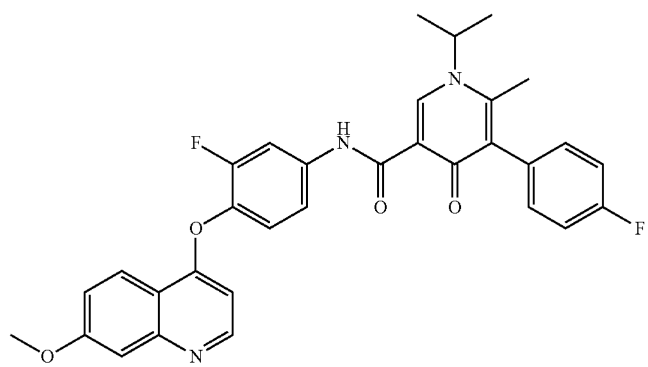 [SMILES: COc1ccc2c(Oc3ccc(NC(=O)c4cn(C(C)C)c(C)c(-c5ccc(F)cc5)c4=O)cc3F)ccnc2c1] | N-[3-fluoro-4-(7-methoxyquinolin-4-yl)oxyphenyl]-5-(4-fluorophenyl)-6-methyl-4-oxo-1-propan-2-ylpyridine-3-carboxamide |
| 107 | 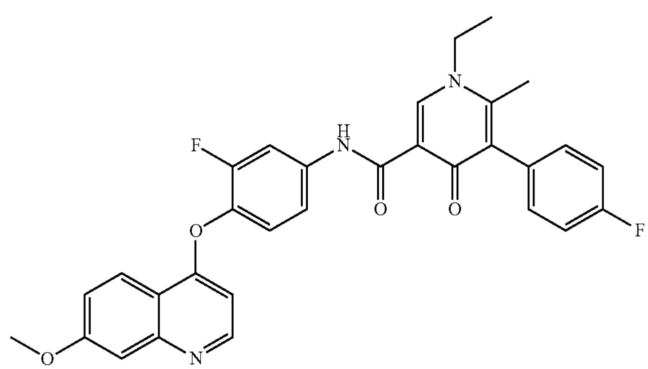 [SMILES: CCn1cc(C(=O)Nc2ccc(Oc3ccnc4cc(OC)ccc34)c(F)c2)c(=O)c(-c2ccc(F)cc2)c1C] | 1-ethyl-N-[3-fluoro-4-(7-methoxyquinolin-4-yl)oxyphenyl]-5-(4-fluorophenyl)-6-methyl-4-oxopyridine-3-carboxamide |
| 108 | 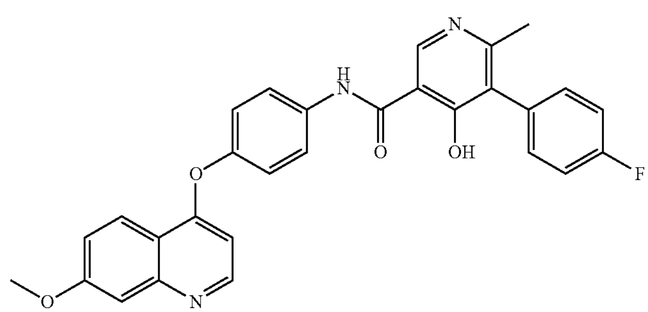 [SMILES: COc1ccc2c(Oc3ccc(NC(=O)c4cnc(C)c(-c5ccc(F)cc5)c4O)cc3)ccnc2c1] | 5-(4-fluorophenyl)-4-hydroxy-N-[4-(7-methoxyquinolin-4-yl)oxyphenyl]-6-methylpyridine-3-carboxamide |
| 109 | 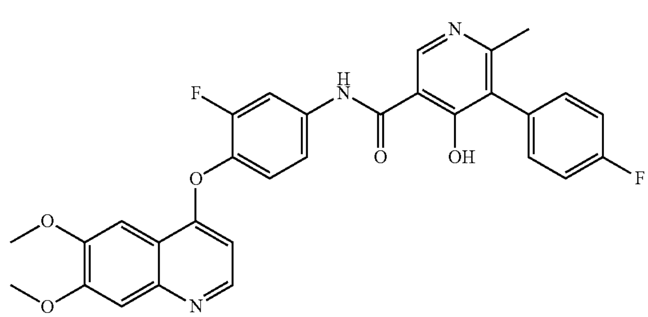 [SMILES: COc1cc2nccc(Oc3ccc(NC(=O)c4cnc(C)c(-c5ccc(F)cc5)c4O)cc3F)c2cc1OC] | N-[4-(6,7-dimethoxyquinolin-4-yl)oxy-3-fluorophenyl]-5-(4-fluorophenyl)-4-hydroxy-6-methylpyridine-3-carboxamide |

TABLE 1-continued

| Cpd # | Structure | IUPAC Name |
|---|---|---|
| 110 | 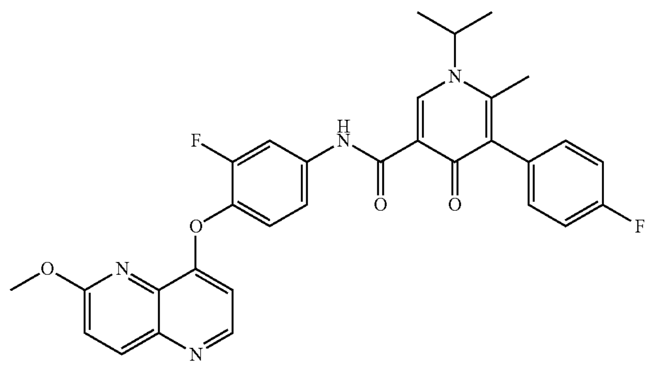 [SMILES: COc1ccc2nccc(Oc3ccc(NC(=O)c4cn(C(C)C)c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-6-methyl-4-oxo-1-propan-2-ylpyridine-3-carboxamide |
| 111 | 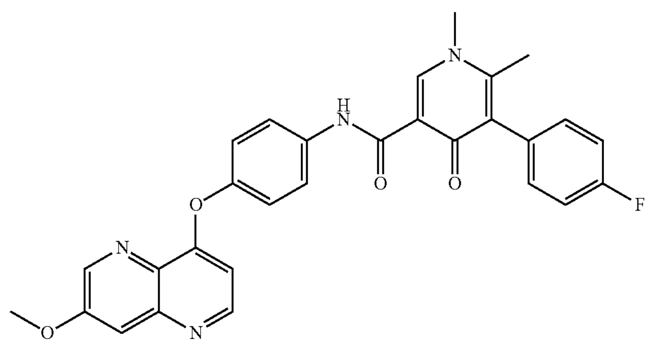 [SMILES: COc1cnc2c(Oc3ccc(NC(=O)c4cn(C)c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-1,6-dimethyl-4-oxopyridine-3-carboxamide |
| 112 | 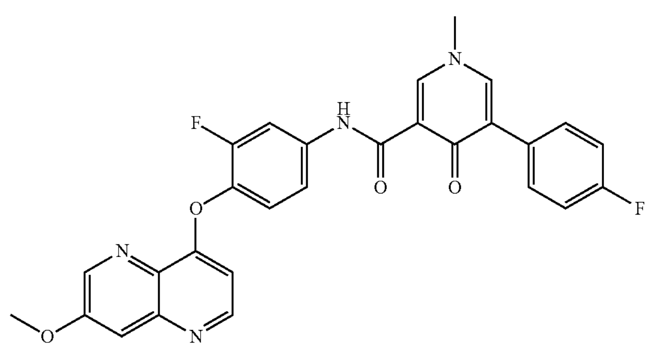 [SMILES: COc1cnc2c(Oc3ccc(NC(=O)c4cn(C)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-methyl-4-oxopyridine-3-carboxamide |
| 113 | 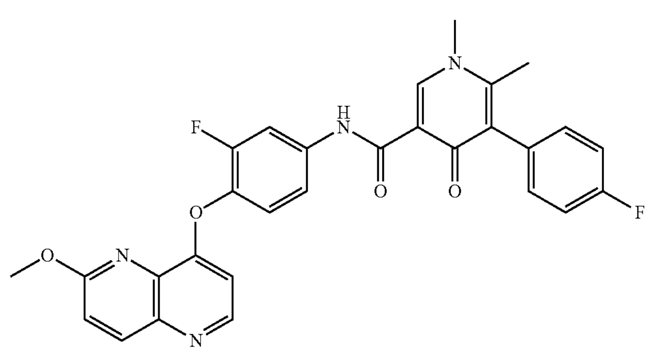 [SMILES: COc1ccc2nccc(Oc3ccc(NC(=O)c4cn(C)c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-1,6-dimethyl-4-oxopyridine-3-carboxamide |

TABLE 1-continued

| Cpd # | Structure | IUPAC Name |
|---|---|---|
| 114 | 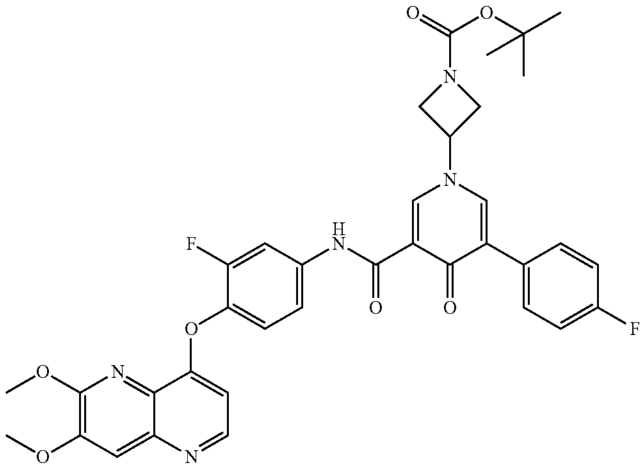 [SMILES: COc1cc2nccc(Oc3ccc(NC(=O)c4cn(C5CN(C(=O)OC(C)(C)C)C5)cc(-c5ccc(F)cc5)c4=O)cc3F)c2nc1OC] | tert-butyl 3-[3-[[4-[(6,7-dimethoxy-1,5-naphthyridin-4-yl)oxy]-3-fluorophenyl]carbamoyl]-5-(4-fluorophenyl)-4-oxopyridin-1-yl]azetidine-1-carboxylate |
| 115 | 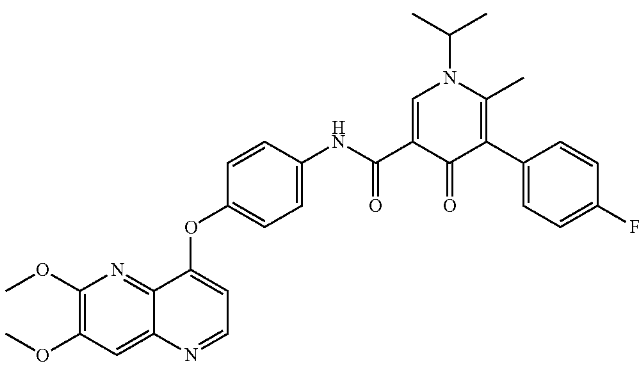 [SMILES: COc1cc2nccc(Oc3ccc(NC(=O)c4cn(C(C)C)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-methyl-4-oxo-1-propan-2-ylpyridine-3-carboxamide |
| 116 | 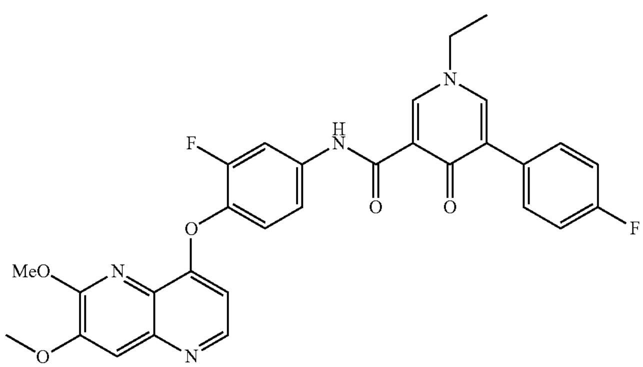 | N-[4-[(6,7-dimethoxy-1,5-naphthyridin-4-yl)oxy]-3-fluorophenyl]-1-ethyl-5-(4-fluorophenyl)-4-oxopyridine-3-carboxamide |
| 117 | 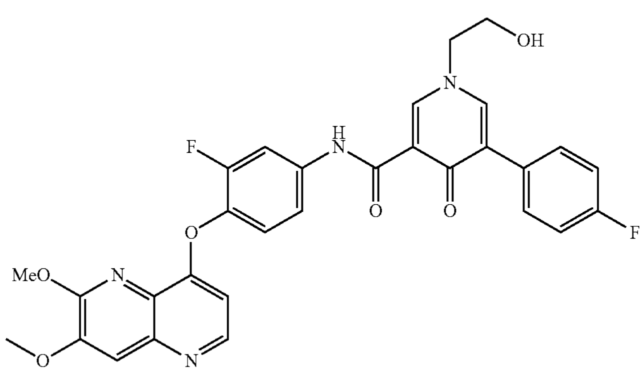 [SMILES: COc1cc2nccc(Oc3ccc(NC(=O)c4cn(CCO)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-hydroxyethyl)-4-oxopyridine-3-carboxamide |

TABLE 1-continued

| Cpd # | Structure | IUPAC Name |
|---|---|---|
| 118 | 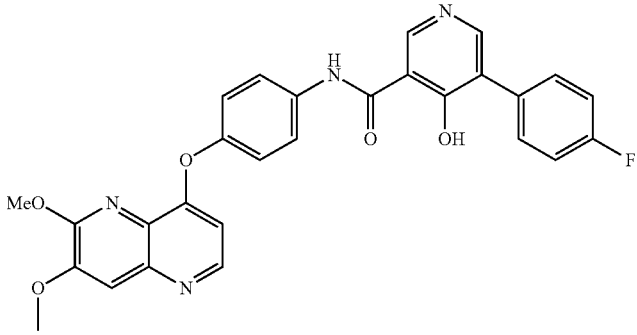 [SMILES: COc1cc2nccc(Oc3ccc(NC(=O)c4cncc(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxypyridine-3-carboxamide |
| 119 | 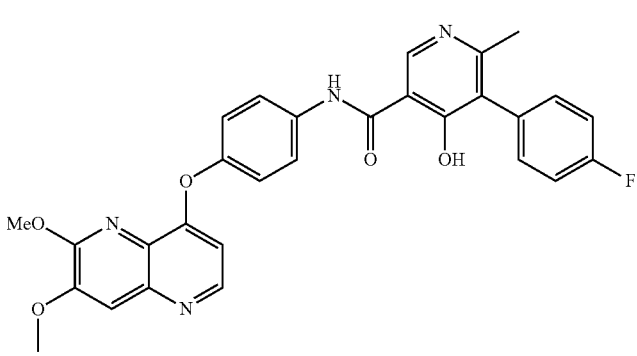 [SMILES: COc1cc2nccc(Oc3ccc(NC(=O)c4cnc(C)c(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxy-6-methylpyridine-3-carboxamide |
| 120 | 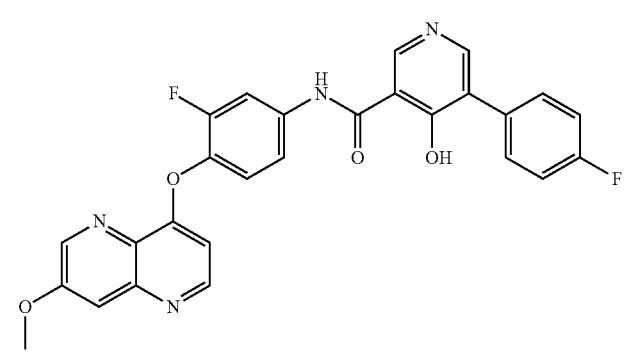 [SMILES: COc1cnc2c(Oc3ccc(NC(=O)c4cncc(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxypyridine-3-carboxamide |
| 121 | 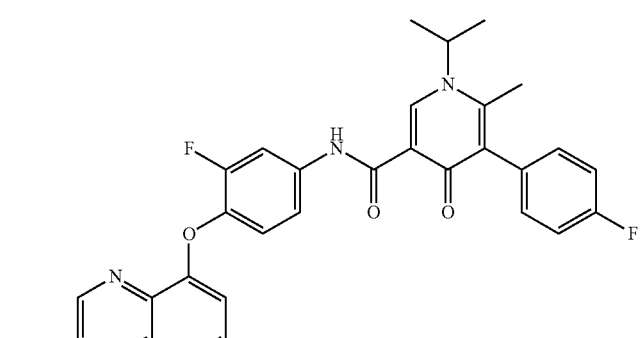 | N-[3-fluoro-4-[(7-methoxy-1,5-naphthyridin-4-yl)oxy]phenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 122 | 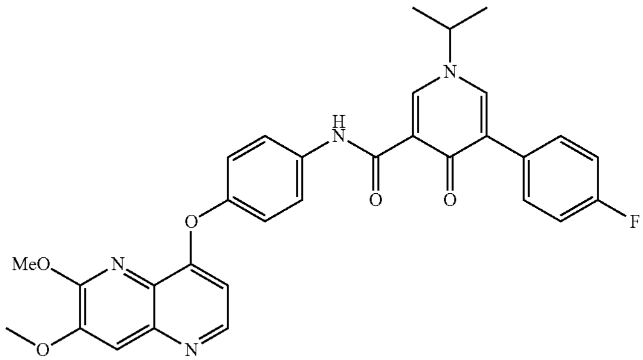 [SMILES: COc1cc2nccc(Oc3ccc(NC(=O)c4cn(C(C)C)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-4-oxo-1-propan-2-ylpyridine-3-carboxamide |
| 123 | 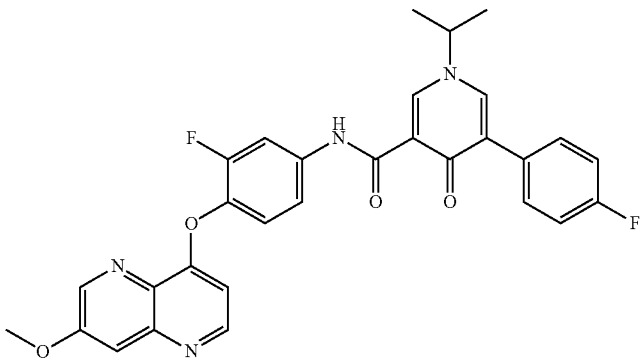 [SMILES: COc1cnc2c(Oc3ccc(NC(=O)c4cn(C(C)C)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-4-oxo-1-propan-2-ylpyridine-3-carboxamide |
| 124 | 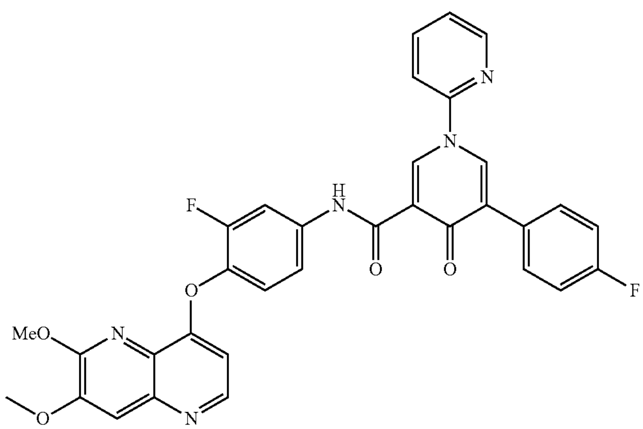 [SMILES: COc1cc2nccc(Oc3ccc(NC(=O)c4cn(-c5ccccn5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-pyridin-2-ylpyridine-3-carboxamide |
| 125 | 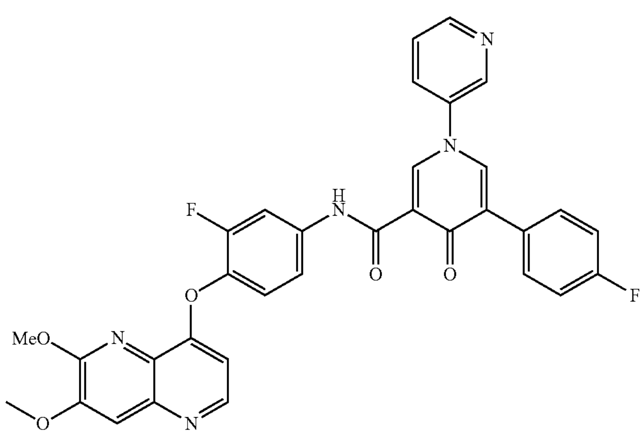 [SMILES: COc1cc2nccc(Oc3ccc(NC(=O)c4cn(-c5cccnc5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-pyridin-3-ylpyridine-3-carboxamide |

TABLE 1-continued

| Cpd # | Structure | IUPAC Name |
|---|---|---|
| 126 | 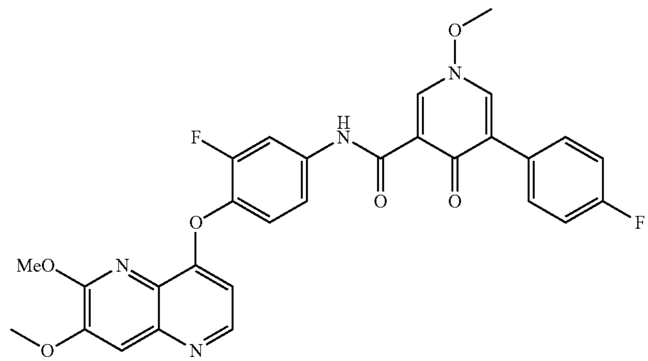 [SMILES: COc1cc2nccc(Oc3ccc(NC(=O)c4cn(OC)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-methoxy-4-oxopyridine-3-carboxamide |
| 127 | 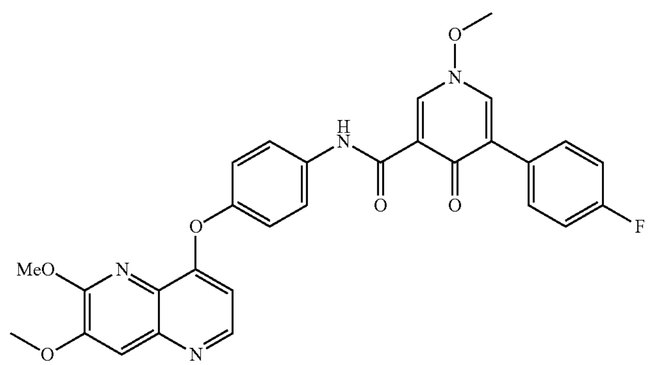 [SMILES: COc1cc2nccc(Oc3ccc(NC(=O)c4cn(OC)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1-methoxy-4-oxopyridine-3-carboxamide |
| 128 | 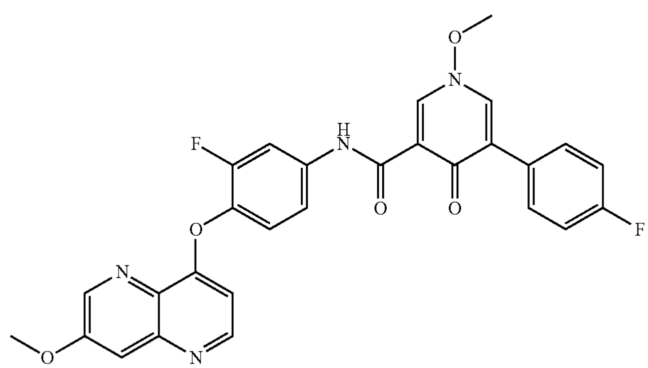 [SMILES: COc1cnc2c(Oc3ccc(NC(=O)c4cn(OC)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-methoxy-4-oxopyridine-3-carboxamide |
| 129 | 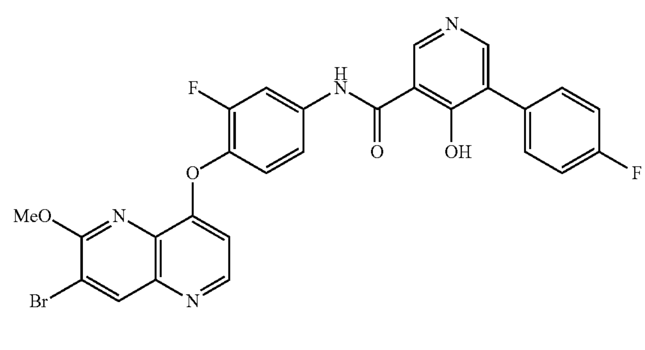 | N-[4-[(7-bromo-6-methoxy-1,5-naphthyridin-4-yl)oxy]-3-fluorophenyl]-5-(4-fluorophenyl)-4-hydroxypyridine-3-carboxamide |

TABLE 1-continued

| Cpd # | Structure | IUPAC Name |
|---|---|---|
| 130 | 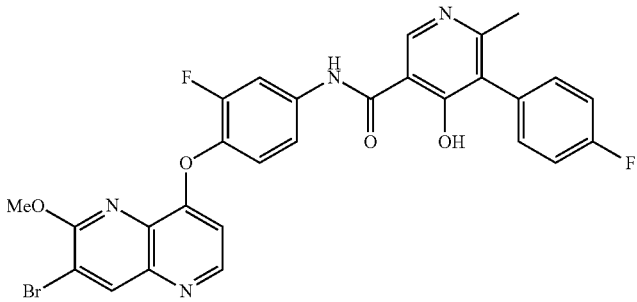 [SMILES: COc1nc2c(Oc3ccc(NC(=O)c4cnc(C)c(-c5ccc(F)cc5)c4O)cc3F)ccnc2cc1Br] | N-[4-[(7-bromo-6-methoxy-1,5-naphthyridin-4-yl)oxy]-3-fluorophenyl]-5-(4-fluorophenyl)-4-hydroxy-6-methylpyridine-3-carboxamide |
| 131 | 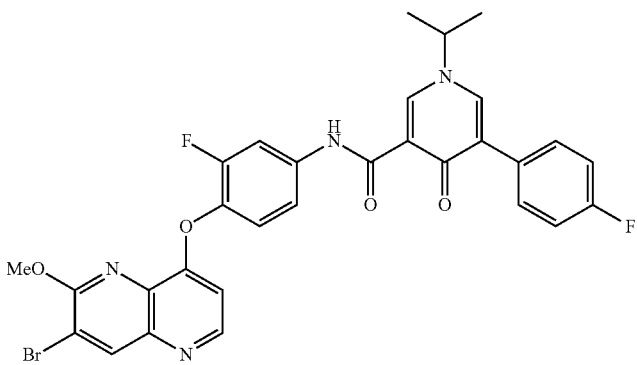 [SMILES: COc1nc2c(Oc3ccc(NC(=O)c4cn(C(C)C)cc(-c5ccc(F)cc5)c4=O)cc3F)ccnc2cc1Br] | N-[4-[(7-bromo-6-methoxy-1,5-naphthyridin-4-yl)oxy]-3-fluorophenyl]-5-(4-fluorophenyl)-4-oxo-1-propan-2-ylpyridine-3-carboxamide |
| 132 | 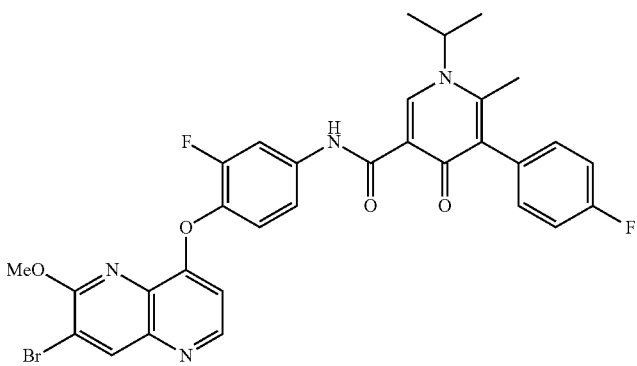 [SMILES: COc1nc2c(Oc3ccc(NC(=O)c4cn(C(C)C)c(C)c(-c5ccc(F)cc5)c4=O)cc3F)ccnc2cc1Br] | N-[4-[(7-bromo-6-methoxy-1,5-naphthyridin-4-yl)oxy]-3-fluorophenyl]-5-(4-fluorophenyl)-6-methyl-4-oxo-1-propan-2-ylpyridine-3-carboxamide |
| 133 | 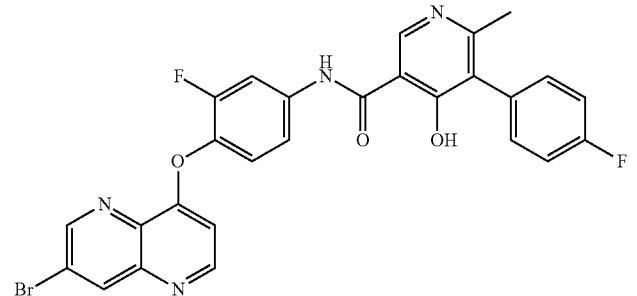 | N-[4-[(7-bromo-1,5-naphthyridin-4-yl)oxy]-3-fluorophenyl]-5-(4-fluorophenyl)-4-hydroxy-6-methylpyridine-3-carboxamide |

TABLE 1-continued

| Cpd # | Structure | IUPAC Name |
|---|---|---|
| 134 | 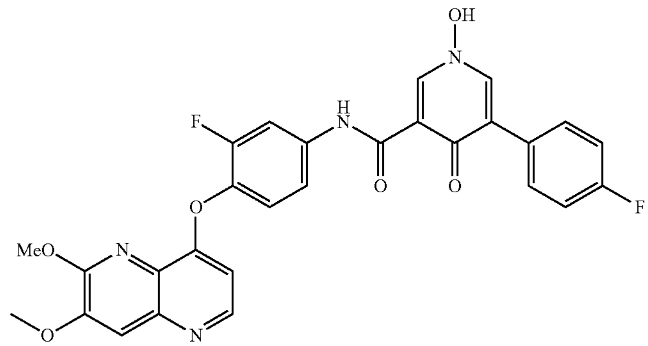 [SMILES: COc1cc2nccc(Oc3ccc(NC(=O)c4cn(O)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-hydroxy-4-oxopyridine-3-carboxamide |
| 135 | 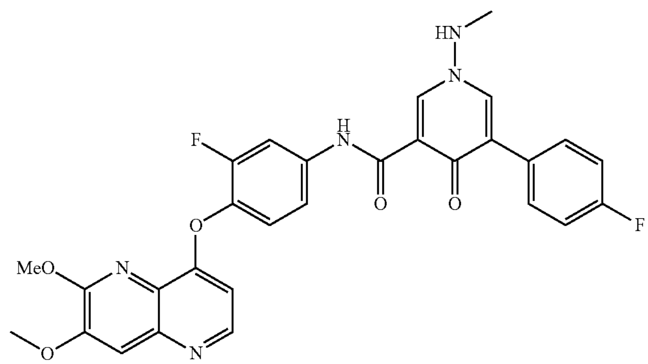 | N-[4-[(6,7-dimethoxy-1,5-naphthyridin-4-yl)oxy]-3-fluorophenyl]-5-(4-fluorophenyl)-1-(methylamino)-4-oxopyridine-3-carboxamide |
| 136 | 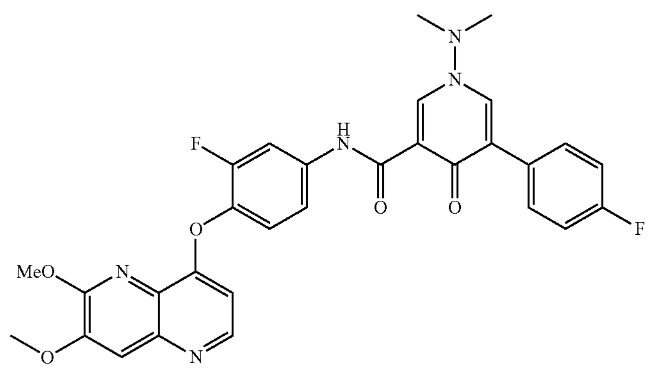 [SMILES: COc1cc2nccc(Oc3ccc(NC(=O)c4cn(N(C)C)cc(-c5ccc(F)cc5)c4=O)cc3F)c2nc1OC] | N-[4-[(6,7-dimethoxy-1,5-naphthyridin-4-yl)oxy]-3-fluorophenyl]-1-(dimethylamino)-5-(4-fluorophenyl)-4-oxopyridine-3-carboxamide |
| 137 | 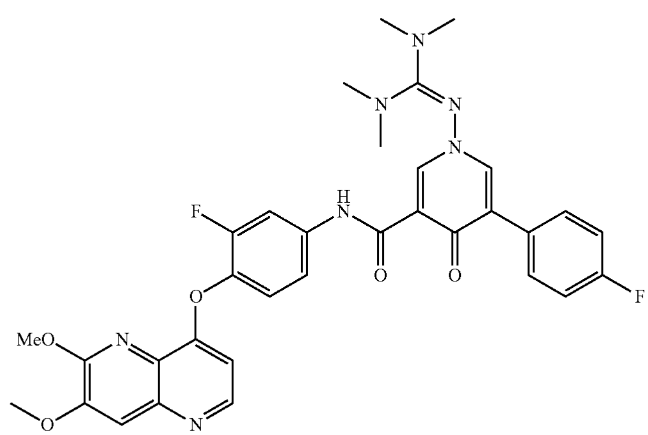 [SMILES: COc1cc2nccc(Oc3ccc(NC(=O)c4cn(N=C(N(C)C)N(C)C)cc(-c5ccc(F)cc5)c4=O)cc3F)c2nc1OC] | 1-[bis(dimethylamino)methylideneamino]-N-[4-[(6,7-dimethoxy-1,5-naphthyridin-4-yl)oxy]-3-fluorophenyl]-5-(4-fluorophenyl)-4-oxopyridine-3-carboxamide |

TABLE 1-continued

| Cpd # | Structure | IUPAC Name |
|---|---|---|
| 138 | 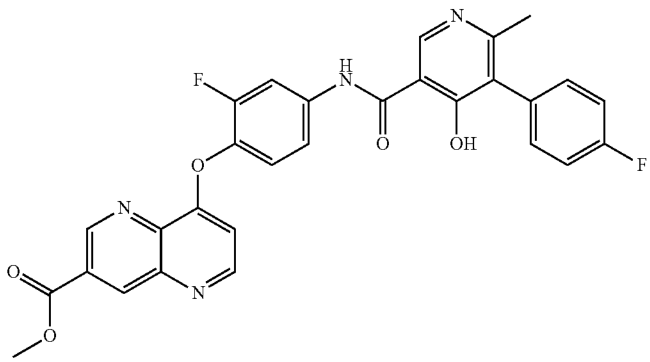 [SMILES: COC(=O)c1cnc2c(Oc3ccc(NC(=O)c4cnc(C)c(-c5ccc(F)cc5)c4O)cc3F)ccnc2c1] | methyl 8-[2-fluoro-4-[[5-(4-fluorophenyl)-4-hydroxy-6-methylpyridine-3-carbonyl]amino]phenoxy]-1,5-naphthyridine-3-carboxylate |
| 139 | 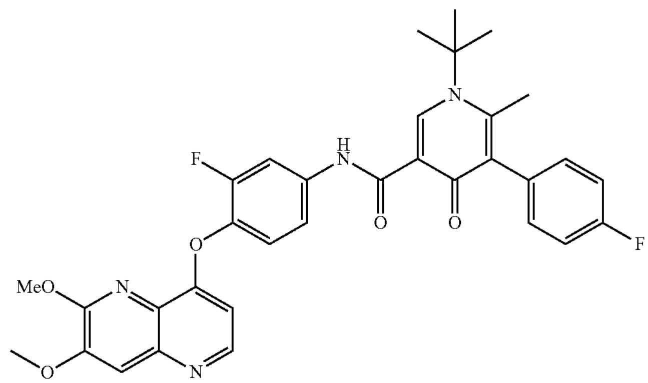 | 1-tert-butyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 140 | 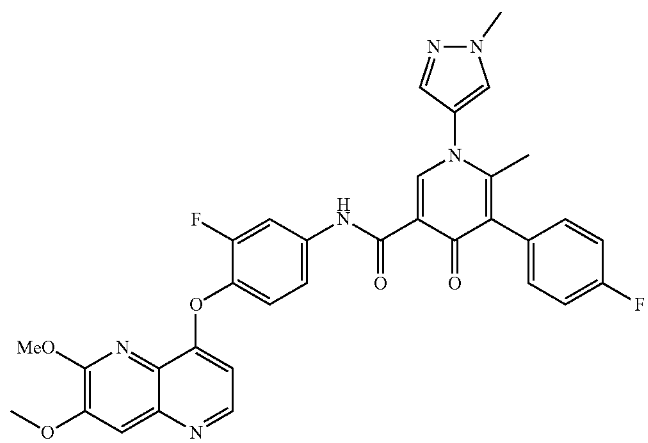 [SMILES: COc1cc2nccc(Oc3ccc(NC(=O)c4cn(-c5cnn(C)c5)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-1-(1-methylpyrazol-4-yl)-4-oxopyridine-3-carboxamide |
| 141 | 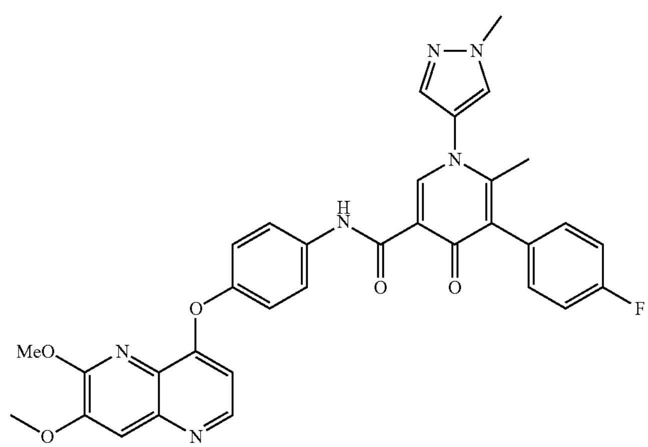 [SMILES: COc1cc2nccc(Oc3ccc(NC(=O)c4cn(-c5cnn(C)c5)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-methyl-1-(1-methylpyrazol-4-yl)-4-oxopyridine-3-carboxamide |

TABLE 1-continued

| Cpd # | Structure | IUPAC Name |
|---|---|---|
| 142 | 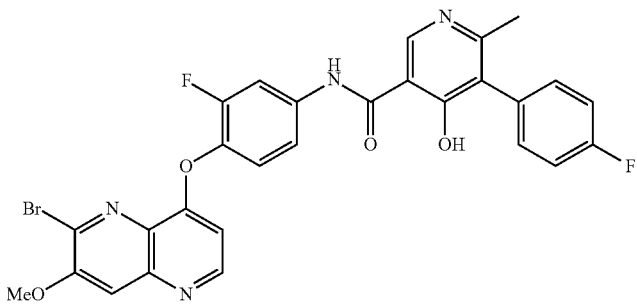 [SMILES: COc1cc2nccc(Oc3ccc(NC(=O)c4cnc(C)c(-c5ccc(F)cc5)c4O)cc3F)c2nc1Br] | N-[4-[(6-bromo-7-methoxy-1,5-naphthyridin-4-yl)oxy]-3-fluorophenyl]-5-(4-fluorophenyl)-4-hydroxy-6-methylpyridine-3-carboxamide |
| 143 | 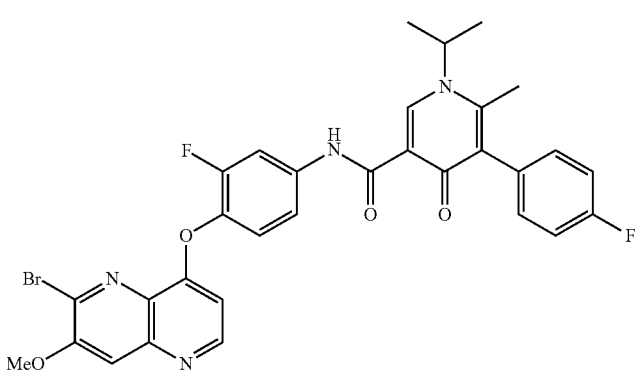 | N-[4-[(6-bromo-7-methoxy-1,5-naphthyridin-4-yl)oxy]-3-fluorophenyl]-5-(4-fluorophenyl)-6-methyl-4-oxo-1-propan-2-ylpyridine-3-carboxamide |
| 144 | 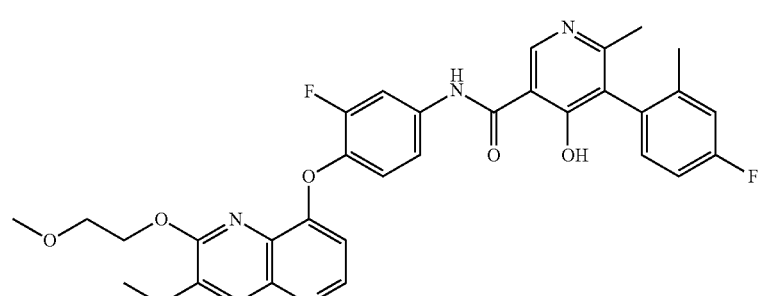 | N-[3-fluoro-4-[[7-methoxy-6-(2-methoxyethoxy)-1,5-naphthyridin-4-yl]oxy]phenyl]-5-(4-fluoro-2-methylphenyl)-4-hydroxy-6-methylpyridine-3-carboxamide |
| 145 | 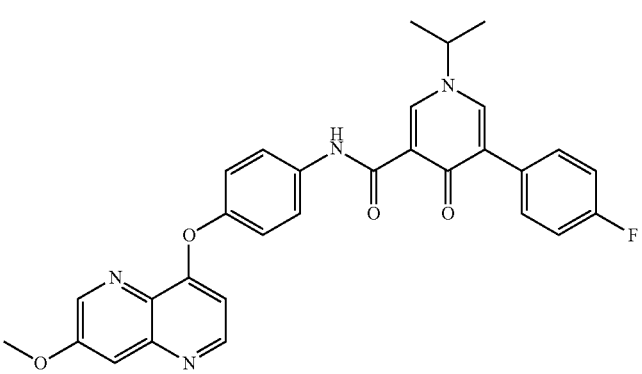 [SMILES: COc1cnc2c(Oc3ccc(NC(=O)c4cn(C(C)C)cc(-c5ccc(F)cc5)c4=O)cc3)ccnc2c1] | 5-(4-fluorophenyl)-N-[4-[(7-methoxy-1,5-naphthyridin-4-yl)oxy]phenyl]-4-oxo-1-propan-2-ylpyridine-3-carboxamide |

TABLE 1-continued

| Cpd # | Structure | IUPAC Name |
|---|---|---|
| 146 | 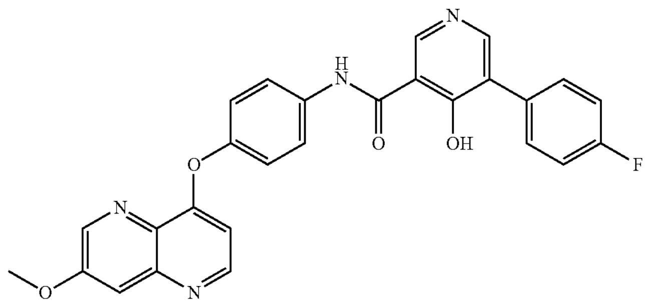 [SMILES: COc1cnc2c(Oc3ccc(NC(=O)c4cncc(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]pyridine-3-carboxamide |
| 147 | 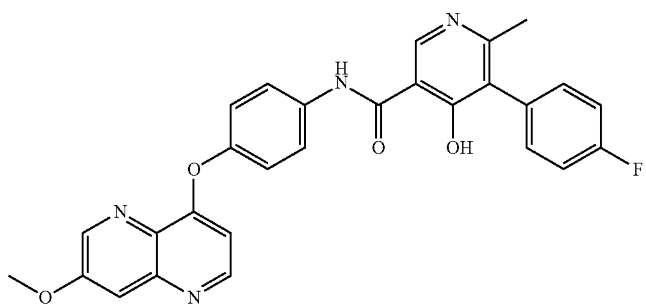 [SMILES: COc1cnc2c(Oc3ccc(NC(=O)c4cnc(C)c(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-6-methylpyridine-3-carboxamide |
| 148 | 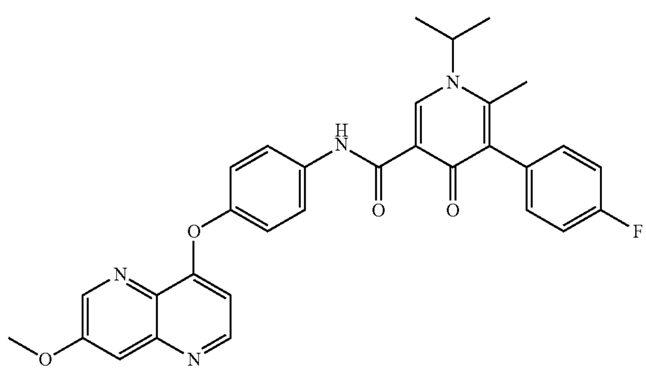 [SMILES: COc1cnc2c(Oc3ccc(NC(=O)c4cn(C(C)C)c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-6-methyl-4-oxo-1-propan-2-ylpyridine-3-carboxamide |
| 149 | 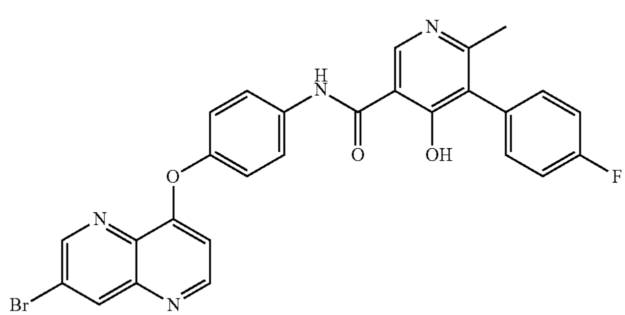 [SMILES: Cc1ncc(C(=O)Nc2ccc(Oc3ccnc4cc(Br)cnc34)cc2)c(O)c1-c1ccc(F)cc1] | N-[4-[(7-bromo-1,5-naphthyridin-4-yl)oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 150 | 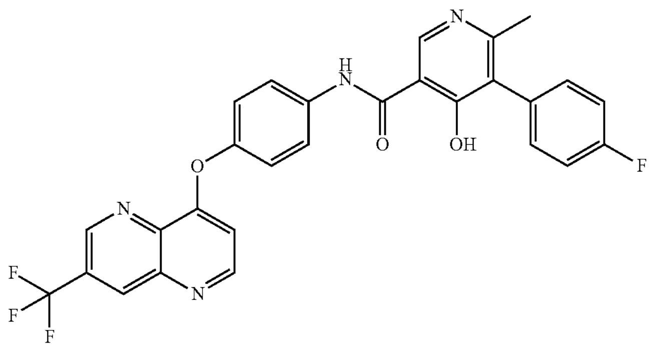 [SMILES: Cc1ncc(C(=O)Nc2ccc(Oc3ccnc4cc(C(F)(F)F)cnc34)cc2)c(O)c1-c1ccc(F)cc1] | 5-(4-fluorophenyl)-4-hydroxy-6-methyl-N-4-[[7-(trifluoromethyl)-1,5-naphthyridin-4-yl]oxy]phenyl]pyridine-3-carboxamide |
| 151 | 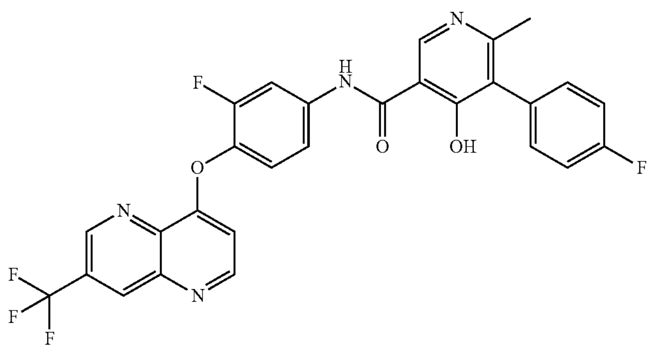 [SMILES: Cc1ncc(C(=O)Nc2ccc(Oc3ccnc4cc(C(F)(F)F)cnc34)c(F)c2)c(O)c1-c1ccc(F)cc1] | 5-(4-fluorophenyl)-N-[3-fluoro-4-[[7-(trifluoromethyl)-1,5-naphthyridin-4-yl]oxy]phenyl]-4-hydroxy-6-methylpyridine-3-carboxamide |
| 152 | 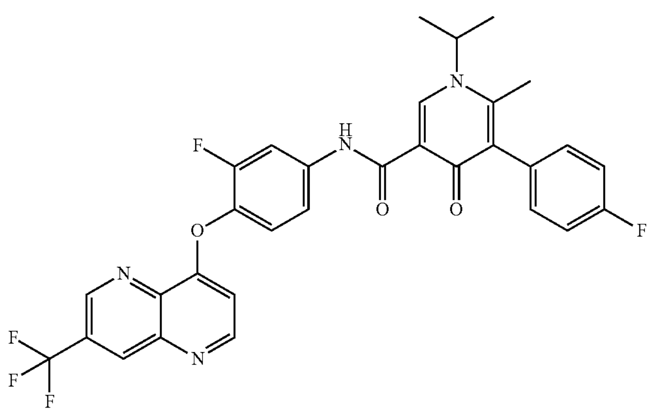 [SMILES: Cc1c(-c2ccc(F)cc2)c(=O)c(C(=O)Nc2ccc(Oc3ccnc4cc(C(F)(F)F)cnc34)c(F)c2)cn1C(C)C] | 5-(4-fluorophenyl)-N-[3-fluoro-4-[[7-(trifluoromethyl)-1,5-naphthyridin-4-yl]oxy]phenyl]-6-methyl-4-oxo-1-propan-2-ylpyridine-3-carboxamide |
| 153 | 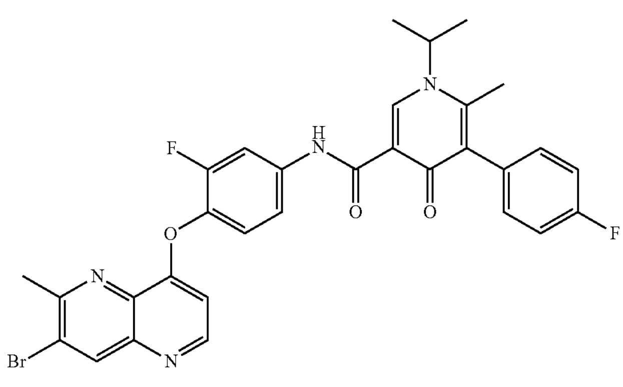 [SMILES: Cc1nc2c(Oc3ccc(NC(=O)c4cn(C(C)C)c(C)c(-c5ccc(F)cc5)c4=O)cc3F)ccnc2cc1Br] | N-[4-[(7-bromo-6-methyl-1,5-naphthyridin-4-yl)oxy]-3-fluorophenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 154 | 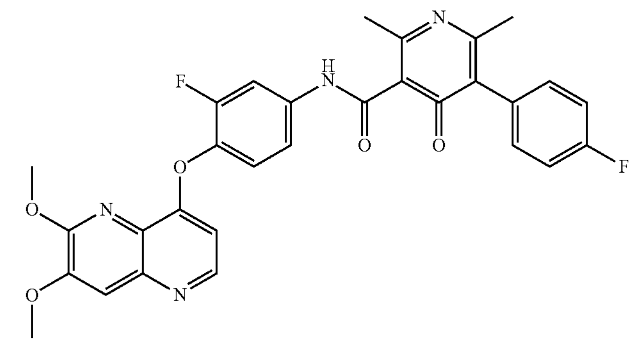 | N-[4-[(6,7-dimethoxy-1,5-naphthyridin-4-yl)oxy]-3-fluorophenyl]-5-(4-fluorophenyl)-4-hydroxy-2,6-dimethylpyridine-3-carboxamide |
| 155 | 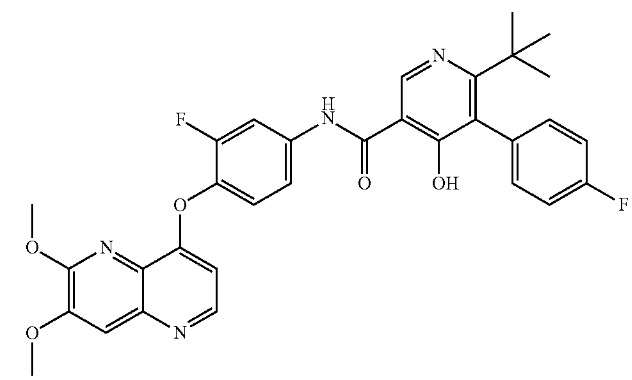 [SMILES: COc1cc2nccc(Oc3ccc(NC(=O)c4cnc(C(C)(C)C)c(-c5ccc(F)cc5)c4O)cc3F)c2nc1OC] | 6-tert-butyl-N-[4-[(6,7-dimethoxy-1,5-naphthyridin-4-yl)oxy]-3-fluorophenyl]-5-(4-fluorophenyl)-4-hydroxypyridine-3-carboxamide |
| 156 | 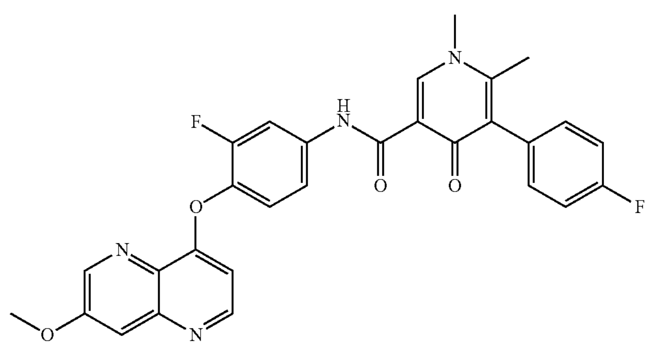 [SMILES: COc1cnc2c(Oc3ccc(NC(=O)c4cn(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,6-dimethyl-4-oxopyridine-3-carboxamide |
| 157 | 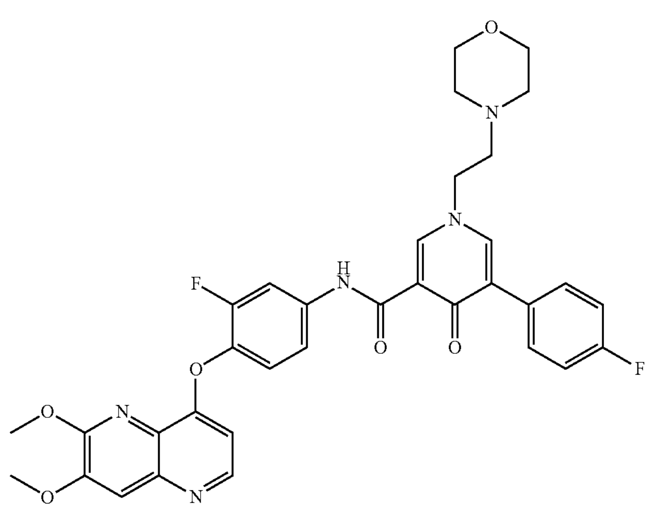 [SMILES: COc1cc2nccc(Oc3ccc(NC(=O)c4cn(CCN5CCOCC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-morpholin-4-ylethyl)-4-oxopyridine-3-carboxamide |

TABLE 1-continued

| Cpd # | Structure | IUPAC Name |
|---|---|---|
| 158 | 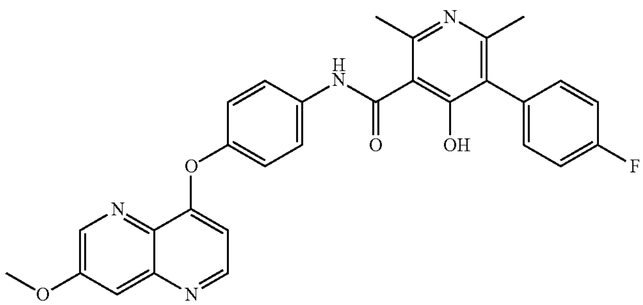 [SMILES: COc1cnc2c(Oc3ccc(NC(=O)c4c(C)nc(C)c(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-2,6-dimethylpyridine-3-carboxamide |
| 159 | 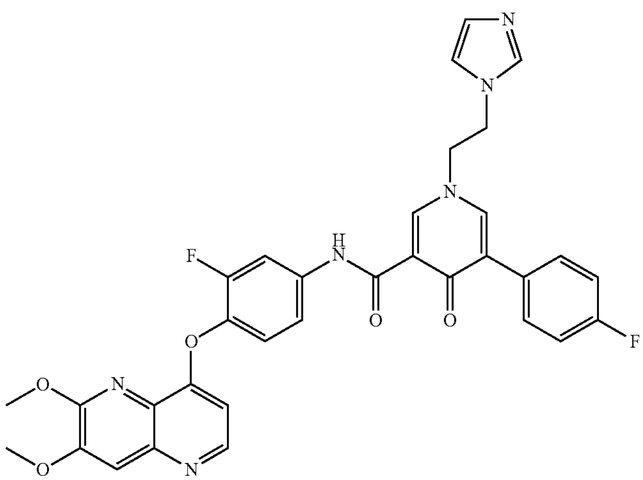 [SMILES: COc1cc2nccc(Oc3ccc(NC(=O)c4cn(CCn5ccnc5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-imidazol-1-ylethyl)-4-oxopyridine-3-carboxamide |
| 160 | 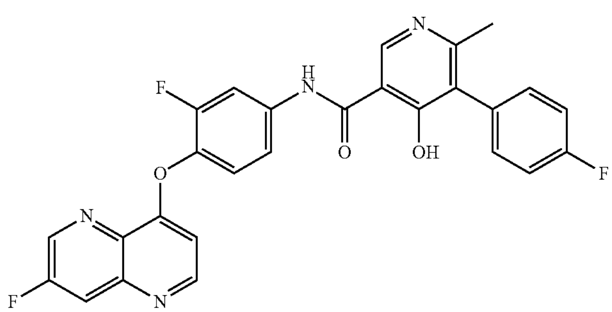 [SMILES: Cc1ncc(C(=O)Nc2ccc(Oc3ccnc4cc(F)cnc34)c(F)c2)c(O)c1-c1ccc(F)cc1] | N-[3-fluoro-4-[(7-fluoro-1,5-naphthyridin-4-yl)oxy]phenyl]-5-(4-fluorophenyl)-4-hydroxy-6-methylpyridine-3-carboxamide |
| 161 | 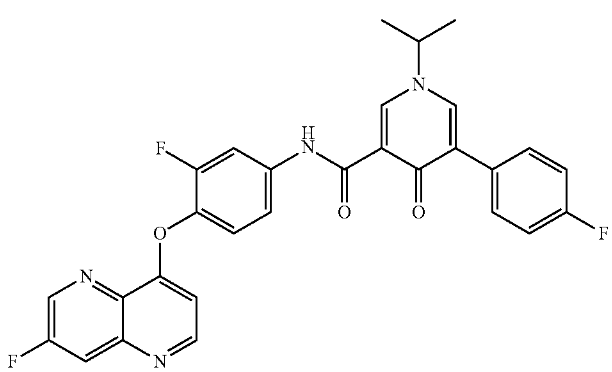 [SMILES: CC(C)n1cc(C(=O)Nc2ccc(Oc3ccnc4cc(F)cnc34)c(F)c2)c(=O)c(-c2ccc(F)cc2)c1] | N-[3-fluoro-4-[(7-fluoro-1,5-naphthyridin-4-yl)oxy]phenyl]-5-(4-fluorophenyl)-4-oxo-1-propan-2-ylpyridine-3-carboxamide |

| Cpd # | Structure | IUPAC Name |
|---|---|---|
| 162 | 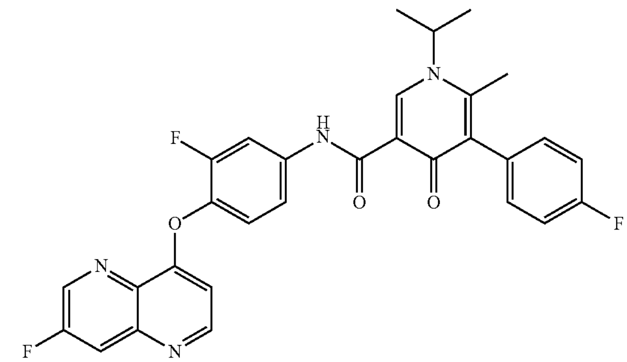 [SMILES: Cc1c(-c2ccc(F)cc2)c(=O)c(C(=O)Nc2ccc(Oc3ccnc4cc(F)cnc34)c(F)c2)cn1C(C)C] | N-[3-fluoro-4-[(7-fluoro-1,5-naphthyridin-4-yl)oxy]phenyl]-5-(4-fluorophenyl)-6-methyl-4-oxo-1-propan-2-ylpyridine-3-carboxamide |
| 163 | 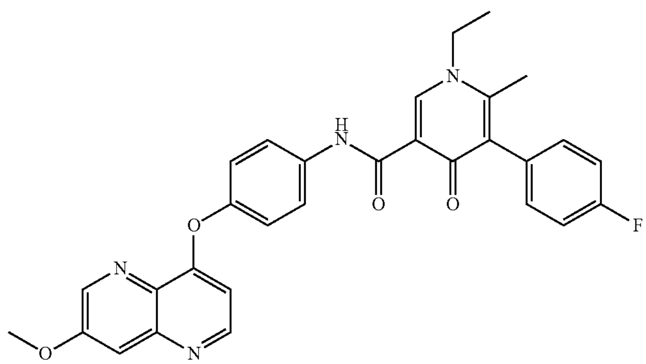 [SMILES: CCn1cc(C(=O)Nc2ccc(Oc3ccnc4cc(OC)cnc34)cc2)c(=O)c(-c2ccc(F)cc2)c1C] | 1-ethyl-5-(4-fluorophenyl)-N-[4-[(7-methoxy-1,5-naphthyridin-4-yl)oxy]phenyl]-6-methyl-4-oxopyridine-3-carboxamide |
| 164 | 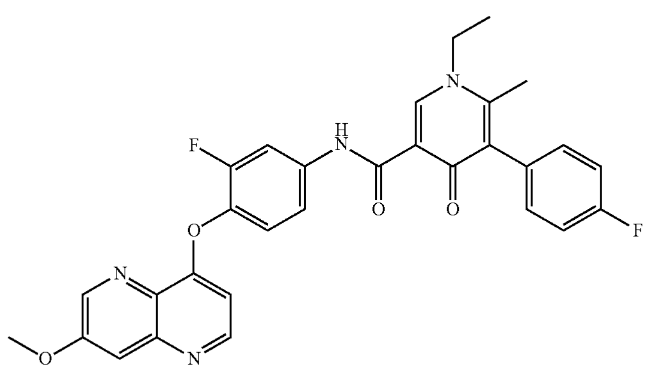 [SMILES: CCn1cc(C(=O)Nc2ccc(Oc3ccnc4cc(OC)cnc34)c(F)c2)c(=O)c(-c2ccc(F)cc2)c1C] | 1-ethyl-N-[3-fluoro-4-[(7-methoxy-1,5-naphthyridin-4-yl)oxy]phenyl]-5-(4-fluorophenyl)-6-methyl-4-oxopyridine-3-carboxamide |
| 165 | 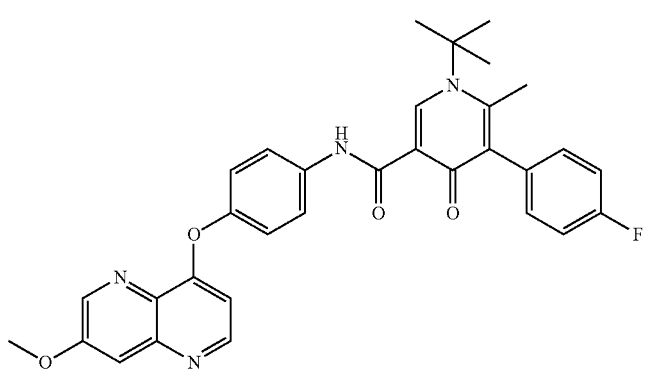 [SMILES: COc1cnc2c(Oc3ccc(NC(=O)c4cn(C(C)(C)C)c(C)c(-c5ccc(F)cc5)c4=O)cc3)ccnc2c1] | 1-tert-butyl-5-(4-fluorophenyl)-N-[4-[(7-methoxy-1,5-naphthyridin-4-yl)oxy]phenyl]-6-methyl-4-oxopyridine-3-carboxamide |

TABLE 1-continued

| Cpd # | Structure | IUPAC Name |
|---|---|---|
| 166 | 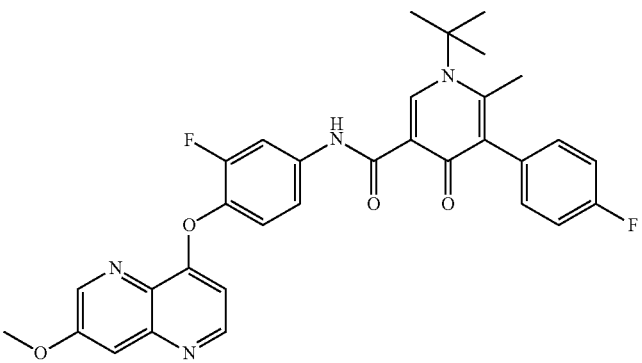 [SMILES: COc1cnc2c(Oc3ccc(NC(=O)c4cn(C(C)(C)C)c(C)c(-c5ccc(F)cc5)c4=O)cc3F)ccnc2c1] | 1-tert-butyl-N-[3-fluoro-4-[(7-methoxy-1,5-naphthyridin-4-yl)oxy]phenyl]-5-(4-fluorophenyl)-6-methyl-4-oxopyridine-3-carboxamide |
| 167 | 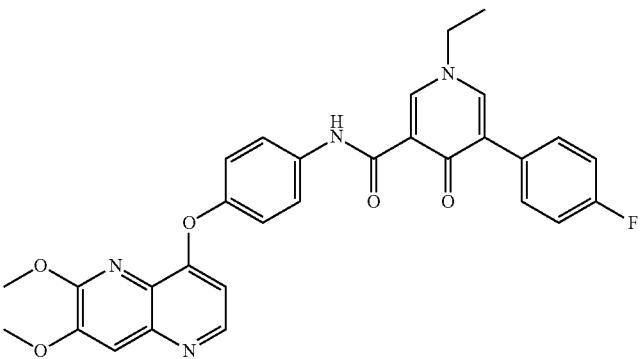 [SMILES: CCn1cc(C(=O)Nc2ccc(Oc3ccnc4cc(OC)c(OC)nc34)cc2)c(=O)c(-c2ccc(F)cc2)c1] | N-[4-[(6,7-dimethoxy-1,5-naphthyridin-4-yl)oxy]phenyl]-1-ethyl-5-(4-fluorophenyl)-4-oxopyridine-3-carboxamide |
| 168 | 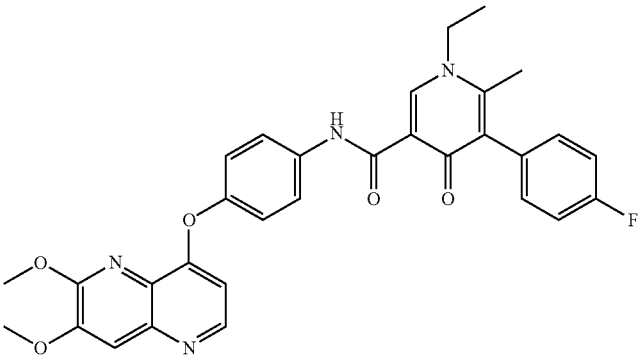 [SMILES: CCn1cc(C(=O)Nc2ccc(Oc3ccnc4cc(OC)c(OC)nc34)cc2)c(=O)c(-c2ccc(F)cc2)c1C] | N-[4-[(6,7-dimethoxy-1,5-naphthyridin-4-yl)oxy]phenyl]-1-ethyl-5-(4-fluorophenyl)-6-methyl-4-oxopyridine-3-carboxamide |
| 169 | 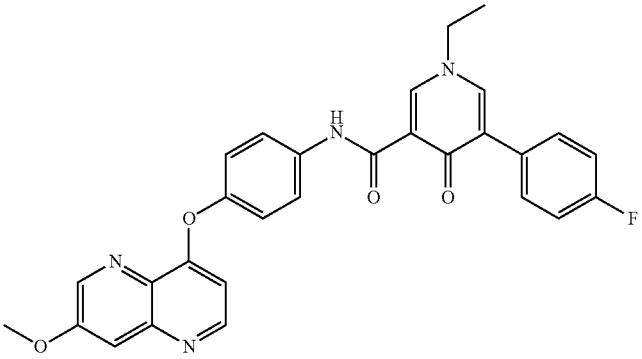 [SMILES: CCn1cc(C(=O)Nc2ccc(Oc3ccnc4cc(OC)cnc34)cc2)c(=O)c(-c2ccc(F)cc2)c1] | 1-ethyl-5-(4-fluorophenyl)-N-[4-[(7-methoxy-1,5-naphthyridin-4-yl)oxy]phenyl]-4-oxopyridine-3-carboxamide |

TABLE 1-continued

| Cpd # | Structure | IUPAC Name |
|---|---|---|
| 170 | 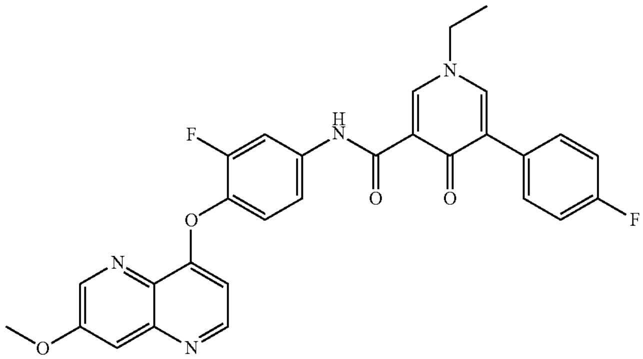 | 1-ethyl-N-[3-fluoro-4-[(7-methoxy-1,5-naphthyridin-4-yl)oxy]phenyl]-5-(4-fluorophenyl)-4-oxopyridine-3-carboxamide |
| 171 | 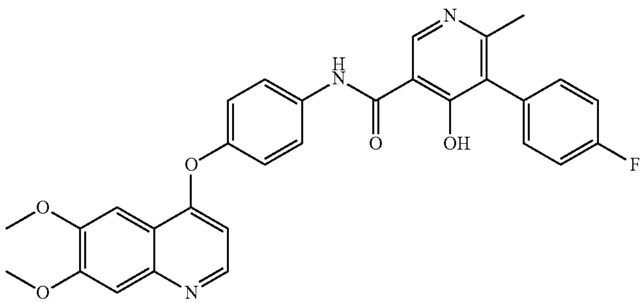 [SMILES: COc1cc2nccc(Oc3ccc(NC(=O)c4cnc(C)c(-c5ccc(F)cc5)c4O)cc3)c2cc1OC] | N-[4-(6,7-dimethoxyquinolin-4-yl)oxyphenyl]-5-(4-fluorophenyl)-4-hydroxy-6-methylpyridine-3-carboxamide |
| 172 | 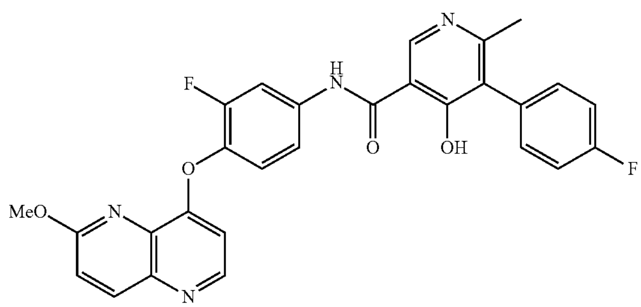 [SMILES: COc1ccc2nccc(Oc3ccc(NC(=O)c4cnc(C)c(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-6-methylpyridine-3-carboxamide |
| 173 | 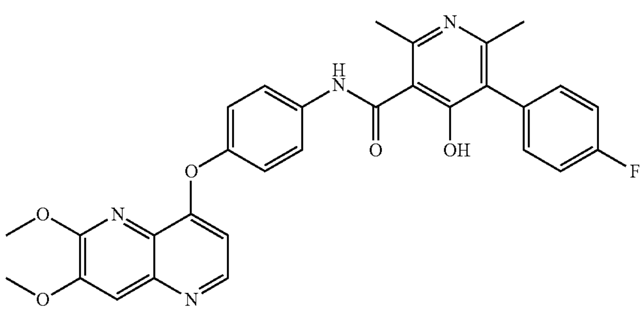 [SMILES: COc1cc2nccc(Oc3ccc(NC(=O)c4c(C)nc(C)c(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxy-2,6-dimethylpyridine-3-carboxamide |
| 174 | 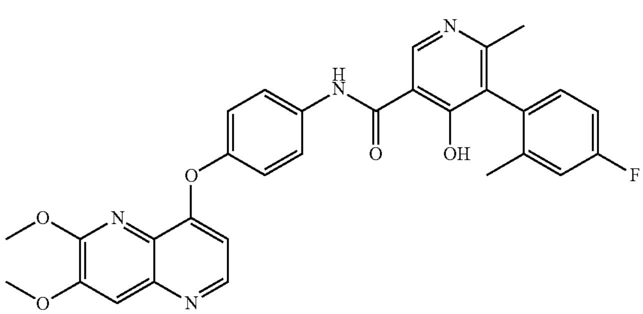 [SMILES: COc1cc2nccc(Oc3ccc(NC(=O)c4cnc(C)c(-c5ccc(F)cc5C)c4O)cc3)c2nc1OC] | N-[4-[(6,7-dimethoxy-1,5-naphthyridin-4-yl)oxy]phenyl]-5-(4-fluoro-2-methylphenyl)-4-hydroxy-6-methylpyridine-3-carboxamide |

TABLE 1-continued

| Cpd # | Structure | IUPAC Name |
|---|---|---|
| 175 | 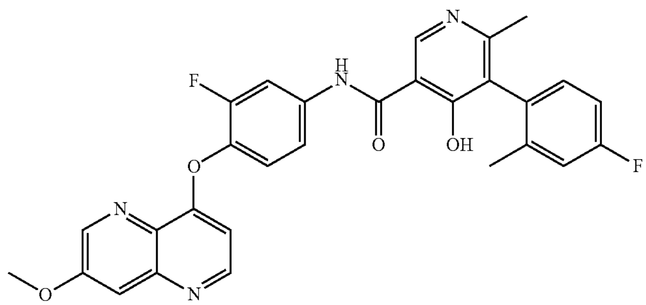 [SMILES: COc1cnc2c(Oc3ccc(NC(=O)c4cnc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |
| 176 | 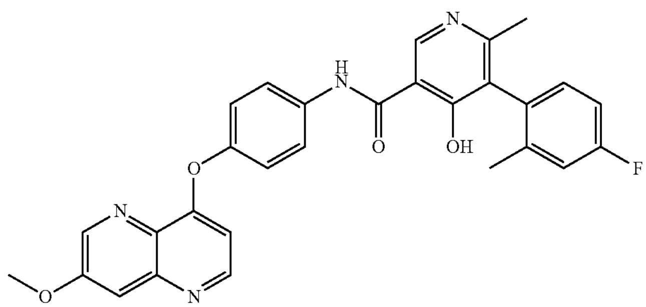 [SMILES: COc1cnc2c(Oc3ccc(NC(=O)c4cnc(C)c(-c5ccc(F)cc5C)c4O)cc3)ccnc2c1] | 5-(4-fluoro-2-methylphenyl)-4-hydroxy-N-[4-[(7-methoxy-1,5-naphthyridin-4-yl)oxy]phenyl]-6-methylpyridine-3-carboxamide |
| 177 | 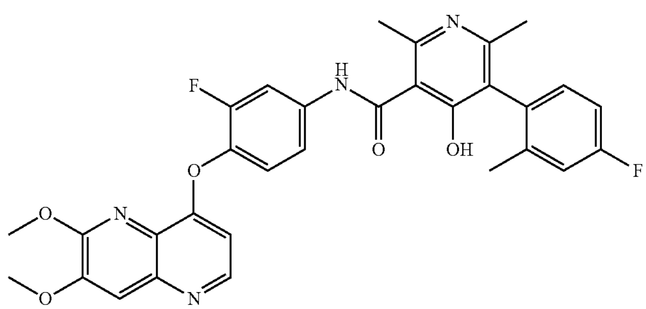 [SMILES: COc1cc2nccc(Oc3ccc(NC(=O)c4c(C)nc(C)c(-c5ccc(F)cc5C)c4O)cc3F)c2nc1OC] | N-[4-[(6,7-dimethoxy-1,5-naphthyridin-4-yl)oxy]-3-fluorophenyl]-5-(4-fluoro-2-methylphenyl)-4-hydroxy-2,6-dimethylpyridine-3-carboxamide |
| 178 | 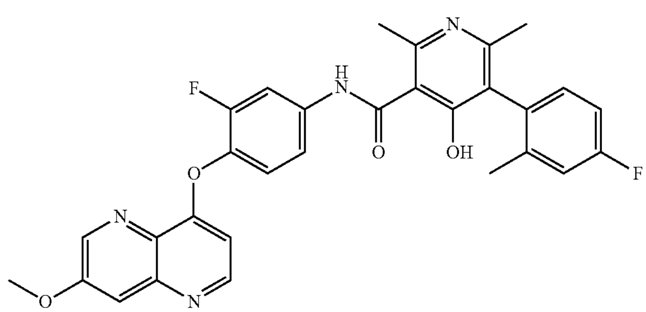 [SMILES: COc1cnc2c(Oc3ccc(NC(=O)c4c(C)nc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 179 | 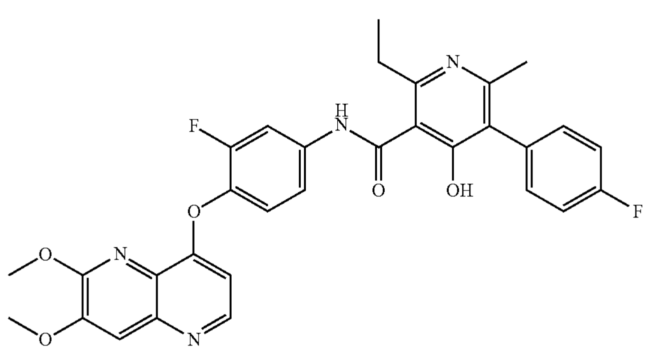 [SMILES: CCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-ethyl-5-(4-fluorophenyl)-4-hydroxy-6-methylpyridine-3-carboxamide |

TABLE 1-continued

| Cpd # | Structure | IUPAC Name |
|---|---|---|
| 180 | 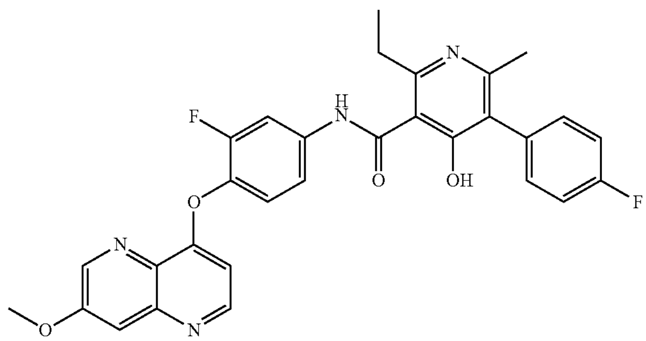 [SMILES: CCc1nc(C)c(-c2ccc(F)cc2)c(O)c1C(=O)Nc1ccc(Oc2ccnc3cc(OC)cnc23)c(F)c1] | 2-ethyl-N-[3-fluoro-4-[(7-methoxy-1,5-naphthyridin-4-yl)oxy]phenyl]-5-(4-fluorophenyl)-4-hydroxy-6-methylpyridine-3-carboxamide |
| 181 | 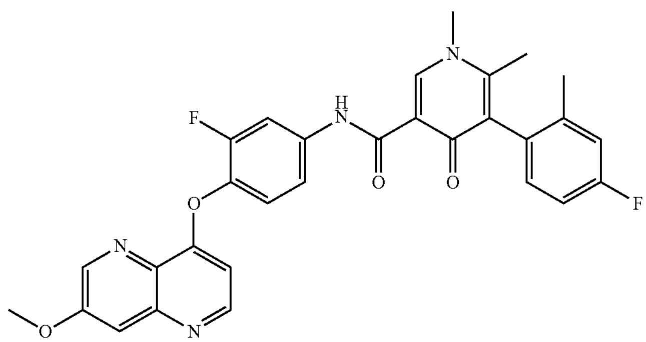 [SMILES: COc1cnc2c(Oc3ccc(NC(=O)c4cn(C)c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-1,6-dimethyl-4-oxopyridine-3-carboxamide |
| 182 | 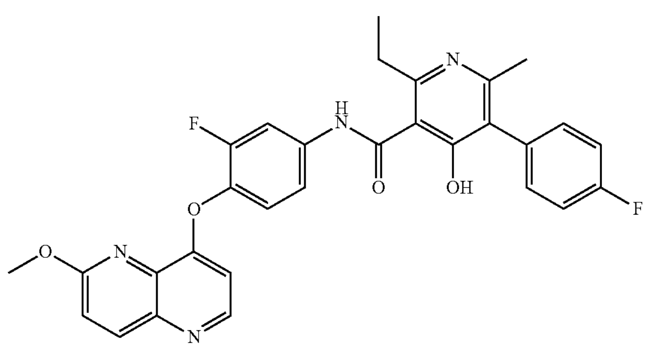 [SMILES: CCc1nc(C)c(-c2ccc(F)cc2)c(O)c1C(=O)Nc1ccc(Oc2ccnc3ccc(OC)nc23)c(F)c1] | 2-ethyl-N-[3-fluoro-4-[(6-methoxy-1,5-naphthyridin-4-yl)oxy]phenyl]-5-(4-fluorophenyl)-4-hydroxy-6-methylpyridine-3-carboxamide |
| 183 | 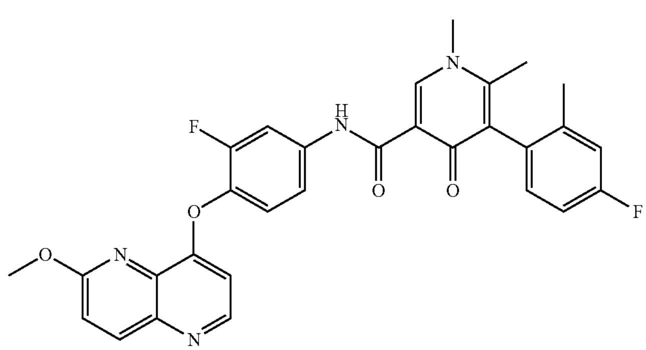 [SMILES: COc1ccc2nccc(Oc3ccc(NC(=O)c4cn(C)c(C)c(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-1,6-dimethyl-4-oxopyridine-3-carboxamide |

TABLE 1-continued

| Cpd # | Structure | IUPAC Name |
|---|---|---|
| 184 | 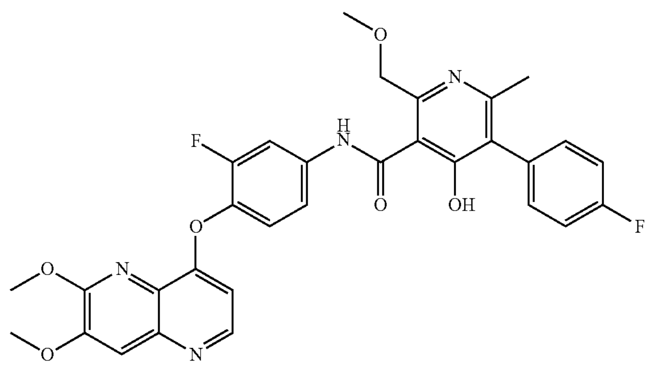 [SMILES: COCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-hydroxy-2-(methoxymethyl)-6-methylpyridine-3-carboxamide |
| 185 | 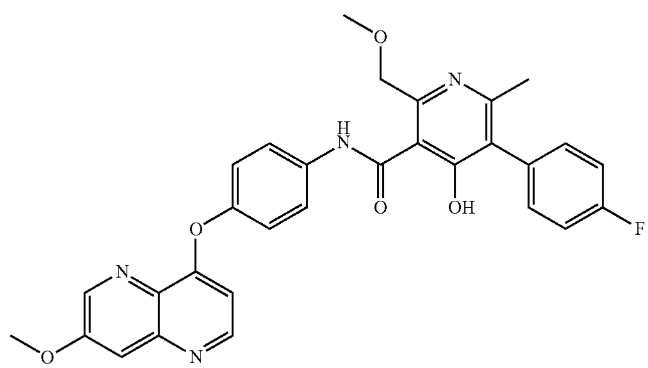 [SMILES: COCc1nc(C)c(-c2ccc(F)cc2)c(O)c1C(=O)Nc1ccc(Oc2ccnc3cc(OC)cnc23)cc1] | 5-(4-fluorophenyl)-4-hydroxy-2-(methoxymethyl)-N-[4-[(7-methoxy-1,5-naphthyridin-4-yl)oxy]phenyl]-6-methylpyridine-3-carboxamide |
| 186 | 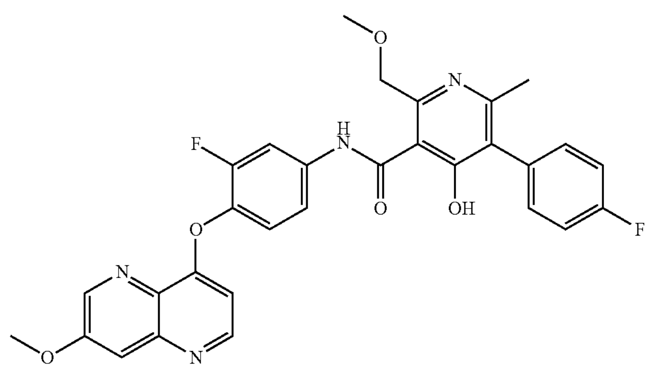 [SMILES: COCc1nc(C)c(-c2ccc(F)cc2)c(O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-5-(4-fluorophenyl)-4-hydroxy-2-(methoxymethyl)-6-methylpyridine-3-carboxamide |
| 187 | 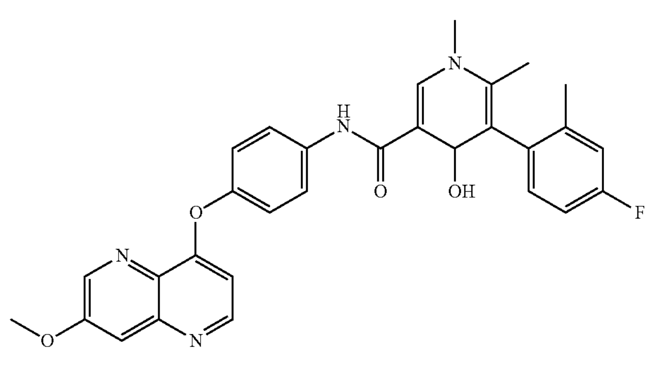 [SMILES: COc1cnc2c(Oc3ccc(NC(=O)C4=CN(C)C(C)=C(c5ccc(F)cc5C)C4O)cc3)ccnc2c1] | 5-(4-fluoro-2-methylphenyl)-N-[4-[(7-methoxy-1,5-naphthyridin-4-yl)oxy]phenyl]-1,6-dimethyl-4-oxopyridine-3-carboxamide |

TABLE 1-continued

| Cpd # | Structure | IUPAC Name |
|---|---|---|
| 188 | 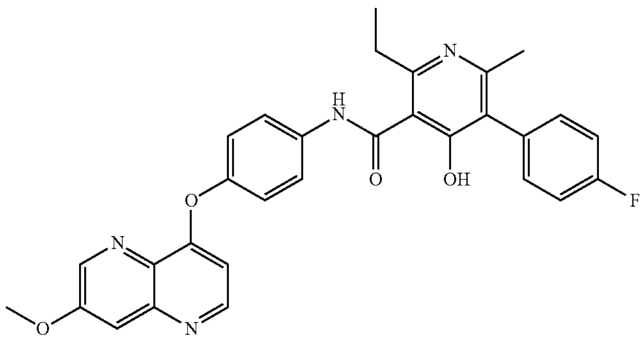 [SMILES: CCc1nc(C)c(-c2ccc(F)cc2)c(O)c1C(=O)Nc1ccc(Oc2ccnc3cc(OC)cnc23)cc1] | 2-ethyl-5-(4-fluorophenyl)-4-hydroxy-N-[4-[(7-methoxy-1,5-naphthyridin-4-yl)oxy]phenyl]-6-methylpyridine-3-carboxamide |
| 189 | 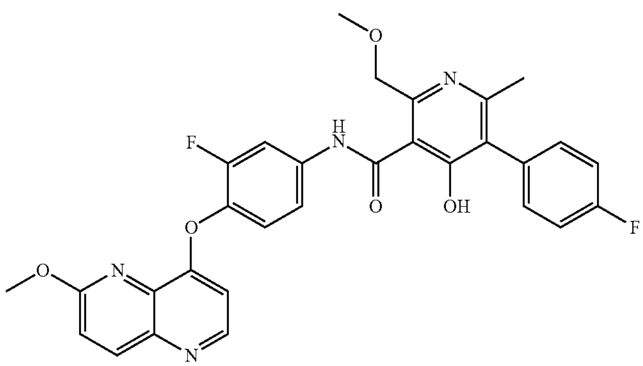 | N-[3-fluoro-4-[(6-methoxy-1,5-naphthyridin-4-yl)oxy]phenyl]-5-(4-fluorophenyl)-4-hydroxy-2-(methoxymethyl)-6-methylpyridine-3-carboxamide |
| 190 | 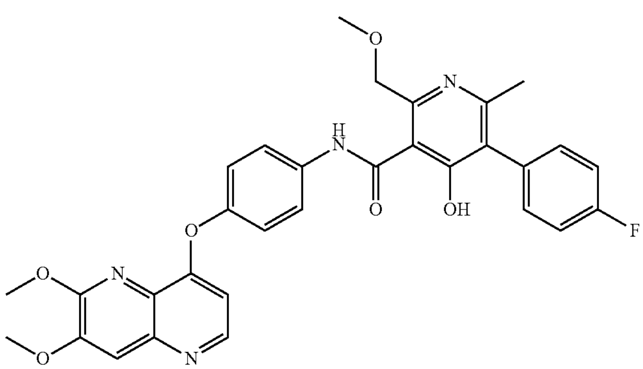 [SMILES: COCc1nc(C)c(-c2ccc(F)cc2)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-5-(4-fluorophenyl)-4-hydroxy-2-(methoxymethyl)-6-methylpyridine-3-carboxamide |
| 191 | 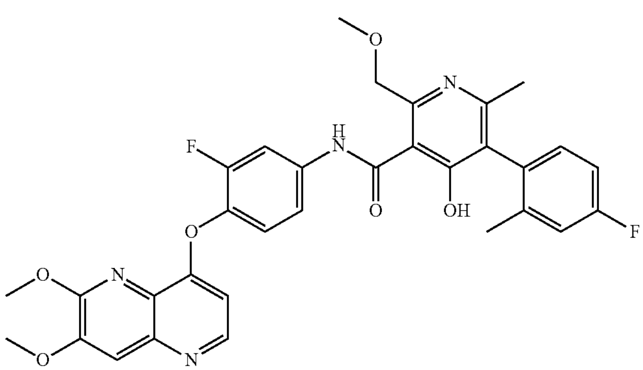 [SMILES: COCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluoro-2-methylphenyl)-4-hydroxy-2-(methoxymethyl)-6-methylpyridine-3-carboxamide |

TABLE 1-continued

| Cpd # | Structure | IUPAC Name |
|---|---|---|
| 192 | 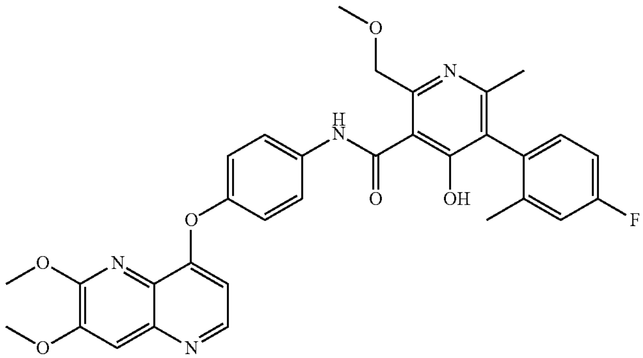 [SMILES: COCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-5-(4-fluoro-2-methylphenyl)-4-hydroxy-2-(methoxymethyl)-6-methylpyridine-3-carboxamide |
| 193 | 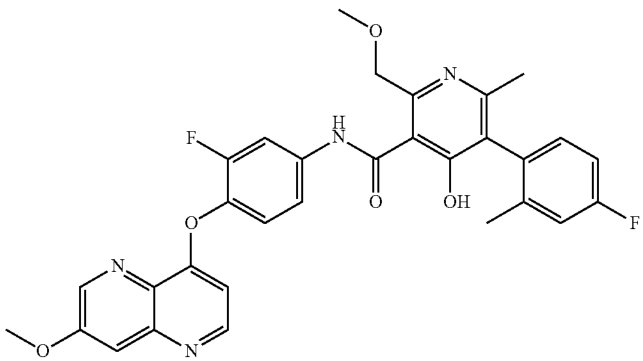 [SMILES: COCc1nc(C)c(-c2ccc(F)cc2C)c(O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-5-(4-fluoro-2-methylphenyl)-4-hydroxy-2-(methoxymethyl)-6-methylpyridine-3-carboxamide |
| 194 | 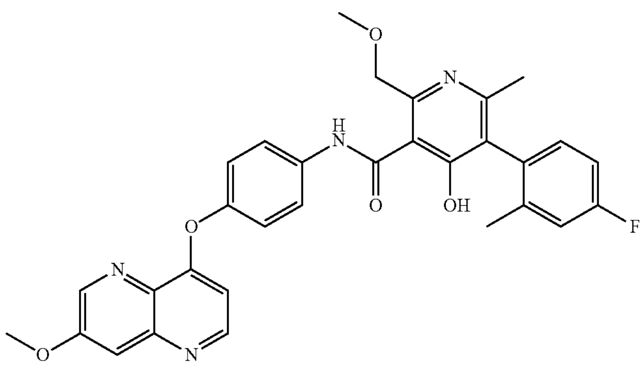 [SMILES: COCc1nc(C)c(-c2ccc(F)cc2C)c(O)c1C(=O)Nc1ccc(Oc2ccnc3cc(OC)cnc23)cc1] | 5-(4-fluoro-2-methylphenyl)-4-hydroxy-2-(methoxymethyl)-N-[4-[(7-methoxy-1,5-naphthyridin-4-yl)oxy]phenyl]-6-methylpyridine-3-carboxamide |
| 195 | 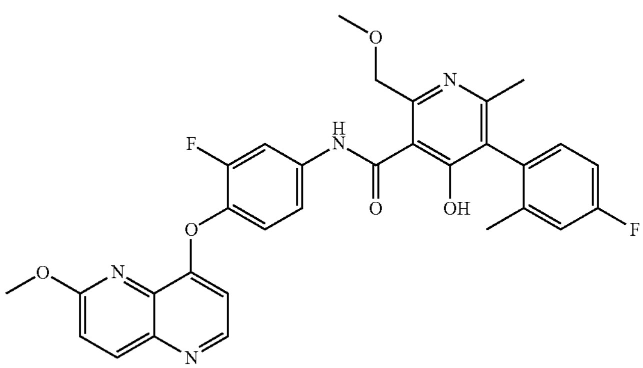 [SMILES: COCc1nc(C)c(-c2ccc(F)cc2C)c(O)c1C(=O)Nc1ccc(Oc2ccnc3ccc(OC)nc23)c(F)c1] | N-[3-fluoro-4-[(6-methoxy-1,5-naphthyridin-4-yl)oxy]phenyl]-5-(4-fluoro-2-methylphenyl)-4-hydroxy-2-(methoxymethyl)-6-methylpyridine-3-carboxamide |

| Cpd # | Structure | IUPAC Name |
|---|---|---|
| 196 | 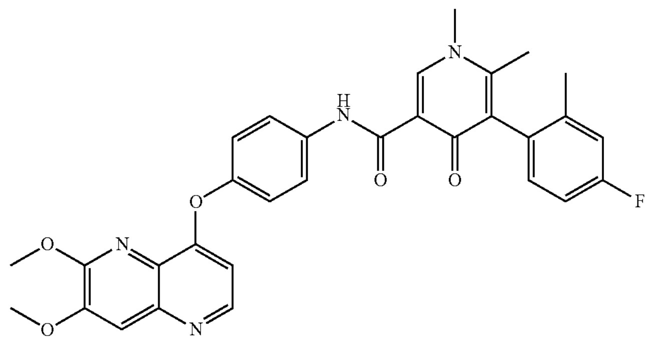 [SMILES: COc1cc2nccc(Oc3ccc(NC(=O)c4cn(C)c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-1,6-dimethyl-4-oxopyridine-3-carboxamide |
| 197 | 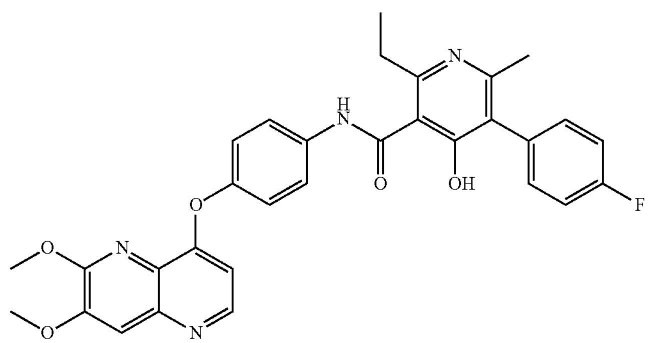 [SMILES: CCc1nc(C)c(-c2ccc(F)cc2)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-ethyl-5-(4-fluorophenyl)-4-hydroxy-6-methylpyridine-3-carboxamide |
| 198 | 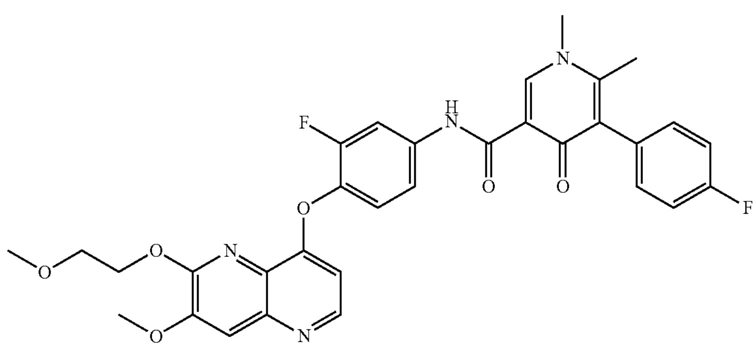 [SMILES: COCCOc1nc2c(Oc3ccc(NC(=O)c4cn(C)c(C)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-1,6-dimethyl-4-oxopyridine-3-carboxamide |
| 199 | 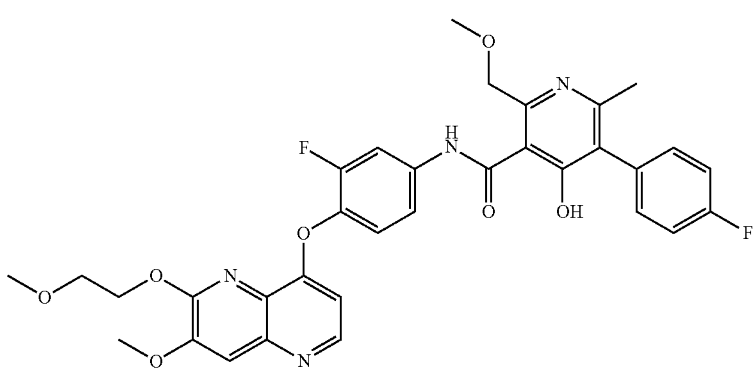 [SMILES: COCCOc1nc2c(Oc3ccc(NC(=O)c4c(COC)nc(C)c(-c5ccc(F)cc5)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide |

TABLE 1-continued

| Cpd # | Structure | IUPAC Name |
|---|---|---|
| 200 | 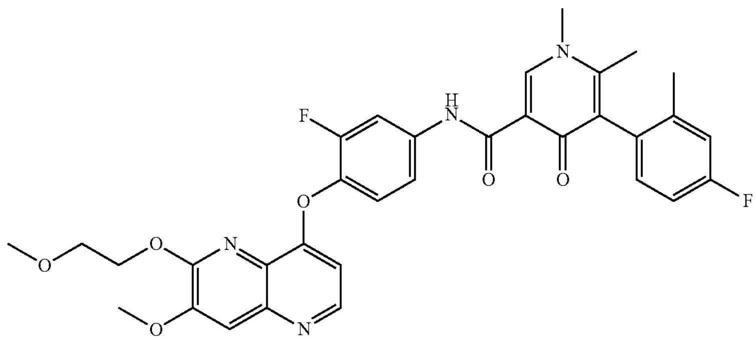 [SMILES: COCCOc1nc2c(Oc3ccc(NC(=O)c4cn(C)c(C)c(-c5ccc(F)cc5C)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-1,6-dimethyl-4-oxopyridine-3-carboxamide |
| 201 | 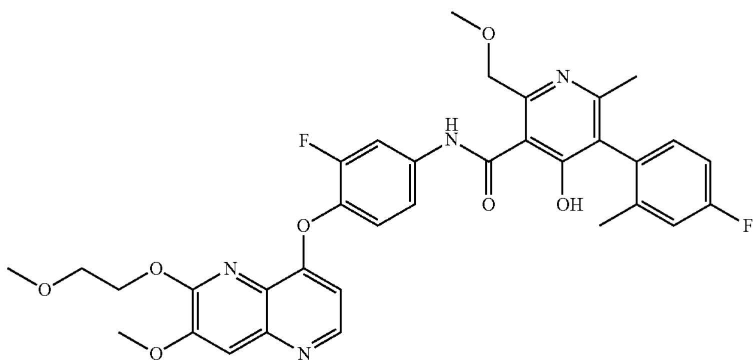 [SMILES: COCCOc1nc2c(Oc3ccc(NC(=O)c4c(COC)nc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-4-hydroxy-2-(methoxymethyl)-6-methylpyridine-3-carboxamide |
| 202 | 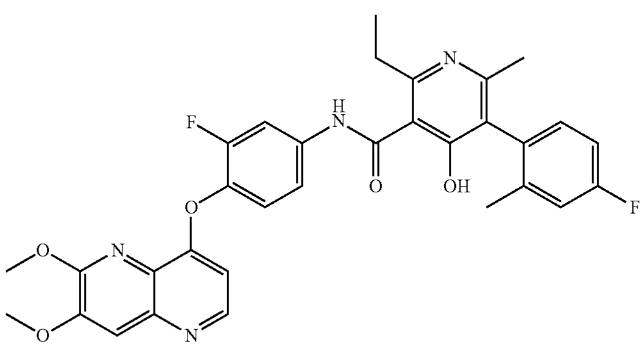 [SMILES: CCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-ethyl-5-(4-fluoro-2-methylphenyl)-4-hydroxy-6-methylpyridine-3-carboxamide |
| 203 | 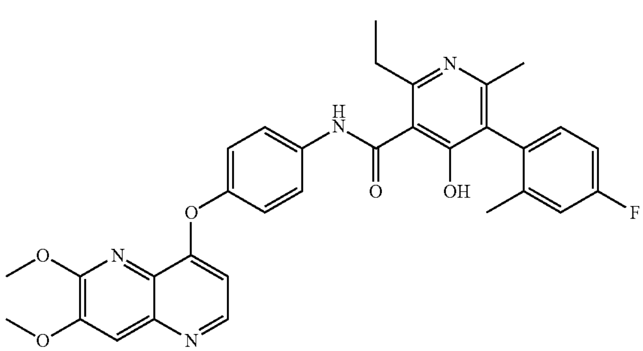 [SMILES: CCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-ethyl-5-(4-fluoro-2-methylphenyl)-4-hydroxy-6-methylpyridine-3-carboxamide |

TABLE 1-continued

| Cpd # | Structure | IUPAC Name |
|---|---|---|
| 204 | 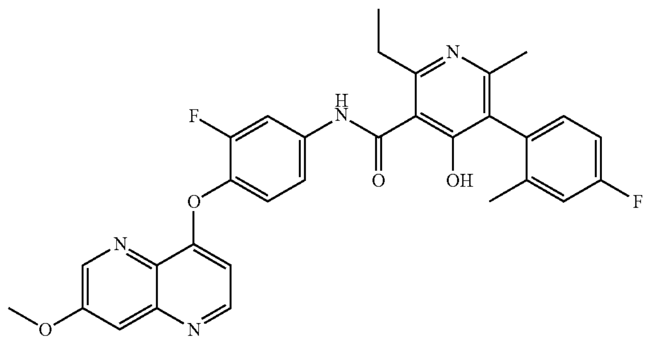 [SMILES: CCc1nc(C)c(-c2ccc(F)cc2C)c(O)c1C(=O)Nc1ccc(Oc2ccnc3cc(OC)cnc23)c(F)c1] | 2-ethyl-N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |
| 205 | 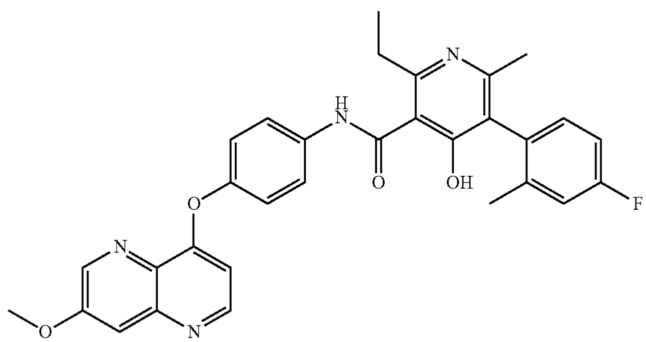 [SMILES: CCc1nc(C)c(-c2ccc(F)cc2C)c(O)c1C(=O)Nc1ccc(Oc2ccnc3cc(OC)cnc23)cc1] | 2-ethyl-5-(4-fluoro-2-methylphenyl)-4-hydroxy-N-[4-[(7-methoxy-1,5-naphthyridin-4-yl)oxy]phenyl]-6-methylpyridine-3-carboxamide |
| 206 | 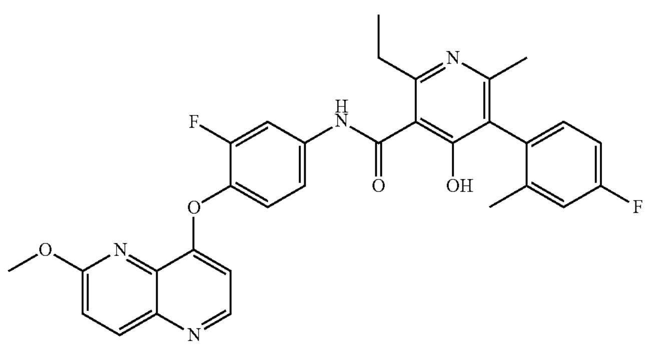 [SMILES: CCc1nc(C)c(-c2ccc(F)cc2C)c(O)c1C(=O)Nc1ccc(Oc2ccnc3ccc(OC)nc23)c(F)c1] | 2-ethyl-N-[3-fluoro-4-[(6-methoxy-1,5-naphthyridin-4-yl)oxy]phenyl]-5-(4-fluoro-2-methylphenyl)-4-hydroxy-6-methylpyridine-3-carboxamide |
| 207 | 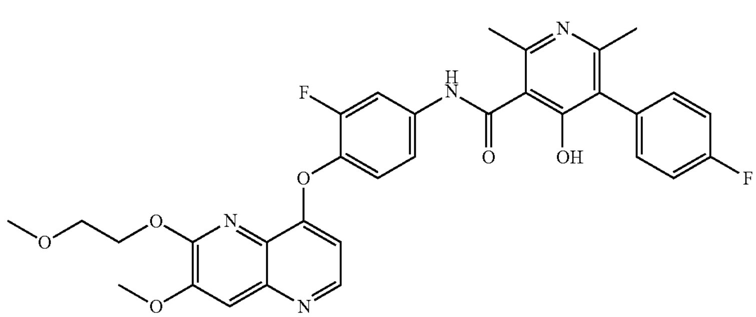 [SMILES: COCCOc1nc2c(Oc3ccc(NC(=O)c4c(C)nc(C)c(-c5ccc(F)cc5)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-2,6-dimethylpyridine-3-carboxamide |

TABLE 1-continued

| Cpd # | Structure | IUPAC Name |
|---|---|---|
| 208 | 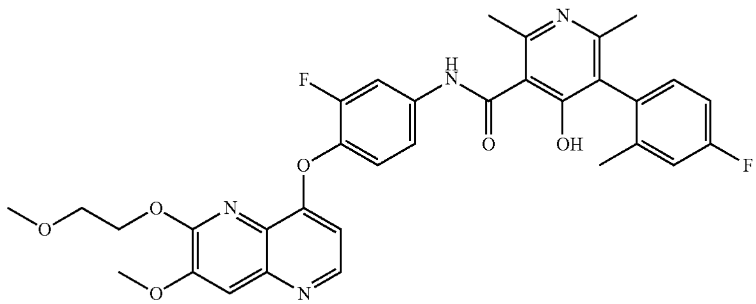 [SMILES: COCCOc1nc2c(Oc3ccc(NC(=O)c4c(C)nc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-4-hydroxy-2,6-dimethylpyridine-3-carboxamide |
| 209 | 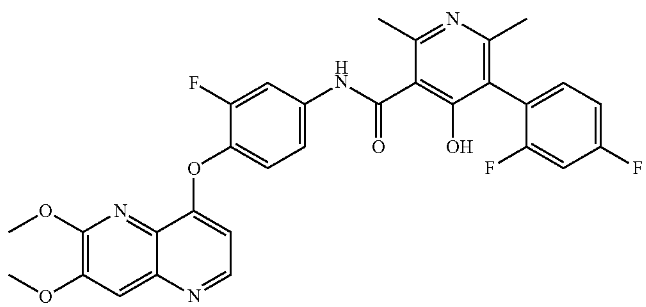 [SMILES: COc1cc2nccc(Oc3ccc(NC(=O)c4c(C)nc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-3-fluorophenyl]-4-hydroxy-2,6-dimethylpyridine-3-carboxamide |
| 210 | 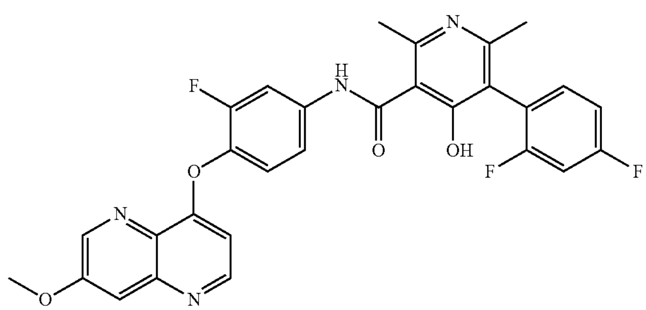 | 5-(2,4-difluorophenyl)-N-[3-fluoro-4-[(7-methoxy-1,5-naphthyridin-4-yl)oxy]phenyl]-4-hydroxy-2,6-dimethylpyridine-3-carboxamide |
| 211 | 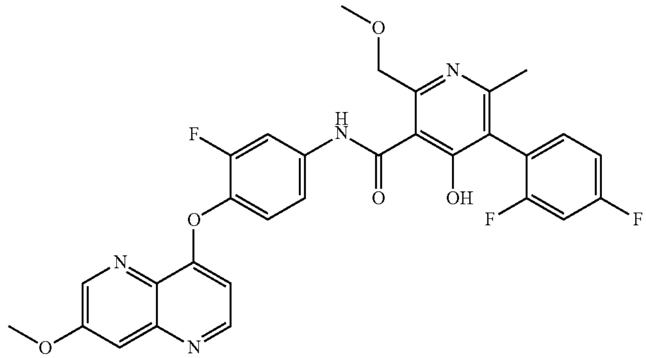 | 5-(2,4-difluorophenyl)-N-[3-fluoro-4-[(7-methoxy-1,5-naphthyridin-4-yl)oxy]phenyl]-4-hydroxy-2-(methoxymethyl)-6-methylpyridine-3-carboxamide |

TABLE 1-continued

| Cpd # | Structure | IUPAC Name |
|---|---|---|
| 212 | 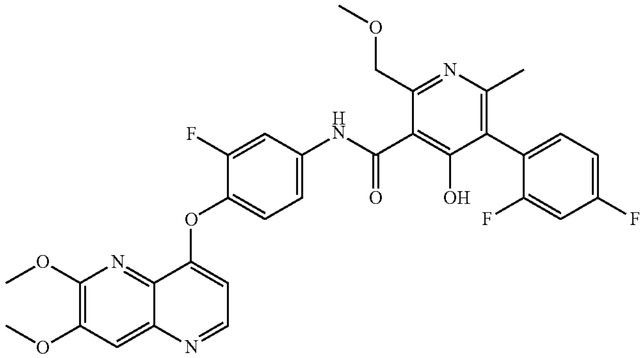 | 5-(2,4-difluorophenyl)-N-[4-[(6,7-dimethoxy-1,5-naphthyridin-4-yl)oxy]-3-fluorophenyl]-4-hydroxy-2-(methoxymethyl)-6-methylpyridine-3-carboxamide |
| 213 | 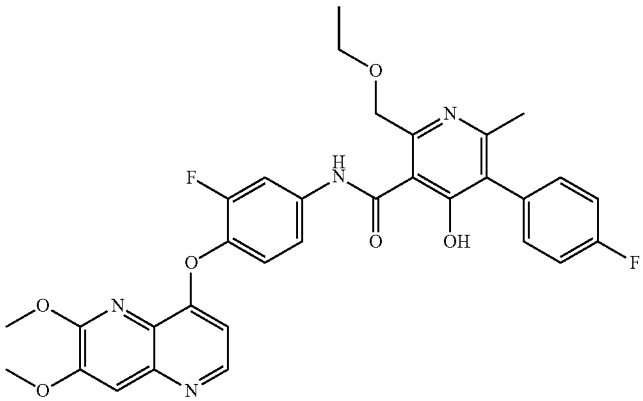 [SMILES: CCOCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(ethoxymethyl)-5-(4-fluorophenyl)-4-hydroxy-6-methylpridine-3-carboxamide |
| 214 | 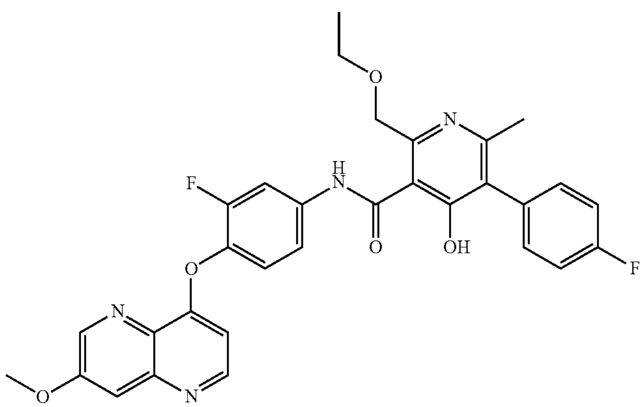 [SMILES: CCOCc1nc(C)c(-c2ccc(F)cc2)c(O)c1C(=O)Nc1ccc(Oc2ccnc3cc(OC)cnc23)c(F)c1] | 2-(ethoxymethyl)-N-[3-fluoro-4-[(7-methoxy-1,5-naphthyridin-4-yl)oxy]phenyl]-5-(4-fluorophenyl)-4-hydroxy-6-methylpyridine-3-carboxamide |
| 215 | 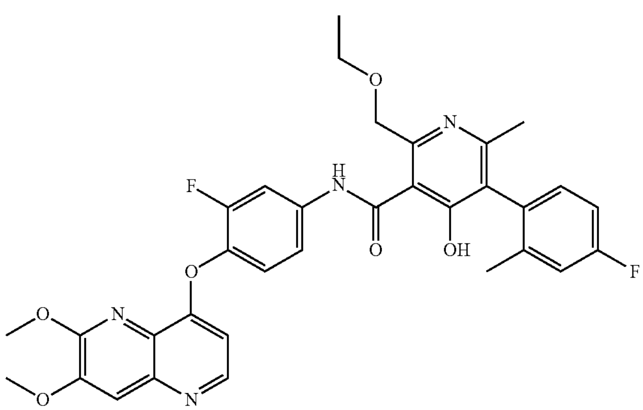 [SMILES: CCOCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(ethoxymethyl)-5-(4-fluoro-2-methylphenyl)-4-hydroxy-6-methylpyridine-3-carboxamide |

TABLE 1-continued

| Cpd # | Structure | IUPAC Name |
|---|---|---|
| 216 | 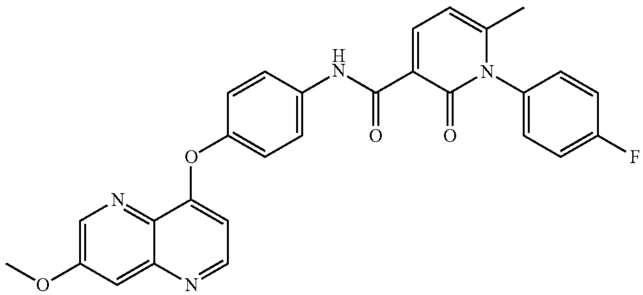 [SMILES: COc1cnc2c(Oc3ccc(NC(=O)c4ccc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-6-methyl-2-oxopyridine-3-carboxamide |
| 217 | 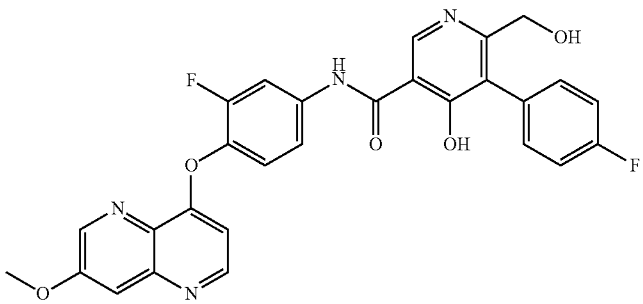 [SMILES: COc1cnc2c(Oc3ccc(NC(=O)c4cnc(CO)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-(hydroxymethyl)pyridine-3-carboxamide |
| 218 | 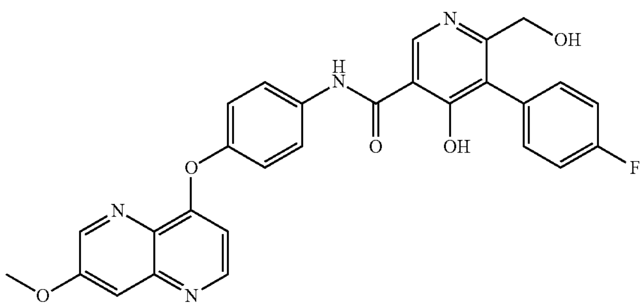 [SMILES: COc1cnc2c(Oc3ccc(NC(=O)c4cnc(CO)c(-c5ccc(F)cc5)c4O)cc3)ccnc2c1] | 5-(4-fluorophenyl)-4-hydroxy-6-(hydroxymethyl)-N-[4-[(7-methoxy-1,5-naphthyridin-4-yl)oxy]phenyl]pyridine-3-carboxamide |
| 219 | 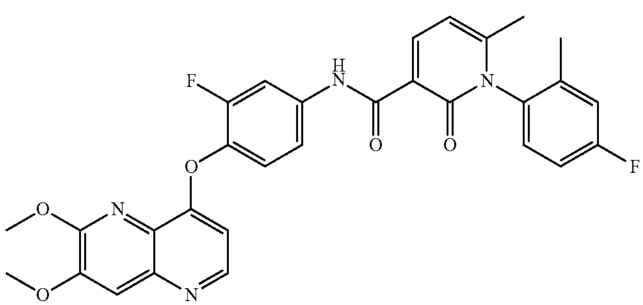 [SMILES: COc1cc2nccc(Oc3ccc(NC(=O)c4ccc(C)n(-c5ccc(F)cc5C)c4=O)cc3F)c2nc1OC] | N-[4-[(6,7-dimethoxy-1,5-naphthyridin-4-yl)oxy]-3-fluorophenyl]-1-(4-fluoro-2-methylphenyl)-6-methyl-2-oxopyridine-3-carboxamide |
| 220 | 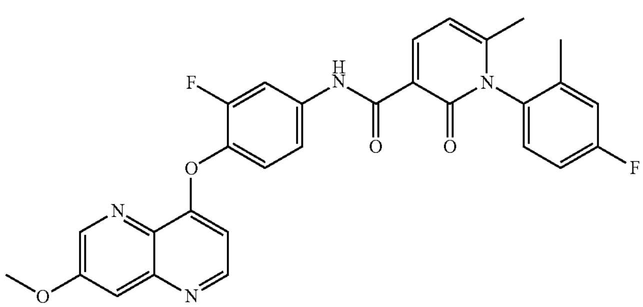 [SMILES: COc1cnc2c(Oc3ccc(NC(=O)c4ccc(C)n(-c5ccc(F)cc5C)c4=O)cc3F)ccnc2c1] | N-[3-fluoro-4-[(7-methoxy-1,5-naphthyridin-4-yl)oxy]phenyl]-1-(4-fluoro-2-methylphenyl)-6-methyl-2-oxopyridine-3-carboxamide |

TABLE 1-continued

| Cpd # | Structure | IUPAC Name |
|---|---|---|
| 221 | 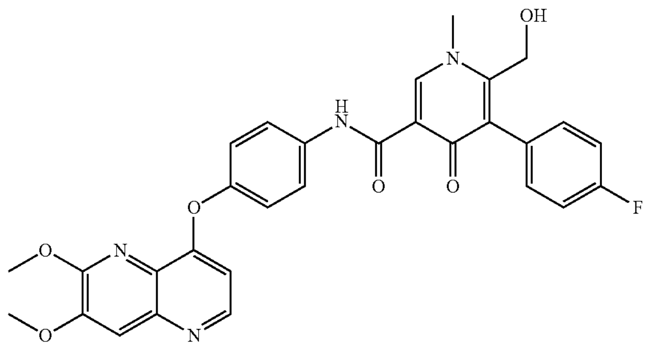 [SMILES: COc1cc2nccc(Oc3ccc(NC(=O)c4cn(C)c(CO)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-(hydroxymethyl)-1-methyl-4-oxopyridine-3-carboxamide |
| 222 | 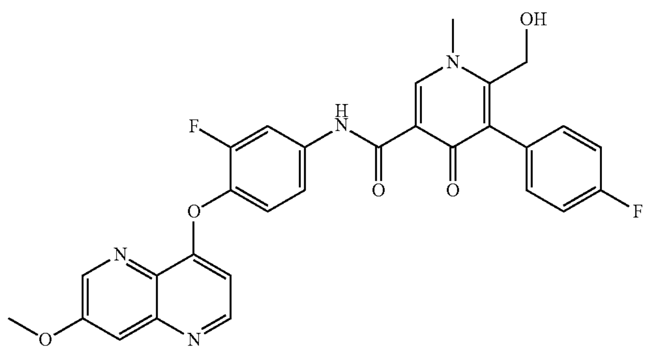 [SMILES: COc1cnc2c(Oc3ccc(NC(=O)c4cn(C)c(CO)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-(hydroxymethyl)-1-methyl-4-oxopyridine-3-carboxamide |
| 223 | 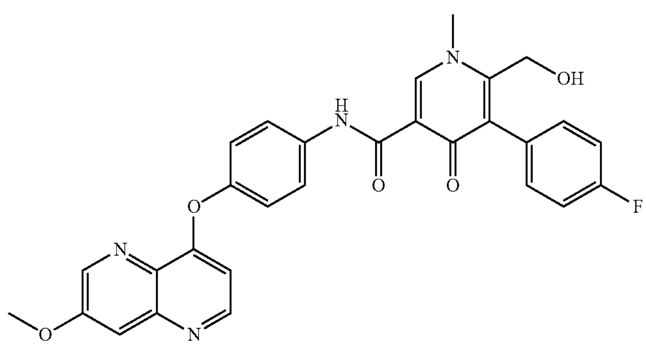 [SMILES: COc1cnc2c(Oc3ccc(NC(=O)c4cn(C)c(CO)c(-c5ccc(F)cc5)c4=O)cc3)ccnc2c1] | 5-(4-fluorophenyl)-6-(hydroxymethyl)-N-[4-[(7-methoxy-1,5-naphthyridin-4-yl)oxy]phenyl]-1-methyl-4-oxopyridine-3-carboxamide |
| 224 | 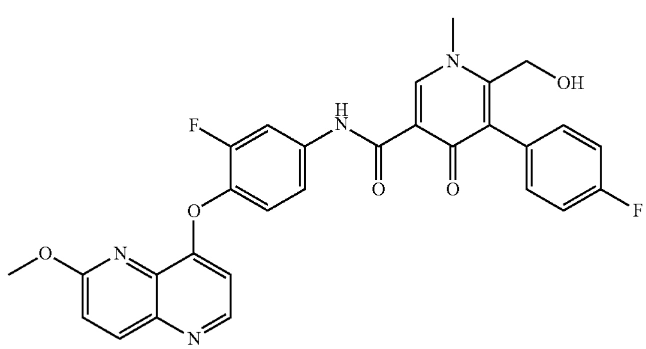 [SMILES: COc1ccc2nccc(Oc3ccc(NC(=O)c4cn(C)c(CO)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-6-(hydroxymethyl)-1-methyl-4-oxopyridine-3-carboxamide |

TABLE 1-continued

| Cpd # | Structure | IUPAC Name |
|---|---|---|
| 225 | 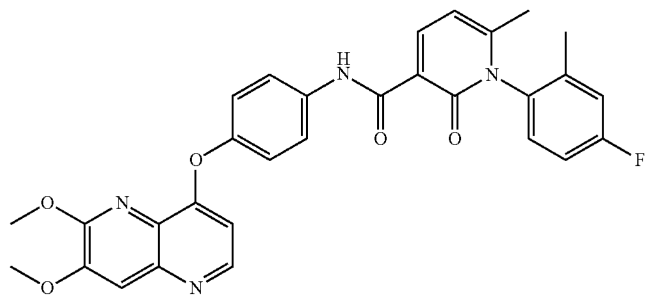 [SMILES: COc1cc2nccc(Oc3ccc(NC(=O)c4ccc(C)n(-c5ccc(F)cc5C)c4=O)cc3)c2nc1OC] | N-[4-[(6,7-dimethoxy-1,5-naphthyridin-4-yl)oxy]phenyl]-1-(4-fluoro-2-methylphenyl)-6-methyl-2-oxopyridine-3-carboxamide |
| 226 | 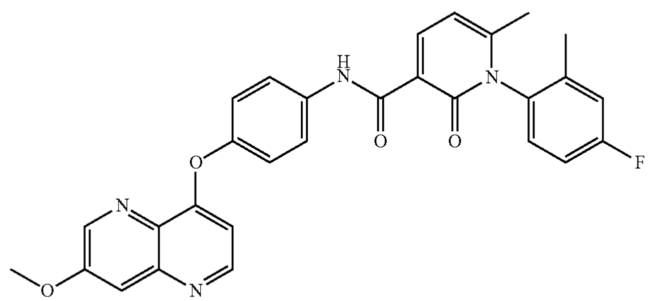 [SMILES: COc1cnc2c(Oc3ccc(NC(=O)c4ccc(C)n(-c5ccc(F)cc5C)c4=O)cc3)ccnc2c1] | 1-(4-fluoro-2-methylphenyl)-N-[4-[(7-methoxy-1,5-naphthyridin-4-yl)oxy]phenyl]-6-methyl-2-oxopyridine-3-carboxamide |
| 227 | 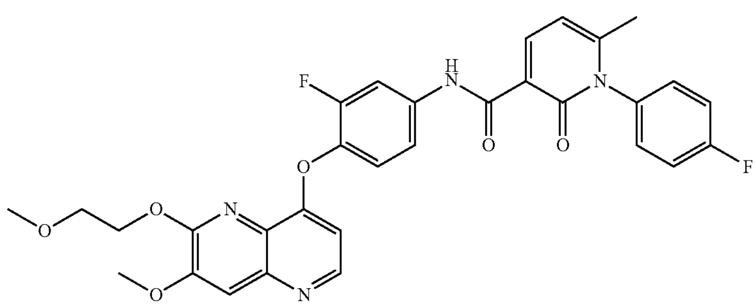 [SMILES: COCCOc1nc2c(Oc3ccc(NC(=O)c4ccc(C)n(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-1-(4-fluorophenyl)-6-methyl-2-oxopyridine-3-carboxamide |
| 228 | 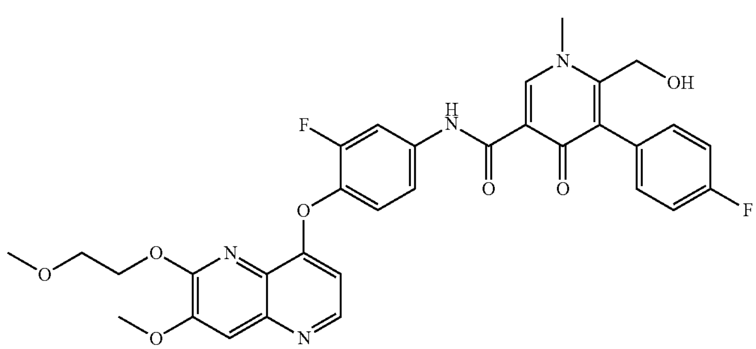 [SMILES: COCCOc1nc2c(Oc3ccc(NC(=O)c4cn(C)c(CO)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-6-(hydroxymethyl)-1-methyl-4-oxopyridine-3-carboxamide |
| 229 | 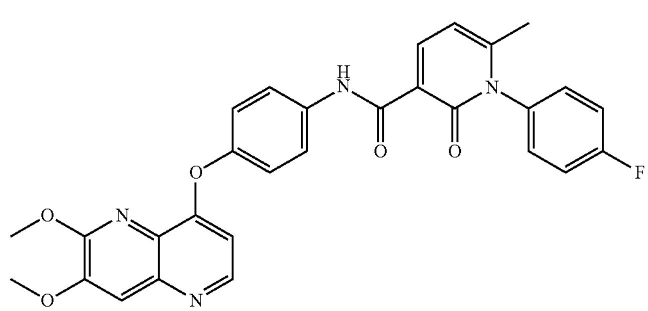 | N-[4-[(6,7-dimethoxy-1,5-naphthyridin-4-yl)oxy]phenyl]-1-(4-fluorophenyl)-6-methyl-2-oxopyridine-3-carboxamide |

TABLE 1-continued

| Cpd # | Structure | IUPAC Name |
|---|---|---|
| 230 | 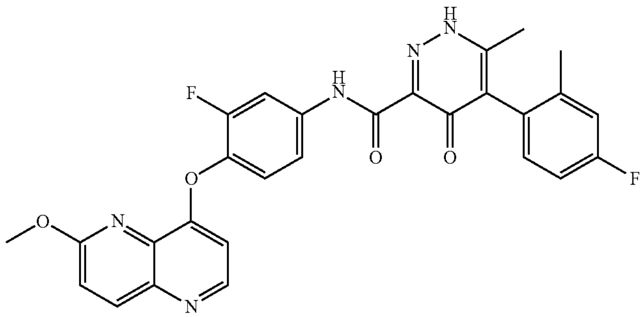 [SMILES: COc1ccc2nccc(Oc3ccc(NC(=O)c4n[nH]c(C)c(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-6-methyl-4-oxo-1H-pyridazine-3-carboxamide |
| 231 | 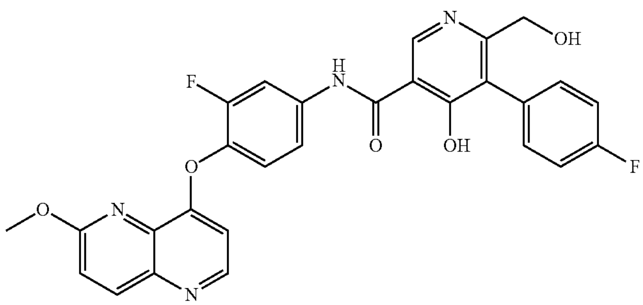 [SMILES: COc1ccc2nccc(Oc3ccc(NC(=O)c4cnc(CO)c(-c5ccc(F)cc5)c4O)cc3F)c2n1] | N-[3-fluoro-4-[(6-methoxy-1,5-naphthyridin-4-yl)oxy]phenyl]-4-hydroxy-6-(hydroxymethyl)pyridine-3-carboxamide |
| 232 | 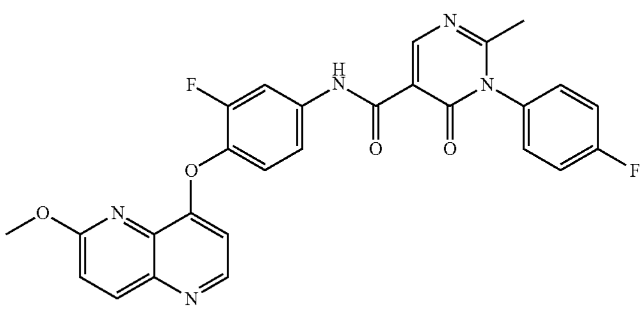 [SMILES: COc1ccc2nccc(Oc3ccc(NC(=O)c4cnc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-2-methyl-6-oxopyrimidine-5-carboxamide |
| 233 | 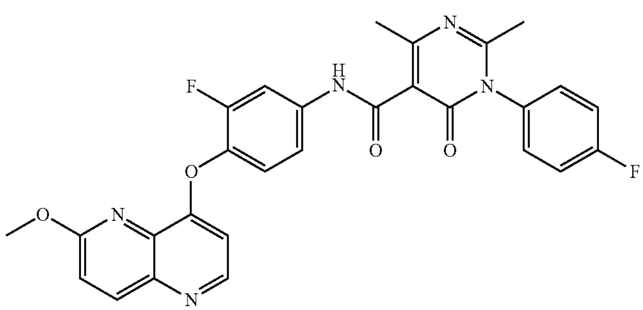 [SMILES: COc1ccc2nccc(Oc3ccc(NC(=O)c4c(C)nc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-2,4-dimethyl-6-oxopyrimidine-5-carboxamide |
| 234 | 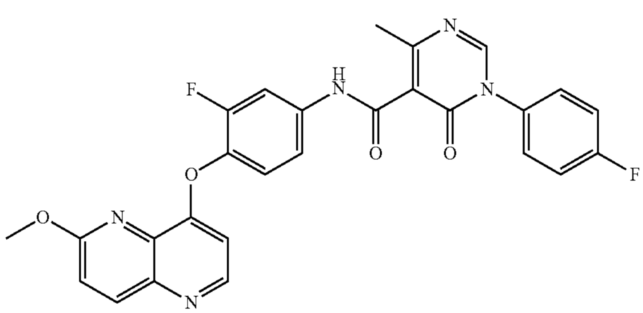 [SMILES: COc1ccc2nccc(Oc3ccc(NC(=O)c4c(C)ncn(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-4-methyl-6-oxopyrimidine-5-carboxamide |

TABLE 1-continued

| Cpd # | Structure | IUPAC Name |
|---|---|---|
| 235 | 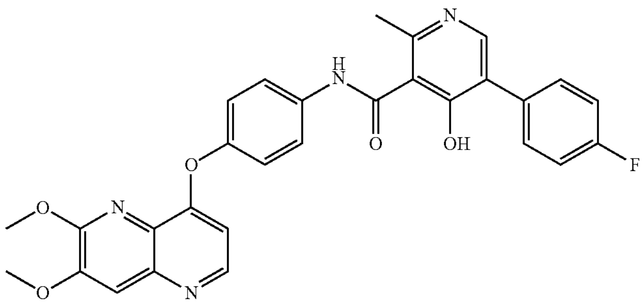 [SMILES: COc1cc2nccc(Oc3ccc(NC(=O)c4c(C)ncc(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxy-2-methylpyridine-3-carboxamide |
| 236 | 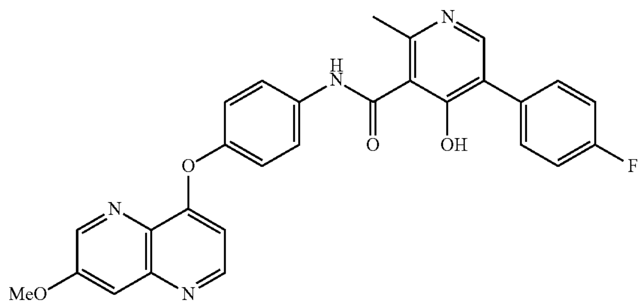 [SMILES: COc1cnc2c(Oc3ccc(NC(=O)c4c(C)ncc(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-2-methylpyridine-3-carboxamide |
| 237 | 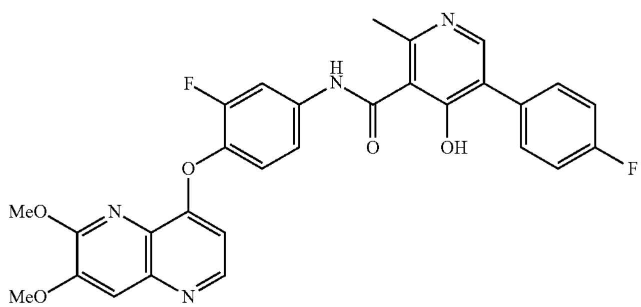 [SMILES: COc1cc2nccc(Oc3ccc(NC(=O)c4c(C)ncc(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-2-methylpyridine-3-carboxamide |
| 238 | 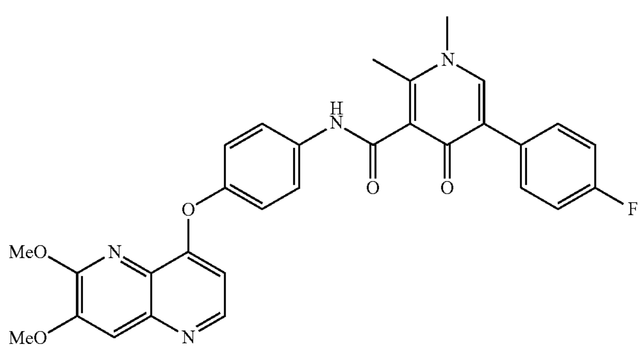 [SMILES: COc1cc2nccc(Oc3ccc(NC(=O)c4c(C)n(C)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,2-dimethyl-4-oxopyridine-3-carboxamide |
| 239 | 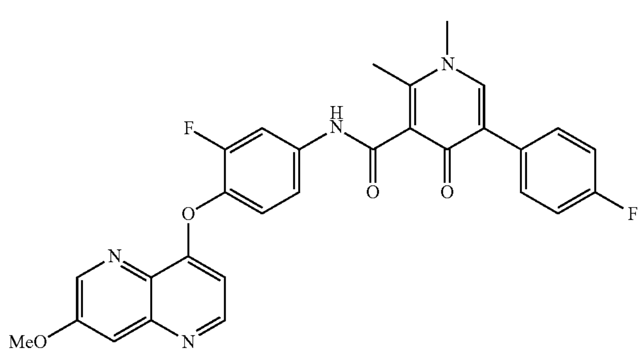 [SMILES: COc1cnc2c(Oc3ccc(NC(=O)c4c(C)n(C)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,2-dimethyl-4-oxopyridine-3-carboxamide |

TABLE 1-continued

| Cpd # | Structure | IUPAC Name |
|---|---|---|
| 240 | 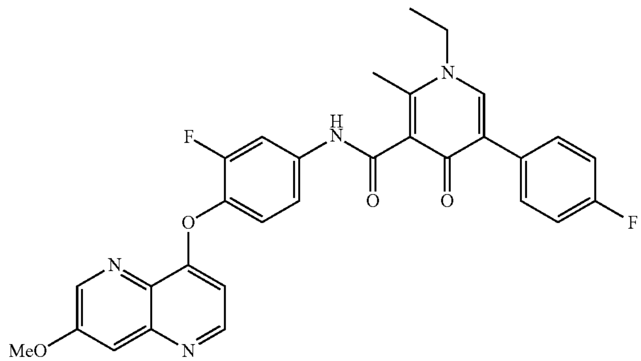 [SMILES: CCn1cc(-c2ccc(F)cc2)c(=O)c(C(=O)Nc2ccc(Oc3ccnc4cc(OC)cnc34)c(F)c2)c1C] | 1-ethyl-N-[3-fluoro-4-[(7-methoxy-1,5-naphthyridin-4-yl)oxy]phenyl]-5-(4-fluorophenyl)-2-methyl-4-oxopyridine-3-carboxamide |
| 241 | 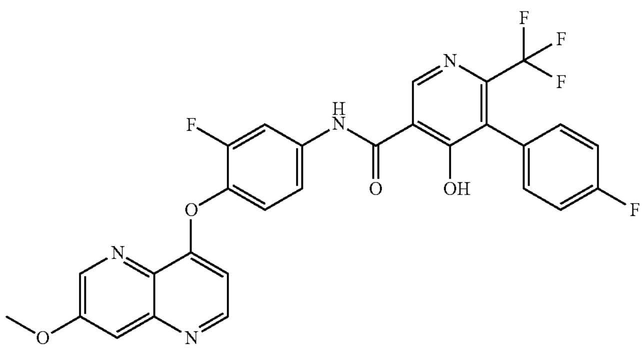 [SMILES: COc1cnc2c(Oc3ccc(NC(=O)c4cnc(C(F)(F)F)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-(trifluoromethyl)pyridine-3-carboxamide |
| 242 | 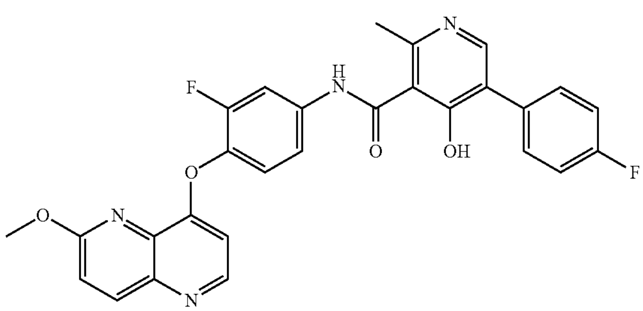 [SMILES: COc1ccc2nccc(Oc3ccc(NC(=O)c4c(C)ncc(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-2-methylpyridine-3-carboxamide |
| 243 | 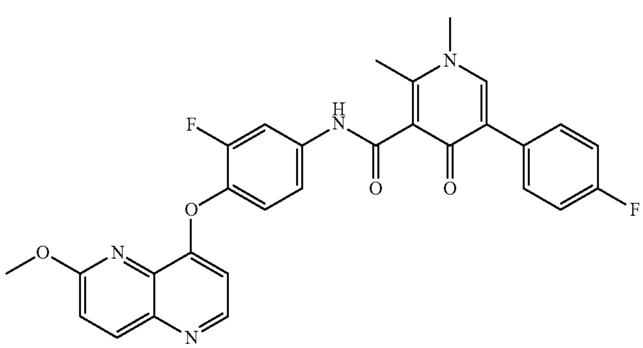 [SMILES: COc1ccc2nccc(Oc3ccc(NC(=O)c4c(C)n(C)cc(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-1,2-dimethyl-4-oxopyridine-3-carboxamide |

TABLE 1-continued

| Cpd # | Structure | IUPAC Name |
|---|---|---|
| 244 | 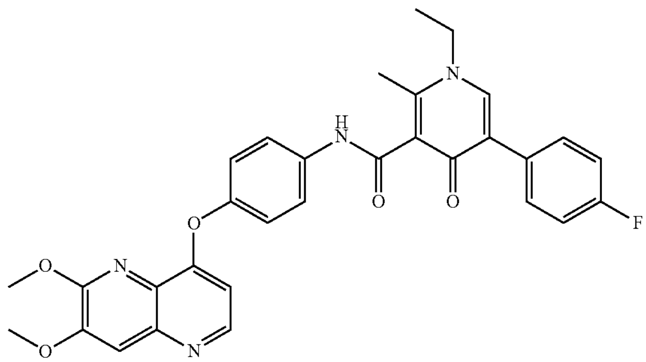 [SMILES: CCn1cc(-c2ccc(F)cc2)c(=O)c(C(=O)Nc2ccc(Oc3ccnc4cc(OC)c(OC)nc34)cc2)c1C] | N-[4-[(6,7-dimethoxy-1,5-naphthyridin-4-yl)oxy]phenyl]-1-ethyl-5-(4-fluorophenyl)-2-methyl-4-oxopyridine-3-carboxamide |
| 245 | 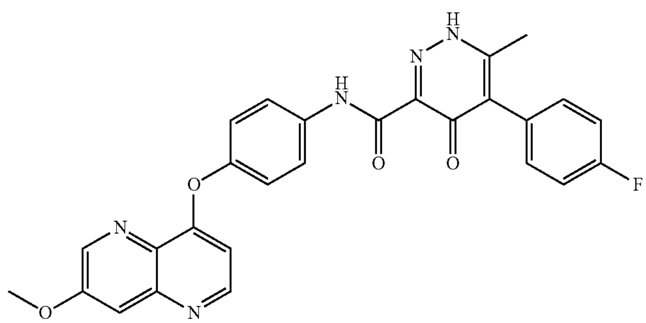 [SMILES: COc1cnc2c(Oc3ccc(NC(=O)c4n[nH]c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-6-methyl-4-oxo-1H-pyridazine-3-carboxamide |
| 246 | 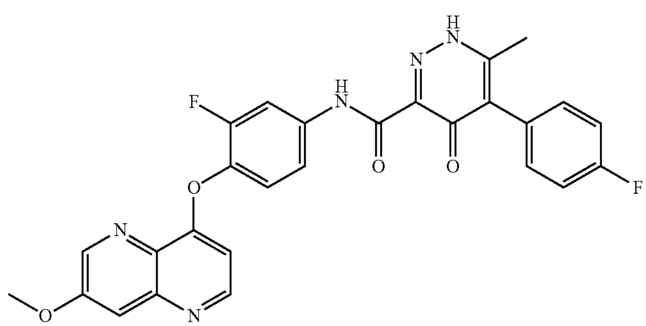 [SMILES: COc1cnc2c(Oc3ccc(NC(=O)c4n[nH]c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1H-pyridazine-3-carboxamide |
| 247 | 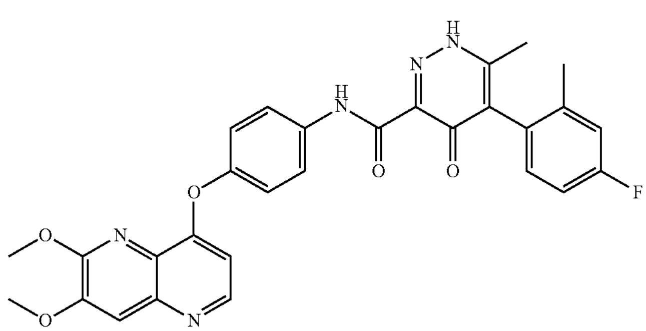 [SMILES: COc1cc2nccc(Oc3ccc(NC(=O)c4n[nH]c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-6-methyl-4-oxo-1H-pyridazine-3-carboxamide |

TABLE 1-continued

| Cpd # | Structure | IUPAC Name |
|---|---|---|
| 248 | 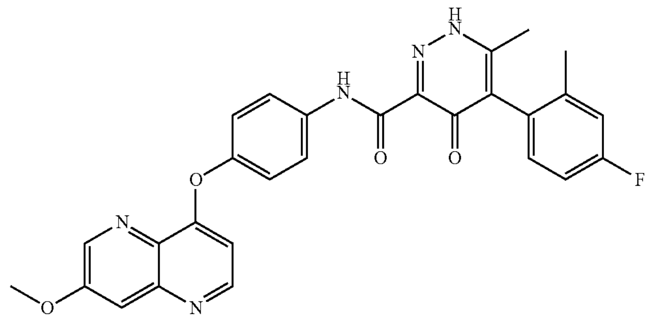 [SMILES: COc1cnc2c(Oc3ccc(NC(=O)c4n[nH]c(C)c(-c5ccc(F)cc5C)c4=O)cc3)ccnc2c1] | 5-(4-fluoro-2-methylphenyl)-N-[4-[(7-methoxy-1,5-naphthyridin-4-yl)oxy]phenyl]-6-methyl-4-oxo-1H-pyridazine-3-carboxamide |
| 249A | 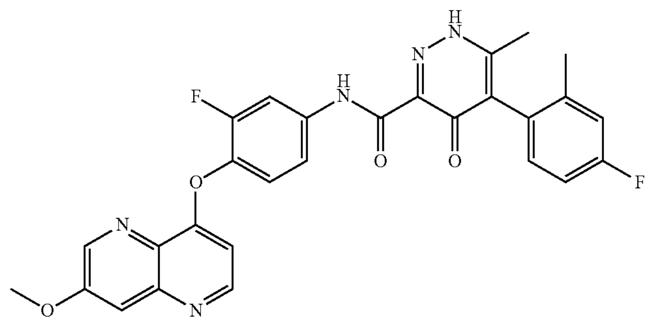 | N-[3-fluoro-4-[(7-methoxy-1,5-naphthyridin-4-yl)oxy]phenyl]-5-(4-fluoro-2-methylphenyl)-6-methyl-4-oxo-1H-pyridazine-3-carboxamide |
| 249B | 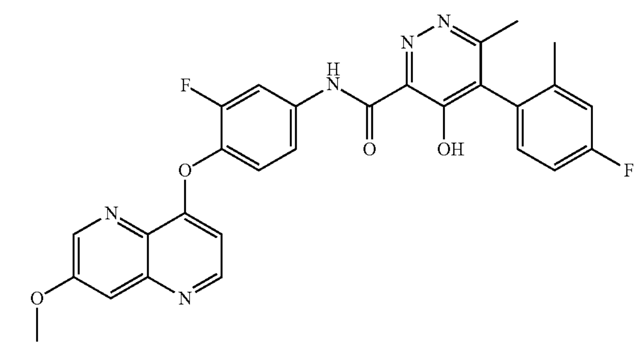 [SMILES: COc1cnc2c(Oc3ccc(NC(=O)c4nnc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropoisomer 1 |
| 249C | 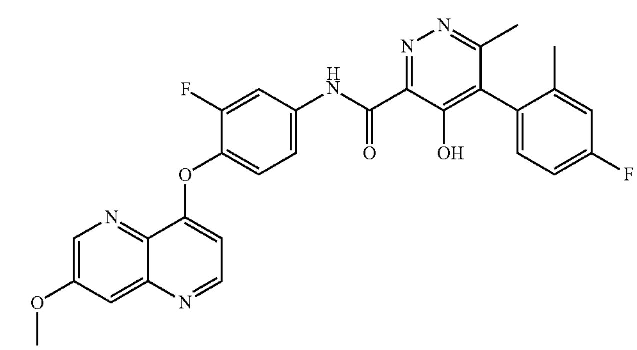 [SMILES: COc1cnc2c(Oc3ccc(NC(=O)c4nnc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropisomer 2 |

TABLE 1-continued

| Cpd # | Structure | IUPAC Name |
|---|---|---|
| 250 | 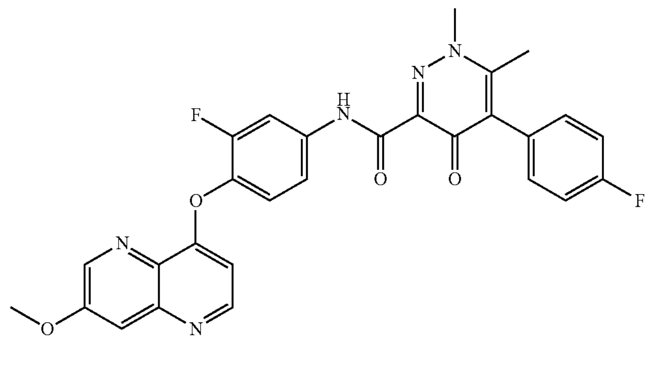 [SMILES: COc1cnc2c(Oc3ccc(NC(=O)c4nn(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,6-dimethyl-4-oxopyridazine-3-carboxamide |
| 251 | 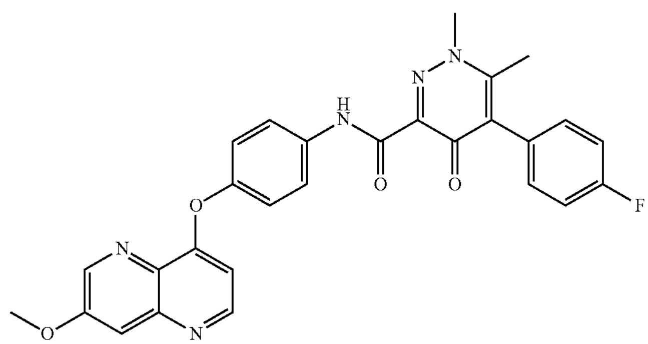 [SMILES: COc1cnc2c(Oc3ccc(NC(=O)c4nn(C)c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-1,6-dimethyl-4-oxopyridazine-3-carboxamide |
| 252 | 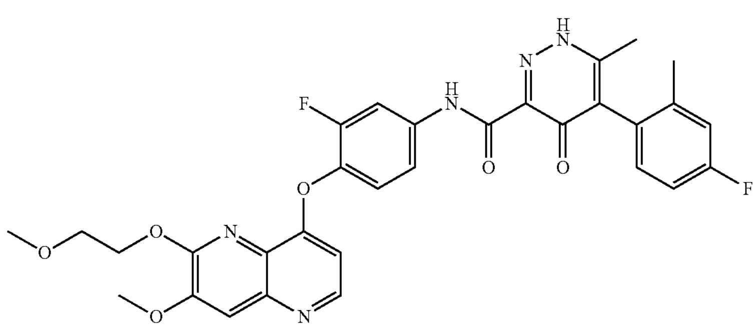 [SMILES: COCCOc1nc2c(Oc3ccc(NC(=O)c4n[nH]c(C)c(-c5ccc(F)cc5C)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-6-methyl-4-oxo-1H-pyridazine-3-carboxamide |
| 253 | 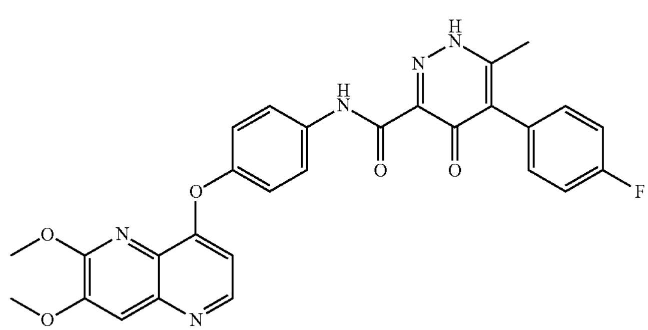 [SMILES: COc1cc2nccc(Oc3ccc(NC(=O)c4n[nH]c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-methyl-4-oxo-1H-pyridazine-3-carboxamide |

TABLE 1-continued

| Cpd # | Structure | IUPAC Name |
|---|---|---|
| 254 | 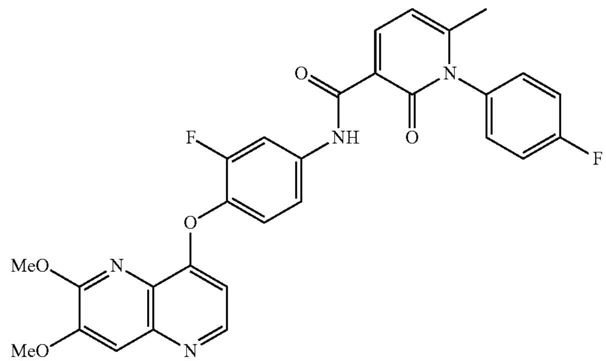 | N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 255 | 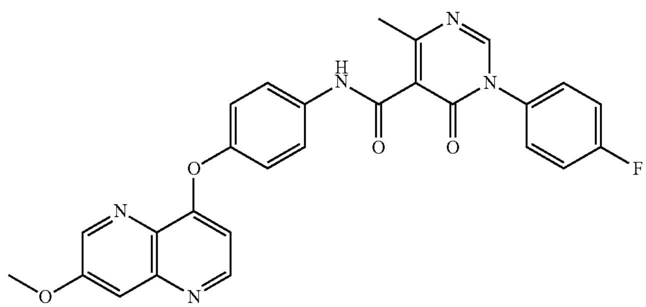 [SMILES: COc1cnc2c(Oc3ccc(NC(=O)c4c(C)ncn(-c5ccc(F)cc5)c4=O)cc3)ccnc2c1] | 1-(4-fluorophenyl)-N-[4-[(7-methoxy-1,5-naphthyridin-4-yl)oxy]phenyl]-4-methyl-6-oxopyrimidine-5-carboxamide |
| 256 | 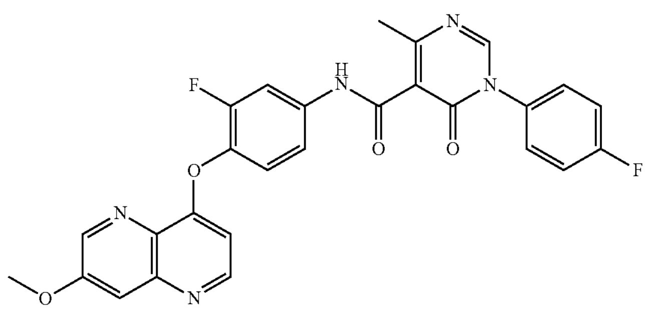 [SMILES: COc1cnc2c(Oc3ccc(NC(=O)c4c(C)ncn(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4-methyl-6-oxopyrimidine-5-carboxamide |
| 257 | 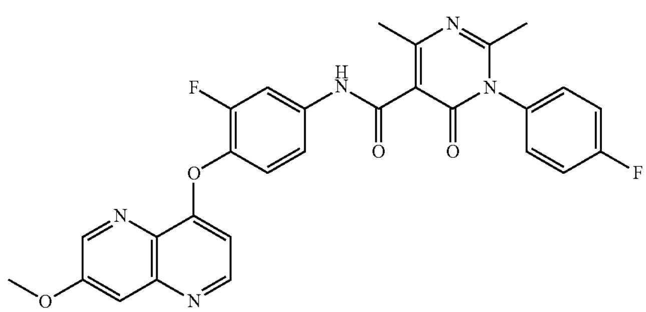 [SMILES: COc1cnc2c(Oc3ccc(NC(=O)c4c(C)nc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-2,4-dimethyl-6-oxopyrimidine-5-carboxamide |
| 258 | 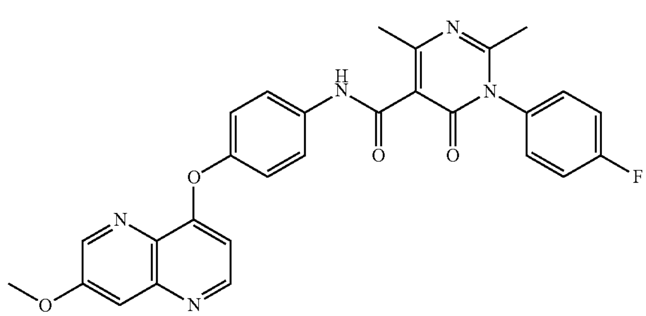 [SMILES: COc1cnc2c(Oc3ccc(NC(=O)c4c(C)nc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-2,4-dimethyl-6-oxopyrimidine-5-carboxamide |

TABLE 1-continued

| Cpd # | Structure | IUPAC Name |
|---|---|---|
| 259 | 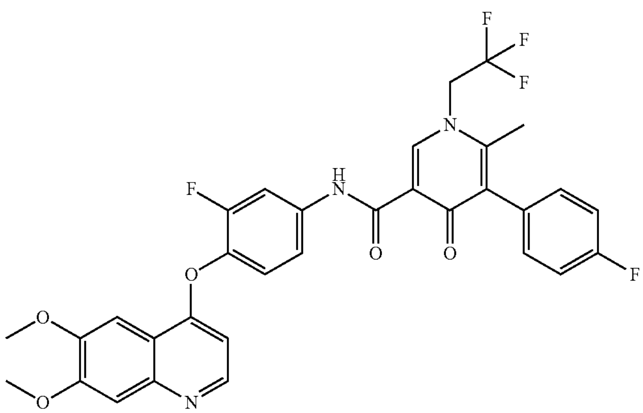 [SMILES: COc1cc2nccc(Oc3ccc(NC(=O)c4cn(CC(F)(F)F)c(C)c(-c5ccc(F)cc5)c4=O)cc3F)c2cc1OC] | N-[4-(6,7-dimethoxyquinolin-4-yl)oxy-3-fluorophenyl]-5-(4-fluorophenyl)-6-methyl-4-oxo-1-(2,2,2-trifluoroethyl)pyridine-3-carboxamide |
| 260 | 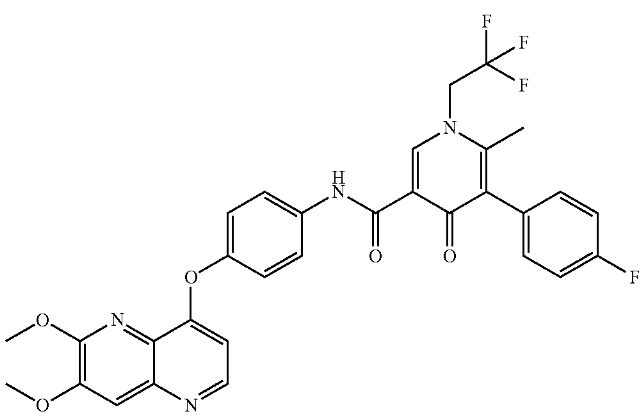 [SMILES: COc1cc2nccc(Oc3ccc(NC(=O)c4cn(CC(F)(F)F)c(C)c(-c5ccc(F)cc5)c4=O)cc3)c2nc1OC] | N-[4-(6,7-dimethoxyquinolin-4-yl)oxyphenyl]-5-(4-fluorophenyl)-6-methyl-4-oxo-1-(2,2,2-trifluoroethyl)pyridine-3-carboxamide |
| 261 | 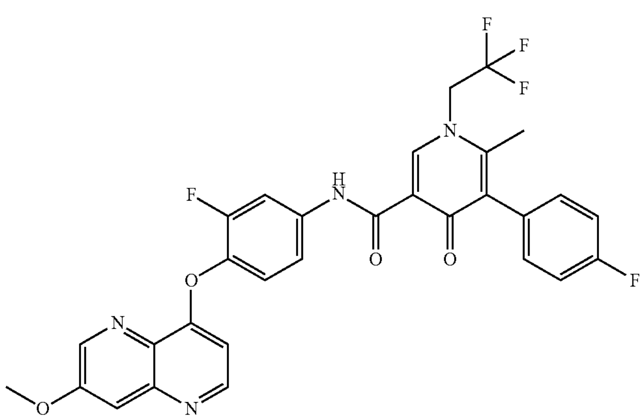 [SMILES: COc1cnc2c(Oc3ccc(NC(=O)c4cn(CC(F)(F)F)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1-(2,2,2-trifluoroethyl)pyridine-3-carboxamide |
| 262 | 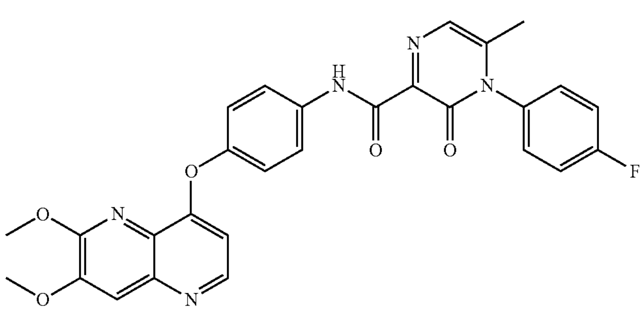 [SMILES: COc1cc2nccc(Oc3ccc(NC(=O)c4ncc(C)n(-c5ccc(F)cc5)c4=O)cc3)c2nc1OC] | N-[4-[(6,7-dimethoxy-1,5-naphthyridin-4-yl)oxy]phenyl]-4-(4-fluorophenyl)-5-methyl-3-oxopyrazine-2-carboxamide |

TABLE 1-continued

| Cpd # | Structure | IUPAC Name |
|---|---|---|
| 263 | 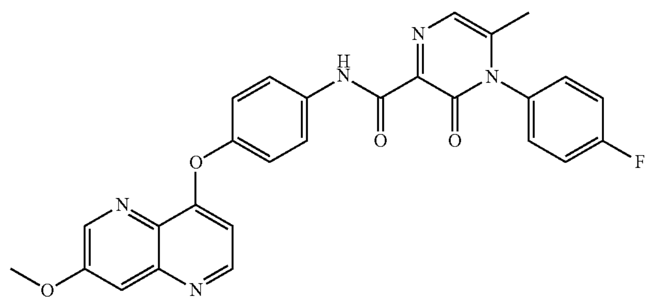 [SMILES: COc1cnc2c(Oc3ccc(NC(=O)c4ncc(C)n(-c5ccc(F)cc5)c4=O)cc3)ccnc2c1] | 4-(4-fluorophenyl)-N-[4-[(7-methoxy-1,5-naphthyridin-4-yl)oxy]phenyl]-5-methyl-3-oxopyrazine-2-carboxamide |
| 264 | 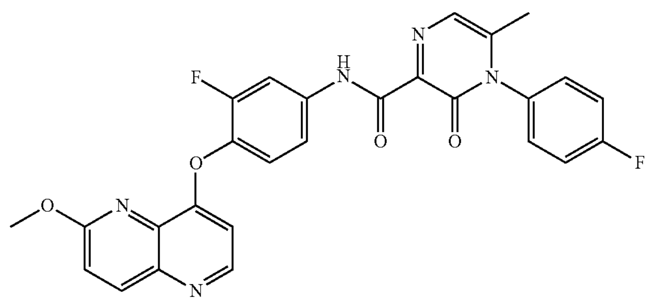 [SMILES: COc1ccc2nccc(Oc3ccc(NC(=O)c4ncc(C)n(-c5ccc(F)cc5)c4=O)cc3F)c2n1] | N-[3-fluoro-4-[(6-methoxy-1,5-naphthyridin-4-yl)oxy]phenyl]-4-(4-fluorophenyl)-5-methyl-3-oxopyrazine-2-carboxamide |
| 265 | 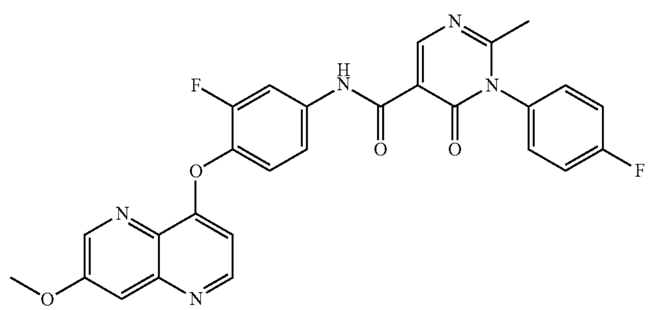 [SMILES: COc1cnc2c(Oc3ccc(NC(=O)c4cnc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-2-methyl-6-oxopyrimidine-5-carboxamide |
| 266 | 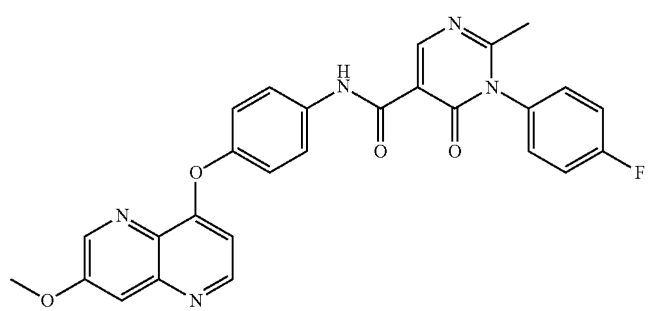 [SMILES: COc1cnc2c(Oc3ccc(NC(=O)c4cnc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-2-methyl-6-oxopyrimidine-5-carboxamide |
| 267 | 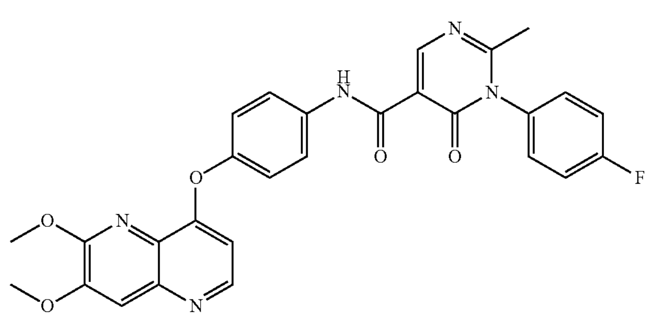 [SMILES: COc1cc2nccc(Oc3ccc(NC(=O)c4cnc(C)n(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-2-methyl-6-oxopyrimidine-5-carboxamide |

TABLE 1-continued

| Cpd # | Structure | IUPAC Name |
|---|---|---|
| 268 | 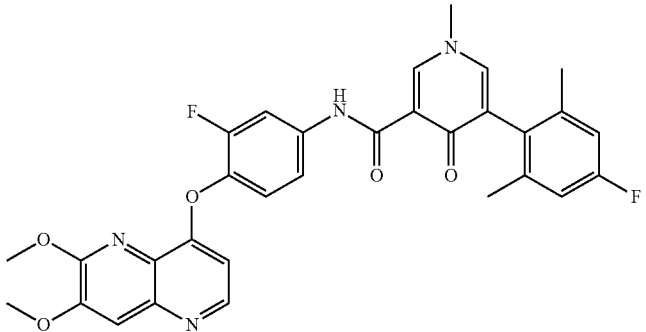 [SMILES: COc1cc2nccc(Oc3ccc(NC(=O)c4cn(C)cc(-c5c(C)cc(F)cc5C)c4=O)cc3F)c2nc1OC] | N-[4-[(6,7-dimethoxy-1,5-naphthyridin-4-yl)oxy]-3-fluorophenyl]-5-(4-fluoro-2,6-dimethylphenyl)-1-methyl-4-oxopyridine-3-carboxamide |
| 269 | 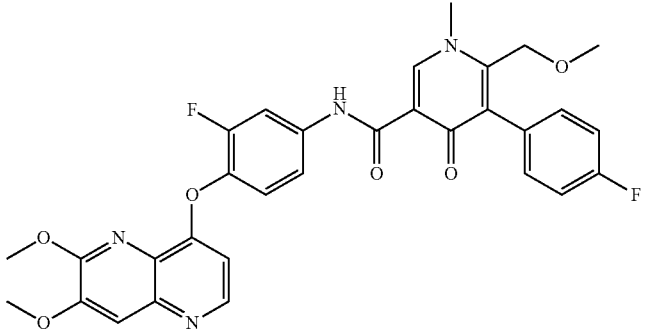 | N-[4-[(6,7-dimethoxy-1,5-naphthyridin-4-yl)oxy]-3-fluorophenyl]-5-(4-fluorophenyl)-6-(methoxymethyl)-1-methyl-4-oxopyridine-3-carboxamide |
| 270 | 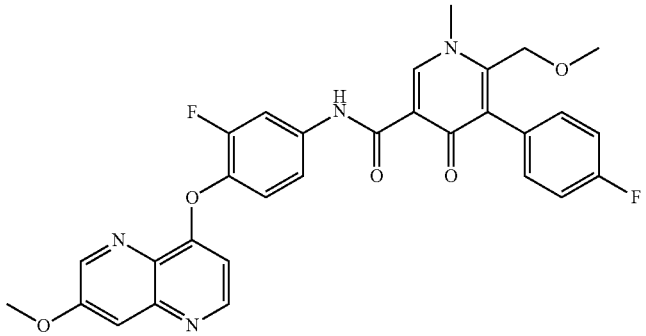 [SMILES: COCc1c(-c2ccc(F)cc2)c(=O)c(C(=O)Nc2ccc(Oc3ccnc4cc(OC)cnc34)c(F)c2)cn1C] | N-[3-fluoro-4-[(7-methoxy-1,5-naphthyridin-4-yl)oxy]phenyl]-5-(4-fluorophenyl)-6-(methoxymethyl)-1-methyl-4-oxopyridine-3-carboxamide |
| 271 | 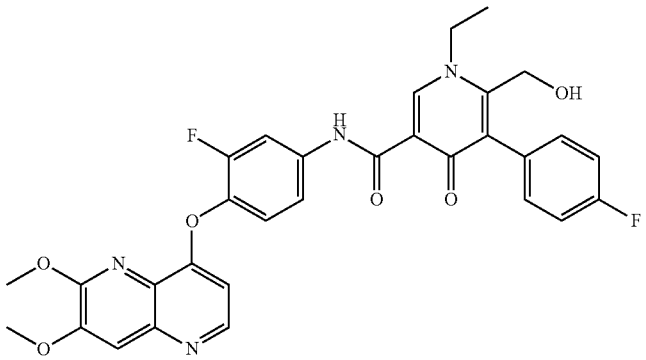 [SMILES: CCn1cc(C(=O)Nc2ccc(Oc3ccnc4cc(OC)c(OC)nc34)c(F)c2)c(=O)c(-c2ccc(F)cc2)c1CO] | N-[4-[(6,7-dimethoxy-1,5-naphthyridin-4-yl)oxy]-3-fluorophenyl]-1-ethyl-5-(4-fluorophenyl)-6-(hydroxymethyl)-4-oxopyridine-3-carboxamide |

TABLE 1-continued

| Cpd # | Structure | IUPAC Name |
|---|---|---|
| 272 | 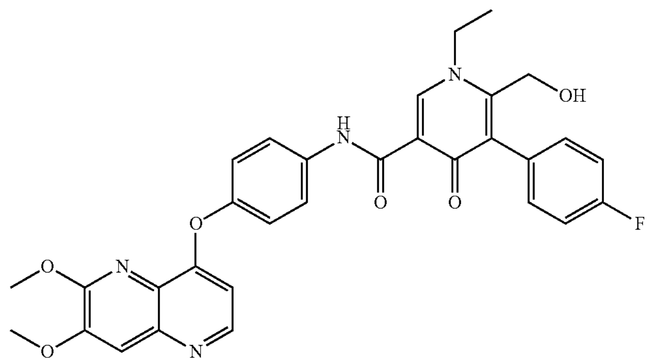 [SMILES: CCn1cc(C(=O)Nc2ccc(Oc3ccnc4cc(OC)c(OC)nc34)cc2)c(=O)c(-c2ccc(F)cc2)c1CO] | N-[4-[(6,7-dimethoxy-1,5-naphthyridin-4-yl)oxy]phenyl]-1-ethyl-5-(4-fluorophenyl)-6-(hydroxymethyl)-4-oxopyridine-3-carboxamide |
| 273 | 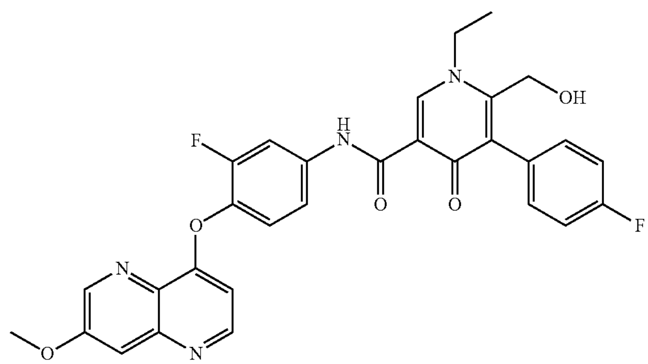 [SMILES: CCn1cc(C(=O)Nc2ccc(Oc3ccnc4cc(OC)cnc34)c(F)c2)c(=O)c(-c2ccc(F)cc2)c1CO] | 1-ethyl-N-[3-fluoro-4-[(7-methoxy-1,5-naphthyridin-4-yl)oxy]phenyl]-5-(4-fluorophenyl)-6-(hydroxymethyl)-4-oxopyridine-3-carboxamide |
| 274 | 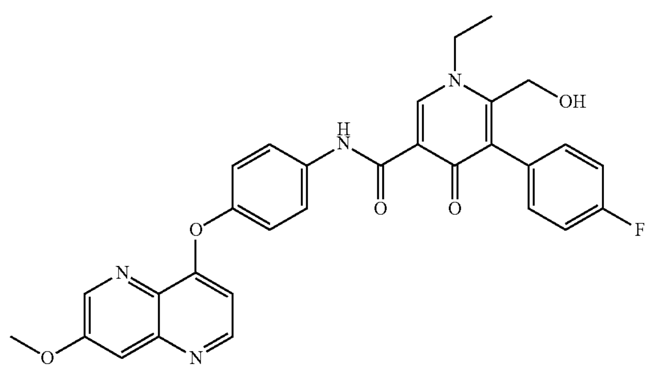 [SMILES: CCn1cc(C(=O)Nc2ccc(Oc3ccnc4cc(OC)cnc34)cc2)c(=O)c(-c2ccc(F)cc2)c1CO] | 1-ethyl-5-(4-fluorophenyl)-6-(hydroxymethyl)-N-[4-[(7-methoxy-1,5-naphthyridin-4-yl)oxy]phenyl]-4-oxopyridine-3-carboxamide |
| 275 | 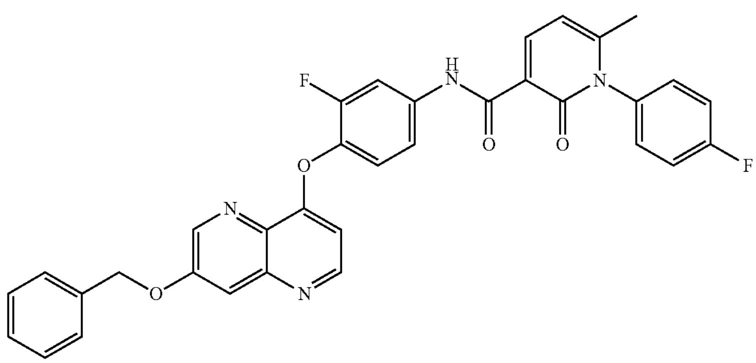 [SMILES: Cc1ccc(C(=O)Nc2ccc(Oc3ccnc4cc(OCc5ccccc5)cnc34)c(F)c2)c(=O)n1-c1ccc(F)cc1] | 1-(4-fluorophenyl)-N-[3-fluoro-4-[(7-phenylmethoxy-1,5-naphthyridin-4-yl)oxy]phenyl]-6-methyl-2-oxopyridine-3-carboxamide |

TABLE 1-continued

| Cpd # | Structure | IUPAC Name |
|---|---|---|
| 276 | 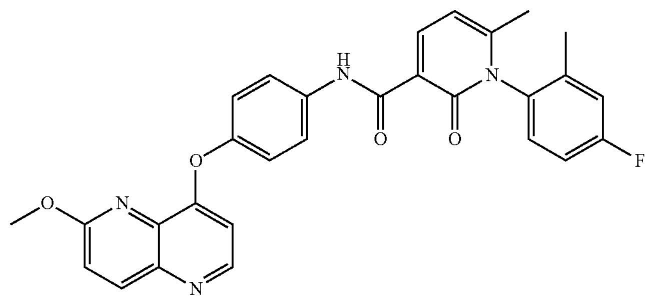 [SMILES: COc1ccc2nccc(Oc3ccc(NC(=O)c4ccc(C)n(-c5ccc(F)cc5C)c4=O)cc3)c2n1] | 1-(4-fluoro-2-methylphenyl)-N-[4-[(6-methoxy-1,5-naphthyridin-4-yl)oxy]phenyl]-6-methyl-2-oxopyridine-3-carboxamide |
| 277 | 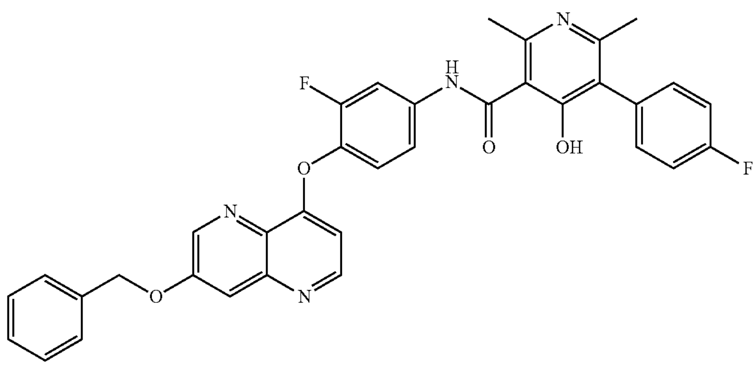 [SMILES: Cc1nc(C)c(-c2ccc(F)cc2)c(O)c1C(=O)Nc1ccc(Oc2ccnc3cc(OCc4ccccc4)cnc23)c(F)c1] | 5-(4-fluorophenyl)-N-[3-fluoro-4-[(7-phenylmethoxy-1,5-naphthyridin-4-yl)oxy]phenyl]-4-hydroxy-2,6-dimethylpyridine-3-carboxamide |
| 278 | 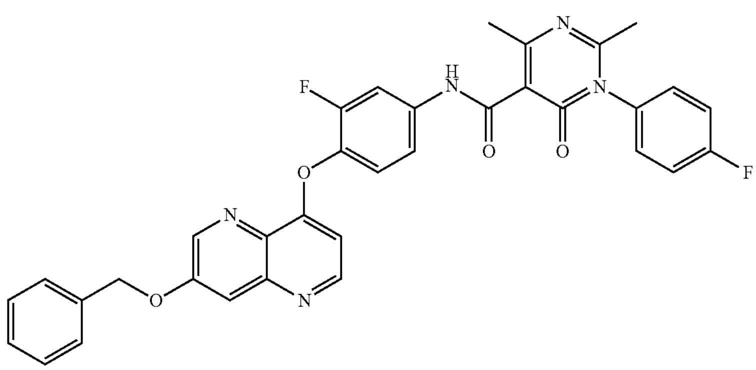 | 1-(4-fluorophenyl)-N-[3-fluoro-4-[(7-phenylmethoxy-1,5-naphthyridin-4-yl)oxy]phenyl]-2,4-dimethyl-6-oxopyrimidine-5-carboxamide |
| 279 | 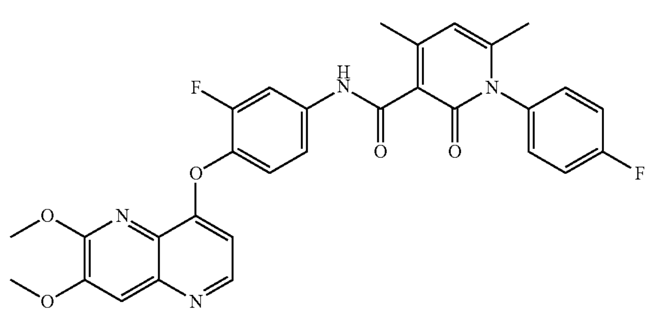 [SMILES: COc1cc2nccc(Oc3ccc(NC(=O)c4c(C)cc(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |

TABLE 1-continued

| Cpd # | Structure | IUPAC Name |
|---|---|---|
| 280 | 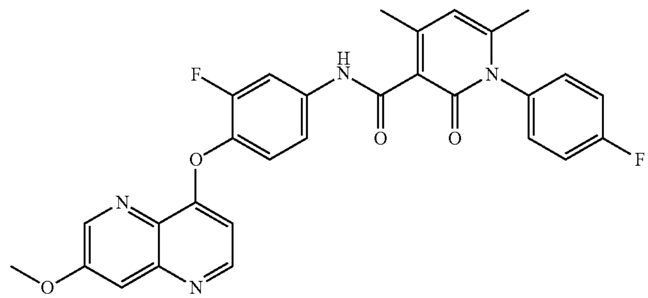 [SMILES: COc1cnc2c(Oc3ccc(NC(=O)c4c(C)cc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 281 | 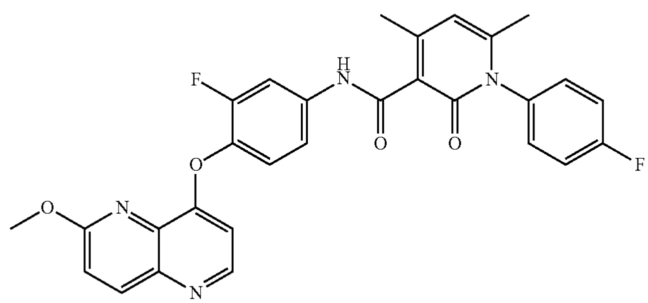 [SMILES: COc1ccc2nccc(Oc3ccc(NC(=O)c4c(C)cc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-4,6-dimethyl-2-oxopyridine-3-carboxamide |
| 282 | 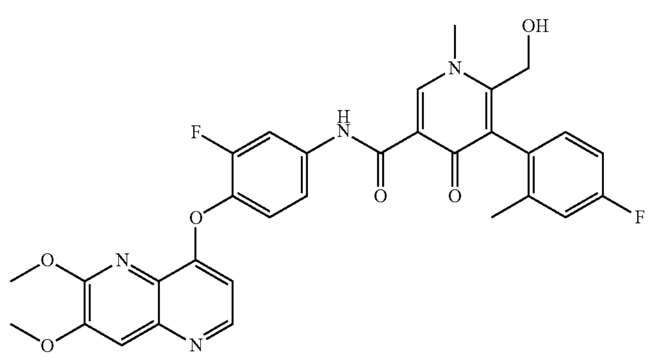 [SMILES: COc1cc2nccc(Oc3ccc(NC(=O)c4cn(C)c(CO)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-6-(hydroxymethyl)-1-methyl-4-oxopyridine-3-carboxamide |
| 283 | 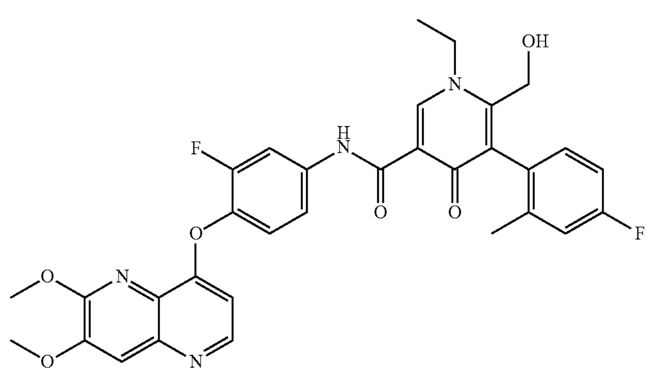 [SMILES: CCn1cc(C(=O)Nc2ccc(Oc3ccnc4cc(OC)c(OC)nc34)c(F)c2)c(=O)c(-c2ccc(F)cc2C)c1CO] | N-[4-[(6,7-dimethoxy-1,5-naphthyridin-4-yl)oxy]-3-fluorophenyl]-1-ethyl-5-(4-fluoro-2-methylphenyl)-6-(hydroxymethyl)-4-oxopyridine-3-carboxamide |

TABLE 1-continued

| Cpd # | Structure | IUPAC Name |
| --- | --- | --- |
| 284 | 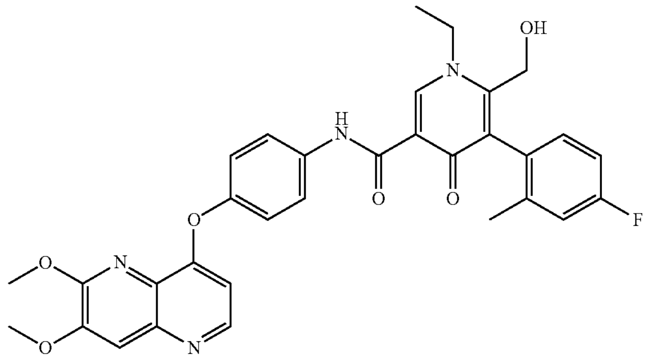 [SMILES: CCn1cc(C(=O)Nc2ccc(Oc3ccnc4cc(OC)c(OC)nc34)cc2)c(=O)c(-c2ccc(F)cc2C)c1CO] | N-[4-[(6,7-dimethoxy-1,5-naphthyridin-4-yl)oxy]phenyl]-1-ethyl-5-(4-fluoro-2-methylphenyl)-6-(hydroxymethyl)-4-oxopyridine-3-carboxamide |
| 285 | 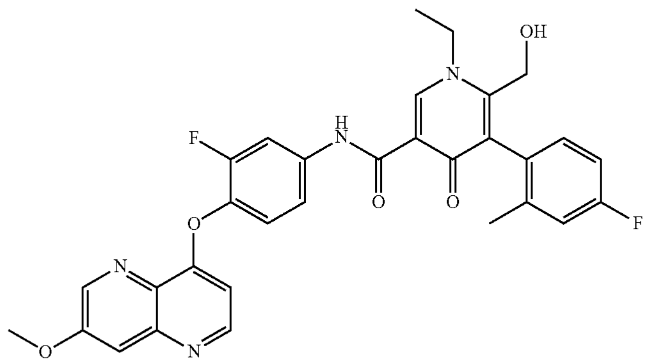 [SMILES: CCn1cc(C(=O)Nc2ccc(Oc3ccnc4cc(OC)cnc34)c(F)c2)c(=O)c(-c2ccc(F)cc2C)c1CO] | 1-ethyl-N-[3-fluoro-4-[(7-methoxy-1,5-naphthyridin-4-yl)oxy]phenyl]-5-(4-fluoro-2-methylphenyl)-6-(hydroxymethyl)-4-oxopyridine-3-carboxamide |
| 286 | 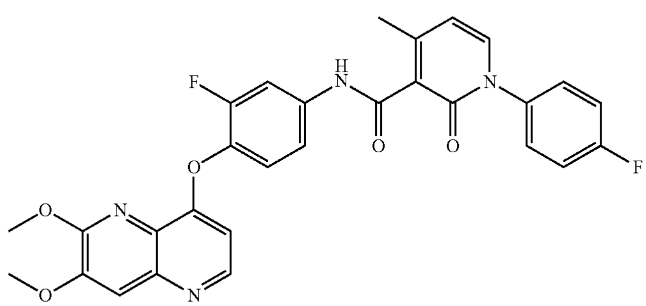 | N-[4-[(6,7-dimethoxy-1,5-naphthyridin-4-yl)oxy]-3-fluorophenyl]-1-(4-fluorophenyl)-4-methyl-2-oxopyridine-3-carboxamide |
| 287 | 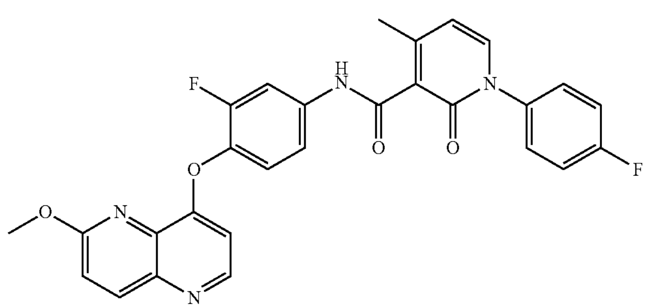 [SMILES: COc1ccc2nccc(Oc3ccc(NC(=O)c4c(C)ccn(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-4-methyl-2-oxopyridine-3-carboxamide |

TABLE 1-continued

| Cpd # | Structure | IUPAC Name |
|---|---|---|
| 288 | 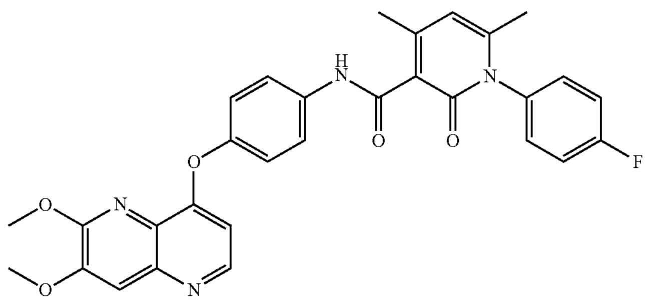 | N-[4-[(6,7-dimethoxy-1,5-naphthyridin-4-yl)oxy]phenyl]-1-(4-fluorophenyl)-4,6-dimethyl-2-oxopyridine-3-carboxamide |
| 289 | 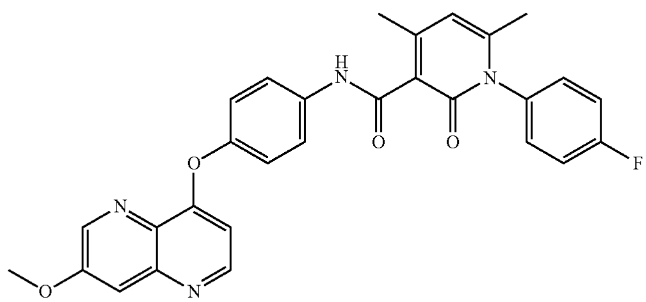 [SMILES: COc1cnc2c(Oc3ccc(NC(=O)c4c(C)cc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-4,6-dimethyl-2-oxopyridine-3-carboxamide |
| 290 | 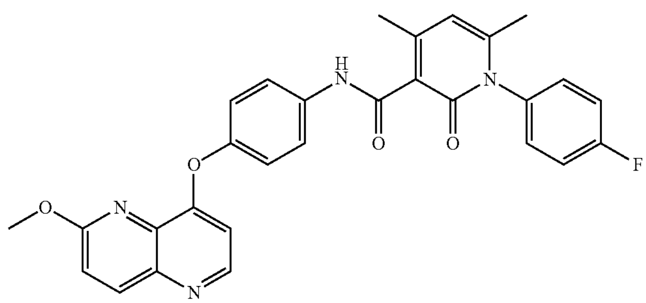 [SMILES: COc1ccc2nccc(Oc3ccc(NC(=O)c4c(C)cc(C)n(-c5ccc(F)cc5)c4=O)cc3)c2n1] | 1-(4-fluorophenyl)-N-[4-[(6-methoxy-1,5-naphthyridin-4-yl)oxy]phenyl]-4,6-dimethyl-2-oxopyridine-3-carboxamide |
| 291 | 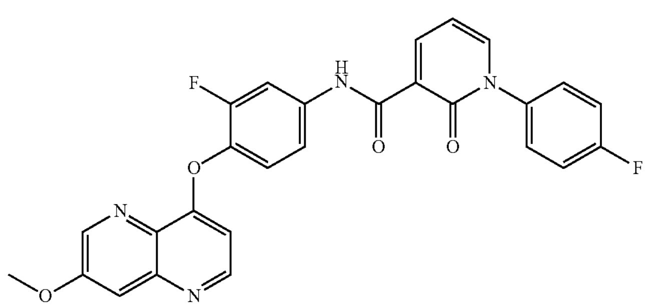 | N-[3-fluoro-4-[(7-methoxy-1,5-naphthyridin-4-yl)oxy]phenyl]-1-(4-fluorophenyl)-2-oxopyridine-3-carboxamide |
| 292 | 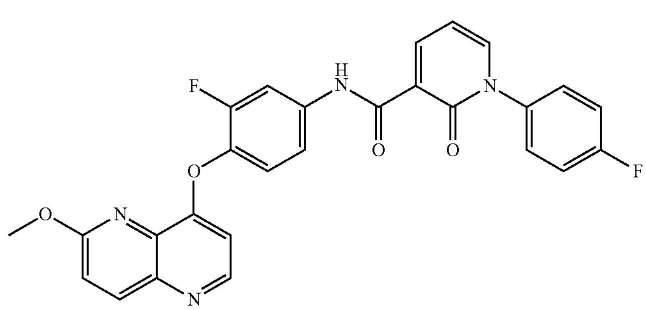 [SMILES: COc1ccc2nccc(Oc3ccc(NC(=O)c4cccn(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-2-oxopyridine-3-carboxamide |

TABLE 1-continued

| Cpd # | Structure | IUPAC Name |
|---|---|---|
| 293 | 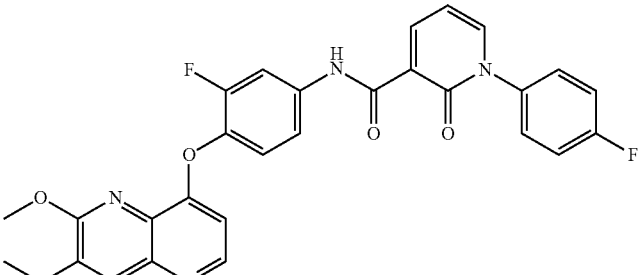 | N-[4-[(6,7-dimethoxy-1,5-naphthyridin-4-yl)oxy]-3-fluorophenyl]-1-(4-fluorophenyl)-2-oxopyridine-3-carboxamide |
| 294 | 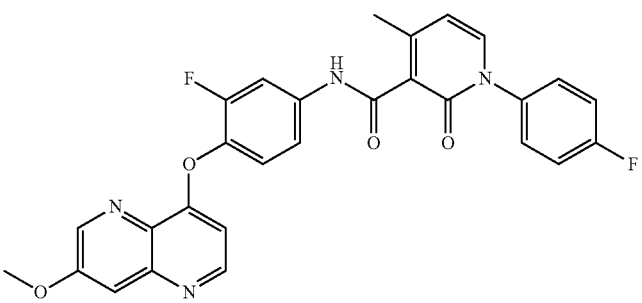 | N-[3-fluoro-4-[(7-methoxy-1,5-naphthyridin-4-yl)oxy]phenyl]-1-(4-fluorophenyl)-4-methyl-2-oxopyridine-3-carboxamide |
| 295 | 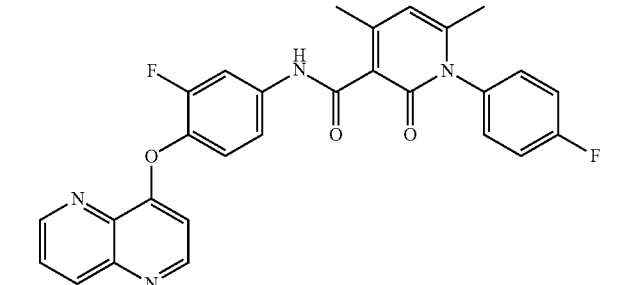 | N-[3-fluoro-4-(1,5-naphthyridin-4-yloxy)phenyl]-1-(4-fluorophenyl)-4,6-dimethyl-2-oxopyridine-3-carboxamide |
| 296 | 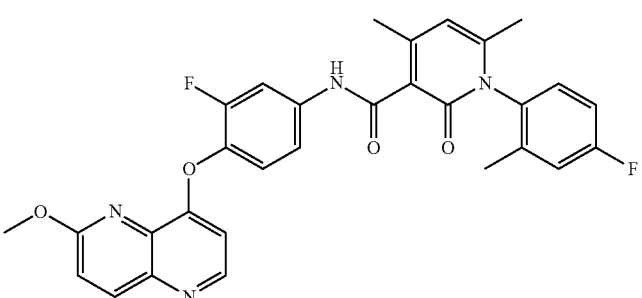 | N-[3-fluoro-4-[(6-methoxy-1,5-naphthyridin-4-yl)oxy]phenyl]-1-(4-fluoro-2-methylphenyl)-4,6-dimethyl-2-oxopyridine-3-carboxamide |
| 297 | 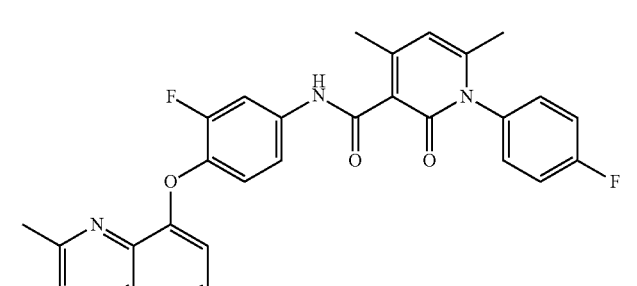 | N-[3-fluoro-4-[(6-methyl-1,5-naphthyridin-4-yl)oxy]phenyl]-1-(4-fluorophenyl)-4,6-dimethyl-2-oxopyridine-3-carboxamide |

TABLE 1-continued

| Cpd # | Structure | IUPAC Name |
|---|---|---|
| 298 | 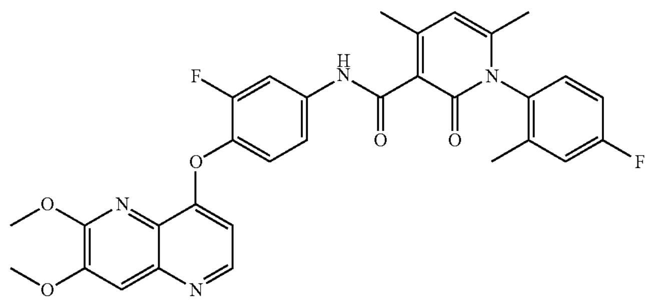 [SMILES: COc1cc2nccc(Oc3ccc(NC(=O)c4c(C)cc(C)n(-c5ccc(F)cc5C)c4=O)cc3F)c2nc1OC] | N-[4-[(6,7-dimethoxy-1,5-naphthyridin-4-yl)oxy]-3-fluorophenyl]-1-(4-fluoro-2-methylphenyl)-4,6-dimethyl-2-oxopyridine-3-carboxamide |
| 299 | 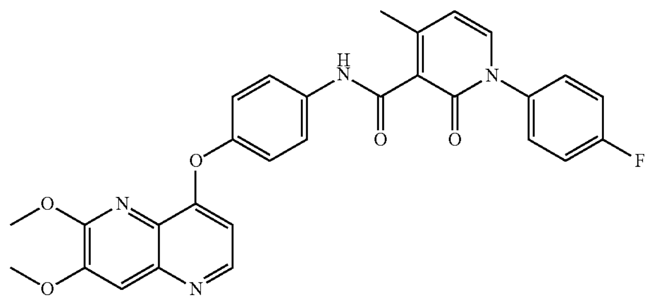 [SMILES: COc1cc2nccc(Oc3ccc(NC(=O)c4c(C)ccn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-4-methyl-2-oxopyridine-3-carboxamide |
| 300 | 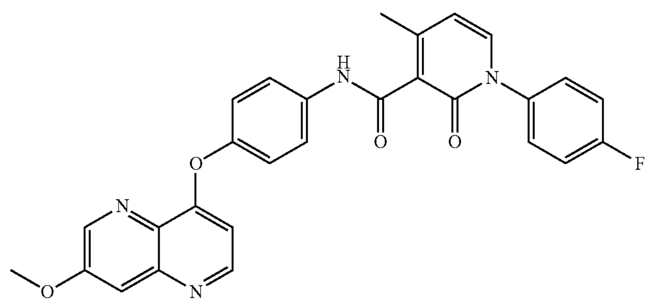 [SMILES: COc1cnc2c(Oc3ccc(NC(=O)c4c(C)ccn(-c5ccc(F)cc5)c4=O)cc3)ccnc2c1] | 1-(4-fluorophenyl)-N-[4-[(7-methoxy-1,5-naphthyridin-4-yl)oxy]phenyl]-4-methyl-2-oxopyridine-3-carboxamide |
| 301 | 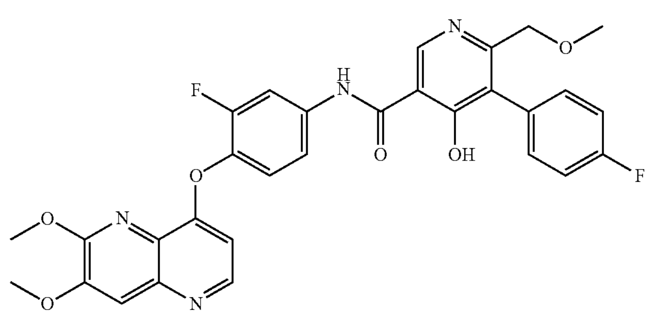 [SMILES: COCc1ncc(C(=O)Nc2ccc(Oc3ccnc4cc(OC)c(OC)nc34)c(F)c2)c(O)c1-c1ccc(F)cc1] | N-[4-[(6,7-dimethoxy-1,5-naphthyridin-4-yl)oxy]-3-fluorophenyl]-5-(4-fluorophenyl)-4-hydroxy-6-(methoxymethyl)pyridine-3-carboxamide |
| 302 | 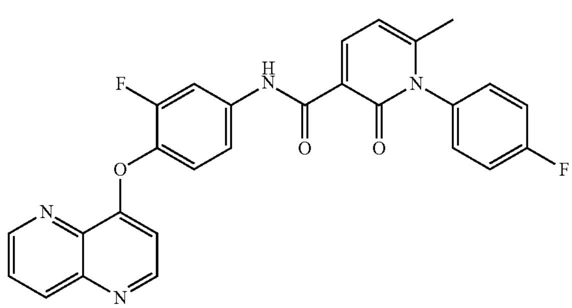 [SMILES: Cc1ccc(C(=O)Nc2ccc(Oc3ccnc4cccnc34)c(F)c2)c(=O)n1-c1ccc(F)cc1] | N-[3-fluoro-4-(1,5-naphthyridin-4-yloxy)phenyl]-1-(4-fluorophenyl)-6-methyl-2-oxopyridine-3-carboxamide |

TABLE 1-continued

| Cpd # | Structure | IUPAC Name |
|---|---|---|
| 303 | 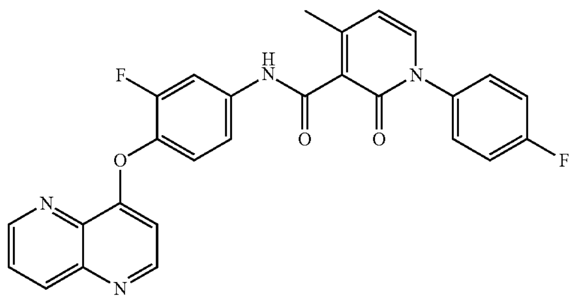 [SMILES: Cc1ccn(-c2ccc(F)cc2)c(=O)c1C(=O)Nc1ccc(Oc2ccnc3cccnc23)c(F)c1] | N-[3-fluoro-4-(1,5-naphthyridin-4-yloxy)phenyl]-1-(4-fluorophenyl)-4-methyl-2-oxopyridine-3-carboxamide |
| 304 | 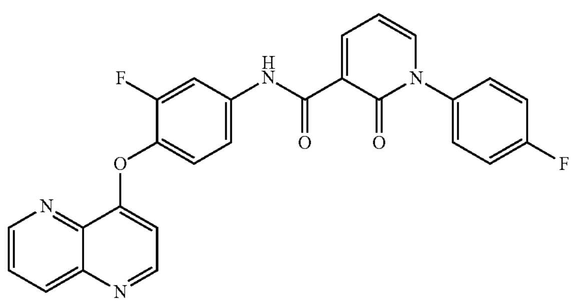 | N-[3-fluoro-4-(1,5-naphthyridin-4-yloxy)phenyl]-1-(4-fluorophenyl)-2-oxopyridine-3-carboxamide |
| 305 | 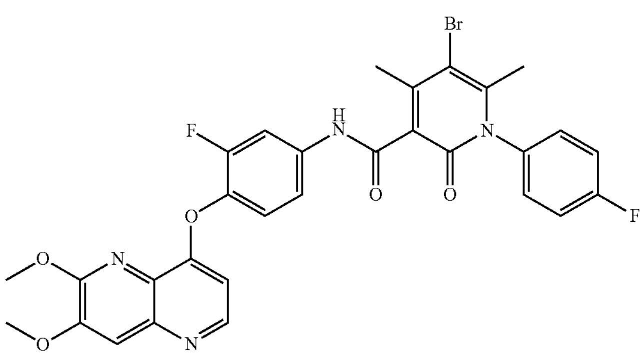 | 5-bromo-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 306 | 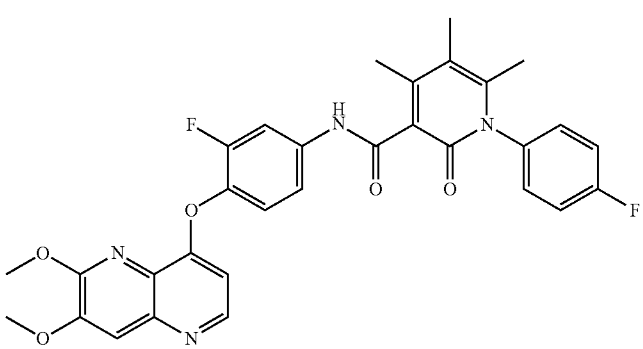 [SMILES: COc1cc2nccc(Oc3ccc(NC(=O)c4c(C)c(C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4,5,6-trimethyl-2-oxopyridine-3-carboxamide |

TABLE 1-continued

| Cpd # | Structure | IUPAC Name |
|---|---|---|
| 307 | 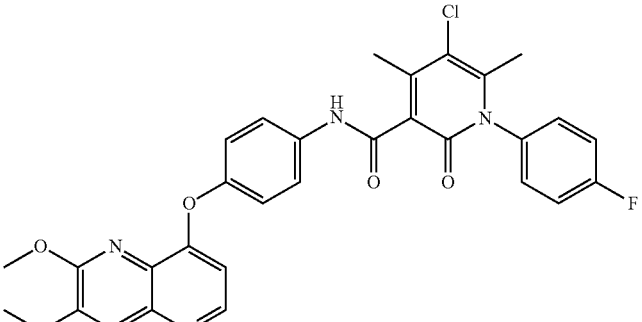 | 5-chloro-N-[4-[(6,7-dimethoxy-1,5-naphthyridin-4-yl)oxy]phenyl]-1-(4-fluorophenyl)-4,6-dimethyl-2-oxopyridine-3-carboxamide |
| 308 | 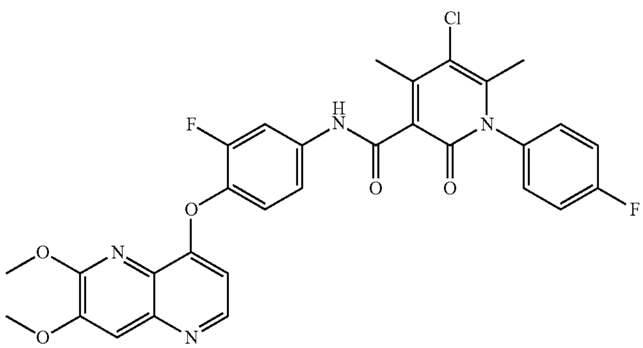 | 5-chloro-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 309 | 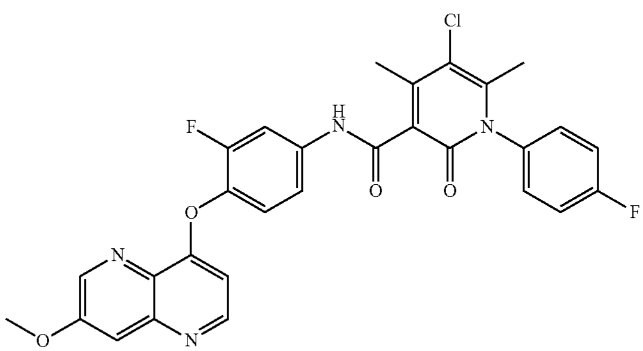 | 5-chloro-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 310 | 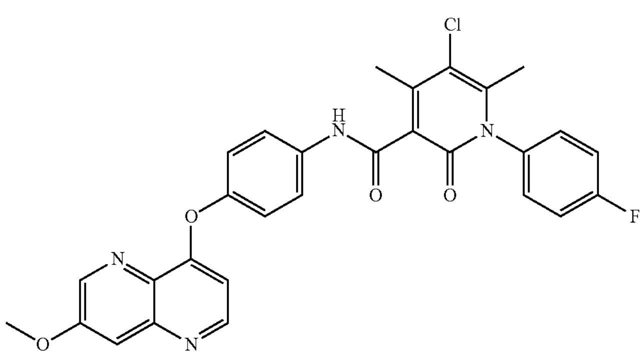 [SMILES: COc1cnc2c(Oc3ccc(NC(=O)c4c(C)c(Cl)c(C)n(-c5ccc(F)cc5)c4=O)cc3)ccnc2c1] | 5-chloro-1-(4-fluorophenyl)-N-[4-[(7-methoxy-1,5-naphthyridin-4-yl)oxy]phenyl]-4,6-dimethyl-2-oxopyridine-3-carboxamide |

TABLE 1-continued

| Cpd # | Structure | IUPAC Name |
|---|---|---|
| 311 | 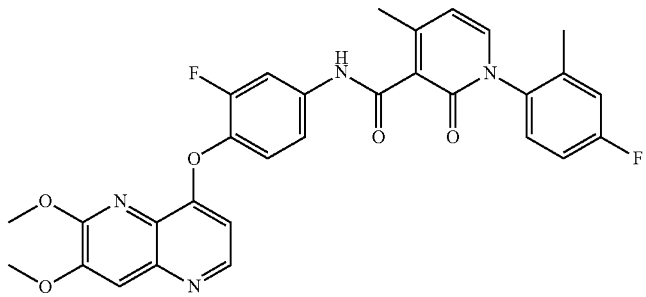 [SMILES: COc1cc2nccc(Oc3ccc(NC(=O)c4c(C)ccn(-c5ccc(F)cc5C)c4=O)cc3F)c2nc1OC] | N-[4-[(6,7-dimethoxy-1,5-naphthyridin-4-yl)oxy]-3-fluorophenyl]-1-(4-fluoro-2-methylphenyl)-4-methyl-2-oxopyridine-3-carboxamide |
| 312 | 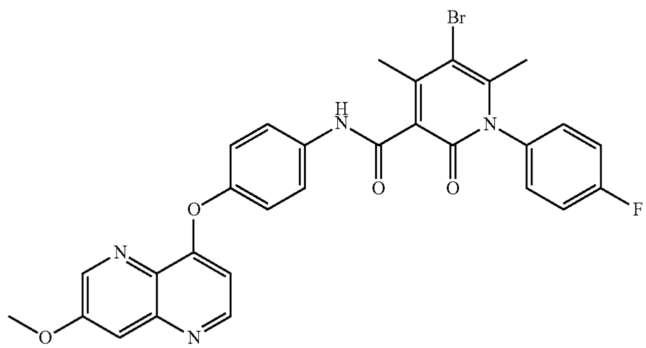 | 5-bromo-1-(4-fluorophenyl)-N-[4-[(7-methoxy-1,5-naphthyridin-4-yl)oxy]phenyl]-4,6-dimethyl-2-oxopyridine-3-carboxamide |
| 313 | 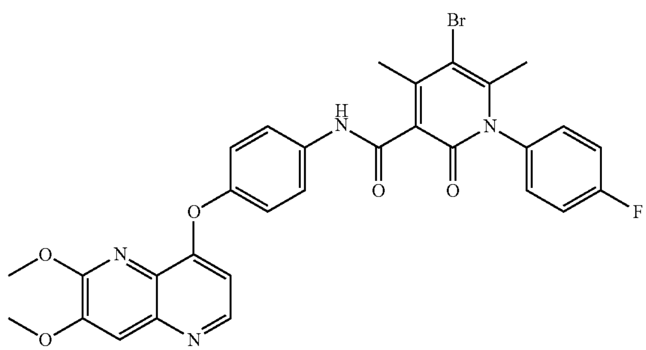 | 5-bromo-N-[4-[(6,7-dimethoxy-1,5-naphthyridin-4-yl)oxy]phenyl]-1-(4-fluorophenyl)-4,6-dimethyl-2-oxopyridine-3-carboxamide |
| 314 | 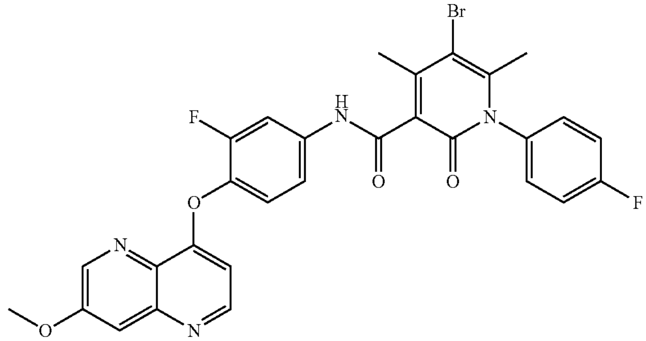 | 5-bromo-N-[3-fluoro-4-[(7-methoxy-1,5-naphthyridin-4-yl)oxy]phenyl]-1-(4-fluorophenyl)-4,6-dimethyl-2-oxopyridine-3-carboxamide |

TABLE 1-continued

| Cpd # | Structure | IUPAC Name |
|---|---|---|
| 315 | 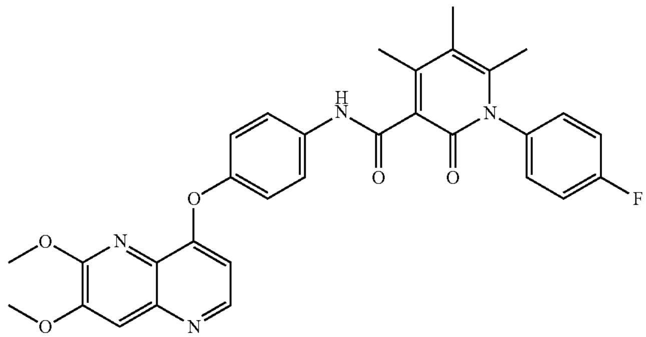 | N-[4-[(6,7-dimethoxy-1,5-naphthyridin-4-yl)oxy]phenyl]-1-(4-fluorophenyl)-4,5,6-trimethyl-2-oxopyridine-3-carboxamide |
| 316 | 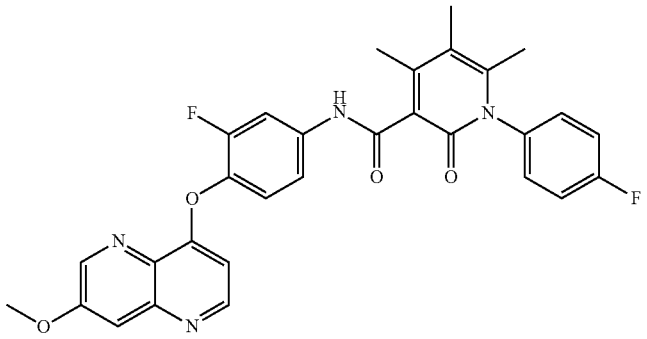 [SMILES: COc1cnc2c(Oc3ccc(NC(=O)c4c(C)c(C)c(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4,5,6-trimethyl-2-oxopyridine-3-carboxamide |
| 317 | 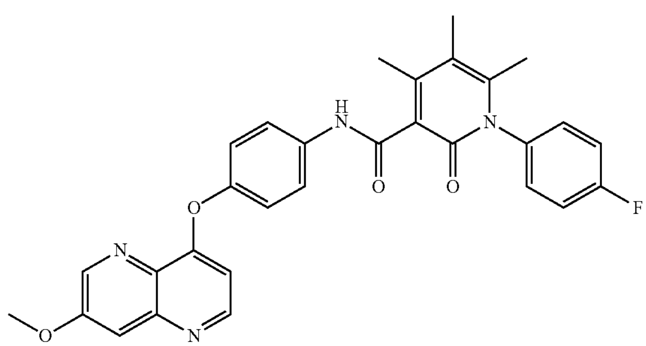 [SMILES: COc1cnc2c(Oc3ccc(NC(=O)c4c(C)c(C)c(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-4,5,6-trimethyl-2-oxopyridine-3-carboxamide |
| 318 | 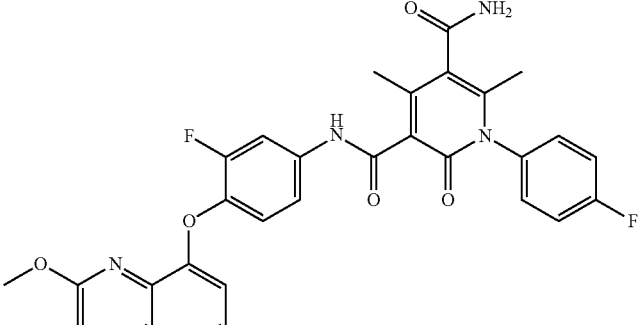 | 5-N-[4-[(6,7-dimethoxy-1,5-naphthyridin-4-yl)oxy]-3-fluorophenyl]-1-(4-fluorophenyl)-2,4-dimethyl-6-oxopyridine-3,5-dicarboxamide |

TABLE 1-continued

| Cpd # | Structure | IUPAC Name |
| --- | --- | --- |
| 319 | 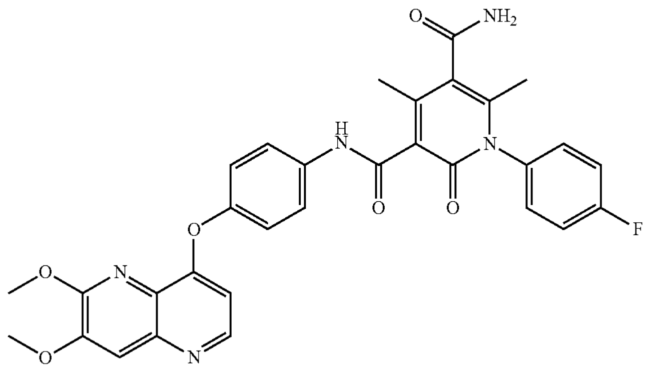 [SMILES: COc1cc2nccc(Oc3ccc(NC(=O)c4c(C)c(C(N)=O)c(C)n(-c5ccc(F)cc5)c4=O)cc3)c2nc1OC] | 5-N-[4-[(6,7-dimethoxy-1,5-naphthyridin-4-yl)oxy]phenyl]-1-(4-fluorophenyl)-2,4-dimethyl-6-oxopyridine-3,5-dicarboxamide |
| 320 | 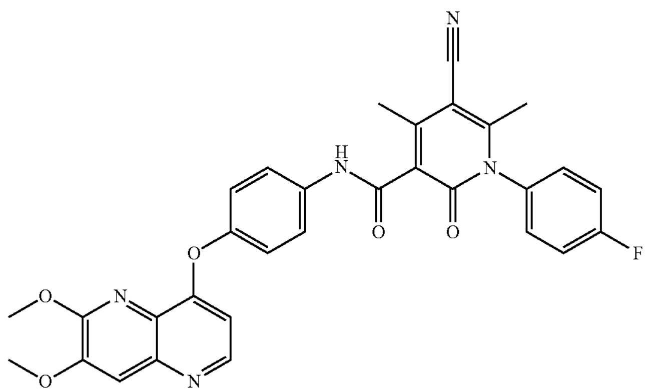 [SMILES: COc1cc2nccc(Oc3ccc(NC(=O)c4c(C)c(C#N)c(C)n(-c5ccc(F)cc5)c4=O)cc3)c2nc1OC] | 5-cyano-N-[4-[(6,7-dimethoxy-1,5-naphthyridin-4-yl)oxy]phenyl]-1-(4-fluorophenyl)-4,6-dimethyl-2-oxopyridine-3-carboxamide |
| 321 | 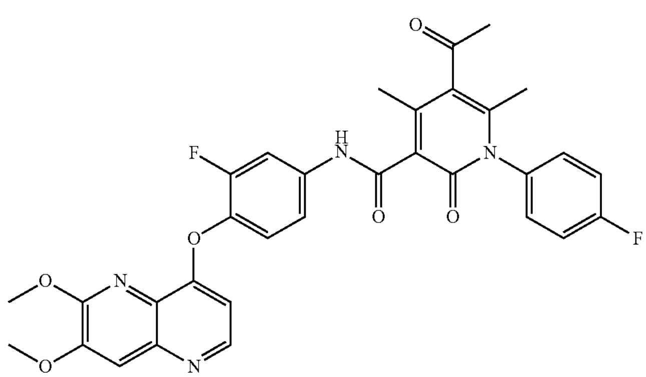 [SMILES: COc1cc2nccc(Oc3ccc(NC(=O)c4c(C)c(C(C)=O)c(C)n(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 322 | 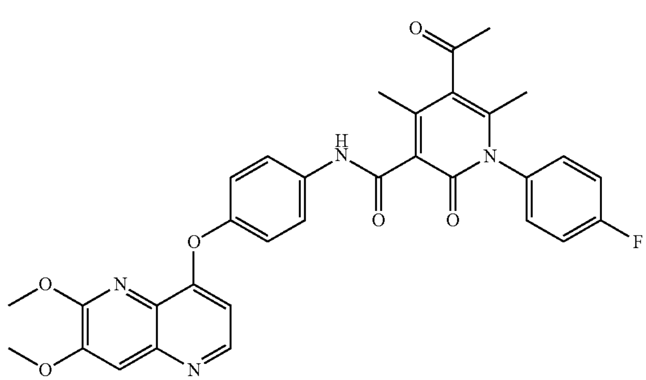 [SMILES: COc1cc2nccc(Oc3ccc(NC(=O)c4c(C)c(C(C)=O)c(C)n(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-4,6-dimethyl-2-oxopyridine-3-carboxamide |

| Cpd # | Structure | IUPAC Name |
|---|---|---|
| 323 | 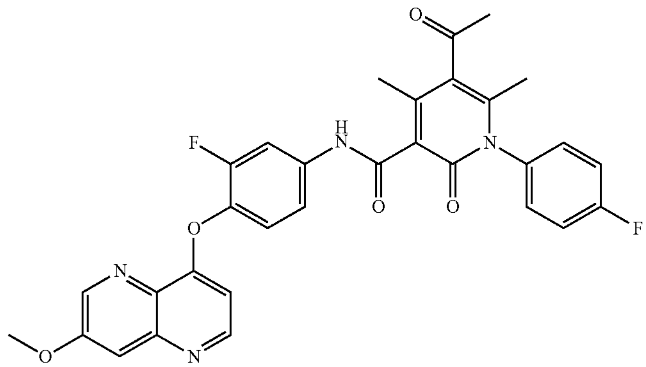 [SMILES: COc1cnc2c(Oc3ccc(NC(=O)c4c(C)c(C(C)=O)c(C)n(-c5ccc(F)cc5)c4=O)cc3F)ccnc2c1] | 5-acetyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 324 | 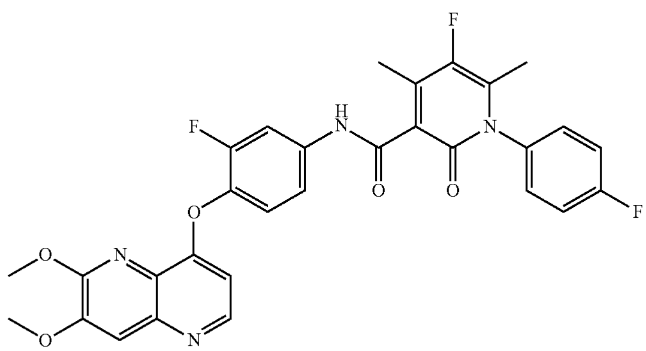 | N-[4-[(6,7-dimethoxy-1,5-naphthyridin-4-yl)oxy]-3-fluorophenyl]-5-fluoro-1-(4-fluorophenyl)-4,6-dimethyl-2-oxopyridine-3-carboxamide |
| 325 | 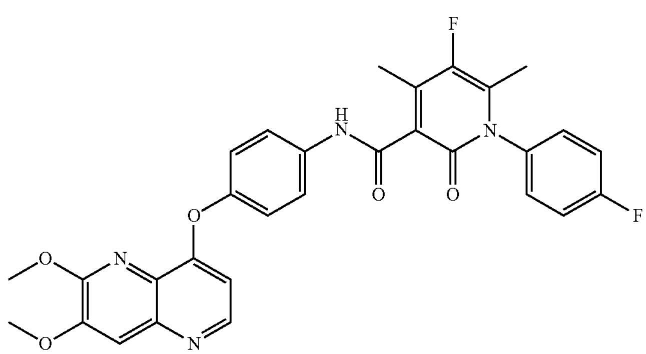 | N-[4-[(6,7-dimethoxy-1,5-naphthyridin-4-yl)oxy]phenyl]-5-fluoro-1-(4-fluorophenyl)-4,6-dimethyl-2-oxopyridine-3-carboxamide |
| 326 | 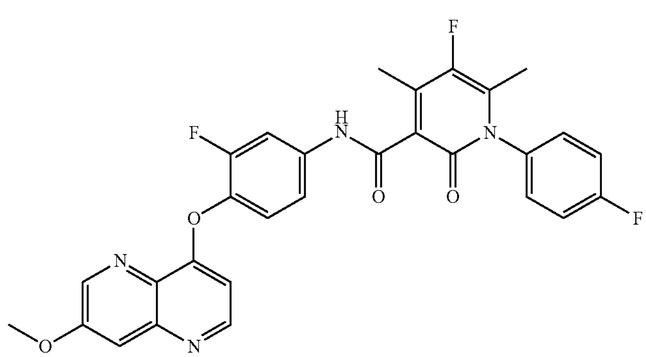 [SMILES: COc1cnc2c(Oc3ccc(NC(=O)c4c(C)c(F)c(C)n(-c5ccc(F)cc5)c4=O)cc3F)ccnc2c1] | 5-fluoro-N-[3-fluoro-4-[(7-methoxy-1,5-naphthyridin-4-yl)oxy]phenyl]-1-(4-fluorophenyl)-4,6-dimethyl-2-oxopyridine-3-carboxamide |

TABLE 1-continued

| Cpd # | Structure | IUPAC Name |
|---|---|---|
| 327 | 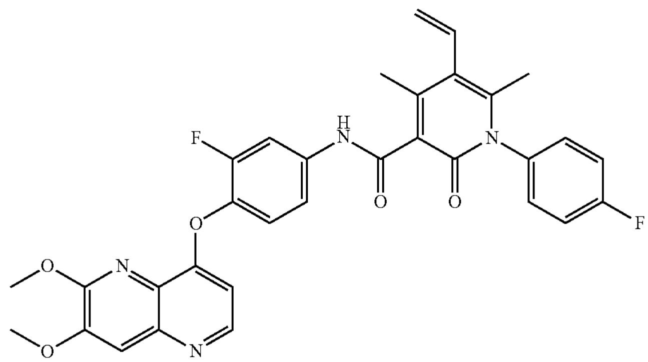 [SMILES: C=Cc1c(C)c(C(=O)Nc2ccc(Oc3ccnc4cc(OC)c(OC)nc34)c(F)c2)c(=O)n(-c2ccc(F)cc2)c1C] | N-[4-[(6,7-dimethoxy-1,5-naphthyridin-4-yl)oxy]-3-fluorophenyl]-5-ethenyl-1-(4-fluorophenyl)-4,6-dimethyl-2-oxopyridine-3-carboxamide |
| 328 | 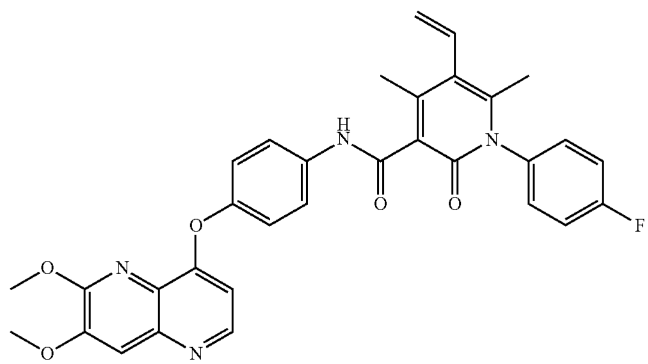 [SMILES: C=Cc1c(C)c(C(=O)Nc2ccc(Oc3ccnc4cc(OC)c(OC)nc34)cc2)c(=O)n(-c2ccc(F)cc2)c1C] | N-[4-[(6,7-dimethoxy-1,5-naphthyridin-4-yl)oxy]phenyl]-5-ethenyl-1-(4-fluorophenyl)-4,6-dimethyl-2-oxopyridine-3-carboxamide |
| 329 | 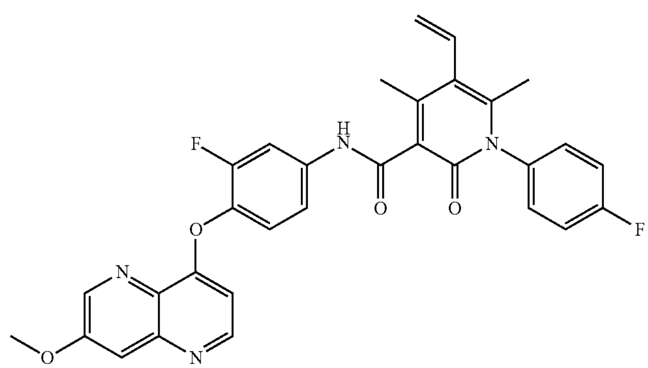 [SMILES: C=Cc1c(C)c(C(=O)Nc2ccc(Oc3ccnc4cc(OC)cnc34)c(F)c2)c(=O)n(-c2ccc(F)cc2)c1C] | 5-ethenyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 330 | 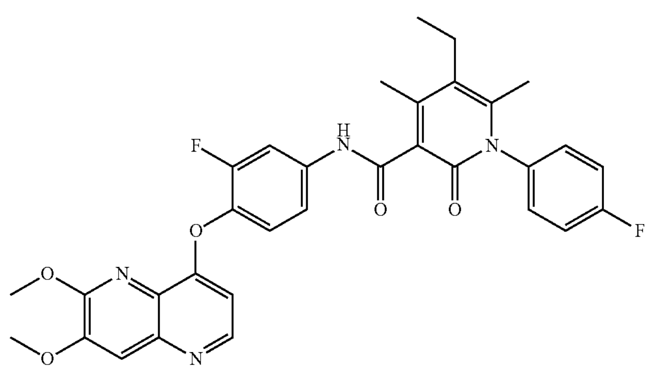 [SMILES: CCc1c(C)c(C(=O)Nc2ccc(Oc3ccnc4cc(OC)c(OC)nc34)c(F)c2)c(=O)n(-c2ccc(F)cc2)c1C] | N-[4-[(6,7-dimethoxy-1,5-naphthyridin-4-yl)oxy]-3-fluorophenyl]-5-ethyl-1-(4-fluorophenyl)-4,6-dimethyl-2-oxopyridine-3-carboxamide |

TABLE 1-continued

| Cpd # | Structure | IUPAC Name |
|---|---|---|
| 331 | 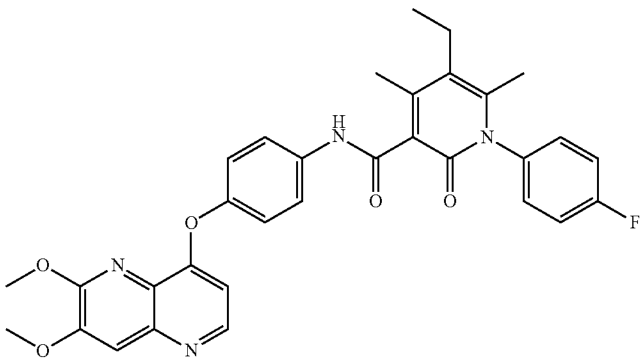 [SMILES: CCc1c(C)c(C(=O)Nc2ccc(Oc3ccnc4cc(OC)c(OC)nc34)cc2)c(=O)n(-c2ccc(F)cc2)c1C] | N-[4-[(6,7-dimethoxy-1,5-naphthyridin-4-yl)oxy]phenyl]-5-ethyl-1-(4-fluorophenyl)-4,6-dimethyl-2-oxopyridine-3-carboxamide |
| 332 | 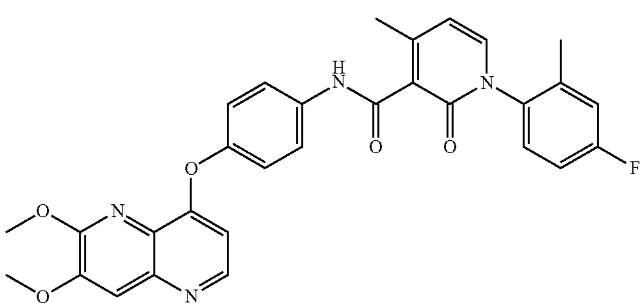 [SMILES: COc1cc2nccc(Oc3ccc(NC(=O)c4c(C)ccn(-c5ccc(F)cc5C)c4=O)cc3)c2nc1OC] | N-[4-[(6,7-dimethoxy-1,5-naphthyridin-4-yl)oxy]phenyl]-1-(4-fluoro-2-methylphenyl)-4-methyl-2-oxopyridine-3-carboxamide |
| 333 | 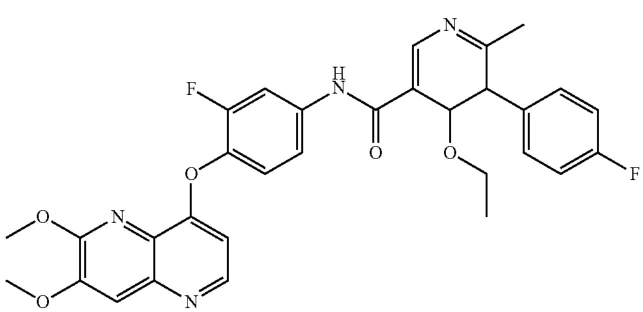 [SMILES: CCOC1C(C(=O)Nc2ccc(Oc3ccnc4cc(OC)c(OC)nc34)c(F)c2)=CN=C(C)C1c1ccc(F)cc1] | N-[4-[(6,7-dimethoxy-1,5-naphthyridin-4-yl)oxy]-3-fluorophenyl]-4-ethoxy-5-(4-fluorophenyl)-6-methylpyridine-3-carboxamide |
| 334 | 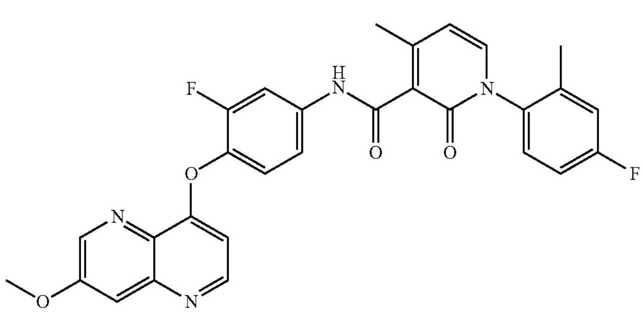 [SMILES: COc1cnc2c(Oc3ccc(NC(=O)c4c(C)ccn(-c5ccc(F)cc5C)c4=O)cc3F)ccnc2c1] | N-[3-fluoro-4-[(7-methoxy-1,5-naphthyridin-4-yl)oxy]phenyl]-1-(4-fluoro-2-methylphenyl)-4-methyl-2-oxopyridine-3-carboxamide |

TABLE 1-continued

| Cpd # | Structure | IUPAC Name |
|---|---|---|
| 335 | 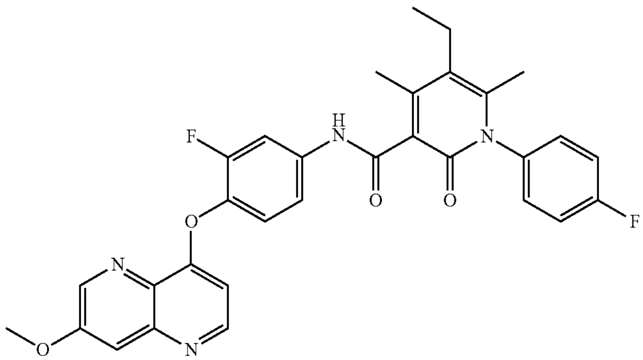 [SMILES: CCc1c(C)c(C(=O)Nc2ccc(Oc3ccnc4cc(OC)cnc34)c(F)c2)c(=O)n(-c2ccc(F)cc2)c1C] | 5-ethyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 336 | 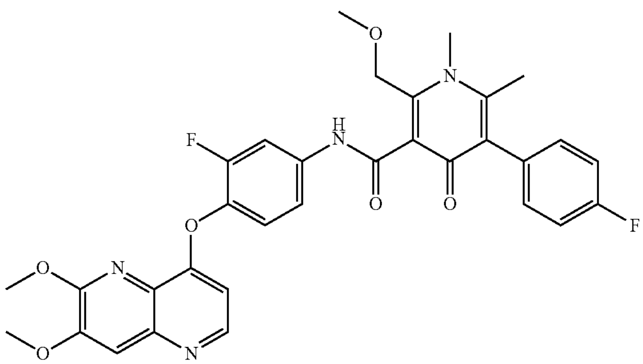 [SMILES: COCc1c(C(=O)Nc2ccc(Oc3ccnc4cc(OC)c(OC)nc34)c(F)c2)c(=O)c(-c2ccc(F)cc2)c(C)n1C] | N-[4-[(6,7-dimethoxy-1,5-naphthyridin-4-yl)oxy]-3-fluorophenyl]-5-(4-fluorophenyl)-2-(methoxymethyl)-1,6-dimethyl-4-oxopyridine-3-carboxamide |
| 337 | 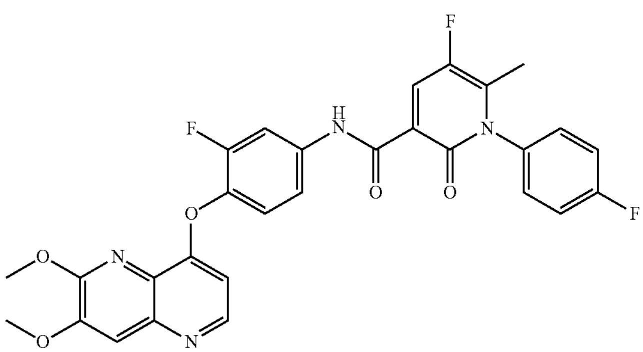 [SMILES: COc1cc2nccc(Oc3ccc(NC(=O)c4cc(F)c(C)n(-c5ccc(F)cc5)c4=O)cc3F)c2nc1OC] | N-[4-[(6,7-dimethoxy-1,5-naphthyridin-4-yl)oxy]-3-fluorophenyl]-5-fluoro-1-(4-fluorophenyl)-6-methyl-2-oxopyridine-3-carboxamide |
| 338 | 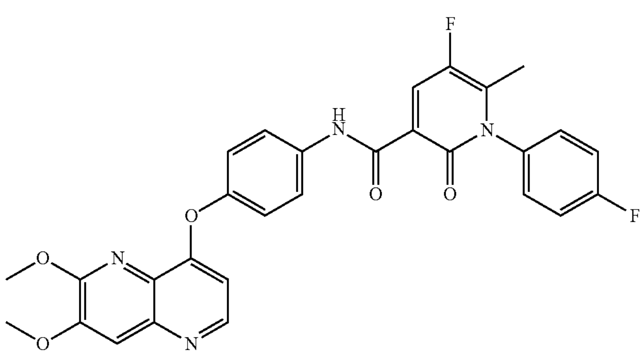 [SMILES: COc1cc2nccc(Oc3ccc(NC(=O)c4cc(F)c(C)n(-c5ccc(F)cc5)c4=O)cc3)c2nc1OC] | N-[4-[(6,7-dimethoxy-1,5-naphthyridin-4-yl)oxy]phenyl]-5-fluoro-1-(4-fluorophenyl)-6-methyl-2-oxopyridine-3-carboxamide |

TABLE 1-continued

| Cpd # | Structure | IUPAC Name |
|---|---|---|
| 339 | 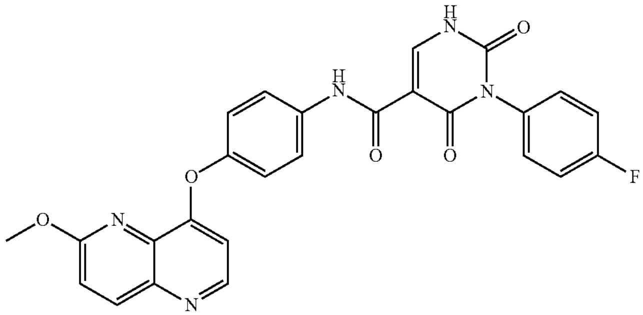 [SMILES: COc1ccc2nccc(Oc3ccc(NC(=O)c4c[nH]c(=O)n(-c5ccc(F)cc5)c4=O)cc3)c2n1] | 3-(4-fluorophenyl)-N-[4-[(6-methoxy-1,5-naphthyridin-4-yl)oxy]phenyl]-2,4-dioxo-1H-pyrimidine-5-carboxamide |
| 340 | 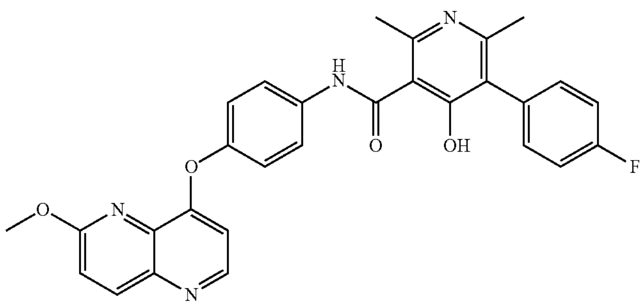 [SMILES: COc1ccc2nccc(Oc3ccc(NC(=O)c4c(C)nc(C)c(-c5ccc(F)cc5)c4O)cc3)c2n1] | 5-(4-fluorophenyl)-4-hydroxy-N-[4-[(6-methoxy-1,5-naphthyridin-4-yl)oxy]phenyl]-2,6-dimethylpyridine-3-carboxamide |
| 341 | 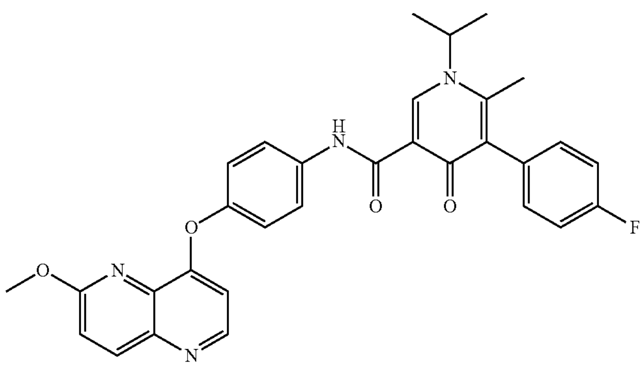 [SMILES: COc1ccc2nccc(Oc3ccc(NC(=O)c4cn(C(C)C)c(C)c(-c5ccc(F)cc5)c4=O)cc3)c2n1] | 5-(4-fluorophenyl)-N-[4-[(6-methoxy-1,5-naphthyridin-4-yl)oxy]phenyl]-6-methyl-4-oxo-1-propan-2-ylpyridine-3-carboxamide |
| 342 | 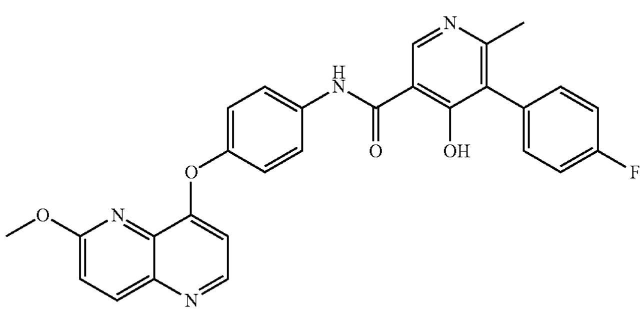 [SMILES: COc1ccc2nccc(Oc3ccc(NC(=O)c4cnc(C)c(-c5ccc(F)cc5)c4O)cc3)c2n1] | 5-(4-fluorophenyl)-4-hydroxy-N-[4-[(6-methoxy-1,5-naphthyridin-4-yl)oxy]phenyl]-6-methylpyridine-3-carboxamide |
| 343 | 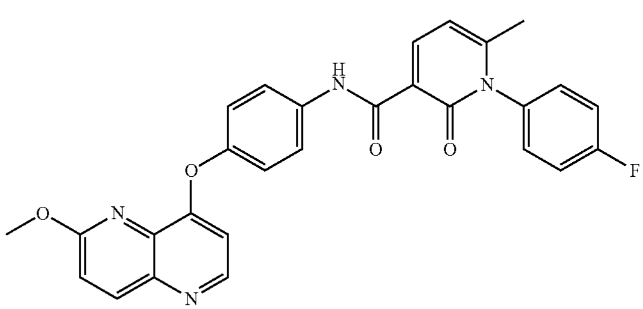 [SMILES: COc1ccc2nccc(Oc3ccc(NC(=O)c4ccc(C)n(-c5ccc(F)cc5)c4=O)cc3)c2n1] | 1-(4-fluorophenyl)-N-[4-[(6-methoxy-1,5-naphthyridin-4-yl)oxy]phenyl]-6-methyl-2-oxopyridine-3-carboxamide |

TABLE 1-continued

| Cpd # | Structure | IUPAC Name |
|---|---|---|
| 344 | 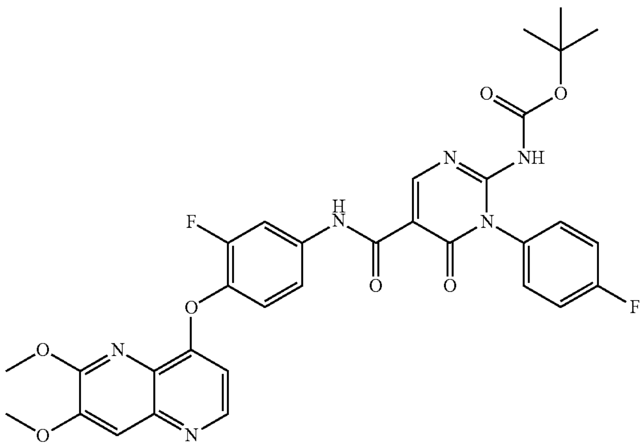 [SMILES: COc1cc2nccc(Oc3ccc(NC(=O)c4cnc(NC(=O)OC(C)(C)C)n(-c5ccc(F)cc5)c4=O)cc3F)c2nc1OC] | tert-butyl N-[5-[[4-[(6,7-dimethoxy-1,5-naphthyridin-4-yl)oxy]-3-fluorophenyl]icarbamoyl]-1-(4-fluorophenyl)-6-oxopyrimidin-2-yl]carbamate |
| 345 | 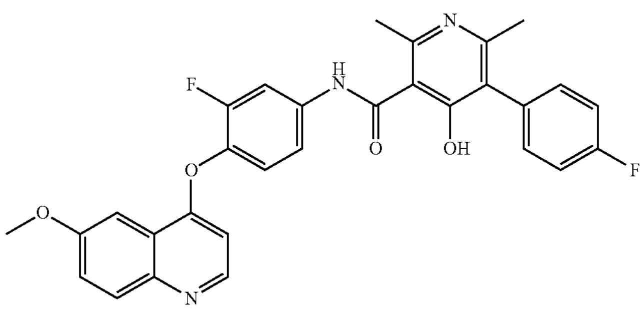 [SMILES: COc1ccc2nccc(Oc3ccc(NC(=O)c4c(C)nc(C)c(-c5ccc(F)cc5)c4O)cc3F)c2c1] | N-[3-fluoro-4-(6-methoxyquinolin-4-yl)oxyphenyl]-5-(4-fluorophenyl)-4-hydroxy-2,6-dimethylpyridine-3-carboxamide |
| 346 | 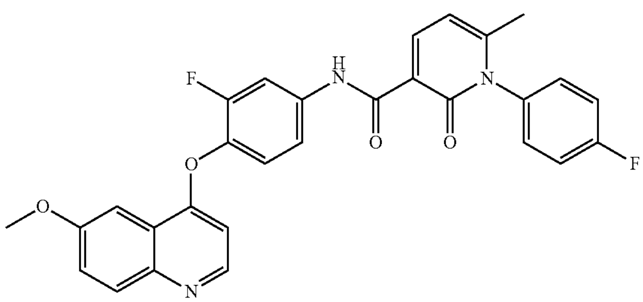 [SMILES: COc1ccc2nccc(Oc3ccc(NC(=O)c4ccc(C)n(-c5ccc(F)cc5)c4=O)cc3F)c2c1] | N-[3-fluoro-4-(6-methoxyquinolin-4-yl)oxyphenyl]-1-(4-fluorophenyl)-6-methyl-2-oxopyridine-3-carboxamide |
| 347 | 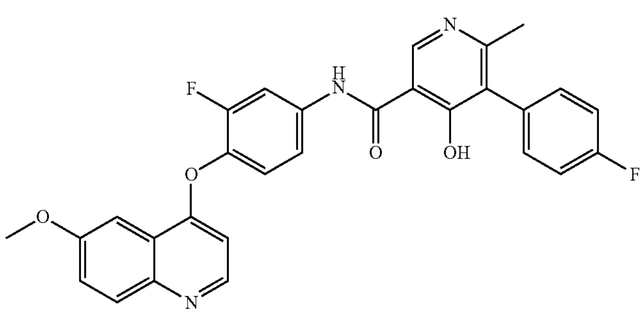 | N-[3-fluoro-4-(6-methoxyquinolin-4-yl)oxyphenyl]-5-(4-fluorophenyl)-4-hydroxy-6-methylpyridine-3-carboxamide |

TABLE 1-continued

| Cpd # | Structure | IUPAC Name |
|---|---|---|
| 348 | 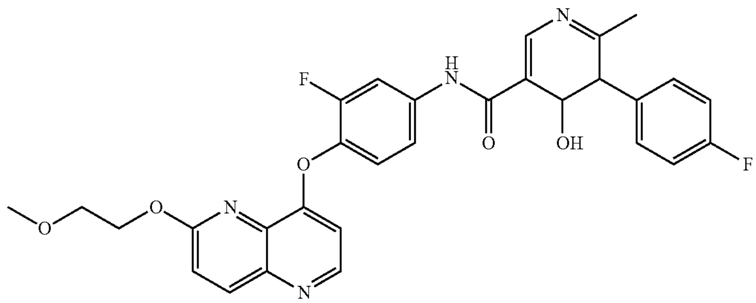 [SMILES: COCCOc1ccc2nccc(Oc3ccc(NC(=O)C4=CN=C(C)C(c5ccc(F)cc5)C4O)cc3F)c2n1] | N-[3-fluoro-4-[[6-(2-methoxyethoxy)-1,5-naphthyridin-4-yl]oxy]phenyl]-5-(4-fluorophenyl)-4-hydroxy-6-methylpyridine-3-carboxamide |
| 349 | 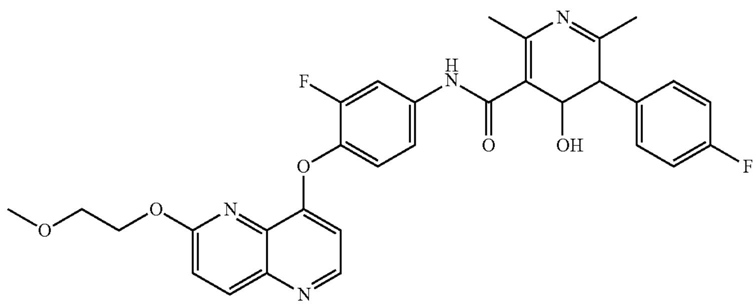 [SMILES: COCCOc1ccc2nccc(Oc3ccc(NC(=O)C4=C(C)N=C(C)C(c5ccc(F)cc5)C4O)cc3F)c2n1] | N-[3-fluoro-4-[[6-(2-methoxyethoxy)-1,5-naphthyridin-4-yl]oxy]phenyl]-5-(4-fluorophenyl)-4-hydroxy-2,6-dimethylpyridine-3-carboxamide |
| 350 | 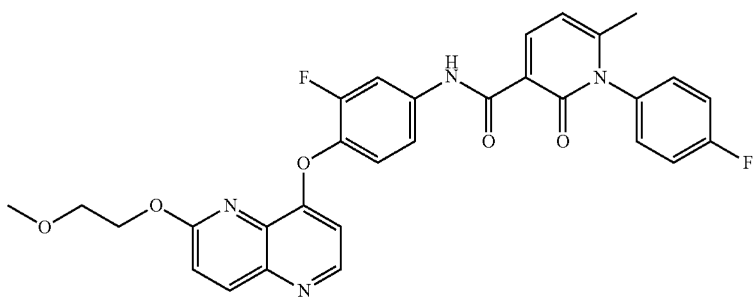 [SMILES: COCCOc1ccc2nccc(Oc3ccc(NC(=O)c4ccc(C)n(-c5ccc(F)cc5)c4=O)cc3F)c2n1] | N-[3-fluoro-4-[[6-(2-methoxyethoxy)-1,5-naphthyridin-4-yl]oxy]phenyl]-1-(4-fluorophenyl)-6-methyl-2-oxopyridine-3-carboxamide |
| 351 | 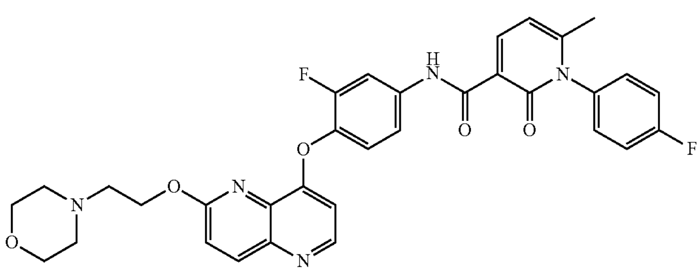 [SMILES: Cc1ccc(C(=O)Nc2ccc(Oc3ccnc4ccc(OCCN5CCOCC5)nc34)c(F)c2)c(=O)n1-c1ccc(F)cc1] | N-[3-fluoro-4-[[6-(2-morpholin-4-ylethoxy)-1,5-naphthyridin-4-yl]oxy]phenyl]-1-(4-fluorophenyl)-6-methyl-2-oxopyridine-3-carboxamide |
| 352 | 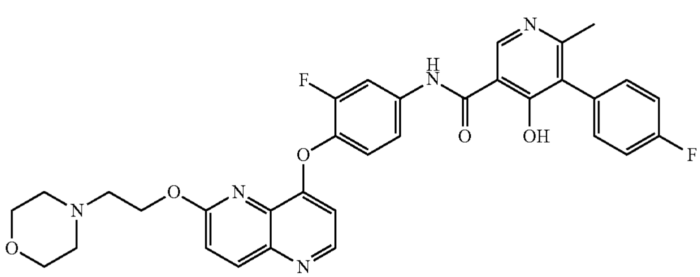 [SMILES: Cc1ncc(C(=O)Nc2ccc(Oc3ccnc4ccc(OCCN5CCOCC5)nc34)c(F)c2)c(O)c1-c1ccc(F)cc1] | N-[3-fluoro-4-[[6-(2-morpholin-4-ylethoxy)-1,5-naphthyridin-4-yl]oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 353 | 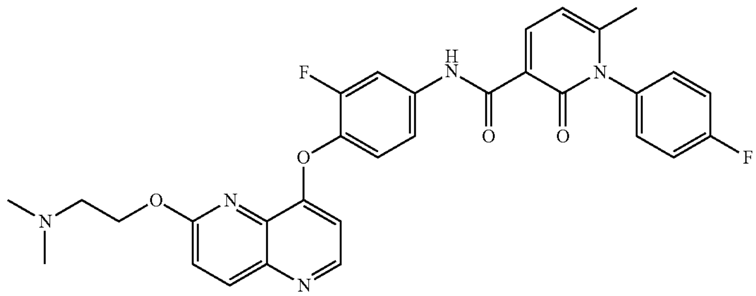 [SMILES: Cc1ccc(C(=O)Nc2ccc(Oc3ccnc4ccc(OCCN(C)C)nc34)c(F)c2)c(=O)n1-c1ccc(F)cc1] | N-[4-[[6-[2-(dimethylamino)ethoxy]-1,5-naphthyridin-4-yl]oxy]-3-fluorophenyl]-1-(4-fluorophenyl)-6-methyl-2-oxopyridine-3-carboxamide |
| 354 | 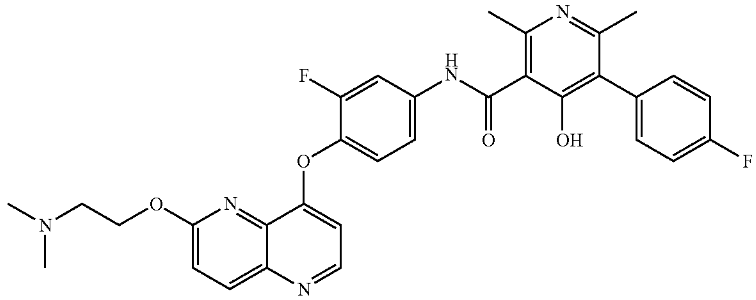 [SMILES: Cc1nc(C)c(-c2ccc(F)cc2)c(O)c1C(=O)Nc1ccc(Oc2ccnc3ccc(OCCN(C)C)nc23)c(F)c1] | N-[4-[[6-[2-(dimethylamino)ethoxy]-1,5-naphthyridin-4-yl]oxy]-3-fluorophenyl]-5-(4-fluorophenyl)-4-hydroxy-2,6-dimethylpyridine-3-carboxamide |
| 355 | 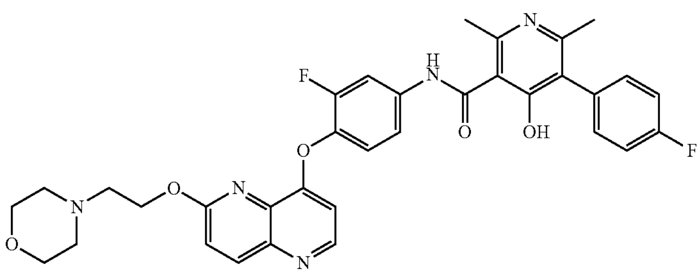 [SMILES: Cc1nc(C)c(-c2ccc(F)cc2)c(O)c1C(=O)Nc1ccc(Oc2ccnc3ccc(OCCN4CCOCC4)nc23)c(F)c1] | N-[3-fluoro-4-[[6-(2-morpholin-4-ylethoxy)-1,5-naphthyridin-4-yl)oxy]phenyl]-5-(4-fluorophenyl)-4-hydroxy-2,6-dimethylpyridine-3-carboxamide |
| 356 | 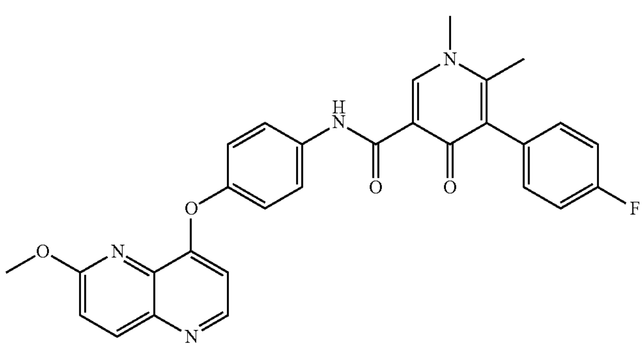 [SMILES: COc1ccc2nccc(Oc3ccc(NC(=O)c4cn(C)c(C)c(-c5ccc(F)cc5)c4=O)cc3)c2n1] | 5-(4-fluorophenyl)-N-[4-[(6-methoxy-1,5-naphthyridin-4-yl)oxy]phenyl]-1,6-dimethyl-4-oxopyridine-3-carboxamide |
| 357 | 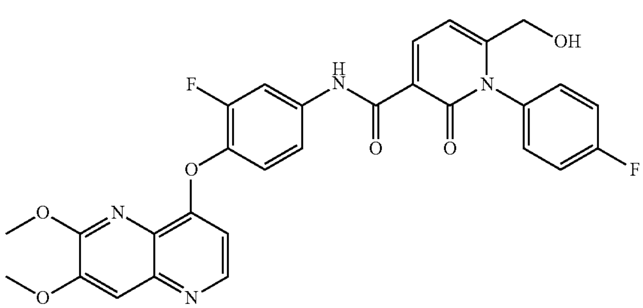 [SMILES: COc1cc2nccc(Oc3ccc(NC(=O)c4ccc(CO)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-6-(hydroxymethyl)-2-oxopyridine-3-carboxamide |

TABLE 1-continued

| Cpd # | Structure | IUPAC Name |
|---|---|---|
| 358 | 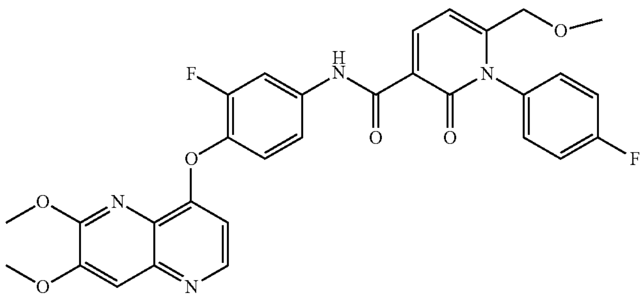 [SMILES: COCc1ccc(C(=O)Nc2ccc(Oc3ccnc4cc(OC)c(OC)nc34)c(F)c2)c(=O)n1-c1ccc(F)cc1] | N-[4-[(6,7-dimethoxy-1,5-naphthyridin-4-yl)oxy]-3-fluorophenyl]-1-(4-fluorophenyl)-6-(methoxymethyl)-2-oxopyridine-3-carboxamide |
| 359 | 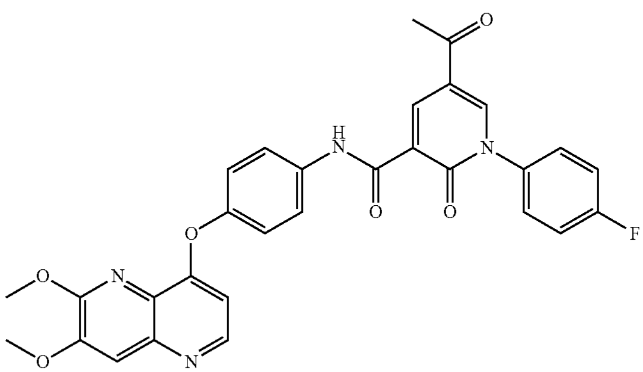 [SMILES: COc1cc2nccc(Oc3ccc(NC(=O)c4cc(C(C)=O)cn(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-2-oxopyridine-3-carboxamide |
| 360 | 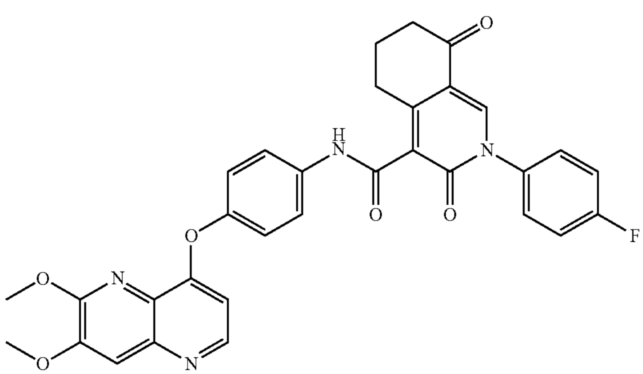 [SMILES: COc1cc2nccc(Oc3ccc(NC(=O)c4c5c(cn(-c6ccc(F)cc6)c4=O)C(=O)CCC5)cc3)c2nc1OC] | N-[4-[(6,7-dimethoxy-1,5-naphthyridin-4-yl)oxy]phenyl]-2-(4-fluorophenyl)-3,8-dioxo-6,7-dihydro-5H-isoquinoline-4-carboxamide |
| 361 | 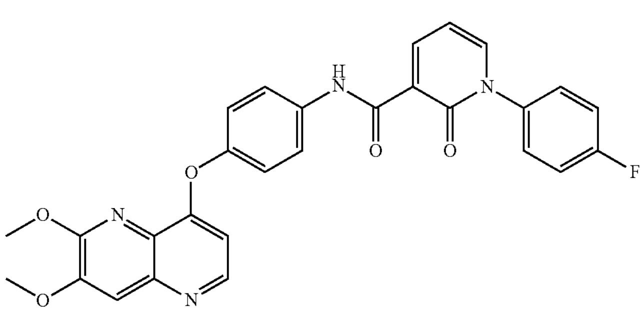 [SMILES: COc1cc2nccc(Oc3ccc(NC(=O)c4cccn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-2-oxopyridine-3-carboxamide |

TABLE 1-continued

| Cpd # | Structure | IUPAC Name |
|---|---|---|
| 362 | 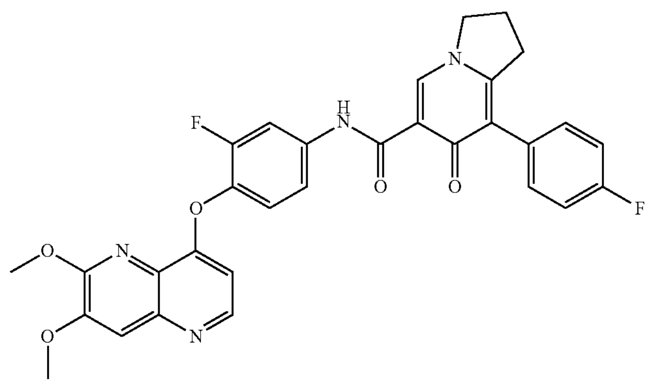 [SMILES: COc1cc2nccc(Oc3ccc(NC(=O)c4cn5c(c(-c6ccc(F)cc6)c4=O)CCC5)cc3F)c2nc1OC] | N-[4-[(6,7-dimethoxy-1,5-naphthyridin-4-yl)oxy]-3-fluorophenyl]-8-(4-fluorophenyl)-7-oxo-2,3-dihydro-1H-indolizine-6-carboxamide |
| 363 | 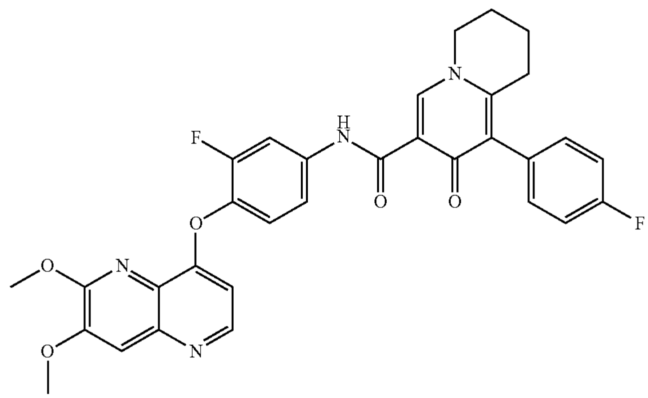 [SMILES: COc1cc2nccc(Oc3ccc(NC(=O)c4cn5c(c(-c6ccc(F)cc6)c4=O)CCCC5)cc3F)c2nc1OC] | N-[4-[(6,7-dimethoxy-1,5-naphthyridin-4-yl)oxy]-3-fluorophenyl]-1-(4-fluorophenyl)-2-oxo-6,7,8,9-tetrahydroquinolizine-3-carboxamide |
| 364 | 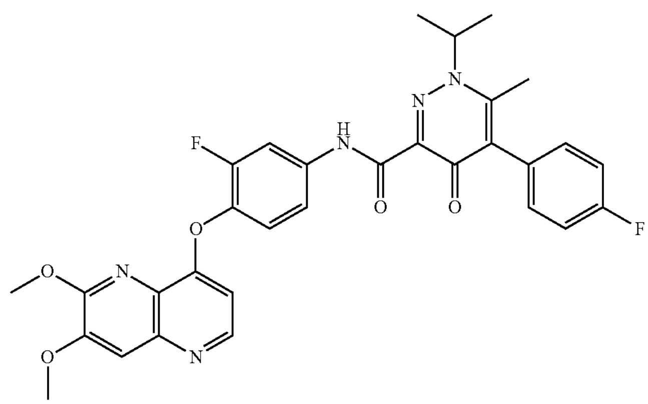 [SMILES: COc1cc2nccc(Oc3ccc(NC(=O)c4nn(C(C)C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-4-oxo-1-propan-2-ylpyridazine-3-carboxamide |
| 365 | 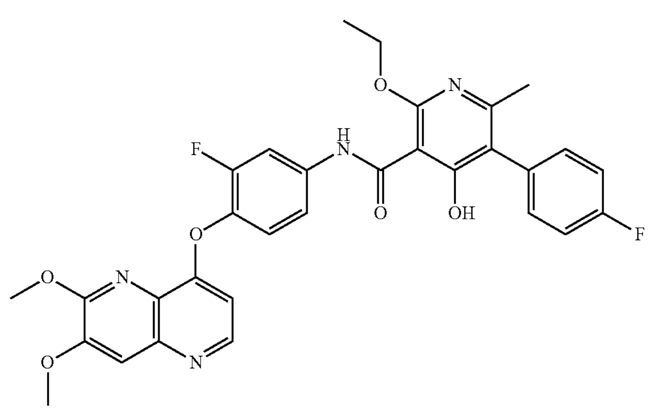 [SMILES: CCOc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-ethoxy-5-(4-fluorophenyl)-4-hydroxy-6-methylpyridine-3-carboxamide |

TABLE 1-continued

| Cpd # | Structure | IUPAC Name |
|---|---|---|
| 366 | 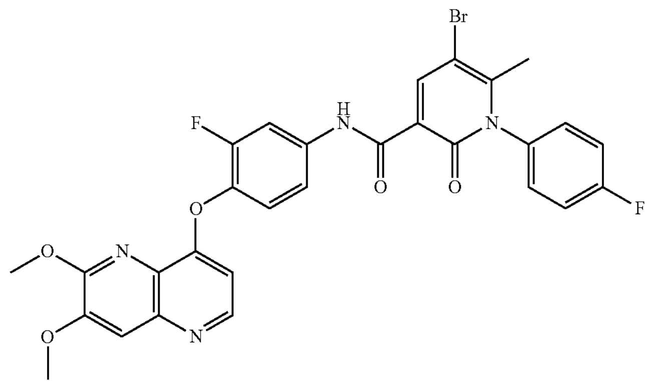 [SMILES: COc1cc2nccc(Oc3ccc(NC(=O)c4cc(Br)c(C)n(-c5ccc(F)cc5)c4=O)cc3F)c2nc1OC] | 5-bromo-N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 367 | 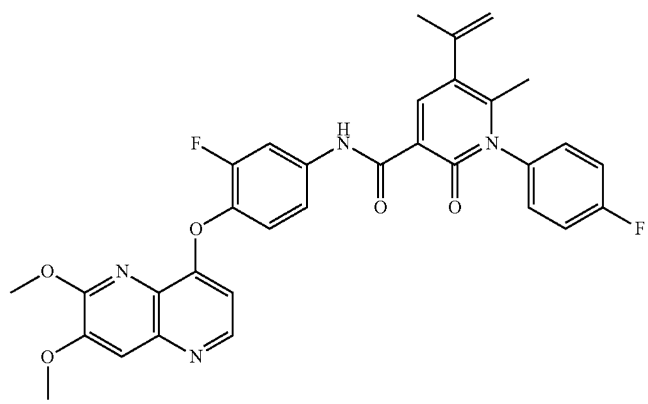 | N-[4-[(6,7-dimethoxy-1,5-naphthyridin-4-yl)oxy]-3-fluorophenyl]-1-(4-fluorophenyl)-6-methyl-2-oxo-5-prop-1-en-2-ylpyridine-3-carboxamide |
| 368 | 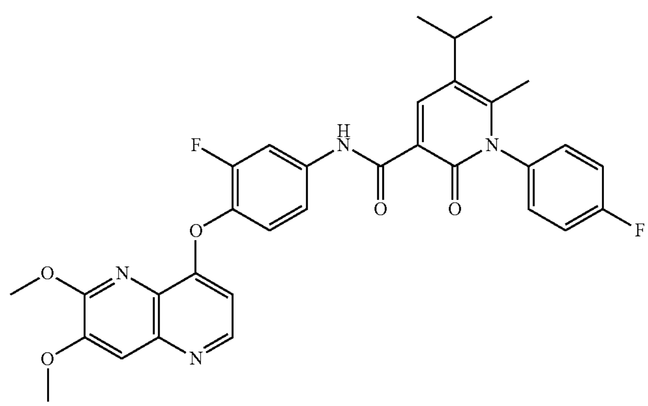 [SMILES: COc1cc2nccc(Oc3ccc(NC(=O)c4cc(C(C)C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-6-methyl-2-oxo-5-propan-2-ylpyridine-3-carboxamide |
| 369 | 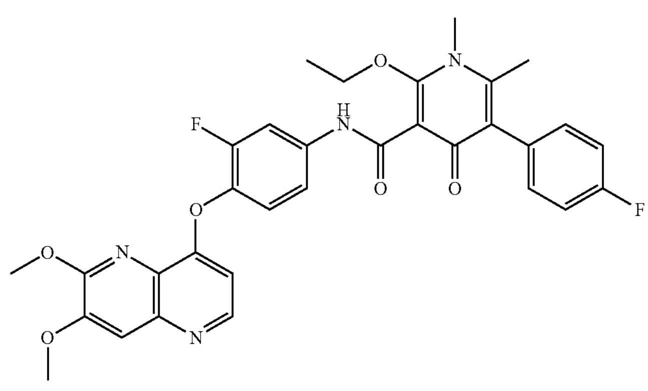 [SMILES: CCOc1c(C(=O)Nc2ccc(Oc3ccnc4cc(OC)c(OC)nc34)c(F)c2)c(=O)c(-c2ccc(F)cc2)c(C)n1C] | N-[4-[(6,7-dimethoxy-1,5-naphthyridin-4-yl)oxy]-3-fluorophenyl]-2-ethoxy-5-(4-fluorophenyl)-1,6-dimethyl-4-oxopyridine-3-carboxamide |

TABLE 1-continued

| Cpd # | Structure | IUPAC Name |
| --- | --- | --- |
| 370 | 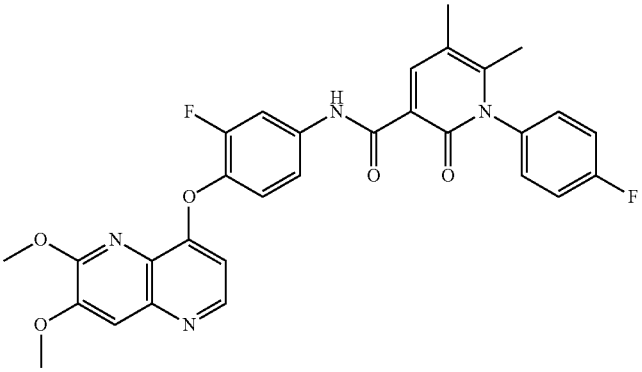 [SMILES: COc1cc2nccc(Oc3ccc(NC(=O)c4cc(C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-5,6-dimethyl-2-oxopyridine-3-carboxamide |
| 371 | 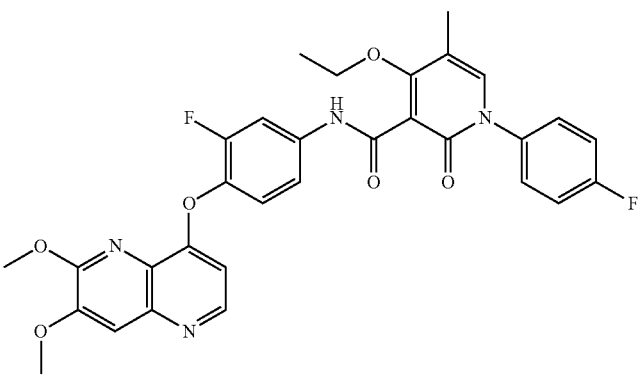 [SMILES: CCOc1c(C)cn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-1-(4-fluorophenyl)-5-methyl-2-oxopyridine-3-carboxamide |
| 372 | 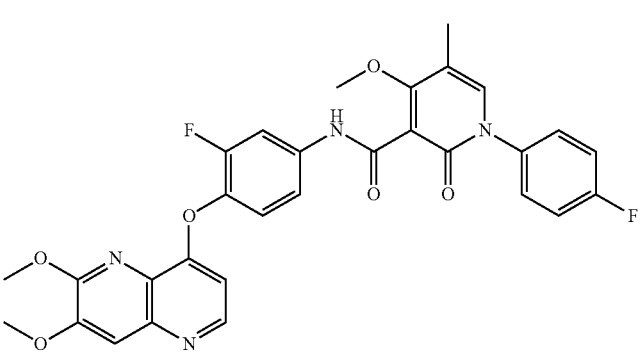 [SMILES: COc1cc2nccc(Oc3ccc(NC(=O)c4c(OC)c(C)cn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4-methoxy-5-methyl-2-oxopyridine-3-carboxamide |
| 373 | 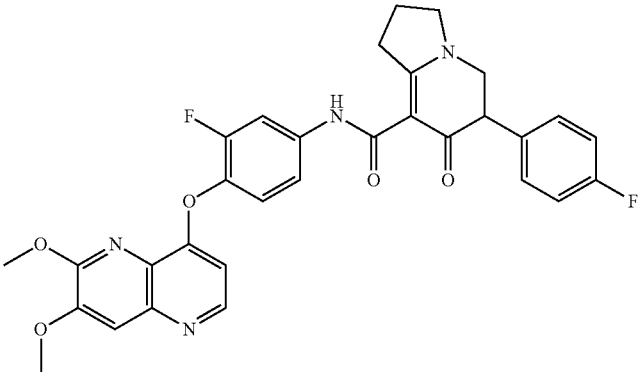 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide |

TABLE 1-continued

| Cpd # | Structure | IUPAC Name |
|---|---|---|
| 374 | 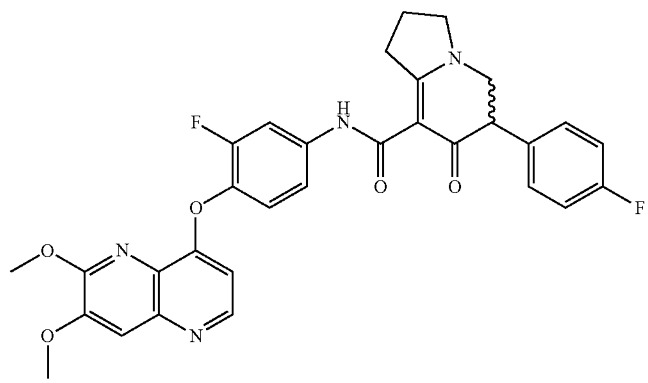 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 1 |
| 375 | 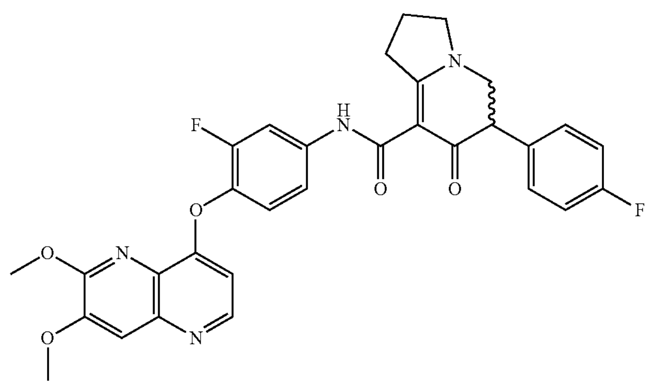 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 2 |
| 376 | 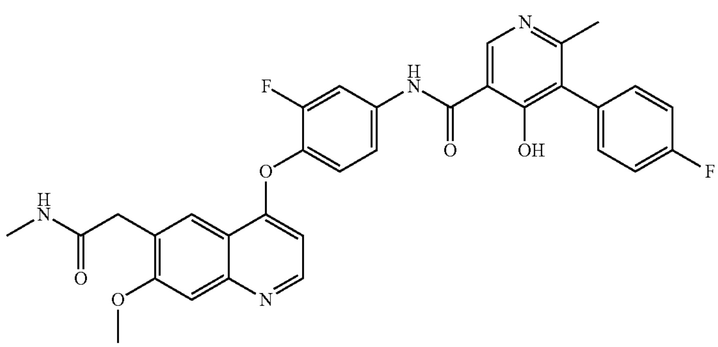 | N-[3-fluoro-4-[7-methoxy-6-[2-(methylamino)-2-oxoethyl]quinolin-4-yl]oxyphenyl]-5-(4-fluorophenyl)-4-hydroxy-6-methylpyridine-3-carboxamide |
| 377 | 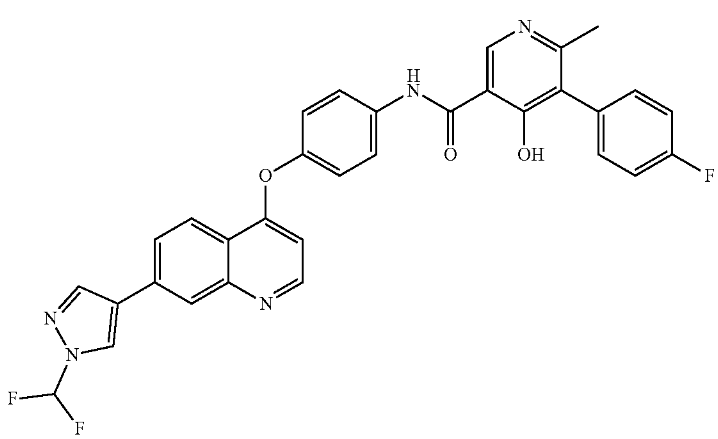 | N-[4-[7-[1-(difluoromethyl)pyrazol-4-yl]quinolin-4-yl]oxyphenyl]-5-(4-fluorophenyl)-4-hydroxy-6-methylpyridine-3-carboxamide |

TABLE 1-continued

| Cpd # | Structure | IUPAC Name |
|---|---|---|
| 378 | 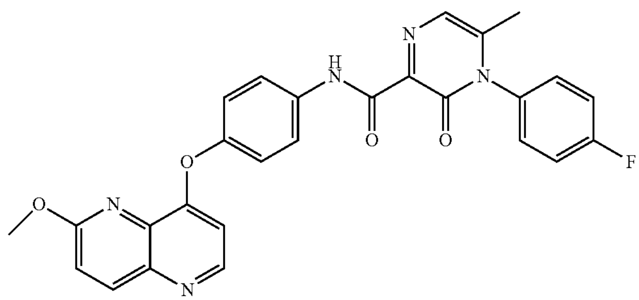 [SMILES: COc1ccc2nccc(Oc3ccc(NC(=O)c4ncc(C)n(-c5ccc(F)cc5)c4=O)cc3)c2n1] | 4-(4-fluorophenyl)-N-[4-[(6-methoxy-1,5-naphthyridin-4-yl)oxy]phenyl]-5-methyl-3-oxopyrazine-2-carboxamide |
| 379 | 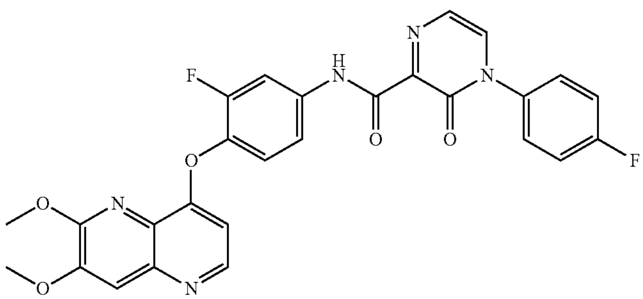 [SMILES: COc1cc2nccc(Oc3ccc(NC(=O)c4nccn(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-3-oxopyrazine-2-carboxamide |
| 380 | 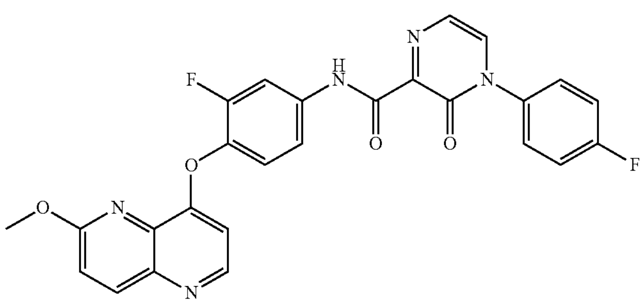 [SMILES: COc1ccc2nccc(Oc3ccc(NC(=O)c4nccn(-c5ccc(F)cc5)c4=O)cc3F)c2n1] | N-[3-fluoro-4-[(6-methoxy-1,5-naphthyridin-4-yl)oxy]phenyl]-4-(4-fluorophenyl)-3-oxopyrazine-2-carboxamide |
| 381 | 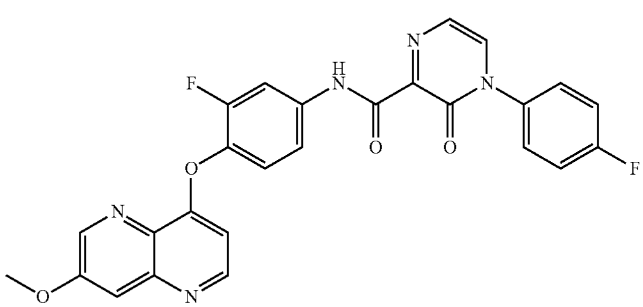 [SMILES: COc1cnc2c(Oc3ccc(NC(=O)c4nccn(-c5ccc(F)cc5)c4=O)cc3F)ccnc2c1] | N-[3-fluoro-4-[(7-methoxy-1,5-naphthyridin-4-yl)oxy]phenyl]-4-(4-fluorophenyl)-3-oxopyrazine-2-carboxamide |
| 382 | 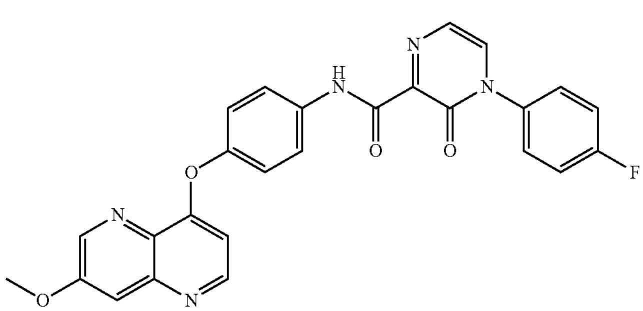 [SMILES: COc1cnc2c(Oc3ccc(NC(=O)c4nccn(-c5ccc(F)cc5)c4=O)cc3)ccnc2c1] | 4-(4-fluorophenyl)-N-[4-[(7-methoxy-1,5-naphthyridin-4-yl)oxy]phenyl]-3-oxopyrazine-2-carboxamide |

TABLE 1-continued

| Cpd # | Structure | IUPAC Name |
|---|---|---|
| 383 | 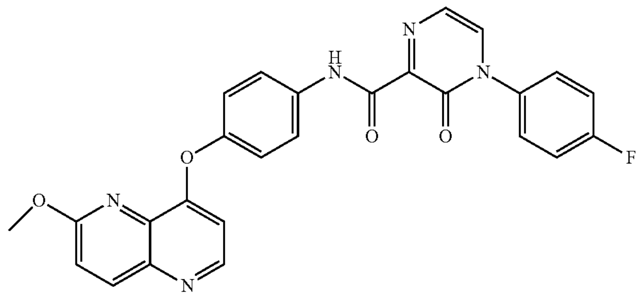 [SMILES: COc1ccc2nccc(Oc3ccc(NC(=O)c4nccn(-c5ccc(F)cc5)c4=O)cc3)c2n1] | 4-(4-fluorophenyl)-N-[4-[(6-methoxy-1,5-naphthyridin-4-yl)oxy]phenyl]-3-oxopyrazine-2-carboxamide |
| 384 | 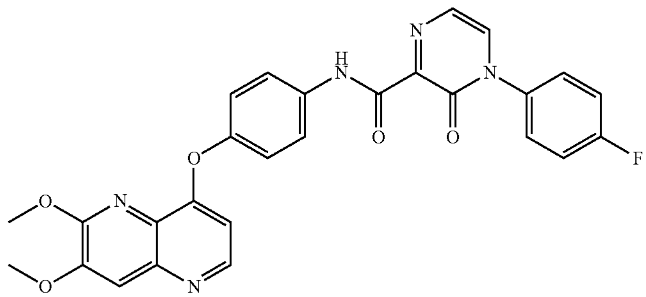 [SMILES: COc1cc2nccc(Oc3ccc(NC(=O)c4nccn(-c5ccc(F)cc5)c4=O)cc3)c2nc1OC] | N-[4-[(6,7-dimethoxy-1,5-naphthyridin-4-yl)oxy]phenyl]-4-(4-fluorophenyl)-3-oxopyrazine-2-carboxamide |
| 385 | 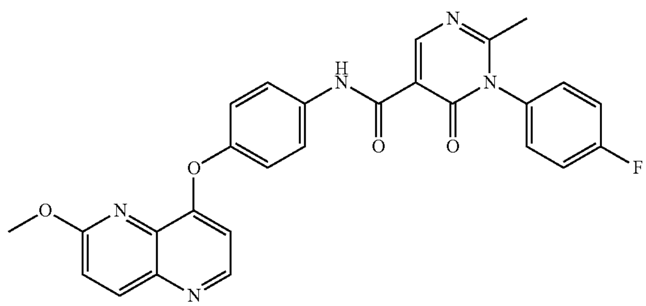 [SMILES: COc1ccc2nccc(Oc3ccc(NC(=O)c4cnc(C)n(-c5ccc(F)cc5)c4=O)cc3)c2n1] | 1-(4-fluorophenyl)-N-[4-[(6-methoxy-1,5-naphthyridin-4-yl)oxy]phenyl]-2-methyl-6-oxopyrimidine-5-carboxamide |
| 386 | 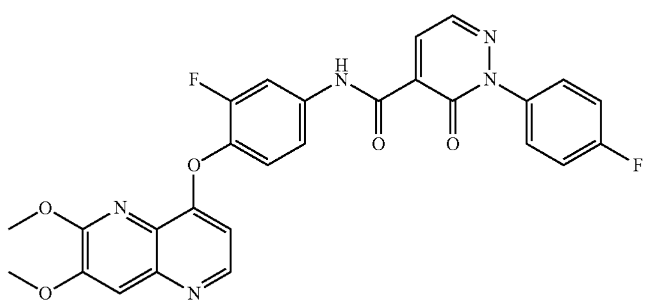 [SMILES: COc1cc2nccc(Oc3ccc(NC(=O)c4ccnn(-c5ccc(F)cc5)c4=O)cc3F)c2nc1OC] | N-[4-[(6,7-dimethoxy-1,5-naphthyridin-4-yl)oxy]-3-fluorophenyl]-2-(4-fluorophenyl)-3-oxopyridazine-4-carboxamide |
| 387 | 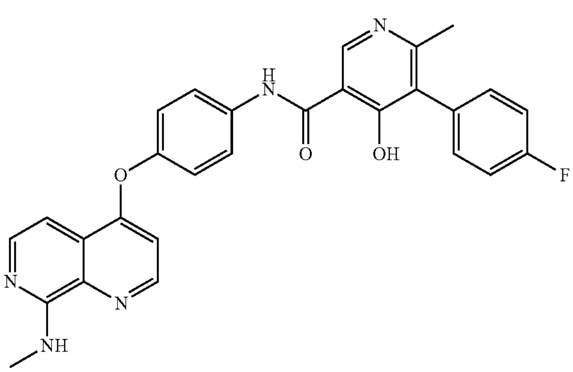 [SMILES: CNc1nccc2c(Oc3ccc(NC(=O)c4cnc(C)c(-c5ccc(F)cc5)c4O)cc3)ccnc12] | 5-(4-fluorophenyl)-4-hydroxy-6-methyl-N-[4-[[8-(methylamino)-1,7-naphthyridin-4-yl]oxy]phenyl]pyridine-3-carboxamide |

TABLE 1-continued

| Cpd # | Structure | IUPAC Name |
|---|---|---|
| 388 | 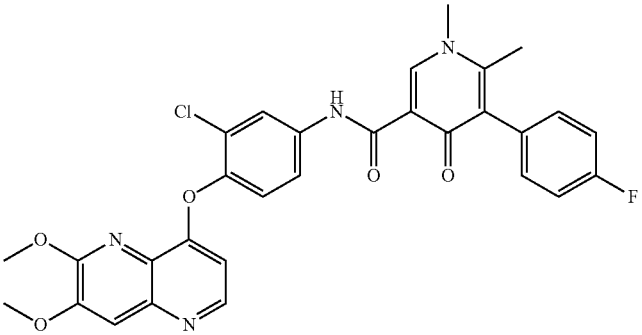 | N-[3-chloro-4-[(6,7-dimethoxy-1,5-naphthyridin-4-yl)oxy]phenyl]-5-(4-fluorophenyl)-1,6-dimethyl-4-oxopyridine-3-carboxamide |
| 389 | 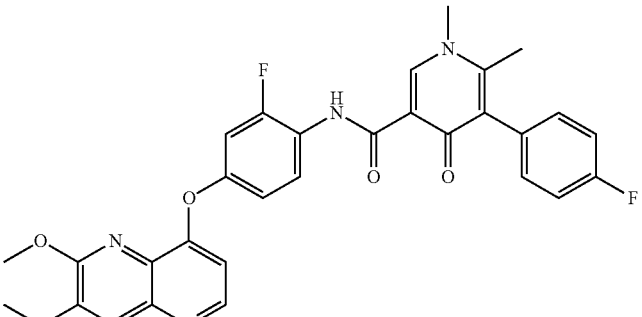 | N-[4-[(6,7-dimethoxy-1,5-naphthyridin-4-yl)oxy]-2-fluorophenyl]-5-(4-fluorophenyl)-1,6-dimethyl-4-oxopyridine-3-carboxamide |
| 390 | 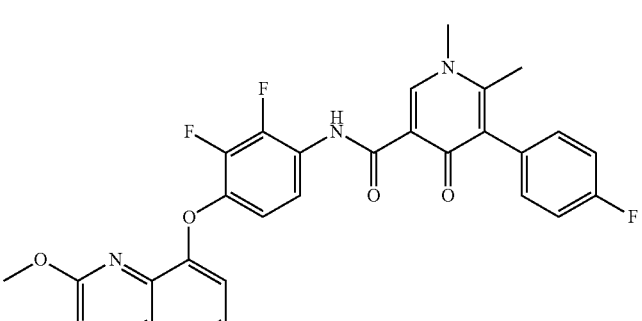 | N-[4-[(6,7-dimethoxy-1,5-naphthyridin-4-yl)oxy]-2,3-difluorophenyl]-5-(4-fluorophenyl)-1,6-dimethyl-4-oxopyridine-3-carboxamide |
| 391 | 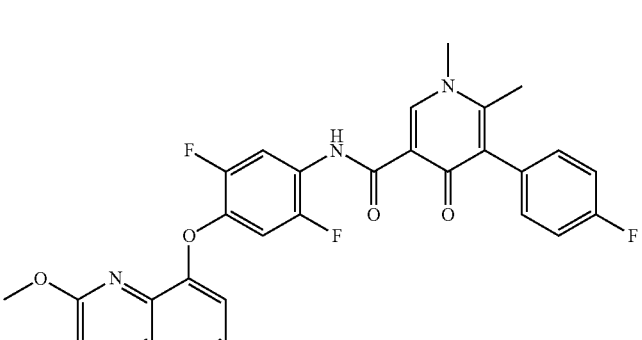 | N-[4-[(6,7-dimethoxy-1,5-naphthyridin-4-yl)oxy]-2,5-difluorophenyl]-5-(4-fluorophenyl)-1,6-dimethyl-4-oxopyridine-3-carboxamide |

TABLE 1-continued

| Cpd # | Structure | IUPAC Name |
|---|---|---|
| 392 | 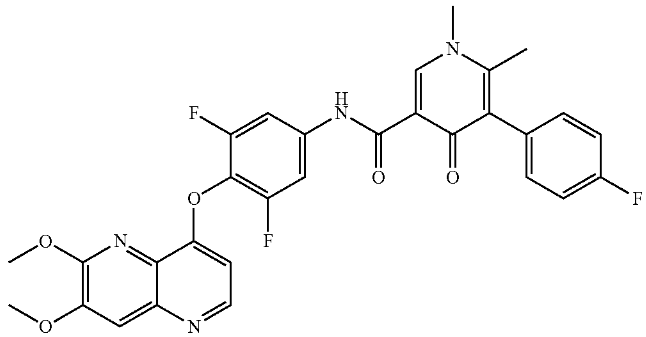 [SMILES: COc1cc2nccc(Oc3c(F)cc(NC(=O)c4cn(C)c(C)c(-c5ccc(F)cc5)c4=O)cc3F)c2nc1OC] | N-[4-[(6,7-dimethoxy-1,5-naphthyridin-4-yl)oxy]-3,5-difluorophenyl]-5-(4-fluorophenyl)-1,6-dimethyl-4-oxopyridine-3-carboxamide |
| 393 | 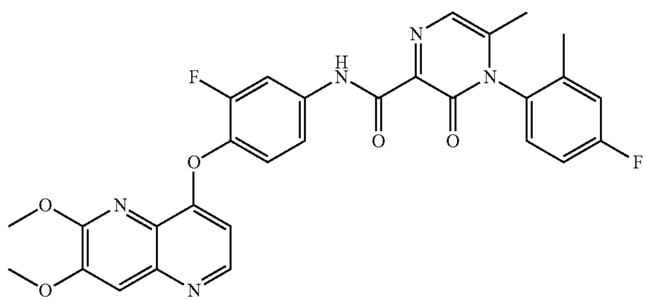 [SMILES: COc1cc2nccc(Oc3ccc(NC(=O)c4ncc(C)n(-c5ccc(F)cc5C)c4=O)cc3F)c2nc1OC] | N-[4-[(6,7-dimethoxy-1,5-naphthyridin-4-yl)oxy]-3-fluorophenyl]-4-(4-fluoro-2-methylphenyl)-5-methyl-3-oxopyrazine-2-carboxamide |
| 394 | 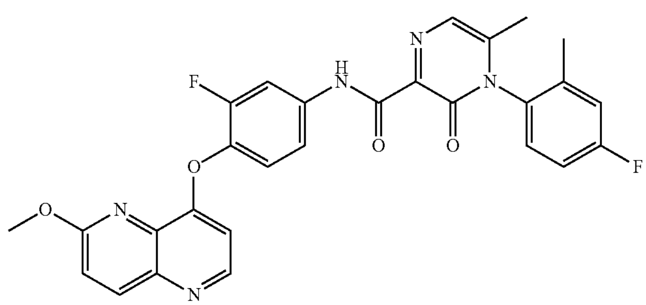 [SMILES: COc1ccc2nccc(Oc3ccc(NC(=O)c4ncc(C)n(-c5ccc(F)cc5C)c4=O)cc3F)c2n1] | N-[3-fluoro-4-[(6-methoxy-1,5-naphthyridin-4-yl)oxy]phenyl]-4-(4-fluoro-2-methylphenyl)-5-methyl-3-oxopyrazine-2-carboxamide |
| 395 | 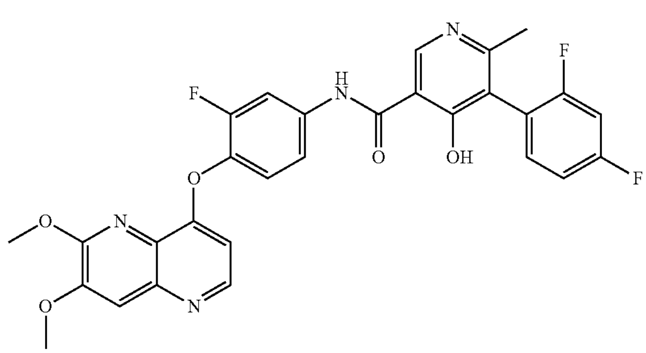 [SMILES: COc1cc2nccc(Oc3ccc(NC(=O)c4cnc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-3-fluorophenyl]-4-hydroxy-6-methylpyridine-3-carboxamide |

TABLE 1-continued

| Cpd # | Structure | IUPAC Name |
|---|---|---|
| 396 | 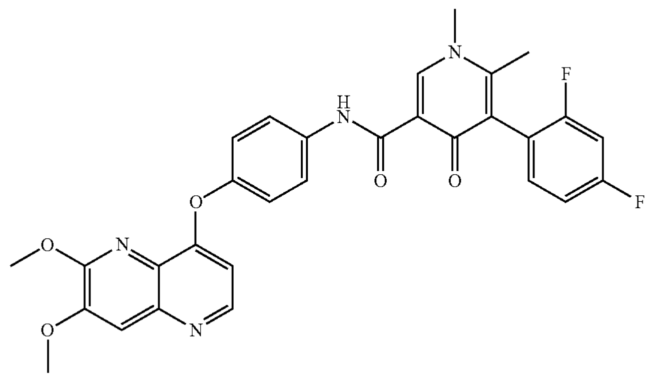 [SMILES: COc1cc2nccc(Oc3ccc(NC(=O)c4cn(C)c(C)c(-c5ccc(F)cc5F)c4=O)cc3)c2nc1OC] | 5-(2,4-difluorophenyl)-N-[4-[(6,7-dimethoxy-1,5-naphthyridin-4-yl)oxy]phenyl]-1,6-dimethyl-4-oxopyridine-3-carboxamide |
| 397 | 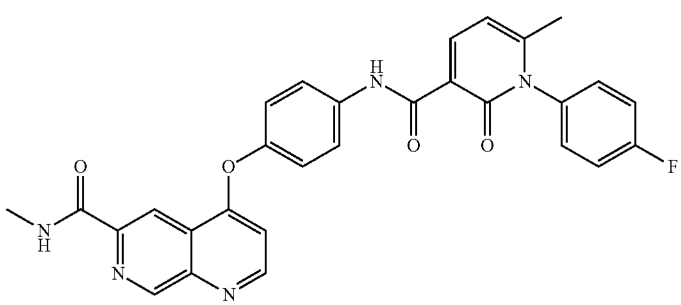 [SMILES: CNC(=O)c1cc2c(Oc3ccc(NC(=O)c4ccc(C)n(-c5ccc(F)cc5)c4=O)cc3)ccnc2cn1] | 4-[4-[[1-(4-fluorophenyl)-6-methyl-2-oxopyridine-3-carbonyl]amino]phenoxy]-N-methyl-1,7-naphthyridine-6-carboxamide |
| 398 | 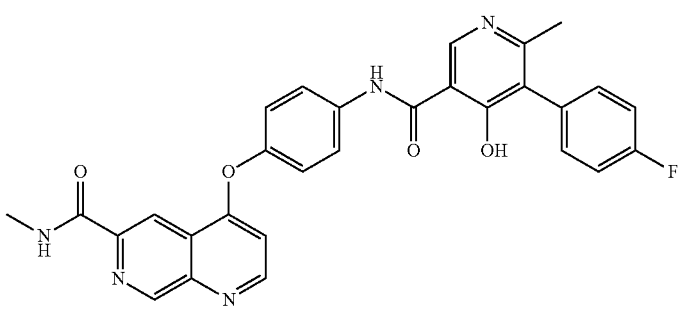 [SMILES: CNC(=O)c1cc2c(Oc3ccc(NC(=O)c4cnc(C)c(-c5ccc(F)cc5)c4O)cc3)ccnc2cn1] | 4-[4-[[5-(4-fluorophenyl)-4-hydroxy-6-methylpyridine-3-carbonyl]amino]phenoxy]-N-methyl-1,7-naphthyridine-6-carboxamide |
| 399 | 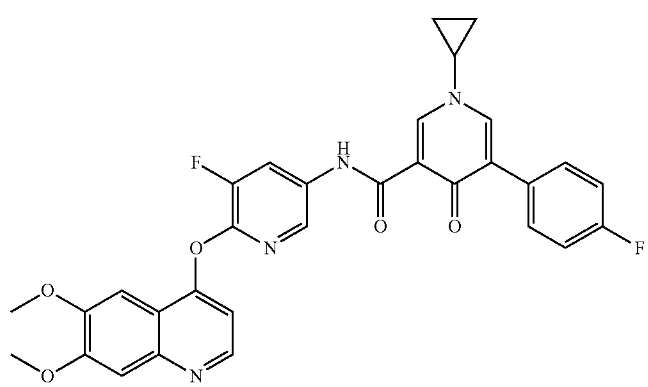 [SMILES: COc1cc2nccc(Oc3ncc(NC(=O)c4cn(C5CC5)cc(-c5ccc(F)cc5)c4=O)cc3F)c2cc1OC] | 1-cyclopropyl-N-[6-(6,7-dimethoxyquinolin-4-yl)oxy-5-fluoropyridin-3-yl]-5-(4-fluorophenyl)-4-oxopyridine-3-carboxamide |

TABLE 1-continued
| Cpd # | Structure | IUPAC Name |
|---|---|---|
| 400 | 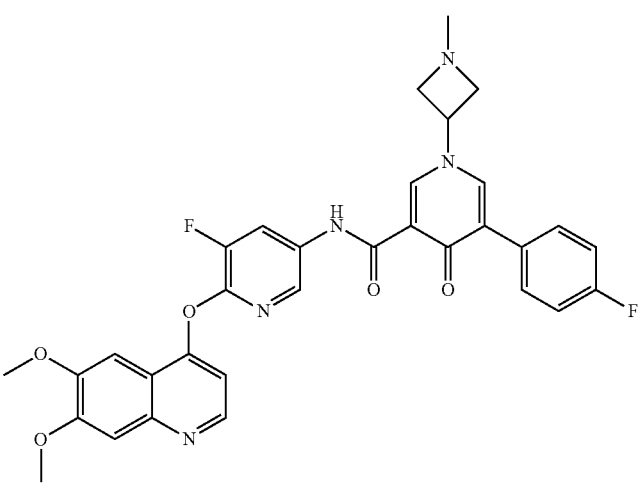 [SMILES: COc1cc2nccc(Oc3ncc(NC(=O)c4cn(C5CN(C)C5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylazetidin-3-yl)-4-oxopyridine-3-carboxamide |
| 401 | 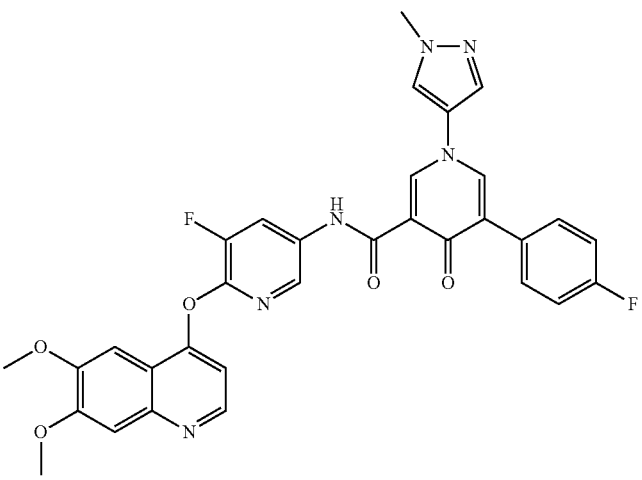 [SMILES: COc1cc2nccc(Oc3ncc(NC(=O)c4cn(-c5cnn(C)c5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylpyrazol-4-yl)-4-oxopyridine-3-carboxamide |
| 402 | 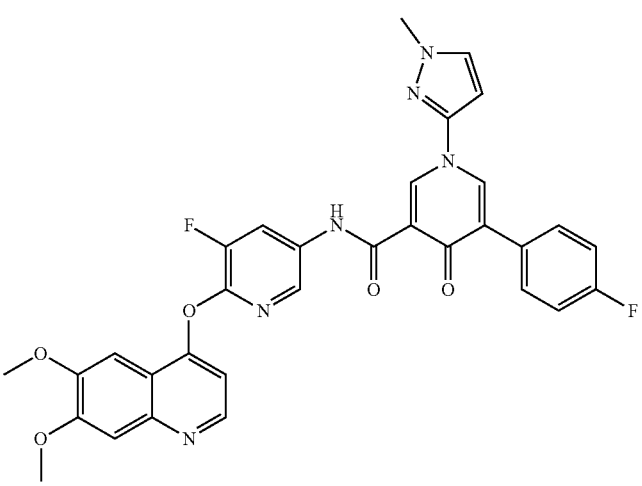 [SMILES: COc1cc2nccc(Oc3ncc(NC(=O)c4cn(-c5ccn(C)n5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylpyrazol-3-yl)-4-oxopyridine-3-carboxamide |

TABLE 1-continued

| Cpd # | Structure | IUPAC Name |
|---|---|---|
| 403 | 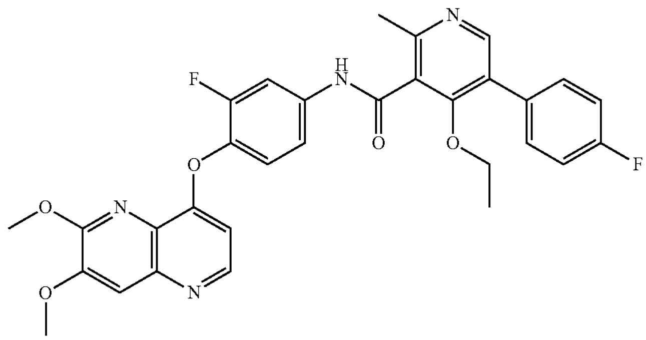 [SMILES: CCOc1c(-c2ccc(F)cc2)cnc(C)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-5-(4-fluorophenyl)-2-methylpyridine-3-carboxamide |
| 404 | 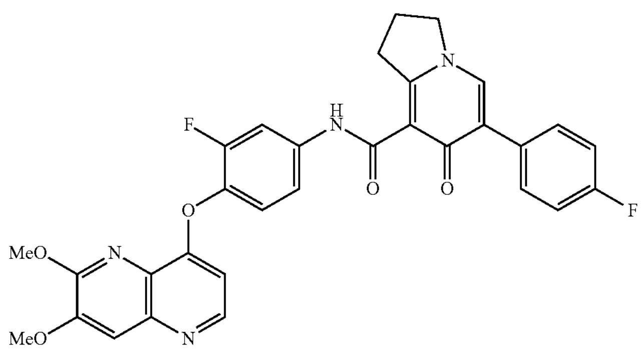 [SMILES: COc1cc2nccc(Oc3ccc(NC(=O)c4c5n(cc(-c6ccc(F)cc6)c4=O)CCC5)cc3F)c2nc1OC] | N-[4-[(6,7-dimethoxy-1,5-naphthyridin-4-yl)oxy]-3-fluorophenyl]-6-(4-fluorophenyl)-7-oxo-2,3-dihydro-1H-indolizine-8-carboxamide |
| 405 | 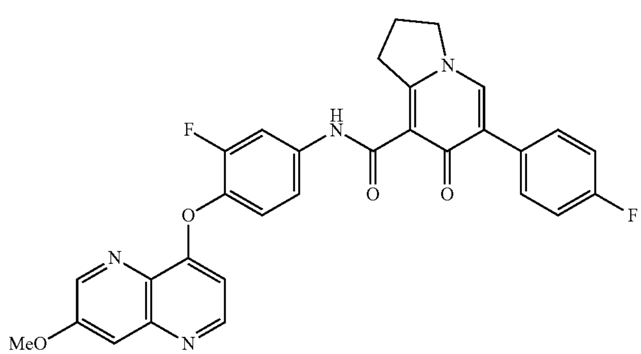 [SMILES: COc1cnc2c(Oc3ccc(NC(=O)c4c5n(cc(-c6ccc(F)cc6)c4=O)CCC5)cc3F)ccnc2c1] | N-[3-fluoro-4-[(7-methoxy-1,5-naphthyridin-4-yl)oxy]phenyl]-6-(4-fluorophenyl)-7-oxo-2,3-dihydro-1H-indolizine-8-carboxamide |
| 406 | 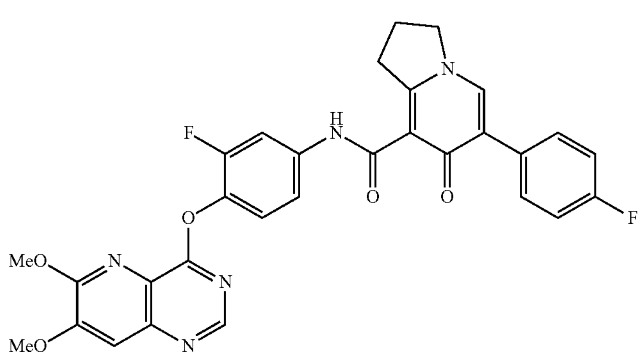 | N-[4-(6,7-dimethoxyquinazolin-4-yl)oxy-3-fluorophenyl]-6-(4-fluorophenyl)-7-oxo-2,3-dihydro-1H-indolizine-8-carboxamide |

TABLE 1-continued

| Cpd # | Structure | IUPAC Name |
|---|---|---|
| 407 | 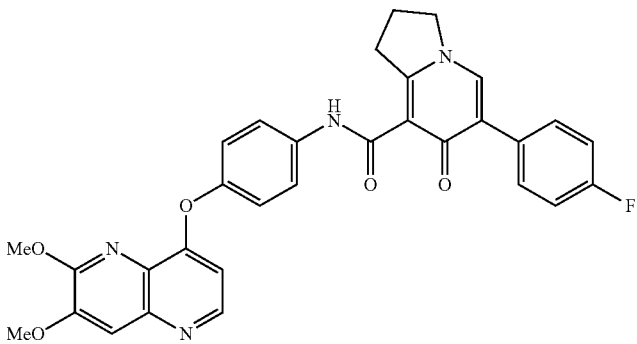 [SMILES: COc1cc2nccc(Oc3ccc(NC(=O)c4c5n(cc(-c6ccc(F)cc6)c4=O)CCC5)cc3)c2nc1OC] | N-[4-[(6,7-dimethoxy-1,5-naphthyridin-4-yl)oxy]phenyl]-6-(4-fluorophenyl)-7-oxo-2,3-dihydro-1H-indolizine-8-carboxamide |
| 408 | 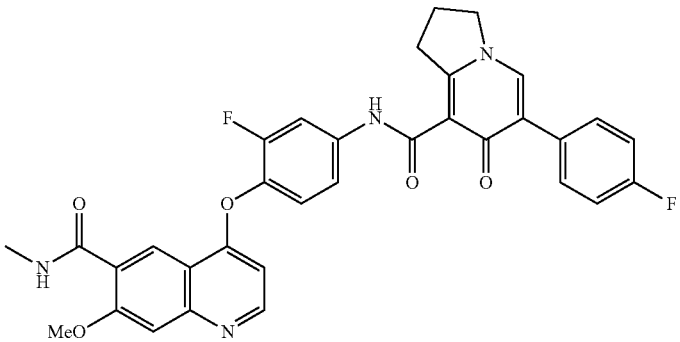 [SMILES: CNC(=O)c1cc2c(Oc3ccc(NC(=O)c4c5n(cc(-c6ccc(F)cc6)c4=O)CCC5)cc3F)ccnc2cc1OC] | 4-[2-fluoro-4-[[6-(4-fluorophenyl)-7-oxo-2,3-dihydro-1H-indolizine-8-carbonyl]amino]phenoxy]-7-methoxy-N-methylquinoline-6-carboxamide |
| 409 | 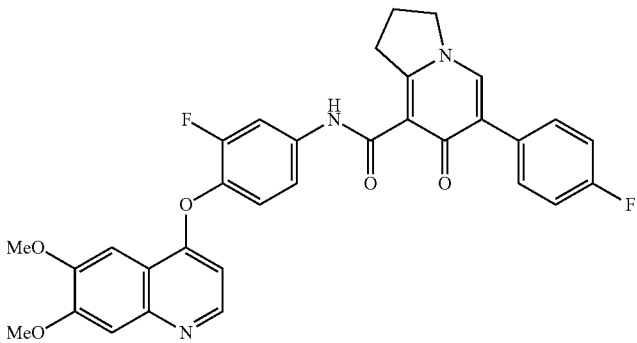 [SMILES: COc1cc2nccc(Oc3ccc(NC(=O)c4c5n(cc(-c6ccc(F)cc6)c4=O)CCC5)cc3F)c2cc1OC] | N-[4-(6,7-dimethoxyquinolin-4-yl)oxy-3-fluorophenyl]-6-(4-fluorophenyl)-7-oxo-2,3-dihydro-1H-indolizine-8-carboxamide |
| 410 | 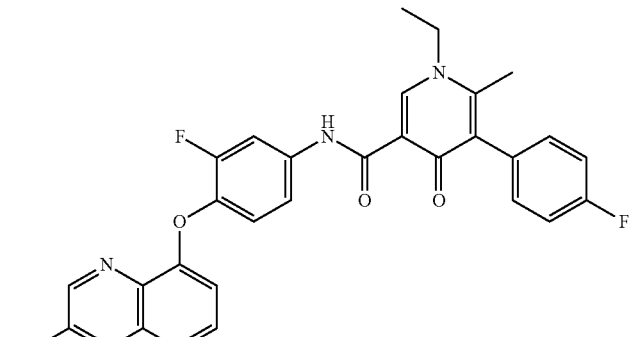 | 1-ethyl-N-[3-fluoro-4-[(7-hydroxy-1,5-naphthyridin-4-yl)oxy]phenyl]-5-(4-fluorophenyl)-6-methyl-4-oxopyridine-3-carboxamide |

TABLE 1-continued

| Cpd # | Structure | IUPAC Name |
|---|---|---|
| 411 | 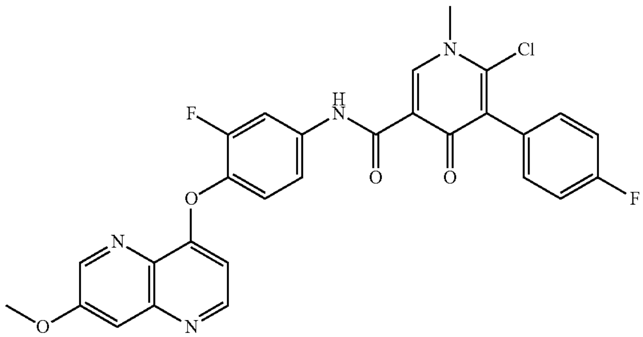 [SMILES: COc1cnc2c(Oc3ccc(NC(=O)c4cn(C)c(Cl)c(-c5ccc(F)cc5)c4=O)cc3F)ccnc2c1] | 6-chloro-N-[3-fluoro-4-[(7-methoxy-1,5-naphthyridin-4-yl)oxy]phenyl]-5-(4-fluorophenyl)-1-methyl-4-oxopyridine-3-carboxamide |
| 412 | 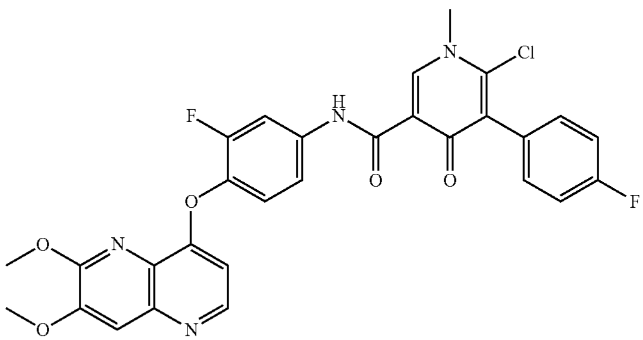 [SMILES: COc1cc2nccc(Oc3ccc(NC(=O)c4cn(C)c(Cl)c(-c5ccc(F)cc5)c4=O)cc3F)c2nc1OC] | 6-chloro-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 413 | 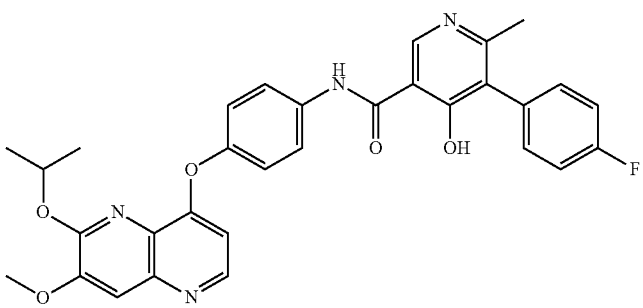 [SMILES: COc1cc2nccc(Oc3ccc(NC(=O)c4cnc(C)c(-c5ccc(F)cc5)c4O)cc3)c2nc1OC(C)C] | 5-(4-fluorophenyl)-4-hydroxy-N-[4-[(7-methoxy-6-propan-2-yloxy-1,5-naphthyridin-4-yl)oxy]phenyl]-6-methylpyridine-3-carboxamide |
| 414 | 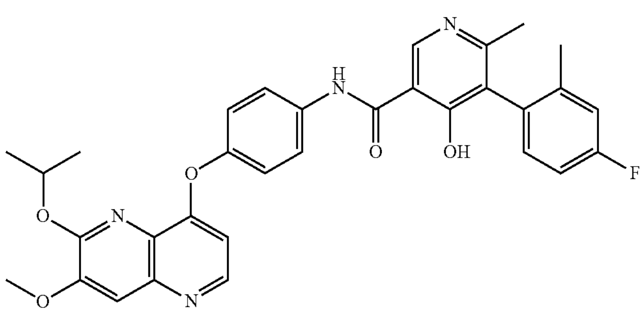 [SMILES: COc1cc2nccc(Oc3ccc(NC(=O)c4cnc(C)c(-c5ccc(F)cc5C)c4O)cc3)c2nc1OC(C)C] | 5-(4-fluoro-2-methylphenyl)-4-hydroxy-N-[4-[(7-methoxy-6-propan-2-yloxy-1,5-naphthyridin-4-yl)oxy]phenyl]-6-methylpyridine-3-carboxamide |
| 415 | 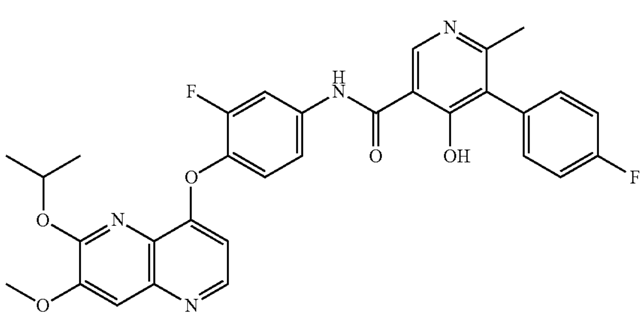 [SMILES: COc1cc2nccc(Oc3ccc(NC(=O)c4cnc(C)c(-c5ccc(F)cc5)c4O)cc3F)c2nc1OC(C)C] | N-[3-fluoro-4-[(7-methoxy-6-propan-2-yloxy-1,5-naphthyridin-4-yl)oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 416 | 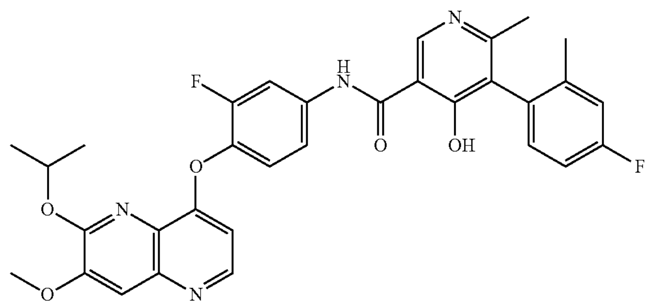 [SMILES: COc1cc2nccc(Oc3ccc(NC(=O)c4cnc(C)c(-c5ccc(F)cc5C)c4O)cc3F)c2nc1OC(C)C] | N-[3-fluoro-4-[(7-methoxy-6-propan-2-yloxy-1,5-naphthyridin-4-yl)oxy]phenyl]-5-(4-fluoro-2-methylphenyl)-4-hydroxy-6-methylpyridine-3-carboxamide |
| 417 | 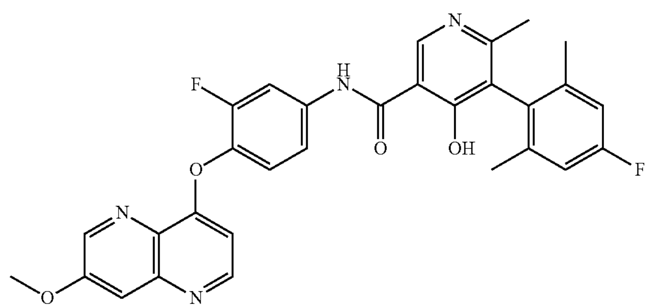 [SMILES: COc1cnc2c(Oc3ccc(NC(=O)c4cnc(C)c(-c5c(C)cc(F)cc5C)c4O)cc3F)ccnc2c1] | 5-(4-fluoro-2,6-dimethylphenyl)-N-[3-fluoro-4-[(7-methoxy-1,5-naphthyridin-4-yl)oxy]phenyl]-4-hydroxy-6-methylpyridine-3-carboxamide |
| 418 | 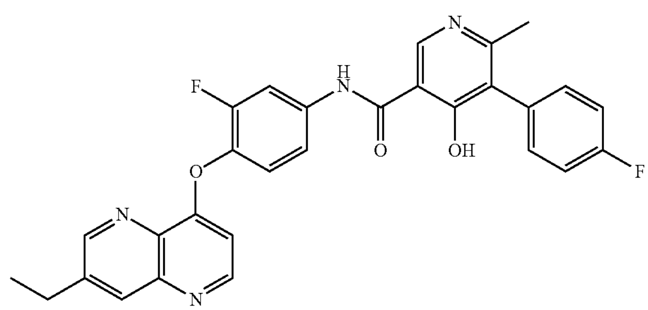 | N-[4-[(7-ethyl-1,5-naphthyridin-4-yl)oxy]-3-fluorophenyl]-5-(4-fluorophenyl)-4-hydroxy-6-methylpyridine-3-carboxamide |
| 419 | 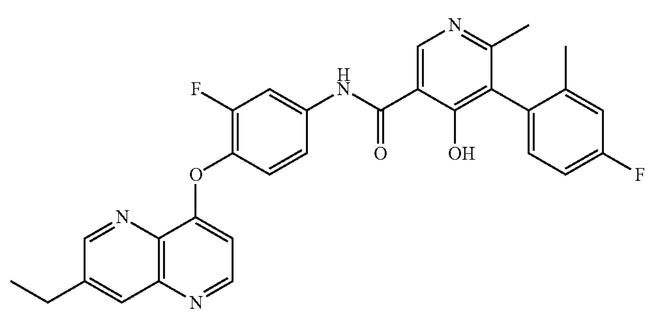 [SMILES: CCc1cnc2c(Oc3ccc(NC(=O)c4cnc(C)c(-c5ccc(F)cc5C)c4O)cc3F)ccnc2c1] | N-[4-[(7-ethyl-1,5-naphthyridin-4-yl)oxy]-3-fluorophenyl]-5-(4-fluoro-2-methylphenyl)-4-hydroxy-6-methylpyridine-3-carboxamide |
| 420 | 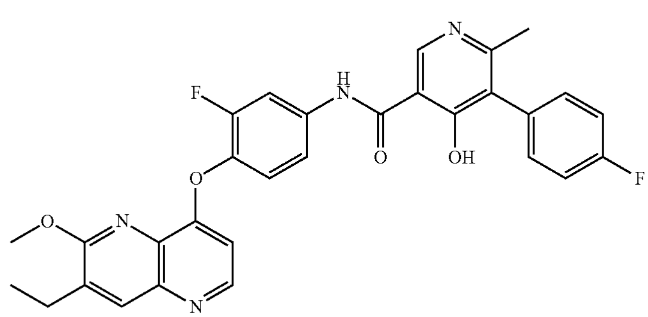 [SMILES: CCc1cc2nccc(Oc3ccc(NC(=O)c4cnc(C)c(-c5ccc(F)cc5)c4O)cc3F)c2nc1OC] | N-[4-[(7-ethyl-6-methoxy-1,5-naphthyridin-4-yl)oxy]-3-fluorophenyl]-5-(4-fluorophenyl)-4-hydroxy-6-methylpyridine-3-carboxamide |

TABLE 1-continued

| Cpd # | Structure | IUPAC Name |
|---|---|---|
| 421 | 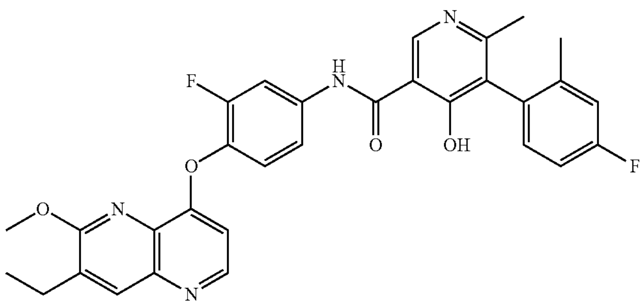 [SMILES: CCc1cc2nccc(Oc3ccc(NC(=O)c4cnc(C)c(-c5ccc(F)cc5C)c4O)cc3F)c2nc1OC] | N-[4-[(7-ethyl-6-methoxy-1,5-naphthyridin-4-yl)oxy]-3-fluorophenyl]-5-(4-fluoro-2-methylphenyl)-4-hydroxy-6-methylpyridine-3-carboxamide |
| 422 | 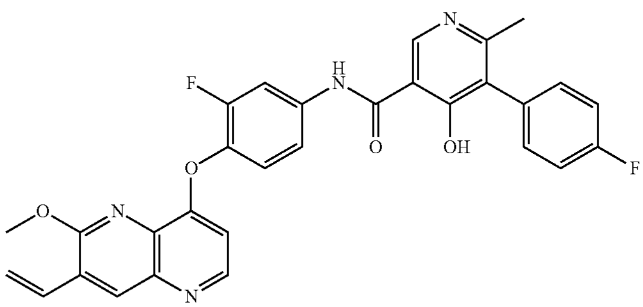 [SMILES: C=Cc1cc2nccc(Oc3ccc(NC(=O)c4cnc(C)c(-c5ccc(F)cc5)c4O)cc3F)c2nc1OC] | N-[4-[(7-ethenyl-6-methoxy-1,5-naphthyridin-4-yl)oxy]-3-fluorophenyl]-5-(4-fluorophenyl)-4-hydroxy-6-methylpyridine-3-carboxamide |
| 423 | 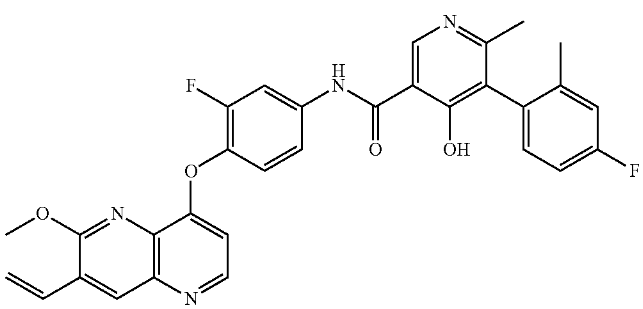 [SMILES: C=Cc1cc2nccc(Oc3ccc(NC(=O)c4cnc(C)c(-c5ccc(F)cc5C)c4O)cc3F)c2nc1OC] | N-[4-[(7-ethenyl-6-methoxy-1,5-naphthyridin-4-yl)oxy]-3-fluorophenyl]-5-(4-fluoro-2-methylphenyl)-4-hydroxy-6-methylpyridine-3-carboxamide |
| 424 | 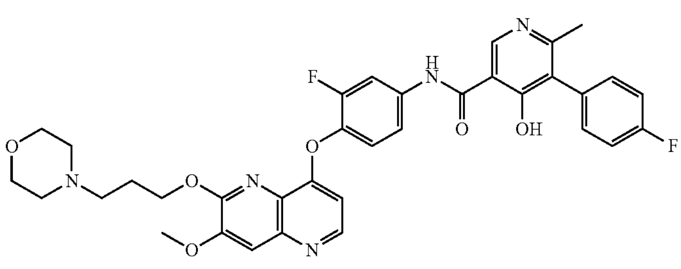 [SMILES: COc1cc2nccc(Oc3ccc(NC(=O)c4cnc(C)c(-c5ccc(F)cc5)c4O)cc3F)c2nc1OCCCN1CCOCC1] | N-[3-fluoro-4-[[7-methoxy-6-(3-morpholin-4-ylpropoxy)-1,5-naphthyridin-4-yl]oxy]phenyl]-5-(4-fluorophenyl)-4-hydroxy-6-methylpyridine-3-carboxamide |
| 425 | 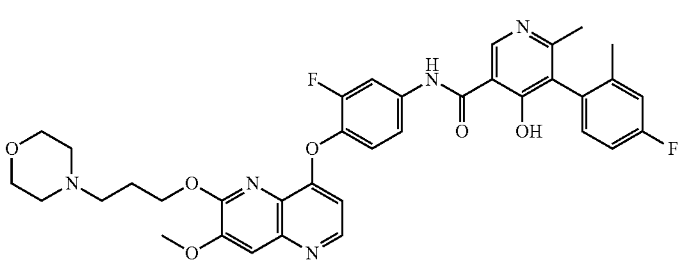 [SMILES: COc1cc2nccc(Oc3ccc(NC(=O)c4cnc(C)c(-c5ccc(F)cc5C)c4O)cc3F)c2nc1OCCCN1CCOCC1] | N-[3-fluoro-4-[[7-methoxy-6-(3-morpholin-4-ylpropoxy)-1,5-naphthyridin-4-yl]oxy]phenyl]-5-(4-fluoro-2-methylphenyl)-4-hydroxy-6-methylpyridine-3-carboxamide |

TABLE 1-continued

| Cpd # | Structure | IUPAC Name |
|---|---|---|
| 426 | 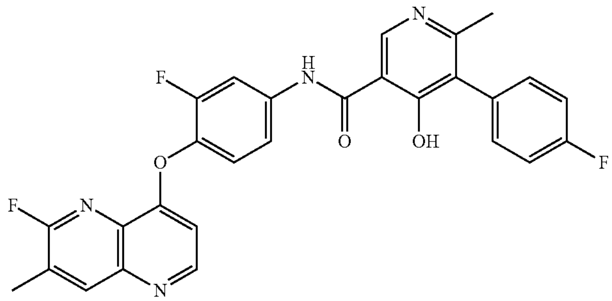 [SMILES: Cc1cc2nccc(Oc3ccc(NC(=O)c4cnc(C)c(-c5ccc(F)cc5)c4O)cc3F)c2nc1F] | N-[3-fluoro-4-[(6-fluoro-7-methyl-1,5-naphthyridin-4-yl)oxy]phenyl]-5-(4-fluorophenyl)-4-hydroxy-6-methylpyridine-3-carboxamide |
| 427 | 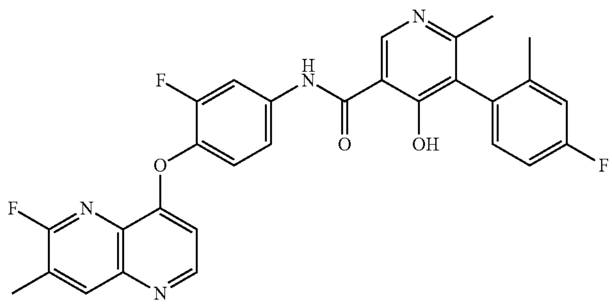 [SMILES: Cc1cc(F)ccc1-c1c(C)ncc(C(=O)Nc2ccc(Oc3ccnc4cc(C)c(F)nc34)c(F)c2)c1O] | N-[3-fluoro-4-[(6-fluoro-7-methyl-1,5-naphthyridin-4-yl)oxy]phenyl]-5-(4-fluoro-2-methylphenyl)-4-hydroxy-6-methylpyridine-3-carboxamide |
| 428 | 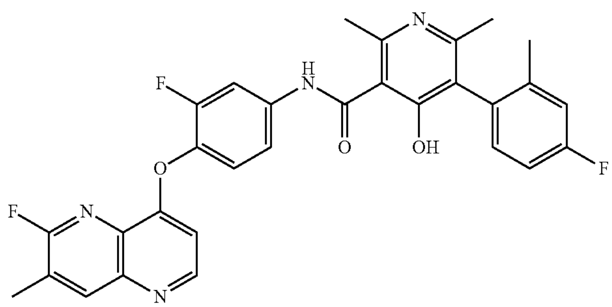 [SMILES: Cc1cc(F)ccc1-c1c(C)nc(C)c(C(=O)Nc2ccc(Oc3ccnc4cc(C)c(F)nc34)c(F)c2)c1O] | N-[3-fluoro-4-[(6-fluoro-7-methyl-1,5-naphthyridin-4-yl)oxy]phenyl]-5-(4-fluoro-2-methylphenyl)-4-hydroxy-2,6-dimethylpyridine-3-carboxamide |
| 429 | 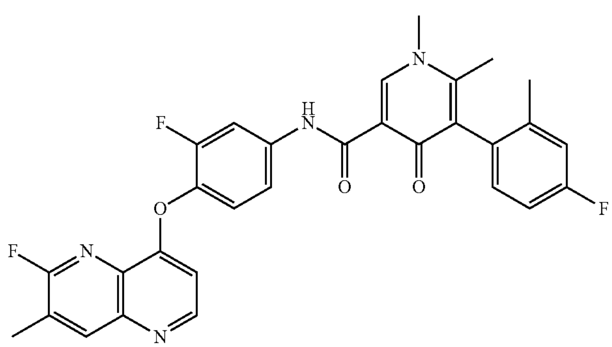 [SMILES: Cc1cc(F)ccc1-c1c(C)n(C)cc(C(=O)Nc2ccc(Oc3ccnc4cc(C)c(F)nc34)c(F)c2)c1=O] | N-[3-fluoro-4-[(6-fluoro-7-methyl-1,5-naphthyridin-4-yl)oxy]phenyl]-5-(4-fluoro-2-methylphenyl)-1,6-dimethyl-4-oxopyridine-3-carboxamide |
| 430 | 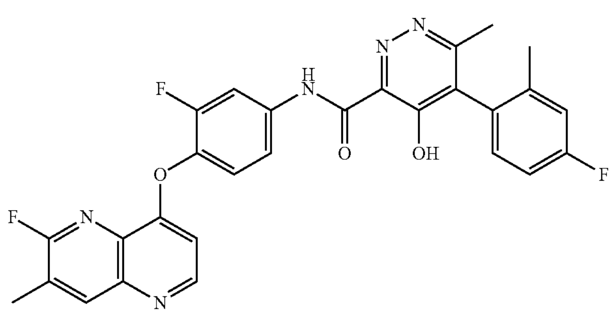 | N-[3-fluoro-4-[(6-fluoro-7-methyl-1,5-naphthyridin-4-yl)oxy]phenyl]-5-(4-fluoro-2-methylphenyl)-4-hydroxy-6-methylpyridazine-3-carboxamide |

TABLE 1-continued

| Cpd # | Structure | IUPAC Name |
|---|---|---|
| 431 | 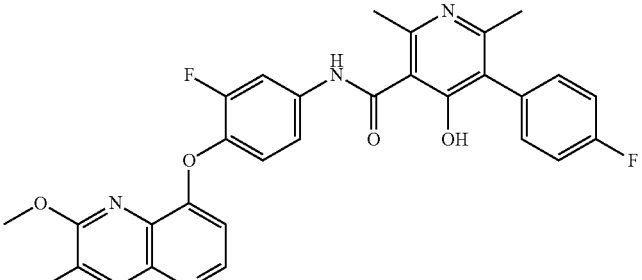 | N-[3-fluoro-4-[(7-hydroxy-6-methoxy-1,5-naphthyridin-4-yl)oxy]phenyl]-5-(4-fluorophenyl)-4-hydroxy-2,6-dimethylpyridine-3-carboxamide |
| 432 | 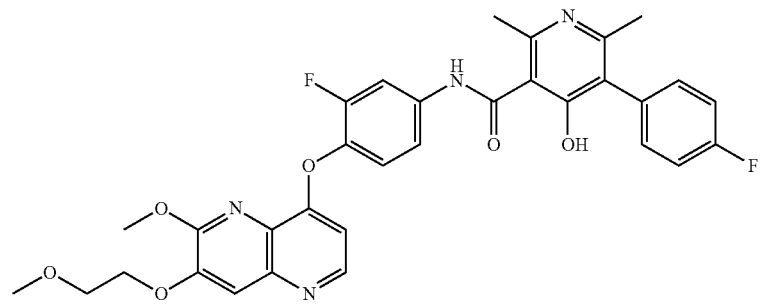 [SMILES: COCCOc1cc2nccc(Oc3ccc(NC(=O)c4c(C)nc(C)c(-c5ccc(F)cc5)c4O)cc3F)c2nc1OC] | N-[3-fluoro-4-[[6-methoxy-7-(2-methoxyethoxy)-1,5-naphthyridin-4-yl]oxy]phenyl]-5-(4-fluorophenyl)-4-hydroxy-2,6-dimethylpyridine-3-carboxamide |
| 433 | 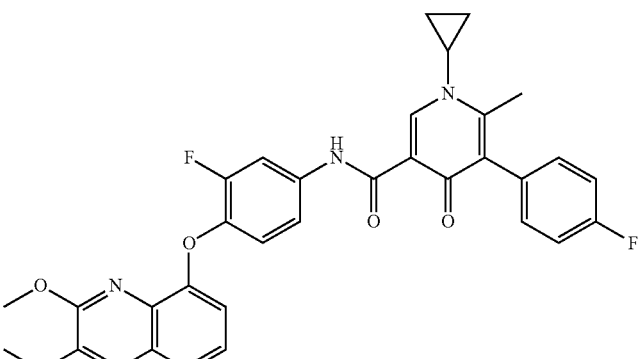 | 1-cyclopropyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 434 | 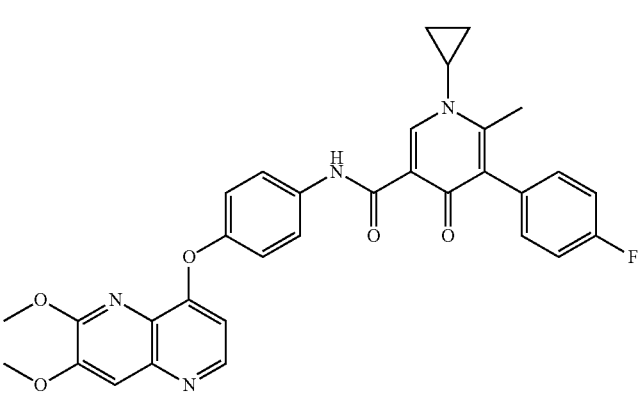 [SMILES: COc1cc2nccc(Oc3ccc(NC(=O)c4cn(C5CC5)c(C)c(-c5ccc(F)cc5)c4=O)cc3)c2nc1OC] | 1-cyclopropyl-N-[4-[(6,7-dimethoxy-1,5-naphthyridin-4-yl)oxy]phenyl]-5-(4-fluorophenyl)-6-methyl-4-oxopyridine-3-carboxamide |

TABLE 1-continued

| Cpd # | Structure | IUPAC Name |
|---|---|---|
| 435 | 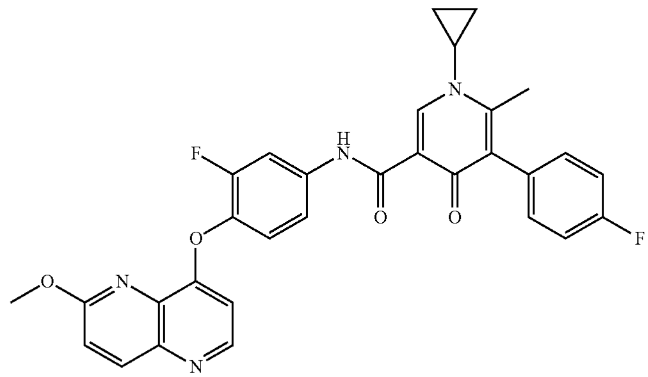 [SMILES: COc1ccc2nccc(Oc3ccc(NC(=O)c4cn(C5CC5)c(C)c(-c5ccc(F)cc5)c4=O)cc3F)c2n1] | 1-cyclopropyl-N-[3-fluoro-4-[(6-methoxy-1,5-naphthyridin-4-yl)oxy]phenyl]-5-(4-fluorophenyl)-6-methyl-4-oxopyridine-3-carboxamide |
| 436 | 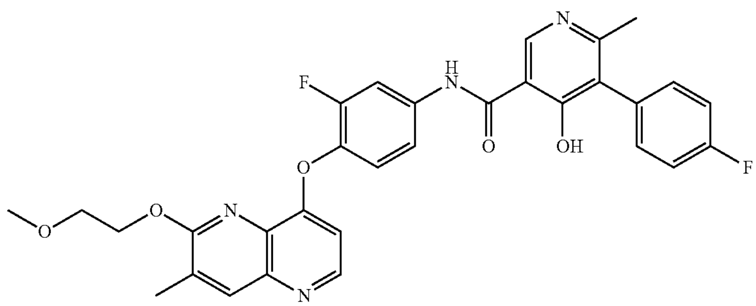 [SMILES: COCCOc1nc2c(Oc3ccc(NC(=O)c4cnc(C)c(-c5ccc(F)cc5)c4O)cc3F)ccnc2cc1C] | N-[3-fluoro-4-[[6-(2-methoxyethoxy)-7-methyl-1,5-naphthyridin-4-yl]oxy]phenyl]-5-(4-fluorophenyl)-4-hydroxy-6-methylpyridine-3-carboxamide |
| 437 | 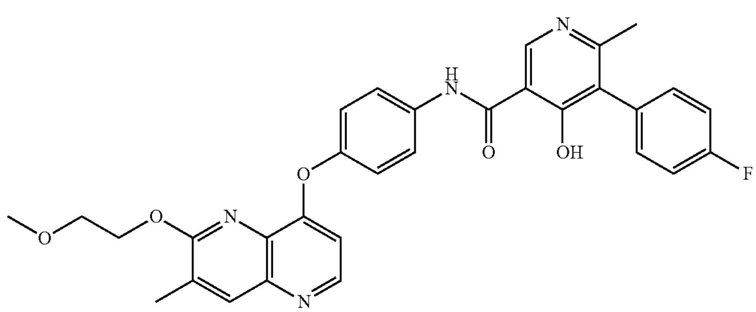 [SMILES: COCCOc1nc2c(Oc3ccc(NC(=O)c4cnc(C)c(-c5ccc(F)cc5)c4O)cc3)ccnc2cc1C] | 5-(4-fluorophenyl)-4-hydroxy-N-[4-[[6-(2-methoxyethoxy)-7-methyl-1,5-naphthyridin-4-yl]oxy]phenyl]-6-methylpyridine-3-carboxamide |
| 438 | 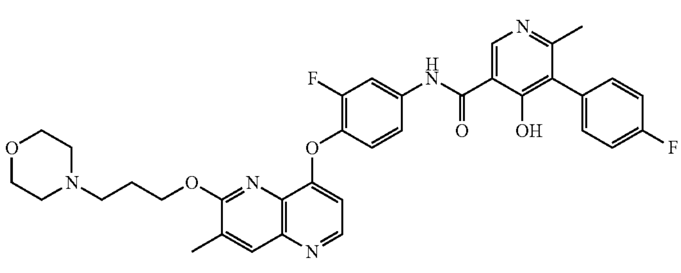 [SMILES: Cc1cc2nccc(Oc3ccc(NC(=O)c4cnc(C)c(-c5ccc(F)cc5)c4O)cc3F)c2nc1OCCCN1CCOCC1] | N-[3-fluoro-4-[[7-methyl-6-(3-morpholin-4-ylpropoxy)-1,5-naphthyridin-4-yl]oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 439 | 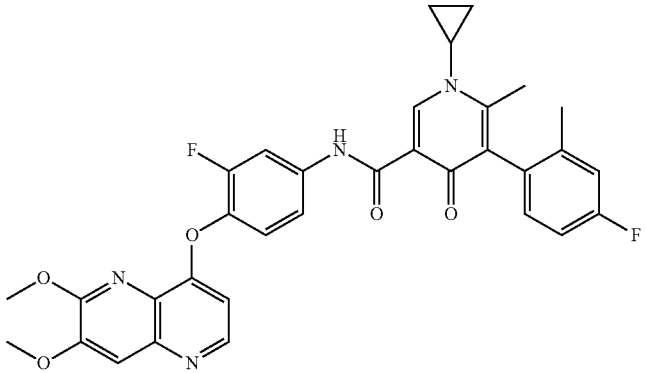 [SMILES: COc1cc2nccc(Oc3ccc(NC(=O)c4cn(C5CC5)c(C)c(-c5ccc(F)cc5C)c4=O)cc3F)c2nc1OC] | 1-cyclopropyl-N-[4-[(6,7-dimethoxy-1,5-naphthyridin-4-yl)oxy]-3-fluorophenyl]-5-(4-fluoro-2-methylphenyl)-6-methyl-4-oxopyridine-3-carboxamide |
| 440 | 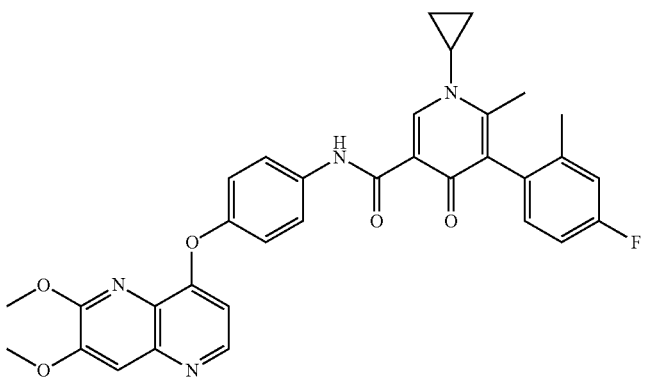 [SMILES: COc1cc2nccc(Oc3ccc(NC(=O)c4cn(C5CC5)c(C)c(-c5ccc(F)cc5C)c4=O)cc3)c2nc1OC] | 1-cyclopropyl-N-[4-[(6,7-dimethoxy-1,5-naphthyridin-4-yl)oxy]phenyl]-5-(4-fluoro-2-methylphenyl)-6-methyl-4-oxopyridine-3-carboxamide |
| 441 | 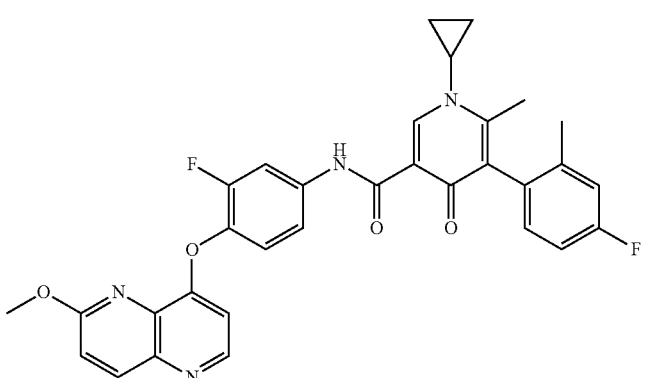 | 1-cyclopropyl-N-[3-fluoro-4-[(6-methoxy-1,5-naphthyridin-4-yl)oxy]phenyl]-5-(4-fluoro-2-methylphenyl)-6-methyl-4-oxopyridine-3-carboxamide |
| 442 | 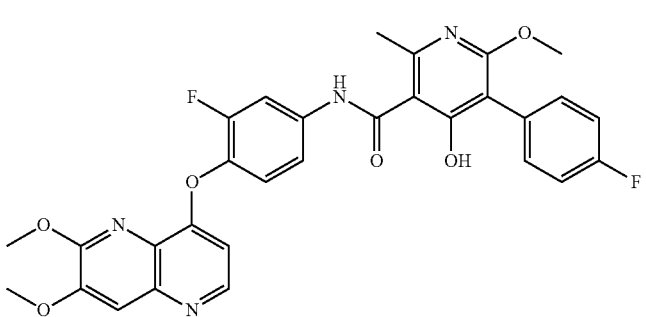 [SMILES: COc1cc2nccc(Oc3ccc(NC(=O)c4c(C)nc(OC)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-methoxy-2-methylpyridine-3-carboxamide |

TABLE 1-continued

| Cpd # | Structure | IUPAC Name |
|---|---|---|
| 443 | 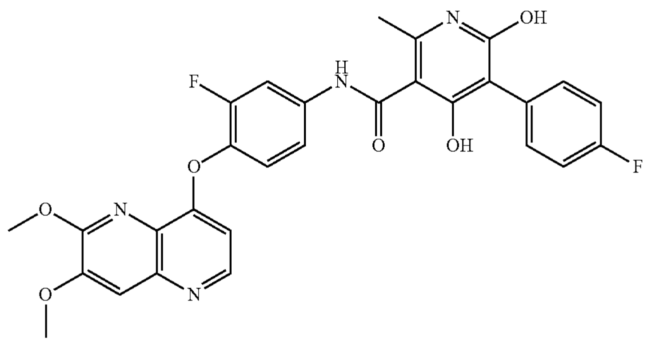 [SMILES: COc1cc2nccc(Oc3ccc(NC(=O)c4c(C)nc(O)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4,6-dihydroxy-2-methylpyridine-3-carboxamide |
| 444 | 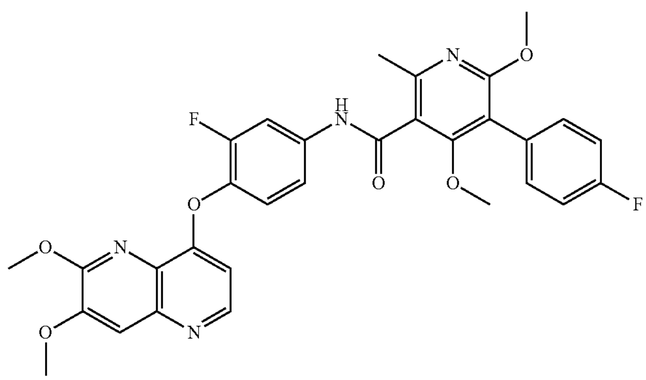 [SMILES: COc1cc2nccc(Oc3ccc(NC(=O)c4c(C)nc(OC)c(-c5ccc(F)cc5)c4OC)cc3F)c2nc1OC] | N-[4-[(6,7-dimethoxy-1,5-naphthyridin-4-yl)oxy]-3-fluorophenyl]-5-(4-fluorophenyl)-4,6-dimethoxy-2-methylpyridine-3-carboxamide |
| 445 | 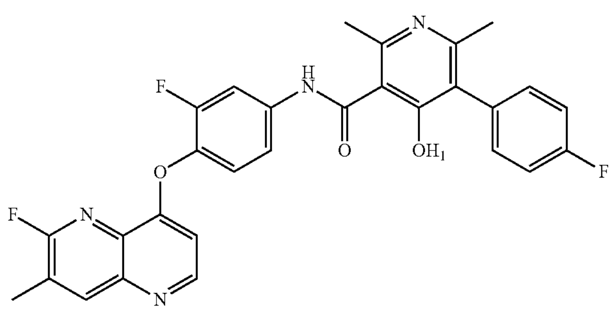 [SMILES: Cc1cc2nccc(Oc3ccc(NC(=O)c4c(C)nc(C)c(-c5ccc(F)cc5)c4O)cc3F)c2nc1F] | N-[3-fluoro-4-[(6-fluoro-7-methyl-1,5-naphthyridin-4-yl)oxy]phenyl]-5-(4-fluorophenyl)-4-hydroxy-2,6-dimethylpyridine-3-carboxamide |
| 446 | 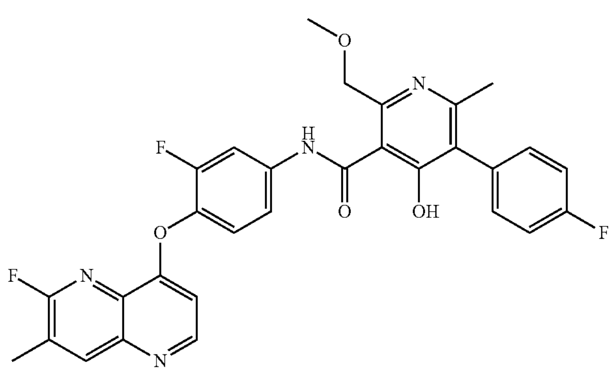 [SMILES: COCc1nc(C)c(-c2ccc(F)cc2)c(O)c1C(=O)Nc1ccc(Oc2ccnc3cc(C)c(F)nc23)c(F)c1] | N-[3-fluoro-4-[(6-fluoro-7-methyl-1,5-naphthyridin-4-yl)oxy]phenyl]-5-(4-fluorophenyl)-4-hydroxy-2-(methoxymethyl)-6-methylpyridine-3-carboxamide |

TABLE 1-continued

| Cpd # | Structure | IUPAC Name |
|---|---|---|
| 447 | 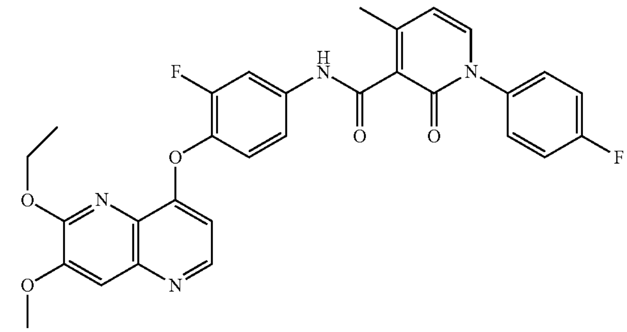 [SMILES: CCOc1nc2c(Oc3ccc(NC(=O)c4c(C)ccn(-c5ccc(F)cc5)c4=O)cc3F)ccnc2cc1OC] | N-[4-[(6-ethoxy-7-methoxy-1,5-naphthyridin-4-yl)oxy]-3-fluorophenyl]-1-(4-fluorophenyl)-4-methyl-2-oxopyridine-3-carboxamide |
| 448 | 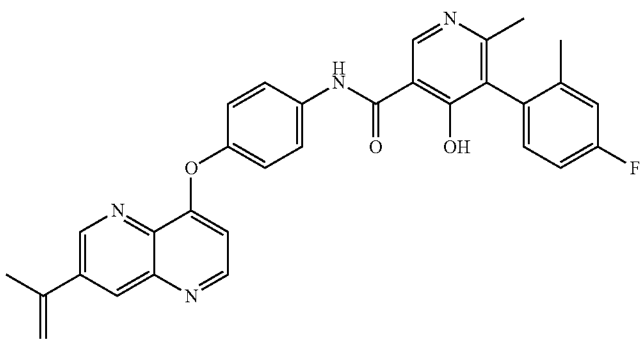 [SMILES: C=C(C)c1cnc2c(Oc3ccc(NC(=O)c4cnc(C)c(-c5ccc(F)cc5C)c4O)cc3)ccnc2c1] | 5-(4-fluoro-2-methylphenyl)-4-hydroxy-6-methyl-N-[4-[(7-prop-1-en-2-yl-1,5-naphthyridin-4-yl)oxy]phenyl]pyridine-3-carboxamide |
| 449 | 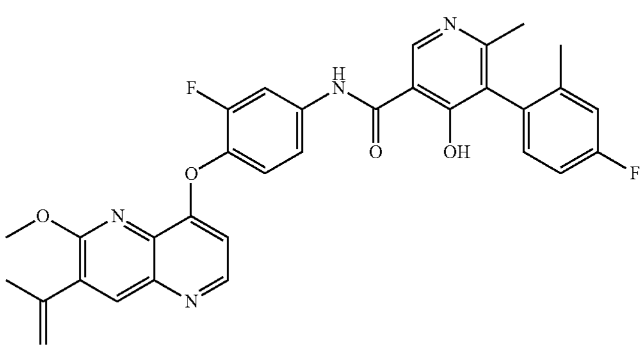 | N-[3-fluoro-4-[(6-methoxy-7-prop-1-en-2-yl-1,5-naphthyridin-4-yl)oxy]phenyl]-5-(4-fluoro-2-methylphenyl)-4-hydroxy-6-methylpyridine-3-carboxamide |
| 450 | 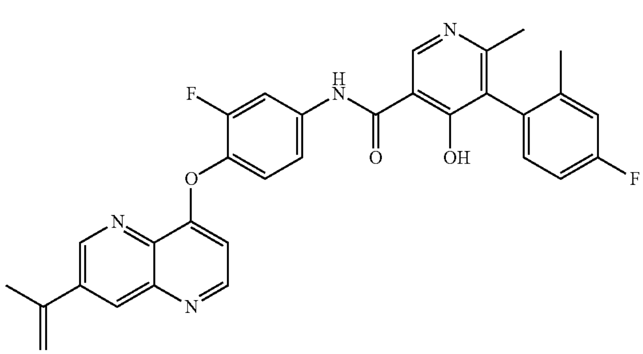 [SMILES: C=C(C)c1cnc2c(Oc3ccc(NC(=O)c4cnc(C)c(-c5ccc(F)cc5C)c4O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-4-hydroxy-6-methylpyridine-3-carboxamide |

TABLE 1-continued

| Cpd # | Structure | IUPAC Name |
|---|---|---|
| 451 | 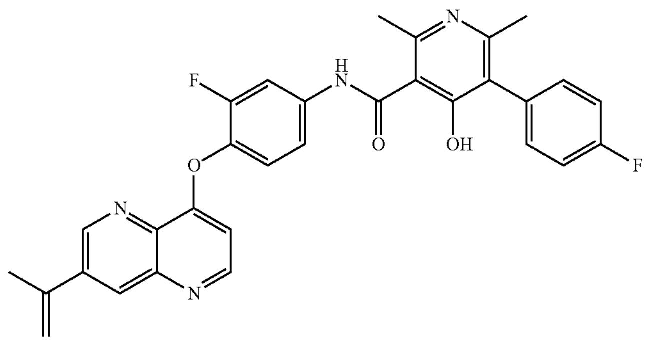 [SMILES: C=C(C)c1cnc2c(Oc3ccc(NC(=O)c4c(C)nc(C)c(-c5ccc(F)cc5)c4O)cc3F)ccnc2c1] | 5-(4-fluorophenyl)-N-[3-fluoro-4-[(7-prop-1-en-2-yl-1,5-naphthyridin-4-yl)oxy]phenyl]-4-hydroxy-2,6-dimethylpyridine-3-carboxamide |
| 452 | 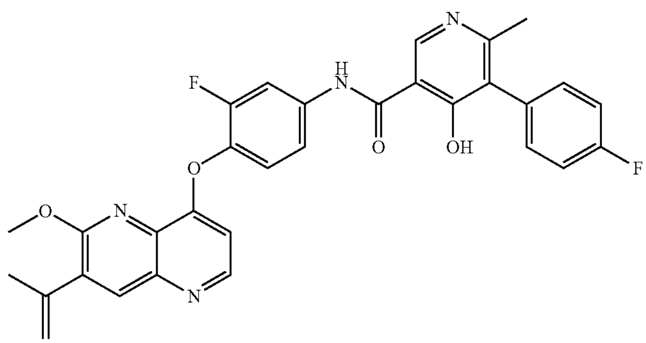 [SMILES: C=C(C)c1cc2nccc(Oc3ccc(NC(=O)c4cnc(C)c(-c5ccc(F)cc5)c4O)cc3F)c2nc1OC] | N-[3-fluoro-4-[(6-methoxy-7-prop-1-en-2-yl-1,5-naphthyridin-4-yl)oxy]phenyl]-5-(4-fluorophenyl)-4-hydroxy-6-methylpyridine-3-carboxamide |
| 453 | 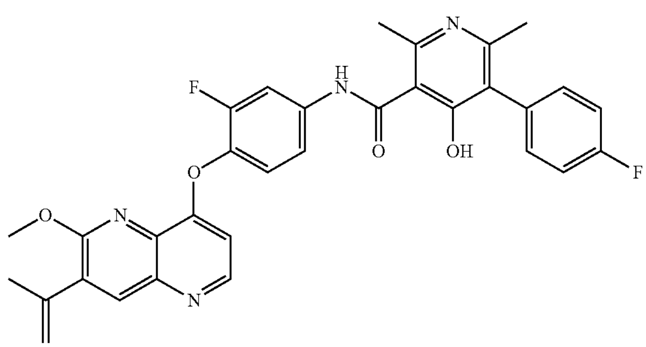 [SMILES: C=C(C)c1cc2nccc(Oc3ccc(NC(=O)c4c(C)nc(C)c(-c5ccc(F)cc5)c4O)cc3F)c2nc1OC] | N-[3-fluoro-4-[(6-methoxy-7-prop-1-en-2-yl-1,5-naphthyridin-4-yl)oxy]phenyl]-5-(4-fluorophenyl)-4-hydroxy-2,6-dimethylpyridine-3-carboxamide |
| 454 | 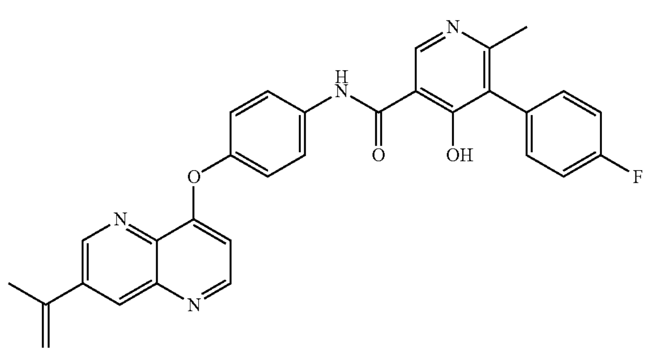 [SMILES: C=C(C)c1cnc2c(Oc3ccc(NC(=O)c4cnc(C)c(-c5ccc(F)cc5)c4O)cc3)ccnc2c1] | 5-(4-fluorophenyl)-4-hydroxy-6-methyl-N-[4-[(7-prop-1-en-2-yl-1,5-naphthyridin-4-yl)oxy]phenyl]pyridine-3-carboxamide |

TABLE 1-continued

| Cpd # | Structure | IUPAC Name |
|---|---|---|
| 455 | 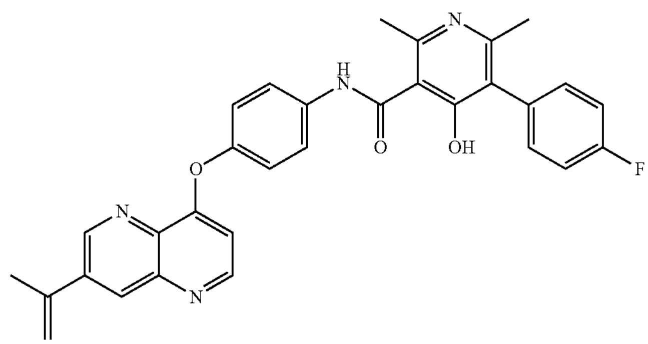 [SMILES: C=C(C)c1cnc2c(Oc3ccc(NC(=O)c4c(C)nc(C)c(-c5ccc(F)cc5)c4O)cc3)ccnc2c1] | 5-(4-fluorophenyl)-4-hydroxy-2,6-dimethyl-N-[4-[(7-prop-1-en-2-yl-1,5-naphthyridin-4-yl)oxy]phenyl]pyridine-3-carboxamide |
| 456 | 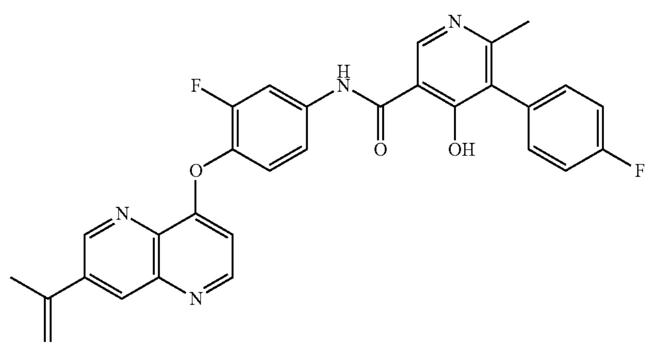 [SMILES: C=C(C)c1cnc2c(Oc3ccc(NC(=O)c4cnc(C)c(-c5ccc(F)cc5)c4O)cc3F)ccnc2c1] | 5-(4-fluorophenyl)-N-[3-fluoro-4-[(7-prop-1-en-2-yl-1,5-naphthyridin-4-yl)oxy]phenyl]-4-hydroxy-6-methylpyridine-3-carboxamide |
| 457 | 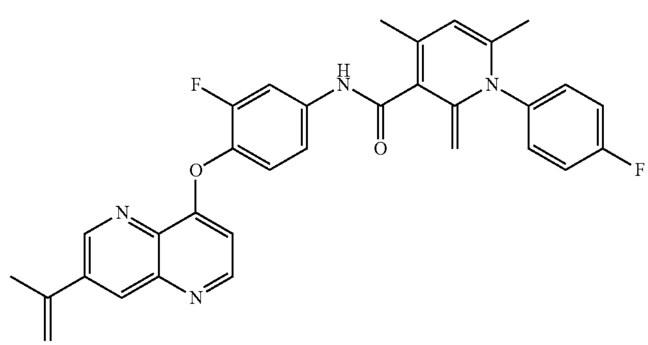 [SMILES: C=C(C)c1cnc2c(Oc3ccc(NC(=O)C4=C(C)C=C(C)N(c5ccc(F)cc5)C4=C)cc3F)ccnc2c1] | 1-(4-fluorophenyl)-N-[3-fluoro-4-[(7-prop-1-en-2-yl-1,5-naphthyridin-4-yl)oxy]phenyl]-4,6-dimethyl-2-oxopyridine-3-carboxamide |
| 458 | 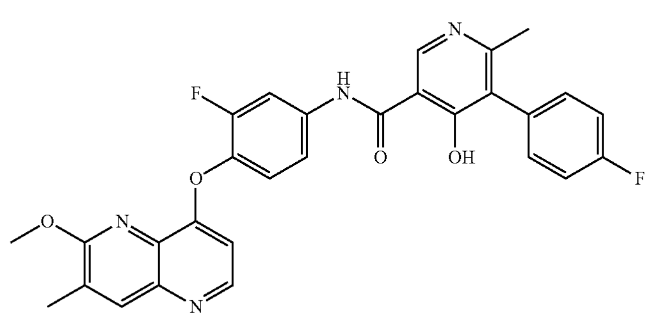 [SMILES: COc1nc2c(Oc3ccc(NC(=O)c4cnc(C)c(-c5ccc(F)cc5)c4O)cc3F)ccnc2cc1C] | N-[3-fluoro-4-[(6-methoxy-7-methyl-1,5-naphthyridin-4-yl)oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 459 | 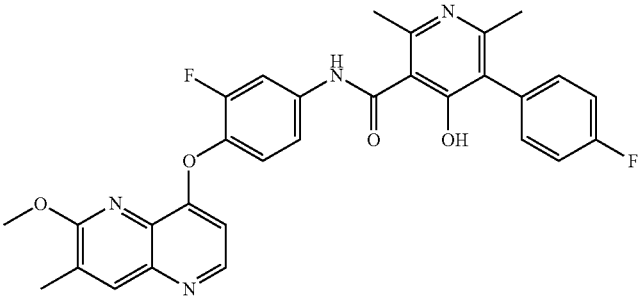 [SMILES: COc1nc2c(Oc3ccc(NC(=O)c4c(C)nc(C)c(-c5ccc(F)cc5)c4O)cc3F)ccnc2cc1C] | N-[3-fluoro-4-[(6-methoxy-7-methyl-1,5-naphthyridin-4-yl)oxy]phenyl]-5-(4-fluorophenyl)-4-hydroxy-2,6-dimethylpyridine-3-carboxamide |
| 460 | 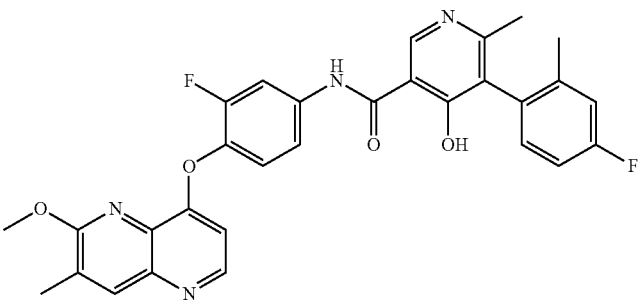 [SMILES: COc1nc2c(Oc3ccc(NC(=O)c4cnc(C)c(-c5ccc(F)cc5C)c4O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-4-hydroxy-6-methylpyridine-3-carboxamide |
| 461 | 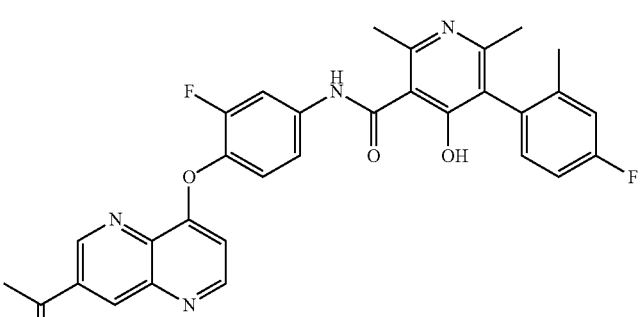 | 5-(4-fluoro-2-methylphenyl)-N-[3-fluoro-4-[(7-prop-1-en-2-yl-1,5-naphthyridin-4-yl)oxy]phenyl]-4-hydroxy-2,6-dimethylpyridine-3-carboxamide |
| 462 | 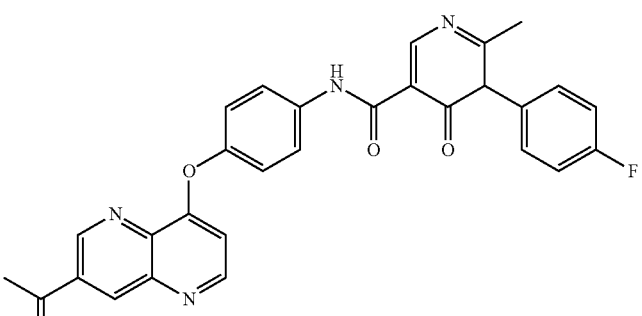 | 1-(4-fluorophenyl)-2-methyl-6-oxo-N-[4-[(7-prop-1-en-2-yl-1,5-naphthyridin-4-yl)oxy]phenyl]pyrimidine-5-carboxamide |

TABLE 1-continued

| Cpd # | Structure | IUPAC Name |
|---|---|---|
| 463 | 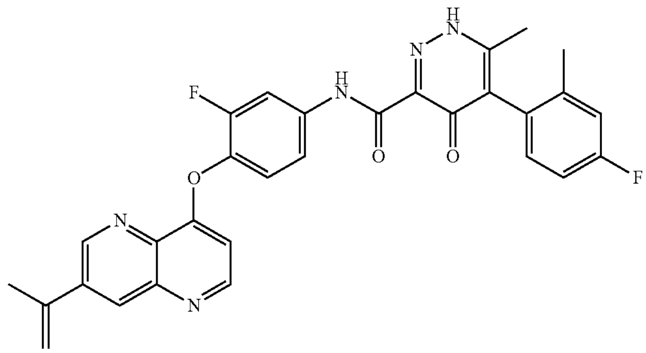 [SMILES: C=C(C)c1cnc2c(Oc3ccc(NC(=O)c4n[nH]c(C)c(-c5ccc(F)cc5C)c4=O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-6-methyl-4-oxo-1H-pyridazine-3-carboxamide |
| 464 | 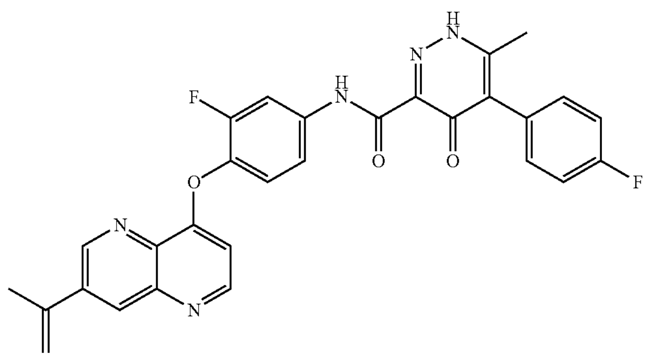 [SMILES: C=C(C)c1cnc2c(Oc3ccc(NC(=O)c4n[nH]c(C)c(-c5ccc(F)cc5)c4=O)cc3F)ccnc2c1] | 5-(4-fluorophenyl)-N-[3-fluoro-4-[(7-prop-1-en-2-yl-1,5-naphthyridin-4-yl)oxy]phenyl]-6-methyl-4-oxo-1H-pyridazine-3-carboxamide |
| 465 | 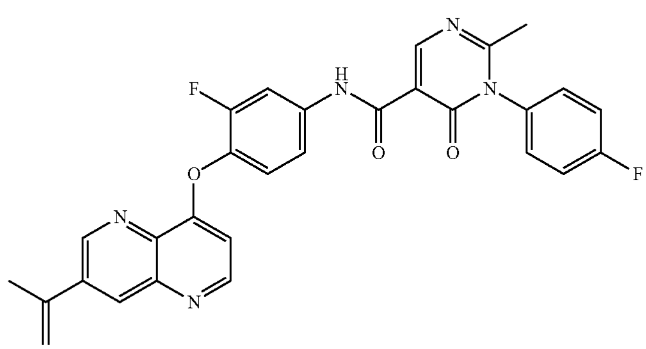 [SMILES: C=C(C)c1cnc2c(Oc3ccc(NC(=O)c4cnc(C)n(-c5ccc(F)cc5)c4=O)cc3F)ccnc2c1] | 1-(4-fluorophenyl)-N-[3-fluoro-4-[(7-prop-1-en-2-yl-1,5-naphthyridin-4-yl)oxy]phenyl]-2-methyl-6-oxopyrimidine-5-carboxamide |
| 466 | 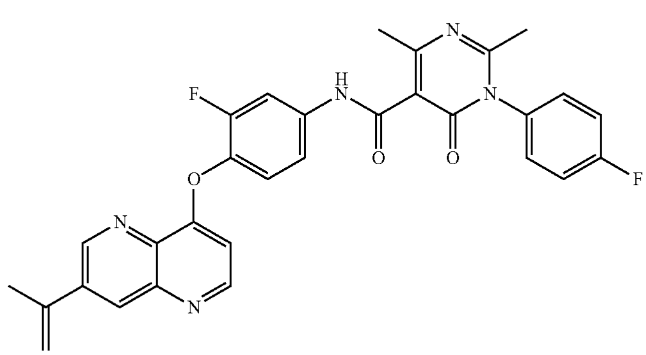 [SMILES: C=C(C)c1cnc2c(Oc3ccc(NC(=O)c4c(C)nc(C)n(-c5ccc(F)cc5)c4=O)cc3F)ccnc2c1] | 1-(4-fluorophenyl)-N-[3-fluoro-4-[(7-prop-1-en-2-yl-1,5-naphthyridin-4-yl)oxy]phenyl]-2,4-dimethyl-6-oxopyrimidine-5-carboxamide |

TABLE 1-continued

| Cpd # | Structure | IUPAC Name |
|---|---|---|
| 467 | 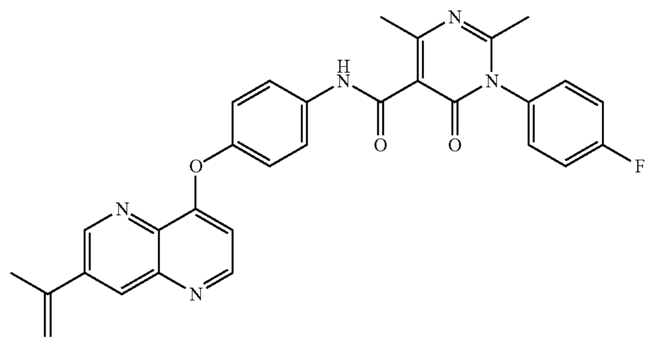 [SMILES: C=C(C)c1cnc2c(Oc3ccc(NC(=O)c4c(C)nc(C)n(-c5ccc(F)cc5)c4=O)cc3)ccnc2c1] | 1-(4-fluorophenyl)-2,4-dimethyl-6-oxo-N-[4-[(7-prop-1-en-2-yl-1,5-naphthyridin-4-yl)oxy]phenyl]pyrimidine-5-carboxamide |
| 468 | 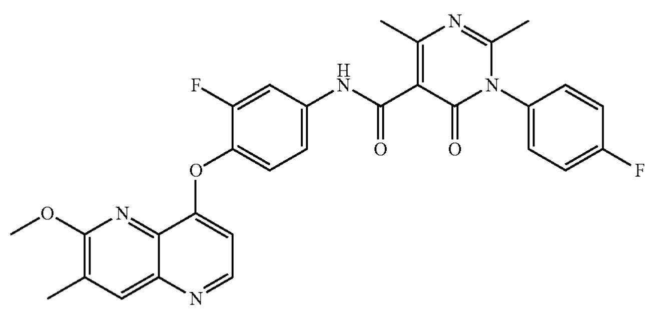 [SMILES: COc1nc2c(Oc3ccc(NC(=O)c4c(C)nc(C)n(-c5ccc(F)cc5)c4=O)cc3F)ccnc2cc1C] | N-[3-fluoro-4-[(6-methoxy-7-methyl-1,5-naphthyridin-4-yl)oxy]phenyl]-1-(4-fluorophenyl)-2,4-dimethyl-6-oxopyrimidine-5-carboxamide |
| 469 | 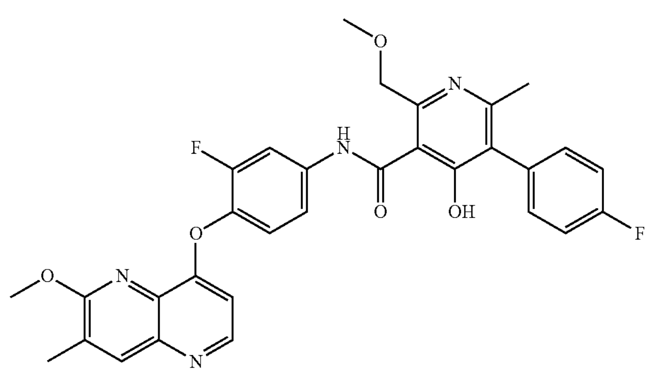 [SMILES: COCc1nc(C)c(-c2ccc(F)cc2)c(O)c1C(=O)Nc1ccc(Oc2ccnc3cc(C)c(OC)nc23)c(F)c1] | N-[3-fluoro-4-[(6-methoxy-7-methyl-1,5-naphthyridin-4-yl)oxy]phenyl]-5-(4-fluorophenyl)-4-hydroxy-2-(methoxymethyl)-6-methylpyridine-3-carboxamide |
| 470 | 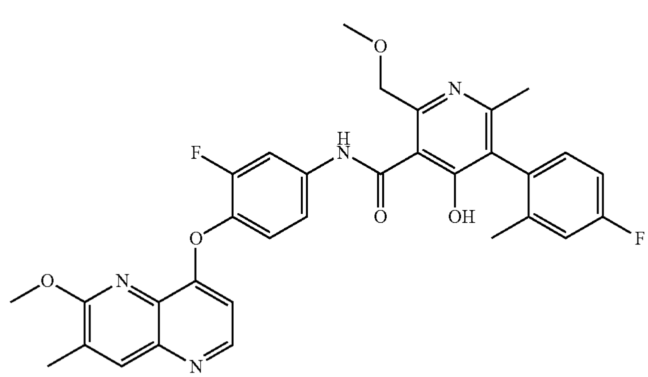 [SMILES: COCc1nc(C)c(-c2ccc(F)cc2C)c(O)c1C(=O)Nc1ccc(Oc2ccnc3cc(C)c(OC)nc23)c(F)c1] | N-[3-fluoro-4-[(6-methoxy-7-methyl-1,5-naphthyridin-4-yl)oxy]phenyl]-5-(4-fluoro-2-methylphenyl)-4-hydroxy-2-(methoxymethyl)-6-methylpyridine-3-carboxamide |

TABLE 1-continued

| Cpd # | Structure | IUPAC Name |
|---|---|---|
| 471 | 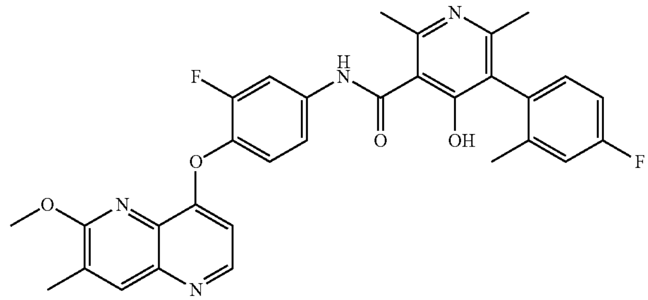 [SMILES: COc1nc2c(Oc3ccc(NC(=O)c4c(C)nc(C)c(-c5ccc(F)cc5C)c4O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-4-hydroxy-2,6-dimethylpyridine-3-carboxamide |
| 472 | 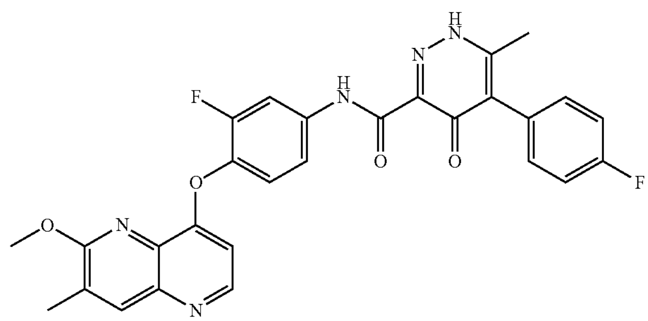 [SMILES: COc1nc2c(Oc3ccc(NC(=O)c4n[nH]c(C)c(-c5ccc(F)cc5)c4=O)cc3F)ccnc2cc1C] | N-[3-fluoro-4-[(6-methoxy-7-methyl-1,5-naphthyridin-4-yl)oxy]phenyl]-5-(4-fluorophenyl)-6-methyl-4-oxo-1H-pyridazine-3-carboxamide |
| 473 | 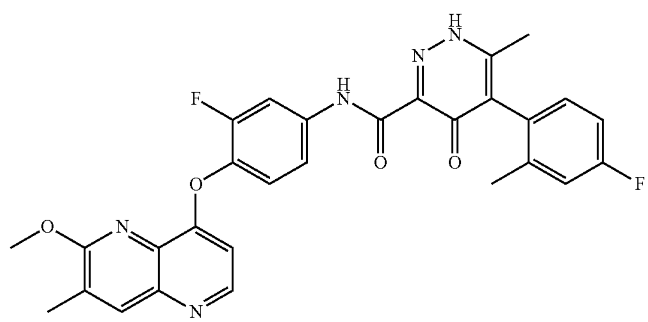 [SMILES: COc1nc2c(Oc3ccc(NC(=O)c4n[nH]c(C)c(-c5ccc(F)cc5C)c4=O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-6-methyl-4-oxo-1H-pyridazine-3-carboxamide |
| 474 | 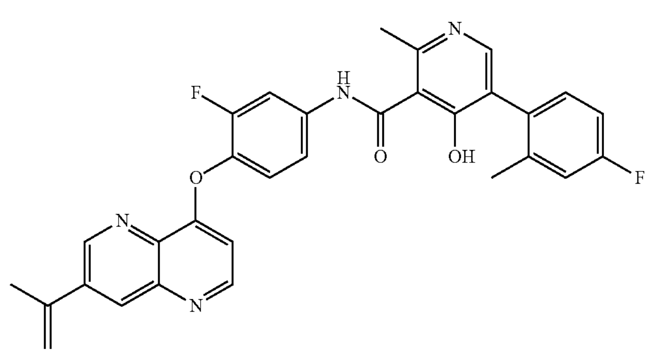 [SMILES: C=C(C)c1cnc2c(Oc3ccc(NC(=O)c4c(C)ncc(-c5ccc(F)cc5C)c4O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-4-hydroxy-2-methylpyridine-3-carboxamide |

TABLE 1-continued

| Cpd # | Structure | IUPAC Name |
|---|---|---|
| 475 | 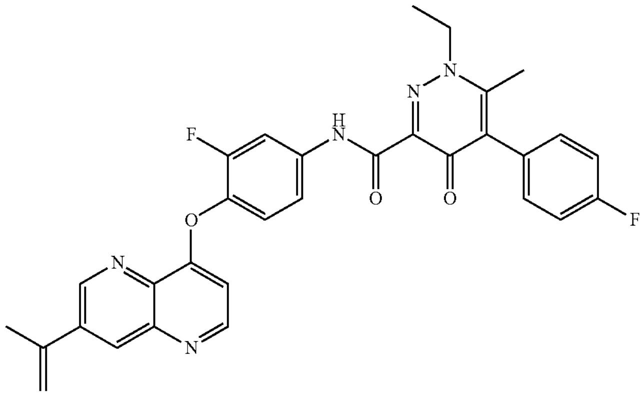 [SMILES: C=C(C)c1cnc2c(Oc3ccc(NC(=O)c4nn(CC)c(C)c(-c5ccc(F)cc5)c4=O)cc3F)ccnc2c1] | 1-ethyl-5-(4-fluorophenyl)-N-[3-fluoro-4-[(7-prop-1-en-2-yl-1,5-naphthyridin-4-yl)oxy]phenyl]-6-methyl-4-oxopyridazine-3-carboxamide |
| 476 | 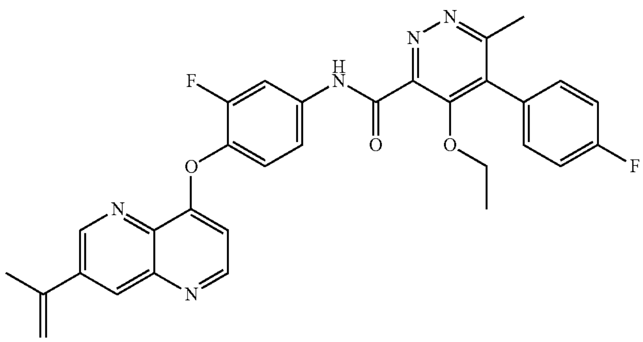 [SMILES: C=C(C)c1cnc2c(Oc3ccc(NC(=O)c4nnc(C)c(-c5ccc(F)cc5)c4OCC)cc3F)ccnc2c1] | 4-ethoxy-5-(4-fluorophenyl)-N-[3-fluoro-4-[(7-prop-1-en-2-yl-1,5-naphthyridin-4-yl)oxy]phenyl]-6-methylpyridazine-3-carboxamide |
| 477 | 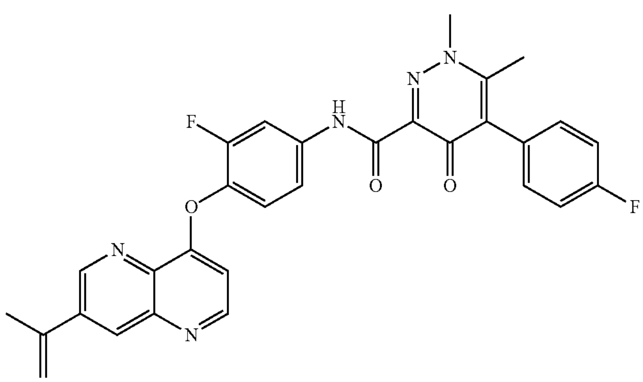 [SMILES: C=C(C)c1cnc2c(Oc3ccc(NC(=O)c4nn(C)c(C)c(-c5ccc(F)cc5)c4=O)cc3F)ccnc2c1] | 5-(4-fluorophenyl)-N-[3-fluoro-4-[(7-prop-1-en-2-yl-1,5-naphthyridin-4-yl)oxy]phenyl]-1,6-dimethyl-4-oxopyridazine-3-carboxamide |
| 478 | 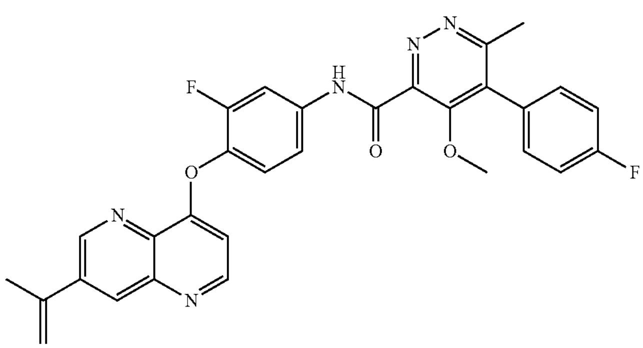 [SMILES: C=C(C)c1cnc2c(Oc3ccc(NC(=O)c4nnc(C)c(-c5ccc(F)cc5)c4OC)cc3F)ccnc2c1] | 5-(4-fluorophenyl)-N-[3-fluoro-4-[(7-prop-1-en-2-yl-1,5-naphthyridin-4-yl)oxy]phenyl]-4-methoxy-6-methylpyridazine-3-carboxamide |

TABLE 1-continued

| Cpd # | Structure | IUPAC Name |
|---|---|---|
| 479 | 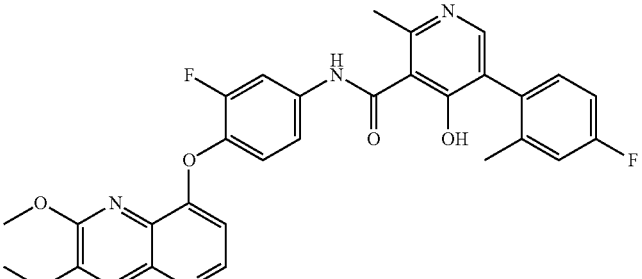 | N-[4-[(6,7-dimethoxy-1,5-naphthyridin-4-yl)oxy]-3-fluorophenyl]-5-(4-fluoro-2-methylphenyl)-4-hydroxy-2-methylpyridine-3-carboxamide |
| 480 | 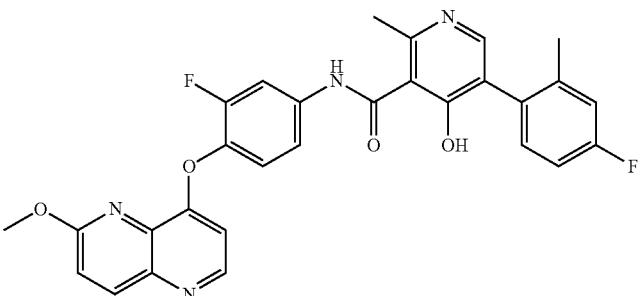 | N-[3-fluoro-4-[(6-methoxy-1,5-naphthyridin-4-yl)oxy]phenyl]-5-(4-fluoro-2-methylphenyl)-4-hydroxy-2-methylpyridine-3-carboxamide |
| 481 | 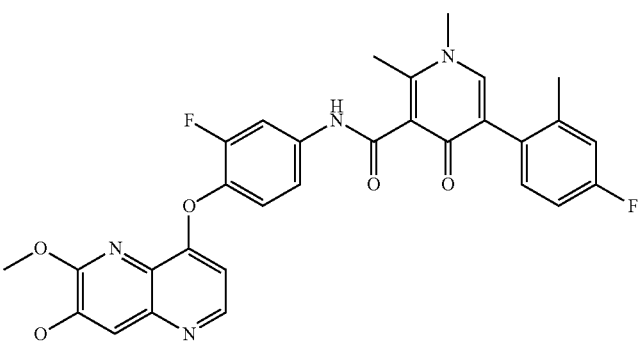 | N-[4-[(6,7-dimethoxy-1,5-naphthyridin-4-yl)oxy]-3-fluorophenyl]-5-(4-fluoro-2-methylphenyl)-1,2-dimethyl-4-oxopyridine-3-carboxamide |
| 482 | 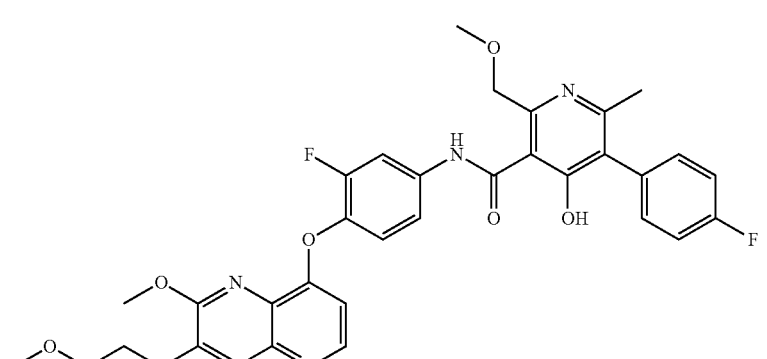 | N-[3-fluoro-4-[[6-methoxy-7-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide |

TABLE 1-continued

| Cpd # | Structure | IUPAC Name |
|---|---|---|
| 483 | 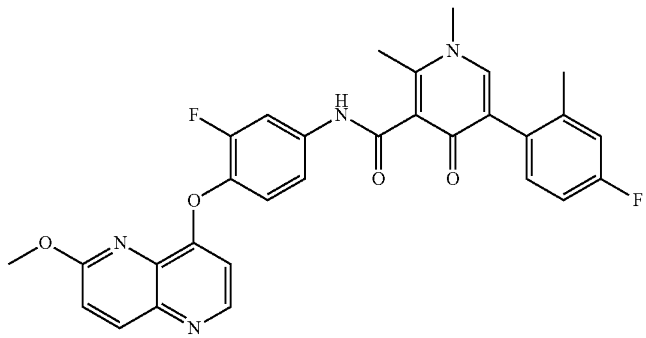 [SMILES: COc1ccc2nccc(Oc3ccc(NC(=O)c4c(C)n(C)cc(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-1,2-dimethyl-4-oxopyridine-3-carboxamide |
| 484 | 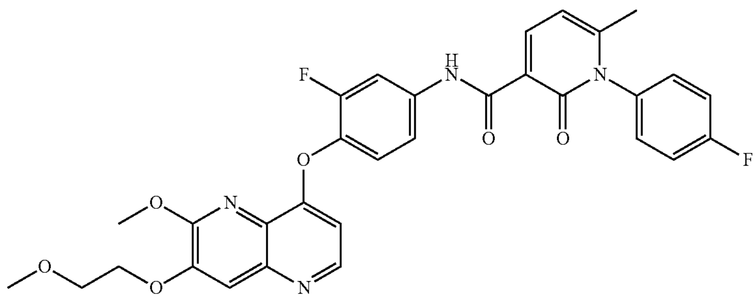 [SMILES: COCCOc1cc2nccc(Oc3ccc(NC(=O)c4ccc(C)n(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-1-(4-fluorophenyl)-6-methyl-2-oxopyridine-3-carboxamide |
| 485 | 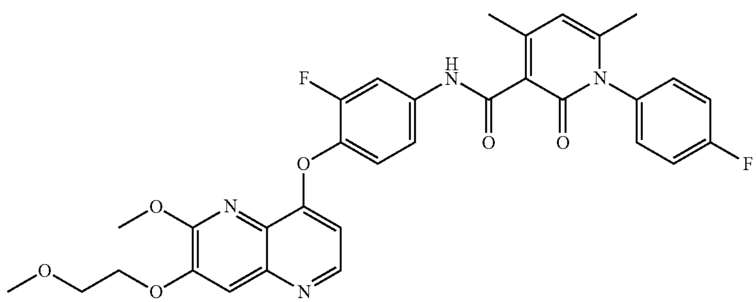 [SMILES: COCCOc1cc2nccc(Oc3ccc(NC(=O)c4c(C)cc(C)n(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-1-(4-fluorophenyl)-4,6-dimethyl-2-oxopyridine-3-carboxamide |
| 486 | 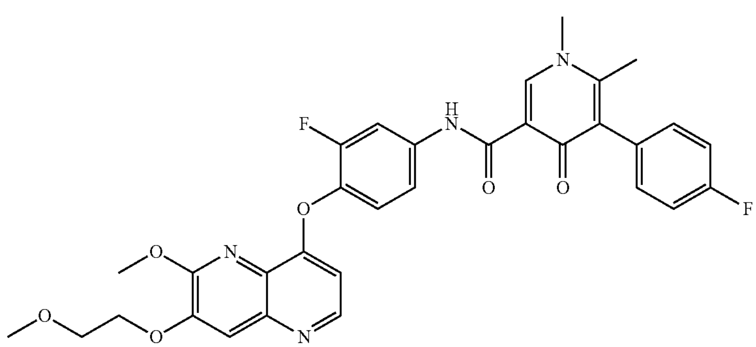 [SMILES: COCCOc1cc2nccc(Oc3ccc(NC(=O)c4cn(C)c(C)c(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-5-(4-fluorophenyl)-1,6-dimethyl-4-oxopyridine-3-carboxamide |
| 487 | 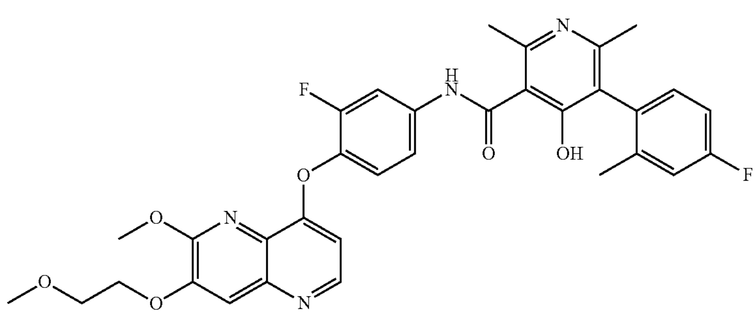 [SMILES: COCCOc1cc2nccc(Oc3ccc(NC(=O)c4c(C)nc(C)c(-c5ccc(F)cc5C)c4O)cc3F)c2nc1OC] | N-[3-fluoro-4-[[6-methoxy-7-(2-methoxyethoxy)-1,5-naphthyridin-4-yl]oxy]phenyl]-5-(4-fluoro-2-methylphenyl)-4-hydroxy-2,6-dimethylpyridine-3-carboxamide |

TABLE 1-continued

| Cpd # | Structure | IUPAC Name |
|---|---|---|
| 488 | 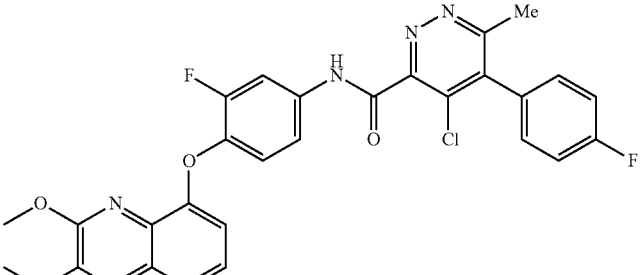 | 4-chloro-N-[4-[(6,7-dimethoxy-1,5-naphthyridin-4-yl)oxy]-3-fluorophenyl]-5-(4-fluorophenyl)-6-methylpyridazine-3-carboxamide |
| 489 | 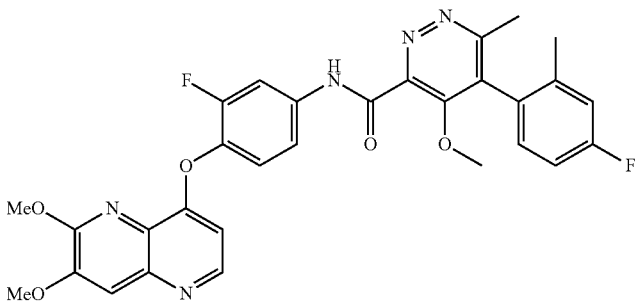 [SMILES: COc1cc2nccc(Oc3ccc(NC(=O)c4nnc(C)c(-c5ccc(F)cc5C)c4OC)cc3F)c2nc1OC] | N-[4-[(6,7-dimethoxy-1,5-naphthyridin-4-yl)oxy]-3-fluorophenyl]-5-(4-fluoro-2-methylphenyl)-4-methoxy-6-methylpyridazine-3-carboxamide |
| 491 | 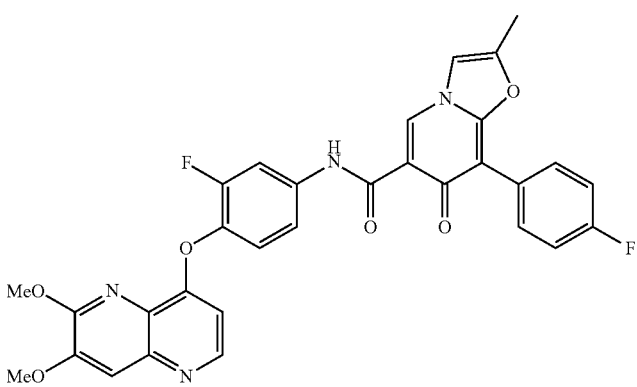 [SMILES: COc1cc2nccc(Oc3ccc(NC(=O)c4cn5cc(C)oc5c(-c5ccc(F)cc5)c4=O)cc3F)c2nc1OC] | N-[4-[(6,7-dimethoxy-1,5-naphthyridin-4-yl)oxy]-3-fluorophenyl]-8-(4-fluorophenyl)-2-methyl-7-oxo-[1,3]oxazolo[3,2-a]pyridine-6-carboxamide |
| 493 | 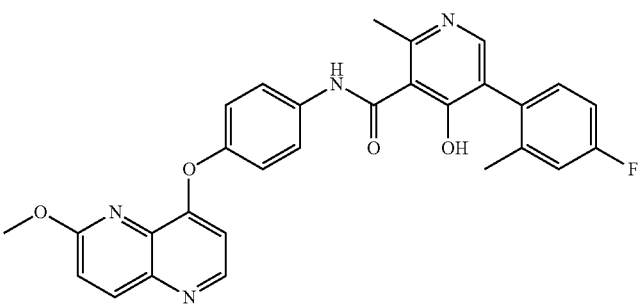 [SMILES: COc1ccc2nccc(Oc3ccc(NC(=O)c4c(C)ncc(-c5ccc(F)cc5C)c4O)cc3)c2n1] | 5-(4-fluoro-2-methylphenyl)-4-hydroxy-N-[4-[(6-methoxy-1,5-naphthyridin-4-yl)oxy]phenyl]-2-methylpyridine-3-carboxamide |
| 494 | 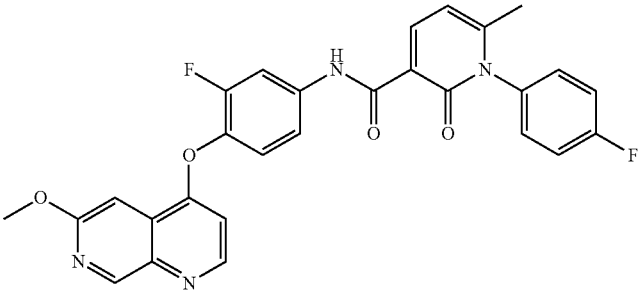 [SMILES: COc1cc2c(Oc3ccc(NC(=O)c4ccc(C)n(-c5ccc(F)cc5)c4=O)cc3F)ccnc2cn1] | N-[3-fluoro-4-[(6-methoxy-1,7-naphthyridin-4-yl)oxy]phenyl]-1-(4-fluorophenyl)-6-methyl-2-oxopyridine-3-carboxamide |

| Cpd # | Structure | IUPAC Name |
|---|---|---|
| 496 | 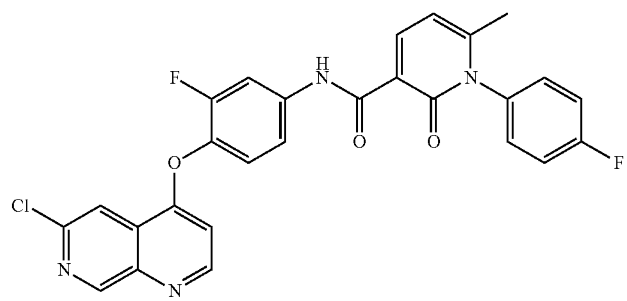 [SMILES: Cc1ccc(C(=O)Nc2ccc(Oc3ccnc4cnc(Cl)cc34)c(F)c2)c(=O)n1-c1ccc(F)cc1] | N-[4-[(6-chloro-1,7-naphthyridin-4-yl)oxy]-3-fluorophenyl]-1-(4-fluorophenyl)-6-methyl-2-oxopyridine-3-carboxamide |
| 497 | 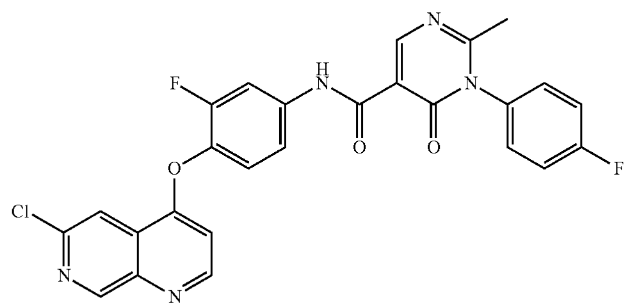 [SMILES: Cc1ncc(C(=O)Nc2ccc(Oc3ccnc4cnc(Cl)cc34)c(F)c2)c(=O)n1-c1ccc(F)cc1] | N-[4-[(6-chloro-1,7-naphthyridin-4-yl)oxy]-3-fluorophenyl]-1-(4-fluorophenyl)-2-methyl-6-oxopyrimidine-5-carboxamide |
| 498 | 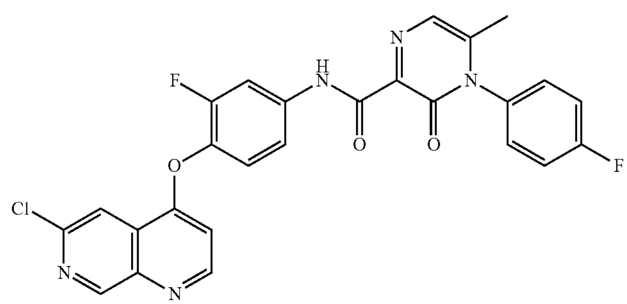 [SMILES: Cc1cnc(C(=O)Nc2ccc(Oc3ccnc4cnc(Cl)cc34)c(F)c2)c(=O)n1-c1ccc(F)cc1] | N-[4-[(6-chloro-1,7-naphthyridin-4-yl)oxy]-3-fluorophenyl]-4-(4-fluorophenyl)-5-methyl-3-oxopyrazine-2-carboxamide |
| 499 | 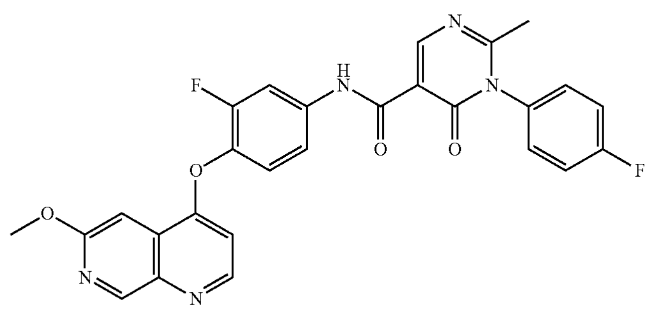 [SMILES: COc1cc2c(Oc3ccc(NC(=O)c4cnc(C)n(-c5ccc(F)cc5)c4=O)cc3F)ccnc2cn1] | N-[3-fluoro-4-[(6-methoxy-1,7-naphthyridin-4-yl)oxy]phenyl]-1-(4-fluorophenyl)-2-methyl-6-oxopyrimidine-5-carboxamide |
| 500 | 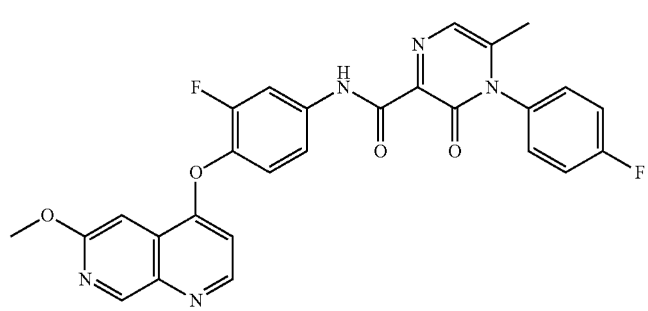 [SMILES: COc1cc2c(Oc3ccc(NC(=O)c4ncc(C)n(-c5ccc(F)cc5)c4=O)cc3F)ccnc2cn1] | N-[3-fluoro-4-[(6-methoxy-1,7-naphthyridin-4-yl)oxy]phenyl]-4-(4-fluorophenyl)-5-methyl-3-oxopyrazine-2-carboxamide |

TABLE 1-continued

| Cpd # | Structure | IUPAC Name |
|---|---|---|
| 501 | 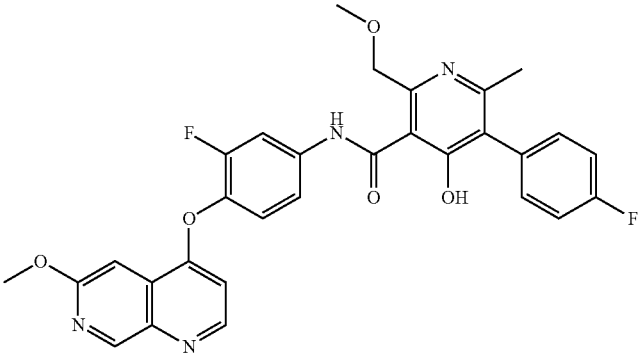 [SMILES: COCc1nc(C)c(-c2ccc(F)cc2)c(O)c1C(=O)Nc1ccc(Oc2ccnc3cnc(OC)cc23)c(F)c1] | N-[3-fluoro-4-[(6-methoxy-1,7-naphthyridin-4-yl)oxy]phenyl]-5-(4-fluorophenyl)-4-hydroxy-2-(methoxymethyl)-6-methylpyridine-3-carboxamide |
| 502 | 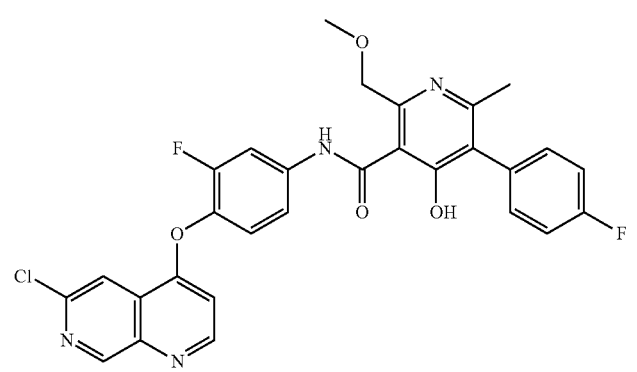 [SMILES: COCc1nc(C)c(-c2ccc(F)cc2)c(O)c1C(=O)Nc1ccc(Oc2ccnc3cnc(Cl)cc23)c(F)c1] | N-[4-[(6-chloro-1,7-naphthyridin-4-yl)oxy]-3-fluorophenyl]-5-(4-fluorophenyl)-4-hydroxy-2-(methoxymethyl)-6-methylpyridine-3-carboxamide |
| 503 | 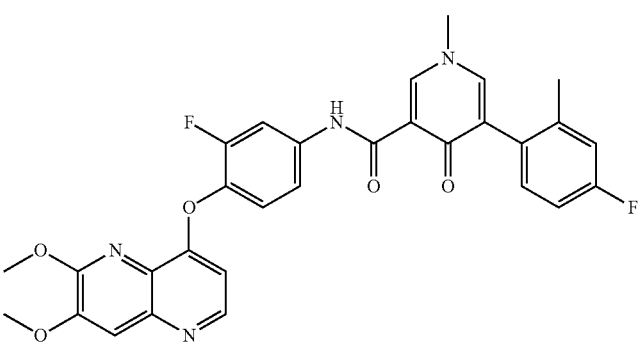 [SMILES: COc1cc2nccc(Oc3ccc(NC(=O)c4cn(C)cc(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1-methyl-4-oxopyridine-3-carboxamide |
| 504 | 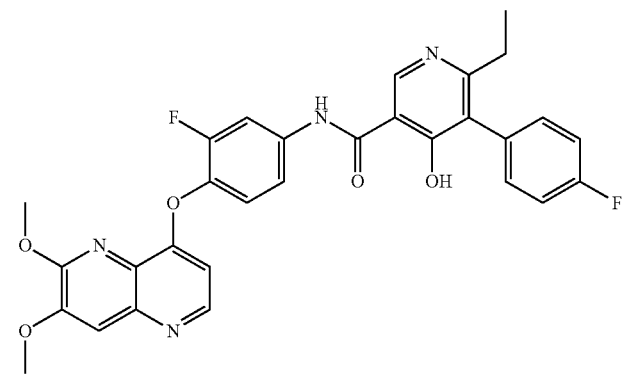 [SMILES: CCc1ncc(C(=O)Nc2ccc(Oc3ccnc4cc(OC)c(OC)nc34)c(F)c2)c(O)c1-c1ccc(F)cc1] | N-[4-[(6,7-dimethoxy-1,5-naphthyridin-4-yl)oxy]-3-fluorophenyl]-6-ethyl-5-(4-fluorophenyl)-4-hydroxypyridine-3-carboxamide |

TABLE 1-continued

| Cpd # | Structure | IUPAC Name |
|---|---|---|
| 505 | 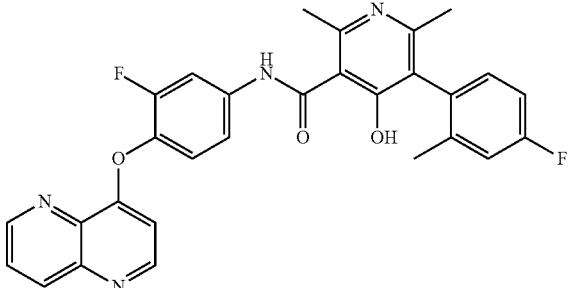 | 5-(4-fluoro-2-methylphenyl)-N-[3-fluoro-4-(1,5-naphthyridin-4-yloxy)phenyl]-4-hydroxy-2,6-dimethylpyridine-3-carboxamide |
| 506 | 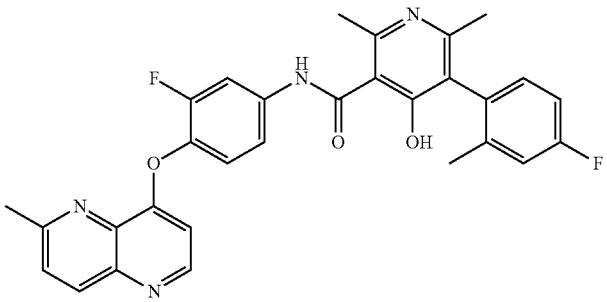 [SMILES: Cc1ccc2nccc(Oc3ccc(NC(=O)c4c(C)nc(C)c(-c5ccc(F)cc5C)c4O)cc3F)c2n1] | N-[3-fluoro-4-[(6-methyl-1,5-naphthyridin-4-yl)oxy]phenyl]-5-(4-fluoro-2-methylphenyl)-4-hydroxy-2,6-dimethylpyridine-3-carboxamide |
| 507 | 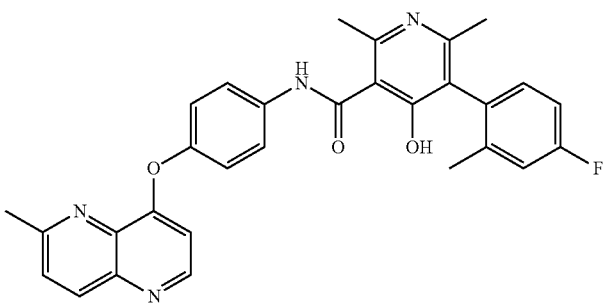 [SMILES: Cc1ccc2nccc(Oc3ccc(NC(=O)c4c(C)nc(C)c(-c5ccc(F)cc5C)c4O)cc3)c2n1] | 5-(4-fluoro-2-methylphenyl)-4-hydroxy-2,6-dimethyl-N-[4-[(6-methyl-1,5-naphthyridin-4-yl)oxy]phenyl]pyridine-3-carboxamide |
| 508 | 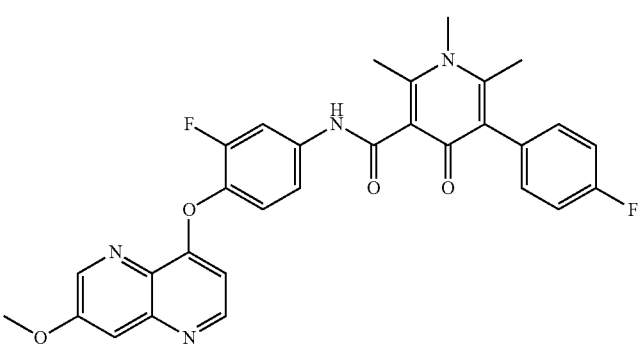 [SMILES: COc1cnc2c(Oc3ccc(NC(=O)c4c(C)n(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,2,6-trimethyl-4-oxopyridine-3-carboxamide |
| 509 | 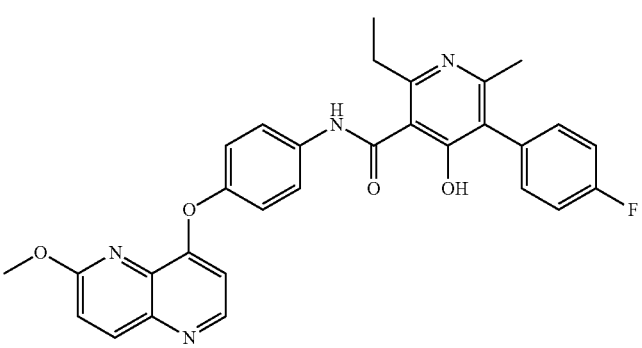 [SMILES: CCc1nc(C)c(-c2ccc(F)cc2)c(O)c1C(=O)Nc1ccc(Oc2ccnc3ccc(OC)nc23)cc1] | 2-ethyl-5-(4-fluorophenyl)-4-hydroxy-N-[4-[(6-methoxy-1,5-naphthyridin-4-yl)oxy]phenyl]-6-methylpyridine-3-carboxamide |

TABLE 1-continued

| Cpd # | Structure | IUPAC Name |
|---|---|---|
| 510 | 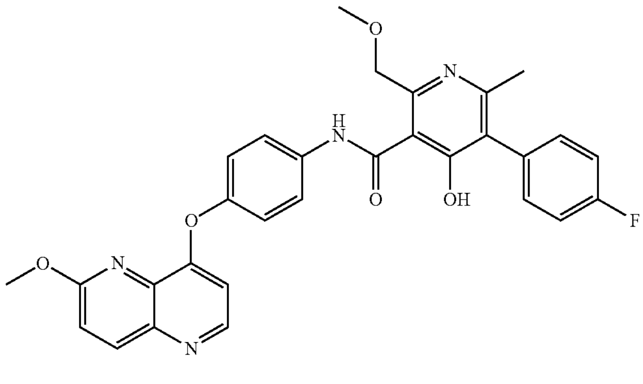 [SMILES: COCc1nc(C)c(-c2ccc(F)cc2)c(O)c1C(=O)Nc1ccc(Oc2ccnc3ccc(OC)nc23)cc1] | 5-(4-fluorophenyl)-4-hydroxy-2-(methoxymethyl)-N-[4-[(6-methoxy-1,5-naphthyridin-4-yl)oxy]phenyl]-6-methylpyridine-3-carboxamide |
| 511 | 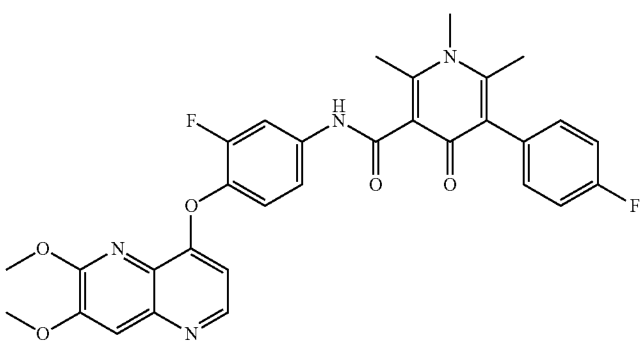 [SMILES: COc1cc2nccc(Oc3ccc(NC(=O)c4c(C)n(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,2,6-trimethyl-4-oxopyridine-3-carboxamide |
| 512 | 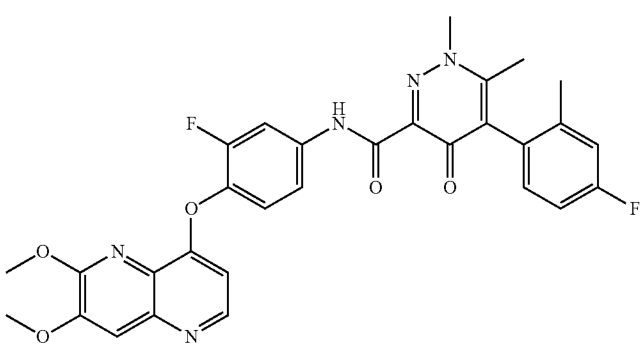 | N-[4-[(6,7-dimethoxy-1,5-naphthyridin-4-yl)oxy]-3-fluorophenyl]-5-(4-fluoro-2-methylphenyl)-1,6-dimethyl-4-oxopyridazine-3-carboxamide |
| 513 | 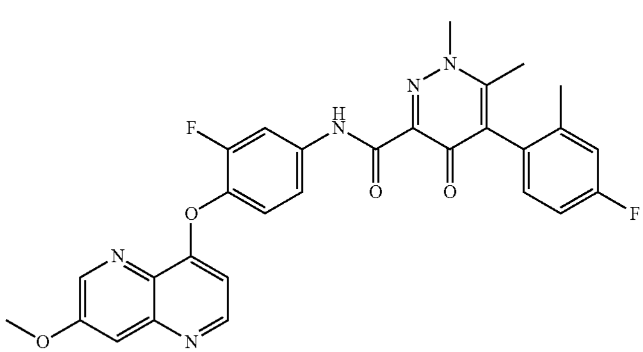 [SMILES: COc1cnc2c(Oc3ccc(NC(=O)c4nn(C)c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-1,6-dimethyl-4-oxopyridazine-3-carboxamide |

TABLE 1-continued

| Cpd # | Structure | IUPAC Name |
|---|---|---|
| 514 | 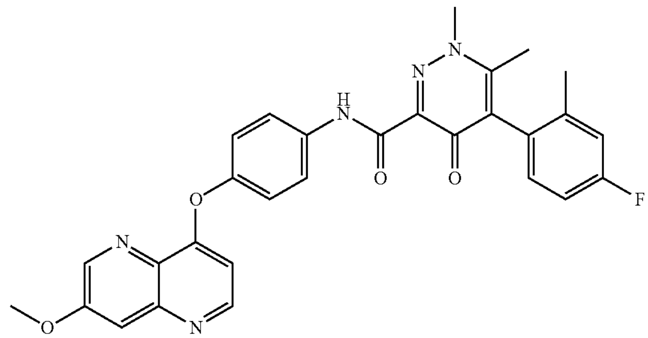 | 5-(4-fluoro-2-methylphenyl)-N-[4-[(7-methoxy-1,5-naphthyridin-4-yl)oxy]phenyl]-1,6-dimethyl-4-oxopyridazine-3-carboxamide |
| 515 | 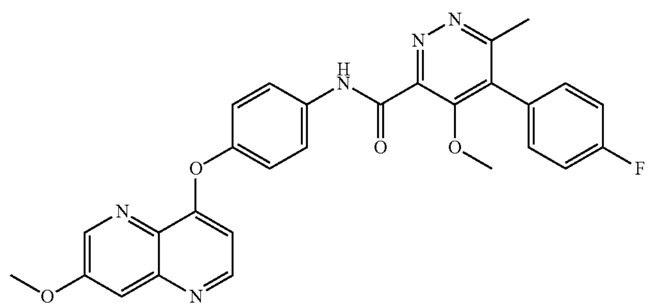 [SMILES: COc1cnc2c(Oc3ccc(NC(=O)c4nnc(C)c(-c5ccc(F)cc5)c4OC)cc3)ccnc2c1] | 5-(4-fluorophenyl)-4-methoxy-N-[4-[(7-methoxy-1,5-naphthyridin-4-yl)oxy]phenyl]-6-methylpyridazine-3-carboxamide |
| 516 | 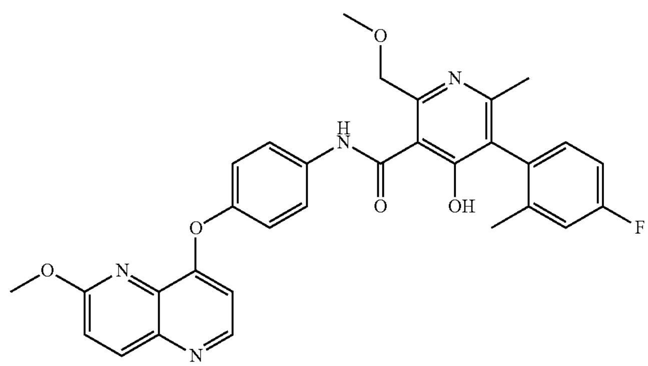 [SMILES: COCc1nc(C)c(-c2ccc(F)cc2C)c(O)c1C(=O)Nc1ccc(Oc2ccnc3ccc(OC)nc23)cc1] | 5-(4-fluoro-2-methylphenyl)-4-hydroxy-2-(methoxymethyl)-N-[4-[(6-methoxy-1,5-naphthyridin-4-yl)oxy]phenyl]-6-methylpyridine-3-carboxamide |
| 517 | 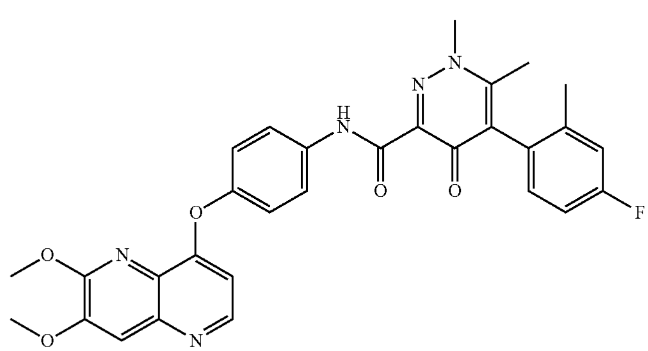 [SMILES: COc1cc2nccc(Oc3ccc(NC(=O)c4nn(C)c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-1,6-dimethyl-4-oxopyridazine-3-carboxamide |

TABLE 1-continued

| Cpd # | Structure | IUPAC Name |
|---|---|---|
| 518 | 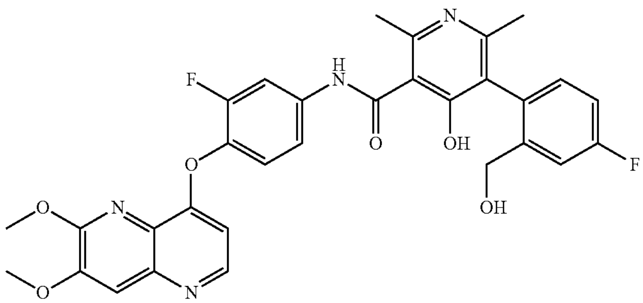 [SMILES: COc1cc2nccc(Oc3ccc(NC(=O)c4c(C)nc(C)c(-c5ccc(F)cc5CO)c4O)cc3F)c2nc1OC] | N-[4-[(6,7-dimethoxy-1,5-naphthyridin-4-yl)oxy]-3-fluorophenyl]-5-[4-fluoro-2-(hydroxymethyl)phenyl]-4-hydroxy-2,6-dimethylpyridine-3-carboxamide |
| 519 | 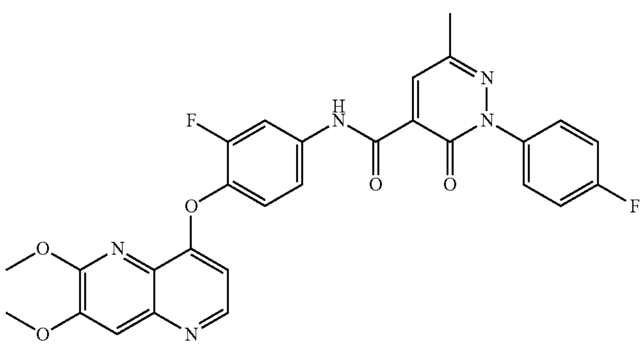 [SMILES: COc1cc2nccc(Oc3ccc(NC(=O)c4cc(C)nn(-c5ccc(F)cc5)c4=O)cc3F)c2nc1OC] | N-[4-[(6,7-dimethoxy-1,5-naphthyridin-4-yl)oxy]-3-fluorophenyl]-2-(4-fluorophenyl)-6-methyl-3-oxopyridazine-4-carboxamide |
| 520 | 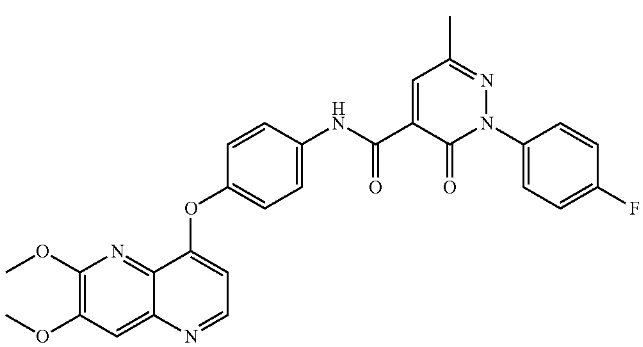 [SMILES: COc1cc2nccc(Oc3ccc(NC(=O)c4cc(C)nn(-c5ccc(F)cc5)c4=O)cc3)c2nc1OC] | N-[4-[(6,7-dimethoxy-1,5-naphthyridin-4-yl)oxy]phenyl]-2-(4-fluorophenyl)-6-methyl-3-oxopyridazine-4-carboxamide |
| 521 | 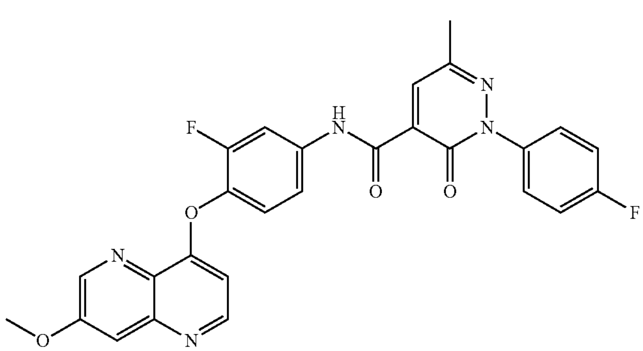 [SMILES: COc1cnc2c(Oc3ccc(NC(=O)c4cc(C)nn(-c5ccc(F)cc5)c4=O)cc3F)ccnc2c1] | N-[3-fluoro-4-[(7-methoxy-1,5-naphthyridin-4-yl)oxy]phenyl]-2-(4-fluorophenyl)-6-methyl-3-oxopyridazine-4-carboxamide |

TABLE 1-continued

| Cpd # | Structure | IUPAC Name |
|---|---|---|
| 522 | 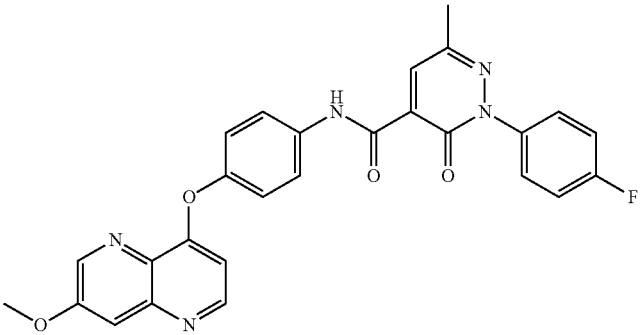 [SMILES: COc1cnc2c(Oc3ccc(NC(=O)c4cc(C)nn(-c5ccc(F)cc5)c4=O)cc3)ccnc2c1] | 2-(4-fluorophenyl)-N-[4-[(7-methoxy-1,5-naphthyridin-4-yl)oxy]phenyl]-6-methyl-3-oxopyridazine-4-carboxamide |
| 523 | 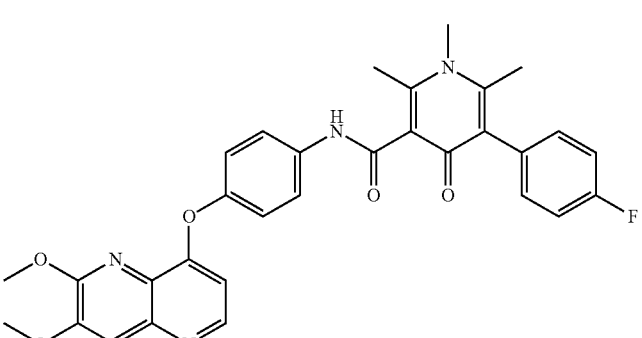 | N-[4-[(6,7-dimethoxy-1,5-naphthyridin-4-yl)oxy]phenyl]-5-(4-fluorophenyl)-1,2,6-trimethyl-4-oxopyridine-3-carboxamide |
| 524 | 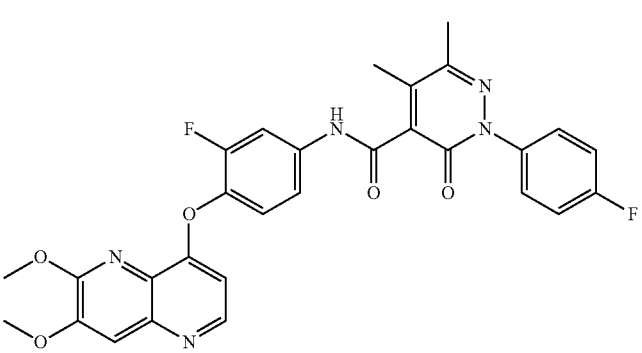 [SMILES: COc1cc2nccc(Oc3ccc(NC(=O)c4c(C)c(C)nn(-c5ccc(F)cc5)c4=O)cc3F)c2nc1OC] | N-[4-[(6,7-dimethoxy-1,5-naphthyridin-4-yl)oxy]-3-fluorophenyl]-2-(4-fluorophenyl)-5,6-dimethyl-3-oxopyridazine-4-carboxamide |
| 525 | 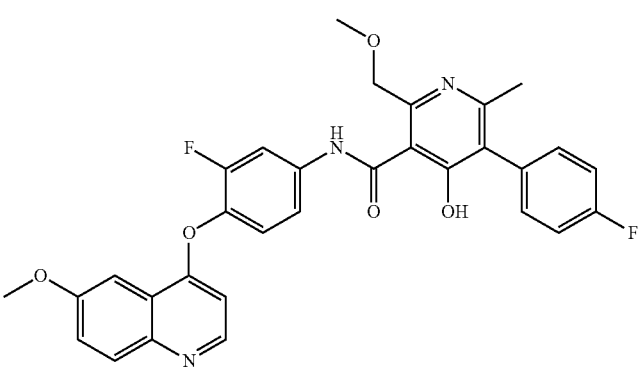 | N-[3-fluoro-4-(6-methoxyquinolin-4-yl)oxyphenyl]-5-(4-fluorophenyl)-4-hydroxy-2-(methoxymethyl)-6-methylpyridine-3-carboxamide |

TABLE 1-continued

| Cpd # | Structure | IUPAC Name |
|---|---|---|
| 526 | 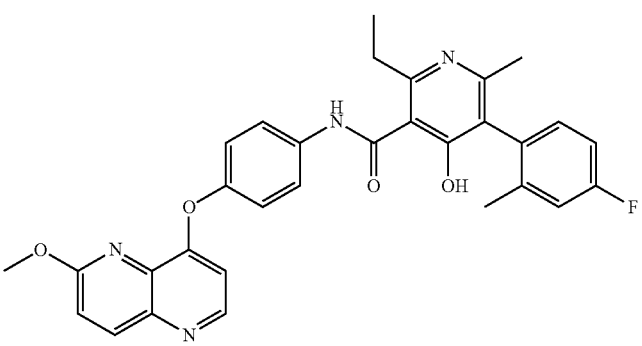 [SMILES: CCc1nc(C)c(-c2ccc(F)cc2C)c(O)c1C(=O)Nc1ccc(Oc2ccnc3ccc(OC)nc23)cc1] | 2-ethyl-5-(4-fluoro-2-methylphenyl)-4-hydroxy-N-[4-[(6-methoxy-1,5-naphthyridin-4-yl)oxy]phenyl]-6-methylpyridine-3-carboxamide |
| 527 | 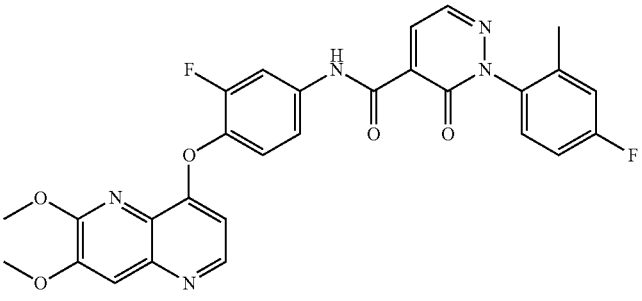 | N-[4-[(6,7-dimethoxy-1,5-naphthyridin-4-yl)oxy]-3-fluorophenyl]-2-(4-fluoro-2-methylphenyl)-3-oxopyridazine-4-carboxamide |
| 528 | 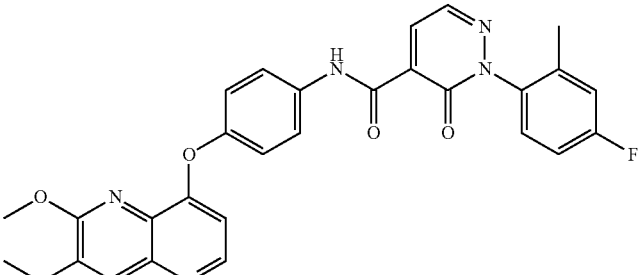 | N-[4-[(6,7-dimethoxy-1,5-naphthyridin-4-yl)oxy]phenyl]-2-(4-fluoro-2-methylphenyl)-3-oxopyridazine-4-carboxamide |
| 529 | 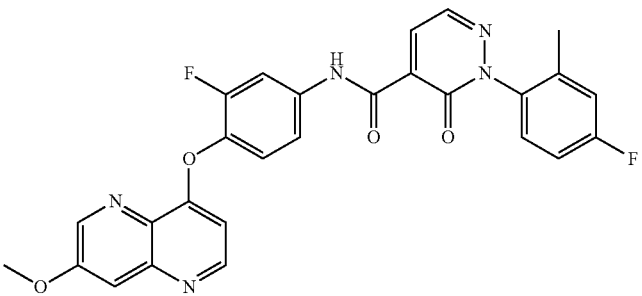 [SMILES: COc1cnc2c(Oc3ccc(NC(=O)c4ccnn(-c5ccc(F)cc5C)c4=O)cc3F)ccnc2c1] | N-[3-fluoro-4-[(7-methoxy-1,5-naphthyridin-4-yl)oxy]phenyl]-2-(4-fluoro-2-methylphenyl)-3-oxopyridazine-4-carboxamide |
| 530 | 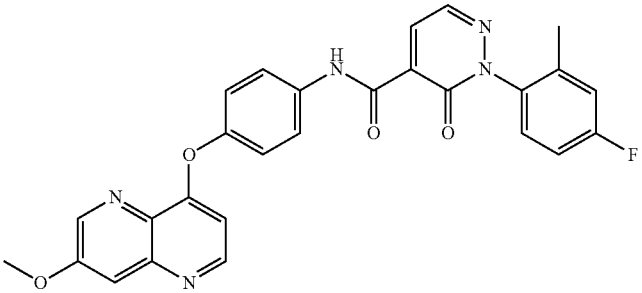 [SMILES: COc1cnc2c(Oc3ccc(NC(=O)c4ccnn(-c5ccc(F)cc5C)c4=O)cc3)ccnc2c1] | 2-(4-fluoro-2-methylphenyl)-N-[4-[(7-methoxy-1,5-naphthyridin-4-yl)oxy]phenyl]-3-oxopyridazine-4-carboxamide |

TABLE 1-continued

| Cpd # | Structure | IUPAC Name |
|---|---|---|
| 531 | 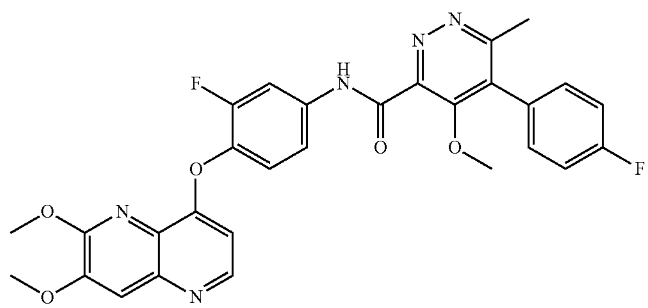 [SMILES: COc1cc2nccc(Oc3ccc(NC(=O)c4nnc(C)c(-c5ccc(F)cc5)c4OC)cc3F)c2nc1OC] | N-[4-[(6,7-dimethoxy-1,5-naphthyridin-4-yl)oxy]-3-fluorophenyl]-5-(4-fluorophenyl)-4-methoxy-6-methylpyridazine-3-carboxamide |
| 532 | 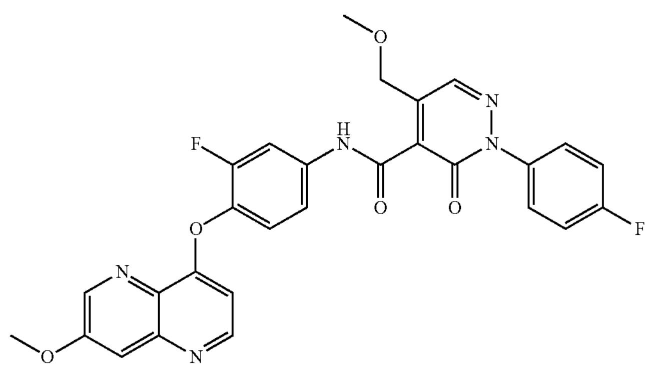 [SMILES: COCc1cnn(-c2ccc(F)cc2)c(=O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-2-(4-fluorophenyl)-5-(methoxymethyl)-3-oxopyridazine-4-carboxamide |
| 533 | 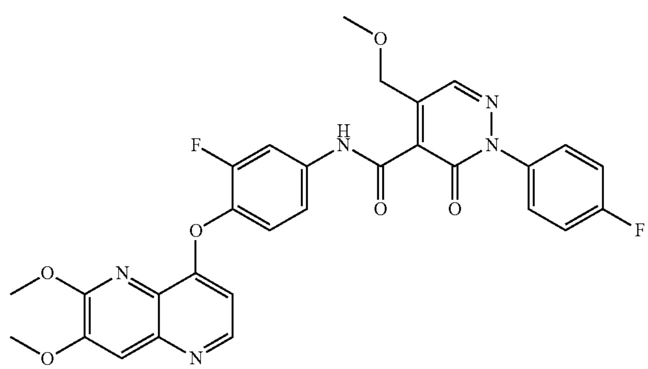 [SMILES: COCc1cnn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(4-fluorophenyl)-5-(methoxymethyl)-3-oxopyridazine-4-carboxamide |
| 534 | 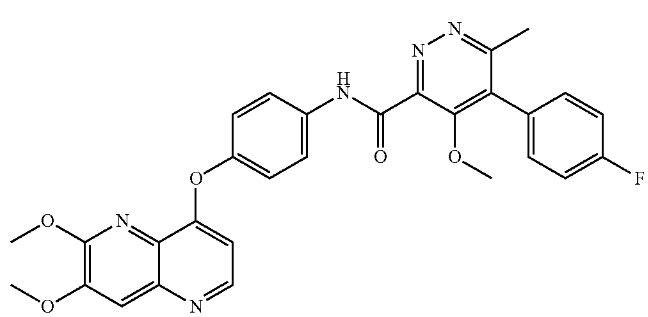 [SMILES: COc1cc2nccc(Oc3ccc(NC(=O)c4nnc(C)c(-c5ccc(F)cc5)c4OC)cc3)c2nc1OC] | N-[4-[(6,7-dimethoxy-1,5-naphthyridin-4-yl)oxy]phenyl]-5-(4-fluorophenyl)-4-methoxy-6-methylpyridazine-3-carboxamide |

TABLE 1-continued

| Cpd # | Structure | IUPAC Name |
|---|---|---|
| 537 | 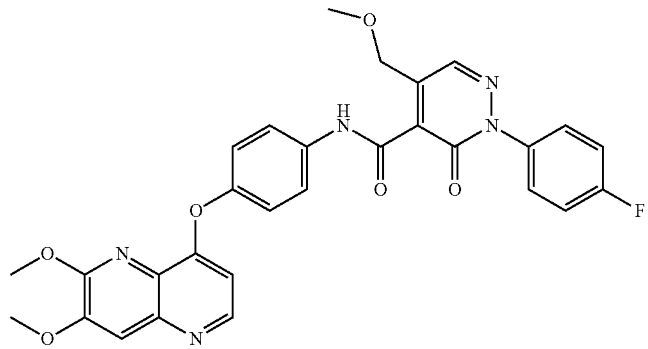 [SMILES: COCc1cnn(-c2ccc(F)cc2)c(=O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-(4-fluorophenyl)-5-(methoxymethyl)-3-oxopyridazine-4-carboxamide |
| 538 | 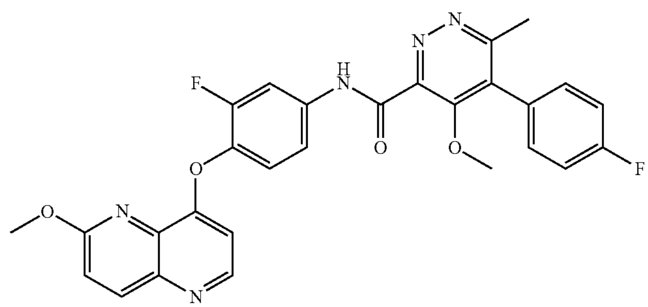 [SMILES: COc1ccc2nccc(Oc3ccc(NC(=O)c4nnc(C)c(-c5ccc(F)cc5)c4OC)cc3F)c2n1] | N-[3-fluoro-4-[(6-methoxy-1,5-naphthyridin-4-yl)oxy]phenyl]-5-(4-fluorophenyl)-4-methoxy-6-methylpyridazine-3-carboxamide |
| 539 | 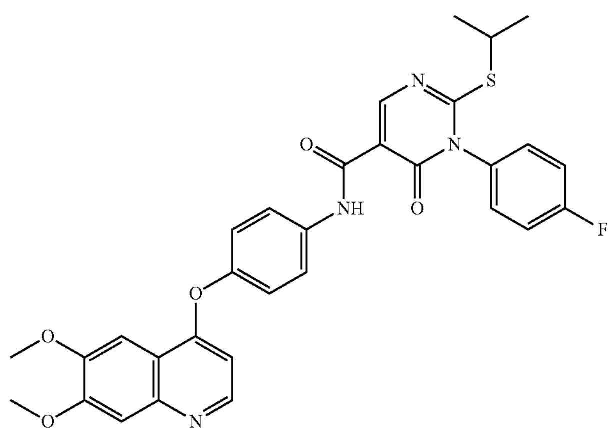 [SMILES: COc1cc2nccc(Oc3ccc(NC(=O)c4cnc(SC(C)C)n(-c5ccc(F)cc5)c4=O)cc3)c2cc1OC] | N-[4-(6,7-dimethoxyquinolin-4-yl)oxyphenyl]-1-(4-fluorophenyl)-6-oxo-2-propan-2-ylsulfanylpyrimidine-5-carboxamide |
| 540 | 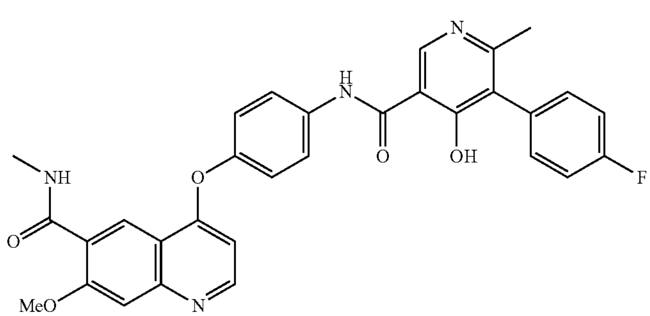 [SMILES: CNC(=O)c1cc2c(Oc3ccc(NC(=O)c4cnc(C)c(-c5ccc(F)cc5)c4O)cc3)ccnc2cc1OC] | 4-[4-[[5-(4-fluorophenyl)-4-hydroxy-6-methylpyridine-3-carbonyl]amino]phenoxy]-7-methoxy-N-methylquinoline-6-carboxamide |

TABLE 1-continued

| Cpd # | Structure | IUPAC Name |
|---|---|---|
| 541 | 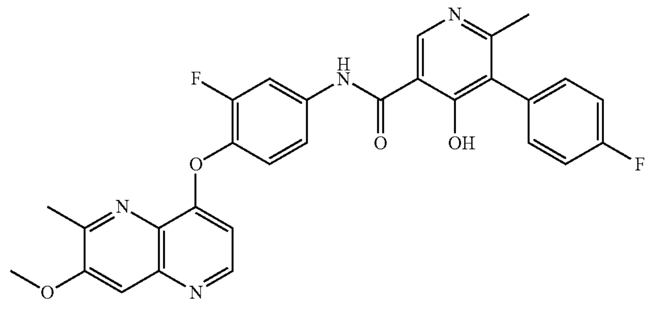 [SMILES: COc1cc2nccc(Oc3ccc(NC(=O)c4cnc(C)c(-c5ccc(F)cc5)c4O)cc3F)c2nc1C] | N-[3-fluoro-4-[(7-methoxy-6-methyl-1,5-naphthyridin-4-yl)oxy]phenyl]-5-(4-fluorophenyl)-4-hydroxy-6-methylpyridine-3-carboxamide |
| 542 | 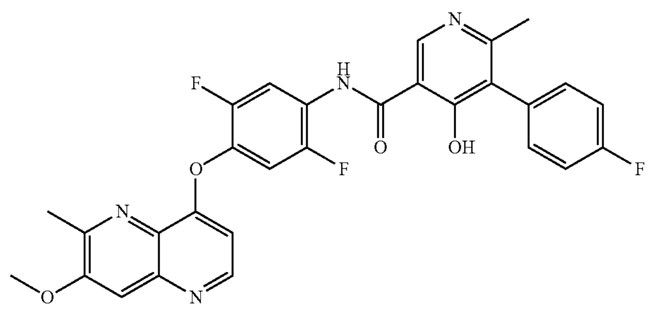 [SMILES: COc1cc2nccc(Oc3cc(F)c(NC(=O)c4cnc(C)c(-c5ccc(F)cc5)c4O)cc3F)c2nc1C] | N-[2,5-difluoro-4-[(7-methoxy-6-methyl-1,5-naphthyridin-4-yl)oxy]phenyl]-5-(4-fluorophenyl)-4-hydroxy-6-methylpyridine-3-carboxamide |
| 543 | 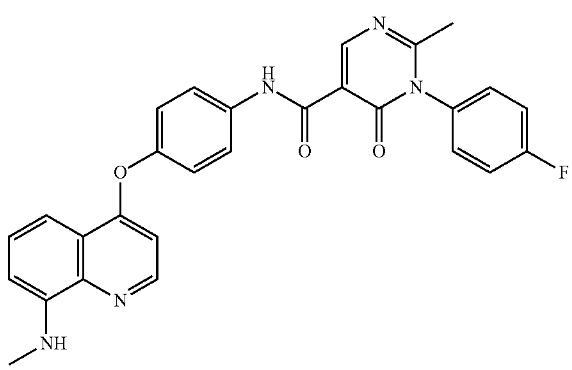 [SMILES: CNc1cccc2c(Oc3ccc(NC(=O)c4cnc(C)n(-c5ccc(F)cc5)c4=O)cc3)ccnc12] | 1-(4-fluorophenyl)-2-methyl-N-[4-[[8-(methylamino)-1,7-naphthyridin-4-yl]oxy]phenyl]-6-oxopyrimidine-5-carboxamide |
| 544 | 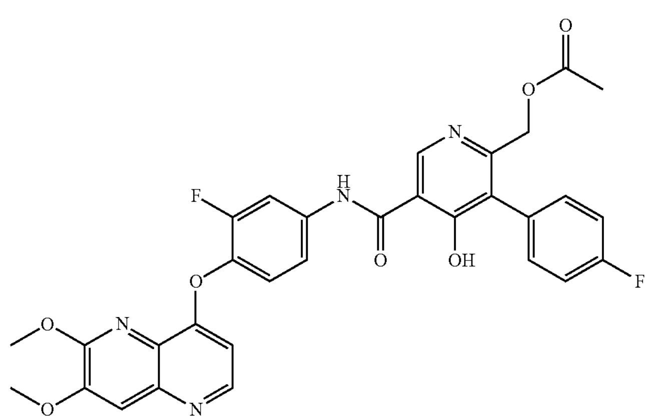 [SMILES: COc1cc2nccc(Oc3ccc(NC(=O)c4cnc(COC(C)=O)c(-c5ccc(F)cc5)c4O)cc3F)c2nc1OC] | [5-[[4-[(6,7-dimethoxy-1,5-naphthyridin-4-yl)oxy]-3-fluorophenyl]carbamoyl]-3-(4-fluorophenyl)-4-hydroxypyridin-2-yl]methyl acetate |

| Cpd # | Structure | IUPAC Name |
| --- | --- | --- |
| 551 | 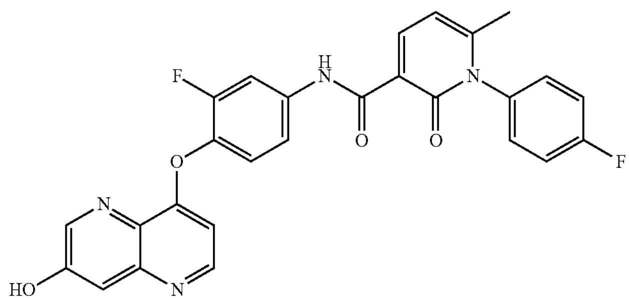 [SMILES: Cc1ccc(C(=O)Nc2ccc(Oc3ccnc4cc(O)cnc34)c(F)c2)c(=O)n1-c1ccc(F)cc1] | N-[3-fluoro-4-[(7-hydroxy-1,5-naphthyridin-4-yl)oxy]phenyl]-1-(4-fluorophenyl)-6-methyl-2-oxopyridine-3-carboxamide |
| 552 | 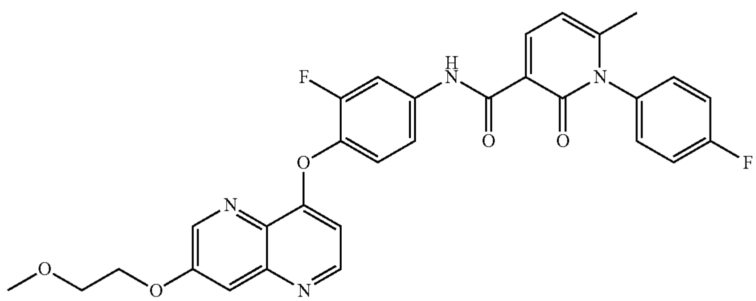 [SMILES: COCCOc1cnc2c(Oc3ccc(NC(=O)c4ccc(C)n(-c5ccc(F)cc5)c4=O)cc3F)ccnc2c1] | N-[3-fluoro-4-[[7-(2-methoxyethoxy)-1,5-naphthyridin-4-yl]oxy]phenyl]-1-(4-fluorophenyl)-6-methyl-2-oxopyridine-3-carboxamide |
| 553 | 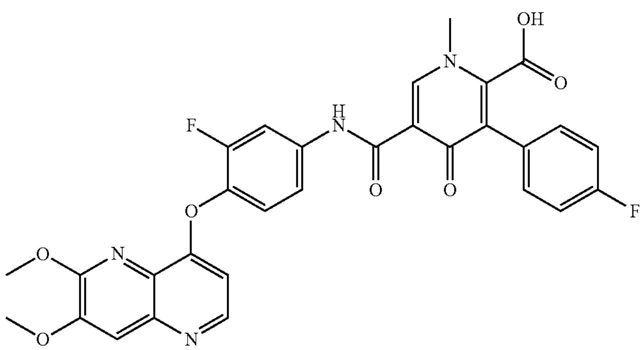 [SMILES: COc1cc2nccc(Oc3ccc(NC(=O)c4cn(C)c(C(=O)O)c(-c5ccc(F)cc5)c4=O)cc3F)c2nc1OC] | 5-[[4-[(6,7-dimethoxy-1,5-naphthyridin-4-yl)oxy]-3-fluorophenyl]carbamoyl]-3-(4-fluorophenyl)-1-methyl-4-oxopyridine-2-carboxylic acid |
| 554 | 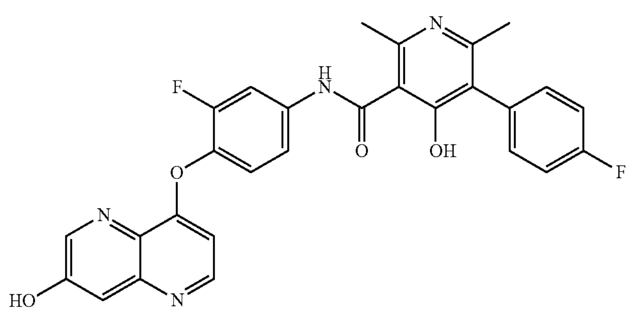 [SMILES: Cc1nc(C)c(-c2ccc(F)cc2)c(O)c1C(=O)Nc1ccc(Oc2ccnc3cc(O)cnc23)c(F)c1] | N-[3-fluoro-4-[(7-hydroxy-1,5-naphthyridin-4-yl)oxy]phenyl]-5-(4-fluorophenyl)-4-hydroxy-2,6-dimethylpyridine-3-carboxamide |
| 555 | 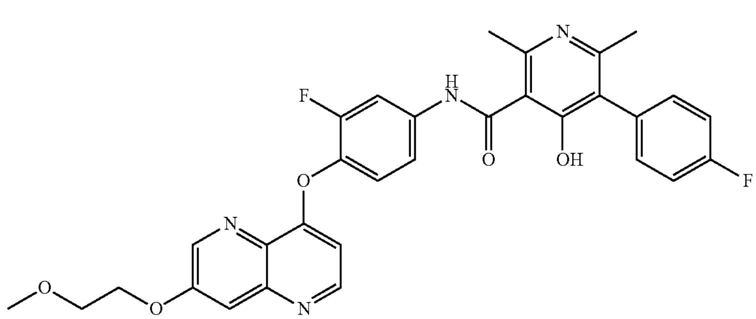 [SMILES: COCCOc1cnc2c(Oc3ccc(NC(=O)c4c(C)nc(C)c(-c5ccc(F)cc5)c4O)cc3F)ccnc2c1] | N-[3-fluoro-4-[[7-(2-methoxyethoxy)-1,5-naphthyridin-4-yl]oxy]phenyl]-5-(4-fluorophenyl)-4-hydroxy-2,6-dimethylpyridine-3-carboxamide |

TABLE 1-continued

| Cpd # | Structure | IUPAC Name |
|---|---|---|
| 556 | 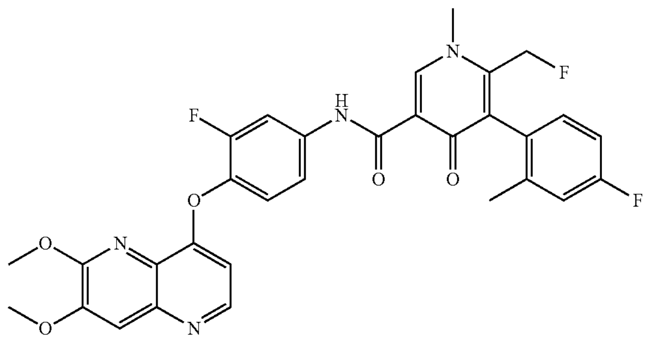 [SMILES: COc1cc2nccc(Oc3ccc(NC(=O)c4cn(C)c(CF)c(-c5ccc(F)cc5C)c4=O)cc3F)c2nc1OC] | N-[4-[(6,7-dimethoxy-1,5-naphthyridin-4-yl)oxy]-3-fluorophenyl]-6-(fluoromethyl)-5-(4-fluoro-2-methylphenyl)-1-methyl-4-oxopyridine-3-carboxamide |
| 557 | 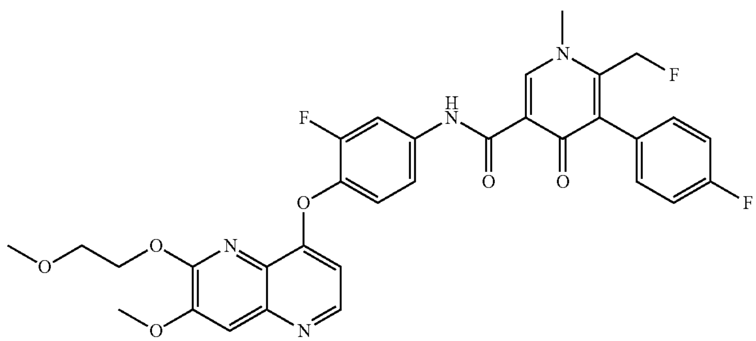 [SMILES: COCCOc1nc2c(Oc3ccc(NC(=O)c4cn(C)c(CF)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-6-(fluoromethyl)-5-(4-fluorophenyl)-1-methyl-4-oxopyridine-3-carboxamide |
| 558 | 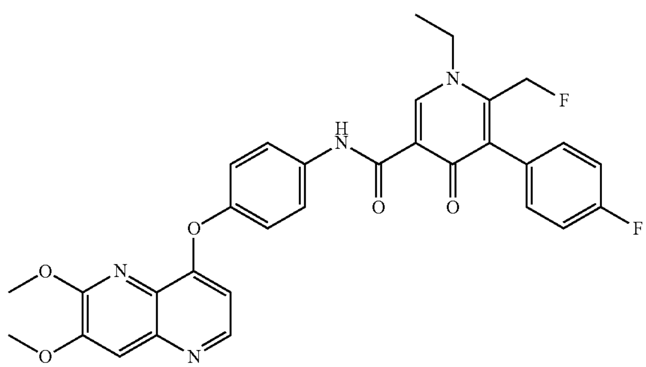 [SMILES: CCn1cc(C(=O)Nc2ccc(Oc3ccnc4cc(OC)c(OC)nc34)cc2)c(=O)c(-c2ccc(F)cc2)c1CF] | N-[4-[(6,7-dimethoxy-1,5-naphthyridin-4-yl)oxy]phenyl]-1-ethyl-6-(fluoromethyl)-5-(4-fluorophenyl)-4-oxopyridine-3-carboxamide |
| 559 | 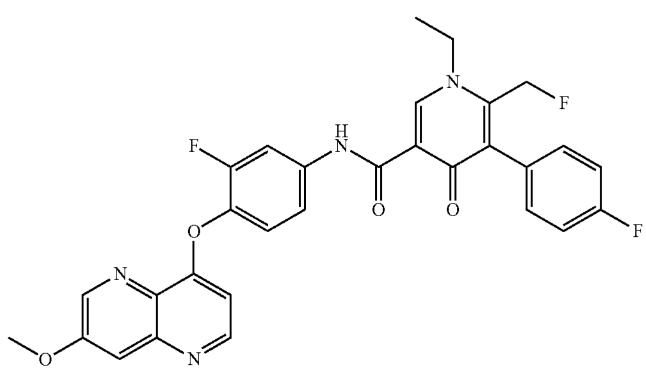 [SMILES: CCn1cc(C(=O)Nc2ccc(Oc3ccnc4cc(OC)cnc34)c(F)c2)c(=O)c(-c2ccc(F)cc2)c1CF] | 1-ethyl-N-[3-fluoro-4-[(7-methoxy-1,5-naphthyridin-4-yl)oxy]phenyl]-6-(fluoromethyl)-5-(4-fluorophenyl)-4-oxopyridine-3-carboxamide |

TABLE 1-continued

| Cpd # | Structure | IUPAC Name |
|---|---|---|
| 560 | 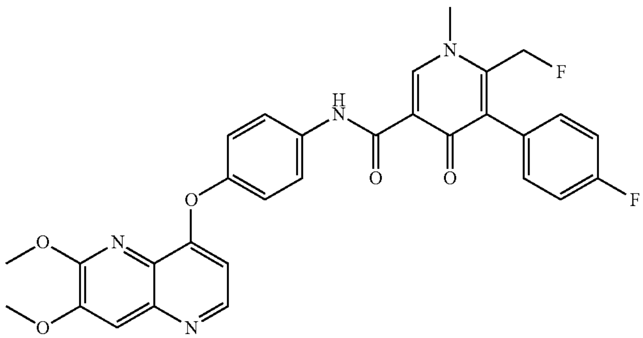 [SMILES: COc1cc2nccc(Oc3ccc(NC(=O)c4cn(C)c(CF)c(-c5ccc(F)cc5)c4=O)cc3)c2nc1OC] | N-[4-[(6,7-dimethoxy-1,5-naphthyridin-4-yl)oxy]phenyl]-6-(fluoromethyl)-5-(4-fluorophenyl)-1-methyl-4-oxopyridine-3-carboxamide |
| 561 | 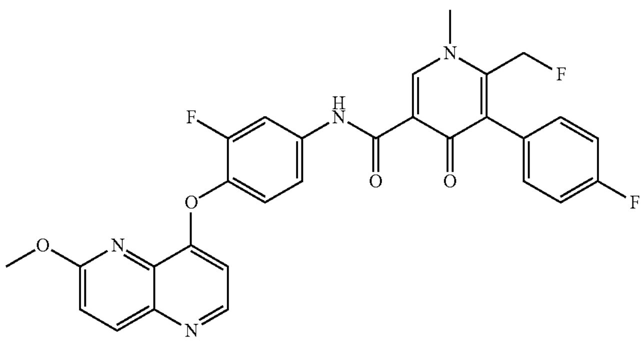 [SMILES: COc1ccc2nccc(Oc3ccc(NC(=O)c4cn(C)c(CF)c(-c5ccc(F)cc5)c4=O)cc3F)c2n1] | N-[3-fluoro-4-[(6-methoxy-1,5-naphthyridin-4-yl)oxy]phenyl]-6-(fluoromethyl)-5-(4-fluorophenyl)-1-methyl-4-oxopyridine-3-carboxamide |
| 562 | 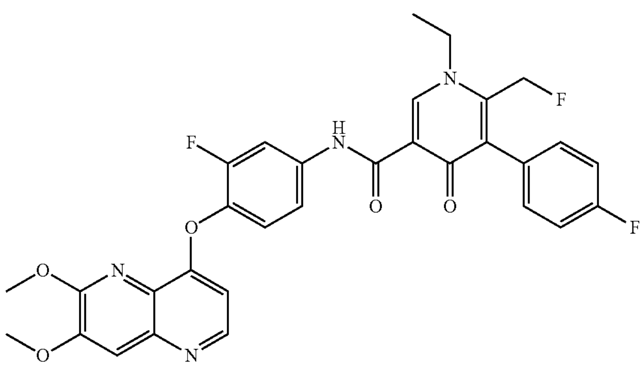 [SMILES: CCn1cc(C(=O)Nc2ccc(Oc3ccnc4cc(OC)c(OC)nc34)c(F)c2)c(=O)c(-c2ccc(F)cc2)c1CF] | N-[4-[(6,7-dimethoxy-1,5-naphthyridin-4-yl)oxy]-3-fluorophenyl]-1-ethyl-6-(fluoromethyl)-5-(4-fluorophenyl)-4-oxopyridine-3-carboxamide |
| 563 | 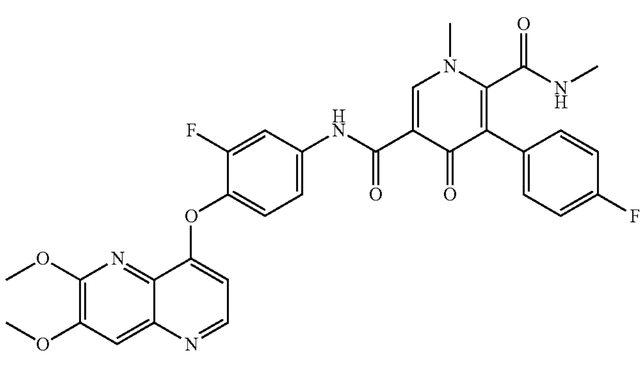 [SMILES: CNC(=O)c1c(-c2ccc(F)cc2)c(=O)c(C(=O)Nc2ccc(Oc3ccnc4cc(OC)c(OC)nc34)c(F)c2)cn1C] | 5-N-[4-[(6,7-dimethoxy-1,5-naphthyridin-4-yl)oxy]-3-fluorophenyl]-3-(4-fluorophenyl)-2-N,1-dimethyl-4-oxopyridine-2,5-dicarboxamide |

TABLE 1-continued

| Cpd # | Structure | IUPAC Name |
|---|---|---|
| 564 | 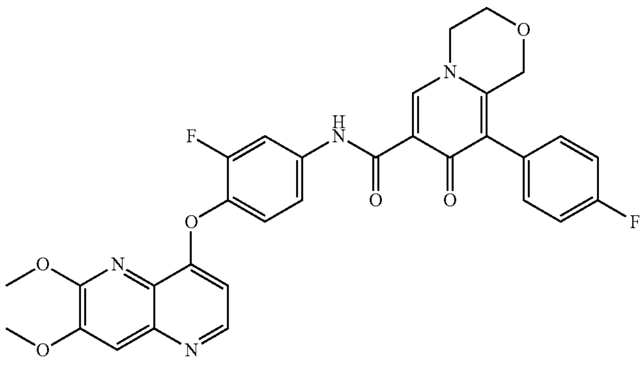 [SMILES: COc1cc2nccc(Oc3ccc(NC(=O)c4cn5c(c(-c6ccc(F)cc6)c4=O)COCC5)cc3F)c2nc1OC] | N-[4-[(6,7-dimethoxy-1,5-naphthyridin-4-yl)oxy]-3-fluorophenyl]-9-(4-fluorophenyl)-8-oxo-3,4-dihydro-1H-pyrido[2,1-c][1,4]oxazine-7-carboxamide |
| 565 | 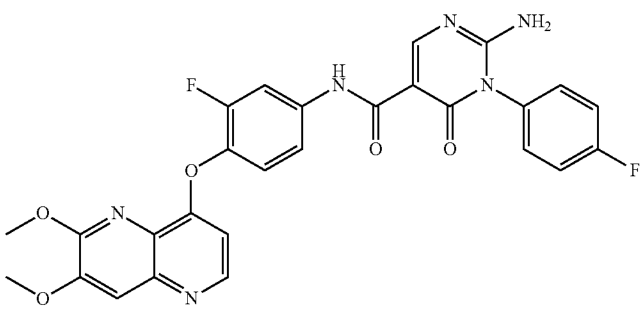 [SMILES: COc1cc2nccc(Oc3ccc(NC(=O)c4cnc(N)n(-c5ccc(F)cc5)c4=O)cc3F)c2nc1OC] | 2-amino-N-[4-[(6,7-dimethoxy-1,5-naphthyridin-4-yl)oxy]-3-fluorophenyl]-1-(4-fluorophenyl)-6-oxopyrimidine-5-carboxamide |
| 566 | 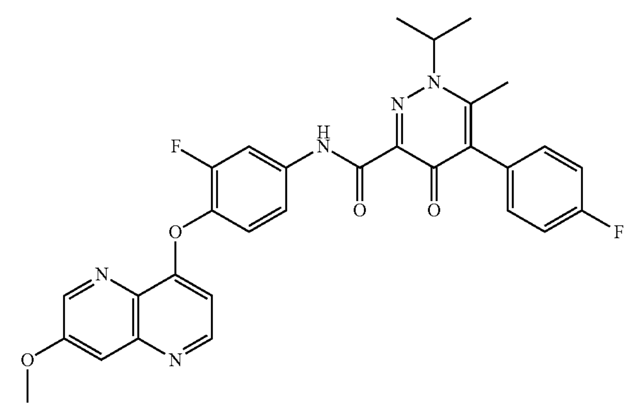 [SMILES: COc1cnc2c(Oc3ccc(NC(=O)c4nn(C(C)C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1-propan-2-ylpyridazine-3-carboxamide |
| 567 | 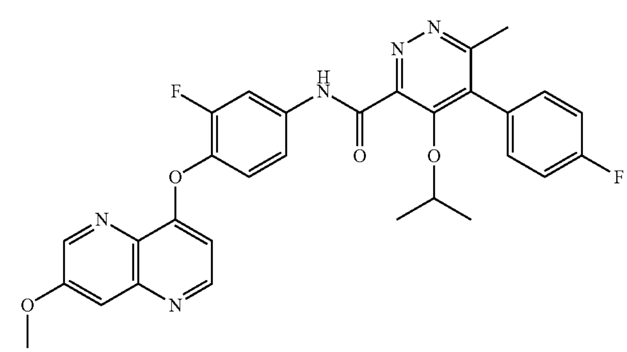 [SMILES: COc1cnc2c(Oc3ccc(NC(=O)c4nnc(C)c(-c5ccc(F)cc5)c4OC(C)C)cc3F)ccnc2c1] | N-[3-fluoro-4-[(7-methoxy-1,5-naphthyridin-4-yl)oxy]phenyl]-5-(4-fluorophenyl)-6-methyl-4-propan-2-yloxypyridazine-3-carboxamide |

| Cpd # | Structure | IUPAC Name |
|---|---|---|
| 568 | 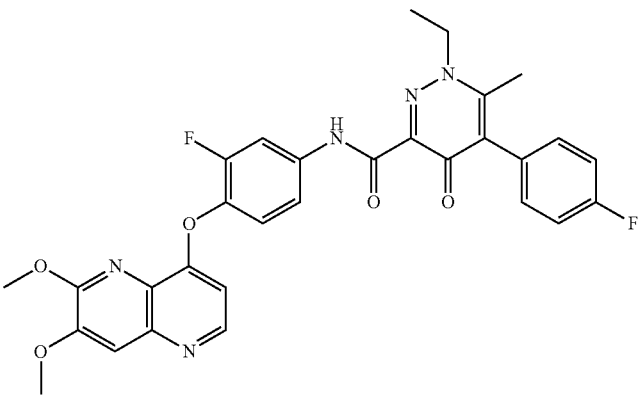 [SMILES: CCn1nc(C(=O)Nc2ccc(Oc3ccnc4cc(OC)c(OC)nc34)c(F)c2)c(=O)c(-c2ccc(F)cc2)c1C] | N-[4-[(6,7-dimethoxy-1,5-naphthyridin-4-yl)oxy]-3-fluorophenyl]-1-ethyl-5-(4-fluorophenyl)-6-methyl-4-oxopyridazine-3-carboxamide |
| 569 | 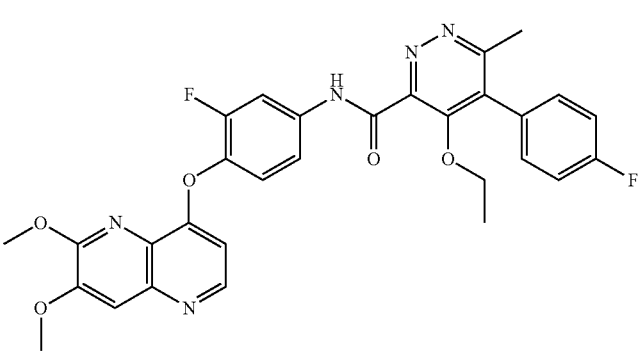 [SMILES: CCOc1c(C(=O)Nc2ccc(Oc3ccnc4cc(OC)c(OC)nc34)c(F)c2)nnc(C)c1-c1ccc(F)cc1] | N-[4-[(6,7-dimethoxy-1,5-naphthyridin-4-yl)oxy]-3-fluorophenyl]-4-ethoxy-5-(4-fluorophenyl)-6-methylpyridazine-3-carboxamide |
| 570 | 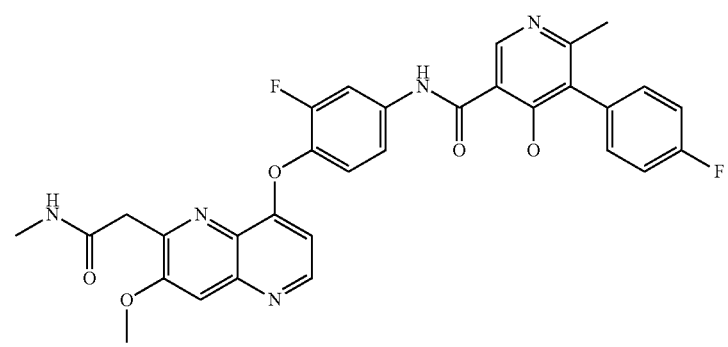 [SMILES: CNC(=O)Cc1nc2c(Oc3ccc(NC(=O)c4cnc(C)c(-c5ccc(F)cc5)c4O)cc3F)ccnc2cc1OC] | N-[3-fluoro-4-[[7-methoxy-6-[2-(methylamino)-2-oxoethyl]-1,5-naphthyridin-4-yl]oxy]phenyl]-5-(4-fluorophenyl)-4-hydroxy-6-methylpyridine-3-carboxamide |
| 571 | 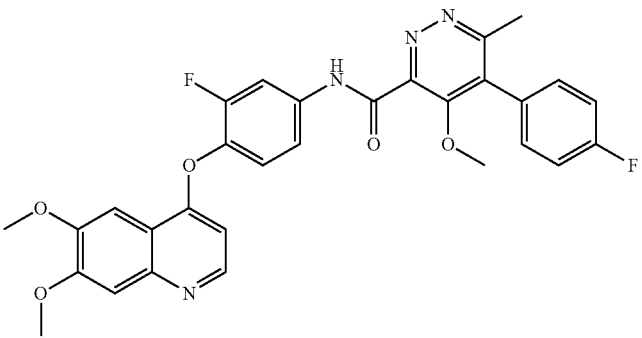 [SMILES: COc1cc2nccc(Oc3ccc(NC(=O)c4nnc(C)c(-c5ccc(F)cc5)c4OC)cc3F)c2cc1OC] | N-[4-(6,7-dimethoxyquinolin-4-yl)oxy-3-fluorophenyl]-5-(4-fluorophenyl)-4-methoxy-6-methylpyridazine-3-carboxamide |

TABLE 1-continued

| Cpd # | Structure | IUPAC Name |
|---|---|---|
| 572 | 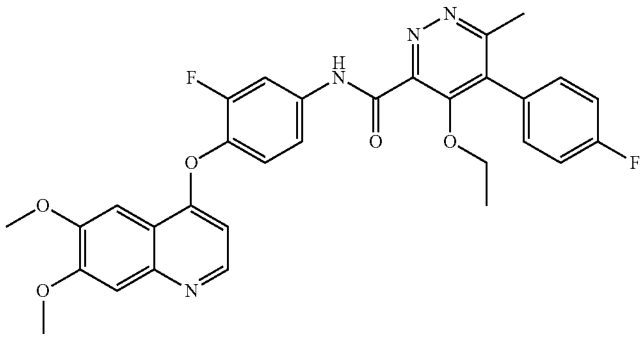 [SMILES: CCOc1c(C(=O)Nc2ccc(Oc3ccnc4cc(OC)c(OC)cc34)c(F)c2)nnc(C)c1-c1ccc(F)cc1] | N-[4-(6,7-dimethoxyquinolin-4-yl)oxy-3-fluorophenyl]-4-ethoxy-5-(4-fluorophenyl)-6-methylpyridazine-3-carboxamide |
| 573 | 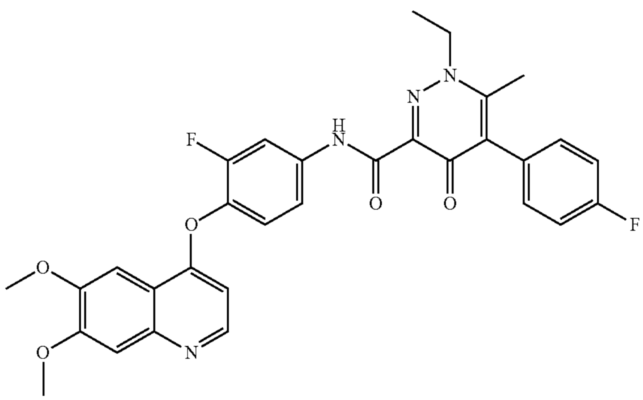 [SMILES: CCn1nc(C(=O)Nc2ccc(Oc3ccnc4cc(OC)c(OC)cc34)c(F)c2)c(=O)c(-c2ccc(F)cc2)c1C] | N-[4-(6,7-dimethoxyquinolin-4-yl)oxy-3-fluorophenyl]-1-ethyl-5-(4-fluorophenyl)-6-methyl-4-oxopyridazine-3-carboxamide |
| 574 | 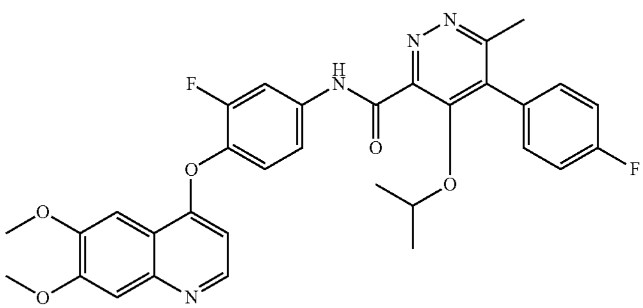 [SMILES: COc1cc2nccc(Oc3ccc(NC(=O)c4nnc(C)c(-c5ccc(F)cc5)c4OC(C)C)cc3F)c2cc1OC] | N-[4-(6,7-dimethoxyquinolin-4-yl)oxy-3-fluorophenyl]-5-(4-fluorophenyl)-6-methyl-4-propan-2-yloxypyridazine-3-carboxamide |
| 575 | 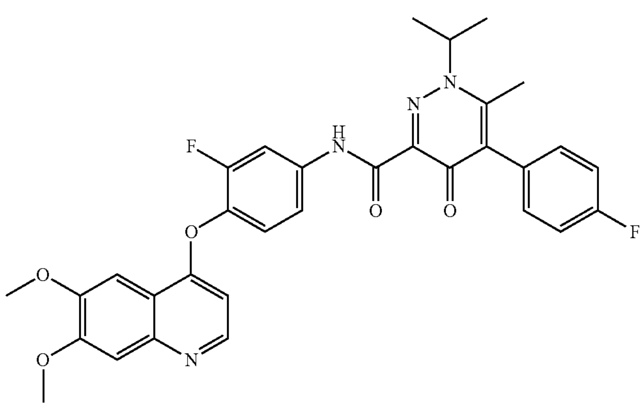 [SMILES: COc1cc2nccc(Oc3ccc(NC(=O)c4nn(C(C)C)c(C)c(-c5ccc(F)cc5)c4=O)cc3F)c2cc1OC] | N-[4-(6,7-dimethoxyquinolin-4-yl)oxy-3-fluorophenyl]-5-(4-fluorophenyl)-6-methyl-4-oxo-1-propan-2-ylpyridazine-3-carboxamide |

TABLE 1-continued

| Cpd # | Structure | IUPAC Name |
|---|---|---|
| 576 | 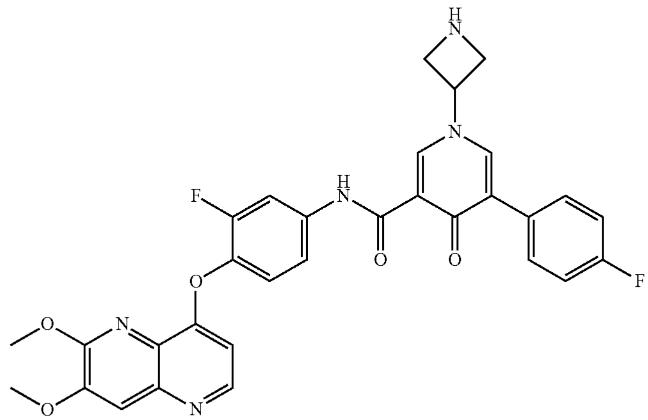 [SMILES: COc1cc2nccc(Oc3ccc(NC(=O)c4cn(C5CNC5)cc(-c5ccc(F)cc5)c4=O)cc3F)c2nc1OC] | 1-(azetidin-3-yl)-N-[4-[(6,7-dimethoxy-1,5-naphthyridin-4-yl)oxy]-3-fluorophenyl]-5-(4-fluorophenyl)-4-oxopyridine-3-carboxamide |
| 577 | 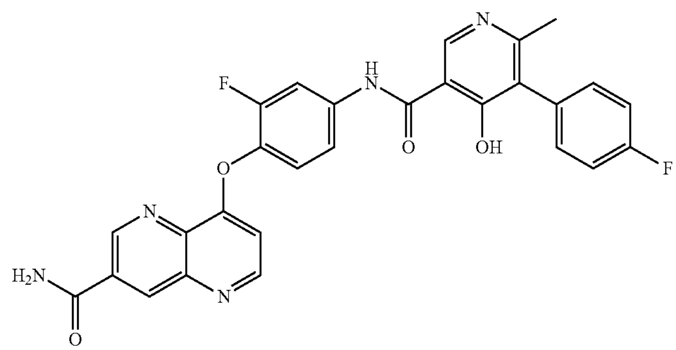 [SMILES: Cc1ncc(C(=O)Nc2ccc(Oc3ccnc4cc(C(N)=O)cnc34)c(F)c2)c(O)c1-c1ccc(F)cc1] | 8-[2-fluoro-4-[[5-(4-fluorophenyl)-4-hydroxy-6-methylpyridine-3-carbonyl]amino]phenoxy]-1,5-naphthyridine-3-carboxamide |
| 578 | 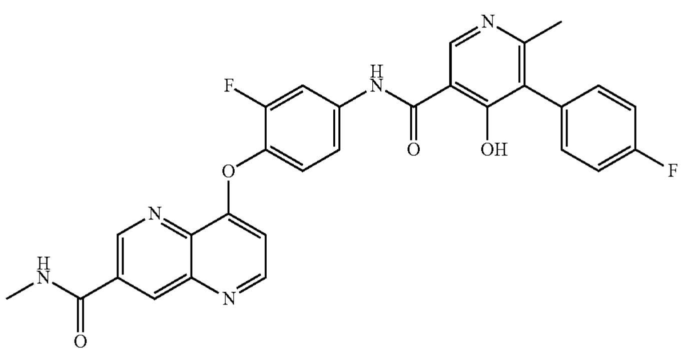 [SMILES: CNC(=O)c1cnc2c(Oc3ccc(NC(=O)c4cnc(C)c(-c5ccc(F)cc5)c4O)cc3F)ccnc2c1] | 8-[2-fluoro-4-[[5-(4-fluorophenyl)-4-hydroxy-6-methylpyridine-3-carbonyl]amino]phenoxy]-N-methyl-1,5-naphthyridine-3-carboxamide |
| 579 | 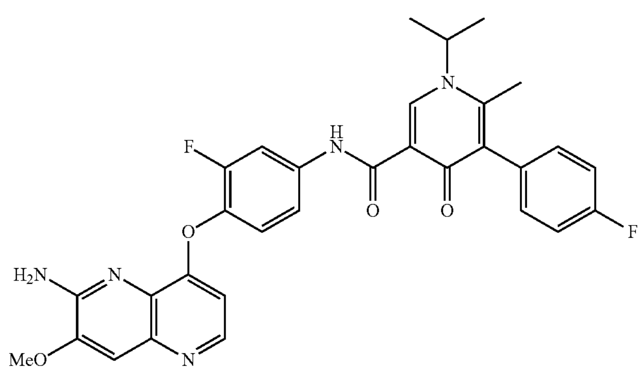 [SMILES: COc1cc2nccc(Oc3ccc(NC(=O)c4cn(C(C)C)c(C)c(-c5ccc(F)cc5)c4=O)cc3F)c2nc1N] | N-[4-[(6-amino-7-methoxy-1,5-naphthyridin-4-yl)oxy]-3-fluorophenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 580 | 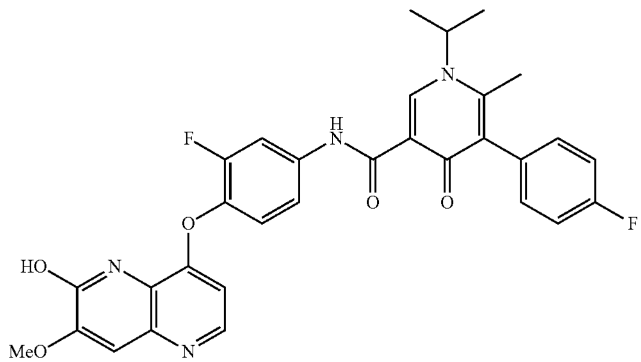 | N-[3-fluoro-4-[(6-hydroxy-7-methoxy-1,5-naphthyridin-4-yl)oxy]phenyl]-5-(4-fluorophenyl)-6-methyl-4-oxo-1-propan-2-ylpyridine-3-carboxamide |
| 581 | 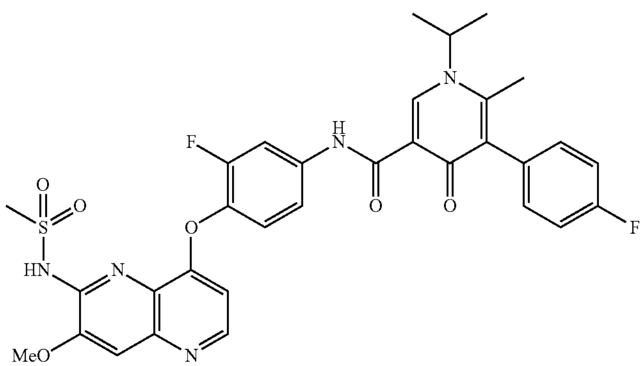 [SMILES: COc1cc2nccc(Oc3ccc(NC(=O)c4cn(C(C)C)c(C)c(-c5ccc(F)cc5)c4=O)cc3F)c2nc1NS(C)(=O)=O] | N-[3-fluoro-4-[[6-(methanesulfonamido)-7-methoxy-1,5-naphthyridin-4-yl]oxy]phenyl]-5-(4-fluorophenyl)-6-methyl-4-oxo-1-propan-2-ylpyridine-3-carboxamide |
| 582 | 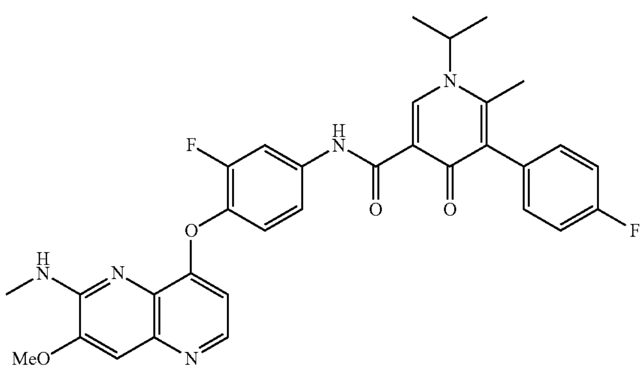 [SMILES: CNc1nc2c(Oc3ccc(NC(=O)c4cn(C(C)C)c(C)c(-c5ccc(F)cc5)c4=O)cc3F)ccnc2cc1OC] | N-[3-fluoro-4-[[7-methoxy-6-(methylamino)-1,5-naphthyridin-4-yl]oxy]phenyl]-5-(4-fluorophenyl)-6-methyl-4-oxo-1-propan-2-ylpyridine-3-carboxamide |
| 583 | 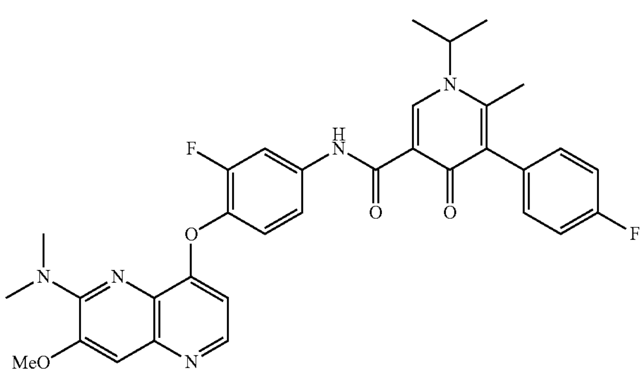 [SMILES: COc1cc2nccc(Oc3ccc(NC(=O)c4cn(C(C)C)c(C)c(-c5ccc(F)cc5)c4=O)cc3F)c2nc1N(C)C] | N-[4-[[6-(dimethylamino)-7-methoxy-1,5-naphthyridin-4-yl]oxy]-3-fluorophenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 584 | 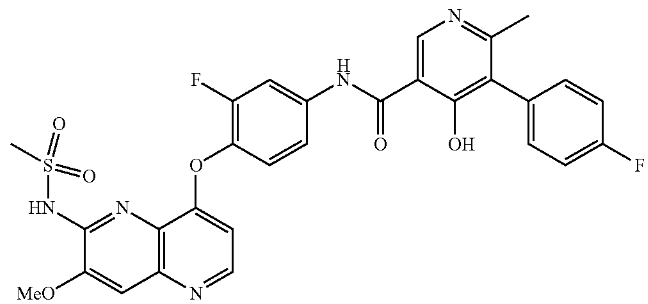 [SMILES: COc1cc2nccc(Oc3ccc(NC(=O)c4cnc(C)c(-c5ccc(F)cc5)c4O)cc3F)c2nc1NS(C)(=O)=O] | N-[3-fluoro-4-[[6-(methanesulfonamido)-7-methoxy-1,5-naphthyridin-4-yl]oxy]phenyl]-5-(4-fluorophenyl)-4-hydroxy-6-methylpyridine-3-carboxamide |
| 585 | 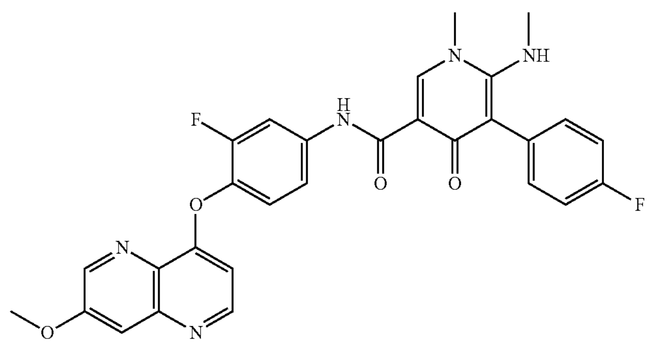 [SMILES: CNc1c(-c2ccc(F)cc2)c(=O)c(C(=O)Nc2ccc(Oc3ccnc4cc(OC)cnc34)c(F)c2)cn1C] | N-[3-fluoro-4-[(7-methoxy-1,5-naphthyridin-4-yl)oxy]phenyl]-5-(4-fluorophenyl)-1-methyl-6-(methylamino)-4-oxopyridine-3-carboxamide |
| 586 | 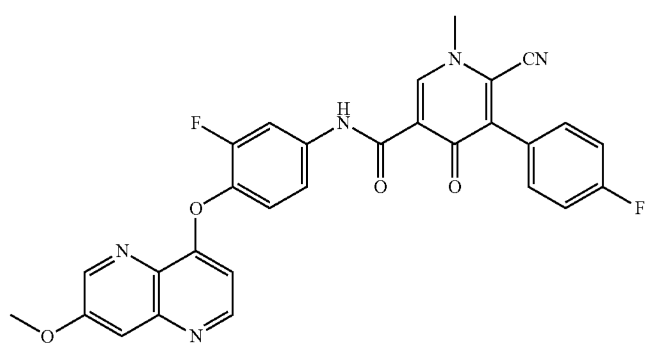 [SMILES: COc1cnc2c(Oc3ccc(NC(=O)c4cn(C)c(C#N)c(-c5ccc(F)cc5)c4=O)cc3F)ccnc2c1] | 6-cyano-N-[3-fluoro-4-[(7-methoxy-1,5-naphthyridin-4-yl)oxy]phenyl]-5-(4-fluorophenyl)-1-methyl-4-oxopyridine-3-carboxamide |
| 587 | 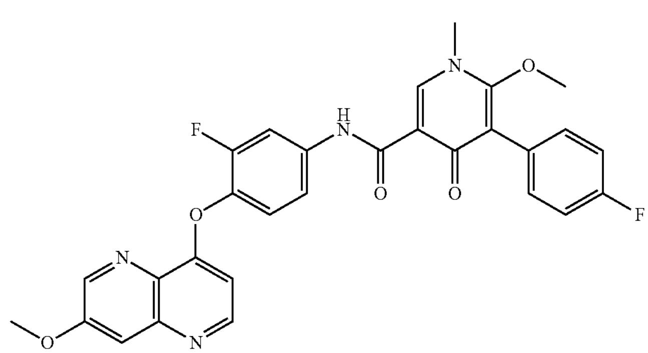 [SMILES: COc1cnc2c(Oc3ccc(NC(=O)c4cn(C)c(OC)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methoxy-1-methyl-4-oxopyridine-3-carboxamide |

TABLE 1-continued

| Cpd # | Structure | IUPAC Name |
|---|---|---|
| 588 | 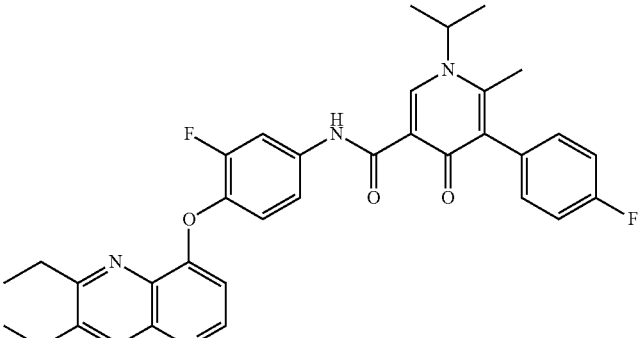 | N-[4-[(6-ethyl-7-methoxy-1,5-naphthyridin-4-yl)oxy]-3-fluorophenyl]-5-(4-fluorophenyl)-6-methyl-4-oxo-1-propan-2-ylpyridine-3-carboxamide |
| 589 | 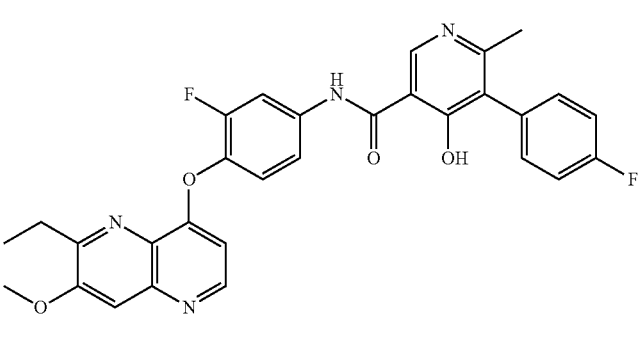 [SMILES: CCc1nc2c(Oc3ccc(NC(=O)c4cnc(C)c(-c5ccc(F)cc5)c4O)cc3F)ccnc2cc1OC] | N-[4-[(6-ethyl-7-methoxy-1,5-naphthyridin-4-yl)oxy]-3-fluorophenyl]-5-(4-fluorophenyl)-4-hydroxy-6-methylpyridine-3-carboxamide |
| 590 | 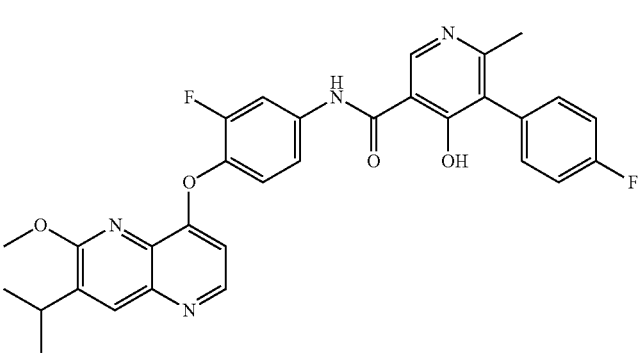 | N-[3-fluoro-4-[(6-methoxy-7-propan-2-yl-1,5-naphthyridin-4-yl)oxy]phenyl]-5-(4-fluorophenyl)-4-hydroxy-6-methylpyridine-3-carboxamide |
| 591 | 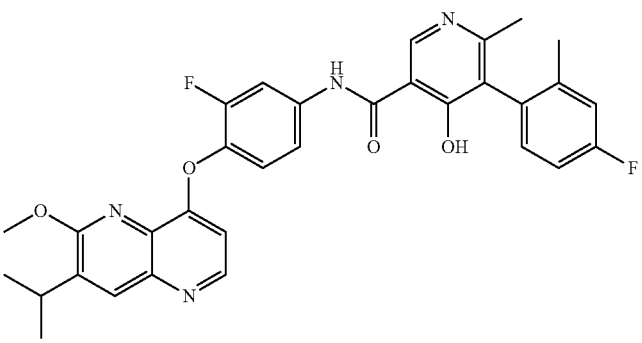 [SMILES: COc1nc2c(Oc3ccc(NC(=O)c4cnc(C)c(-c5ccc(F)cc5C)c4O)cc3F)ccnc2cc1C(C)C] | N-[3-fluoro-4-[(6-methoxy-7-propan-2-yl-1,5-naphthyridin-4-yl)oxy]phenyl]-5-(4-fluoro-2-methylphenyl)-4-hydroxy-6-methylpyridine-3-carboxamide |

TABLE 1-continued

| Cpd # | Structure | IUPAC Name |
|---|---|---|
| 592 | 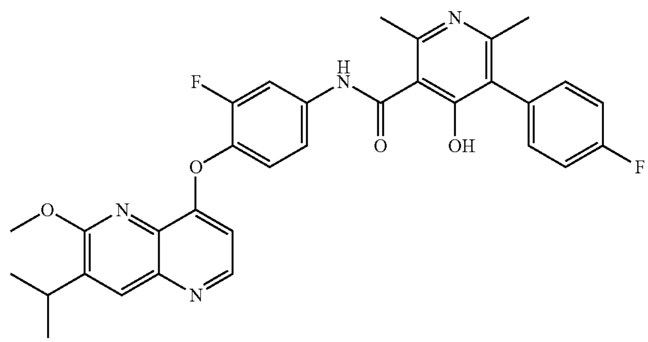 [SMILES: COc1nc2c(Oc3ccc(NC(=O)c4c(C)nc(C)c(-c5ccc(F)cc5)c4O)cc3F)ccnc2cc1C(C)C] | N-[3-fluoro-4-[(6-methoxy-7-propan-2-yl-1,5-naphthyridin-4-yl)oxy]phenyl]-5-(4-fluorophenyl)-4-hydroxy-2,6-dimethylpyridine-3-carboxamide |
| 593 | 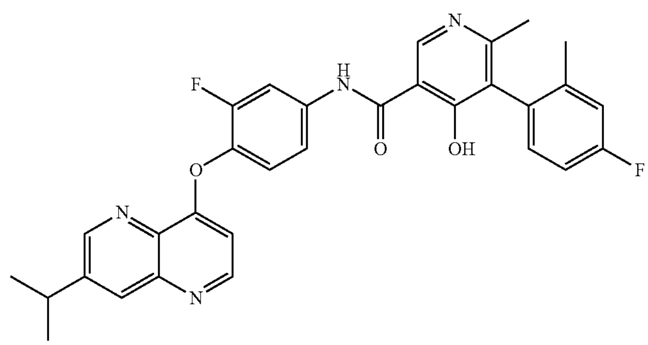 [SMILES: Cc1cc(F)ccc1-c1c(C)ncc(C(=O)Nc2ccc(Oc3ccnc4cc(C(C)C)cnc34)c(F)c2)c1O] | 5-(4-fluoro-2-methylphenyl)-N-[3-fluoro-4-[(7-propan-2-yl-1,5-naphthyridin-4-yl)oxy]phenyl]-4-hydroxy-6-methylpyridine-3-carboxamide |
| 594 | 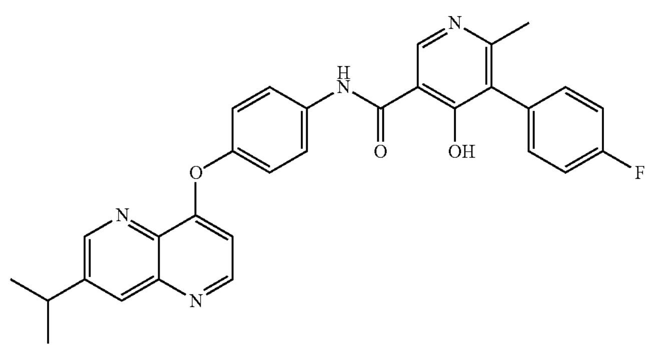 | 5-(4-fluorophenyl)-4-hydroxy-6-methyl-N-[4-[(7-propan-2-yl-1,5-naphthyridin-4-yl)oxy]phenyl]pyridine-3-carboxamide |
| 595 | 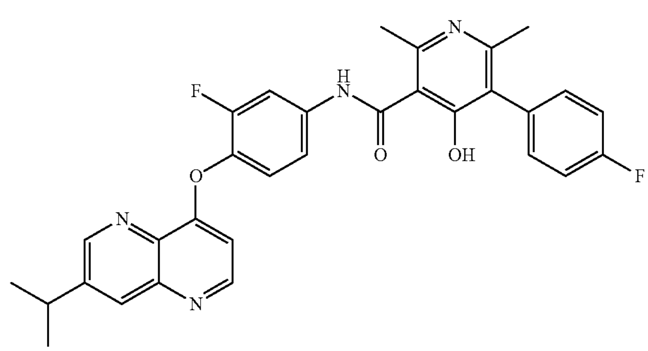 [SMILES: Cc1nc(C)c(-c2ccc(F)cc2)c(O)c1C(=O)Nc1ccc(Oc2ccnc3cc(C(C)C)cnc23)c(F)c1] | 5-(4-fluorophenyl)-N-[3-fluoro-4-[(7-propan-2-yl-1,5-naphthyridin-4-yl)oxy]phenyl]-4-hydroxy-2,6-dimethylpyridine-3-carboxamide |

TABLE 1-continued

| Cpd # | Structure | IUPAC Name |
|---|---|---|
| 596 | 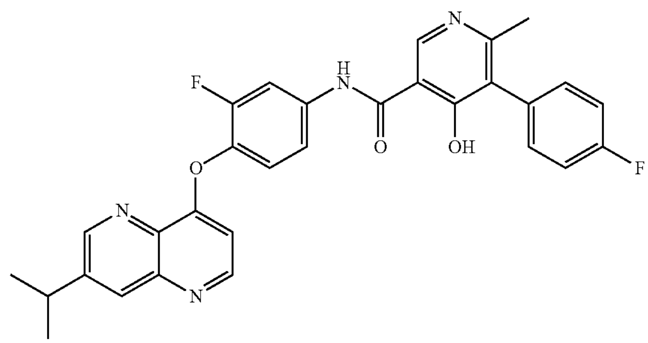 | 5-(4-fluorophenyl)-N-[3-fluoro-4-[(7-propan-2-yl-1,5-naphthyridin-4-yl)oxy]phenyl]-4-hydroxy-6-methylpyridine-3-carboxamide |
| 597 | 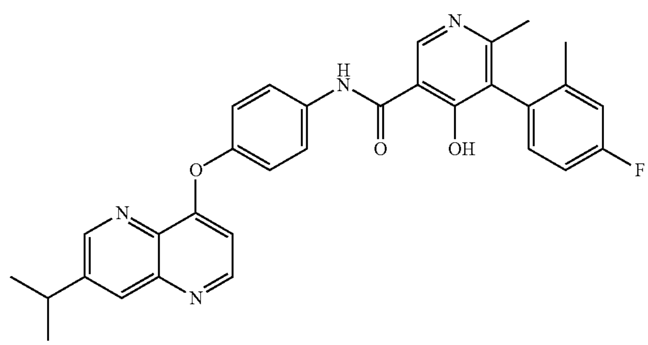 [SMILES: Cc1cc(F)ccc1-c1c(C)ncc(C(=O)Nc2ccc(Oc3ccnc4cc(C(C)C)cnc34)cc2)c1O] | 5-(4-fluoro-2-methylphenyl)-4-hydroxy-6-methyl-N-[4-[(7-propan-2-yl-1,5-naphthyridin-4-yl)oxy]phenyl]pyridine-3-carboxamide |
| 598 | 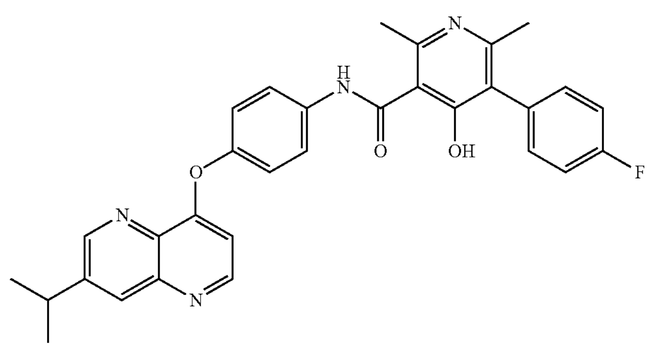 [SMILES: Cc1nc(C)c(-c2ccc(F)cc2)c(O)c1C(=O)Nc1ccc(Oc2ccnc3cc(C(C)C)cnc23)cc1] | 5-(4-fluorophenyl)-4-hydroxy-2,6-dimethyl-N-[4-[(7-propan-2-yl-1,5-naphthyridin-4-yl)oxy]phenyl]pyridine-3-carboxamide |
| 599 | 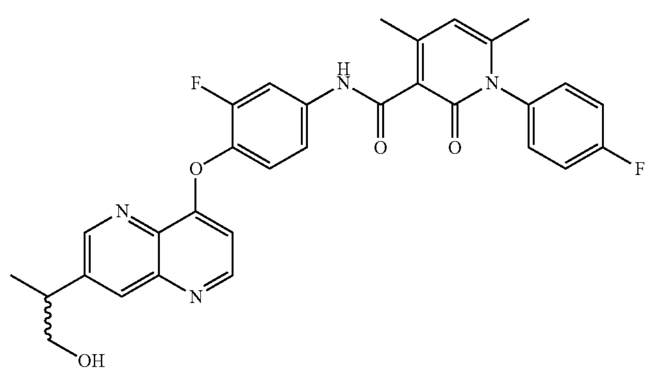 [SMILES: Cc1cc(C)n(-c2ccc(F)cc2)c(=O)c1C(=O)Nc1ccc(Oc2ccnc3cc(C(C)CO)cnc23)c(F)c1] | N-[3-fluoro-4-[[7-(1-hydroxypropan-2-yl)-1,5-naphthyridin-4-yl]oxy]phenyl]-1-(4-fluorophenyl)-4,6-dimethyl-2-oxopyridine-3-carboxamide |

TABLE 1-continued

| Cpd # | Structure | IUPAC Name |
|---|---|---|
| 600 | 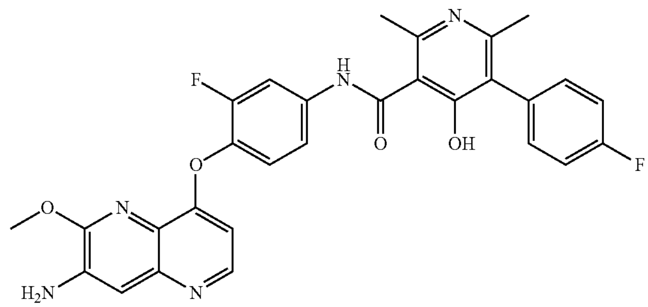 [SMILES: COc1nc2c(Oc3ccc(NC(=O)c4c(C)nc(C)c(-c5ccc(F)cc5)c4O)cc3F)ccnc2cc1N] | N-[4-[(7-amino-6-methoxy-1,5-naphthyridin-4-yl)oxy]-3-fluorophenyl]-5-(4-fluorophenyl)-4-hydroxy-2,6-dimethylpyridine-3-carboxamide |
| 601 | 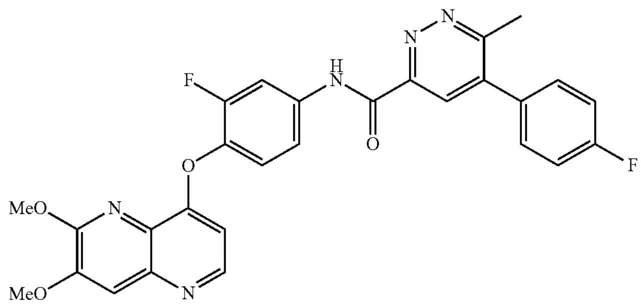 [SMILES: COc1cc2nccc(Oc3ccc(NC(=O)c4cc(-c5ccc(F)cc5)c(C)nn4)cc3F)c2nc1OC] | N-[4-[(6,7-dimethoxy-1,5-naphthyridin-4-yl)oxy]-3-fluorophenyl]-5-(4-fluorophenyl)-6-methylpyridazine-3-carboxamide |
| 602 | 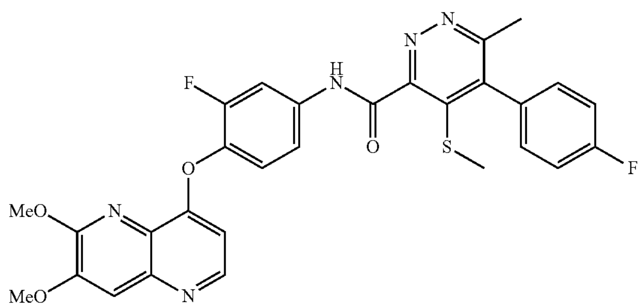 [SMILES: COc1cc2nccc(Oc3ccc(NC(=O)c4nnc(C)c(-c5ccc(F)cc5)c4SC)cc3F)c2nc1OC] | N-[4-[(6,7-dimethoxy-1,5-naphthyridin-4-yl)oxy]-3-fluorophenyl]-5-(4-fluorophenyl)-6-methyl-4-methylsulfanylpyridazine-3-carboxamide |
| 603 | 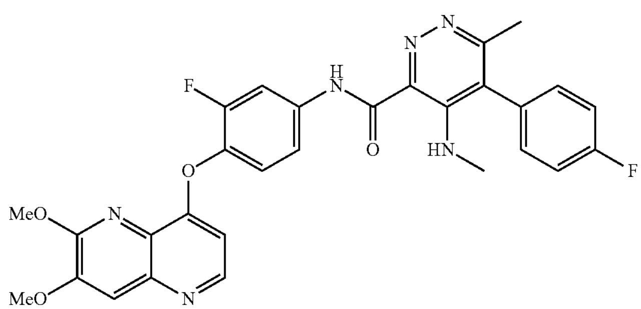 [SMILES: CNc1c(C(=O)Nc2ccc(Oc3ccnc4cc(OC)c(OC)nc34)c(F)c2)nnc(C)c1-c1ccc(F)cc1] | N-[4-[(6,7-dimethoxy-1,5-naphthyridin-4-yl)oxy]-3-fluorophenyl]-5-(4-fluorophenyl)-6-methyl-4-(methylamino)pyridazine-3-carboxamide |
| 604 | 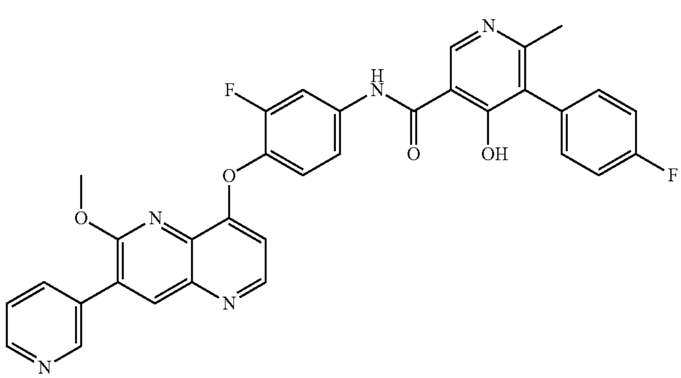 [SMILES: COc1nc2c(Oc3ccc(NC(=O)c4cnc(C)c(-c5ccc(F)cc5)c4O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 605 | 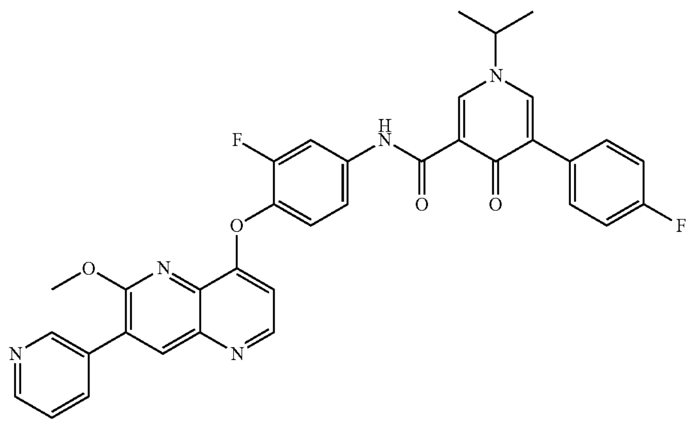 [SMILES: COc1nc2c(Oc3ccc(NC(=O)c4cn(C(C)C)cc(-c5ccc(F)cc5)c4=O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-4-oxo-1-propan-2-ylpyridine-3-carboxamide |
| 606 | 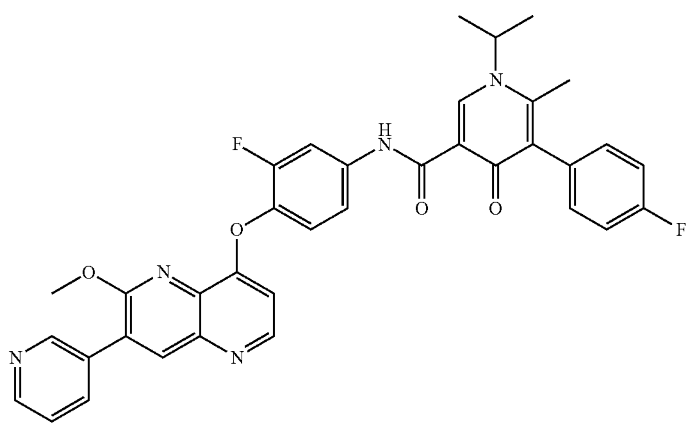 [SMILES: COc1nc2c(Oc3ccc(NC(=O)c4cn(C(C)C)c(C)c(-c5ccc(F)cc5)c4=O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-6-methyl-4-oxo-1-propan-2-ylpyridine-3-carboxamide |
| 607 | 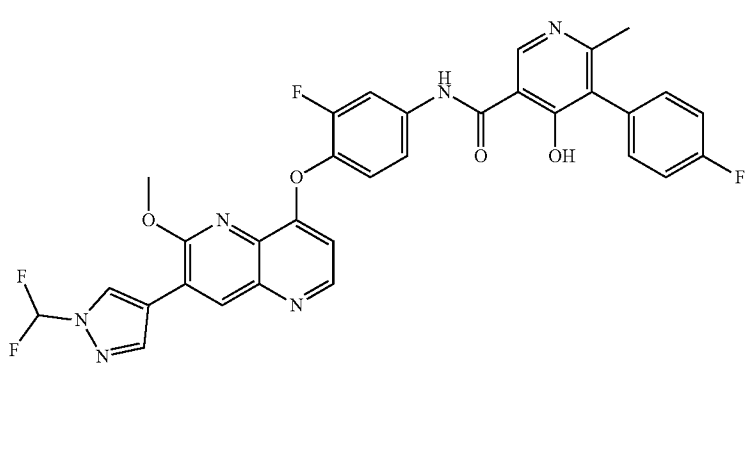 [SMILES: COc1nc2c(Oc3ccc(NC(=O)c4cnc(C)c(-c5ccc(F)cc5)c4O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-4-hydroxy-6-methylpyridine-3-carboxamide |

TABLE 1-continued

| Cpd # | Structure | IUPAC Name |
|---|---|---|
| 608 | 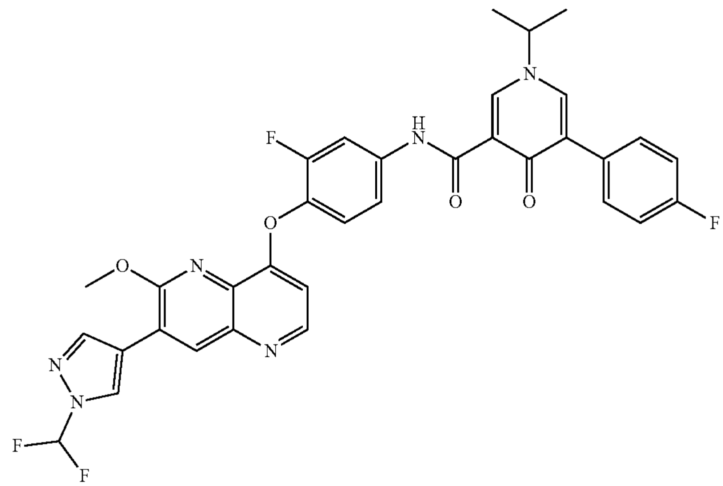 [SMILES: COc1nc2c(Oc3ccc(NC(=O)c4cn(C(C)C)cc(-c5ccc(F)cc5)c4=O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-4-oxo-1-propan-2-ylpyridine-3-carboxamide |
| 609 | 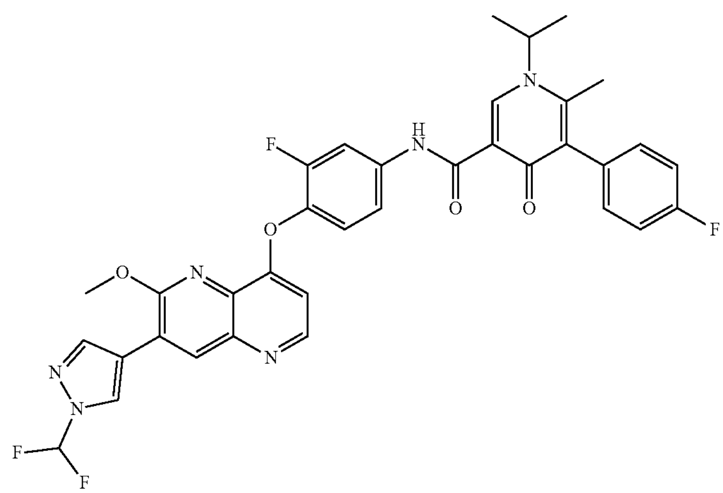 [SMILES: COc1nc2c(Oc3ccc(NC(=O)c4cn(C(C)C)c(C)c(-c5ccc(F)cc5)c4=O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-6-methyl-4-oxo-1-propan-2-ylpyridine-3-carboxamide |
| 610 | 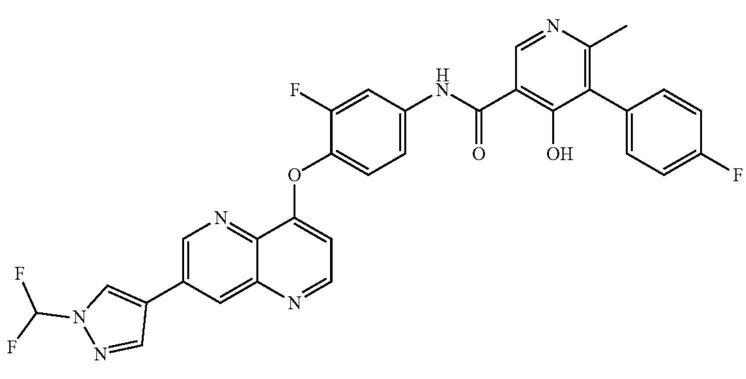 [SMILES: Cc1ncc(C(=O)Nc2ccc(Oc3ccnc4cc(-c5cnn(C(F)F)c5)cnc34)c(F)c2)c(O)c1-c1ccc(F)cc1] | N-[4-[[7-[1-(difluoromethyl)pyrazol-4-yl]-1,5-naphthyridin-4-yl]oxy]-3-fluorophenyl]-5-(4-fluorophenyl)-4-hydroxy-6-methylpyridine-3-carboxamide |

TABLE 1-continued

| Cpd # | Structure | IUPAC Name |
|---|---|---|
| 611 | 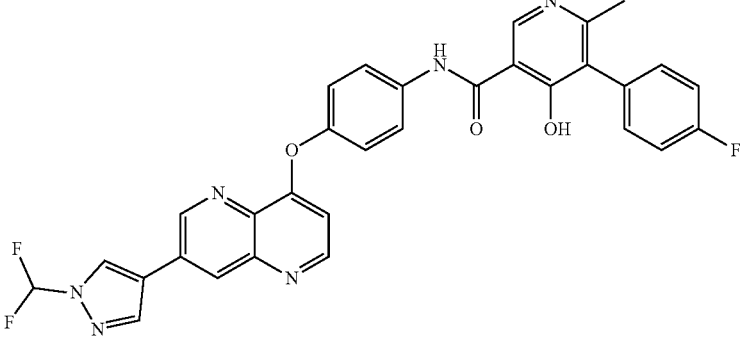 | N-[4-[[7-[1-(difluoromethyl)pyrazol-4-yl]-1,5-naphthyridin-4-yl]oxy]phenyl]-5-(4-fluorophenyl)-4-hydroxy-6-methylpyridine-3-carboxamide |
| 612 | 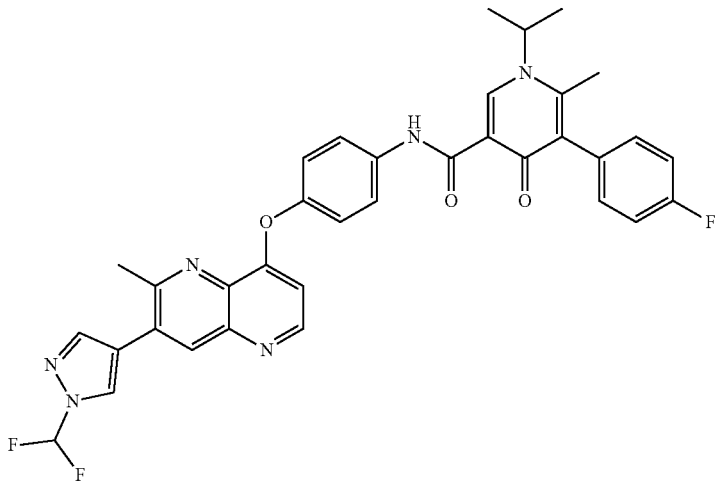 [SMILES: Cc1nc2c(Oc3ccc(NC(=O)c4cn(C(C)C)c(C)c(-c5ccc(F)cc5)c4=O)cc3)ccnc2cc1-c1cnn(C(F)F)c1] | N-[4-[[7-[1-(difluoromethyl)pyrazol-4-yl]-6-methyl-1,5-naphthyridin-4-yl]oxy]phenyl]-5-(4-fluorophenyl)-6-methyl-4-oxo-1-propan-2-ylpyridine-3-carboxamide |
| 613 | 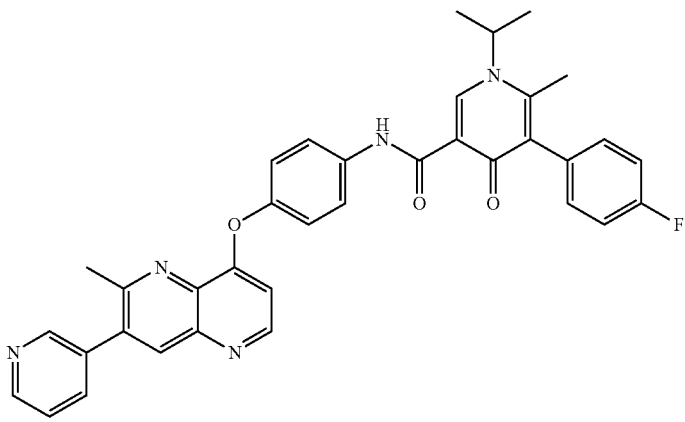 [SMILES: Cc1nc2c(Oc3ccc(NC(=O)c4cn(C(C)C)c(C)c(-c5ccc(F)cc5)c4=O)cc3)ccnc2cc1-c1cccnc1] | 5-(4-fluorophenyl)-6-methyl-N-[4-[(6-methyl-7-pyridin-3-yl-1,5-naphthyridin-4-yl)oxy]phenyl]-4-oxo-1-propan-2-ylpyridine-3-carboxamide |

TABLE 1-continued

| Cpd # | Structure | IUPAC Name |
|---|---|---|
| 614 | 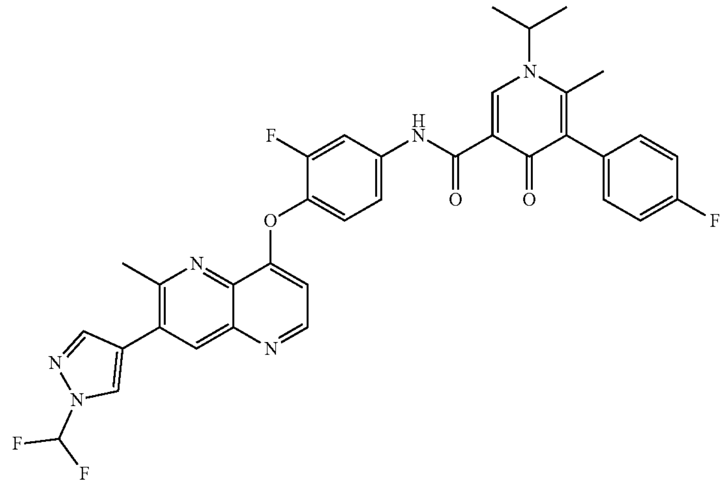 [SMILES: Cc1nc2c(Oc3ccc(NC(=O)c4cn(C(C)C)c(C)c(-c5ccc(F)cc5)c4=O)cc3F)ccnc2cc1-c1cnn(C(F)F)c1] | N-[4-[[7-[1-(difluoromethyl)pyrazol-4-yl]-6-methyl-1,5-naphthyridin-4-yl]oxy]-3-fluorophenyl]-5-(4-fluorophenyl)-6-methyl-4-oxo-1-propan-2-ylpyridine-3-carboxamide |
| 615 | 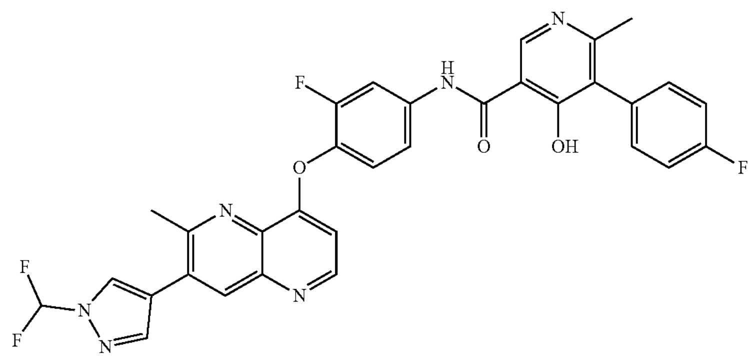 [SMILES: Cc1nc2c(Oc3ccc(NC(=O)c4cnc(C)c(-c5ccc(F)cc5)c4O)cc3F)ccnc2cc1-c1cnn(C(F)F)c1] | N-[4-[[7-[1-(difluoromethyl)pyrazol-4-yl]-6-methyl-1,5-naphthyridin-4-yl]oxy]-3-fluorophenyl]-5-(4-fluorophenyl)-4-hydroxy-6-methylpyridine-3-carboxamide |
| 616 | 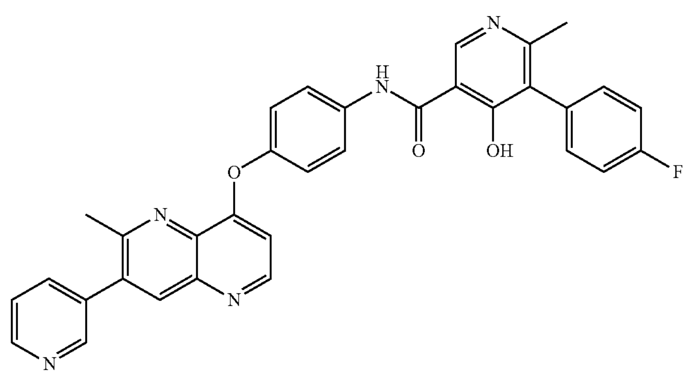 [SMILES: Cc1nc2c(Oc3ccc(NC(=O)c4cnc(C)c(-c5ccc(F)cc5)c4O)cc3)ccnc2cc1-c1cccnc1] | 5-(4-fluorophenyl)-4-hydroxy-6-methyl-N-4-[(6-methyl-7-pyridin-3-yl-1,5-naphthyridin-4-yl)oxy]phenyl]pyridine-3-carboxamide |
| 617 | 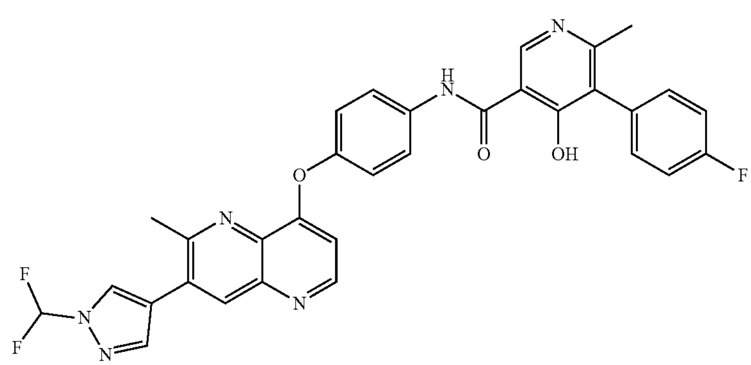 [SMILES: Cc1nc2c(Oc3ccc(NC(=O)c4cnc(C)c(-c5ccc(F)cc5)c4O)cc3)ccnc2cc1-c1cnn(C(F)F)c1] | N-[4-[[7-[1-(difluoromethyl)pyrazol-4-yl]-6-methyl-1,5-naphthyridin-4-yl]oxy]phenyl]-5-(4-fluorophenyl)-4-hydroxy-6-methylpyridine-3-carboxamide |

TABLE 1-continued

| Cpd # | Structure | IUPAC Name |
|---|---|---|
| 618 | 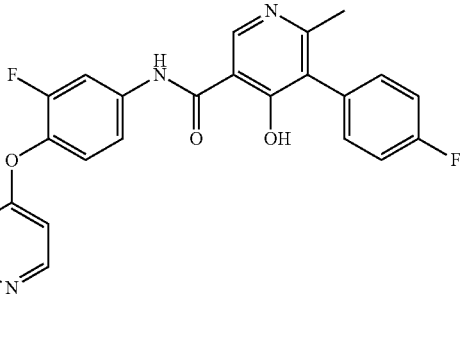 | N-[3-fluoro-4-[(6-methyl-7-pyridin-3-yl-1,5-naphthyridin-4-yl)oxy]phenyl]-5-(4-fluorophenyl)-4-hydroxy-6-methylpyridine-3-carboxamide |
| 619 | 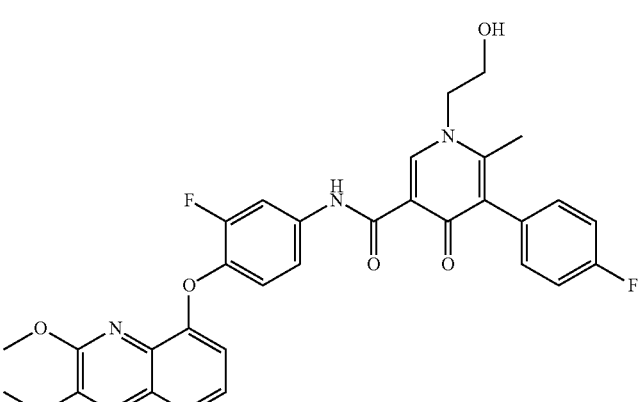 | N-[4-[(6,7-dimethoxy-1,5-naphthyridin-4-yl)oxy]-3-fluorophenyl]-5-(4-fluorophenyl)-1-(2-hydroxyethyl)-6-methyl-4-oxopyridine-3-carboxamide |
| 620 | 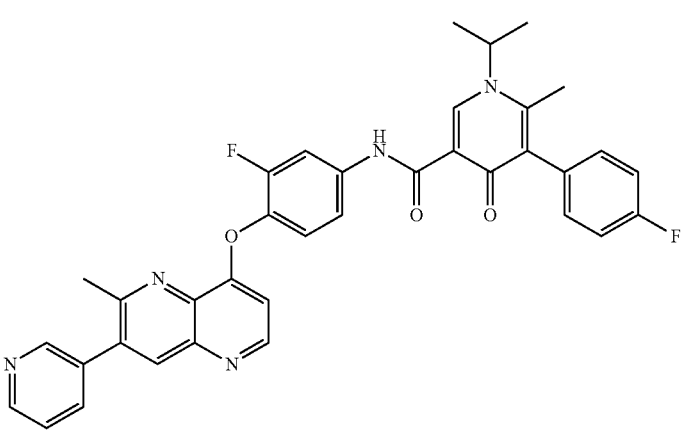 [SMILES: Cc1nc2c(Oc3ccc(NC(=O)c4cn(C(C)C)c(C)c(-c5ccc(F)cc5)c4=O)cc3F)ccnc2cc1-c1cccnc1] | N-[3-fluoro-4-[(6-methyl-7-pyridin-3-yl-1,5-naphthyridin-4-yl)oxy]phenyl]-5-(4-fluorophenyl)-6-methyl-4-oxo-1-propan-2-ylpyridine-3-carboxamide |

TABLE 1-continued

| Cpd # | Structure | IUPAC Name |
|---|---|---|
| 621 | 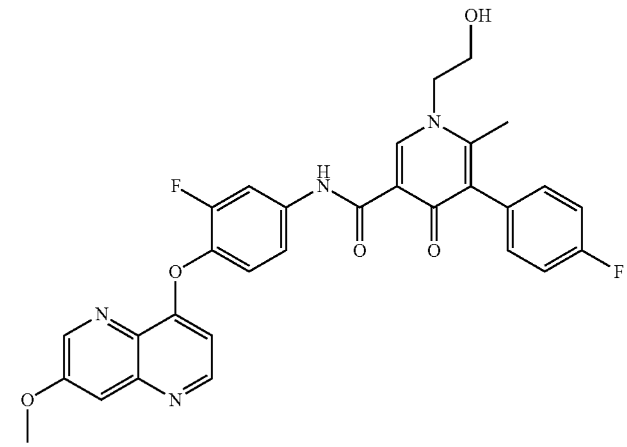 [SMILES: COc1cnc2c(Oc3ccc(NC(=O)c4cn(CCO)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-(2-hydroxyethyl)-6-methyl-4-oxopyridine-3-carboxamide |
| 622 | 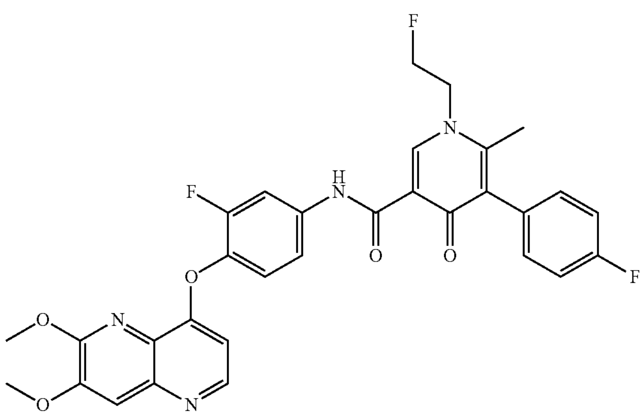 [SMILES: COc1cc2nccc(Oc3ccc(NC(=O)c4cn(CCF)c(C)c(-c5ccc(F)cc5)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluorophenyl)-6-methyl-4-oxopyridine-3-carboxamide |
| 623 | 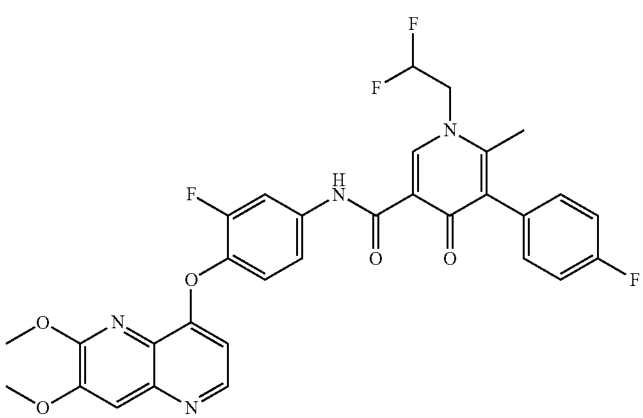 [SMILES: COc1cc2nccc(Oc3ccc(NC(=O)c4cn(CC(F)F)c(C)c(-c5ccc(F)cc5)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluorophenyl)-6-methyl-4-oxopyridine-3-carboxamide |

TABLE 1-continued

| Cpd # | Structure | IUPAC Name |
|---|---|---|
| 624 | 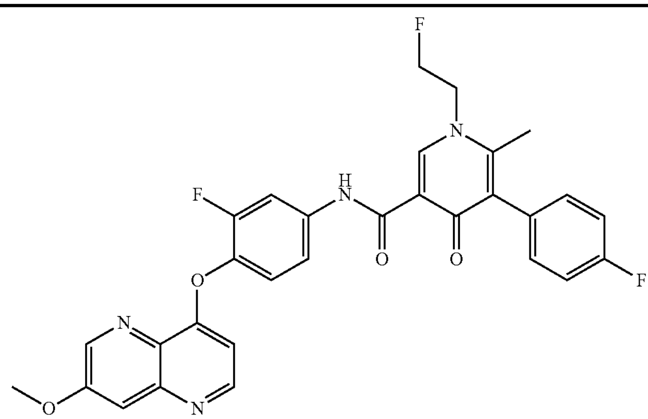 | 1-(2-fluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide |
| 625 | 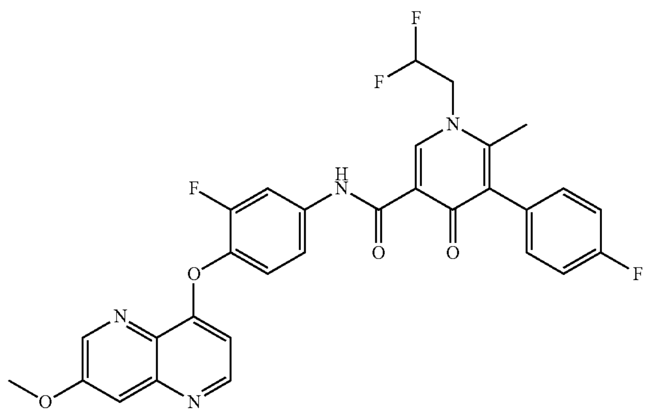 [SMILES: COc1cnc2c(Oc3ccc(NC(=O)c4cn(CC(F)F)c(C)c(-c5ccc(F)cc5)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide |
| 626 | 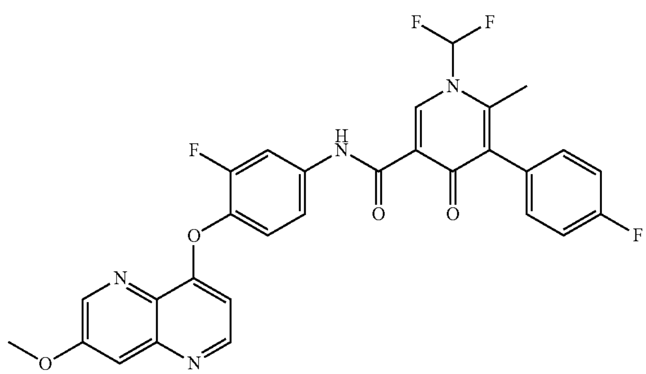 [SMILES: COc1cnc2c(Oc3ccc(NC(=O)c4cn(C(F)F)c(C)c(-c5ccc(F)cc5)c4=O)cc3F)ccnc2c1] | 1-(difluoromethyl)-N-[3-fluoro-4-[(7-methoxy-1,5-naphthyridin-4-yl)oxy]phenyl]-5-(4-fluorophenyl)-6-methyl-4-oxopyridine-3-carboxamide |
| 627 | 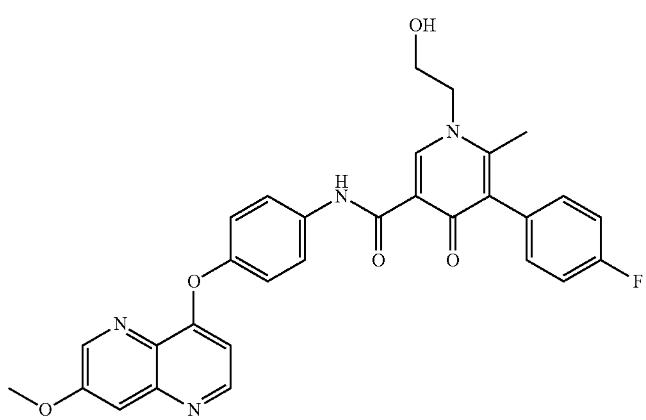 [SMILES: COc1cnc2c(Oc3ccc(NC(=O)c4cn(CCO)c(C)c(-c5ccc(F)cc5)c4=O)cc3)ccnc2c1] | 5-(4-fluorophenyl)-1-(2-hydroxyethyl)-N-[4-[(7-methoxy-1,5-naphthyridin-4-yl)oxy]phenyl]-6-methyl-4-oxopyridine-3-carboxamide |

TABLE 1-continued
| Cpd # | Structure | IUPAC Name |
|---|---|---|
| 628 | 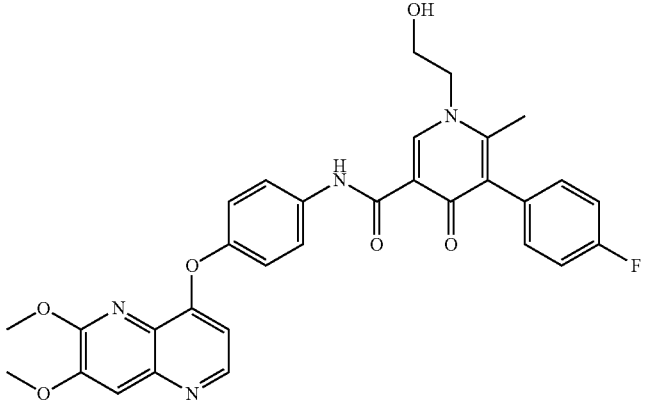 [SMILES: COc1cc2nccc(Oc3ccc(NC(=O)c4cn(CCO)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1-(2-hydroxyethyl)-6-methyl-4-oxopyridine-3-carboxamide |
| 629 | 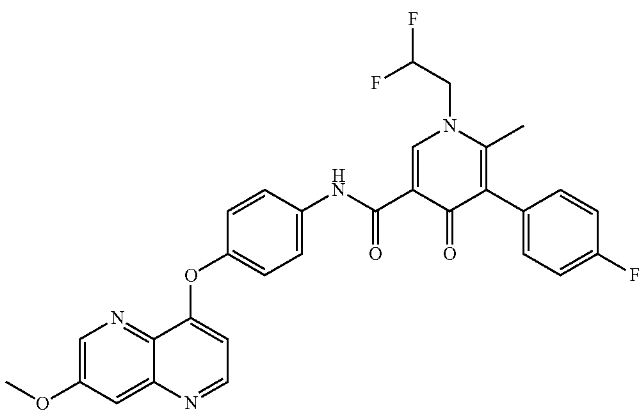 [SMILES: COc1cnc2c(Oc3ccc(NC(=O)c4cn(CC(F)F)c(C)c(-c5ccc(F)cc5)c4=O)cc3)ccnc2c1] | 1-(2,2-difluoroethyl)-5-(4-fluorophenyl)-N-[4-[(7-methoxy-1,5-naphthyridin-4-yl)oxy]phenyl]-6-methyl-4-oxopyridine-3-carboxamide |
| 630 | 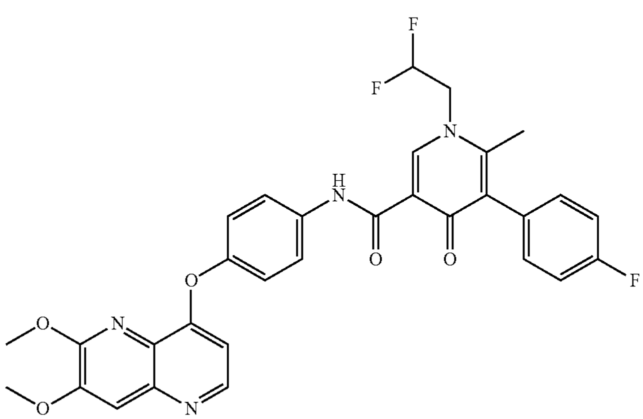 [SMILES: COc1cc2nccc(Oc3ccc(NC(=O)c4cn(CC(F)F)c(C)c(-c5ccc(F)cc5)c4=O)cc3)c2nc1OC] | 1-(2,2-difluoroethyl)-N-[4-[(6,7-dimethoxy-1,5-naphthyridin-4-yl)oxy]phenyl]-5-(4-fluorophenyl)-6-methyl-4-oxopyridine-3-carboxamide |

TABLE 1-continued

| Cpd # | Structure | IUPAC Name |
|---|---|---|
| 631 | 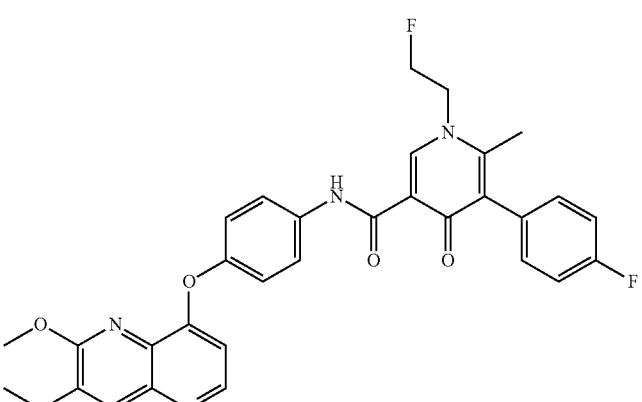 | N-[4-[(6,7-dimethoxy-1,5-naphthyridin-4-yl)oxy]phenyl]-1-(2-fluoroethyl)-5-(4-fluorophenyl)-6-methyl-4-oxopyridine-3-carboxamide |
| 632 | 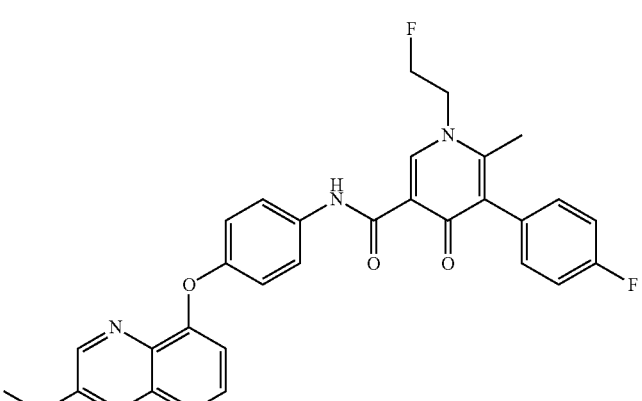 | 1-(2-fluoroethyl)-5-(4-fluorophenyl)-N-[4-[(7-methoxy-1,5-naphthyridin-4-yl)oxy]phenyl]-6-methyl-4-oxopyridine-3-carboxamide |
| 633 | 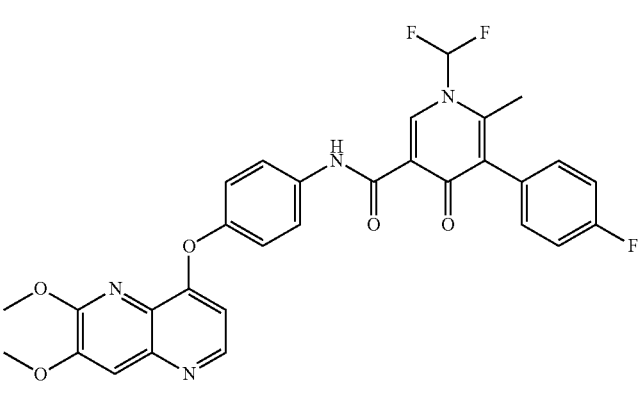 [SMILES: COc1cc2nccc(Oc3ccc(NC(=O)c4cn(C(F)F)c(C)c(-c5ccc(F)cc5)c4=O)cc3)c2nc1OC] | 1-(difluoromethyl)-N-[4-[(6,7-dimethoxy-1,5-naphthyridin-4-yl)oxy]phenyl]-5-(4-fluorophenyl)-6-methyl-4-oxopyridine-3-carboxamide |
| 634 | 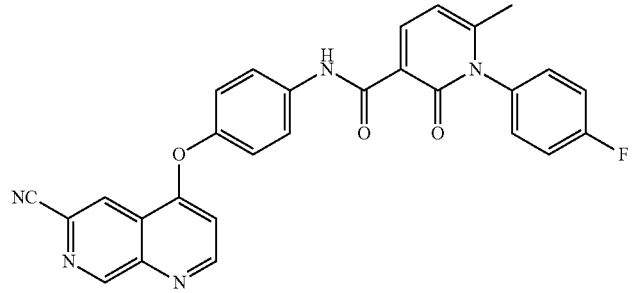 [SMILES: Cc1ccc(C(=O)Nc2ccc(Oc3ccnc4cnc(C#N)cc34)cc2)c(=O)n1-c1ccc(F)cc1] | N-[4-[(6-cyano-1,7-naphthyridin-4-yl)oxy]phenyl]-1-(4-fluorophenyl)-6-methyl-2-oxopyridine-3-carboxamide |

TABLE 1-continued

| Cpd # | Structure | IUPAC Name |
|---|---|---|
| 635 | 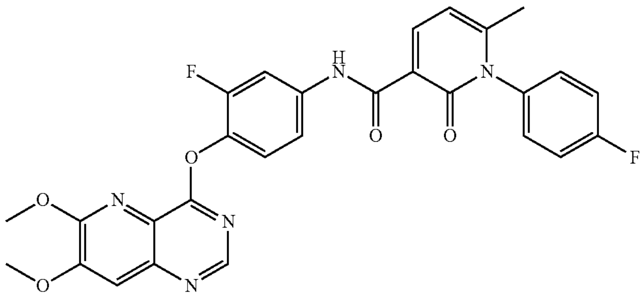 [SMILES: COc1cc2ncnc(Oc3ccc(NC(=O)c4ccc(C)n(-c5ccc(F)cc5)c4=O)cc3F)c2nc1OC] | N-[4-(6,7-dimethoxypyrido[3,2-d]pyrimidin-4-yl)oxy-3-fluorophenyl]-1-(4-fluorophenyl)-6-methyl-2-oxopyridine-3-carboxamide |
| 636 | 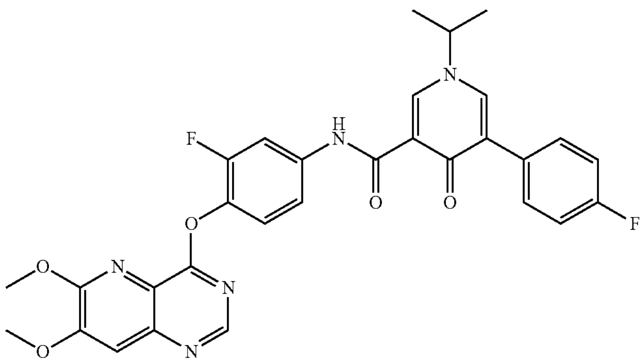 [SMILES: COc1cc2ncnc(Oc3ccc(NC(=O)c4cn(C(C)C)cc(-c5ccc(F)cc5)c4=O)cc3F)c2nc1OC] | N-[4-(6,7-dimethoxypyrido[3,2-d]pyrimidin-4-yl)oxy-3-fluorophenyl]-5-(4-fluorophenyl)-4-oxo-1-propan-2-ylpyridine-3-carboxamide |
| 637 | 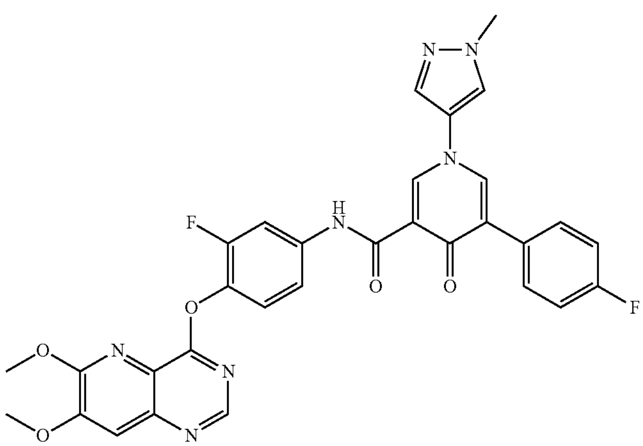 [SMILES: COc1cc2ncnc(Oc3ccc(NC(=O)c4cn(-c5cnn(C)c5)cc(-c5ccc(F)cc5)c4=O)cc3F)c2nc1OC] | N-[4-(6,7-dimethoxyprido[3,2-d]pyrimidin-4-yl)oxy-3-fluorophenyl]-5-(4-fluorophenyl)-1-(1-methylpyrazol-4-yl)-4-oxopyridine-3-carboxamide |
| 638 | 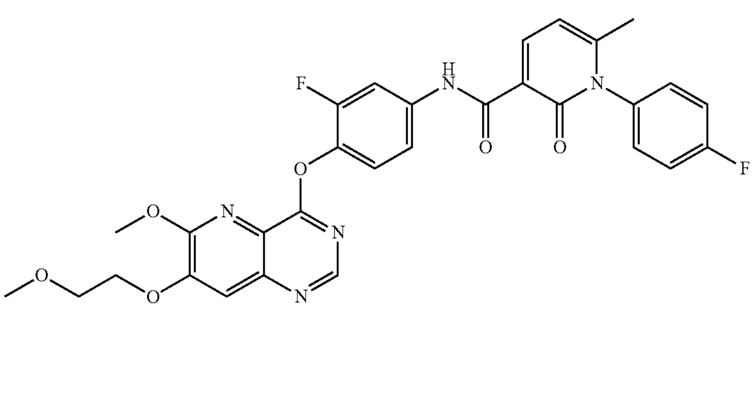 [SMILES: COCCOc1cc2ncnc(Oc3ccc(NC(=O)c4ccc(C)n(-c5ccc(F)cc5)c4=O)cc3F)c2nc1OC] | N-[3-fluoro-4-[6-methoxy-7-(2-methoxyethoxy)pyrido[3,2-d]pyrimidin-4-yl]oxyphenyl]-1-(4-fluorophenyl)-6-methyl-2-oxopyridine-3-carboxamide |

TABLE 1-continued

| Cpd # | Structure | IUPAC Name |
|---|---|---|
| 639 | 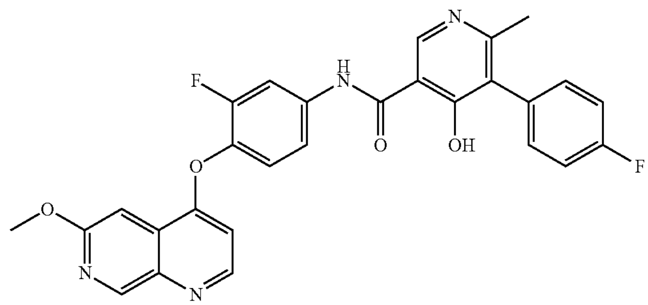 | N-[3-fluoro-4-[(6-methoxy-1,7-naphthyridin-4-yl)oxy]phenyl]-5-(4-fluorophenyl)-4-hydroxy-6-methylpyridine-3-carboxamide |
| 640 | 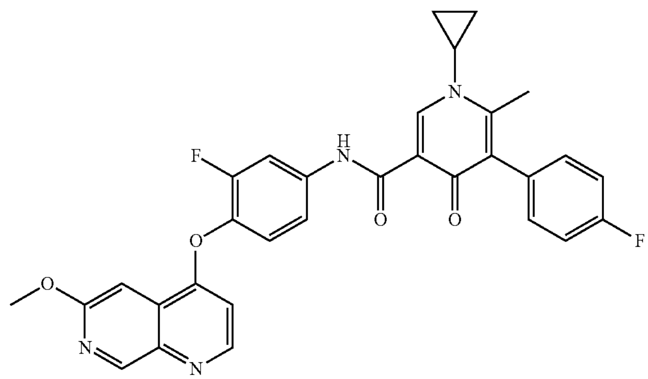 [SMILES: COc1cc2c(Oc3ccc(NC(=O)c4cn(C5CC5)c(C)c(-c5ccc(F)cc5)c4=O)cc3F)ccnc2cn1] | 1-cyclopropyl-N-[3-fluoro-4-[(6-methoxy-1,7-naphthyridin-4-yl)oxy]phenyl]-5-(4-fluorophenyl)-6-methyl-4-oxopyridine-3-carboxamide |
| 641 | 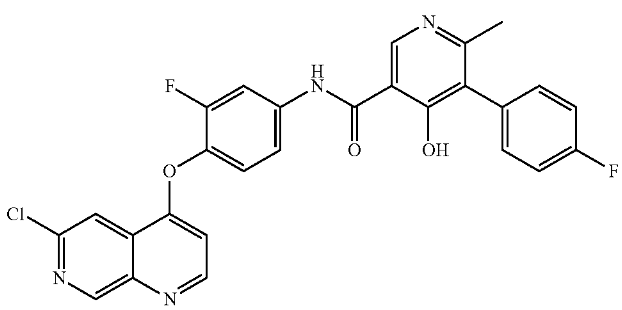 [SMILES: Cc1ncc(C(=O)Nc2ccc(Oc3ccnc4cnc(Cl)cc34)c(F)c2)c(O)c1-c1ccc(F)cc1] | N-[4-[(6-chloro-1,7-naphthyridin-4-yl)oxy]-3-fluorophenyl]-5-(4-fluorophenyl)-4-hydroxy-6-methylpyridine-3-carboxamide |
| 642 | 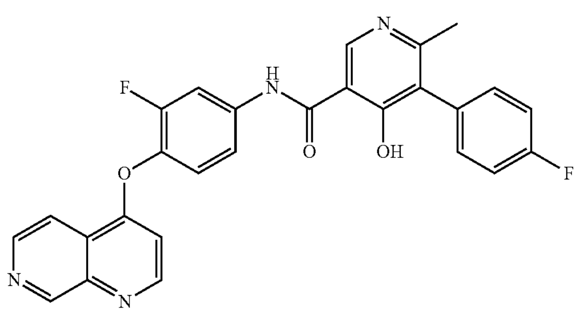 [SMILES: Cc1ncc(C(=O)Nc2ccc(Oc3ccnc4cnccc34)c(F)c2)c(O)c1-c1ccc(F)cc1] | N-[3-fluoro-4-(1,7-naphthyridin-4-yloxy)phenyl]-5-(4-fluorophenyl)-4-hydroxy-6-methylpyridine-3-carboxamide |
| 643 | 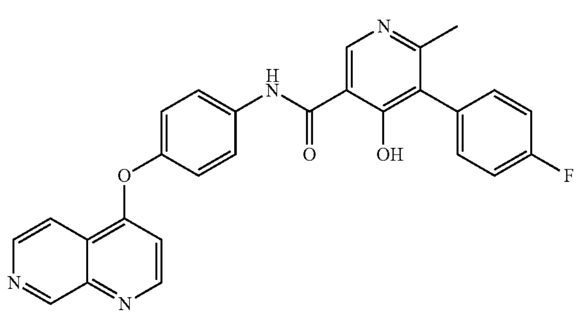 [SMILES: Cc1ncc(C(=O)Nc2ccc(Oc3ccnc4cnccc34)cc2)c(O)c1-c1ccc(F)cc1] | 5-(4-fluorophenyl)-4-hydroxy-6-methyl-N-[4-(1,7-naphthyridin-4-yloxy)phenyl]pyridine-3-carboxamide |

TABLE 1-continued

| Cpd # | Structure | IUPAC Name |
|---|---|---|
| 644 | 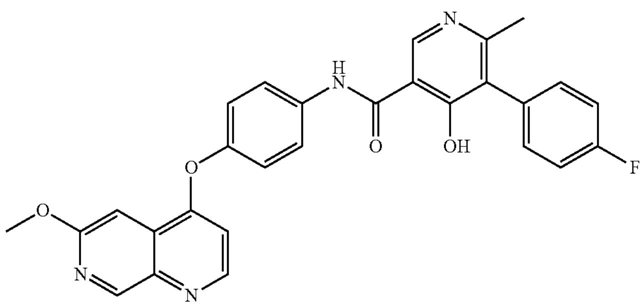 [SMILES: COc1cc2c(Oc3ccc(NC(=O)c4cnc(C)c(-c5ccc(F)cc5)c4O)cc3)ccnc2cn1] | 5-(4-fluorophenyl)-4-hydroxy-N-[4-[(6-methoxy-1,7-naphthyridin-4-yl)oxy]phenyl]-6-methylpyridine-3-carboxamide |
| 645 | 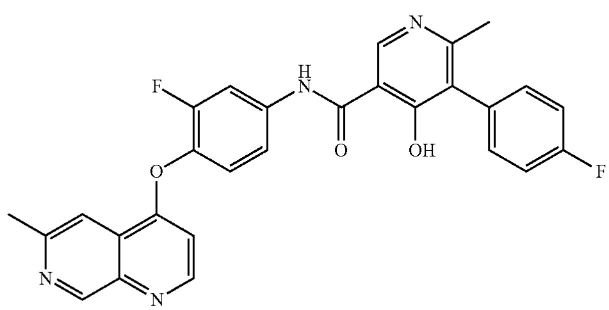 [SMILES: Cc1cc2c(Oc3ccc(NC(=O)c4cnc(C)c(-c5ccc(F)cc5)c4O)cc3F)ccnc2cn1] | N-[3-fluoro-4-[(6-methyl-1,7-naphthyridin-4-yl)oxy]phenyl]-5-(4-fluorophenyl)-4-hydroxy-6-methylpyridine-3-carboxamide |
| 646 | 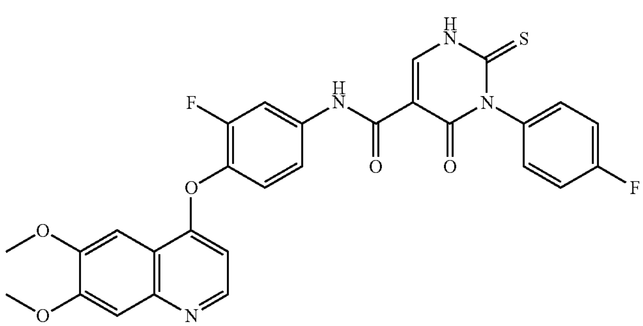 [SMILES: COc1cc2nccc(Oc3ccc(NC(=O)c4c[nH]c(=S)n(-c5ccc(F)cc5)c4=O)cc3F)c2cc1OC] | N-[4-(6,7-dimethoxyquinolin-4-yl)oxy-3-fluorophenyl]-3-(4-fluorophenyl)-4-oxo-2-sulfanylidene-1H-pyrimidine-5-carboxamide |
| 647 | 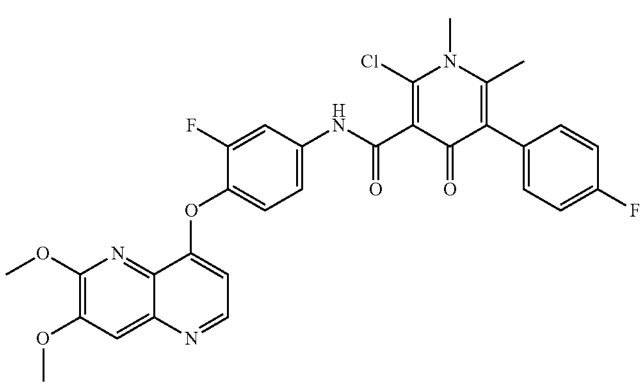 [SMILES: COc1cc2nccc(Oc3ccc(NC(=O)c4c(Cl)n(C)c(C)c(-c5ccc(F)cc5)c4=O)cc3F)c2nc1OC] | 2-chloro-N-[4-[(6,7-dimethoxy-1,5-naphthyridin-4-yl)oxy]-3-fluorophenyl]-5-(4-fluorophenyl)-1,6-dimethyl-4-oxopyridine-3-carboxamide |

TABLE 1-continued

| Cpd # | Structure | IUPAC Name |
|---|---|---|
| 648 | 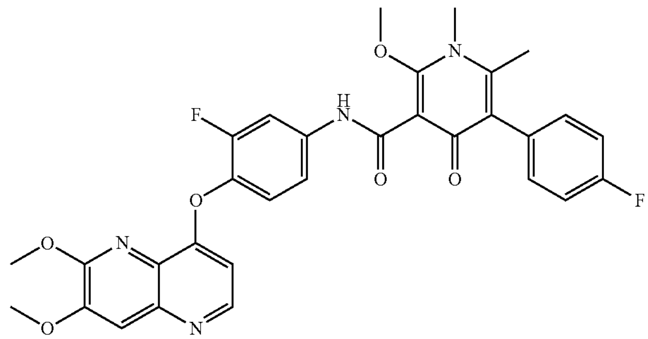 [SMILES: COc1cc2nccc(Oc3ccc(NC(=O)c4c(OC)n(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-2-methoxy-1,6-dimethyl-4-oxopyridine-3-carboxamide |
| 649 | 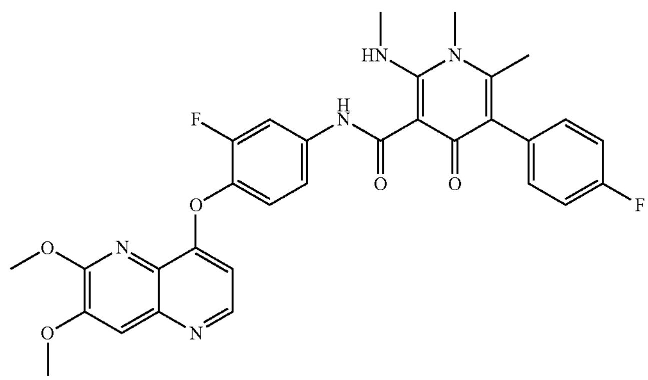 | N-[4-[(6,7-dimethoxy-1,5-naphthyridin-4-yl)oxy]-3-fluorophenyl]-5-(4-fluorophenyl)-1,6-dimethyl-2-(methylamino)-4-oxopyridine-3-carboxamide |
| 650 | 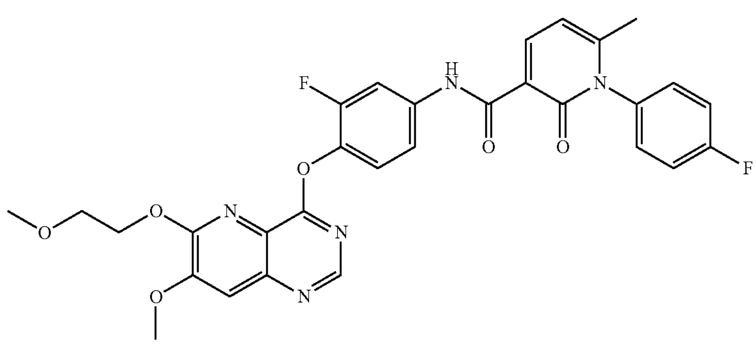 [SMILES: COCCOc1nc2c(Oc3ccc(NC(=O)c4ccc(C)n(-c5ccc(F)cc5)c4=O)cc3F)ncnc2cc1OC] | N-[3-fluoro-4-[7-methoxy-6-(2-methoxyethoxy)pyrido[3,2-d]pyrimidin-4-yl]oxyphenyl]-1-(4-fluorophenyl)-6-methyl-2-oxopyridine-3-carboxamide |
| 651 | 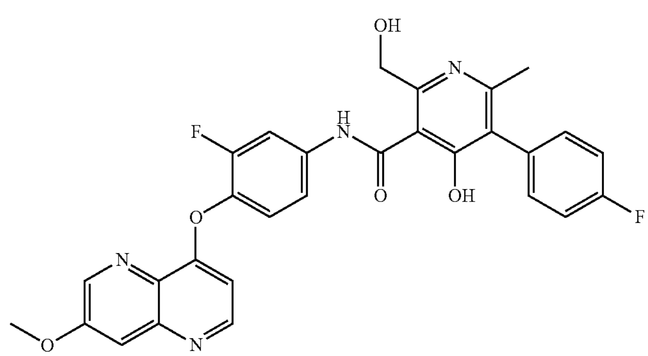 [SMILES: COc1cnc2c(Oc3ccc(NC(=O)c4c(CO)nc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2-(hydroxymethyl)-6-methylpyridine-3-carboxamide |

TABLE 1-continued

| Cpd # | Structure | IUPAC Name |
|---|---|---|
| 652 | 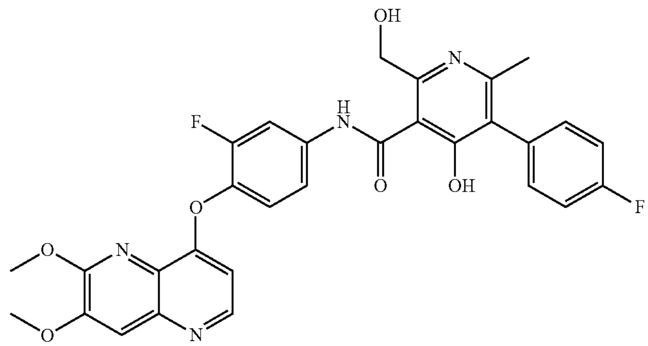 [SMILES: COc1cc2nccc(Oc3ccc(NC(=O)c4c(CO)nc(C)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-2-(hydroxymethyl)-6-methylpyridine-3-carboxamide |
| 653 | 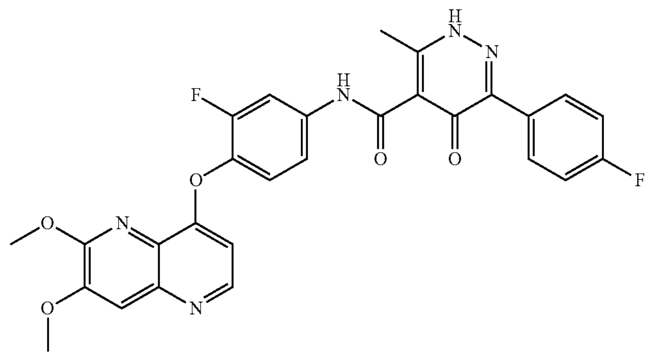 [SMILES: COc1cc2nccc(Oc3ccc(NC(=O)c4c(C)[nH]nc(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-6-methyl-4-oxo-1H-pyridazine-5-carboxamide |
| 654 | 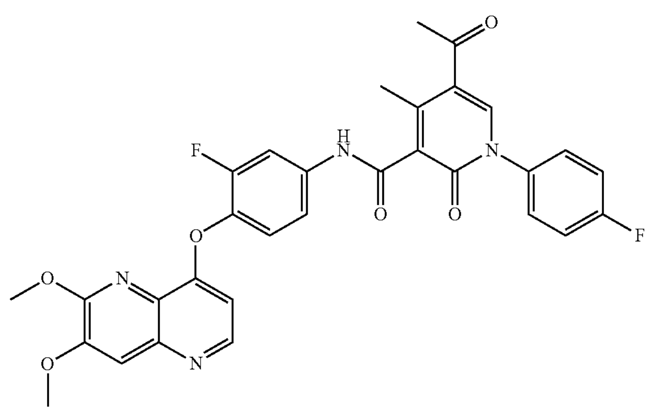 [SMILES: COc1cc2nccc(Oc3ccc(NC(=O)c4c(C)c(C(C)=O)cn(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4-methyl-2-oxopyridine-3-carboxamide |
| 655 | 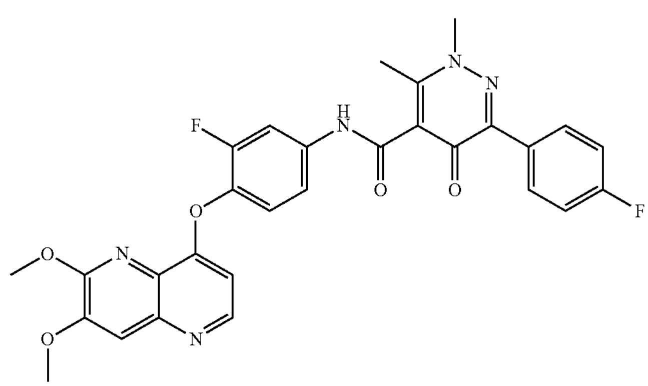 [SMILES: COc1cc2nccc(Oc3ccc(NC(=O)c4c(C)n(C)nc(-c5ccc(F)cc5)c4=O)cc3F)c2nc1OC] | N-[4-[(6,7-dimethoxy-1,5-naphthyridin-4-yl)oxy]-3-fluorophenyl]-6-(4-fluorophenyl)-2,3-dimethyl-5-oxopyridazine-4-carboxamide |

TABLE 1-continued

| Cpd # | Structure | IUPAC Name |
|---|---|---|
| 656 | 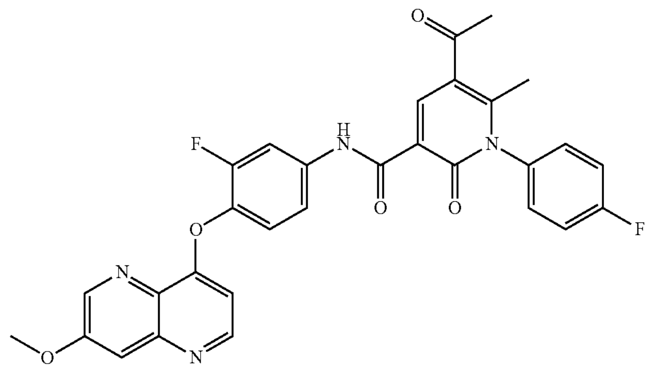 [SMILES: COc1cnc2c(Oc3ccc(NC(=O)c4cc(C(C)=O)c(C)n(-c5ccc(F)cc5)c4=O)cc3F)ccnc2c1] | 5-acetyl-N-[3-fluoro-4-[(7-methoxy-1,5-naphthyridin-4-yl)oxy]phenyl]-1-(4-fluorophenyl)-6-methyl-2-oxopyridine-3-carboxamide |
| 657 | 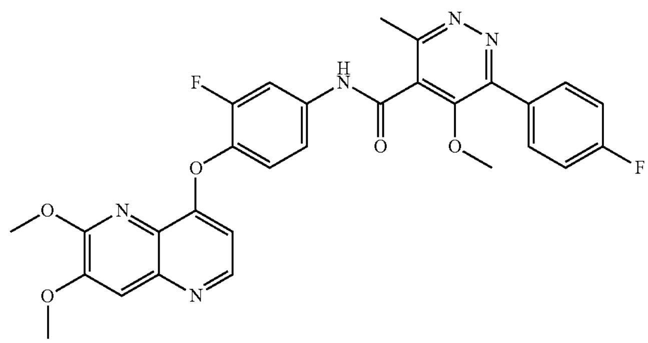 [SMILES: COc1cc2nccc(Oc3ccc(NC(=O)c4c(C)nnc(-c5ccc(F)cc5)c4OC)cc3F)c2nc1OC] | N-[4-[(6,7-dimethoxy-1,5-naphthyridin-4-yl)oxy]-3-fluorophenyl]-6-(4-fluorophenyl)-5-methoxy-3-methylpyridazine-4-carboxamide |
| 658 | 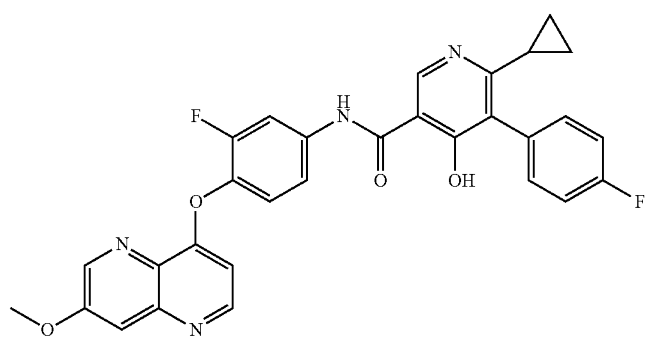 [SMILES: COc1cnc2c(Oc3ccc(NC(=O)c4cnc(C5CC5)c(-c5ccc(F)cc5)c4O)cc3F)ccnc2c1] | 6-cyclopropyl-N-[3-fluoro-4-[(7-methoxy-1,5-naphthyridin-4-yl)oxy]phenyl]-5-(4-fluorophenyl)-4-hydroxypyridine-3-carboxamide |
| 659 | 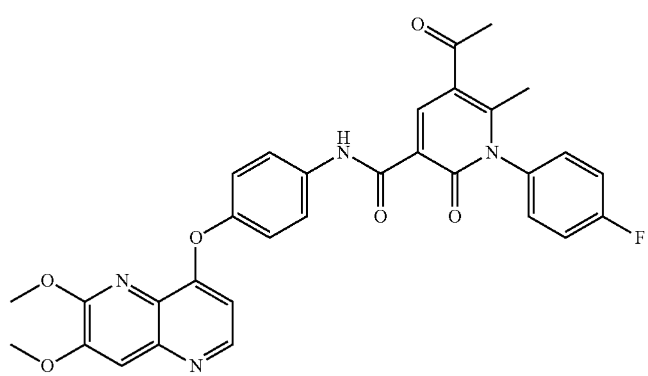 [SMILES: COc1cc2nccc(Oc3ccc(NC(=O)c4cc(C(C)=O)c(C)n(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-6-methyl-2-oxopyridine-3-carboxamide |

TABLE 1-continued

| Cpd # | Structure | IUPAC Name |
|---|---|---|
| 660 | 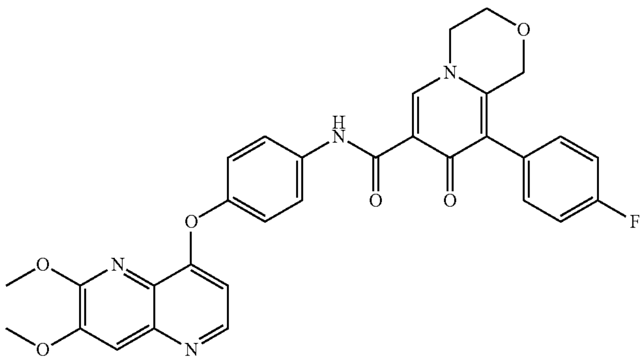 [SMILES: COc1cc2nccc(Oc3ccc(NC(=O)c4cn5c(c(-c6ccc(F)cc6)c4=O)COCC5)cc3)c2nc1OC] | N-[4-[(6,7-dimethoxy-1,5-naphthyridin-4-yl)oxy]phenyl]-9-(4-fluorophenyl)-8-oxo-3,4-dihydro-1H-pyrido[2,1-c][1,4]oxazine-7-carboxamide |
| 661 | 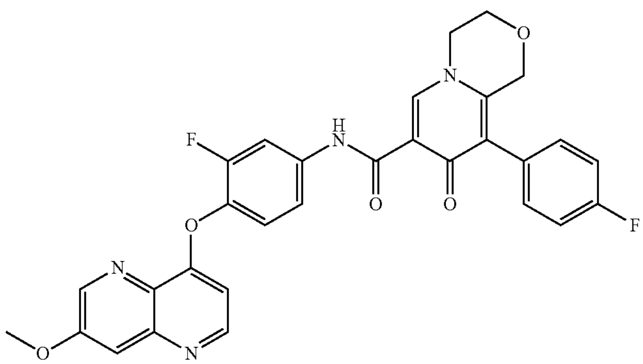 [SMILES: COc1cnc2c(Oc3ccc(NC(=O)c4cn5c(c(-c6ccc(F)cc6)c4=O)COCC5)cc3F)ccnc2c1] | N-[3-fluoro-4-[(7-methoxy-1,5-naphthyridin-4-yl)oxy]phenyl]-9-(4-fluorophenyl)-8-oxo-3,4-dihydro-1H-pyrido[2,1-c][1,4]oxazine-7-carboxamide |
| 662 | 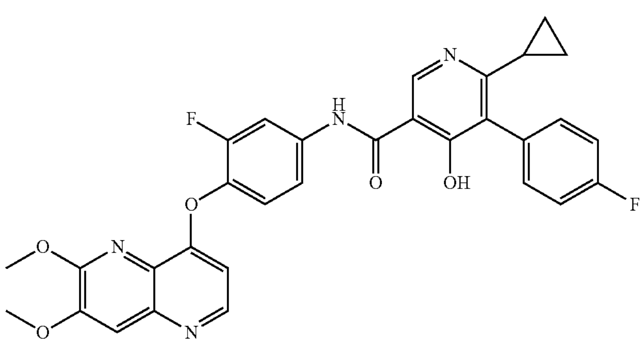 [SMILES: COc1cc2nccc(Oc3ccc(NC(=O)c4cnc(C5CC5)c(-c5ccc(F)cc5)c4O)cc3F)c2nc1OC] | 6-cyclopropyl-N-[4-[(6,7-dimethoxy-1,5-naphthyridin-4-yl)oxy]-3-fluorophenyl]-5-(4-fluorophenyl)-4-hydroxypyridine-3-carboxamide |
| 663 | 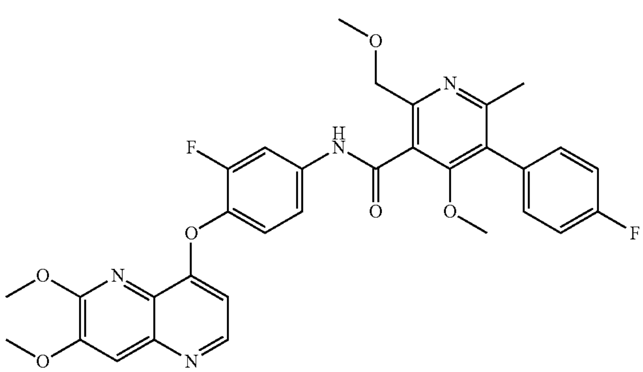 [SMILES: COCc1nc(C)c(-c2ccc(F)cc2)c(OC)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-methoxy-2-(methoxymethyl)-6-methylpyridine-3-carboxamide |

TABLE 1-continued

| Cpd # | Structure | IUPAC Name |
|---|---|---|
| 664 | 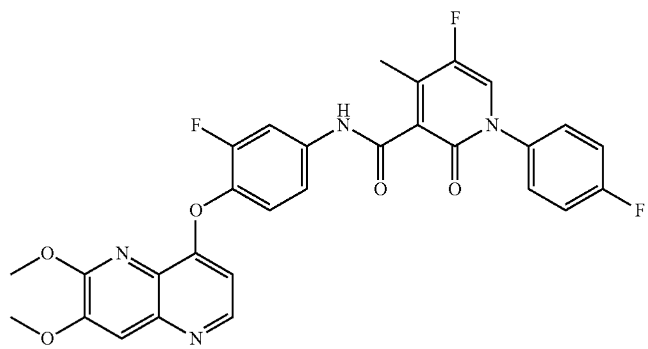 [SMILES: COc1cc2nccc(Oc3ccc(NC(=O)c4c(C)c(F)cn(-c5ccc(F)cc5)c4=O)cc3F)c2nc1OC] | N-[4-[(6,7-dimethoxy-1,5-naphthyridin-4-yl)oxy]-3-fluorophenyl]-5-fluoro-1-(4-fluorophenyl)-4-methyl-2-oxopyridine-3-carboxamide |
| 665 | 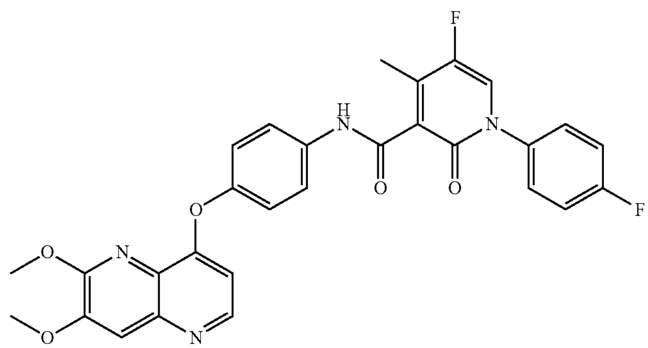 [SMILES: COc1cc2nccc(Oc3ccc(NC(=O)c4c(C)c(F)cn(-c5ccc(F)cc5)c4=O)cc3)c2nc1OC] | N-[4-[(6,7-dimethoxy-1,5-naphthyridin-4-yl)oxy]phenyl]-5-fluoro-1-(4-fluorophenyl)-4-methyl-2-oxopyridine-3-carboxamide |
| 666 | 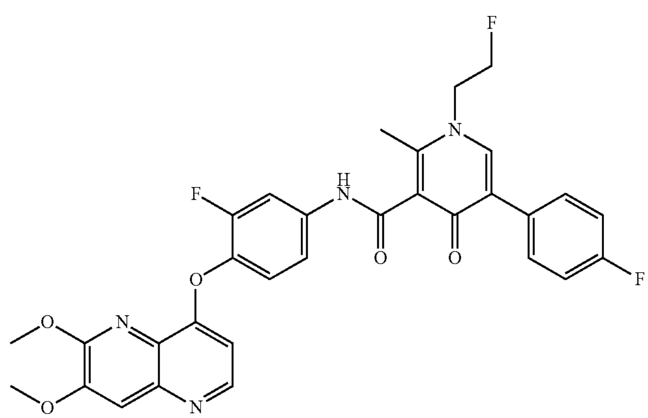 [SMILES: COc1cc2nccc(Oc3ccc(NC(=O)c4c(C)n(CCF)cc(-c5ccc(F)cc5)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluorophenyl)-2-methyl-4-oxopyridine-3-carboxamide |
| 667 | 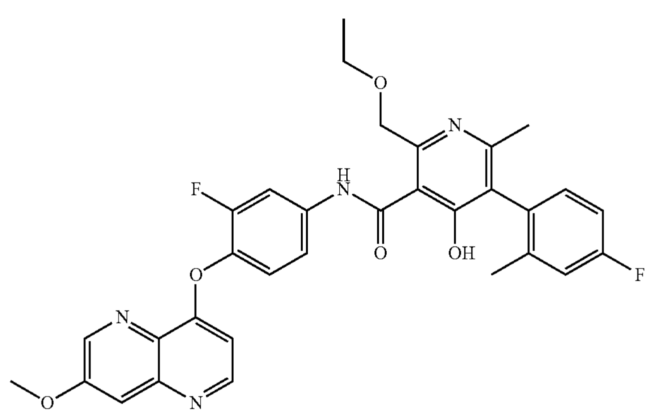 [SMILES: CCOCc1nc(C)c(-c2ccc(F)cc2C)c(O)c1C(=O)Nc1ccc(Oc2ccnc3cc(OC)cnc23)c(F)c1] | 2-(ethoxymethyl)-N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |

TABLE 1-continued

| Cpd # | Structure | IUPAC Name |
|---|---|---|
| 668 | 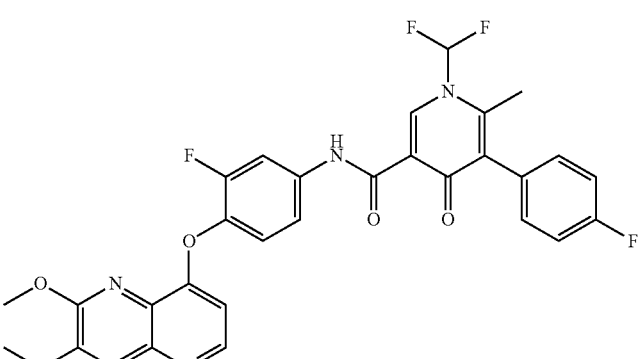 | 1-(difluoromethyl)-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 669 | 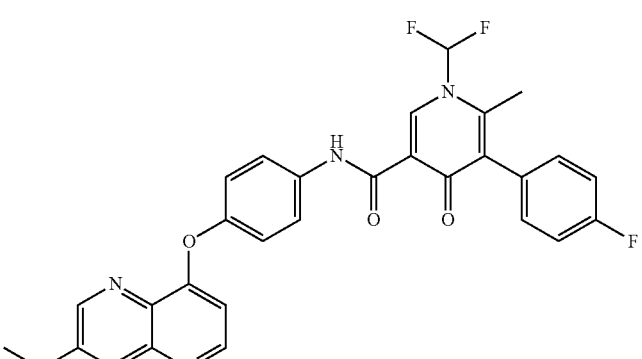 | 1-(difluoromethyl)-5-(4-fluorophenyl)-N-[4-[(7-methoxy-1,5-naphthyridin-4-yl)oxy]phenyl]-6-methyl-4-oxopyridine-3-carboxamide |
| 670 | 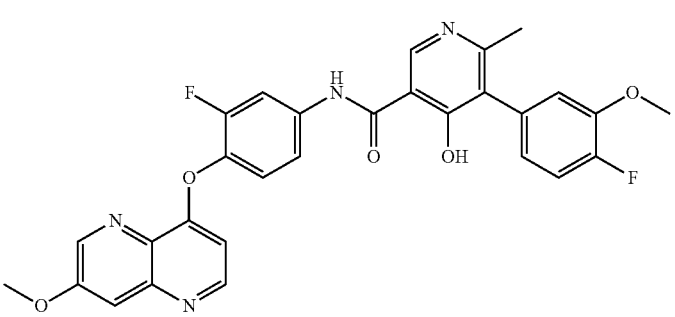 | N-[3-fluoro-4-[(7-methoxy-1,5-naphthyridin-4-yl)oxy]phenyl]-5-(4-fluoro-3-methoxyphenyl)-4-hydroxy-6-methylpyridine-3-carboxamide |
| 671 | 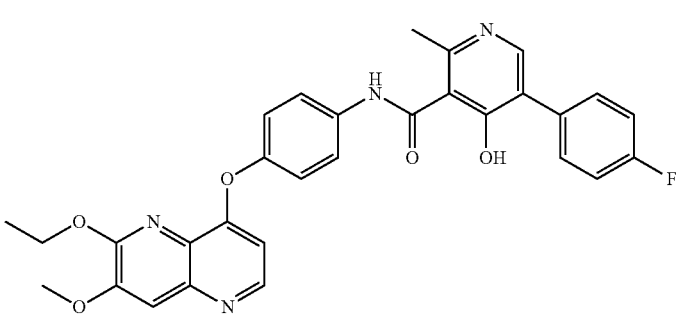 [SMILES: CCOc1nc2c(Oc3ccc(NC(=O)c4c(C)ncc(-c5ccc(F)cc5)c4O)cc3)ccnc2cc1OC] | N-[4-[(6-ethoxy-7-methoxy-1,5-naphthyridin-4-yl)oxy]phenyl]-5-(4-fluorophenyl)-4-hydroxy-2-methylpyridine-3-carboxamide |

| Cpd # | Structure | IUPAC Name |
|---|---|---|
| 672 | 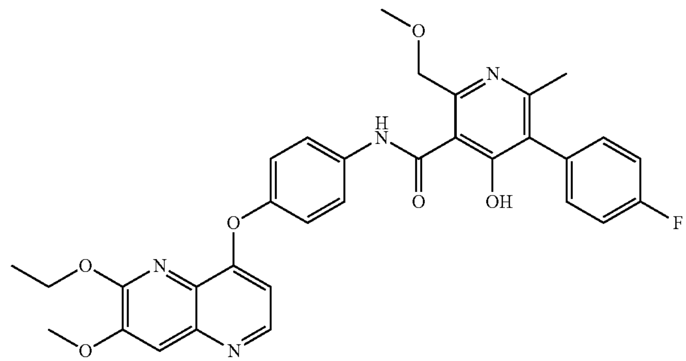 [SMILES: CCOc1nc2c(Oc3ccc(NC(=O)c4c(COC)nc(C)c(-c5ccc(F)cc5)c4O)cc3)ccnc2cc1OC] | N-[4-[(6-ethoxy-7-methoxy-1,5-naphthyridin-4-yl)oxy]phenyl]-5-(4-fluorophenyl)-4-hydroxy-2-(methoxymethyl)-6-methylpyridine-3-carboxamide |
| 673 | 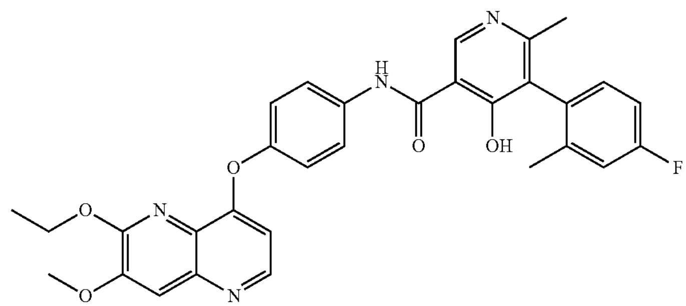 [SMILES: CCOc1nc2c(Oc3ccc(NC(=O)c4cnc(C)c(-c5ccc(F)cc5C)c4O)cc3)ccnc2cc1OC] | N-[4-[(6-ethoxy-7-methoxy-1,5-naphthyridin-4-yl)oxy]phenyl]-5-(4-fluoro-2-methylphenyl)-4-hydroxy-6-methylpyridine-3-carboxamide |
| 674 | 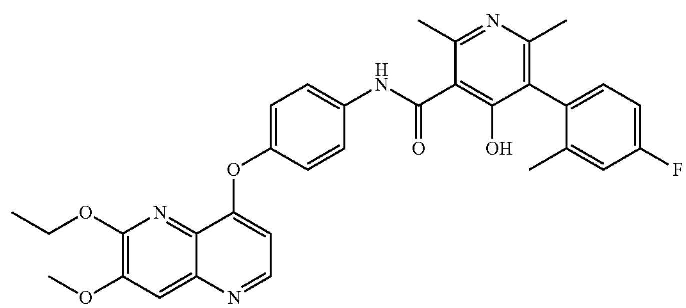 [SMILES: CCOc1nc2c(Oc3ccc(NC(=O)c4c(C)nc(C)c(-c5ccc(F)cc5C)c4O)cc3)ccnc2cc1OC] | N-[4-[(6-ethoxy-7-methoxy-1,5-naphthyridin-4-yl)oxy]phenyl]-5-(4-fluoro-2-methylphenyl)-4-hydroxy-2,6-dimethylpyridine-3-carboxamide |
| 675 | 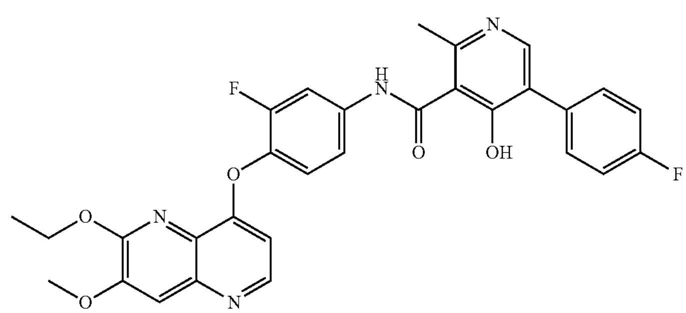 [SMILES: CCOc1nc2c(Oc3ccc(NC(=O)c4c(C)ncc(-c5ccc(F)cc5)c4O)cc3F)ccnc2cc1OC] | N-[4-[(6-ethoxy-7-methoxy-1,5-naphthyridin-4-yl)oxy]-3-fluorophenyl]-5-(4-fluorophenyl)-4-hydroxy-2-methylpyridine-3-carboxamide |

TABLE 1-continued

| Cpd # | Structure | IUPAC Name |
|---|---|---|
| 676 | 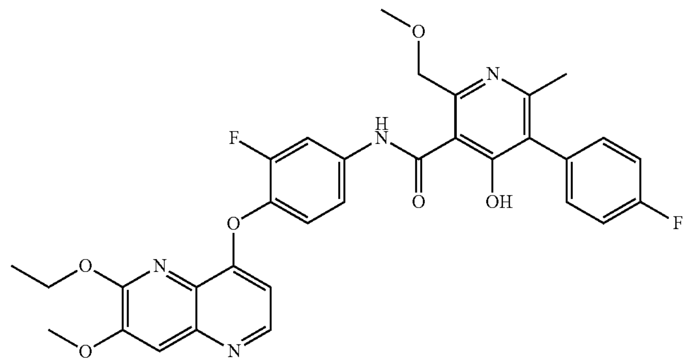 [SMILES: CCOc1nc2c(Oc3ccc(NC(=O)c4c(COC)nc(C)c(-c5ccc(F)cc5)c4O)cc3F)ccnc2cc1OC] | N-[4-[(6-ethoxy-7-methoxy-1,5-naphthyridin-4-yl)oxy]-3-fluorophenyl]-5-(4-fluorophenyl)-4-hydroxy-2-(methoxymethyl)-6-methylpyridine-3-carboxamide |
| 677 | 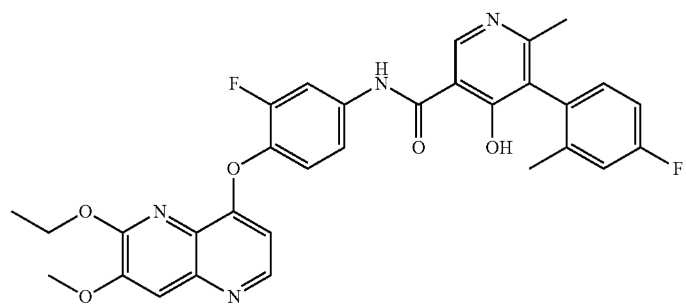 [SMILES: CCOc1nc2c(Oc3ccc(NC(=O)c4cnc(C)c(-c5ccc(F)cc5C)c4O)cc3F)ccnc2cc1OC] | N-[4-[(6-ethoxy-7-methoxy-1,5-naphthyridin-4-yl)oxy]-3-fluorophenyl]-5-(4-fluoro-2-methylphenyl)-4-hydroxy-6-methylpyridine-3-carboxamide |
| 678 | 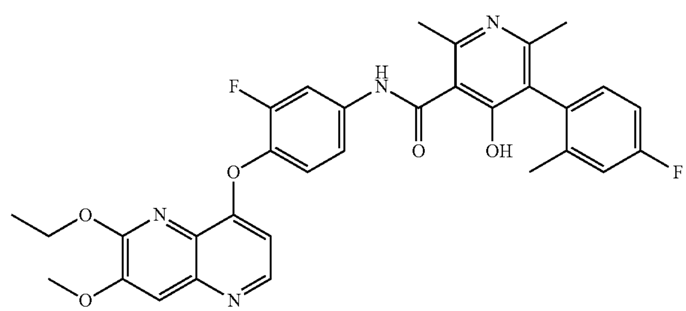 [SMILES: CCOc1nc2c(Oc3ccc(NC(=O)c4c(C)nc(C)c(-c5ccc(F)cc5C)c4O)cc3F)ccnc2cc1OC] | N-[4-[(6-ethoxy-7-methoxy-1,5-naphthyridin-4-yl)oxy]-3-fluorophenyl]-5-(4-fluoro-2-methylphenyl)-4-hydroxy-2,6-dimethylpyridine-3-carboxamide |
| 679 | 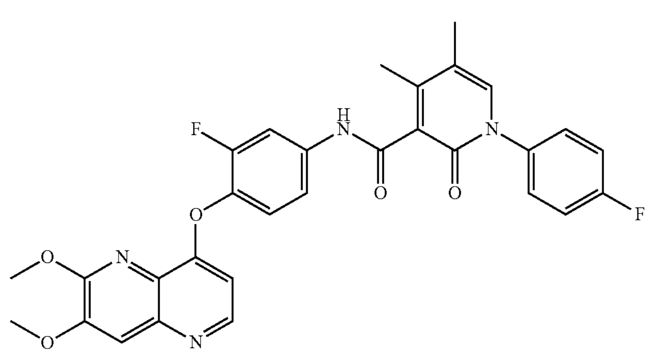 [SMILES: COc1cc2nccc(Oc3ccc(NC(=O)c4c(C)c(C)cn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4,5-dimethyl-2-oxopyridine-3-carboxamide |

| Cpd # | Structure | IUPAC Name |
|---|---|---|
| 680 | 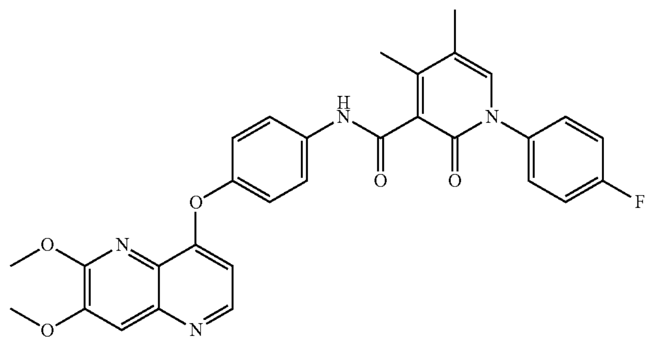 [SMILES: COc1cc2nccc(Oc3ccc(NC(=O)c4c(C)c(C)cn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-4,5-dimethyl-2-oxopyridine-3-carboxamide |
| 681 | 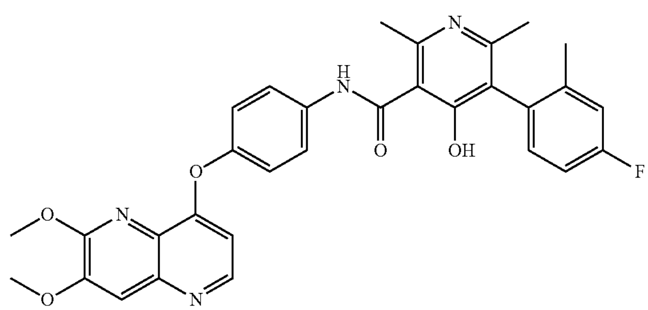 [SMILES: COc1cc2nccc(Oc3ccc(NC(=O)c4c(C)nc(C)c(-c5ccc(F)cc5C)c4O)cc3)c2nc1OC] | N-[4-[(6,7-dimethoxy-1,5-naphthyridin-4-yl)oxy]phenyl]-5-(4-fluoro-2-methylphenyl)-4-hydroxy-2,6-dimethylpyridine-3-carboxamide |
| 682 | 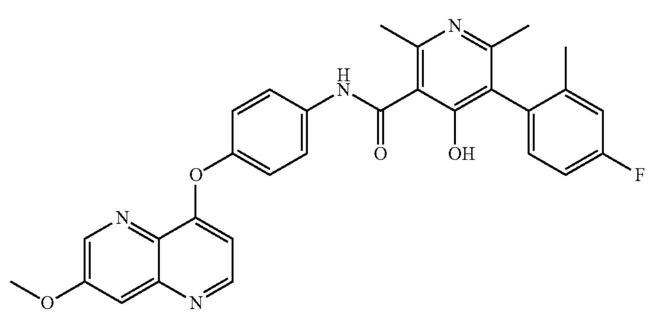 [SMILES: COc1cnc2c(Oc3ccc(NC(=O)c4c(C)nc(C)c(-c5ccc(F)cc5C)c4O)cc3)ccnc2c1] | 5-(4-fluoro-2-methylphenyl)-4-hydroxy-N-[4-[(7-methoxy-1,5-naphthyridin-4-yl)oxy]phenyl]-2,6-dimethylpyridine-3-carboxamide |
| 683 | 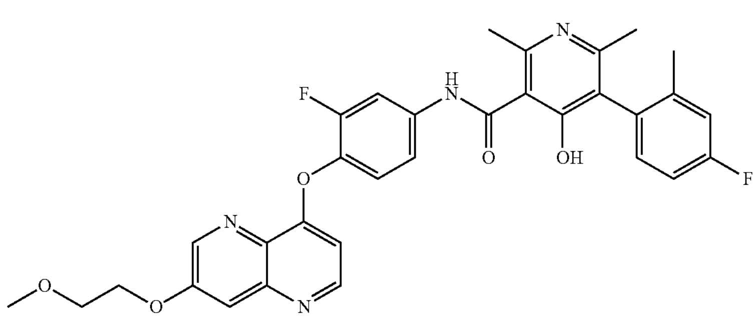 [SMILES: COCCOc1cnc2c(Oc3ccc(NC(=O)c4c(C)nc(C)c(-c5ccc(F)cc5C)c4O)cc3F)ccnc2c1] | N-[3-fluoro-4-[[7-(2-methoxyethoxy)-1,5-naphthyridin-4-yl]oxy]phenyl]-5-(4-fluoro-2-methylphenyl)-4-hydroxy-2,6-dimethylpyridine-3-carboxamide |

TABLE 1-continued

| Cpd # | Structure | IUPAC Name |
|---|---|---|
| 684 | 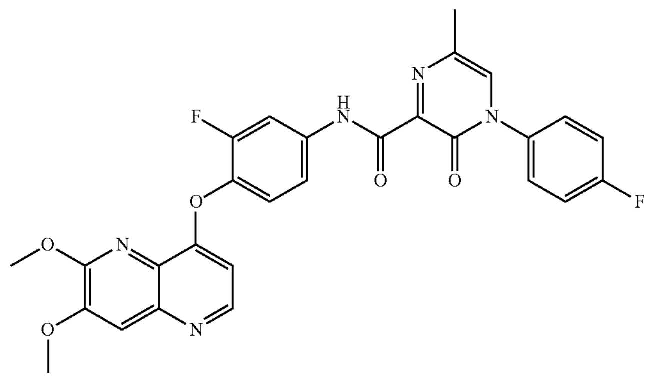 [SMILES: COc1cc2nccc(Oc3ccc(NC(=O)c4nc(C)cn(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-6-methyl-3-oxopyrazine-2-carboxamide |
| 685 | 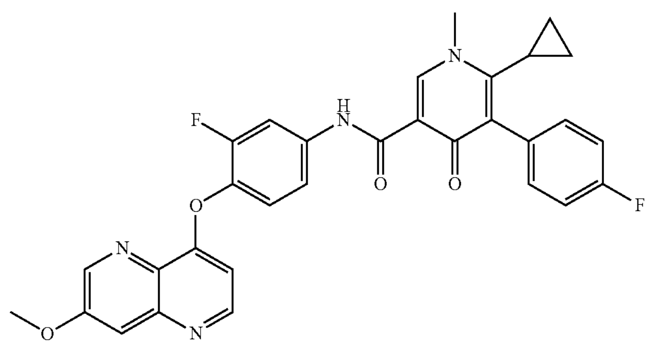 [SMILES: COc1cnc2c(Oc3ccc(NC(=O)c4cn(C)c(C5CC5)c(-c5ccc(F)cc5)c4=O)cc3F)ccnc2c1] | 6-cyclopropyl-N-[3-fluoro-4-[(7-methoxy-1,5-naphthyridin-4-yl)oxy]phenyl]-5-(4-fluorophenyl)-1-methyl-4-oxopyridine-3-carboxamide |
| 686 | 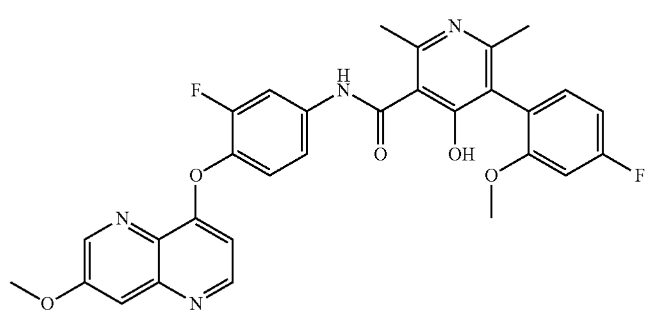 [SMILES: COc1cnc2c(Oc3ccc(NC(=O)c4c(C)nc(C)c(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-2,6-dimethylpyridine-3-carboxamide |
| 687 | 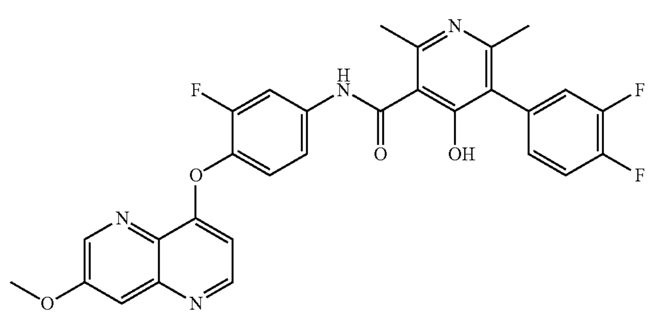 [SMILES: COc1cnc2c(Oc3ccc(NC(=O)c4c(C)nc(C)c(-c5ccc(F)c(F)c5)c4O)cc3F)ccnc2c1] | 5-(3,4-difluorophenyl)-N-[3-fluoro-4-[(7-methoxy-1,5-naphthyridin-4-yl)oxy]phenyl]-4-hydroxy-2,6-dimethylpyridine-3-carboxamide |

TABLE 1-continued

| Cpd # | Structure | IUPAC Name |
|---|---|---|
| 688 | 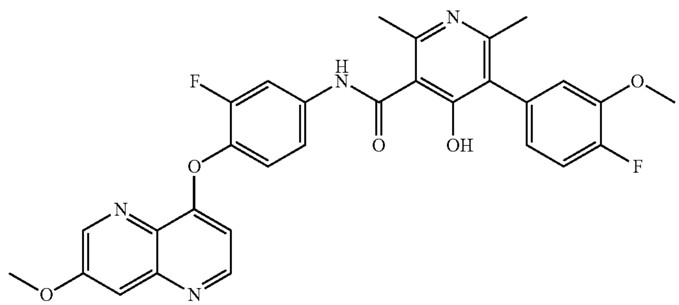 | N-[3-fluoro-4-[(7-methoxy-1,5-naphthyridin-4-yl)oxy]phenyl]-5-(4-fluoro-3-methoxyphenyl)-4-hydroxy-2,6-dimethylpyridine-3-carboxamide |
| 689 | 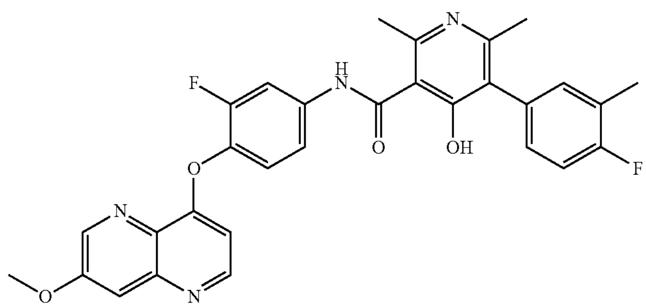 | N-[3-fluoro-4-[(7-methoxy-1,5-naphthyridin-4-yl)oxy]phenyl]-5-(4-fluoro-3-methylphenyl)-4-hydroxy-2,6-dimethylpyridine-3-carboxamide |
| 690 | 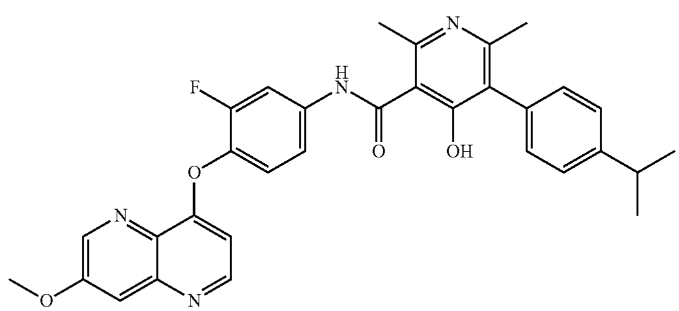 [SMILES: COc1cnc2c(Oc3ccc(NC(=O)c4c(C)nc(C)c(-c5ccc(C(C)C)cc5)c4O)cc3F)ccnc2c1] | N-[3-fluoro-4-[(7-methoxy-1,5-naphthyridin-4-yl)oxy]phenyl]-4-hydroxy-2,6-dimethyl-5-(4-propan-2-ylphenyl)pyridine-3-carboxamide |
| 691 | 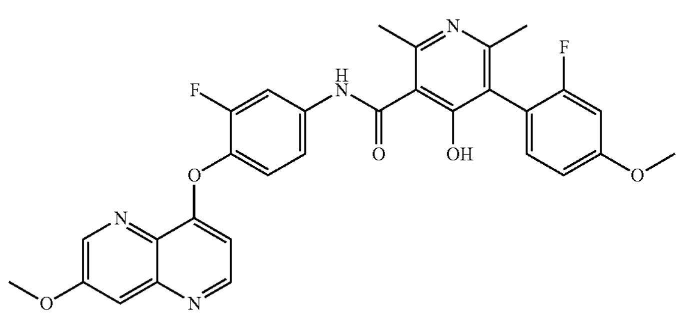 | N-[3-fluoro-4-[(7-methoxy-1,5-naphthyridin-4-yl)oxy]phenyl]-5-(2-fluoro-4-methoxyphenyl)-4-hydroxy-2,6-dimethylpyridine-3-carboxamide |
| 692 | 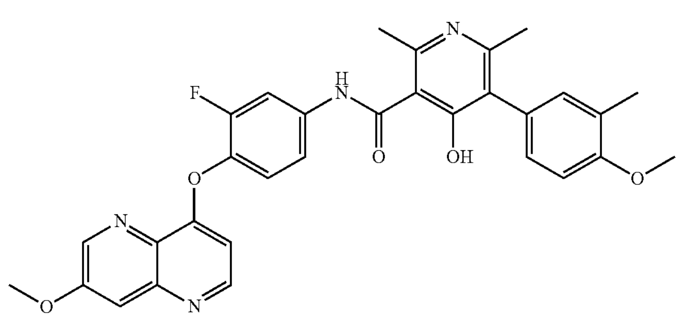 | N-[3-fluoro-4-[(7-methoxy-1,5-naphthyridin-4-yl)oxy]phenyl]-4-hydroxy-5-(4-methoxy-3-methylphenyl)-2,6-dimethylpyridine-3-carboxamide |

TABLE 1-continued

| Cpd # | Structure | IUPAC Name |
|---|---|---|
| 693 | 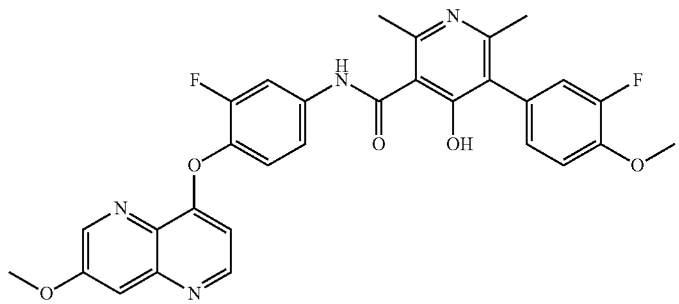 | N-[3-fluoro-4-[(7-methoxy-1,5-naphthyridin-4-yl)oxy]phenyl]-5-(3-fluoro-4-methoxyphenyl)-4-hydroxy-2,6-dimethylpyridine-3-carboxamide |
| 694 | 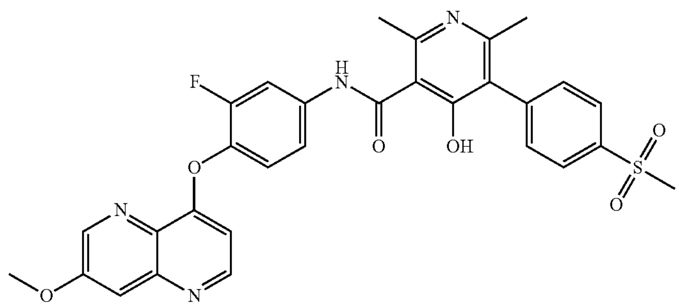 | N-[3-fluoro-4-[(7-methoxy-1,5-naphthyridin-4-yl)oxy]phenyl]-4-hydroxy-2,6-dimethyl-5-(4-methylsulfonylphenyl)pyridine-3-carboxamide |
| 695 | 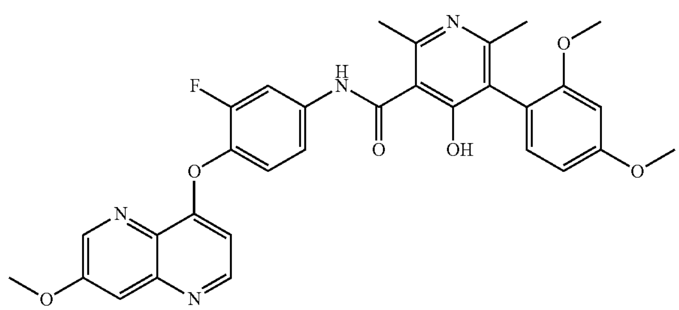 | 5-(2,4-dimethoxyphenyl)-N-[3-fluoro-4-[(7-methoxy-1,5-naphthyridin-4-yl)oxy]phenyl]-4-hydroxy-2,6-dimethylpyridine-3-carboxamide |
| 696 | 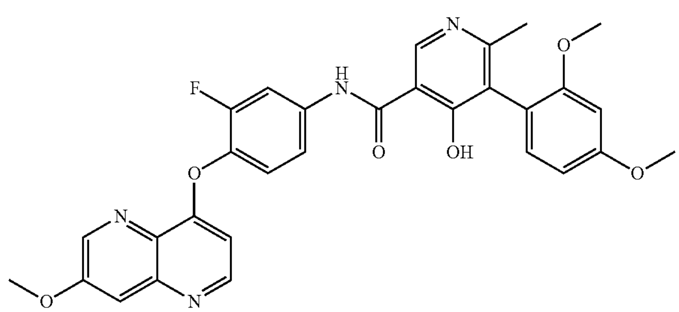 | 5-(2,4-dimethoxyphenyl)-N-[3-fluoro-4-[(7-methoxy-1,5-naphthyridin-4-yl)oxy]phenyl]-4-hydroxy-6-methylpyridine-3-carboxamide |
| 697 | 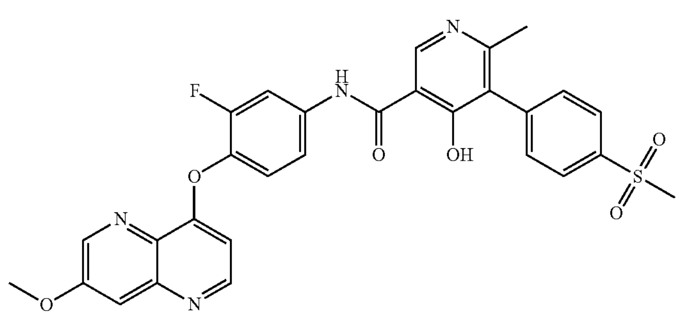 | N-[3-fluoro-4-[(7-methoxy-1,5-naphthyridin-4-yl)oxy]phenyl]-4-hydroxy-6-methyl-5-(4-methylsulfonylphenyl)pyridine-3-carboxamide |

TABLE 1-continued

| Cpd # | Structure | IUPAC Name |
|---|---|---|
| 698 | 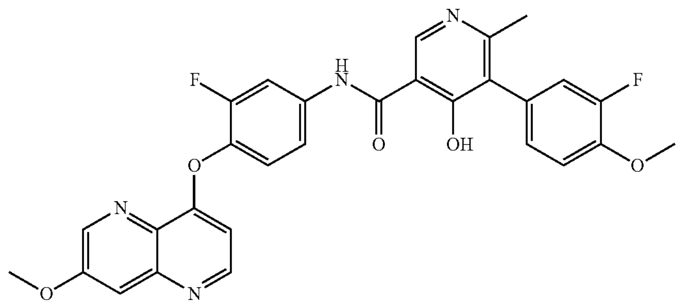 | N-[3-fluoro-4-[(7-methoxy-1,5-naphthyridin-4-yl)oxy]phenyl]-5-(3-fluoro-4-methoxyphenyl)-4-hydroxy-6-methylpyridine-3-carboxamide |
| 699 | 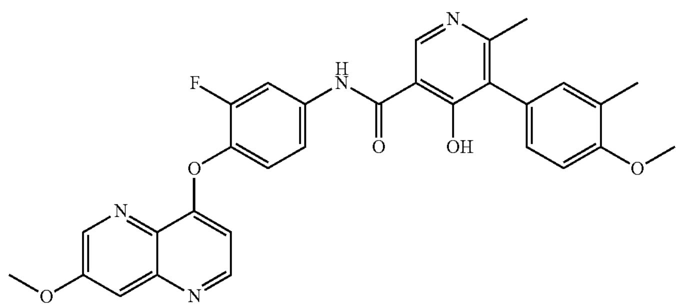 | N-[3-fluoro-4-[(7-methoxy-1,5-naphthyridin-4-yl)oxy]phenyl]-4-hydroxy-5-(4-methoxy-3-methylphenyl)-6-methylpyridine-3-carboxamide |
| 700 | 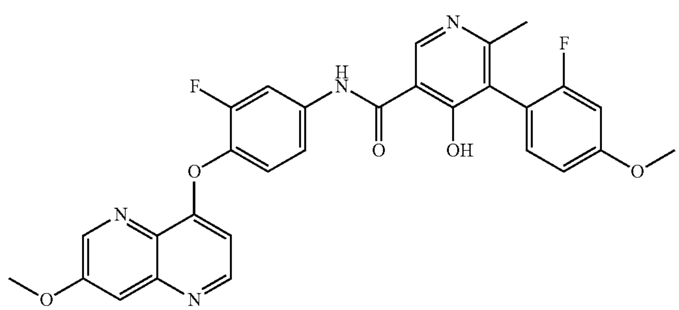 | N-[3-fluoro-4-[(7-methoxy-1,5-naphthyridin-4-yl)oxy]phenyl]-5-(2-fluoro-4-methoxyphenyl)-4-hydroxy-6-methylpyridine-3-carboxamide |
| 701 | 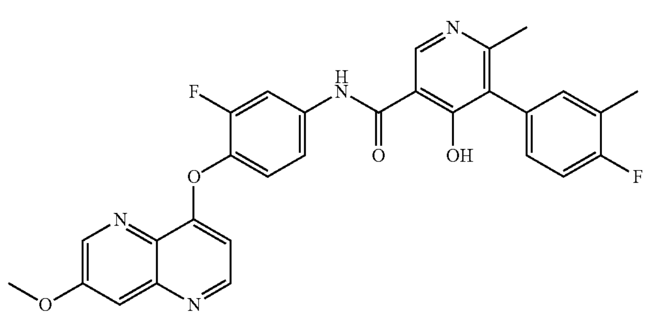 | N-[3-fluoro-4-[(7-methoxy-1,5-naphthyridin-4-yl)oxy]phenyl]-5-(4-fluoro-3-methylphenyl)-4-hydroxy-6-methylpyridine-3-carboxamide |

TABLE 1-continued

| Cpd # | Structure | IUPAC Name |
|---|---|---|
| 702 | 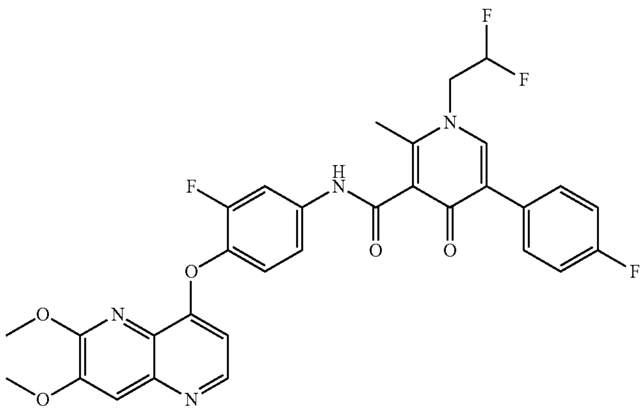 [SMILES: COc1cc2nccc(Oc3ccc(NC(=O)c4c(C)n(CC(F)F)cc(-c5ccc(F)cc5)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluorophenyl)-2-methyl-4-oxopyridine-3-carboxamide |
| 703 | 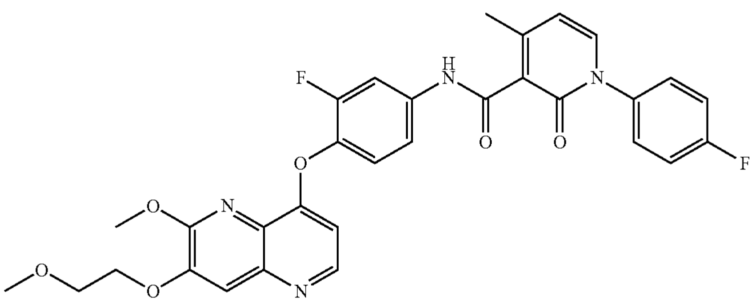 [SMILES: COCCOc1cc2nccc(Oc3ccc(NC(=O)c4c(C)ccn(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-1-(4-fluorophenyl)-4-methyl-2-oxopyridine-3-carboxamide |
| 704 | 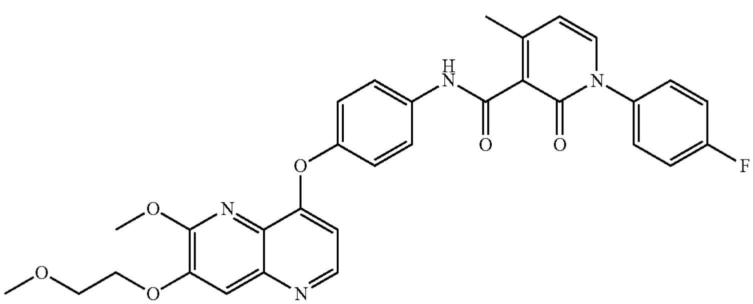 [SMILES: COCCOc1cc2nccc(Oc3ccc(NC(=O)c4c(C)ccn(-c5ccc(F)cc5)c4=O)cc3)c2nc1OC] | 1-(4-fluorophenyl)-N-[4-[[6-methoxy-7-(2-methoxyethoxy)-1,5-naphthyridin-4-yl]oxy]phenyl]-4-methyl-2-oxopyridine-3-carboxamide |
| 705 | 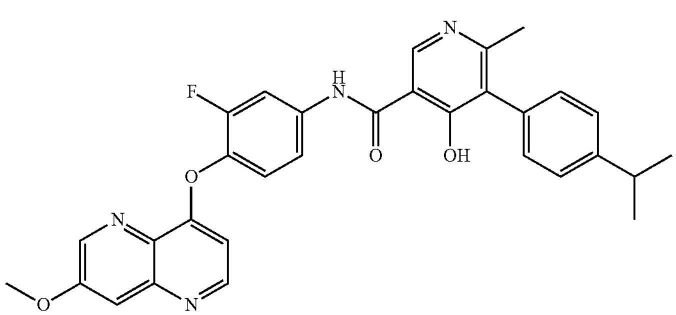 [SMILES: COc1cnc2c(Oc3ccc(NC(=O)c4cnc(C)c(-c5ccc(C(C)C)cc5)c4O)cc3F)ccnc2c1] | N-[3-fluoro-4-[(7-methoxy-1,5-naphthyridin-4-yl)oxy]phenyl]-4-hydroxy-6-methyl-5-(4-propan-2-ylphenyl)pyridine-3-carboxamide |

| Cpd # | Structure | IUPAC Name |
|---|---|---|
| 706 | 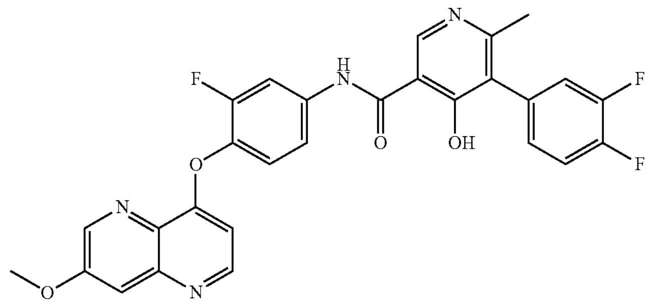 | 5-(3,4-difluorophenyl)-N-[3-fluoro-4-[(7-methoxy-1,5-naphthyridin-4-yl)oxy]phenyl]-4-hydroxy-6-methylpyridine-3-carboxamide |
| 707 | 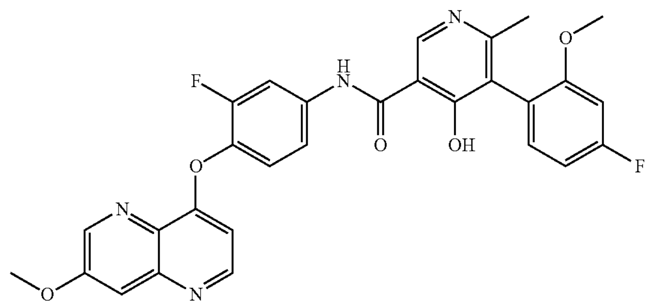 [SMILES: COc1cnc2c(Oc3ccc(NC(=O)c4cnc(C)c(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-6-methylpyridine-3-carboxamide |
| 708 | 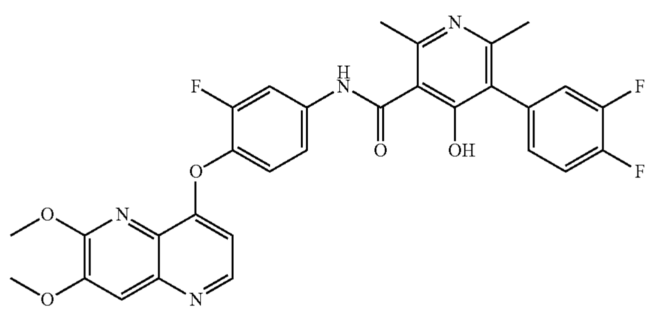 | 5-(3,4-difluorophenyl)-N-[4-[(6,7-dimethoxy-1,5-naphthyridin-4-yl)oxy]-3-fluorophenyl]-4-hydroxy-2,6-dimethylpyridine-3-carboxamide |
| 709 | 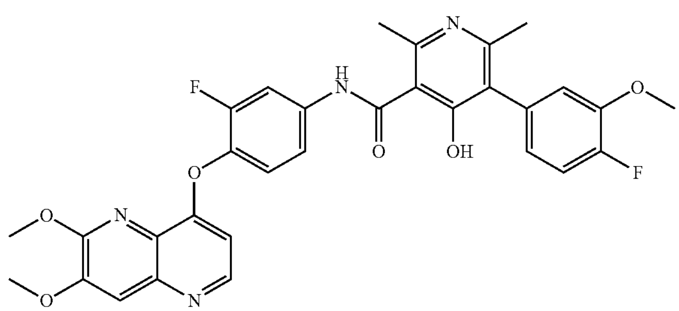 | N-[4-[(6,7-dimethoxy-1,5-naphthyridin-4-yl)oxy]-3-fluorophenyl]-5-(4-fluoro-3-methoxyphenyl)-4-hydroxy-2,6-dimethylpyridine-3-carboxamide |
| 710 | 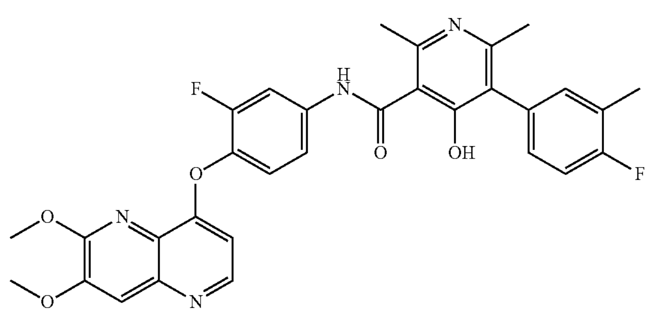 | N-[4-[(6,7-dimethoxy-1,5-naphthyridin-4-yl)oxy]-3-fluorophenyl]-5-(4-fluoro-3-methylphenyl)-4-hydroxy-2,6-dimethylpyridine-3-carboxamide |

TABLE 1-continued

| Cpd # | Structure | IUPAC Name |
|---|---|---|
| 711 | 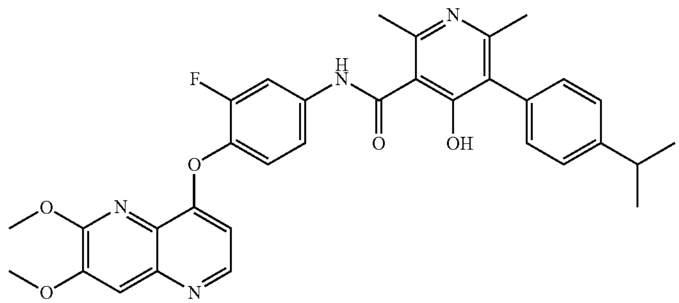 [SMILES: COc1cc2nccc(Oc3ccc(NC(=O)c4c(C)nc(C)c(-c5ccc(C(C)C)cc5)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(4-propan-2-ylphenyl)pyridine-3-carboxamide |
| 712 | 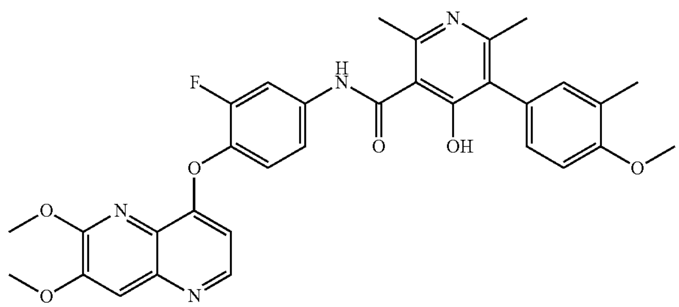 | N-[4-[(6,7-dimethoxy-1,5-naphthyridin-4-yl)oxy]-3-fluorophenyl]-4-hydroxy-5-(4-methoxy-3-methylphenyl)-2,6-dimethylpyridine-3-carboxamide |
| 713 | 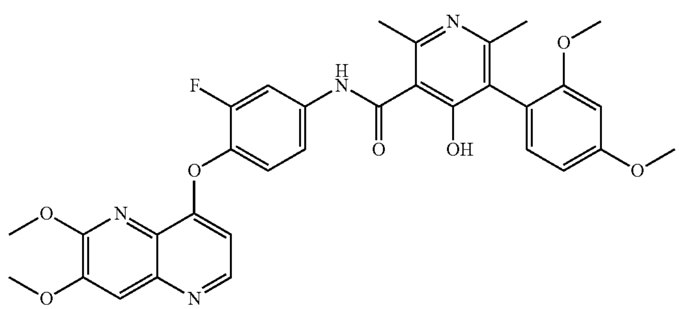 | N-[4-[(6,7-dimethoxy-1,5-naphthyridin-4-yl)oxy]-3-fluorophenyl]-5-(2,4-dimethoxyphenyl)-4-hydroxy-2,6-dimethylpyridine-3-carboxamide |
| 714 | 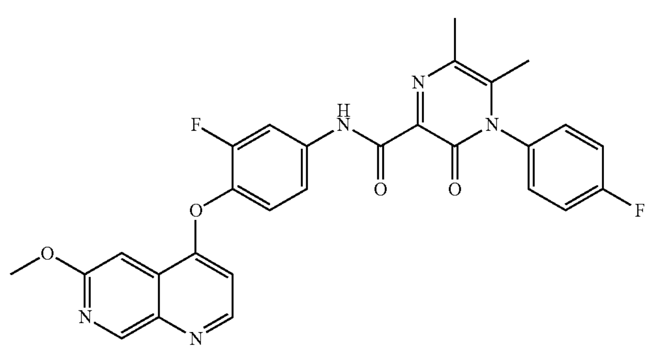 [SMILES: COc1cc2c(Oc3ccc(NC(=O)c4nc(C)c(C)n(-c5ccc(F)cc5)c4=O)cc3F)ccnc2cn1] | N-[3-fluoro-4-[(6-methoxy-1,7-naphthyridin-4-yl)oxy]phenyl]-4-(4-fluorophenyl)-5,6-dimethyl-3-oxopyrazine-2-carboxamide |

TABLE 1-continued

| Cpd # | Structure | IUPAC Name |
|---|---|---|
| 715 | 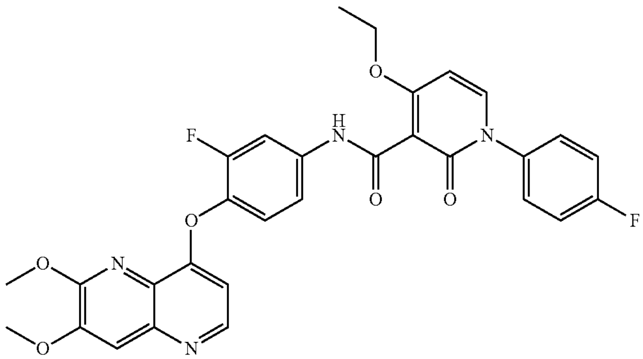 [SMILES: CCOc1ccn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-1-(4-fluorophenyl)-2-oxopyridine-3-carboxamide |
| 716 | 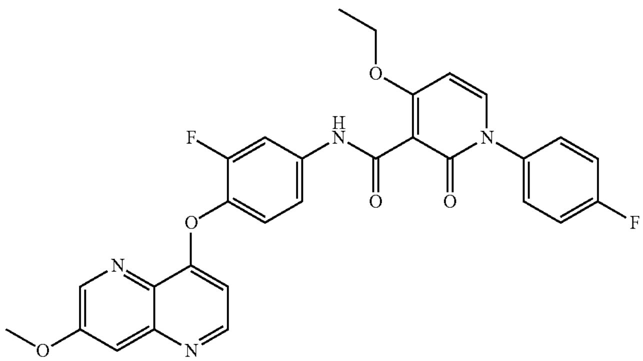 [SMILES: CCOc1ccn(-c2ccc(F)cc2)c(=O)c1C(=O)Nc1ccc(Oc2ccnc3cc(OC)cnc23)c(F)c1] | 4-ethoxy-N-[3-fluoro-4-[(7-methoxy-1,5-naphthyridin-4-yl)oxy]phenyl]-1-(4-fluorophenyl)-2-oxopyridine-3-carboxamide |
| 717 | 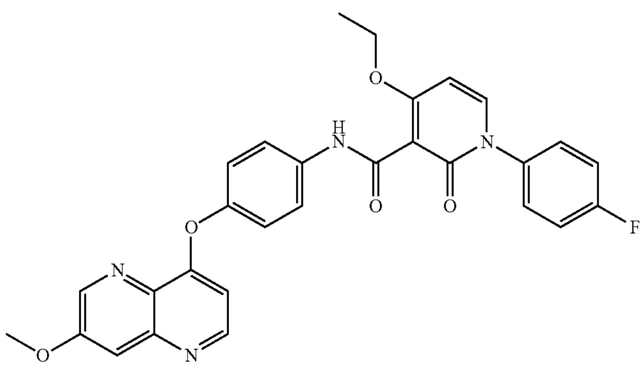 [SMILES: CCOc1ccn(-c2ccc(F)cc2)c(=O)c1C(=O)Nc1ccc(Oc2ccnc3cc(OC)cnc23)cc1] | 4-ethoxy-1-(4-fluorophenyl)-N-[4-[(7-methoxy-1,5-naphthyridin-4-yl)oxy]phenyl]-2-oxopyridine-3-carboxamide |
| 718 | 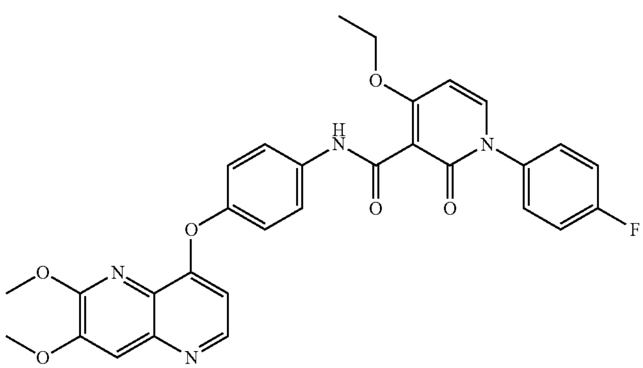 [SMILES: CCOc1ccn(-c2ccc(F)cc2)c(=O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-4-ethoxy-1-(4-fluorophenyl)-2-oxopyridine-3-carboxamide |

TABLE 1-continued

| Cpd # | Structure | IUPAC Name |
|---|---|---|
| 719 | 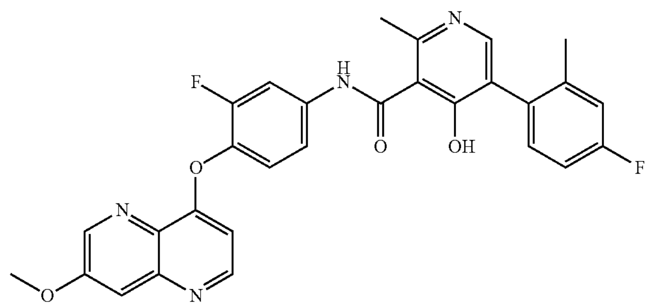 [SMILES: COc1cnc2c(Oc3ccc(NC(=O)c4c(C)ncc(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-2-methylpyridine-3-carboxamide |
| 720 | 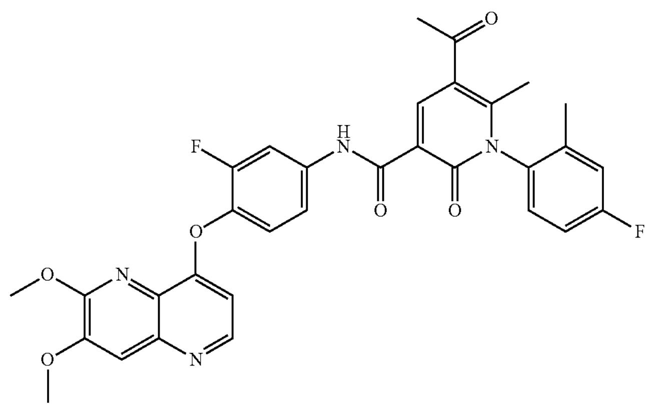 [SMILES: COc1cc2nccc(Oc3ccc(NC(=O)c4cc(C(C)=O)c(C)n(-c5ccc(F)cc5C)c4=O)cc3F)c2nc1OC] | 5-acetyl-N-[4-[(6,7-dimethoxy-1,5-naphthyridin-4-yl)oxy]-3-fluorophenyl]-1-(4-fluoro-2-methylphenyl)-6-methyl-2-oxopyridine-3-carboxamide |
| 721 | 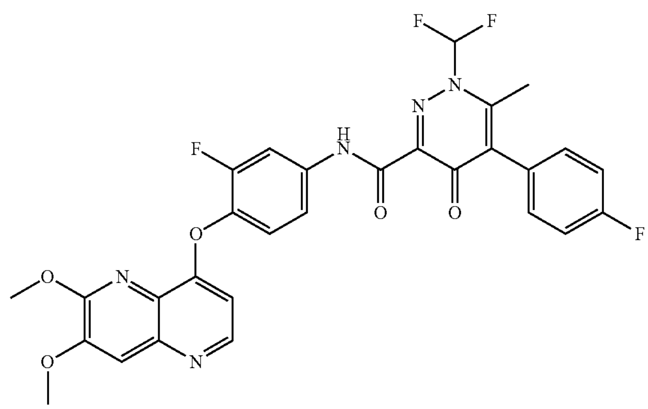 [SMILES: COc1cc2nccc(Oc3ccc(NC(=O)c4nn(C(F)F)c(C)c(-c5ccc(F)cc5)c4=O)cc3F)c2nc1OC] | 1-(difluoromethyl)-N-[4-[(6,7-dimethoxy-1,5-naphthyridin-4-yl)oxy]-3-fluorophenyl]-5-(4-fluorophenyl)-6-methyl-4-oxopyridazine-3-carboxamide |
| 722 | 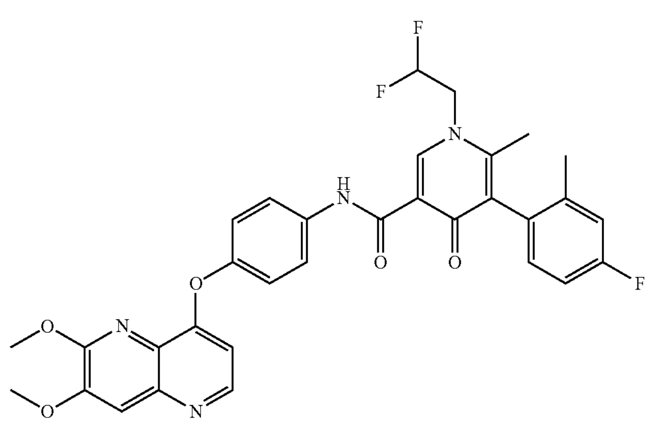 [SMILES: COc1cc2nccc(Oc3ccc(NC(=O)c4cn(CC(F)F)c(C)c(-c5ccc(F)cc5C)c4=O)cc3)c2nc1OC] | 1-(2,2-difluoroethyl)-N-[4-[(6,7-dimethoxy-1,5-naphthyridin-4-yl)oxy]phenyl]-5-(4-fluoro-2-methylphenyl)-6-methyl-4-oxopyridine-3-carboxamide |

TABLE 1-continued

| Cpd # | Structure | IUPAC Name |
|---|---|---|
| 723 | 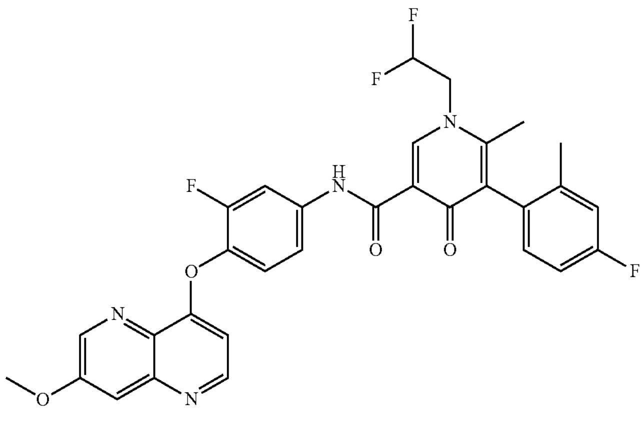 [SMILES: COc1cnc2c(Oc3ccc(NC(=O)c4cn(CC(F)F)c(C)c(-c5ccc(F)cc5C)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluoro-2-methylphenyl)-6-methyl-4-oxopyridine-3-carboxamide |
| 724 | 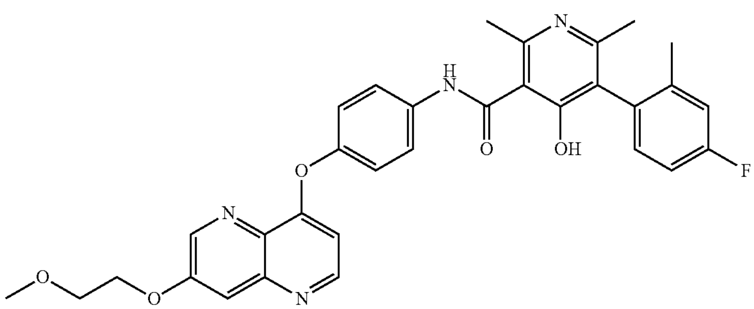 [SMILES: COCCOc1cnc2c(Oc3ccc(NC(=O)c4c(C)nc(C)c(-c5ccc(F)cc5C)c4O)cc3)ccnc2c1] | 5-(4-fluoro-2-methylphenyl)-4-hydroxy-N-[4-[[7-(2-methoxyethoxy)-1,5-naphthyridin-4-yl]oxy]phenyl]-2,6-dimethylpyridine-3-carboxamide |
| 725 | 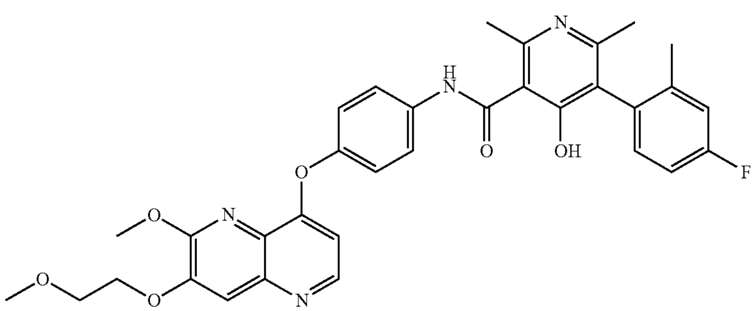 [SMILES: COCCOc1cc2nccc(Oc3ccc(NC(=O)c4c(C)nc(C)c(-c5ccc(F)cc5C)c4O)cc3)c2nc1OC] | 5-(4-fluoro-2-methylphenyl)-4-hydroxy-N-[4-[[6-methoxy-7-(2-methoxyethoxy)-1,5-naphthyridin-4-yl]oxy]phenyl]-2,6-dimethylpyridine-3-carboxamide |
| 726 | 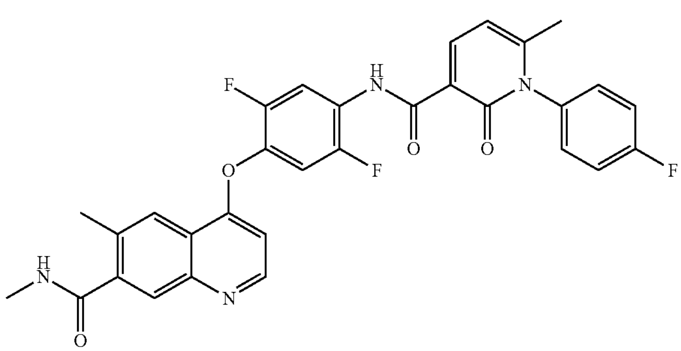 [SMILES: CNC(=O)c1cc2nccc(Oc3cc(F)c(NC(=O)c4ccc(C)n(-c5ccc(F)cc5)c4=O)cc3F)c2cc1C] | 4-[2,5-difluoro-4-[[1-(4-fluorophenyl)-6-methyl-2-oxopyridine-3-carbonyl]amino]phenoxy]-N,6-dimethylquinoline-7-carboxamide |

TABLE 1-continued

| Cpd # | Structure | IUPAC Name |
|---|---|---|
| 727 | 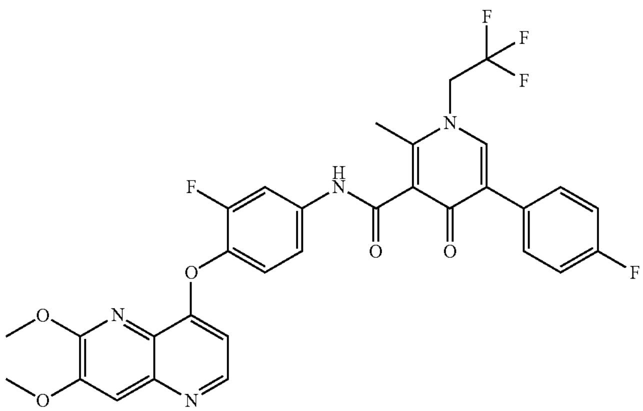 [SMILES: COc1cc2nccc(Oc3ccc(NC(=O)c4c(C)n(CC(F)(F)F)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-2-methyl-4-oxo-1-(2,2,2-trifluoroethyl)pyridine-3-carboxamide |
| 728 | 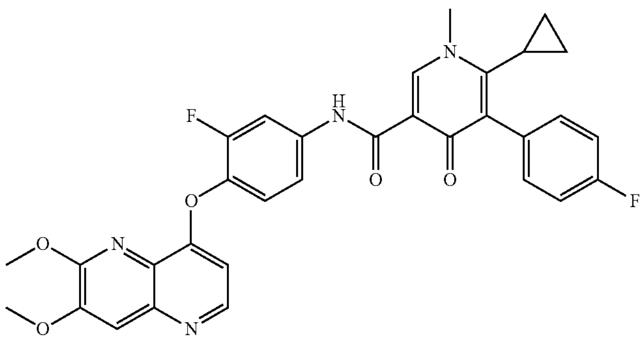 [SMILES: COc1cc2nccc(Oc3ccc(NC(=O)c4cn(C)c(C5CC5)c(-c5ccc(F)cc5)c4=O)cc3F)c2nc1OC] | 6-cyclopropyl-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 729 | 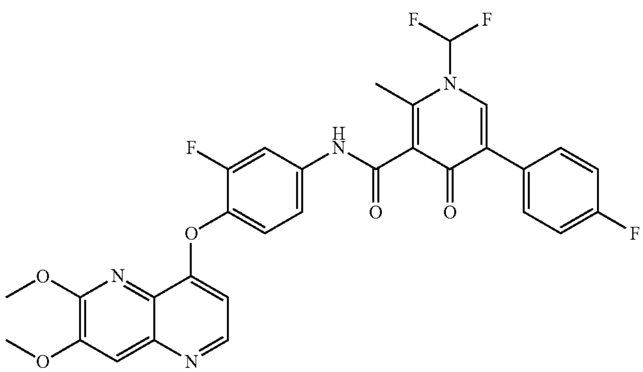 [SMILES: COc1cc2nccc(Oc3ccc(NC(=O)c4c(C)n(C(F)F)cc(-c5ccc(F)cc5)c4=O)cc3F)c2nc1OC] | 1-(difluoromethyl)-N-[4-[(6,7-dimethoxy-1,5-naphthyridin-4-yl)oxy]-3-fluorophenyl]-5-(4-fluorophenyl)-2-methyl-4-oxopyridine-3-carboxamide |
| 730 | 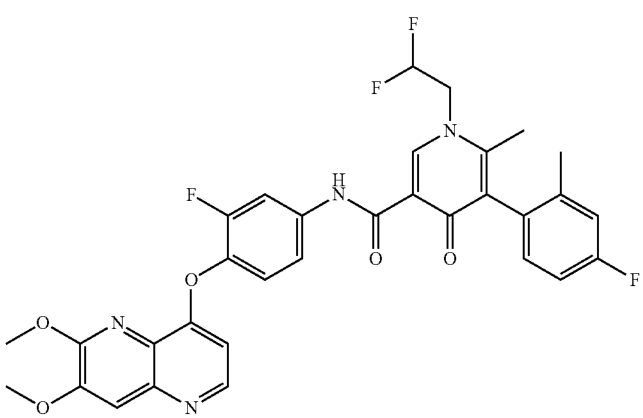 [SMILES: COc1cc2nccc(Oc3ccc(NC(=O)c4cn(CC(F)F)c(C)c(-c5ccc(F)cc5C)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluoro-2-methylphenyl)-6-methyl-4-oxopyridine-3-carboxamide |

TABLE 1-continued

| Cpd # | Structure | IUPAC Name |
|---|---|---|
| 731 | 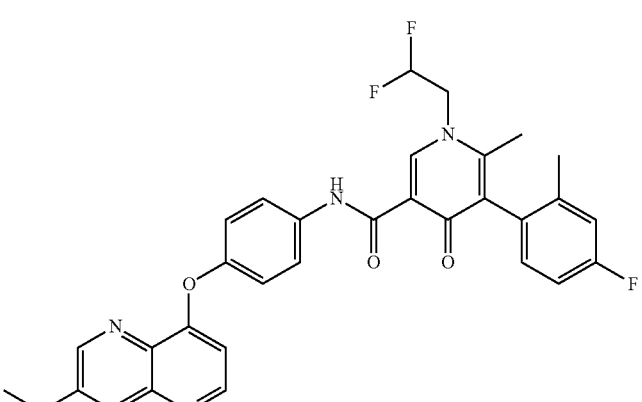 | 1-(2,2-difluoroethyl)-5-(4-fluoro-2-methylphenyl)-N-[4-[(7-methoxy-1,5-naphthyridin-4-yl)oxy]phenyl]-6-methyl-4-oxopyridine-3-carboxamide |
| 732 | 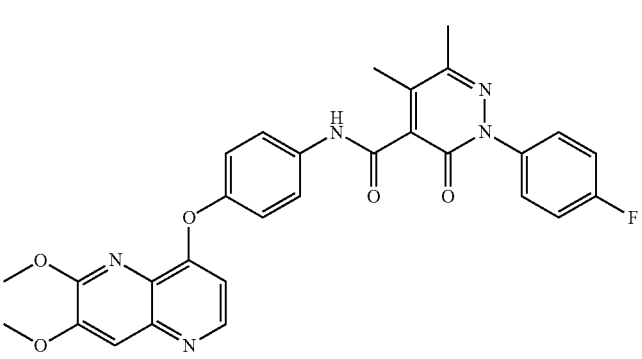 [SMILES: COc1cc2nccc(Oc3ccc(NC(=O)c4c(C)c(C)nn(-c5ccc(F)cc5)c4=O)cc3)c2nc1OC] | N-[4-[(6,7-dimethoxy-1,5-naphthyridin-4-yl)oxy]phenyl]-2-(4-fluorophenyl)-5,6-dimethyl-3-oxopyridazine-4-carboxamide |
| 733 | 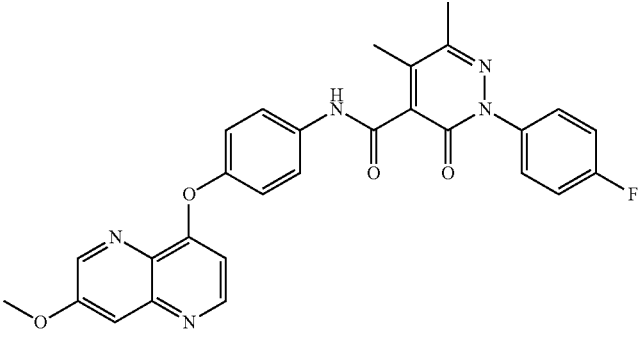 [SMILES: COc1cnc2c(Oc3ccc(NC(=O)c4c(C)c(C)nn(-c5ccc(F)cc5)c4=O)cc3)ccnc2c1] | 2-(4-fluorophenyl)-N-[4-[(7-methoxy-1,5-naphthyridin-4-yl)oxy]phenyl]-5,6-dimethyl-3-oxopyridazine-4-carboxamide |
| 734 | 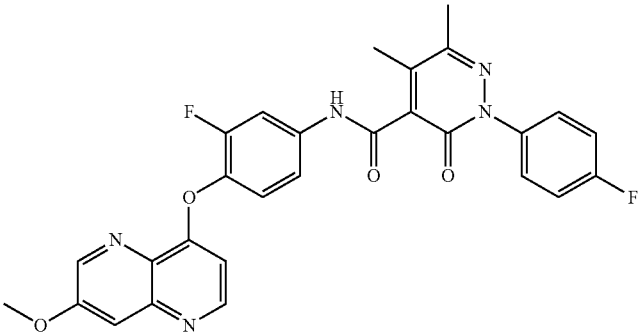 [SMILES: COc1cnc2c(Oc3ccc(NC(=O)c4c(C)c(C)nn(-c5ccc(F)cc5)c4=O)cc3F)ccnc2c1] | N-[3-fluoro-4-[(7-methoxy-1,5-naphthyridin-4-yl)oxy]phenyl]-2-(4-fluorophenyl)-5,6-dimethyl-3-oxopyridazine-4-carboxamide |

TABLE 1-continued

| Cpd # | Structure | IUPAC Name |
|---|---|---|
| 735 | 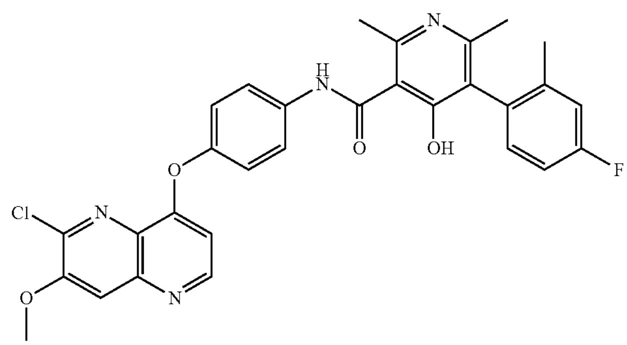 [SMILES: COc1cc2nccc(Oc3ccc(NC(=O)c4c(C)nc(C)c(-c5ccc(F)cc5C)c4O)cc3)c2nc1Cl] | N-[4-[(6-chloro-7-methoxy-1,5-naphthyridin-4-yl)oxy]phenyl]-5-(4-fluoro-2-methylphenyl)-4-hydroxy-2,6-dimethylpyridine-3-carboxamide |
| 736 | 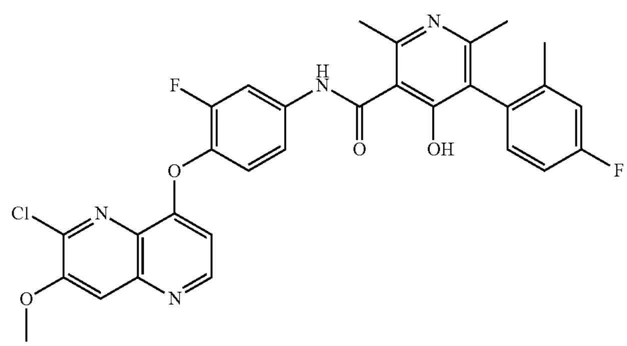 [SMILES: COc1cc2nccc(Oc3ccc(NC(=O)c4c(C)nc(C)c(-c5ccc(F)cc5C)c4O)cc3F)c2nc1Cl] | N-[4-[(6-chloro-7-methoxy-1,5-naphthyridin-4-yl)oxy]-3-fluorophenyl]-5-(4-fluoro-2-methylphenyl)-4-hydroxy-2,6-dimethylpyridine-3-carboxamide |
| 737 | 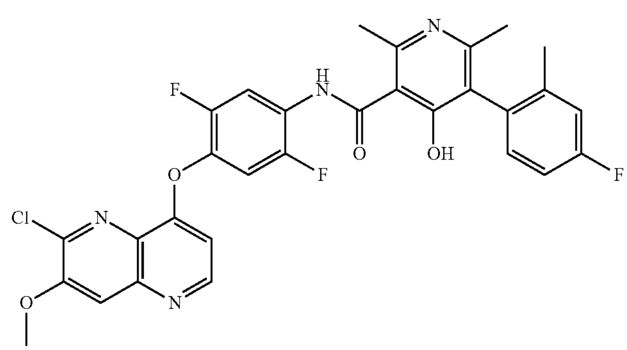 [SMILES: COc1cc2nccc(Oc3cc(F)c(NC(=O)c4c(C)nc(C)c(-c5ccc(F)cc5C)c4O)cc3F)c2nc1Cl] | N-[4-[(6-chloro-7-methoxy-1,5-naphthyridin-4-yl)oxy]-2,5-difluorophenyl]-5-(4-fluoro-2-methylphenyl)-4-hydroxy-2,6-dimethylpyridine-3-carboxamide |
| 738 | 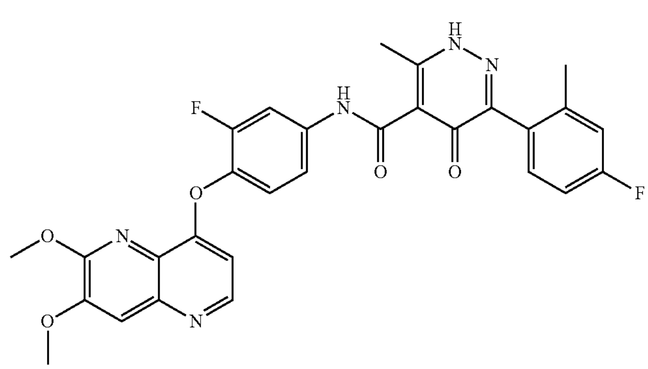 [SMILES: COc1cc2nccc(Oc3ccc(NC(=O)c4c(C)[nH]nc(-c5ccc(F)cc5C)c4=O)cc3F)c2nc1OC] | N-[4-[(6,7-dimethoxy-1,5-naphthyridin-4-yl)oxy]-3-fluorophenyl]-3-(4-fluoro-2-methylphenyl)-6-methyl-4-oxo-1H-pyridazine-5-carboxamide |

TABLE 1-continued

| Cpd # | Structure | IUPAC Name |
|---|---|---|
| 739 | 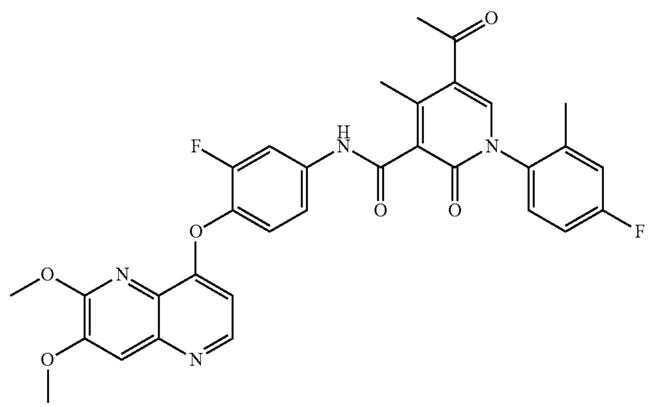 [SMILES: COc1cc2nccc(Oc3ccc(NC(=O)c4c(C)c(C(C)=O)cn(-c5ccc(F)cc5C)c4=O)cc3F)c2nc1OC] | 5-acetyl-N-[4-[(6,7-dimethoxy-1,5-naphthyridin-4-yl)oxy]-3-fluorophenyl]-1-(4-fluoro-2-methylphenyl)-4-methyl-2-oxopyridine-3-carboxamide |
| 740 | 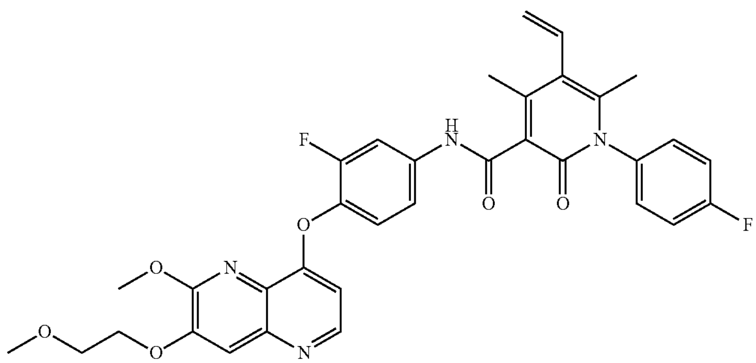 [SMILES: C=Cc1c(C)c(C(=O)Nc2ccc(Oc3ccnc4cc(OCCOC)c(OC)nc34)c(F)c2)c(=O)n(-c2ccc(F)cc2)c1C] | 5-ethenyl-N-[3-fluoro-4-[[6-methoxy-7-(2-methoxyethoxy)-1,5-naphthyridin-4-yl]oxy]phenyl]-1-(4-fluorophenyl)-4,6-dimethyl-2-oxopyridine-3-carboxamide |
| 741 | 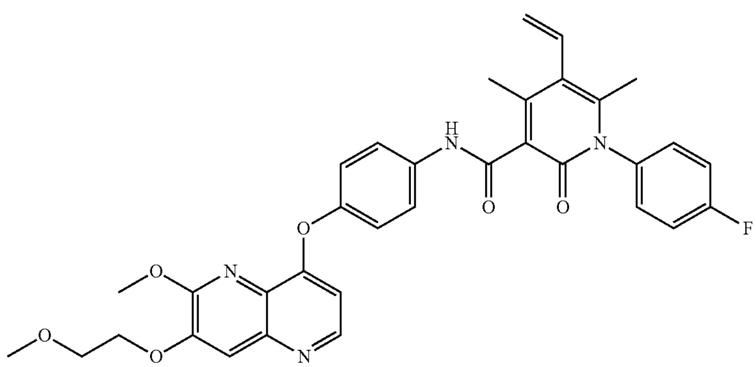 [SMILES: C=Cc1c(C)c(C(=O)Nc2ccc(Oc3ccnc4cc(OCCOC)c(OC)nc34)cc2)c(=O)n(-c2ccc(F)cc2)c1C] | 5-ethenyl-1-(4-fluorophenyl)-N-[4-[[6-methoxy-7-(2-methoxyethoxy)-1,5-naphthyridin-4-yl]oxy]phenyl]-4,6-dimethyl-2-oxopyridine-3-carboxamide |
| 742 | 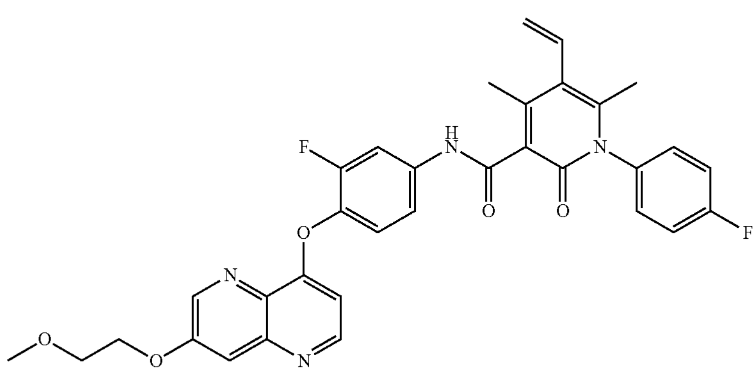 [SMILES: C=Cc1c(C)c(C(=O)Nc2ccc(Oc3ccnc4cc(OCCOC)cnc34)c(F)c2)c(=O)n(-c2ccc(F)cc2)c1C] | 5-ethenyl-N-[3-fluoro-4-[[7-(2-methoxyethoxy)-1,5-naphthyridin-4-yl]oxy]phenyl]-1-(4-fluorophenyl)-4,6-dimethyl-2-oxopyridine-3-carboxamide |

TABLE 1-continued

| Cpd # | Structure | IUPAC Name |
|---|---|---|
| 743 | 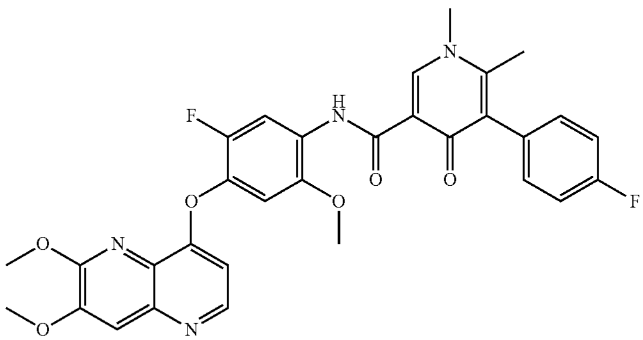 [SMILES: COc1cc(Oc2ccnc3cc(OC)c(OC)nc23)c(F)cc1NC(=O)c1cn(C)c(C)c(-c2ccc(F)cc2)c1=O] | N-[4-[(6,7-dimethoxy-1,5-naphthyridin-4-yl)oxy]-5-fluoro-2-methoxyphenyl]-5-(4-fluorophenyl)-1,6-dimethyl-4-oxopyridine-3-carboxamide |
| 744 | 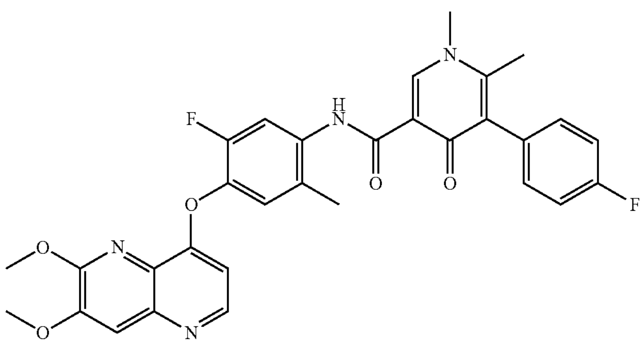 [SMILES: COc1cc2nccc(Oc3cc(C)c(NC(=O)c4cn(C)c(C)c(-c5ccc(F)cc5)c4=O)cc3F)c2nc1OC] | N-[4-[(6,7-dimethoxy-1,5-naphthyridin-4-yl)oxy]-5-fluoro-2-methylphenyl]-5-(4-fluorophenyl)-1,6-dimethyl-4-oxopyridine-3-carboxamide |
| 745 | 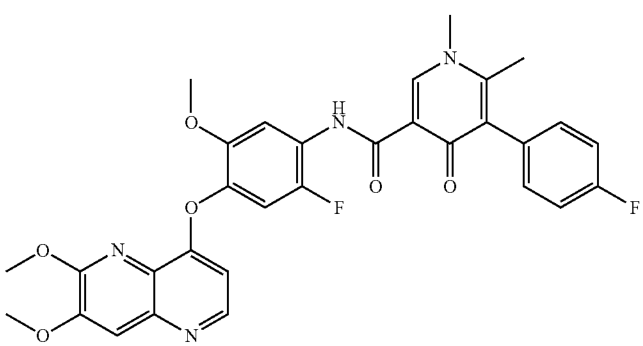 [SMILES: COc1cc(NC(=O)c2cn(C)c(C)c(-c3ccc(F)cc3)c2=O)c(F)cc1Oc1ccnc2cc(OC)c(OC)nc12] | N-[4-[(6,7-dimethoxy-1,5-naphthyridin-4-yl)oxy]-2-fluoro-5-methoxyphenyl]-5-(4-fluorophenyl)-1,6-dimethyl-4-oxopyridine-3-carboxamide |
| 746 | 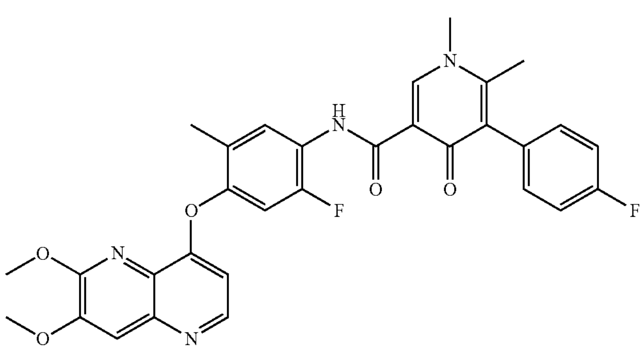 [SMILES: COc1cc2nccc(Oc3cc(F)c(NC(=O)c4cn(C)c(C)c(-c5ccc(F)cc5)c4=O)cc3C)c2nc1OC] | N-[4-[(6,7-dimethoxy-1,5-naphthyridin-4-yl)oxy]-2-fluoro-5-methylphenyl]-5-(4-fluorophenyl)-1,6-dimethyl-4-oxopyridine-3-carboxamide |

TABLE 1-continued

| Cpd # | Structure | IUPAC Name |
|---|---|---|
| 747 | 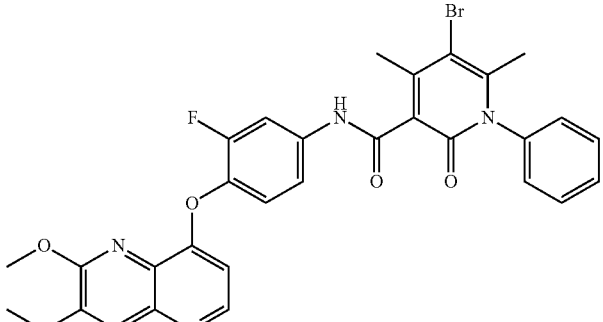 | 5-bromo-N-[4-[(6,7-dimethoxy-1,5-naphthyridin-4-yl)oxy]-3-fluorophenyl]-4,6-dimethyl-2-oxo-1-phenylpyridine-3-carboxamide |
| 748 | 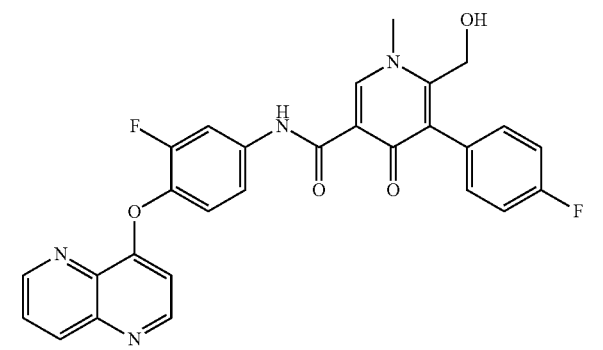 [SMILES: Cn1cc(C(=O)Nc2ccc(Oc3ccnc4cccnc34)c(F)c2)c(=O)c(-c2ccc(F)cc2)c1CO] | N-[3-fluoro-4-(1,5-naphthyridin-4-yloxy)phenyl]-5-(4-fluorophenyl)-6-(hydroxymethyl)-1-methyl-4-oxopyridine-3-carboxamide |
| 749 | 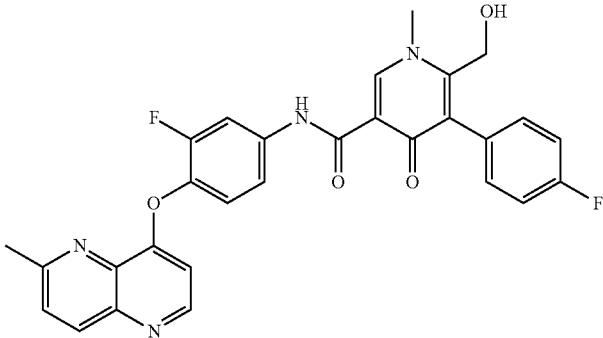 [SMILES: Cc1ccc2nccc(Oc3ccc(NC(=O)c4cn(C)c(CO)c(-c5ccc(F)cc5)c4=O)cc3F)c2n1] | N-[3-fluoro-4-[(6-methyl-1,5-naphthyridin-4-yl)oxy]phenyl]-5-(4-fluorophenyl)-6-(hydroxymethyl)-1-methyl-4-oxopyridine-3-carboxamide |
| 750 | 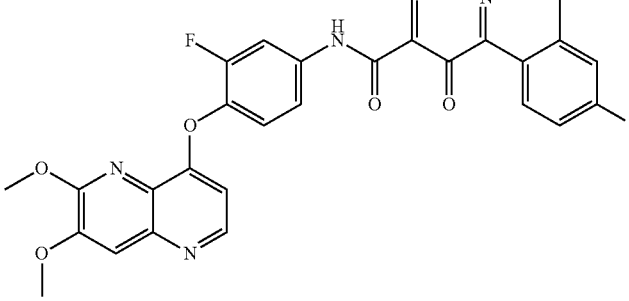 | N-[4-[(6,7-dimethoxy-1,5-naphthyridin-4-yl)oxy]-3-fluorophenyl]-6-(4-fluoro-2-methylphenyl)-2,3-dimethyl-5-oxopyridazine-4-carboxamide |

TABLE 1-continued

| Cpd # | Structure | IUPAC Name |
|---|---|---|
| 751 | 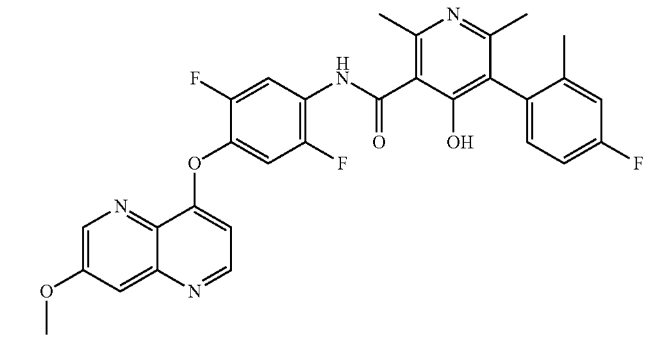 [SMILES: COc1cnc2c(Oc3cc(F)c(NC(=O)c4c(C)nc(C)c(-c5ccc(F)cc5C)c4O)cc3F)ccnc2c1] | N-[2,5-difluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 752 | 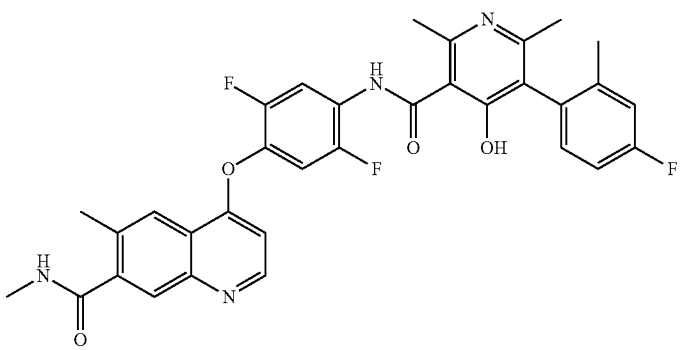 [SMILES: CNC(=O)c1cc2nccc(Oc3cc(F)c(NC(=O)c4c(C)nc(C)c(-c5ccc(F)cc5C)c4O)cc3F)c2cc1C] | 4-[2,5-difluoro-4-[[5-(4-fluoro-2-methylphenyl)-4-hydroxy-2,6-dimethylpyridine-3-carbonyl]amino]phenoxy]-N,6-dimethylquinoline-7-carboxamide |
| 753 | 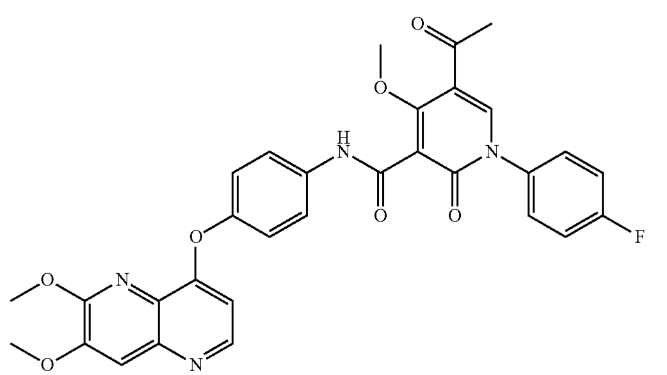 [SMILES: COc1cc2nccc(Oc3ccc(NC(=O)c4c(OC)c(C(C)=O)cn(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-4-methoxy-2-oxopyridine-3-carboxamide |
| 754 | 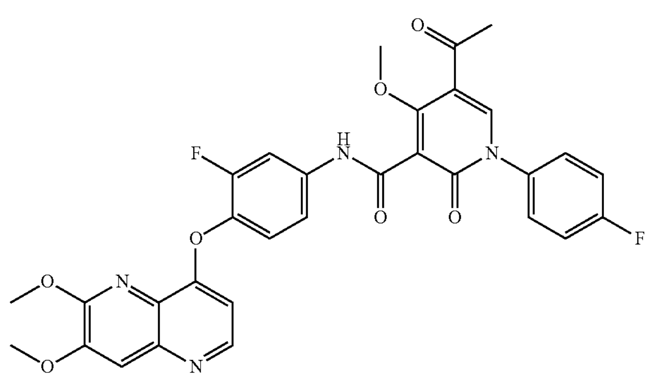 [SMILES: COc1cc2nccc(Oc3ccc(NC(=O)c4c(OC)c(C(C)=O)cn(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4-methoxy-2-oxopyridine-3-carboxamide |

TABLE 1-continued

| Cpd # | Structure | IUPAC Name |
|---|---|---|
| 755 | 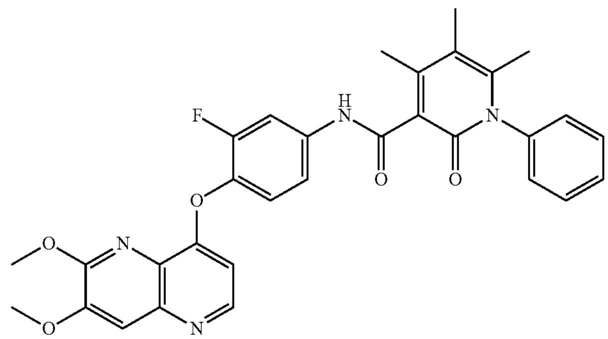 [SMILES: COc1cc2nccc(Oc3ccc(NC(=O)c4c(C)c(C)c(C)n(-c5ccccc5)c4=O)cc3F)c2nc1OC] | N-[4-[(6,7-dimethoxy-1,5-naphthyridin-4-yl)oxy]-3-fluorophenyl]-4,5,6-trimethyl-2-oxo-1-phenylpyridine-3-carboxamide |
| 756 | 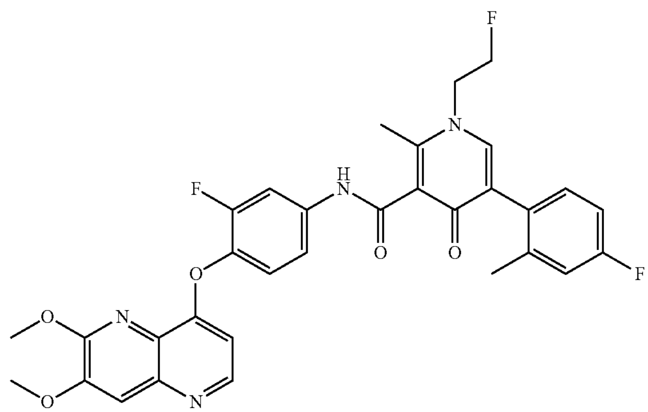 [SMILES: COc1cc2nccc(Oc3ccc(NC(=O)c4c(C)n(CCF)cc(-c5ccc(F)cc5C)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluoro-2-methylphenyl)-2-methyl-4-oxopyridine-3-carboxamide |
| 757 | 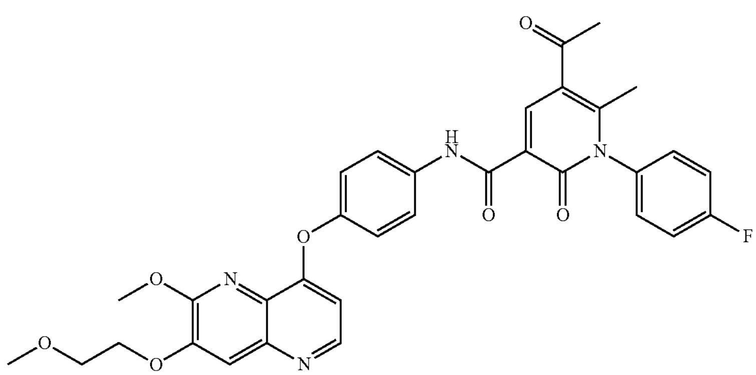 [SMILES: COCCOc1cc2nccc(Oc3ccc(NC(=O)c4cc(C(C)=O)c(C)n(-c5ccc(F)cc5)c4=O)cc3)c2nc1OC] | 5-acetyl-1-(4-fluorophenyl)-N-[4-[[6-methoxy-7-(2-methoxyethoxy)-1,5-naphthyridin-4-yl]oxy]phenyl]-6-methyl-2-oxopyridine-3-carboxamide |
| 758 | 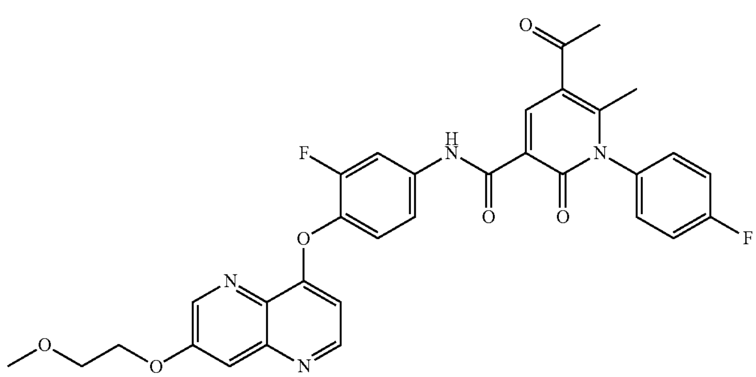 [SMILES: COCCOc1cnc2c(Oc3ccc(NC(=O)c4cc(C(C)=O)c(C)n(-c5ccc(F)cc5)c4=O)cc3F)ccnc2c1] | 5-acetyl-N-[3-fluoro-4-[[7-(2-methoxyethoxy)-1,5-naphthyridin-4-yl]oxy]phenyl]-1-(4-fluorophenyl)-6-methyl-2-oxopyridine-3-carboxamide |

TABLE 1-continued

| Cpd # | Structure | IUPAC Name |
|---|---|---|
| 759 | 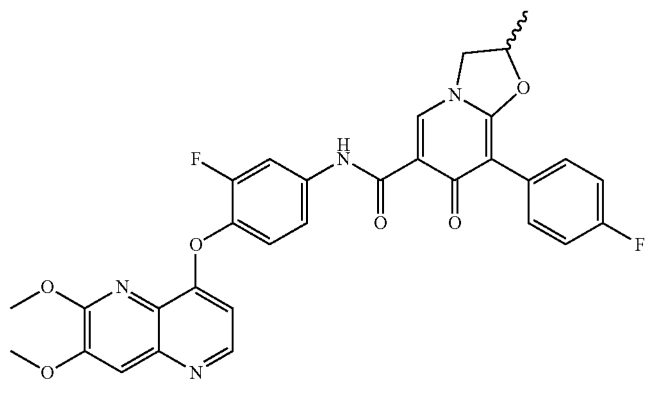 [SMILES: COc1cc2nccc(Oc3ccc(NC(=O)c4cn5c(c(-c6ccc(F)cc6)c4=O)OC(C)C5)cc3F)c2nc1OC] | N-[4-[(6,7-dimethoxy-1,5-naphthyridin-4-yl)oxy]-3-fluorophenyl]-8-(4-fluorophenyl)-2-methyl-7-oxo-2,3-dihydro-[1,3]oxazolo[3,2-a]pyridine-6-carboxamide |
| 760 | 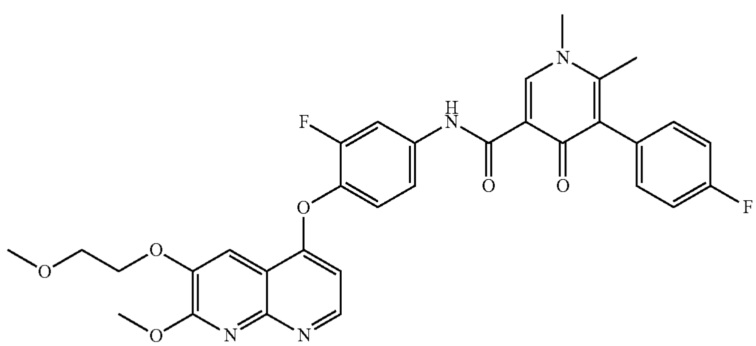 [SMILES: COCCOc1cc2c(Oc3ccc(NC(=O)c4cn(C)c(C)c(-c5ccc(F)cc5)c4=O)cc3F)ccnc2nc1OC] | N-[3-fluoro-4-[[7-methoxy-6-(2-methoxyethoxy)-1,8-naphthyridin-4-yl]oxy]phenyl]-5-(4-fluorophenyl)-1,6-dimethyl-4-oxopyridine-3-carboxamide |
| 761 | 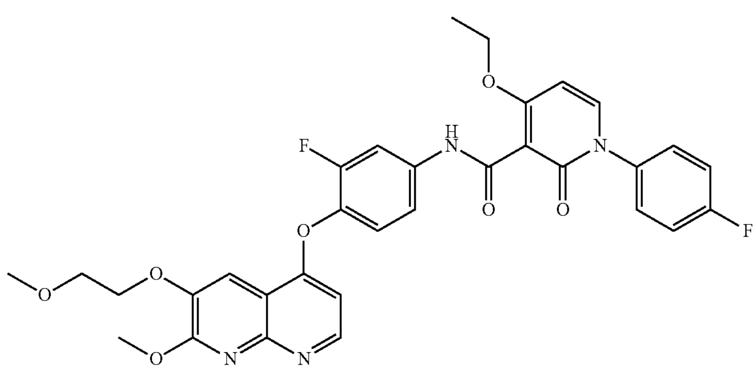 [SMILES: CCOc1ccn(-c2ccc(F)cc2)c(=O)c1C(=O)Nc1ccc(Oc2ccnc3nc(OC)c(OCCOC)cc23)c(F)c1] | 4-ethoxy-N-[3-fluoro-4-[[7-methoxy-6-(2-methoxyethoxy)-1,8-naphthyridin-4-yl]oxy]phenyl]-1-(4-fluorophenyl)-2-oxopyridine-3-carboxamide |
| 762 | 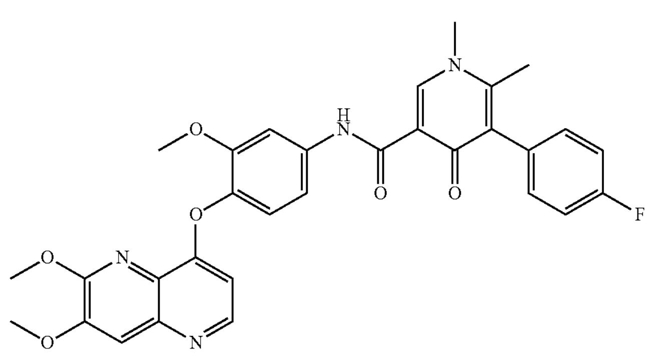 [SMILES: COc1cc(NC(=O)c2cn(C)c(C)c(-c3ccc(F)cc3)c2=O)ccc1Oc1ccnc2cc(OC)c(OC)nc12] | N-[4-[(6,7-dimethoxy-1,5-naphthyridin-4-yl)oxy]-3-methoxyphenyl]-5-(4-fluorophenyl)-1,6-dimethyl-4-oxopyridine-3-carboxamide |

TABLE 1-continued

| Cpd # | Structure | IUPAC Name |
|---|---|---|
| 763 | 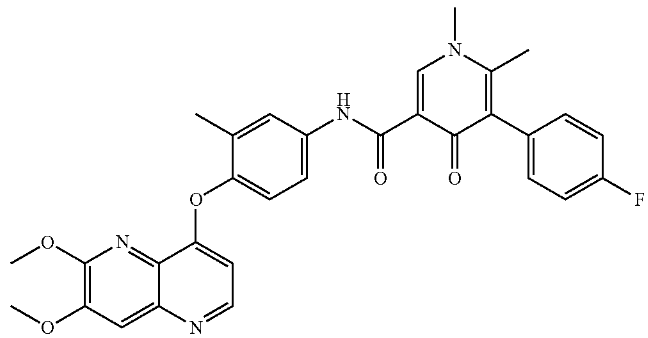 [SMILES: COc1cc2nccc(Oc3ccc(NC(=O)c4cn(C)c(C)c(-c5ccc(F)cc5)c4=O)cc3C)c2nc1OC] | N-[4-[(6,7-dimethoxy-1,5-naphthyridin-4-yl)oxy]-3-methylphenyl]-5-(4-fluorophenyl)-1,6-dimethyl-4-oxopyridine-3-carboxamide |
| 764 | 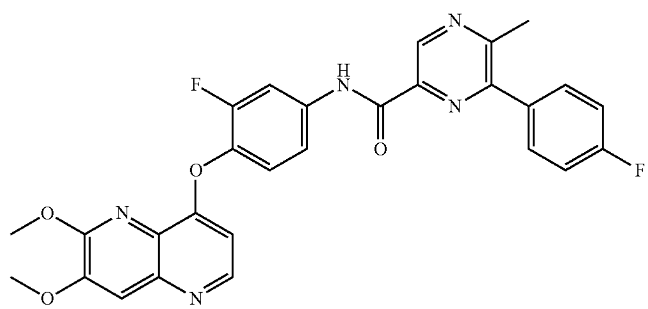 [SMILES: COc1cc2nccc(Oc3ccc(NC(=O)c4cnc(C)c(-c5ccc(F)cc5)n4)cc3F)c2nc1OC] | N-[4-[(6,7-dimethoxy-1,5-naphthyridin-4-yl)oxy]-3-fluorophenyl]-6-(4-fluorophenyl)-5-methylpyrazine-2-carboxamide |
| 765 | 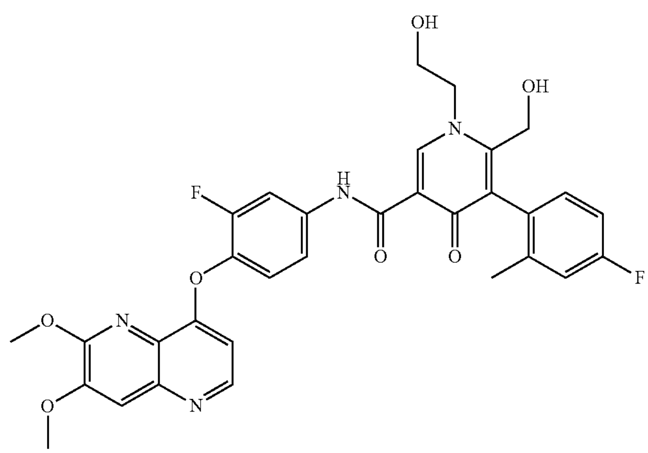 [SMILES: COc1cc2nccc(Oc3ccc(NC(=O)c4cn(CCO)c(CO)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1-(2-hydroxyethyl)-6-(hydroxymethyl)-4-oxopyridine-3-carboxamide |
| 766 | 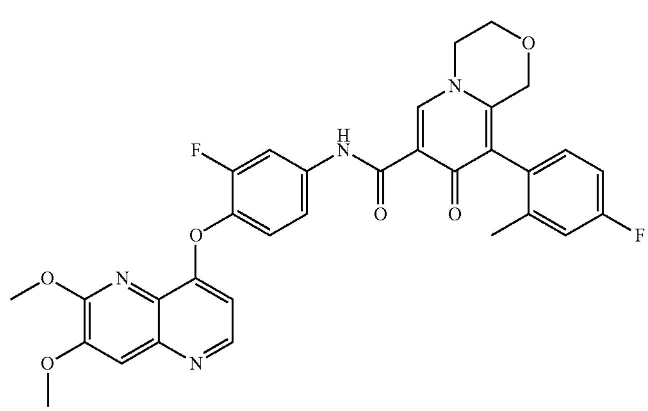 [SMILES: COc1cc2nccc(Oc3ccc(NC(=O)c4cn5c(c(-c6ccc(F)cc6C)c4=O)COCC5)cc3F)c2nc1OC] | N-[4-[(6,7-dimethoxy-1,5-naphthyridin-4-yl)oxy]-3-fluorophenyl]-9-(4-fluoro-2-methylphenyl)-8-oxo-3,4-dihydro-1H-pyrido[2,1-c][1,4]oxazine-7-carboxamide |

TABLE 1-continued

| Cpd # | Structure | IUPAC Name |
|---|---|---|
| 767 | 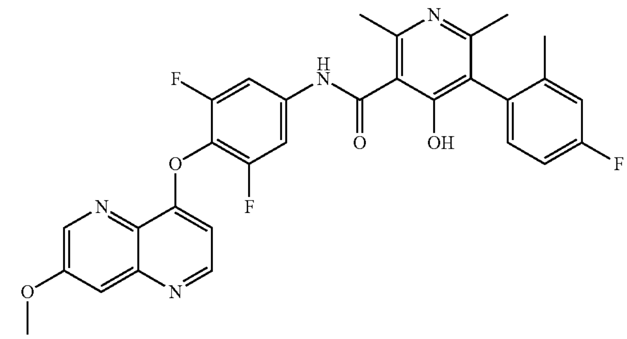 [SMILES: COc1cnc2c(Oc3c(F)cc(NC(=O)c4c(C)nc(C)c(-c5ccc(F)cc5C)c4O)cc3F)ccnc2c1] | N-[3,5-difluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 768 | 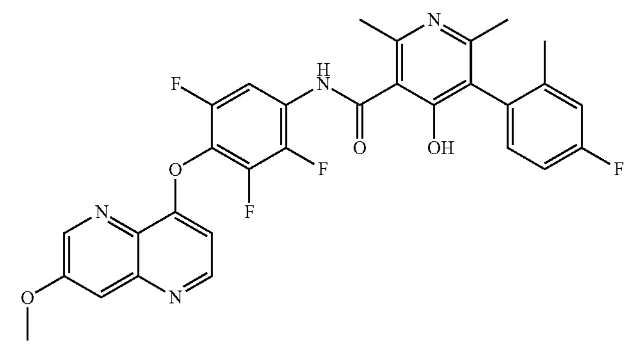 [SMILES: COc1cnc2c(Oc3c(F)cc(NC(=O)c4c(C)nc(C)c(-c5ccc(F)cc5C)c4O)c(F)c3F)ccnc2c1] | 5-(4-fluoro-2-methylphenyl)-4-hydroxy-2,6-dimethyl-N-[2,3,5-trifluoro-4-[(7-methoxy-1,5-naphthyridin-4-yl)oxy]phenyl]pyridine-3-carboxamide |
| 769 | 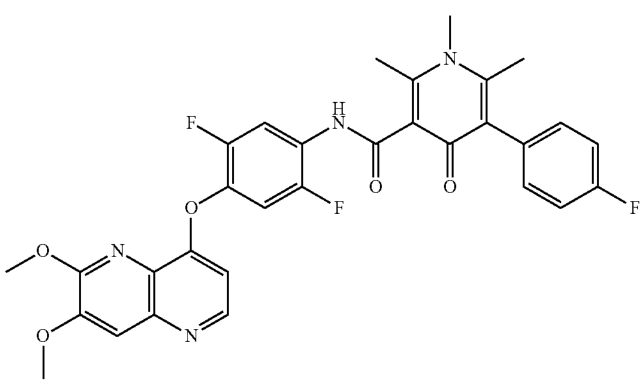 [SMILES: COc1cc2nccc(Oc3cc(F)c(NC(=O)c4c(C)n(C)c(C)c(-c5ccc(F)cc5)c4=O)cc3F)c2nc1OC] | N-[4-[(6,7-dimethoxy-1,5-naphthyridin-4-yl)oxy]-2,5-difluorophenyl]-5-(4-fluorophenyl)-1,2,6-trimethyl-4-oxopyridine-3-carboxamide |
| 770 | 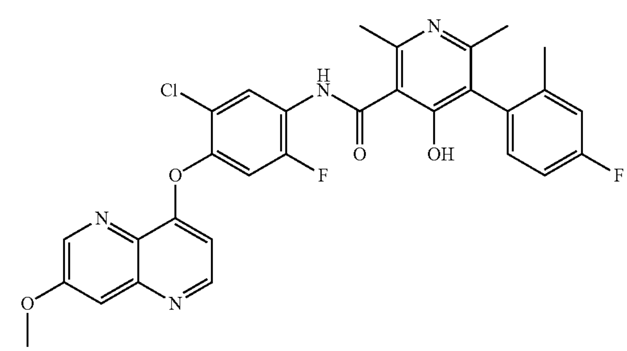 [SMILES: COc1cnc2c(Oc3cc(F)c(NC(=O)c4c(C)nc(C)c(-c5ccc(F)cc5C)c4O)cc3Cl)ccnc2c1] | N-[5-chloro-2-fluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |

TABLE 1-continued

| Cpd # | Structure | IUPAC Name |
|---|---|---|
| 771 | 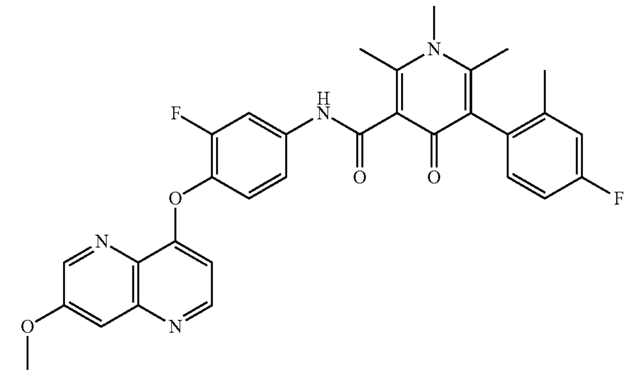 [SMILES: COc1cnc2c(Oc3ccc(NC(=O)c4c(C)n(C)c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-1,2,6-trimethyl-4-oxopyridine-3-carboxamide |
| 772 | 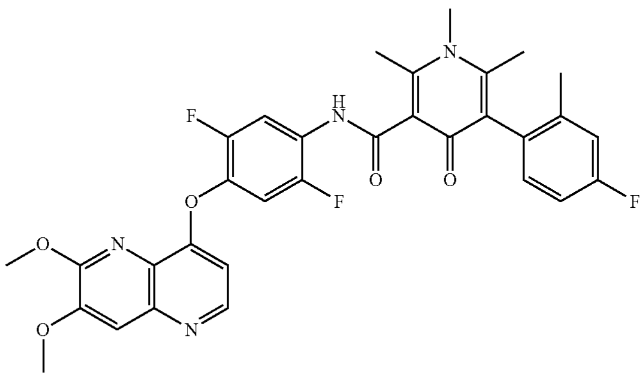 [SMILES: COc1cc2nccc(Oc3cc(F)c(NC(=O)c4c(C)n(C)c(C)c(-c5ccc(F)cc5C)c4=O)cc3F)c2nc1OC] | N-[4-[(6,7-dimethoxy-1,5-naphthyridin-4-yl)oxy]-2,5-difluorophenyl]-5-(4-fluoro-2-methylphenyl)-1,2,6-trimethyl-4-oxopyridine-3-carboxamide |
| 773 | 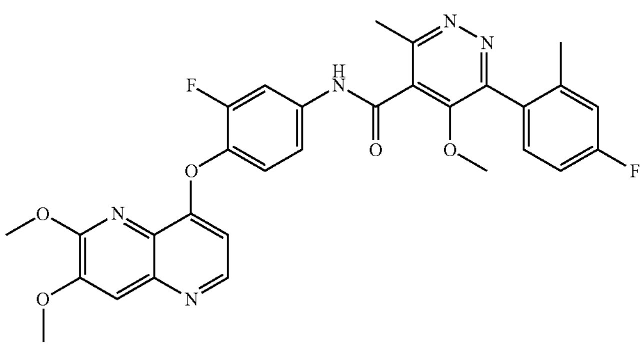 [SMILES: COc1cc2nccc(Oc3ccc(NC(=O)c4c(C)nnc(-c5ccc(F)cc5C)c4OC)cc3F)c2nc1OC] | N-[4-[(6,7-dimethoxy-1,5-naphthyridin-4-yl)oxy]-3-fluorophenyl]-6-(4-fluoro-2-methylphenyl)-5-methoxy-3-methylpyridazine-4-carboxamide |
| 774 | 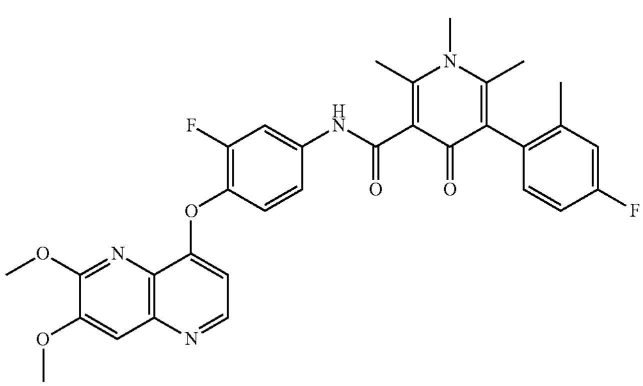 [SMILES: COc1cc2nccc(Oc3ccc(NC(=O)c4c(C)n(C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1,2,6-trimethyl-4-oxopyridine-3-carboxamide |

TABLE 1-continued

| Cpd # | Structure | IUPAC Name |
|---|---|---|
| 775 | 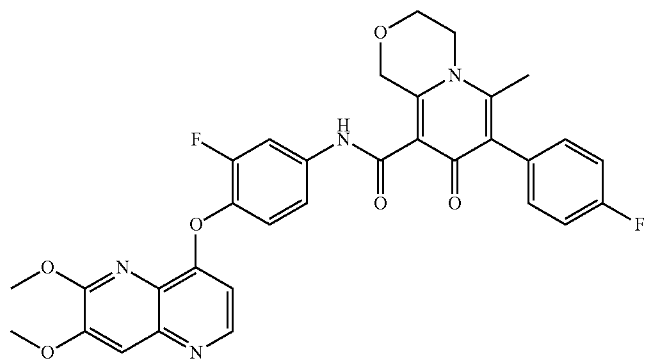 [SMILES: COc1cc2nccc(Oc3ccc(NC(=O)c4c5n(c(C)c(-c6ccc(F)cc6)c4=O)CCOC5)cc3F)c2nc1OC] | N-[4-[(6,7-dimethoxy-1,5-naphthyridin-4-yl)oxy]-3-fluorophenyl]-7-(4-fluorophenyl)-6-methyl-8-oxo-3,4-dihydro-1H-pyrido[2,1-c][1,4]oxazine-9-carboxamide |
| 776 | 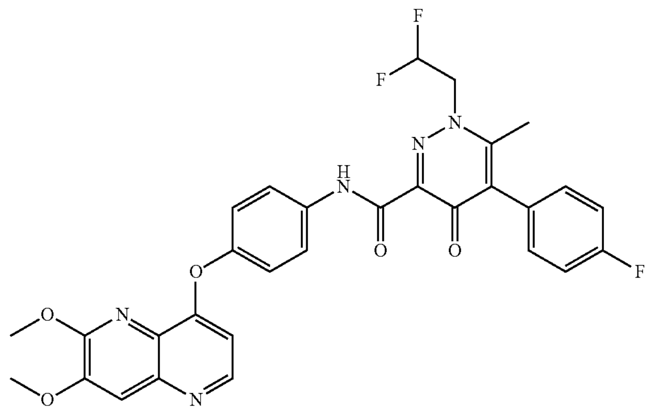 [SMILES: COc1cc2nccc(Oc3ccc(NC(=O)c4nn(CC(F)F)c(C)c(-c5ccc(F)cc5)c4=O)cc3)c2nc1OC] | 1-(2,2-difluoroethyl)-N-[4-[(6,7-dimethoxy-1,5-naphthyridin-4-yl)oxy]phenyl]-5-(4-fluorophenyl)-6-methyl-4-oxopyridazine-3-carboxamide |
| 777 | 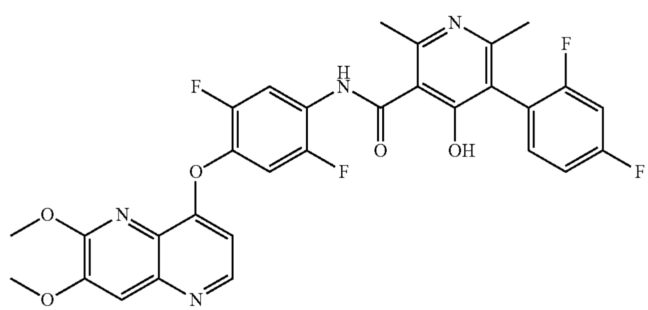 [SMILES: COc1cc2nccc(Oc3cc(F)c(NC(=O)c4c(C)nc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-2,5-difluorophenyl]-4-hydroxy-2,6-dimethylpyridine-3-carboxamide |
| 778 | 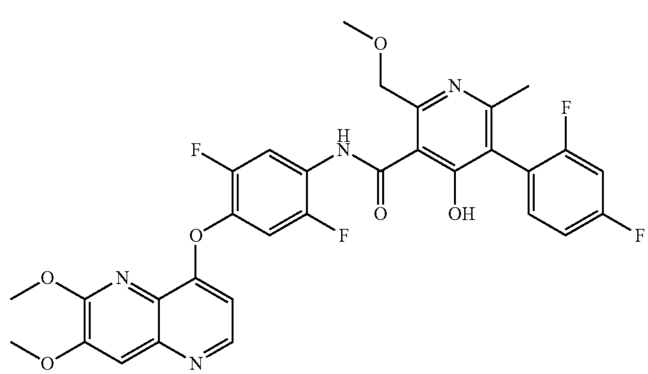 [SMILES: COCc1nc(C)c(-c2ccc(F)cc2F)c(O)c1C(=O)Nc1cc(F)c(Oc2ccnc3cc(OC)c(OC)nc23)cc1F] | 5-(2,4-difluorophenyl)-N-[4-[(6,7-dimethoxy-1,5-naphthyridin-4-yl)oxy]-2,5-difluorophenyl]-4-hydroxy-2-(methoxymethyl)-6-methylpyridine-3-carboxamide |

TABLE 1-continued

| Cpd # | Structure | IUPAC Name |
|---|---|---|
| 779 | 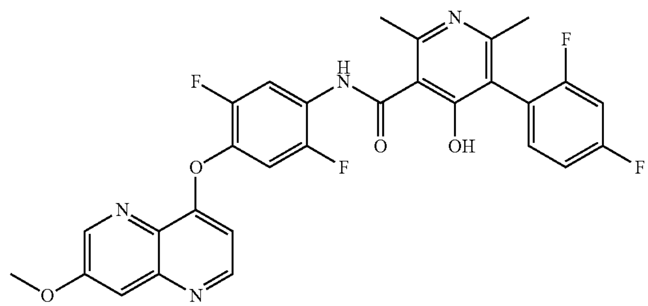 [SMILES: COc1cnc2c(Oc3cc(F)c(NC(=O)c4c(C)nc(C)c(-c5ccc(F)cc5F)c4O)cc3F)ccnc2c1] | N-[2,5-difluoro-4-[(7-methoxy-1,5-naphthyridin-4-yl)oxy]phenyl]-5-(2,4-difluorophenyl)-4-hydroxy-2,6-dimethylpyridine-3-carboxamide |
| 780 | 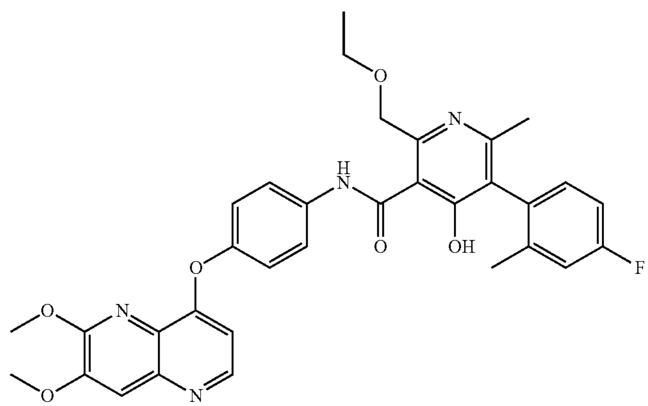 [SMILES: CCOCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-(ethoxymethyl)-5-(4-fluoro-2-methylphenyl)-4-hydroxy-6-methylpyridine-3-carboxamide |
| 781 | 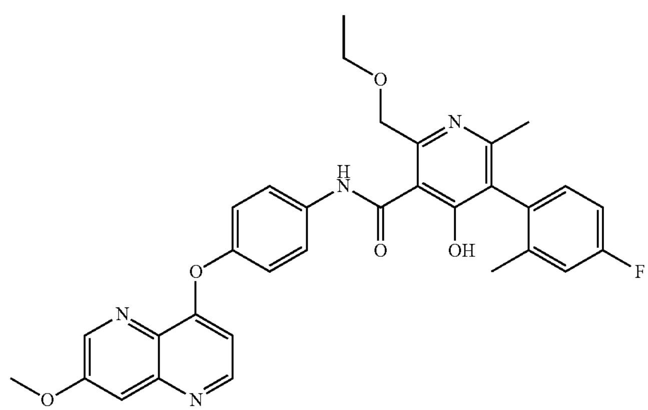 [SMILES: CCOCc1nc(C)c(-c2ccc(F)cc2C)c(O)c1C(=O)Nc1ccc(Oc2ccnc3cc(OC)cnc23)cc1] | 2-(ethoxymethyl)-5-(4-fluoro-2-methylphenyl)-4-hydroxy-N-[4-[(7-methoxy-1,5-naphthyridin-4-yl)oxy]phenyl]-6-methylpyridine-3-carboxamide |
| 782 | 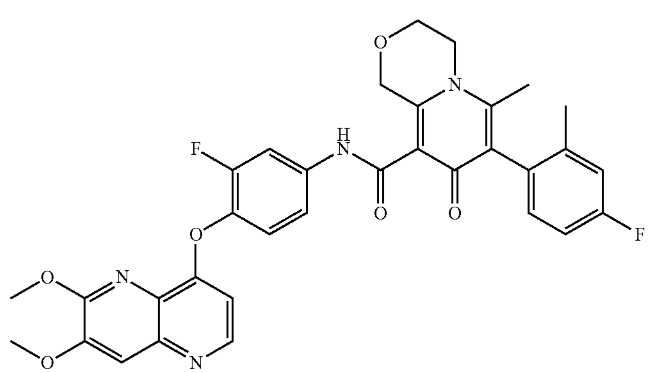 [SMILES: COc1cc2nccc(Oc3ccc(NC(=O)c4c5n(c(C)c(-c6ccc(F)cc6C)c4=O)CCOC5)cc3F)c2nc1OC] | N-[4-[(6,7-dimethoxy-1,5-naphthyridin-4-yl)oxy]-3-fluorophenyl]-7-(4-fluoro-2-methylphenyl)-6-methyl-8-oxo-3,4-dihydro-1H-pyrido[2,1-c][1,4]oxazine-9-carboxamide |

TABLE 1-continued

| Cpd # | Structure | IUPAC Name |
|---|---|---|
| 783 | 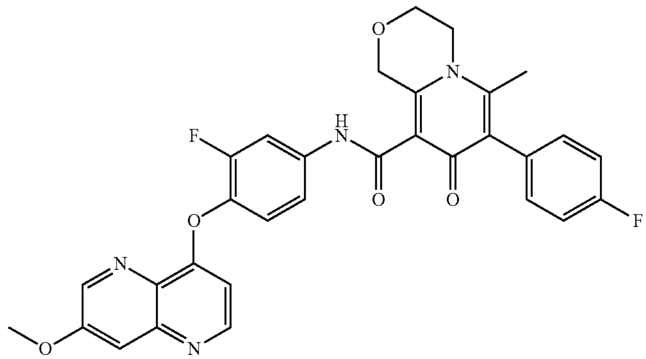 | N-[3-fluoro-4-[(7-methoxy-1,5-naphthyridin-4-yl)oxy]phenyl]-7-(4-fluorophenyl)-6-methyl-8-oxo-3,4-dihydro-1H-pyrido[2,1-c][1,4]oxazine-9-carboxamide |
| 784 | 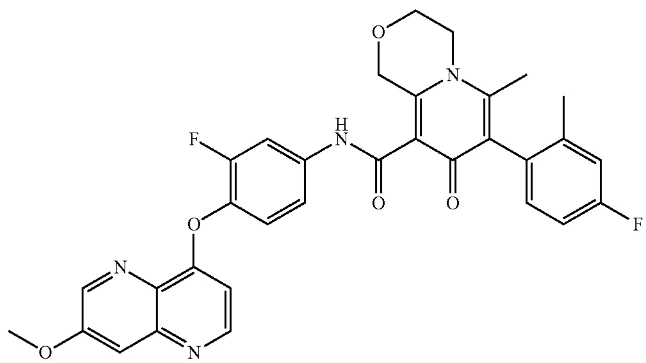 [SMILES: COc1cnc2c(Oc3ccc(NC(=O)c4c5n(c(C)c(-c6ccc(F)cc6C)c4=O)CCOC5)cc3F)ccnc2c1] | N-[3-fluoro-4-[(7-methoxy-1,5-naphthyridin-4-yl)oxy]phenyl]-7-(4-fluoro-2-methylphenyl)-6-methyl-8-oxo-3,4-dihydro-1H-pyrido[2,1-c][1,4]oxazine-9-carboxamide |
| 785 | 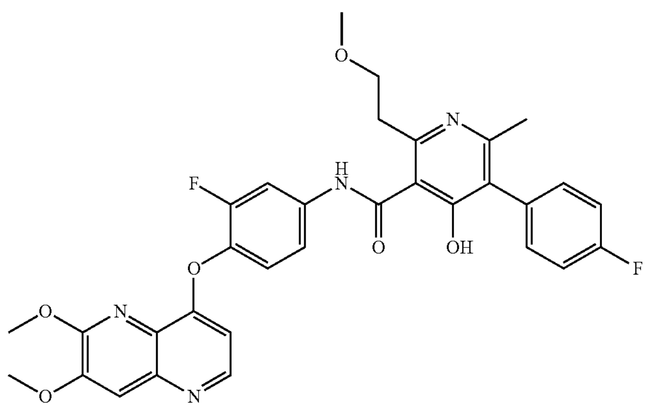 [SMILES: COCCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-hydroxy-2-(2-methoxyethyl)-6-methylpyridine-3-carboxamide |
| 786 | 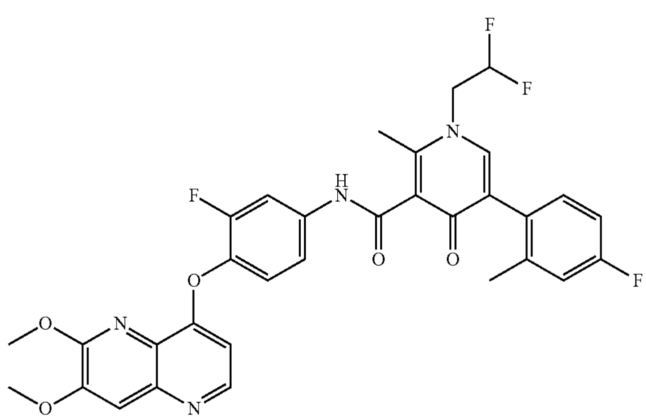 [SMILES: COc1cc2nccc(Oc3ccc(NC(=O)c4c(C)n(CC(F)F)cc(-c5ccc(F)cc5C)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluoro-2-methylphenyl)-2-methyl-4-oxopyridine-3-carboxamide |

TABLE 1-continued
| Cpd # | Structure | IUPAC Name |
|---|---|---|
| 787 | 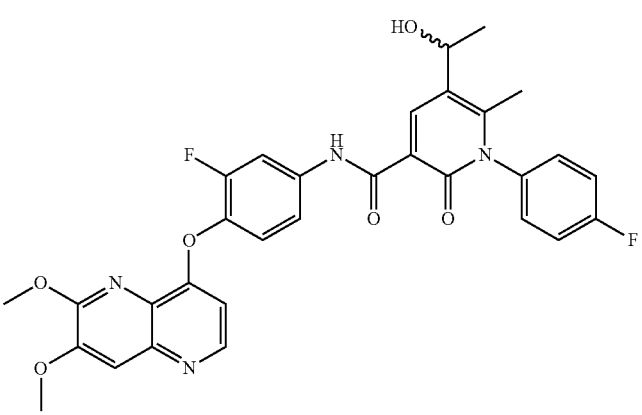 [SMILES: COc1cc2nccc(Oc3ccc(NC(=O)c4cc(C(C)O)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-5-(1-hydroxyethyl)-6-methyl-2-oxopyridine-3-carboxamide |
| 788 | 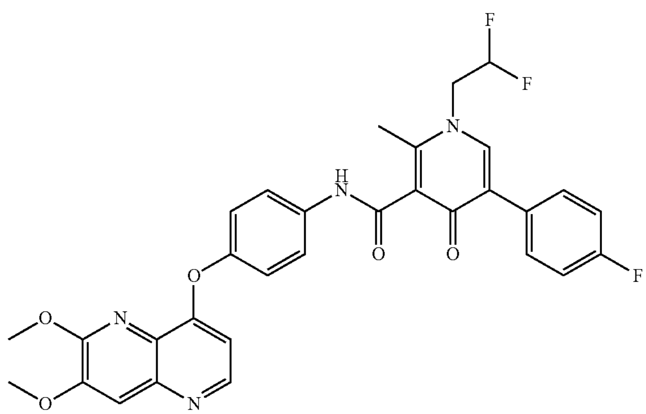 [SMILES: COc1cc2nccc(Oc3ccc(NC(=O)c4c(C)n(CC(F)F)cc(-c5ccc(F)cc5)c4=O)cc3)c2nc1OC] | 1-(2,2-difluoroethyl)-N-[4-[(6,7-dimethoxy-1,5-naphthyridin-4-yl)oxy]phenyl]-5-(4-fluorophenyl)-2-methyl-4-oxopyridine-3-carboxamide |
| 789 | 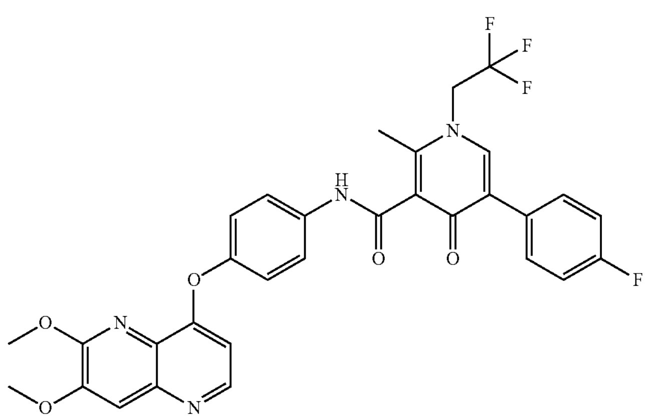 [SMILES: COc1cc2nccc(Oc3ccc(NC(=O)c4c(C)n(CC(F)(F)F)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-2-methyl-4-oxo-1-(2,2,2-trifluoroethyl)pyridine-3-carboxamide |

TABLE 1-continued

| Cpd # | Structure | IUPAC Name |
|---|---|---|
| 790 | 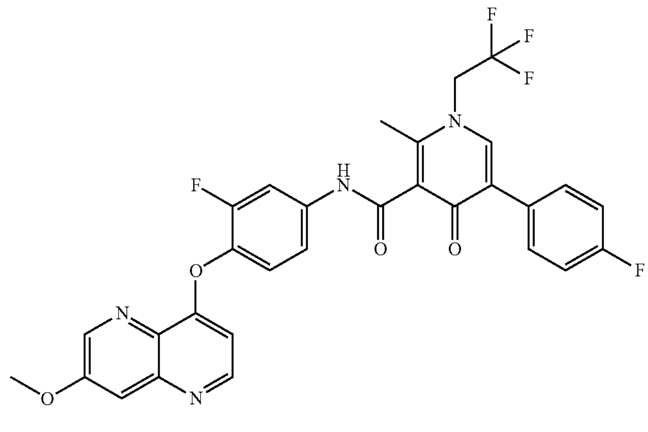 [SMILES: COc1cnc2c(Oc3ccc(NC(=O)c4c(C)n(CC(F)(F)F)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-2-methyl-4-oxo-1-(2,2,2-trifluoroethyl)pyridine-3-carboxamide |
| 791 | 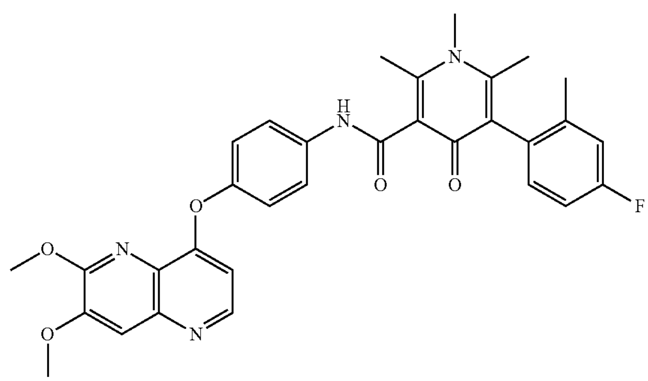 [SMILES: COc1cc2nccc(Oc3ccc(NC(=O)c4c(C)n(C)c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-1,2,6-trimethyl-4-oxopyridine-3-carboxamide |
| 792 | 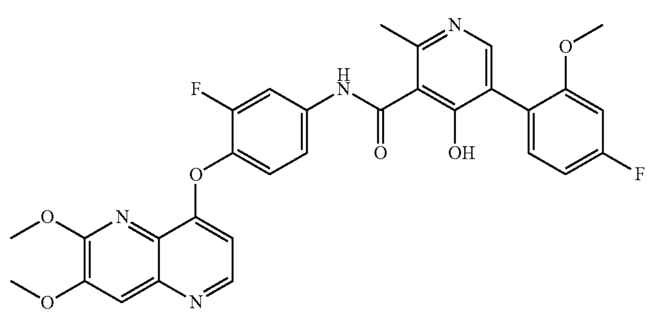 [SMILES: COc1cc(F)ccc1-c1cnc(C)c(C(=O)Nc2ccc(Oc3ccnc4cc(OC)c(OC)nc34)c(F)c2)c1O] | N-[4-[(6,7-dimethoxy-1,5-naphthyridin-4-yl)oxy]-3-fluorophenyl]-5-(4-fluoro-2-methoxyphenyl)-4-hydroxy-2-methylpyridine-3-carboxamide |
| 793 | 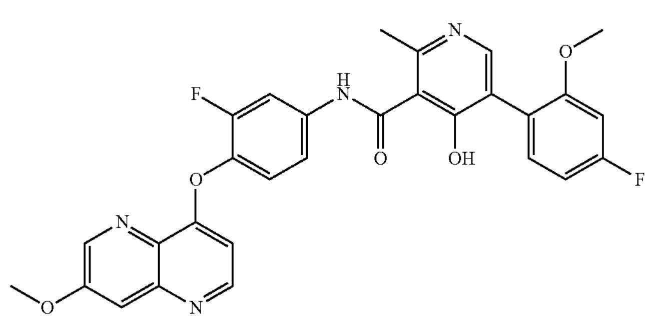 [SMILES: COc1cnc2c(Oc3ccc(NC(=O)c4c(C)ncc(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-2-methylpyridine-3-carboxamide |

TABLE 1-continued

| Cpd # | Structure | IUPAC Name |
|---|---|---|
| 794 | 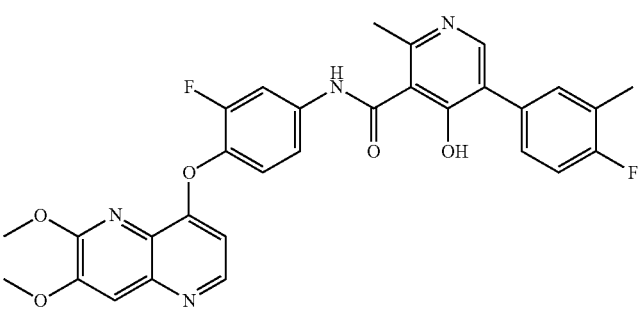 | N-[4-[(6,7-dimethoxy-1,5-naphthyridin-4-yl)oxy]-3-fluorophenyl]-5-(4-fluoro-3-methylphenyl)-4-hydroxy-2-methylpyridine-3-carboxamide |
| 795 | 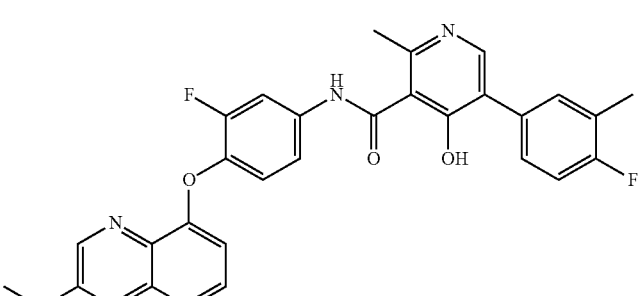 | N-[3-fluoro-4-[(7-methoxy-1,5-naphthyridin-4-yl)oxy]phenyl]-5-(4-fluoro-3-methylphenyl)-4-hydroxy-2-methylpyridine-3-carboxamide |
| 796 | 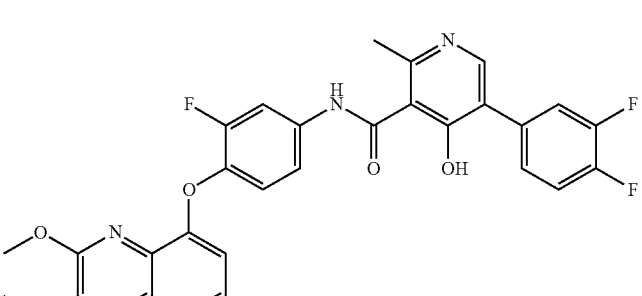 | 5-(3,4-difluorophenyl)-N-[4-[(6,7-dimethoxy-1,5-naphthyridin-4-yl)oxy]-3-fluorophenyl]-4-hydroxy-2-methylpyridine-3-carboxamide |
| 797 | 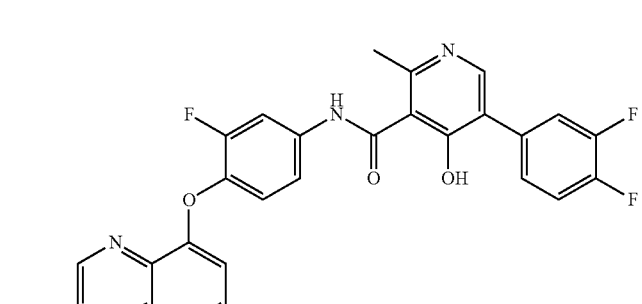 | 5-(3,4-difluorophenyl)-N-[3-fluoro-4-[(7-methoxy-1,5-naphthyridin-4-yl)oxy]phenyl]-4-hydroxy-2-methylpyridine-3-carboxamide |

TABLE 1-continued

| Cpd # | Structure | IUPAC Name |
|---|---|---|
| 798 | 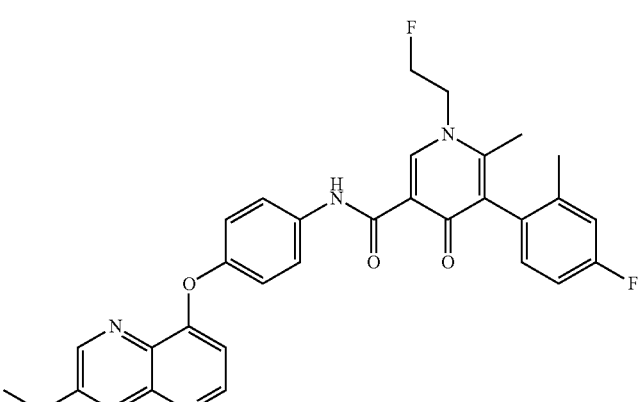 | 1-(2-fluoroethyl)-5-(4-fluoro-2-methylphenyl)-N-[4-[(7-methoxy-1,5-naphthyridin-4-yl)oxy]phenyl]-6-methyl-4-oxopyridine-3-carboxamide |
| 799 | 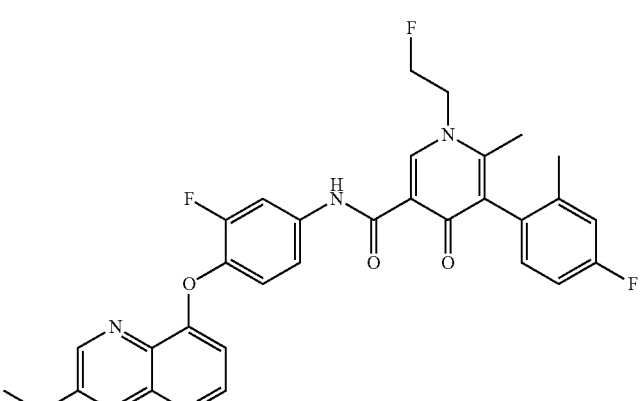 | 1-(2-fluoroethyl)-N-[3-fluoro-4-[(7-methoxy-1,5-naphthyridin-4-yl)oxy]phenyl]-5-(4-fluoro-2-methylphenyl)-6-methyl-4-oxopyridine-3-carboxamide |
| 800 | 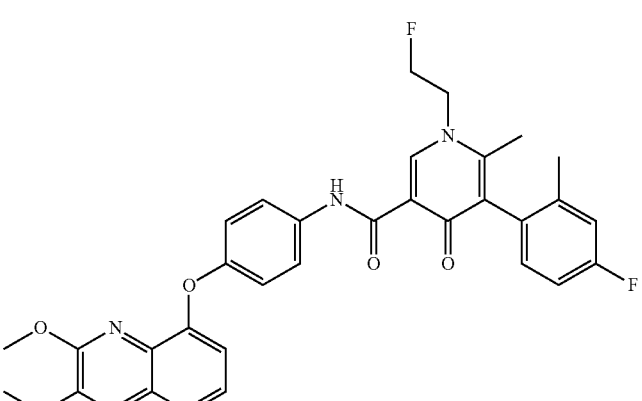 | N-[4-[(6,7-dimethoxy-1,5-naphthyridin-4-yl)oxy]phenyl]-1-(2-fluoroethyl)-5-(4-fluoro-2-methylphenyl)-6-methyl-4-oxopyridine-3-carboxamide |

TABLE 1-continued

| Cpd # | Structure | IUPAC Name |
|---|---|---|
| 801 | 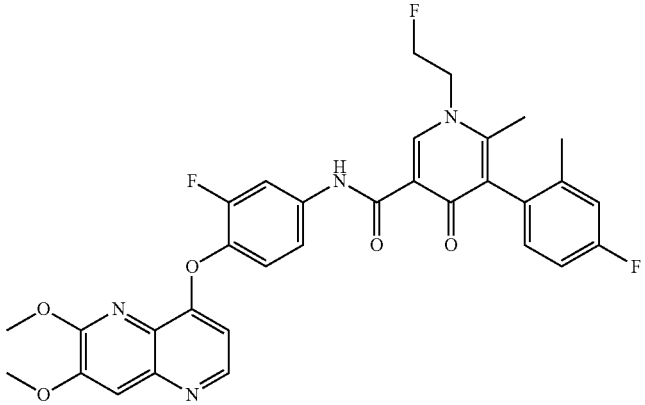 [SMILES: COc1cc2nccc(Oc3ccc(NC(=O)c4cn(CCF)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluoro-2-methylphenyl)-6-methyl-4-oxopyridine-3-carboxamide |
| 802 | 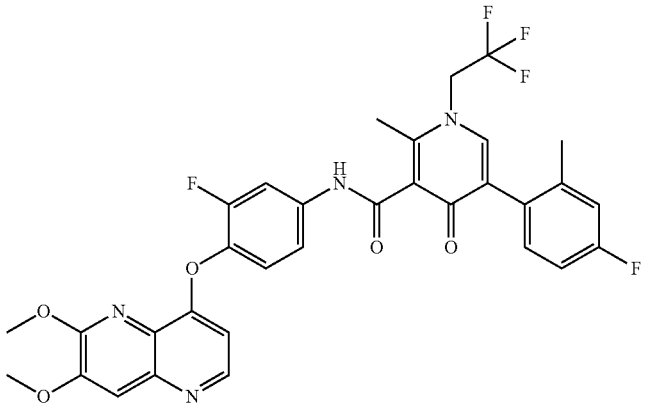 [SMILES: COc1cc2nccc(Oc3ccc(NC(=O)c4c(C)n(CC(F)(F)F)cc(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-2-methyl-4-oxo-1-(2,2,2-trifluoroethyl)pyridine-3-carboxamide |
| 803 | 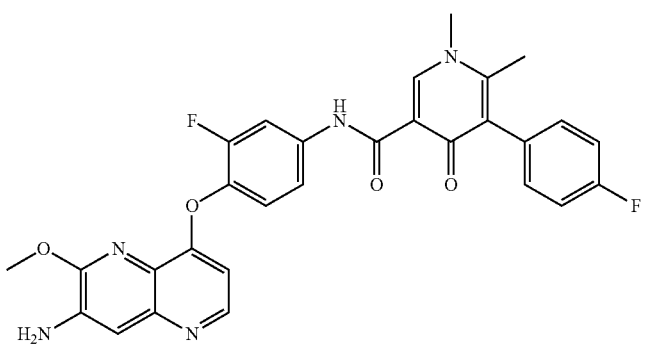 [SMILES: COc1nc2c(Oc3ccc(NC(=O)c4cn(C)c(C)c(-c5ccc(F)cc5)c4=O)cc3F)ccnc2cc1N] | N-[4-[(7-amino-6-methoxy-1,5-naphthyridin-4-yl)oxy]-3-fluorophenyl]-5-(4-fluorophenyl)-1,6-dimethyl-4-oxopyridine-3-carboxamide |
| 804 | 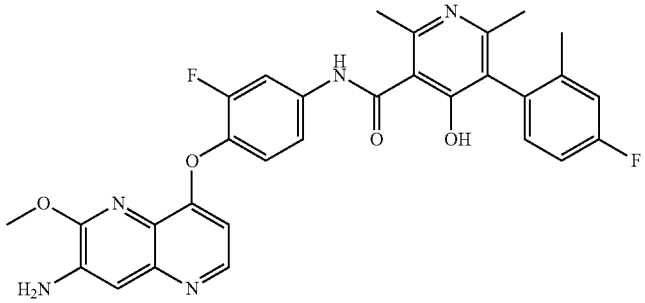 [SMILES: COc1nc2c(Oc3ccc(NC(=O)c4c(C)nc(C)c(-c5ccc(F)cc5C)c4O)cc3F)ccnc2cc1N] | N-[4-[(7-amino-6-methoxy-1,5-naphthyridin-4-yl)oxy]-3-fluorophenyl]-5-(4-fluoro-2-methylphenyl)-4-hydroxy-2,6-dimethylpyridine-3-carboxamide |

TABLE 1-continued

| Cpd # | Structure | IUPAC Name |
|---|---|---|
| 805 | 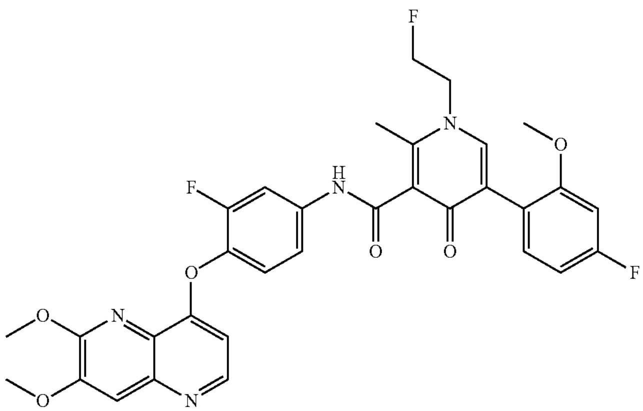 [SMILES: COc1cc(F)ccc1-c1cn(CCF)c(C)c(C(=O)Nc2ccc(Oc3ccnc4cc(OC)c(OC)nc34)c(F)c2)c1=O] | N-[4-[(6,7-dimethoxy-1,5-naphthyridin-4-yl)oxy]-3-fluorophenyl]-1-(2-fluoroethyl)-5-(4-fluoro-2-methoxyphenyl)-2-methyl-4-oxopyridine-3-carboxamide |
| 806 | 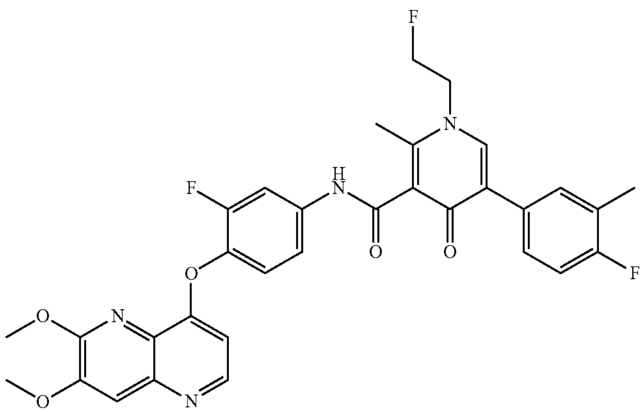 | N-[4-[(6,7-dimethoxy-1,5-naphthyridin-4-yl)oxy]-3-fluorophenyl]-1-(2-fluoroethyl)-5-(4-fluoro-3-methylphenyl)-2-methyl-4-oxopyridine-3-carboxamide |
| 807 | 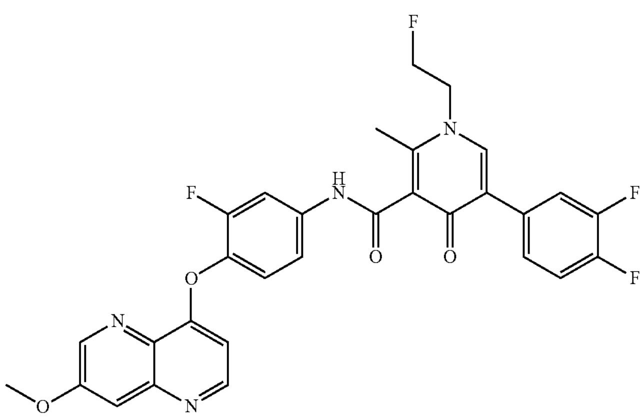 | 5-(3,4-difluorophenyl)-1-(2-fluoroethyl)-N-[3-fluoro-4-[(7-methoxy-1,5-naphthyridin-4-yl)oxy]phenyl]-2-methyl-4-oxopyridine-3-carboxamide |
| 808 | 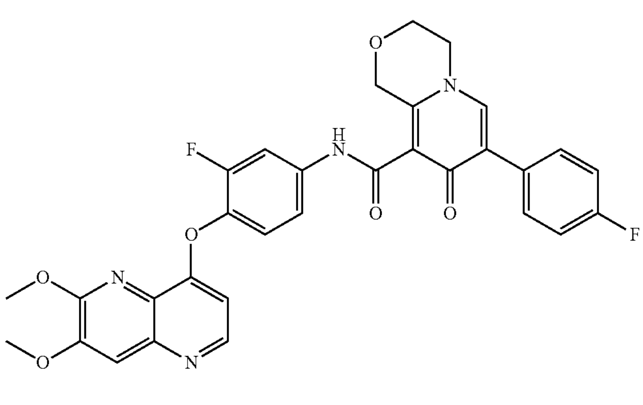 [SMILES: COc1cc2nccc(Oc3ccc(NC(=O)c4c5n(cc(-c6ccc(F)cc6)c4=O)CCOC5)cc3F)c2nc1OC] | N-[4-[(6,7-dimethoxy-1,5-naphthyridin-4-yl)oxy]-3-fluorophenyl]-7-(4-fluorophenyl)-8-oxo-3,4-dihydro-1H-pyrido[2,1-c][1,4]oxazine-9-carboxamide |

TABLE 1-continued

| Cpd # | Structure | IUPAC Name |
|---|---|---|
| 809 | 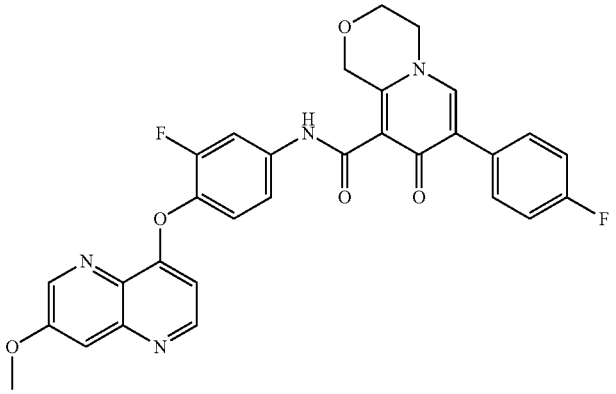 [SMILES: COc1cnc2c(Oc3ccc(NC(=O)c4c5n(cc(-c6ccc(F)cc6)c4=O)CCOC5)cc3F)ccnc2c1] | N-[3-fluoro-4-[(7-methoxy-1,5-naphthyridin-4-yl)oxy]phenyl]-7-(4-fluorophenyl)-8-oxo-3,4-dihydro-1H-pyrido[2,1-c][1,4]oxazine-9-carboxamide |
| 810 | 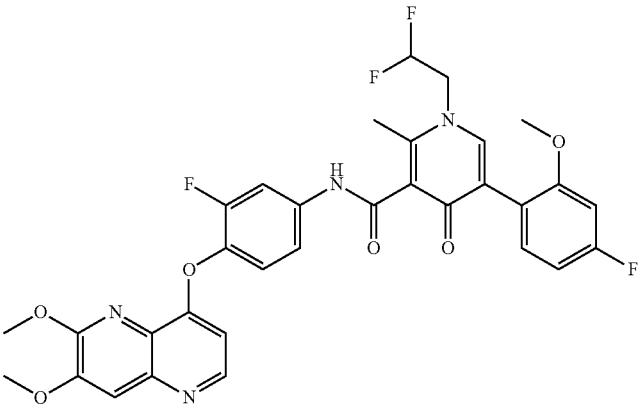 [SMILES: COc1cc(F)ccc1-c1cn(CC(F)F)c(C)c(C(=O)Nc2ccc(Oc3ccnc4cc(OC)c(OC)nc34)c(F)c2)c1=O] | 1-(2,2-difluoroethyl)-N-[4-[(6,7-dimethoxy-1,5-naphthyridin-4-yl)oxy]-3-fluorophenyl]-5-(4-fluoro-2-methoxyphenyl)-2-methyl-4-oxopyridine-3-carboxamide |
| 811 | 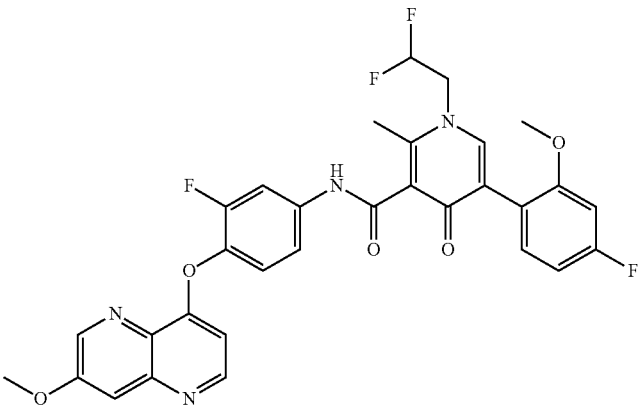 [SMILES: COc1cnc2c(Oc3ccc(NC(=O)c4c(C)n(CC(F)F)cc(-c5ccc(F)cc5OC)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluoro-2-methoxyphenyl)-2-methyl-4-oxopyridine-3-carboxamide |

TABLE 1-continued

| Cpd # | Structure | IUPAC Name |
|---|---|---|
| 812 | 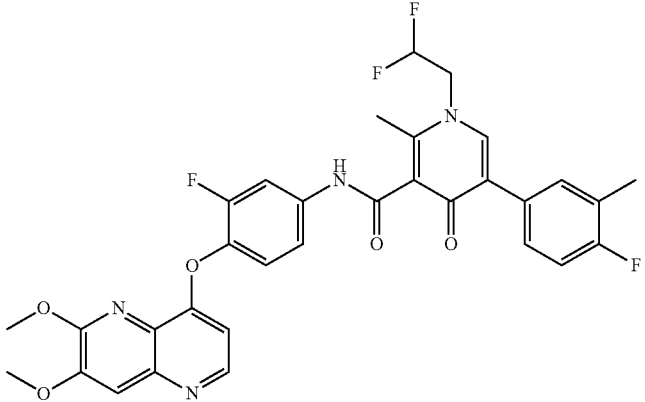 | 1-(2,2-difluoroethyl)-N-[4-[(6,7-dimethoxy-1,5-naphthyridin-4-yl)oxy]-3-fluorophenyl]-5-(4-fluoro-3-methylphenyl)-2-methyl-4-oxopyridine-3-carboxamide |
| 813 | 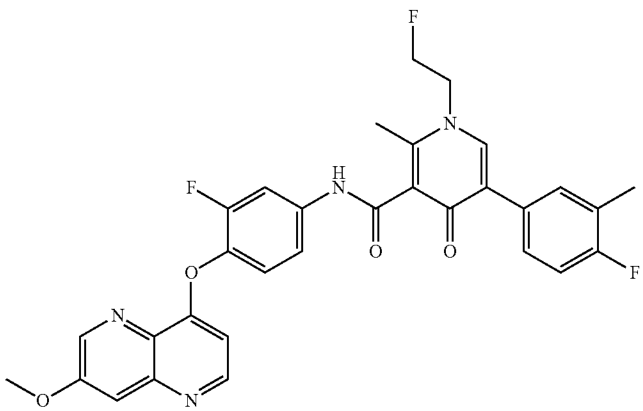 | 1-(2-fluoroethyl)-N-[3-fluoro-4-[(7-methoxy-1,5-naphthyridin-4-yl)oxy]phenyl]-5-(4-fluoro-3-methylphenyl)-2-methyl-4-oxopyridine-3-carboxamide |
| 814 | 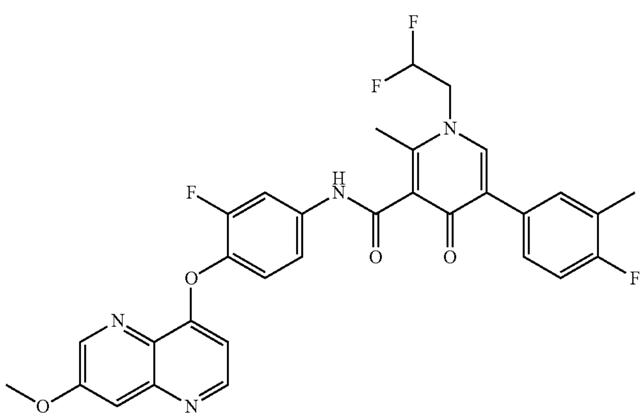 | 1-(2,2-difluoroethyl)-N-[3-fluoro-4-[(7-methoxy-1,5-naphthyridin-4-yl)oxy]phenyl]-5-(4-fluoro-3-methylphenyl)-2-methyl-4-oxopyridine-3-carboxamide |

TABLE 1-continued

| Cpd # | Structure | IUPAC Name |
|---|---|---|
| 815 | 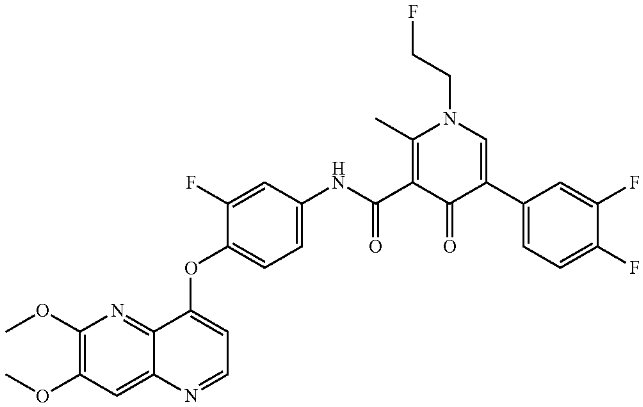 | 5-(3,4-difluorophenyl)-N-[4-[(6,7-dimethoxy-1,5-naphthyridin-4-yl)oxy]-3-fluorophenyl]-1-(2-fluoroethyl)-2-methyl-4-oxopyridine-3-carboxamide |
| 816 | 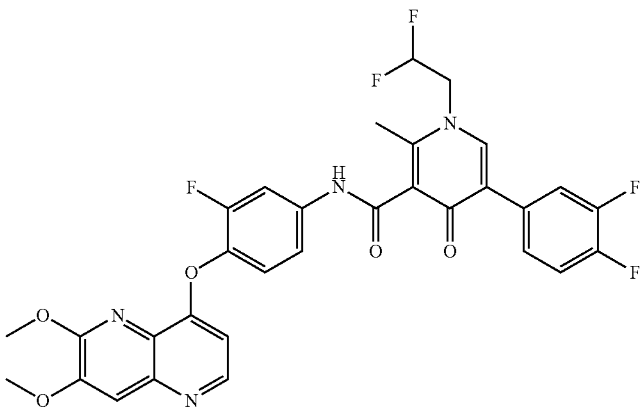 | 1-(2,2-difluoroethyl)-5-(3,4-difluorophenyl)-N-[4-[(6,7-dimethoxy-1,5-naphthyridin-4-yl)oxy]-3-fluorophenyl]-2-methyl-4-oxopyridine-3-carboxamide |
| 817 | 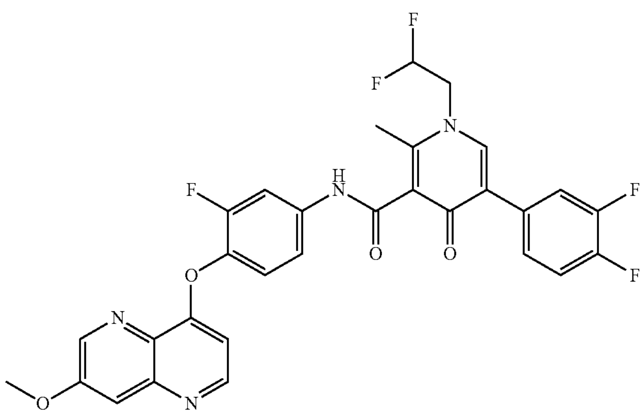 | 1-(2,2-difluoroethyl)-5-(3,4-difluorophenyl)-N-[3-fluoro-4-[(7-methoxy-1,5-naphthyridin-4-yl)oxy]phenyl]-2-methyl-4-oxopyridine-3-carboxamide |
| 818 | 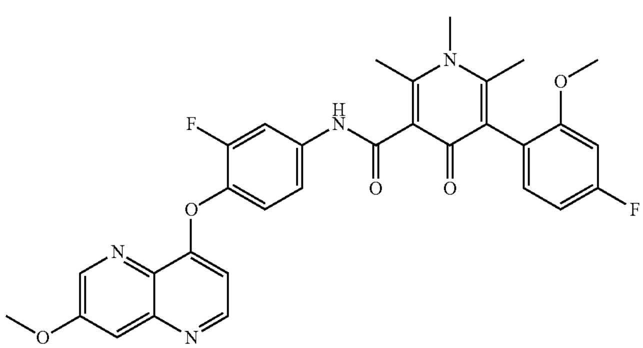 [SMILES: COc1cnc2c(Oc3ccc(NC(=O)c4c(C)n(C)c(C)c(-c5ccc(F)cc5OC)c4=O)cc3F)ccnc2c1] | N-[3-fluoro-4-[(7-methoxy-1,5-naphthyridin-4-yl)oxy]phenyl]-5-(4-fluoro-2-methoxyphenyl)-1,2,6-trimethyl-4-oxopyridine-3-carboxamide |

TABLE 1-continued

| Cpd # | Structure | IUPAC Name |
|---|---|---|
| 819 | 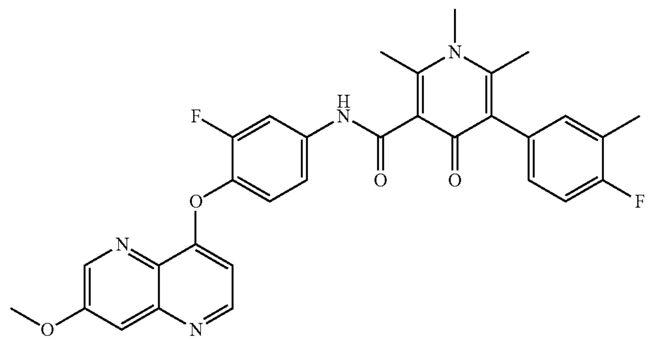 | N-[3-fluoro-4-[(7-methoxy-1,5-naphthyridin-4-yl)oxy]phenyl]-5-(4-fluoro-3-methylphenyl)-1,2,6-trimethyl-4-oxopyridine-3-carboxamide |
| 820 | 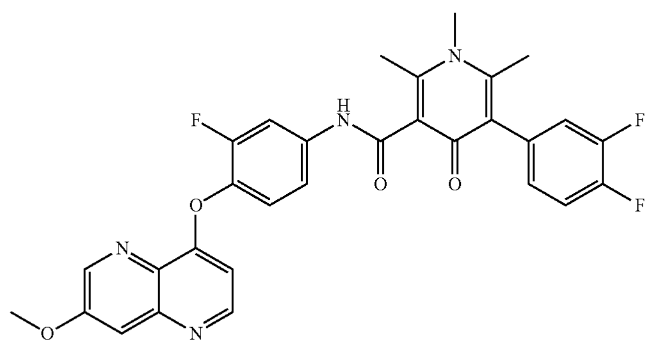 | 5-(3,4-difluorophenyl)-N-[3-fluoro-4-[(7-methoxy-1,5-naphthyridin-4-yl)oxy]phenyl]-1,2,6-trimethyl-4-oxopyridine-3-carboxamide |
| 821 | 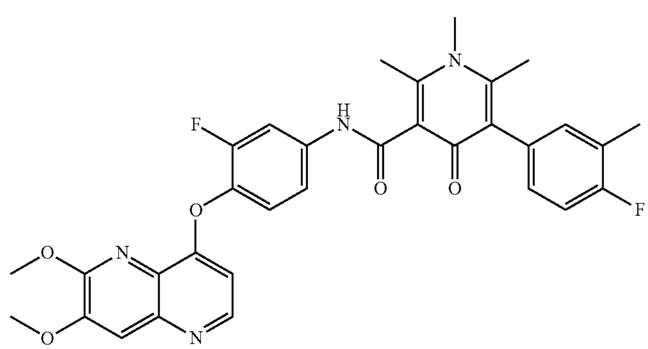 | N-[4-[(6,7-dimethoxy-1,5-naphthyridin-4-yl)oxy]-3-fluorophenyl]-5-(4-fluoro-3-methylphenyl)-1,2,6-trimethyl-4-oxopyridine-3-carboxamide |
| 822 | 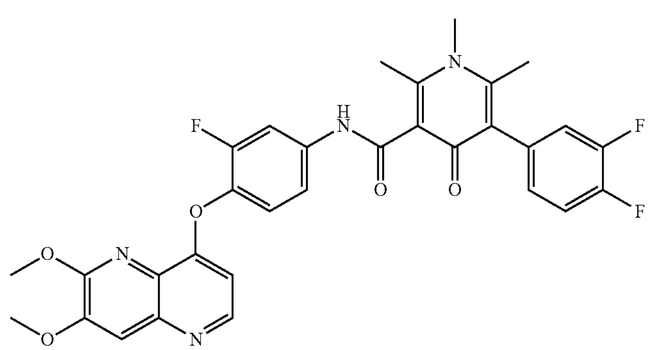 | 5-(3,4-difluorophenyl)-N-[4-[(6,7-dimethoxy-1,5-naphthyridin-4-yl)oxy]-3-fluorophenyl]-1,2,6-trimethyl-4-oxopyridine-3-carboxamide |

TABLE 1-continued

| Cpd # | Structure | IUPAC Name |
|---|---|---|
| 823 | 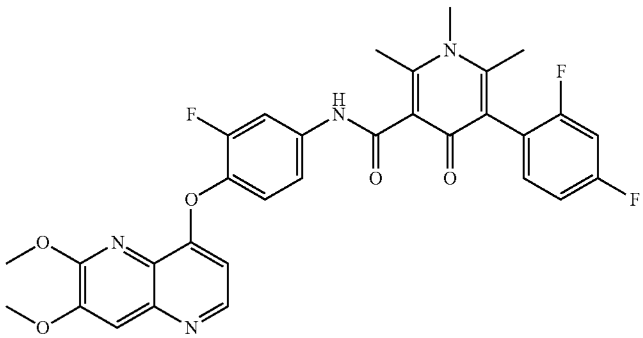 [SMILES: COc1cc2nccc(Oc3ccc(NC(=O)c4c(C)n(C)c(C)c(-c5ccc(F)cc5F)c4=O)cc3F)c2nc1OC] | 5-(2,4-difluorophenyl)-N-[4-[(6,7-dimethoxy-1,5-naphthyridin-4-yl)oxy]-3-fluorophenyl]-1,2,6-trimethyl-4-oxopyridine-3-carboxamide |
| 824 | 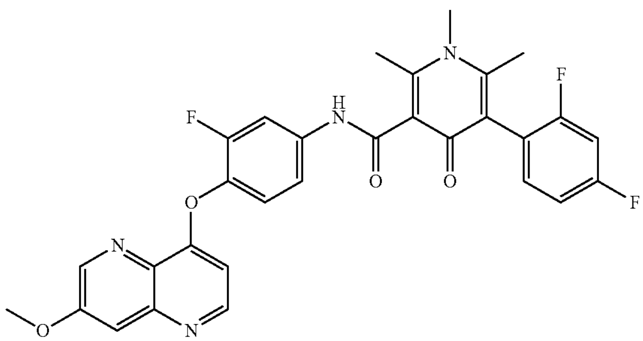 [SMILES: COc1cnc2c(Oc3ccc(NC(=O)c4c(C)n(C)c(C)c(-c5ccc(F)cc5F)c4=O)cc3F)ccnc2c1] | 5-(2,4-difluorophenyl)-N-[3-fluoro-4-[(7-methoxy-1,5-naphthyridin-4-yl)oxy]phenyl]-1,2,6-trimethyl-4-oxopyridine-3-carboxamide |

Some embodiments provide for a compound of Table 1 or a pharmaceutically acceptable salt, a stereoisomer, or a mixture of stereoisomers thereof.

In some embodiments, provided is a compound, or a pharmaceutically acceptable salt or a stereoisomer thereof, of Table 2:

TABLE 2

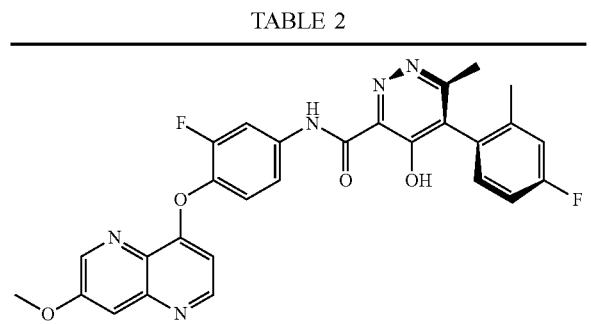

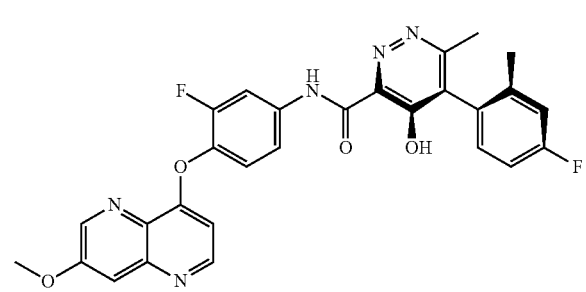

TABLE 2-continued

In some embodiments, provided is a compound, or a pharmaceutically acceptable salt thereof, of Table 3:

TABLE 3

| Cpd # | Structure | IUPAC Name |
|---|---|---|
| 490 | 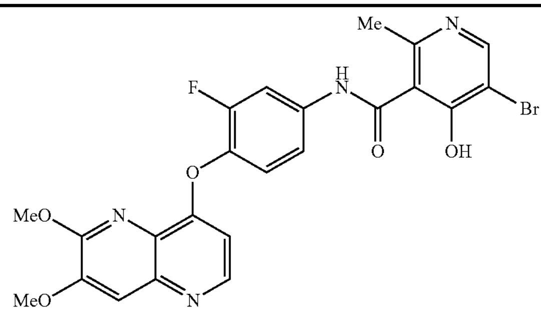 | 5-bromo-N-[4-[(6,7-dimethoxy-1,5-naphthyridin-4-yl)oxy]-3-fluorophenyl]-4-hydroxy-2-methylpyridine-3-carboxamide |
| 492 | 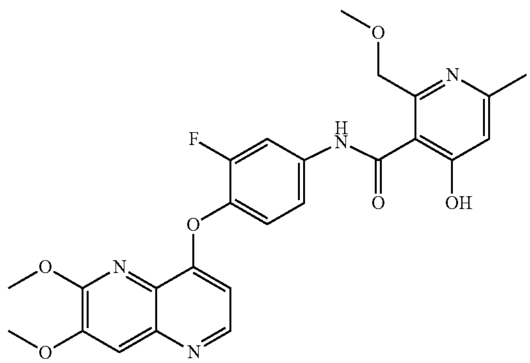 | N-[4-[(6,7-dimethoxy-1,5-naphthyridin-4-yl)oxy]-3-fluorophenyl]-4-hydroxy-2-(methoxymethyl)-6-methylpyridine-3-carboxamide |
| 535 | 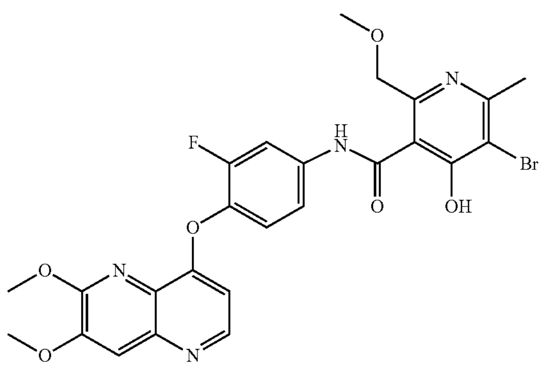 [SMILES: COCc1nc(C)c(Br)c(O)c1C(=O)Nc1ccc(Oc2ccnc3cc(OC)c(OC)nc23)c(F)c1] | 5-bromo-N-[4-[(6,7-dimethoxy-1,5-naphthyridin-4-yl)oxy]-3-fluorophenyl]-4-hydroxy-2-(methoxymethyl)-6-methylpyridine-3-carboxamide |
| 536 | 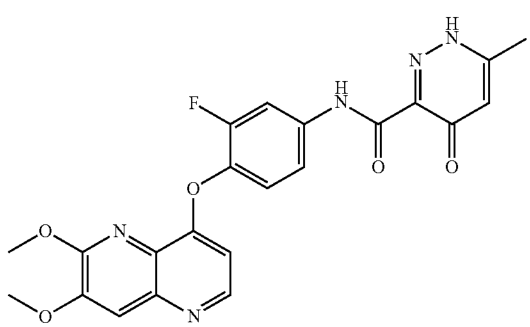 | N-[4-[(6,7-dimethoxy-1,5-naphthyridin-4-yl)oxy]-3-fluorophenyl]-6-methyl-4-oxo-1H-pyridazine-3-carboxamide |

Treatment Methods and Uses

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one or ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

Some embodiments provide for a method of modulating in vivo activity of a protein kinase in a subject, the method comprising: administering to the subject a therapeutically effective amount of a compound as described herein, or a pharmaceutically acceptable salt or stereoisomer thereof, or a pharmaceutical composition as described herein.

Some embodiments provide for methods of modulating in vivo activity of a protein kinase in a subject, the method comprising administering to the subject a therapeutically effective amount of a compound as described herein, or a pharmaceutically acceptable salt, stereoisomer, or mixture of stereoisomers thereof, or a pharmaceutical composition as described herein.

Some embodiments provide for a method of treating a disease, disorder, or syndrome in a subject, the method comprising: administering to the subject in need thereof a therapeutically effective amount of a compound as described herein, or a pharmaceutically acceptable salt or stereoisomer thereof, or a pharmaceutical composition as described herein, wherein the disease, disorder, or syndrome is mediated at least in part by modulating in vivo activity of a protein kinase.

Some embodiments provide for methods of treating a disease, disorder, or syndrome in a subject, the method comprising administering to the subject in need thereof a therapeutically effective amount of a compound as described herein, or a pharmaceutically acceptable salt, stereoisomer, or mixture of stereoisomers thereof, or a pharmaceutical composition as described herein, wherein the disease, disorder, or syndrome is mediated at least in part by modulating in vivo activity of a protein kinase.

In some embodiments, the protein kinase is AXL, KDR, Mer, or Met. In some embodiments, the disease is cancer.

Some embodiments provide for methods of treating a disease, disorder, or syndrome in a subject, the method comprising: administering to the subject in need thereof a therapeutically effective amount of a compound as described herein, or a pharmaceutically acceptable salt or stereoisomer thereof, or a pharmaceutical composition as described herein, in combination with a therapeutic agent or therapy.

Some embodiments provide for methods of treating a disease, disorder, or syndrome in a subject, the method comprising: administering to the subject in need thereof a therapeutically effective amount of a compound as described herein, or a pharmaceutically acceptable salt, stereoisomer, or mixture of stereoisomers thereof, or a pharmaceutical composition as described herein, in combination with a therapeutic agent or therapy.

In some embodiments, the therapeutic agent is an immunotherapeutic agent or a cancer vaccine. In some embodiments, the immunotherapeutic agent is an anti-PD-1 antibody or anti-PD-L1 antibody.

Provided herein are methods for treating cancer.

"Cancer" includes tumor types such as tumor types including breast, colon, renal, lung, squamous cell myeloid leukemia, hemangiomas, melanomas, astrocytomas, and glioblastomas as well as other cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia, renal cell carcinoma), bladder and urethra (squamous cell carcinoma, transitional cell carcinoma, adenocarcinoma), prostate (adenocarcinoma, sarcoma, small cell carcinoma of the prostate), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma; as well as cancers of the thyroid including medullary thyroid cancer. Thus, the term "cancerous cell," as provided herein, includes a cell afflicted by any one of the above-identified conditions.

In one embodiment, the cancer is selected from ovarian cancer, prostate cancer, lung cancer, medullary thyroid cancer, liver cancer, gastrointestinal cancer, pancreatic cancer, bone cancer, hematologic cancer, skin cancer, kidney cancer, breast cancer, colon cancer, and fallopian tube cancer.

In some embodiments, the cancer is clear cell carcinoma, clear cell renal cell carcinoma, non-clear cell carcinoma, non-clear cell renal cell carcinoma, urothelial carcinoma, salivary gland cancer, penile squamous cell carcinoma, neuroendocrine tumors, adrenocortical carcinoma, or merkel cell carcinoma.

In another embodiment, the disease or disorder is ovarian cancer.

In another embodiment, the disease or disorder is prostate cancer.

In another embodiment, the disease or disorder is lung cancer.

In another embodiment, the disease or disorder is medullary thyroid cancer.

In another embodiment, the disease or disorder is liver cancer.

In another embodiment, the disease or disorder is gastrointestinal cancer.

In another embodiment, the disease or disorder is pancreatic cancer.

In another embodiment, the disease or disorder is bone cancer.

In another embodiment, the disease or disorder is hematologic cancer.

In another embodiment, the disease or disorder is skin cancer.

In another embodiment, the disease or disorder is kidney cancer.

In another embodiment, the disease or disorder is breast cancer.

In another embodiment, the disease or disorder is colon cancer. In another embodiment, the disease or disorder is fallopian cancer. In another embodiment, the disease or disorder is liver cancer, wherein the liver cancer is hepatocellular carcinoma, cholangiocarcinoma, hepatoblastoma, angiosarcoma, hepatocellular adenoma, or hemagioma.

In another embodiment, the disease or disorder is gastrointestinal cancer, wherein the gastrointestinal cancer is cancer of the esophagus which is squamous cell carcinoma, adenocarcinoma, or leiomyosarcoma; cancer of the stomach which is carcinoma, or lymphoma; cancer of the pancreas, which is ductal adenocarcinoma, insulinoma, gucagonoma, gastrinoma, carcinoid tumors, or vipoma; cancer of the small bowel, which is adenocarcinoma, lymphoma, carcinoid tumors, Karposi's sarcoma, leiomyoma, hemagioma, lipoma, or cancer of the large bowel, which is adenocarcinoma, tubular adenoma, villous adenoma, hamartoma, or leiomyoma.

In another embodiment, the disease or disorder is cancer of the pancreas, wherein the cancer of the pancreas is ductal adenocarcinoma, insulinoma, gucagonoma, gastrinoma, carcinoid tumors, or vipoma.

In another embodiment, the disease or disorder is bone cancer, wherein the bone cancer is osteosarcoma, fibrosarcoma, malignant fibrous histiocytoma, chondrosarcoma, Ewing's sarcoma, malignant reticulum cell sarcoma, multiple myeloma, malignant giant cell tumor chordoma, osteocartiliginous exostoses, chondroblastoma, chondromyxofibroma, or osteoid osteoma.

In another embodiment, the disease or disorder is hematologic cancer, wherein the hematologic cancer is myeloid leukemia, acute lymphoblastic leukemia, chronic lymphocytic leukemia, myeloproliferative diseases, multiple myeloma, or myelodysplastic syndrome.

In another embodiment, the disease or disorder is skin cancer, wherein the skin cancer is malignant melanoma, basal cell carcinoma, squamous cell carcinoma, or Karposi's sarcoma.

In another embodiment, the disease or disorder is a renal tumor or renal cell carcinoma.

In another embodiment, the disease or disorder is breast cancer.

In another embodiment, the disease or disorder is a colon cancer tumor.

In another embodiment, the disease or disorder is fallopian tube carcinoma.

Combination Therapies

A compound as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of a compound as described herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs and in publicly available sources such as Cancer Principles and Practice of Oncology by V. T. Devita and S. Hellman (editors), 1 1$^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound as disclosed herein, or a pharmaceutically acceptable salt, stereoisomer, or mixture of stereoisomers thereof, and at least one immunotherapy. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to rituximab (Rituxan), an antibody against the CD20 antigen used to treat, for example, B cell non-Hodgkin lymphoma; trastuzumab (Herceptin), an antibody against the HER2 protein used to treat, for example, advanced breast cancer; alemtuzumab (Campath), an antibody against the CD52 antigen used to treat, for example, B cell chronic lymphocytic leukemia (B-CLL); cetuximab (Erbitux), an antibody against the EGFR protein used, for example, in combination with irinotecan to treat, for example, advanced colorectal cancer and head and neck cancers; and bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody ibritumomab tiuxetan (Zevalin) which delivers radioactivity directly to cancerous B lymphocytes and is used to treat, for example, B cell non-Hodgkin lymphoma; radiolabeled antibody tositumomab (Bexxar) which is used to treat, for example, certain types of non-Hodgkin lymphoma; and immunotoxin gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN® (trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITETXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-1 14 is a primatized anti-CD80 antibody (IDEC Pharm/Mitsubishi); ZEVALIN™ is a radiolabeled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA (ruplizumab) is a humanized anti-CD40L IgG antibody (Biogen); ANTE- GREN™ is a humanized anti-VLA-4 IgG antibody (Elan); and CAT-152 is a human anti-TGF-beta$_2$ antibody (Cambridge Ab Tech).

Immunotherapies that can be used in combination with a compound as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IF A); QS-21; DETOX; Levamisole; and Dinitrophenyl (DNP), and combinations thereof, such as, for example, combinations of, interleukins, for example, IL-2 with other cytokines, such as IFN-alpha.

In various embodiments, an immunological therapy or an immunological therapeutic agent can include, one or more of the following: an adoptive cell transfer, an angiogenesis inhibitor, *Bacillus*-Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The function or at least one of the functions of the immunological therapy or immunological therapeutic agent, collectively referred to herein as an "immunotherapeutic agent."

In various embodiments described herein, an exemplary immunotherapeutic agent is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art). In some embodiments, the immunotherapeutic agent can be an antibody that modulates a costimulatory molecule, bind to an antigen on the surface of an immune cell, or a cancer cell. In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Bamase-barstar, a scFv-Fc, a sc(Fab)2, a Trimeric antibody construct, a Triabody antibody construct, a Trimerbody antibody construct, a Tribody antibody construct, a Collabody antibody construct, a (scFv-TNFa)3, or a F(ab)3/DNL antibody construct.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity. In some embodiments, the immunotherapeutic agent is an antibody modulator that targets PD-1, PD-L1, PD-L2, CEACAM (e g., CEACAM-1, -3 and/or -5), CTLA-4, TIM-3, LAG-3, VISTA, BTLA, TIGIT, LAIR1, CD160, 2B4, TGF beta, 0X40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors.

In some embodiments, the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, 0X40, ICOS, SLAM (e.g., SLAMF7), HVEM, LIGHT, CD2, CD27, CD28, CDS, ICAM-1, LFA-1(CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of 0X40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide. In some embodiments, the immunotherapeutic agent is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an 0X40 agonist (e.g., an anti-0X40 antibody molecule), or (xii) a CD27 agonist (e.g., an anti-CD27 antibody molecule). In one embodiment, the immunomodulator is an inhibitor of PD-1, PD-L1, PD-L2, CTLA-4, TIM-3, LAG-3, CEACAM (e.g., CEACAM-1, -3 and/or -5), VISTA, BTLA, TIGIT, LAIR, CD 160, 2B4 and/or TGF beta. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CEACAM (e.g., CEACAM-1, -3 and/or -5), CTLA-4, TIM-3, LAG-3, VISTA, BTLA, TIGIT, LAIR1, CD 160, 2B4, TGF beta, or a combination thereof.

In one embodiment, the treatment method includes the co-administration of a compound as disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{88}$, $Sm^{153}$, $Bi^{22}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agents" include chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX, AstraZeneca), sunitib (SETTENT®, Pfizer/Sugen), letrozole (FEMARA®, Novartis), imatinib mesylate (GLEEVEC®, Novartis), fmasunate (VATALANIB®, Novartis), oxaliplatin (ELOXATIN®, Sanofi), 5-FET (5-fluorouracil), leucovorin, rapamycin (Sirolimus, RAPAMUNE®, Wyeth), lapatinib (TYKERB®, GSK572016, Glaxo Smith Kline), lonafamib (SCH 66336), sorafenib (NEXAVAR, Bayer Labs), gefitinib (IRESSA®, AstraZeneca), AG1478; alkylating agents such as thiotepa and CYTOXAN®; cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; cally statin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5 alpha-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancrati statin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega I (Angew Chem. Inti. Ed. Engl. 1994 33: 183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Ore.); razoxane; rhizoxin; sizofuran; spirogermanium; tenuazonic acid; triaziquone; 2,2',2''-trichlorotriethylamine; trichothecenes especially T-2 toxin, verracurin A, roridin A and anguidine); urethan; vindesine; dacarbazine; mannomustine; mitobronitol; mitolactol; pipobroman; gacytosine; arabinoside "Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluorom ethyl ornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifme citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN, LEUVECTIN®, and VAXID®; PROLEUKIN®, rIL-2; a topoisomerase 1 inhibitor such as LEIRTOTECAN®; ABARELIX®; and (ix) pharmaceutically acceptable salts, acids and derivatives of any of the above.

Chemotherapeutic agents also include antibodies, as described above, including alemtuzumab (Campath), bevacizumab (AVASTIN®, Genentech); cetuximab (ERBITETX®, Imclone); panitumumab (VECTIBIX®, Amgen), rituximab (RITETXAN®, Genentech/Biogen Idee), pertuzumab (OMNITARG, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nivolumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-8744695, Wyeth Research and Abbott Laboratories) which is a recombinant exclusively human-sequence, full-length IgG$_1$ λ antibody genetically modified to recognize interleukin-12 p40 protein.

Chemotherapeutic agents also include "tyrosine kinase inhibitors" including the EGFR inhibitors; small molecule HER2 tyrosine kinase inhibitor such as mubritonib (TAK165, Takeda); CP-724.714, (Axon Medchem BV, an oral selective inhibitor of the ErbB2 receptor tyrosine kinase); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SLTTENT®, available from Pfizer); VEGF receptor tyrosine kinase inhibitors such as vatalanib (PTK787/ZK222584, available from Novartis/Schering AG); MAPK extracellular regulated kinase 1 inhibitor Cl-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; antisense molecules (e.g. those that bind to HER-encoding nucleic acid); quinoxalines (U.S. Pat. No. 5,804,396); tryphostins (U.S. Pat. No. 5,804,396); affmitac (ISIS 3521; Isis/Lilly); PKI166 (Novartis); Semaxinib (Pfizer); INC-1C11 (Imclone), rapamycin (sirolimus, RAPAMUNE); or as described in any of the following patent publications: ET.S. U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca). Tyrosine kinase inhibitors also include erlotinib (Tarceva®), gefitinib (Iressa), dasatinib (Sprycel), nilotinib (Tasigna), crizotinib (Xalkori®), ruxolitinib (Jakafi®), vemurafenib (Zelboraf®), Vandetanib (Caprelsa), pazopanib (Votrient®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, veliparib, vismodegib, volasertib, cobimetinib (Cotellic®), and others.

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNF alpha) blockers such as etanercept (Enbrel), infliximab (Remicade), adalimumab (1-Iumira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-1 3) blockers such as lebrikizumab; Interferon alpha (IFN) blockers such as Rontalizumab; Beta 7 integrin blockers such as rhuMAb Beta7; IgE pathway blockers such as Anti-Ml prime; Secreted homotrimeric LTa3 and membrane bound heterotrimer LTa1/132 blockers such as Anti-lymphotoxin alpha (LTa); miscellaneous investigational agents such as thioplatin, PS-341, phenylbutyrate, ET-I8-OCH3, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifamib (R11577); orafenib, ABT510; Bcl-2 inhibitor such as oblimersen sodium (GENASENSE) pixantrone; farnesyltransferase inhibitors such as lonafamib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin. [000354] Chemotherapeutic agents also include Poly ADP ribose polymerase (PARP) inhibitors: olaparib (Lynparza®), rucaprib (Rubraca®) niraparib (Zejula®), talzoparib (Talzenna®).

In some embodiments, compounds as disclosed herein may be used in combination therapy with any of the kinase inhibitors disclosed herein for the treatment of diseases such as cancer. Exemplary kinase inhibitors include imatinib, baricitinib gefitinib, erlotinib, sorafenib, dasatinib, sunitinib, lapatinib, nilotinib, pirfenidone, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib, pexidartinib, ribociclib, temsirolimus, XL-092, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, a CK1 inhibitor, a CK1-a inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, for treatment of cancer, compounds as disclosed herein may be used in combination with inhibitors of PD-1 or inhibitors of PD-L1, e.g., an anti-PD-1 monoclonal antibody, an anti-PD-1 bispecific antibody or an anti-PD-L1 monoclonal antibody, an anti-PD-L1 bispecific antibody, for example, nivolumab (Opdivo), pembrolizumab (Keytruda, MK-3475), atezolizumab, avelumab, AB122, AMP-224, AMP-514, PDR001, durvalumab, pidilizumab (Imfinzi®, CT-011), CK-301, BMS 936559, and MPDL3280A; CTLA-4 inhibitors, e.g., an anti-CTLA-4 antibody, for example, ipilimumab (Yervoy) and tremelimumab; and phosphatidylserine inhibitors, for example, bavituximab (PGN401); antibodies to cytokines (IL-10, TGF-b, and the like); other anti-cancer agents such as cemiplimab. In some embodiments, the anti-PD-1 monoclonal antibody is nivolumab or pembrolizumab.

In some embodiments, a compound as described herein can be used in combination with a vaccination protocol for the treatment of cancer. In some embodiments, a compound as described herein can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa*.

In some embodiments, compounds as disclosed herein may be used in combination with inhibitors of PARP, for example, olaparib (Lynparza®), rucaprib (Rubraca®), niraparib (Zejula®), talzoparib (Talzenna®) for the treatment of cancer.

In some embodiments, compounds as disclosed herein may be used in combination with esaxerenone (XL-550) or XL-888 for the treatment of cancer.

In some embodiments, the compounds as disclosed herein can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS-R, IGF-1R, IR-R, PDGFαR, PDGFβ/R, CSFIR, KIT, FLK-II, KDR/FLK-1, FLK-4, fit-1, FGFR1, FGFR2, FGFR3, FGFR4, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYR, FRK, JAK, ABL, ALK, CDK7, CDK12, KRAS, and B-Raf.

Pharmaceutical Compositions and Modes of Administration

Compounds provided herein are usually administered in the form of pharmaceutical compositions. Thus, provided herein are also pharmaceutical compositions that comprise one or more of the compounds described herein or a pharmaceutically acceptable salt, a stereoisomer, or a mixture of stereoisomers thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, a stereoisomer, or a mixture of stereoisomers thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, a stereoisomer, or a mixture of stereoisomers thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, a stereoisomer, or a mixture of stereoisomers thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Preparation of compounds as disclosed herein can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of formula (I), formula (I'), formula (I'''), or any subformulas as disclosed herein and certain intermediates can be prepared, for example, using a process as illustrated in Schemes 1A-5C. The variables employed in the Schemes below are as defined throughout the specification.

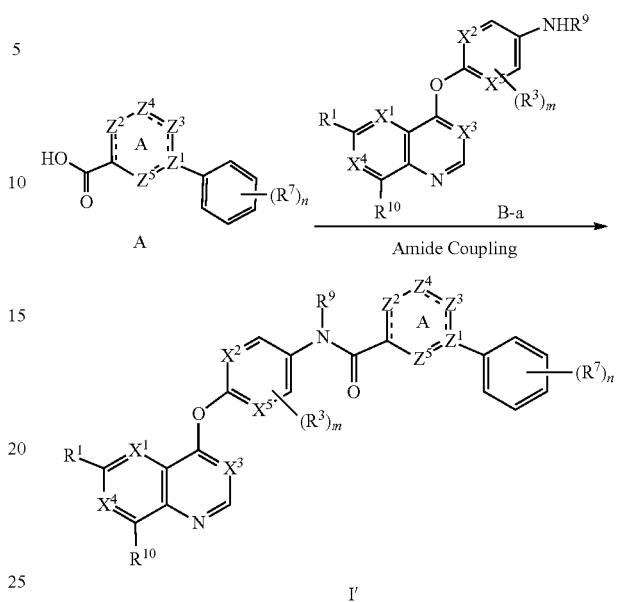

As shown in Scheme 1A, a compound of formula (I') can be synthesized from carboxylic acid A and aniline B-a by standard methods to form amide bonds using coupling agents appropriate for this transformation that are well known in the art such as HATU in the presence of a base such as DIEA in organic solvents such as DMF at room or elevated temperatures.

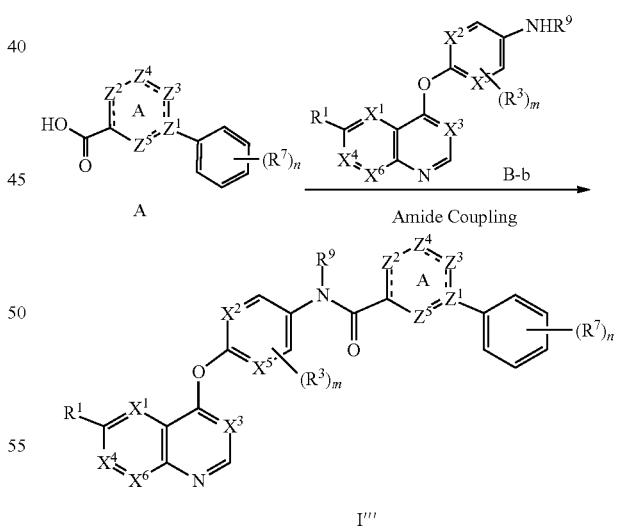

As shown in Scheme 1B, a compound of formula (I''') can be synthesized from carboxylic acid A and aniline B-b by standard methods to form amide bonds using coupling agents appropriate for this transformation that are well known in the art such as HATU in the presence of a base such as DIEA in organic solvents such as DMF at room or elevated temperatures.

Scheme 1C.

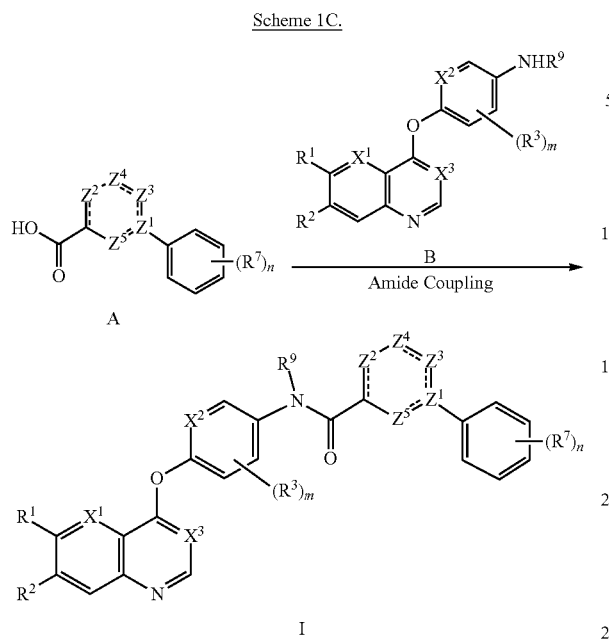

As shown in Scheme 1C, a compound of formula (I) can be synthesized from carboxylic acid A and aniline B by standard methods to form amide bonds using coupling agents appropriate for this transformation that are well known in the art such as HATU in the presence of a base such as DIEA in organic solvents such as DMF at room or elevated temperatures.

In some embodiments, provided is a process for preparing a compound of formula (I'), comprising contacting a compound of formula A with a compound of formula B-a, under conditions suitable to provide a compound of formula (I').

In some embodiments, provided is a process for preparing a compound of formula (I'''), comprising contacting a compound of formula A with a compound of formula B-b, under conditions suitable to provide a compound of formula (I''').

In some embodiments, provided is a process for preparing a compound of formula (I), comprising contacting a compound of formula A with a compound of formula B, under conditions suitable to provide a compound of formula (I).

Scheme 2A.

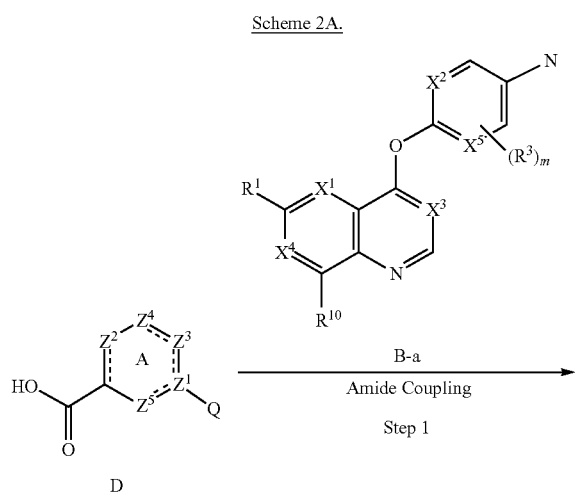

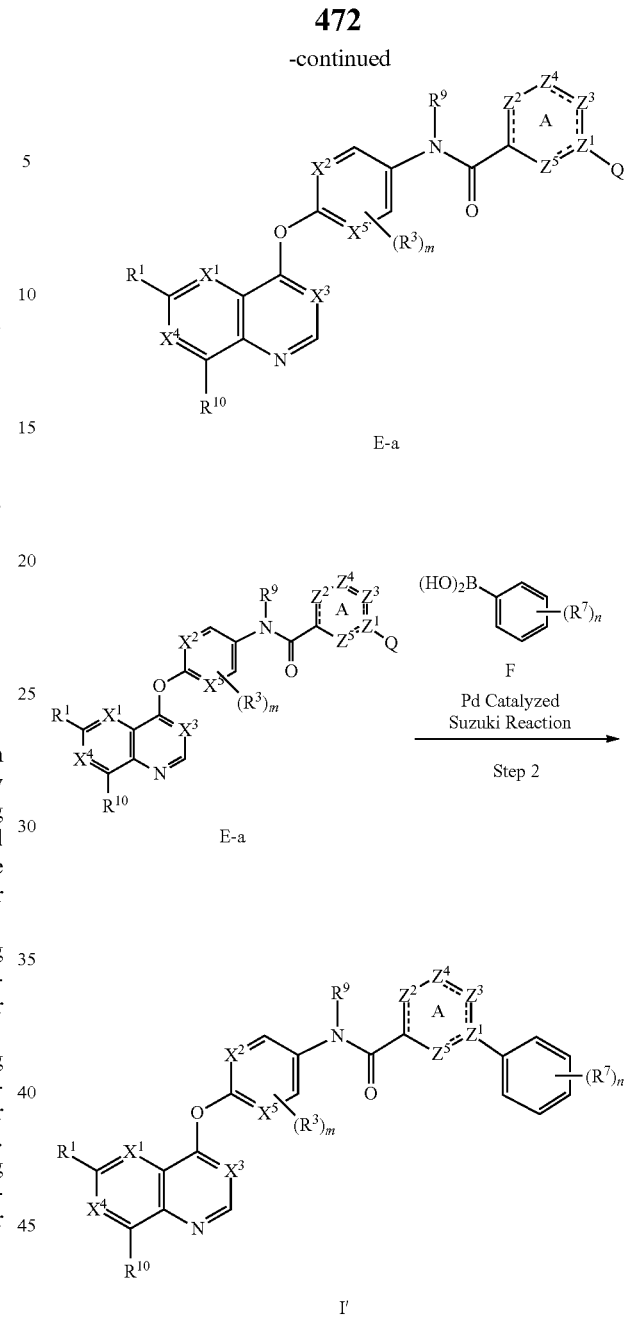

As shown in Scheme 2A, a compound of formula (I') can be made from a two-step process starting from bromocarboxylic acid D, where Q is a leaving group (including Cl, Br, I, triflate and the like), and aniline B-a which are coupled together by standard methods to form amide bonds using coupling agents appropriate for this transformation that are well known in the art such as HATU in the presence of a base such as DIEA in organic solvents such as DMF at room or elevated temperatures to form a compound of formula E-a. In a second step, compounds of formula E-a can be converted to compounds of formula (I') by coupling with boron compounds of the formula F using coupling chemistry known to those skilled in the art. Typical procedures to accomplish this type of coupling involve the use palladium-containing complexes as a catalyst in the presence of an inorganic base such as tripotassium phosphate in a mixture of water and a water-miscible solvent such as dioxane.

Scheme 2B.

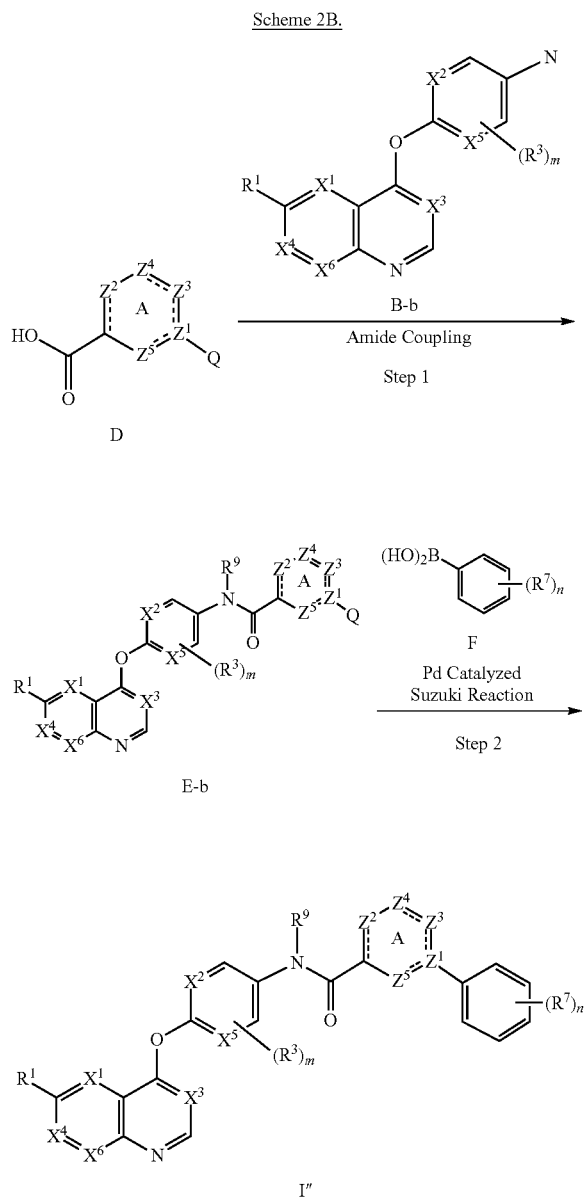

Scheme 2C.

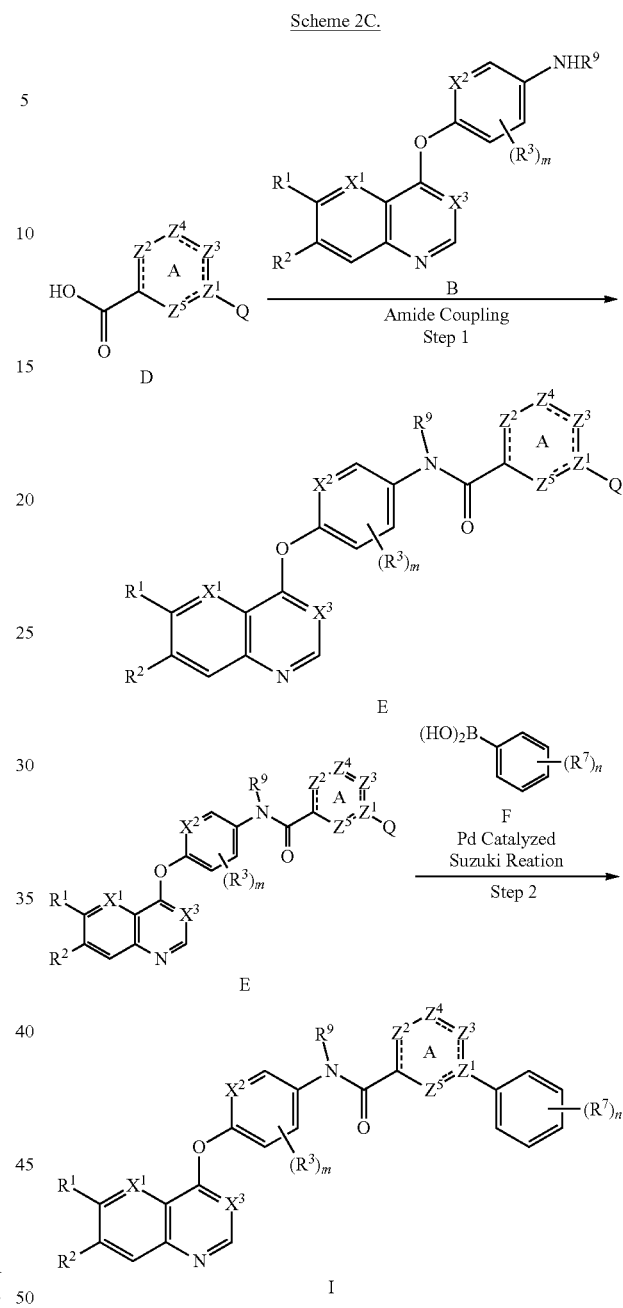

As shown in Scheme 2B, a compound of formula (I''') can be made from a two-step process starting from bromocarboxylic acid D, where Q is a leaving group (including Cl, Br, I, triflate and the like), and aniline B-b which are coupled together by standard methods to form amide bonds using coupling agents appropriate for this transformation that are well known in the art such as HATU in the presence of a base such as DIEA in organic solvents such as DMF at room or elevated temperatures to form a compound of formula E-b. In a second step, compounds of formula E-b can be converted to compounds of formula (I''') by coupling with boron compounds of the formula F using coupling chemistry known to those skilled in the art. Typical procedures to accomplish this type of coupling involve the use palladium-containing complexes as a catalyst in the presence of an inorganic base such as tripotassium phosphate in a mixture of water and a water-miscible solvent such as dioxane.

As shown in Scheme 2C, a compound of formula (I) can be made from a two-step process starting from bromocarboxylic acid D, where Q is a leaving group, including Cl, Br, I or triflate, and aniline B which are coupled together by standard methods to form amide bonds using coupling agents appropriate for this transformation that are well known in the art such as HATU in the presence of a base such as DIEA in organic solvents such as DMF at room or elevated temperatures to form a compound of formula E. In a second step, compounds of formula E can be converted to compounds of formula (I) by coupling with boron compounds of the formula F using coupling chemistry known to those skilled in the art. Typical procedures to accomplish this type of coupling involve the use palladium-containing complexes as a catalyst in the presence of an inorganic base such as tripotassium phosphate in a mixture of water and a water-miscible solvent such as dioxane.

In some embodiments, provided is a process for preparing a compound of formula (I'), comprising:
  contacting a compound of formula D with a compound of formula B-a, under conditions suitable to provide a compound of formula E-a; and
  contacting a compound of formula E-a with a compound of formula F, under conditions suitable to provide a compound of Formula (I').

In some embodiments, provided is a process for preparing a compound of formula (I'''), comprising:
  contacting a compound of formula D with a compound of formula B-b, under conditions suitable to provide a compound of formula E-b; and
  contacting a compound of formula E-b with a compound of formula F, under conditions suitable to provide a compound of Formula (I''').

In some embodiments, provided is a process for preparing a compound of formula (I), comprising:
  contacting a compound of formula D with a compound of formula B, under conditions suitable to provide a compound of formula E; and
  contacting a compound of formula E with a compound of formula F, under conditions suitable to provide a compound of Formula (I).

Scheme 3.

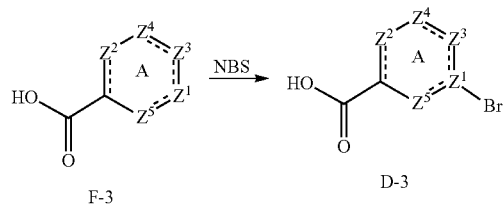

As shown in Scheme 3, a compound of formula D-3 (Q=Br) can be prepared from carboxylic acid F-3 through treatment with NBS in an appropriate solvent typically at room temperature.

Scheme 4A.

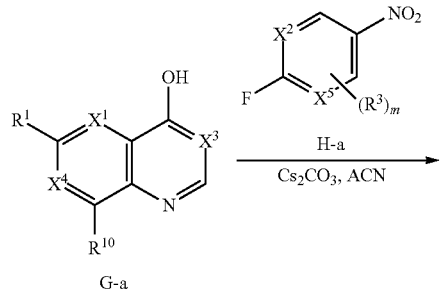

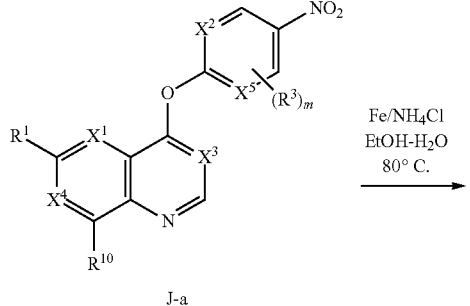

As shown in Scheme 4A, a compound of formula J-a can be prepared by reacting a compound of formula G-a with a compound of formula H-a in the presence of a base such as cesium carbonate in an appropriate organic solvent, typically at room temperature. A compound of formula B-a can be made from a compound of formula J-a by reducing the nitro group with a mixture of ammonium chloride and iron typically in a solvent mixture of water and an alcohol such as methanol or ethanol at elevated temperatures.

Scheme 4B.

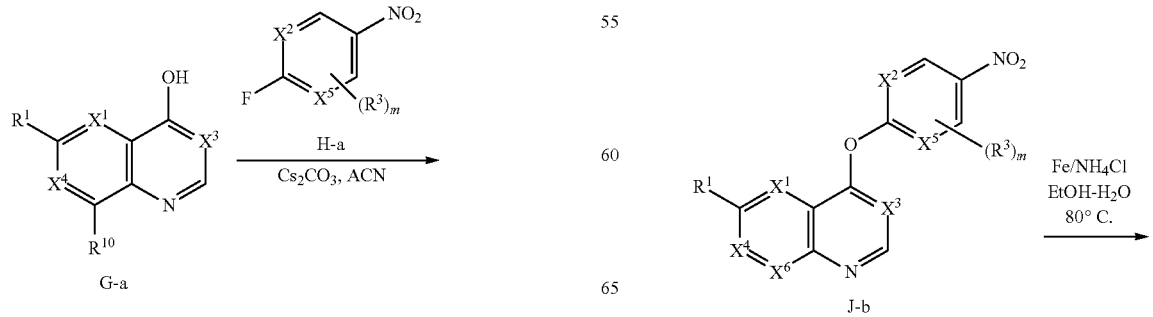

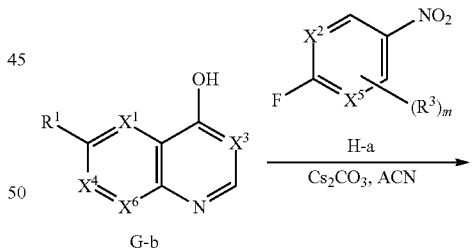

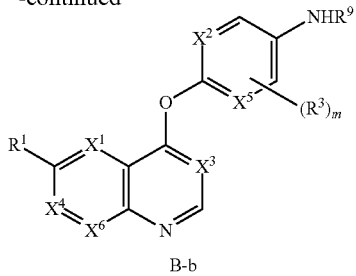

As shown in Scheme 4B, a compound of formula J-b can be prepared by reacting a compound of formula G-b with a compound of formula H-a in the presence of a base such as cesium carbonate in an appropriate organic solvent, typically at room temperature. A compound of formula B-b can be made from a compound of formula J-b by reducing the nitro group with a mixture of ammonium chloride and iron typically in a solvent mixture of water and an alcohol such as methanol or ethanol at elevated temperatures.

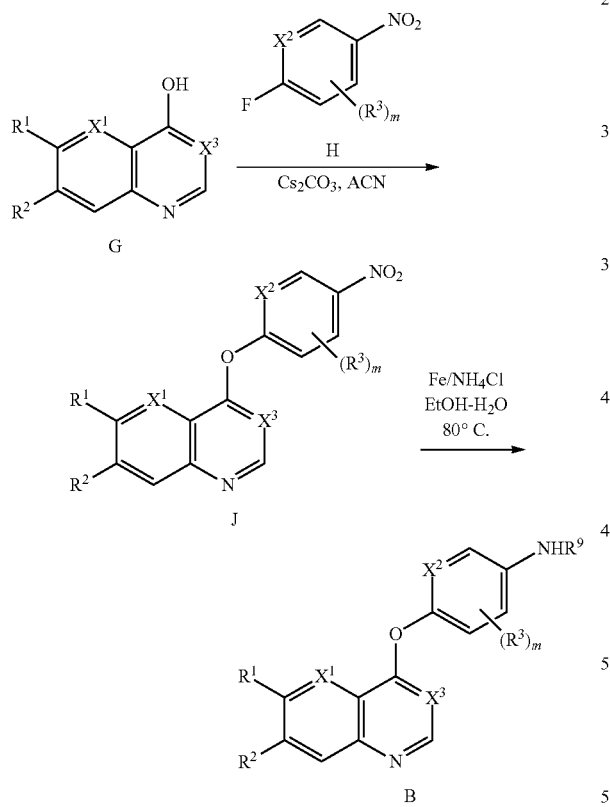

As shown in Scheme 4C, a compound of formula J can be prepared by reacting a compound of formula G with a compound of formula H in the presence of a base such as cesium carbonate in an appropriate organic solvent, typically at room temperature. A compound of formula B can be made from a compound of formula J by reducing the nitro group with a mixture of ammonium chloride and iron typically in a solvent mixture of water and an alcohol such as methanol or ethanol at elevated temperatures.

In some embodiments, provided is a process for preparing a compound of formula B-a, comprising:

contacting a compound of formula G-a with a compound of formula H-a, under conditions suitable to provide a compound of formula J-a; and reducing a compound of formula J-a under conditions suitable to provide a compound of formula B-a.

In some embodiments, provided is a process for preparing a compound of formula B-b, comprising:

contacting a compound of formula G-b with a compound of formula H-a, under conditions suitable to provide a compound of formula J-b; and reducing a compound of formula J-b under conditions suitable to provide a compound of formula B-b.

In some embodiments, provided is a process for preparing a compound of formula B, comprising:

contacting a compound of formula G with a compound of formula H, under conditions suitable to provide a compound of formula J; and reducing a compound of formula J under conditions suitable to provide a compound of formula B.

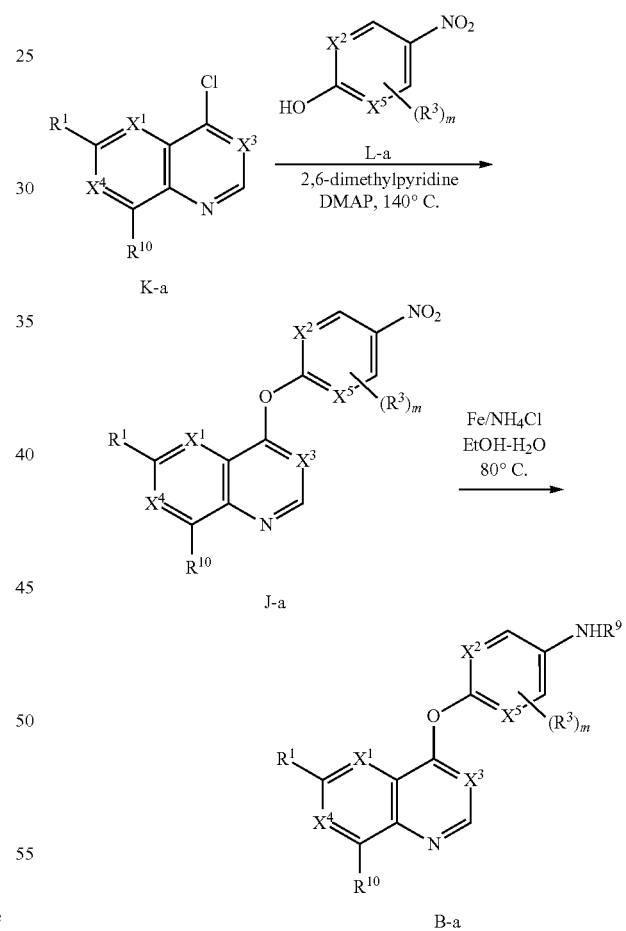

As shown in Scheme 5A, a compound of formula J-a can also be synthesized by reacting a compound of formula K-a with a compound of formula L-a in an appropriate solvent such as 2,6-dimethylpyridine in the presence of a catalytic amount of dimethylaminopyridine at elevated temperatures. A compound of formula B-a can be prepared from a compound of formula J-a by reducing the nitro group with a mixture of ammonium chloride and iron typically in a solvent mixture of water and an alcohol such as methanol or ethanol at elevated temperatures.

Scheme 5B.

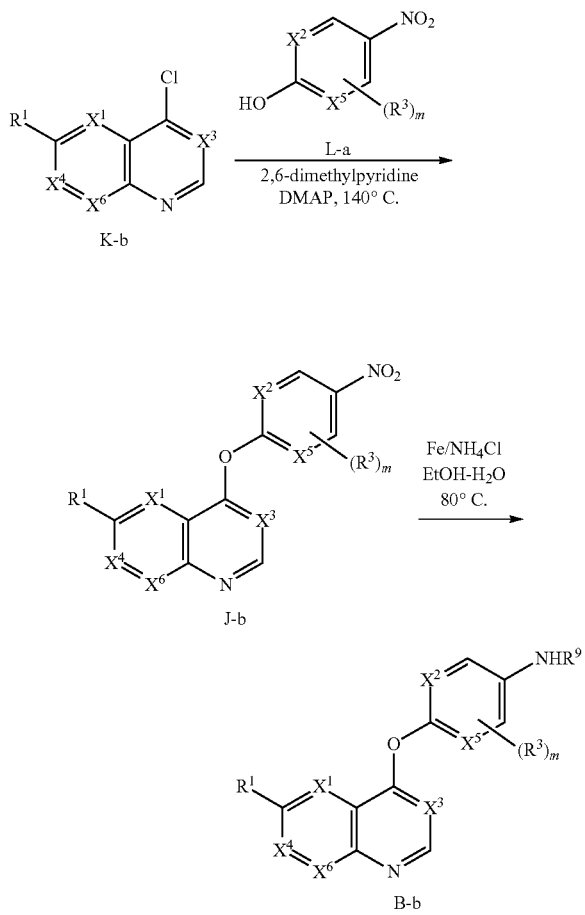

As shown in Scheme 5B, a compound of formula J-b can also be synthesized by reacting a compound of formula K-b with a compound of formula L-a in an appropriate solvent such as 2,6-dimethylpyridine in the presence of a catalytic amount of dimethylaminopyridine at elevated temperatures. A compound of formula B-b can be prepared from a compound of formula J-b by reducing the nitro group with a mixture of ammonium chloride and iron typically in a solvent mixture of water and an alcohol such as methanol or ethanol at elevated temperatures.

Scheme 5C.

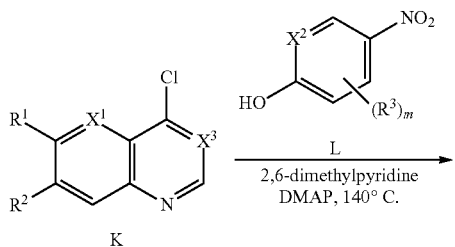

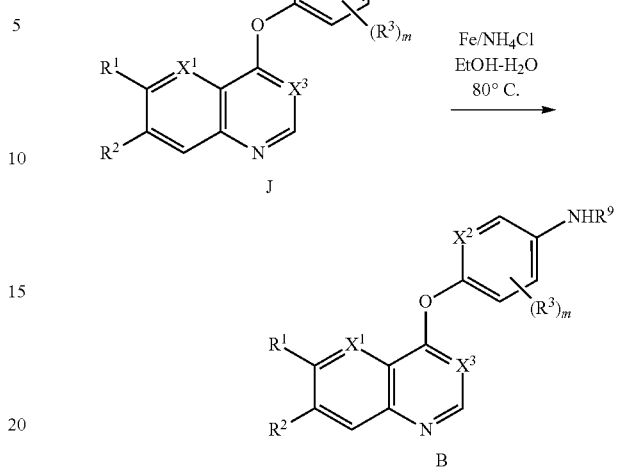

As shown in Scheme 5C, a compound of formula J can also be synthesized by reacting a compound of formula K with a compound of formula L in an appropriate solvent such as 2,6-dimethylpyridine in the presence of a catalytic amount of dimethylaminopyridine at elevated temperatures. A compound of formula B can be prepared from a compound of formula J by reducing the nitro group with a mixture of ammonium chloride and iron typically in a solvent mixture of water and an alcohol such as methanol or ethanol at elevated temperatures.

In some embodiments, provided is a process for preparing a compound of formula B-a, comprising:
    contacting a compound of formula K-a with a compound of formula L-a, under conditions suitable to provide a compound of formula J-a; and
    reducing a compound of formula J-a under conditions suitable to provide a compound of formula B-a.

In some embodiments, provided is a process for preparing a compound of formula B-b, comprising:
    contacting a compound of formula K-b with a compound of formula L-a, under conditions suitable to provide a compound of formula J-b; and
    reducing a compound of formula J-b under conditions suitable to provide a compound of formula B-b.

In some embodiments, provided is a process for preparing a compound of formula B, comprising:
    contacting a compound of formula K with a compound of formula L, under conditions suitable to provide a compound of formula J; and
    reducing a compound of formula J under conditions suitable to provide a compound of formula B.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Synthetic Examples

The following examples are provided for the purpose of further illustration and are not intended to limit the scope of the claimed invention.

Intermediate Synthesis—General Procedures

General Procedure A: 4-Pyridone Carboxylic Acids (PA1)

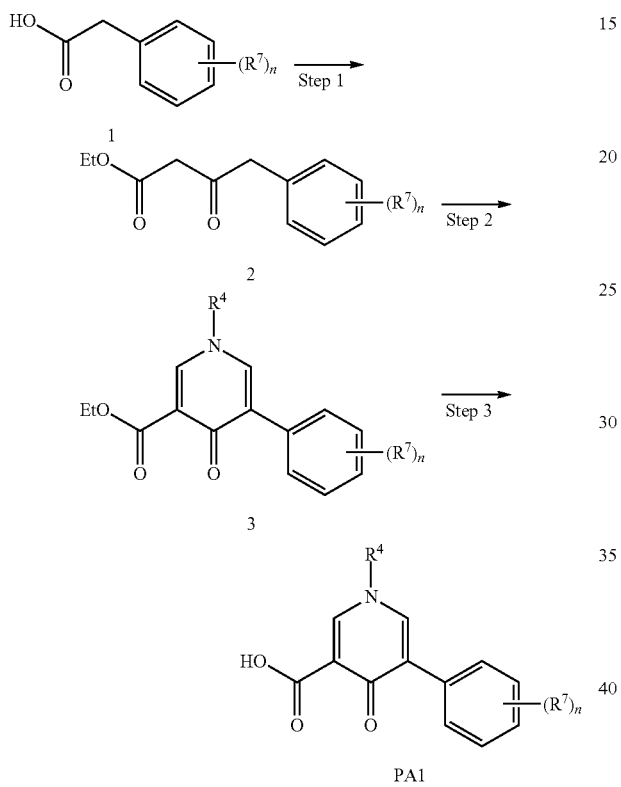

Step 1: To a stirred solution of Compound 1 (65 mmol, 1 eq), Meldrum's acid (9.4 g, 65 mmol, 1 eq) and DMAP (15.8 g, 130 mmol, 2 eq) in DCM (200 mL, 3 mL/mmol of 1) was added DCC (13.4 g, 65 mmol, 1 eq) in portions. After stirring at room temperature overnight, the reaction mixture was filtered through Celite. The filtrate was washed with aq. 1N HCl (2×), water and aq. saturated NaCl. The resulting organic solution was dried over anhyd $Na_2SO_4$ and concentrated under vacuum to provide the acyl Meldrum's acid derivative. This material was then dissolved in absolute EtOH (250 mL, 3.8 mL/mmol of 1) and the resulting solution refluxed overnight. The mixture was concentrated under vacuum and the resulting residue purified by silica gel column chromatography, eluted with 0-15% EtOAc in hexanes, to give Compound 2.

Step 2: N,N-Dimethylformamide dimethylacetal (DMF-DMA) (2-10 eq) was added to a solution of Compound 2 (1 eq) in toluene (2-3 mL/mmol of substrate (2)) at room temperature. The mixture was stirred at 90-100° C. overnight. The volatiles were removed under reduced pressure and EtOH (2-4 mL/mmol of 2 used) was added, followed by addition of amine, $R^4$—$NH_2$ (1-3 eq). The mixture was stirred at 60° C. until the rearrangement was complete as monitored by LC-MS and/or TLC (several hours). The solvent was removed under reduced pressure and the residue was purified by silica gel column chromatography, eluted with 0-100% EtOAc in hexanes to give Compound 3.

Step 3: Compound 3 (1 eq) was mixed with NaOH (2M, 1-20 eq) in THF or MeOH (5-20 mL/mmol of 3) and stirred at room temperature until hydrolysis was complete as monitored by LC-MS and/or TLC. The mixture was diluted with water (5-20 mL/mmol of 3) and washed with an organic solvent such as EtOAc or DCM (2×). The aqueous phase was acidified to pH 2 with aq. 6M HCl. If acidification gave a precipitate, the resulting suspension was filtered, and the material was washed with water and dried to give Compound PAL. If acidification did not give a filterable precipitate, the aqueous solution was extracted with an organic solvent such as EtOAc or DCM (3×). The combined extracts were dried over anhyd. $Na_2SO_4$ and concentrated under vacuum to give crude Compound PA1 which was generally used in subsequent reactions without further purification.

Example of General Procedure A: 5-(4-Fluorophenyl)-1-isopropyl-4-oxo-1,4-dihydropyridine-3-carboxylic acid (PA1-3)

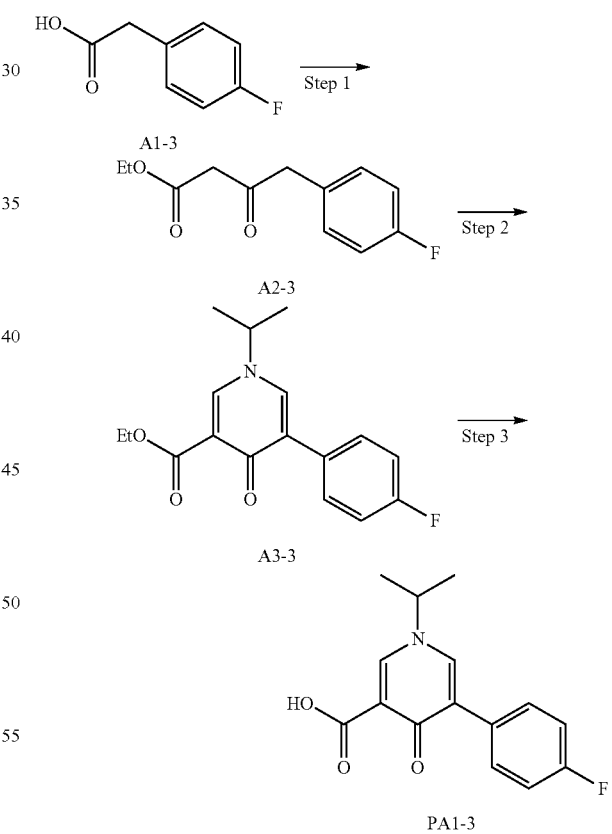

Step 1: Ethyl 4-(4-fluorophenyl)-3-oxobutanoate (A2-3): To a stirred solution of Compound A1-3 (10 g, 65 mmol, 1 eq), Meldrum's acid (9.4 g, 65 mmol, 1 eq) and DMAP (15.8 g, 130 mmol, 2 eq) in DCM (200 mL), was added DCC (13.4 g, 65 mmol, 1 eq) in portions. After stirring at room temperature overnight, the reaction mixture was filtered through Celite and the filtrate was washed with aq. 1 N HCl (2×), washed with water, washed with aq. saturated NaCl, dried over anhyd. Na₂SO₄ and concentrated to provide the acyl Meldrum's acid derivative. This solid was dissolved in absolute EtOH (250 mL) and the resulting solution refluxed overnight. The reaction mixture was concentrated, and the resulting residue was purified by silica gel column chromatography (0-15% EtOAc in hexanes) to give Compound A2-3. MS for $C_{12}H_{13}FO_3$: m/z 225 (MH+).

Step 2: Ethyl 5-(4-fluorophenyl)-1-isopropyl-4-oxo-1,4-dihydropyridine-3-carboxylate (A3-3): DMF-DMA (1.0 mL, 13 mmol, 5.8 eq) was added to a solution of Compound A2-3 (500 mg, 2.23 mmol, 1 eq) in toluene (5 mL) at room temperature, and the mixture was stirred at 100° C. overnight. The reaction mixture was concentrated under reduced pressure to dryness and EtOH (8 mL) was added, followed by the addition of isopropylamine (0.5 mL, 6.1 mmol, 2.7 eq). The mixture was stirred at 60° C. for 8 h, concentrated under reduced pressure and the resulting residue was purified by silica gel column chromatography (0-100% EtOAc in hexanes) to give Compound A3-3. MS for $C_{17}H_{18}FNO_3$: m/z 304 (MH+).

Step 3: 5-(4-Fluorophenyl)-1-isopropyl-4-oxo-1,4-dihydropyridine-3-carboxylic acid (PA1-3): A mixture of Compound A3-3 (480 mg, 1.58 mmol, 1 eq) and aq 2 N NaOH (5 mL) in MeOH (15 mL) was stirred at room temperature for 1 h and then concentrated to remove most of the MeOH. The resulting residue was diluted with water (15 mL) and washed with EtOAc. The aqueous phase was acidified to pH 2 with aq. 6 N HCl and extracted with EtOAc (3×). The combined organic extracts were dried over anhyd. Na₂SO₄ and concentrated to give Compound PA1-3, which was used in subsequent reactions without further purification. MS for $C_{15}H_{14}FNO_3$: m/z 276 (MH+).

The following intermediates were made following General Procedure A for the synthesis of 4-pyridone carboxylic acids, PA1:

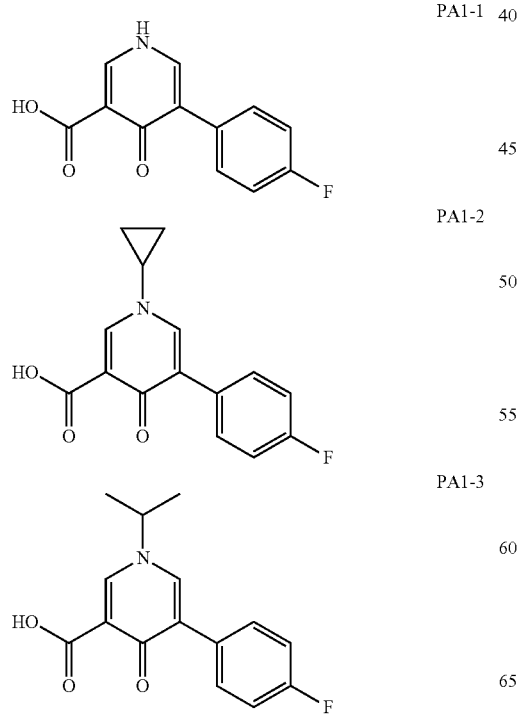

PA1-1

PA1-2

PA1-3

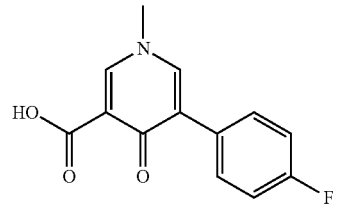

PA1-4

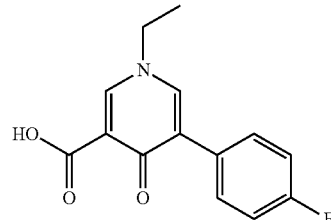

PA1-5

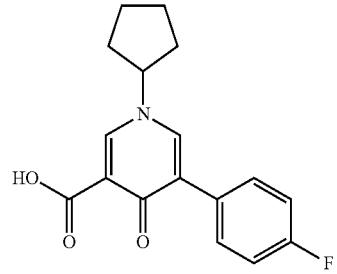

PA1-6

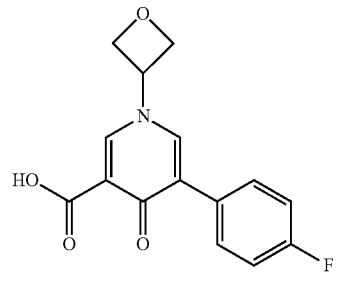

PA1-7

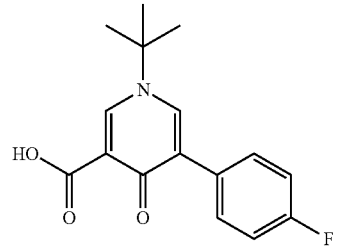

PA1-8

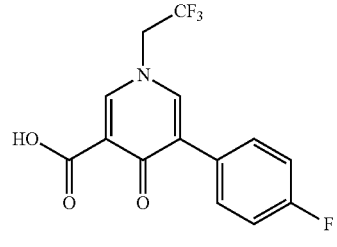

PA1-9

PA1-10
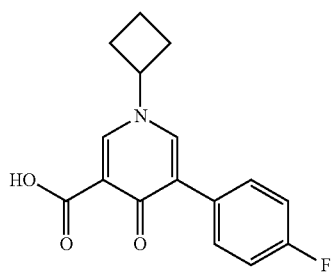
PA1-11
PA1-12
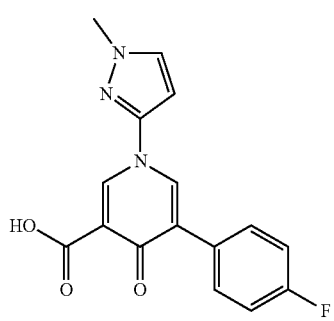
PA1-13
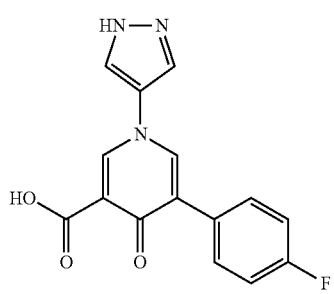
PA1-14
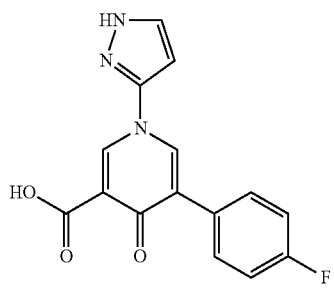
PA1-15
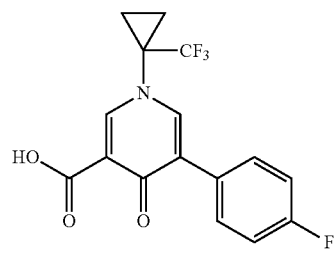
PA1-16
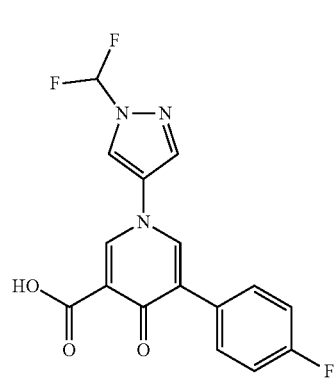
PA1-17
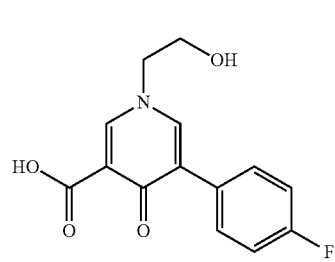
PA1-18
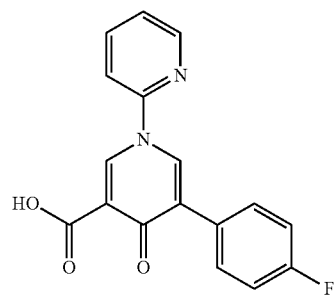
PA1-19
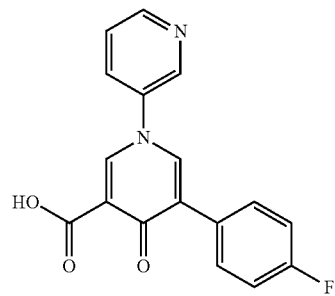

PA1-20
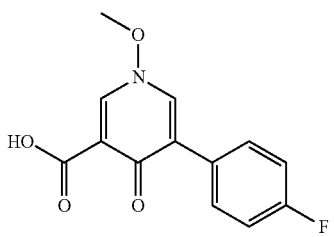

PA1-21
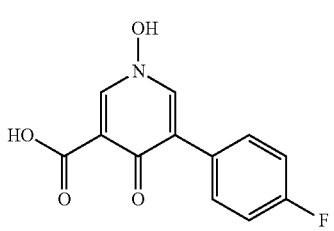

PA1-22
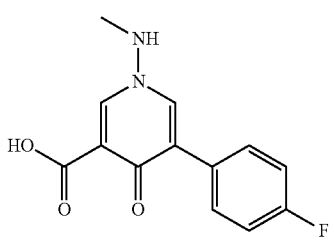

PA1-23
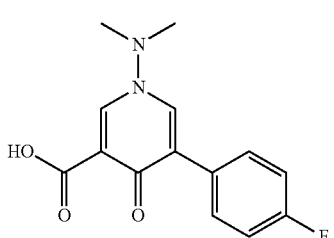

PA1-24
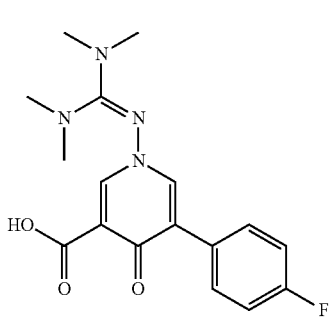

PA1-25
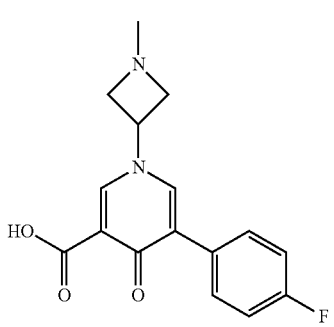

PA1-26
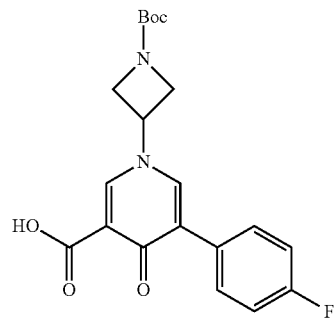

PA1-27
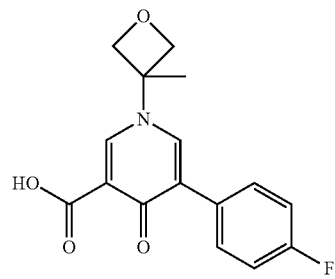

PA1-28
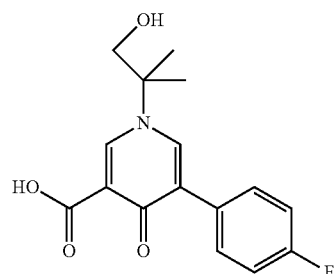

5-(4-Fluorophenyl)-4-oxo-1,4-dihydropyridine-3-carboxylic acid (PA1-1): MS for $C_{12}H_8FNO_3$: m/z 234 (MH+).

1-Cyclopropyl-5-(4-fluorophenyl)-4-oxo-1,4-dihydropyridine-3-carboxylic acid (PA-2): MS for $C_{15}H_{12}FNO_3$: m/z 274 (MH+).

5-(4-Fluorophenyl)-1-isopropyl-4-oxo-1,4-dihydropyridine-3-carboxylic acid (PA1-3): MS for $C_{13}H_{14}FNO_3$: m/z 276 (MH+).

5-(4-Fluorophenyl)-1-methyl-4-oxo-1,4-dihydropyridine-3-carboxylic acid (PA1-4): MS for $C_{13}H_{10}FNO_3$: m/z 248 (MH+).

1-Ethyl-5-(4-fluorophenyl)-4-oxo-1,4-dihydropyridine-3-carboxylic acid (PA1-5): MS for $C_{14}H_{12}FNO_3$: m/z 262 (MH+).

1-Cyclopentyl-5-(4-fluorophenyl)-4-oxo-1,4-dihydropyridine-3-carboxylic acid (PA1-6): MS for $C_{17}H_{16}FNO_3$: m/z 302 (MH+).

5-(4-Fluorophenyl)-1-(oxetan-3-yl)-4-oxo-1,4-dihydropyridine-3-carboxylic acid (PA-7): MS for $C_{15}H_{12}FNO_4$: m/z 290 (MH+).

1-(tert-Butyl)-5-(4-fluorophenyl)-4-oxo-1,4-dihydropyridine-3-carboxylic acid (PA-8): MS for $C_{16}H_{16}FNO_3$: m/z 290 (MH+).

5-(4-Fluorophenyl)-4-oxo-1-(2,2,2-trifluoroethyl)-1,4-dihydropyridine-3-carboxylic acid (PA1-9): MS for $C_{14}H_9F_4NO_3$: m/z 316 (MH+).

1-Cyclobutyl-5-(4-fluorophenyl)-4-oxo-1,4-dihydropyridine-3-carboxylic acid (PA1-10): MS for $C_{16}H_{14}FNO_3$: m/z 288 (MH+).

5-(4-Fluorophenyl)-1-(1-methyl-1H-pyrazol-4-yl)-4-oxo-1,4-dihydropyridine-3-carboxylic acid (PA1-11): MS for $C_{16}H_{12}FN_3O_3$: m/z 314 (MH+).

5-(4-Fluorophenyl)-1-(1-methyl-1H-pyrazol-3-yl)-4-oxo-1,4-dihydropyridine-3-carboxylic acid (PA1-12): MS for $C_{16}H_{12}FN_3O_3$: m/z 314 (MH+).

5-(4-Fluorophenyl)-4-oxo-1-(1H-pyrazol-4-yl)-1,4-dihydropyridine-3-carboxylic acid (PA1-13): MS for $C_{15}H_{10}FN_3O_3$: m/z 300 (MH+).

5-(4-Fluorophenyl)-4-oxo-1-(1H-pyrazol-3-yl)-1,4-dihydropyridine-3-carboxylic acid (PA1-14): MS for $C_{15}H_{10}FN_3O_3$: m/z 300 (MH+).

5-(4-Fluorophenyl)-4-oxo-1-(1-(trifluoromethyl)cyclopropyl)-1,4-dihydropyridine-3-carboxylic acid (PA1-15): MS for $C_{16}H_{11}F_4NO_3$: m/z 342 (MH+).

1-(1-(Difluoromethyl)-1H-pyrazol-4-yl)-5-(4-fluorophenyl)-4-oxo-1,4-dihydropyridine-3-carboxylic acid (PA1-16): MS for $C_{16}H_{10}F_3N_3O_3$: m/z 350 (MH+).

5-(4-Fluorophenyl)-1-(2-hydroxyethyl)-4-oxo-1,4-dihydropyridine-3-carboxylic acid (PA1-17): MS for $C_{14}H_{12}FNO_4$: m/z 278 (MH+).

5-(4-Fluorophenyl)-4-oxo-4H-[1,2'-bipyridine]-3-carboxylic acid (PA1-18): MS for $C_{17}H_{11}FN_2O_3$: m/z 311 (MH+).

5-(4-Fluorophenyl)-4-oxo-4H-[1,3'-bipyridine]-3-carboxylic acid (PA1-19): MS for $C_{17}H_{11}FN_2O_3$: m/z 311 (MH+).

5-(4-Fluorophenyl)-1-methoxy-4-oxo-1,4-dihydropyridine-3-carboxylic acid (PA1-20): MS for $C_{13}H_{10}FNO_4$: m/z 264 (MH+).

5-(4-Fluorophenyl)-1-hydroxy-4-oxo-1,4-dihydropyridine-3-carboxylic acid (PA1-21): MS for $C_{12}H_8FNO_4$: m/z 250 (MH+).

5-(4-Fluorophenyl)-1-(methylamino)-4-oxo-1,4-dihydropyridine-3-carboxylic acid (PA1-22): MS for $C_{13}H_{11}FN_2O_3$: m/z 263 (MH+).

1-(Dimethylamino)-5-(4-fluorophenyl)-4-oxo-1,4-dihydropyridine-3-carboxylic acid (PA1-23): MS for $C_{14}H_{13}FN_2O_3$: m/z 277 (MH+).

1-((bis(Dimethylamino)methylene)amino)-5-(4-fluorophenyl)-4-oxo-1,4-dihydropyridine-3-carboxylic acid (PA1-24): MS for $C_{17}H_{19}FN_4O_3$: m/z 347 (MH+).

5-(4-Fluorophenyl)-1-(1-methylazetidin-3-yl)-4-oxo-1,4-dihydropyridine-3-carboxylic acid (PA1-25): MS for $C_{16}H_{15}FN_2O_3$: m/z 303 (MH+).

1-(1-(tert-Butoxycarbonyl)azetidin-3-yl)-5-(4-fluorophenyl)-4-oxo-1,4-dihydropyridine-3-carboxylic acid (PA1-26): MS for $C_{12}H_{21}FN_2O_5$: m/z 389 (MH+).

5-(4-Fluorophenyl)-1-(3-methyloxetan-3-yl)-4-oxo-1,4-dihydropyridine-3-carboxylic acid (PA1-27): MS for $C_{16}H_{14}FNO_4$: m/z 304 (MH+).

5-(4-Fluorophenyl)-1-(1-hydroxy-2-methylpropan-2-yl)-4-oxo-1,4-dihydropyridine-3-carboxylic acid (PA1-28): MS for $C_{16}H_{16}FNO_4$: m/z 306 (MH+).

General Procedure B: 5-Bromo-4-Pyridone Carboxylic Acids (PA2)

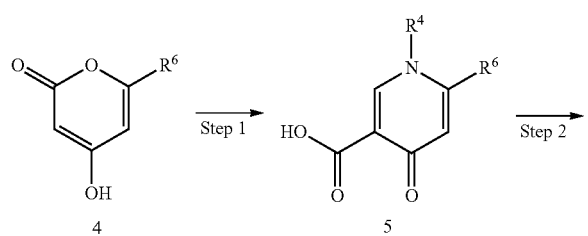

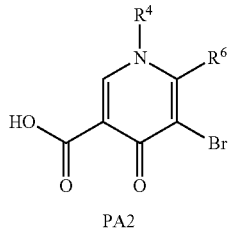

Step 1: To a solution of Compound 4 (100 mmol) in toluene (35 mL) was added DMF-DMA (14 ml, 105 mmol). The resulting solution was stirred at room temperature for 3 h and then concentrated. A mixture of this material (50 mmol), amine $R^4$—$NH_2$ (61 mmol) and sodium tert-butoxide (5.6 g, 58 mmol) in EtOH (30 mL) was stirred at 90° C. for 24 h, cooled to room temperature, concentrated and treated with water and DCM. The phases were separated, and the aqueous layer was acidified to pH 2 with aq. 6 N HCl and extracted with DCM. The combined DCM extracts were washed with water, aq. saturated NaCl, dried over anhyd. $Na_2SO_4$ and concentrated to give the crude Compound 5.

Step 2: To a solution of crude Compound 5 (31.3 mmol) in DCE (100 mL) was added solid NBS (9.0 g, 50.6 mmol) in portions. The mixture was stirred at room temperature overnight, diluted with DCM, washed with water, aq. saturated NaCl, dried over anhyd. $Na_2SO_4$ and concentrated to give the crude Compound PA2 which was generally used in subsequent reactions without further purification.

Example of General Procedure B: 5-Bromo-1-isopropyl-6-methyl-4-oxo-1,4-dihydropyridine-3-carboxylic acid (PA2-2)

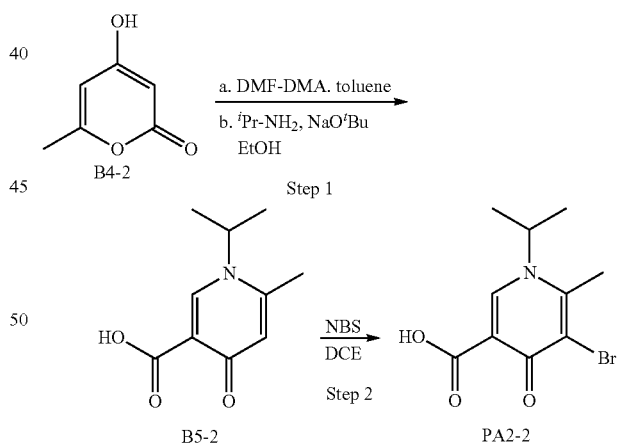

Step 1: 1-Isopropyl-6-methyl-4-oxo-1,4-dihydropyridine-3-carboxylic acid (B5-2): To a suspension of Compound B4-2 (15 g, 119 mmol, 1 eq) in toluene (40 mL) was added DMF-DMA (15.2 g, 127 mmol, 1.1 eq). The resulting mixture was stirred at 15° C. for 2 h. The reaction mixture was concentrated under reduced pressure and co-evaporated with toluene (50 mL) 3 times and DCM (50 mL) 2 times to give the enamine intermediate, (E)-3-((dimethylamino)methylene)-6-methyl-2H-pyran-2,4(3H)-dione. This enamine intermediate (11 g, 60.7 mmol, 1 eq) was suspended in EtOH (50 mL), and i-PrNH$_2$ (7.9 mL, 92 mmol, 1.5 eq) was added, followed by the addition of t-BuONa (8.6 g, 90 mmol, 1.5 eq). The resulting suspension was stirred at 90° C. for 15 h. The reaction mixture was concentrated under reduced pressure. To the resulting residue was diluted with water (150 mL) and acidified with aq. 4 N HCl to pH 2-3 and extracted with DCM (2×50 mL). The combined organic extracts were concentrated under reduced pressure to give Compound B5-2, which was used in subsequent reactions without further purification.

Step 2: 5-Bromo-1-isopropyl-6-methyl-4-oxo-1,4-dihydropyridine-3-carboxylic acid (PA2-2). Compound PA2-2 was synthesized from Compound B5-2 using a closely related version of General Procedure B as outlined in General Procedure B1 below. $^1$H NMR (400 MHz, CDCl$_3$) δ 15.31 (br s, 1H), 8.59 (s, 1H), 4.80-4.70 (m, 1H), 2.80 (s, 3H), 1.58 (s, 3H), 1.57 (s, 3H); MS for $C_{10}H_{20}BrNO_3$: m/z 275.8 (MH+).

General Procedure B1: Bromination of 4-Pyridone Carboxylic Acids or Esters (PA2a)

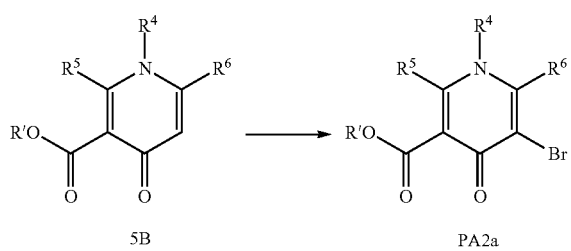

Step 1: Commercially available pyridone carboxylic acids or esters or any pyridone carboxylic acids or esters (5B) generated by the methods described within were brominated using NBS in appropriate organic solvents such as, but not limited to, DCE, NMP or ACN. To a solution of crude 5B (1 eq) in solvent (1.1-3.2 mL/mmol of 5B) was added solid NBS (1-1.6 eq) in portions. The resulting mixture was stirred at room temperature (30 min to overnight). Upon completion of the reaction as monitored by LC-MS and/or TLC, the reaction mixture was typically worked up by one of the following methods or a very similar variation. Method 1: The reaction mixture was diluted with DCM, washed with water, washed with aq saturated NaCl, dried over anhyd. Na$_2$SO$_4$ and concentrated to give crude brominated product PA2a. Method 2: To the reaction mixture was added water and the resulting mixture was stirred at room temperature for 15 min. The resulting precipitate was filtered, washed with water and allowed to air-dry to give crude brominated product PA2a. Regardless of the method of work up, the crude PA2a was generally used in subsequent reactions without further purification.

Example of General Procedure B: Ethyl 5-bromo-6-(tert-butyl)-4-oxo-1,4-dihydropyridine-3-carboxylate (PA2a-3)

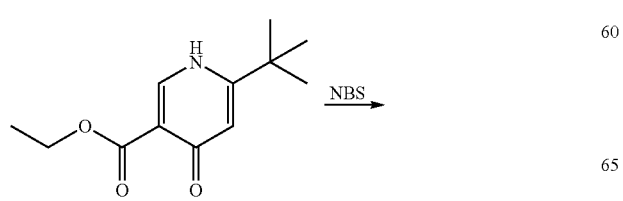

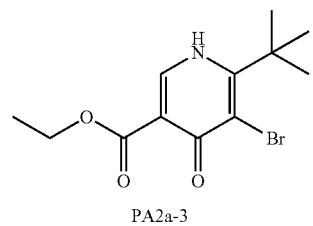

PA2a-3

Ethyl 5-bromo-6-(tert-butyl)-4-oxo-1,4-dihydropyridine-3-carboxylate (PA2a-3): To a solution of commercially available ethyl 6-(tert-butyl)-4-oxo-1,4-dihydropyridine-3-carboxylate (1 g, 4.48 mmol, 1 eq) in NMP (5 mL) was added NBS (797 mg, 4.48 mmol, 1 eq) in one portion. The reaction mixture was stirred at room temperature for 1 h. The reaction was quenched with water and continued stirring for another 15 min. The resulting solid was filtered, washed with water and allowed to dry in the open air to give Compound PA2a-3. MS for $C_{12}H_{16}BrNO_3$: m/z: 302 (MH+).

The following intermediates were made following General Procedure B or General Procedure B1 for the synthesis of 5-bromo 4-pyridone carboxylic acids, PA2 or PA2a:

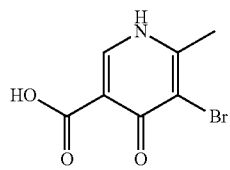

PA2-1

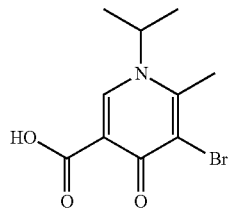

PA2-2

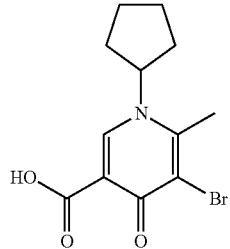

PA2-3

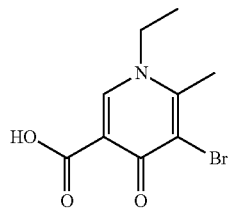

PA2-4

-continued

PA2-5
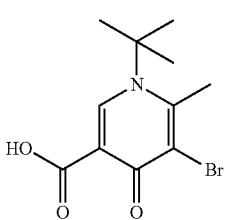

PA2-6
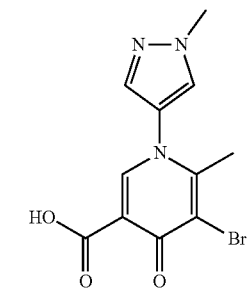

PA2-7
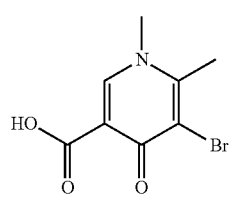

PA2-8
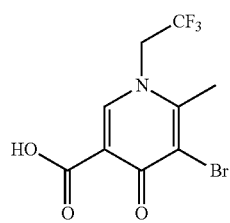

PA2-9
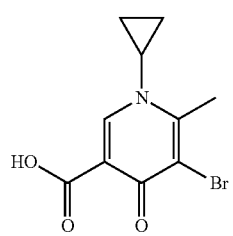

5-Bromo-6-methyl-4-oxo-1,4-dihydropyridine-3-carboxylic acid (PA2-1): MS for $C_7H_6BrNO_3$: m/z 232/234 (MH+).

5-Bromo-1-isopropyl-6-methyl-4-oxo-1,4-dihydropyridine-3-carboxylic acid (PA2-2): MS $C_{10}H_{12}BrNO_3$: m/z 274/276 (MH+).

5-Bromo-1-cyclopentyl-6-methyl-4-oxo-1,4-dihydropyridine-3-carboxylic acid (PA2-3): MS for $C_{12}H_{14}BrNO_3$: m/z 300/302 (MH+).

5-Bromo-1-ethyl-6-methyl-4-oxo-1,4-dihydropyridine-3-carboxylic acid (PA2-4): MS for $C_9H_{10}BrNO_3$: m/z 260/262 (MH+).

5-Bromo-1-(tert-butyl)-6-methyl-4-oxo-1,4-dihydropyridine-3-carboxylic acid (PA2-5): MS for $C_{12}H_{16}BrNO_3$: m/z 302 (MH+).

5-Bromo-6-methyl-1-(1-methyl-1H-pyrazol-4-yl)-4-oxo-1,4-dihydropyridine-3-carboxylic acid (PA2-6): MS for $C_{11}H_{10}BrN_3O_3$: m/z 312/314 (MH+).

5-Bromo-1,6-dimethyl-4-oxo-1,4-dihydropyridine-3-carboxylic acid (PA2-7): MS for $C_8H_8BrNO$: m/z 246/248 (MH+).

5-Bromo-6-methyl-4-oxo-1-(2,2,2-trifluoroethyl)-1,4-dihydropyridine-3-carboxylic acid (PA2-8): MS for $C_9H_7BrF_3NO_3$: m/z 314.1/316.1 (MH+).

5-Bromo-1-cyclopropyl-6-methyl-4-oxo-1,4-dihydropyridine-3-carboxylic acid (PA2-9): MS for $C_{10}H_{10}BrNO_3$: m/z 272.2/274.2 (MH+).

General Procedure C: 4-Pyridone Carboxylic Acids (PA3)

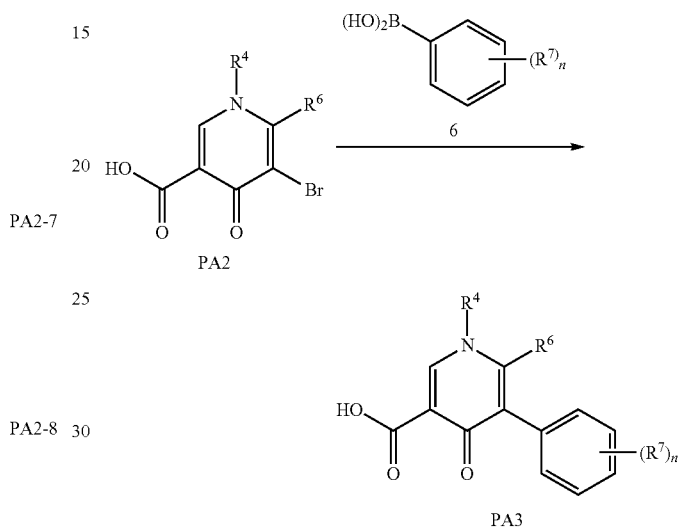

A mixture of compound PA2 (12.8 mmol), boronic acid 6 (14.3 mmol), $K_2CO_3$, (4.0 g, 29.0 mmol), $Pd(PPh_3)_4$ (1.2 g, 1.0 mmol) in water (20 mL) and dioxane (40 mL) was degassed with nitrogen for 5 min and then stirred at 90° C. until the reaction was complete as monitored by LC-MS and/or TLC. The reaction mixture was filtered through Celite and the filtrate was concentrated under vacuum to remove dioxane. The resulting residue was diluted with aq. NaOH (20 mL, 2.0 M) and washed with EtOAc (2×). The aqueous phase was then acidified to pH 2-3 with aq. 6 M HCl. The resulting precipitate was filtered, washed with water and dried to give Compound PA3 which was typically used in subsequent reactions without further purification.

Example of General Procedure C: 5-(4-Fluorophenyl)-1-isopropyl-6-methyl-4-oxo-1,4-dihydropyridine-3-carboxylic acid (PA3-2)

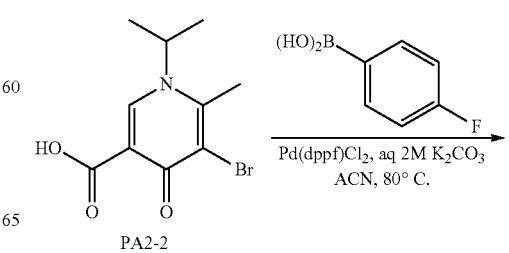

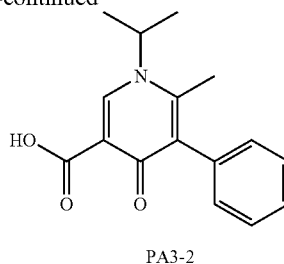

PA3-2

5-(4-Fluorophenyl)-1-isopropyl-6-methyl-4-oxo-1,4-dihydropyridine-3-carboxylic acid (PA3-2): Compound PA3-2 was synthesized using a closely related version of General Procedure C as outlined in General Procedure C below. MS for $C_{16}H_{16}FNO_3$: m/z 289.9 (MH+).

General Procedure C1: Suzuki reactions with 5-bromo-4-pyridone carboxylic acids or esters

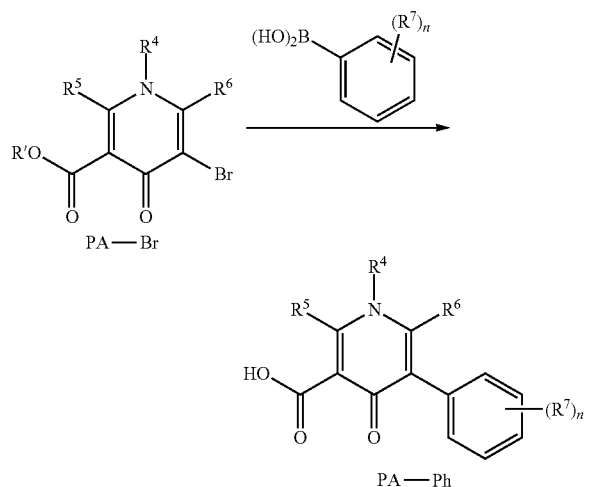

PA—Br

PA—Ph

To a solution of compound PA-Br, which can include compounds of type PA2 or PA2, (1 eq) and an appropriately substituted phenyl boronic acid or ester (1.1-2.5 eq) in an appropriate solvent mixture such as, but not limited to, 2:1 dioxane:water or 4:1 ACN:water (1.8-4.7 mL/mmol of PA-Br) was added an appropriate base (2-3 eq) and palladium catalyst (0.03-0.08 eq). Appropriate bases include, but are not limited to, $K_2CO_3$, $K_3PO_4$ or $KH_2PO_4$. Appropriate palladium sources include, but are not limited to, $Pd(PPh_3)_4$, $Pd(dppf)Cl_2$, $Pd(dppf)Cl_2$—$CH_2Cl_2$, $Pd_2(dba)_3$ or $Amphos_2PdCl_2$. The resulting mixture was degassed with nitrogen and then stirred at 80-100° C. until the reaction was complete as monitored by LC-MS and/or TLC. The resulting reaction mixture was worked up by one of the following methods or a very similar variation. Method 1: The reaction mixture was filtered through Celite and the filtrate was concentrated under vacuum to remove dioxane. The resulting residue was diluted with aq. 2 N NaOH (1.6 mL/mmol of PA-Br used) and washed with EtOAc (2×). The aqueous phase was then acidified to pH 2-3 with aq. 6 N HCl. The resulting precipitate was filtered, washed with water and dried to give crude PA-Ph. Method 2: The reaction mixture was diluted with water (1.8 mL/mmol of PA-Br used), the resulting mixture was washed with EtOAc and the layers were separated. The organic layer was extracted with aq. 1 N NaOH (2×). The combined aqueous phases were washed with EtOAc (3×). The resulting aqueous phase was then acidified with aq. 6 N HCl to pH 2-3. The resulting precipitate was filtered and allowed to air-dry to give crude PA-Ph. Method 3: Where PA-Br is a carboxylic ester (R' is Me or Et) that was partially hydrolyzed to the carboxylic acid during the reaction, to push the hydrolysis to completion, 1 N NaOH (3.0 mL/mmol of PA-Br used) was added to the reaction mixture and heating continued at 60° C. for another 30 min or until the hydrolysis was complete as monitored by LC-MS and/or TLC. The reaction mixture was cooled to room temperature, diluted with water (3.0 mL/mmol of PA-Br used) and washed with EtOAc (3×). The aqueous phase was acidified using aq. 6 N HCl to pH 2. The resulting solid was filtered and dried to give PA-Ph. Regardless of the method of work up, the crude PA-Ph was generally used in subsequent reactions without further purification.

Example of General Procedure C: 6-(tert-Butyl)-5-(4-fluorophenyl)-4-oxo-1,4-dihydropyridine-3-carboxylic acid (PA5-3)

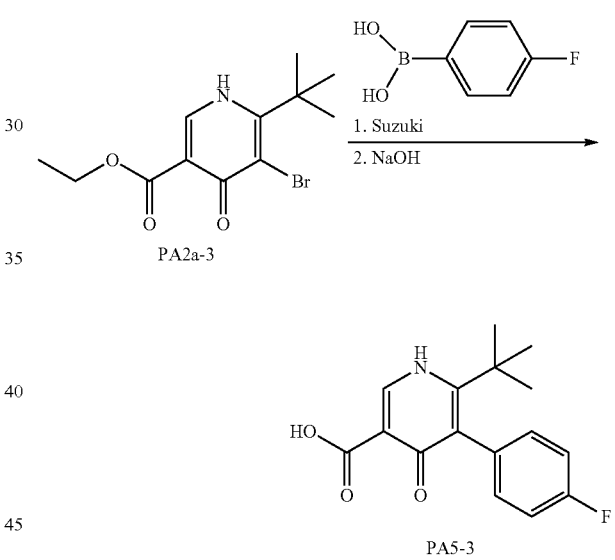

PA2a-3

PA5-3

6-(tert-Butyl)-5-(4-fluorophenyl)-4-oxo-1,4-dihydropyridine-3-carboxylic acid (PA5-3) To a solution of Compound PA2a-3 (200 mg, 0.66 mmol, 1 eq) in 2:1 dioxane:water (3.0 mL) was added (4-fluorophenyl)boronic acid (184 mg, 1.32 mmol, 2 eq), $K_2CO_3$ (274 mg, 1.98 mmol, 3 eq) and $Pd(PPh_3)_4$ (23 mg, 0.02 mmol, 0.03 eq). The resulting mixture was purged with nitrogen three times and heated to 90° C. overnight. The ester was partially hydrolyzed. To the reaction mixture was added aq. 1 N NaOH (2 mL) and the heating was continued at 60° C. for another 30 min to push the hydrolysis of the ester to completion. The reaction mixture was cooled to room temperature, diluted with water (2 mL) and washed with EtOAc (3×). The aqueous phase was acidified with aq. 6 N HCl to pH 2. The solid that formed was filtered and allowed to dry in the open air to give PA5-3. MS for $C_{16}H_{16}FNO_3$: m/z: 290 (MH+).

The following intermediates were made following General Procedure C or General Procedure C1:

-continued
PA3-1
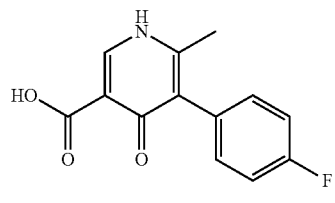
PA3-2
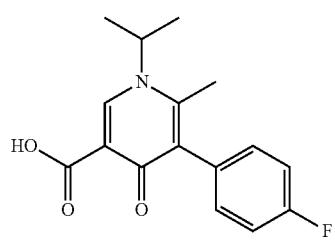
PA3-4
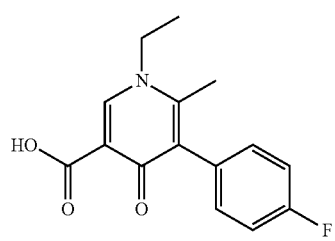
PA3-5
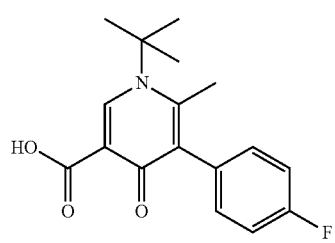
PA3-6
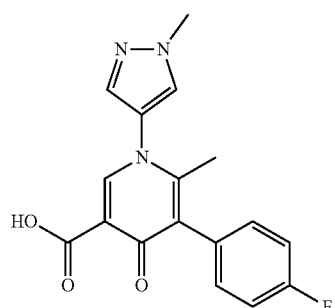
PA3-7
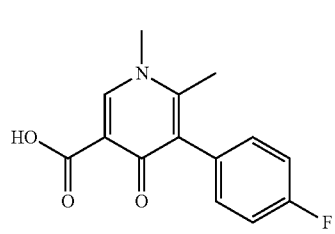
PA3-8
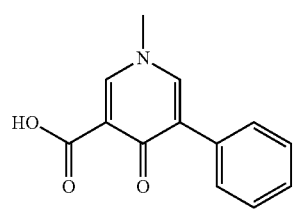
PA3-9
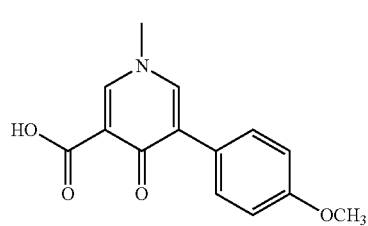
PA3-10
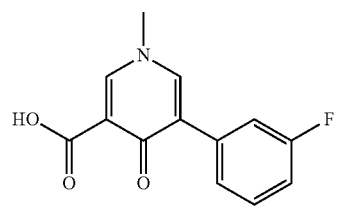
PA3-11
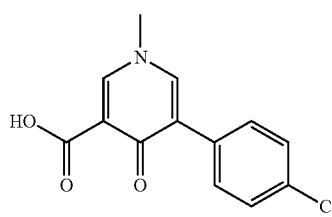
PA3-12
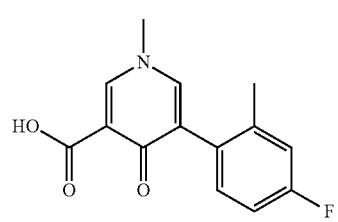
PA3-13
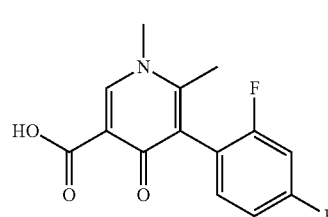
PA5-1
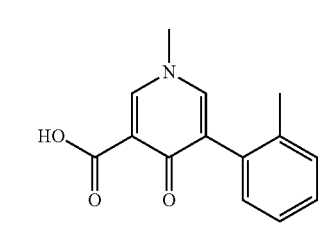

-continued

PA5-3

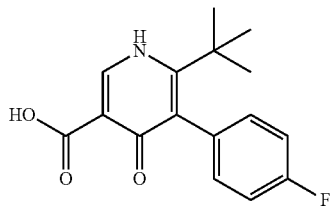

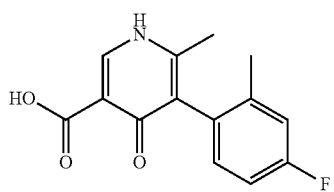

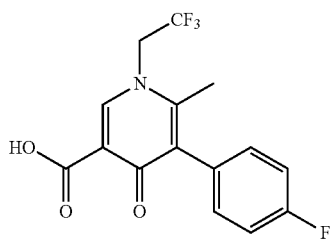

PA7-6

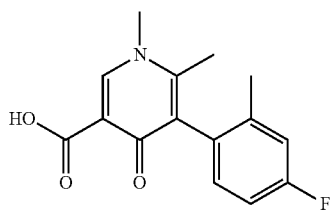

PA7-7

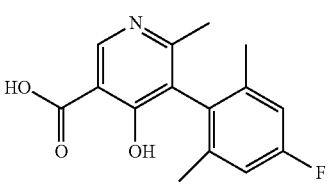

PA7-20

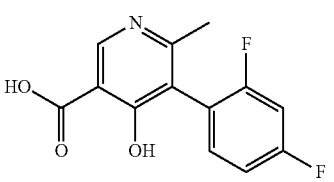

PA7-22

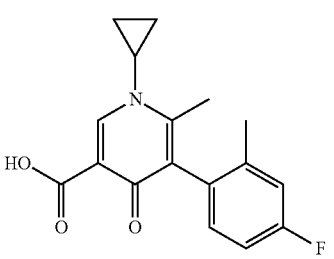

PA7-32

-continued

PA7-35

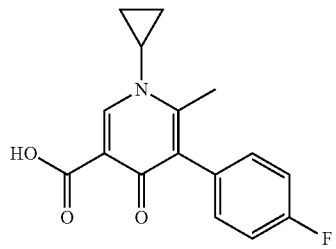

PA7-1  5-(4-Fluorophenyl)-6-methyl-4-oxo-1,4-dihydropyridine-3-carboxylic acid (PA3-1): MS for $C_{13}H_{10}FNO_3$: m/z 247.9 (MH+).

5-(4-Fluorophenyl)-1-isopropyl-6-methyl-4-oxo-1,4-dihydropyridine-3-carboxylic acid (PA3-2): MS for $C_{16}H_{16}FNO_3$: m/z 290 (MH+).

1-Ethyl-5-(4-fluorophenyl)-6-methyl-4-oxo-1,4-dihydropyridine-3-carboxylic acid (PA3-4): MS for $C_{15}H_{14}FNO_3$: m/z 276 (MH+).

1-(tert-Butyl)-5-(4-fluorophenyl)-6-methyl-4-oxo-1,4-dihydropyridine-3-carboxylic acid (PA3-5): MS for $C_{17}H_{18}FNO_3$: m/z 304 (MH+).

5-(4-Fluorophenyl)-6-methyl-1-(1-methyl-1H-pyrazol-4-yl)-4-oxo-1,4-dihydropyridine-3-carboxylic acid (PA3-6): MS for $C_{17}H_4FN_3O_3$: m/z 328 (MH+).

5-(4-fluorophenyl)-1,6-dimethyl-4-oxo-1,4-dihydropyridine-3-carboxylic acid (PA3-7): MS for $C_{14}H_{12}FNO_3$: m/z 262 (MH+).

1-Methyl-4-oxo-5-phenyl-1,4-dihydropyridine-3-carboxylic acid (PA3-8): MS for $C_{13}HNO_3$: m/z 230 (MH+).

5-(4-Methoxyphenyl)-1-methyl-4-oxo-1,4-dihydropyridine-3-carboxylic acid (PA3-9): MS for $C_{14}H_{13}NO_4$: m/z 260 (MH+).

5-(3-Fluorophenyl)-1-methyl-4-oxo-1,4-dihydropyridine-3-carboxylic acid (PA3-10): MS for $C_{13}H_{10}FNO_3$: m/z 248 (MH+).

5-(4-Chlorophenyl)-1-methyl-4-oxo-1,4-dihydropyridine-3-carboxylic acid (PA3-11): MS for $C_{13}H_{10}ClNO_3$: m/z 264 (MH+).

5-(4-Fluoro-2-methylphenyl)-1-methyl-4-oxo-1,4-dihydropyridine-3-carboxylic acid (PA3-12): MS for $C_{14}H_{12}FNO_3$: m/z 262 (MH+).

5-(2,4-Difluorophenyl)-1,6-dimethyl-4-oxo-1,4-dihydropyridine-3-carboxylic acid (PA3-13).

1-Methyl-4-oxo-5-(o-tolyl)-1,4-dihydropyridine-3-carboxylic acid (PA5-1): calculated MS for $C_{14}H_{13}NO_3$: m/z 244 (MH+)

6-(tert-Butyl)-5-(4-fluorophenyl)-4-oxo-1,4-dihydropyridine-3-carboxylic acid (PA5-3): MS for $C_{16}H_{16}FNO_3$: m/z 290 (MH+).

5-(4-Fluoro-2-methylphenyl)-6-methyl-4-oxo-1,4-dihydropyridine-3-carboxylic acid (PA7-1): MS for $C_{14}H_{12}FNO_3$: m/z 262 (MH+).

5-(4-Fluorophenyl)-6-methyl-4-oxo-1-(2,2,2-trifluoroethyl)-1,4-dihydropyridine-3-carboxylic acid (PA7-6): MS for $C_{15}HF_4NO_3$: m/z 330.3 (MH+).

5-(4-Fluoro-2-methylphenyl)-1,6-dimethyl-4-oxo-1,4-dihydropyridine-3-carboxylic acid (PA7-7): MS for $C_{15}H_{14}FNO_3$: m/z 276 (MH+).

5-(4-Fluoro-2,6-dimethylphenyl)-4-hydroxy-6-methylnicotinic acid (PA7-20): In this particular case, the amount of catalyst used ($Pd_2(dba)_3$) was increased to 0.46 eq and the reaction was heated at 100° C. overnight. After work-up the crude product was purified by prep HPLC. MS for $C_{15}H_{14}FNO_3$: m/z 276.3 (MH+).

5-(2,4-Difluorophenyl)-4-hydroxy-6-methylnicotinic acid (PA7-22): MS for $C_{13}H_9F_2NO_3$: m/z 266.2 (MH+).

1-Cyclopropyl-5-(4-fluoro-2-methylphenyl)-6-methyl-4-oxo-1,4-dihydropyridine-3-carboxylic acid (PA7-32): MS for $C_{17}H_{16}FNO_3$: m/z 302.3 (MH+).

1-Cyclopropyl-5-(4-fluorophenyl)-6-methyl-4-oxo-1,4-dihydropyridine-3-carboxylic acid (PA7-35): MS for $C_{16}H_{14}FNO_3$: m/z 288.3 (MH+).

General Procedure C2: 4-Hydroxy-2H-pyran-2-one method to form 2,6-disubstituted 4-hydroxypyridines (PA5-a)

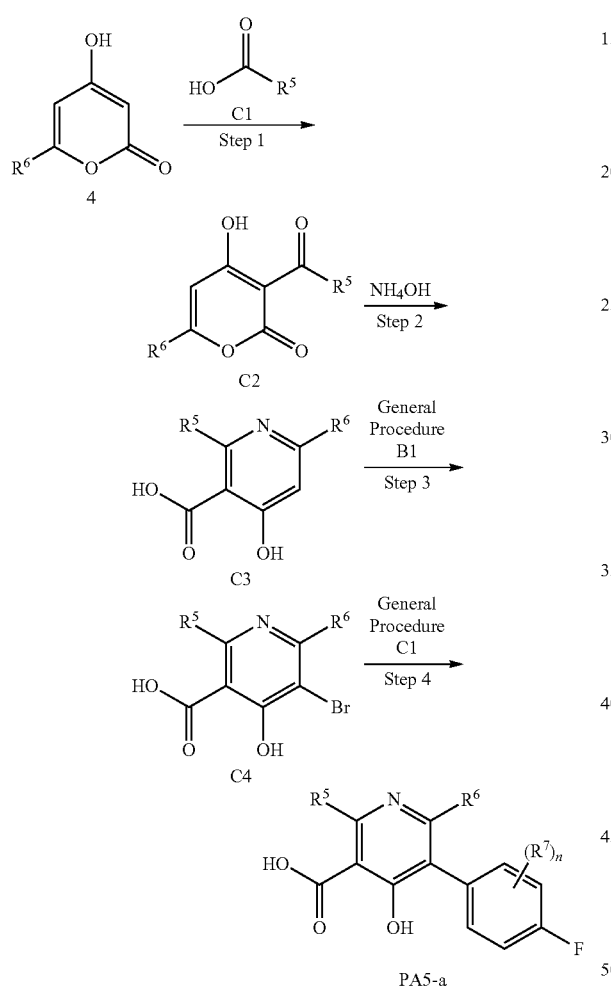

Step 1: To a solution of Compound 4 (1 eq) in toluene (1.2 mL/mmol of 4) was added acid C1 (1 eq), DCC (1 eq) and DMAP (1 eq). The resulting mixture was heated to 50° C. The resulting solid crude product was filtered and then purified by flash silica gel column chromatography to give Compound C2.

Step 2: To a solution of Compound C2 (1 eq) in water (1.0-3.2 mL/mmol of $C_2$) was added 30-40% ammonium hydroxide in water (0.9-1.0 mL/mmol of $C_2$). The resulting mixture was heated to reflux overnight. The reaction mixture was cooled to room temperature and solvent was partially removed in vacuo. The resulting reaction mixture was cooled to 0° C. and acidified using aq. 6 N HCl to pH 2. The resulting solid was filtered and dried in the open air to give Compound C3.

Step 3: See General Procedure B above for the bromination of 4-pyridone carboxylic acids or esters.

Step 4: See General Procedure C1 above for Suzuki reactions with 5-bromo-4-pyridone carboxylic acids or esters.

Example A of General Procedure C2: 5-(4-Fluorophenyl)-2-(methoxymethyl)-6-methyl-4-oxo-1,4-dihydropyridine-3-carboxylic acid (PA5-11)

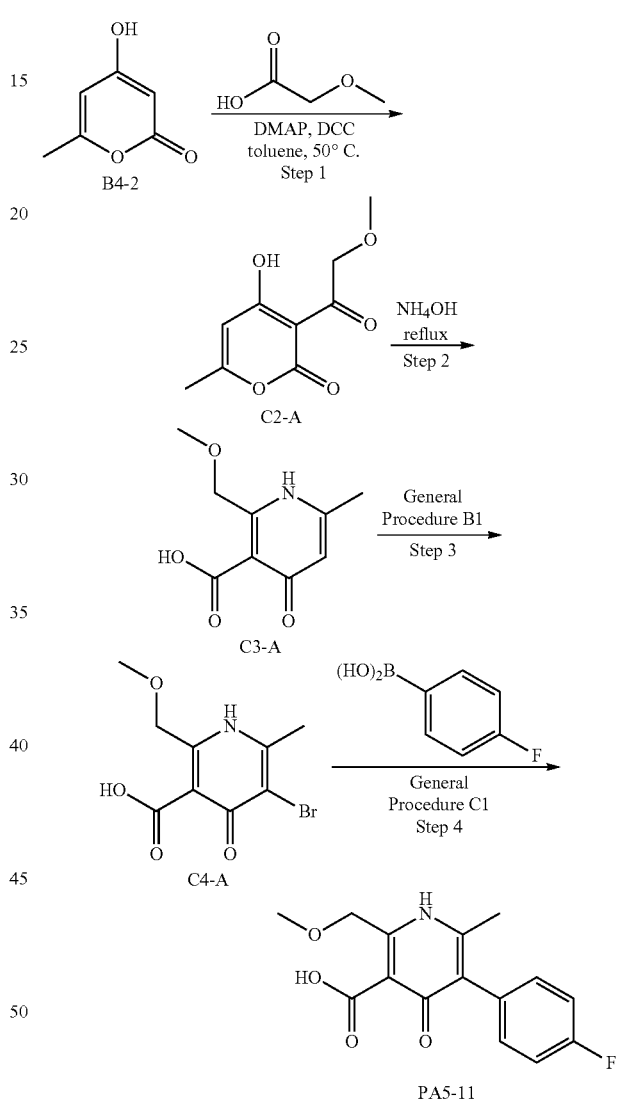

Step 1: 4-Hydroxy-3-(2-methoxyacetyl)-6-methyl-2H-pyran-2-one ($C_2$-A): To a solution of Compound B4-2 (10 g, 79 mmol, 1 eq) in toluene (100 mL) was added 2-methoxyacetic acid (7.1 g, 79 mmol, 1 eq), DCC (16.3 g, 79 mmol, 1 eq) and DMAP (9.6 g, 79 mmol, 1 eq). The resulting mixture was heated to 50° C. The resulting solid was filtered and then purified by flash silica gel column chromatography (0-100% EtOAc/hexanes) to give Compound C2-A. MS for $C_9H_{10}O_5$: m/z 199 (MH+).

Step 2: 2-(Methoxymethyl)-6-methyl-4-oxo-1,4-dihydropyridine-3-carboxylic acid (C3-A): To a solution of Compound C2-A (12.5 g, 63 mmol, 1 eq) in water (200 mL) was added ammonium hydroxide (40% in water, 60 mL). The resulting mixture was heated to reflux overnight. After allowing the reaction mixture to cool to room temperature, the solvent was partially removed under vacuum. The resulting mixture was cooled to 0° C. and acidified to pH 2 using aq. 6 N HCl. The resulting solid was filtered and allowed to dry in the open air to give Compound C3-A. MS for $C_9H_{11}NO_4$: m/z 198 (MH+).

Step 3: 5-Bromo-2-(methoxymethyl)-6-methyl-4-oxo-1,4-dihydropyridine-3-carboxylic acid (C4-A): Compound C4-A was synthesized from Compound C3-A using General Procedure B1. MS for $C_9H_{10}BrNO_4$: m/z 276 (MH+).

Step 4: 5-(4-Fluorophenyl)-2-(methoxymethyl)-6-methyl-4-oxo-1,4-dihydropyridine-3-carboxylic acid (PA5-11): Compound PA5-11 was synthesized from Compound C4-A using General Procedure C1. MS for $C_{15}H_{14}FNO_4$: m/z 292 (MH+).

Example B of General Procedure C2: 5-(4-Fluoro-2-methylphenyl)-2,6-dimethyl-4-oxo-1,4-dihydropyridine-3-carboxylic acid (PA7-2)

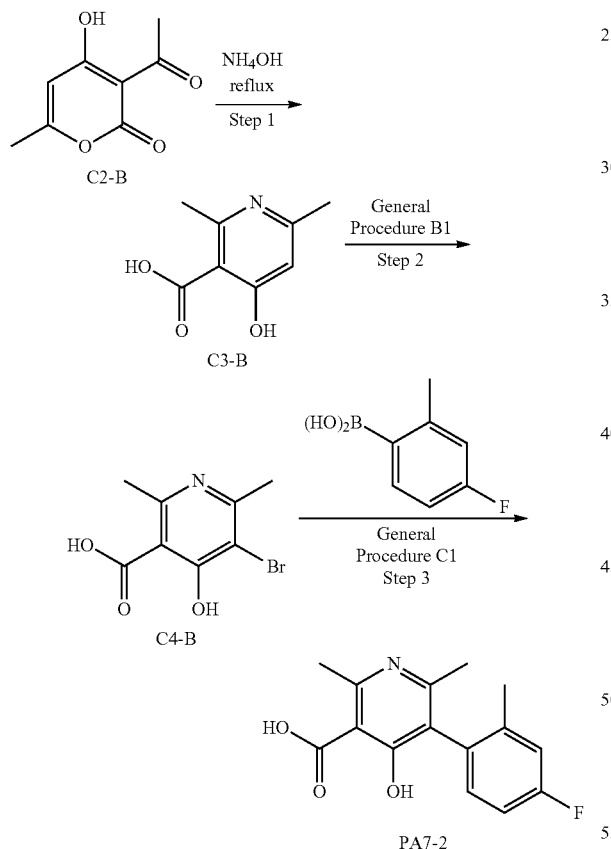

Step 1: 2,6-Dimethyl-4-oxo-1,4-dihydropyridine-3-carboxylic acid ($C_3$—B): To a solution of commercially available Compound C2-B (10 g, 59.88 mmol) in water (60 mL) was added ammonium hydroxide (60 mL, 30% in water). The resulting mixture was heated to reflux overnight. The mixture was partially concentrated and then acidified to pH 2 with aq. 6 M HCl. The resulting precipitate was filtered and allowed to dry in the open air to afford Compound C3-B as a white solid (2.5 g, 25% yield). MS for $C_8H_9NO_3$: m/z 168 (MH+).

Step 2: 5-Bromo-2,6-dimethyl-4-oxo-1,4-dihydropyridine-3-carboxylic acid (C4-B): Compound C4-B was synthesized from Compound C3-B using General Procedure B1. MS for $C_8H_8BrNO_3$: m/z 246 (MH+).

Step 3: 5-(4-Fluoro-2-methylphenyl)-2,6-dimethyl-4-oxo-1,4-dihydropyridine-3-carboxylic acid (PA7-2): Compound PA7-2 was synthesized from Compound C4-B using a procedure similar to General Procedure C1. Specifically, to a solution of Compound C4-B (1 g, 4.1 mmol) in dioxane/water (10 mL/5 mL) was added (4-fluoro-2-methylphenyl)boronic acid (10.2 mmol, 2.5 eq), Pd(Amphos)Cl$_2$ (0.24 mmol, 0.06 eq) and K$_3$PO$_4$ (12.2 mmol, 3 eq). The resulting mixture was heated to 90° C. overnight. The resulting phases were separated. The organic phase was diluted with EtOAc and extracted with aq. 1 N NaOH (2×). The combined aqueous layers (original aqueous phase from the crude reaction mixture and the aqueous extracts) were combined and washed with EtOAc (3×) and then acidified to pH 2 using aq. 6 M HCl. The resulting precipitate was filtered and allowed to dry in the open air to give Compound PA7-2 as a white solid (642 mg. 57% yield). MS for $C_{15}H_{14}FNO_3$: m/z 276 (MH+).

The following intermediates were made following General Procedure C2 for the 4-hydroxy-2H-pyran-2-one method to form 2,6-disubstituted 4-hydroxypyridines: PA5-a,

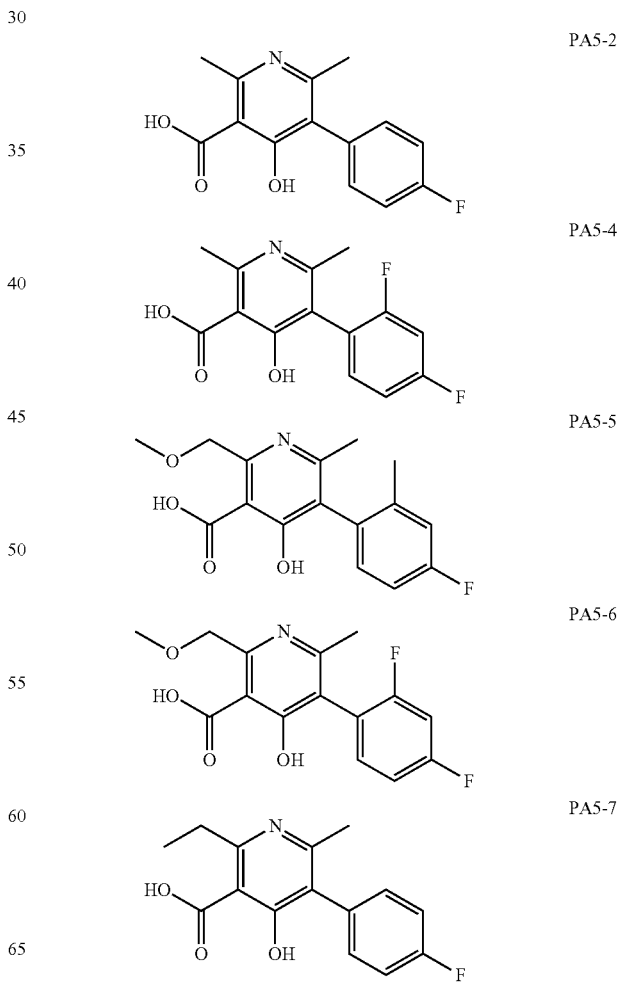

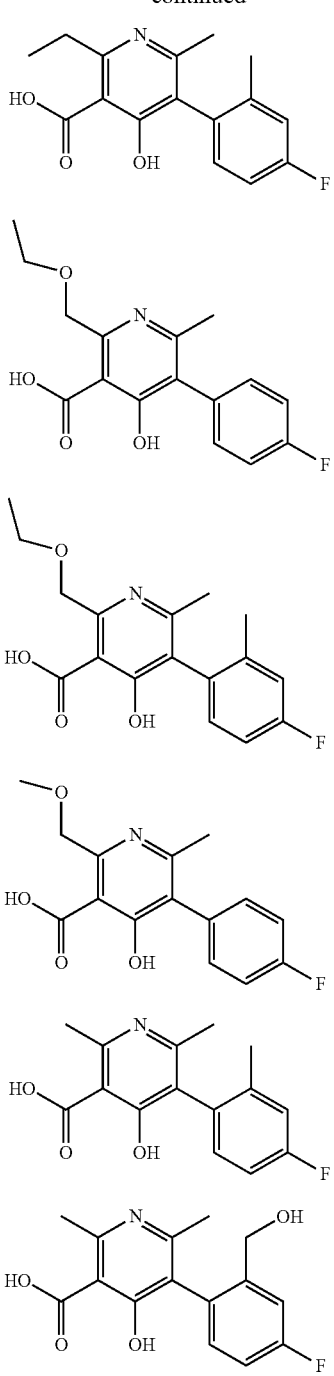

5-(4-Fluorophenyl)-2,6-dimethyl-4-oxo-1,4-dihydropyridine-3-carboxylic acid (PA5-2): MS for $C_{14}H_{12}FNO_3$: m/z 262 (MH+).

5-(2,4-Difluorophenyl)-2,6-dimethyl-4-oxo-1,4-dihydropyridine-3-carboxylic acid (PA5-4): MS for $C_{14}H_{11}F_2NO_3$: m/z 280 (MH+).

5-(4-Fluoro-2-methylphenyl)-2-(methoxymethyl)-6-methyl-4-oxo-1,4-dihydropyridine-3-carboxylic acid (PA5-5): MS for $C_{16}H_{16}FNO_4$: m/z 306 (MH+).

5-(2,4-Difluorophenyl)-2-(methoxymethyl)-6-methyl-4-oxo-1,4-dihydropyridine-3-carboxylic acid (PA5-6): MS for $C_{15}H_{13}F_2NO_4$: m/z 310 (MH+).

2-Ethyl-5-(4-fluorophenyl)-6-methyl-4-oxo-1,4-dihydropyridine-3-carboxylic acid (PA5-7): MS for $C_{15}H_{14}FNO_3$: m/z 276 (MH+).

2-Ethyl-5-(4-fluoro-2-methylphenyl)-6-methyl-4-oxo-1,4-dihydropyridine-3-carboxylic acid (PA5-8): MS for $C_{16}H_{16}FNO_3$: m/z 290 (MH+).

2-(Ethoxymethyl)-5-(4-fluorophenyl)-6-methyl-4-oxo-1,4-dihydropyridine-3-carboxylic acid (PA5-9): MS for $C_{16}H_{16}FNO_4$: m/z 306 (MH+).

2-(Ethoxymethyl)-5-(4-fluoro-2-methylphenyl)-6-methyl-4-oxo-1,4-dihydropyridine-3-carboxylic acid (PA5-10): MS for $C_{17}H_{18}FNO_4$: m/z 320 (MH+).

5-(4-Fluorophenyl)-2-(methoxymethyl)-6-methyl-4-oxo-1,4-dihydropyridine-3-carboxylic acid (PA5-11): MS for $C_{15}H_{14}FNO_4$: m/z 292 (MH+).

5-(4-Fluoro-2-methylphenyl)-2,6-dimethyl-4-oxo-1,4-dihydropyridine-3-carboxylic acid (PA7-2): MS for $C_{15}H_{14}FNO_3$: m/z 276 (MH+).

5-(4-Fluoro-2-(hydroxymethyl)phenyl)-4-hydroxy-2,6-dimethylnicotinic acid (PA7-21): MS for $C_{15}H_{14}FNO_4$: m/z 292 (MH+).

General Procedure D: 4-Pyridone Carboxylic Acids (PA4)

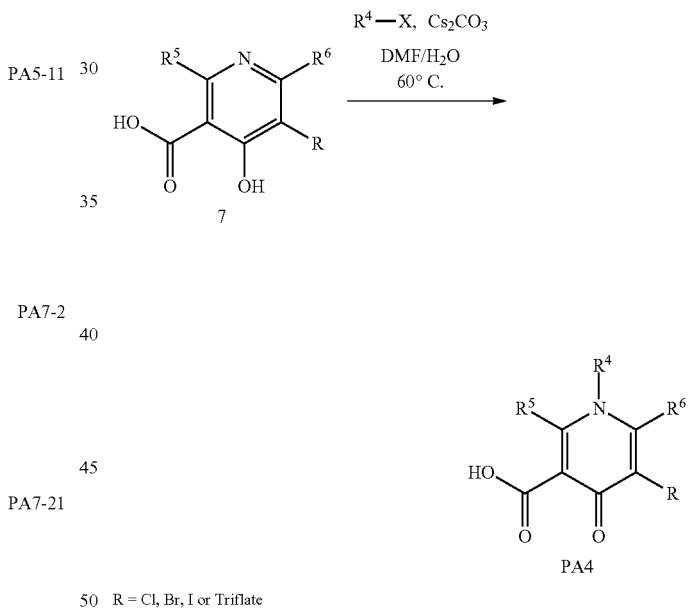

R = Cl, Br, I or Triflate

To a solution of pyridine acid 7 in (8.1 mmol) in DMF (10 mL)/water (10 mL) was added alkyl halide ($R^4$—X) (2 eq) and cesium carbonate (3 eq). The resulting mixture was heated to 60° C. overnight. The reaction mixture was allowed to cool to room temperature and filtered through Celite. The filtrate was concentrated under vacuum. The crude residue was brought up in MeOH (5 mL) and 1 N NaOH (5 mL) was added. The resulting mixture was stirred at room temperature for 1 h. MeOH was removed in vacuo and the resulting aqueous mixture was washed with EtOAc (3×). The aqueous phase was acidified with aq. 6 N HCl to pH 2-3. The resulting material was filtered and allowed to air-dry to give Compound PA4 which was generally used in subsequent reactions without further purification.

Example of General Procedure D: 5-Bromo-1-methyl-4-oxo-1,4-dihydropyridine-3-carboxylic acid (PA4-1)

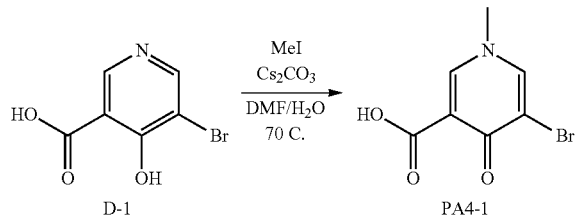

5-Bromo-1-methyl-4-oxo-1,4-dihydropyridine-3-carboxylic acid (PA4-1): To a solution of Compound D-1 (4.8 g, 22 mmol, 1 eq) in 2:1 DMF:water (30 mL) was added $Cs_2CO_3$ (21.4 g, 65.6 mmol, 3 eq) and MeI (9.3 g, 65.6 mmol, 3 eq). The resulting mixture was heated to 70° C. for 10 min. The reaction mixture was allowed to cool to room temperature, diluted with water (10 ml) and washed with EtOAc (3×). The aqueous phase was acidified to pH 3-4 using aq. 6 N HCl. The resulting solid was filtered and allowed to dry in the open air to give Compound PA4-1 as a light-yellow solid (4.1 g, 82% yield). MS for $C_7H_6BrNO_3$: m/z 232/234 (MH+).

General Procedure E: 4-Pyridone Carboxylic Acids (PA5)

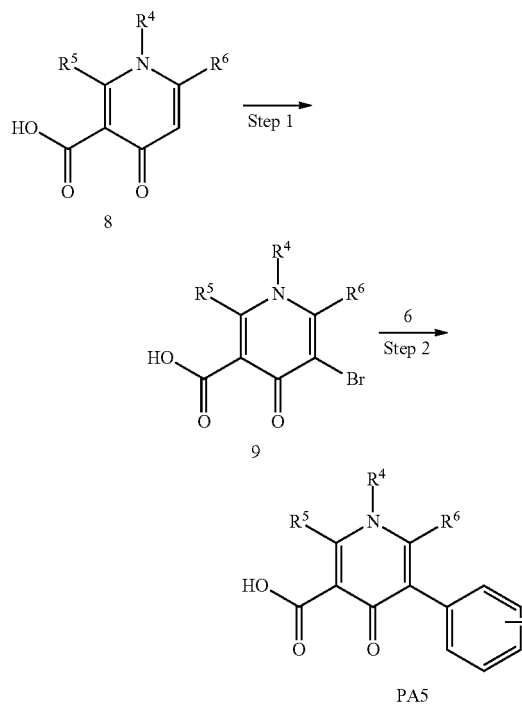

Step 1: Following procedures similar to Step 2 of General Procedure B or General Procedure B1, pyridone carboxylic acids 8 (32.7 mmol) were brominated using NBS (1 eq) in an organic solvent such as NMP or ACN (0.5M) for 30 min. Upon completion of the reaction as determined by monitoring with LC-MS, water was added to the reaction mixture and the resulting mixture was stirred at room temperature for 15 min. The resulting precipitate was filtered, washed with water and allowed to air-dry to afford Compound 9 which was generally used in subsequent reactions without further purification. The same procedure can also be carried out on esters of Compound 8.

Step 2: Following procedures similar to General Procedure C or General Procedure C1, Compound 9 recovered from Step 1 was dissolved in a mixture of dioxane and water (40/20 mL, 1:1 vv). Boronic acid 6 (1.5-2.5 eq) was added to the resulting solution of Compound 9 followed by the addition of $K_2CO_3$ or $KH_3PO_4$ (3 eq) and a palladium source such as tetrakis or $Amphos_2PdCl_2$ (0.06 eq). The reaction mixture was purged with nitrogen 3 times and then heated to 90° C. for 1 h. Upon completion of the reaction as monitored by LC-MS, the reaction mixture was allowed to cool to room temperature followed by dilution with water (60 mL). The resulting mixture was washed with EtOAc and layers were separated. The organic layer was extracted with 1 N NaOH (2×). The combined aqueous phases were washed with EtOAc (3×). The resulting aqueous phase was then acidified with aq. 6 N HCl to pH 2-3. The resulting precipitate was filtered and allowed to air-dry to give Compound PA5 which was generally used in subsequent reactions without further purification.

General Procedure F: 4-Pyridone Carboxylic Acids (PA6)

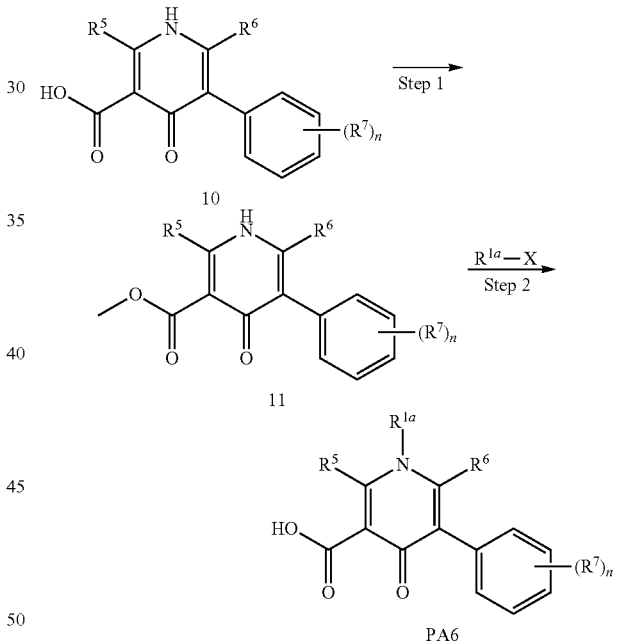

Step 1: Note: Compound 10 in this procedure can be any PA1, PA2, or PA5 synthesized according to the previous general procedures where $R^4$ is hydrogen. To a solution of Compound 10 (2.18 mmol) in anhyd. MeOH (5 mL) was added HCl (2 mL, 4 M in dioxane). The resulting mixture was stirred at room temperature overnight. Solvents were removed under reduced pressure and the resulting crude Compound 11 was used for the next step without further purification.

Step 2: To Compound 11 (0.38 mmol) in DMF (2 mL) was added alkyl halide $R^{1a}$—X (1.2 eq) and $Cs_2CO_3$ (3 eq). The resulting mixture was heated to 60° C. overnight. The reaction mixture was allowed to cool to room temperature and filtered through Celite. The filtrate was concentrated under reduced pressure. The resulting crude residue was brought up in MeOH (1 mL) and aq. 1 N NaOH (1 mL) was added. The resulting mixture was stirred at room temperature for 1 h. MeOH was removed under vacuum and remaining aqueous mixture was washed with EtOAc (3×). The resulting aqueous phase was acidified with aq. 6 N HCl to pH 2-3. The resulting precipitate was filtered and air-dried to give crude Compound PA6 which was generally used in subsequent reactions without further purification.

General Procedure F1: N-Alkylation 4-Hydroxypyridines (PA6-a)

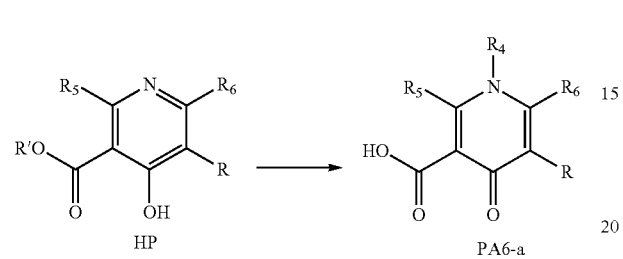

To a solution of a hydroxypyridine (HP) carboxylic acid (R' =H) or ester (R' typically=Me or Et) (1 eq) in an appropriate solvent (1.4-5.3 mL/mmol of HP) such as, but not limited to, DMF, a 2:1 mixture of DMF and water, or ACN was added alkyl halide ($R^4$—X) (1.2-3 eq) and an appropriate base such as, but not limited to, $Cs_2CO_3$ or $K_2CO_3$ (3 eq). The resulting mixture was heated to 60-70° C. until reaction was complete as monitored by LC-MS and/or TLC. After cooling to room temperature, the reaction mixture was worked up using one of the following methods depending on whether HP was a carboxylic acid, an ester, or whether the ester formed from the carboxylic acid as a side product during the alkylation reaction. Method 1 (HP=carboxylic acid): The cooled reaction mixture was diluted with water and washed with EtOAc (3×). The aqueous phase was acidified to pH 3-4 with aq. 6 N HCl. The resulting solid was filtered and dried to give Compound PA6-a. Method 2 (HP=Me or Et ester or side product ester formed during the alkylation reaction): The cooled reaction mixture was diluted with water and extracted with EtOAc (3×). The combined organic extracts were washed with water, washed with aq. saturated NaCl, dried over anhyd. $Na_2SO_4$ and concentrated in vacuo. The crude residue was dissolved in MeOH (0.6-5.2 mL/mmol of HP used) to which was added aq. 1 N NaOH (0.6-5.2 mL/mmol of HP used) The resulting mixture was stirred at room temperature long enough to ensure complete hydrolysis of the ester to the corresponding carboxylic acid as monitored by LC-MS and/or TLC. MeOH was removed in vacuo and the resulting aqueous mixture was washed with EtOAc (3×). The aqueous phase was acidified with aq. 6 N HCl to pH 2-7. The resulting material was filtered, and the resulting solid allowed to air-dry to give crude Compound PA6-a. Regardless of the method, crude PA6-a was generally used in subsequent reactions without further purification. The carboxylic acids of HP can be generated by any of the methods described within. The esters of HP can be generated en route to the carboxylic acids previously described such as intermediate C3 in General Procedure C or can be generated from the acids by standard esterification techniques. For example, to form the methyl ester of the carboxylic acid of HP, the acid can be dissolved in anhyd. MeOH to which is added 4 M HCl in dioxane. After stirring the resulting mixture at room temperature overnight, the corresponding crude methyl ester is recovered by concentration of the reaction mixture under vacuum.

Example of General Procedure F1: 5-(4-Fluorophenyl)-1-(2-morpholinoethyl)-4-oxo-1,4-dihydropyridine-3-carboxylic acid (PA6-1)

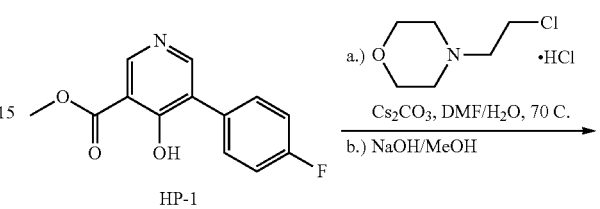

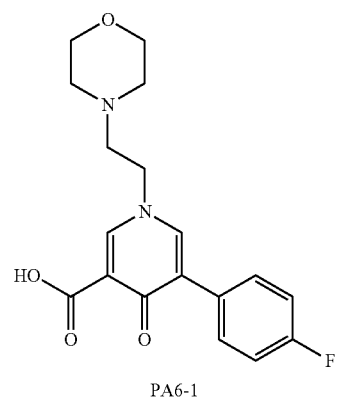

5-(4-Fluorophenyl)-1-(2-morpholinoethyl)-4-oxo-1,4-dihydropyridine-3-carboxylic acid (PA6-1): To a solution of Compound HP-1 (100 mg, 0.38 mmol, 1 eq) in DMF (2 mL) was added $Cs_2CO_3$ (375 mg, 1.15 mmol, 3 eq) and 4-(2-chloroethyl)morpholine hydrochloride (86 mg, 0.46 mmol, 1.2 eq). The resulting mixture was heated to 60° C. for 15 min. The reaction mixture was allowed to cool to room temperature, diluted with water (3 ml) and extracted with EtOAc (3×). The combined organic extracts were washed with water, washed with aq. saturated NaCl, dried over anhyd. $Na_2SO_4$ and concentrated. The resulting residue was dissolved in MeOH (2 mL) and 1 N NaOH (2 mL) was added. The resulting solution was stirred at room temperature for 2 h. The solvent was partially removed, and the resulting aqueous mixture was washed with EtOAc (3×). The aqueous layer was acidified with aq. 6 N HCl to pH neutral. The resulting precipitate was filtered and allowed to dry in the open air to give Compound PA6-1 (66 mg, 50% yield) which was used in subsequent steps without further purification. MS of $C_{18}H_{19}FN_2O_4$: m/z: 347 (MH+).

The following intermediates were made following General Procedure F or General Procedure F1 for the synthesis of 4-pyridone carboxylic acids PA6 or PA6-a:

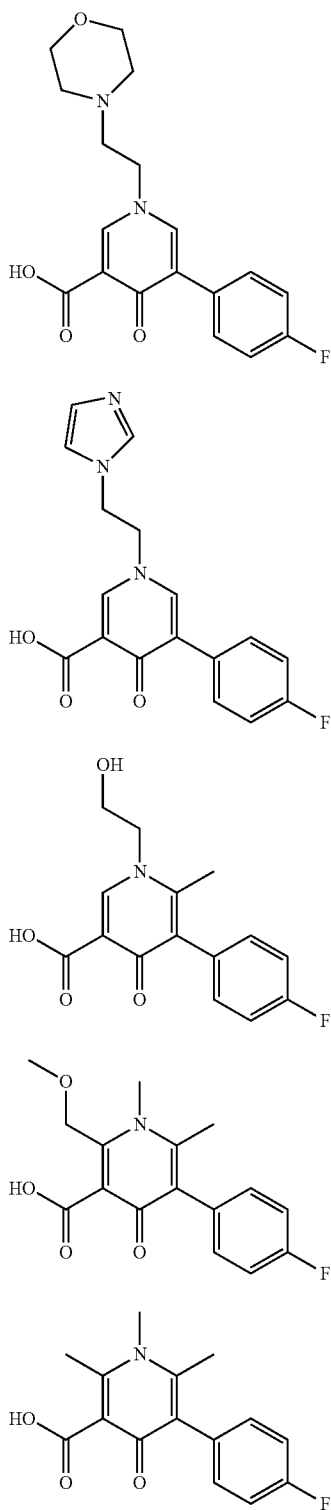

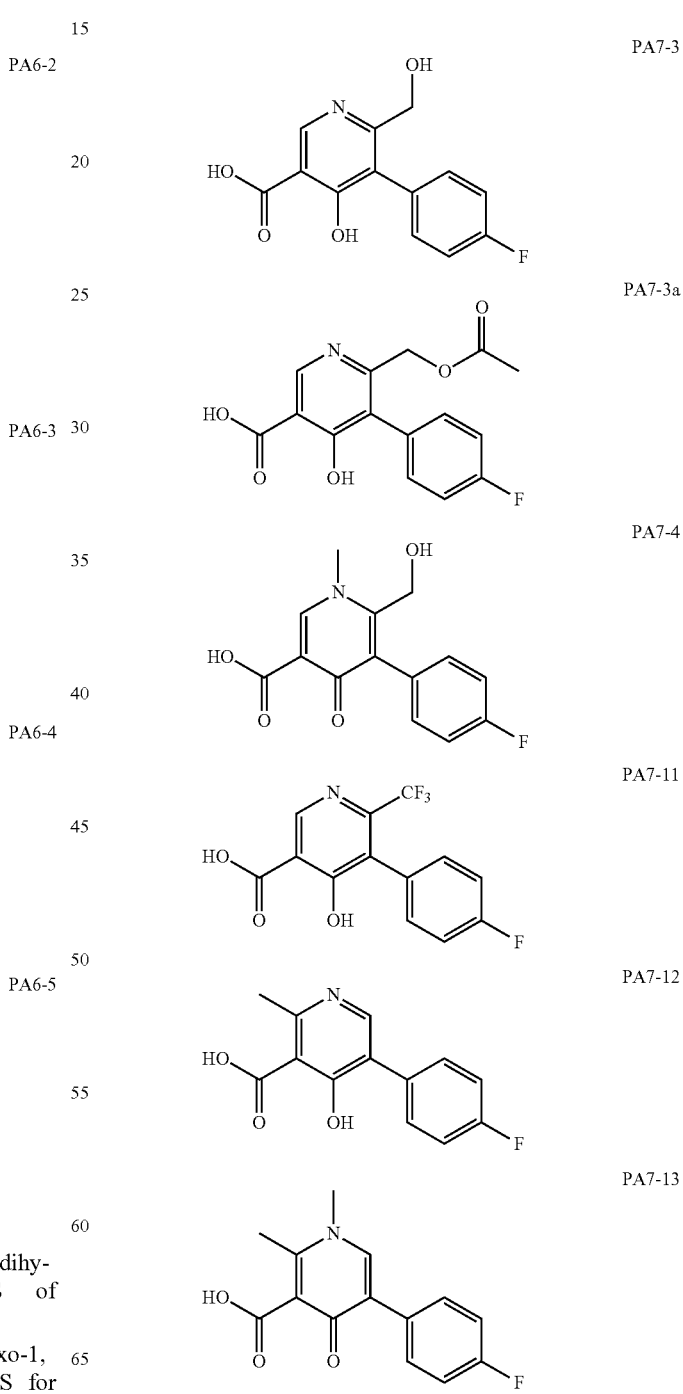

5-(4-Fluorophenyl)-1-(2-morpholinoethyl)-4-oxo-1,4-dihydropyridine-3-carboxylic acid (PA6-1): MS of $C_{18}H_{19}FN_2O_4$: m/z: 347 (MH+).

1-(2-(1H-Imidazol-1-yl)ethyl)-5-(4-fluorophenyl)-4-oxo-1,4-dihydropyridine-3-carboxylic acid (PA6-2): MS for $C_{17}H_{14}FN_3O_3$: m/z 328 (MH+).

5-(4-Fluorophenyl)-1-(2-hydroxyethyl)-6-methyl-4-oxo-1,4-dihydropyridine-3-carboxylic acid (PA6-3): MS for $C_{15}H_{14}FNO_4$: m/z 292 (MH+).

5-(4-Fluorophenyl)-2-(methoxymethyl)-1,6-dimethyl-4-oxo-1,4-dihydropyridine-3-carboxylic acid (PA6-4): MS for $C_{16}H_{16}FNO_4$: m/z 306.1 (MH+).

5-(4-Fluorophenyl)-1,2,6-trimethyl-4-oxo-1,4-dihydropyridine-3-carboxylic acid (PA6-5): MS for $C_{15}H_{14}FNO_3$: m/z 276 (MH+).

The following additional intermediates have been made using the synthetic methods detailed in Examples 5-61:

-continued
PA7-14
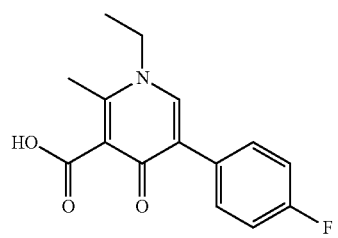
PA7-15
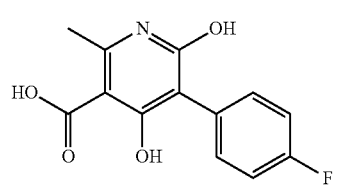
PA7-16
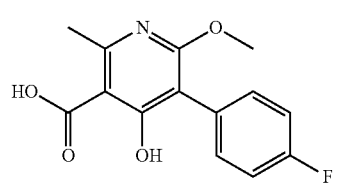
PA7-17
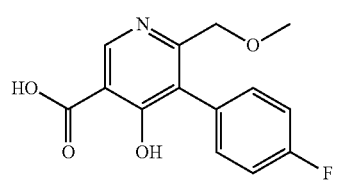
PA7-18
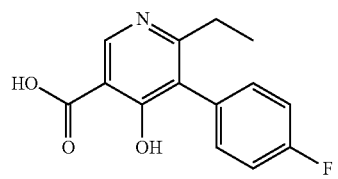
PA7-19
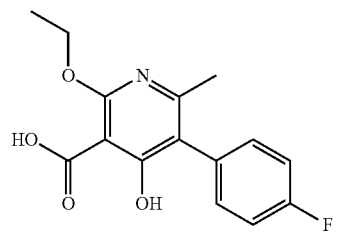
PA7-23
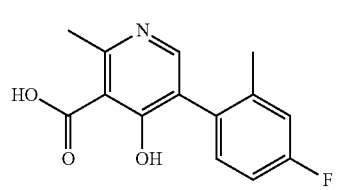
PA7-24
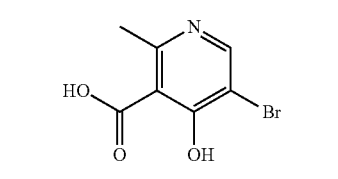
-continued
PA7-25
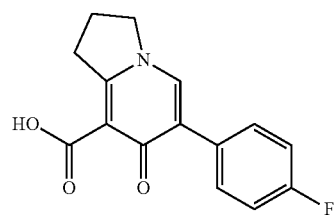
PA7-26
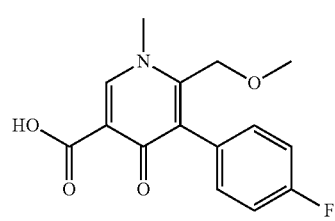
PA7-27
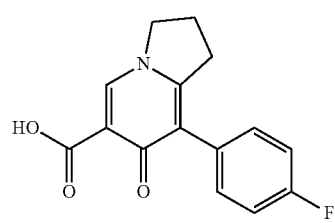
PA7-28
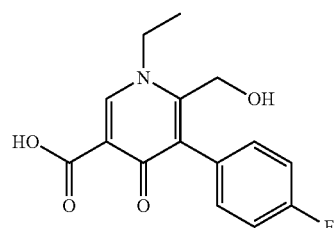
PA7-29
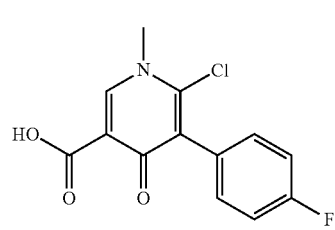
PA7-30
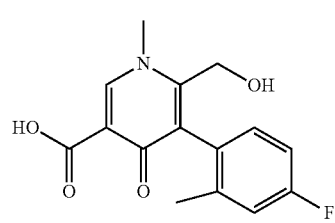
PA7-31
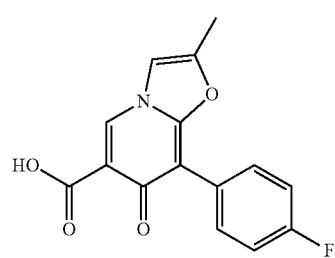

PA7-33
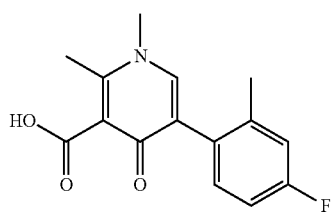
PA7-34
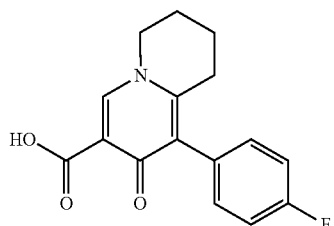
PA7-36
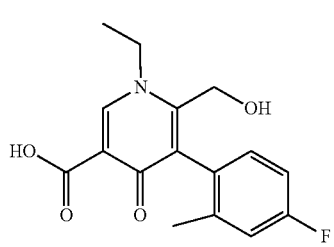
PA7-37
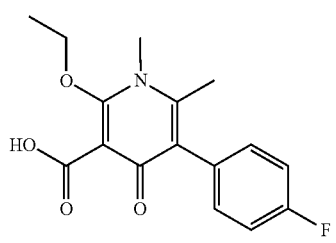
PA7-38
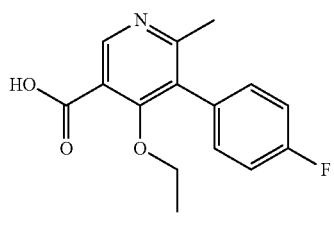
PA7-39
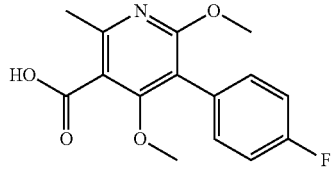
PA7-40
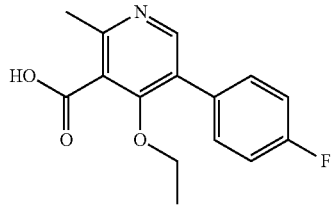
PA7-41
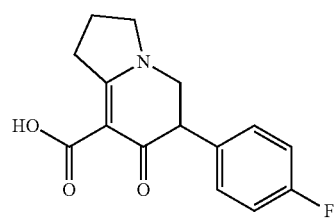
HA1-1
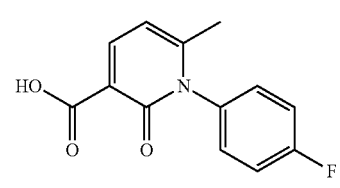
HA1-2
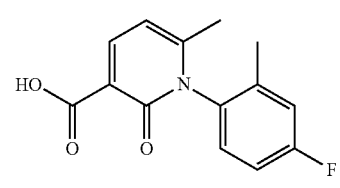
HA1-3
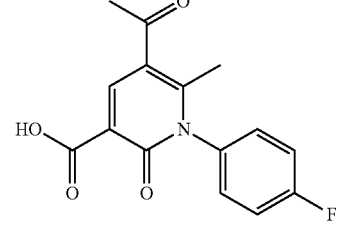
HA1-4
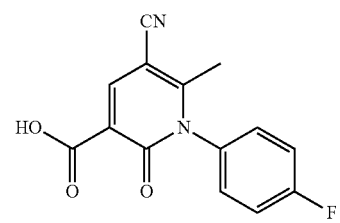
HA1-5
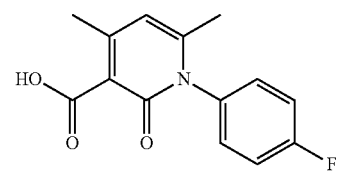
HA1-6
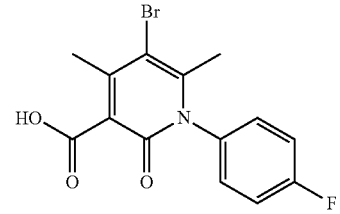

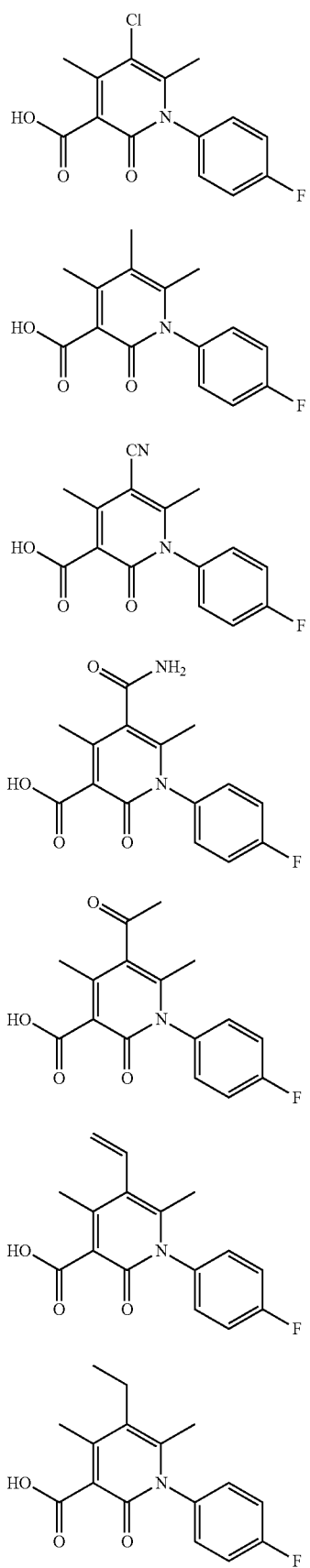
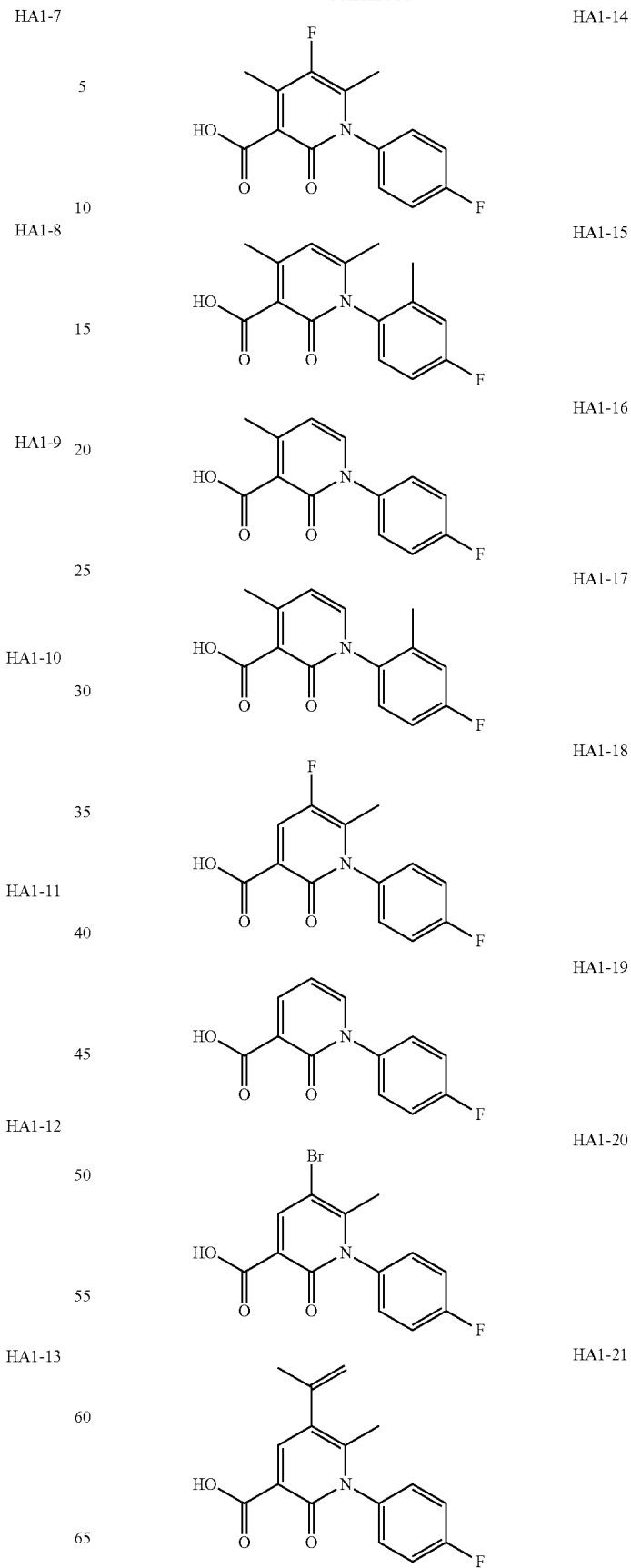

| | |
|---|---|
| HA1-22 | HA1-29 |
| HA1-23 | HA2-1 |
| HA1-24 | HA2-2 |
| HA1-25 | HA2-3 |
| HA1-26 | HA2-3B |
| HA1-27 | HA2-4A |
| HA1-28 | HA2-4B |

HA2-5
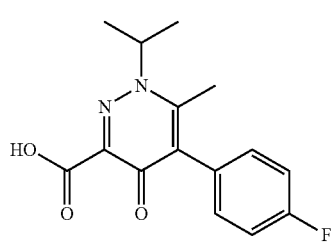
HA2-6A
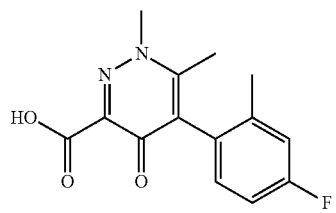
HA2-6B
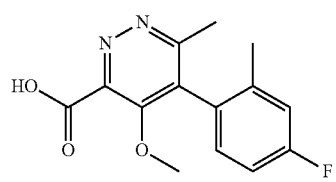
HA2-7
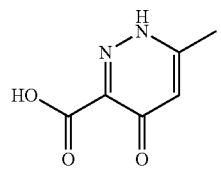
HA2-11
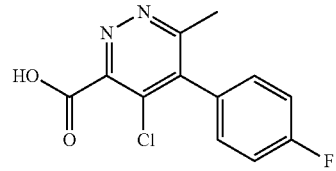
HA2-12
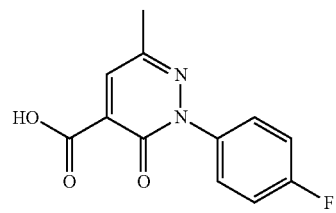
HA2-13
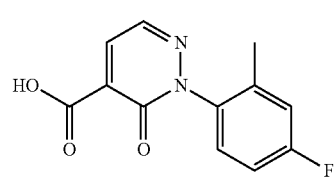
HA2-14
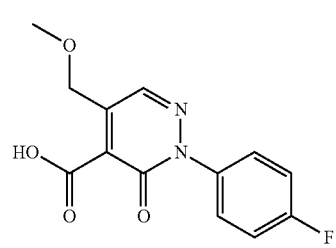
HA2-15
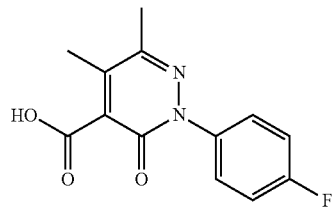
HA2-16
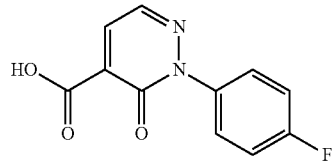
HA3-1
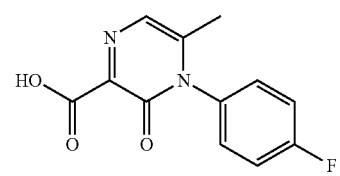
HA3-2
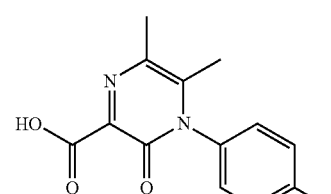
HA3-3
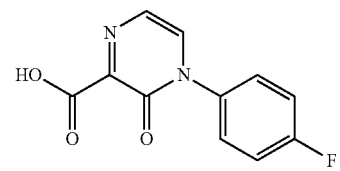
HA3-4
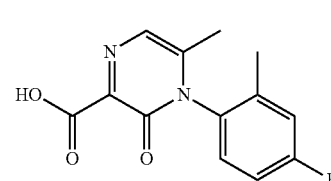
HA4-1
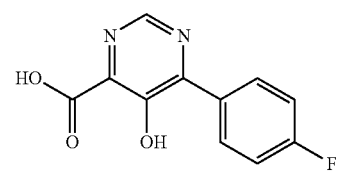
HA4-2
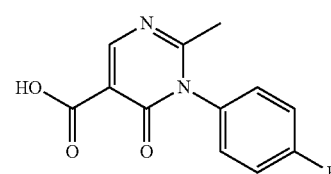

-continued

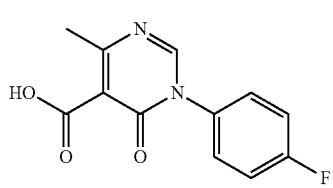
HA4-3

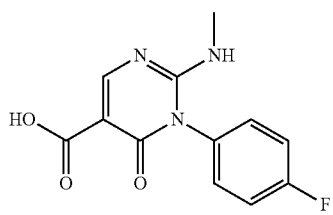
HA4-4

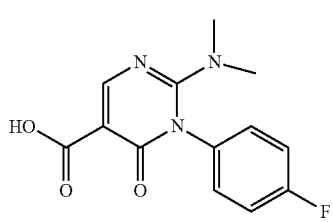
HA4-5

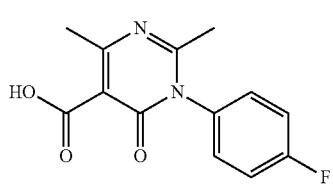
HA4-6

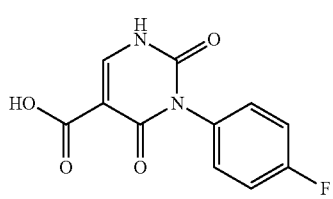
HA4-7

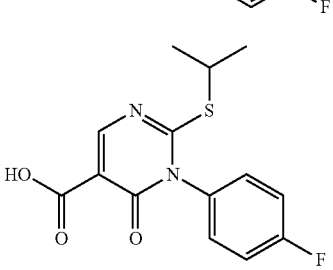
HA4-9

HA4-10

General Procedure G: 4-((1,5-Naphthyridin-4-yl)oxy)anilines (NA1)

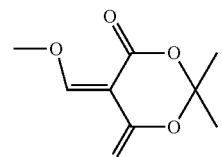

Step 1: A mixture of Compound 12 (32 mmol, 1 eq) and Compound 13 (5.92 g, 32 mmol, 1 eq) in toluene (50 mL, 1.5-1.6 mL/mmol of 12) was stirred at 105° C. for 1.5 h and cooled to room temperature. Hexane (50 mL, 1.5-1.6 mL/mmol of 12 used) was added and the suspension filtered. This material was mixed with Ph$_2$O (50 mL, 1.5-1.6 mL/mmol of 12 used) and the resulting mixture was stirred at 220-230° C. for 1 h, cooled to room temperature and poured into Et$_2$O (100 mL, 3.0-3.2 mL/mmol of 12 used). The resulting suspension was filtered, washed with Et$_2$O and dried to give Compound 14. Compound 13 can easily be generated from heating Meldrum's acid (1 eq) in trimethyl orthoformate (10 eq) at 110° C. for 1-2 h.

Step 2: A mixture of Compound 14 (4.8 mmol, 1 eq), Compound 15 (6.8 mmol, 1.4 eq), and Cs$_2$CO$_3$ (6.6 g, 20 mmol, 4.2 eq) in acetonitrile (20 mL, 4.2 mL/mmol of 14) was stirred at room temperature overnight. EtOAc (80 mL, 16-17 mL/mmol of 14 was used) was added and the resulting mixture filtered. The filtrate was evaporated, and residue purified by silica gel column chromatography to give Compound 16.

Step 3: A mixture of Compound 16 (1.8 mmol, 1 eq), NH₄Cl (500 mg, 9.3 mmol, 5.2 eq), and Fe (260 mg, 4.6 mmol, 2.6 eq) in MeOH/water (20/5 mL) (11 mL MeOH/mmol of 16 and 2.8 mL water/mmol of 16) was refluxed for 1 h and then cooled to room temperature. The resulting mixture was filtered through Celite and the filtrate concentrated to remove MeOH. To the residue was added aq. saturated NaHCO₃ (6 mL, 3.3 mL/mmol of 16 used) and the resulting aqueous mixture was extracted with EtOAc. The organic extract was dried over anhyd. Na₂SO₄ and evaporated give Compound NA1.

Example of General Procedure G: 4-((6,7-Dimethoxy-1,5-naphthyridin-4-yl)oxy)-3-fluoroaniline (NA1-1)

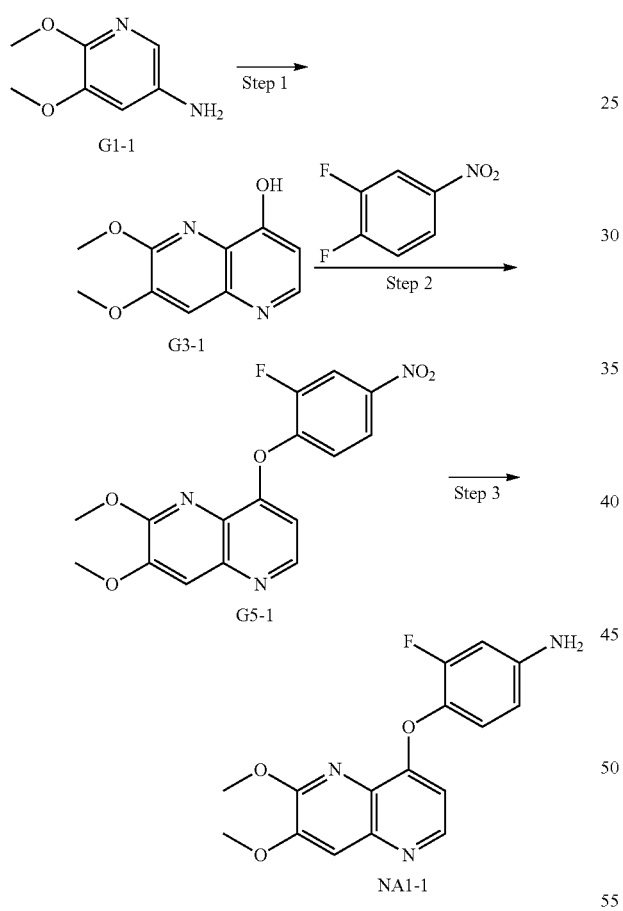

Step 1: 6,7-Dimethoxy-1,5-naphthyridin-4-ol (G3-1): A mixture of 2,2-dimethyl-1,3-dioxane-4,6-dione (2.7 g, 18.7 mmol, 1 eq) in trimethoxymethane (19.6 g, 185 mmol, 20.3 mL, 10 eq) was stirred at 110° C. for 1.5 h to form a yellow solution of Compound 13. Compound G1-1 (2.8 g, 18.5 mmol, 1 eq) was added to the above solution and the mixture was stirred at 110° C. for 0.5 h. The resulting brown suspension was filtered and the solid washed with petroleum ether (2×30 mL) and dried under vacuum to give the intermediate 5-[(E)-(5,6-dimethoxy-3-pyridyl)iminomethyl]-2,2-dimethyl-1,3-dioxane-4,6-dione. A portion of this compound (2.2 g, 7.1 mmol) in Ph₂O (25 mL) was stirred at 230° C. for 0.5 h. To the reaction mixture was added methyl tert-butyl ether (MTBE) (100 mL) and the mixture stirred for 5 min and then filtered. The resulting solid was washed with MTBE (2×30 mL) and dried under vacuum to give Compound G3-1 from the intermediate 5-[(E)-(5,6-dimethoxy-3-pyridyl)iminomethyl]-2,2-dimethyl-1,3-dioxane-4,6-dione). ¹H NMR (400 MHz, DMSO-d₆) δ 11.62 (br s, 1H), 7.93-7.79 (m, 1H), 7.27 (s, 1H), 6.28-6.08 (m, 1H), 3.94 (s, 3H), 3.88 (s, 3H).

Step 2: 8-(2-Fluoro-4-nitrophenoxy)-2,3-dimethoxy-1,5-naphthyridine (G5-1): To mixture of Compound G3-1 (2.1 g, 10.2 mmol, 1 eq) and 1,2-difluoro-4-nitro-benzene (1.6 g, 10.2 mmol, 1.13 mL, 1 eq) in ACN (50 mL) was added Cs₂CO₃ (6.6 g, 20.4 mmol, 2 eq) and the resulting mixture was stirred at room temperature for 15 h. The reaction mixture was filtered, and any solids washed with ACN (2×30 mL) and the resulting filtrate was concentrated under reduced pressure. The residue was purified by column chromatography on silica gel (petroleum ether:EtOAc) to give Compound G5-1. ¹H NMR (400 MHz, CDCl₃) δ 8.70 (d, 1H), 8.12 (dd, 1H), 8.01-7.96 (m, 1H), 7.53 (s, 1H), 7.17 (d, 1H), 7.03 (dd, 1H), 4.02 (s, 3H), 3.75 (s, 3H).

Step 3: 4-((6,7-Dimethoxy-1,5-naphthyridin-4-yl)oxy)-3-fluoroaniline (NA1-1): To a mixture of Compound G5-1 (1.4 g, 3.9 mmol, 1 eq) in EtOH (20 mL) and water (5 mL) was added Fe (1.1 g, 19 mmol, 5 eq) and NH₄Cl (2.1 g, 39 mmol, 10 eq) and the resulting mixture was stirred at 80° C. for 15 h. The reaction mixture was filtered, and the filter cake was washed with MeOH (2×30 mL) and the filtrate concentrated under reduced pressure. The resulting solid was washed with water (2×50 mL) and dried under vacuum to give Compound NA1-1, which was used in subsequent reactions without further purification. MS of C₁₆H₁₄FN₃O₃: m/z: 315.9 (MH+).

The following intermediates were made following General Procedure G for the synthesis of 4-((1,5-Naphthyridin-4-yl)oxy)anilines NA1:

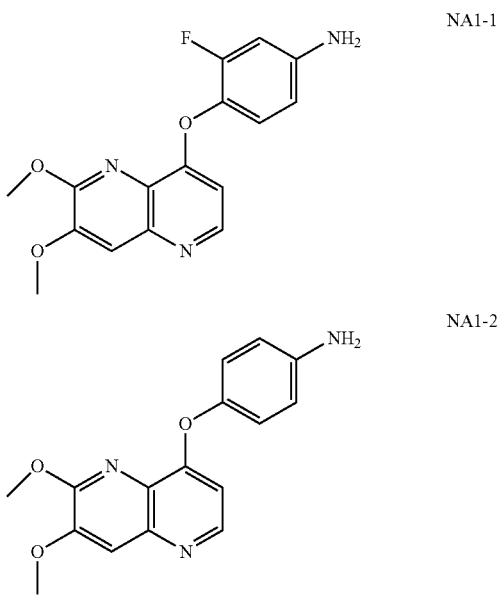

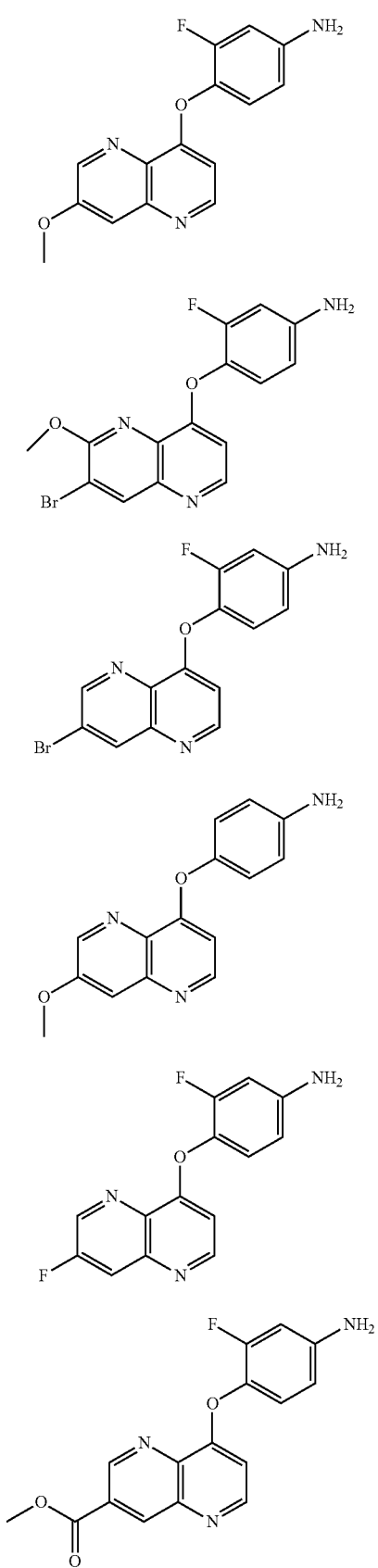
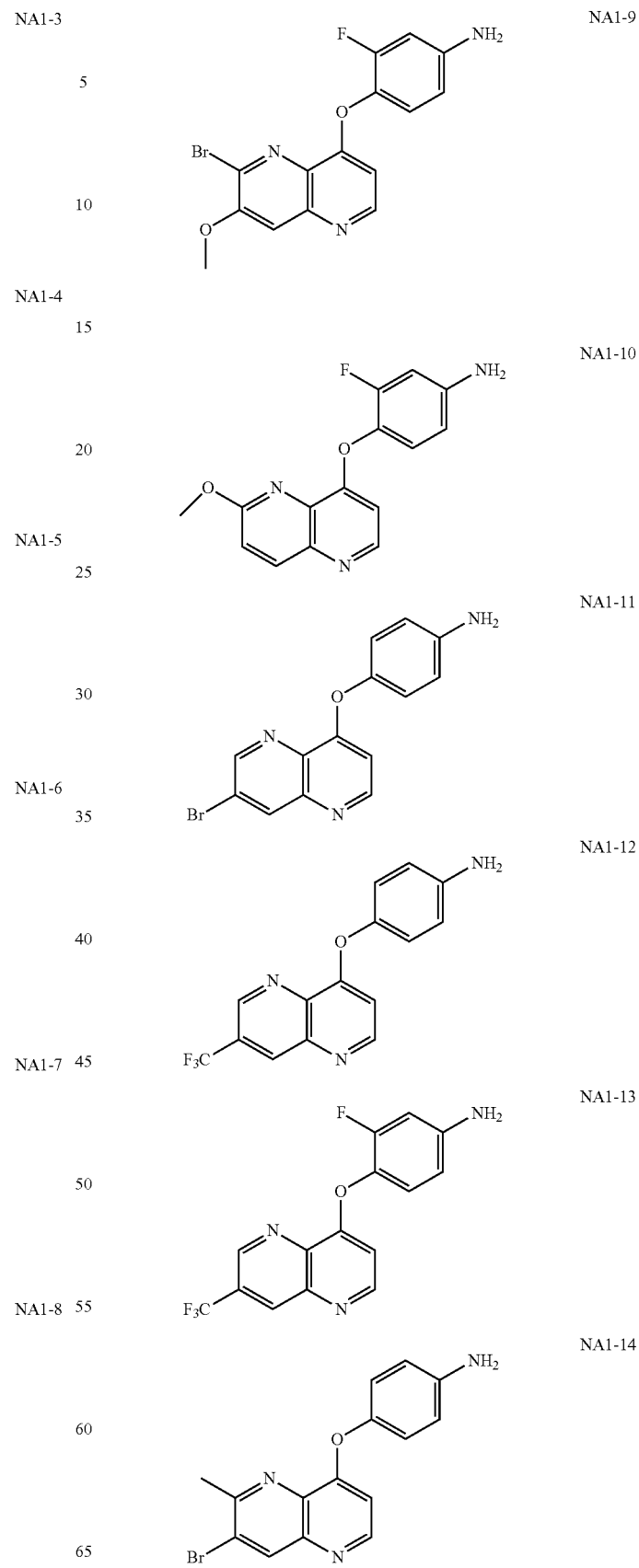

NA1-15 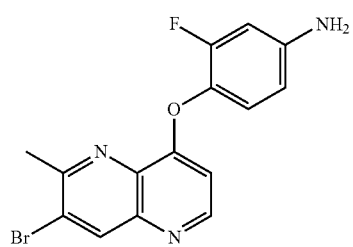
NA1-17 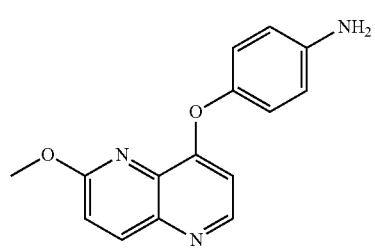
NA1-20 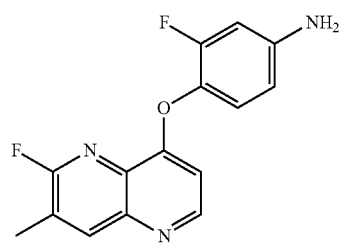
NA1-21 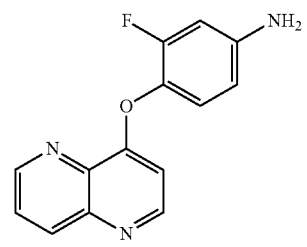
NA1-26 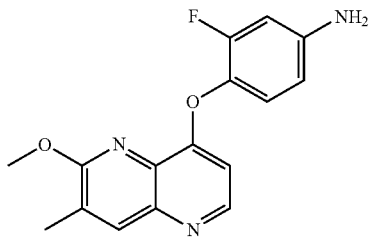
NA1-33 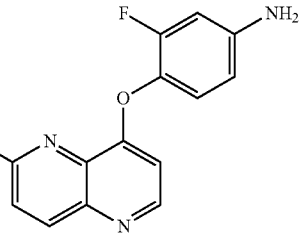
NA1-34 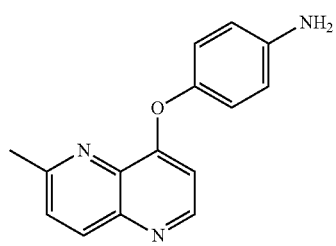
NA1-44 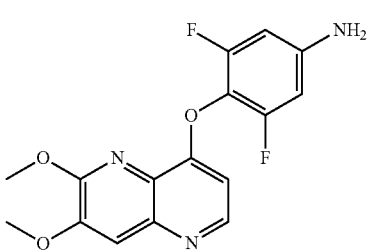
NA1-45 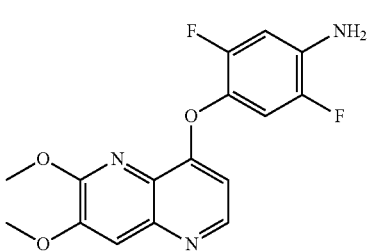
NA1-46 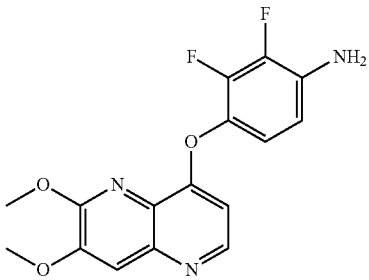
NA1-47 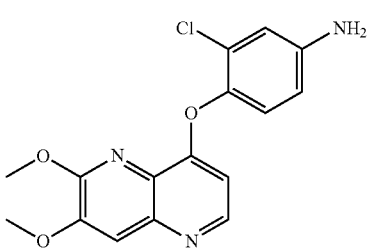
NA1-48 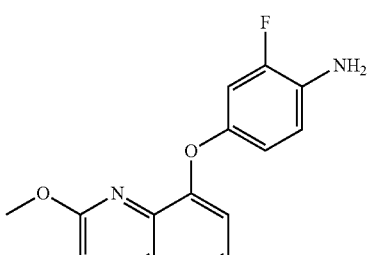
4-((6,7-Dimethoxy-1,5-naphthyridin-4-yl)oxy)-3-fluoroaniline (NA1-1): MS for $C_{16}H_{14}FN_3O_3$: m/z 316 (MH+).

4-((6,7-Dimethoxy-1,5-naphthyridin-4-yl)oxy)aniline (NA1-2): MS for C₁₆H₁₅N₃O₃: m/z 298 (MH+).

3-Fluoro-4-((7-methoxy-1,5-naphthyridin-4-yl)oxy)aniline (NA-3): MS for C₁₅H₁₂FN₃O₂: m/z 286 (MH+).

4-((7-Bromo-6-methoxy-1,5-naphthyridin-4-yl)oxy)-3-fluoroaniline (NA1-4): MS for C₁₅H₁₁BrFN₃O₂: m/z 364/366 (MH+).

4-((7-Bromo-1,5-naphthyridin-4-yl)oxy)-3-fluoroaniline (NA1-5): MS for C₁₄H₉BrFN₃O: m/z 334/336 (MH+).

4-((7-Methoxy-1,5-naphthyridin-4-yl)oxy)aniline (NA1-6): MS for C₁₅H₁₃N₃O₂: m/z 268 (MH+).

3-Fluoro-4-((7-fluoro-1,5-naphthyridin-4-yl)oxy)aniline (NA-7): MS for C₁₄H₉F₂N₃O: m/z 274 (MH+).

Methyl 8-(4-amino-2-fluorophenoxy)-1,5-naphthyridine-3-carboxylate (NA1-8): MS for C₁₆H₁₂FN₃O₃: m/z 314 (MH+).

4-((6-Bromo-7-methoxy-1,5-naphthyridin-4-yl)oxy)-3-fluoroaniline (NA1-9): MS for C₁₅H₁₁BrFN₃O₂: m/z 364/366 (MH+).

3-Fluoro-4-((6-methoxy-1,5-naphthyridin-4-yl)oxy)aniline (NA-10): MS for C₁₅H₁₂FN₃O₂: m/z 286.0 (MH+).

4-((7-Bromo-1,5-naphthyridin-4-yl)oxy)aniline (NA1-11): MS for C₁₄H₁₀BrN₃O: m/z 316/318 (MH+).

4-((7-(Trifluoromethyl)-1,5-naphthyridin-4-yl)oxy)aniline (NA1-12): MS for C₁₅H₁₀F₃N₃O: m/z 306 (MH+).

3-Fluoro-4-((7-(trifluoromethyl)-1,5-naphthyridin-4-yl)oxy)aniline (NA1-13): MS for C₁₅H₉F₄N₃O: m/z 324 (MH+).

4-((7-Bromo-6-methyl-1,5-naphthyridin-4-yl)oxy)aniline (NA1-14): MS for C₁₅H₁₂BrN₃O: m/z 330/332 (MH+).

4-((7-Bromo-6-methyl-1,5-naphthyridin-4-yl)oxy)-3-fluoroaniline (NA1-15): MS for C₁₅H₁₁BrFN₃O: m/z 348/350 (MH+).

4-((6-Methoxy-1,5-naphthyridin-4-yl)oxy)aniline (NA1-17): MS for C₁₅H₁₃N₃O₂: m/z 268 (MH+).

3-Fluoro-4-((6-fluoro-7-methyl-1,5-naphthyridin-4-yl)oxy)aniline (NA1-20): MS for C₁₅H₁₁F₂N₃O: m/z 288 (MH+).

4-((1,5-Naphthyridin-4-yl)oxy)-3-fluoroaniline (NA1-21): MS for C₁₄H₁₀FN₃O: m/z 256 (MH+).

3-Fluoro-4-((6-methoxy-7-methyl-1,5-naphthyridin-4-yl)oxy)aniline (NA1-26): MS for C₁₆H₁₄FN₃O₂: m/z 300 (MH+).

3-Fluoro-4-((6-methyl-1,5-naphthyridin-4-yl)oxy)aniline (NA1-33): MS for C₁₅H₁₂FN₃O: m/z 270 (MH+).

4-((6-Methyl-1,5-naphthyridin-4-yl)oxy)aniline (NA1-34): MS for C₁₅H₁₃N₃O: m/z 252 (MH+).

4-((6,7-Dimethoxy-1,5-naphthyridin-4-yl)oxy)-3,5-difluoroaniline (NA1-44): MS for C₁₆H₁₃F₂N₃O₃: m/z 333.9 (MH+).

4-((6,7-Dimethoxy-1,5-naphthyridin-4-yl)oxy)-2,5-difluoroaniline (NA1-45): MS for C₁₆H₁₃F₂N₃O₃: m/z 334.0 (MH+).

4-((6,7-Dimethoxy-1,5-naphthyridin-4-yl)oxy)-2,3-difluoroaniline (NA1-46): MS for C₁₆H₁₃F₂N₃O₃: m/z 333.9 (MH+).

3-Chloro-4-((6,7-dimethoxy-1,5-naphthyridin-4-yl)oxy)aniline (NA1-47): MS for C₁₆H₁₄ClN₃O₃: m/z 331.9 (MH+).

4-((6,7-Dimethoxy-1,5-naphthyridin-4-yl)oxy)-2-fluoroaniline (NA1-48): MS for C₁₆H₁₄FN₃O₃: m/z 316.0 (MH+).

The following additional intermediates have been made using the synthetic methods detailed in Examples 61-71:

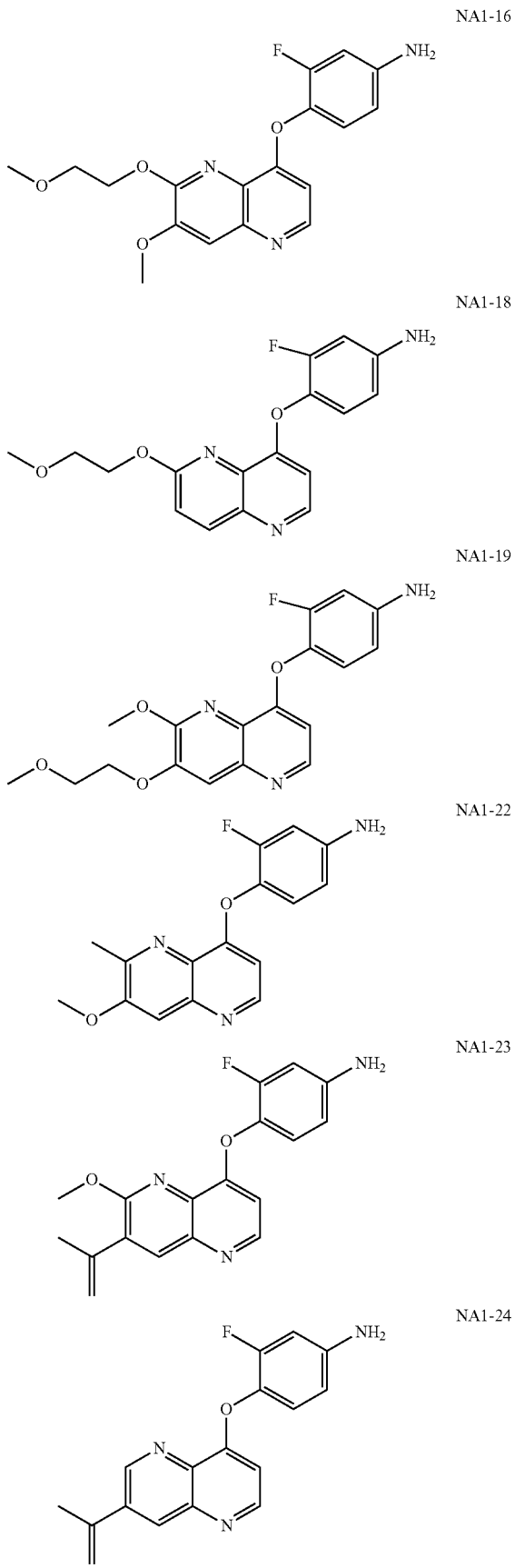

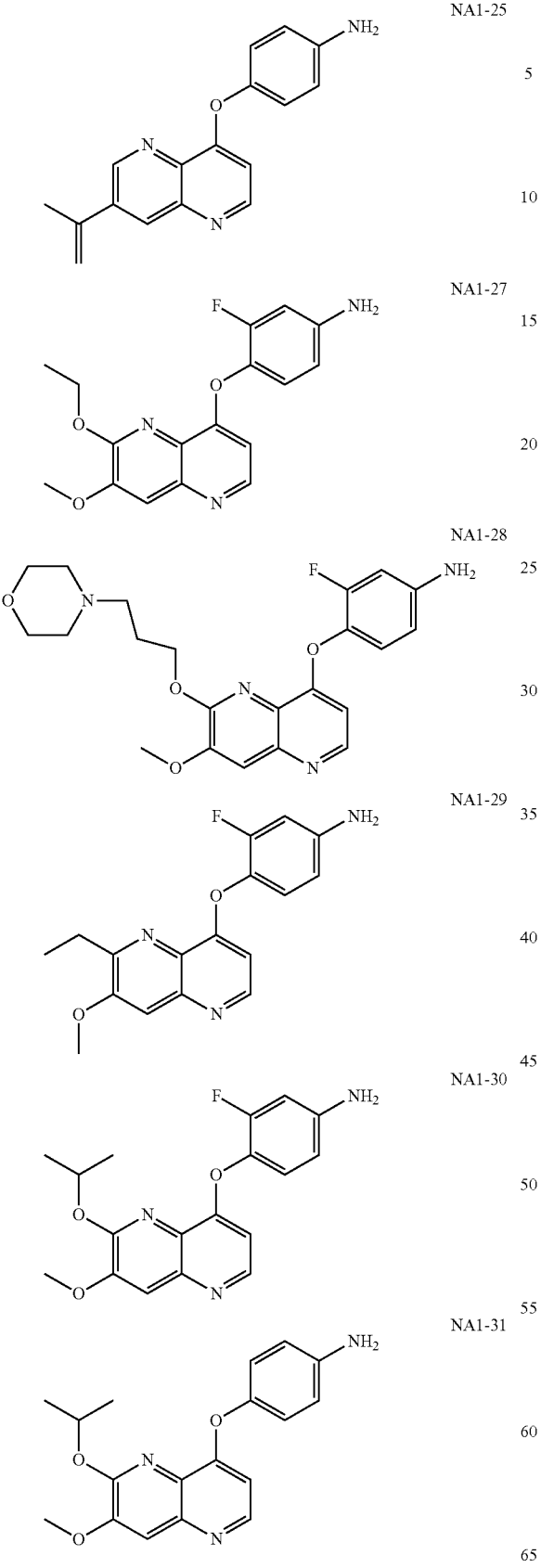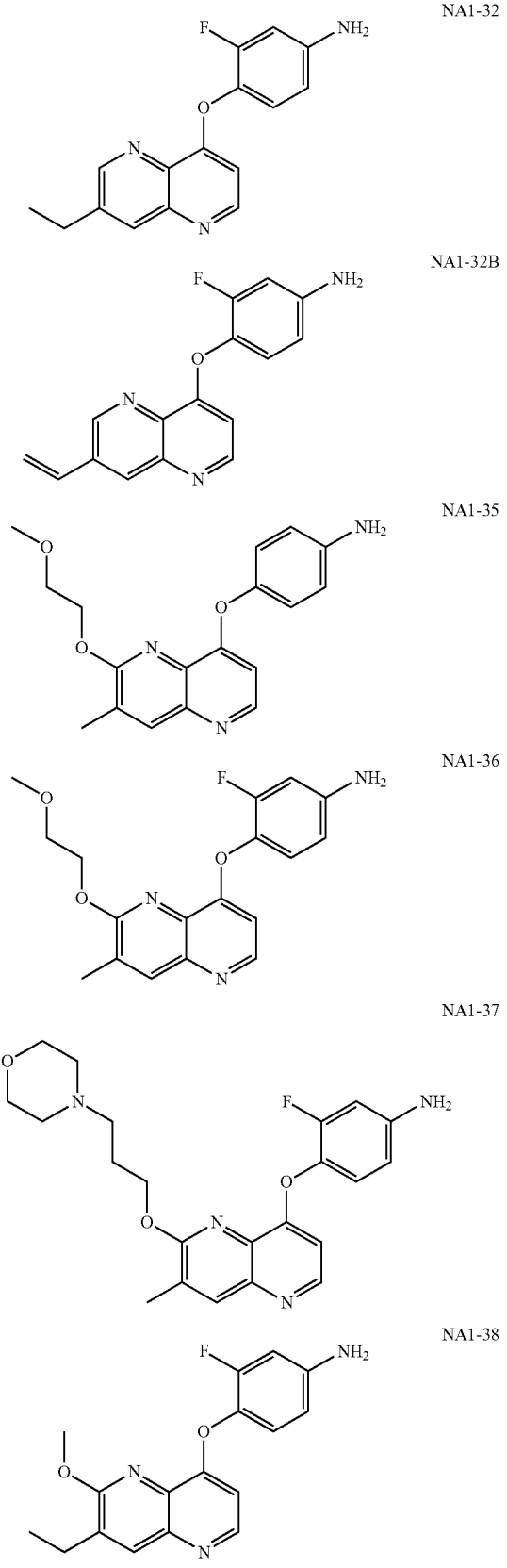

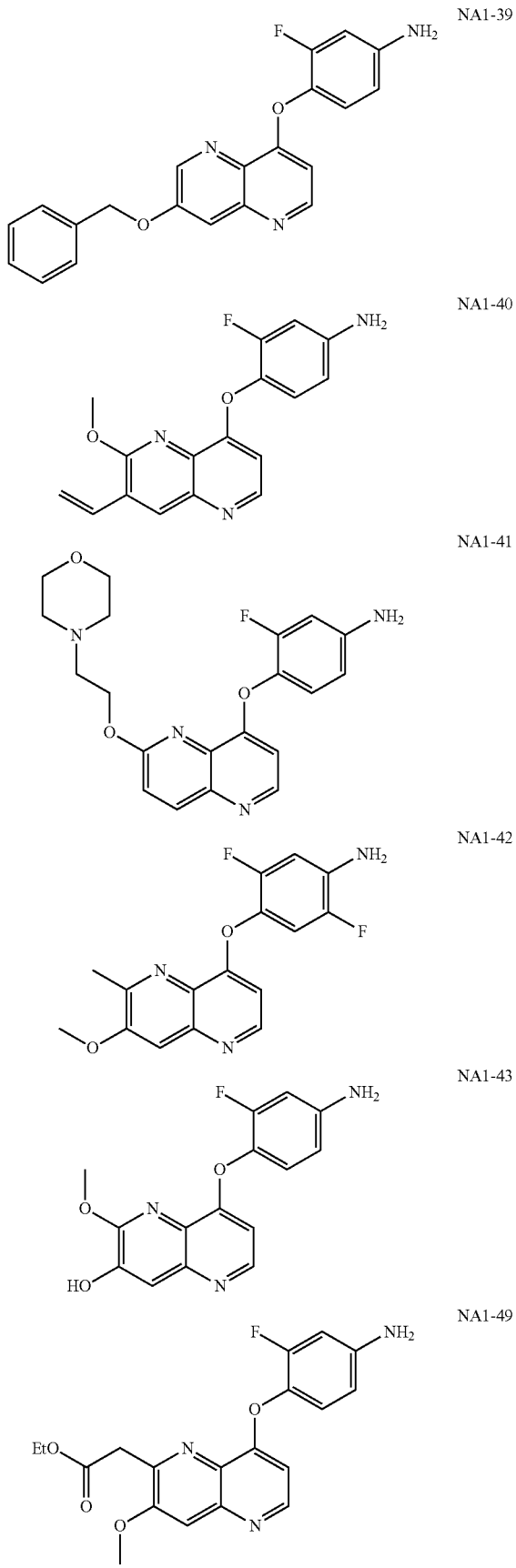
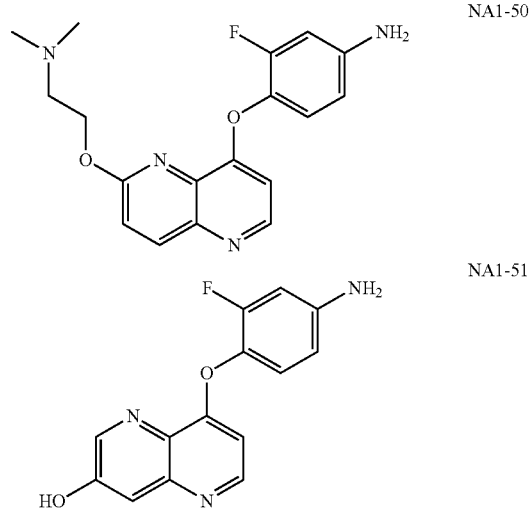

General Procedure H: 4-(Quinolin-4-yloxy)aniline (QA1)

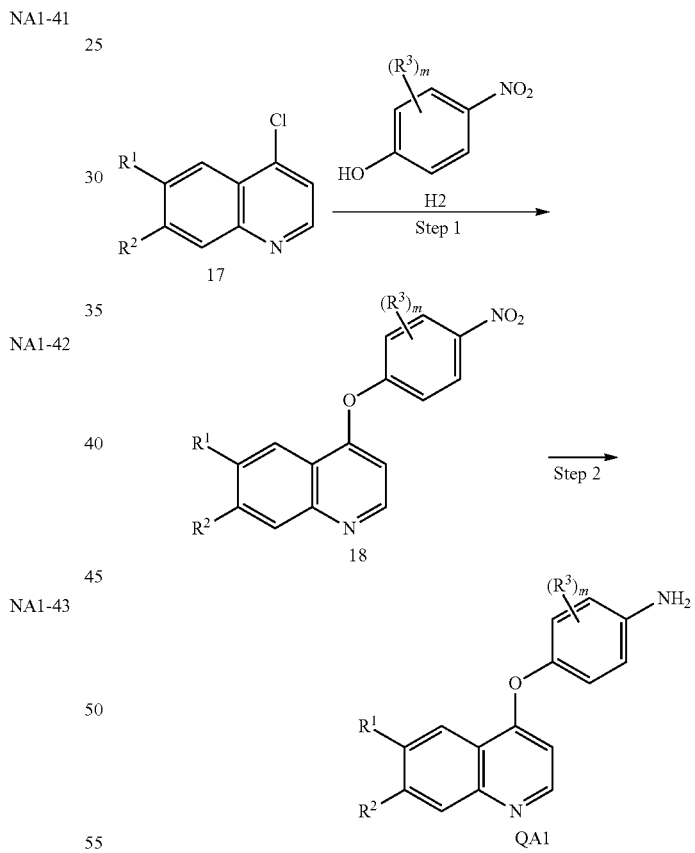

Step 1: To a mixture of Compound 17 (44.7 mmol, 1 eq) and Compound H2 (62.5 mmol, 1.4 eq) in 2,6-dimethylpyridine (50 mL) was added DMAP (1.10 g, 9.0 mmol, 0.2 eq). The mixture was stirred at 140° C. for 36 h. The reaction was cooled to room temperature, MeOH (32 g) was added, followed by aq. $K_2CO_3$ (4 g in water (62 g)). The resulting mixture was stirred at 0° C. for 2 h. The resulting mixture was filtered and washed with water (200 mL) to give the Compound 18.

Step 1 can also be performed as follows: A mixture of Compound 17 (1 eq) and Compound H2 (1.2-1.4 eq) in an appropriate solvent such as, but not limited to, 2,6-dimethylpyridine or diphenyl ether (1.1-2.2 mL/mmol of 17) was stirred at 140° C. for typically 36-66 h. DMAP (0.2 eq) can also be optionally added as a catalyst. Upon completion of the reaction as monitored by LC-MS and/or TLC, the reaction mixture was allowed to cool to room temperature and typically worked up by one of the following methods or a similar variation. Method 1: MeOH (0.9 mL/mmol of 17 used) was added, followed by aq. 6.5% $K_2CO_3$ (1.4 mL/mmol of 17 used). The resulting mixture was stirred at 0° C. for 2 h. The resulting mixture was filtered and washed with water (4.5 mL/mmol of 17 used) to give Compound 18. Method 2: The mixture was diluted with MTBE (2.2 mL/mmol of 17 used) and filtered. The resulting solid was washed with MTBE (0.4 mL/mmol of 17 used) and dried under vacuum to give Compound 18. Regardless of the method of work up, the crude Compound 18 was generally used in subsequent reactions without further purification.

Step 2: To a mixture of Compound 18 (6.1 mmol, 1 eq) in EtOH (40 mL) and water (8 mL) was added Fe (1.71 g, 30.6 mmol, 5.0 eq) and $NH_4Cl$ (2.62 g, 49.0 mmol, 8.0 eq). The mixture was stirred at 85° C. for 3 h. The reaction was filtered, and the filtrate was dried over anhyd. $Na_2SO_4$ and concentrated to give crude product. To this crude product was added EtOAc (150 mL) and DCM (150 mL). The resulting mixture was filtered, and the filtrate was concentrated to give Compound QA1.

Step 2 can also be performed as follows: To a mixture of Compound 18 (1 eq) in EtOH (4.5-6.5 mL/mmol of 18) and water (1.1-1.3 mL/mmol of 18) was added Fe (5.0 eq) and $NH_4Cl$ (8-10 eq). The mixture was stirred at 85° C. for 3-4 h. Upon completion of the reaction as monitored by LC-MS and/or TLC, the reaction mixture was allowed to cool to room temperature and typically worked up by one of the following methods or a similar variation. Method 1: The reaction was filtered, and the filtrate was dried over anhyd. $Na_2SO_4$ and concentrated to give crude product. To this crude product was added EtOAc (25 mL/mmol of 18 used) and DCM (25 mL/mmol of 18 used). The resulting mixture was filtered, and the filtrate was concentrated to give Compound QA1. Method 2: The mixture was filtered through Celite, the filtrate was concentrated under vacuum and the residue was dissolved in EtOAc (11.2 mL/mmol of 18 used). The organic layer was washed with aq. saturated $NaHCO_3$ (6.7 mL/mmol of 18 used), washed with water (6.7 mL/mmol of 18 used), washed with aq. saturated NaCl (6.7 mL/mmol of 18 used), dried over anhyd. $Na_2SO_4$ and concentrated under vacuum to give Compound QA1. Regardless of the method of work up, the crude Compound QA1 was generally used in subsequent reactions without further purification.

Example of General Procedure H: 4-((6,7-Dimethoxyquinolin-4-yl)oxy)-3-fluoroaniline (QA1-1)

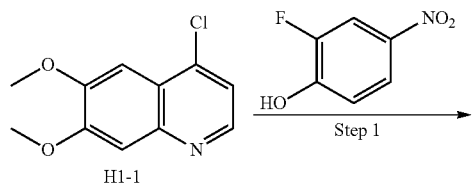

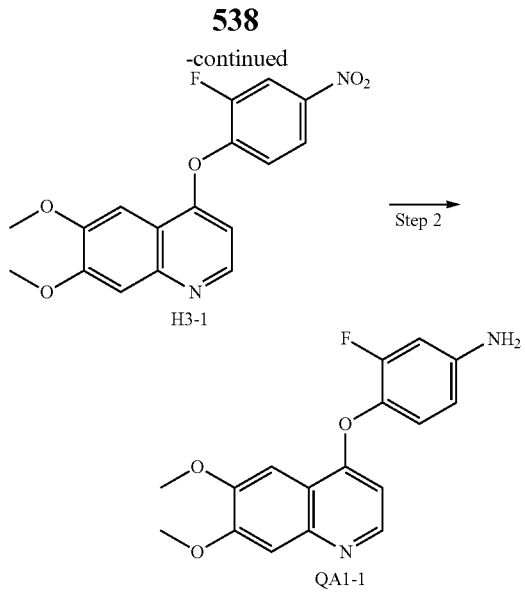

Step 1: 4-(2-Fluoro-4-nitrophenoxy)-6,7-dimethoxyquinoline (H3-1): A suspension of Compound H1-1 (10 g, 45 mmol, 1 eq) and 2-fluoro-4-nitro-phenol (8.4 g, 54 mmol, 1.2 eq) in $Ph_2O$ (100 mL) was heated and stirred at 140° C. for 66 h. After cooling to room temperature, the mixture was diluted with MTBE (100 mL) and filtered. The filtered cake was washed with MTBE (20 mL) and dried under vacuum to give Compound H3-1, which was used in subsequent steps without further purification. $^1$H NMR (400 MHz, DMSO-$d_6$) δ 8.89 (d, 1H), 8.56 (dd, 1H), 8.35-8.27 (m, 1H), 7.89 (t, 1H), 7.79-7.71 (m, 2H), 7.17 (d, 1H), 4.04 (d, 6H); MS for $C_{17}H_{13}FN_2O_5$: m/z 344.9 (MH+).

Step 2: 4-((6,7-Dimethoxyquinolin-4-yl)oxy)-3-fluoroaniline (QA1-1): Fe (12.5 g, 223 mmol, 5 eq) was added to a mixture of Compound H3-1 (16.2 g, 45 mmol, 1 eq) and $NH_4Cl$ (23.9 g, 447 mmol, 10 eq) in EtOH (200 mL) and water (50 mL). The mixture was heated and stirred at 85° C. for 3.5 h. After cooling to room temperature, the mixture was filtered through a pad of Celite. The filtrate was concentrated under vacuum and the residue was dissolved in EtOAc (500 mL). The organic layer was washed with aq. $NaHCO_3$ (300 mL), washed with water (300 mL), washed with aq. saturated NaCl (300 mL), dried over anhyd. $Na_2SO_4$ and concentrated under vacuum to give Compound QA1-1, which was used in subsequent reactions without further purification. MS for $C_{17}H_{15}FN_2O_3$: m/z 315.0 (MH+).

The following intermediates were made following General Procedure H for the synthesis of 4-(quinolin-4-yloxy)anilines QA1:

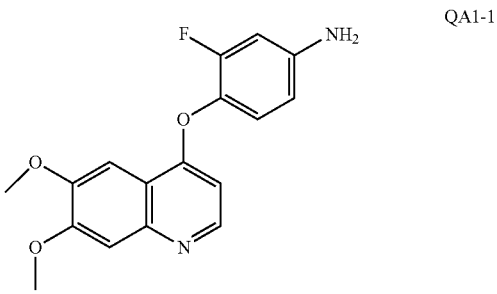

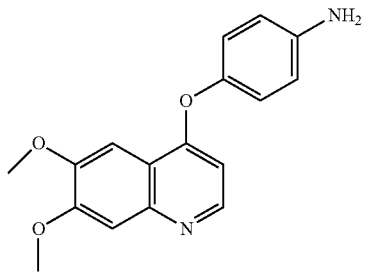 QA1-2

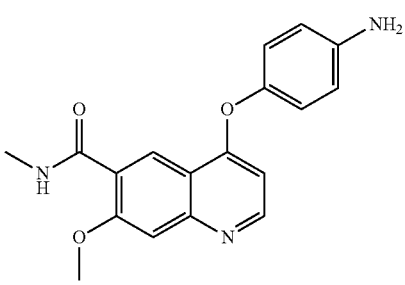 QA1-5

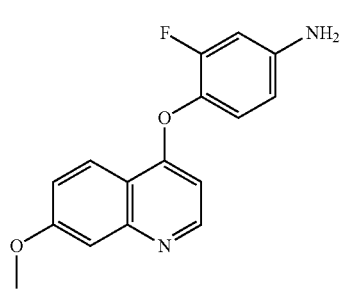 QA1-3

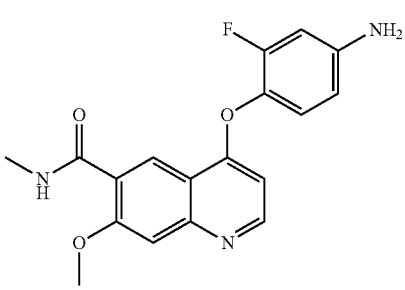 QA1-6

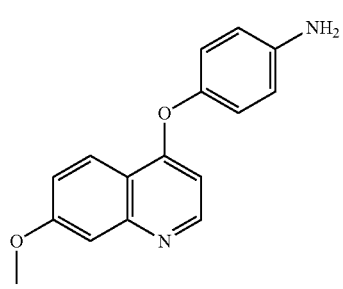 QA1-4

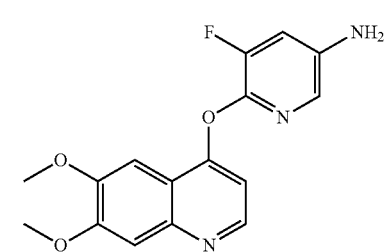 QA1-8

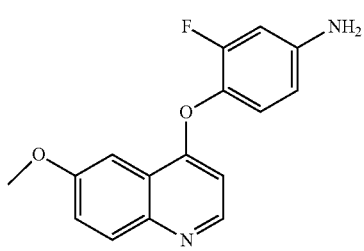 QA1-7

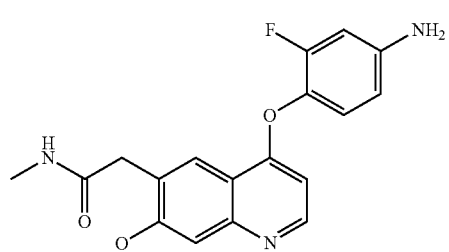 QA1-9

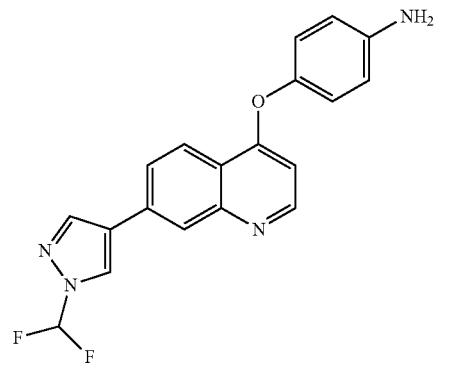 QA1-10

4-((6,7-Dimethoxyquinolin-4-yl)oxy)-3-fluoroaniline (QA1-1): MS for $C_{17}H_{15}FN_2O_3$: m/z 315 (MH+).

4-((6,7-Dimethoxyquinolin-4-yl)oxy)aniline (QA1-2): MS for $C_{17}H_{16}N_2O_3$: m/z 297.2 (MH+).

3-Fluoro-4-((7-methoxyquinolin-4-yl)oxy)aniline (QA1-3): MS for $C_{16}H_{13}FN_2O_2$: m/z 285 (MH+).

4-((7-Methoxyquinolin-4-yl)oxy)aniline (QA1-4): MS for $C_{16}H_{14}N_2O_2$: m/z 267 (MH+).

3-Fluoro-4-((6-methoxyquinolin-4-yl)oxy)aniline (QA1-7): MS for $C_{16}H_{13}FN_2O_2$, m/z 285 (MH+).

The following additional intermediates have been made using the synthetic methods detailed in Examples 72-80:

NA3-1

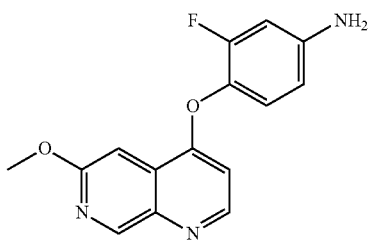

NA3-2

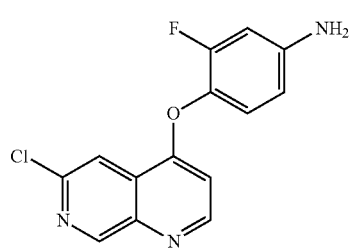

NA3-3

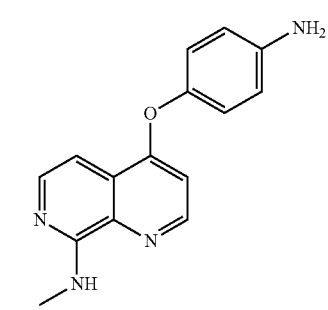

NA3-4

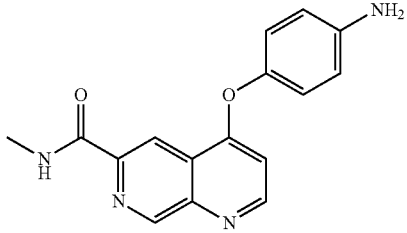

QA2-1

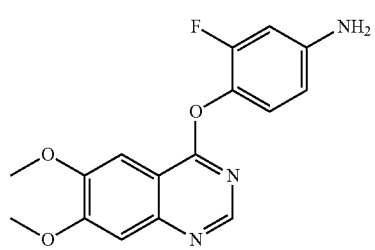

General Procedure I: 4-Hydroxyphenyl Carboxamides (I3)

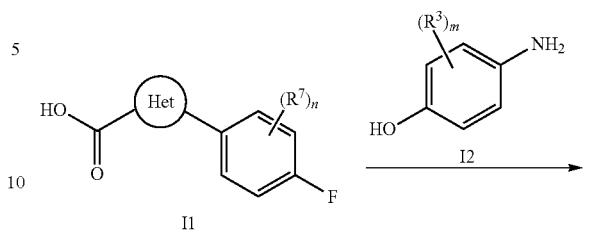

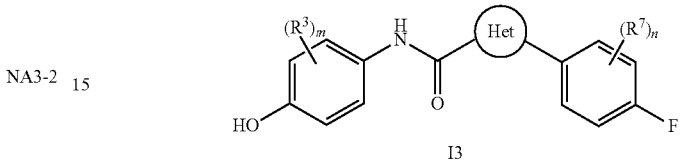

Compound I1 can be any of the heterocyclic acids described herein (i.e. PA-Br, PA-Ph, PA1, PA2, PA3, PA4, PA5, PA6, PA7, HA1, HA2, HA3, HA4, and the like). The hydroxyl of Compound 12 can optionally be protected with a benzyl group, which is then removed after the coupling reaction by standard hydrogenation techniques. To a mixture of Compound 2 (1 eq) and Compound I1 (1.1 eq) in DMF (2.2 mL/mmol of 12) was added HATU (1.1 eq) and DIEA (3 eq). The resulting solution was stirred at 25° C. for 12-15 h. The reaction mixture was diluted with EtOAc (54 mL/mmol of 12 used) and washed with a 1:1 mixture of water:aq. saturated NaCl (4×108 mL/mmol of 12 used). The organic layer was dried over anhyd. $Na_2SO_4$ and concentrated. The resulting residue was purified by silica gel column chromatography to give Compound 13.

Example of General Procedure I: 1-(4-fluorophenyl)-N-(4-hydroxyphenyl)-6-methyl-2-oxo-1,2-dihydropyridine-3-carboxamide (I3-1)

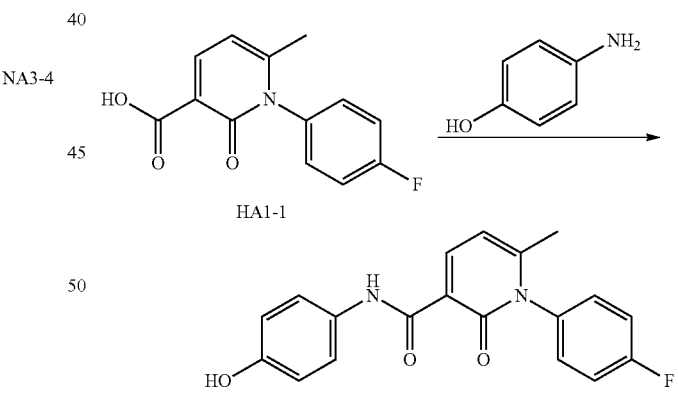

1-(4-fluorophenyl)-N-(4-hydroxyphenyl)-6-methyl-2-oxo-1,2-dihydropyridine-3-carboxamide (I3-1): To a mixture of 4-aminophenol (100 mg, 0.92 mmol, 0.14 mL, 1 eq) and Compound HA-1 (249 mg, 1.0 mmol, 1.1 eq) in DMF (2 mL) was added HATU (383 mg, 1.0 mmol, 1.1 eq) and DIEA (355 mg, 2.8 mmol, 0.48 mL, 3 eq). The resulting solution was stirred at 25° C. for 15 h. The reaction mixture was diluted with EtOAc (50 mL) and washed with a 1:1 mixture of water:aq. saturated NaCl (4×100 mL). The organic layer was dried over anhyd. $Na_2SO_4$, filtered and concentrated. The resulting residue was purified by silica gel column chromatography (DCM:MeOH) to give Compound I3-1. MS for $C_{19}H_{15}FN_2O_3$: m/z 339.1 (MH+).

The following compounds were made using General Procedure I to form compounds of formula I3:

I3-2
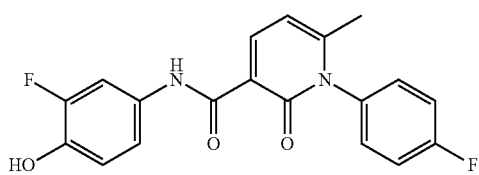

I3-3
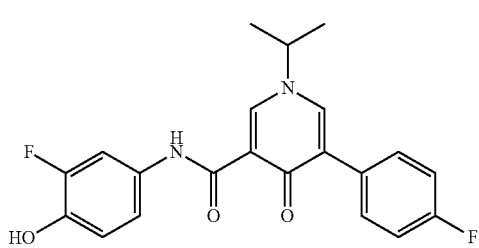

I3-4
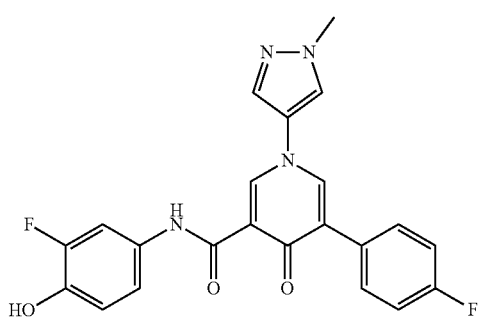

I3-5
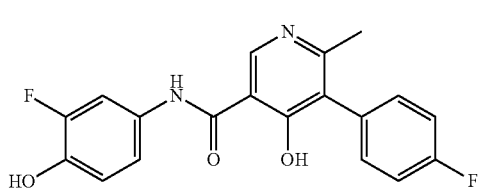

I3-6
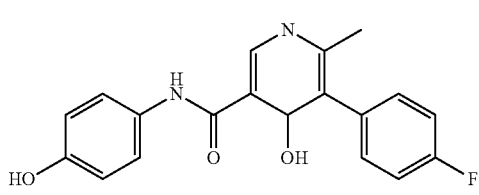

I3-7
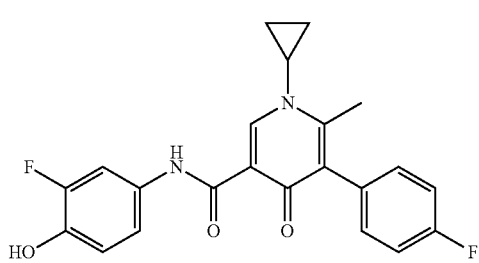

N-(3-Fluoro-4-hydroxyphenyl)-1-(4-fluorophenyl)-6-methyl-2-oxo-1,2-dihydropyridine-3-carboxamide (I3-2):

The 4-aminophenol was replaced with 4-amino-2-fluorophenol. MS for $C_{19}H_{14}F_2N_2O_3$: m/z 357 (MH+).

N-(3-Fluoro-4-hydroxyphenyl)-5-(4-fluorophenyl)-1-isopropyl-4-oxo-1,4-dihydropyridine-3-carboxamide (I3-3): Compound HA1-1 was replaced with PA-3. The 4-aminophenol was replaced with 4-amino-2-fluorophenol.

N-(3-Fluoro-4-hydroxyphenyl)-5-(4-fluorophenyl)-1-(1-methyl-1H-pyrazol-4-yl)-4-oxo-1,4-dihydropyridine-3-carboxamide (I3-4): Compound HA1-1 was replaced with PA-11. The 4-aminophenol was replaced with 4-amino-2-fluorophenol.

N-(3-Fluoro-4-hydroxyphenyl)-5-(4-fluorophenyl)-4-hydroxy-6-methylnicotinamide (I3-5): Compound HA1-1 was replaced with PA3-1. The 4-aminophenol was replaced with 4-amino-2-fluorophenol. MS for $C_{19}H_{14}F_2N_2O_3$: m/z 357 (MH+).

5-(4-Fluorophenyl)-4-hydroxy-N-(4-hydroxyphenyl)-6-methylnicotinamide (I3-6): Compound HA-1 was replaced with PA3-1. MS for $C_{19}H_{15}FN_2O_3$: m/z 339 (MH+).

1-Cyclopropyl-N-(3-fluoro-4-hydroxyphenyl)-5-(4-fluorophenyl)-6-methyl-4-oxo-1,4-dihydropyridine-3-carboxamide (I3-7): Compound HA-1 was replaced with PA7-35. The 4-aminophenol was replaced with 4-(benzyloxy)-3-fluoroaniline to initially form N-(4-(benzyloxy)-3-fluorophenyl)-1-cyclopropyl-5-(4-fluorophenyl)-6-methyl-4-oxo-1,4-dihydropyridine-3-carboxamide which was subsequently subject to standard hydrogenation techniques to give Compound I3-7. MS for $C_{22}H_{18}F_2N_2O_3$: m/z 397 (MH+).

General Procedure J: SNAr Reaction with I3 (J2)

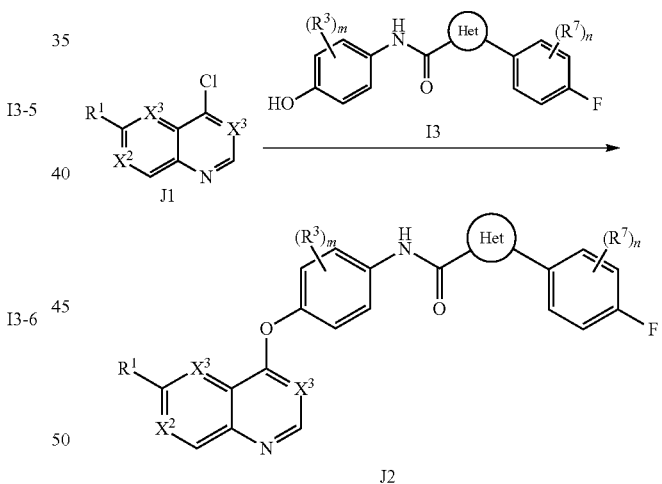

To a solution of Compound J1 (1 eq) and Compound I3 (0.9-1.1 eq) in an appropriate solvent such as, but not limited to DMF or THF (2.7-5.0 mL/mmol of J1) was added $Cs_2CO_3$ (2-6 eq). The reaction mixture was heated to 60-80° C. until the reaction was complete as determined by LC-MS and/or TLC. The reaction mixture was diluted with water and extracted with EtOAc (3×135 mL/mmol of J1 used). The combined organic layers were washed with aq. saturated NaCl (270 mL/mmol of J1 used), dried over anhyd. $Na_2SO_4$ and concentrated. Alternatively, the reaction mixture can be diluted with EtOAc and filtered. The filtrate is then washed with water (2×), dried over anhyd. $Na_2SO_4$ and concentrated. In a modification of the reaction, a mixture of Compound J1 (1 eq), Compound I3 (1 eq), DIEA (4.8 eq)

and DMSO (16 mL/mmol of J1) was heated at 100° C. until the reaction was complete as determined by LC-MS and/or TLC. The reaction mixture was diluted with water (167 mL/mmol of J1 used), sonicated, filtered and the resulting solid was washed with water. Regardless of which reaction or work up was used, the resulting residue/solid was purified by prep-HPLC to give Compound J2.

Example 1: N-[4-[(6,7-Dimethoxy-1,5-naphthyridin-4-yl)oxy]-3-fluorophenyl]-5-(4-fluorophenyl)-6-methyl-4-oxo-1-propan-2-ylpyridine-3-carboxamide (21)

Compound NA1-1 (360 mg, 1.14 mmol), Compound PA2-2 (360 mg, 1.31 mmol) and HATU (1.15 g, 3.03 mmol) in DMF (4 mL) was added DIEA (1.0 mL, 5.7 mmol) and the reaction was stirred at room temperature until reaction completion as monitored by LC-MS or TLC. Aq. saturated NaHCO$_3$ (10 mL) and water (10 mL) were added and resulting suspension was filtered. The resulting material was washed with water and dried to give crude Compound 19 which was used in the next step without further purification. MS for C$_{26}$H$_{24}$BrFN$_4$O$_5$: m/z 571/573 (MH+).

Step 2: N-(4-(((6,7-Dimethoxy-1,5-naphthyridin-4-yl)oxy)-3-fluorophenyl)-5-(4-fluorophenyl)-1-isopropyl-6-methyl-4-oxo-1,4-dihydropyridine-3-carboxamide (21): A

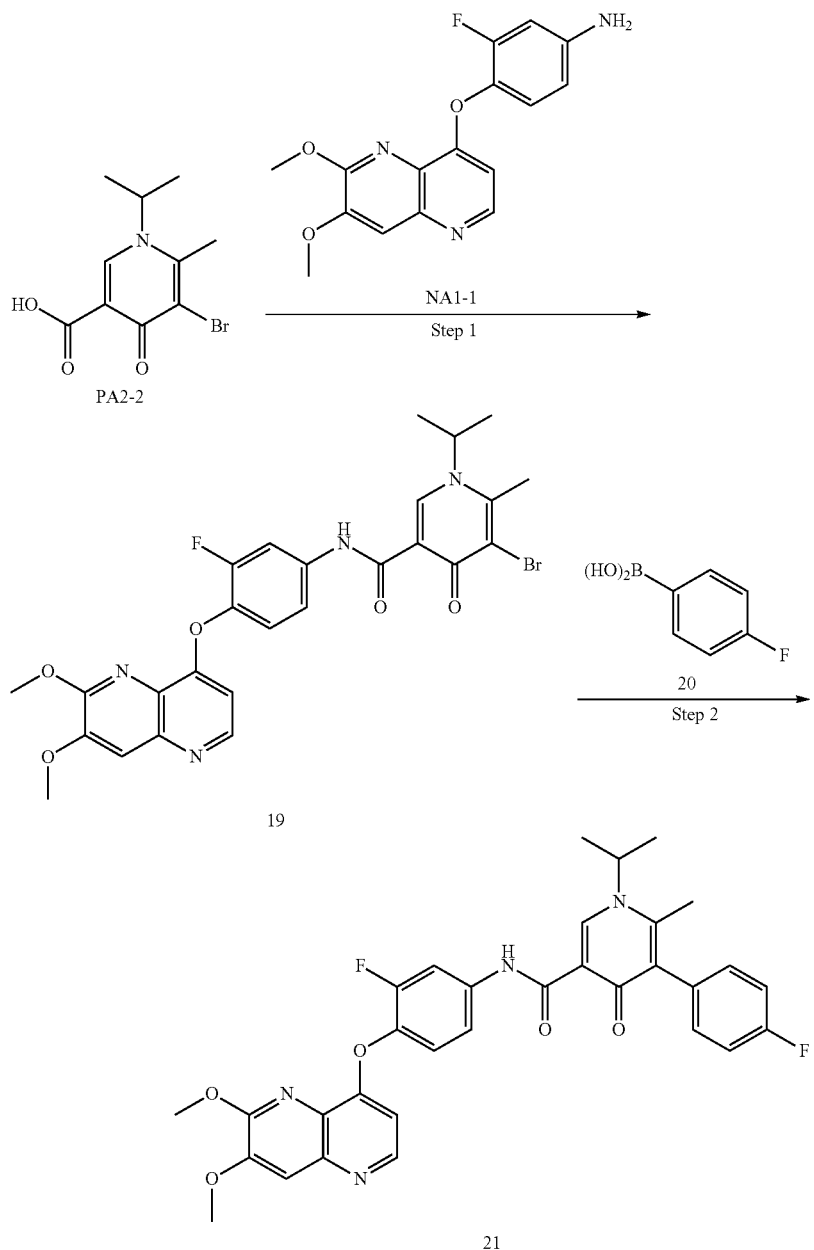

Step 1: 5-Bromo-N-(4-(((6,7-dimethoxy-1,5-naphthyridin-4-yl)oxy)-3-fluorophenyl)-1-isopropyl-6-methyl-4-oxo-1,4-dihydropyridine-3-carboxamide (19). To a mixture of mixture of Compound 19 (57 mg, 0.10 mmol), Compound 20 (70 mg, 0.50 mmol), K$_3$PO$_4$, (64 mg, 0.30 mmol), XPhos Pd G2 (20 mg, 0.1 mmol), water (0.5 mL) and dioxane (3.0 mL) was degassed with nitrogen for 3 minutes and then stirred at 90° C. for 5 h. The mixture was extracted with EtOAc (2×) and the combined extracts concentrated. The residue was purified by silica gel column chromatography, eluted with EtOAc and further purified by Prep HPLC to give Compound 21. $^1$H NMR (400 MHz, DMSO-d$_6$) δ 13.05 (s, 1H), 8.63 (d, 1H), 8.48 (d, 1H), 7.94 (dd, 1H), 7.58 (s, 1H), 7.34 (d, 1H), 7.40-7.15 (m, 5H), 6.76 (d, 1H), 4.72 (q, 1H), 3.90 (s, 3H), 3.86 (s, 3H), 2.22 (s, 3H), 1.44 (d, 6H); MS for $C_{32}H_{28}F_2N_4O_5$: m/z 587 (MH+).

The following compounds were made following a method analogous to that used to synthesize Compound 21 in Example 1 in two steps from Compounds NA1-1 and PA2-2. Where HCl salts are indicated, the target compounds were general converted to the HCl salts by first dissolving the compound in 20% MeOH in DCM, passing it through an Agilent PL-HCO3 ion exchange column and concentrating under reduced pressure (alternatively, the compound was dissolved in DCM and washed with aq. saturated sodium bicarbonate and then concentrated). Secondly, HCl (4 M in Dioxane, 0.5 mL; or 1 M aqueous, 1 mL) was added and the volatile solvents were removed under reduced pressure and the resulting residue dried under high vacuum to give the desired final product as the hydrochloride salt.

N-[4-(6,7-Dimethoxyquinolin-4-yl)oxy-3-fluorophenyl]-5-(4-fluorophenyl)-6-methyl-4-oxo-1-propan-2-ylpyridine-3-carboxamide (22): Compound NA1-1 was replaced with Compound QA1-1. $^1$H NMR (400 MHz, DMSO-d$_6$) δ 13.10 (s, 1H), 8.64 (s, 1H), 8.41 (d, 1H), 7.98 (dd, 1H), 7.44-7.10 (m, 8H), 6.42 (d, 1H), 4.72 (p, 1H), 3.88 (s, 6H), 2.22 (s, 3H), 1.45 (d, 6H); MS for $C_{33}H_{29}F_2N_3O_5$: m/z 586 (MH+).

5-(3,4-Dichlorophenyl)-N-[4-(6,7-dimethoxyquinolin-4-yl)oxy-3-fluorophenyl]-6-methyl-4-oxo-1-propan-2-ylpyridine-3-carboxamide (23): Compound NA1-1 was replaced with Compound QA1-1. Compound 20 was replaced with (3,4-dichlorophenyl)boronic acid. $^1$H NMR (400 MHz, DMSO-d$_6$) δ 13.06 (s, 1H), 8.78-8.57 (m, 2H), 8.05 (d, 1H), 7.75-7.59 (m, 2H), 7.47 (dd, 4H), 7.18 (d, 1H), 6.84 (d, 1H), 4.74 (p, 1H), 3.96 (d, 6H), 2.25 (s, 3H), 1.45 (d, 6H); MS for $C_{33}H_{28}FN_3O_5$: m/z 636 (MH+).

5-(3-Chloro-4-fluorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide (24): Compound 20 was replaced with (3-chloro-4-fluorophenyl)boronic acid. $^1$H NMR (400 MHz, DMSO-d$_6$) δ 12.96 (s, 1H), 8.64 (s, 1H), 8.48 (d, 1H), 7.94 (dd, 1H), 7.58 (s, 1H), 7.49-7.07 (m, 5H), 6.77 (d, 1H), 4.72 (p, 1H), 3.90 (s, 3H), 3.86 (s, 3H), 2.24 (s, 3H), 1.44 (d, 6H); MS for $C_{32}H_{27}CF_2N_4O_5$: m/z 621 (MH+).

5-(3,4-Dichlorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide (25): Compound 20 was replaced with (3,4-dichlorophenyl)boronic acid. $^1$H NMR (400 MHz, DMSO-d$_6$) δ 12.93 (s, 1H), 8.64 (s, 1H), 8.48 (d, 1H), 7.95 (d, 1H), 7.66 (d, 1H), 7.58 (s, 1H), 7.47 (d, 1H), 7.35 (d, 1H), 7.29-7.12 (m, 2H), 6.77 (d, 1H), 4.82-4.62 (m, 1H), 3.90 (s, 3H), 3.86 (s, 3H), 2.25 (s, 3H), 1.44 (d, 6H); MS for $C_{32}H_{27}Cl_2FN_4O_5$: m/z 637 (MH+).

N-[4-[(6,7-Dimethoxy-1,5-naphthyridin-4-yl)oxy]-3-fluorophenyl]-5-(4-fluorophenyl)-4-hydroxy-6-methylpyridine-3-carboxamide (26): Compound PA2-2 was replaced with Compound PA2-3. $^1$H NMR (400 MHz, DMSO-d$_6$) δ 13.01 (s, 1H), 8.58 (d, 1H), 8.48 (d, 1H), 7.94 (d, 1H), 7.58 (d, 1H), 7.33 (d, 1H), 7.22 (dd, 5H), 6.77 (t, 1H), 4.83 (t, 1H), 3.90 (d, 3H), 3.86 (d, 3H), 2.30-2.10 (m, 5H), 1.74 (d, 6H). MS for $C_{34}H_{30}F_2N_4O_5$: m/z 613 (MH+).

5-(3-Chloro-4-fluorophenyl)-1-cyclopentyl-N-[4-[(6,7-dimethoxy-1,5-naphthyridin-4-yl)oxy]-3-fluorophenyl]-6-methyl-4-oxopyridine-3-carboxamide (27): Compound PA2-2 was replaced with Compound PA2-3. Compound 20 was replaced with (3-chloro-4-fluorophenyl)boronic acid. $^1$H NMR (400 MHz, DMSO-d$_6$) δ 12.92 (s, 1H), 8.57 (s, 1H), 8.48 (d, 1H), 7.94 (d, 1H), 7.58 (s, 1H), 7.52-7.11 (m, 5H), 6.76 (d, 1H), 4.94-4.73 (m, 1H), 3.89 (s, 3H), 3.85 (s, 3H), 2.25 (s, 3H), 2.25-2.10 (m, 2H), 1.90-1.60 (m, 6H); MS for $C_{34}H_{29}CF_2N_4O_5$: m/z 647 (MH+).

N-[4-[(6,7-Dimethoxy-1,5-naphthyridin-4-yl)oxy]-3-fluorophenyl]-5-(4-fluorophenyl)-4-hydroxy-6-methylpyridine-3-carboxamide (28): Compound PA2-2 was replaced with Compound PA2-1. $^1$H NMR (400 MHz, DMSO-d$_6$) δ 13.09 (s, 1H), 12.54 (s, 1H), 8.51-8.36 (m, 2H), 7.94 (dd, 1H), 7.58 (s, 1H), 7.34 (ddd, 1H), 7.28-7.07 (m, 5H), 6.75 (dd, 1H), 3.90 (s, 3H), 3.87 (s, 3H), 2.11 (s, 3H); MS for $C_{29}H_{22}F_2N_4O_5$: m/z 545 (MH+).

N-[4-[(6,7-Dimethoxy-1,5-naphthyridin-4-yl)oxy]-3-fluorophenyl]-6-methyl-4-oxo-5-phenyl-1-propan-2-ylpyridine-3-carboxamide hydrochloride (29): Compound 20 was replaced with phenylboronic acid. $^1$H NMR (400 MHz, CD$_3$OD) δ 8.89 (s, 1H), 8.74 (d, 1H), 8.11 (dd, 1H), 7.61 (s, 1H), 7.57-7.35 (m, 6H), 7.25 (ddd, 2H), 4.92 (t, 1H), 4.19 (s, 3H), 4.16 (s, 3H), 2.37 (s, 3H), 1.63 (dd, 6H); MS for $C_{32}H_{29}FN_4O_5$: m/z 569.3 (MH+).

N-[4-[(6,7-Dimethoxy-1,5-naphthyridin-4-yl)oxy]-3-fluorophenyl]-5-(3-fluorophenyl)-6-methyl-4-oxo-1-propan-2-ylpyridine-3-carboxamide hydrochloride (30): Compound 20 was replaced with (3-fluorophenyl)boronic acid. $^1$H NMR (400 MHz, CD$_3$OD) δ 8.89 (s, 1H), 8.74 (d, 1H), 8.11 (dd, 1H), 7.60 (s, 1H), 7.58-7.38 (m, 2H), 7.28-7.11 (m, 2H), 7.11-6.98 (m, 2H), 6.71-6.43 (m, 1H), 4.92 (q, 1H), 4.19 (s, 3H), 4.16 (s, 3H), 2.38 (s, 3H), 1.63 (d, 6H); MS for $C_{32}H_{28}F_2N_4O_5$: m/z 587.3 (MH+).

N-[4-[(6,7-dimethoxy-1,5-naphthyridin-4-yl)oxy]-3-fluorophenyl]-5-(4-methoxyphenyl)-6-methyl-4-oxo-1-propan-2-ylpyridine-3-carboxamide hydrochloride (31): Compound 20 was replaced with (4-methoxyphenyl)boronic acid. H NMR (400 MHz, CD$_3$OD) δ 8.75 (s, 1H), 8.62 (d, 1H), 7.99 (d, 1H), 7.51 (s, 1H), 7.37 (dt, 2H), 7.12 (d, 1H), 7.07 (dd, 2H), 6.98-6.91 (m, 2H), 4.86-4.77 (m, 1H), 4.07 (s, 3H), 4.04 (s, 3H), 3.76 (s, 3H), 2.27 (d, 3H), 1.56-1.43 (m, 6H); MS for $C_{33}H_{31}FN_4O_6$: m/z 599.3 (MH+).

N-[4-[(6,7-Dimethoxy-1,5-naphthyridin-4-yl)oxy]-3-fluorophenyl]-5-(4-fluoro-2-methylphenyl)-6-methyl-4-oxo-1-propan-2-ylpyridine-3-carboxamide hydrochloride (32): Compound 20 was replaced with (4-fluoro-2-methylphenyl)boronic acid. $^1$H NMR (400 MHz, CD$_3$OD) δ 8.91 (s, 1H), 8.74 (d, 1H), 8.11 (dd, 1H), 7.63 (s, 1H), 7.57-7.40 (m, 2H), 7.23 (d, 1H), 7.19-6.99 (m, 3H), 4.92 (q, 1H), 4.19 (s, 3H), 4.16 (s, 3H), 2.30 (s, 3H), 2.14 (s, 3H), 1.63 (d, 6H); MS for $C_{33}H_3F_2N_4O_5$: m/z 601.3 (MH+).

N-[4-[(6,7-Dimethoxy-1,5-naphthyridin-4-yl)oxy]-3-fluorophenyl]-1-methyl-4-oxo-5-phenylpyridine-3-carboxamide hydrochloride (33): Compound 33 can be made by replacing Compound PA2-2 with Compound PA4-1 and replacing Compound 20 with phenylboronic acid. Compound 33 was also made using the method exemplified in Example 2 where Compound PA1-2 was replaced with Compound PA3-8. $^1$H NMR (400 MHz, CD$_3$OD) δ 8.75 (dd, 2H), 8.13 (dd, 1H), 8.04 (d, 1H), 7.70-7.61 (m, 3H), 7.58-7.36 (m, 5H), 7.24 (dd, 1H), 4.20 (s, 3H), 4.16 (s, 3H), 4.00 (s, 3H); MS for $C_{29}H_{23}FN_4O_5$: m/z 527.1 (MH+).

N-[4-[(6,7-Dimethoxy-1,5-naphthyridin-4-yl)oxy]-3-fluorophenyl]-5-(4-methoxyphenyl)-1-methyl-4-oxopyridine-3-carboxamide hydrochloride (34): Compound 34 can be made by replacing Compound PA2-2 with Compound PA4-1 and replacing Compound 20 with (3-fluorophenyl)boronic acid. Compound 34 was also made using the method exemplified in Example 2 where Compound PA1-2 was replaced with Compound PA3-9. $^1$H NMR (400 MHz, CD$_3$OD) δ 8.74 (d, 1H), 8.70 (d, 1H), 8.12 (dd, 1H), 7.98 (d, 1H), 7.68-7.55 (m, 3H), 7.56-7.42 (m, 2H), 7.22 (d, 1H), 7.10-7.00 (m, 2H), 4.19 (s, 3H), 4.16 (s, 3H), 3.98 (s, 3H), 3.86 (s, 3H); MS for $C_{30}H_{25}FN_4O_6$: m/z 557.1 (MH+).

N-[4-[(6,7-Dimethoxy-1,5-naphthyridin-4-yl)oxy]-3-fluorophenyl]-5-(3-fluorophenyl)-1-methyl-4-oxopyridine-3-carboxamide hydrochloride (35): Compound 35 can be made by replacing Compound PA2-2 with Compound PA4-1 and replacing Compound 20 with (4-methoxyphenyl)boronic acid. Compound 35 was also made using the method exemplified in Example 2 where Compound PA1-2 was replaced with Compound PA3-10. $^1$H NMR (400 MHz, CD$_3$OD) δ 8.74 (d, 1H), 8.67 (d, 1H), 8.15-8.03 (m, 2H), 7.61 (s, 1H), 7.56-7.36 (m, 5H), 7.21-7.04 (m, 2H), 4.15 (s, 3H), 4.12 (s, 3H), 4.00 (s, 3H); MS for $C_{29}H_{22}F_2N_4O_5$: m/z 545.1 (MH+).

N-[4-[(6,7-Dimethoxy-1,5-naphthyridin-4-yl)oxy]-3-fluorophenyl]-1,6-dimethyl-4-oxo-5-phenylpyridine-3-carboxamide hydrochloride (36): Compound QA1-1 was replaced with Compound NA1-1. Compound PA2-2 was replaced with Compound PA2-7. Compound 20 was replaced with phenylboronic acid. $^1$H NMR (400 MHz, CD$_3$OD) δ 8.80 (s, 1H), 8.74 (d, 1H), 8.10 (dd, 1H), 7.62 (s, 1H), 7.48 (ddt, 5H), 7.31-7.24 (m, 2H), 7.22 (dd, 1H), 4.19 (s, 3H), 4.16 (s, 3H), 3.96 (s, 3H), 2.30 (s, 3H); MS for $C_{30}H_{25}FN_4O_5$: m/z 541.2 (MH+).

N-[4-[(6,7-Dimethoxy-1,5-naphthyridin-4-yl)oxy]-3-fluorophenyl]-5-(3-fluorophenyl)-1,6-dimethyl-4-oxopyridine-3-carboxamide hydrochloride (37): Compound QA1-1 was replaced with Compound NA1-1. Compound PA2-2 was replaced with Compound PA2-7. Compound 20 was replaced with (3-fluorophenyl)boronic acid. $^1$H NMR (400 MHz, CD$_3$OD) δ 8.81 (s, 1H), 8.74 (d, 1H), 8.10 (dd, 1H), 7.61 (s, 1H), 7.58-7.39 (m, 3H), 7.27-7.13 (m, 2H), 7.14-7.01 (m, 2H), 4.19 (s, 3H), 4.16 (s, 3H), 3.96 (s, 3H), 2.32 (s, 3H); MS for $C_{30}H_{24}F_2N_4O_5$: m/z 559.2 (MH+).

5-(4-Chlorophenyl)-N-[4-[(6,7-dimethoxy-1,5-naphthyridin-4-yl)oxy]-3-fluorophenyl]-1-methyl-4-oxopyridine-3-carboxamide hydrochloride (38): Compound 38 can be made by replacing Compound PA2-2 with Compound PA4-1 and replacing Compound 20 with (4-chlorophenyl)boronic acid. Compound 38 was also made using the method exemplified in Example 2 where Compound PA1-2 was replaced with Compound PA3-11. $^1$H NMR (400 MHz, CD$_3$OD) δ 8.77-8.70 (m, 2H), 8.14 (dd, 1H), 8.07 (d, 1H), 7.67 (d, 2H), 7.61 (s, 1H), 7.58-7.43 (m, 4H), 7.24 (dd, 1H), 4.20 (s, 3H), 4.17 (s, 3H), 4.00 (s, 3H); MS for $C_{29}H_{22}ClFN_4O_5$: m/z 561 (MH+).

N-[4-[(6,7-Dimethoxy-1,5-naphthyridin-4-yl)oxy]phenyl]-1-methyl-4-oxo-5-phenylpyridine-3-carboxamide hydrochloride (39): Compound NA1-1 was replaced with Compound NA1-2. Compound 39 can be made by replacing Compound PA2-2 with Compound PA4-1 and replacing Compound 20 with phenylboronic acid. Compound 39 was also made using the method exemplified in Example 2 where Compound PA1-2 was replaced with Compound PA3-8. $^1$H NMR (400 MHz, CD$_3$OD) δ 8.75 (d, 1H), 8.70 (d, 1H), 8.04 (d, 1H), 8.00-7.91 (m, 2H), 7.69-7.61 (m, 2H), 7.60 (s, 1H), 7.54-7.39 (m, 3H), 7.39-7.30 (m, 2H), 7.15 (d, 1H), 4.22 (s, 3H), 4.16 (s, 3H), 4.01 (s, 3H); MS for $C_{29}H_{24}N_4O_5$: m/z 509.2 (MH+).

N-[3-Fluoro-4-[(7-methoxy-1,5-naphthyridin-4-yl)oxy]phenyl]-1-methyl-4-oxo-5-phenylpyridine-3-carboxamide hydrochloride (40): Compound NA1-1 was replaced with Compound NA1-3. Compound 40 can be made by replacing Compound PA2-2 with Compound PA4-1 and replacing Compound 20 with phenylboronic acid. Compound 40 was also made using the method exemplified in Example 2 where Compound PA1-2 was replaced with Compound PA3-8. $^1$H NMR (400 MHz, CD$_3$OD) δ 9.04-8.96 (m, 2H), 8.76 (d, 1H), 8.17 (dd, 1H), 8.05 (d, 1H), 7.81 (d, 1H), 7.69-7.61 (m, 2H), 7.61-7.37 (m, 5H), 7.27 (dd, 1H), 4.19 (s, 3H), 4.01 (s, 3H); MS for $C_{28}H_{21}FN_4O_4$: m/z 497.2 (MH+).

N-[4-[(6,7-Dimethoxy-1,5-naphthyridin-4-yl)oxy]-3-fluorophenyl]-5-(4-fluoro-2,6-dimethylphenyl)-1-methyl-4-oxopyridine-3-carboxamide (268): Compound PA2-2 was replaced with Compound PA4-1. Compound 20 was replaced with (4-fluoro-2,6-dimethylphenyl)boronic acid. MS for $C_{31}H_{26}F_2N_4O_5$: m/z 559.2 (MH+).

N-[3-Fluoro-4-[(6-methoxy-1,7-naphthyridin-4-yl)oxy]phenyl]-5-(4-fluorophenyl)-4-hydroxy-2-(methoxymethyl)-6-methylpyridine-3-carboxamide (501): Compound NA1-1 was replaced with Compound NA3-1. Compound PA2-2 was replaced with Compound C4-A. $^1$H NMR (400 MHz, DMSO-d$_6$) δ 13.41 (s, 1H), 11.48 (s, 1H), 9.18 (s, 1H), 8.65 (d, 1H), 8.04 (d, 1H), 7.48-7.40 (m, 3H), 7.34-7.21 (m, 4H), 6.75 (d, 1H), 5.05 (s, 2H), 4.02 (s, 3H), 3.50 (d, 3H), 2.24 (s, 3H); MS for $C_{30}H_{24}F_2N_4O_5$: m/z 559.2 (MH+).

N-[4-[(6-Chloro-1,7-naphthyridin-4-yl)oxy]-3-fluorophenyl]-5-(4-fluorophenyl)-4-hydroxy-2-(methoxymethyl)-6-methylpyridine-3-carboxamide (502): Compound NA1-1 was replaced with Compound NA3-2. Compound PA2-2 was replaced with Compound C4-A. MS for $C_{29}H_{21}ClF_2N_4O_4$: m/z 563.0 (MH+).

Example 2: 1-Cyclopropyl-N-[4-[(6,7-dimethoxy-1,5-naphthyridin-4-yl)oxy]-3-fluorophenyl]-5-(4-fluorophenyl)-4-oxopyridine-3-carboxamide (41)

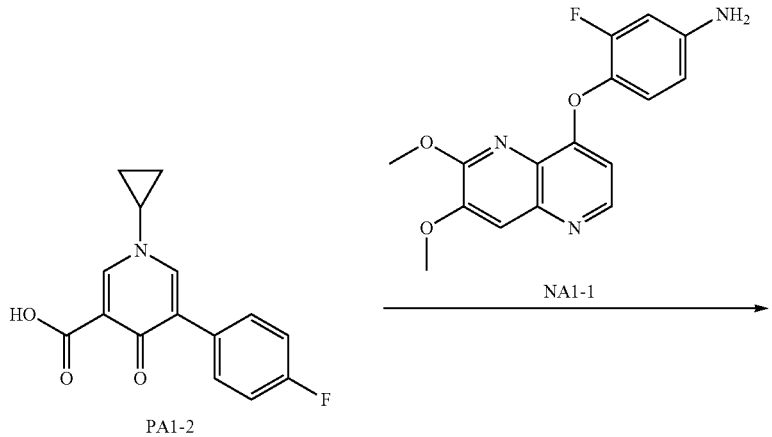

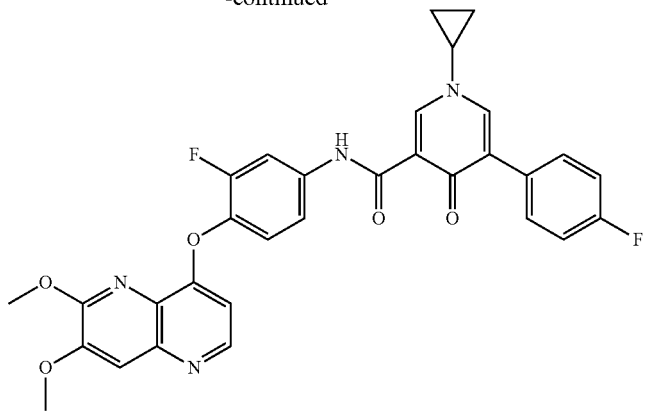

41

1-Cyclopropyl-N-[4-[(6,7-dimethoxy-1,5-naphthyridin-4-yl)oxy]-3-fluorophenyl]-5-(4-fluorophenyl)-4-oxopyridine-3-carboxamide (41). Compound NA1-1 was coupled to Compound PA1-2 using standard HATU coupling procedures similar to that used in Step 1 of Example 1 for coupling Compound NA1-1 to Compound PA2-2. After the reaction was complete and the reaction mixture was poured into the aq. saturated NaHCO$_3$ and the resulting suspension was filtered, the recovered material was purified by silica gel column chromatography or prep-HPLC to give Compound 41. $^1$H NMR (400 MHz, DMSO-d$_6$) δ 12.98 (s, 1H), 8.57 (s, 1H), 8.49 (d, 1H), 8.07 (s, 1H), 7.96 (d, 1H), 7.67 (d, 2H), 7.59 (s, 1H), 7.39 (d, 1H), 7.24 (dt, 3H), 6.78 (d, 1H), 3.90 (s, 3H), 3.88 (s, 3H), 3.81 (t, 1H), 1.18 (s, 2H), 1.01 (d, 2H); MS for C$_{31}$H$_{24}$F$_2$N$_4$O$_5$: m/z 571 (MH+).

The following compounds were made following a method analogous to that used to synthesize Compound 41 in Example 2 in one step from Compounds NA1-1 and PA1-2. Where HCl salts are indicated, the target compounds were generally converted to the HCl salts by first dissolving the compound in 20% MeOH in DCM, passing it through an Agilent PL-HCO3 ion exchange column and concentrating under reduced pressure (alternatively, the compound was dissolved in DCM and washed with aq. saturated sodium bicarbonate and then concentrated). Secondly, HCl (4 M in Dioxane, 0.5 mL; or 1 M aqueous, 1 mL) was added and the volatile solvents were removed under reduced pressure and the resulting residue dried under high vacuum to give the desired final product as the hydrochloride salt.

N-[4-[(6,7-Dimethoxy-1,5-naphthyridin-4-yl)oxy]-3-fluorophenyl]-5-(4-fluorophenyl)-4-hydroxypyridine-3-carboxamide (42): Compound PA1-2 was replaced with Compound PA1-1. $^1$H NMR (400 MHz, DMSO-d$_6$) δ 13.10 (s, 1H), 12.61 (t, 1H), 8.56 (d, 1H), 8.49 (d, 1H), 8.03 (d, 1H), 8.01-7.93 (m, 1H), 7.64 (dd, 2H), 7.59 (s, 1H), 7.38 (d, 1H), 7.23 (dt, 3H), 6.78 (d, 1H), 3.89 (d, 6H); MS for C$_{28}$H$_{20}$F$_2$N$_4$O$_5$: m/z 531 (MH+).

N-[4-(6,7-Dimethoxyquinolin-4-yl)oxy-3-fluorophenyl]-5-(4-fluorophenyl)-4-oxo-1-propan-2-ylpyridine-3-carboxamide (43): Compound NA1-1 was replaced with Compound QA1-1. Compound PA1-2 was replaced with Compound PA1-3. $^1$H NMR (400 MHz, DMSO-d$_6$) δ 13.17 (s, 1H), 8.71 (d, 1H), 8.42 (d, 1H), 8.21 (d, 1H), 8.00 (dd, 1H), 7.67 (dd, 2H), 7.49-7.32 (m, 4H), 7.22 (t, 2H), 6.43 (d, 1H), 4.58 (p, 1H), 3.88 (d, 6H), 1.45 (d, 6H); MS for C$_{32}$H$_{27}$F$_2$N$_3$O$_5$: m/z 572 (MH+).

N-[4-[(6,7-Dimethoxy-1,5-naphthyridin-4-yl)oxy]-3-fluorophenyl]-5-(4-fluorophenyl)-4-oxo-1-propan-2-ylpyridine-3-carboxamide (44): Compound PA1-2 was replaced with Compound PA1-3. $^1$H NMR (400 MHz, DMSO-d$_6$) δ 13.11 (s, 1H), 8.70 (d, 1H), 8.48 (d, 1H), 8.21 (d, 1H), 8.01-7.92 (m, 1H), 7.66 (dd, 2H), 7.58 (s, 1H), 7.38 (d, 1H), 7.24 (dt, 3H), 6.77 (d, 1H), 4.61-4.54 (m, 1H), 3.92-3.85 (m, 6H), 1.45 (d, 6H); MS for C$_{31}$H$_{26}$F$_2$N$_4$O$_5$: m/z 573 (MH+).

N-[4-[(6,7-Dimethoxy-1,5-naphthyridin-4-yl)oxy]-3-fluorophenyl]-5-(4-fluorophenyl)-1-methyl-4-oxopyridine-3-carboxamide (45): Compound PA1-2 was replaced with Compound PA1-4. $^1$H NMR (400 MHz, DMSO-d$_6$) δ 13.13 (s, 1H), 8.63 (d, 1H), 8.48 (d, 1H), 8.09 (d, 1H), 7.96 (dd, 1H), 7.71-7.61 (m, 2H), 7.58 (s, 1H), 7.38 (dt, 1H), 7.31-7.17 (m, 3H), 6.76 (d, 1H), 3.90 (s, 3H), 3.90 (s, 3H), 3.90 (s, 3H); MS for C$_{29}$H$_{22}$F$_2$N$_4$O$_5$: m/z 545 (MH+).

1-Cyclopentyl-N-[4-[(6,7-dimethoxy-1,5-naphthyridin-4-yl)oxy]-3-fluorophenyl]-5-(4-fluorophenyl)-4-oxopyridine-3-carboxamide (46): Compound PA1-2 was replaced with Compound PA1-6. $^1$H NMR (400 MHz, DMSO-d$_6$) δ 13.16 (s, 1H), 8.74 (s, 1H), 8.56 (d, 1H), 8.22 (d, 1H), 8.05 (d, 1H), 7.74 (dd, 2H), 7.66 (s, 1H), 7.46 (d, 1H), 7.32 (dt, 3H), 6.85 (d, 1H), 4.78 (t, 1H), 3.98 (s, 3H), 3.95 (s, 3H), 2.24 (s, 2H), 1.92 (d, 4H), 1.68 (s, 2H); MS for C$_{33}$H$_{28}$F$_2$N$_4$O$_5$: m/z 599 (MH+).

N-[4-[(6,7-Dimethoxy-1,5-naphthyridin-4-yl)oxy]-3-fluorophenyl]-5-(4-fluorophenyl)-1-(oxetan-3-yl)-4-oxopyridine-3-carboxamide (47): Compound PA1-2 was replaced with Compound PA1-7. $^1$H NMR (400 MHz, DMSO-d$_6$) δ 12.98 (s, 1H), 8.78 (d, 1H), 8.49 (t, 1H), 8.30 (d, 1H), 7.97 (d, 1H), 7.79-7.63 (m, 2H), 7.59 (d, 1H), 7.40 (d, 1H), 7.26 (dt, 3H), 6.77 (d, 1H), 5.52 (q, 1H), 4.90 (dt, 4H), 4.01-3.81 (m, 6H); MS for C$_{31}$H$_{24}$F$_2$N$_4$O$_6$: m/z 587 (MH+).

1-tert-Butyl-N-[4-[(6,7-dimethoxy-1,5-naphthyridin-4-yl)oxy]-3-fluorophenyl]-5-(4-fluorophenyl)-4-oxopyridine-3-carboxamide (48): Compound PA1-2 was replaced with Compound PA1-8. $^1$H NMR (400 MHz, CDCl$_3$) δ 13.09 (s, 1H), 8.96 (d, 1H), 8.53 (d, 1H), 8.07 (d, 2H), 7.84 (d, 1H), 7.58 (dd, 2H), 7.53-7.37 (m, 1H), 7.22 (m, 3H), 6.92 (s, 1H), 4.20 (s, 3H), 4.14 (s, 3H), 1.76 (s, 9H); MS for C$_{32}$H$_{28}$F$_2$N$_4$O$_5$: m/z 587 (MH+).

N-[4-[(6,7-Dimethoxy-1,5-naphthyridin-4-yl)oxy]-3-fluorophenyl]-5-(4-fluorophenyl)-4-oxo-1-(2,2,2-trifluoroethyl)pyridine-3-carboxamide (49): Compound PA1-2 was replaced with Compound PA1-9. $^1$H NMR (400 MHz, CDCl$_3$) δ 12.52 (s, 1H), 8.56 (d, 1H), 8.44 (d, 1H), 7.90 (d, 1H), 7.78 (s, 1H), 7.46 (q, 3H), 7.32 (d, 1H), 7.11 (q, 3H), 6.76 (d, 1H), 4.47 (q, 2H), 4.07 (d, 3H), 4.00 (s, 3H); MS for $C_{30}H_{21}F_5N_4O_5$: m/z 613 (MH+).

1-Cyclobutyl-N-[4-[(6,7-dimethoxy-1,5-naphthyridin-4-yl)oxy]-3-fluorophenyl]-5-(4-fluorophenyl)-4-oxopyridine-3-carboxamide (50): Compound PA1-2 was replaced with Compound PA1-10. $^1$H NMR (400 MHz, DMSO-$d_6$) δ 13.06 (s, 1H), 8.62 (d, 1H), 8.48 (d, 1H), 8.17 (d, 1H), 7.96 (dd, 1H), 7.71-7.61 (m, 2H), 7.58 (s, 1H), 7.38 (ddd, 1H), 7.33-7.10 (m, 3H), 6.77 (d, 1H), 4.84 (p, 1H), 3.90 (s, 3H), 3.87 (s, 3H), 2.53-2.29 (m, 4H), 1.88-1.55 (m, 2H); MS for $C_{32}H_{26}F_2N_4O_5$: m/z 585 (MH+).

N-[4-[(6,7-Dimethoxy-1,5-naphthyridin-4-yl)oxy]-3-fluorophenyl]-5-(4-fluorophenyl)-1-(1-methylpyrazol-4-yl)-4-oxopyridine-3-carboxamide (51): Compound PA1-2 was replaced with Compound PA1-11. $^1$H NMR (400 MHz, DMSO-$d_6$) δ 12.95 (s, 1H), 8.74 (d, 1H), 8.56 (d, 1H), 8.49 (s, 1H), 8.34 (d, 1H), 8.08 (d, 1H), 8.07-7.97 (m, 1H), 7.86-7.71 (m, 2H), 7.66 (s, 1H), 7.55-7.43 (m, 1H), 7.43-7.22 (m, 3H), 6.86 (d, 1H), 3.98 (s, 3H), 3.95 (s, 3H), 3.92 (s, 3H); MS for $C_{32}H_{24}F_2N_6O_5$: m/z 611 (MH+).

N-[4-[(6,7-Dmethoxy-1,5-naphthyridin-4-yl)oxy]-3-fluorophenyl]-5-(4-fluorophenyl)-1-(1-methylazetidin-3-yl)-4-oxopyridine-3-carboxamide (52): Compound PA1-2 was replaced with Compound PA1-25. $^1$H NMR (400 MHz, DMSO-$d_6$) δ 13.04 (s, 1H), 8.92 (d, 1H), 8.48 (d, 1H), 8.28 (d, 1H), 7.97 (dd, 1H), 7.72-7.61 (m, 2H), 7.59 (s, 1H), 7.39 (ddd, 1H), 7.32-7.13 (m, 3H), 6.77 (d, 1H), 4.93 (tt, 1H), 3.90 (s, 3H), 3.87 (s, 3H), 3.64-3.41 (m, 4H), 2.27 (s, 3H). MS for $C_{32}H_{27}F_2N_5O_5$: m/z 600 (MH+).

N-[4-[(6,7-Dimethoxy-1,5-naphthyridin-4-yl)oxy]-3-fluorophenyl]-5-(4-fluorophenyl)-1-(1-methylpyrazol-3-yl)-4-oxopyridine-3-carboxamide (53): Compound PA1-2 was replaced with Compound PA1-12. $^1$H NMR (400 MHz, DMSO-$d_6$) δ 12.76 (s, 1H), 9.07 (d, 1H), 8.49 (d, 1H), 8.43 (d, 1H), 7.98 (dd, 1H), 7.86 (d, 1H), 7.75-7.63 (m, 2H), 7.59 (s, 1H), 7.42 (ddd, 1H), 7.26 (dt, 3H), 6.87 (d, 1H), 6.82-6.74 (m, 1H), 3.90 (s, 3H), 3.87 (s, 3H), 3.86 (s, 3H); MS for $C_{32}H_{24}F_2N_6O_5$: m/z 611 (MH+).

N-[4-[(6,7-Dimethoxy-1,5-naphthyridin-4-yl)oxy]-3-fluorophenyl]-5-(4-fluorophenyl)-1-(3-methyloxetan-3-yl)-4-oxopyridine-3-carboxamide (54): Compound PA1-2 was replaced with Compound PA-27. $^1$H NMR (400 MHz, CDCl$_3$) δ 12.81 (s, 1H), 8.50 (d, 1H), 8.37 (d, 1H), 7.98 (s, 1H), 7.93 (q, 1H), 7.46 (m, 2H), 7.35 (m, 1H), 7.28 (d, 1H), 7.17 (t, 2H), 7.08 (t, 1H), 6.81 (d, 1H), 5.06 (d, 2H), 4.65 (d, 2H), 4.09 (s, 3H), 4.02 (s, 3H), 1.93 (s, 3H); MS for $C_{32}H_{26}F_2N_4O_6$: m/z 601.2 (MH+).

N-[4-(6,7-Dimethoxyquinolin-4-yl)oxy-3-fluorophenyl]-5-(4-fluorophenyl)-1-(3-methyloxetan-3-yl)-4-oxopyridine-3-carboxamide (55): Compound NA1-1 was replaced with Compound QA1-1. Compound PA1-2 was replaced with Compound PA1-27. $^1$H NMR (400 MHz, CDCl$_3$) δ 2.74 (s, 1H), 8.40 (d, 1H), 8.37 (d, 1H), 7.90 (q, 1H), 7.51 (s, 1H), 7.46 (m, 2H), 7.35 (m, 2H), 7.26 (d, 1H), 7.13 (m, 3H), 6.38 (d, 1H), 5.06 (d, 2H), 4.65 (d, 2H), 3.98 (d, 3H), 3.40 (s, 3H), 1.93 (s, 3H); MS for $C_{33}H_{27}F_2N_3O_6$: m/z 600.2 (MH+).

N-[4-[(6,7-Dimethoxy-1,5-naphthyridin-4-yl)oxy]-3-fluorophenyl]-5-(4-fluorophenyl)-1-(1-hydroxy-2-methylpropan-2-yl)-4-oxopyridine-3-carboxamide (56): Compound PA1-2 was replaced with Compound PA1-28. $^1$H NMR (400 MHz, CDCl$_3$) δ 12.89 (s, 1H), 8.78 (d, 1H), 8.35 (d, 1H), 7.87 (q, 1H), 7.75 (d, 1H), 7.40 (m, 3H), 7.25 (m, 1H), 7.18 (s, 1H), 7.07 (m, 3H), 6.64 (d, 1H), 4.03 (s, 3H), 3.93 (s, 3H), 3.77 (s, 2H), 1.63 (s, 6H); MS for $C_{32}H_{28}F_2N_4O_6$: m/z 603.3 (MH+).

N-[4-(6,7-Dimethoxyquinolin-4-yl)oxy-3-fluorophenyl]-5-(4-fluorophenyl)-1-(1-hydroxy-2-methylpropan-2-yl)-4-oxopyridine-3-carboxamide (57): Compound NA1-1 was replaced with Compound QA1-1. Compound PA1-2 was replaced with Compound PA1-28. $^1$H NMR (400 MHz, CDCl$_3$) δ 12.88 (s, 1H), 8.78 (d, 1H), 8.25 (d, 1H), 7.91 (dd, 1H), 7.71 (d, 1H), 7.49 (s, 1H), 7.35-7.29 (m, 2H), 7.27 (s, 1H), 7.18 (s, 1H), 7.14 (t, 1H), 7.01 (t, 2H), 6.30 (dd, 1H), 3.98 (s, 3H), 3.96 (d, 1H), 3.94 (s, 3H), 3.79 (s, 2H), 1.63 (s, 6H); MS for $C_{33}H_{29}F_2N_3O_6$: m/z 602.3 (MH+).

N-[4-[(6,7-Dimethoxy-1,5-naphthyridin-4-yl)oxy]-3-fluorophenyl]-5-(4-fluorophenyl)-1,6-dimethyl-4-oxopyridine-3-carboxamide (58): Compound PA1-2 was replaced with Compound PA3-7. $^1$H NMR (400 MHz, CD$_3$OD) δ 13.11 (s, 1H), 8.79 (s, 1H), 8.70 (d, 1H), 8.19-8.00 (m, 2H), 7.58 (s, 1H), 7.52-7.36 (m, 2H), 7.35-7.20 (m, 3H), 7.17 (d, 1H), 4.17 (s, 3H), 4.14 (s, 3H), 3.96 (s, 3H), 2.31 (s, 3H); MS for $C_{30}H_{24}F_2N_4O_5$: m/z 559.2 (MH+).

N-[4-[(6,7-Dimethoxy-1,5-naphthyridin-4-yl)oxy]-3-fluorophenyl]-5-(4-fluorophenyl)-4-oxo-1-[1-(trifluoromethyl)cyclopropyl]pyridine-3-carboxamide (59): Compound PA1-2 was replaced with Compound PA1-15. $^1$H NMR (400 MHz, DMSO-$d_6$) δ 12.61 (s, 1H), 8.62 (d, 1H), 8.49 (d, 1H), 8.27 (d, 1H), 7.96 (dd, 1H), 7.69-7.60 (m, 2H), 7.58 (s, 1H), 7.40 (dd, 1H), 7.25 (dt, 3H), 6.78 (d, 1H), 3.90 (s, 3H), 3.86 (s, 3H), 1.86 (s, 2H), 1.75-1.52 (m, 2H). MS for $C_{32}H_{23}F_5N_4O_5$: m/z 639 (MH+).

1-[1-(Difluoromethyl)pyrazol-4-yl]-N-[4-[(6,7-dimethoxy-1,5-naphthyridin-4-yl)oxy]-3-fluorophenyl]-5-(4-fluorophenyl)-4-oxopyridine-3-carboxamide (60): Compound PA1-2 was replaced with Compound PA1-16. $^1$H NMR (400 MHz, DMSO-$d_6$) δ 12.80 (s, 1H), 9.03 (s, 1H), 8.78 (d, 1H), 8.49 (d, 1H), 8.44 (s, 1H), 8.37 (d, 1H), 8.24-7.78 (m, 2H), 7.78-7.65 (m, 2H), 7.59 (s, 1H), 7.42 (dd, 1H), 7.26 (dt, 3H), 6.78 (d, 1H), 3.90 (s, 3H), 3.87 (d, 3H). MS for $C_{32}H_{22}F_4N_6O_5$: m/z 647 (MH+).

N-[4-[(6,7-Dimethoxy-1,5-naphthyridin-4-yl)oxy]-3-fluorophenyl]-5-(4-fluorophenyl)-4-oxo-1-(1H-pyrazol-3-yl)pyridine-3-carboxamide (61): Compound PA1-2 was replaced with Compound PA-14. $^1$H NMR (400 MHz, DMSO-$d_6$) δ 13.21 (s, 1H), 12.78 (s, 1H), 9.11 (d, 1H), 8.55-8.44 (m, 2H), 7.98 (dd, 1H), 7.95-7.89 (m, 1H), 7.79-7.65 (m, 2H), 7.59 (s, 1H), 7.48-7.35 (m, 1H), 7.26 (dt, 3H), 6.91 (t, 1H), 6.79 (d, 1H), 3.90 (s, 3H), 3.87 (d, 3H). MS for $C_{31}H_{22}F_2N_6O_5$: m/z 597 (MH+).

N-[4-[(6,7-Dimethoxy-1,5-naphthyridin-4-yl)oxy]-3-fluorophenyl]-5-(4-fluorophenyl)-4-oxo-1-(1H-pyrazol-4-yl)pyridine-3-carboxamide (62): Compound PA1-2 was replaced with Compound PA-13. $^1$H NMR (400 MHz, DMSO-$d_6$) δ 13.34 (s, 1H), 12.98 (s, 1H), 8.78 (d, 1H), 8.61-8.49 (m, 2H), 8.37 (d, 1H), 8.15 (d, 1H), 8.06 (dd, 1H), 7.83-7.74 (m, 2H), 7.66 (s, 1H), 7.49 (ddd, 1H), 7.42-7.22 (m, 3H), 6.86 (d, 1H), 3.98 (s, 3H), 3.95 (s, 3H). MS for $C_{31}H_{22}F_2N_6O_5$: m/z 597 (MH+).

N-[4-[(6,7-Dimethoxy-1,5-naphthyridin-4-yl)oxy]-3-fluorophenyl]-1-ethyl-5-(4-fluorophenyl)-6-methyl-4-oxopyridine-3-carboxamide (63): Compound PA1-2 was replaced with Compound PA3-4. $^1$H NMR (400 MHz, DMSO-$d_6$) δ 13.15 (s, 1H), 8.78 (s, 1H), 8.55 (d, 1H), 8.01 (dd, 1H), 7.66 (s, 1H), 7.42 (dd, 1H), 7.39-7.19 (m, 5H), 6.83 (d, 1H), 4.28 (q, 2H), 3.97 (s, 3H), 3.95 (s, 3H), 2.26 (s, 3H), 1.40 (t, 3H); MS for $C_{30}H_{26}F_2N_4O_5$: m/z 573 (MH+).

N-[3-Fluoro-4-[(7-methoxy-1,5-naphthyridin-4-yl)oxy]phenyl]-5-(4-fluorophenyl)-4-hydroxy-6-methylpyridine-3-carboxamide (64): Compound NA1-1 was replaced with Compound NA1-3. Compound PA1-2 was replaced with Compound PA3-1. $^1$H NMR (400 MHz, DMSO-$d_6$) δ 13.25

(s, 1H), 12.56 (s, 1H), 8.76 (d, 1H), 8.71 (d, 1H), 8.57 (s, 1H), 8.06 (dd, 1H), 7.81 (d, 1H), 7.54-7.17 (m, 6H), 6.75 (dd, 1H), 4.01 (s, 3H), 2.19 (s, 3H); MS for $C_{28}H_{20}F_2N_4O_4$: m/z 515 (MH+).

N-[4-[(6,7-Dimethoxy-1,5-naphthyridin-4-yl)oxy]phenyl]-5-(4-fluorophenyl)-1,6-dimethyl-4-oxopyridine-3-carboxamide (65): Compound NA1-1 was replaced with Compound NA1-2. Compound PA1-2 was replaced with Compound PA3-7. $^1$H NMR (400 MHz, CD$_3$OD) δ 8.90 (s, 1H), 8.70 (d, 1H), 7.93 (d, 2H), 7.62 (s, 1H), 7.39-7.22 (m, 6H), 7.14 (d, 1H), 4.21 (s, 3H), 4.16 (s, 3H), 4.00 (s, 3H), 2.34 (s, 3H); MS for $C_{30}H_{25}FN_4O_5$: m/z 541.2 (MH+).

N-[3-Fluoro-4-[(7-methoxy-1,5-naphthyridin-4-yl)oxy]phenyl]-5-(4-fluorophenyl)-4-hydroxy-2,6-dimethylpyridine-3-carboxamide (66): Compound NA1-1 was replaced with Compound NA1-3. Compound PA1-2 was replaced with Compound PA5-2. $^1$H NMR (400 MHz, CD$_3$OD) δ 9.00 (d, 1H), 8.96 (d, 1H), 8.11 (d, 1H), 7.78 (d, 1H), 7.50 (d, 2H), 7.33 (dd, 2H), 7.25 (t, 3H), 4.19 (s, 3H), 2.83 (s, 3H), 2.27 (s, 3H); MS for $C_{29}H_{22}F_2N_4O_4$: m/z 529.2 (MH+).

N-[3-Fluoro-4-[(6-methoxy-1,5-naphthyridin-4-yl)oxy]phenyl]-5-(4-fluorophenyl)-4-hydroxy-2,6-dimethylpyridine-3-carboxamide (67): Compound NA1-1 was replaced with Compound NA1-10. Compound PA1-2 was replaced with Compound PA5-2. $^1$H NMR (DMSO-d$_6$) δ:13.35 (s, 1H), 11.96 (s, 1H), 8.63 (d, 1H), 8.29 (d, 1H), 8.00 (dd, 1H), 7.38 (dd, 1H), 7.35-7.20 (m, 6H), 6.96 (d, 1H), 3.94 (s, 3H), 2.75 (s, 3H), 2.15 (s, 3H); MS for $C_{29}H_{22}F_2N_4O_4$: m/z 529.2 (MH+).

N-[3-Fluoro-4-[[7-methoxy-6-(2-methoxyethoxy)-1,5-naphthyridin-4-yl]oxy]phenyl]-5-(4-fluorophenyl)-4-hydroxy-6-methylpyridine-3-carboxamide (68): Compound NA1-1 was replaced with Compound NA1-16. Compound PA1-2 was replaced with Compound PA3-1. $^1$H NMR (400 MHz, DMSO-d$_6$) δ 13.2 (s, 1H), 12.6 (s, 1H), 8.56 (s, 1H), 8.55 (d, 1H), 8.01 (dd, 1H), 7.66 (s, 1H), 7.40 (dd, 1H), 7.36-7.22 (m, 5H), 6.86 (d, 1H), 4.46 (t, 2H), 3.98 (s, 3H), 3.65 (t, 2H), 3.28 (s, 3H), 2.18 (s, 3H); MS for $C_{31}H_{26}F_2N_4O_6$: m/z 589 (MH+).

N-[4-[(6,7-Dimethoxy-1,5-naphthyridin-4-yl)oxy]-3-fluorophenyl]-5-(4-fluoro-2-methylphenyl)-4-hydroxy-6-methylpyridine-3-carboxamide (69): Compound PA1-2 was replaced with Compound PA7-1. MS for $C_{30}H_{24}F_2N_4O_5$: m/z 559 (MH+).

N-[3-Fluoro-4-[(6-methoxy-1,5-naphthyridin-4-yl)oxy]phenyl]-5-(4-fluoro-2-methylphenyl)-4-hydroxy-2,6-dimethylpyridine-3-carboxamide (70): Compound NA1-1 was replaced with Compound NA1-10. Compound PA1-2 was replaced with Compound PA7-2. MS for $C_{30}H_{24}F_2N_4O_4$: m/z 543 (MH+).

N-[4-[(6,7-Dimethoxy-1,5-naphthyridin-4-yl)oxy]-3-fluorophenyl]-5-(4-fluorophenyl)-4-hydroxy-6-(hydroxymethyl)pyridine-3-carboxamide (71): Compound PA1-2 was replaced with Compound PA7-3. Compound 71 may also be obtained by replacing Compound PA1-2 with Compound PA7-3a with subsequent hydrolysis of the acetyl group to give the hydroxyl using standard methods such as stirring in the presence of LiOH in a mixture of water and THF at room temperature. $^1$H NMR (400 MHz, DMSO-d$_6$) δ 13.20 (s, 1H), 12.30 (s, 1H), 8.58 (s, 1H), 8.55 (dd, 1H), 8.01 (dd, 1H), 7.66 (d, 1H), 7.42 (d, 1H), 7.37-7.22 (m, 5H), 6.83 (d, 1H), 5.97 (s, 1H), 4.34 (s, 2H), 3.97 (s, 3H), 3.95 (s, 3H); MS for $C_{29}H_{22}F_2N_4O_6$: m/z 561 (MH+).

N-[4-[(6,7-Dimethoxy-1,5-naphthyridin-4-yl)oxy]-3-fluorophenyl]-5-(4-fluorophenyl)-6-(hydroxymethyl)-1-methyl-4-oxopyridine-3-carboxamide (72): Compound PA1-2 was replaced with Compound PA7-4. MS for $C_{30}H_{24}F_2N_4O_6$: m/z 575 (MH+).

N-[4-[(6,7-Dimethoxy-1,5-naphthyridin-4-yl)oxy]-3-fluorophenyl]-5-(4-fluorophenyl)-6-methyl-4-oxo-1-(2,2,2-trifluoroethyl)pyridine-3-carboxamide (74): Compound PA1-2 was replaced with Compound PA7-6. MS for $C_{31}H_{23}F_5N_4O_5$: m/z 627 (MH+).

N-[4-[(6,7-Dimethoxy-1,5-naphthyridin-4-yl)oxy]-3-fluorophenyl]-5-(4-fluoro-2-methylphenyl)-1,6-dimethyl-4-oxopyridine-3-carboxamide (75): Compound PA1-2 was replaced with Compound PA7-7. MS for $C_{30}H_{26}F_2N_4O_5$: m/z 573 (MH+).

N-[4-[(6,7-Dimethoxy-1,5-naphthyridin-4-yl)oxy]-3-fluorophenyl]-5-(4-fluorophenyl)-4-hydroxy-6-(trifluoromethyl)pyridine-3-carboxamide (79): Compound PA1-2 was replaced with Compound PA7-11. MS for $C_{29}H_{19}F_5N_4O_5$: m/z 599 (MH+).

N-[3-Fluoro-4-[(7-methoxy-1,5-naphthyridin-4-yl)oxy]phenyl]-5-(4-fluorophenyl)-4-hydroxy-2-methylpyridine-3-carboxamide (80): Compound NA1-1 was replaced with Compound NA1-3. Compound PA1-2 was replaced with Compound PA7-12. $^1$H NMR (400 MHz, DMSO-d$_6$) δ 12.84 (s, 1H), 12.34 (d, 1H), 8.77 (t, 1H), 8.74-8.65 (m, 1H), 8.04 (dd, 1H), 7.94 (d, 1H), 7.81 (t, 1H), 7.75-7.59 (m, 2H), 7.54-7.41 (m, 1H), 7.39 (d, 1H), 7.26 (td, 2H), 6.76 (d, 1H), 4.02 (s, 3H), 2.67 (s, 3H); MS for $C_{28}H_{20}F_2N_4O_4$: m/z 515 (MH+).

N-[4-[(6,7-Dimethoxy-1,5-naphthyridin-4-yl)oxy]-3-fluorophenyl]-5-(4-fluorophenyl)-1,2-dimethyl-4-oxopyridine-3-carboxamide (81): Compound PA1-2 was replaced with Compound PA7-13. MS for $C_{30}H_{24}F_2N_4O_5$: m/z 559 (MH+).

N-[4-[(6,7-Dimethoxy-1,5-naphthyridin-4-yl)oxy]-3-fluorophenyl]-1-ethyl-5-(4-fluorophenyl)-2-methyl-4-oxopyridine-3-carboxamide (82): Compound PA1-2 was replaced with Compound PA7-14. MS for $C_{30}H_{26}F_2N_4O_5$: m/z 573 (MH+).

N-[3-Fluoro-4-[(7-methoxy-1,5-naphthyridin-4-yl)oxy]phenyl]-1-(4-fluorophenyl)-6-methyl-2-oxopyridine-3-carboxamide (83): Compound NA1-1 was replaced with Compound NA-3. Compound PA1-2 was replaced with Compound HA1-1. $^1$H NMR (400 MHz, DMSO-d$_6$) δ 12.08 (s, 1H), 8.74 (d, 1H), 8.70 (d, 1H), 8.51 (d, 1H), 8.05 (dd, 1H), 7.79 (d, 1H), 7.55-7.35 (m, 6H), 6.73 (t, 2H), 4.00 (s, 3H), 2.09 (s, 3H); MS for $C_{28}H_{20}F_2N_4O_4$: m/z 515.2 (MH+).

N-[3-Fluoro-4-[(6-methoxy-1,5-naphthyridin-4-yl)oxy]phenyl]-1-(4-fluorophenyl)-6-methyl-2-oxopyridine-3-carboxamide (84): Compound NA1-1 was replaced with Compound NA1-10. Compound PA1-2 was replaced with Compound HA-1. MS for $C_{28}H_{20}F_2N_4O_4$: m/z 515 (MH+).

N-[3-Fluoro-4-[(6-methoxy-1,5-naphthyridin-4-yl)oxy]phenyl]-1-(4-fluoro-2-methylphenyl)-6-methyl-2-oxopyridine-3-carboxamide (85): Compound NA1-1 was replaced with Compound NA1-10. Compound PA1-2 was replaced with Compound HA-2. MS for $C_{29}H_{22}F_2N_4O_4$: m/z 529 (MH+).

5-Acetyl-N-[4-[(6,7-dimethoxy-1,5-naphthyridin-4-yl)oxy]-3-fluorophenyl]-1-(4-fluorophenyl)-6-methyl-2-oxopyridine-3-carboxamide (86): Compound PA1-2 was replaced with Compound HA-3. $^1$H NMR (400 MHz, DMSO-d$_6$) δ 11.68 (s, 1H), 8.94 (s, 1H), 8.55 (d, 1H), 8.02 (dd, 1H), 7.64 (s, 1H), 7.53-7.44 (m, 5H), 7.34-7.29 (m, 1H), 6.84 (d, 1H), 3.96 (s, 3H), 3.91 (s, 3H), 2.63 (s, 3H), 2.31 (s, 3H); MS for $C_{31}H_{24}F_2N_4O_6$: m/z 587.3 (MH+).

5-Cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide (87): Compound 87 can be made by replacing Compound PA1-2 with Compound HA1-4. Alternatively, Compound 87 was made from Compound 366 as detailed in Example 85. MS for $C_{30}H_{21}F_2N_5O_5$: m/z 570.1 (MH+).

N-[4-[(6,7-Dimethoxy-1,5-naphthyridin-4-yl)oxy]-3-fluorophenyl]-5-(4-fluorophenyl)-6-methyl-4-oxo-1H-pyridazine-3-carboxamide (88): Compound PA1-2 was replaced with Compound HA2-1. $^1$H NMR (400 MHz, DMSO-$d_6$) δ 14.14 (s, 1H), 12.70 (s, 1H), 8.57 (d, 1H), 8.02 (d, 1H), 7.66 (s, 1H), 7.48 (d, 1H), 7.42 (t, 2H), 7.34 (dt, 3H), 6.86 (d, 1H), 3.98 (s, 3H), 3.95 (s, 3H), 2.29 (s, 3H); MS for $C_{28}H_{21}F_2N_5O_5$: m/z 546.2 (MH+).

N-[3-Fluoro-4-[(6-methoxy-1,5-naphthyridin-4-yl)oxy]phenyl]-5-(4-fluorophenyl)-6-methyl-4-oxo-1H-pyridazine-3-carboxamide (89): Compound NA1-1 was replaced with Compound NA1-10. Compound PA1-2 was replaced with Compound HA2-1. MS for $C_{27}H_9F_2N_5O_4$: m/z 516.2 (MH+).

N-[4-[(6,7-Dimethoxy-1,5-naphthyridin-4-yl)oxy]-3-fluorophenyl]-5-(4-fluoro-2-methylphenyl)-6-methyl-4-oxo-1H-pyridazine-3-carboxamide (90): Compound PA1-2 was replaced with Compound HA2-2. MS for $C_{29}H_{23}F_2N_5O_5$: m/z 560 (MH+).

N-[4-[(6,7-Dimethoxy-1,5-naphthyridin-4-yl)oxy]phenyl]-5-(4-fluorophenyl)-1,6-dimethyl-4-oxopyridazine-3-carboxamide (91): Compound NA1-1 was replaced with Compound NA1-2. Compound PA1-2 was replaced with Compound HA2-3. MS for $C_{29}H_{24}FN_5O_5$: m/z 542 (MH+).

N-[4-[(6,7-Dimethoxy-1,5-naphthyridin-4-yl)oxy]-3-fluorophenyl]-5-(4-fluorophenyl)-1,6-dimethyl-4-oxopyridazine-3-carboxamide (92): Compound PA1-2 was replaced with Compound HA2-3. MS for $C_{29}H_{23}F_2N_5O_5$: m/z 560 (MH+).

N-[4-[(6,7-Dimethoxy-1,5-naphthyridin-4-yl)oxy]-3-fluorophenyl]-4-(4-fluorophenyl)-5-methyl-3-oxopyrazine-2-carboxamide (93): Compound PA1-2 was replaced with Compound HA3-1. MS for $C_{28}H_{21}F_2N_5O_5$: m/z 546.1 (MH+).

N-[3-Fluoro-4-[(7-methoxy-1,5-naphthyridin-4-yl)oxy]phenyl]-4-(4-fluorophenyl)-5-methyl-3-oxopyrazine-2-carboxamide (94): Compound NA1-1 was replaced with Compound NA1-3. Compound PA1-2 was replaced with Compound HA3-1. MS for $C_{27}H_9F_2N_5O_4$: m/z 516.1 (MH+).

N-[4-[(6,7-Dimethoxy-1,5-naphthyridin-4-yl)oxy]-3-fluorophenyl]-4-(4-fluorophenyl)-5,6-dimethyl-3-oxopyrazine-2-carboxamide (95): Compound PA1-2 was replaced with Compound HA3-2. MS for $C_{29}H_{23}F_2N_5O_5$: m/z 560.0 (MH+).

N-[4-[(6,7-Dimethoxy-1,5-naphthyridin-4-yl)oxy]-3-fluorophenyl]-6-(4-fluorophenyl)-5-hydroxypyrimidine-4-carboxamide (96): Compound PA1-2 was replaced with Compound HA4-1. MS for $C_{27}H_{19}F_2N_5O_5$: m/z 532.1 (MH+).

N-[4-[(6,7-Dimethoxy-1,5-naphthyridin-4-yl)oxy]-3-fluorophenyl]-1-(4-fluorophenyl)-2-methyl-6-oxopyrimidine-5-carboxamide (97): Compound PA1-2 was replaced with Compound HA4-2. MS for $C_{28}H_{21}F_2N_5O_5$: m/z 546 (MH+).

N-[4-[(6,7-Dimethoxy-1,5-naphthyridin-4-yl)oxy]-3-fluorophenyl]-1-(4-fluorophenyl)-4-methyl-6-oxopyrimidine-5-carboxamide (98): Compound PA1-2 was replaced with Compound HA4-3. MS for $C_{28}H_{21}F_2N_5O_5$: m/z 546 (MH+).

N-[4-[(6,7-Dimethoxy-1,5-naphthyridin-4-yl)oxy]-3-fluorophenyl]-1-(4-fluorophenyl)-2-(methylamino)-6-oxopyrimidine-5-carboxamide (99): Compound PA1-2 was replaced with Compound HA4-4. $^1$H NMR (400 MHz, DMSO-$d_6$) δ 11.20 (s, 1H), 8.73 (s, 1H), 8.55 (d, 1H), 7.98 (dd, 1H), 7.65 (s, 1H), 7.5-7.35 (m, 5H), 7.29 (t, 1H), 7.05 (d, 1H), 6.81 (d, 1H), 3.97 (s, 3H), 3.94 (s, 3H), 2.85 (d, 3H); MS for $C_{28}H_{22}F_2N_6O_5$: m/z 561 (MH+).

N-[4-[(6,7-Dimethoxy-1,5-naphthyridin-4-yl)oxy]-3-fluorophenyl]-2-(dimethylamino)-1-(4-fluorophenyl)-6-oxopyrimidine-5-carboxamide (100): Compound PA1-2 was replaced with Compound HA4-5. MS for $C_{29}H_{24}F_2N_6O_5$: m/z 575.2 (MH+).

N-[4-[(6,7-Dimethoxy-1,5-naphthyridin-4-yl)oxy]-3-fluorophenyl]-1-(4-fluorophenyl)-2,4-dimethyl-6-oxopyrimidine-5-carboxamide (101): Compound PA1-2 was replaced with Compound HA4-6. MS for $C_{29}H_{23}F_2N_5O_5$: m/z 560 (MH+).

N-[4-[(6,7-Dimethoxy-1,5-naphthyridin-4-yl)oxy]-3-fluorophenyl]-3-(4-fluorophenyl)-2,4-dioxo-1H-pyrimidine-5-carboxamide (102): Compound PA1-2 was replaced with Compound HA4-7. MS for $C_{27}H_9F_2N_5O_6$: m/z 548.2 (MH+).

N-[3-Fluoro-4-[(6-methoxy-1,5-naphthyridin-4-yl)oxy]phenyl]-3-(4-fluorophenyl)-2,4-dioxo-1H-pyrimidine-5-carboxamide (103): Compound NA1-1 was replaced with Compound NA1-10. Compound PA1-2 was replaced with Compound HA4-7. MS for $C_{26}H_{17}F_2N_5O_5$: m/z 518.2 (MH+).

N-[4-[(6,7-Dimethoxy-1,5-naphthyridin-4-yl)oxy]-3-fluorophenyl]-3-(4-fluorophenyl)-4-oxo-2-sulfanylidene-1H-pyrimidine-5-carboxamide (104): Compound PA1-2 can be replaced with Compound HA4-8.

N-[3-Fluoro-4-(7-methoxyquinolin-4-yl)oxyphenyl]-5-(4-fluorophenyl)-4-hydroxy-6-methylpyridine-3-carboxamide (105): Compound NA1-1 was replaced with Compound QA1-3. Compound PA1-2 was replaced with Compound PA3-1. $^1$H NMR (400 MHz, CDCl$_3$) δ 12.98 (s, 1H), 8.69-8.56 (m, 3H), 8.35 (d, 1H), 8.00 (dd, 1H), 7.53 (d, 1H), 7.43-7.27 (m, 2H), 7.27-7.13 (m, 4H), 6.58 (d, 1H), 4.02 (s, 3H), 3.03 (br. s, 1H), 2.24 (s, 3H); MS for $C_{29}H_{21}F_2N_3O_4$: m/z 514.2 (MH+).

N-[3-Fluoro-4-(7-methoxyquinolin-4-yl)oxyphenyl]-5-(4-fluorophenyl)-6-methyl-4-oxo-1-propan-2-ylpyridine-3-carboxamide (106): Compound NA1-1 was replaced with Compound QA-3. Compound PA1-2 was replaced with Compound PA3-2. MS for $C_{32}H_{27}F_2N_3O_4$: m/z 556.2 (MH+).

1-Ethyl-N-[3-fluoro-4-(7-methoxyquinolin-4-yl)oxyphenyl]-5-(4-fluorophenyl)-6-methyl-4-oxopyridine-3-carboxamide (107): Compound NA1-1 was replaced with Compound QA1-3. Compound PA1-2 was replaced with Compound PA3-4. $^1$H NMR (400 MHz, DMSO-$d_6$) δ 13.29 (s, 1H), 8.98 (d, 1H), 8.80 (s, 1H), 8.51 (d, 1H), 8.13 (dd, 1H), 7.79 (d, 1H), 7.59 (tdd, 3H), 7.28 (d, 4H), 7.01 (d, 1H), 4.29 (q, 2H), 4.04 (s, 3H), 2.27 (s, 3H), 1.40 (t, 3H); MS for $C_{31}H_{25}F_2N_3O_4$: m/z 542.2 (MH+).

5-(4-Fluorophenyl)-4-hydroxy-N-[4-(7-methoxyquinolin-4-yl)oxyphenyl]-6-methylpyridine-3-carboxamide (108): Compound NA1-1 was replaced with Compound QA1-4. Compound PA1-2 was replaced with Compound PA3-1. MS for $C_{29}H_{22}FN_3O_4$: m/z 496.2 (MH+).

N-[4-(6,7-Dimethoxyquinolin-4-yl)oxy-3-fluorophenyl]-5-(4-fluorophenyl)-4-hydroxy-6-methylpyridine-3-carboxamide (109): Compound NA1-1 was replaced with Compound QA-1. Compound PA1-2 was replaced with Compound PA3-1. MS for $C_{30}H_{23}F_2N_3O_5$: m/z 544.2 (MH+).

N-[3-Fluoro-4-[(6-methoxy-1,5-naphthyridin-4-yl)oxy]phenyl]-5-(4-fluorophenyl)-6-methyl-4-oxo-1-propan-2- ylpyridine-3-carboxamide (110): Compound NA1-1 was replaced with Compound NA1-10. Compound PA1-2 was replaced with Compound PA3-2. MS for $C_{31}H_{26}F_2N_4O_4$: m/z 557.2 (MH+).

5-(4-Fluorophenyl)-N-[4-[(7-methoxy-1,5-naphthyridin-4-yl)oxy]phenyl]-1,6-dimethyl-4-oxopyridine-3-carboxamide (111): Compound NA1-1 was replaced with Compound NA1-6. Compound PA1-2 was replaced with Compound PA3-7. MS for $C_{29}H_{23}FN_4O_4$: m/z 511 (MH+).

N-[3-Fluoro-4-[(7-methoxy-1,5-naphthyridin-4-yl)oxy]phenyl]-5-(4-fluorophenyl)-1-methyl-4-oxopyridine-3-carboxamide (112): Compound NA1-1 was replaced with Compound NA1-3. Compound PA1-2 was replaced with Compound PA-4. MS for $C_{28}H_{20}F_2N_4O_4$: m/z 515 (MH+).

N-[3-Fluoro-4-[(6-methoxy-1,5-naphthyridin-4-yl)oxy]phenyl]-5-(4-fluorophenyl)-1,6-dimethyl-4-oxopyridine-3-carboxamide (113): Compound NA1-1 was replaced with Compound NA1-10. Compound PA1-2 was replaced with Compound PA3-7. MS for $C_{29}H_{22}F_2N_4O_4$: m/z 529 (MH+).

tert-Butyl 3-[3-[[4-[(6,7-dimethoxy-1,5-naphthyridin-4-yl)oxy]-3-fluorophenyl]carbamoyl]-5-(4-fluorophenyl)-4-oxopyridin-1-yl]azetidine-1-carboxylate (114): Compound PA1-2 was replaced with Compound PA1-26. MS for $C_{36}H_{33}F_2N_5O_7$: m/z 686 (MH+).

N-[4-[(6,7-Dimethoxy-1,5-naphthyridin-4-yl)oxy]phenyl]-5-(4-fluorophenyl)-6-methyl-4-oxo-1-propan-2-ylpyridine-3-carboxamide (115): Compound NA1-1 was replaced with Compound NA1-2. Compound PA1-2 was replaced with Compound PA3-2. $^1$H NMR (400 MHz, DMSO-$d_6$) δ 12.91 (s, 1H), 8.63 (s, 1H), 8.54 (d, 1H), 7.75-7.64 (m, 2H), 7.58 (s, 1H), 7.28-7.06 (m, 6H), 6.81 (d, 1H), 4.70 (m, 1H), 3.92 (s, 3H), 3.89 (s, 3H), 2.22 (s, 3H), 1.44 (d, 6H); MS for $C_{32}H_{29}FN_4O_5$: m/z 569 (MH+).

N-[4-[(6,7-Dimethoxy-1,5-naphthyridin-4-yl)oxy]-3-fluorophenyl]-1-ethyl-5-(4-fluorophenyl)-4-oxopyridine-3-carboxamide (116): Compound PA1-2 was replaced with Compound PA1-5. MS for $C_{30}H_{24}F_2N_4O_5$: m/z 559 (MH+).

N-[4-[(6,7-Dimethoxy-1,5-naphthyridin-4-yl)oxy]-3-fluorophenyl]-5-(4-fluorophenyl)-1-(2-hydroxyethyl)-4-oxopyridine-3-carboxamide (117): Compound PA1-2 was replaced with Compound PA1-17. MS for $C_{30}H_{24}F_2N_4O_6$: m/z 575 (MH+).

N-[4-[(6,7-Dimethoxy-1,5-naphthyridin-4-yl)oxy]phenyl]-5-(4-fluorophenyl)-4-hydroxypyridine-3-carboxamide (118): Compound NA1-1 was replaced with Compound NA1-2. Compound PA1-2 was replaced with Compound PA1-1. MS for $C_{28}H_{21}FN_4O_5$: m/z 513 (MH+).

N-[4-[(6,7-Dimethoxy-1,5-naphthyridin-4-yl)oxy]phenyl]-5-(4-fluorophenyl)-4-hydroxy-6-methylpyridine-3-carboxamide (119): Compound NA1-1 was replaced with Compound NA-2. Compound PA1-2 was replaced with Compound PA3-1. $^1$H NMR (400 MHz, DMSO-$d_6$) δ 13.04 (s, 1H), 12.56 (s, 1H), 8.54 (t, 2H), 7.82-7.69 (m, 2H), 7.64 (s, 1H), 7.35-7.23 (m, 4H), 7.21-7.08 (m, 2H), 6.80 (d, 1H), 3.97 (s, 3H), 3.94 (s, 3H), 2.18 (s, 3H); MS for $C_{29}H_{23}FN_4O_5$: m/z 527 (MH+).

N-[3-Fluoro-4-[(7-methoxy-1,5-naphthyridin-4-yl)oxy]phenyl]-5-(4-fluorophenyl)-4-hydroxypyridine-3-carboxamide (120): Compound NA1-1 was replaced with Compound NA1-3. Compound PA1-2 was replaced with Compound PA-1. MS for $C_{27}H_{11}F_2N_4O_4$: m/z 501 (MH+).

N-[3-Fluoro-4-[(7-methoxy-1,5-naphthyridin-4-yl)oxy]phenyl]-5-(4-fluorophenyl)-6-methyl-4-oxo-1-propan-2-ylpyridine-3-carboxamide (121): Compound NA1-1 was replaced with Compound NA1-3. Compound PA1-2 was replaced with Compound PA3-2. MS for $C_{30}H_{26}F_2N_4O_4$: m/z 557 (MH+).

N-[4-[(6,7-Dimethoxy-1,5-naphthyridin-4-yl)oxy]phenyl]-5-(4-fluorophenyl)-4-oxo-1-propan-2-ylpyridine-3-carboxamide (122): Compound NA1-1 was replaced with Compound NA-2. Compound PA1-2 was replaced with Compound PA1-3. MS for $C_{31}H_{27}FN_4O_5$: m/z 555 (MH+).

N-[3-Fluoro-4-[(7-methoxy-1,5-naphthyridin-4-yl)oxy]phenyl]-5-(4-fluorophenyl)-4-oxo-1-propan-2-ylpyridine-3-carboxamide (123): Compound NA1-1 was replaced with Compound NA-3. Compound PA1-2 was replaced with Compound PA-3. MS for $C_{30}H_{24}F_2N_4O_4$: m/z 543 (MH+).

N-[4-[(6,7-Dimethoxy-1,5-naphthyridin-4-yl)oxy]-3-fluorophenyl]-5-(4-fluorophenyl)-4-oxo-1-pyridin-2-ylpyridine-3-carboxamide (124): Compound PA1-2 was replaced with Compound PA1-18. MS for $C_{33}H_{23}F_2N_5O_5$: m/z 608 (MH+).

N-[4-[(6,7-Dimethoxy-1,5-naphthyridin-4-yl)oxy]-3-fluorophenyl]-5-(4-fluorophenyl)-4-oxo-1-pyridin-3-ylpyridine-3-carboxamide (125): Compound PA1-2 was replaced with Compound PA1-19. $^1$H NMR (400 MHz, DMSO-$d_6$) δ 12.91 (s, 1H), 9.07 (d, 1H), 8.85 (d, 1H), 8.76 (dd, 1H), 8.57 (d, 1H), 8.50 (d, 1H), 8.32 (dt, 1H), 8.07 (dd, 1H), 7.89-7.79 (m, 2H), 7.72-7.61 (m, 2H), 7.51 (d, 1H), 7.34 (dt, 3H), 6.86 (d, 1H), 3.98 (s, 3H), 3.95 (s, 3H); MS for $C_{33}H_{23}F_2N_5O_5$: m/z 608 (MH+).

N-[4-[(6,7-Dimethoxy-1,5-naphthyridin-4-yl)oxy]-3-fluorophenyl]-5-(4-fluorophenyl)-1-methoxy-4-oxopyridine-3-carboxamide (126): Compound PA1-2 was replaced with Compound PA1-20. MS for $C_{29}H_{22}F_2N_4O_6$: m/z 561 (MH+).

N-[4-[(6,7-Dimethoxy-1,5-naphthyridin-4-yl)oxy]phenyl]-5-(4-fluorophenyl)-1-methoxy-4-oxopyridine-3-carboxamide (127): Compound NA1-1 was replaced with Compound NA1-2. Compound PA1-2 was replaced with Compound PA-20. MS for $C_{29}H_{23}FN_4O_6$: m/z 543 (MH+).

N-[3-Fluoro-4-[(7-methoxy-1,5-naphthyridin-4-yl)oxy]phenyl]-5-(4-fluorophenyl)-1-methoxy-4-oxopyridine-3-carboxamide (128): Compound NA1-1 was replaced with Compound NA1-3. Compound PA1-2 was replaced with Compound PA-20. MS for $C_{28}H_{20}F_2N_4O_5$: m/z 531 (MH+).

N-[4-[(7-Bromo-6-methoxy-1,5-naphthyridin-4-yl)oxy]-3-fluorophenyl]-5-(4-fluorophenyl)-4-hydroxypyridine-3-carboxamide (129): Compound NA1-1 was replaced with Compound NA1-4. Compound PA1-2 was replaced with Compound PA1-1. MS for $C_{27}H_{17}BrF_2N_4O_4$: m/z 579/581 (MH+).

N-[4-[(7-Bromo-6-methoxy-1,5-naphthyridin-4-yl)oxy]-3-fluorophenyl]-5-(4-fluorophenyl)-4-hydroxy-6-methylpyridine-3-carboxamide (130): Compound NA1-1 was replaced with Compound NA1-4. Compound PA1-2 was replaced with Compound PA3-1. MS for $C_{28}H_{19}BrF_2N_4O_4$: m/z 593/595 (MH+).

N-[4-[(7-Bromo-6-methoxy-1,5-naphthyridin-4-yl)oxy]-3-fluorophenyl]-5-(4-fluorophenyl)-4-oxo-1-propan-2-ylpyridine-3-carboxamide (131): Compound NA1-1 was replaced with Compound NA1-4. Compound PA1-2 was replaced with Compound PA1-3. MS for $C_{30}H_{23}BrF_2N_4O_4$: m/z 621/623 (MH+).

N-[4-[(7-Bromo-6-methoxy-1,5-naphthyridin-4-yl)oxy]-3-fluorophenyl]-5-(4-fluorophenyl)-6-methyl-4-oxo-1-propan-2-ylpyridine-3-carboxamide (132): Compound NA1-1 was replaced with Compound NA1-4. Compound PA-2 was replaced with Compound PA3-2. MS for $C_{31}H_{25}BrF_2N_4O_4$: m/z 635/637 (MH+).

N-[4-[(7-Bromo-1,5-naphthyridin-4-yl)oxy]-3-fluorophenyl]-5-(4-fluorophenyl)-4-hydroxy-6-methylpyridine-3-carboxamide (133): Compound NA1-1 was replaced with Compound NA1-5. Compound PA1-2 was replaced with Compound PA3-1. MS for $C_{27}H_{17}BrF_2N_4O_3$: m/z 563/565 (MH+).

N-[4-[(6,7-Dimethoxy-1,5-naphthyridin-4-yl)oxy]-3-fluorophenyl]-5-(4-fluorophenyl)-1-hydroxy-4-oxopyridine-3-carboxamide (134): Compound PA1-2 was replaced with Compound PA1-21. $^1$H NMR (400 MHz, DMSO-d$_6$) δ 13.41 (s, 1H), 13.19 (s, 1H), 8.65 (d, 1H), 8.56 (d, 1H), 8.38 (d, 1H), 8.03 (dd, 1H), 7.79-7.69 (m, 2H), 7.66 (s, 1H), 7.45 (dd, 1H), 7.32 (dt, 3H), 6.85 (d, 1H), 3.98 (s, 3H), 3.95 (s, 3H); MS for $C_{28}H_{20}F_2N_4O_6$: m/z 547 (MH+).

N-[4-[(6,7-Dimethoxy-1,5-naphthyridin-4-yl)oxy]-3-fluorophenyl]-5-(4-fluorophenyl)-1-(methylamino)-4-oxopyridine-3-carboxamide (135): Compound PA1-2 was replaced with Compound PA1-22. $^1$H NMR (400 MHz, DMSO-d$_6$) δ 13.10 (s, 1H), 8.72 (d, 1H), 8.56 (d, 1H), 8.23 (d, 1H), 8.04 (dd, 1H), 7.80-7.70 (m, 2H), 7.66 (s, 1H), 7.51-7.41 (m, 1H), 7.32 (dt, 3H), 7.13 (d, 1H), 6.85 (d, 1H), 3.98 (s, 3H), 3.95 (s, 3H), 2.90 (d, 3H); MS for $C_{29}H_{23}F_2N_5O_5$: m/z 560 (MH+).

N-[4-[(6,7-Dimethoxy-1,5-naphthyridin-4-yl)oxy]-3-fluorophenyl]-1-(dimethylamino)-5-(4-fluorophenyl)-4-oxopyridine-3-carboxamide (136): Compound PA1-2 was replaced with Compound PA1-23. MS for $C_{30}H_{25}F_2N_5O_5$: m/z 574 (MH+).

1-[bis(Dimethylamino)methylideneamino]-N-[4-[(6,7-dimethoxy-1,5-naphthyridin-4-yl)oxy]-3-fluorophenyl]-5-(4-fluorophenyl)-4-oxopyridine-3-carboxamide (137): Compound PA-2 was replaced with Compound PA-24. MS for $C_{33}H_{31}F_2N_7O5$: m/z 644 (MH+).

Methyl 8-[2-fluoro-4-[[5-(4-fluorophenyl)-4-hydroxy-6-methylpyridine-3-carbonyl]amino]phenoxy]-1,5-naphthyridine-3-carboxylate (138): Compound NA1-1 was replaced with Compound NA1-8. Compound PA1-2 was replaced with Compound PA3-1. MS for $C_{29}H_{20}F_2N_4O_5$: m/z 543 (MH+).

1-tert-Butyl-N-[4-[(6,7-dimethoxy-1,5-naphthyridin-4-yl)oxy]-3-fluorophenyl]-5-(4-fluorophenyl)-6-methyl-4-oxopyridine-3-carboxamide (139): Compound PA1-2 was replaced with Compound PA3-5. MS for $C_{33}H_3F_2N_4O_5$: m/z 601 (MH+).

N-[4-[(6,7-Dimethoxy-1,5-naphthyridin-4-yl)oxy]-3-fluorophenyl]-5-(4-fluorophenyl)-6-methyl-1-(1-methylpyrazol-4-yl)-4-oxopyridine-3-carboxamide (140): Compound PA1-2 was replaced with Compound PA3-6. $^1$H NMR (400 MHz, DMSO-d$_6$) δ 12.91 (s, 1H), 8.55 (d, 1H), 8.47 (s, 1H), 8.26 (s, 1H), 8.00 (dd, 1H), 7.85 (s, 1H), 7.66 (s, 1H), 7.45 (dt, 1H), 7.39-7.21 (m, 5H), 6.83 (d, 1H), 3.97 (s, 3H), 3.94 (s, 6H), 2.01 (s, 3H); MS for $C_{33}H_{26}F_2N_6O_5$: m/z 625 (MH+).

N-[4-[(6,7-Dimethoxy-1,5-naphthyridin-4-yl)oxy]phenyl]-5-(4-fluorophenyl)-6-methyl-1-(1-methylpyrazol-4-yl)-4-oxopyridine-3-carboxamide (141): Compound NA1-1 was replaced with Compound NA1-2. Compound PA1-2 was replaced with Compound PA3-6. MS for $C_{33}H_{27}FN_6O_5$: m/z 607 (MH+).

N-[4-[(6-Bromo-7-methoxy-1,5-naphthyridin-4-yl)oxy]-3-fluorophenyl]-5-(4-fluorophenyl)-4-hydroxy-6-methylpyridine-3-carboxamide (142): Compound NA1-1 was replaced with Compound NA1-9. Compound PA1-2 was replaced with Compound PA3-1. MS for $C_{28}H_{19}BrF_2N_4O_4$: m/z 593/595 (MH+).

N-[4-[(6-Bromo-7-methoxy-1,5-naphthyridin-4-yl)oxy]-3-fluorophenyl]-5-(4-fluorophenyl)-6-methyl-4-oxo-1-propan-2-ylpyridine-3-carboxamide (143): Compound NA1-1 was replaced with Compound NA1-9. Compound PA-2 was replaced with Compound PA3-2. MS for $C_{31}H_{25}BrF_2N_4O_4$: m/z 635/637 (MH+).

N-[3-Fluoro-4-[[7-methoxy-6-(2-methoxyethoxy)-1,5-naphthyridin-4-yl]oxy]phenyl]-5-(4-fluoro-2-methylphenyl)-4-hydroxy-6-methylpyridine-3-carboxamide (144): Compound NA1-1 was replaced with Compound NA1-16. Compound PA-2 was replaced with Compound PA7-1. MS for $C_{32}H_{28}F_2N_4O_6$: m/z 603 (MH+).

5-(4-Fluorophenyl)-N-[4-[(7-methoxy-1,5-naphthyridin-4-yl)oxy]phenyl]-4-oxo-1-propan-2-ylpyridine-3-carboxamide (145): Compound NA1-1 was replaced with Compound NA1-6. Compound PA1-2 was replaced with Compound PA-3. MS for $C_{30}H_{25}FN_4O_4$: m/z 525 (MH+).

5-(4-Fluorophenyl)-4-hydroxy-N-[4-[(7-methoxy-1,5-naphthyridin-4-yl)oxy]phenyl]pyridine-3-carboxamide (146): Compound NA1-1 was replaced with Compound NA1-6. Compound PA1-2 was replaced with Compound PA1-1. MS for $C_{27}H_{19}FN_4O_4$: m/z 483 (MH+).

5-(4-Fluorophenyl)-4-hydroxy-N-[4-[(7-methoxy-1,5-naphthyridin-4-yl)oxy]phenyl]-6-methylpyridine-3-carboxamide (147): Compound NA-1 was replaced with Compound NA1-6. Compound PA1-2 was replaced with Compound PA3-1. MS for $C_{28}H_{21}FN_4O_4$: m/z 497 (MH+).

5-(4-Fluorophenyl)-N-[4-[(7-methoxy-1,5-naphthyridin-4-yl)oxy]phenyl]-6-methyl-4-oxo-1-propan-2-ylpyridine-3-carboxamide (148): Compound NA1-1 was replaced with Compound NA1-6. Compound PA1-2 was replaced with Compound PA3-2. MS for $C_{31}H_{27}FN_4O_4$: m/z 538.2 (MH+).

N-[4-[(7-Bromo-1,5-naphthyridin-4-yl)oxy]phenyl]-5-(4-fluorophenyl)-4-hydroxy-6-methylpyridine-3-carboxamide (149): Compound NA-1 was replaced with Compound NA-11. Compound PA1-2 was replaced with Compound PA3-1. MS for $C_{27}H_{18}FN_4O_3$: m/z 545 (MH+).

5-(4-Fluorophenyl)-4-hydroxy-6-methyl-N-[4-[[7-(trifluoromethyl)-1,5-naphthyridin-4-yl]oxy]phenyl]pyridine-3-carboxamide (150): Compound NA1-1 was replaced with Compound NA1-12. Compound PA1-2 was replaced with Compound PA3-1. MS for $C_{28}H_{18}F_4N_4O_3$: m/z 535 (MH+).

5-(4-Fluorophenyl)-N-[3-fluoro-4-[[7-(trifluoromethyl)-1,5-naphthyridin-4-yl]oxy]phenyl]-4-hydroxy-6-methylpyridine-3-carboxamide (151): Compound NA1-1 was replaced with Compound NA1-13. Compound PA1-2 was replaced with Compound PA3-1. MS for $C_{28}H_{17}F_5N_4O_3$: m/z 553 (MH+).

5-(4-Fluorophenyl)-N-[3-fluoro-4-[[7-(trifluoromethyl)-1,5-naphthyridin-4-yl]oxy]phenyl]-6-methyl-4-oxo-1-propan-2-ylpyridine-3-carboxamide (152): Compound NA-1 was replaced with Compound NA1-13. Compound PA-2 was replaced with Compound PA3-2. MS for $C_{31}H_{23}F_5N_4O_3$: m/z 595 (MH+).

N-[4-[(7-Bromo-6-methyl-1,5-naphthyridin-4-yl)oxy]-3-fluorophenyl]-5-(4-fluorophenyl)-6-methyl-4-oxo-1-propan-2-ylpyridine-3-carboxamide (153): Compound NA-1 was replaced with Compound NA1-15. Compound PA-2 was replaced with Compound PA3-2. MS for $C_{31}H_{25}BrF_2N_4O_3$: m/z 619 (MH+).

N-[4-[(6,7-Dimethoxy-1,5-naphthyridin-4-yl)oxy]-3-fluorophenyl]-5-(4-fluorophenyl)-4-hydroxy-2,6-dimethylpyridine-3-carboxamide (154): Compound PA1-2 was replaced with Compound PA5-2. MS for $C_{30}H_{24}F_2N_4O_5$: m/z 559.2 (MH+).

6-tert-Butyl-N-[4-[(6,7-dimethoxy-1,5-naphthyridin-4-yl)oxy]-3-fluorophenyl]-5-(4-fluorophenyl)-4-hydroxypyridine-3-carboxamide (155): Compound PA1-2 was replaced with Compound PA5-3. MS for $C_{32}H_{28}F_2N_4O_5$: m/z 587.3 (MH+).

N-[3-Fluoro-4-[(7-methoxy-1,5-naphthyridin-4-yl)oxy]phenyl]-5-(4-fluorophenyl)-1,6-dimethyl-4-oxopyridine-3-carboxamide (156): Compound NA1-1 was replaced with Compound NA1-3. Compound PA1-2 was replaced with Compound PA3-7. MS for $C_{29}H_{22}F_2N_4O_4$: m/z 529.2 (MH+).

N-[4-[(6,7-Dimethoxy-1,5-naphthyridin-4-yl)oxy]-3-fluorophenyl]-5-(4-fluorophenyl)-1-(2-morpholin-4-yl-ethyl)-4-oxopyridine-3-carboxamide (157): Compound PA1-2 was replaced with Compound PA6-1. MS for $C_{34}H_{31}F_2N_5O_6$: m/z 644.1 (MH+).

5-(4-Fluorophenyl)-4-hydroxy-N-[4-[(7-methoxy-1,5-naphthyridin-4-yl)oxy]phenyl]-2,6-dimethylpyridine-3-carboxamide (158): Compound NA1-1 was replaced with Compound NA1-6. Compound PA1-2 was replaced with Compound PA5-2. $^1$H NMR (400 MHz, CD$_3$OD) δ 8.98 (d, 1H), 8.92 (d, 1H), 8.01-7.88 (m, 2H), 7.78 (d, 1H), 7.47-7.32 (m, 4H), 7.28 (t, 2H), 7.18 (d, 1H), 4.19 (s, 3H), 2.81 (s, 3H), 2.31 (s, 3H); MS for $C_{29}H_{23}FN_4O_4$: m/z 511.2 (MH+).

N-[4-[(6,7-Dimethoxy-1,5-naphthyridin-4-yl)oxy]-3-fluorophenyl]-5-(4-fluorophenyl)-1-(2-imidazol-1-ylethyl)-4-oxopyridine-3-carboxamide (159): Compound PA1-2 was replaced with Compound PA6-2. MS for $C_{33}H_{26}F_2N_6O_5$: m/z 625.2 (MH+).

N-[3-Fluoro-4-[(7-fluoro-1,5-naphthyridin-4-yl)oxy]phenyl]-5-(4-fluorophenyl)-4-hydroxy-6-methylpyridine-3-carboxamide (160): Compound NA1-1 was replaced with Compound NA1-7. Compound PA1-2 was replaced with Compound PA3-1. $^1$H NMR (400 MHz, CD$_3$OD) δ 9.00 (d, 1H), 8.80 (d, 1H), 8.63 (s, 1H), 8.18 (dd, 1H), 8.06 (dd, 1H), 7.53-7.38 (m, 2H), 7.33 (dd, 2H), 7.24 (t, 2H), 6.92 (d, 1H), 2.27 (s, 3H); MS for $C_{27}H_7F_3N_4O_3$: m/z 503.2 (MH+).

N-[3-Fluoro-4-[(7-fluoro-1,5-naphthyridin-4-yl)oxy]phenyl]-5-(4-fluorophenyl)-4-oxo-1-propan-2-ylpyridine-3-carboxamide (161): Compound NA1-1 was replaced with Compound NA1-7. Compound PA1-2 was replaced with Compound PA-3. MS for $C_{29}H_{21}F_3N_4O_3$: m/z 531.2 (MH+).

N-[3-Fluoro-4-[(7-fluoro-1,5-naphthyridin-4-yl)oxy]phenyl]-5-(4-fluorophenyl)-6-methyl-4-oxo-1-propan-2-ylpyridine-3-carboxamide (162): Compound NA1-1 was replaced with Compound NA1-7. Compound PA1-2 was replaced with Compound PA3-2. MS for $C_{30}H_{23}F_3N_4O_3$: m/z 545.2 (MH+).

1-Ethyl-5-(4-fluorophenyl)-N-[4-[(7-methoxy-1,5-naphthyridin-4-yl)oxy]phenyl]-6-methyl-4-oxopyridine-3-carboxamide (163): Compound NA1-1 was replaced with Compound NA1-6. Compound PA1-2 was replaced with Compound PA3-4. $^1$H NMR (400 MHz, CD$_3$OD) δ 8.81 (s, 1H), 8.72 (d, 1H), 8.68 (d, 1H), 7.87 (d, 2H), 7.76 (d, 1H), 7.36-7.20 (m, 6H), 6.81 (d, 1H), 4.32 (q, 2H), 4.08 (s, 3H), 2.34 (s, 3H), 1.54 (t, 3H); MS for $C_{30}H_{25}FN_4O_4$: m/z 525.2 (MH+).

1-Ethyl-N-[3-fluoro-4-[(7-methoxy-1,5-naphthyridin-4-yl)oxy]phenyl]-5-(4-fluorophenyl)-6-methyl-4-oxopyridine-3-carboxamide (164): Compound NA1-1 was replaced with Compound NA1-3. Compound PA1-2 was replaced with Compound PA3-4. MS for $C_{30}H_{24}F_2N_4O_4$: m/z 543.2 (MH+).

1-tert-Butyl-5-(4-fluorophenyl)-N-[4-[(7-methoxy-1,5-naphthyridin-4-yl)oxy]phenyl]-6-methyl-4-oxopyridine-3-carboxamide (165): Compound NA1-1 was replaced with Compound NA1-6. Compound PA1-2 was replaced with Compound PA3-5. MS for $C_{32}H_{29}FN_4O_4$: m/z 553.2 (MH+).

1-tert-Butyl-N-[3-fluoro-4-[(7-methoxy-1,5-naphthyridin-4-yl)oxy]phenyl]-5-(4-fluorophenyl)-6-methyl-4-oxopyridine-3-carboxamide (166): Compound NA1-1 was replaced with Compound NA1-3. Compound PA1-2 was replaced with Compound PA3-5. MS for $C_{32}H_{28}F_2N_4O_4$: m/z 571.2 (MH+).

N-[4-[(6,7-Dimethoxy-1,5-naphthyridin-4-yl)oxy]phenyl]-1-ethyl-5-(4-fluorophenyl)-4-oxopyridine-3-carboxamide (167): Compound NA1-1 was replaced with Compound NA1-2. Compound PA1-2 was replaced with Compound PA-5. MS for $C_{30}H_{25}FN_4O_5$: m/z 541.2 (MH+).

N-[4-[(6,7-Dimethoxy-1,5-naphthyridin-4-yl)oxy]phenyl]-1-ethyl-5-(4-fluorophenyl)-6-methyl-4-oxopyridine-3-carboxamide (168): Compound NA1-1 was replaced with Compound NA1-2. Compound PA1-2 was replaced with Compound PA3-4. MS for $C_{31}H_{27}FN_4O_5$: m/z 555.2 (MH+).

1-Ethyl-5-(4-fluorophenyl)-N-[4-[(7-methoxy-1,5-naphthyridin-4-yl)oxy]phenyl]-4-oxopyridine-3-carboxamide (169): Compound NA1-1 was replaced with Compound NA1-6. Compound PA1-2 was replaced with Compound PA-5. MS for $C_{29}H_{23}FN_4O_4$: m/z 511.2 (MH+).

1-Ethyl-N-[3-fluoro-4-[(7-methoxy-1,5-naphthyridin-4-yl)oxy]phenyl]-5-(4-fluorophenyl)-4-oxopyridine-3-carboxamide (170): Compound NA1-1 was replaced with Compound NA1-3. Compound PA1-2 was replaced with Compound PA-5. MS for $C_{29}H_{22}F_2N_4O_4$: m/z 529.2 (MH+).

N-[4-(6,7-Dimethoxyquinolin-4-yl)oxyphenyl]-5-(4-fluorophenyl)-4-hydroxy-6-methylpyridine-3-carboxamide (171): Compound NA1-1 was replaced with Compound QA-2. Compound PA1-2 was replaced with Compound PA3-1. MS for $C_{30}H_{24}FN_3O_5$: m/z 526 (MH+).

N-[3-Fluoro-4-[(6-methoxy-1,5-naphthyridin-4-yl)oxy]phenyl]-5-(4-fluorophenyl)-4-hydroxy-6-methylpyridine-3-carboxamide (172): Compound NA1-1 was replaced with Compound NA1-10. Compound PA1-2 was replaced with Compound PA3-1. MS for $C_{28}H_{20}F_2N_4O_4$: m/z 515.2 (MH+).

N-[4-[(6,7-Dimethoxy-1,5-naphthyridin-4-yl)oxy]phenyl]-5-(4-fluorophenyl)-4-hydroxy-2,6-dimethylpyridine-3-carboxamide (173): Compound NA1-1 was replaced with Compound NA1-2. Compound PA1-2 was replaced with Compound PA5-2. MS for $C_{30}H_{25}FN_4O_5$: m/z 541.2 (MH+).

N-[4-[(6,7-Dimethoxy-1,5-naphthyridin-4-yl)oxy]phenyl]-5-(4-fluoro-2-methylphenyl)-4-hydroxy-6-methylpyridine-3-carboxamide (174): Compound NA1-1 was replaced with Compound NA1-2. Compound PA1-2 was replaced with Compound PA7-1. MS for $C_{30}H_{25}FN_4O_5$: m/z 541 (MH+).

N-[3-Fluoro-4-[(7-methoxy-1,5-naphthyridin-4-yl)oxy]phenyl]-5-(4-fluoro-2-methylphenyl)-4-hydroxy-6-methylpyridine-3-carboxamide (175): Compound NA1-1 was replaced with Compound NA1-3. Compound PA1-2 was replaced with Compound PA7-1. MS for $C_{29}H_{22}F_2N_4O_4$: m/z 529 (MH+).

5-(4-Fluoro-2-methylphenyl)-4-hydroxy-N-[4-[(7-methoxy-1,5-naphthyridin-4-yl)oxy]phenyl]-6-methylpyridine-3-carboxamide (176): Compound NA1-1 was replaced with Compound NA1-6. Compound PA1-2 was replaced with Compound PA7-1. MS for $C_{29}H_{23}FN_4O_4$: m/z 511 (MH+).

N-[4-[(6,7-Dimethoxy-1,5-naphthyridin-4-yl)oxy]-3-fluorophenyl]-5-(4-fluoro-2-methylphenyl)-4-hydroxy-2,6-dimethylpyridine-3-carboxamide (177): Compound PA1-2 was replaced with Compound PA7-2. MS for $C_{30}H_{26}F_2N_4O_5$: m/z 573 (MH+).

N-[3-Fluoro-4-[(7-methoxy-1,5-naphthyridin-4-yl)oxy]phenyl]-5-(4-fluoro-2-methylphenyl)-4-hydroxy-2,6-dimethylpyridine-3-carboxamide (178): Compound NA1-1 was replaced with Compound NA1-3. Compound PA1-2 was replaced with Compound PA7-2. MS for $C_{30}H_{24}F_2N_4O_4$: m/z 543 (MH+).

N-[4-[(6,7-Dimethoxy-1,5-naphthyridin-4-yl)oxy]-3-fluorophenyl]-2-ethyl-5-(4-fluorophenyl)-4-hydroxy-6-methylpyridine-3-carboxamide (179): Compound PA1-2 was replaced with Compound PA5-7. MS for $C_{31}H_{26}F_2N_4O_5$: m/z 573 (MH+).

2-Ethyl-N-[3-fluoro-4-[(7-methoxy-1,5-naphthyridin-4-yl)oxy]phenyl]-5-(4-fluorophenyl)-4-hydroxy-6-methylpyridine-3-carboxamide (180): Compound NA-1 was replaced with Compound NA1-3. Compound PA1-2 was replaced with Compound PA5-7. MS for $C_{30}H_{24}F_2N_4O_4$: m/z 543 (MH+).

N-[3-Fluoro-4-[(7-methoxy-1,5-naphthyridin-4-yl)oxy]phenyl]-5-(4-fluoro-2-methylphenyl)-1,6-dimethyl-4-oxopyridine-3-carboxamide (181): Compound NA-1 was replaced with Compound NA1-3. Compound PA1-2 was replaced with Compound PA7-7. MS for $C_{30}H_{24}F_2N_4O_4$: m/z 543 (MH+).

2-Ethyl-N-[3-fluoro-4-[(6-methoxy-1,5-naphthyridin-4-yl)oxy]phenyl]-5-(4-fluorophenyl)-4-hydroxy-6-methylpyridine-3-carboxamide (182): Compound NA-1 was replaced with Compound NA1-10. Compound PA1-2 was replaced with Compound PA5-7. MS for $C_{30}H_{24}F_2N_4O_4$: m/z 543 (MH+).

N-[3-Fluoro-4-[(6-methoxy-1,5-naphthyridin-4-yl)oxy]phenyl]-5-(4-fluoro-2-methylphenyl)-1,6-dimethyl-4-oxopyridine-3-carboxamide (183): Compound NA-1 was replaced with Compound NA1-10. Compound PA1-2 was replaced with Compound PA7-7. MS for $C_{30}H_{24}F_2N_4O_4$: m/z 543 (MH+).

N-[4-[(6,7-Dimethoxy-1,5-naphthyridin-4-yl)oxy]-3-fluorophenyl]-5-(4-fluorophenyl)-4-hydroxy-2-(methoxymethyl)-6-methylpyridine-3-carboxamide (184): Compound PA1-2 was replaced with Compound PA5-11. MS for $C_{31}H_{26}F_2N_4O_6$: m/z 589 (MH+).

5-(4-Fluorophenyl)-4-hydroxy-2-(methoxymethyl)-N-[4-[(7-methoxy-1,5-naphthyridin-4-yl)oxy]phenyl]-6-methylpyridine-3-carboxamide (185): Compound NA1-1 was replaced with Compound NA1-6. Compound PA1-2 was replaced with Compound PA5-11. MS for $C_{30}H_{25}FN_4O_5$: m/z 541 (MH+).

N-[3-Fluoro-4-[(7-methoxy-1,5-naphthyridin-4-yl)oxy]phenyl]-5-(4-fluorophenyl)-4-hydroxy-2-(methoxymethyl)-6-methylpyridine-3-carboxamide (186): Compound NA-1 was replaced with Compound NA1-3. Compound PA-2 was replaced with Compound PA5-11. MS for $C_{30}H_{24}F_2N_4O_5$: m/z 559 (MH+).

5-(4-Fluoro-2-methylphenyl)-N-[4-[(7-methoxy-1,5-naphthyridin-4-yl)oxy]phenyl]-1,6-dimethyl-4-oxopyridine-3-carboxamide (187): Compound NA1-1 was replaced with Compound NA1-6. Compound PA1-2 was replaced with Compound PA7-7. MS for $C_{30}H_{25}FN_4O_4$: m/z 525 (MH+).

2-Ethyl-5-(4-fluorophenyl)-4-hydroxy-N-[4-[(7-methoxy-1,5-naphthyridin-4-yl)oxy]phenyl]-6-methylpyridine-3-carboxamide (188): Compound NA1-1 was replaced with Compound NA1-6. Compound PA1-2 was replaced with Compound PA5-7. MS for $C_{30}H_{25}FN_4O_4$: m/z 525 (MH+).

N-[3-Fluoro-4-[(6-methoxy-1,5-naphthyridin-4-yl)oxy]phenyl]-5-(4-fluorophenyl)-4-hydroxy-2-(methoxymethyl)-6-methylpyridine-3-carboxamide (189): Compound NA1-1 was replaced with Compound NA1-10. Compound PA1-2 was replaced with Compound PA5-11. MS for $C_{30}H_{24}F_2N_4O_5$: m/z 559 (MH+).

N-[4-[(6,7-Dimethoxy-1,5-naphthyridin-4-yl)oxy]phenyl]-5-(4-fluorophenyl)-4-hydroxy-2-(methoxymethyl)-6-methylpyridine-3-carboxamide (190): Compound NA1-1 was replaced with Compound NA1-2. Compound PA1-2 was replaced with Compound PA5-11. MS for $C_{31}H_{27}FN_4O_6$: m/z 571 (MH+).

N-[4-[(6,7-Dimethoxy-1,5-naphthyridin-4-yl)oxy]-3-fluorophenyl]-5-(4-fluoro-2-methylphenyl)-4-hydroxy-2-(methoxymethyl)-6-methylpyridine-3-carboxamide (191): Compound PA1-2 was replaced with Compound PA5-5. MS for $C_{32}H_{28}F_2N_4O_6$: m/z 603 (MH+).

N-[4-[(6,7-Dimethoxy-1,5-naphthyridin-4-yl)oxy]phenyl]-5-(4-fluoro-2-methylphenyl)-4-hydroxy-2-(methoxymethyl)-6-methylpyridine-3-carboxamide (192): Compound NA1-1 was replaced with Compound NA1-2. Compound PA1-2 was replaced with Compound PA5-5. MS for $C_{32}H_{29}FN_4O_6$: m/z 585 (MH+).

N-[3-Fluoro-4-[(7-methoxy-1,5-naphthyridin-4-yl)oxy]phenyl]-5-(4-fluoro-2-methylphenyl)-4-hydroxy-2-(methoxymethyl)-6-methylpyridine-3-carboxamide (193): Compound NA1-1 was replaced with Compound NA1-3. Compound PA1-2 was replaced with Compound PA5-5. MS for $C_{31}H_{26}F_2N_4O_5$: m/z 573 (MH+).

5-(4-Fluoro-2-methylphenyl)-4-hydroxy-2-(methoxymethyl)-N-[4-[(7-methoxy-1,5-naphthyridin-4-yl)oxy]phenyl]-6-methylpyridine-3-carboxamide (194): Compound NA1-1 was replaced with Compound NA1-6. Compound PA1-2 was replaced with Compound PA5-5. $^1$H NMR (400 MHz, CD$_3$OD) δ 9.01-8.91 (m, 2H), 8.02-7.95 (m, 2H), 7.86 (d, 1H), 7.48-7.40 (m, 2H), 7.32-7.11 (m, 4H), 5.0 (s, 2H), 4.20 (d, 3H), 3.58 (d, 3H), 2.38 (d, 3H), 2.20 (s, 3H); MS for $C_{31}H_{27}FN_4O_5$: m/z 555 (MH+).

N-[3-Fluoro-4-[(6-methoxy-1,5-naphthyridin-4-yl)oxy]phenyl]-5-(4-fluoro-2-methylphenyl)-4-hydroxy-2-(methoxymethyl)-6-methylpyridine-3-carboxamide (195): Compound NA1-1 was replaced with Compound NA1-10. Compound PA1-2 was replaced with Compound PA5-5. $^1$H NMR (400 MHz, CD$_3$OD) δ 8.89 (d, 1H), 8.45 (d, 1H), 8.14-8.06 (m, 1H), 7.66 (d, 1H), 7.59-7.47 (m, 2H), 7.40 (d, 1H), 7.20 (q, 2H), 7.11 (dd, 1H), 5.02 (s, 2H), 4.19 (s, 3H), 3.61 (s, 3H), 2.31 (s, 3H), 2.19 (s, 3H); MS for $C_{31}H_{26}F_2N_4O_5$: m/z 573 (MH+).

N-[4-[(6,7-Dimethoxy-1,5-naphthyridin-4-yl)oxy]phenyl]-5-(4-fluoro-2-methylphenyl)-1,6-dimethyl-4-oxopyridine-3-carboxamide (196): Compound NA1-1 was replaced with Compound NA1-2. Compound PA1-2 was replaced with Compound PA7-7. MS for $C_{31}H_{27}FN_4O_5$: m/z 555 (MH+).

N-[4-[(6,7-Dimethoxy-1,5-naphthyridin-4-yl)oxy]phenyl]-2-ethyl-5-(4-fluorophenyl)-4-hydroxy-6-methylpyridine-3-carboxamide (197): Compound NA1-1 was replaced with Compound NA1-2. Compound PA1-2 was replaced with Compound PA5-7. MS for $C_{31}H_{27}F_2N_4O_5$: m/z 555 (MH+).

N-[3-Fluoro-4-[[7-methoxy-6-(2-methoxyethoxy)-1,5-naphthyridin-4-yl]oxy]phenyl]-5-(4-fluorophenyl)-1,6-dimethyl-4-oxopyridine-3-carboxamide (198): Compound NA-1 was replaced with Compound NA1-16. Compound PA1-2 was replaced with Compound PA3-7. MS for $C_{32}H_{28}F_2N_4O_6$: m/z 603 (MH+).

N-[3-Fluoro-4-[[7-methoxy-6-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide (199): Compound NA1-1 was replaced with Compound NA1-16. Compound PA1-2 was replaced with Compound PA5-11. MS for $C_{33}H_{30}F_2N_4O_7$: m/z 633 (MH+).

N-[3-Fluoro-4-[[7-methoxy-6-(2-methoxyethoxy)-1,5-naphthyridin-4-yl]oxy]phenyl]-5-(4-fluoro-2-methylphenyl)-1,6-dimethyl-4-oxopyridine-3-carboxamide (200): Compound NA1-1 was replaced with Compound NA1-16. Compound PA1-2 was replaced with Compound PA7-7. MS for $C_{33}H_{30}F_2N_4O_6$: m/z 617 (MH+).

N-[3-Fluoro-4-[[7-methoxy-6-(2-methoxyethoxy)-1,5-naphthyridin-4-yl]oxy]phenyl]-5-(4-fluoro-2-methylphenyl)-4-hydroxy-2-(methoxymethyl)-6-methylpyridine-3-carboxamide (201): Compound NA1-1 was replaced with Compound NA1-16. Compound PA1-2 was replaced with Compound PA5-5. MS for $C_{34}H_{32}F_2N_4O_7$: m/z 647 (MH+).

N-[4-[(6,7-Dimethoxy-1,5-naphthyridin-4-yl)oxy]-3-fluorophenyl]-2-ethyl-5-(4-fluoro-2-methylphenyl)-4-hydroxy-6-methylpyridine-3-carboxamide (202): Compound PA1-2 was replaced with Compound PA5-8. MS for $C_{32}H_{28}F_2N_4O_5$: m/z 587 (MH+).

N-[4-[(6,7-Dimethoxy-1,5-naphthyridin-4-yl)oxy]phenyl]-2-ethyl-5-(4-fluoro-2-methylphenyl)-4-hydroxy-6-methylpyridine-3-carboxamide (203): Compound NA1-1 was replaced with Compound NA1-2. Compound PA1-2 was replaced with Compound PA5-8. MS for $C_{32}H_{29}FN_4O_5$: m/z 569 (MH+).

2-Ethyl-N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide (204): Compound NA1-1 was replaced with Compound NA1-3. Compound PA1-2 was replaced with Compound PA5-8. MS for $C_{30}H_{26}F_2N_4O_4$: m/z 557 (MH+).

2-Ethyl-5-(4-fluoro-2-methylphenyl)-4-hydroxy-N-[4-[(7-methoxy-1,5-naphthyridin-4-yl)oxy]phenyl]-6-methylpyridine-3-carboxamide (205): Compound NA1-1 was replaced with Compound NA1-6. Compound PA1-2 was replaced with Compound PA5-8. $^1$H NMR (400 MHz, CD$_3$OD) δ 9.00-8.94 (m, 2H), 8.02 (d, 2H), 7.91 (d, 1H), 7.45 (d, 2H), 7.34-7.11 (m, 4H), 4.20 (s, 3H), 3.12-3.02 (m, 2H), 2.39 (s, 3H), 2.21 (s, 3H), 1.49 (t, 3H); MS for $C_{31}H_{27}FN_4O_4$: m/z 539 (MH+).

2-Ethyl-N-[3-fluoro-4-[(6-methoxy-1,5-naphthyridin-4-yl)oxy]phenyl]-5-(4-fluoro-2-methylphenyl)-4-hydroxy-6-methylpyridine-3-carboxamide (206): Compound NA1-1 was replaced with Compound NA1-10. Compound PA1-2 was replaced with Compound PA5-8. MS for $C_{31}H_{26}F_2N_4O_4$: m/z 557 (MH+).

N-[3-Fluoro-4-[[7-methoxy-6-(2-methoxyethoxy)-1,5-naphthyridin-4-yl]oxy]phenyl]-5-(4-fluorophenyl)-4-hydroxy-2,6-dimethylpyridine-3-carboxamide (207): Compound NA1-1 was replaced with Compound NA1-16. Compound PA1-2 was replaced with Compound PA5-2. MS for $C_{32}H_{28}F_2N_4O_6$: m/z 603 (MH+).

N-[3-Fluoro-4-[[7-methoxy-6-(2-methoxyethoxy)-1,5-naphthyridin-4-yl]oxy]phenyl]-5-(4-fluoro-2-methylphenyl)-4-hydroxy-2,6-dimethylpyridine-3-carboxamide (208): Compound NA1-1 was replaced with Compound NA1-16. Compound PA1-2 was replaced with Compound PA7-2. MS for $C_{33}H_{30}F_2N_4O_6$: m/z 617 (MH+).

5-(2,4-Difluorophenyl)-N-[4-[(6,7-dimethoxy-1,5-naphthyridin-4-yl)oxy]-3-fluorophenyl]-4-hydroxy-2,6-dimethylpyridine-3-carboxamide (209): Compound PA1-2 was replaced with Compound PA5-4. MS for $C_{30}H_{23}F_3N_4O_5$: m/z 577 (MH+).

5-(2,4-Difluorophenyl)-N-[3-fluoro-4-[(7-methoxy-1,5-naphthyridin-4-yl)oxy]phenyl]-4-hydroxy-2,6-dimethylpyridine-3-carboxamide (210): Compound NA1-1 was replaced with Compound NA1-3. Compound PA1-2 was replaced with Compound PA5-4. $^1$H NMR (400 MHz, DMSO-d$_6$) δ 13.22 (s, 1H), 12.05 (s, 1H), 8.77-8.67 (m, 2H), 8.02 (d, 1H), 7.79 (d, 1H), 7.37 (dq, 4H), 7.16 (t, 1H), 6.73 (d, 1H), 4.00 (d, 3H), 2.76 (d, 3H), 2.13 (s, 3H); MS for $C_{29}H_{20}F_3N_4O_4$: m/z 547 (MH+).

5-(2,4-Difluorophenyl)-N-[3-fluoro-4-[(7-methoxy-1,5-naphthyridin-4-yl)oxy]phenyl]-4-hydroxy-2-(methoxymethyl)-6-methylpyridine-3-carboxamide (211): Compound NA1-1 was replaced with Compound NA1-3. Compound PA1-2 was replaced with Compound PA5-6. $^1$H NMR (400 MHz, DMSO-d$_6$) δ 13.24 (s, 1H), 11.59 (s, 1H), 8.77-8.64 (m, 2H), 8.11-7.88 (m, 1H), 7.80 (d, 1H), 7.37 (dq, 4H), 7.17 (t, 1H), 6.73 (d, 1H), 5.05 (s, 2H), 4.00 (d, 3H), 3.50 (d, 3H), 2.22 (s, 3H); MS for $C_{30}H_{23}F_3N_4O_5$: m/z 577 (MH+).

5-(2,4-Difluorophenyl)-N-[4-[(6,7-dimethoxy-1,5-naphthyridin-4-yl)oxy]-3-fluorophenyl]-4-hydroxy-2-(methoxymethyl)-6-methylpyridine-3-carboxamide (212): Compound PA1-2 was replaced with Compound PA5-6. MS for $C_{31}H_{25}F_3N_4O_6$: m/z 607 (MH+).

N-[4-[(6,7-Dimethoxy-1,5-naphthyridin-4-yl)oxy]-3-fluorophenyl]-2-(ethoxymethyl)-5-(4-fluorophenyl)-4-hydroxy-6-methylpyridine-3-carboxamide (213): Compound PA1-2 was replaced with Compound PA5-9. $^1$H NMR (400 MHz, DMSO-d$_6$) δ 13.70 (s, 1H), 11.39 (s, 1H), 8.54 (d, 1H), 7.98 (dd, 1H), 7.65 (s, 1H), 7.36 (dd, 1H), 7.32-7.19 (m, 5H), 6.79 (d, 1H), 5.02 (s, 2H), 3.96 (d, 6H), 3.66 (q, 2H), 2.20 (s, 3H), 1.23 (t, 3H); MS for $C_{32}H_{28}F_2N_4O_6$: m/z 603 (MH+).

2-(Ethoxymethyl)-N-[3-fluoro-4-[(7-methoxy-1,5-naphthyridin-4-yl)oxy]phenyl]-5-(4-fluorophenyl)-4-hydroxy-6-methylpyridine-3-carboxamide (214): Compound NA-1 was replaced with Compound NA1-3. Compound PA-2 was replaced with Compound PA5-9. MS for $C_{31}H_{26}F_2N_4O_5$: m/z 573 (MH+).

N-[4-[(6,7-Dimethoxy-1,5-naphthyridin-4-yl)oxy]-3-fluorophenyl]-2-(ethoxymethyl)-5-(4-fluoro-2-methylphenyl)-4-hydroxy-6-methylpyridine-3-carboxamide (215): Compound PA1-2 was replaced with Compound PA5-10. MS for $C_{33}H_{30}F_2N_4O_6$: m/z 617 (MH+).

1-(4-Fluorophenyl)-N-[4-[(7-methoxy-1,5-naphthyridin-4-yl)oxy]phenyl]-6-methyl-2-oxopyridine-3-carboxamide (216): Compound NA1-1 was replaced with Compound NA1-6. Compound PA1-2 was replaced with Compound HA1-1. MS for $C_{28}H_{21}FN_4O_4$: m/z 497.2 (MH+).

N-[3-Fluoro-4-[(7-methoxy-1,5-naphthyridin-4-yl)oxy]phenyl]-5-(4-fluorophenyl)-4-hydroxy-6-(hydroxymethyl)pyridine-3-carboxamide (217): Compound NA-1 was replaced with Compound NA1-3. Compound PA1-2 was replaced with Compound PA7-3a with subsequent hydrolysis of the acetyl group to give the hydroxyl using standard methods such as stirring in the presence of LiOH in a mixture of water and THF at room temperature. MS for $C_{28}H_{20}F_2N_4O_5$: m/z 531.2 (MH+).

5-(4-Fluorophenyl)-4-hydroxy-6-(hydroxymethyl)-N-[4-[(7-methoxy-1,5-naphthyridin-4-yl)oxy]phenyl]pyridine-3-carboxamide (218): Compound NA1-1 was replaced with Compound NA1-6. Compound PA1-2 was replaced with Compound PA7-3. In this particular case, the HATU coupling method was replaced with standard amide coupling techniques using T$_3$P and DIEA in DCM with stirring at room temperature, followed by heating at 45° C. MS for $C_{28}H_{21}FN_4O_5$: m/z 513.2 (MH+).

N-[4-[(6,7-Dimethoxy-1,5-naphthyridin-4-yl)oxy]-3-fluorophenyl]-1-(4-fluoro-2-methylphenyl)-6-methyl-2-oxopyridine-3-carboxamide (219): Compound PA1-2 was replaced with Compound HA1-2. MS for $C_{30}H_{24}F_2N_4O_5$: m/z 559 (MH+).

N-[3-Fluoro-4-[(7-methoxy-1,5-naphthyridin-4-yl)oxy]phenyl]-1-(4-fluoro-2-methylphenyl)-6-methyl-2-oxopyridine-3-carboxamide (220): Compound NA-1 was replaced with Compound NA1-3. Compound PA1-2 was replaced with Compound HA1-2. MS for $C_{29}H_{22}F_2N_4O_4$: m/z 529.2 (MH+).

N-[4-[(6,7-Dimethoxy-1,5-naphthyridin-4-yl)oxy]phenyl]-5-(4-fluorophenyl)-6-(hydroxymethyl)-1-methyl-4-oxopyridine-3-carboxamide (221): Compound NA-1 was replaced with Compound NA1-2. Compound PA1-2 was replaced with Compound PA7-4. MS for $C_{30}H_{25}FN_4O_6$: m/z 557.2 (MH+).

N-[3-Fluoro-4-[(7-methoxy-1,5-naphthyridin-4-yl)oxy]phenyl]-5-(4-fluorophenyl)-6-(hydroxymethyl)-1-methyl-4-oxopyridine-3-carboxamide (222): Compound NA-1 was replaced with Compound NA1-3. Compound PA1-2 was replaced with Compound PA7-4. MS for $C_{29}H_{22}F_2N_4O_5$: m/z 545.2 (MH+).

5-(4-Fluorophenyl)-6-(hydroxymethyl)-N-[4-[(7-methoxy-1,5-naphthyridin-4-yl)oxy]phenyl]-1-methyl-4-oxopyridine-3-carboxamide (223): Compound NA-1 was replaced with Compound NA1-6. Compound PA1-2 was replaced with Compound PA7-4. MS for $C_{29}H_{23}FN_4O_5$: m/z 527.2 (MH+).

N-[3-Fluoro-4-[(6-methoxy-1,5-naphthyridin-4-yl)oxy]phenyl]-5-(4-fluorophenyl)-6-(hydroxymethyl)-1-methyl-4-oxopyridine-3-carboxamide (224): Compound NA1-1 was replaced with Compound NA1-10. Compound PA1-2 was replaced with Compound PA7-4. MS for $C_{29}H_{22}F_2N_4O_5$: m/z 545.2 (MH+).

N-[4-[(6,7-Dimethoxy-1,5-naphthyridin-4-yl)oxy]phenyl]-1-(4-fluoro-2-methylphenyl)-6-methyl-2-oxopyridine-3-carboxamide (225): Compound NA1-1 was replaced with Compound NA-2. Compound PA1-2 was replaced with Compound HA-2. MS for $C_{30}H_{25}FN_4O_5$: m/z 541.2 (MH+).

1-(4-Fluoro-2-methylphenyl)-N-[4-[(7-methoxy-1,5-naphthyridin-4-yl)oxy]phenyl]-6-methyl-2-oxopyridine-3-carboxamide (226): Compound NA1-1 was replaced with Compound NA1-6. Compound PA1-2 was replaced with Compound HA-2. MS for $C_{29}H_{23}FN_4O_4$: m/z 511 (MH+).

N-[3-Fluoro-4-[[7-methoxy-6-(2-methoxyethoxy)-1,5-naphthyridin-4-yl]oxy]phenyl]-1-(4-fluorophenyl)-6-methyl-2-oxopyridine-3-carboxamide (227): Compound NA1-1 was replaced with Compound NA1-16. Compound PA1-2 was replaced with Compound HA-1. MS for $C_{30}H_{26}F_2N_4O_6$: m/z 589.2 (MH+).

N-[3-Fluoro-4-[[7-methoxy-6-(2-methoxyethoxy)-1,5-naphthyridin-4-yl]oxy]phenyl]-5-(4-fluorophenyl)-6-(hydroxymethyl)-1-methyl-4-oxopyridine-3-carboxamide (228): Compound NA1-1 was replaced with Compound NA1-16. Compound PA1-2 was replaced with Compound PA7-4. $^1$H NMR (400 MHz, DMSO-d$_6$) δ 13.04 (s, 1H), 8.81 (s, 1H), 8.56 (d, 1H), 8.01 (d, 1H), 7.66 (s, 1H), 7.42 (d, 1H), 7.34-7.26 (m, 5H), 6.86 (m, 1H), 5.65 (s, 1H), 4.48-4.44 (m, 2H), 4.32 (s, 2H), 4.05 (s, 3H), 3.98 (s, 3H), 3.65 (s, 2H), 3.30-3.25 (m, 3H); MS for $C_{32}H_{28}F_2N_4O_7$: m/z 619.2 (MH+).

N-[4-[(6,7-Dimethoxy-1,5-naphthyridin-4-yl)oxy]phenyl]-1-(4-fluorophenyl)-6-methyl-2-oxopyridine-3-carboxamide (229): Compound NA1-1 was replaced with Compound NA1-2. Compound PA1-2 was replaced with Compound HA-1. MS for $C_{29}H_{23}FN_4O_5$: m/z 527.2 (MH+).

N-[3-Fluoro-4-[(6-methoxy-1,5-naphthyridin-4-yl)oxy]phenyl]-5-(4-fluoro-2-methylphenyl)-6-methyl-4-oxo-1H-pyridazine-3-carboxamide (230): Compound NA1-1 was replaced with Compound NA1-10. Compound PA1-2 was replaced with Compound HA2-2. MS for $C_{28}H_{21}F_2N_5O_4$: m/z 530 (MH+).

N-[3-Fluoro-4-[(6-methoxy-1,5-naphthyridin-4-yl)oxy]phenyl]-5-(4-fluorophenyl)-4-hydroxy-6-(hydroxymethyl)pyridine-3-carboxamide (231): Compound NA1-1 was replaced with Compound NA1-10. Compound PA1-2 was replaced with Compound PA7-3a with subsequent hydrolysis of the acetyl group to give the hydroxyl using standard methods such as stirring in the presence of LiOH in a mixture of water and THF at room temperature. $^1$H NMR (400 MHz, DMSO-d$_6$) δ 13.22 (s, 1H), 8.62 (d, 1H), 8.58 (s, 1H), 8.29 (d, 1H), 8.03 (d, 1H), 7.43 (d, 1H), 7.31 (tt, 7H), 6.97 (d, 1H), 6.07 (s, 1H), 4.34 (s, 2H), 3.94 (s, 3H); MS for $C_{28}H_{20}F_2N_4O_5$: m/z 531 (MH+).

N-[3-Fluoro-4-[(6-methoxy-1,5-naphthyridin-4-yl)oxy]phenyl]-1-(4-fluorophenyl)-2-methyl-6-oxopyrimidine-5-carboxamide (232): Compound NA1-1 was replaced with Compound NA1-10. Compound PA1-2 was replaced with Compound HA4-2. $^1$H NMR (400 MHz, CDCl$_3$) δ 11.17 (s, 1H), 9.08 (d, 1H), 8.60 (dd, 1H), 8.22 (dd, 1H), 7.92 (dt, 1H), 7.41-7.25 (m, 5H), 7.23-7.13 (m, 2H), 6.86 (d, 1H), 4.03 (d, 3H), 2.37 (d, 3H); MS for $C_{27}H_{19}F_2N_5O_4$: m/z 516 (MH+).

N-[3-Fluoro-4-[(6-methoxy-1,5-naphthyridin-4-yl)oxy]phenyl]-1-(4-fluorophenyl)-2,4-dimethyl-6-oxopyrimidine-5-carboxamide (233): Compound NA1-1 was replaced with Compound NA1-10. Compound PA1-2 was replaced with Compound HA4-6. MS for $C_{28}H_{21}F_2N_5O_4$: m/z 530 (MH+).

N-[3-Fluoro-4-[(6-methoxy-1,5-naphthyridin-4-yl)oxy]phenyl]-1-(4-fluorophenyl)-4-methyl-6-oxopyrimidine-5-carboxamide (234): Compound NA1-1 was replaced with Compound NA1-10. Compound PA1-2 was replaced with Compound HA4-3. MS for $C_{27}H_{19}F_2N_5O_4$: m/z 516 (MH+).

N-[4-[(6,7-Dimethoxy-1,5-naphthyridin-4-yl)oxy]phenyl]-5-(4-fluorophenyl)-4-hydroxy-2-methylpyridine-3-carboxamide (235): Compound NA1-1 was replaced with Compound NA1-2. Compound PA1-2 was replaced with Compound PA7-12. MS for $C_{29}H_{23}FN_4O_5$: m/z 527 (MH+).

5-(4-Fluorophenyl)-4-hydroxy-N-[4-[(7-methoxy-1,5-naphthyridin-4-yl)oxy]phenyl]-2-methylpyridine-3-carboxamide (236): Compound NA1-1 was replaced with Compound NA1-6. Compound PA1-2 was replaced with Compound PA7-12. MS for $C_{28}H_{21}FN_4O_4$: m/z 497 (MH+).

N-[4-[(6,7-Dimethoxy-1,5-naphthyridin-4-yl)oxy]-3-fluorophenyl]-5-(4-fluorophenyl)-4-hydroxy-2-methylpyridine-3-carboxamide (237): Compound PA1-2 was replaced with Compound PA7-12. MS for $C_{29}H_{22}F_2N_4O_5$: m/z 545 (MH+).

N-[4-[(6,7-Dimethoxy-1,5-naphthyridin-4-yl)oxy]phenyl]-5-(4-fluorophenyl)-1,2-dimethyl-4-oxopyridine-3-carboxamide (238): Compound NA1-1 was replaced with Compound NA-2. Compound PA1-2 was replaced with Compound PA7-13. MS for $C_{30}H_{25}FN_4O_5$: m/z 541 (MH+).

N-[3-Fluoro-4-[(7-methoxy-1,5-naphthyridin-4-yl)oxy]phenyl]-5-(4-fluorophenyl)-1,2-dimethyl-4-oxopyridine-3-carboxamide (239): Compound NA1-1 was replaced with Compound NA1-3. Compound PA1-2 was replaced with Compound PA7-13. MS for $C_{29}H_{22}F_2N_4O_4$: m/z 529 (MH+).

1-Ethyl-N-[3-fluoro-4-[(7-methoxy-1,5-naphthyridin-4-yl)oxy]phenyl]-5-(4-fluorophenyl)-2-methyl-4-oxopyridine-3-carboxamide (240): Compound NA1-1 was replaced with Compound NA1-3. Compound PA1-2 was replaced with Compound PA7-14. MS for $C_{30}H_{24}F_2N_4O_4$: m/z 543 (MH+).

N-[3-Fluoro-4-[(7-methoxy-1,5-naphthyridin-4-yl)oxy]phenyl]-5-(4-fluorophenyl)-4-hydroxy-6-(trifluoromethyl)pyridine-3-carboxamide (241): Compound NA1-1 was replaced with Compound NA1-3. Compound PA1-2 was replaced with Compound PA7-11. MS for $C_{28}H_{17}F_5N_4O_4$: m/z 569 (MH+).

N-[3-Fluoro-4-[(6-methoxy-1,5-naphthyridin-4-yl)oxy]phenyl]-5-(4-fluorophenyl)-4-hydroxy-2-methylpyridine-3-carboxamide (242): Compound NA1-1 was replaced with Compound NA1-10. Compound PA1-2 was replaced with Compound PA7-12. MS for $C_{28}H_{20}F_2N_4O_4$: m/z 515.2 (MH+).

N-[3-Fluoro-4-[(6-methoxy-1,5-naphthyridin-4-yl)oxy]phenyl]-5-(4-fluorophenyl)-1,2-dimethyl-4-oxopyridine-3-carboxamide (243): Compound NA1-1 was replaced with Compound NA1-10. Compound PA1-2 was replaced with Compound PA7-13. MS for $C_{29}H_{22}F_2N_4O_4$: m/z 529.2 (MH+).

N-[4-[(6,7-Dimethoxy-1,5-naphthyridin-4-yl)oxy]phenyl]-1-ethyl-5-(4-fluorophenyl)-2-methyl-4-oxopyridine-3-carboxamide (244): Compound NA1-1 was replaced with Compound NA-2. Compound PA1-2 was replaced with Compound PA7-14. $^1$H NMR (400 MHz, DMSO-d$_6$) δ 10.69 (s, 1H), 8.44 (d, 1H), 8.01 (s, 1H), 7.79-7.66 (m, 4H), 7.57 (s, 1H), 7.25-7.05 (m, 4H), 6.67 (d, 1H), 4.04 (q, 2H), 3.91 (s, 3H), 3.90 (s, 3H), 3.25 (s, 4H), 1.29 (t, 3H); MS for $C_{31}H_{27}FN_4O_5$: m/z 555.2 (MH+).

5-(4-Fluorophenyl)-N-[4-[(7-methoxy-1,5-naphthyridin-4-yl)oxy]phenyl]-6-methyl-4-oxo-1H-pyridazine-3-carboxamide (245): Compound NA1-1 was replaced with Compound NA1-6. Compound PA1-2 was replaced with Compound HA2-1. MS for $C_{27}H_{20}FN_5O_4$: m/z 498 (MH+).

N-[3-Fluoro-4-[(7-methoxy-1,5-naphthyridin-4-yl)oxy]phenyl]-5-(4-fluorophenyl)-6-methyl-4-oxo-1H-pyridazine-3-carboxamide (246): Compound NA1-1 was replaced with Compound NA1-3. Compound PA1-2 was replaced with Compound HA2-1. $^1$H NMR (400 MHz, DMSO-d$_6$) δ 14.16 (s, 1H), 12.74 (s, 1H), 8.95-8.63 (m, 2H), 8.05 (d, 1H), 7.81 (s, 1H), 7.63-7.22 (m, 6H), 6.78 (d, 1H), 4.02 (s, 3H), 2.29 (s, 3H); MS for $C_{27}H_9F_2N_5O_4$: m/z 516 (MH+).

N-[4-[(6,7-Dimethoxy-1,5-naphthyridin-4-yl)oxy]phenyl]-5-(4-fluoro-2-methylphenyl)-6-methyl-4-oxo-1H-pyridazine-3-carboxamide (247): Compound NA1-1 was replaced with Compound NA1-2. Compound PA1-2 was replaced with Compound HA2-2. MS for $C_{29}H_{24}FN_5O_5$: m/z 542 (MH+).

5-(4-Fluoro-2-methylphenyl)-N-[4-[(7-methoxy-1,5-naphthyridin-4-yl)oxy]phenyl]-6-methyl-4-oxo-1H-pyridazine-3-carboxamide (248): Compound NA1-1 was replaced with Compound NA1-6. Compound PA1-2 was replaced with Compound HA2-2. MS for $C_{28}H_{22}FN_5O_4$: m/z 512 (MH+).

N-[3-Fluoro-4-[(7-methoxy-1,5-naphthyridin-4-yl)oxy]phenyl]-5-(4-fluoro-2-methylphenyl)-6-methyl-4-oxo-1H-pyridazine-3-carboxamide, racemate (249A): Compound NA1-1 was replaced with Compound NA1-3. Compound PA1-2 was replaced with Compound HA2-2. MS for $C_{28}H_{21}F_2N_5O_4$: m/z 530 (MH+).

The following two atropisomers were recovered from the chiral SFC separation of Compound 249A. Absolute stereochemistry was not determined:

N-[3-Fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropisomer 1 (249B): MS for $C_{28}H_{21}F_2N_5O_4$: m/z 530.1 (MH+). Analytical chiral SFC (Chiralcel OJ-3, 100×4.6 mm, 3 m; Mobile phase: A=CO$_2$, B=EtOH (0.05% DEA), Gradient 5-40% B in 4 min and hold at 40% for 2.5 min, flow rate=2.8 mL/min) retention time=3.375 min.

N-[3-Fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropisomer 2 (249C): MS for $C_{28}H_{21}F_2N_5O_4$: m/z 530.1 (MH+). Analytical chiral SFC (Chiralcel OJ-3, 100×4.6 mm, 3 m; Mobile phase: A=CO$_2$, B=EtOH (0.05% DEA), Gradient 5-40% B in 4 min and hold at 40% for 2.5 min, flow rate=2.8 mL/min) retention time=4.303 min.

N-[3-Fluoro-4-[(7-methoxy-1,5-naphthyridin-4-yl)oxy]phenyl]-5-(4-fluorophenyl)-1,6-dimethyl-4-oxopyridazine-3-carboxamide (250): Compound NA1-1 was replaced with Compound NA1-3. Compound PA1-2 was replaced with Compound HA2-3. MS for $C_{28}H_{21}F_2N_5O_4$: m/z 530 (MH+).

5-(4-Fluorophenyl)-N-[4-[(7-methoxy-1,5-naphthyridin-4-yl)oxy]phenyl]-1,6-dimethyl-4-oxopyridazine-3-carboxamide (251): Compound NA1-1 was replaced with Compound NA1-6. Compound PA1-2 was replaced with Compound HA2-3. MS for $C_{28}H_{22}FN_5O_4$: m/z 512 (MH+).

N-[3-Fluoro-4-[[7-methoxy-6-(2-methoxyethoxy)-1,5-naphthyridin-4-yl]oxy]phenyl]-5-(4-fluoro-2-methylphenyl)-6-methyl-4-oxo-1H-pyridazine-3-carboxamide (252): Compound NA1-1 was replaced with Compound NA1-16. Compound PA1-2 was replaced with Compound HA2-2. MS for $C_{31}H_{27}F_2N_5O_6$: m/z 604 (MH+).

N-[4-[(6,7-Dimethoxy-1,5-naphthyridin-4-yl)oxy]phenyl]-5-(4-fluorophenyl)-6-methyl-4-oxo-1H-pyridazine-3-carboxamide (253): Compound NA1-1 was replaced with Compound NA1-2. Compound PA1-2 was replaced with Compound HA2-1. MS for $C_{28}H_{22}FN_5O_5$: m/z 528 (MH+).

N-[4-[(6,7-Dimethoxy-1,5-naphthyridin-4-yl)oxy]-3-fluorophenyl]-1-(4-fluorophenyl)-6-methyl-2-oxopyridine-3-carboxamide (254): Compound PA1-2 was replaced with Compound HA1-1. $^1$H NMR (400 MHz, DMSO-d$_6$) δ 12.04 (s, 1H), 8.54 (d, 1H), 8.49 (d, 1H), 7.99 (d, 1H), 7.64 (s, 1H), 7.46 (m, 5H), 7.30 (m, 1H), 6.81 (d, 1H), 6.72 (d, 1H), 3.95 (s, 3H), 3.92 (s, 3H), 2.08 (s, 3H); MS for $C_{29}H_{22}F_2N_4O_5$: m/z 545 (MH+).

1-(4-Fluorophenyl)-N-[4-[(7-methoxy-1,5-naphthyridin-4-yl)oxy]phenyl]-4-methyl-6-oxopyrimidine-5-carboxamide (255): Compound NA1-1 was replaced with Compound NA1-6. Compound PA1-2 was replaced with Compound HA4-3. MS for $C_{27}H_{20}FN_5O_4$: m/z 498 (MH+).

N-[3-Fluoro-4-[(7-methoxy-1,5-naphthyridin-4-yl)oxy]phenyl]-1-(4-fluorophenyl)-4-methyl-6-oxopyrimidine-5-carboxamide (256): Compound NA1-1 was replaced with Compound NA1-3. Compound PA1-2 was replaced with Compound HA4-3. $^1$H NMR (400 MHz, DMSO-d$_6$) δ 10.87 (s, 1H), 8.74 (d, 1H), 8.72-8.65 (m, 1H), 8.52 (s, 1H), 7.94 (dd, 1H), 7.79 (d, 1H), 7.58 (dd, 2H), 7.53-7.35 (m, 4H), 6.76 (d, 1H), 4.00 (s, 3H), 2.38 (s, 3H); MS for $C_{27}H_9F_2N_5O_4$: m/z 516 (MH+).

N-[3-Fluoro-4-[(7-methoxy-1,5-naphthyridin-4-yl)oxy]phenyl]-1-(4-fluorophenyl)-2,4-dimethyl-6-oxopyrimidine-5-carboxamide (257): Compound NA1-1 was replaced with Compound NA1-3. Compound PA1-2 was replaced with Compound HA4-6. MS for $C_{28}H_{20}F_2N_5O_4$: m/z 530 (MH+).

1-(4-Fluorophenyl)-N-[4-[(7-methoxy-1,5-naphthyridin-4-yl)oxy]phenyl]-2,4-dimethyl-6-oxopyrimidine-5-carboxamide (258): Compound NA1-1 was replaced with Compound NA1-6. Compound PA1-2 was replaced with Compound HA4-6. MS for $C_{28}H_{22}FN_5O_4$: m/z 512 (MH+).

N-[4-(6,7-Dimethoxyquinolin-4-yl)oxy-3-fluorophenyl]-5-(4-fluorophenyl)-6-methyl-4-oxo-1-(2,2,2-trifluoroethyl)pyridine-3-carboxamide (259): Compound NA1-1 was replaced with Compound QA1-1. Compound PA1-2 was replaced with Compound PA7-6. MS for $C_{32}H_{24}F_5N_3O_5$: m/z 626 (MH+).

N-[4-(6,7-Dimethoxyquinolin-4-yl)oxyphenyl]-5-(4-fluorophenyl)-6-methyl-4-oxo-1-(2,2,2-trifluoroethyl)pyridine-3-carboxamide (260): Compound NA1-1 was replaced with Compound QA1-2. Compound PA1-2 was replaced with Compound PA7-6. MS for $C_{32}H_{25}F_4N_3O_5$: m/z 608 (MH+).

N-[3-Fluoro-4-[(7-methoxy-1,5-naphthyridin-4-yl)oxy]phenyl]-5-(4-fluorophenyl)-6-methyl-4-oxo-1-(2,2,2-trifluoroethyl)pyridine-3-carboxamide (261): Compound NA1-1 was replaced with Compound NA1-3. Compound PA1-2 was replaced with Compound PA7-6. MS for $C_{30}H_{21}F_5N_4O_4$: m/z 597 (MH+).

N-[4-[(6,7-Dimethoxy-1,5-naphthyridin-4-yl)oxy]phenyl]-4-(4-fluorophenyl)-5-methyl-3-oxopyrazine-2-carboxamide (262): Compound NA1-1 was replaced with Compound NA1-2. Compound PA1-2 was replaced with Compound HA3-1. $^1$H NMR (400 MHz, DMSO-d$_6$) δ 11.38 (s, 1H), 8.54 (d, 1H), 7.81 (d, 2H), 7.74 (s, 1H), 7.64 (s, 1H), 7.56-7.44 (m, 4H), 7.20 (d, 2H), 6.80 (d, 1H), 3.98-3.95 (m, 3H), 3.93 (s, 3H), 2.04 (s, 3H); MS for $C_{28}H_{22}FN_5O_5$: m/z 528.1 (MH+).

4-(4-Fluorophenyl)-N-[4-[(7-methoxy-1,5-naphthyridin-4-yl)oxy]phenyl]-5-methyl-3-oxopyrazine-2-carboxamide (263): Compound NA1-1 was replaced with Compound NA1-6. Compound PA1-2 was replaced with Compound HA3-1. MS for $C_{27}H_{20}FN_5O_4$: m/z 498.2 (MH+).

N-[3-Fluoro-4-[(6-methoxy-1,5-naphthyridin-4-yl)oxy]phenyl]-4-(4-fluorophenyl)-5-methyl-3-oxopyrazine-2-carboxamide (264): Compound NA1-1 was replaced with Compound NA1-10. Compound PA1-2 was replaced with Compound HA3-1. MS for $C_{27}H_9F_2N_5O_4$: m/z 516.1 (MH+).

N-[3-Fluoro-4-[(7-methoxy-1,5-naphthyridin-4-yl)oxy]phenyl]-1-(4-fluorophenyl)-2-methyl-6-oxopyrimidine-5-carboxamide (265): Compound NA1-1 was replaced with Compound NA1-3. Compound PA1-2 was replaced with Compound HA4-2. $^1$H NMR (400 MHz, DMSO-d$_6$) δ 11.29 (s, 1H), 8.84 (s, 1H), 8.74 (d, 1H), 8.70 (d, 1H), 8.03 (dd, 1H), 7.80 (d, 1H), 7.61 (dd, 2H), 7.55 (br d, 1H), 7.48 (t, 2H), 7.41 (t, 1H), 6.74 (d, 1H), 4.00 (s, 3H), 2.23 (s, 3H); MS for $C_{27}H_{19}F_2N_5O_4$: m/z 516.1 (MH+).

1-(4-Fluorophenyl)-N-[4-[(7-methoxy-1,5-naphthyridin-4-yl)oxy]phenyl]-2-methyl-6-oxopyrimidine-5-carboxamide (266): Compound NA1-1 was replaced with Compound NA1-6. Compound PA1-2 was replaced with Compound HA4-2. MS for $C_{27}H_{20}FN_5O_4$: m/z 498.1 (MH+).

N-[4-[(6,7-Dimethoxy-1,5-naphthyridin-4-yl)oxy]phenyl]-1-(4-fluorophenyl)-2-methyl-6-oxopyrimidine-5-carboxamide (267): Compound NA1-1 was replaced with Compound NA-2. Compound PA1-2 was replaced with Compound HA4-2. $^1$H NMR (400 MHz, CD$_3$OD) δ 8.92 (s, 1H), 8.80 (d, 1H), 7.70-7.58 (m, 7H), 7.41 (d, 1H), 7.11 (t, 2H), 4.15 (d, 6H), 2.41 (s, 3H); MS for $C_{28}H_{22}FN_5O_5$: m/z 528.2 (MH+).

N-[4-[(6,7-Dimethoxy-1,5-naphthyridin-4-yl)oxy]-3-fluorophenyl]-5-(4-fluorophenyl)-6-(methoxymethyl)-1-methyl-4-oxopyridine-3-carboxamide (269): Compound PA1-2 was replaced with Compound PA7-26. MS for $C_{31}H_{26}F_2N_4O_6$: m/z 589.2 (MH+).

N-[3-Fluoro-4-[(7-methoxy-1,5-naphthyridin-4-yl)oxy]phenyl]-5-(4-fluorophenyl)-6-(methoxymethyl)-1-methyl-4-oxopyridine-3-carboxamide (270): Compound NA1-1 was replaced with Compound PA7-26. MS for $C_{30}H_{24}F_2N_4O_5$: m/z 559.2 (MH+).

N-[4-[(6,7-Dimethoxy-1,5-naphthyridin-4-yl)oxy]-3-fluorophenyl]-1-ethyl-5-(4-fluorophenyl)-6-(hydroxymethyl)-4-oxopyridine-3-carboxamide (271): Compound PA1-2 was replaced with Compound PA7-28. $^1$H NMR (400 MHz, DMSO-d$_6$) δ 13.03 (s, 1H), 8.82 (s, 1H), 8.55 (d, 1H), 8.02 (dd, 1H), 7.66 (s, 1H), 7.47-7.40 (m, 1H), 7.37-7.24 (m, 5H), 6.83 (d, 1H), 5.70 (t, 1H), 4.41 (q, 2H), 4.32 (d, 2H), 3.98 (s, 3H), 3.95 (s, 3H), 1.47 (t, 3H); MS for $C_{31}H_{26}F_2N_4O_6$: m/z 589.2 (MH+).

N-[4-[(6,7-Dimethoxy-1,5-naphthyridin-4-yl)oxy]phenyl]-1-ethyl-5-(4-fluorophenyl)-6-(hydroxymethyl)-4-oxopyridine-3-carboxamide (272): Compound NA1-1 was replaced with Compound NA1-2. Compound PA1-2 was replaced with Compound PA7-28. MS for $C_{31}H_{27}FN_4O_6$: m/z 571.2 (MH+).

1-Ethyl-N-[3-fluoro-4-[(7-methoxy-1,5-naphthyridin-4-yl)oxy]phenyl]-5-(4-fluorophenyl)-6-(hydroxymethyl)-4-oxopyridine-3-carboxamide (273): Compound NA1-1 was replaced with Compound NA1-3. Compound PA1-2 was replaced with Compound PA7-28. MS for $C_{30}H_{24}F_2N_4O_5$: m/z 559.2 (MH+).

1-Ethyl-5-(4-fluorophenyl)-6-(hydroxymethyl)-N-[4-[(7-methoxy-1,5-naphthyridin-4-yl)oxy]phenyl]-4-oxopyridine-3-carboxamide (274): Compound NA1-1 was replaced with Compound NA1-6. Compound PA1-2 was replaced with Compound PA7-28. $^1$H NMR (400 MHz, DMSO-d$_6$) δ 12.90 (s, 1H), 8.81 (s, 1H), 8.74 (d, 1H), 8.70 (d, 1H), 7.83 (d, 2H), 7.79 (d, 1H), 7.38-7.22 (m, 6H), 6.75 (d, 1H), 5.69 (t, 1H), 4.41 (d, 2H), 4.32 (d, 2H), 4.01 (s, 3H), 1.47 (t, 3H); MS for $C_{30}H_{25}FN_4O_5$: m/z 541.2 (MH+).

1-(4-Fluorophenyl)-N-[3-fluoro-4-[(7-phenylmethoxy-1,5-naphthyridin-4-yl)oxy]phenyl]-6-methyl-2-oxopyridine-3-carboxamide (275): Compound NA1-1 was replaced with Compound NA1-39. Compound PA1-2 was replaced with Compound HA-1. MS for $C_{34}H_{24}F_2N_4O_4$: m/z 591.2 (MH+).

1-(4-Fluoro-2-methylphenyl)-N-[4-[(6-methoxy-1,5-naphthyridin-4-yl)oxy]phenyl]-6-methyl-2-oxopyridine-3-carboxamide (276): Compound NA1-1 was replaced with Compound NA1-17. Compound PA1-2 was replaced with Compound HA1-2. MS for $C_{29}H_{23}FN_4O_4$: m/z 511.2 (MH+).

5-(4-Fluorophenyl)-N-[3-fluoro-4-[(7-phenylmethoxy-1,5-naphthyridin-4-yl)oxy]phenyl]-4-hydroxy-2,6-dimethylpyridine-3-carboxamide (277): Compound NA1-1 was replaced with Compound NA1-39. Compound PA1-2 was replaced with Compound PA5-2. MS for $C_{35}H_{26}F_2N_4O_4$: m/z 605.2 (MH+).

1-(4-Fluorophenyl)-N-[3-fluoro-4-[(7-phenylmethoxy-1,5-naphthyridin-4-yl)oxy]phenyl]-2,4-dimethyl-6-oxopyrimidine-5-carboxamide (278): Compound NA1-1 was replaced with Compound NA1-39. Compound PA1-2 was replaced with Compound HA4-6. MS for $C_{34}H_{25}F_2N_5O_4$: m/z 606.2 (MH+).

N-[4-[(6,7-Dimethoxy-1,5-naphthyridin-4-yl)oxy]-3-fluorophenyl]-1-(4-fluorophenyl)-4,6-dimethyl-2-oxopyridine-3-carboxamide (279): Compound PA1-2 was replaced with Compound HA1-5. MS for $C_{30}H_{24}F_2N_4O_5$: m/z 559.2 (MH+).

N-[3-Fluoro-4-[(7-methoxy-1,5-naphthyridin-4-yl)oxy]phenyl]-1-(4-fluorophenyl)-4,6-dimethyl-2-oxopyridine-3-carboxamide (280): Compound NA1-1 was replaced with Compound NA1-3. Compound PA1-2 was replaced with Compound HA1-5. MS for $C_{29}H_{22}F_2N_4O_4$: m/z 529.2 (MH+).

N-[3-Fluoro-4-[(6-methoxy-1,5-naphthyridin-4-yl)oxy]phenyl]-1-(4-fluorophenyl)-4,6-dimethyl-2-oxopyridine-3-carboxamide (281): Compound NA1-1 was replaced with Compound NA1-10. Compound PA1-2 was replaced with Compound HA1-5. MS for $C_{29}H_{22}F_2N_4O_4$: m/z 529.2 (MH+).

N-[4-[(6,7-Dimethoxy-1,5-naphthyridin-4-yl)oxy]-3-fluorophenyl]-5-(4-fluoro-2-methylphenyl)-6-(hydroxymethyl)-1-methyl-4-oxopyridine-3-carboxamide (282): Compound PA1-2 was replaced with Compound PA7-30. MS for $C_{31}H_{26}F_2N_4O_6$: m/z 589.2 (MH+).

N-[4-[(6,7-Dimethoxy-1,5-naphthyridin-4-yl)oxy]-3-fluorophenyl]-1-ethyl-5-(4-fluoro-2-methylphenyl)-6-(hydroxymethyl)-4-oxopyridine-3-carboxamide (283): Compound PA1-2 was replaced with Compound PA7-36. $^1$H NMR (400 MHz, DMSO-$d_6$) δ 13.05 (s, 1H), 8.83 (s, 1H), 8.56 (d, 1H), 8.02 (d, 1H), 7.66 (d, 1H), 7.44 (d, 1H), 7.33 (t, 1H), 7.18 (d, 1H), 7.14-7.06 (m, 2H), 6.84 (s, 1H), 5.62 (s, 1H), 4.41 (d, 2H), 4.31 (d, 1H), 4.17 (d, 1H), 3.98 (s, 3H), 3.95 (s, 3H), 2.06 (s, 3H), 1.47 (t, 3H); MS for $C_{32}H_{28}F_2N_4O_6$: m/z 603.2 (MH+).

N-[4-[(6,7-Dimethoxy-1,5-naphthyridin-4-yl)oxy]phenyl]-1-ethyl-5-(4-fluoro-2-methylphenyl)-6-(hydroxymethyl)-4-oxopyridine-3-carboxamide (284): Compound NA1-1 was replaced with Compound NA1-2. Compound PA1-2 was replaced with Compound PA7-36. MS for $C_{32}H_{29}FN_4O_6$: m/z 585.2 (MH+).

1-Ethyl-N-[3-fluoro-4-[(7-methoxy-1,5-naphthyridin-4-yl)oxy]phenyl]-5-(4-fluoro-2-methylphenyl)-6-(hydroxymethyl)-4-oxopyridine-3-carboxamide (285): Compound NA1-1 was replaced with Compound NA1-3. Compound PA1-2 was replaced with Compound PA7-36. MS for $C_{31}H_{26}F_2N_4O_5$: m/z 573.2 (MH+).

N-[4-[(6,7-Dimethoxy-1,5-naphthyridin-4-yl)oxy]-3-fluorophenyl]-1-(4-fluorophenyl)-4-methyl-2-oxopyridine-3-carboxamide (286): Compound PA1-2 was replaced with Compound HA1-16. MS for $C_{29}H_{22}F_2N_4O_5$: m/z 545.2 (MH+).

N-[3-Fluoro-4-[(6-methoxy-1,5-naphthyridin-4-yl)oxy]phenyl]-1-(4-fluorophenyl)-4-methyl-2-oxopyridine-3-carboxamide (287): Compound NA1-1 was replaced with Compound NA1-10. Compound PA1-2 was replaced with Compound HA1-16. $^1$H NMR (400 MHz, DMSO-$d_6$) δ 10.88 (s, 1H), 8.61 (dd, 1H), 8.30 (dd, 1H), 7.96 (d, 1H), 7.75 (d, 1H), 7.56-7.30 (m, 7H), 6.95 (d, 1H), 6.39 (d, 1H), 3.97 (d, 3H), 2.32 (d, 3H); MS for $C_{28}H_{20}F_2N_4O_4$: m/z 515 (MH+).

N-[4-[(6,7-Dimethoxy-1,5-naphthyridin-4-yl)oxy]phenyl]-1-(4-fluorophenyl)-4,6-dimethyl-2-oxopyridine-3-carboxamide (288): Compound NA1-1 was replaced with Compound NA-2. Compound PA1-2 was replaced with Compound HA-5. MS for $C_{30}H_{25}FN_4O_5$: m/z 541.2 (MH+).

1-(4-Fluorophenyl)-N-[4-[(7-methoxy-1,5-naphthyridin-4-yl)oxy]phenyl]-4,6-dimethyl-2-oxopyridine-3-carboxamide (289): Compound NA1-1 was replaced with Compound NA1-6. Compound PA1-2 was replaced with Compound HA-5. MS for $C_{29}H_{23}FN_4O_4$: m/z 511.2 (MH+).

1-(4-Fluorophenyl)-N-[4-[(6-methoxy-1,5-naphthyridin-4-yl)oxy]phenyl]-4,6-dimethyl-2-oxopyridine-3-carboxamide (290): Compound NA1-1 was replaced with Compound NA1-17. Compound PA1-2 was replaced with Compound HA1-5. $^1$H NMR (400 MHz, DMSO-$d_6$) δ 10.99 (s, 1H), 8.59 (dd, 1H), 8.28 (dd, 1H), 7.79 (dd, 2H), 7.45-7.34 (m, 4H), 7.31 (dd, 1H), 7.25-7.17 (m, 2H), 6.90 (dd, 1H), 6.38 (s, 1H), 3.95 (d, 3H), 2.38 (d, 3H), 1.98 (s, 3H); MS for $C_{29}H_{23}FN_4O_4$: m/z 511.2 (MH+).

N-[3-Fluoro-4-[(7-methoxy-1,5-naphthyridin-4-yl)oxy]phenyl]-1-(4-fluorophenyl)-2-oxopyridine-3-carboxamide (291): Compound NA1-1 was replaced with Compound NA1-3. Compound PA1-2 was replaced with Compound HA1-19. $^1$H NMR (400 MHz, DMSO-$d_6$) δ 12.13 (s, 1H), 8.81-8.75 (m, 1H), 8.72 (d, 1H), 8.61 (d, 1H), 8.15 (d, 1H), 8.07 (d, 1H), 7.84-7.78 (m, 1H), 7.67-7.59 (m, 2H), 7.53 (d, 1H), 7.48-7.38 (m, 3H), 6.79-6.71 (m, 2H), 4.01 (s, 3H); MS for $C_{27}H_{18}F_2N_4O_4$: m/z 501.2 (MH+).

N-[3-Fluoro-4-[(6-methoxy-1,5-naphthyridin-4-yl)oxy]phenyl]-1-(4-fluorophenyl)-2-oxopyridine-3-carboxamide (292): Compound NA1-1 was replaced with Compound NA1-10. Compound PA1-2 was replaced with Compound HA1-19. $^1$H NMR (400 MHz, DMSO-$d_6$) δ 12.11 (s, 1H), 8.63 (d, 1H), 8.60 (d, 1H), 8.30 (d, 1H), 8.18-8.11 (m, 1H), 8.04 (d, 1H), 7.62 (dd, 2H), 7.54-7.29 (m, 5H), 6.99 (d, 1H), 6.75 (dd, 1H), 3.93 (s, 3H); MS for $C_{27}H_{18}F_2N_4O_4$: m/z 501.2 (MH+).

N-[4-[(6,7-Dimethoxy-1,5-naphthyridin-4-yl)oxy]-3-fluorophenyl]-1-(4-fluorophenyl)-2-oxopyridine-3-carboxamide (293): Compound PA1-2 was replaced with Compound HA1-19. $^1$H NMR (400 MHz, DMSO-$d_6$) δ 12.10 (s, 1H), 8.64-8.58 (m, 1H), 8.56 (d, 1H), 8.14 (dd, 1H), 8.03 (d, 1H), 7.68-7.58 (m, 3H), 7.45 (q, 3H), 7.33 (t, 1H), 6.85 (d, 1H), 6.74 (s, 1H), 3.98 (s, 3H), 3.94 (s, 3H); MS for $C_{28}H_{20}F_2N_4O_5$: m/z 531.2 (MH+).

N-[3-Fluoro-4-[(7-methoxy-1,5-naphthyridin-4-yl)oxy]phenyl]-1-(4-fluorophenyl)-4-methyl-2-oxopyridine-3-carboxamide (294): Compound NA1-1 was replaced with Compound NA-3. Compound PA1-2 was replaced with Compound HA1-16. MS for $C_{28}H_{20}F_2N_4O_4$: m/z 515.2 (MH+).

N-[3-Fluoro-4-(1,5-naphthyridin-4-yloxy)phenyl]-1-(4-fluorophenyl)-4,6-dimethyl-2-oxopyridine-3-carboxamide (295): Compound NA1-1 was replaced with Compound NA1-21. Compound PA1-2 was replaced with Compound HA1-5. $^1$H NMR (400 MHz, DMSO-$d_6$) δ 11.22 (s, 1H), 9.03 (dd, 1H), 8.79 (dd, 1H), 8.46 (dd, 1H), 8.00 (d, 1H), 7.88 (dd, 1H), 7.51 (d, 1H), 7.46-7.35 (m, 5H), 6.92 (d, 1H), 6.40 (s, 1H), 2.39 (d, 3H), 1.99 (s, 3H); MS for $C_{28}H_{20}F_2N_4O_3$: m/z 499.2 (MH+).

N-[3-Fluoro-4-[(6-methoxy-1,5-naphthyridin-4-yl)oxy]phenyl]-1-(4-fluoro-2-methylphenyl)-4,6-dimethyl-2-oxopyridine-3-carboxamide (296): Compound NA1-1 was replaced with Compound NA1-10. Compound PA1-2 was replaced with Compound HA1-15. MS for $C_{30}H_{24}F_2N_4O_4$: m/z 543.2 (MH+).

N-[3-Fluoro-4-[(6-methyl-1,5-naphthyridin-4-yl)oxy]phenyl]-1-(4-fluorophenyl)-4,6-dimethyl-2-oxopyridine-3-carboxamide (297): Compound NA1-1 was replaced with Compound NA1-33. Compound PA1-2 was replaced with Compound HA1-5. MS for $C_{29}H_{22}F_2N_4O_3$: m/z 513.2 (MH+).

N-[4-[(6,7-Dimethoxy-1,5-naphthyridin-4-yl)oxy]-3-fluorophenyl]-1-(4-fluoro-2-methylphenyl)-4,6-dimethyl-2-oxopyridine-3-carboxamide (298): Compound PA1-2 was replaced with Compound HA1-15. $^1$H NMR (400 MHz, DMSO-$d_6$) δ 11.11 (s, 1H), 8.46 (d, 1H), 7.87 (d, 1H), 7.58 (s, 1H), 7.38 (d, 1H), 7.30-7.11 (m, 4H), 6.72 (d, 1H), 6.35 (s, 1H), 3.92-3.89 (m, 3H), 3.89 (s, 3H), 2.33 (s, 3H), 1.97 (s, 3H), 1.85 (s, 3H); MS for $C_{31}H_{26}F_2N_4O_5$: m/z 573.2 (MH+).

N-[4-[(6,7-Dimethoxy-1,5-naphthyridin-4-yl)oxy]phenyl]-1-(4-fluorophenyl)-4-methyl-2-oxopyridine-3-carboxamide (299): Compound NA1-1 was replaced with Compound NA1-2. Compound PA1-2 was replaced with Compound HA-16. MS for $C_{29}H_{23}FN_4O_5$: m/z 527.2 (MH+).

1-(4-Fluorophenyl)-N-[4-[(7-methoxy-1,5-naphthyridin-4-yl)oxy]phenyl]-4-methyl-2-oxopyridine-3-carboxamide (300): Compound NA1-1 was replaced with Compound NA1-6. Compound PA1-2 was replaced with Compound HA-16. MS for $C_{28}H_{21}FN_4O_4$: m/z 497.2 (MH+).

N-[4-[(6,7-Dimethoxy-1,5-naphthyridin-4-yl)oxy]-3-fluorophenyl]-5-(4-fluorophenyl)-4-hydroxy-6-(methoxymethyl)pyridine-3-carboxamide (301): Compound PA1-2 was replaced with Compound PA7-17. MS for $C_{30}H_{24}F_2N_4O_6$: m/z 575.2 (MH+).

N-[3-Fluoro-4-(1,5-naphthyridin-4-yloxy)phenyl]-1-(4-fluorophenyl)-6-methyl-2-oxopyridine-3-carboxamide (302): Compound NA1-1 was replaced with Compound NA1-21. Compound PA1-2 was replaced with Compound HA-1. MS for $C_{27}H_{18}F_2N_4O_3$: m/z 485.2 (MH+).

N-[3-Fluoro-4-(1,5-naphthyridin-4-yloxy)phenyl]-1-(4-fluorophenyl)-4-methyl-2-oxopyridine-3-carboxamide (303): Compound NA1-1 was replaced with Compound NA1-21. Compound PA1-2 was replaced with Compound HA1-16. MS for $C_{27}H_{11}F_2N_4O_3$: m/z 485.2 (MH+).

N-[3-Fluoro-4-(1,5-naphthyridin-4-yloxy)phenyl]-1-(4-fluorophenyl)-2-oxopyridine-3-carboxamide (304): Compound NA1-1 was replaced with Compound NA1-21. Compound PA1-2 was replaced with Compound HA1-19. MS for $C_{26}H_{16}F_2N_4O_3$: m/z 471.2 (MH+).

5-Bromo-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide (305): Compound PA1-2 was replaced with Compound HA-6. MS for $C_{30}H_{23}BrF_2N_4O_5$: m/z 639.2 (MH+).

N-[4-[(6,7-Dimethoxy-1,5-naphthyridin-4-yl)oxy]-3-fluorophenyl]-1-(4-fluorophenyl)-4,5,6-trimethyl-2-oxopyridine-3-carboxamide (306): Compound PA1-2 was replaced with Compound HA1-8. $^1$H NMR (400 MHz, DMSO-d$_6$) δ 10.70 (s, 1H), 8.52 (d, 1H), 7.92 (dd, 1H), 7.65 (s, 1H), 7.50-7.43 (m, 1H), 7.43-7.24 (m, 5H), 6.78 (d, 1H), 4.03-3.93 (m, 6H), 2.23 (s, 3H), 2.08 (s, 3H), 1.96 (s, 3H); MS for $C_{31}H_{26}F_2N_4O_5$: m/z 573.2 (MH+).

5-Chloro-N-[4-[(6,7-dimethoxy-1,5-naphthyridin-4-yl)oxy]phenyl]-1-(4-fluorophenyl)-4,6-dimethyl-2-oxopyridine-3-carboxamide (307): Compound NA1-1 was replaced with Compound NA1-2. Compound PA1-2 was replaced with Compound HA1-7. MS for $C_{30}H_{24}ClFN_4O_5$: m/z 575.2 (MH+).

5-Chloro-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide (308): Compound PA1-2 was replaced with Compound HA-7. MS for $C_{30}H_{23}ClF_2N_4O_5$: m/z 593.2 (MH+).

5-Chloro-N-[3-fluoro-4-[(7-methoxy-1,5-naphthyridin-4-yl)oxy]phenyl]-1-(4-fluorophenyl)-4,6-dimethyl-2-oxopyridine-3-carboxamide (309): Compound NA1-1 was replaced with Compound NA1-3. Compound PA1-2 was replaced with Compound HA1-7. MS for $C_{29}H_{21}ClF_2N_4O_4$: m/z 563.2 (MH+).

5-Chloro-1-(4-fluorophenyl)-N-[4-[(7-methoxy-1,5-naphthyridin-4-yl)oxy]phenyl]-4,6-dimethyl-2-oxopyridine-3-carboxamide (310): Compound NA1-1 was replaced with Compound NA1-6. Compound PA1-2 was replaced with Compound HA1-7. MS for $C_{29}H_{22}ClFN_4O_4$: m/z 545.2 (MH+).

N-[4-[(6,7-Dimethoxy-1,5-naphthyridin-4-yl)oxy]-3-fluorophenyl]-1-(4-fluoro-2-methylphenyl)-4-methyl-2-oxopyridine-3-carboxamide (311): Compound PA1-2 was replaced with Compound HA1-17. MS for $C_{30}H_{24}F_2N_4O_5$: m/z 559.2 (MH+).

5-Bromo-1-(4-fluorophenyl)-N-[4-[(7-methoxy-1,5-naphthyridin-4-yl)oxy]phenyl]-4,6-dimethyl-2-oxopyridine-3-carboxamide (312): Compound NA1-1 was replaced with Compound NA1-6. Compound PA1-2 was replaced with Compound HA1-6. MS for $C_{29}H_{22}BrFN_4O_4$: m/z 591 (MH+).

5-Bromo-N-[4-[(6,7-dimethoxy-1,5-naphthyridin-4-yl)oxy]phenyl]-1-(4-fluorophenyl)-4,6-dimethyl-2-oxopyridine-3-carboxamide (313): Compound NA1-1 was replaced with Compound NA1-2. Compound PA1-2 was replaced with Compound HA1-6. MS for $C_{30}H_{24}BrFN_4O_5$: m/z 621.2 (MH+).

5-Bromo-N-[3-fluoro-4-[(7-methoxy-1,5-naphthyridin-4-yl)oxy]phenyl]-1-(4-fluorophenyl)-4,6-dimethyl-2-oxopyridine-3-carboxamide (314): Compound NA1-1 was replaced with Compound NA1-3. Compound PA1-2 was replaced with Compound HA1-6. MS for $C_{29}H_{21}BrF_2N_4O_4$: m/z 609.2 (MH+).

N-[4-[(6,7-Dimethoxy-1,5-naphthyridin-4-yl)oxy]phenyl]-1-(4-fluorophenyl)-4,5,6-trimethyl-2-oxopyridine-3-carboxamide (315): Compound NA1-1 was replaced with Compound NA1-2. Compound PA1-2 was replaced with Compound HA1-8. MS for $C_{31}H_{27}FN_4O_5$: m/z 555 (MH+).

N-[3-Fluoro-4-[(7-methoxy-1,5-naphthyridin-4-yl)oxy]phenyl]-1-(4-fluorophenyl)-4,5,6-trimethyl-2-oxopyridine-3-carboxamide (316): Compound NA1-1 was replaced with Compound NA1-3. Compound PA1-2 was replaced with Compound HA1-8. $^1$H NMR (400 MHz, DMSO-d$_6$) δ 10.73 (s, 1H), 8.74 (d, 1H), 8.69 (d, 1H), 7.95 (dd, 1H), 7.79 (d, 1H), 7.50 (dd, 1H), 7.40 (td, 3H), 7.33-7.25 (m, 2H), 6.74 (d, 1H), 4.00 (s, 3H), 2.24 (s, 3H), 2.08 (s, 3H), 1.96 (s, 3H); MS for $C_{30}H_{24}F_2N_4O_4$: m/z 543 (MH+).

1-(4-Fluorophenyl)-N-[4-[(7-methoxy-1,5-naphthyridin-4-yl)oxy]phenyl]-4,5,6-trimethyl-2-oxopyridine-3-carboxamide (317): Compound NA1-1 was replaced with Compound NA1-6. Compound PA1-2 was replaced with Compound HA-8. MS for $C_{30}H_{25}FN_4O_4$: m/z 525 (MH+).

5-N-[4-[(6,7-Dimethoxy-1,5-naphthyridin-4-yl)oxy]-3-fluorophenyl]-1-(4-fluorophenyl)-2,4-dimethyl-6-oxopyridine-3,5-dicarboxamide (318): Compound PA1-2 was replaced with Compound HA1-10. MS for $C_{31}H_{25}F_2N_5O_6$: m/z 602.2 (MH+).

5-N-[4-[(6,7-Dimethoxy-1,5-naphthyridin-4-yl)oxy]phenyl]-1-(4-fluorophenyl)-2,4-dimethyl-6-oxopyridine-3,5-dicarboxamide (319): Compound NA1-1 was replaced with Compound NA1-2. Compound PA1-2 was replaced with Compound HA1-10. MS for $C_{31}H_{26}FN_5O_6$: m/z 584.2 (MH+).

5-Cyano-N-[4-[(6,7-dimethoxy-1,5-naphthyridin-4-yl)oxy]phenyl]-1-(4-fluorophenyl)-4,6-dimethyl-2-oxopyridine-3-carboxamide (320): Compound NA1-1 was replaced with Compound NA1-2. Compound PA1-2 was replaced with Compound HA1-9. MS for $C_{31}H_{24}FN_5O_5$: m/z 566.2 (MH+).

5-Acetyl-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide (321): Compound PA1-2 was replaced with Compound HA1-11. $^1$H NMR (400 MHz, DMSO-d$_6$) δ 10.77 (s, 1H), 8.52 (d, 1H), 7.91 (dd, 1H), 7.65 (s, 1H), 7.49-7.31 (m, 6H), 6.78 (d, 1H), 3.97 (d, 6H), 2.54 (s, 3H), 2.15 (s, 3H), 1.90 (s, 3H); MS for $C_{32}H_{26}F_2N_4O_6$: m/z 601.2 (MH+).

5-Acetyl-N-[4-[(6,7-dimethoxy-1,5-naphthyridin-4-yl)oxy]phenyl]-1-(4-fluorophenyl)-4,6-dimethyl-2-oxopyridine-3-carboxamide (322): Compound NA1-1 was replaced with Compound NA1-2. Compound PA1-2 was replaced with Compound HA1-11. $^1$H NMR (400 MHz, DMSO-d$_6$) δ 10.49 (s, 1H), 8.44 (d, 1H), 7.69 (d, 2H), 7.57 (s, 1H), 7.39-7.25 (m, 4H), 7.12 (d, 2H), 6.68 (d, 1H), 3.89 (s, 3H), 3.89 (s, 3H), 2.47 (s, 3H), 2.08 (s, 3H), 1.83 (s, 3H); MS for $C_{32}H_{27}FN_4O_6$: m/z 583.2 (MH+).

5-Acetyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide (323): Compound NA1-1 was replaced with Compound NA1-3. Compound PA-2 was replaced with Compound HA1-11. MS for $C_{31}H_{24}F_2N_4O_5$: m/z 571.2 (MH+).

N-[4-[(6,7-Dimethoxy-1,5-naphthyridin-4-yl)oxy]-3-fluorophenyl]-5-fluoro-1-(4-fluorophenyl)-4,6-dimethyl-2-oxopyridine-3-carboxamide (324): Compound PA1-2 was replaced with Compound HA1-14. MS for $C_{30}H_{23}F_3N_4O_5$: m/z 577.2 (MH+).

N-[4-[(6,7-Dimethoxy-1,5-naphthyridin-4-yl)oxy]phenyl]-5-fluoro-1-(4-fluorophenyl)-4,6-dimethyl-2-oxopyridine-3-carboxamide (325): Compound NA1-1 was replaced with Compound NA1-2. Compound PA1-2 was replaced with Compound HA1-14. $^1$H NMR (400 MHz, DMSO-d$_6$) δ 10.82 (s, 1H), 8.52 (d, 1H), 7.76 (d, 2H), 7.64 (s, 1H), 7.47-7.36 (m, 4H), 7.19 (d, 2H), 6.76 (d, 1H), 3.97 (s, 3H), 3.95 (s, 3H), 2.34 (d, 3H), 1.96 (d, 3H); MS for $C_{30}H_{24}F_2N_4O_5$: m/z 559.2 (MH+).

5-Fluoro-N-[3-fluoro-4-[(7-methoxy-1,5-naphthyridin-4-yl)oxy]phenyl]-1-(4-fluorophenyl)-4,6-dimethyl-2-oxopyridine-3-carboxamide (326): Compound NA1-1 was replaced with Compound NA1-3. Compound PA1-2 was replaced with Compound HA1-14. MS for $C_{29}H_{21}F_3N_4O_4$: m/z 547.2 (MH+).

N-[4-[(6,7-Dimethoxy-1,5-naphthyridin-4-yl)oxy]-3-fluorophenyl]-5-ethenyl-1-(4-fluorophenyl)-4,6-dimethyl-2-oxopyridine-3-carboxamide (327): Compound PA1-2 was replaced with Compound HA1-12. MS for $C_{32}H_{26}F_2N_4O_5$: m/z 585.2 (MH+).

N-[4-[(6,7-Dimethoxy-1,5-naphthyridin-4-yl)oxy]phenyl]-5-ethenyl-1-(4-fluorophenyl)-4,6-dimethyl-2-oxopyridine-3-carboxamide (328): Compound NA1-1 was replaced with Compound NA1-2. Compound PA1-2 was replaced with Compound HA1-12. MS for $C_{32}H_{27}FN_4O_5$: m/z 567.2 (MH+).

5-Ethenyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide (329): Compound NA1-1 was replaced with Compound NA1-3. Compound PA1-2 was replaced with Compound HA1-12. $^1$H NMR (400 MHz, DMSO-d$_6$) δ 10.77 (s, 1H), 8.75 (d, 1H), 8.69 (d, 1H), 7.95 (dd, 1H), 7.80 (d, 1H), 7.50 (d, 1H), 7.41 (t, 3H), 7.34 (dd, 2H), 6.75 (d, 1H), 6.61 (dd, 1H), 5.63 (dd, 1H), 5.38-5.29 (m, 1H), 4.01 (s, 3H), 2.21 (s, 3H), 2.01 (s, 3H); MS for $C_{31}H_{24}F_2N_4O_4$: m/z 555.2 (MH+).

N-[4-[(6,7-Dimethoxy-1,5-naphthyridin-4-yl)oxy]-3-fluorophenyl]-5-ethyl-1-(4-fluorophenyl)-4,6-dimethyl-2-oxopyridine-3-carboxamide (330): Compound PA1-2 was replaced with Compound HA1-13. MS for $C_{32}H_{28}F_2N_4O_5$: m/z 587.2 (MH+).

N-[4-[(6,7-Dimethoxy-1,5-naphthyridin-4-yl)oxy]phenyl]-5-ethyl-1-(4-fluorophenyl)-4,6-dimethyl-2-oxopyridine-3-carboxamide (331): Compound NA1-1 was replaced with Compound NA1-2. Compound PA1-2 was replaced with Compound HA1-13. MS for $C_{32}H_{29}FN_4O_5$: m/z 569.2 (MH+).

N-[4-[(6,7-Dimethoxy-1,5-naphthyridin-4-yl)oxy]phenyl]-1-(4-fluoro-2-methylphenyl)-4-methyl-2-oxopyridine-3-carboxamide (332): Compound NA1-1 was replaced with Compound NA-2. Compound PA1-2 was replaced with Compound HA-17. MS for $C_{30}H_{25}FN_4O_5$: m/z 541.2 (MH+).

N-[4-[(6,7-Dimethoxy-1,5-naphthyridin-4-yl)oxy]-3-fluorophenyl]-4-ethoxy-5-(4-fluorophenyl)-6-methylpyridine-3-carboxamide (333): Compound PA1-2 was replaced with Compound PA7-38. MS for $C_{30}H_{26}F_2N_4O_5$: m/z 571 [M-H]−.

N-[3-Fluoro-4-[(7-methoxy-1,5-naphthyridin-4-yl)oxy]phenyl]-1-(4-fluoro-2-methylphenyl)-4-methyl-2-oxopyridine-3-carboxamide (334): Compound NA1-1 was replaced with Compound NA1-3. Compound PA1-2 was replaced with Compound HA1-17. $^1$H NMR (400 MHz, DMSO-d$_6$) δ 10.94 (s, 1H), 8.75 (d, 1H), 8.70 (d, 1H), 7.97 (dd, 1H), 7.80 (d, 1H), 7.63 (d, 1H), 7.51 (dd, 1H), 7.42 (t, 1H), 7.31 (dd, 2H), 7.20 (td, 1H), 6.76 (d, 1H), 6.39 (d, 1H), 4.01 (s, 3H), 2.35 (s, 3H), 2.12 (s, 3H); MS for $C_{29}H_{22}F_2N_4O_4$: m/z 529 (MH+).

5-Ethyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide (335): Compound NA1-1 was replaced with Compound NA1-3. Compound PA1-2 was replaced with Compound HA1-13. MS for $C_{30}H_{26}F_2N_4O_4$: m/z 557 (MH+).

N-[4-[(6,7-Dimethoxy-1,5-naphthyridin-4-yl)oxy]-3-fluorophenyl]-5-(4-fluorophenyl)-2-(methoxymethyl)-1,6-dimethyl-4-oxopyridine-3-carboxamide (336): Compound PA1-2 was replaced with Compound PA6-4. MS for $C_{32}H_{28}F_2N_4O_6$: m/z 603.2 (MH+).

N-[4-[(6,7-Dimethoxy-1,5-naphthyridin-4-yl)oxy]-3-fluorophenyl]-5-fluoro-1-(4-fluorophenyl)-6-methyl-2-oxopyridine-3-carboxamide (337): Compound PA1-2 was replaced with Compound HA1-18. MS for $C_{29}H_{21}F_3N_4O_5$: m/z 563.1 (MH+).

N-[4-[(6,7-Dimethoxy-1,5-naphthyridin-4-yl)oxy]phenyl]-5-fluoro-1-(4-fluorophenyl)-6-methyl-2-oxopyridine-3-carboxamide (338): Compound NA1-1 was replaced with Compound NA-2. Compound PA1-2 was replaced with Compound HA1-18. MS for $C_{29}H_{22}F_2N_4O_5$: m/z 545.1 (MH+).

3-(4-Fluorophenyl)-N-[4-[(6-methoxy-1,5-naphthyridin-4-yl)oxy]phenyl]-2,4-dioxo-1H-pyrimidine-5-carboxamide (339): Compound NA1-1 was replaced with Compound NA1-17. Compound PA1-2 was replaced with Compound HA4-7. MS for $C_{26}H_{18}FN_5O_5$: m/z 500 (MH+).

5-(4-Fluorophenyl)-4-hydroxy-N-[4-[(6-methoxy-1,5-naphthyridin-4-yl)oxy]phenyl]-2,6-dimethylpyridine-3-carboxamide (340): Compound NA1-1 was replaced with Compound NA1-17. Compound PA1-2 was replaced with Compound PA5-2. MS for $C_{29}H_{23}FN_4O_4$: m/z 511 (MH+).

5-(4-Fluorophenyl)-N-[4-[(6-methoxy-1,5-naphthyridin-4-yl)oxy]phenyl]-6-methyl-4-oxo-1-propan-2-ylpyridine-3-carboxamide (341): Compound NA1-1 was replaced with Compound NA1-17. Compound PA1-2 was replaced with Compound PA3-2. MS for $C_{31}H_{27}FN_4O_4$: m/z 539 (MH+).

5-(4-Fluorophenyl)-4-hydroxy-N-[4-[(6-methoxy-1,5-naphthyridin-4-yl)oxy]phenyl]-6-methylpyridine-3-carboxamide (342): Compound NA1-1 was replaced with Compound NA1-17. Compound PA1-2 was replaced with Compound PA3-1. MS for $C_{28}H_{20}FN_4O_4$: m/z 497 (MH+).

1-(4-Fluorophenyl)-N-[4-[(6-methoxy-1,5-naphthyridin-4-yl)oxy]phenyl]-6-methyl-2-oxopyridine-3-carboxamide (343): Compound NA1-1 was replaced with Compound NA1-17. Compound PA1-2 was replaced with Compound HA-1. MS for $C_{28}H_{21}FN_4O_4$: m/z 497 (MH+).

tert-Butyl N-[5-[[4-[(6,7-dimethoxy-1,5-naphthyridin-4-yl)oxy]-3-fluorophenyl]carbamoyl]-1-(4-fluorophenyl)-6-oxopyrimidin-2-yl]carbamate (344): Compound PA1-2 was replaced with Compound HA4-9. $^{1}$H NMR (400 MHz, CDCl$_3$) δ 13.43 (s, 1H), 10.86 (s, 1H), 8.55 (d, 1H), 7.92-7.84 (m, 1H), 7.57 (s, 1H), 7.27 (s, 6H), 7.18 (t, 1H), 6.78 (d, 1H), 4.11 (d, 3H), 4.05 (s, 3H), 1.46 (s, 9H); MS for $C_{32}H_{28}F_2N_6O_7$: m/z 647 (MH+).

N-[3-Fluoro-4-(6-methoxyquinolin-4-yl)oxyphenyl]-5-(4-fluorophenyl)-4-hydroxy-2,6-dimethylpyridine-3-carboxamide (345): Compound NA1-1 was replaced with Compound QA-7. Compound PA1-2 was replaced with Compound PA5-2. MS for $C_{30}H_{23}F_2N_3O_4$: m/z 528 (MH+).

N-[3-Fluoro-4-(6-methoxyquinolin-4-yl)oxyphenyl]-1-(4-fluorophenyl)-6-methyl-2-oxopyridine-3-carboxamide (346): Compound NA1-1 was replaced with Compound QA1-7. Compound PA1-2 was replaced with Compound HA1-1. $^{1}$H NMR (400 MHz, CDCl$_3$) δ 11.96 (s, 1H), 8.65 (d, 1H), 8.55 (d, 1H), 8.03-7.95 (m, 2H), 7.63 (d, 1H), 7.45-7.16 (m, 7H), 6.55-6.49 (m, 2H), 3.99 (s, 3H), 2.14 (s, 3H); MS for $C_{29}H_{20}F_2N_3O_4$: m/z 514 (MH+).

N-[3-Fluoro-4-(6-methoxyquinolin-4-yl)oxyphenyl]-5-(4-fluorophenyl)-4-hydroxy-6-methylpyridine-3-carboxamide (347): Compound NA1-1 was replaced with Compound QA1-7. Compound PA1-2 was replaced with Compound PA3-1. MS for $C_{29}H_{20}F_2N_3O_4$: m/z 514 (MH+).

N-[3-Fluoro-4-[[6-(2-methoxyethoxy)-1,5-naphthyridin-4-yl]oxy]phenyl]-5-(4-fluorophenyl)-4-hydroxy-6-methylpyridine-3-carboxamide (348): Compound NA1-1 was replaced with Compound NA1-18. Compound PA1-2 was replaced with Compound PA3-1. MS for $C_{30}H_{24}F_2N_4O_5$: m/z 559 (MH+).

N-[3-Fluoro-4-[[6-(2-methoxyethoxy)-1,5-naphthyridin-4-yl]oxy]phenyl]-1-(4-fluorophenyl)-6-methyl-2-oxopyridine-3-carboxamide (349): Compound NA1-1 was replaced with Compound NA1-18. Compound PA1-2 was replaced with Compound PA5-2. MS for $C_{30}H_{26}F_2N_4O_5$: m/z 573 (MH+).

N-[3-Fluoro-4-[[6-(2-morpholin-4-ylethoxy)-1,5-naphthyridin-4-yl]oxy]phenyl]-1-(4-fluorophenyl)-6-methyl-2-oxopyridine-3-carboxamide (350): Compound NA1-1 was replaced with Compound NA1-18. Compound PA1-2 was replaced with Compound HA-1. MS for $C_{30}H_{24}F_2N_4O_5$: m/z 559 (MH+).

N-[3-Fluoro-4-[[6-(2-morpholin-4-ylethoxy)-1,5-naphthyridin-4-yl]oxy]phenyl]-5-(4-fluorophenyl)-4-hydroxy-6-methylpyridine-3-carboxamide (351): Compound NA1-1 was replaced with Compound NA1-41. Compound PA-2 was replaced with Compound HA1-1. MS for $C_{33}H_{29}F_2N_5O_5$: m/z 614 (MH+).

N-[4-[[6-[2-(Dimethylamino)ethoxy]-1,5-naphthyridin-4-yl]oxy]-3-fluorophenyl]-1-(4-fluorophenyl)-6-methyl-2-oxopyridine-3-carboxamide (352): Compound NA1-1 was replaced with Compound NA1-41. Compound PA1-2 was replaced with Compound PA3-1. MS for $C_{33}H_{29}F_2N_5O_5$: m/z 614 (MH+).

N-[4-[[6-[2-(Dimethylamino)ethoxy]-1,5-naphthyridin-4-yl]oxy]-3-fluorophenyl]-5-(4-fluorophenyl)-4-hydroxy-2,6-dimethylpyridine-3-carboxamide (353): Compound NA1-1 was replaced with Compound NA1-50. Compound PA-2 was replaced with Compound HA1-1. MS for $C_{31}H_{27}F_2N_5O_4$: m/z 572 (MH+).

N-[3-Fluoro-4-[[6-(2-morpholin-4-ylethoxy)-1,5-naphthyridin-4-yl]oxy]phenyl]-5-(4-fluorophenyl)-4-hydroxy-2,6-dimethylpyridine-3-carboxamide (354): Compound NA1-1 was replaced with Compound NA1-50. Compound PA1-2 was replaced with Compound PA5-2. $^{1}$H NMR (400 MHz, CDCl$_3$) δ 13.33 (s, 1H), 11.13 (s, 1H), 8.51 (d, 1H), 8.44 (s, 1H), 8.15 (d, 1H), 7.80 (d, 1H), 7.24 (d, 1H), 7.08 (dtt, 6H), 6.78 (d, 1H), 4.62 (t, 2H), 3.07 (d, 2H), 2.77 (s, 3H), 2.57 (s, 5H), 2.06 (s, 3H); MS for $C_{32}H_{29}F_2N_5O_4$: m/z 586 (MH+).

5-(4-Fluorophenyl)-N-[4-[(6-methoxy-1,5-naphthyridin-4-yl)oxy]phenyl]-1,6-dimethyl-4-oxopyridine-3-carboxamide (355): Compound NA1-1 was replaced with Compound NA1-41. Compound PA1-2 was replaced with Compound PA5-2. MS for $C_{34}H_{31}F_2N_5O_5$: m/z 628 (MH+).

N-[4-[(6,7-Dimethoxy-1,5-naphthyridin-4-yl)oxy]-3-fluorophenyl]-1-(4-fluorophenyl)-6-(hydroxymethyl)-2-oxopyridine-3-carboxamide (356): Compound NA1-1 was replaced with Compound NA1-17. Compound PA1-2 was replaced with Compound PA3-7. MS for $C_{29}H_{23}FN_4O_4$: m/z 511 (MH+).

N-[4-[(6,7-Dimethoxy-1,5-naphthyridin-4-yl)oxy]-3-fluorophenyl]-1-(4-fluorophenyl)-6-(methoxymethyl)-2-oxopyridine-3-carboxamide (357): Compound PA1-2 was replaced with Compound HA1-25. MS for $C_{29}H_{22}F_2N_4O_6$: m/z 561 (MH+).

N-[4-[(6,7-Dimethoxy-1,5-naphthyridin-4-yl)oxy]-3-fluorophenyl]-1-(4-fluorophenyl)-6-(methoxymethyl)-2-oxopyridine-3-carboxamide (358): Compound PA1-2 was replaced with Compound HA1-26. MS for $C_{30}H_{24}F_2N_4O_6$: m/z 575 (MH+).

5-Acetyl-N-[4-[(6,7-dimethoxy-1,5-naphthyridin-4-yl)oxy]phenyl]-1-(4-fluorophenyl)-2-oxopyridine-3-carboxamide (359): Compound NA1-1 was replaced with Compound NA1-2. Compound PA1-2 was replaced with Compound HA-24. MS for $C_{30}H_{23}FN_4O_6$: m/z 555.1 (MH+).

N-[4-[(6,7-Dimethoxy-1,5-naphthyridin-4-yl)oxy]phenyl]-2-(4-fluorophenyl)-3,8-dioxo-6,7-dihydro-5H-isoquinoline-4-carboxamide (360): Compound NA1-1 was replaced with Compound NA1-2. Compound PA1-2 was replaced with Compound HA-29. MS for $C_{32}H_{25}FN_4O_6$: m/z 581.2 (MH+).

N-[4-[(6,7-Dimethoxy-1,5-naphthyridin-4-yl)oxy]phenyl]-1-(4-fluorophenyl)-2-oxopyridine-3-carboxamide (361): Compound NA1-1 was replaced with Compound NA1-2. Compound PA1-2 was replaced with Compound HA-19. MS for $C_{28}H_{21}FN_4O_5$: m/z 513.0 (MH+).

N-[4-[(6,7-Dimethoxy-1,5-naphthyridin-4-yl)oxy]-3-fluorophenyl]-8-(4-fluorophenyl)-7-oxo-2,3-dihydro-1H-indolizine-6-carboxamide (362): Compound PA1-2 was replaced with Compound PA7-27. MS for $C_{31}H_{24}F_2N_4O_5$: m/z 571.1 (MH+).

N-[4-[(6,7-Dimethoxy-1,5-naphthyridin-4-yl)oxy]-3-fluorophenyl]-1-(4-fluorophenyl)-2-oxo-6,7,8,9-tetrahydroquinolizine-3-carboxamide (363): Compound PA1-2 was replaced with Compound PA7-34. MS for $C_{32}H_{26}F_2N_4O_5$: m/z 585.1 (MH+).

N-[4-[(6,7-Dimethoxy-1,5-naphthyridin-4-yl)oxy]-3-fluorophenyl]-5-(4-fluorophenyl)-6-methyl-4-oxo-1-propan-2-ylpyridazine-3-carboxamide (364): Compound PA1-2 was replaced with Compound HA2-5. MS for $C_{31}H_{27}F_2N_5O_5$: m/z 588.2 (MH+).

N-[4-[(6,7-Dimethoxy-1,5-naphthyridin-4-yl)oxy]-3-fluorophenyl]-2-ethoxy-5-(4-fluorophenyl)-4-hydroxy-6-methylpyridine-3-carboxamide (365): Compound PA1-2 was replaced with Compound PA7-19. MS for $C_{31}H_{26}F_2N_4O_6$: m/z 589.2 (MH+).

5-Bromo-N-[4-[(6,7-dimethoxy-1,5-naphthyridin-4-yl)oxy]-3-fluorophenyl]-1-(4-fluorophenyl)-6-methyl-2-oxopyridine-3-carboxamide (366): Compound PA1-2 was replaced with Compound HA1-20. MS for $C_{29}H_{20}BrF_2N_4O_5$: m/z 625.1 (MH+).

N-[4-[(6,7-Dimethoxy-1,5-naphthyridin-4-yl)oxy]-3-fluorophenyl]-1-(4-fluorophenyl)-6-methyl-2-oxo-5-prop-1-en-2-ylpyridine-3-carboxamide (367): Compound PA1-2 was replaced with Compound HA1-21. $^1$H NMR (400 MHz, CD$_3$OD) δ 12.24 (s, 1H), 8.68 (d, 1H), 8.48 (s, 1H), 8.06 (dd, 1H), 7.57 (s, 1H), 7.45-7.37 (m, 6H), 7.14 (d, 1H), 5.41-5.39 (m, 1H), 5.04 (s, 1H), 4.14 (s, 3H), 4.12 (s, 3H), 2.15 (s, 3H), 2.10 (s, 3H); MS for $C_{32}H_{26}F_2N_4O_5$: m/z 585.1 (MH+).

N-[4-[(6,7-Dimethoxy-1,5-naphthyridin-4-yl)oxy]-3-fluorophenyl]-1-(4-fluorophenyl)-6-methyl-2-oxo-5-propan-2-ylpyridine-3-carboxamide (368): Compound PA1-2 was replaced with Compound HA1-22. MS for $C_{32}H_{28}F_2N_4O_5$: m/z 587.1 (MH+).

N-[4-[(6,7-Dimethoxy-1,5-naphthyridin-4-yl)oxy]-3-fluorophenyl]-2-ethoxy-5-(4-fluorophenyl)-1,6-dimethyl-4-oxopyridine-3-carboxamide (369): Compound PA1-2 was replaced with Compound PA7-37. $^1$H NMR (400 MHz, DMSO-d$_6$) δ 10.91 (s, 1H), 8.80 (d, 1H), 7.99 (d, 1H), 7.90-7.79 (m, 1H), 7.59-7.46 (m, 2H), 7.38-7.25 (m, 4H), 7.21-7.11 (m, 1H), 4.40 (q, 2H), 4.07 (s, 3H), 4.05 (s, 3H), 3.50 (s, 3H), 2.19 (s, 3H), 1.30 (t, 3H); MS for $C_{32}H_{28}F_2N_4O_6$: m/z 603.1 (MH+).

N-[4-[(6,7-Dimethoxy-1,5-naphthyridin-4-yl)oxy]-3-fluorophenyl]-1-(4-fluorophenyl)-5,6-dimethyl-2-oxopyridine-3-carboxamide (370): Compound PA1-2 was replaced with Compound HA1-23. MS for $C_{30}H_{24}F_2N_4O_5$: m/z 559.3 (MH+).

N-[4-[(6,7-Dimethoxy-1,5-naphthyridin-4-yl)oxy]-3-fluorophenyl]-4-ethoxy-1-(4-fluorophenyl)-5-methyl-2-oxopyridine-3-carboxamide (371): Compound PA1-2 was replaced with Compound HA1-27. MS for $C_{30}H_{26}F_2N_4O_6$: m/z 589.1 (MH+).

N-[4-[(6,7-Dimethoxy-1,5-naphthyridin-4-yl)oxy]-3-fluorophenyl]-1-(4-fluorophenyl)-4-methoxy-5-methyl-2-oxopyridine-3-carboxamide (372): Compound PA1-2 was replaced with Compound HA1-28. MS for $C_{30}H_{24}F_2N_4O_6$: m/z 575.2 (MH+).

N-[4-[(6,7-Dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, racemate (373): Compound PA1-2 was replaced with Compound PA7-41. $^1$H NMR (400 MHz, CD$_3$OD) δ=8.65 (d, 1H), 7.98-7.89 (m, 1H), 7.57 (s, 1H), 7.37-7.27 (m, 4H), 7.14-7.05 (m, 3H), 4.16 (s, 3H), 4.11 (s, 3H), 3.98-3.89 (m, 2H), 3.88-3.65 (m, 3H), 3.55 (br t, 2H), 2.25-2.14 (m, 2H); MS for $C_{31}H_{26}F_2N_4O_5$: m/z 573.1 (MH+).

The following two compounds were recovered from the chiral separation of Compound 373. Absolute stereochemistry was not determined:

N-[4-[(6,7-Dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 1 (374): MS for $C_{30}H_{26}F_2N_4O_5$: m/z 573.2 (MH+). Analytical chiral SFC (Chiralcel OD-3, 50×4.6 mm, 3 m; Mobile phase: A=CO$_2$, B=EtOH (0.05% DEA), Isocratic 40%, flow rate=4.0 mL/min) retention time=1.345 min.

N-[4-[(6,7-Dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 2 (375): MS for $C_{30}H_{26}F_2N_4O_5$: m/z 573.1 (MH+). Analytical chiral SFC (Chiralcel OD-3, 50×4.6 mm, 3 m; Mobile phase: A=CO$_2$, B=EtOH (0.05% DEA), Isocratic 40%, flow rate=4.0 mL/min) retention time=4.971 min.

N-[3-Fluoro-4-[7-methoxy-6-[2-(methylamino)-2-oxoethyl]quinolin-4-yl]oxyphenyl]-5-(4-fluorophenyl)-4-hydroxy-6-methylpyridine-3-carboxamide (376): Compound NA1-1 was replaced with Compound QA1-9. Compound PA1-2 was replaced with Compound PA3-1. MS for $C_{32}H_{26}FN_4O_5$: m/z 585.1 (MH+).

N-[4-[7-[1-(Difluoromethyl)pyrazol-4-yl]quinolin-4-yl]oxyphenyl]-5-(4-fluorophenyl)-4-hydroxy-6-methylpyridine-3-carboxamide (377): Compound NA1-1 was replaced with Compound QA1-10. Compound PA1-2 was replaced with Compound PA3-1. MS for $C_{32}H_{22}F_3N_5O_3$: m/z 582.1 (MH+).

4-(4-Fluorophenyl)-N-[4-[(6-methoxy-1,5-naphthyridin-4-yl)oxy]phenyl]-5-methyl-3-oxopyrazine-2-carboxamide (378): Compound NA1-1 was replaced with Compound NA1-17. Compound PA1-2 was replaced with Compound HA3-1. $^1$H NMR (400 MHz, CDCl$_3$) δ 11.65 (s, 1H), 8.57 (d, 1H), 8.20 (d, 1H), 7.87-7.79 (m, 3H), 7.41-7.31 (m, 2H), 7.29 (br s, 1H), 7.25 (br s, 1H), 7.16 (dd, 3H), 6.86 (d, 1H), 4.02 (s, 3H), 2.16 (s, 3H); MS for $C_{27}H_{20}FN_5O_4$: m/z 498.1 (MH+).

N-[4-[(6,7-Dimethoxy-1,5-naphthyridin-4-yl)oxy]-3-fluorophenyl]-4-(4-fluorophenyl)-3-oxopyrazine-2-carboxamide (379): Compound PA1-2 was replaced with Compound HA3-3. $^1$H NMR (400 MHz, DMSO-d$_6$) δ 11.29 (s, 1H), 8.55 (d, 1H), 8.04-7.93 (m, 2H), 7.67-7.60 (m, 4H), 7.53 (br d, 1H), 7.45 (br t, 2H), 7.37 (br t, 1H), 6.84 (br d, 1H), 3.97 (s, 3H), 3.95 (s, 3H); MS for $C_{27}H_{19}F_2N_5O_5$: m/z 532.1 (MH+).

N-[3-Fluoro-4-[(6-methoxy-1,5-naphthyridin-4-yl)oxy]phenyl]-4-(4-fluorophenyl)-3-oxopyrazine-2-carboxamide (380): Compound NA1-1 was replaced with Compound NA1-10. Compound PA1-2 was replaced with Compound HA3-3. MS for $C_{26}H_{17}F_2N_5O_4$: m/z 502.0 (MH+).

N-[3-Fluoro-4-[(7-methoxy-1,5-naphthyridin-4-yl)oxy]phenyl]-4-(4-fluorophenyl)-3-oxopyrazine-2-carboxamide (381): Compound NA1-1 was replaced with Compound NA1-3. Compound PA1-2 was replaced with Compound HA3-3. MS for $C_{26}H_{17}F_2N_5O_4$: m/z 502.1 (MH+).

4-(4-Fluorophenyl)-N-[4-[(7-methoxy-1,5-naphthyridin-4-yl)oxy]phenyl]-3-oxopyrazine-2-carboxamide (382): Compound NA1-1 was replaced with Compound NA1-6. Compound PA1-2 was replaced with Compound HA3-3. $^1$H NMR (400 MHz, DMSO-d$_6$) δ 11.20 (s, 1H), 8.73 (d, 1H), 8.70 (d, 1H), 7.98 (d, 1H), 7.85 (d, 2H), 7.79 (d, 1H), 7.67-7.62 (m, 3H), 7.45 (t, 2H), 7.28 (d, 2H), 6.76 (d, 1H), 4.00 (s, 3H); MS for $C_{26}H_{10}FN_5O_4$: m/z 484.1 (MH+).

4-(4-Fluorophenyl)-N-[4-[(6-methoxy-1,5-naphthyridin-4-yl)oxy]phenyl]-3-oxopyrazine-2-carboxamide (383): Compound NA1-1 was replaced with Compound NA1-17. Compound PA1-2 was replaced with Compound HA3-3. $^1$H NMR (400 MHz, DMSO-d$_6$) δ 11.16 (s, 1H), 8.61 (d, 1H), 8.28 (d, 1H), 7.97 (d, 1H), 7.82 (d, 2H), 7.70-7.60 (m, 3H), 7.44 (t, 2H), 7.30 (d, 1H), 7.24 (d, 2H), 6.94 (d, 1H), 3.93 (s, 3H); MS for $C_{26}H_{10}FN_5O_4$: m/z 484.0 (MH+).

N-[4-[(6,7-Dimethoxy-1,5-naphthyridin-4-yl)oxy]phenyl]-4-(4-fluorophenyl)-3-oxopyrazine-2-carboxamide (384): Compound NA1-1 was replaced with Compound NA1-2. Compound PA1-2 was replaced with Compound HA3-3. MS for $C_{27}H_{20}FN_5O_5$: m/z 514.1 (MH+).

1-(4-Fluorophenyl)-N-[4-[(6-methoxy-1,5-naphthyridin-4-yl)oxy]phenyl]-2-methyl-6-oxopyrimidine-5-carboxamide (385): Compound NA1-1 was replaced with Compound NA1-17. Compound PA1-2 was replaced with Compound HA4-2. $^1$H NMR (400 MHz, DMSO-d$_6$) δ 11.18 (s, 1H), 8.82 (s, 1H), 8.61 (d, 1H), 8.27 (d, 1H), 7.80 (d, 2H), 7.61 (dd, 2H), 7.47 (t, 2H), 7.29 (d, 1H), 7.21 (d, 2H), 6.94 (d, 1H), 3.91 (s, 3H), 2.22 (s, 3H); MS for $C_{27}H_{20}FN_5O_4$: m/z 498.0 (MH+).

N-[4-[(6,7-Dimethoxy-1,5-naphthyridin-4-yl)oxy]-3-fluorophenyl]-2-(4-fluorophenyl)-3-oxopyridazine-4-carboxamide (386): Compound PA1-2 was replaced with Compound HA2-16. $^1$H NMR (400 MHz, CD$_3$OD) δ 12.00 (s, 1H), 8.73 (d, 1H), 8.37 (d, 1H), 8.32 (d, 1H), 8.12 (dd, 1H), 7.71-7.65 (m, 2H), 7.60 (s, 1H), 7.59-7.54 (m, 1H), 7.48 (t, 1H), 7.30 (t, 2H), 7.23 (d, 1H), 4.17 (s, 3H), 4.14 (s, 3H). MS for $C_{27}H_{19}F_2N_5O_5$: m/z 532.1 (MH+).

5-(4-Fluorophenyl)-4-hydroxy-6-methyl-N-[4-[[8-(methylamino)-1,7-naphthyridin-4-yl]oxy]phenyl]pyridine-3-carboxamide (387): Compound NA1-1 was replaced with Compound NA3-3. Compound PA1-2 was replaced with Compound PA3-1. $^1$H NMR (400 MHz, DMSO-d$_6$) δ 13.08 (s, 1H), 12.75 (d, 1H), 10.03 (d, 1H), 8.76 (d, 1H), 8.53 (d, 1H), 7.86 (d, 2H), 7.75 (d, 1H), 7.38 (d, 1H), 7.33-7.24 (m, 6H), 7.07 (d, 1H), 3.18 (d, 3H), 2.18 (s, 3H); MS for $C_{28}H_{22}FN_5O_3$: m/z 496.0 (MH+).

N-[3-Chloro-4-[(6,7-dimethoxy-1,5-naphthyridin-4-yl)oxy]phenyl]-5-(4-fluorophenyl)-1,6-dimethyl-4-oxopyridine-3-carboxamide (388): Compound NA1-1 was replaced with Compound NA1-47. Compound PA1-2 was replaced with Compound PA3-7. $^1$H NMR (400 MHz, DMSO-d$_6$) δ 13.25 (br s, 1H), 8.78 (br s, 2H), 8.24 (br s, 1H), 7.85 (br s, 1H), 7.65 (br s, 1H), 7.51-6.98 (m, 6H), 4.03 (br s, 6H), 3.66-3.63 (m, 3H), 2.21 (br s, 3H); MS for $C_{30}H_{24}ClFN_4O_5$: m/z 575.1 (MH+).

N-[4-[(6,7-Dimethoxy-1,5-naphthyridin-4-yl)oxy]-2-fluorophenyl]-5-(4-fluorophenyl)-1,6-dimethyl-4-oxopyridine-3-carboxamide (389): Compound NA1-1 was replaced with Compound NA1-48. Compound PA1-2 was replaced with Compound PA3-7. MS for $C_{30}H_{24}F_2N_4O_5$: m/z 559.2 (MH+).

N-[4-[(6,7-Dimethoxy-1,5-naphthyridin-4-yl)oxy]-2,3-difluorophenyl]-5-(4-fluorophenyl)-1,6-dimethyl-4-oxopyridine-3-carboxamide (390): Compound NA1-1 was replaced with Compound NA1-46. Compound PA1-2 was replaced with Compound PA3-7. MS for $C_{30}H_{23}F_3N_4O_5$: m/z 577.1 (MH+).

N-[4-[(6,7-Dimethoxy-1,5-naphthyridin-4-yl)oxy]-2,5-difluorophenyl]-5-(4-fluorophenyl)-1,6-dimethyl-4-oxopyridine-3-carboxamide (391): Compound NA1-1 was replaced with Compound NA1-45. Compound PA1-2 was replaced with Compound PA3-7. MS for $C_{30}H_{23}F_3N_4O_5$: m/z 577.1 (MH+).

N-[4-[(6,7-Dimethoxy-1,5-naphthyridin-4-yl)oxy]-3,5-difluorophenyl]-5-(4-fluorophenyl)-1,6-dimethyl-4-oxopyridine-3-carboxamide (392): Compound NA1-1 was replaced with Compound NA1-44. Compound PA1-2 was replaced with Compound PA3-7. $^1$H NMR (400 MHz, CDCl$_3$) δ 12.91 (s, 1H), 8.62 (s, 1H), 8.53 (d, 1H), 7.56-7.48 (m, 3H), 7.20 (d, 4H), 6.78 (d, 1H), 4.09 (s, 3H), 4.02 (s, 3H), 3.86 (s, 3H), 2.28 (s, 3H); MS for $C_{30}H_{23}F_3N_4O_5$: m/z 577.1 (MH+).

N-[4-[(6,7-Dimethoxy-1,5-naphthyridin-4-yl)oxy]-3-fluorophenyl]-4-(4-fluoro-2-methylphenyl)-5-methyl-3-oxopyrazine-2-carboxamide (393): Compound PA1-2 was replaced with Compound HA3-4. MS for $C_{29}H_{23}F_2N_5O_5$: m/z 560.1 (MH+).

N-[3-Fluoro-4-[(6-methoxy-1,5-naphthyridin-4-yl)oxy]phenyl]-4-(4-fluoro-2-methylphenyl)-5-methyl-3-oxopyrazine-2-carboxamide (394): Compound NA1-1 was replaced with Compound NA1-10. Compound PA1-2 was replaced with Compound HA3-4. $^1$H NMR (400 MHz, CD$_3$OD) δ 8.92-8.81 (m, 1H), 8.49-8.38 (m, 1H), 8.13 (br d, 1H), 7.86 (br s, 1H), 7.70-7.54 (m, 2H), 7.50 (br t, 1H), 7.43-7.26 (m, 3H), 7.22 (m, 1H), 4.15 (s, 3H), 2.13 (br s, 6H); MS for $C_{28}H_{20}F_2N_5O_4$: m/z 530.3 (MH+).

5-(2,4-Difluorophenyl)-N-[4-[(6,7-dimethoxy-1,5-naphthyridin-4-yl)oxy]-3-fluorophenyl]-4-hydroxy-6-methylpyridine-3-carboxamide (395): Compound PA1-2 was replaced with Compound PA7-22. MS for $C_{29}H_{21}F_3N_4O_5$: m/z 563.0 (MH+).

5-(2,4-Difluorophenyl)-N-[4-[(6,7-dimethoxy-1,5-naphthyridin-4-yl)oxy]phenyl]-1,6-dimethyl-4-oxopyridine-3-carboxamide (396): Compound NA1-1 was replaced with Compound NA1-2. Compound PA1-2 was replaced with Compound PA3-13. $^1$H NMR (400 MHz, DMSO-d$_6$) δ 12.86 (s, 1H), 8.79 (s, 1H), 8.53 (d, 1H), 7.77 (br d, 2H), 7.63 (s, 1H), 7.39-7.26 (m, 2H), 7.18 (br d, 3H), 6.79 (d, 1H), 3.97-3.89 (m, 9H), 2.21 (s, 3H); MS for $C_{30}H_{24}F_2N_4O_5$: m/z 559.1 (MH+).

4-[4-[[1-(4-Fluorophenyl)-6-methyl-2-oxopyridine-3-carbonyl]amino]phenoxy]-N-methyl-1,7-naphthyridine-6-carboxamide (397): Compound NA1-1 was replaced with Compound NA3-4. Compound PA1-2 was replaced with Compound HA-1. MS for $C_{29}H_{22}FN_5O_4$: m/z 524.1 (MH+).

4-[4-[[5-(4-Fluorophenyl)-4-hydroxy-6-methylpyridine-3-carbonyl]amino]phenoxy]-N-methyl-1,7-naphthyridine-6-carboxamide (398): Compound NA1-1 was replaced with Compound NA3-4. Compound PA1-2 was replaced with Compound PA3-1. MS for $C_{29}H_{22}FN_5O_4$: m/z 524.1 (MH+).

1-Cyclopropyl-N-[6-(6,7-dimethoxyquinolin-4-yl)oxy-5-fluoropyridin-3-yl]-5-(4-fluorophenyl)-4-oxopyridine-3-carboxamide (399): Compound NA1-1 was replaced with Compound QA1-8. MS for $C_{31}H_{24}F_2N_4O_5$: m/z 571 (MH+).

N-[6-(6,7-Dimethoxyquinolin-4-yl)oxy-5-fluoropyridin-3-yl]-5-(4-fluorophenyl)-1-(1-methylazetidin-3-yl)-4-oxopyridine-3-carboxamide (400): Compound NA1-1 was replaced with Compound QA1-8. Compound PA1-2 was replaced with Compound PA-25. MS for $C_{32}H_{27}F_2N_5O_5$: m/z 600 (MH+).

N-[6-(6,7-Dimethoxyquinolin-4-yl)oxy-5-fluoropyridin-3-yl]-5-(4-fluorophenyl)-1-(1-methylpyrazol-4-yl)-4-oxopyridine-3-carboxamide (401): Compound NA1-1 was replaced with Compound QA1-8. Compound PA1-2 was replaced with Compound PA1-11. MS for $C_{32}H_{24}F_2N_6O5$: m/z 611 (MH+).

N-[6-(6,7-Dimethoxyquinolin-4-yl)oxy-5-fluoropyridin-3-yl]-5-(4-fluorophenyl)-1-(1-methylpyrazol-3-yl)-4-oxopyridine-3-carboxamide (402): Compound NA1-1 was replaced with Compound QA1-8. Compound PA1-2 was replaced with Compound PA1-12. MS for $C_{32}H_{24}F_2N_6O5$: m/z 611 (MH+).

N-[4-[(6,7-Dimethoxy-1,5-naphthyridin-4-yl)oxy]-3-fluorophenyl]-4-ethoxy-5-(4-fluorophenyl)-2-methylpyridine-3-carboxamide (403): Compound PA1-2 was replaced with Compound PA7-40. MS for $C_{31}H_{26}F_2N_4O_5$: m/z 573 (MH+).

N-[4-[(6,7-Dimethoxy-1,5-naphthyridin-4-yl)oxy]-3-fluorophenyl]-6-(4-fluorophenyl)-7-oxo-2,3-dihydro-1H-indolizine-8-carboxamide (404): Compound PA1-2 was replaced with Compound PA7-25. MS for $C_{31}H_{24}F_2N_4O_5$: m/z 571 (MH+).

N-[3-Fluoro-4-[(7-methoxy-1,5-naphthyridin-4-yl)oxy]phenyl]-6-(4-fluorophenyl)-7-oxo-2,3-dihydro-1H-indolizine-8-carboxamide (405): Compound NA1-1 was replaced with Compound NA1-3. Compound PA1-2 was replaced with Compound PA7-25. MS for $C_{30}H_{22}F_2N_4O_4$: m/z 541 (MH+).

N-[4-(6,7-Dimethoxyquinazolin-4-yl)oxy-3-fluorophenyl]-6-(4-fluorophenyl)-7-oxo-2,3-dihydro-1H-indolizine-8-carboxamide (406): Compound NA1-1 was replaced with Compound QA2-1. Compound PA1-2 was replaced with Compound PA7-25. MS for $C_{31}H_{24}F_2N_4O_5$: m/z 571 (MH+).

N-[4-[(6,7-Dimethoxy-1,5-naphthyridin-4-yl)oxy]phenyl]-6-(4-fluorophenyl)-7-oxo-2,3-dihydro-1H-indolizine-8-carboxamide (407): Compound NA1-1 was replaced with Compound NA1-2. Compound PA1-2 was replaced with Compound PA7-25. MS for $C_{31}H_{25}FN_4O_5$: m/z 553 (MH+).

4-[2-Fluoro-4-[[6-(4-fluorophenyl)-7-oxo-2,3-dihydro-1H-indolizine-8-carbonyl]amino]phenoxy]-7-methoxy-N-methylquinoline-6-carboxamide (408): Compound NA1-1 was replaced with Compound QA1-6. Compound PA1-2 was replaced with Compound PA7-25. MS for $C_{33}H_{26}F_2N_4O_5$: m/z 597 (MH+).

N-[4-(6,7-Dimethoxyquinolin-4-yl)oxy-3-fluorophenyl]-6-(4-fluorophenyl)-7-oxo-2,3-dihydro-1H-indolizine-8-carboxamide (409): Compound NA1-1 was replaced with Compound QA1-1. Compound PA1-2 was replaced with Compound PA7-25. MS for $C_{32}H_{25}F_2N_3O_5$: m/z 570 (MH+).

1-Ethyl-N-[3-fluoro-4-[(7-hydroxy-1,5-naphthyridin-4-yl)oxy]phenyl]-5-(4-fluorophenyl)-6-methyl-4-oxopyridine-3-carboxamide (410): Compound NA1-1 was replaced with Compound NA1-51. Compound PA1-2 was replaced with Compound PA3-4. $^1$H NMR (400 MHz, DMSO-d$_6$) δ 13.2 (s, 1H), 11.3 (s, 1H), 8.80 (s, 1H), 8.76 (d, 2H), 8.08 (d, 1H), 7.64 (d, 1H), 7.51 (d, 1H), 7.45 (t, 1H), 7.29 (d, 4H), 6.83 (s, 1H), 4.29 (q, 2H), 2.27 (s, 3H), 1.40 (t, 3H); MS for $C_{29}H_{22}F_2N_4O_4$: m/z 529 (MH+).

6-Chloro-N-[3-fluoro-4-[(7-methoxy-1,5-naphthyridin-4-yl)oxy]phenyl]-5-(4-fluorophenyl)-1-methyl-4-oxopyridine-3-carboxamide (411): Compound NA1-1 was replaced with Compound NA1-3. Compound PA1-2 was replaced with Compound PA7-29. $^1$H NMR (400 MHz, DMSO-d$_6$) δ 12.8 (s, 1H), 8.96 (s, 1H), 8.76 (d, 1H), 8.72 (s, 1H), 8.05 (dd, 1H), 7.81 (d, 1H), 7.54-7.47 (m, 1H), 7.47-7.27 (m, 5H), 6.76 (dd, 1H), 4.01 (s, 6H); MS for $C_{28}H_9CF_2N_4O_4$: m/z 549 (MH+).

6-Chloro-N-[4-[(6,7-dimethoxy-1,5-naphthyridin-4-yl)oxy]-3-fluorophenyl]-5-(4-fluorophenyl)-1-methyl-4-oxopyridine-3-carboxamide (412): Compound PA1-2 was replaced with Compound PA7-29. $^1$H NMR (400 MHz, DMSO-d$_6$) δ 12.7 (s, 1H), 8.95 (s, 1H), 8.56 (d, 1H), 8.01 (dd, 1H), 7.66 (s, 1H), 7.45 (d, 1H), 7.39-7.27 (m, 5H), 6.84 (d, 1H), 4.01 (s, 3H), 3.97 (s, 3H), 3.94 (s, 3H); MS for $C_{29}H_{21}ClF_2N_4O_5$: m/z 579 (MH+).

5-(4-Fluorophenyl)-4-hydroxy-N-[4-[(7-methoxy-6-propan-2-yloxy-1,5-naphthyridin-4-yl)oxy]phenyl]-6-methylpyridine-3-carboxamide (413): Compound NA1-1 was replaced with Compound NA1-31. Compound PA1-2 was replaced with Compound PA3-1. MS for $C_{31}H_{27}FN_4O_5$: m/z 555 (MH+).

5-(4-Fluoro-2-methylphenyl)-4-hydroxy-N-[4-[(7-methoxy-6-propan-2-yloxy-1,5-naphthyridin-4-yl)oxy]phenyl]-6-methylpyridine-3-carboxamide (414): Compound NA1-1 was replaced with Compound NA1-31. Compound PA1-2 was replaced with Compound PA7-1. MS for $C_{32}H_{29}FN_4O_5$: m/z 569 (MH+).

N-[3-Fluoro-4-[(7-methoxy-6-propan-2-yloxy-1,5-naphthyridin-4-yl)oxy]phenyl]-5-(4-fluorophenyl)-4-hydroxy-6-methylpyridine-3-carboxamide (415): Compound NA1-1 was replaced with Compound NA1-30. Compound PA1-2 was replaced with Compound PA3-1. MS for $C_{31}H_{26}F_2N_4O_5$: m/z 573 (MH+).

N-[3-Fluoro-4-[(7-methoxy-6-propan-2-yloxy-1,5-naphthyridin-4-yl)oxy]phenyl]-5-(4-fluoro-2-methylphenyl)-4-hydroxy-6-methylpyridine-3-carboxamide (416): Compound NA1-1 was replaced with Compound NA1-30. Compound PA1-2 was replaced with Compound PA7-1. $^1$H NMR (400 MHz, DMSO-d$_6$) δ 13.22 (s, 1H), 12.6 (s, 1H), 8.57 (s, 1H), 8.56 (s, 1H), 8.00 (dd, 1H), 7.62 (s, 1H), 7.35 (d, 1H), 7.27-7.03 (m, 4H), 6.92 (d, 1H), 5.29 (p, 1H), 3.95 (s, 3H), 2.06 (s, 6H), 1.27 (dd, 6H); MS for $C_{32}H_{28}F_2N_4O_5$: m/z 587 (MH+).

5-(4-Fluoro-2,6-dimethylphenyl)-N-[3-fluoro-4-[(7-methoxy-1,5-naphthyridin-4-yl)oxy]phenyl]-4-hydroxy-6-methylpyridine-3-carboxamide (417): Compound NA1-1 was replaced with Compound NA1-3. Compound PA1-2 was replaced with Compound PA7-20. MS for $C_{30}H_{24}F_2N_4O_4$: m/z 543 (MH+).

N-[4-[(7-Ethyl-1,5-naphthyridin-4-yl)oxy]-3-fluorophenyl]-5-(4-fluorophenyl)-4-hydroxy-6-methylpyridine-3-carboxamide (418): Compound NA1-1 was replaced with Compound NA-32. Compound PA1-2 was replaced with Compound PA3-1. MS for $C_{29}H_{22}F_2N_4O_3$: m/z 513 (MH+).

N-[4-[(7-Ethyl-1,5-naphthyridin-4-yl)oxy]-3-fluorophenyl]-5-(4-fluoro-2-methylphenyl)-4-hydroxy-6-methylpyridine-3-carboxamide (419): Compound NA1-1 was replaced with Compound NA1-32. Compound PA1-2 was replaced with Compound PA7-1. MS for $C_{30}H_{24}F_2N_4O_3$: m/z 527 (MH+).

N-[4-[(7-Ethyl-6-methoxy-1,5-naphthyridin-4-yl)oxy]-3-fluorophenyl]-5-(4-fluorophenyl)-4-hydroxy-6-methylpyridine-3-carboxamide (420): Compound NA1-1 was replaced with Compound NA1-38. Compound PA1-2 was replaced with Compound PA3-1. MS for $C_{30}H_{24}F_2N_4O_4$: m/z 543 (MH+).

N-[4-[(7-Ethyl-6-methoxy-1,5-naphthyridin-4-yl)oxy]-3-fluorophenyl]-5-(4-fluoro-2-methylphenyl)-4-hydroxy-6-methylpyridine-3-carboxamide (421): Compound NA1-1 was replaced with Compound NA1-38. Compound PA1-2 was replaced with Compound PA7-1. MS for $C_{31}H_{26}F_2N_4O_4$: m/z 557 (MH+).

N-[4-[(7-Ethenyl-6-methoxy-1,5-naphthyridin-4-yl)oxy]-3-fluorophenyl]-5-(4-fluorophenyl)-4-hydroxy-6-methylpyridine-3-carboxamide (422): Compound NA1-1 was replaced with Compound NA1-40. Compound PA1-2 was replaced with Compound PA3-1. MS for $C_{30}H_{22}F_2N_4O_4$: m/z 541 (MH+).

N-[4-[(7-Ethenyl-6-methoxy-1,5-naphthyridin-4-yl)oxy]-3-fluorophenyl]-5-(4-fluoro-2-methylphenyl)-4-hydroxy-6-methylpyridine-3-carboxamide (423): Compound NA1-1 was replaced with Compound NA1-40. Compound PA1-2 was replaced with Compound PA7-1. MS for $C_{31}H_{24}F_2N_4O_4$: m/z 555 (MH+).

N-[3-Fluoro-4-[[7-methoxy-6-(3-morpholin-4-ylpropoxy)-1,5-naphthyridin-4-yl]oxy]phenyl]-5-(4-fluorophenyl)-4-hydroxy-6-methylpyridine-3-carboxamide (424): Compound NA1-1 was replaced with Compound NA1-28. Compound PA1-2 was replaced with Compound PA3-1. MS for $C_{35}H_{33}F_2N_5O_6$: m/z 658 (MH+).

N-[3-Fluoro-4-[[7-methoxy-6-(3-morpholin-4-ylpropoxy)-1,5-naphthyridin-4-yl]oxy]phenyl]-5-(4-fluoro-2-methylphenyl)-4-hydroxy-6-methylpyridine-3-carboxamide (425): Compound NA1-1 was replaced with Compound NA1-28. Compound PA1-2 was replaced with Compound PA7-1. $^1$H NMR (400 MHz, DMSO-d$_6$) δ 13.18 (s, 1H), 12.64 (s, 1H), 8.60-8.53 (m, 2H), 8.01 (d, 1H), 7.64 (s, 1H), 7.38 (d, 1H), 7.27 (t, 1H), 7.17 (d, 1H), 7.12-7.05 (m, 2H), 6.88 (d, 1H), 4.34 (t, 2H), 3.97 (s, 3H), 3.49 (t, 4H), 2.40-2.27 (m, 6H), 2.07 (s, 6H), 1.87 (m, 2H); MS for $C_{36}H_{35}F_2N_5O_6$: m/z 672 (MH+).

N-[3-Fluoro-4-[(6-fluoro-7-methyl-1,5-naphthyridin-4-yl)oxy]phenyl]-5-(4-fluorophenyl)-4-hydroxy-6-methylpyridine-3-carboxamide (426): Compound NA1-1 was replaced with Compound NA1-20. Compound PA1-2 was replaced with Compound PA3-1 MS for $C_{28}H_{19}F_3N_4O_3$: m/z 517 (MH+).

N-[3-Fluoro-4-[(6-fluoro-7-methyl-1,5-naphthyridin-4-yl)oxy]phenyl]-5-(4-fluoro-2-methylphenyl)-4-hydroxy-6-methylpyridine-3-carboxamide (427): Compound NA1-1 was replaced with Compound NA1-20. Compound PA1-2 was replaced with Compound PA7-1. MS for $C_{29}H_{21}F_3N_4O_3$: m/z 531 (MH+).

N-[3-Fluoro-4-[(6-fluoro-7-methyl-1,5-naphthyridin-4-yl)oxy]phenyl]-5-(4-fluoro-2-methylphenyl)-4-hydroxy-2,6-dimethylpyridine-3-carboxamide (428): Compound NA1-1 was replaced with Compound NA1-20. Compound PA1-2 was replaced with Compound PA7-2. MS for $C_{30}H_{23}F_3N_4O_3$: m/z 545 (MH+).

N-[3-Fluoro-4-[(6-fluoro-7-methyl-1,5-naphthyridin-4-yl)oxy]phenyl]-5-(4-fluoro-2-methylphenyl)-1,6-dimethyl-4-oxopyridine-3-carboxamide (429): Compound NA1-1 was replaced with Compound NA1-20. Compound PA1-2 was replaced with Compound PA7-7. MS for $C_{30}H_{23}F_3N_4O_3$: m/z 545 (MH+).

N-[3-Fluoro-4-[(6-fluoro-7-methyl-1,5-naphthyridin-4-yl)oxy]phenyl]-5-(4-fluoro-2-methylphenyl)-4-hydroxy-6-methylpyridazine-3-carboxamide (430): Compound NA1-1 was replaced with Compound NA1-20. Compound PA1-2 was replaced with Compound HA2-2. $^1$H NMR (400 MHz, DMSO-d$_6$) δ 14.21 (s, 1H), 12.83 (s, 1H), 8.74 (d, 1H), 8.49 (d, 1H), 8.06 (d, 1H), 7.54 (d, 1H), 7.46 (t, 1H), 7.25-7.07 (m, 3H), 6.92 (d, 1H), 2.49 (s, 3H), 2.16 (s, 3H), 2.11 (s, 3H); MS for $C_{28}H_{20}F_3N_5O_3$: m/z 532 (MH+).

N-[3-Fluoro-4-[(7-hydroxy-6-methoxy-1,5-naphthyridin-4-yl)oxy]phenyl]-5-(4-fluorophenyl)-4-hydroxy-2,6-dimethylpyridine-3-carboxamide (431): Compound NA1-1 was replaced with Compound NA1-43. Compound PA1-2 was replaced with Compound PA5-2. MS for $C_{29}H_{22}F_2N_4O_5$: m/z 545 (MH+).

N-[3-Fluoro-4-[[6-methoxy-7-(2-methoxyethoxy)-1,5-naphthyridin-4-yl]oxy]phenyl]-5-(4-fluorophenyl)-4-hydroxy-2,6-dimethylpyridine-3-carboxamide (432): Compound NA1-1 was replaced with Compound NA1-19. Compound PA1-2 was replaced with Compound PA5-2. MS for $C_{32}H_{28}F_2N_4O_6$: m/z 603 (MH+).

1-Cyclopropyl-N-[4-[(6,7-dimethoxy-1,5-naphthyridin-4-yl)oxy]-3-fluorophenyl]-5-(4-fluorophenyl)-6-methyl-4-oxopyridine-3-carboxamide (433): Compound PA1-2 was replaced with Compound PA7-35. MS for $C_{32}H_{26}F_2N_4O_5$: m/z 585 (MH+).

1-Cyclopropyl-N-[4-[(6,7-dimethoxy-1,5-naphthyridin-4-yl)oxy]phenyl]-5-(4-fluorophenyl)-6-methyl-4-oxopyridine-3-carboxamide (434): Compound NA1-1 was replaced with Compound NA1-2. Compound PA1-2 was replaced with Compound PA7-35. $^1$H NMR (400 MHz, DMSO-d$_6$) δ 12.87 (s, 1H), 8.60 (s, 1H), 8.54 (dd, 1H), 7.77 (d, 2H), 7.65 (d, 1H), 7.34-7.25 (m, 4H), 7.18 (d, 2H), 6.81 (dd, 1H), 3.97 (s, 3H), 3.94 (s, 3H), 2.43 (m, 1H), 2.37 (s, 3H), 1.26-1.18 (m, 4H); MS for $C_{32}H_{27}FN_4O_5$: m/z 567 (MH+).

1-Cyclopropyl-N-[3-fluoro-4-[(6-methoxy-1,5-naphthyridin-4-yl)oxy]phenyl]-5-(4-fluorophenyl)-6-methyl-4-oxopyridine-3-carboxamide (435): Compound NA1-1 was replaced with Compound NA1-10. Compound PA1-2 was replaced with Compound PA7-35. MS for $C_{31}H_{24}F_2N_4O_4$: m/z 555 (MH+).

N-[3-Fluoro-4-[[6-(2-methoxyethoxy)-7-methyl-1,5-naphthyridin-4-yl]oxy]phenyl]-5-(4-fluorophenyl)-4-hydroxy-6-methylpyridine-3-carboxamide (436): Compound NA1-1 was replaced with Compound NA1-36. Compound PA1-2 was replaced with Compound PA3-1. MS for $C_{31}H_{26}F_2N_4O_5$: m/z 573 (MH+).

5-(4-Fluorophenyl)-4-hydroxy-N-[4-[[6-(2-methoxyethoxy)-7-methyl-1,5-naphthyridin-4-yl]oxy]phenyl]-6-methylpyridine-3-carboxamide (437): Compound NA1-1 was replaced with Compound NA1-35. Compound PA1-2 was replaced with Compound PA3-1. MS for $C_{31}H_{27}FN_4O_5$: m/z 555 (MH+).

N-[3-Fluoro-4-[[7-methyl-6-(3-morpholin-4-ylpropoxy)-1,5-naphthyridin-4-yl]oxy]phenyl]-5-(4-fluorophenyl)-4-hydroxy-6-methylpyridine-3-carboxamide (438): Compound NA1-1 was replaced with Compound NA1-37. Compound PA1-2 was replaced with Compound PA3-1. MS for $C_{35}H_{33}F_2N_5O_5$: m/z 642 (MH+).

1-Cyclopropyl-N-[4-[(6,7-dimethoxy-1,5-naphthyridin-4-yl)oxy]-3-fluorophenyl]-5-(4-fluoro-2-methylphenyl)-6-methyl-4-oxopyridine-3-carboxamide (439): Compound PA1-2 was replaced with Compound PA7-32. MS for $C_{33}H_{28}F_2N_4O_5$: m/z 599 (MH+).

1-Cyclopropyl-N-[4-[(6,7-dimethoxy-1,5-naphthyridin-4-yl)oxy]phenyl]-5-(4-fluoro-2-methylphenyl)-6-methyl-4-oxopyridine-3-carboxamide (440): Compound NA-1 was replaced with Compound NA1-2. Compound PA1-2 was replaced with Compound PA7-32. MS for $C_{33}H_{29}FN_4O_5$: m/z 581 (MH+).

1-Cyclopropyl-N-[3-fluoro-4-[(6-methoxy-1,5-naphthyridin-4-yl)oxy]phenyl]-5-(4-fluoro-2-methylphenyl)-6-methyl-4-oxopyridine-3-carboxamide (441): Compound NA1-1 was replaced with Compound NA1-10. Compound PA1-2 was replaced with Compound PA7-32. MS for $C_{32}H_{26}F_2N_4O_4$: m/z 569 (MH+).

N-[4-[(6,7-Dimethoxy-1,5-naphthyridin-4-yl)oxy]-3-fluorophenyl]-5-(4-fluorophenyl)-4-hydroxy-6-methoxy-2-methylpyridine-3-carboxamide (442): Compound PA1-2 was replaced with Compound PA7-16. MS for $C_{30}H_{24}F_2N_4O_6$: m/z 575 (MH+).

N-[4-[(6,7-Dimethoxy-1,5-naphthyridin-4-yl)oxy]-3-fluorophenyl]-5-(4-fluorophenyl)-4,6-dihydroxy-2-methylpyridine-3-carboxamide (443): Compound PA1-2 was replaced with Compound PA7-15. MS for $C_{29}H_{22}F_2N_4O_6$: m/z 561 (MH+).

N-[4-[(6,7-Dimethoxy-1,5-naphthyridin-4-yl)oxy]-3-fluorophenyl]-5-(4-fluorophenyl)-4,6-dimethoxy-2-methylpyridine-3-carboxamide (444): Compound PA1-2 was replaced with Compound PA7-39. MS for $C_{30}H_{26}F_2N_4O_6$: m/z 589 (MH+).

N-[3-Fluoro-4-[(6-fluoro-7-methyl-1,5-naphthyridin-4-yl)oxy]phenyl]-5-(4-fluorophenyl)-4-hydroxy-2,6-dimethylpyridine-3-carboxamide (445): Compound NA-1 was replaced with Compound NA1-20. Compound PA1-2 was replaced with Compound PA5-2. MS for $C_{29}H_{21}F_3N_4O_3$: m/z 531 (MH+).

N-[3-Fluoro-4-[(6-fluoro-7-methyl-1,5-naphthyridin-4-yl)oxy]phenyl]-5-(4-fluorophenyl)-4-hydroxy-2-(methoxymethyl)-6-methylpyridine-3-carboxamide (446): Compound NA1-1 was replaced with Compound NA1-20. Compound PA-2 was replaced with Compound PA5-11. MS for $C_{30}H_{23}F_3N_4O_4$: m/z 561 (MH+).

N-[4-[(6-Ethoxy-7-methoxy-1,5-naphthyridin-4-yl)oxy]-3-fluorophenyl]-1-(4-fluorophenyl)-4-methyl-2-oxopyridine-3-carboxamide (447): Compound NA1-1 was replaced with Compound NA1-27. Compound PA1-2 was replaced with Compound HA-16. MS for $C_{30}H_{24}F_2N_4O_5$: m/z 559 (MH+).

5-(4-Fluoro-2-methylphenyl)-4-hydroxy-6-methyl-N-[4-[(7-prop-1-en-2-yl-1,5-naphthyridin-4-yl)oxy]phenyl]pyridine-3-carboxamide (448): Compound NA-1 was replaced with Compound NA1-25. Compound PA1-2 was replaced with Compound PA7-1. MS for $C_{31}H_{25}FN_4O_3$: m/z 521 (MH+).

N-[3-Fluoro-4-[(6-methoxy-7-prop-1-en-2-yl-1,5-naphthyridin-4-yl)oxy]phenyl]-5-(4-fluoro-2-methylphenyl)-4-hydroxy-6-methylpyridine-3-carboxamide (449): Compound NA1-1 was replaced with Compound NA1-23. Compound PA1-2 was replaced with Compound PA7-1. MS for $C_{32}H_{26}F_2N_4O_4$: m/z 569 (MH+).

5-(4-Fluoro-2-methylphenyl)-N-[3-fluoro-4-[(7-prop-1-en-2-yl-1,5-naphthyridin-4-yl)oxy]phenyl]-4-hydroxy-6-methylpyridine-3-carboxamide (450): Compound NA1-1 was replaced with Compound NA1-24. Compound PA1-2 was replaced with Compound PA7-1. MS for $C_{31}H_{24}F_2N_4O_3$: m/z 539 (MH+).

5-(4-Fluorophenyl)-N-[3-fluoro-4-[(7-prop-1-en-2-yl-1,5-naphthyridin-4-yl)oxy]phenyl]-4-hydroxy-2,6-dimethylpyridine-3-carboxamide (451): Compound NA1-1 was replaced with Compound NA1-24. Compound PA1-2 was replaced with Compound PA5-2. $^1$H NMR (400 MHz, DMSO-d$_6$) δ 13.4 (s, 1H), 11.6 (s, 1H), 9.19 (s, 1H), 8.71 (d, 1H), 8.30 (s, 1H), 7.96 (d, 1H), 7.33 (m, 2H), 7.18 (m, 4H), 6.79 (d, 1H), 5.81 (s, 1H), 5.37 (s, 1H), 2.68 (s, 3H), 2.22 (s, 3H), 2.08 (s, 3H); MS for $C_{31}H_{24}F_2N_4O_3$: m/z 539 (MH+).

N-[3-Fluoro-4-[(6-methoxy-7-prop-1-en-2-yl-1,5-naphthyridin-4-yl)oxy]phenyl]-5-(4-fluorophenyl)-4-hydroxy-6-methylpyridine-3-carboxamide (452): Compound NA1-1 was replaced with Compound NA1-23. Compound PA1-2 was replaced with Compound PA3-1. MS for $C_{31}H_{24}F_2N_4O_4$: m/z 555 (MH+).

N-[3-Fluoro-4-[(6-methoxy-7-prop-1-en-2-yl-1,5-naphthyridin-4-yl)oxy]phenyl]-5-(4-fluorophenyl)-4-hydroxy-2,6-dimethylpyridine-3-carboxamide (453): Compound NA1-1 was replaced with Compound NA1-23. Compound PA1-2 was replaced with Compound PA5-2. MS for $C_{32}H_{26}F_2N_4O_4$: m/z 569 (MH+).

5-(4-Fluorophenyl)-4-hydroxy-6-methyl-N-[4-[(7-prop-1-en-2-yl-1,5-naphthyridin-4-yl)oxy]phenyl]pyridine-3-carboxamide (454): Compound NA1-1 was replaced with Compound NA1-25. Compound PA1-2 was replaced with Compound PA3-1. MS for $C_{30}H_{23}FN_4O_3$: m/z 507 (MH+).

5-(4-Fluorophenyl)-4-hydroxy-2,6-dimethyl-N-[4-[(7-prop-1-en-2-yl-1,5-naphthyridin-4-yl)oxy]phenyl]pyridine-3-carboxamide (455): Compound NA1-1 was replaced with Compound NA1-25. Compound PA1-2 was replaced with Compound PA5-2. $^1$H NMR (400 MHz, DMSO-d$_6$) δ 13.4 (s, 1H), 11.9 (s, 1H), 9.25 (s, 1H), 8.77 (d, 1H), 8.37 (s, 1H), 7.81 (d, 2H), 7.25 (m, 6H), 6.85 (d, 1H), 5.88 (s, 1H), 5.44 (s, 1H), 2.75 (s, 3H), 2.30 (s, 3H), 2.14 (s, 3H); MS for $C_{31}H_{25}FN_4O_3$: m/z 521 (MH+).

5-(4-Fluorophenyl)-N-[3-fluoro-4-[(7-prop-1-en-2-yl-1,5-naphthyridin-4-yl)oxy]phenyl]-4-hydroxy-6-methylpyridine-3-carboxamide (456): Compound NA1-1 was replaced with Compound NA1-24. Compound PA1-2 was replaced with Compound PA3-1. MS for $C_{30}H_{22}F_2N_4O_3$: m/z 525 (MH+).

1-(4-Fluorophenyl)-N-[3-fluoro-4-[(7-prop-1-en-2-yl-1,5-naphthyridin-4-yl)oxy]phenyl]-4,6-dimethyl-2-oxopyridine-3-carboxamide (457): Compound NA1-1 was replaced with Compound NA1-24. Compound PA1-2 was replaced with Compound HA-5. MS for $C_{31}H_{24}F_2N_4O_3$: m/z 539 (MH+).

N-[3-Fluoro-4-[(6-methoxy-7-methyl-1,5-naphthyridin-4-yl)oxy]phenyl]-5-(4-fluorophenyl)-4-hydroxy-6-methylpyridine-3-carboxamide (458): Compound NA1-1 was replaced with Compound NA1-26. Compound PA1-2 was replaced with Compound PA3-1. MS for $C_{29}H_{22}F_2N_4O_4$: m/z 529 (MH+).

N-[3-Fluoro-4-[(6-methoxy-7-methyl-1,5-naphthyridin-4-yl)oxy]phenyl]-5-(4-fluorophenyl)-4-hydroxy-2,6-dimethylpyridine-3-carboxamide (459): Compound NA1-1 was replaced with Compound NA1-26. Compound PA1-2 was replaced with Compound PA5-2. MS for $C_{30}H_{24}F_2N_4O_4$: m/z 543 (MH+).

N-[3-Fluoro-4-[(6-methoxy-7-methyl-1,5-naphthyridin-4-yl)oxy]phenyl]-5-(4-fluoro-2-methylphenyl)-4-hydroxy-6-methylpyridine-3-carboxamide (460): Compound NA1-1 was replaced with Compound NA1-26. Compound PA1-2 was replaced with Compound PA7-1. MS for $C_{30}H_{24}F_2N_4O_4$: m/z 543 (MH+).

5-(4-Fluoro-2-methylphenyl)-N-[3-fluoro-4-[(7-prop-1-en-2-yl-1,5-naphthyridin-4-yl)oxy]phenyl]-4-hydroxy-2,6-dimethylpyridine-3-carboxamide (461): Compound NA1-1 was replaced with Compound NA1-24. Compound PA1-2 was replaced with Compound PA7-2. $^1$H NMR (400 MHz, DMSO-d$_6$) δ 13.6 (s, 1H), 12.0 (s, 1H), 9.26 (s, 1H), 8.78 (d, 1H), 8.37 (s, 1H), 8.03 (dd, 1H), 7.39 (m, 2H), 7.15 (d, 1H), 7.06 (m, 2H), 6.86 (d, 1H), 5.88 (s, 1H), 5.44 (s, 1H), 2.79 (s, 3H), 2.29 (s, 3H), 2.07 (s, 3H), 2.03 (s, 3H); MS for $C_{32}H_{26}F_2N_4O_3$: m/z 553 (MH+).

1-(4-Fluorophenyl)-2-methyl-6-oxo-N-[4-[(7-prop-1-en-2-yl-1,5-naphthyridin-4-yl)oxy]phenyl]pyrimidine-5-carboxamide (462): Compound NA1-1 was replaced with Compound NA1-25. Compound PA1-2 was replaced with Compound HA4-2. MS for $C_{29}H_{22}FN_5O_3$: m/z 508 (MH+).

5-(4-Fluoro-2-methylphenyl)-N-[3-fluoro-4-[(7-prop-1-en-2-yl-1,5-naphthyridin-4-yl)oxy]phenyl]-6-methyl-4-oxo-1H-pyridazine-3-carboxamide (463): Compound NA1-1 was replaced with Compound NA1-24. Compound PA1-2 was replaced with Compound HA2-2. $^1$H NMR (400 MHz, DMSO-d$_6$) δ 14.2 (s, 1H), 12.9 (s, 1H), 9.27 (s, 1H), 8.79 (d, 1H), 8.38 (s, 1H), 8.06 (dd, 1H), 7.52 (d, 1H), 7.45 (m, 1H), 7.19 (m, 2H), 7.10 (m, 1H), 6.91 (d, 1H), 5.89 (s, 1H), 5.44 (s, 1H), 2.99 (s, 3H), 2.15 (s, 3H), 2.10 (s, 3H); MS for $C_{30}H_{23}F_2N_5O_3$: m/z 540 (MH+).

5-(4-Fluorophenyl)-N-[3-fluoro-4-[(7-prop-1-en-2-yl-1,5-naphthyridin-4-yl)oxy]phenyl]-6-methyl-4-oxo-1H-pyridazine-3-carboxamide (464): Compound NA1-1 was replaced with Compound NA1-24. Compound PA1-2 was replaced with Compound HA2-1. MS for $C_{29}H_{20}F_2N_5O_3$: m/z 526 (MH+).

1-(4-Fluorophenyl)-N-[3-fluoro-4-[(7-prop-1-en-2-yl-1,5-naphthyridin-4-yl)oxy]phenyl]-2-methyl-6-oxopyrimidine-5-carboxamide (465): Compound NA1-1 was replaced with Compound NA1-24. Compound PA1-2 was replaced with Compound HA4-2. MS for $C_{29}H_{21}F_2N_5O_3$: m/z 526 (MH+).

1-(4-Fluorophenyl)-N-[3-fluoro-4-[(7-prop-1-en-2-yl-1,5-naphthyridin-4-yl)oxy]phenyl]-2,4-dimethyl-6-oxopyrimidine-5-carboxamide (466): Compound NA1-1 was replaced with Compound NA1-24. Compound PA1-2 was replaced with Compound HA4-6. MS for $C_{30}H_{23}F_2N_5O_3$: m/z 540 (MH+).

1-(4-Fluorophenyl)-2,4-dimethyl-6-oxo-N-[4-[(7-prop-1-en-2-yl-1,5-naphthyridin-4-yl)oxy]phenyl]pyrimidine-5-carboxamide (467): Compound NA1-1 was replaced with Compound NA1-25. Compound PA1-2 was replaced with Compound HA4-6. MS for $C_{30}H_{24}FN_5O_3$: m/z 522 (MH+).

N-[3-Fluoro-4-[(6-methoxy-7-methyl-1,5-naphthyridin-4-yl)oxy]phenyl]-1-(4-fluorophenyl)-2,4-dimethyl-6-oxopyrimidine-5-carboxamide (468): Compound NA1-1 was replaced with Compound NA1-26. Compound PA1-2 was replaced with Compound HA4-6. $^1$H NMR (400 MHz, DMSO-d$_6$) δ 12.9 (s, 1H), 8.58 (d, 1H), 8.13 (s, 1H), 8.01 (dd, 1H), 7.46 (dd, 1H), 7.34 (m, 1H), 7.15 (m, 4H), 6.94 (d, 1H), 3.93 (s, 3H), 2.35 (s, 3H), 2.14 (s, 3H), 2.09 (s, 3H); MS for C$_{29}$H$_{23}$F$_2$N$_5$O$_4$: m/z 544 (MH+).

N-[3-Fluoro-4-[(6-methoxy-7-methyl-1,5-naphthyridin-4-yl)oxy]phenyl]-5-(4-fluorophenyl)-4-hydroxy-2-(methoxymethyl)-6-methylpyridine-3-carboxamide (469): Compound NA1-1 was replaced with Compound NA1-26. Compound PA1-2 was replaced with Compound PA5-11. MS for C$_{31}$H$_{26}$F$_2$N$_4$O$_5$: m/z 573 (MH+).

N-[3-Fluoro-4-[(6-methoxy-7-methyl-1,5-naphthyridin-4-yl)oxy]phenyl]-5-(4-fluoro-2-methylphenyl)-4-hydroxy-2-(methoxymethyl)-6-methylpyridine-3-carboxamide (470): Compound NA1-1 was replaced with Compound NA1-26. Compound PA1-2 was replaced with Compound PA5-5. MS for C$_{32}$H$_{28}$F$_2$N$_4$O$_5$: m/z 587 (MH+).

N-[3-Fluoro-4-[(6-methoxy-7-methyl-1,5-naphthyridin-4-yl)oxy]phenyl]-5-(4-fluoro-2-methylphenyl)-4-hydroxy-2,6-dimethylpyridine-3-carboxamide (471): Compound NA1-1 was replaced with Compound NA1-26. Compound PA1-2 was replaced with Compound PA7-2. MS for C$_{31}$H$_{26}$F$_2$N$_4$O$_4$: m/z 557 (MH+).

N-[3-Fluoro-4-[(6-methoxy-7-methyl-1,5-naphthyridin-4-yl)oxy]phenyl]-5-(4-fluorophenyl)-6-methyl-4-oxo-1H-pyridazine-3-carboxamide (472): Compound NA1-1 was replaced with Compound NA1-26. Compound PA1-2 was replaced with Compound HA2-1. MS for C$_{28}$H$_{21}$F$_2$N$_5$O$_4$: m/z 530 (MH+).

N-[3-Fluoro-4-[(6-methoxy-7-methyl-1,5-naphthyridin-4-yl)oxy]phenyl]-5-(4-fluoro-2-methylphenyl)-6-methyl-4-oxo-1H-pyridazine-3-carboxamide (473): Compound NA1-1 was replaced with Compound NA1-26. Compound PA1-2 was replaced with Compound HA2-2. MS for C$_{29}$H$_{23}$F$_2$N$_5$O$_4$: m/z 544 (MH+).

5-(4-Fluoro-2-methylphenyl)-N-[3-fluoro-4-[(7-prop-1-en-2-yl-1,5-naphthyridin-4-yl)oxy]phenyl]-4-hydroxy-2-methylpyridine-3-carboxamide (474): Compound NA1-1 was replaced with Compound NA1-24. Compound PA1-2 was replaced with Compound PA7-23. MS for C$_{31}$H$_{24}$F$_2$N$_4$O$_3$: m/z 539 (MH+).

1-Ethyl-5-(4-fluorophenyl)-N-[3-fluoro-4-[(7-prop-1-en-2-yl-1,5-naphthyridin-4-yl)oxy]phenyl]-6-methyl-4-oxopyridazine-3-carboxamide (475): Compound NA1-1 was replaced with Compound NA1-24. Compound PA1-2 was replaced with Compound HA2-4A. $^1$H NMR (400 MHz, DMSO-d$_6$) δ 12.7 (s, 1H), 9.27 (s, 1H), 8.79 (d, 1H), 8.38 (s, 1H), 8.05 (d, 1H), 7.51 (d, 1H), 7.45 (m, 1H), 7.34 (m, 4H), 6.88 (d, 1H), 5.88 (s, 1H), 5.44 (s, 1H), 4.41 (q, 2H), 2.37 (s, 3H), 2.29 (s, 3H), 1.46 (t, 3H); MS for C$_{31}$H$_{25}$F$_2$N$_5$O$_3$: m/z 554 (MH+).

4-Ethoxy-5-(4-fluorophenyl)-N-[3-fluoro-4-[(7-prop-1-en-2-yl-1,5-naphthyridin-4-yl)oxy]phenyl]-6-methylpyridazine-3-carboxamide (476): Compound NA1-1 was replaced with Compound NA1-24. Compound PA1-2 was replaced with Compound HA2-4B. $^1$H NMR (400 MHz, DMSO-d$_6$) δ 11.7 (s, 1H), 9.27 (s, 1H), 8.79 (d, 1H), 8.39 (s, 1H), 7.95 (d, 1H), 7.52 (d, 2H), 7.46 (m, 2H), 7.29 (t, 2H), 6.94 (d, 1H), 5.89 (s, 1H), 5.45 (s, 1H), 4.47 (q, 2H), 2.29 (s, 3H), 2.28 (s, 3H), 1.57 (t, 3H); MS for C$_{30}$H$_{25}$F$_2$N$_5$O$_3$: m/z 554 (MH+).

5-(4-Fluorophenyl)-N-[3-fluoro-4-[(7-prop-1-en-2-yl-1,5-naphthyridin-4-yl)oxy]phenyl]-1,6-dimethyl-4-oxopyridazine-3-carboxamide (477): Compound NA1-1 was replaced with Compound NA1-24. Compound PA1-2 was replaced with Compound HA2-3. MS for C$_{30}$H$_{23}$F$_2$N$_5$O$_3$: m/z 540 (MH+).

5-(4-Fluorophenyl)-N-[3-fluoro-4-[(7-prop-1-en-2-yl-1,5-naphthyridin-4-yl)oxy]phenyl]-4-methoxy-6-methylpyridazine-3-carboxamide (478): Compound NA1-1 was replaced with Compound NA1-24. Compound PA1-2 was replaced with Compound HA2-3B. MS for C$_{30}$H$_{23}$F$_2$N$_5$O$_3$: m/z 540 (MH+).

N-[4-[(6,7-Dimethoxy-1,5-naphthyridin-4-yl)oxy]-3-fluorophenyl]-5-(4-fluoro-2-methylphenyl)-4-hydroxy-2-methylpyridine-3-carboxamide (479): Compound PA1-2 was replaced with Compound PA7-23. MS for C$_{30}$H$_{24}$F$_2$N$_4$O$_5$: m/z 559.2 (MH+).

N-[3-Fluoro-4-[(6-methoxy-1,5-naphthyridin-4-yl)oxy]phenyl]-5-(4-fluoro-2-methylphenyl)-4-hydroxy-2-methylpyridine-3-carboxamide (480): Compound NA1-1 was replaced with Compound NA1-10. Compound PA1-2 was replaced with Compound PA7-23. MS for C$_{29}$H$_{22}$F$_2$N$_4$O$_4$: m/z 529.2 (MH+).

N-[4-[(6,7-Dimethoxy-1,5-naphthyridin-4-yl)oxy]-3-fluorophenyl]-5-(4-fluoro-2-methylphenyl)-1,2-dimethyl-4-oxopyridine-3-carboxamide (481): Compound PA1-2 was replaced with Compound PA7-33. $^1$H NMR (400 MHz, DMSO-d$_6$) δ 11.50 (s, 1H), 8.53 (d, 1H), 7.98-7.91 (m, 1H), 7.89 (s, 1H), 7.65 (s, 1H), 7.47-7.42 (m, 1H), 7.34 (t, 1H), 7.20-6.99 (m, 3H), 6.78 (d, 1H), 3.97 (s, 3H), 3.97 (s, 3H), 3.74 (s, 3H), 2.54 (s, 3H), 2.19 (s, 3H); MS for C$_{31}$H$_{26}$F$_2$N$_4$O$_5$: m/z 573.2 (MH+).

N-[3-Fluoro-4-[[6-methoxy-7-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide (482): Compound NA1-1 was replaced with Compound NA1-19. Compound PA1-2 was replaced with Compound PA5-11. MS for C$_{33}$H$_{30}$F$_2$N$_4$O$_7$: m/z 633.2 (MH+).

N-[3-Fluoro-4-[(6-methoxy-1,5-naphthyridin-4-yl)oxy]phenyl]-5-(4-fluoro-2-methylphenyl)-1,2-dimethyl-4-oxopyridine-3-carboxamide (483): Compound NA1-1 was replaced with Compound NA1-10. Compound PA1-2 was replaced with Compound PA7-33. MS for C$_{30}$H$_{24}$F$_2$N$_4$O$_4$: m/z 543.2 (MH+).

N-[3-Fluoro-4-[[6-methoxy-7-(2-methoxyethoxy)-1,5-naphthyridin-4-yl]oxy]phenyl]-1-(4-fluorophenyl)-6-methyl-2-oxopyridine-3-carboxamide (484): Compound NA1-1 was replaced with Compound NA1-19. Compound PA1-2 was replaced with Compound HA1-1. MS for C$_{31}$H$_{26}$F$_2$N$_4$O$_6$: m/z 589.2 (MH+).

N-[3-Fluoro-4-[[6-methoxy-7-(2-methoxyethoxy)-1,5-naphthyridin-4-yl]oxy]phenyl]-1-(4-fluorophenyl)-4,6-dimethyl-2-oxopyridine-3-carboxamide (485): Compound NA1-1 was replaced with Compound NA1-19. Compound PA1-2 was replaced with Compound HA1-5. MS for C$_{32}$H$_{28}$F$_2$N$_4$O$_6$: m/z 603.2 (MH+).

N-[3-Fluoro-4-[[6-methoxy-7-(2-methoxyethoxy)-1,5-naphthyridin-4-yl]oxy]phenyl]-5-(4-fluorophenyl)-1,6-dimethyl-4-oxopyridine-3-carboxamide (486): Compound NA1-1 was replaced with Compound NA1-19. Compound PA1-2 was replaced with Compound PA3-7. MS for C$_{32}$H$_{28}$F$_2$N$_4$O$_6$: m/z 603.2 (MH+).

N-[3-Fluoro-4-[[6-methoxy-7-(2-methoxyethoxy)-1,5-naphthyridin-4-yl]oxy]phenyl]-5-(4-fluoro-2-methylphenyl)-4-hydroxy-2,6-dimethylpyridine-3-carboxamide (487): Compound NA-1 was replaced with Compound NA1-19. Compound PA1-2 was replaced with Compound PA7-2. MS for C$_{33}$H$_{30}$F$_2$N$_4$O$_6$: m/z 617.2 (MH+).

4-Chloro-N-[4-[(6,7-dimethoxy-1,5-naphthyridin-4-yl)oxy]-3-fluorophenyl]-5-(4-fluorophenyl)-6-methylpyridazine-3-carboxamide (488): Compound PA1-2 was replaced with Compound HA2-11. MS for C$_{28}$H$_{20}$ClF$_2$N$_5$O$_4$: m/z 564.2 (MH+).

N-[4-[(6,7-Dimethoxy-1,5-naphthyridin-4-yl)oxy]-3-fluorophenyl]-5-(4-fluoro-2-methylphenyl)-4-methoxy-6-methylpyridazine-3-carboxamide (489): Compound PA1-2 was replaced with Compound HA2-6B. MS for $C_{30}H_{25}F_2N_5O_5$: m/z 574.1 (MH+).

5-Bromo-N-[4-[(6,7-dimethoxy-1,5-naphthyridin-4-yl)oxy]-3-fluorophenyl]-4-hydroxy-2-methylpyridine-3-carboxamide (490): Compound PA1-2 was replaced with Compound PA7-24. MS for $C_{23}H_{15}BrFN_4O_5$: m/z 531.0 (MH+).

N-[4-[(6,7-Dimethoxy-1,5-naphthyridin-4-yl)oxy]-3-fluorophenyl]-8-(4-fluorophenyl)-2-methyl-7-oxo-[1,3]oxazolo[3,2-a]pyridine-6-carboxamide (491): Compound PA1-2 was replaced with Compound PA7-31. MS for $C_{31}H_{22}F_2N_4O_6$: m/z 585.1 (MH+).

N-[4-[(6,7-Dimethoxy-1,5-naphthyridin-4-yl)oxy]-3-fluorophenyl]-4-hydroxy-2-(methoxymethyl)-6-methylpyridine-3-carboxamide (492): Compound PA1-2 was replaced with Compound E3-1. MS for $C_{25}H_{23}FN_4O_6$: m/z 495.1 (MH+).

5-(4-Fluoro-2-methylphenyl)-4-hydroxy-N-[4-[(6-methoxy-1,5-naphthyridin-4-yl)oxy]phenyl]-2-methylpyridine-3-carboxamide (493): Compound NA1-1 was replaced with Compound NA1-17. Compound PA1-2 was replaced with Compound PA7-23. MS for $C_{29}H_{23}FN_4O_4$: m/z 511.2 (MH+).

N-[3-Fluoro-4-[(6-methoxy-1,7-naphthyridin-4-yl)oxy]phenyl]-1-(4-fluorophenyl)-6-methyl-2-oxopyridine-3-carboxamide (494): Compound NA1-1 was replaced with Compound NA3-1. Compound PA1-2 was replaced with Compound HA-1. MS for $C_{28}H_{20}F_2N_4O_4$: m/z 515.2 (MH+).

N-[4-[(6-Chloro-1,7-naphthyridin-4-yl)oxy]-3-fluorophenyl]-1-(4-fluorophenyl)-6-methyl-2-oxopyridine-3-carboxamide (496): Compound NA1-1 was replaced with Compound NA3-2. Compound PA1-2 was replaced with Compound HA1-1. $^1$H NMR (400 MHz, DMSO-$d_6$) δ 12.06 (s, 1H), 9.25 (s, 1H), 8.80 (d, 1H), 8.44 (d, 1H), 8.23 (d, 1H), 8.03 (dd, 1H), 7.56-7.22 (m, 5H), 6.87 (d, 1H), 6.66 (d, 2H), 2.02 (s, 3H); MS for $C_{27}H_7ClF_2N_4O_3$: m/z 519.0 (MH+).

N-[4-[(6-Chloro-1,7-naphthyridin-4-yl)oxy]-3-fluorophenyl]-1-(4-fluorophenyl)-2-methyl-6-oxopyrimidine-5-carboxamide (497): Compound NA1-1 was replaced with Compound NA3-2. Compound PA1-2 was replaced with Compound HA4-2. MS for $C_{26}H_{16}ClF_2N_5O_3$: m/z 520.0 (MH+).

N-[4-[(6-Chloro-1,7-naphthyridin-4-yl)oxy]-3-fluorophenyl]-4-(4-fluorophenyl)-5-methyl-3-oxopyrazine-2-carboxamide (498): Compound NA1-1 was replaced with Compound NA3-2. Compound PA1-2 was replaced with Compound HA3-1. MS for $C_{26}H_{16}ClF_2N_5O_3$: m/z 520.0 (MH+).

N-[3-Fluoro-4-[(6-methoxy-1,7-naphthyridin-4-yl)oxy]phenyl]-1-(4-fluorophenyl)-2-methyl-6-oxopyrimidine-5-carboxamide (499): Compound NA1-1 was replaced with Compound NA3-1. Compound PA1-2 was replaced with Compound HA4-2. MS for $C_{27}H_{19}F_2N_5O_4$: m/z 516.0 (MH+).

N-[3-Fluoro-4-[(6-methoxy-1,7-naphthyridin-4-yl)oxy]phenyl]-4-(4-fluorophenyl)-5-methyl-3-oxopyrazine-2-carboxamide (500): Compound NA1-1 was replaced with Compound NA3-1. Compound PA1-2 was replaced with Compound HA3-1. MS for $C_{27}H_{19}F_2N_5O_4$: m/z 516.0 (MH+).

N-[4-[(6,7-Dimethoxy-1,5-naphthyridin-4-yl)oxy]-3-fluorophenyl]-5-(4-fluoro-2-methylphenyl)-1-methyl-4-oxopyridine-3-carboxamide (503): Compound PA1-2 was replaced with Compound PA3-12. MS for $C_{30}H_{24}F_2N_4O_5$: m/z 559.2 (MH+).

N-[4-[(6,7-Dimethoxy-1,5-naphthyridin-4-yl)oxy]-3-fluorophenyl]-6-ethyl-5-(4-fluorophenyl)-4-hydroxypyridine-3-carboxamide (504): Compound PA1-2 was replaced with Compound PA7-18. MS for $C_{30}H_{24}F_2N_4O_5$: m/z 559.2 (MH+).

5-(4-Fluoro-2-methylphenyl)-N-[3-fluoro-4-(1,5-naphthyridin-4-yloxy)phenyl]-4-hydroxy-2,6-dimethylpyridine-3-carboxamide (505): Compound NA1-1 was replaced with Compound NA1-21. Compound PA1-2 was replaced with Compound PA7-2. MS for $C_{29}H_{22}F_2N_4O_3$: m/z 513 (MH+).

N-[3-Fluoro-4-[(6-methyl-1,5-naphthyridin-4-yl)oxy]phenyl]-5-(4-fluoro-2-methylphenyl)-4-hydroxy-2,6-dimethylpyridine-3-carboxamide (506): Compound NA1-1 was replaced with Compound NA1-33. Compound PA1-2 was replaced with Compound PA7-2. MS for $C_{30}H_{24}F_2N_4O_3$: m/z 527 (MH+).

5-(4-Fluoro-2-methylphenyl)-4-hydroxy-2,6-dimethyl-N-[4-[(6-methyl-1,5-naphthyridin-4-yl)oxy]phenyl]pyridine-3-carboxamide (507): Compound NA1-1 was replaced with Compound NA1-34. Compound PA1-2 was replaced with Compound PA7-2. MS for $C_{30}H_{25}FN_4O_3$: m/z 509 (MH+).

N-[3-Fluoro-4-[(7-methoxy-1,5-naphthyridin-4-yl)oxy]phenyl]-5-(4-fluorophenyl)-1,2,6-trimethyl-4-oxopyridine-3-carboxamide (508): Compound NA1-1 was replaced with Compound NA1-3. Compound PA1-2 was replaced with Compound PA6-5. MS for $C_{30}H_{24}F_2N_4O_4$: m/z 543 (MH+).

2-Ethyl-5-(4-fluorophenyl)-4-hydroxy-N-[4-[(6-methoxy-1,5-naphthyridin-4-yl)oxy]phenyl]-6-methylpyridine-3-carboxamide (509): Compound NA1-1 was replaced with Compound NA1-17. Compound PA1-2 was replaced with Compound PA5-7. MS for $C_{30}H_{25}FN_4O_4$: m/z 525 (MH+).

5-(4-Fluorophenyl)-4-hydroxy-2-(methoxymethyl)-N-[4-[(6-methoxy-1,5-naphthyridin-4-yl)oxy]phenyl]-6-methylpyridine-3-carboxamide (510): Compound NA1-1 was replaced with Compound NA1-17. Compound PA1-2 was replaced with Compound PA5-11. MS for $C_{30}H_{25}FN_4O_5$: m/z 541 (MH+).

N-[4-[(6,7-Dimethoxy-1,5-naphthyridin-4-yl)oxy]-3-fluorophenyl]-5-(4-fluorophenyl)-1,2,6-trimethyl-4-oxopyridine-3-carboxamide (511): Compound PA1-2 was replaced with Compound PA6-5. MS for $C_{30}H_{26}F_2N_4O_5$: m/z 573 (MH+).

N-[4-[(6,7-Dimethoxy-1,5-naphthyridin-4-yl)oxy]-3-fluorophenyl]-5-(4-fluoro-2-methylphenyl)-1,6-dimethyl-4-oxopyridazine-3-carboxamide (512): Compound PA1-2 was replaced with Compound HA2-6A. MS for $C_{30}H_{25}F_2N_5O_5$: m/z 574 (MH+).

N-[3-Fluoro-4-[(7-methoxy-1,5-naphthyridin-4-yl)oxy]phenyl]-5-(4-fluoro-2-methylphenyl)-1,6-dimethyl-4-oxopyridazine-3-carboxamide (513): Compound NA1-1 was replaced with Compound NA1-3. Compound PA1-2 was replaced with Compound HA2-6A. $^1$H NMR (400 MHz, CD$_3$OD) δ 9.04-8.96 (m, 2H), 8.16-8.08 (m, 1H), 7.80 (d, 1H), 7.59 (dt, 2H), 7.27 (d, 1H), 7.21-7.05 (m, 3H), 4.59 (s, 3H), 4.19 (s, 3H), 2.26 (s, 3H), 2.20 (s, 3H); MS for $C_{29}H_{23}F_2N_5O_4$: m/z 544 (MH+).

5-(4-Fluoro-2-methylphenyl)-N-[4-[(7-methoxy-1,5-naphthyridin-4-yl)oxy]phenyl]-1,6-dimethyl-4-oxopyridazine-3-carboxamide (514): Compound NA1-1 was replaced with Compound NA1-6. Compound PA1-2 was replaced with Compound HA2-6A. $^1$H NMR (400 MHz, CD$_3$OD) δ 9.02-8.90 (m, 2H), 8.00 (dd, 2H), 7.78 (d, 1H), 7.49-7.42 (m, 2H), 7.22-7.06 (m, 4H), 4.58 (d, 3H), 4.19 (d, 3H), 2.33-2.19 (m, 6H); MS for $C_{29}H_{24}FN_5O_4$: m/z 526 (MH+).

5-(4-Fluorophenyl)-4-methoxy-N-[4-[(7-methoxy-1,5-naphthyridin-4-yl)oxy]phenyl]-6-methylpyridazine-3-carboxamide (515): Compound NA1-1 was replaced with Compound NA1-6. Compound PA1-2 was replaced with Compound HA2-3B. MS for $C_{28}H_{22}FN_5O_4$: m/z 512 (MH+).

5-(4-Fluoro-2-methylphenyl)-4-hydroxy-2-(methoxymethyl)-N-[4-[(6-methoxy-1,5-naphthyridin-4-yl)oxy]phenyl]-6-methylpyridine-3-carboxamide (516): Compound NA1-1 was replaced with Compound NA1-17. Compound PA1-2 was replaced with Compound PA5-5. MS for $C_{31}H_{27}FN_4O_5$: m/z 555 (MH+).

N-[4-[(6,7-Dimethoxy-1,5-naphthyridin-4-yl)oxy]phenyl]-5-(4-fluoro-2-methylphenyl)-1,6-dimethyl-4-oxopyridazine-3-carboxamide (517): Compound NA1-1 was replaced with Compound NA1-2. Compound PA1-2 was replaced with Compound HA2-6A. MS for $C_{30}H_{26}FN_5O_5$: m/z 556 (MH+).

N-[4-[(6,7-Dimethoxy-1,5-naphthyridin-4-yl)oxy]-3-fluorophenyl]-5-[4-fluoro-2-(hydroxymethyl)phenyl]-4-hydroxy-2,6-dimethylpyridine-3-carboxamide (518): Compound PA1-2 was replaced with Compound PA7-21. MS for $C_{30}H_{26}F_2N_4O_6$: m/z 589 (MH+).

N-[4-[(6,7-Dimethoxy-1,5-naphthyridin-4-yl)oxy]-3-fluorophenyl]-2-(4-fluorophenyl)-6-methyl-3-oxopyridazine-4-carboxamide (519): Compound PA1-2 was replaced with Compound HA2-12. MS for $C_{28}H_{21}F_2N_5O_5$: m/z 546 (MH+).

N-[4-[(6,7-Dimethoxy-1,5-naphthyridin-4-yl)oxy]phenyl]-2-(4-fluorophenyl)-6-methyl-3-oxopyridazine-4-carboxamide (520): Compound NA1-1 was replaced with Compound NA1-2. Compound PA1-2 was replaced with Compound HA2-12. MS for $C_{28}H_{22}FN_5O_5$: m/z 528 (MH+).

N-[3-Fluoro-4-[(7-methoxy-1,5-naphthyridin-4-yl)oxy]phenyl]-2-(4-fluorophenyl)-6-methyl-3-oxopyridazine-4-carboxamide (521): Compound NA1-1 was replaced with Compound NA1-3. Compound PA1-2 was replaced with Compound HA2-12. $^1$H NMR (400 MHz, CD$_3$OD) δ 12.13 (s, 1H), 8.86 (s, 1H), 8.81 (d, 1H), 8.33 (s, 1H), 8.08 (d, 1H), 7.74 (d, 1H), 7.63 (dd, 2H), 7.53 (d, 1H), 7.44 (t, 1H), 7.28 (t, 2H), 6.99 (d, 1H), 4.12 (s, 3H), 2.55 (s, 3H); MS for $C_{27}H_{19}F_2N_5O_4$: m/z 516 (MH+).

2-(4-Fluorophenyl)-N-[4-[(7-methoxy-1,5-naphthyridin-4-yl)oxy]phenyl]-6-methyl-3-oxopyridazine-4-carboxamide (522): Compound NA1-1 was replaced with Compound NA1-6. Compound PA1-2 was replaced with Compound HA2-12. $^1$H NMR (400 MHz, CD$_3$OD) δ 12.08 (s, 1H), 8.98 (d, 1H), 8.92 (d, 1H), 8.34 (s, 1H), 8.01 (d, 2H), 7.78 (d, 1H), 7.68 (dd, 2H), 7.43 (d, 2H), 7.31 (t, 2H), 7.18 (d, 1H), 4.19 (s, 3H), 2.54 (s, 3H); MS for $C_{27}H_{20}FN_5O_4$: m/z 498 (MH+).

N-[4-[(6,7-Dimethoxy-1,5-naphthyridin-4-yl)oxy]phenyl]-5-(4-fluorophenyl)-1,2,6-trimethyl-4-oxopyridine-3-carboxamide (523): Compound NA1-1 was replaced with Compound NA1-2. Compound PA1-2 was replaced with Compound PA6-5. MS for $C_{31}H_{27}FN_4O_5$: m/z 555 (MH+).

N-[4-[(6,7-Dimethoxy-1,5-naphthyridin-4-yl)oxy]-3-fluorophenyl]-2-(4-fluorophenyl)-5,6-dimethyl-3-oxopyridazine-4-carboxamide (524): Compound PA1-2 was replaced with Compound HA2-15. MS for $C_{29}H_{23}F_2N_5O_5$: m/z 560 (MH+).

N-[3-Fluoro-4-(6-methoxyquinolin-4-yl)oxyphenyl]-5-(4-fluorophenyl)-4-hydroxy-2-(methoxymethyl)-6-methylpyridine-3-carboxamide (525): Compound NA1-1 was replaced with Compound QA1-7. Compound PA1-2 was replaced with Compound PA5-11. MS for $C_{31}H_{25}F_2N_3O_5$: m/z 558 (MH+).

2-Ethyl-5-(4-fluoro-2-methylphenyl)-4-hydroxy-N-[4-[(6-methoxy-1,5-naphthyridin-4-yl)oxy]phenyl]-6-methylpyridine-3-carboxamide (526): Compound NA1-1 was replaced with Compound NA1-17. Compound PA1-2 was replaced with Compound PA5-8. MS for $C_{31}H_{27}FN_4O_4$: m/z 539 (MH+).

N-[4-[(6,7-Dimethoxy-1,5-naphthyridin-4-yl)oxy]-3-fluorophenyl]-2-(4-fluoro-2-methylphenyl)-3-oxopyridazine-4-carboxamide (527): Compound PA1-2 was replaced with Compound HA2-13. MS for $C_{28}H_{21}F_2N_5O_5$: m/z 546 (MH+).

N-[4-[(6,7-Dimethoxy-1,5-naphthyridin-4-yl)oxy]phenyl]-2-(4-fluoro-2-methylphenyl)-3-oxopyridazine-4-carboxamide (528): Compound NA1-1 was replaced with Compound NA1-2. Compound PA1-2 was replaced with Compound HA2-13. MS for $C_{28}H_{22}FN_5O_5$: m/z 528 (MH+).

N-[3-Fluoro-4-[(7-methoxy-1,5-naphthyridin-4-yl)oxy]phenyl]-2-(4-fluoro-2-methylphenyl)-3-oxopyridazine-4-carboxamide (529): Compound NA1-1 was replaced with Compound NA1-3. Compound PA1-2 was replaced with Compound HA2-13. MS for $C_{27}H_{19}F_2N_5O_4$: m/z 516 (MH+).

2-(4-Fluoro-2-methylphenyl)-N-[4-[(7-methoxy-1,5-naphthyridin-4-yl)oxy]phenyl]-3-oxopyridazine-4-carboxamide (530): Compound NA1-1 was replaced with Compound NA1-6. Compound PA1-2 was replaced with Compound HA2-13. MS for $C_{27}H_{20}FN_5O_4$: m/z 498 (MH+).

N-[4-[(6,7-Dimethoxy-1,5-naphthyridin-4-yl)oxy]-3-fluorophenyl]-5-(4-fluorophenyl)-4-methoxy-6-methylpyridazine-3-carboxamide (531): Compound PA1-2 was replaced with Compound HA2-3B. MS for $C_{29}H_{23}F_2N_5O_5$: m/z 560 (MH+).

N-[3-Fluoro-4-[(7-methoxy-1,5-naphthyridin-4-yl)oxy]phenyl]-2-(4-fluorophenyl)-5-(methoxymethyl)-3-oxopyridazine-4-carboxamide (532): Compound NA1-1 was replaced with Compound NA1-3. Compound PA1-2 was replaced with Compound HA2-14. $^1$H NMR (400 MHz, CD$_3$OD) δ 11.90 (s, 1H), 8.83 (d, 1H), 8.69 (d, 1H), 8.58 (s, 1H), 8.01 (dd, 1H), 7.82 (s, 1H), 7.65-7.56 (m, 2H), 7.49-7.41 (m, 1H), 7.34 (t, 1H), 7.28-7.22 (m, 2H), 6.70 (d, 1H), 4.52 (s, 2H), 4.05 (s, 3H), 3.52 (s, 3H); MS for $C_{28}H_{20}F_2N_5O_5$: m/z 546 (MH+).

N-[4-[(6,7-Dimethoxy-1,5-naphthyridin-4-yl)oxy]-3-fluorophenyl]-2-(4-fluorophenyl)-5-(methoxymethyl)-3-oxopyridazine-4-carboxamide (533): Compound PA1-2 was replaced with Compound HA2-14. $^1$H NMR (400 MHz, CD$_3$OD) δ 11.85 (s, 1H), 8.60-8.52 (m, 2H), 7.97 (dd, 1H), 7.69 (s, 1H), 7.64-7.56 (m, 2H), 7.43-7.35 (m, 1H), 7.30-7.18 (m, 3H), 6.82 (d, 1H), 4.52 (s, 2H), 4.09 (d, 6H), 3.51 (s, 3H); MS for $C_{29}H_{23}F_2N_5O_6$: m/z 576 (MH+).

N-[4-[(6,7-Dimethoxy-1,5-naphthyridin-4-yl)oxy]phenyl]-5-(4-fluorophenyl)-4-methoxy-6-methylpyridazine-3-carboxamide (534): Compound NA1-1 was replaced with Compound NA1-2. Compound PA1-2 was replaced with Compound HA2-3B. MS for $C_{29}H_{24}FN_5O_5$: m/z 542 (MH+).

5-Bromo-N-[4-[(6,7-dimethoxy-1,5-naphthyridin-4-yl)oxy]-3-fluorophenyl]-4-hydroxy-2-(methoxymethyl)-6-methylpyridine-3-carboxamide (535): Compound PA1-2 was replaced with Compound C4-A. MS for $C_{25}H_{22}BrFN_4O_6$: m/z 573 (MH+).

N-[4-[(6,7-Dimethoxy-1,5-naphthyridin-4-yl)oxy]-3-fluorophenyl]-6-methyl-4-oxo-1H-pyridazine-3-carboxamide (536): Compound PA1-2 was replaced with Compound HA2-7. MS for $C_{22}H_{18}FN_5O_5$: m/z 452 (MH+).

N-[4-[(6,7-Dimethoxy-1,5-naphthyridin-4-yl)oxy]phenyl]-2-(4-fluorophenyl)-5-(methoxymethyl)-3-oxopyridazine-4-carboxamide (537): Compound NA1-1 was replaced with Compound NA1-2. Compound PA1-2 was replaced with Compound HA2-14. MS for $C_{29}H_{24}FN_5O_6$: m/z 558 (MH+).

N-[3-Fluoro-4-[(6-methoxy-1,5-naphthyridin-4-yl)oxy]phenyl]-5-(4-fluorophenyl)-4-methoxy-6-methylpyridazine-3-carboxamide (538): Compound NA1-1 was replaced with Compound NA1-10. Compound PA1-2 was replaced with Compound HA2-3B. MS for $C_{28}H_{21}F_2N_5O_4$: m/z 530 (MH+).

N-[4-(6,7-Dimethoxyquinolin-4-yl)oxyphenyl]-1-(4-fluorophenyl)-6-oxo-2-propan-2-ylsulfanylpyrimidine-5-carboxamide (539): Compound NA1-1 was replaced with Compound QA1-2. Compound PA1-2 was replaced with Compound HA4-10. MS for $C_{30}H_{27}FN_4O_5S$: m/z 587 (MH+).

4-[4-[[5-(4-Fluorophenyl)-4-hydroxy-6-methylpyridine-3-carbonyl]amino]phenoxy]-7-methoxy-N-methylquinoline-6-carboxamide (540): Compound NA1-1 was replaced with Compound QA1-5. Compound PA1-2 was replaced with Compound PA3-1. MS for $C_{31}H_{25}FN_4O_5$: m/z 553 (MH+).

N-[3-Fluoro-4-[(7-methoxy-6-methyl-1,5-naphthyridin-4-yl)oxy]phenyl]-5-(4-fluorophenyl)-4-hydroxy-6-methylpyridine-3-carboxamide (541): Compound NA1-1 was replaced with Compound NA1-22. Compound PA1-2 was replaced with Compound PA3-1. MS for $C_{29}H_{22}F_2N_4O_4$: m/z 529 (MH+).

N-[2,5-Difluoro-4-[(7-methoxy-6-methyl-1,5-naphthyridin-4-yl)oxy]phenyl]-5-(4-fluorophenyl)-4-hydroxy-6-methylpyridine-3-carboxamide (542): Compound NA1-1 was replaced with Compound NA1-42. Compound PA1-2 was replaced with Compound PA3-1. $^1$H NMR (400 MHz, DMSO-$d_6$) δ 13.48 (s, 1H), 12.67 (s, 1H), 8.70-8.47 (m, 3H), 7.70 (s, 1H), 7.62 (dd, 1H), 7.39-7.15 (m, 4H), 6.79 (dd, 1H), 4.01 (s, 3H), 2.59 (s, 3H), 2.18 (s, 3H); MS for $C_{29}H_{20}F_3N_4O_4$: m/z 547 (MH+).

1-(4-Fluorophenyl)-2-methyl-N-[4-[[8-(methylamino)-1,7-naphthyridin-4-yl]oxy]phenyl]-6-oxopyrimidine-5-carboxamide (543): Compound NA1-1 was replaced with Compound NA3-3. Compound PA1-2 was replaced with Compound HA4-2. $^1$H NMR (400 MHz, DMSO-$d_6$) δ 11.19 (s, 1H), 8.82 (d, 1H), 8.55 (dd, 1H), 7.97 (dd, 1H), 7.90-7.75 (m, 2H), 7.73-7.53 (m, 3H), 7.47 (td, 2H), 7.33-7.16 (m, 2H), 7.07 (dd, 1H), 6.77 (dd, 1H), 2.99 (d, 3H), 2.23 (s, 3H); MS for $C_{27}H_{21}FN_6O_3$: m/z 497 (MH+).

[5-[[4-[(6,7-Dimethoxy-1,5-naphthyridin-4-yl)oxy]-3-fluorophenyl]carbamoyl]-3-(4-fluorophenyl)-4-hydroxypyridin-2-yl]methyl acetate (544): Compound PA1-2 was replaced with Compound PA7-3a. MS for $C_{31}H_{24}F_2N_4O_7$: m/z 603.2 (MH+).

Ethyl 2-(8-(2-fluoro-4-(5-(4-fluorophenyl)-4-hydroxy-6-methylnicotinamido)-phenoxy)-3-methoxy-1,5-naphthyridin-2-yl)acetate (545): Compound NA1-1 was replaced with Compound NA1-49. Compound PA1-2 was replaced with Compound PA3-1. MS for $C_{32}H_{26}F_2N_4O_6$: m/z 601.1 (MH+).

N-(4-((6,7-Dimethoxyquinolin-4-yl)oxy)-3-fluorophenyl)-5-(4-fluorophenyl)-6-methyl-4-oxo-1,4-dihydropyridazine-3-carboxamide (546): Compound NA1-1 was replaced with Compound QA1-1. Compound PA1-2 was replaced with Compound HA2-1. MS for $C_{29}H_{22}F_2N_4O_5$: m/z 545.1 (MH+).

N-(4-((7-Bromo-6-methoxy-1,5-naphthyridin-4-yl)oxy)-3-fluorophenyl)-5-(4-fluorophenyl)-2,6-dimethyl-4-oxo-1,4-dihydropyridine-3-carboxamide (547): Compound NA-1 was replaced with Compound NA1-4. Compound PA1-2 was replaced with Compound PA5-2. MS for $C_{29}H_{21}BrF_2N_4O_4$: m/z 609 (MH+).

N-(4-((7-Bromo-6-methyl-1,5-naphthyridin-4-yl)oxy)phenyl)-5-(4-fluorophenyl)-1-isopropyl-6-methyl-4-oxo-1,4-dihydropyridine-3-carboxamide (548): Compound NA1-1 was replaced with Compound NA1-14. Compound PA1-2 was replaced with Compound PA3-2. MS for $C_{31}H_{26}BrFN_4O_3$: m/z 601 (MH+).

N-(4-((7-Bromo-6-methyl-1,5-naphthyridin-4-yl)oxy)-3-fluorophenyl)-5-(4-fluorophenyl)-4-hydroxy-6-methylnicotinamide (549): Compound NA-1 was replaced with Compound NA1-15. Compound PA1-2 was replaced with Compound PA3-1. MS for $C_{28}H_{19}BrF_2N_4O_3$: m/z 608 (MH+). m/z 577 (MH+).

N-(4-((7-Bromo-6-methyl-1,5-naphthyridin-4-yl)oxy)phenyl)-5-(4-fluorophenyl)-4-hydroxy-6-methylnicotinamide (550): Compound NA1-1 was replaced with Compound NA1-14. Compound PA1-2 was replaced with Compound PA3-1. MS for $C_{28}H_{20}BrFN_4O_3$: m/z 608 (MH+). m/z 559 (MH+).

Additional compounds were made through synthetic modifications made to select compounds listed under Examples 1 and 2. The syntheses of those compounds are detailed in Examples 81-104.

Example 3: N-[4-[(6-Cyano-1,7-naphthyridin-4-yl)oxy]phenyl]-1-(4-fluorophenyl)-6-methyl-2-oxopyridine-3-carboxamide (634)

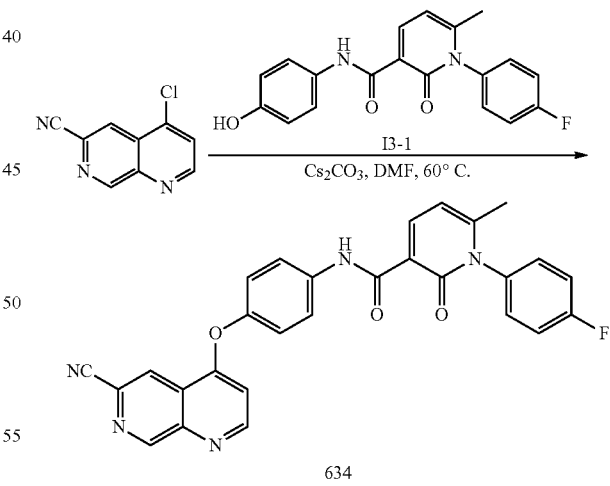

634

N-[4-[(6-Cyano-1,7-naphthyridin-4-yl)oxy]phenyl]-1-(4-fluorophenyl)-6-methyl-2-oxopyridine-3-carboxamide (634): Compound 634 was made by General Procedure J. Specifically, to a solution of 4-chloro-1,7-naphthyridine-6-carbonitrile (70 mg, 0.37 mmol, 1 eq) and Compound I3-1 (137 mg, 0.41 mmol, 1.1 eq) in DMF (1 mL) was added Cs$_2$CO$_3$ (240 mg, 0.74 mmol, 2 eq). The reaction mixture was heated at 60° C. for 12 h. The reaction mixture was diluted with water and extracted with EtOAc (3×50 mL).

The combined organic layers were washed with aq. saturated NaCl (100 mL), dried over anhyd. $Na_2SO_4$ and concentrated. The residue was purified by prep-HPLC (column: Phenomenex Gemini-NX 80*30 mm*3 um; mobile phase: [water (10 mM $NH_4HCO_3$)—ACN]; B %: 43%-73%, 9 min) to give Compound 634. $^1$H NMR (400 MHz, $CD_3OD$) δ 9.42 (s, 1H), 8.92 (d, 1H), 8.82 (s, 1H), 8.58 (d, 1H), 7.86 (d, 2H), 7.44-7.36 (m, 4H), 7.31 (d, 2H), 6.99 (d, 1H), 6.70 (d, 1H), 2.16 (s, 3H); MS for $C_{28}H_{18}FN_5O_3$: m/z 492.1 (MH+).

The following compounds were made using General Procedure J to form compounds of formula J2:

N-[4-(6,7-Dimethoxypyrido[3,2-d]pyrimidin-4-yl)oxy-3-fluorophenyl]-1-(4-fluorophenyl)-6-methyl-2-oxopyridine-3-carboxamide (635): 4-Chloro-1,7-naphthyridine-6-carbonitrile was replaced with 4-chloro-6,7-dimethoxypyrido[3,2-d]pyrimidine (which can be synthesized according to methods known in the art (see, e.g., WO 2019/148036 A1)). Compound I3-1 was replaced with Compound I3-2. MS for $C_{28}H_{21}F_2N_5O_5$: m/z 546 (MH+).

N-[4-(6,7-Dimethoxypyrido[3,2-d]pyrimidin-4-yl)oxy-3-fluorophenyl]-5-(4-fluorophenyl)-4-oxo-1-propan-2-ylpyridine-3-carboxamide (636): 4-Chloro-1,7-naphthyridine-6-carbonitrile was replaced with 4-chloro-6,7-dimethoxypyrido[3,2-d]pyrimidine (which can be synthesized according to methods known in the art (see, e.g., WO 2019/148036 A1)). Compound I3-1 was replaced with Compound I3-3. MS for $C_{30}H_{25}F_2N_5O_5$: m/z 574.0 (MH+).

N-[4-(6,7-Dimethoxypyrido[3,2-d]pyrimidin-4-yl)oxy-3-fluorophenyl]-5-(4-fluorophenyl)-1-(1-methylpyrazol-4-yl)-4-oxopyridine-3-carboxamide (637): 4-Chloro-1,7-naphthyridine-6-carbonitrile was replaced with 4-chloro-6,7-dimethoxypyrido[3,2-d]pyrimidine (which can be synthesized according to methods known in the art (see, e.g., WO 2019/148036 A1)). Compound I3-1 was replaced with Compound I3-4. MS for $C_{31}H_{23}F_2N_7O5$: m/z 612.4 (MH+).

N-[3-Fluoro-4-[6-methoxy-7-(2-methoxyethoxy)pyrido[3,2-d]pyrimidin-4-yl]oxyphenyl]-1-(4-fluorophenyl)-6-methyl-2-oxopyridine-3-carboxamide (638): 4-Chloro-1,7-naphthyridine-6-carbonitrile was replaced with 4-chloro-6-methoxy-7-(2-methoxyethoxy)pyrido[3,2-d]pyrimidine (which can be synthesized according to methods known in the art (see, e.g., WO 2019/148036 A1)). Compound I3-1 was replaced with Compound I3-2. $^1$H NMR (400 MHz, DMSO-$d_6$) δ 12.1 (s, 1H), 8.59 (s, 1H), 8.51 (d, 1H), 7.98 (m, 1H), 7.68 (s, 1H), 7.50 (m, 2H), 7.44 (m, 4H), 6.72 (d, 1H), 4.38 (t, 2H), 4.10 (s, 3H), 3.76 (t, 2H), 3.34 (s, 3H), 2.09 (s, 3H); MS for $C_{30}H_{25}F_2N_5O_6$: m/z 590 (MH+).

N-[3-Fluoro-4-[(6-methoxy-1,7-naphthyridin-4-yl)oxy]phenyl]-5-(4-fluorophenyl)-4-hydroxy-6-methylpyridine-3-carboxamide (639): 4-Chloro-1,7-naphthyridine-6-carbonitrile was replaced with 4-chloro-6-methoxy-1,7-naphthyridine. Compound I3-1 was replaced with Compound I3-5. MS for $C_{28}H_{20}F_2N_4O_4$: m/z 515 (MH+).

1-Cyclopropyl-N-[3-fluoro-4-[(6-methoxy-1,7-naphthyridin-4-yl)oxy]phenyl]-5-(4-fluorophenyl)-6-methyl-4-oxopyridine-3-carboxamide (640): 4-Chloro-1,7-naphthyridine-6-carbonitrile was replaced with 4-chloro-6-methoxy-1,7-naphthyridine. Compound I3-1 was replaced with Compound I3-7. MS for $C_{31}H_{24}F_2N_4O_4$: m/z 555.0 (MH+).

N-[4-[(6-Chloro-1,7-naphthyridin-4-yl)oxy]-3-fluorophenyl]-5-(4-fluorophenyl)-4-hydroxy-6-methylpyridine-3-carboxamide (641): 4-Chloro-1,7-naphthyridine-6-carbonitrile was replaced with 4,6-dichloro-1,7-naphthyridine. Compound I3-1 was replaced with Compound I3-5. MS for $C_{27}H_{17}ClF_2N_4O_3$: m/z 519.0 (MH+).

N-[3-Fluoro-4-(1,7-naphthyridin-4-yloxy)phenyl]-5-(4-fluorophenyl)-4-hydroxy-6-methylpyridine-3-carboxamide (642): 4-Chloro-1,7-naphthyridine-6-carbonitrile was replaced with 4-chloro-1,7-naphthyridine. Compound I3-1 was replaced with Compound I3-5. MS for $C_{27}H_{18}F_2N_4O_3$: m/z 485 (MH+).

5-(4-Fluorophenyl)-4-hydroxy-6-methyl-N-[4-(1,7-naphthyridin-4-yloxy)phenyl]pyridine-3-carboxamide (643): 4-Chloro-1,7-naphthyridine-6-carbonitrile was replaced with 4-chloro-1,7-naphthyridine. Compound I3-1 was replaced with Compound I3-6. MS for $C_{27}H_{19}FN_4O_3$: m/z 467.0 (MH+).

5-(4-Fluorophenyl)-4-hydroxy-N-[4-[(6-methoxy-1,7-naphthyridin-4-yl)oxy]phenyl]-6-methylpyridine-3-carboxamide (644): 4-Chloro-1,7-naphthyridine-6-carbonitrile was replaced with 4-chloro-6-methoxy-1,7-naphthyridine. Compound I3-1 was replaced with Compound I3-6. MS for $C_{28}H_{21}FN_4O_4$: m/z 497 (MH+).

N-[3-Fluoro-4-[(6-methyl-1,7-naphthyridin-4-yl)oxy]phenyl]-5-(4-fluorophenyl)-4-hydroxy-6-methylpyridine-3-carboxamide (645): 4-Chloro-1,7-naphthyridine-6-carbonitrile was replaced with 4-chloro-6-methyl-1,7-naphthyridine. Compound I3-1 was replaced with Compound I3-5. MS for $C_{28}H_{20}F_2N_4O_3$: m/z 499 (MH+).

Example 4: N-[4-(6,7-Dimethoxyquinolin-4-yl)oxy-3-fluorophenyl]-3-(4-fluorophenyl)-4-oxo-2-sulfanylidene-1H-pyrimidine-5-carboxamide (646)

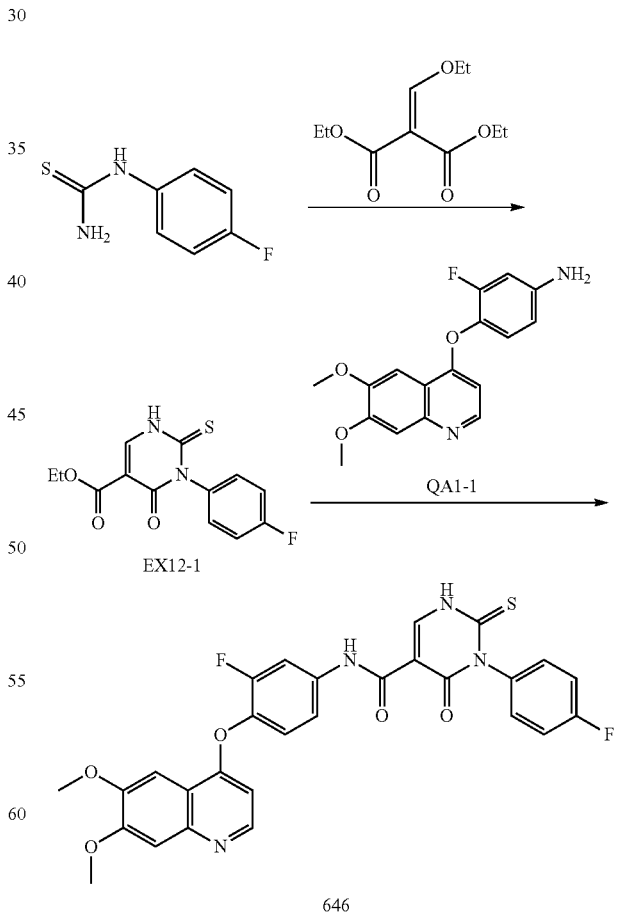

646

Step 1: Ethyl 3-(4-fluorophenyl)-4-oxo-2-thioxo-1,2,3,4-tetrahydropyrimidine-5-carboxylate (EX12-1). A mixture of diethyl 2-(ethoxymethylene)malonate (3.2 mL, 13.8 mmol), 1-(4-fluorophenyl)-thiourea (2.54 g, 15 mmol), and HCl (36% aq., 3.2 mL) in EtOH was refluxed for 6 h. The reaction was cooled to room temperature and filtered. The resulting solid was washed with EtOH and dried to give the Compound EX12-1. MS for $C_{13}HFN_2O_3S$: m/z 295 (MH+).

Step 2: N-[4-(6,7-Dimethoxyquinolin-4-yl)oxy-3-fluorophenyl]-3-(4-fluorophenyl)-4-oxo-2-sulfanylidene-1H-pyrimidine-5-carboxamide (646). To a mixture of Compound EX12-1 (50 mg, 0.17 mmol) and Compound QA1-1 (50 mg, 0.16 mmol) in THF, was added Li[N(SiMe$_3$)$_2$] (2 M in THF, 0.4 mL, 0.8 mmol). The reaction was stirred at room temperature overnight, quenched with aq. saturated NaHCO$_3$ and extracted with EtOAc. The organic extract was concentrated, and the residue purified by silica gel chromatography to give the Compound 646 (83 mg, 93%). $^1$H NMR (400 MHz, DMSO-d$_6$) δ 13.59 (b, 1H), 10.97 (s, 1H), 8.49 (d, 1H), 8.31 (s, 1H), 8.02 (d, 1H), 7.60-7.30 (m, 8H), 6.48 (d, 1H), 3.96 (s, 6H). MS for $C_{28}H_{20}F_2N_4O_5S$: m/z 563 (MH+).

The following compound was made by the same method as Compound 646 in Example 4:

N-[4-[(6,7-Dimethoxy-1,5-naphthyridin-4-yl)oxy]-3-fluorophenyl]-3-(4-fluorophenyl)-4-oxo-2-sulfanylidene-1H-pyrimidine-5-carboxamide (104): Compound QA1-1 was replaced with Compound NA1-1. MS for $C_{27}H_{19}F_2N_5O_5S$: m/z 564 (MH+).

Example 5: 5-(4-Fluorophenyl)-4-hydroxy-6-(hydroxymethyl)nicotinic acid (PA7-3)

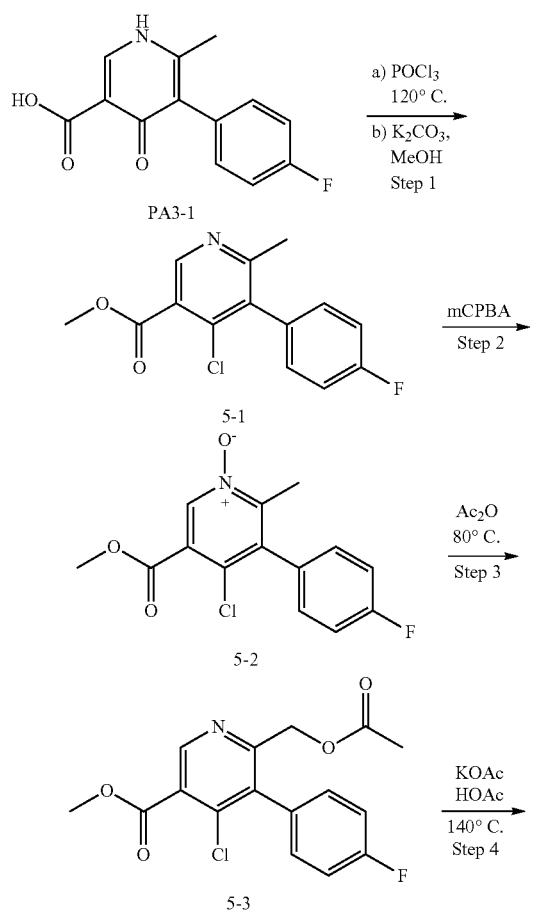

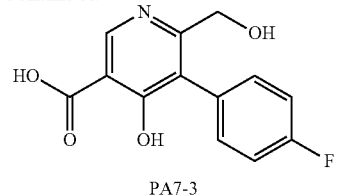

Step 1: Methyl 4-chloro-5-(4-fluorophenyl)-6-methylnicotinate (5-1). A mixture of Compound PA3-1 (2.33 g, 9.42 mmol, 1 eq) and POCl$_3$ (6.7 mL) was heated to 120° C. under microwave irradiation for 25 min. The resulting solution was diluted with DCM and added over 15 min to a mixture of MeOH and K$_2$CO$_3$ at −10° C. The reaction was allowed to warm to room temperature and then concentration in vacuo. The resulting residue was partitioned between and EtOAc (125 mL) and water (125 mL). The organic layer was washed with water (125 mL), washed with aq saturated NaCl (125 mL), dried over anhyd Na$_2$SO$_4$ and concentrated. The resulting residue was purified by silica gel chromatography (0 to 50% EtOAc in hexanes) to give Compound 5-1 (2.78 g, 95%). $^1$H NMR (400 MHz, CDCl$_3$) δ 8.90 (s, 1H), 7.26-7.14 (m, 4H), 3.99 (s, 3H), 2.38 (s, 3H); MS for $C_{14}H_{11}ClFNO_2$: m/z 280 (MH+).

Step 2: 4-Chloro-3-(4-fluorophenyl)-5-(methoxycarbonyl)-2-methylpyridine 1-oxide (5-2). A solution of mCPBA (3.9 g, 16.9 mmol, 1.5 eq) in DCM (26 mL) was added to Compound 5-1 (3.3 g, 11.8 mmol, 1.0 eq) in DCM (26 mL) over 5 min. After the reaction was complete the reaction mixture was adsorbed onto Celite and purified by silica gel chromatography (0 to 100% EtOAc in hexanes) to give Compound 5-2 (2.8 g, 981% yield). $^1$H NMR (400 MHz, CDCl$_3$) δ 8.77 (s, 1H), 7.28-7.15 (m, 4H), 4.00 (s, 3H), 2.35 (s, 3H); MS for $C_{14}H_{11}ClFNO_3$: m/z 296 (MH+).

Step 3: Methyl 6-(acetoxymethyl)-4-chloro-5-(4-fluorophenyl)nicotinate (5-3). A mixture of Compound 5-2 (2.8 g, 9.5 mmol, 1 eq) and acetic anhydride (13 g) was heated at 40° C. for 5 h, 60° C. for 1 h, 80° C. for 1 h, then 40° C. for an additional 12 h. The reaction mixture was adsorbed onto Celite and purified by silica gel Chromatography (0 to 40% EtOAc in hexanes) to give Compound 5-3 (1.8 g, 90% by mass, 50% yield). $^1$H NMR (400 MHz, CDCl$_3$) δ 8.99 (s, 1H), 7.27-7.17 (m, 4H), 4.95 (s, 2H), 4.01 (s, 3H), 2.09 (s, 3H); MS for $C_{16}H_{13}ClFNO_4$: m/z 338 (MH+).

Step 4: 5-(4-Fluorophenyl)-4-hydroxy-6-(hydroxymethyl)nicotinic acid (PA7-3). A mixture of Compound 5-3 (0.94 g, 2.5 mmol, 1 eq), KOAc (0.80 g, 8.1 mmol, 3.2 eq) and acetic acid (1.8 g, 30 mmol, 24 eq) was heated to 140° C. for 1 h, 160° C. for 1 h and 180° C. for 30 min. The reaction mixture was transferred to a separatory funnel, basified with 1M NaOH (pH~13) and washed with EtOAc. The aqueous phase was acidified to pH~2. A precipitate formed and aq saturated NaCl was added to the resulting suspension and further precipitation was observed. The precipitate was isolated via filtration and the mother liquid was extracted with EtOAc (2×). The combined extracts were concentrated and the resulting solid combined with the filtered precipitate to give Compound PA7-3 (0.43 g, 90% by mass, 59% yield). $^1$H NMR (400 MHz, DMSO-d$_6$) δ 12.73 (s, 1H), 8.49 (d, 1H), 7.39-7.24 (m, 4H), 6.11 (s, 1H), 4.39 (s, 2H); MS for $C_{13}H_{10}FNO_4$: m/z 264 (MH+).

Example 6: 6-(Acetoxymethyl)-5-(4-fluorophenyl)-4-hydroxynicotinic acid (PA7-3a)

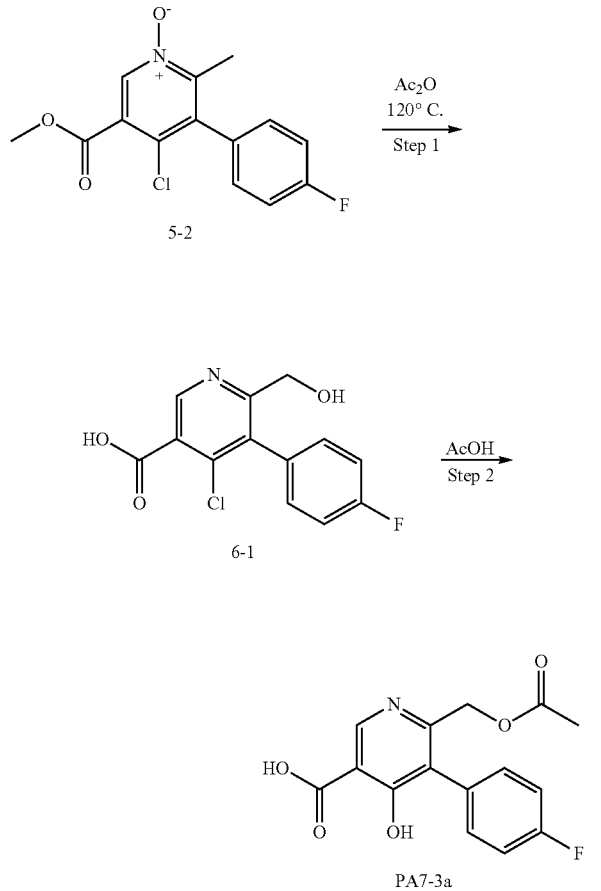

Example 7: 5-(4-Fluorophenyl)-6-(hydroxymethyl)-1-methyl-4-oxo-1,4-dihydropyridine-3-carboxylic acid (PA7-4)

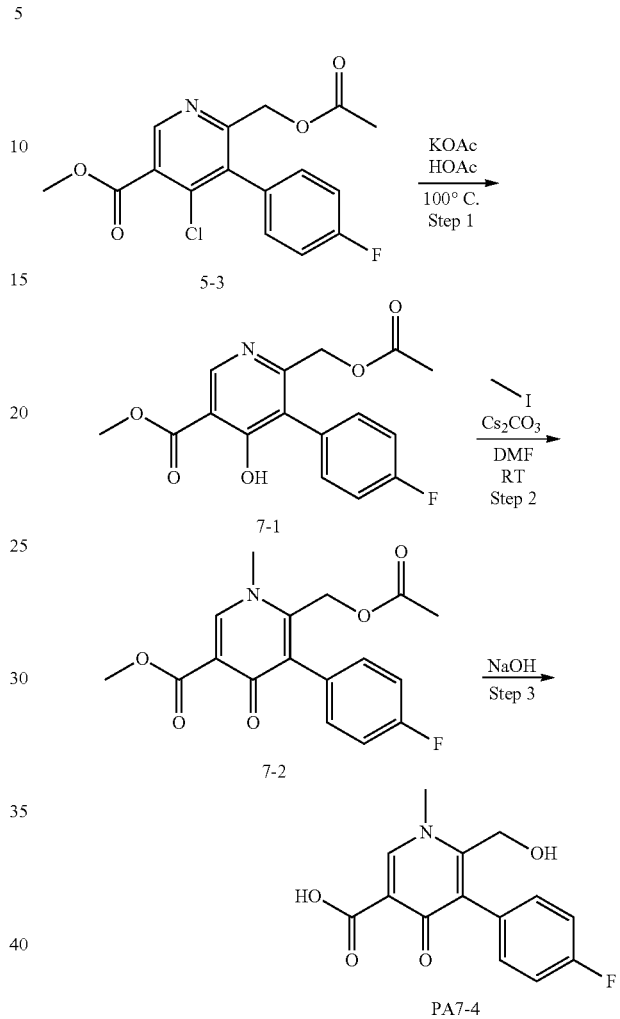

Step 1: 4-Chloro-5-(4-fluorophenyl)-6-(hydroxymethyl) nicotinic acid (6-1). To a solution of Compound 5-2 (3 g, 10.2 mmol, 1 eq) was added acetic anhydride (21.8 g, 213 mmol, 20 mL, 21 eq). The mixture was stirred at 120° C. for 2 h. The reaction mixture was concentrated under reduced pressure. To the resulting residue was added aq NaHCO₃ (200 mL) until a pH of 9-10 was attained. The resulting aq solution was washed with DCM (3×200 mL). The aqueous phase was acidified with 1 N HCl to pH=2 and extracted with DCM (3×200 mL). Both the aqueous phase and combined organic extracts were concentrated under reduced pressure. The resulting residue was purified by column chromatography (SiO₂, Petroleum ether/Ethyl acetate=100/1 to 3/1) to give Compound 6-1 (2 g, 70% yield). MS for $C_{13}H_9ClFNO_3$: m/z 281.8 (MH+).

Step 2: 6-(Acetoxymethyl)-5-(4-fluorophenyl)-4-hydroxynicotinic acid (PA7-3a). A mixture of Compound 6-1 (2 g, 7.1 mmol, 1 eq) in acetic acid (100 mL) was stirred at 120° C. for 16 h under an atmosphere of nitrogen. The reaction mixture was concentrated under reduced pressure. The resulting residue was purified by column chromatography (SiO₂, DCM:MeOH=100/1 to 50/1) to give Compound PA7-3a (230 mg, 10.6% yield). ¹H NMR (400 MHz, DMSO-d₆) δ 8.61 (s, 1H), 7.44-7.22 (m, 5H), 4.89 (s, 2H), 2.03 (s, 3H); MS for $C_{15}H_{12}FNO_5$: m/z 305.9 (MH+).

Step 1: Methyl 6-(acetoxymethyl)-5-(4-fluorophenyl)-4-hydroxynicotinate (7-1). A mixture of Compound 5-3 (1.4 g, 4.15 mmol, 1 eq), KOAc (2.8 g, 28.6 mmol, 6.9 eq) and acetic acid (5 mL) was heated to 100° C. for 14 h. The contents were subsequently cooled and diluted with water (100 mL). Filtration of the resulting precipitate gave Compound 7.1 (1.2 g, 80% by mass, 69% yield). ¹H NMR (400 MHz, DMSO-d₆) δ 11.93 (s, 1H), 8.31 (s, 1H), 7.25 (s, 2H), 7.23 (s, 2H), 4.76 (s, 2H), 3.74 (s, 3H), 2.03 (s, 3H); MS for $C_{16}H_{14}FNO_5$: m/z 320 (MH+).

Step 2: Methyl 6-(acetoxymethyl)-5-(4-fluorophenyl)-1-methyl-4-oxo-1,4-dihydropyridine-3-carboxylate (7-2). A mixture of Compound 7-1 (0.24 g, 0.75 mmol, 1 eq), Cs₂CO₃ (0.33 g, 1.0 mmol, 1.3 eq), DMF (3.0 mL) and methyl iodide (0.12 mL, 1.9 mL, 2.5 eq) was stirred at ambient temperature in a sealed vial. The reaction was allowed to proceed overnight, and then the contents were diluted with aq saturated NaCl (50 mL) and extracted with EtOAc (2×20 mL). The combined extracts were concentrated, and the residue was purified by silica gel chromatography (0% to 100% EtOAc then 0 to 5% MeOH in EtOAc gradient) to give Compound 7-2 (0.16 g, 64% yield). ¹H NMR (400 MHz, CDCl₃) δ 8.30 (s, 1H), 7.18 (ddd, 2H), 7.10 (t, 2H), 4.87 (s, 2H), 3.90 (s, 3H), 3.78 (s, 3H), 2.15 (s, 3H); MS for $C_{17}H_{16}FNO_5$: m/z 334.2 (MH+).

Step 3: 5-(4-Fluorophenyl)-6-(hydroxymethyl)-1-methyl-4-oxo-1,4-dihydropyridine-3-carboxylic acid (PA7-4). Compound 7-2 was converted to Compound PA7-4 using a modification of the ester hydrolysis procedure used in Step 3 of General Procedure A. In this particular case the reaction mixture was heated to reflux for 2 h prior to work up. $^1$H NMR (400 MHz, CD$_3$OD) δ 8.79 (s, 1H), 7.35 (ddd, 2H), 7.28-7.18 (m, 2H), 4.49 (s, 2H), 4.15 (s, 3H); MS for $C_{14}H_{12}FNO_4$: m/z 278 (MH+).

The following compound was made by the same three step procedure as Compound PA7-4 in Example 7:

1-Ethyl-5-(4-fluorophenyl)-6-(hydroxymethyl)-4-oxo-1,4-dihydropyridine-3-carboxylic acid (PA7-28): $^1$H NMR (400 MHz, DMSO-d$_6$) δ 16.34 (s, 1H), 8.86 (s, 1H), 7.39-7.25 (m, 4H), 5.79 (t, 1H), 4.44 (q, 2H), 4.35 (d, 2H), 1.46 (t, 3H); MS for $C_{15}H_{14}FNO_4$: m/z 292 (MH+).

Example 8: 5-(4-Fluoro-2-methylphenyl)-6-(hydroxymethyl)-1-methyl-4-oxo-1,4-dihydropyridine-3-carboxylic acid (PA7-30)

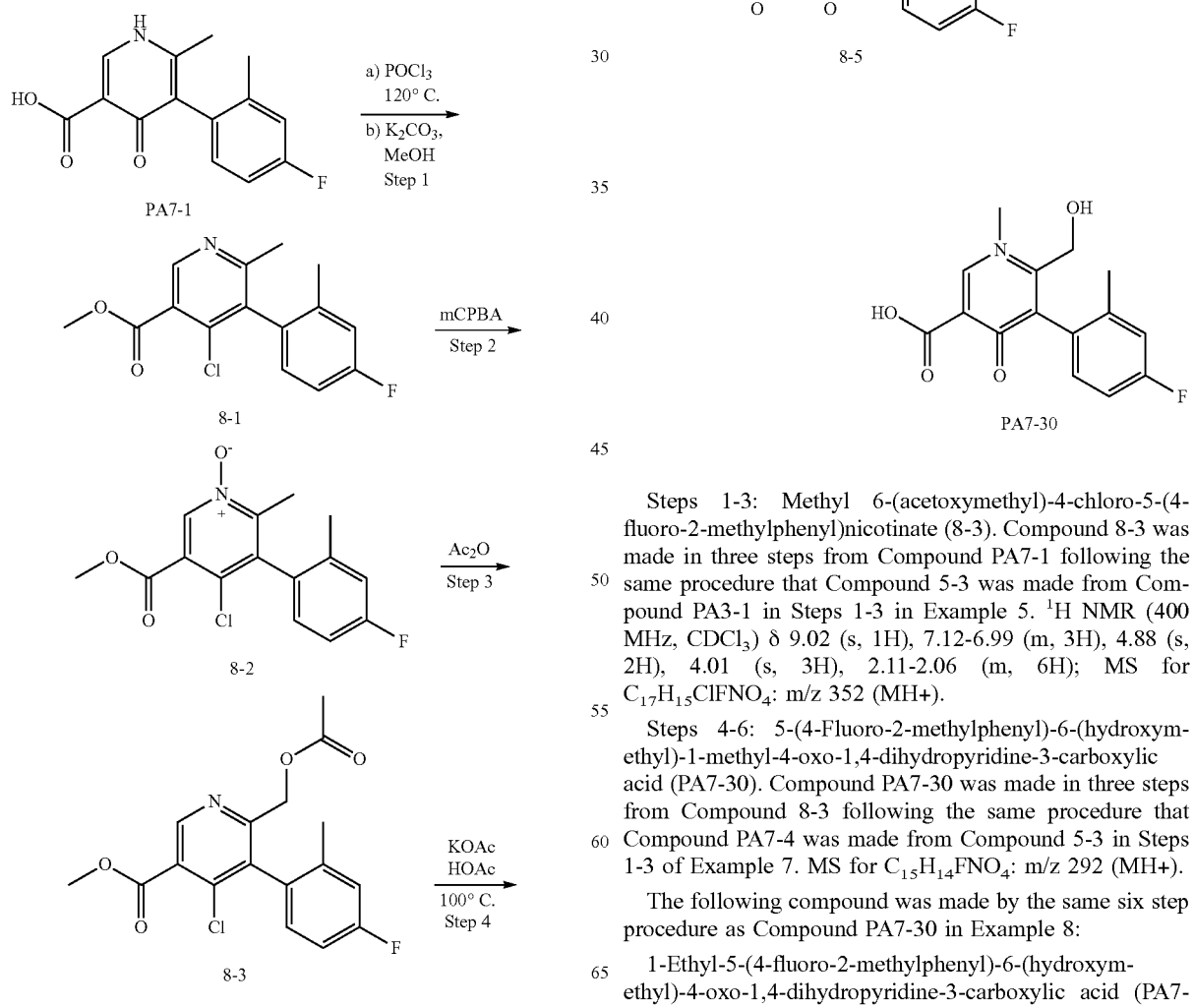

Steps 1-3: Methyl 6-(acetoxymethyl)-4-chloro-5-(4-fluoro-2-methylphenyl)nicotinate (8-3). Compound 8-3 was made in three steps from Compound PA7-1 following the same procedure that Compound 5-3 was made from Compound PA3-1 in Steps 1-3 in Example 5. $^1$H NMR (400 MHz, CDCl$_3$) δ 9.02 (s, 1H), 7.12-6.99 (m, 3H), 4.88 (s, 2H), 4.01 (s, 3H), 2.11-2.06 (m, 6H); MS for $C_{17}H_{15}ClFNO_4$: m/z 352 (MH+).

Steps 4-6: 5-(4-Fluoro-2-methylphenyl)-6-(hydroxymethyl)-1-methyl-4-oxo-1,4-dihydropyridine-3-carboxylic acid (PA7-30). Compound PA7-30 was made in three steps from Compound 8-3 following the same procedure that Compound PA7-4 was made from Compound 5-3 in Steps 1-3 of Example 7. MS for $C_{15}H_{14}FNO_4$: m/z 292 (MH+).

The following compound was made by the same six step procedure as Compound PA7-30 in Example 8:

1-Ethyl-5-(4-fluoro-2-methylphenyl)-6-(hydroxymethyl)-4-oxo-1,4-dihydropyridine-3-carboxylic acid (PA7-36): MS for $C_{16}H_{16}FNO_4$: m/z 306 (MH+).

Example 9: 5-(4-Fluorophenyl)-4-hydroxy-6-(methoxymethyl)nicotinic acid (PA7-17)

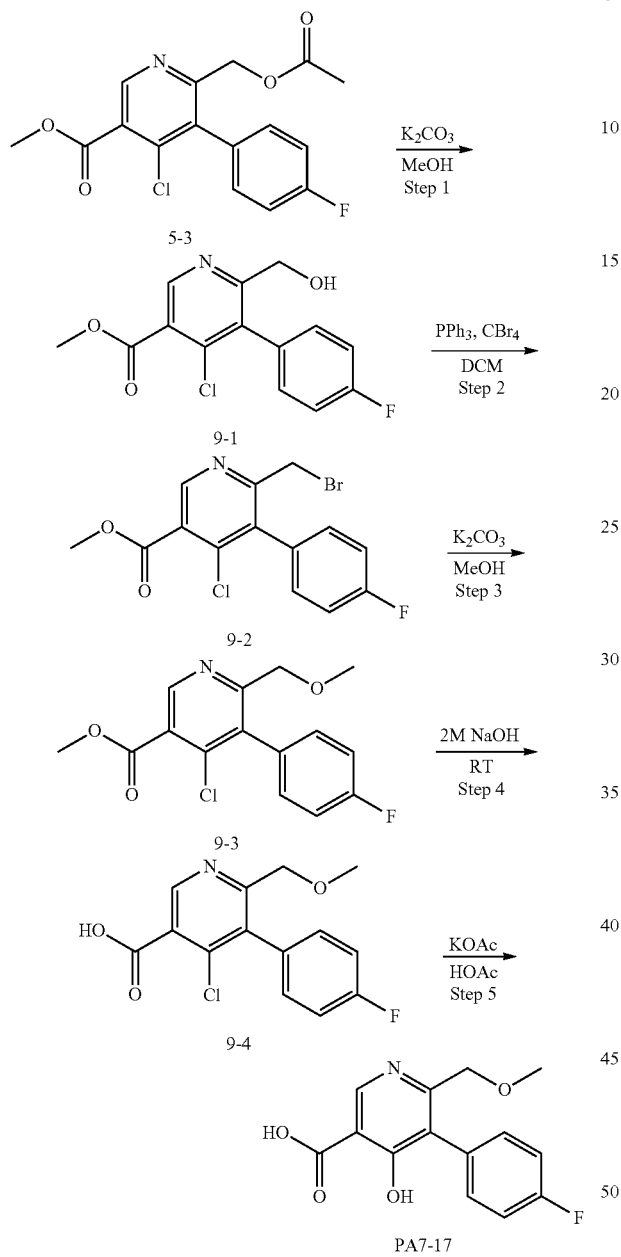

Steps 1: Methyl 4-chloro-5-(4-fluorophenyl)-6-(hydroxymethyl)nicotinate (9-1). A mixture of Compound 5-3 (0.60 g, 1.8 mmol, 1 eq), MeOH (5 mL) and K$_2$CO$_3$ (0.40 g, 2.9 mmol, 1.6 eq) was stirred at ambient temperature for 24 h. The reaction was subsequently diluted with EtOAc, filtered and concentrated. The resulting residue was purified by silica gel chromatography (0% to 100% EtOAc in hexanes) to give Compound 9-1 (0.20 g, 038% yield). MS for C$_{14}$H$_{11}$ClFNO$_3$: m/z 296 (MH+).

Steps 2: Methyl 6-(bromomethyl)-4-chloro-5-(4-fluorophenyl)nicotinate (9-2). To a stirring mixture of Compound 9-1 (0.20 g, 0.68 mmol, 1 eq), DCM (3 mL) and CBr$_4$ (0.65 g, 2.0 mmol, 3 eq) was added PPh$_3$ (0.52 g, 2.0 mmol, 3 eq). After 1 h the crude reaction was purified by silica gel chromatography (0% to 100% EtOAc in hexanes) to give Compound 9-2 (54 mg, 22% yield). MS for C$_{14}$H$_{10}$BrClFNO$_2$: m/z 360 (MH+).

Steps 3: Methyl 4-chloro-5-(4-fluorophenyl)-6-(methoxymethyl)nicotinate (9-3). A mixture of Compound 9-2 (54 mg, 0.15 mmol, 1 eq), MeOH (1 mL) and K$_2$CO$_3$ (0.10 g, 0.31 mmol, 2.1 eq) was stirred at ambient temperature for 1 h. The reaction was subsequently concentrated, diluted with EtOAc, and filtered to give Compound 9-3 which was used in the subsequent step without further purification. MS for C$_{15}$H$_{13}$ClFNO$_3$: m/z 310 (MH+).

Steps 4: 4-Chloro-5-(4-fluorophenyl)-6-(methoxymethyl)nicotinic acid (9-4). Compound 9-3 was converted to Compound 9-4 using a modification of the ester hydrolysis procedure used in Step 3 of General Procedure A. MS for C$_{14}$H$_{11}$ClFNO$_3$: m/z 296 (MH+).

Steps 5: 5-(4-Fluorophenyl)-4-hydroxy-6-(methoxymethyl)nicotinic acid (PA7-17). Compound PA7-17 was made from Compound 9-4 in the same manner that Compound PA7-3 was made from Compound 5-3 in Step 4 of Example 5. MS for C$_{14}$H$_{12}$FNO$_4$: m/z 278 (MH+).

Example 10: 5-(4-Fluorophenyl)-6-(methoxymethyl)-1-methyl-4-oxo-1,4-dihydropyridine-3-carboxylic acid (PA7-26)

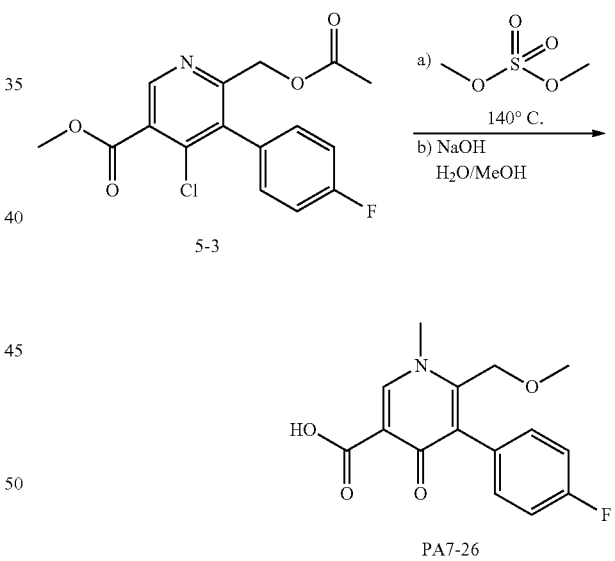

5-(4-Fluorophenyl)-6-(methoxymethyl)-1-methyl-4-oxo-1,4-dihydropyridine-3-carboxylic acid (PA7-26). Compound 5-3 (0.50 g, 1.5 mmol, 1 eq) and dimethyl sulfate (0.66 g, 5.3 mmol, 3.6 mmol) were heated at 140° C. under microwave irradiation for 5 min. Aq 25% NaOH (4 mL) was added to the reaction and the vial contents were heated to 80° C. After 48 h the reaction was cooled, acidified with 1 M HCl to pH-2 and extracted with EtOAc (3×). The combined organic extracts were concentrated, and the resulting residue was purified prep HPLC (C18, 20% to 40% ACN in H$_2$O (+FA)) to give Compound PA7-26 (37 mg, 9% yield). MS for C$_{15}$H$_{14}$FNO$_4$: m/z 292 (MH+).

Example 11: 5-(4-Fluorophenyl)-4-hydroxy-6-(trifluoromethyl)nicotinic acid (PA7-11)

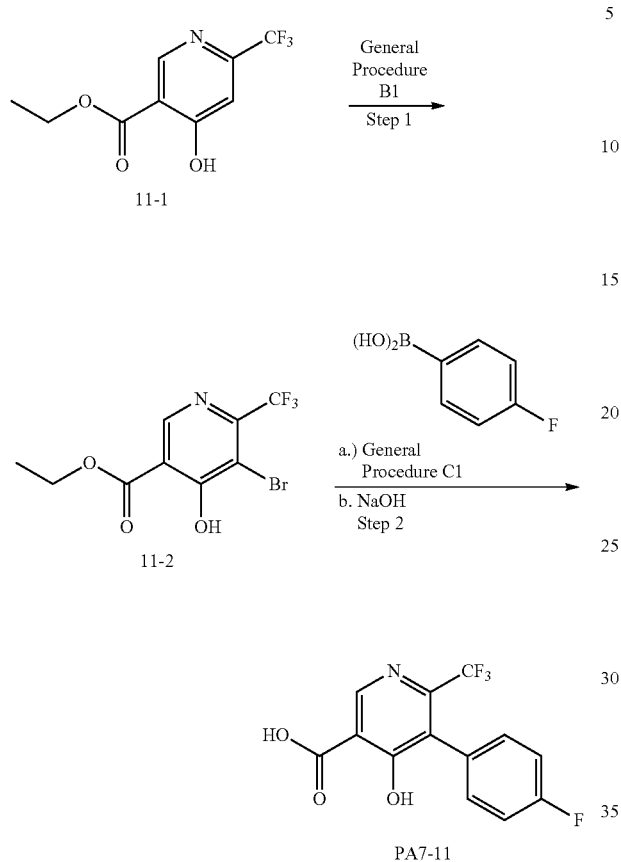

Step 1: Ethyl 5-bromo-4-hydroxy-6-(trifluoromethyl)nicotinate (11-2). Compound 11-2 was synthesized from Compound 11-1 using General Procedure B. MS for $C_9H_7BrF_3NO_3$: m/z 314/316 (MH+).

Step 2: 5-(4-Fluorophenyl)-4-hydroxy-6-(trifluoromethyl)nicotinic acid (PA7-11). The ethyl ester of Compound PA7-11 was synthesized from Compound 11-2 using General Procedure C1. Specifically in this case, a mixture of Compound 11-2 (250 mg, 0.80 mmol), (4-fluorophenyl) boronic acid (270 mg, 1.93 mmol), Pd(PPh$_3$)$_4$ (50 mg, 0.043 mmol) and K$_2$CO$_3$ (600 mg, 4.34 mmol) in dioxane (3 mL) and water (1.5 mL) was degassed with nitrogen for 2 min, followed by stirring at 90° C. overnight forming the ethyl ester of Compound PA7-11. After cooling to room temperature, the ethyl ester was subsequently hydrolyzed by adding NaOH (2 M, 5 mL) to the reaction mixture. The resulting mixture was stirred at room temperature until ester hydrolysis was complete. The mixture was washed with EtOAc (2×) and the aqueous phase was acidified to pH 2-3 and extracted with EtOAc (2×). The combined EtOAc extracts were dried over anhyd Na$_2$SO$_4$, and concentrated. The resulting residue was suspended in a mixture solvent of DCM/hexane (7.5/7.5 mL), sonicated for 2 min, and filtered to give Compound PA7-11 (244 mg, 100% yield). MS for $C_{13}H_7F_4NO_3$: m/z 302.2 (MH+). Example 12:5-(4-Fluorophenyl)-2-methyl-4-oxo-1,4-dihydropyridine-3-carboxylic acid (PA7-12)

General

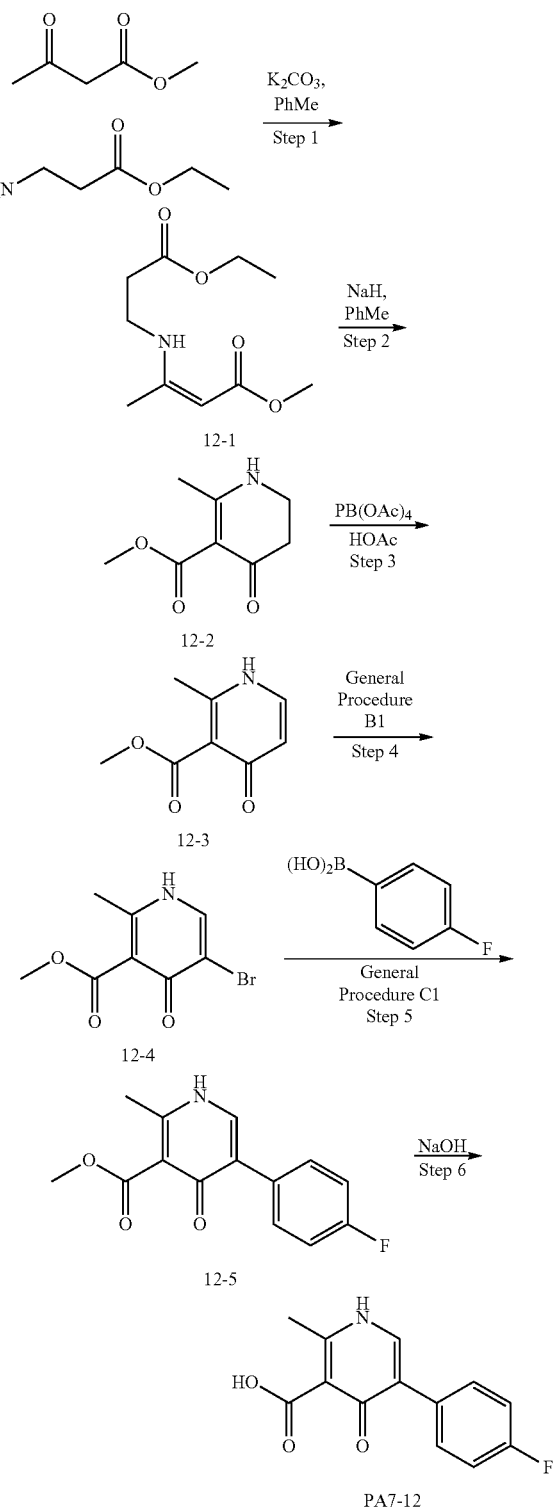

Step 1: Methyl 3-((3-ethoxy-3-oxopropyl)amino)but-2-enoate (12-1): A mixture of 3-aninopropionic acid ethyl ester hydrochloride (15.6 g, 101 mmol), methyl 3-oxobutanoate (10.8 mL, 101 mmol) and anhyd K$_2$CO$_3$ (28.0 g, 203 mmol) in toluene (200 mL) was refluxed with a Dean-Stark trap overnight. The reaction mixture was cooled and diluted with EtOAc (150 mL), filtered and the filtrate was concentrated under reduced pressure to give crude Compound 12-1 (21 g), which was used in the next step without further purification.

Step 2: Methyl 2-methyl-4-oxo-1,4,5,6-tetrahydropyridine-3-carboxylate (12-2): To a solution of crude Compound 12-1 (21 g, 95 mmol) in 200 mL of toluene was added sodium hydride (6.0 g, 60% dispersion in oil, 150 mmol) and the resulting yellow suspension was refluxed overnight. The mixture was concentrated to remove solvent and the residue was treated carefully with water (100 mL), acidified to pH 2 with 6 M HCl and then washed with $Et_2O$ (3×). The aqueous phase was basified with $NaHCO_3$ and extracted with EtOAc (5×). The combined EtOAc extracts were dried over anhyd $Na_2SO_4$, and concentrated to give Compound 12-2 (7.6 g, 46% yield) which was used without further purification. MS for $C_8H_{11}NO_3$: m/z 170 (MH+).

Step 3: Methyl 2-methyl-4-oxo-1,4-dihydropyridine-3-carboxylate (12-3): A mixture of Compound 12-2 (3.6 g, 21 mmol) and lead tetraacetate (20 g, 58 mmol) in 30 mL of acetic acid was stirred at 100° C. overnight and concentrated under reduced pressure to remove acetic acid. The resulting residue was purified by silica gel chromatography (5-15% MeOH in DCM) to give Compound 12-3 (2.0 g, 56%). MS for $C_8H_9NO_3$: m/z 168 (MH+).

Step 4: Methyl 5-bromo-2-methyl-4-oxo-1,4-dihydropyridine-3-carboxylate (12-4): Compound 12-4 was synthesized from Compound 12-3 using General Procedure B1. MS for $C_8H_8BrNO_3$: m/z 246/248 (MH+).

Step 5: Methyl 5-(4-fluorophenyl)-2-methyl-4-oxo-1,4-dihydropyridine-3-carboxylate (12-5): Compound 12-5 was synthesized from Compound 12-4 using General Procedure C1. MS for $C_{14}H_{12}FNO_3$: m/z 262 (MH+).

Step 6: 5-(4-Fluorophenyl)-2-methyl-4-oxo-1,4-dihydropyridine-3-carboxylic acid (PA7-12). Compound 12-5 was converted to Compound PA7-12 by the ester hydrolysis procedure used in Step 3 of General Procedure A. MS for $C_{13}H_{10}FNO_3$: m/z 248 (MH+).

The following compounds were made using the same procedure used to synthesize Compound PA7-12 in Example 12:

5-(4-Fluoro-2-methylphenyl)-4-hydroxy-2-methylnicotinic acid (PA7-23): MS for $C_{14}H_{12}FNO_3$: m/z 262.0 (MH+).

Example 13: 1-Ethyl-5-(4-fluorophenyl)-2-methyl-4-oxo-1,4-dihydropyridine-3-carboxylic acid (PA7-14) and 4-Ethoxy-5-(4-fluorophenyl)-2-methylnicotinic acid (PA7-40)

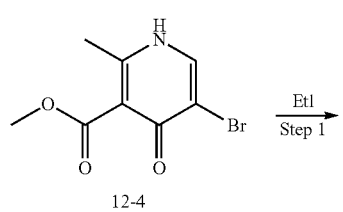

12-4

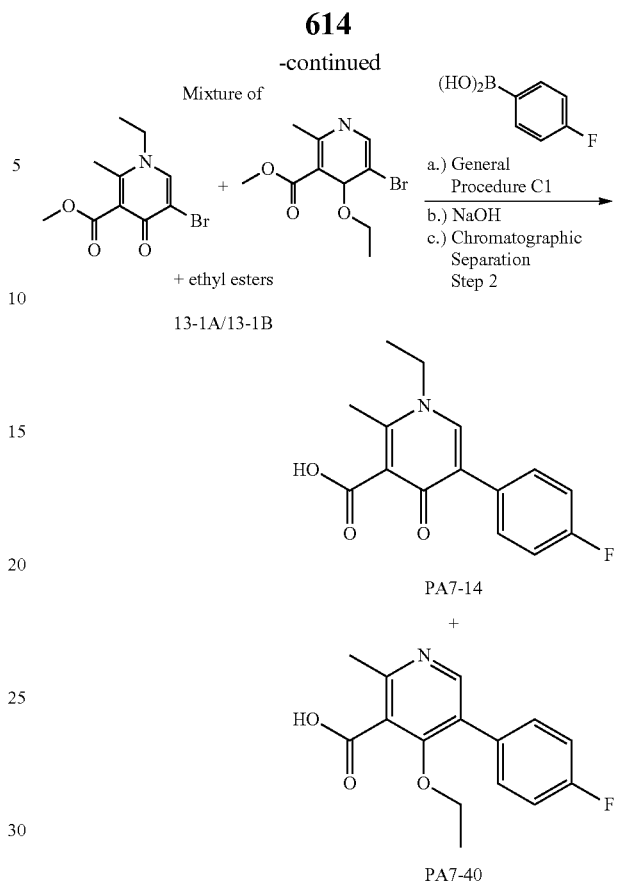

Step 1: Mixture 13-1A/13-1B. To a suspension of Compound 12-4 (180 mg, 0.73 mmol) and $Cs_2CO_3$ (600 mg, 1.84 mmol) in DMF (4 mL), was added EtI (0.5 mL, 6.25 mmol). The resulting mixture was stirred at room temperature for 2 h and then partitioned between DCM and water. The DCM phase was washed with aq saturated NaCl and concentrated to give the mixture 13-1A/13-1B (248 mg). MS for methyl esters $C_{10}H_{12}BrNO_3$: m/z 274/276 (MH+).

Step 2: 1-Ethyl-5-(4-fluorophenyl)-2-methyl-4-oxo-1,4-dihydropyridine-3-carboxylic acid (PA7-14) and 4-Ethoxy-5-(4-fluorophenyl)-2-methylnicotinic acid (PA7-40): A mixture of Compound PA7-14 and Compound PA7-40 was made from the mixture of Compounds 13-1A/13-1B by the same method used to make Compound PA7-11 from Compound 11-2 in Step 2 of Example 11. The mixture of Compound PA7-14 and Compound PA7-40 was subsequently separated by silica gel chromatography (5-15% MeOH in EtOAc) to give pure Compound PA7-14 (46% yield in two steps from Compound 12-4) and pure Compound PA7-40 (26% yield in two steps from Compound 12-4). Compound PA7-14: $^1$H NMR (400 MHz, DMSO-$d_6$) δ 8.40 (s, 1H), 7.77-7.69 (m, 2H), 7.31 (td, 2H), 4.30 (q, 2H), 2.96 (s, 3H), 1.39 (t, 3H); MS for $C_{15}H_{14}FNO_3$: m/z 276.3 (MH+). Compound PA7-40: $^1$H NMR (400 MHz, DMSO-$d_6$) δ 8.25 (s, 1H), 7.57 (dd, 2H), 7.30 (t, 2H), 3.80 (q, 2H), 2.42 (s, 3H), 1.05 (t, 3H); MS for $C_{15}H_{14}FNO_3$: m/z 276.3 (MH+).

The following compounds was made using the same method used to make Compound PA7-14 and/or Compound PA7-40 in Example 13:

5-(4-Fluorophenyl)-1,2-dimethyl-4-oxo-1,4-dihydropyridine-3-carboxylic acid (PA7-13): MS for $C_{14}H_{12}FNO_3$: m/z 262.3 (MH+).

5-(4-Fluoro-2-methylphenyl)-1,2-dimethyl-4-oxo-1,4-dihydropyridine-3-carboxylic acid (PA7-33): MS for $C_{15}H_{14}FNO_3$: m/z 276.2 (MH+).

4-Ethoxy-5-(4-fluorophenyl)-6-methylnicotinic acid (PA7-38): MS for $C_{15}H_{14}FNO_3$: m/z 276.1 (MH+).

Example 14: 5-(4-Fluorophenyl)-4,6-dimethoxy-2-methylnicotinic acid (PA7-39)

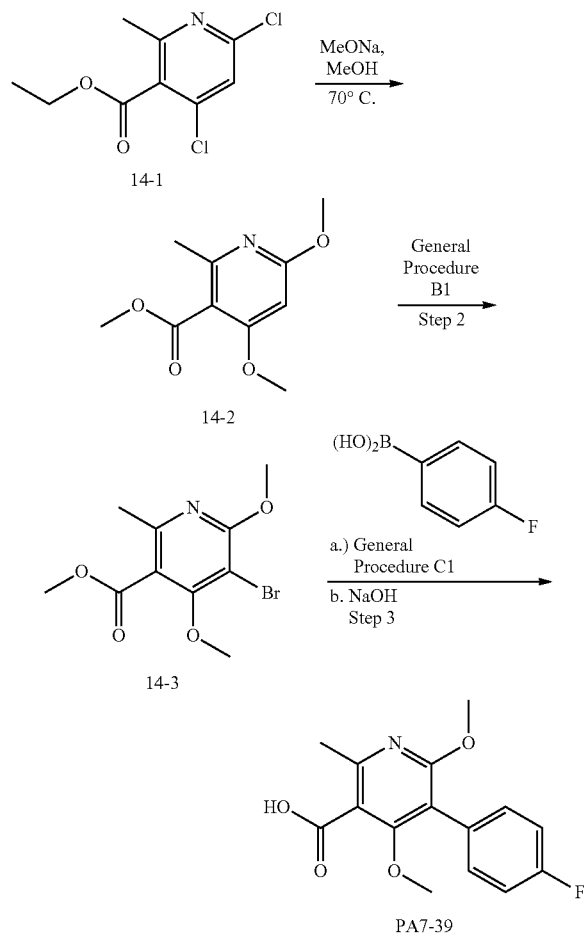

Step 1: Methyl 4,6-dimethoxy-2-methylnicotinate (14-2). A mixture of Compound 14-1 (3.6 g, 15.4 mmol) and NaOMe (1.8M, 30 mL, 54 mmol) was stirred at 70° C. until the reaction was complete and concentrated to remove MeOH. To the resulting residue was added water and the resulting suspension was filtered. The solid was washed with water and dried under vacuum to give Compound 14-2 (3.3 g, 100% yield). MS for $C_{10}H_{13}NO_4$: m/z 212 (MH+).

Step 2: Methyl 5-bromo-4,6-dimethoxy-2-methylnicotinate (14-3): Compound 14-3 was synthesized from Compound 14-2 using General Procedure B. MS for $C_{10}H_{12}BrNO_4$: m/z 290/292 (MH+).

Step 3: 5-(4-Fluorophenyl)-4,6-dimethoxy-2-methylnicotinic acid (PA7-39): Compound PA7-39 was made from Compound 14-3 by the same method used to make Compound PA7-11 from Compound 11-2 in Step 2 of Example 11. MS for $C_{15}H_{14}FNO_4$: m/z 292 (MH).

Example 15: 5-(4-Fluorophenyl)-6-hydroxy-2-methyl-4-oxo-1,4-dihydropyridine-3-carboxylic acid (PA7-15) and 5-(4-Fluorophenyl)-6-methoxy-2-methyl-4-oxo-1,4-dihydropyridine-3-carboxylic acid (PA7-16)

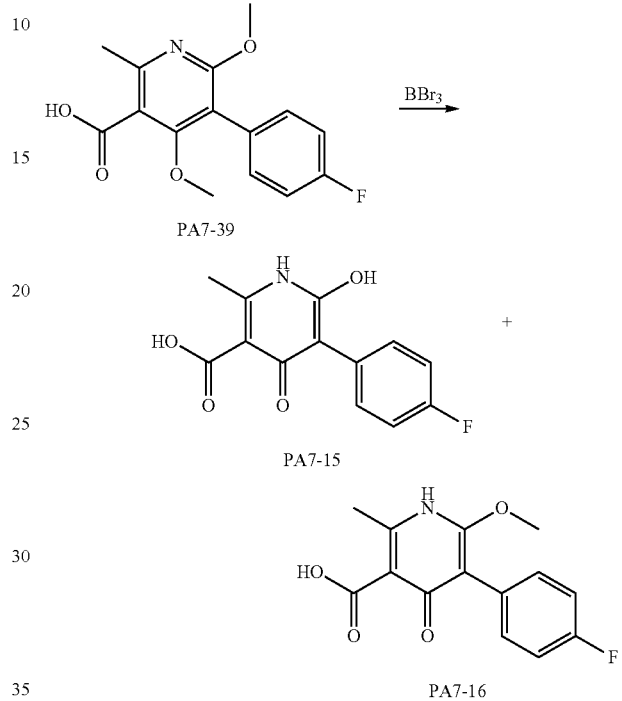

5-(4-Fluorophenyl)-6-hydroxy-2-methyl-4-oxo-1,4-dihydropyridine-3-carboxylic acid (PA7-15) and 5-(4-Fluorophenyl)-6-methoxy-2-methyl-4-oxo-1,4-dihydropyridine-3-carboxylic acid (PA7-16). A mixture of Compound PA7-39 (550 mg, 1.89 mmol) and $BBr_3$ (2 mL, 21.4 mmol) in DCM (6 mL) was stirred at room temperature for 1 h, quenched with water and concentrated in vacuo to remove DCM. To the resulting residue was added 2 M HCl (10 mL) and MeOH (10 mL). The resulting mixture was stirred at room temperature for 4 h and then concentrated to remove MeOH. The resulting residue was extracted with EtOAc (3×) and the combined extracts were concentrated in vacuo. The resulting residue was purified by silica gel chromatography (0-10% MeOH in DCM) to give Compound PA7-15 (82 mg, 15% yield), MS for $C_{13}H_{10}FNO_4$: m/z 264 (MH+) and Compound PA7-16 (176 mg, 33% yield), MS for $C_{14}H_{12}FNO_4$: m/z 278 (MH+).

Example 16: 6-Ethyl-5-(4-fluorophenyl)-4-oxo-1,4-dihydropyridine-3-carboxylic acid (PA7-18)

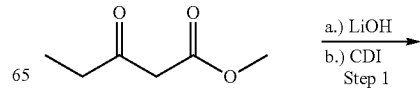

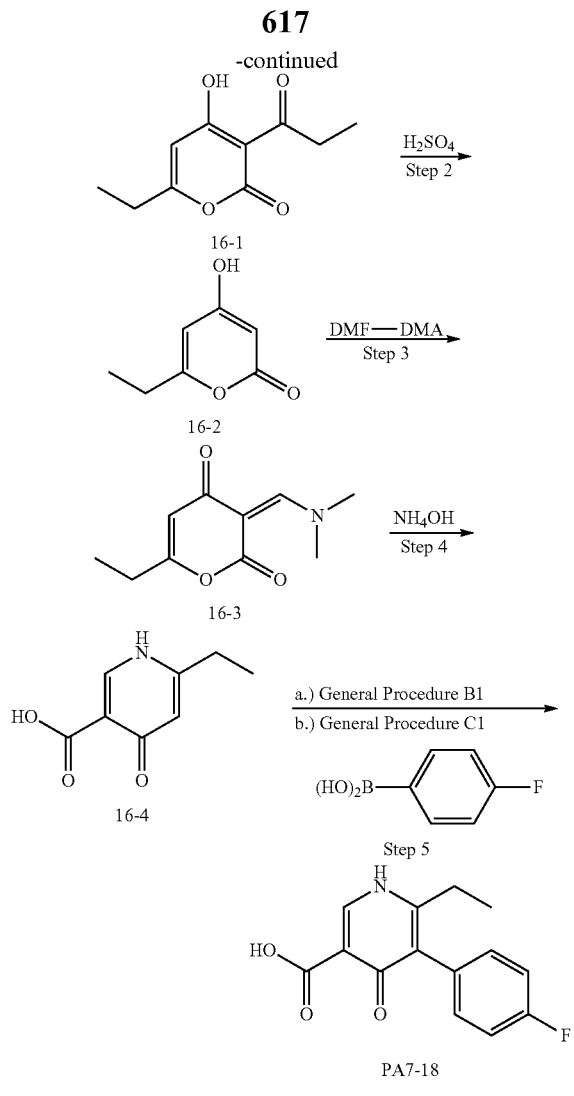

Step 3: (Z)-3-((Dimethylamino)methylene)-6-ethyl-2H-pyran-2,4(3H)-dione (16-3): To Compound 16-2 (1.76 g, 7.69 mmol) in dioxane (20 mL) was added DMF-DMA (2.9 mL). The resulting mixture was stirred at room temperature for 30 min and then concentrated in vacuo to give crude Compound 16-3 which was used in the next step without further purification. MS for $C_{10}H_{13}NO_3$: m/z 196 (MH)

Step 4: 6-Ethyl-4-oxo-1,4-dihydropyridine-3-carboxylic acid (16-4): To crude Compound 16-3 (1.5 g, 7.69 mmol) in water (11 mL) was added ammonium hydroxide (6 eq). The resulting mixture was stirred at room temperature for 1 h. The reaction mixture was then chilled to 0° C. and acidified using 6 N HCl to pH 4. The resulting mixture was extracted with EtOAc (4×). The combined organic extracts were washed with aq saturated NaCl, dried over anhyd $Na_2SO_4$ and concentrated to give Compound 16-4 which was used in the next step without further purification. MS for $C_8H_9NO_3$: m/z 168 (MH)

Step 5: 6-Ethyl-5-(4-fluorophenyl)-4-oxo-1,4-dihydropyridine-3-carboxylic acid (PA7-18): Compound PA7-18 was made in two steps from Compound 16-4. Compound 16-4 was first brominated using General Procedure B1. The resulting bromide was converted to Compound PA7-18 through General Procedure C1. MS for $C_{14}H_{12}FNO_3$: m/z 262 (MH)

Example 17: 5-Bromo-4-hydroxy-2-methylnicotinic acid (PA7-24)

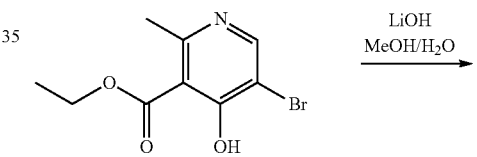

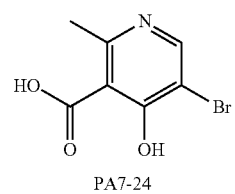

PA7-24

5-Bromo-4-hydroxy-2-methylnicotinic acid (PA7-24): Ethyl 5-bromo-4-hydroxy-2-methyl-pyridine-3-carboxylate can be made in the same manner as the corresponding methyl ester Compound 12-4 in Example 12. To a 20 mL vial equipped with a magnetic stir bar and a pressure relief septum was added ethyl 5-bromo-4-hydroxy-2-methyl-pyridine-3-carboxylate (1.50 g, 5.77 mmol, 1.00 eq), MeOH (10 mL), and water (3 mL). LiOH hydrate (800 mg, 19.07 mmol, 3.31 eq) was added in a single portion, and the reaction was heated to 65° C. for 3 h. The solution was then concentrated to remove most of the MeOH, and the solution was acidified to pH=3 with 6 M HCl. The resulting precipitate was collected by vacuum filtration to give Compound PA7-24 (1.22 g, 91% yield). MS for $C_7H_6BrNO_3$: m/z 232.0 (MH+).

Step 1: 6-ethyl-4-hydroxy-3-propionyl-2H-pyran-2-one (16-1). A solution of methyl 3-oxopentanoate (5 g, 38.46 mmol) in MeOH (20 mL) was charged with 1 M LiOH (10 eq). The resulting mixture was stirred at room temperature for 1 h. MeOH was removed in vacuo and the aqueous layer was washed with EtOAc (3×). The aqueous layer was acidified using 6 N HCl to pH 2-3 and extracted with EtOAc (3×). The combined organic extracts were washed with aq saturated NaCl, dried over anhyd $Na_2SO_4$ and concentrated. The resulting residue was dissolved in THF (50 mL) and to the resulting solution was added 1,1'-carbonyldiimidazole (1.1 eq). The resulting mixture was stirred at room temperature overnight. The crude reaction mixture was diluted with EtOAc, washed with 1 M HCl, washed with aq saturated NaCl, dried over anhyd $Na_2SO_4$ and concentrated to give Compound 16-1 (3.47 g, 46% yield). MS for $C_{10}H_{12}O_4$: m/z 197 (MH+).

Step 2: 6-Ethyl-4-hydroxy-2H-pyran-2-one (16-2): Concentrated $H_2SO_4$ (5 mL) was added to Compound 16-1 (3.47 g, 17.7 mmol) and heated to 130° C. for 30 min. The reaction mixture was allowed to cool to room temperature and poured onto ice. The resulting aqueous mixture was neutralized with 3 N NaOH, extracted with EtOAc, washed with aq saturated NaCl, dried over anhyd $Na_2SO_4$ and concentrated to give Compound 16-2. MS for $C_7H_8O_3$: m/z 141 (MH)

Example 18: 6-(4-Fluorophenyl)-7-oxo-1,2,3,7-tetrahydroindolizine-8-carboxylic acid (PA7-25)

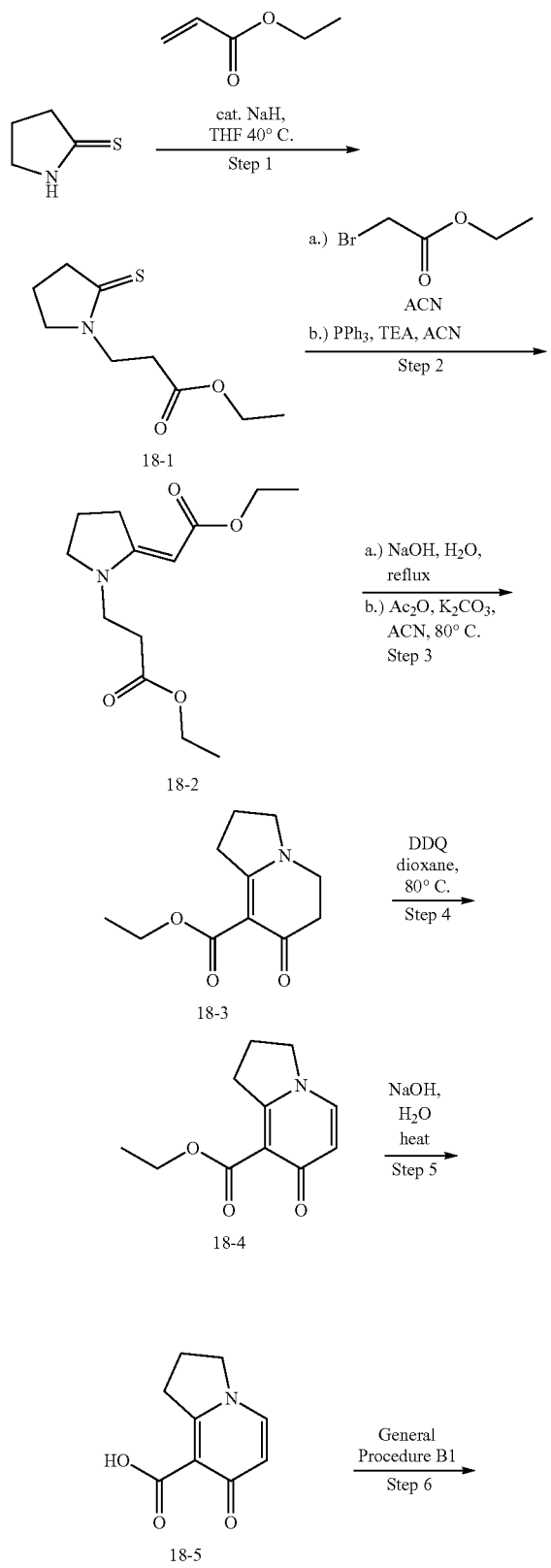

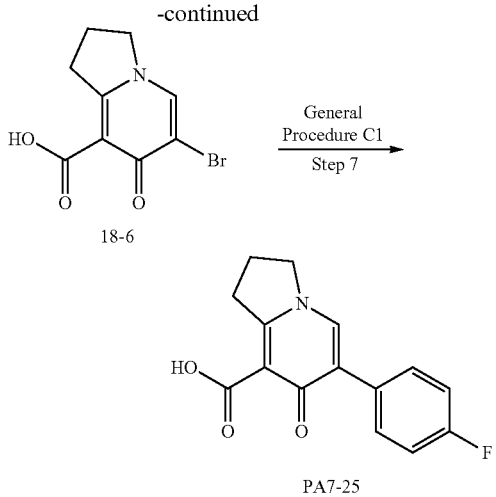

Step 1: Ethyl 3-(2-thioxopyrrolidin-1-yl)propanoate (18-1): To a stirred solution of pyrrolidine-2-thione (500 mg, 4.95 mmol) in dry THF (10 mL) was added a catalytic amount of NaH (60% dispersion in oil, 18 mg, 0.95 mmol) followed by the dropwise addition of ethyl acrylate (0.6 mL, d 0.94 g/mL, 0.56 mmol). The mixture was stirred at 40° C. overnight. The reaction mixture was evaporated to remove the solvent in vacuo. The resulting residue was partitioned between EtOAc and aq NaHCO$_3$ (1 M). The organic phase was separated, washed with aq saturated NaCl and concentrated. The resulting residue was purified by silica gel chromatography (0-50% of EtOAc in hexane) to give Compound 18-1 (0.9 g, 90% yield). $^1$H NMR (400 MHz, CDCl$_3$) δ 4.17 (q, 2H), 4.03 (t, 2H), 3.83 (t, 2H), 3.04 (t, 2H), 2.80 (t, 2H), 2.08 (q, 2H), 1.29 (t, 3H); MS for C$_9$H$_{15}$NO$_2$S: m/z 202 (MH+).

Step 2: Ethyl (E)-3-(2-(2-ethoxy-2-oxoethylidene)pyrrolidin-1-yl)propanoate (18-2): Ethyl bromoacetate (0.6 mL, d 1.51 g/ML, 5.42 mmol) was added dropwise to a stirred solution of Compound 18-1 (0.9 g, 4.48 mmol) in dry ACN (10 mL). The resulting solution was stirred at room temperature overnight. The volatiles were removed in vacuo, and the residue was thoroughly dried under vacuum. This salt was then re-dissolved in dry ACN (10 mL) to which was added triphenylphosphine (1.42 g, 5.42 mmol) and TEA (0.77 mL, 5.5 mmol). The resulting solution was stirred at room for 3 days and concentrated. The residue was partitioned between water and DCM. The organic phase was separated, washed with aq saturated NaCl and evaporated in vacuo. The resulting residue was purified by silica gel chromatography (DCM first to remove Ph$_3$P/Ph$_3$PS, and then with 0-40% EtOAc in hexane) to give Compound 18-2 (1.09 g, 95% yield). MS for C$_{13}$H$_{21}$NO$_4$: m/z 256 (MH+).

Step 3: Ethyl 7-oxo-1,2,3,5,6,7-hexahydroindolizine-8-carboxylate (18-3): A mixture of Compound 18-2 (1.09 g, 4.27 mmol) and NaOH (172 mg, 4.3 mmol) in water (10 mL) was refluxed until hydrolysis was complete followed by cooling to room temperature. The resulting mixture was acidified to pH 3 and extracted with EtOAc (3×). The combined extracts were dried over anhyd Na$_2$SO$_4$ and concentrated. This crude acid was then mixed with K$_2$CO$_3$ (1.2 g, 8.7 mmol) and acetic anhydride (0.5 mL, 5.40 mmol) in ACN (20 mL). The mixture was stirred at 80° C. overnight, cooled to room temperature, quenched with water and extracted with DCM (3×). The combined DCM extracts were dried with Na$_2$SO$_4$ and concentrated to give crude Compound 18-3 (880 mg, 98% yield). $^1$H NMR (400 MHz, CDCl$_3$) δ 4.30 (q, 2H), 3.80 (t, 2H), 3.73 (t, 2H), 3.37 (t, 2H), 2.83 (t, 2H), 2.23 (q, 2H), 1.37 (t, 3H); MS for C$_{11}$H$_{15}$NO$_3$: m/z 210 (MH+).

Step 4: Ethyl 7-oxo-1,2,3,7-tetrahydroindolizine-8-carboxylate (18-4): Compound 18-3 (790 mg, 3.78 mmol) was mixed with DDQ (990 mg, 4.36 mmol) in dioxane (8 mL) and the reaction mixture stirred at 80° C. overnight. After cooling to room temperature, the mixture was partitioned between EtOAc and aq NaHCO$_3$. The aqueous phase was extracted twice with EtOAc, and the combined organic phases were dried over anhyd Na$_2$SO$_4$ and concentrated. The resulting residue was purified by silica gel chromatography (0-10% MeOH in DCM) to give Compound 18-4 (560 mg, 72%). MS for C$_{11}$H$_{13}$NO$_3$: m/z 208 (MH+).

Step 5: 7-oxo-1,2,3,7-tetrahydroindolizine-8-carboxylic acid (18-5). Compound 18-4 was converted to Compound 18-5 by a modification of the ester hydrolysis procedure used in Step 3 of General Procedure A. In this case the reaction was heated at 80° C. overnight, followed by 90° C. for an additional 4 h prior to the usual work-up. MS for C$_9$H$_9$NO$_3$: m/z 180 (MH+).

Step 6: 6-Bromo-7-oxo-1,2,3,7-tetrahydroindolizine-8-carboxylic acid (18-6): Compound 18-6 was synthesized from Compound 18-5 using General Procedure B1. MS for C$_9$H$_8$BrNO$_3$: m/z 258/260 (MH+).

Step 7: 6-(4-Fluorophenyl)-7-oxo-1,2,3,7-tetrahydroindolizine-8-carboxylic acid (PA7-25): Compound PA7-25 was synthesized from Compound 18-6 using General Procedure C1. MS for C$_{15}$H$_{12}$FNO$_3$: m/z 274 (MH+).

Example 19: 6-Chloro-5-(4-fluorophenyl)-1-methyl-4-oxo-1,4-dihydropyridine-3-carboxylic acid

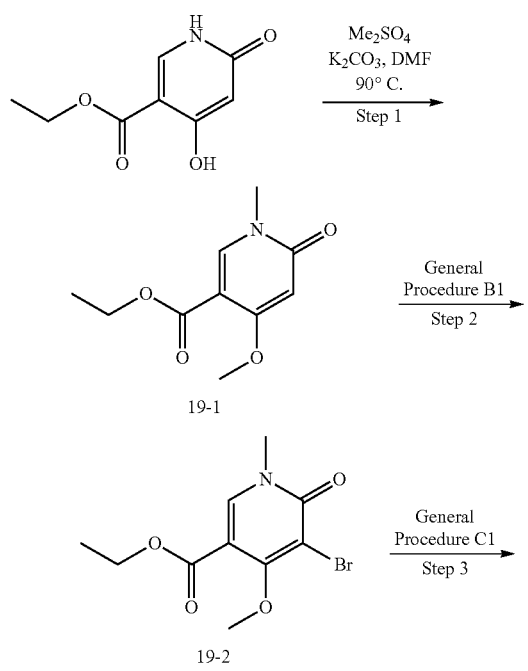

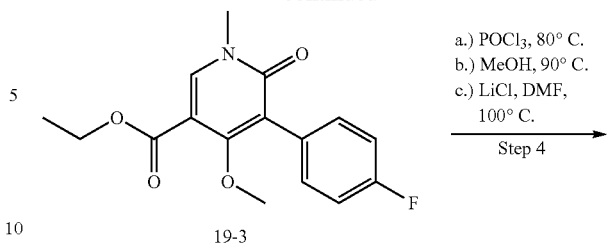

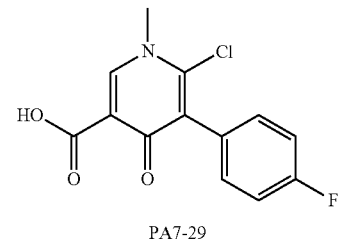

Step 1: Ethyl 4-methoxy-1-methyl-6-oxo-1,6-dihydropyridine-3-carboxylate (19-1): A mixture of ethyl 4-hydroxy-6-oxo-1,6-dihydropyridine-3-carboxylate (3.2 g, 1.75 mmol), dimethyl sulfate (2.1 mL, 2.22 mmol), K$_2$CO$_3$ (7.0 g, 5.1 mmol) in DMF (30 mL) was stirred at 90° C. Upon completion of the reaction as monitored by LC-MS, the mixture was cooled to room temperature and partitioned between EtOAc and water. The phases were separated and the aqueous was further extracted with EtOAc. The combined organic phases were dried over anhyd Na$_2$SO$_4$ and concentrated to give Compound 19-1 which was used without further purification. MS for C$_{10}$H$_{13}$NO$_4$: m/z 212 (MH+).

Step 2: Ethyl 5-bromo-4-methoxy-1-methyl-6-oxo-1,6-dihydropyridine-3-carboxylated (19-2): Compound 19-2 was synthesized from Compound 19-1 using General Procedure B1. MS for C$_{10}$H$_{12}$BrNO$_4$: m/z 290/292 (MH+).

Step 3: Ethyl 5-(4-fluorophenyl)-4-methoxy-1-methyl-6-oxo-1,6-dihydropyridine-3-carboxylate (19-3): Compound 19-3 was synthesized from Compound 19-2 using General Procedure C1. MS for C$_{16}$H$_{16}$FNO$_4$: m/z 306 (MH+).

Step 4: 6-Chloro-5-(4-fluorophenyl)-1-methyl-4-oxo-1,4-dihydropyridine-3-carboxylic acid (PA7-29): A mixture of Compound 19-3 (2.02 g, 6.62 mmol) and POCl$_3$ (10 mL) was stirred at 80° C. for 4 h and then evaporated to dryness. To the resulting residue was added MeOH (5 mL) and the resulting mixture stirred at 90° C. for 1 h and then evaporated to dryness. The resulting residue was mixed with LiCl (3.0 g, 70.8 mmol) in DMF (3 mL) and the resulting mixture stirred at 100° C. for 4 h, cooled to room temperature, quenched with NaOH (1M) to pH>12 and washed with EtOAc (2×). The aqueous phase was acidified to pH 2 with 6 M HCl and extracted with EtOAc (2×). The combined extracts were dried over anhyd Na$_2$SO$_4$ and concentrated to give crude Compound PA7-29 (620 mg, 33% yield), which was used without further purification. MS for C$_{13}$H$_9$FNO$_3$: m/z 282 (MH+).

Example 20: 8-(4-Fluorophenyl)-2-methyl-7-oxo-7H-oxazolo[3,2-a]pyridine-6-carboxylic acid (PA7-31)

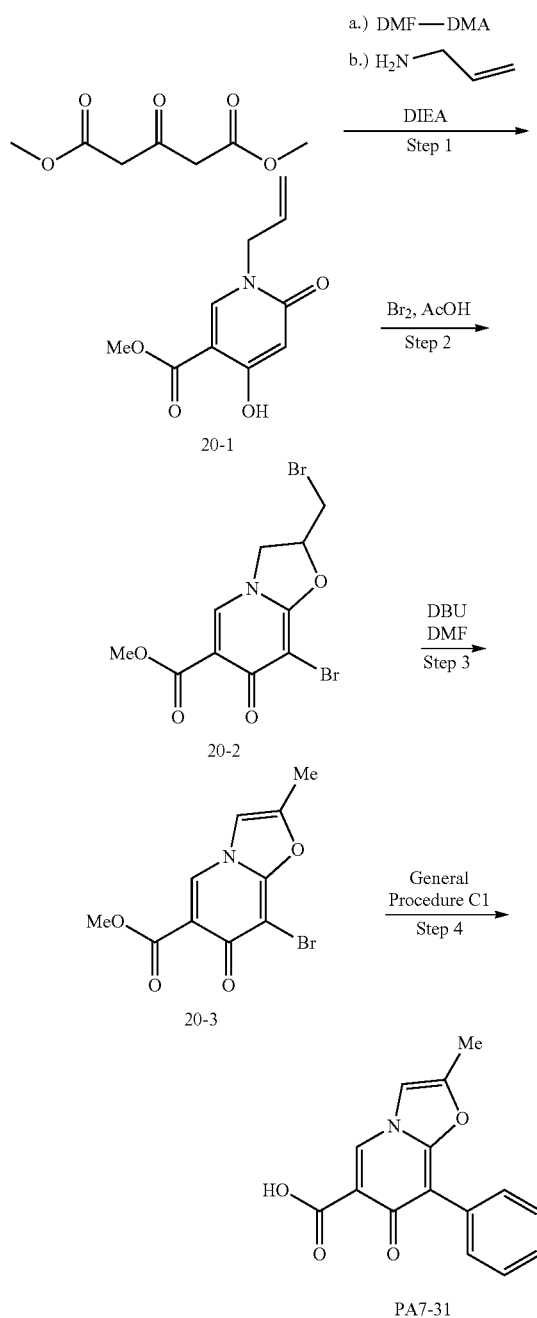

temperature, concentrated and purified by silica gel chromatography (0-100% EtOAc in hexanes) to give Compound 20-1 (2.1 g, 31% yield). $^1$H NMR (400 MHz, CDCl$_3$) δ 10.55 (d, 1H), 8.11 (s, 1H), 6.08-5.80 (m, 2H), 5.43-5.17 (m, 2H), 4.58 (dd, 2H), 3.93 (d, 3H). MS for $C_{10}HNO_4$: m/z 210.0 (MH+).

Step 2: Methyl 8-bromo-2-(bromomethyl)-7-oxo-2,3-dihydro-7H-oxazolo[3,2-a]pyridine-6-carboxylate (20-2): To a 100 mL round bottom flask equipped with a magnetic stir bar was added Compound 20-1 (1.0 g, 4.8 mmol) in acetic acid (5.0 mL). Bromine (1.0 mL, 19 mmol, 4.1 equiv.) was added dropwise, and the reaction was heated to 60° C. for 4 h. The reaction was allowed to cool to room temperature and the resulting suspension was filtered to give Compound 20-2 (780 mg, 44% yield). $^1$H NMR (400 MHz, DMSO-d$_6$) δ 8.42 (s, 1H), 5.53-5.40 (m, 1H), 4.64 (dd, Hz, 1H), 4.28 (dd, 1H), 3.98 (qd, 2H), 3.72 (s, 3H); MS for $C_{10}H_9Br_2NO_4$: m/z 367.8 (MH+).

Step 3: Methyl 8-bromo-2-methyl-7-oxo-7H-oxazolo[3,2-a]pyridine-6-carboxylate (20-3): To a 20-mL vial equipped with a magnetic stir bar and a pressure relief septum was added Compound 20-2 (700 mg, 1.91 mmol) in DMF (5 mL). DBU (1 mL, 6.70 mmol, 3.51 equiv.) was added in a single portion at room temperature and the reaction was stirred at room temperature for 3 h. The reaction was then concentrated, loaded onto silica gel, and purified by silica gel chromatography (gradient 0 to 100% EtOAc in hexanes) to give Compound 20-3 (130 mg, 23.8% yield). $^1$H NMR (400 MHz, DMSO-d$_6$) δ 8.69 (s, 1H), 7.75 (s, 1H), 3.76 (s, 3H), 2.37 (s, 3H).

Step 4: 8-(4-Fluorophenyl)-2-methyl-7-oxo-7H-oxazolo[3,2-a]pyridine-6-carboxylic acid (PA7-31): Compound PA7-31 was synthesized from Compound 20-3 using General Procedure C1. $^1$H NMR (400 MHz, DMSO-d$_6$) δ 9.14 (s, 1H), 7.97 (s, 1H), 7.73 (dd, 2H), 7.33 (t, 2H), 2.40 (s, 3H).

Example 21: 2-Ethoxy-5-(4-fluorophenyl)-6-methyl-4-oxo-1,4-dihydropyridine-3-carboxylic acid (PA7-19)

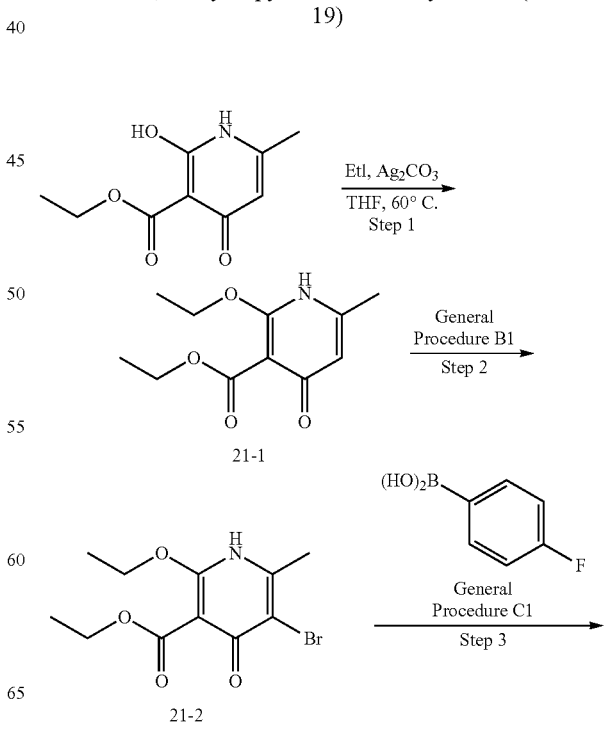

Step 1: Methyl 1-allyl-4-hydroxy-6-oxo-1,6-dihydropyridine-3-carboxylate (20-1): To a 40 mL vial equipped with a magnetic stir bar and a pressure relief septum was added dimethyl 3-oxopentanedioate (5.0 mL, 35 mmol, 1.1 eq) and DMF-DMA (5.5 mL, 41 mmol, 1.3 eq). The mixture was stirred in open air vigorously for 1.5 h at 100° C. The vial was cooled to room temperature and allylamine hydrochloride (3.0 g, 32 mmol, 1.0 eq) was added in a single portion followed by DIEA (10 mL, 56.2 mmol, 1.8 eq). The resulting solution was then heated to 80° C. for 4 h, cooled to room

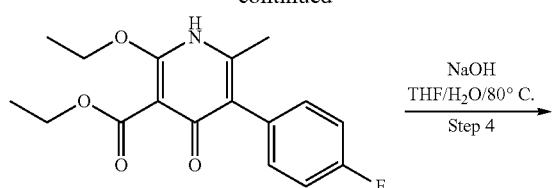

21-3

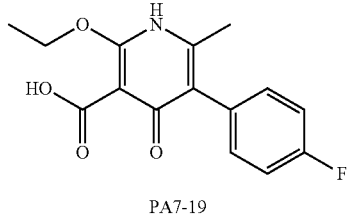

PA7-19

Step 1: Ethyl 2-ethoxy-6-methyl-4-oxo-1,4-dihydropyridine-3-carboxylate (21-1): To a mixture of ethyl 2,4-dihydroxy-6-methyl-pyridine-3-carboxylate (1.2 g, 6.1 mmol, 1 eq) and $Ag_2CO_3$ (840 mg, 3.05 mmol, 0.5 eq) in THF (10 mL) was added iodoethane (7.50 mmol, 0.6 mL, 1.2 eq). The mixture was stirred at 60° C. for 12 h. The mixture was concentrated, and the resulting residue was purified by flash silica gel chromatography (0-10% EtOAc/Petroleum ether) to give Compound 21-1 (638 mg, 46% yield). $^1$H NMR (400 MHz, $CDCl_3$) δ 12.20 (s, 1H), 6.36 (s, 1H), 4.47-4.31 (m, 4H), 2.34 (s, 3H), 1.46-1.36 (m, 6H); MS for $C_{11}H_{15}NO_4$: m/z 226 (MH+).

Step 2: Ethyl 5-bromo-2-ethoxy-6-methyl-4-oxo-1,4-dihydropyridine-3-carboxylate (21-2): Compound 21-2 was synthesized from Compound 21-1 using General Procedure B1. MS for $C_{11}H_{14}BrNO_4$: m/z 305.7 (MH+).

Step 3: Ethyl 2-ethoxy-5-(4-fluorophenyl)-6-methyl-4-oxo-1,4-dihydropyridine-3-carboxylate (21-3): Compound 21-3 was synthesized from Compound 21-2 using General Procedure C1. MS for $C_{17}H_{18}FNO_4$: m/z 320.0 (MH+).

Step 4: 2-Ethoxy-5-(4-fluorophenyl)-6-methyl-4-oxo-1,4-dihydropyridine-3-carboxylic acid (PA7-19): Compound 21-3 was converted to Compound PA7-19 using a modification of the ester hydrolysis procedure used in Step 3 of General Procedure A. In this particular case the reaction mixture was heated to 80° C. prior to work up. MS for $C_{15}H_{14}FNO_4$: m/z 291.9 (MH+).

Example 22: 2-Ethoxy-5-(4-fluorophenyl)-1,6-dimethyl-4-oxo-1,4-dihydropyridine-3-carboxylic acid (PA7-37)

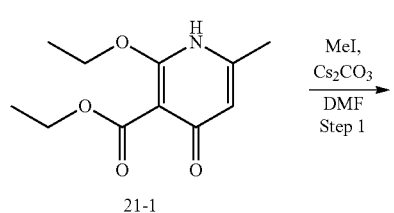

21-1

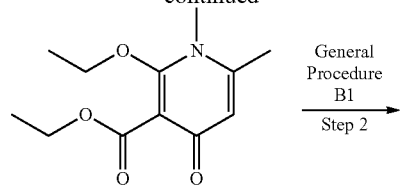

22-1

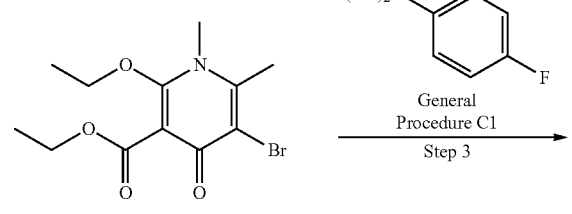

22-2

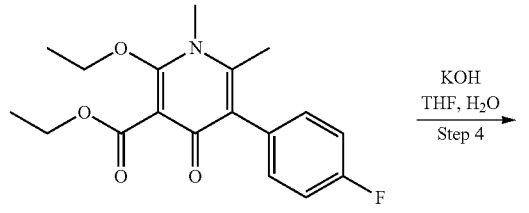

22-3

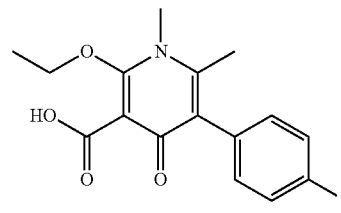

PA7-37

Step 1: Ethyl 2-ethoxy-1,6-dimethyl-4-oxo-1,4-dihydropyridine-3-carboxylate (22-1): To a mixture of Compound 21-1 (154 mg, 0.68 mmol, 1 eq) in DMF (2 mL) was added $Cs_2CO_3$ (267.32 mg, 0.82 mmol, 1.2 eq) and MeI (1.03 g, 7.3 mmol, 0.45 mL, 11 eq). The mixture was stirred at 25° C. for 12 h. The mixture was diluted with water (20 mL) and extracted with EtOAc (3×10 mL). The combined organic extracts were washed with aq saturated NaCl (15 mL), dried over anhyd $Na_2SO_4$, concentrated and purified by flash silica gel chromatography (0-10% EtOAc/Petroleum ether) to give Compound 22-1 (163 mg, 99.6% yield). MS for $C_{12}H_{17}NO_4$: m/z 240.2 (MH+).

Step 2: Ethyl 5-bromo-2-ethoxy-1,6-dimethyl-4-oxo-1,4-dihydropyridine-3-carboxylate (22-2): Compound 22-2 was synthesized from Compound 22-1 using General Procedure B1. MS for $C_{12}H_{16}BrNO_4$: m/z 319.8 (MH+).

Step 3: Ethyl 2-ethoxy-5-(4-fluorophenyl)-1,6-dimethyl-4-oxo-1,4-dihydropyridine-3-carboxylate (22-3): Compound 22-3 was synthesized from Compound 22-2 using General Procedure C1. MS for $C_{18}H_{20}FNO_4$: m/z 333.9 (MH+).

Step 4: 2-Ethoxy-5-(4-fluorophenyl)-1,6-dimethyl-4-oxo-1,4-dihydropyridine-3-carboxylic acid (PA7-37): Compound 21-3 was converted to Compound PA7-19 using a modification of the ester hydrolysis procedure used in Step 3 of General Procedure A. In this particular case the NaOH was replaced with KOH and the reaction mixture was heated to 100° C. prior to work up. MS for $C_{16}H_{16}FNO_4$: m/z 305.9 (MH+).

Example 23: 8-(4-Fluorophenyl)-7-oxo-1,2,3,7-tetrahydroindolizine-6-carboxylic acid (PA7-27)

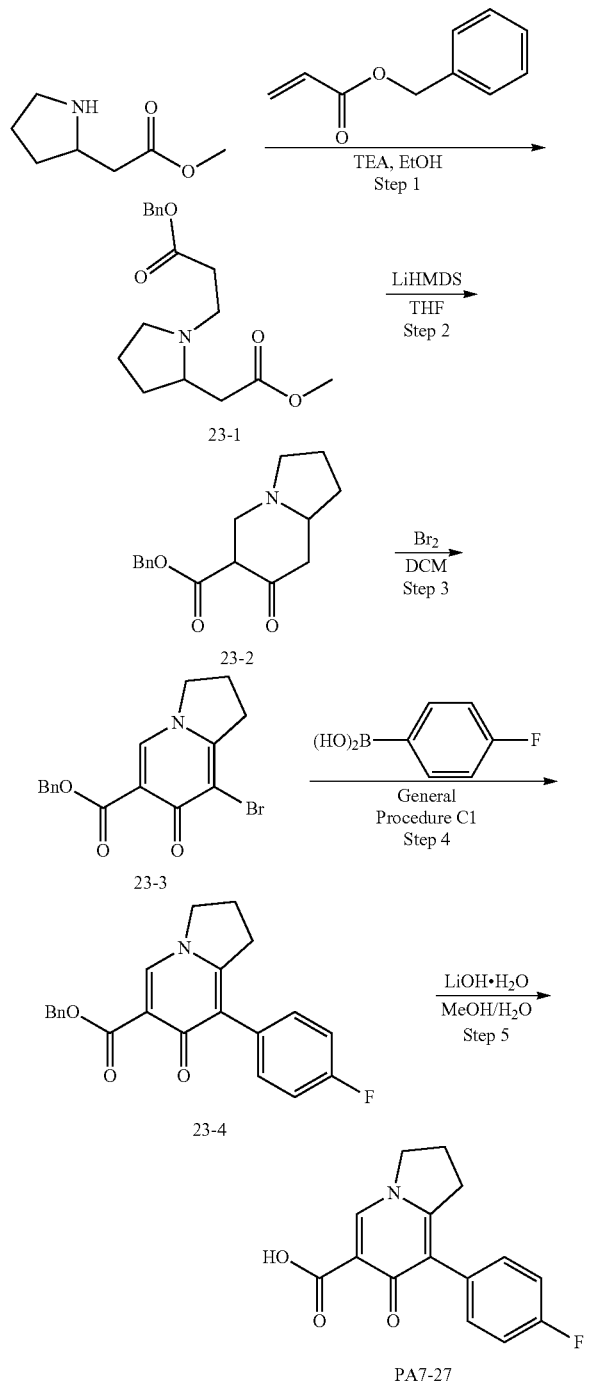

Step 1: Benzyl 3-(2-(2-methoxy-2-oxoethyl)pyrrolidin-1-yl)propanoate (23-1): To a mixture of methyl 2-pyrrolidin-2-ylacetate (1.04 g, 7.3 mmol, 1 eq) and benzyl prop-2-enoate (1.77 g, 11 mmol, 1.5 eq) in EtOH (15 mL) was added TEA (3.67 g, 36 mmol, 5.1 mL, 5 eq) in one portion at 20° C. The mixture was stirred at 20° C. for 16 h. The mixture was concentrated then diluted with water (300 mL) and extracted with EtOAc (3×30 mL). The combined organic extracts were washed with aq saturated NaCl (10 mL), dried over anhyd $Na_2SO_4$, concentrated and the resulting residue was purified by flash silica gel chromatography (0-10% MeOH/DCM) to give Compound 23-1 (1.2 g, 54% yield). MS for $C_{17}H_{23}NO_4$: m/z 306.1 (MH+).

Step 2: Benzyl 7-oxooctahydroindolizine-6-carboxylate (23-2): To a mixture of Compound 23-1 (1.2 g, 4 mmol, 1 eq) in THF (15 mL) was added LiHMDS (1 M, 7.9 mL, 2 eq) slowly in one portion at −78° C. under an atmosphere of nitrogen. The mixture was stirred at −78° C. for 2 h. Conc. HCl (10 mL) and THF (1 mL) was added into the reaction mixture. The mixture was concentrated, then diluted with water (60 mL) and the pH adjust to 8 with the addition of $K_2CO_3$. The resulting mixture was extracted with EtOAc (2×60 mL). The combined organic extracts were washed with aq saturated NaCl (20 mL), dried over anhyd $Na_2SO_4$, concentrated and purified by silica gel column chromatography (3% MeOH in DCM) to give Compound 23-2 (600 mg, 56% yield). MS for $C_{16}H_{19}NO_3$: m/z 274.1 (MH+).

Step 3: Benzyl 8-bromo-7-oxo-1,2,3,7-tetrahydroindolizine-6-carboxylate (23-3): To a mixture of Compound 23-2 (600 mg, 2.2 mmol, 1 eq) in DCM (10 mL) was added $Br_2$ (351 mg, 2.2 mmol, 0.11 mL, 1 eq) in one portion at 20° C. The mixture was stirred at 0-20° C. for 3 h. The mixture was diluted with DCM (50 mL), washed with aq saturated $NaHCO_3$, concentrated and purified by silica gel column chromatography (2% MeOH in DCM) to give Compound 23-3 (170 mg, 22% yield). MS for $C_{16}H_{19}NO_3$: m/z 348.0 (MH+).

Step 4: Benzyl 8-(4-fluorophenyl)-7-oxo-1,2,3,7-tetrahydroindolizine-6-carboxylate (23-4): Compound 23-4 was synthesized from Compound 23-3 using General Procedure C1. MS for $C_{22}H_{18}FNO_3$: m/z 364.1 (MH+).

Step 5: 8-(4-Fluorophenyl)-7-oxo-1,2,3,7-tetrahydroindolizine-6-carboxylic acid (PA7-27): To a mixture of Compound 23-4 (75 mg, 0.21 mmol, 1 eq) in MeOH (6 mL) and water (2 mL) was added LiOH monohydrate (86.61 mg, 2.06 mmol, 10 eq) in one portion at 20° C. under an atmosphere of nitrogen. The mixture was stirred at 20° C. for 12 h. The pH of the resulting mixture was adjusted to pH 4-5 by the addition of aq 2 N HCl. The mixture was then diluted with water (30 mL) and extracted with EtOAc (3×50 mL). The combined EtOAc extracts were concentrated and purified by silica gel column chromatography (5% MeOH in DCM) to give Compound PA7-27 (56 mg, 99% yield). MS for $C_{15}H_{12}FNO_3$: m/z 274.1 (MH+).

The following compound was made by the same technique used to make PA7-27 in Example 23:

1-(4-Fluorophenyl)-2-oxo-6,7,8,9-tetrahydro-2H-quinolizine-3-carboxylic acid (PA7-34): MS for $C_{16}H_{14}FNO_3$: m/z 288.1 (MH+).

Example 24: 6-(4-Fluorophenyl)-7-oxo-1,2,3,5,6,7-hexahydroindolizine-8-carboxylic acid (PA7-41)

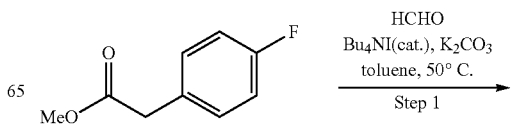

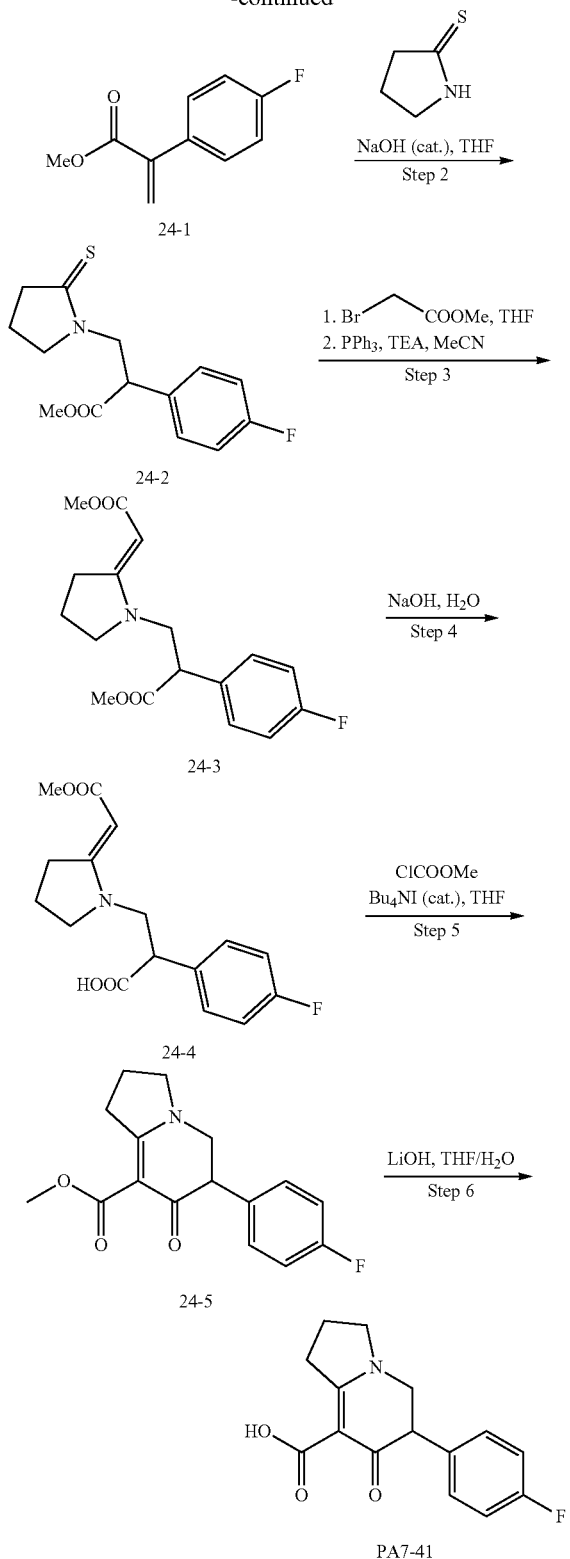

17 h. After cooling to room temperature, the mixture was diluted with water (50 mL) and extracted with toluene (2×50 mL). The organic extracts were dried over anhyd Na₂SO₄, concentrated and the resulting residue was purified by silica gel column chromatography (3% EtOAc in petroleum ether) to give Compound 24-1 (0.61 g, 28% yield). $^1$H NMR (400 MHz, CDCl$_3$) δ 7.45-7.35 (m, 2H), 7.09-7.00 (m, 2H), 6.36 (d, 1H), 5.87 (d, 1H), 3.82 (s, 3H).

Step 2: Methyl 2-(4-fluorophenyl)-3-(2-thioxopyrrolidin-1-yl)propanoate (24-2): Compound 24-1 (610 mg, 3.4 mmol, 1 eq) and pyrrolidine-2-thione (330 mg, 3.3 mmol, 0.96 eq) were dissolved in dry THF (10 mL) followed by the addition of NaOH (20 mg, 0.500 mmol, 0.15 eq). The resulting mixture was stirred at 25-30° C. for 90 h. The mixture was diluted with water (30 mL) and extracted with EtOAc (2×30 mL). The combined organic extracts were concentrated, and the resulting residue was purified by silica gel column chromatography (20% EtOAc in petroleum ether) to give Compound 24-2 (624 mg, 66% yield). $^1$H NMR (400 MHz, CDCl$_3$) δ 7.35-7.27 (m, 2H), 7.07-6.98 (m, 2H), 4.56 (t, 1H), 4.17 (dd, 1H), 3.97 (dd, 1H), 3.75-3.69 (m, 1H), 3.69 (s, 3H), 3.28-3.20 (m, 1H), 3.00-2.89 (m, 2H), 2.00-1.82 (m, 2H).

Step 3: Methyl (E)-2-(4-fluorophenyl)-3-(2-(2-methoxy-2-oxoethylidene)pyrrolidin-1-yl)propanoate (24-3): Methyl 2-bromoacetate (405 mg, 2.6 mmol, 0.25 mL, 1.2 eq) was added to a solution of Compound 24-2 (620 mg, 2.20 mmol, 1 eq) in THF (10 mL) and the mixture was stirred at 20-30° C. for 16 h. The resulting mixture was concentrated under vacuum and the residue was dissolved in ACN (10 mL). PPh$_3$ (636 mg, 2.4 mmol, 1.1 eq) and TEA (268 mg, 2.6 mmol, 0.37 mL, 1.2 eq) were added. The resulting mixture was stirred at 20-30° C. for another 24 h. The mixture was concentrated under vacuum and the resulting residue was purified by silica gel column chromatography (20% EtOAc in petroleum ether) to give Compound 24-3 (564 mg, 73% yield). MS for C$_{17}$H$_{20}$FNO$_4$: m/z 321.9 (MH+).

Step 4: (E)-2-(4-Fluorophenyl)-3-(2-(2-methoxy-2-oxoethylidene)pyrrolidin-1-yl)propanoic acid (24-4): NaOH (65 mg, 1.6 mmol, 1.0 eq) was added to a mixture of Compound 24-3 (560 mg, 1.6 mmol, 1 eq) in water (10 mL). The mixture was heated and stirred at 100° C. for 2 h. After cooling to room temperature, the reaction mixture was lyophilized to give Compound 24-4 (530 mg, 99.8% yield). MS for C$_{16}$H$_{18}$FNO$_4$: m/z 307.9 (MH+).

Step 5: Methyl 6-(4-fluorophenyl)-7-oxo-1,2,3,5,6,7-hexahydroindolizine-8-carboxylate (24-5): Methyl chloroformate (122 mg, 1.3 mmol, 0.1 mL, 1.1 eq) was added to a suspension of Compound 24-4 (400 mg, 1.2 mmol, 1 eq) and tetrabutylammonium; iodide (44 mg, 0.12 mmol, 0.1 eq) in THF (20 mL) under an atmosphere of nitrogen. The mixture was stirred at 20-30° C. for 22 h. The mixture was concentrated under vacuum and the resulting residue was purified by silica gel column chromatography (0-10% EtOH in EtOAc) followed by further purification by prep-HPLC (Venusil ASB Phenyl 150*30 mm*5 um; mobile phase: [water (0.05% HCl)-ACN]; B %: 30%-60%, 9 min) to give Compound 24-5 (130 mg, 87% yield). MS for C$_{16}$H$_{16}$FNO$_3$: m/z 289.9 (MH+).

Step 6: 6-(4-Fluorophenyl)-7-oxo-1,2,3,5,6,7-hexahydroindolizine-8-carboxylic acid (PA7-41): LiOH·H$_2$O (165 mg, 3.9 mmol, 10 eq) was added to a solution of Compound 24-5 (110 mg, 0.38 mmol, 1 eq) in THF (5 mL) and water (1 mL). The mixture was stirred at 60° C. for 18 h. After cooling to room temperature, the mixture was concentrated under vacuum to remove the organic solvent. The residual aqueous layer was diluted with water (10 mL) and extracted Step 1: Methyl 2-(4-fluorophenyl)acrylate (24-1): Formaldehyde (2.70 g, 33 mmol, 2.5 mL, 2.8 eq), tetrabutylammonium; iodide (175 mg, 0.47 mmol, 0.04 eq) and K$_2$CO$_3$ (4.93 g, 36 mmol, 3 eq) were added to a solution of methyl 2-(4-fluorophenyl)acetate (2 g, 12 mmol, 1 eq) in toluene (15 mL). The mixture was warmed and stirred at 50° C. for with EtOAc (2×20 mL). The combined organic extracts were dried over anhyd Na₂SO₄ and concentrated under vacuum to give crude Compound PA7-41 (100 mg, 96% yield). MS for $C_{15}H_{14}FNO_3$: m/z 275.9 (MH+).

Example 25: 1-(4-Fluorophenyl)-6-methyl-2-oxo-1, 2-dihydropyridine-3-carboxylic acid (HA1-1)

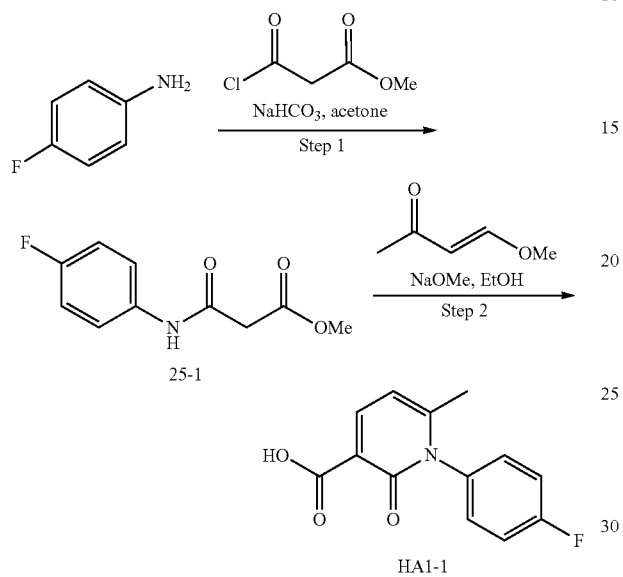

Step 1: Methyl 3-((4-fluorophenyl)amino)-3-oxopropanoate (25-1): To a mixture of 4-fluoroaniline (50 g, 450 mmol, 43 mL, 1 eq) and NaHCO₃ (64 g, 765 mmol, 30 mL, 1.7 eq) in acetone (250 mL) was added methyl 3-chloro-3-oxopropanoate (92 g, 675 mmol, 72 mL, 1.5 eq) dropwise and the resulting solution was stirred at 20° C. for 12 h. Water (200 mL) was added to the reaction mixture and the mixture was concentrated to remove the acetone. Water (200 mL) was again added and the mixture was stirred to precipitate. The resulting solid was filtered, washed with petroleum ether (2×50 mL) and dried to give Compound 25-1 (89 g, 94% yield) which was used in subsequent reactions without further purification. ¹H NMR (400 MHz, DMSO-d₆) δ 10.25 (s, 1H), 7.61-7.54 (m, 2H), 7.19-7.12 (m, 2H), 3.65 (s, 3H), 3.46 (s, 2H); MS for $C_{10}H_{10}FNO_3$: m/z 212.1 (MH+).

Step 2: 1-(4-Fluorophenyl)-6-methyl-2-oxo-1,2-dihydropyridine-3-carboxylic acid (HA1-1): To a solution of Compound 25-1 (1.0 g, 4.7 mmol, 1 eq) in EtOH (10 mL) was added 25% NaOMe in MeOH (2.35 g, 11 mmol, 2.3 eq) followed by the addition of (E)-4-methoxybut-3-en-2-one (521 mg, 5.2 mmol, 0.5 mL, 1.1 eq) and the resulting reaction mixture was stirred at 65° C. for 12 h. The reaction mixture was concentrated to remove the solvent and the pH adjusted 5 with aq HCl solution (3 M). The resulting suspension was filtrated, and the filtrate was concentrated to dryness to give Compound HA1-1 (550 mg, 47% yield) which was used in subsequent reactions without further purification. ¹H NMR (400 MHz, DMSO-d₆) δ 14.21 (s, 1H), 8.40 (d, 1H), 7.54-7.49 (m, 2H), 7.47-7.41 (m, 2H), 6.80 (d, 1H), 2.09 (s, 3H); MS for $C_{13}H_{10}FNO_3$: m/z 248 (MH+).

The following compounds were made using the same synthetic techniques exemplified in Example 25:

1-(4-Fluoro-2-methylphenyl)-6-methyl-2-oxo-1,2-dihydropyridine-3-carboxylic acid (HA1-2): The NaOMe in step 2 was replaced with NaOEt. ¹H NMR (400 MHz, DMSO-d₆) δ 14.15 (s, 1H), 8.45 (d, 1H), 7.45 (dd, 1H), 7.39 (dd, 1H), 7.28 (td, 1H), 6.85 (d, 1H), 2.07 (s, 3H), 2.00 (s, 3H); MS for $C_{14}H_{12}FNO_3$: m/z 262 (MH+).

Example 26: 1-(4-Fluorophenyl)-2-oxo-1,2-dihydropyridine-3-carboxylic acid (HA1-19)

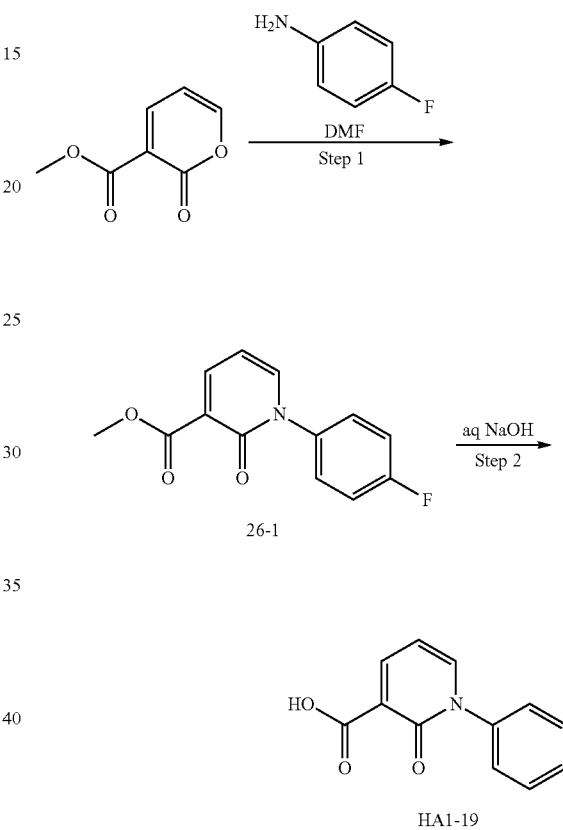

Step 1: Methyl 1-(4-fluorophenyl)-2-oxo-1,2-dihydropyridine-3-carboxylate (26-1): To a solution of methyl 2-oxopyran-3-carboxylate (400 mg, 2.6 mmol, 1 eq) in DMF (5 mL) was added 4-fluoroaniline (317 mg, 2.8 mmol, 0.27 mL, 1.1 eq) dropwise at 0° C. and the resulting mixture was stirred for 2 h at this temperature followed by heating the reaction mixture at 30° C. for 12 h. The resulting solid was filtered, and the filtrate was diluted with DCM (30 mL). The resulting precipitate was filtered and combined with the previously filtered solid. The resulting combined solids were washed with DCM (2×5 mL) and dried under vacuum to give Compound 26-1 (550 mg, 68% yield). ¹H NMR (400 MHz, DMSO-d₆) δ 7.97-8.27 (m, 1H), 7.89-7.97 (m, 1H), 7.21-7.29 (m, 4H), 6.97-7.04 (m, 1H), 3.74 (s, 3H); MS for $C_{13}H_{10}FNO_3$: m/z 248.0 (MH+).

Step 2: 1-(4-Fluorophenyl)-2-oxo-1,2-dihydropyridine-3-carboxylic acid (HA1-19): Compound HA1-19 was made from Compound 26-1 using standard ester hydrolysis conditions such as those used in Step 3 of Example 7. MS for $C_{12}H_8FNO_3$: m/z 234 (MH+).

Example 27: 5-Bromo-1-(4-fluorophenyl)-6-methyl-2-oxo-1,2-dihydropyridine-3-carboxylic acid (HA1-20)

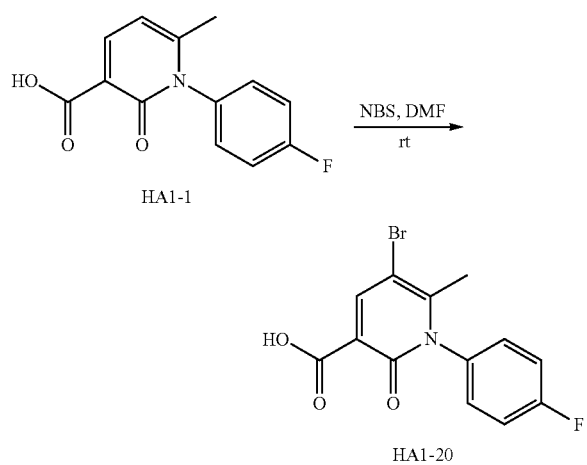 [SMILES: Cc1ccc(C(=O)O)c(=O)n1-c1ccc(F)cc1 ; Cc1c(Br)cc(C(=O)O)c(=O)n1-c1ccc(F)cc1]

5-Bromo-1-(4-fluorophenyl)-6-methyl-2-oxo-1,2-dihydropyridine-3-carboxylic acid (HA1-20): To a mixture of Compound HA-1 (550 mg, 2.2 mmol, 1 eq) in DMF (5 mL) was added NBS (475 mg, 2.7 mmol, 1.2 eq) under an atmosphere of nitrogen. The mixture was stirred at 25° C. for 12 h. The mixture was concentrated to remove the solvent and water (30 mL) was added and the resulting mixture was extracted with DCM (2×20 mL). The combined organic extracts were concentrated to give Compound HA1-20 (700 mg, 96% yield) which was used in subsequent reactions without further purification. MS for $C_{13}H_9BrFNO_3$: m/z 327.9 (MH+).

Example 28: 5-Acetyl-1-(4-fluorophenyl)-6-methyl-2-oxo-1,2-dihydropyridine-3-carboxylic acid (HA1-3)

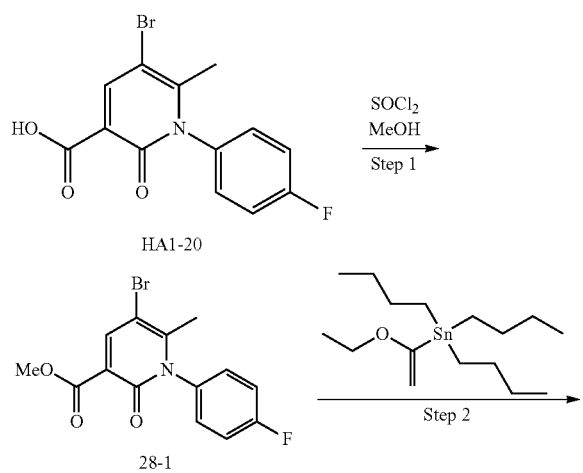

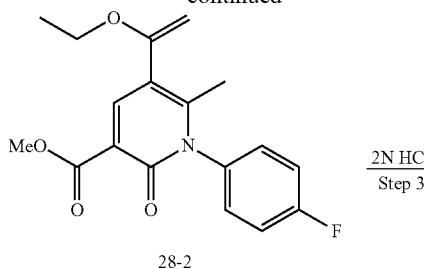

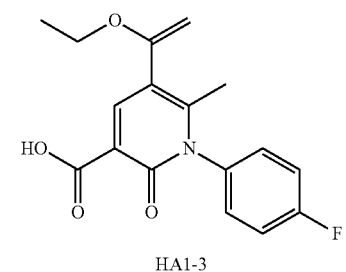

Step 1: Methyl 5-bromo-1-(4-fluorophenyl)-6-methyl-2-oxo-1,2-dihydropyridine-3-carboxylate (28-1): To a mixture of Compound HA1-20 (11.0 g, 33.73 mmol, 1 eq) in MeOH (100 mL) was added thionyl chloride (20 g, 169 mmol, 12.2 mL, 5 eq) at 0° C. and the resulting mixture was stirred at 25° C. for 1 h. The reaction mixture was concentrated to remove the solvent, diluted with water (50 mL) and extracted with DCM (3×50 mL). The combined organic extracts were washed with aq saturated NaCl (30 mL), dried with anhyd $Na_2SO_4$ and concentrated under vacuum. The resulting residue was purified by flash silica gel chromatography (0-30% EtOAc/petroleum ether) to give Compound 28-1 (11.0 g, 96% yield). MS for $C_{14}H_{11}BrFNO_3$: m/z 341.7 (MH+).

Step 2: Methyl 5-(1-ethoxyvinyl)-1-(4-fluorophenyl)-6-methyl-2-oxo-1,2-dihydropyridine-3-carboxylate (28-2): To a solution of Compound 28-1 (200 mg, 0.59 mmol, 1 eq) and tributyl(1-ethoxyvinyl)stannane (0.84 g, 2.33 mmol, 0.78 mL, 3.96 eq) in dioxane (5 mL) was added DPPF (32.6 mg, 0.059 mmol, 0.1 eq), Pd(dppf)Cl$_2$ (43 mg, 0.059 mmol, 0.1 eq) and CuI (11.2 mg, 0.059 mmol, 0.1 eq). The reaction mixture was stirred at 100° C. for 12 h under an atmosphere of nitrogen. Aq saturated KF (20 mL) was added and the mixture was stirred at 25° C. for 1 h, then $NH_3·H_2O$ (5 mL) was added and the mixture was extracted with EtOAc (3×30 mL). The combined organic extracts were washed with aq saturated NaCl (10 mL), dried over $Na_2SO_4$ and concentrated Compound 28-2 (190 mg, 98% yield) which was used in subsequent reactions without further purification. MS for $C_{18}H_{18}FNO_4$: m/z 332.1 (MH+).

Step 3: 5-Acetyl-1-(4-fluorophenyl)-6-methyl-2-oxo-1,2-dihydropyridine-3-carboxylic acid (HA1-3): A mixture of Compound 28-2 (190 mg, 0.57 mmol, 1 eq) in aq HCl (2 M, 5 mL, 17 eq) was stirred at 25° C. for 2 h. The resulting mixture was extracted with DCM (3×20 mL). The combined organic extracts were dried over anhyd $Na_2SO_4$ and concentrated to give Compound HA1-3 (67 mg, 40% yield) which was used in subsequent reactions without further purification. MS for $C_{15}H_{12}FNO_4$: m/z 290.0 (MH+).

Example 29: 1-(4-Fluorophenyl)-5,6-dimethyl-2-oxo-1,2-dihydropyridine-3-carboxylic acid (HA1-23)

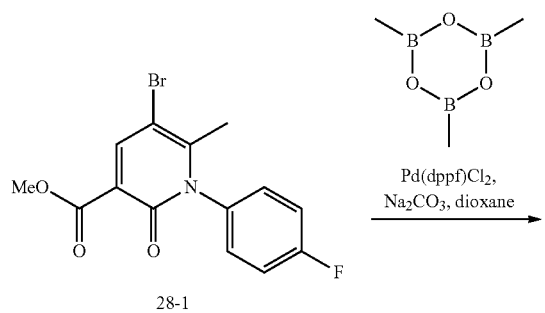

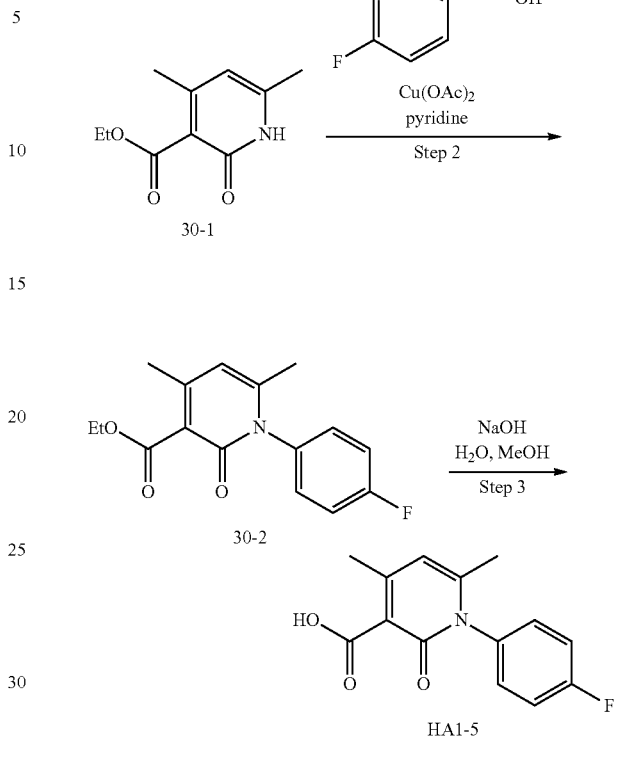

1-(4-Fluorophenyl)-5,6-dimethyl-2-oxo-1,2-dihydropyridine-3-carboxylic acid (HA-23): To a solution of 2,4,6-trimethyl-1,3,5,2,4,6-trioxatriborinane (1.48 g, 5.9 mmol, 1.6 mL, 2 eq) and Compound 28-1 (1.0 g, 2.94 mmol, 1 eq) in dioxane (10 mL) and water (2 mL) was added Na$_2$CO$_3$ (623 mg, 5.9 mmol, 2 eq) and Pd(dppf)Cl$_2$ (108 mg, 0.15 mmol, 0.05 eq) under an atmosphere of nitrogen. The mixture was stirred at 120° C. for 3 h. The reaction mixture was concentrated to remove the solvent, diluted with water (20 mL) and extracted with DCM (3×20 mL). The combined organic extracts were washed with aq saturated NaCl (10 mL), dried with anhyd Na$_2$SO$_4$ and concentrated under vacuum. The resulting residue was purified flash silica gel chromatography (0-10% MeOH/DCM) to give Compound HA1-23 (200 mg, 26% yield). MS for C$_{14}$H$_{12}$FNO$_3$: m/z 261.9 (MH+).

Example 30: 1-(4-Fluorophenyl)-4,6-dimethyl-2-oxo-1,2-dihydropyridine-3-carboxylic (HA1-5)

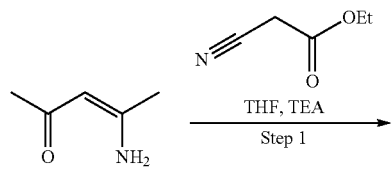

Step 1: Ethyl 4,6-dimethyl-2-oxo-1,2-dihydropyridine-3-carboxylate (30-1): (Z)-4-aminopent-3-en-2-one (5.0 g, 50 mmol, 1 eq) and ethyl 2-cyanoacetate (5.8 g, 51 mmol, 1.02 eq) were added to a stirring solution of THF (56 mL) and TEA (2.0 g, 20 mmol, 0.4 eq). After heating for 48 h, the reaction was cooled to ambient temperature and allowed to sit for 4 days. The resulting mixture was filtered, and the solids were washed with EtOAc to give Compound 30-1 (2.98 g, 30% yield). MS for C$_{10}$H$_{13}$NO$_3$: m/z=196 (MH+).

Step 2: Ethyl 1-(4-fluorophenyl)-4,6-dimethyl-2-oxo-1,2-dihydropyridine-3-carboxylate (30-2): Compound 30-1 (9.0 g, 46 mmol, 1 eq), diacetoxycopper hydrate (10 g, 50 mmol, 1.1 eq), (4-fluorophenyl)boronic acid (16 g, 110 mmol, 2.4 eq), 1,2-dichloroethane (15 mL) and pyridine (40 mL) were heated to 45° C. under an atmosphere of oxygen (1 atm). After overnight reaction the contents were cooled to ambient temperature, diluted with EtOAc and filtered through a short plug of silica gel. The crude product was concentrated onto Celite and purified by silica gel chromatography (220 g, 0% to 2% MeOH in DCM) to give Compound 30-2 (4.2 g, 31% yield). MS for C$_{16}$H$_{16}$FNO$_3$: m/z=290 (MH+).

Step 3: 1-(4-Fluorophenyl)-4,6-dimethyl-2-oxo-1,2-dihydropyridine-3-carboxylic (HA1-5): Compound HA1-5 was made from Compound 30-2 using standard ester hydrolysis conditions such as those used in Step 3 of Example 7. MS for C$_{14}$H$_{12}$FNO$_3$: m/z 262 (MH+).

The following compound was made using the same method used to make Compound HA1-5 in Example 30:

1-(4-Fluoro-2-methylphenyl)-4,6-dimethyl-2-oxo-1,2-dihydropyridine-3-carboxylic acid (HA1-15): MS for C$_{15}$H$_{14}$FNO$_3$: m/z 276 (MH+).

Example 31: 5-Bromo-1-(4-fluorophenyl)-4,6-dimethyl-2-oxo-1,2-dihydropyridine-3-carboxylic acid (HA1-6)

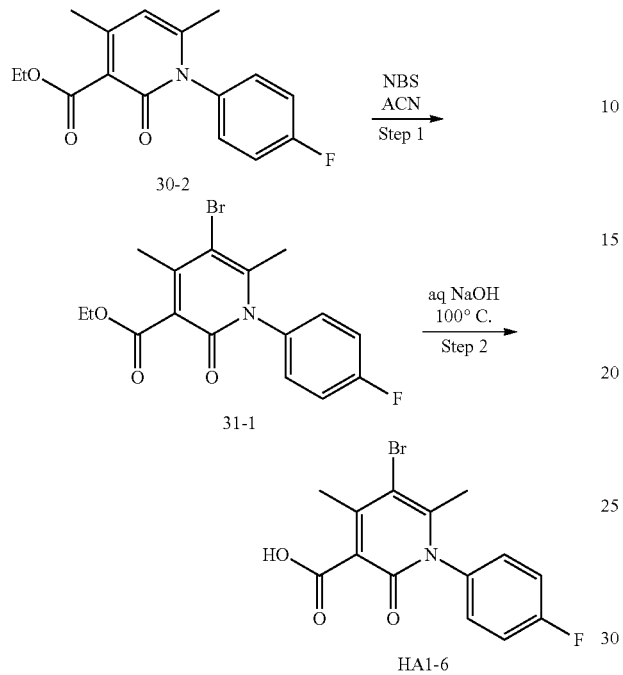

Step 1: Ethyl 5-bromo-1-(4-fluorophenyl)-4,6-dimethyl-2-oxo-1,2-dihydropyridine-3-carboxylate (31-1): To a stirring solution of Compound 30-2 (1.0 g, 3.5 mmol, 1 eq) in ACN (12 mL) at room temperature was added NBS (1.0 g, 5.6 mmol, 1.6 eq) in a single portion. After several hours at room temperature, the reaction was quenched with the addition of aq saturated $Na_2S_2O_3$ (20 mL). The mixture was then diluted with water (80 mL) and extracted with DCM (3×50 mL). The combined organic extracts were dried with anhyd $Na_2SO_4$, concentrated and purified by silica gel chromatography (0% to 40% EtOAc in hexanes) to give Compound 31-1 (1.11 g, 87% yield). H NMR (400 MHz, DMSO-$d_6$) δ 7.42-7.33 (m, 4H), 4.25 (q, 2H), 2.25 (s, 3H), 2.13 (s, 3H), 1.29-1.14 (m, 3H); MS for $C_{16}H_{15}BrFNO_3$: m/z 370 (MH+).

Step 2: 5-Bromo-1-(4-fluorophenyl)-4,6-dimethyl-2-oxo-1,2-dihydropyridine-3-carboxylic acid (HA1-6): Compound HA1-6 was made from Compound 31-1 using standard ester hydrolysis conditions such as those used in Step 3 of Example 7. MS for $C_{14}H_{11}BrFNO_3$: m/z 340 (MH+).

Example 32: 1-(4-Fluorophenyl)-4,5,6-trimethyl-2-oxo-1,2-dihydropyridine-3-carboxylic acid HA1-8)

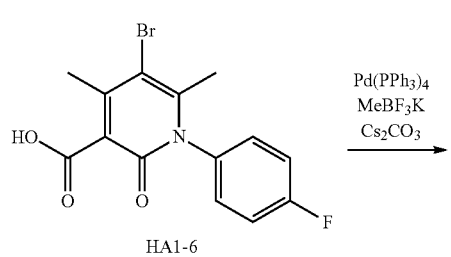

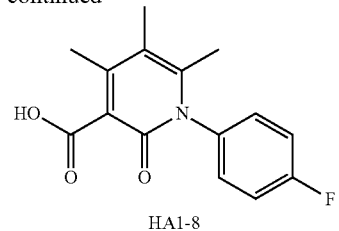

1-(4-Fluorophenyl)-4,5,6-trimethyl-2-oxo-1,2-dihydropyridine-3-carboxylic acid (HA1-8): A mixture of Compound HA1-6 (175 mg, 0.51 mmol, 1 eq), potassium methyltrifluoroborate (0.48 g, 3.9 mmol, 7.7 eq), $Cs_2CO_3$ (0.33 g, 1.0 mmol, 2 eq), tetrakis(triphenylphosphine) palladium(0) (110 mg, 0.095 mmol, 0.19 eq), DMF (0.50 mL), water (0.30 mL) and THF (1.0 mL) was heated to 80° C. under an inert atmosphere. After overnight reaction, the resulting reaction mixture was concentrated, diluted with EtOAc (10 mL) and extracted (2×Veq) with dilute aq NaOH (pH-12). The combined aqueous basic extracts were acidified with concentrated HCl (pH 2) and extracted with EtOAc (3×Veq). The combined organic extracts were purified by prep HPLC (10% to 90% MeCN in water (+FA)) to give Compound HA1-8 (30 mg, 22% yield). MS for $C_{15}H_{14}FNO_3$: m/z 276 (MH+).

Example 33: 5-Chloro-1-(4-fluorophenyl)-4,6-dimethyl-2-oxo-1,2-dihydropyridine-3-carboxylic acid (HA1-7)

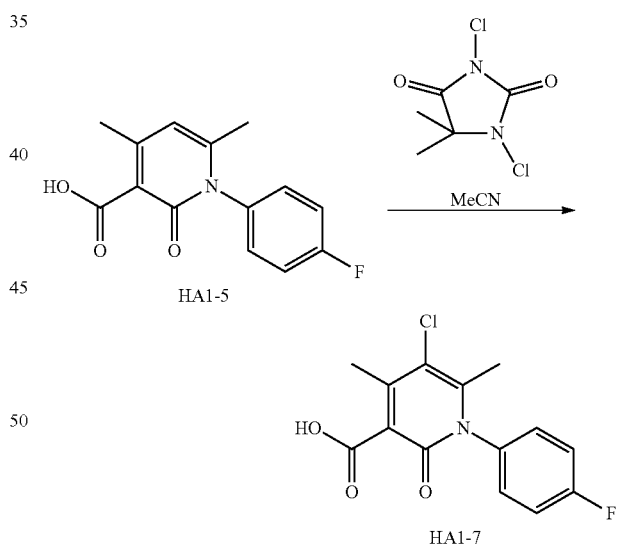

5-Chloro-1-(4-fluorophenyl)-4,6-dimethyl-2-oxo-1,2-dihydropyridine-3-carboxylic acid (HA1-7): To a solution of Compound HA-5 (98 mg, 0.38 mmol, 1 eq) in ACN (1.0 mL) was added a solution of 1,3-dichloro-5,5-dimethylhydantoin (100 mg, 0.5 mmol, 1.3 eq) in ACN (1.0 mL) over 5 min. After 2 h, the reaction was quenched by the addition of an equal volume of aq, saturated $Na_2S_2O_3$. The resulting mixture was stirred for 5 min after which water (20 mL) was added and the resulting mixture was extracted with EtOAc (2×Veq) and concentrated to give Compound HA1-7 (78 mg, 68% yield). MS for $C_{14}H_1ClFNO_3$: m/z 296 (MH+).

Example 34: 5-Cyano-1-(4-fluorophenyl)-4,6-dimethyl-2-oxo-1,2-dihydropyridine-3-carboxylic acid (HA1-9) and 5-Carbamoyl-1-(4-fluorophenyl)-4,6-dimethyl-2-oxo-1,2-dihydropyridine-3-carboxylic acid (HA1-10)

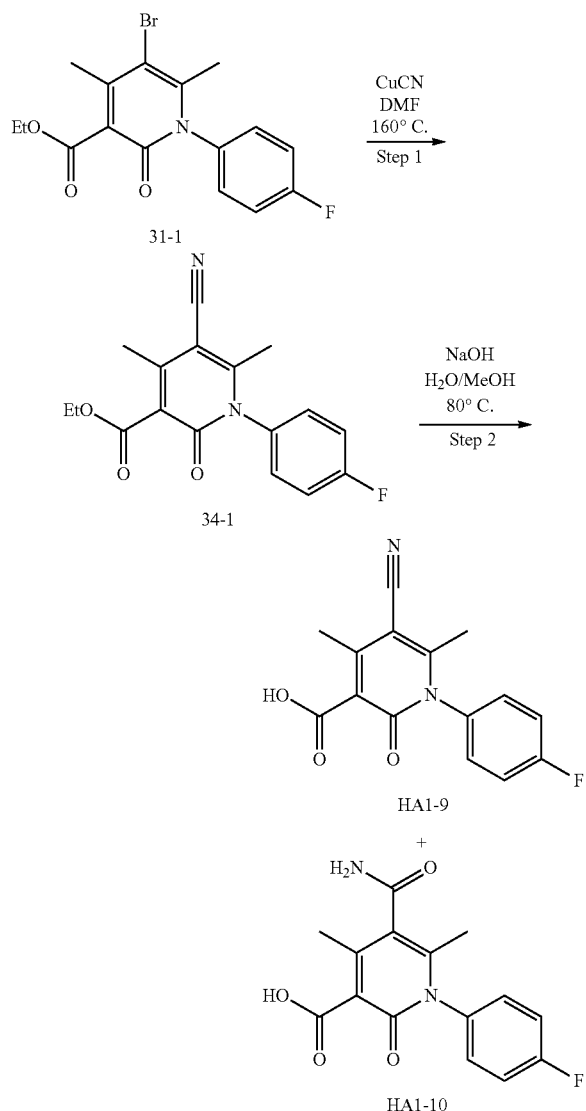

Step 1: Ethyl 5-cyano-1-(4-fluorophenyl)-4,6-dimethyl-2-oxo-1,2-dihydropyridine-3-carboxylate (34-1): A mixture of Compound 31-1 (286 mg, 0.777 mmol, 1.0 eq), copper(I) cyanide (186 mg, 2.08 mmol, 2.7 eq) and DMF (1.0 mL) were heated to 160° C. for 3 h in a microwave reactor. The resulting mixture was subsequently diluted with water and extracted with EtOAc (3×Veq). The combined organic extracts were concentrated and purified by silica gel chromatography (0% to 100% EtOAc in hexanes) to give Compound 34-1 (210 mg, 86.0% Yield). MS for $C_{17}H_{15}FN_2O_3$: m/z 315 (MH+).

Step 2: 5-Cyano-1-(4-fluorophenyl)-4,6-dimethyl-2-oxo-1,2-dihydropyridine-3-carboxylic acid (HA1-9) and 5-Carbamoyl-1-(4-fluorophenyl)-4,6-dimethyl-2-oxo-1,2-dihydropyridine-3-carboxylic acid (HA1-10): Compound 34-1 was subjected to standard ester hydrolysis conditions such as those used in Step 3 of Example 7 to give 90 mg of a mixture of Compound HA1-9 (MS for $C_{15}H_{11}FN_2O_3$: m/z 287 (MH+) and Compound HA1-10 (MS for $C_{15}H_{13}FN_2O_4$: m/z 305 (MH+). The mixture of HA1-9 and HA1-10 was used as is in subsequent reactions without separation or further purification.

Example 35: 5-Acetyl-1-(4-fluorophenyl)-4,6-dimethyl-2-oxo-1,2-dihydropyridine-3-carboxylic acid (HA1-11)

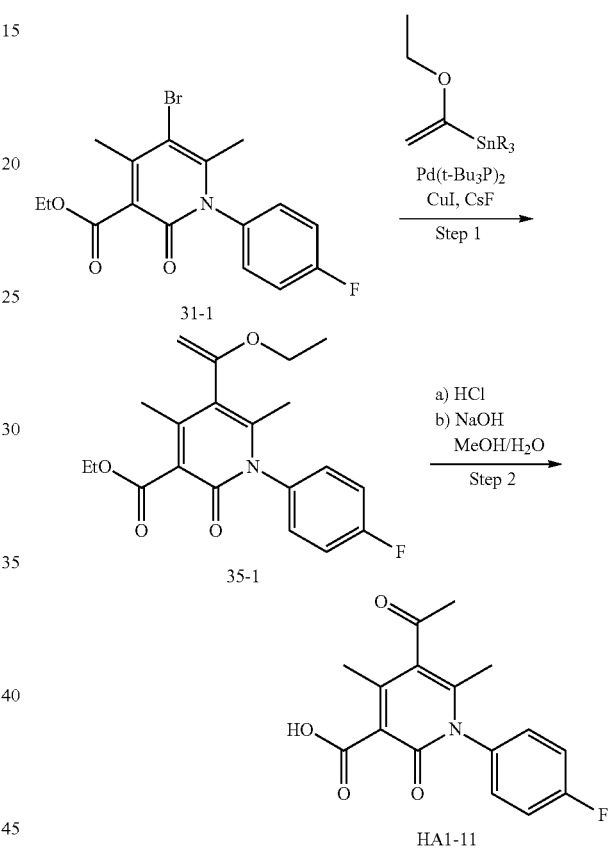

Step 1: Ethyl 5-(1-ethoxyvinyl)-1-(4-fluorophenyl)-4,6-dimethyl-2-oxo-1,2-dihydropyridine-3-carboxylate (35-1): A mixture of cesium fluoride (290 mg, 1.91 mmol, 2.4 eq), copper(I) iodide (15 mg, 0.079 mmol, 0.10 eq), bis(tri-tert-butylphosphine)palladium(0) (45 mg, 0.088 mmol, 0.11 eq), Compound 31-1 (290 mg, 0.788 mmol, 1.0 eq), tributyl(1-ethoxyvinyl)stannane (425 mg, 1.177 mmol, 1.5 eq) and DMF (2 mL) was stirred at 45° C. under an inert atmosphere of argon (1 atm). After overnight reaction, the reaction mixture was diluted with water and extracted with EtOAc (3×Veq). The combined organic extracts were concentrated and purified by silica gel chromatography (0% to 50% EtOAc in hexanes) to give Compound 35-1 (100 mg, 35% Yield). MS for $C_{20}H_{22}FNO_4$: m/z 360.2 (MH+).

Step 2: 5-Acetyl-1-(4-fluorophenyl)-4,6-dimethyl-2-oxo-1,2-dihydropyridine-3-carboxylic acid (HA1-11): To a stirring solution Compound 35-1 (100 mg, 0.28 mmol, 1.0 eq) in MeOH (2.0 mL) was added HCl (50.0 mg, 37 mass %, 0.51 mmol, 1.8 eq) in water (2.0 mL). After stirring for several hours at ambient temperature an LC-MS indicated the Compound 35-1 had been consumed to produce the partially hydrolyzed intermediate. NaOH (260 mg, 6.50 mmol, 23 eq) was subsequently added and the reaction was heated to 80° C. for 2 h. The reaction mixture was then acidified (pH~2) with conc HCl. The resulting mixture was diluted with water (20 mL) and extracted with EtOAc (3×Veq). The combined EtOAc extracts were concentrated and purified by prep HPLC (10% to 60% MeCN in water (FA)) to give Compound HA1-11 (48 mg, 57% Yield). MS for $C_{16}H_{14}FNO_4$: m/z 304 (MH+).

Example 36: 1-(4-Fluorophenyl)-4,6-dimethyl-2-oxo-5-vinyl-1,2-dihydropyridine-3-carboxylic acid (HA1-12)

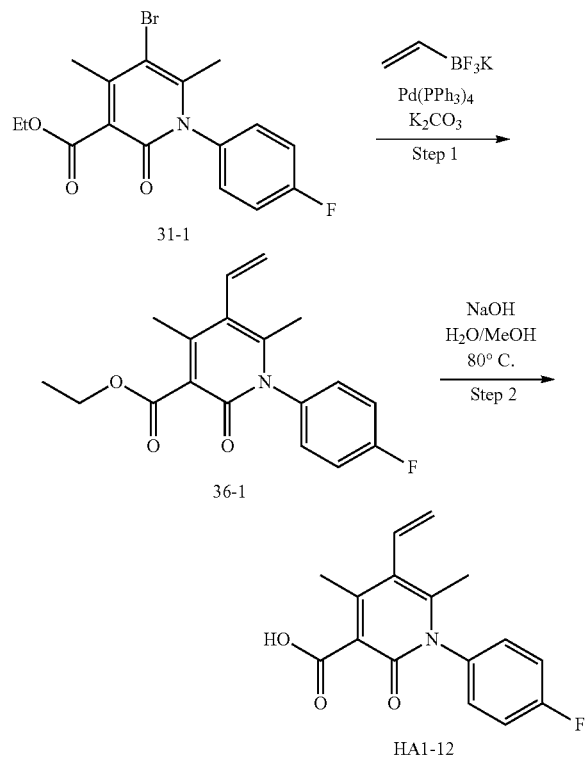

Step 1: Ethyl 1-(4-fluorophenyl)-4,6-dimethyl-2-oxo-5-vinyl-1,2-dihydropyridine-3-carboxylate (36-1): A mixture of Compound 31-1 (300 mg, 0.81 mmol, 1.0 eq), potassium vinyltrifluoroborate (300 mg, 2.2 mmol, 2.8 eq), tetrakis(triphenylphosphine)palladium(0) (90 mg, 0.078 mmol, 0.10 eq), $K_2CO_3$ (250 mg, 1.8 mmol, 2.2 eq), 1,4-dioxane (4.0 mL) and water (1.0 mL) was heated in a microwave reactor for 15 min at 120° C. The resulting mixture was diluted with water and extracted with an equal volume of EtOAc. The organic extract was concentrated and purified by silica gel chromatography (0% to 50% EtOAc in hexanes) to give Compound 36-1 (0.26 g, 99% yield). MS for $C_{18}H_{18}FNO_3$: m/z 316 (MH+).

Step 2: 1-(4-Fluorophenyl)-4,6-dimethyl-2-oxo-5-vinyl-1,2-dihydropyridine-3-carboxylic acid (HA1-12): Compound HA1-12 was made from Compound 36-1 using standard ester hydrolysis conditions such as those used in Step 3 of Example 7. MS for $C_{16}H_{14}FNO_3$: m/z 288 (MH+).

Example 37: 5-Ethyl-1-(4-fluorophenyl)-4,6-dimethyl-2-oxo-1,2-dihydropyridine-3-carboxylic acid-HA1-13)

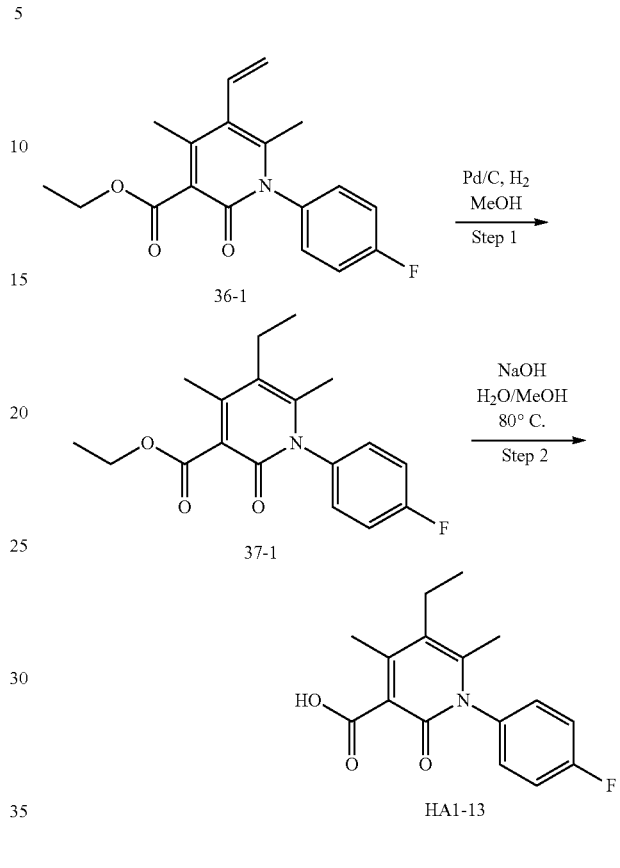

Step 1: Ethyl 5-ethyl-1-(4-fluorophenyl)-4,6-dimethyl-2-oxo-1,2-dihydropyridine-3-carboxylate (37-1): A mixture of Compound 36-1 (114 mg, 0.36 mmol, 1.0 eq), palladium on carbon (20 mg, 10% mass) and MeOH (1.0 mL) was stirred overnight under an atmosphere of hydrogen (1 atm). The reaction was then filtered through a pad of Celite and concentrated. The resulting residue was purified by prep HPLC (10% to 60% ACN in water (+FA)) to give Compound 37-1 (50 mg, 40% yield); MS for $C_{18}H_{20}FNO_3$: m/z 318 (MH+).

Step 2: 5-Ethyl-1-(4-fluorophenyl)-4,6-dimethyl-2-oxo-1,2-dihydropyridine-3-carboxylic acid (HA1-13): Compound HA1-13 was made from Compound 37-1 using standard ester hydrolysis conditions such as those used in Step 3 of Example 7. MS for $C_{16}H_{16}FNO_3$: m/z 290 (MH+).

Example 38: 5-Fluoro-1-(4-fluorophenyl)-4,6-dimethyl-2-oxo-1,2-dihydropyridine-3-carboxylic acid (HA1-14)

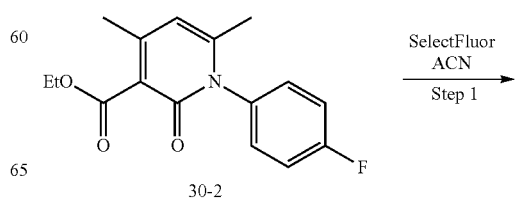

-continued

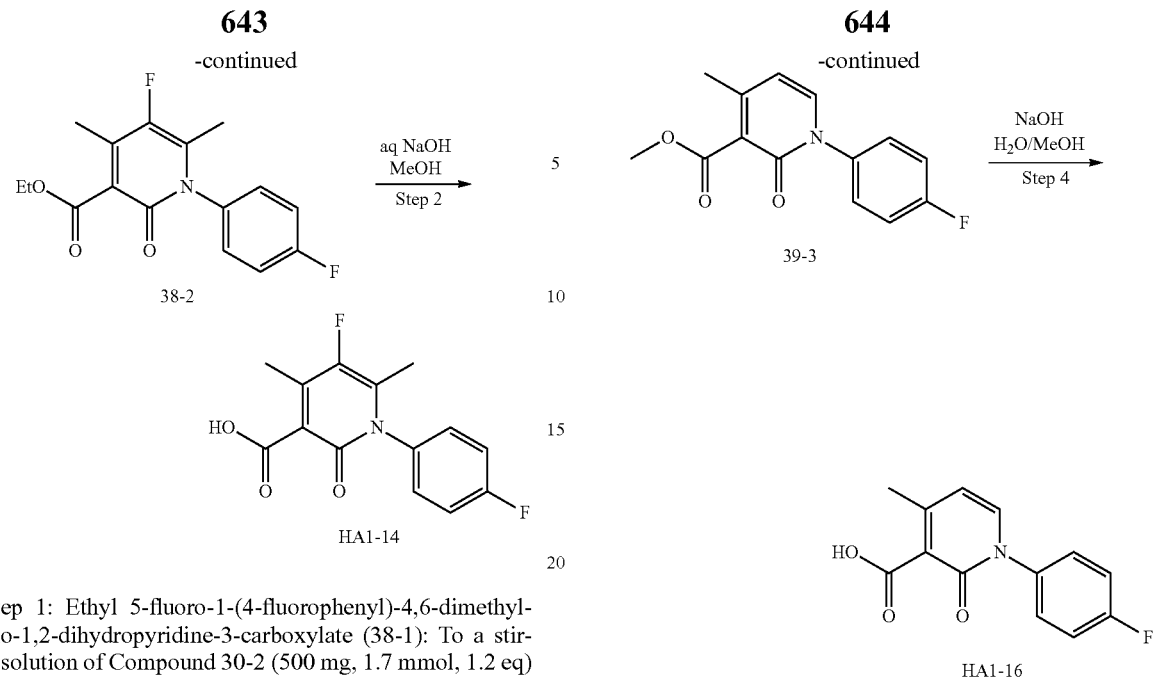

Step 1: Ethyl 5-fluoro-1-(4-fluorophenyl)-4,6-dimethyl-2-oxo-1,2-dihydropyridine-3-carboxylate (38-1): To a stirring solution of Compound 30-2 (500 mg, 1.7 mmol, 1.2 eq) in ACN (6 mL) was added Selectfluor (510 mg, 1.4 mmol, 1.0 eq). After 4 h, the crude reaction mixture was directly purified by silica gel chromatography (0% to 60% EtOAc in hexanes) to give Compound 38-1 (160 mg, 34% yield). $^1$H NMR (400 MHz, DMSO-$d_6$) δ 7.46-7.32 (m, 4H), 4.25 (q, 2H), 2.17 (d, 3H), 1.89 (d, 3H), 1.25 (t, 3H); MS for $C_{16}H_{15}F_2NO_3$: m/z 308 (MH+).

Step 2: 5-Fluoro-1-(4-fluorophenyl)-4,6-dimethyl-2-oxo-1,2-dihydropyridine-3-carboxylic acid (HA1-14): Compound HA1-14 was made from Compound 38-1 using standard ester hydrolysis conditions such as those used in Step 3 of Example 7. MS for $C_{14}HF_2NO_3$: m/z 280 (MH+).

Example 39: 1-(4-Fluorophenyl)-4-methyl-2-oxo-1,2-dihydropyridine-3-carboxylic acid (HA1-16)

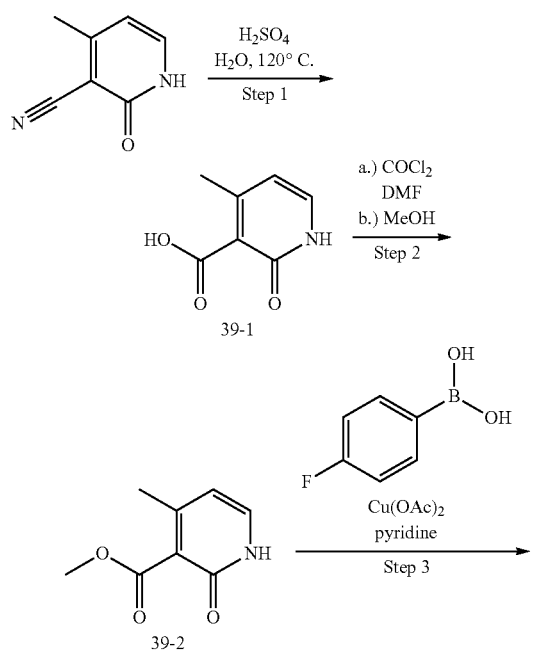

Step 1: 4-Methyl-2-oxo-1,2-dihydropyridine-3-carboxylic acid (39-1): A mixture of 4-methyl-2-oxo-1,2-dihydropyridine-3-carbonitrile (1.2 g, 8.9 mmol, 1 eq), water (3.4 mL) and concentrated sulfuric acid (1.9 mL) was heated to 120° C. for 4 h. The reaction was subsequently cooled, basified with 2 M NaOH (pH~10) and washed with EtOAc (2×Veq). The aqueous layer was acidified with 6 M HCl (pH~2), diluted with aq saturated NaCl and extracted with EtOAc (3×Veq). The combined EtOAc extracts were dried over anhyd $Na_2SO_4$ and concentrated to give Compound 39-1 (0.36 g, 26% yield). MS for $C_7H_7NO_3$: m/z 154 (MH+).

Step 2: Methyl 4-methyl-2-oxo-1,2-dihydropyridine-3-carboxylate (39-2): To a mixture of Compound 39-1 (0.36 g, 2.35 mmol, 1 eq), DCM (8 mL) and DMF (0.10 mL) under an atmosphere of nitrogen was added oxalyl chloride (0.55 mL, 6.4 mmol, 2.7 eq). After stirring for 4 h at ambient temperature, anhyd MeOH (1.0 mL) was added to the reaction in a dropwise fashion. One hour after the addition of MeOH, the contents were concentrated and purified by silica gel chromatography (0 to 100% EtOAc in hexanes followed by 0 to 20% MeOH in EtOAc) to give Compound 39-2 (0.28 g, 71% yield). MS for $C_8H_9NO_3$: m/z 168 (MH+).

Step 3: Methyl 1-(4-fluorophenyl)-4-methyl-2-oxo-1,2-dihydropyridine-3-carboxylate (39-3): Compound 39-3 was made from Compound 39-2 in the same manner Compound 30-2 was made from Compound 30-1 in Example 30. MS for $C_{14}H_{12}FNO_3$: m/z 262 (MH+).

Step 4: 1-(4-Fluorophenyl)-4-methyl-2-oxo-1,2-dihydropyridine-3-carboxylic acid (HA1-16): Compound HA1-16 was made from Compound 39-3 using standard ester hydrolysis conditions such as those used in Step 3 of Example 7. MS for $C_{13}H_{10}FNO_3$: m/z 248 (MH+).

The following compound was made using the same method used to make Compound HA1-16 in Example 39:

1-(4-Fluoro-2-methylphenyl)-4-methyl-2-oxo-1,2-dihydropyridine-3-carboxylic acid (HA1-17 MS for $C_{14}H_{12}FNO_3$: m/z 262 (MH+).

Example 40: 5-Fluoro-1-(4-fluorophenyl)-6-methyl-2-oxo-1,2-dihydropyridine-3-carboxylic acid (HA1-18)

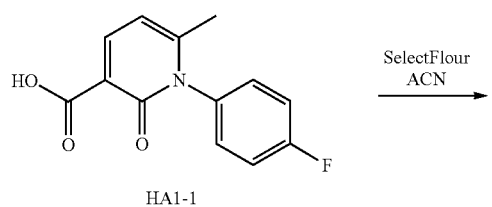

5-Fluoro-1-(4-fluorophenyl)-6-methyl-2-oxo-1,2-dihydropyridine-3-carboxylic acid (HA1-18): Compound HA1-18 was made from Compound HA1-1 by the same method used to convert Compound 30-2 to Compound 38-1 in Step 1 of Example 38. MS for $C_{13}H_9F_2NO_3$: m/z 266 (MH+).

Example 41: 1-(4-Fluorophenyl)-6-methyl-2-oxo-5-(prop-1-en-2-yl)-1,2-dihydropyridine-3-carboxylic acid (HA1-21) and 1-(4-Fluorophenyl)-5-isopropyl-6-methyl-2-oxo-1,2-dihydropyridine-3-carboxylic acid (HA1-22)

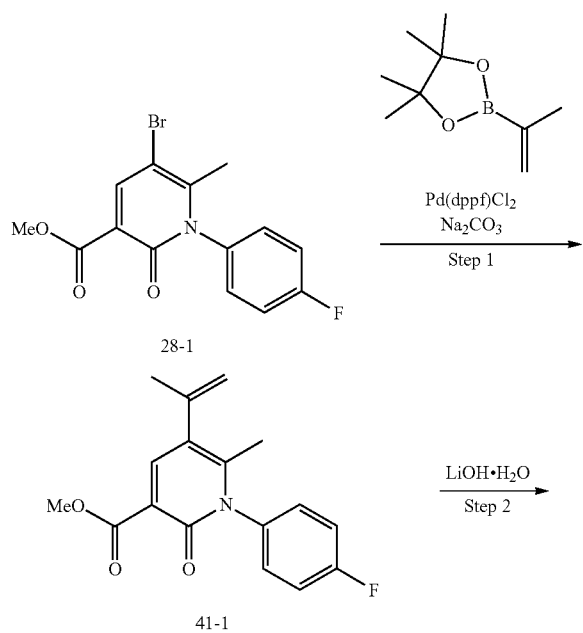

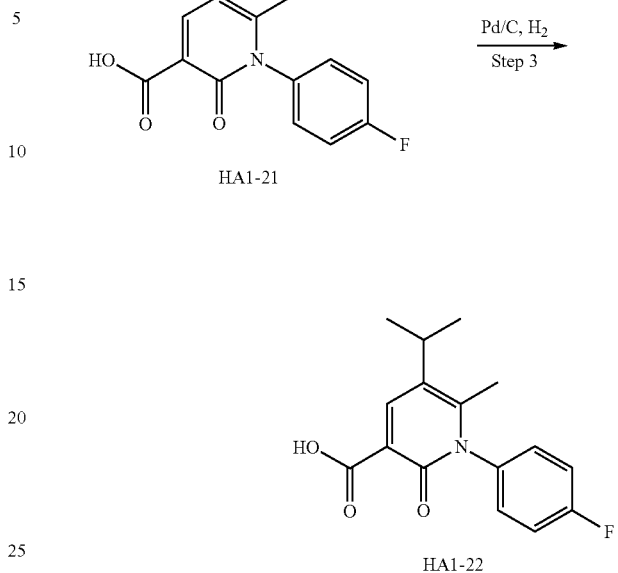

Step 1: Methyl 1-(4-fluorophenyl)-6-methyl-2-oxo-5-(prop-1-en-2-yl)-1,2-dihydropyridine-3-carboxylate (41-1): To a solution of Compound 28-1 (1.0 g, 2.9 mmol, 1 eq) and 2-isopropenyl-4,4,5,5-tetramethyl-1,3,2-dioxaborolane (94.0 mg, 2.9 mmol, 1 eq) in dioxane (10 mL) and water (2 mL) was added Na$_2$CO$_3$ (935 mg, 8.8 mmol, 3 eq) and Pd(dppf)Cl$_2$ (215 mg, 0.29 mmol, 0.1 eq) under an atmosphere of nitrogen. The mixture was stirred at 120° C. for 2 h under microwave irradiation. Water (30 mL) was added and the reaction mixture was extracted with DCM (3×30 mL). The combined organic extracts were washed with aq saturated NaCl (10 mL) concentrated under vacuum to give Compound 41-1 (320 mg, 36% yield). MS for $C_{17}H_{16}FNO_3$: m/z 301.9 (MH+).

Step 2: 1-(4-Fluorophenyl)-6-methyl-2-oxo-5-(prop-1-en-2-yl)-1,2-dihydropyridine-3-carboxylic acid (HA1-21): A mixture of Compound 41-1 (250 mg, 0.83 mmol, 1 eq) and LiOH·H$_2$O (70 mg, 1.7 mmol, 2 eq) in THF (5 mL) and water (2 mL) was stirred at 50° C. for 3 h. The reaction mixture was acidified with aq 2 M HCl solution to pH~6, diluted with water (20 mL) and extracted with DCM (3×20 mL). The combined organic extracts were dried over anhyd Na$_2$SO$_4$ and concentrated to give Compound H1-21 (200 mg, 84% yield). MS for $C_{16}H_{14}FNO_3$: m/z 288.1 (MH+).

1-(4-Fluorophenyl)-5-isopropyl-6-methyl-2-oxo-1,2-dihydropyridine-3-carboxylic acid (HA1-22): To a solution of Compound HA1-21 (150 mg, 0.52 mmol, 1 eq) in MeOH (5 mL) was added 5% Pd/C (10 mg, 0.052 mmol, 0.1 eq) under an atmosphere of nitrogen. The resulting suspension was degassed under vacuum and purged with hydrogen gas several times. The mixture was then stirred under an atmosphere of hydrogen (15 psi) at 25° C. for 12 h. The reaction mixture was filtered, and the filtrate was concentrated under vacuum to give crude Compound HA1-22 (100 mg, 66% yield) which was used in subsequent reactions without further purification. MS for $C_{16}H_{16}FNO_3$: m/z 289.9 (MH+).

Example 42: 5-Acetyl-1-(4-fluorophenyl)-2-oxo-1,2-dihydropyridine-3-carboxylic acid (HA-24)

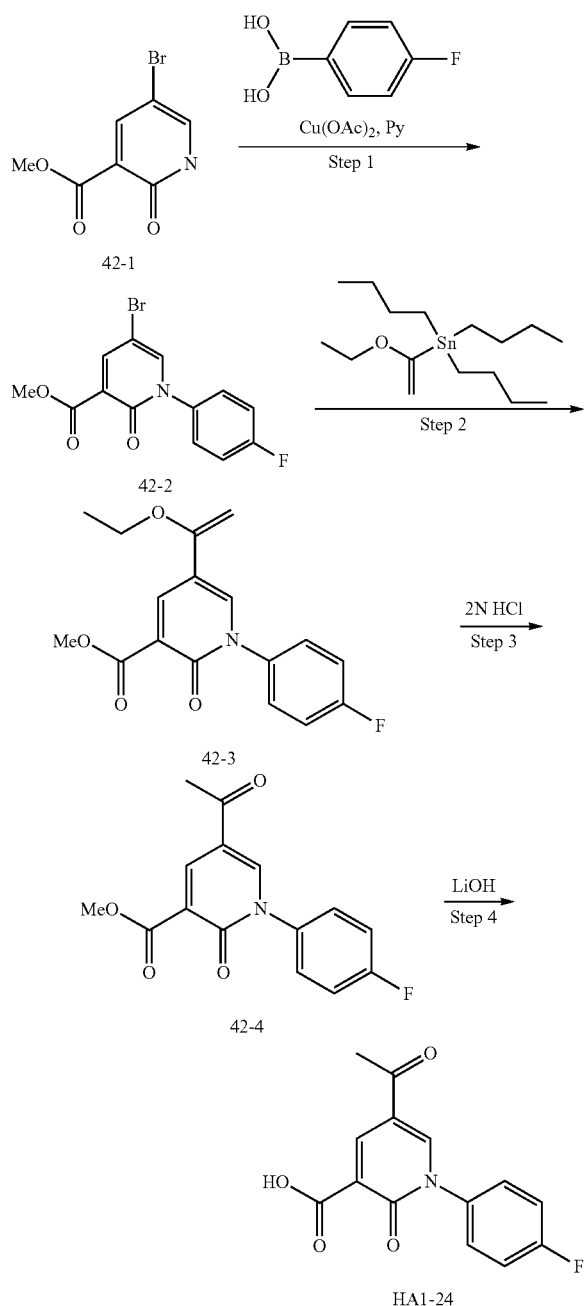

Step 1: Methyl 5-bromo-1-(4-fluorophenyl)-2-oxo-1,2-dihydropyridine-3-carboxylate (42-2): Compound 42-2 was made from Compound 42-1 in the same manner Compound 30-2 was made from Compound 30-1 in Example 30. MS for $C_{13}H_9BrFNO_3$: m/z 327.8 (MH+).

Step 2: Methyl 5-(1-ethoxyvinyl)-1-(4-fluorophenyl)-2-oxo-1,2-dihydropyridine-3-carboxylate (42-3): Compound 42-3 was made from Compound 42-2 in the same manner Compound 28-2 was made from Compound 28-1 in Example 28. MS for $C_{17}H_{16}FNO_4$: m/z 317.9 (MH+).

Step 3: Methyl 5-acetyl-1-(4-fluorophenyl)-2-oxo-1,2-dihydropyridine-3-carboxylate (42-4): Compound 42-4 was made from Compound 42-3 in the same manner Compound HA1-3 was made from Compound 28-2 in Example 28. MS for $C_{15}H_{12}FNO_4$: m/z 289.9 (MH+).

Step 4: 5-Acetyl-1-(4-fluorophenyl)-2-oxo-1,2-dihydropyridine-3-carboxylic acid (HA1-24): Compound HA1-24 was made from Compound 42-4 in the same manner Compound HA1-21 was made from Compound 41-1 in Example 41. MS for $C_{14}H_{10}FNO_4$: m/z 275.9 (MH+).

Example 43: 1-(4-Fluorophenyl)-6-(hydroxymethyl)-2-oxo-1,2-dihydropyridine-3-carboxylic acid (HA1-25)

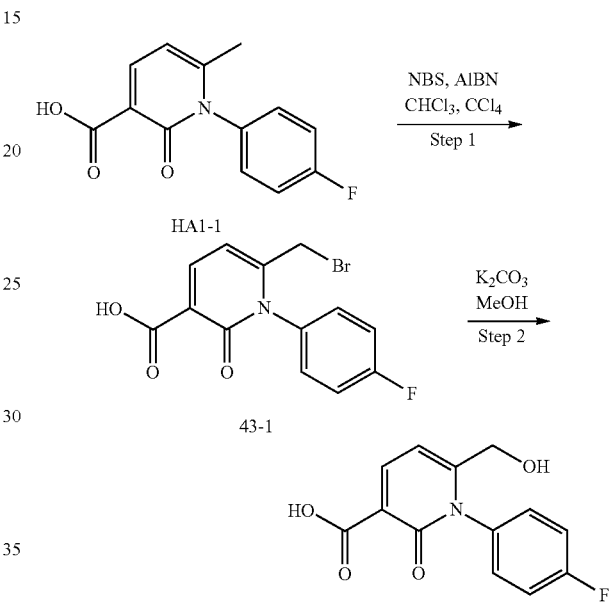

Step 1: 6-(Bromomethyl)-1-(4-fluorophenyl)-2-oxo-1,2-dihydropyridine-3-carboxylic acid (43-1): A 50-mL round bottom flask was charged with NBS (441 mg, 2.5 mmol, 1.2 eq), AIBN (104 mg, 0.6 mmol, 0.3 eq), $CHCl_3$ (5 mL) and $CCl_4$ (15 mL). Compound HA1-1 (500 mg, 2.0 mmol, 1.0 eq) was added in bulk to the stirring reaction which was sealed with a rubber septum and irradiated with a high wattage lamp overnight. The reaction was diluted with DCM and washed with water. The organic phase was extracted with aq 1 N $Na_2CO_3$. The aqueous layer was then acidified with 6 N HCl and extracted twice with DCM. The combined organic extracts were washed with aq saturated NaCl, dried over $Na_2SO_4$ and concentrated to give crude Compound 43-1 which was carried forward without further purification. MS for $C_{13}H_9BrFNO_3$: m/z 326 (MH+).

Step 2: 1-(4-Fluorophenyl)-6-(hydroxymethyl)-2-oxo-1,2-dihydropyridine-3-carboxylic acid (HA1-25): A 20-mL scintillation vial bearing crude Compound 43-1 (198 mg, 0.5 mmol) was charged with $K_2CO_3$ (72.2 mg, 0.52 mmol, 1.1 eq) and a Teflon stir bar. MeOH (5 mL) was added and the reaction was stirred at room temperature overnight. The reaction was then heated to 50° C. and stirred for an additional 18 h. The reaction was reduced under vacuum and the resulting residue partitioned between DCM and water. The phases were separated, and the aqueous layer was further basified with 1 N $Na_2CO_3$ and washed with DCM. The aqueous layer was then carefully acidified with 6 N HCl and extracted with DCM and 15% iPrOH in EtOAc. The organic layers were dried over Na₂SO₄ and concentrated. The resulting residue was purified by prep HPLC (10-90% MeCN in H₂O (0.1% FA) to give Compound HA1-25 (9.4 mg, 7% yield over 2-steps): MS for $C_{13}H_{10}FNO_4$: m/z 264 (MH+).

Example 44: 1-(4-Fluorophenyl)-6-(methoxymethyl)-2-oxo-1,2-dihydropyridine-3-carboxylic acid (HA1-26)

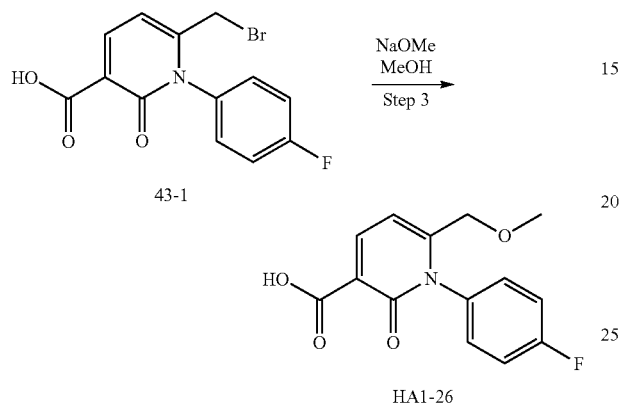

1-(4-Fluorophenyl)-6-(methoxymethyl)-2-oxo-1,2-dihydropyridine-3-carboxylic acid (HA1-26): A 10 mL round bottom flask was heat dried under vacuum and charged with a Teflon stir bar, sodium methoxide (80 mg, 1.5 mmol, 3 eq) and MeOH (3 mL). Compound 43-1 (155 mg, 0.5 mmol, 1.0 eq) was added in bulk and the resulting mixture stirred at room temperature for 10 min until a precipitate formed. The solids were filtered off and the filtrate was concentrated and was dissolved in water and washed with EtOAc. The aqueous layer was acidified to pH~4 and extracted twice with EtOAc. The combined organic layers were washed with aq saturated NaCl, dried over Na₂SO₄ and concentrated. The resulting residue was purified by prep HPLC (15-75% MeCN in H₂O (0.1% FA) to give Compound HA1-26 (29 mg). MS for $C_{14}H_{12}FNO_4$: m/z 278 (MH+).

Example 45: 4-Ethoxy-1-(4-fluorophenyl)-5-methyl-2-oxo-1,2-dihydropyridine-3-carboxylic acid (HA1-27) and 1-(4-Fluorophenyl)-4-methoxy-5-methyl-2-oxo-1,2-dihydropyridine-3-carboxylic acid (HA1-28)

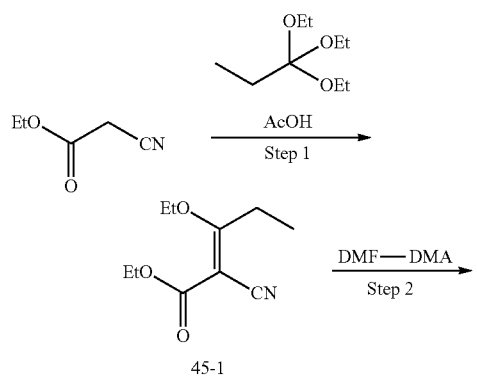

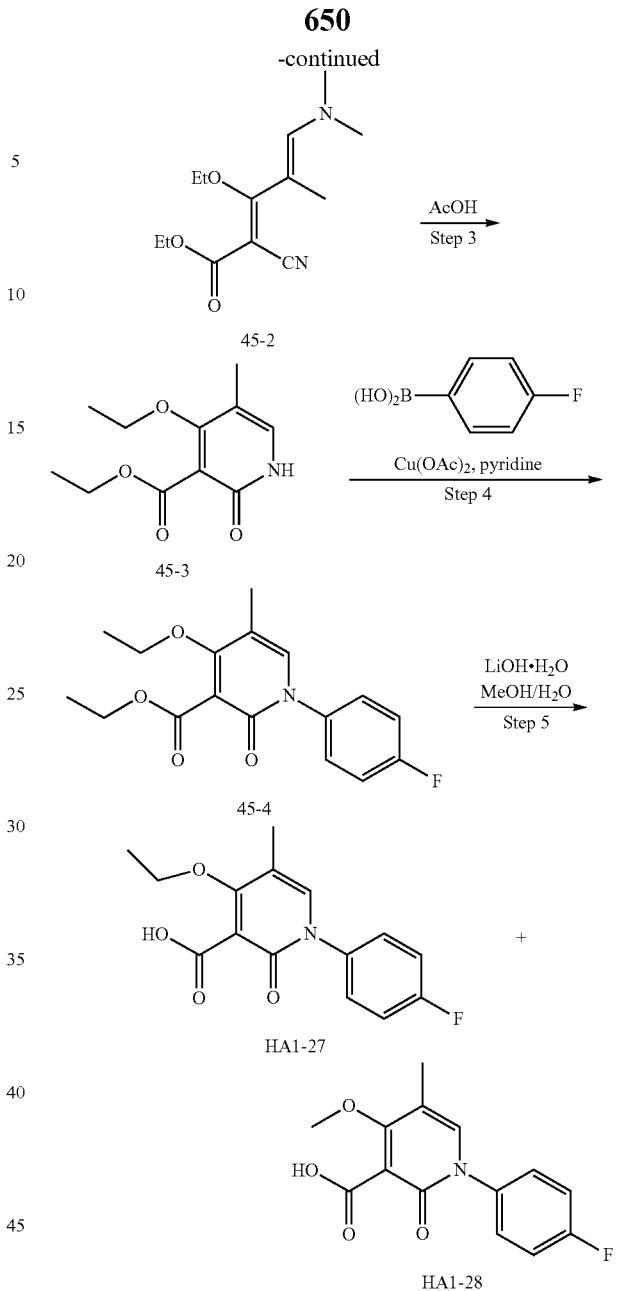

Step 1: Ethyl (Z)-2-cyano-3-ethoxypent-2-enoate (45-1): To a solution of ethyl 2-cyanoacetate (5 g, 44 mmol, 4.7 mL, 1 eq) in AcOH (1.3 g, 22 mmol, 1.3 mL, 0.5 eq) was added 1,1,1-triethoxypropane (15.6 g, 88 mmol, 17.6 mL, 2 eq). The colorless solution was stirred at 130° C. for 20 hr. The reaction mixture was concentrated under reduced pressure to give Compound 45-1 (8.7 g, 100% yield) which was used in subsequent reactions without further purification. MS for $C_{10}H_{15}NO_3$: m/z 198.0 (MH+).

Step 2: Ethyl (2Z,4E)-2-cyano-5-(dimethylamino)-3-ethoxy-4-methylpenta-2,4-dienoate (45-2): A solution of Compound 45-1 (8.72 g, 44.2 mmol, 1 eq) in DMF-DMA (6.85 g, 57.5 mmol, 7.6 mL, 1.3 eq) was stirred at 70° C. for 16 h. The reaction mixture was concentrated to give Compound 45-2 (11 g, 99% yield) which was used in subsequent reactions without further purification. MS for $C_{13}H_{20}N_2O_3$: m/z 253.0 (MH+).

Step 3: Ethyl 4-ethoxy-5-methyl-2-oxo-1,2-dihydropyridine-3-carboxylate (45-3): A mixture of Compound 45-2 (11 g, 44 mmol, 1 eq) in AcOH (50 mL) was stirred at 130° C. for 16 h. The reaction mixture diluted with water (100 mL) and aq saturated NaHCO$_3$ was added to pH=8. The resulting aqueous mixture was extracted with EtOAc (2×80 mL). The combined organic extracts were concentrated and the resulting residue was purified by silica gel column chromatography (petroleum ether:EtOAc=3:1 to 1:1 to DCM:MeOH) followed by further purification by silica gel chromatography DCM:MeOH=1:0-20:1) to give Compound 45-3 (2 g, 41% purity). MS for $C_{11}H_{15}NO_4$: m/z 226.0 (MH+).

Step 4: Ethyl 4-ethoxy-1-(4-fluorophenyl)-5-methyl-2-oxo-1,2-dihydropyridine-3-carboxylate (45-4): Compound 45-4 was made from Compound 45-3 in the same manner Compound 30-2 was made from Compound 30-1 in Example 30. MS for $C_{17}H_{18}FNO_4$: m/z 320.1 (MH+).

Step 5: 4-Ethoxy-1-(4-fluorophenyl)-5-methyl-2-oxo-1,2-dihydropyridine-3-carboxylic acid (HA1-27) and 1-(4-Fluorophenyl)-4-methoxy-5-methyl-2-oxo-1,2-dihydropyridine-3-carboxylic acid (HA1-28): To a solution of Compound 45-4 (130 mg, 0.41 mmol, 1 eq) in MeOH (5 mL) and water (1 mL) was added LiOH·H$_2$O (137 mg, 3.3 mmol, 8 eq). The colorless solution was stirred at 20° C. for 15 h. The reaction residue was concentrated under reduced pressure to remove MeOH. The resulting residue was diluted with water (20 mL) and washed with EtOAc (2×50 mL). The aqueous layer was acidified with 1 N HCl to pH=2 and extracted with EtOAc (2×50 mL). The combined organic extracts were dried over anhyd Na$_2$SO$_4$ and concentrated to give a mixture of Compound HA1-27 and HA1-28 (60 mg) which was used in subsequent reactions without further purification or separation. Compound HA1-27: MS for $C_{15}H_{14}FNO_4$: m/z 291.9 (MH+). Compound HA1-28: MS for $C_{14}H_{12}FNO_4$: m/z 277.9 (MH+).

Example 46: 2-(4-Fluorophenyl)-3,8-dioxo-2,3,5,6,7,8-hexahydroisoquinoline-4-carboxylic acid (HA1-29)

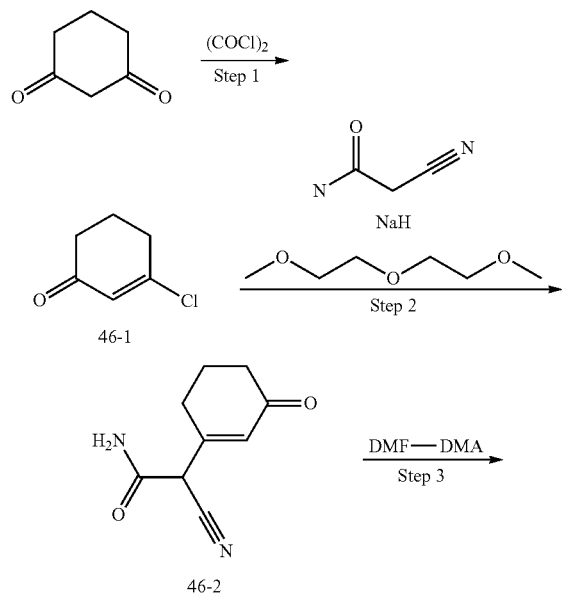

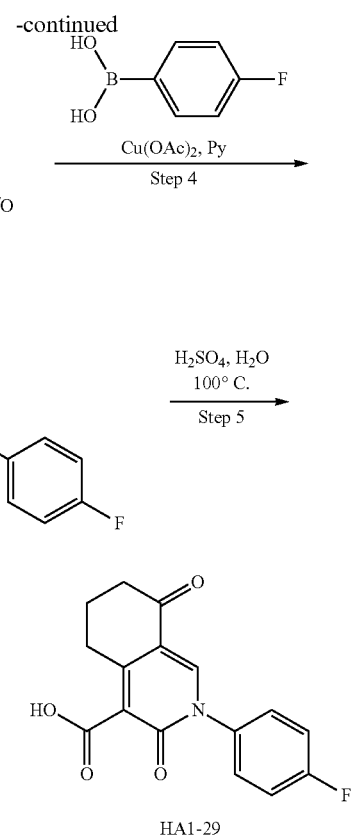

Step 1: 3-Chlorocyclohex-2-en-1-one (46-1): To a solution of cyclohexane-1,3-dione (5 g, 44.6 mmol, 1 eq) in ACN (100 mL) was added oxalyl dichloride (8.49 g, 66.9 mmol, 5.9 mL, 1.5 eq) slowly at 25° C. and the resulting reaction mixture was stirred at 25° C. for 2 h. The reaction mixture was concentrated to give Compound 46-1 (5.6 g, 96% yield) which was used in next step directly without further purification. $^1$H NMR (400 MHz, CDCl$_3$) δ 6.23 (t, 1H), 2.69 (dt, 2H), 2.44-2.36 (m, 2H), 2.14-2.04 (m, 2H).

Step 2: 2-Cyano-2-(3-oxocyclohex-1-en-1-yl)acetamide (46-2): To a solution of 2-cyanoacetamide (3.61 g, 42.9 mmol, 1.0 eq) in diethylene glycol dimethyl ether (100 mL) was added 60% NaH (2.06 g, 51.5 mmol, 1.2 eq) slowly at 0° C. and then Compound 46-1 (5.6 g, 42.9 mmol, 1.0 eq) was added slowly. The reaction mixture was stirred at 25° C. for 15 h. The reaction was diluted with water (300 mL) and extracted with EtOAc (4×200 mL). The combined organic extracts were washed with aq saturated NaCl (2×500 mL) and dried over anhyd Na$_2$SO$_4$. The organic layer was concentrated to about 50 mL, cooled to room temperature and then filtered. The resulting solid was collected and dried in vacuo to give Compound 46-2 (3.1 g, 40% yield). MS for $C_9H_{10}N_2O_2$: m/z 178.8 (MH+).

Step 3: 3,8-Dioxo-2,3,5,6,7,8-hexahydroisoquinoline-4-carbonitrile (46-3): To a solution of Compound 46-2 (2.5 g, 14 mmol, 1 eq) in DMF (7 mL) was added DMF-DMA (2.01 g, 17 mmol, 2.24 mL, 1.2 eq) slowly. The reaction mixture was stirred at 25° C. for 60 h. The reaction mixture was diluted with aq 2.5% NaOH (50 mL) and washed DCM (2×30 mL2). The aqueous layer was acidified by conc HCl to pH=1. The resulting precipitate was filtered, and the resulting solid was triturated with a mixture of MeOH/water (2/1, 30 mL) and then filtered. The solid was collected and dried in vacuo to give Compound 46-3 (960 mg, 36% yield). MS for $C_{10}H_8N_2O_2$: m/z 188.9 (MH+).

Step 4: 2-(4-Fluorophenyl)-3,8-dioxo-2,3,5,6,7,8-hexahydroisoquinoline-4-carbonitrile (46-4): Compound 46-4 was made from Compound 46-3 in the same manner Compound 30-2 was made from Compound 30-1 in Example 30. MS for $C_{16}H_{11}FN_2O_2$: m/z 282.9 (MH+).

Step 5: 2-(4-Fluorophenyl)-3,8-dioxo-2,3,5,6,7,8-hexahydroisoquinoline-4-carboxylic acid (HA1-29): To a solution of Compound 46-4 (160 mg, 0.57 mmol, 1 eq) in water (1 mL) was added $H_2SO_4$ (1 mL) slowly. The reaction mixture was stirred at 100° C. for 8 hr. The reaction mixture was poured into ice water (50 mL) and then extracted with DCM (2×20 mL). The combined DCM extracts were extracted with aq 2 N NaOH (2×20 mL). The combined aqueous extracts were acidified with conc HCl to pH=1, and then extracted with DCM (2×30 mL). The combined organic extracts were washed with aq saturated NaCl (30 mL), dried over anhyd $Na_2SO_4$ and concentrated to give Compound HA1-29 (65 mg, 38% yield). MS for $C_{16}H_{12}FNO_4$: m/z 301.8 (MH+).

Example 47: 5-(4-Fluorophenyl)-6-methyl-4-oxo-1,4-dihydropyridazine-3-carboxylic acid (HA1-2) and 6-Methyl-4-oxo-1,4-dihydropyridazine-3-carboxylic acid (HA2-7)

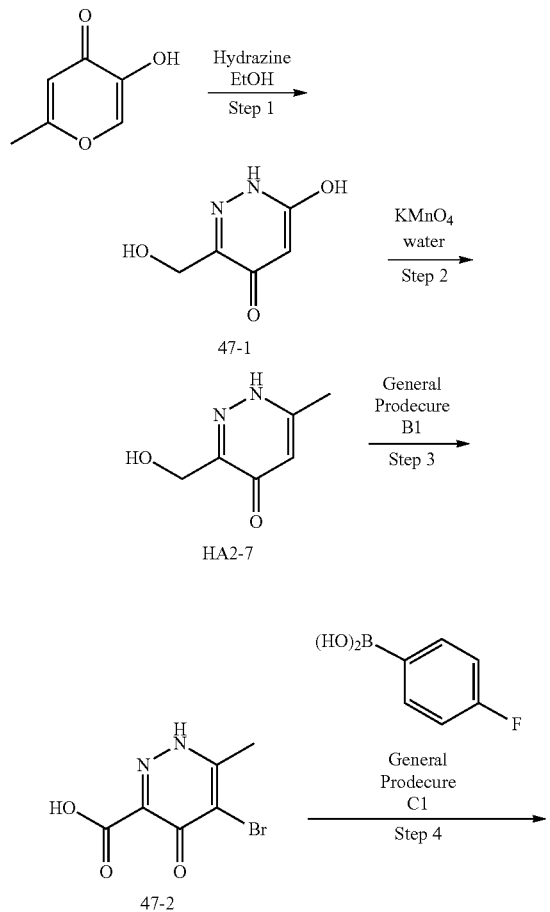

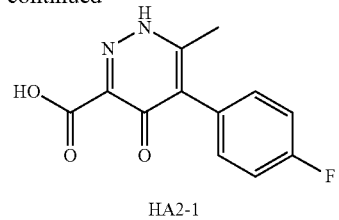

HA2-1

Step 1: 3-(Hydroxymethyl)-6-methylpyridazin-4(1H)-one (47-1): To a solution of 5-hydroxy-2-methyl-4H-pyran-4-one (2.5 g, 19.8 mmol) in EtOH (80 mL) was added hydrazine (4 mL, 60% in water). The resulting mixture was heated to reflux for 90 min. The reaction mixture was allowed to cool to room temperature. The resulting precipitate was filtered and allowed to dry in the open air to afford Compound 47-1 (1.4 g, 51% yield). MS for $C_{61}H_8N_2O_2$: m/z 141 (MH+).

Step 2: 6-Methyl-4-oxo-1,4-dihydropyridazine-3-carboxylic acid (HA2-7): To a solution of Compound 47-1 (1.4 g, 10 mmol) in water (56 mL) at 75° C. was added $KMnO_4$ (17.2 mmol, 1.8 eq) in water (84 mL) dropwise over 20 min. The mixture was allowed to cool to room temperature and filtered through a Celite pad. The solvent was partially removed, and the resulting mixture was acidified using 6 M HCl to pH 2. The solution was chilled to 0° C. along with scraping the side of the flask to facilitate precipitation. The resulting solid was filtered and allowed to dry in the open air to afford Compound HA2-7 (912 mg, 59% yield). MS for $C_6H_6N_2O_3$: m/z 155 (MH+).

Step 3: 5-Bromo-6-methyl-4-oxo-1,4-dihydropyridazine-3-carboxylic acid (47-2): Compound 47-2 was synthesized from Compound HA2-7 using General Procedure B1. MS for $C_6H_5BrN_2O_3$: m/z 233 (MH+).

Step 4: 5-(4-Fluorophenyl)-6-methyl-4-oxo-1,4-dihydropyridazine-3-carboxylic acid (HA1-2): Compound HA1-2 was synthesized from Compound 47-2 using General Procedure C1. MS for $C_{12}H_9FN_2O_3$: m/z 249 (MH+).

The following compound was made using the same method as that used to make Compound HA2-1 in Example 47:

5-(4-Fluoro-2-methylphenyl)-6-methyl-4-oxo-1,4-dihydropyridazine-3-carboxylic acid (HA2-2): MS for $C_{13}H_{11}FN_2O_3$: m/z 263 (MH+).

Example 48: 5-(4-Fluorophenyl)-1,6-dimethyl-4-oxo-1,4-dihydropyridazine-3-carboxylic acid (HA2-3) and 5-(4-Fluorophenyl)-4-methoxy-6-methylpyridazine-3-carboxylic acid (HA2-3B)

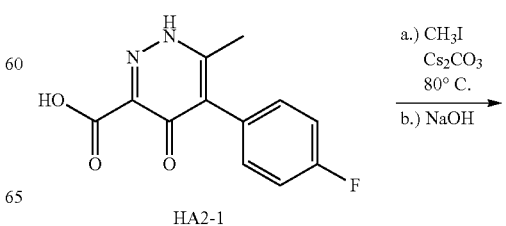

HA2-1

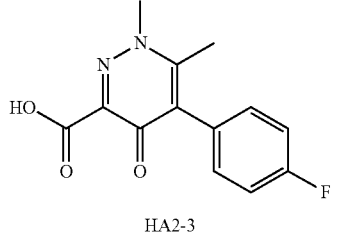

HA2-3

+

Example 49: 4-Chloro-5-(4-fluorophenyl)-6-methylpyridazine-3-carboxylic acid (HA2-11)

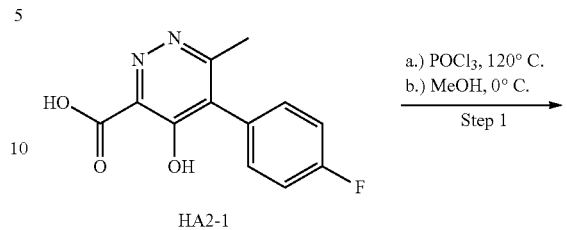

HA2-1

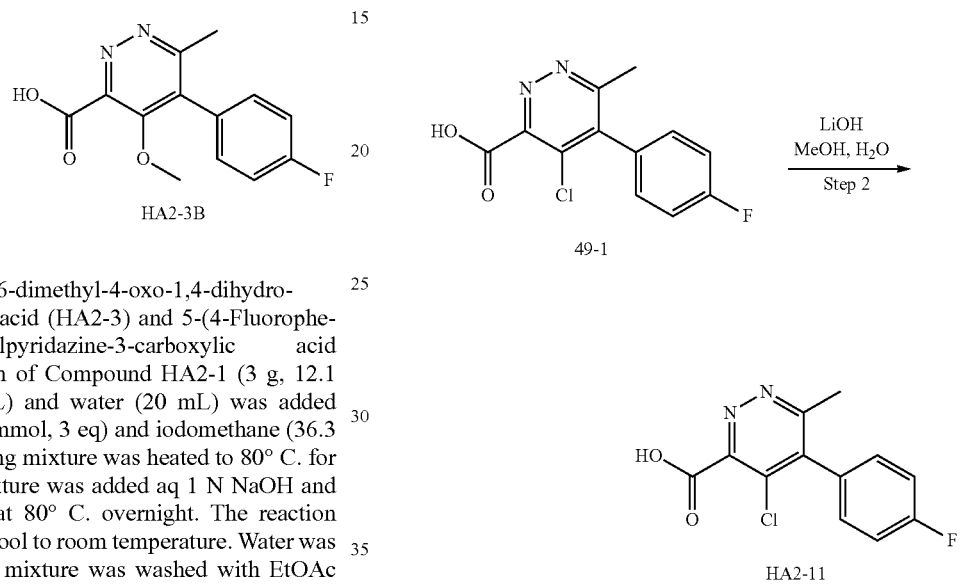

5-(4-Fluorophenyl)-1,6-dimethyl-4-oxo-1,4-dihydropyridazine-3-carboxylic acid (HA2-3) and 5-(4-Fluorophenyl)-4-methoxy-6-methylpyridazine-3-carboxylic acid (HA2-3B): To a solution of Compound HA2-1 (3 g, 12.1 mmol) in DMF (20 mL) and water (20 mL) was added cesium carbonate (36.3 mmol, 3 eq) and iodomethane (36.3 mmol, 3 eq). The resulting mixture was heated to 80° C. for 3 h. To this reaction mixture was added aq 1 N NaOH and stirring was continued at 80° C. overnight. The reaction mixture was allowed to cool to room temperature. Water was added and the resulting mixture was washed with EtOAc (3×). The aqueous phase was acidified using aq 6 M HCl to pH 2. The resulting solid was filtered and allowed to dry in the open air to give a 1:2 mixture of Compound HA2-3: Compound HA2-3B (1.85 g). MS for $C_{13}H_{11}FN_2O_3$: m/z 263 (MH+). This mixture of Compound HA2-3 and HA2-3B was used in subsequent reactions without separation of the regioisomers.

The following compounds were made using the same process that was used to make the mixture of Compounds HA2-3 and HA2-3B in Example 48. The resulting mixture of regioisomers can either be separated at this stage or used as mixtures in subsequent reactions.

1-Ethyl-5-(4-fluorophenyl)-6-methyl-4-oxo-1,4-dihydropyridazine-3-carboxylic acid (HA2-4A): MS for $C_{14}H_{13}FN_2O_3$: m/z 277 (MH+).

4-Ethoxy-5-(4-fluorophenyl)-6-methylpyridazine-3-carboxylic acid (HA2-4B): MS for $C_{14}H_{13}FN_2O_3$: m/z 277 (MH+).

5-(4-Fluorophenyl)-1-isopropyl-6-methyl-4-oxo-1,4-dihydropyridazine-3-carboxylic acid (HA2-5): MS for $C_{15}H_{15}FN_2O_3$: m/z 291.0 (MH+).

5-(4-Fluoro-2-methylphenyl)-1,6-dimethyl-4-oxo-1,4-dihydropyridazine-3-carboxylic acid (HA2-6A): MS for $C_{14}H_{13}FN_2O_3$: m/z 277 (MH+).

5-(4-Fluoro-2-methylphenyl)-4-methoxy-6-methylpyridazine-3-carboxylic acid (HA2-6B): $^1$H NMR (400 MHz, DMSO-$d_6$) δ 7.31-7.12 (m, 3H), 4.68 (s, 3H), 2.22 (s, 3H), 2.07 (s, 3H); MS for $C_{14}H_{13}FN_2O_3$: m/z 277 (MH+).

Step 1: Methyl 4-chloro-5-(4-fluorophenyl)-6-methylpyridazine-3-carboxylate (49-1): To a 5 mL microwave vial equipped with a magnetic stir bar was added Compound HA2-1 (687 mg, 2.8 mmol) and phosphoryl chloride (3.5 mL, 37 mmol, 13.5 eq). The vial was purged with nitrogen, sealed and placed in the microwave reactor at 120° C. for 30 min. The resulting dark brown solution was slowly added to MeOH (40 mL) at 0° C. The resulting solution was allowed to warm to room temperature and stirred for 30 min. The reaction was then concentrated under reduced pressure and purified by silica gel column chromatography (0-50% EtOAc in hexanes) to give Compound 49-1 (405 mg, 52% yield). H NMR (400 MHz, CDCl$_3$) δ 7.30-7.20 (m, 4H), 4.09 (s, 3H), 2.58 (s, 3H). MS for $C_{13}H_{10}ClFN_2O_2$: m/z 281.0 (MH+).

Step 2: 4-Chloro-5-(4-fluorophenyl)-6-methylpyridazine-3-carboxylic acid (HA2-11): To a 20-mL vial equipped with a magnetic stir bar and a pressure relief septum was added a solution of Compound 49-1 (256 mg, 0.912 mmol) in MeOH (5 mL) and water (1 mL). LiOH·H$_2$O (60 mg, 1.4 mmol, 1.6 eq) was added in a single portion and the reaction was allowed to proceed at room temperature for 30 min. The resulting solution was adjusted to pH=3 with aq 6 M HCl and concentrated to near dryness. The resulting mixture was diluted with water (10 mL). The resulting suspension was filtered to give Compound HA2-11 (223 mg, 92% yield). $^1$H NMR (400 MHz, DMSO-d6) δ 7.63-7.25 (m, 4H), 2.44 (s, 3H). MS for $C_{12}H_8ClFN_2O_2$: m/z 267.0 (MH+).

Example 50: 2-(4-Fluorophenyl)-5,6-dimethyl-3-oxo-2,3-dihydropyridazine-4-carboxylic acid (HA2-15)

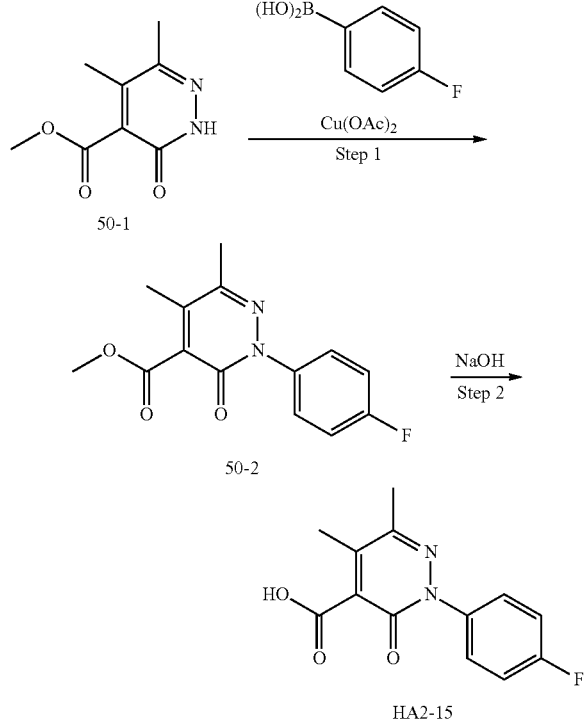

Example 51: 2-(4-Fluorophenyl)-5-(methoxymethyl)-3-oxo-2,3-dihydropyridazine-4-carboxylic acid (HA2-14)

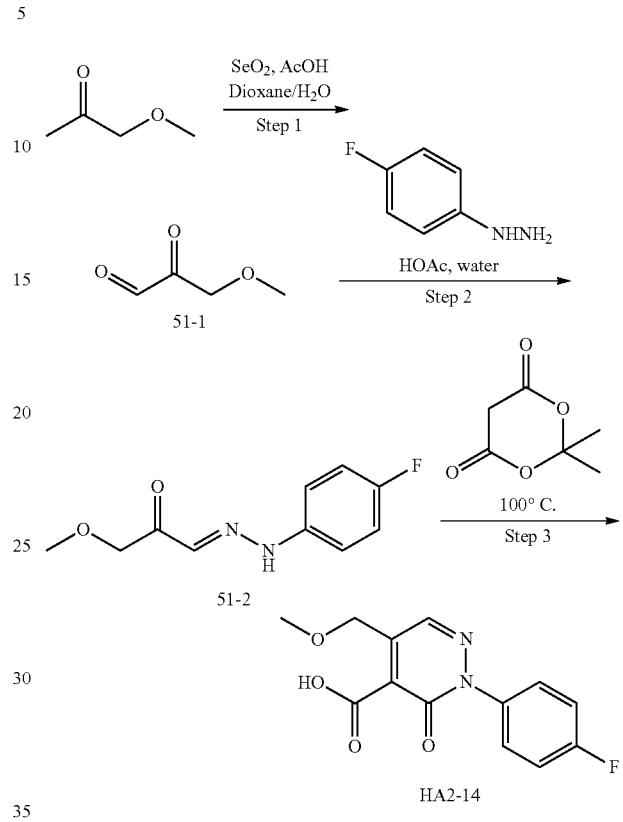

Step 1: Methyl 2-(4-fluorophenyl)-5,6-dimethyl-3-oxo-2,3-dihydropyridazine-4-carboxylate (50-2): To a solution of Compound 50-1 (100 mg, 0.55 mmol) in DMA (2 mL) was added (4-fluorophenyl)boronic acid (0.66 mmol, 1.2 eq) and copper (II) acetate (0.66 mmol, 1.2 eq). Oxygen gas was bubbled into the resulting mixture for 5 min and then the mixture was heated to 90° C. under an atmosphere of oxygen for 30 min. The reaction mixture was allowed to cool to room temperature and filtered through a Celite pad. The solvent was removed under reduced pressure and resulting crude residue was purified by flash silica gel chromatography (0-100% EtOAc/hexanes) to give Compound 50-2 (50 mg, 33% yield). MS for $C_{14}H_{13}FN_2O_3$: m/z 277 (MH+).

Step 2: 2-(4-Fluorophenyl)-5,6-dimethyl-3-oxo-2,3-dihydropyridazine-4-carboxylic acid (HA2-15): Compound 50-2 was converted to Compound HA2-15 using the ester hydrolysis procedure used in Step 3 of General Procedure A. MS for $C_{13}H_{11}FN_2O_3$: m/z 263 (MH+).

The following compounds were made using similar techniques to those used to make Compound HA2-15 in Example 50:

2-(4-Fluorophenyl)-6-methyl-3-oxo-2,3-dihydropyridazine-4-carboxylic acid (HA2-12): MS for $C_{12}H_9FN_2O_3$: m/z 249 (MH+).

2-(4-Fluorophenyl)-3-oxo-2,3-dihydropyridazine-4-carboxylic acid (HA2-16): MS for $C_{11}H_7FN_2O_3$: m/z 234.8 (MH+).

2-(4-Fluoro-2-methylphenyl)-3-oxo-2,3-dihydropyridazine-4-carboxylic acid (HA2-13): MS for $C_{12}H_9FN_2O_3$: m/z 249 (MH+).

Step 1: 3-Methoxy-2-oxopropanal (51-1): To a solution of selenium dioxide (2.80 g, 25.2 mmol) in dioxane (14 mL) and AcOH/water (0.5 mL/0.5 mL (1:1 v/v)) was added 1-methoxypropan-2-one (1.86 g, 21 mmol) slowly. The resulting mixture was stirred at 100° C. overnight. The resulting reaction mixture was allowed to cool to room temperature, filtered through a Celite pad to give a solution of Compound 51-1 which was used directly in the next step without further purification.

Step 2: (E)-1-(2-(4-Fluorophenyl)hydrazinylidene)-3-methoxypropan-2-one (51-2): To the crude solution of Compound 51-1 from step 1 was added water (30 mL), AcOH (1.2 mL) and (4-fluorophenyl)hydrazine (21 mmol, 1 eq). The resulting mixture was stirred at room temperature overnight. The resulting solids were filtered to give Compound 51-2 (3.53 g, 80% yield over 2 steps). MS for $C_{10}H_{11}FN_2O_2$: m/z 211 (MH+).

Step 3: 2-(4-Fluorophenyl)-5-(methoxymethyl)-3-oxo-2,3-dihydropyridazine-4-carboxylic acid (HA2-14): To a solution of Compound 51-2 (3.53 g, 17 mmol) in toluene (20 mL) was added AcOH (0.5 mL) and Meldrum's acid (16.81 mmol, 1 eq). The resulting mixture was heated to 100° C. overnight. Solvent was removed under reduced pressure, aq 1 N NaOH (20 mL) was added and the resulting mixture was washed with EtOAc (3×). The aqueous phase was acidified with aq 6 M HCl to pH 1-2 and extracted with EtOAc (3×). The combined EtOAc extracts were washed with aq saturated NaCl, dried over anhyd $Na_2SO_4$ and concentrated to give Compound HA2-14 (1.2 g, 26% yield). MS for $C_{13}H_{11}FN_2O_4$: m/z 279 (MH+).

Example 52: 4-(4-Fluorophenyl)-5-methyl-3-oxo-3,4-dihydropyrazine-2-carboxylic acid (HA3-1)

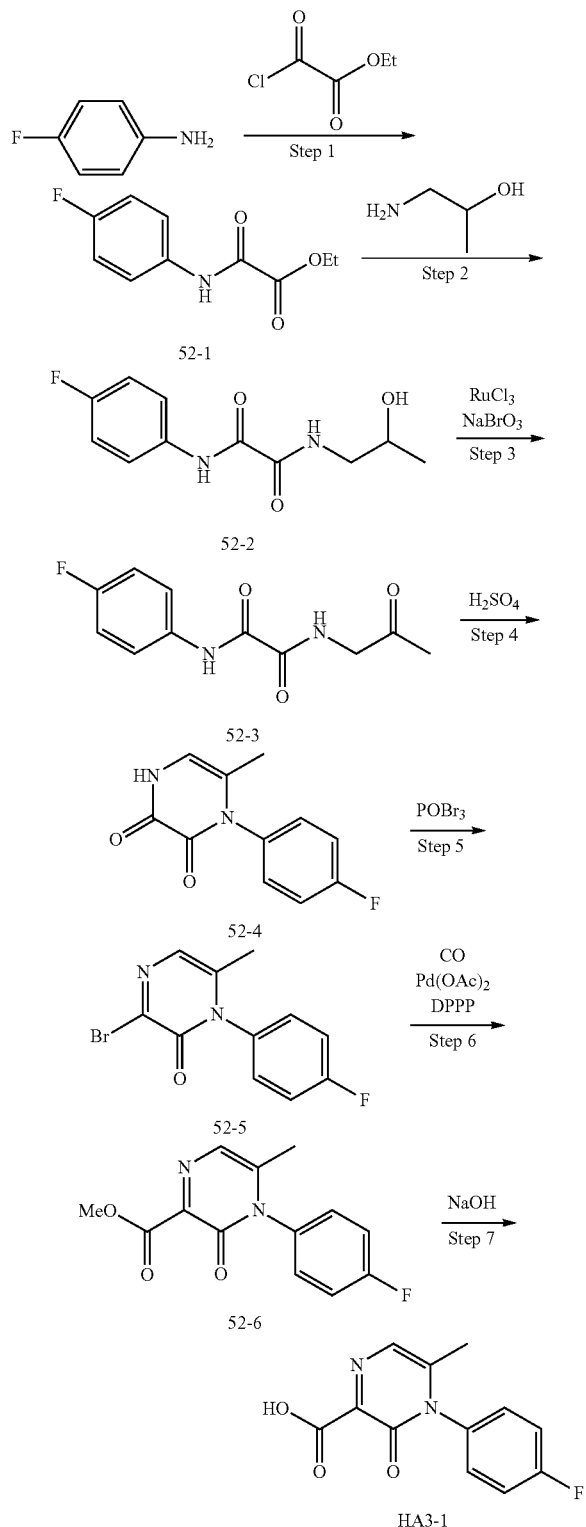

Step 1: Ethyl 2-((4-fluorophenyl)amino)-2-oxoacetate (52-1): To a solution of 4-fluoroaniline (10 g, 90 mmol, 8.6 mL, 1 eq) and TEA (13.7 g, 135 mmol, 18.8 mL, 1.5 eq) in EtOAc (150 mL) was added ethyl 2-chloro-2-oxo-acetate (14.7 g, 108 mmol, 12 mL, 1.2 eq) at 0° C. dropwise. The resulting white suspension was stirred at 20° C. for 15 h. The reaction mixture was quenched with water (100 mL) and extracted with EtOAc (3×50 mL). The combined organic extracts were washed with aq saturated NaCl (100 mL), dried over anhyd $Na_2SO_4$ and concentrated under reduced pressure to 30 mL. EtOAc (40 mL) and petroleum ether (120 mL) were added and the resulting mixture stirred for 5 min. The resulting solid was filtered, washed with petroleum ether (2×30 mL) and dried under vacuum to give Compound 52-1 (16.3 g, 86% yield). MS for $C_{10}H_{10}FNO_3$: m/z 211.8 (MH+).

Step 2: $N^1$-(4-Fluorophenyl)-$N^2$-(2-hydroxypropyl)oxalamide (52-2): To a mixture of Compound 52-1 (11.3 g, 53.5 mmol, 1 eq) in EtOH (100 mL) was added 1-aminopropan-2-ol (4.42 g, 58.9 mmol, 4.6 mL, 1.1 eq) at 70° C. dropwise. The mixture was stirred at 80° C. for 3 h. The reaction mixture was concentrated under reduced pressure until 30 mL remained. Petroleum ether (150 mL) was added and the resulting mixture was stirred for 1 h. The resulting solid was filtered, washed with petroleum ether (2×30 mL) and dried under vacuum to give Compound 52-2 (12.2 g, 95% yield). $^1$H NMR (400 MHz, $CDCl_3$) δ 9.26 (br s, 1H), 7.92 (br s, 1H), 7.65-7.57 (m, 2H), 7.13-7.03 (m, 2H), 4.08-3.98 (m, 1H), 3.60-3.50 (m, 1H), 3.35-3.25 (m, 1H), 2.11 (br s, 1H), 1.27 (d, 3H).

Step 3: $N^1$-(4-Fluorophenyl)-$N^2$-(2-oxopropyl)oxalamide (52-3): To a mixture of Compound 52-2 (10.2 g, 42.5 mmol, 1 eq) in ACN (100 mL) was added a solution of $RuCl_3$ (132 mg, 0.64 mmol, 0.015 eq) in water (10 mL) followed by a solution of sodium bromate (7.05 g, 47 mmol, 1.1 eq) in water (20 mL). The purple mixture was stirred at 20° C. for 19 h. The reaction mixture was concentrated under reduced pressure to remove ACN. To the resulting residue was added water (200 mL) and the mixture was stirred for 2 h. Solids were filtered and washed with water (2×50 mL). The filtrate was concentrated under reduced pressure to give Compound 52-3 (9 g, 89% yield) which was used in subsequent reactions without further purification. MS for $C_{11}H_{11}FN_2O_3$: m/z 238.9 (MH+).

Step 4: 1-(4-Fluorophenyl)-6-methyl-1,4-dihydropyrazine-2,3-dione (52-4): A mixture of Compound 52-3 (9 g, 38 mmol, 1 eq) in conc $H_2SO_4$ (10 mL) was stirred at 55° C. for 1.5 h. The resulting mixture was cooled to 0° C. and water (150 mL) was added slowly. The resulting solids were filtered, washed with water (3×30 mL) and dried under vacuum to give Compound 52-4 (7.3 g, 88% yield) which was used in subsequent reactions without further purification. $^1$H NMR (400 MHz, $CDCl_3$) δ 7.13 (d, 4H), 6.11 (s, 1H), 1.65 (s, 3H).

Step 5: 3-Bromo-1-(4-fluorophenyl)-6-methylpyrazin-2(1H)-one (52-5): To a mixture of Compound 52-4 (7.3 g, 33 mmol, 1 eq) in ACN (70 mL) was added a solution of $POBr_3$ (10.4 g, 36.5 mmol, 1.1 eq) in ACN (30 mL). The mixture was stirred at 65° C. for 6 h. The reaction mixture was added to aq saturated $NaHCO_3$ (200 mL) at 0° C. slowly. The mixture was stirred for 0.5 h, then extracted with EtOAc (2×150 mL). The combined organic extracts were dried over anhyd $Na_2SO_4$ and concentrated under reduced pressure. The resulting residue was purified by silica gel column (petroleum ether:EtOAc=30:1 to 1:1) to give Compound 52-5 (6.3 g, 62% yield). MS for $C_{11}H_8BrFN_2O$: m/z 282.8 (MH+).

Step 6: Methyl 4-(4-fluorophenyl)-5-methyl-3-oxo-3,4-dihydropyrazine-2-carboxylate (52-6): To a mixture of Compound 52-5 (2.3 g, 8.1 mmol, 1 eq) in MeOH (30 mL)

was added 1,3-bis(diphenylphosphino)propane (DPPP) (36.9 mg, 0.09 mmol, 0.011 eq) and TEA (2.5 g, 24 mmol, 3.4 mL, 3 eq) followed by the addition of Pd(OAc)$_2$ (18.2 mg, 0.08 mmol, 0.01 eq). The mixture was stirred at 70° C. for 60 h under CO (50 Psi). The reaction mixture was concentrated under reduced pressure. The resulting residue was diluted with water (150 mL), then extracted with DCM (2×80 mL). The combined organic extracts were dried over anhyd Na$_2$SO$_4$, concentrated and purified by silica gel column chromatography (petroleum ether:EtOAc=3:1 to 0:1) to give Compound 52-6(1.55 g, 58% yield). MS for C$_{13}$H$_{11}$FN$_2$O$_3$: m/z 262.9 (MH+).

Step 7: 4-(4-Fluorophenyl)-5-methyl-3-oxo-3,4-dihydropyrazine-2-carboxylic acid (HA3-1): Compound 52-6 was converted to Compound HA3-1 using the ester hydrolysis procedure used in Step 3 of General Procedure A. MS for C$_{12}$H$_9$FN$_2$O$_3$: m/z 248.9 (MH+).

The following compounds were made using techniques similar to those used to make Compound H3-1 in Example 52:

4-(4-Fluorophenyl)-3-oxo-3,4-dihydropyrazine-2-carboxylic acid (HA3-3): MS for C$_{11}$H$_7$FN$_2$O$_3$: m/z 234.9 (MH+).

4-(4-Fluoro-2-methylphenyl)-5-methyl-3-oxo-3,4-dihydropyrazine-2-carboxylic acid (HA3-4): MS for C$_{13}$H$_{11}$FN$_2$O$_3$: m/z 262.9 (MH+).

Example 53: 4-(4-Fluorophenyl)-5,6-dimethyl-3-oxo-3,4-dihydropyrazine-2-carboxylic acid (HA3-2)

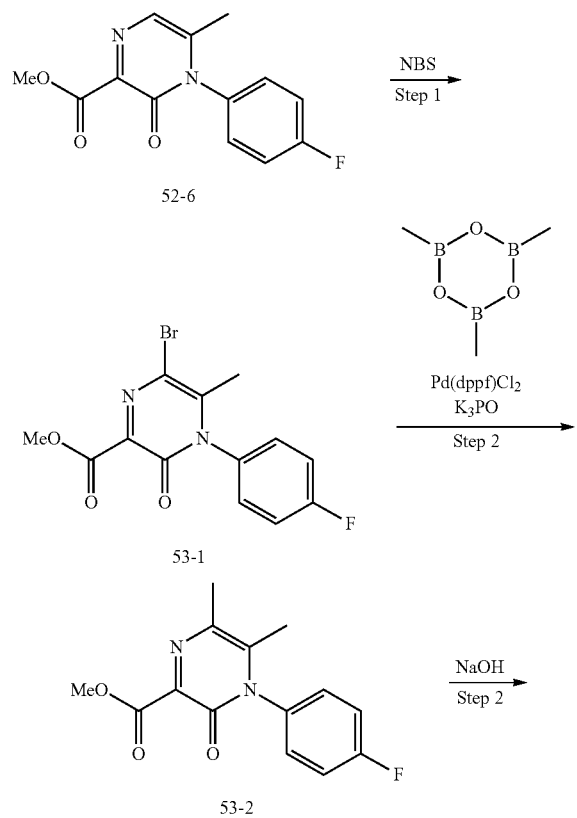

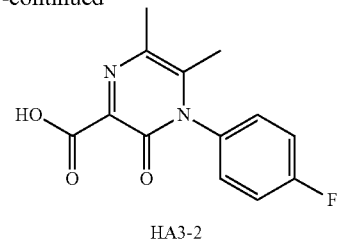

HA3-2

Step 1: Methyl 6-bromo-4-(4-fluorophenyl)-5-methyl-3-oxo-3,4-dihydropyrazine-2-carboxylate (53-1): To a solution of Compound 52-6 (0.5 g, 1.9 mmol, 1 eq) in DMF (5 mL) was added NBS (339 mg, 1.9 mmol, 1 eq) and the mixture was stirred at 25° C. for 2.5 h. The reaction mixture was diluted with water (80 mL) and stirred for 0.5 h. The mixture was then extracted with DCM (3×50 mL). The combined organic extracts were dried over anhyd Na$_2$SO$_4$, concentrated under reduced pressure and purified by silica gel column chromatography (petroleum ether:EtOAc=10:1 to 1:1) to give Compound 53-1 (580 mg, 89% yield). $^1$H NMR (400 MHz, CDCl$_3$) δ 7.26-7.21 (m, 2H), 7.17-7.12 (m, 2H), 3.93 (s, 3H), 2.21 (s, 3H).

Step 2: Methyl 4-(4-fluorophenyl)-5,6-dimethyl-3-oxo-3,4-dihydropyrazine-2-carboxylate (53-2): To a mixture of Compound 53-1 (280 mg, 0.82 mmol, 1 eq), 2,4,6-trimethyl-1,3,5,2,4,6-trioxatriborinane in (3.5 M in THF) (0.23 mL, 1.6 mmol, 2 eq) and dioxane (4 mL) was added K$_3$PO$_4$ (348 mg, 1.6 mmol, 2 eq) followed by Pd(dppf)Cl$_2$ (60 mg, 0.082 mmol, 0.1 eq) under an atmosphere of nitrogen. The mixture was stirred at 90° C. for 15 h under an atmosphere of nitrogen. The reaction mixture was diluted with water (50 mL) and extracted with EtOAc (2×50 mL). The combined organic extracts were dried over anhyd Na$_2$SO$_4$, concentrated under reduced pressure and purified flash silica gel chromatography (0-50% EtOAc gradient) to give Compound 53-2 (150 mg, 56% yield). MS for C$_{14}$H$_{13}$FN$_2$O$_3$: m/z 276.9 (MH+).

Step 3: 4-(4-Fluorophenyl)-5,6-dimethyl-3-oxo-3,4-dihydropyrazine-2-carboxylic acid (HA3-2): Compound 53-2 was converted to Compound HA3-2 using the ester hydrolysis procedure used in Step 3 of General Procedure A. MS for C$_{13}$H$_{11}$FN$_2$O$_3$: m/z 262.9 (MH+).

Example 54: 6-(4-Fluorophenyl)-5-hydroxypyrimidine-4-carboxylic acid (HA4-1)

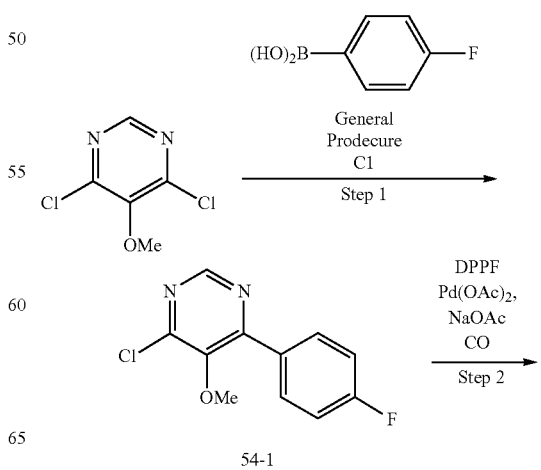

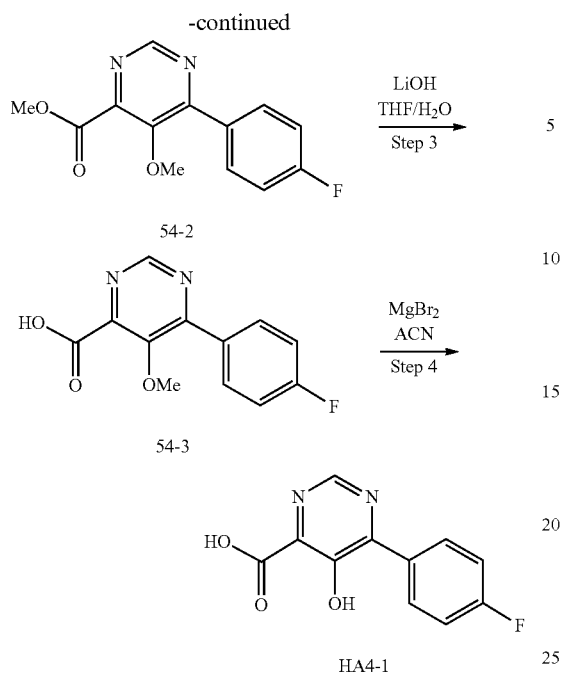

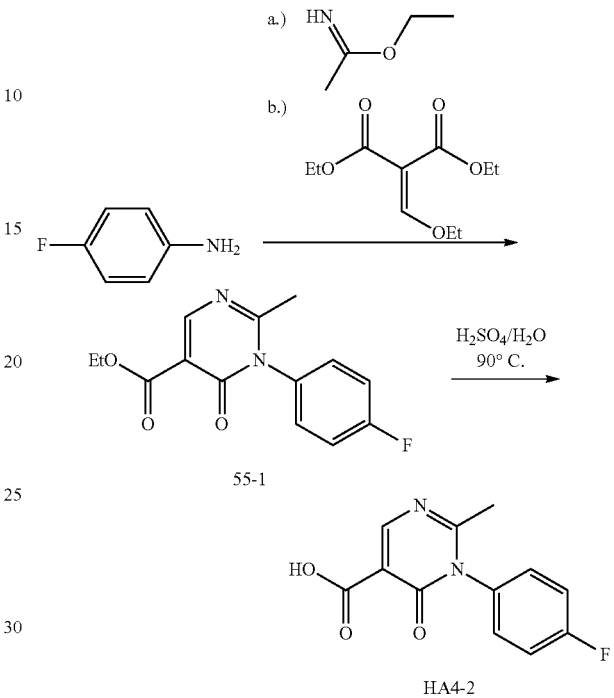

Example 55: 1-(4-Fluorophenyl)-2-methyl-6-oxo-1,6-dihydropyrimidine-5-carboxylic acid, Sodium salt (HA4-2)

Step 1: 4-Chloro-6-(4-fluorophenyl)-5-methoxypyrimidine (54-1): Compound 54-1 was synthesized from 4,6-dichloro-5-methoxypyrimidine using General Procedure C1. MS for $C_{11}H_8ClFN_2O$: m/z 238.9 (MH+).

Step 2: Methyl 6-(4-fluorophenyl)-5-methoxypyrimidine-4-carboxylate (54-2): To a mixture of Compound 54-1 (635 mg, 2.7 mmol, 1 eq) and MeOH (5.54 g, 172 mmol, 7 mL, 65 eq) in DMF (7 mL) was added cyclopentyl(diphenyl) phosphane; iron (DPPF) (295 mg, 0.53 mmol, 0.2 eq), diacetoxypalladium (61 mg, 0.27 mmol, 0.1 eq) and sodium acetate (656 mg, 8 mmol, 3 eq). The mixture was degassed under vacuum and purged with CO several times. The mixture was stirred at 75° C. for 13 h under CO (50 psi). The mixture was diluted with water (70 mL) and extracted with EtOAc (3×20 mL). The combined organic extracts were washed with aq saturated NaCl (30 mL), dried over anhyd $Na_2SO_4$ and concentrated. The resulting residue was purified by flash silica gel chromatography (0-10% EtOAc gradient in petroleum ether) to give Compound 54-2 (660 mg, 94% yield). MS for $C_{13}H_{11}FN_2O_3$: m/z 262.9 (MH+).

Step 3: 6-(4-Fluorophenyl)-5-methoxypyrimidine-4-carboxylic acid (54-3): Compound 54-3 was made from Compound 54-2 in a manner similar to the way that Compound HA2-11 was made from Compound 49-1 in Example 49. MS for $C_{12}H_9FN_2O_3$: m/z 248.9 (MH+).

Step 4: 6-(4-Fluorophenyl)-5-hydroxypyrimidine-4-carboxylic acid (HA4-1): To a mixture of Compound 54-3 (189 mg, 0.76 mmol, 1 eq) in ACN (4 mL) was added $MgBr_2$ (280 mg, 1.5 mmol, 2 eq). The mixture was stirred at 50° C. for 1 h. The mixture was diluted with water (10 mL), the pH was adjusted to pH=3 with aq 1.0 M HCl and the resulting mixture was extracted with EtOAc (3×10 mL). The combined organic extracts were washed with aq saturated NaCl (20 mL), dried over anhyd $Na_2SO_4$ and concentrated to give Compound HA4-1 (113 mg, 63% yield) which was used in subsequent reactions without further purification. MS for $C_{11}H_7FN_2O_3$: m/z 234.9 (MH+).

Step 1: Ethyl 1-(4-fluorophenyl)-2-methyl-6-oxo-1,6-dihydropyrimidine-5-carboxylate (55-1): A mixture of 4-fluoroaniline (11 g, 99 mmol, 1 eq), ethyl ethanimidate HCl (12 g, 99 mmol, 1 eq) and TEA (11 g, 109 mmol, 1.1 eq) in EtOH (40 mL) was stirred at 20° C. for 64 h. Diethyl 2-(ethoxymethylene)propanedioate (23.6 g, 109 mmol, 1.1 eq) was then added to the mixture and stirring was continued at 80° C. for 7 h. The reaction mixture was diluted with water (300 mL) and extracted with EtOAc (3×150 mL). The combined organic extracts were washed with aq saturated NaCl (50 mL), dried over $Na_2SO_4$ and concentrated under reduced pressure. The resulting residue was purified by silica gel column chromatography (petroleum ether/EtOAc=5/1 to 5/4) to give Compound 55-1(5.0 g, 18 mmol, 18% yield). MS for $C_{14}H_{13}FN_2O_3$: m/z 276.9 (MH+).

Step 2: 1-(4-Fluorophenyl)-2-methyl-6-oxo-1,6-dihydropyrimidine-5-carboxylic acid (HA4-2): A mixture of Compound 55-1 (1 g, 3.62 mmol, 1 eq), water (500 mg, 28 mmol, 0.5 mL, 7.7 eq) and $H_2SO_4$ (5 mL) was stirred at 90° C. for 3.5 h. The reaction mixture was added dropwise to ice (300 mL) at 0° C., and the pH was adjusted to pH=7-8 slowly with $NaHCO_3$ at 0° C. The resulting mixture was washed with EtOAc (3×20 mL). The aqueous phase was carefully acidified with aq 2 M HCl to pH=4-5 and then extracted with EtOAc (4×50 mL). The combined EtOAc extracts were washed with aq saturated NaCl (15 mL), dried over anhyd $Na_2SO_4$ and concentrated in vacuo to give crude Compound HA4-2 (690 mg, 77% yield) which was used into the next step without further purification. H NMR (400 MHz, $CDCl_3$) δ 12.56 (br s, 1H), 8.88 (br s, 1H), 7.44-7.13 (m, 4H), 2.34 (br s, 3H).

Example 56: 1-(4-Fluorophenyl)-2-(methylamino)-6-oxo-1,6-dihydropyrimidine-5-carboxylic acid (HA4-4)

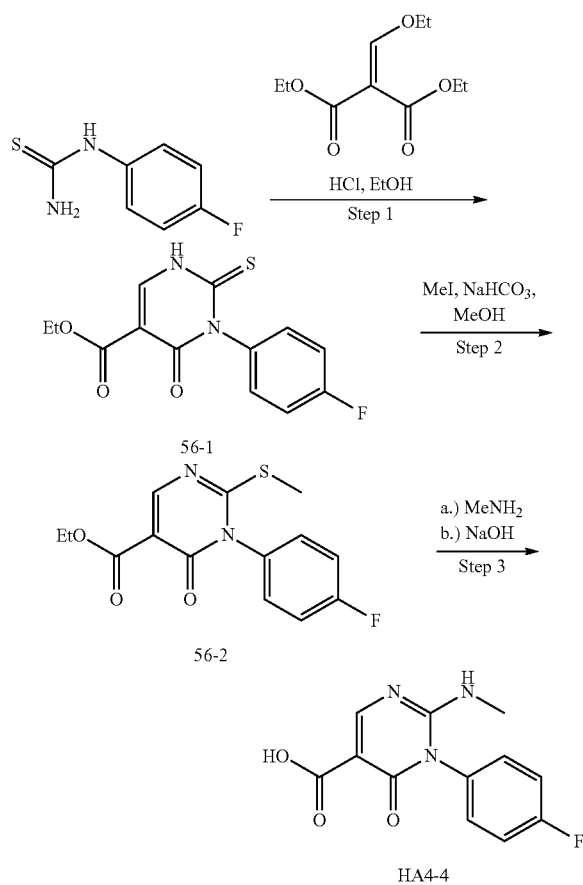

Step 1: Ethyl 3-(4-fluorophenyl)-4-oxo-2-thioxo-1,2,3,4-tetrahydropyrimidine-5-carboxylate (56-1): A mixture of diethyl 2-(ethoxymethylene)malonate (3.2 mL, 13.8 mmol), 1-(4-fluorophenyl)-thiourea (2.54 g, 15 mmol), and HCl (36% aq, 3.2 mL) in EtOH was refluxed for 6 h. The reaction was cooled to room temperature and filtered. The resulting solid was washed with EtOH and dried to give Compound 56-1 (2.6 g, 64% yield). MS for $C_{13}HFN_2O_3S$: m/z 295 (MH+).

Step 2: Ethyl 1-(4-fluorophenyl)-2-(methylthio)-6-oxo-1,6-dihydropyrimidine-5-carboxylate (56-2): To a mixture of Compound 56-1 (1.5 g, 5.1 mmol), aq saturated $NaHCO_3$ (4 mL) and MeOH was added MeI (1.0 mL, 16.1 mmol). The reaction was stirred at room temperature overnight and concentrated to remove MeOH and excess MeI. The resulting solid was filtered, washed with water and dried to give Compound 56-2 (1.51 g, 96% yield). MS for $C_{14}H_{13}FN_2O_3S$: m/z 309 (MH+).

Step 3: 1-(4-Fluorophenyl)-2-(methylamino)-6-oxo-1,6-dihydropyrimidine-5-carboxylic acid (HA4-4): A mixture of Compound 56-2 (130 mg, 0.447 mmol) and $MeNH_2$ (8 M solution in EtOH, 1.0 mL) was stirred at 50° C. for 20 min and then concentrated to remove all volatiles. To the resulting residue was added aq NaOH (2 M, 1 mL) and MeOH (2 mL). The resulting mixture was stirred at room temperature for 4 h, concentrated to remove most of the MeOH and acidified with aq HCl (6 M) to pH~2. The resulting solids were filtered, washed with water and dried to give Compound HA4-4 (70 mg, 63% yield). MS for $C_{12}H_{10}FN_3O_3$: m/z 264 (MH+).

The following compound was made using the same method employed to make Compound HA4-4 from Compound 56-2 in Example 56:

2-(Dimethylamino)-1-(4-fluorophenyl)-6-oxo-1,6-dihydropyrimidine-5-carboxylic acid (HA4-5): MS for $C_{13}H_{12}FN_3O_3$: m/z 278 (MH+).

Example 57: 1-(4-Fluorophenyl)-2-(isopropylthio)-6-oxo-1,6-dihydropyrimidine-5-carboxylic acid (HA4-10)

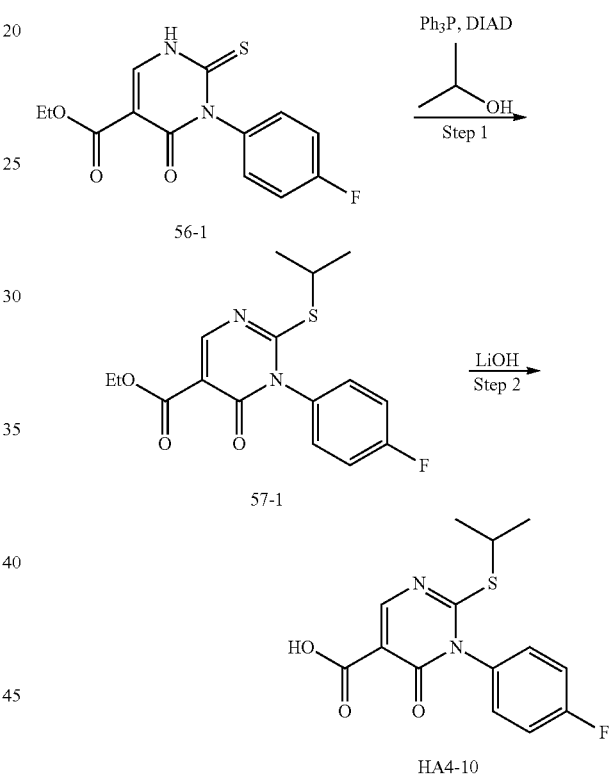

Step 1: Ethyl 1-(4-fluorophenyl)-2-(isopropylthio)-6-oxo-1,6-dihydropyrimidine-5-carboxylate (57-1): Compound 56-1 (294 mg, 1.0 mmol), triphenylphosphine (400 mg, 1.52 mmol) and isopropanol (120 mg, 2.0 mmol) were dissolved in anhydrous DCM (5 mL). The resulting solution was cooled to 0° C. Diisopropyl azodicarboxylate (DIAD) (202 mg, 1.0 mmol) was added dropwise. The mixture is stirred at 0° C. for 2 h, and then water was added. The resulting mixture was extracted with EtOAc. The combined EtOAc extracts were washed with aq saturated NaCl and concentrated. The resulting residue was purified by flash column chromatography to give Compound 57-1 (270 mg, 80%).

Step 2: 1-(4-Fluorophenyl)-2-(isopropylthio)-6-oxo-1,6-dihydropyrimidine-5-carboxylic acid: Compound HA4-10 was made from Compound 57-1 in a manner similar to the way that Compound HA2-11 was made from Compound 49-1 in Example 49.

Example 58: 3-(4-Fluorophenyl)-2,4-dioxo-1,2,3,4-tetrahydropyrimidine-5-carboxylic acid (HA4-7)

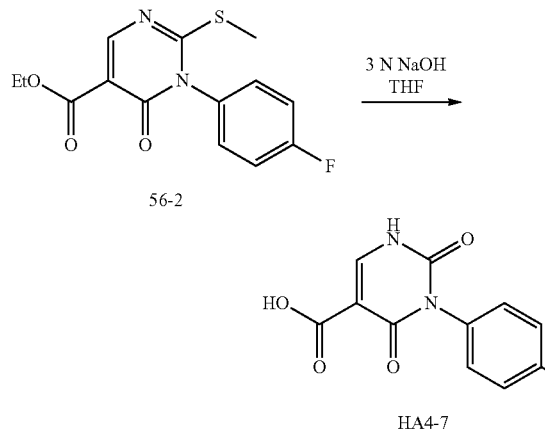

3-(4-Fluorophenyl)-2,4-dioxo-1,2,3,4-tetrahydropyrimidine-5-carboxylic acid (HA4-7): A 20-mL scintillation vial was charged with a Teflon stir bar, Compound 56-2 (207 mg, 0.670 mmol) and THF (4.4 mL). Aq 3 N NaOH (2.2 mL) was added and the reaction was stirred at room temperature for 20 h. The reaction was diluted with water and washed with DCM. The aqueous layer was acidified with aq 1 N HCl and extracted twice with EtOAc. The combined EtOAc extracts were washed with aq saturated NaCl, dried over anhyd $Na_2SO_4$ and concentrated to give Compound HA4-7 (158 mg, 94% yield). MS for $C_{11}H_7FN_2O_4$: m/z 251 (MH+).

Example 59: 2-((tert-Butoxycarbonyl)amino)-1-(4-fluorophenyl)-6-oxo-1,6-dihydropyrimidine-5-carboxylic acid (HA4-9)

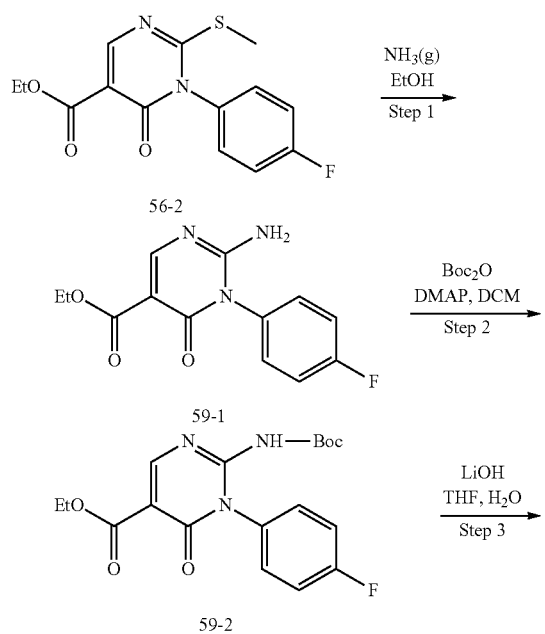

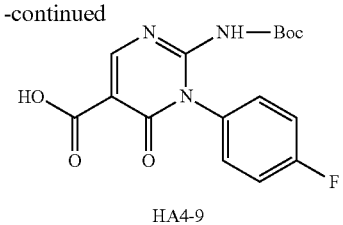

Step 1: Ethyl 2-amino-1-(4-fluorophenyl)-6-oxo-1,6-dihydropyrimidine-5-carboxylate (59-1): A sealed tube reaction vessel was charged with a Teflon stir bar and Compound 56-2 (99 mg, 0.32 mmol). The vessel was sealed with a rubber septum and the material was suspended in 5 mL of EtOH. Ammonia gas was bubbled into the solution until all material was dissolved then the vessel was capped and stirred at room temperature overnight. The reaction was concentrated to give Compound 59-1 (88 mg, 99% yield). MS for $C_{13}H_{12}FN_3O_3$: m/z 278 (MH+).

Step 2: Ethyl 2-((tert-butoxycarbonyl)amino)-1-(4-fluorophenyl)-6-oxo-1,6-dihydropyrimidine-5-carboxylate (59-2): A 4 mL scintillation vial was charged with Compound 59-1 (50 mg, 0.180 mmol), DMAP (5.5 mg, 0.045 mmol, 0.25 eq) and a Teflon stir bar. The material was suspended in DCM and a 1 M solution of $Boc_2O$ in THF (0.27 mL, 0.27 mmol, 1.5 eq) was added to the stirring reaction. The reaction was stirred at room temperature for 3 h then diluted with DCM and MeOH and concentrated in the presence of silica gel (500 mg). The resulting powder was loaded onto a silica gel column and the reaction product was purified by silica gel column chromatography (eluting with 0-50% EtOAc in hexanes) to give Compound 59-2 (34 mg, 50% yield). MS for $C_{11}H_{20}FN_3O_5$: m/z 378 (MH+).

Step 3: 2-((tert-Butoxycarbonyl)amino)-1-(4-fluorophenyl)-6-oxo-1,6-dihydropyrimidine-5-carboxylic acid (HA4-9): Compound HA4-9 was made from Compound 59-2 in a manner similar to the way that Compound HA2-11 was made from Compound 49-1 in Example 49. MS for $C_{16}H_{16}FN_3O_5$: m/z 350 (MH+).

Example 60: 1-(4-Fluorophenyl)-2,4-dimethyl-6-oxo-1,6-dihydropyrimidine-5-carboxylic acid (HA4-6)

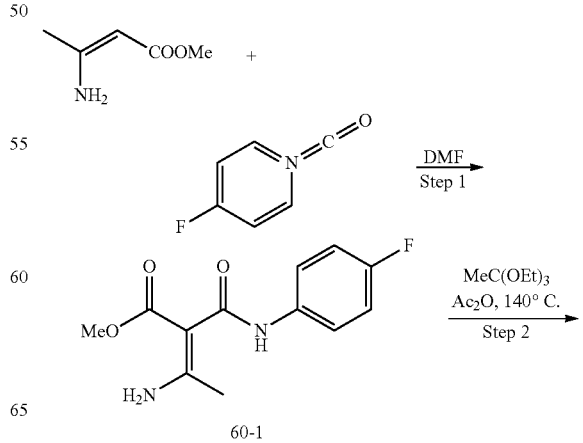

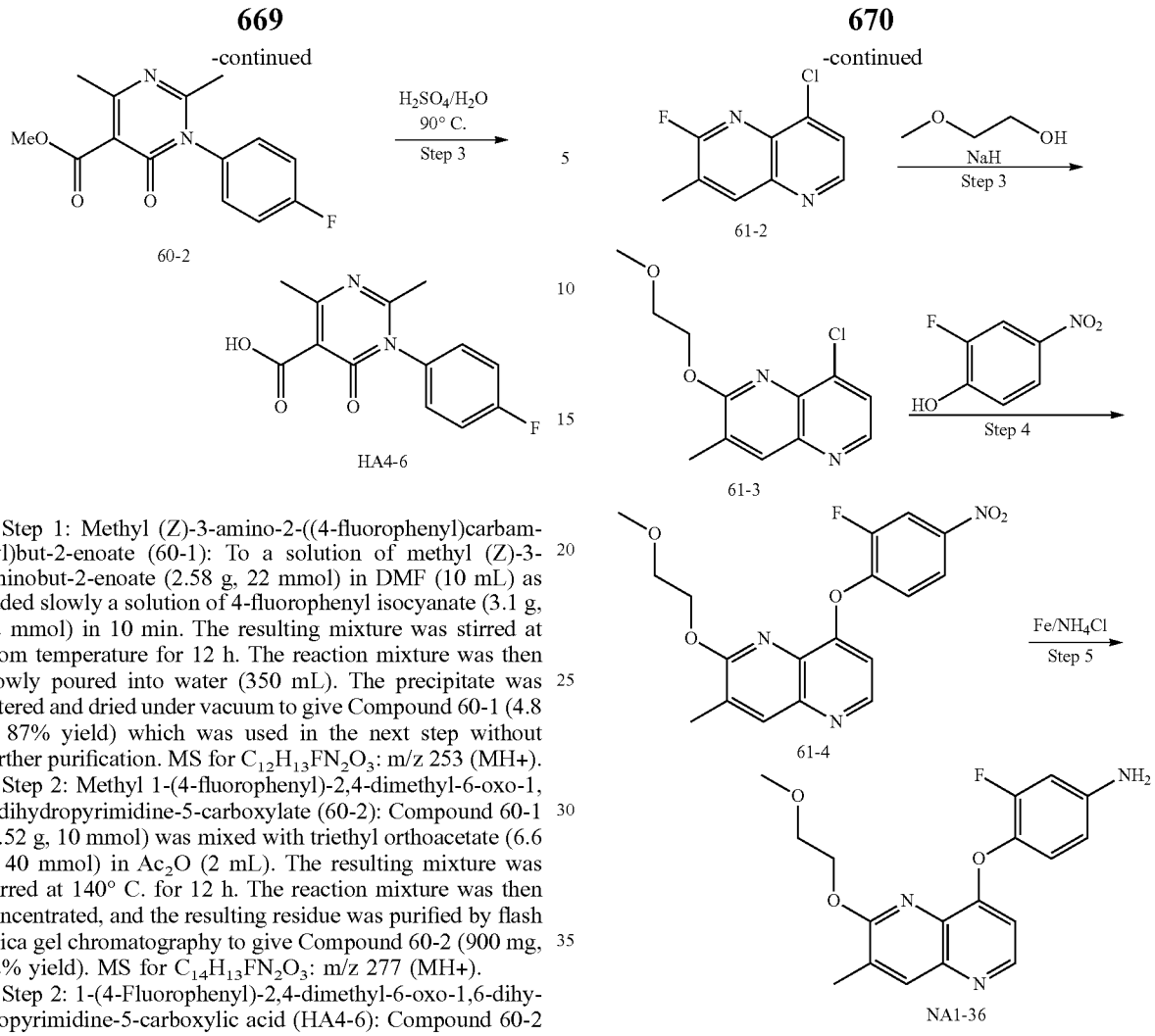

Step 1: Methyl (Z)-3-amino-2-((4-fluorophenyl)carbamoyl)but-2-enoate (60-1): To a solution of methyl (Z)-3-aminobut-2-enoate (2.58 g, 22 mmol) in DMF (10 mL) as added slowly a solution of 4-fluorophenyl isocyanate (3.1 g, 22 mmol) in 10 min. The resulting mixture was stirred at room temperature for 12 h. The reaction mixture was then slowly poured into water (350 mL). The precipitate was filtered and dried under vacuum to give Compound 60-1 (4.8 g, 87% yield) which was used in the next step without further purification. MS for $C_{12}H_{13}FN_2O_3$: m/z 253 (MH+).

Step 2: Methyl 1-(4-fluorophenyl)-2,4-dimethyl-6-oxo-1,6-dihydropyrimidine-5-carboxylate (60-2): Compound 60-1 (2.52 g, 10 mmol) was mixed with triethyl orthoacetate (6.6 g, 40 mmol) in $Ac_2O$ (2 mL). The resulting mixture was stirred at 140° C. for 12 h. The reaction mixture was then concentrated, and the resulting residue was purified by flash silica gel chromatography to give Compound 60-2 (900 mg, 32% yield). MS for $C_{14}H_{13}FN_2O_3$: m/z 277 (MH+).

Step 2: 1-(4-Fluorophenyl)-2,4-dimethyl-6-oxo-1,6-dihydropyrimidine-5-carboxylic acid (HA4-6): Compound 60-2 (50 mg, 1.81 mmol) was mixed with $H_2SO_4$ (2 g) and water (135 mg). The resulting mixture was stirred at 90° C. for 4 h. After it was cooled to room temperature, water was slowly added, and the resulting precipitate was filtered and dried under vacuum to give Compound HA4-6 (250 mg, 52% yield). MS for $C_{13}H_{11}FN_2O_3$: m/z 263 (MH+).

The following compound was made in the same manner as Compound HA4-6 in Example 60:

Same procedures: 1-(4-Fluorophenyl)-4-methyl-6-oxo-1,6-dihydropyrimidine-5-carboxylic acid (HA4-3): MS for $C_{12}H_9FN_2O_3$: m/z 249 (MH+).

Example 61: 3-Fluoro-4-((6-(2-methoxyethoxy)-7-methyl-1,5-naphthyridin-4-yl)oxy)aniline (NA1-36)

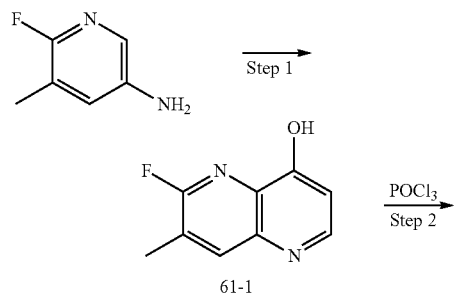

Step 1: 6-Fluoro-7-methyl-1,5-naphthyridin-4-ol (61-1): Compound 61-1 was made from 6-fluoro-5-methylpyridin-3-amine using Step 1 of General Procedure G.

Step 2: 8-Chloro-2-fluoro-3-methyl-1,5-naphthyridine (61-2): A mixture of Compound 61-1 (560 mg, 3.14 mmol), $POCl_3$ (1.5 g, 9.8 mmol) and DIEA (1.74 mL, 10 mmol) in toluene (10 mL) was stirred at 100° C. for 30 min, then cooled to room temperature and concentrated. The resulting residue was purified by silica gel chromatography (0-70% EtOAc in hexanes) to give Compound 61-2 (586 mg, 94% yield). MS for $C_9H_6ClFN_2$: m/z 197 (MH+).

Step 3: 8-Chloro-2-(2-methoxyethoxy)-3-methyl-1,5-naphthyridine (61-3): To a solution of 2-methoxyethanol (150 mg, 2 mmol) in DMF (4 mL) was added NaH (60%, 90 mg, 2.25 mmol) with stirring at 100° C., followed by the addition of Compound 61-2 (256 mg, 1.3 mmol). The resulting mixture was stirred at room temperature for 10 min. The reaction was then quenched with water. The resulting solid was filtered, washed with water and dried to give Compound 62-3 (330 mg, 100% yield). MS for $C_{12}H_{13}ClN_2O_2$: m/z 253 (MH+).

Step 4: 8-(2-Fluoro-4-nitrophenoxy)-2-(2-methoxyethoxy)-3-methyl-1,5-naphthyridine (61-4): Compound 61-4 was made from Compound 61-3 using step 1 of General Procedure H.

Step 5: 3-Fluoro-4-((6-(2-methoxyethoxy)-7-methyl-1,5-naphthyridin-4-yl)oxy)aniline (NA1-36): Compound NA-36 was made from Compound 61-4 using step 3 of General Procedure G. MS for $C_{11}H_{11}FN_3O_3$: m/z 344 (MH+).

The following compounds were made in a similar fashion to that of Compound NA1-36 in Example 61.

4-((6-(2-Methoxyethoxy)-7-methyl-1,5-naphthyridin-4-yl)oxy)aniline (NA-35): MS for $C_{11}H_{19}N_3O_3$: m/z 326 (MH+).

3-Fluoro-4-((7-methyl-6-(3-morpholinopropoxy)-1,5-naphthyridin-4-yl)oxy)aniline (NA1-37): MS for $C_{22}H_{25}FN_4O_3$: m/z 413 (MH+).

Example 62:3-Fluoro-4-((7-methoxy-6-(3-morpholinopropoxy)-1,5-naphthyridin-4-yl)oxy)aniline (NA1-28)

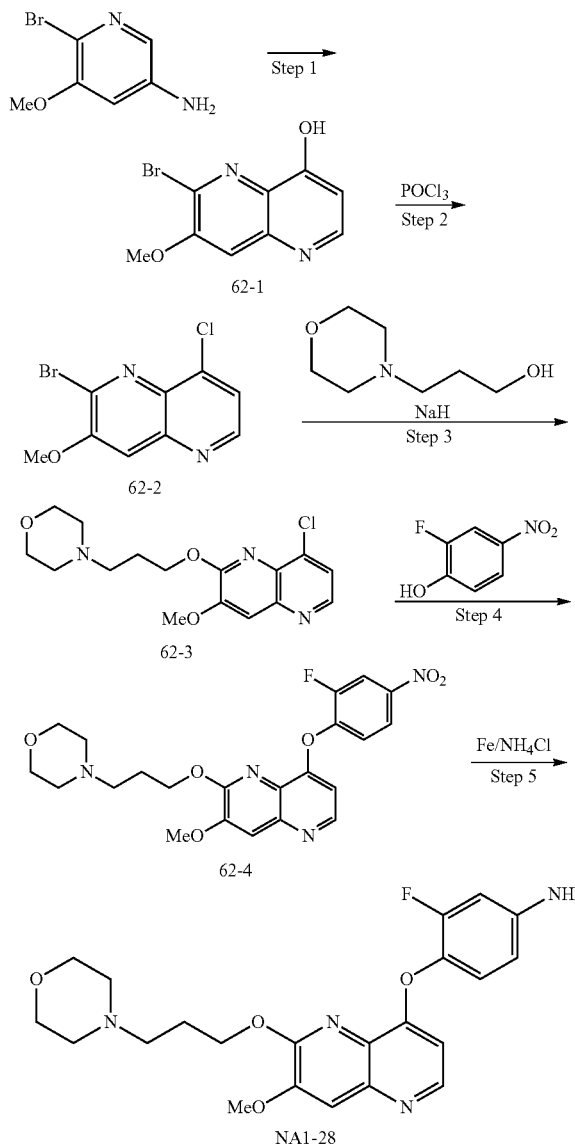

Step 1: 6-Bromo-7-methoxy-1,5-naphthyridin-4-ol (62-1): Compound 62-1 was made from 6-bromo-5-methoxy-pyridin-3-amine using step 1 of General Procedure G. MS for $C_9H_7BrN_2O_2$, found 255/257 (MH+).

Step 2: 2-Bromo-8-chloro-3-methoxy-1,5-naphthyridine (62-2): Compound 62-2 was made from Compound 62-1 in the same manner that Compound 61-2 was made from Compound 61-1 in Example 61. MS for $C_9H_6BrCN_2O$: 275 (MH+).

Step 3: 4-(3-((8-Chloro-3-methoxy-1,5-naphthyridin-2-yl)oxy)propyl)morpholine (62-3): To a solution of 3-morpholinopropan-1-ol (125 mg, 0.86 mmol) in DMF (2 mL) was slowly added NaH (60% in oil, 38 mg, 0.95 mmol). The resulting suspension was stirred at room temperature for 5 min, followed by addition of Compound 62-2 (110 mg, 0.40 mmol). The mixture was stirred at room temperature for 30 min, quenched with aq NaHCO3 and extracted with EtOAc (2×). The combined extracts were washed with aq saturated NaCl and concentrated. The resulting residue was purified by silica gel chromatography (0-5% MeOH in EtOAc) to give Compound 62-3 (104 mg, 77% yield). MS for $C_{16}H_{20}ClN_3O_3$: 338 (MH+).

Step 4: 4-(3-((8-(2-Fluoro-4-nitrophenoxy)-3-methoxy-1,5-naphthyridin-2-yl)oxy)propyl)morpholine (62-4): Compound 62-4 was made from Compound 62-3 using step 1 of General Procedure H.

Step 5: 3-Fluoro-4-((7-methoxy-6-(3-morpholino-propoxy)-1,5-naphthyridin-4-yl)oxy)aniline (NA1-28): Compound NA-28 was made from Compound 62-4 using step 3 of General Procedure G. MS for $C_{22}H_{25}FN_4O_4$: 429 (MH+).

The following compounds were made in a similar fashion to that of Compound NA1-28 in Example 62.

3-Fluoro-4-((7-methoxy-6-(2-methoxyethoxy)-1,5-naphthyridin-4-yl)oxy)aniline (NA1-16): MS for $C_{18}H_{18}FN_3O_4$: 360 (MH+).

4-((6-Ethoxy-7-methoxy-1,5-naphthyridin-4-yl)oxy)-3-fluoroaniline (NA-27): MS for $C_{17}H_{16}FN_3O_3$: 330 (MH+).

3-Fluoro-4-((6-isopropoxy-7-methoxy-1,5-naphthyridin-4-yl)oxy)aniline (NA1-30): MS for $C_{11}HFN_3O_3$: 344 (MH+).

4-((6-Isopropoxy-7-methoxy-1,5-naphthyridin-4-yl)oxy)aniline (NA1-31): MS for $C_{18}H_{19}N_3O_3$: 326 (MH+).

Example 63:3-Fluoro-4-((6-(2-methoxyethoxy)-1,5-naphthyridin-4-yl)oxy)aniline(NA1-18)

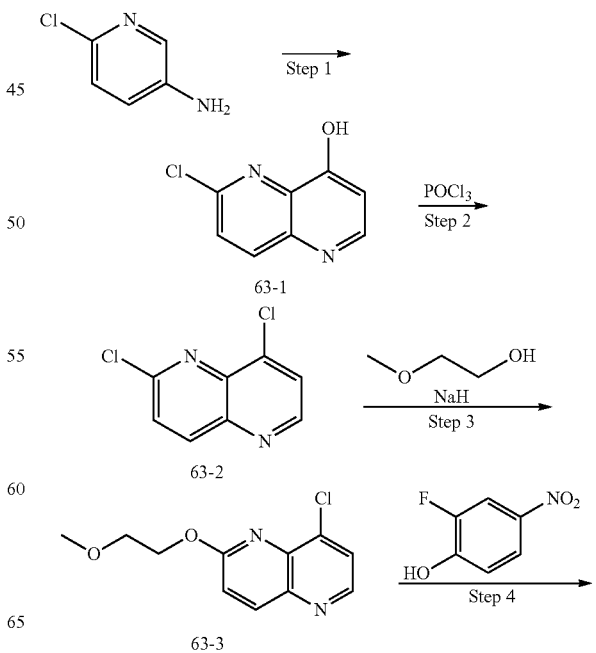

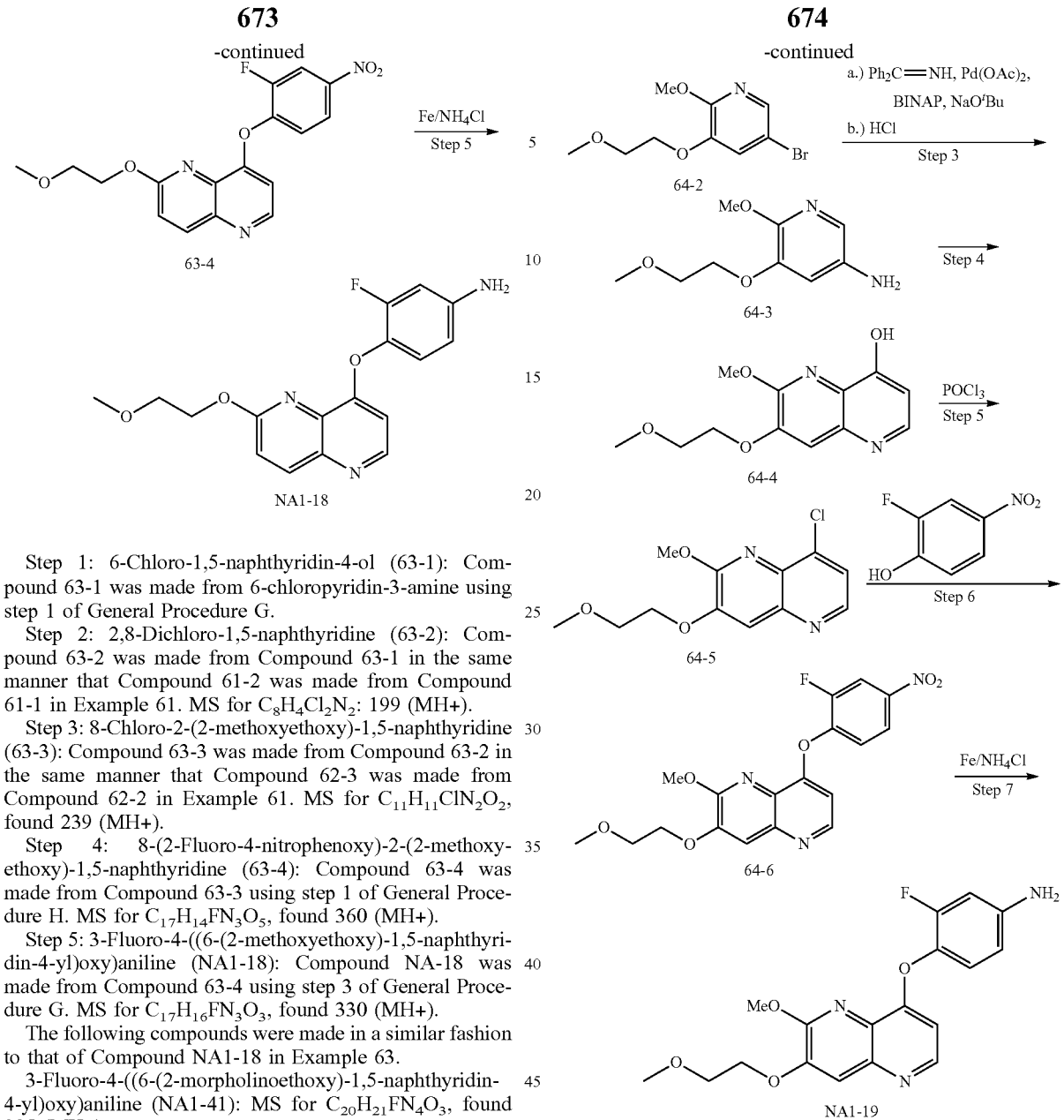

Step 1: 6-Chloro-1,5-naphthyridin-4-ol (63-1): Compound 63-1 was made from 6-chloropyridin-3-amine using step 1 of General Procedure G.

Step 2: 2,8-Dichloro-1,5-naphthyridine (63-2): Compound 63-2 was made from Compound 63-1 in the same manner that Compound 61-2 was made from Compound 61-1 in Example 61. MS for $C_8H_4Cl_2N_2$: 199 (MH+).

Step 3: 8-Chloro-2-(2-methoxyethoxy)-1,5-naphthyridine (63-3): Compound 63-3 was made from Compound 63-2 in the same manner that Compound 62-3 was made from Compound 62-2 in Example 61. MS for $C_{11}H_{11}ClN_2O_2$, found 239 (MH+).

Step 4: 8-(2-Fluoro-4-nitrophenoxy)-2-(2-methoxyethoxy)-1,5-naphthyridine (63-4): Compound 63-4 was made from Compound 63-3 using step 1 of General Procedure H. MS for $C_{17}H_{14}FN_3O_5$, found 360 (MH+).

Step 5: 3-Fluoro-4-((6-(2-methoxyethoxy)-1,5-naphthyridin-4-yl)oxy)aniline (NA1-18): Compound NA-18 was made from Compound 63-4 using step 3 of General Procedure G. MS for $C_{17}H_{16}FN_3O_3$, found 330 (MH+).

The following compounds were made in a similar fashion to that of Compound NA1-18 in Example 63.

3-Fluoro-4-((6-(2-morpholinoethoxy)-1,5-naphthyridin-4-yl)oxy)aniline (NA1-41): MS for $C_{20}H_{21}FN_4O_3$, found 385 (MH+).

4-((6-(2-(Dimethylamino)ethoxy)-1,5-naphthyridin-4-yl)oxy)-3-fluoroaniline (NA1-50): MS for $C_{18}H_{19}FN_4O_2$, found 343 (MH+).

Example 64:3-Fluoro-4-((6-methoxy-7-(2-methoxyethoxy)-1,5-naphthyridin-4-yl)oxy)aniline (NA1-19)

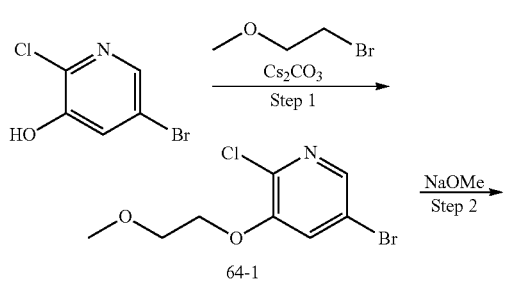

Step 1: 5-Bromo-2-chloro-3-(2-methoxyethoxy)pyridine (64-1): A mixture of 5-bromo-2-chloropyridin-3-ol (2.10 g, 10.0 mmol), 1-bromo-2-methoxyethane (1.50 g, 10.8 mmol) and $Cs_2CO_3$ (6.6 g, 20.2 mmol) in DMF was stirred at 80° C. for 2 h, quenched with water and extracted with EtOAc (2×). The combined extracts were washed with aq saturated NaCl, dried over anhyd $Na_2SO_4$ and concentrated to give crude Compound 64-1 (2.68 g, 100% yield). MS for $C_8H_9BrClNO_2$, found 268 (MH+).

Step 2: 5-Bromo-2-methoxy-3-(2-methoxyethoxy)pyridine (64-2): Compound 64-1 (2.68 g, 10.0 mmol) was mixed with NaOMe (3.0 g, 55.5 mmol) in MeOH (40 mL) and heated at 80° C. overnight. The reaction mixture was concentrated to remove MeOH. The residue was partitioned between water and EtOAc. The EtOAc solution was washed with aq saturated NaCl, dried over anhyd $Na_2SO_4$ and concentrated to give crude Compound 64-2 (3.0 g) contaminated with residual solvent. MS for $C_9H_{12}BrNO_3$, found 262/264 (MH+).

Step 3: 6-Methoxy-5-(2-methoxyethoxy)pyridin-3-amine (64-3): Compound 64-2 (3.0 g, crude) was mixed with diphenylmethanimine (3.6 g, 20 mmol), Pd(OAc)$_2$ (360 mg, 1.61 mmol), BINAP (1.3 g, 2.08 mmol) and NaO$^t$Bu (1.6 g, 16.7 mmol) in toluene (60 mL). The resulting mixture was degassed with nitrogen and stirred at 85° C. overnight. The resulting reaction mixture was partitioned between water and EtOAc. The organic phase was separated and evaporated to dryness. To the resulting residue was added THF (40 mL) and HCl (aq, 2M, 40 mL) and resulting mixture was stirred at room temperature overnight. The pH of the resulting reaction mixture was adjusted to pH 10 with NaHCO$_3$ and extracted with EtOAc. The extract was concentrated, and the resulting residue purified by silica gel chromatography (0-90% EtOAc in hexanes) to give Compound 64-3 (1.4 g). MS for $C_9H_{14}N_2O_3$, found 199 (MH+).

Step 4: 6-Methoxy-7-(2-methoxyethoxy)-1,5-naphthyridin-4-ol (64-4): Compound 64-4 was made from Compound 64-3 using step 1 of General Procedure G. MS for $C_{12}H_{14}N_2O_4$, found 251 (MH+).

Step 5: 8-Chloro-2-methoxy-3-(2-methoxyethoxy)-1,5-naphthyridine (64-5): Compound 64-5 was made from Compound 64-4 in the same manner that Compound 61-2 was made from Compound 61-1 in Example 61. MS for $C_{12}H_{13}ClN_2O_3$, 269 (MH+).

Step 6: 8-(2-Fluoro-4-nitrophenoxy)-2-methoxy-3-(2-methoxyethoxy)-1,5-naphthyridine (64-6): Compound 64-6 was made from Compound 64-5 using step 1 of General Procedure H. Step 7: 3-Fluoro-4-((6-methoxy-7-(2-methoxyethoxy)-1,5-naphthyridin-4-yl)oxy)aniline (NA1-19): Compound NA-19 was made from Compound 64-6 using step 3 of General Procedure G. MS for $C_{18}H_{18}FN_3O_4$, 360 (MH+).

Example 65: 3-Fluoro-4-((7-methoxy-6-methyl-1,5-naphthyridin-4-yl)oxy)aniline (NA1-22)

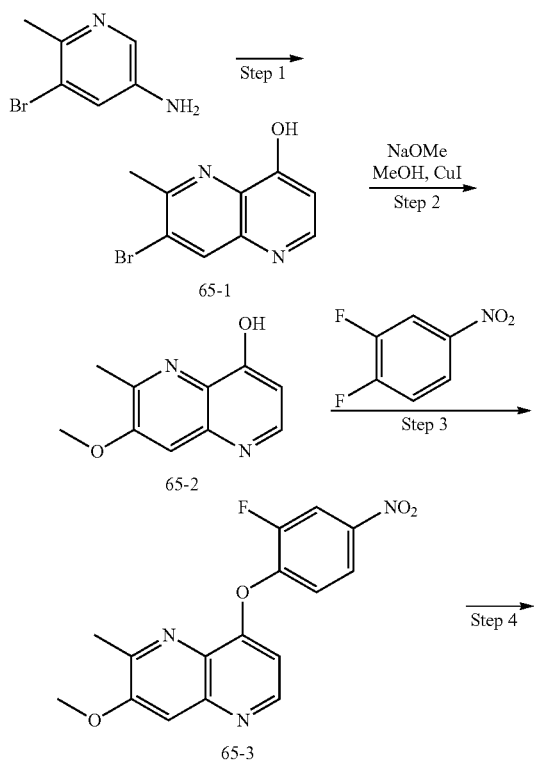

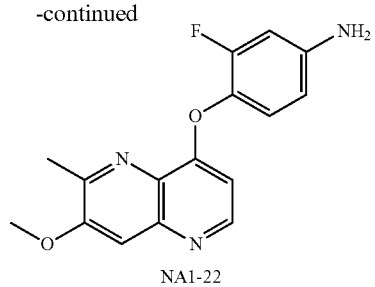

NA1-22

Step 1: 7-Bromo-6-methyl-1,5-naphthyridin-4-ol (65-1): Compound 65-1 was made from 5-bromo-6-methylpyridin-3-amine using step 1 of General Procedure G.

Step 2: 7-Methoxy-6-methyl-1,5-naphthyridin-4-ol (65-2): To a mixture of Compound 65-1 (100 mg, 0.418 mmol) and CuI (38 mg, 0.20 mmol) in DMF (2 mL) was added freshly prepared sodium methoxide in MeOH (1.2 mL, 3.5 M). The resulting mixture was stirred at 120° C. for 1 h. The mixture was concentrated, and the residue was washed with 5% MeOH in DCM. The organic phase was concentrated to give crude Compound 65-2 (40 mg, 50% yield) which was used in the next step without further purification. MS for $C_{10}H_{10}N_2O_2$, found: 191 (MH+).

Step 3: 8-(2-Fluoro-4-nitrophenoxy)-3-methoxy-2-methyl-1,5-naphthyridine (65-3): Compound 65-3 was made from Compound 65-2 using step 2 of General Procedure G.

Step 4: 3-Fluoro-4-((7-methoxy-6-methyl-1,5-naphthyridin-4-yl)oxy)aniline (NA1-22): Compound NA-22 was made from Compound 65-3 using step 3 of General Procedure G. MS for $C_{16}H_{14}FN_3O_2$, found 300 (MH+).

The following compounds were made in a similar fashion to that of Compound NA1-22 in Example 65.

2,5-Difluoro-4-((7-methoxy-6-methyl-1,5-naphthyridin-4-yl)oxy)aniline (NA1-42): MS for $C_{16}H_{13}F_2N_3O_2$, found 318 (MH+).

Example 66: 3-Fluoro-4-((6-methoxy-7-vinyl-1,5-naphthyridin-4-yl)oxy)aniline (NA1-40)

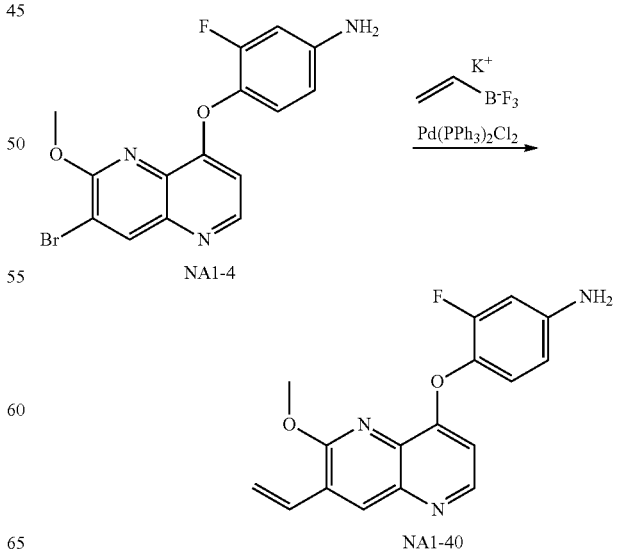

3-Fluoro-4-((6-methoxy-7-vinyl-1,5-naphthyridin-4-yl)oxy)aniline (NA1-40): A mixture of Compound NA1-4 (330 mg, 0.91 mmol), Pd(PPh$_3$)$_2$Cl$_2$ (72 mg, 0.10 mmol), potassium vinyltriflouroborate (230 mg, 1.72 mmol), and CsF (500 mg, 3.3 mmol) in dioxane/water (2/1 mL) was stirred at 85° C. for 2 h and then cooled to room temperature. The resulting mixture was diluted with aq Na$_2$CO$_3$ (2M, 2 mL) and extracted twice with EtOAc. The combined organic extracts were dried over anhyd Na$_2$SO$_4$ and concentrated to give crude Compound NA1-40 which was used without further purification. MS for C$_{17}$H$_{14}$FN$_3$O$_2$: m/z 312 (MH+).

The following compounds were made in a similar fashion to that used to make Compound NA1-40 in Example 66.

3-Fluoro-4-((7-vinyl-1,5-naphthyridin-4-yl)oxy)aniline (NA1-32B): Compound NA1-4 was replaced with Compound NA1-5. MS for C$_{16}$H$_{12}$FN$_3$O: m/z 282 (MH+).

3-Fluoro-4-((6-methoxy-7-(prop-1-en-2-yl)-1,5-naphthyridin-4-yl)oxy)aniline (NA1-23): The potassium vinyltriflouroborate was replaced with potassium isopropenyltrifluoroborate. MS for C$_{18}$H$_{16}$FN$_3$O$_2$: m/z 326 (MH+).

3-Fluoro-4-((7-(prop-1-en-2-yl)-1,5-naphthyridin-4-yl)oxy)aniline (NA1-24): The potassium vinyltriflouroborate was replaced with potassium isopropenyltrifluoroborate and Compound NA1-4 was replaced with Compound NA1-5. MS for C$_{17}$H$_{14}$FN$_3$O: m/z 296 (MH+).

4-((7-(Prop-1-en-2-yl)-1,5-naphthyridin-4-yl)oxy)aniline (NA1-25): The potassium vinyltriflouroborate was replaced with potassium isopropenyltrifluoroborate and Compound NA1-4 was replaced with Compound NA1-11. MS for C$_{17}$H$_{15}$N$_3$O: m/z 278 (MH+).

Example 67: 4-((7-Ethyl-6-methoxy-1,5-naphthyridin-4-yl)oxy)-3-fluoroaniline (NA1-38)

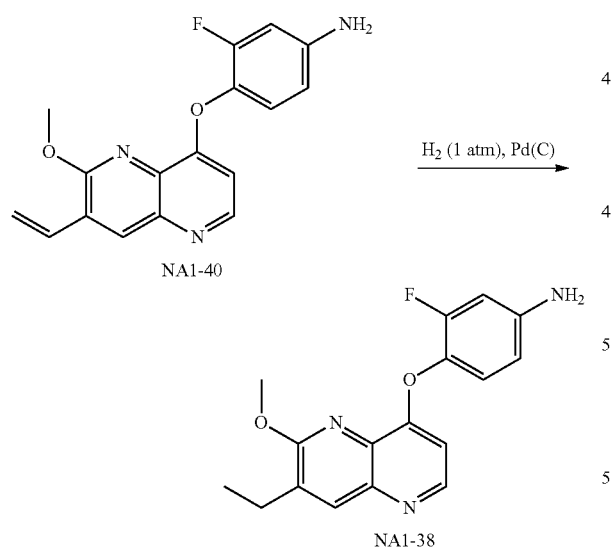

4-((7-Ethyl-6-methoxy-1,5-naphthyridin-4-yl)oxy)-3-fluoroaniline (NA1-38): Crude Compound NA-40 was mixed with Pd (10% on C, 53% wet, 107 mg) in EtOAc (15 mL) and the resulting suspension was degassed under vacuum for 2 min then stirred under an atmosphere of hydrogen at room temperature overnight. The reaction mixture was filtered, and the filtrate was concentrated. The resulting residue was purified by silica gel chromatography to give Compound NA1-38 (155 mg, 54% yield over 2 steps from Compound NA-4). MS for C$_{17}$H$_{16}$FN$_3$O$_2$: m/z 314 (MH+).

The following compound was made in a manner very similar to that used to make Compound NA1-38 in Example 67.

4-((7-Ethyl-1,5-naphthyridin-4-yl)oxy)-3-fluoroaniline (NA1-32): Compound NA1-40 was replaced with Compound NA1-32B. MS for C$_{16}$H$_{14}$FN$_3$O: m/z 284 (MH+).

Example 68: 8-(4-Amino-2-fluorophenoxy)-2-methoxy-1,5-naphthyridin-3-ol (NA1-43)

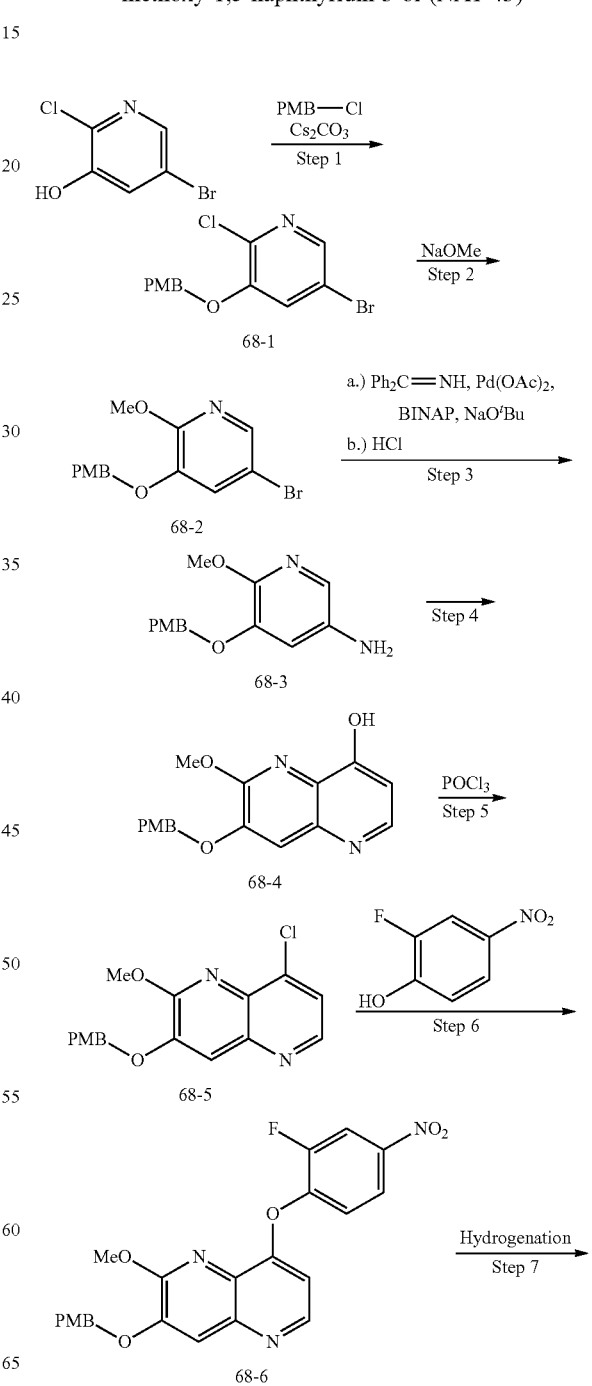

-continued

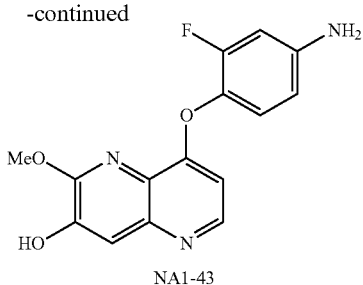

NA1-43

Steps 1-6: 8-(2-Fluoro-4-nitrophenoxy)-2-methoxy-3-((4-methoxybenzyl)oxy)-1,5-naphthyridine (68-6): Compound 68-6 was made in 6 steps from 5-bromo-2-chloropyridin-3-ol following the same 6-step procedure used to make Compound 64-6 from 5-bromo-2-chloropyridin-3-ol in Example 64. The 1-bromo-2-methoxyethane was replaced with 4-methoxybenzyl chloride. Step 7: 8-(4-Amino-2-fluorophenoxy)-2-methoxy-1,5-naphthyridin-3-ol (NA1-43): The nitro group if Compound 68-6 was reduced and the PMB protecting group was removed to give Compound NA1-43 in a single step using standard hydrogenation conditions such as those used in Step 6 of Example 71. MS for $C_{15}H_{12}FN_3O_3$, found 302 (MH+).

Example 69: 8-(4-Amino-2-fluorophenoxy)-1,5-naphthyridin-3-ol (NA1-51)

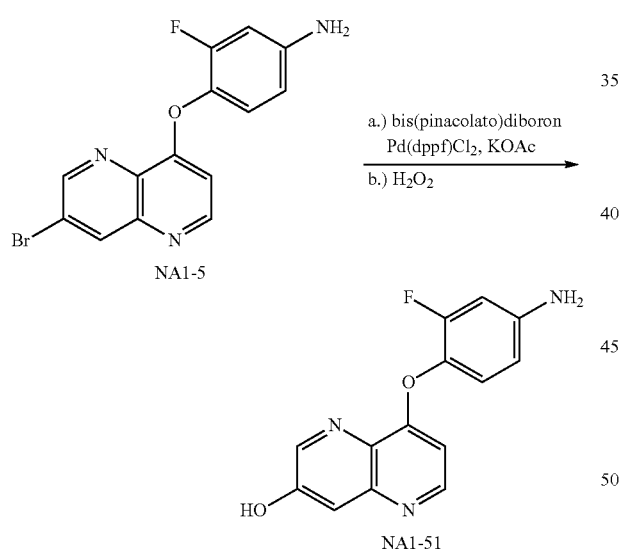

8-(4-Amino-2-fluorophenoxy)-1,5-naphthyridin-3-ol (NA1-51): A mixture of Compound NA1-5 (375 mg, 1.12 mmol), bis(pinacolato)diboron (700 mg, 2.75 mmol), Pd(dppf)Cl$_2$ (78 mg, 0.11 mmol) and KOAc (250 mg, 2.55 mmol) in 1,4-dioxane (6.0 mL) was stirred at 85° C. for 2 h under an atmosphere of nitrogen. The reaction mixture was cooled to room temperature and 30% aq hydrogen peroxide (0.25 mL) and aq saturated NaHCO$_3$ (5.0 mL) were added. The mixture was stirred at room temperature for 5 h and then partitioned between aq saturated NaCl and EtOAc. The EtOAc layer was collected, dried over anhyd Na$_2$SO$_4$ and evaporated to remove the solvent. The resulting residue was purified by silica gel column chromatography (EtOAc-hexane) to give Compound NA1-51 (122 mg, 40% yield). MS for $C_{14}H_{10}FN_3O_2$, m/z 272 (MH+).

Example 70:4-((7-(Benzyloxy)-1,5-naphthyridin-4-yl)oxy)-3-fluoroaniline (NA1-39)

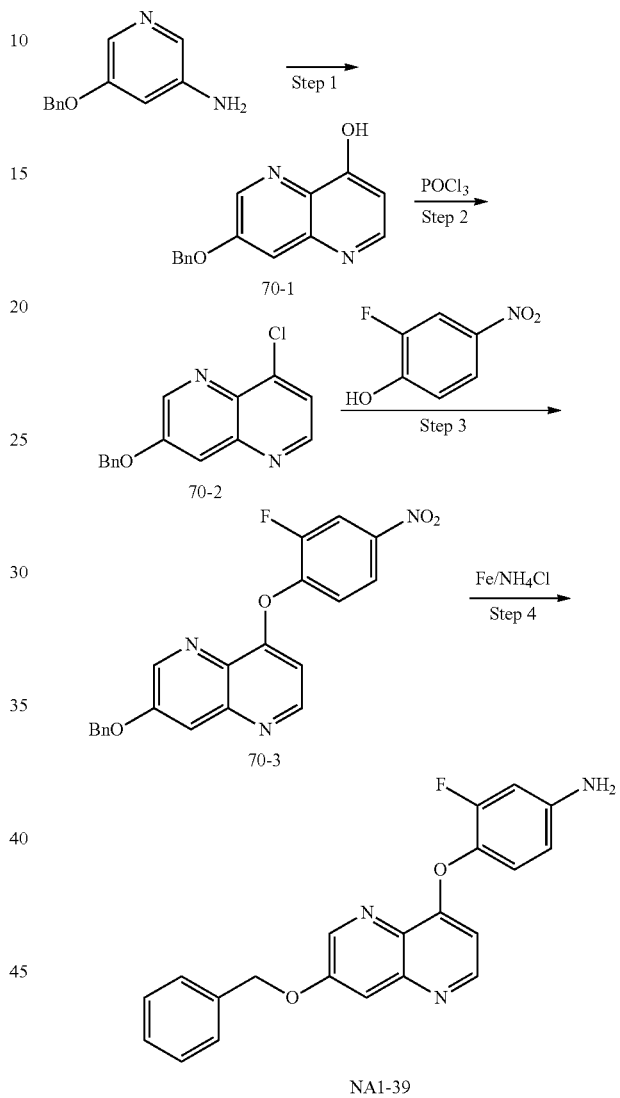

Step 1: 7-(Benzyloxy)-1,5-naphthyridin-4-ol (70-1): Compound 70-1 was made from 5-(benzyloxy)pyridin-3-amine using step 1 of General Procedure G. MS for $C_{15}H_{12}N_2O_2$: 252.8 (MH+).

Step 2: 3-(Benzyloxy)-8-chloro-1,5-naphthyridine (70-2): Compound 70-2 was made from Compound 70-1 in the same manner that Compound 61-2 was made from Compound 61-1 in Example 61. MS for $C_{15}H_{11}ClN_2O$, m/z 271 (MH+).

Step 3: 3-(Benzyloxy)-8-(2-fluoro-4-nitrophenoxy)-1,5-naphthyridine (70-3): Compound 70-3 was made from Compound 70-2 using step 1 of General Procedure H. MS for $C_{21}H_{14}FN_3O_4$, m/z for 392 (MH+).

Step 4: 4-((7-(Benzyloxy)-1,5-naphthyridin-4-yl)oxy)-3-fluoroaniline (NA1-39): Compound NA-39 was made from Compound 70-3 using step 3 of General Procedure G. MS for $C_{21}H_{16}FN_3O_2$, m/z 362 (MH+).

Example 71: Ethyl 2-(8-(4-amino-2-fluorophenoxy)-3-methoxy-1,5-naphthyridin-2-yl)acetate (NA1-49)

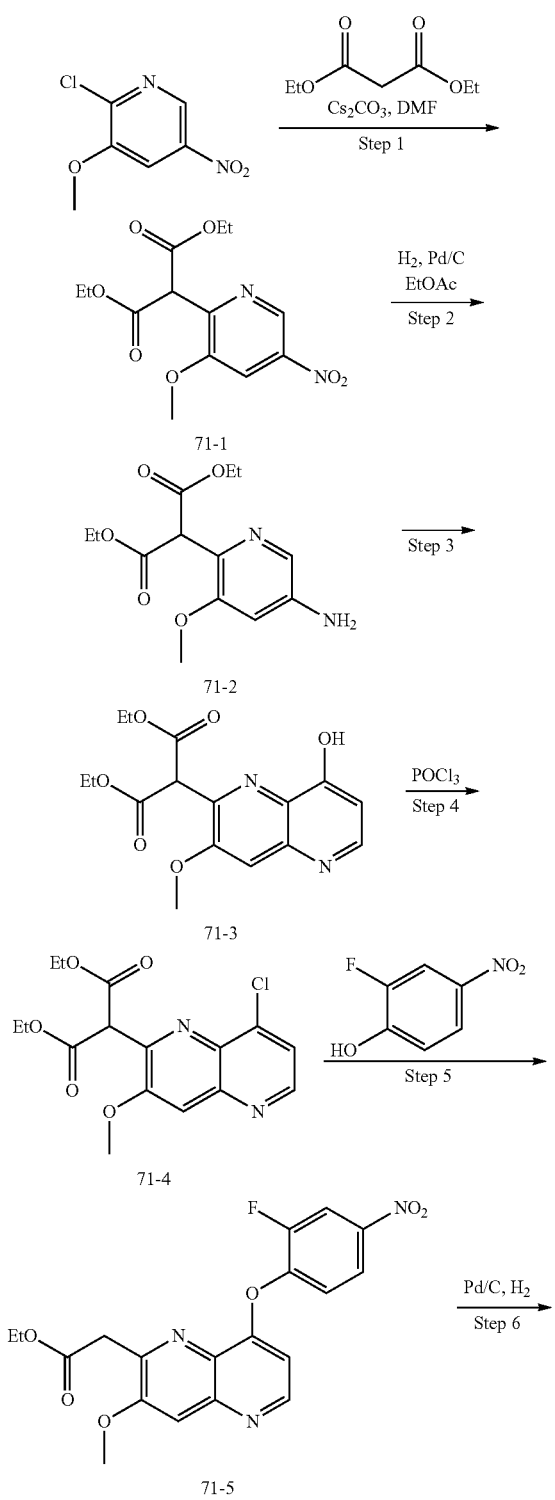

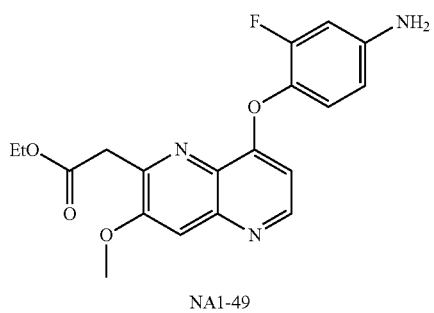 [SMILES: CCOC(=O)Cc1nc2c(Oc3ccc(N)cc3F)ccnc2cc1OC]

NA1-49

Step 1: Diethyl 2-(3-methoxy-5-nitropyridin-2-yl)malonate (71-1): To a mixture of diethyl malonate (4.1 g, 25 mmol, 3.85 mL, 1.2 eq) in DMF (50 mL) was added $Cs_2CO_3$ (15.2 g, 47 mmol, 2.2 eq). The resulting mixture was stirred at 70° C. under an atmosphere of nitrogen for 30 min. 2-Chloro-3-methoxy-5-nitro-pyridine (4 g, 21 mmol, 1 eq) was added and the resulting mixture was stirred for 8.5 h. The solution was poured into water (200 mL) and the resulting mixture was stirred vigorously for 1 h. The resulting solids were filtered, washed with water (100 mL) and dried in the air to give crude Compound 71-1 (7.81 g). $^1$H NMR (400 MHz, $CDCl_3$) δ 9.02 (d, 1H), 7.94 (d, 1H), 5.15 (s, 1H), 4.29 (q, 4H), 3.97 (s, 3H), 1.28 (t, 6H).

Step 2: Diethyl 2-(5-amino-3-methoxypyridin-2-yl)malonate (71-2): To a mixture of Compound 71-1 (4.4 g, 14.2 mmol, 1 eq) in EtOAc (5 mL) was added 10% Pd/C (400 mg) in one portion at 25° C. under an atmosphere of hydrogen (15 psi). The mixture was stirred at 25° C. for 3 h. The reaction was filtered and washed with MeOH (70 mL). The filtrate was concentrated to give Compound 71-2 (3.9 g, 97% yield) which was used in subsequent reactions without further purification. MS for $C_{13}H_{18}N_2O_5$, m/z 283.1 (MH+).

Step 3: Diethyl 2-(8-hydroxy-3-methoxy-1,5-naphthyridin-2-yl)malonate (71-3): Compound 71-3 was made from Compound 71-2 using step 1 of General Procedure G.

Step 4: Diethyl 2-(8-chloro-3-methoxy-1,5-naphthyridin-2-yl)malonate (71-4): Compound 71-4 was made from Compound 71-3 in the same manner that Compound 61-2 was made from Compound 61-1 in Example 61. MS for $C_{16}H_{17}CN_2O_5$ m/z 353.0 (MH+).

Step 5: Ethyl 2-(8-(2-fluoro-4-nitrophenoxy)-3-methoxy-1,5-naphthyridin-2-yl)acetate (71-5): Compound 71-5 was made from Compound 71-4 using step 1 of General Procedure H. MS for $C_{19}H_{16}FN_3O_6$, m/z for 402.0 (MH+).

Step 6: Ethyl 2-(8-(4-amino-2-fluorophenoxy)-3-methoxy-1,5-naphthyridin-2-yl)acetate (NA1-49): To a mixture of Compound 71-5 (100 mg, 0.25 mmol, 1 eq) in EtOAc (20 mL) was added 10% Pd/C (100 mg) in one portion at 25° C. under an atmosphere of hydrogen (15 Psi). The mixture was stirred at 25° C. for 60 min. The reaction mixture was filtered and washed with EtOAc (20 mL). The filtrate was concentrated under reduced pressure to give Compound NA1-49 (90 mg, 97% yield) which was used in subsequent steps without further purification. MS for $C_{19}H_{18}FN_3O_4$, m/z 372.0 (MH+).

Example 72: 4-(4-Amino-2-fluorophenoxy)-7-methoxy-N-methylquinoline-6-carboxamide (QA1-6)

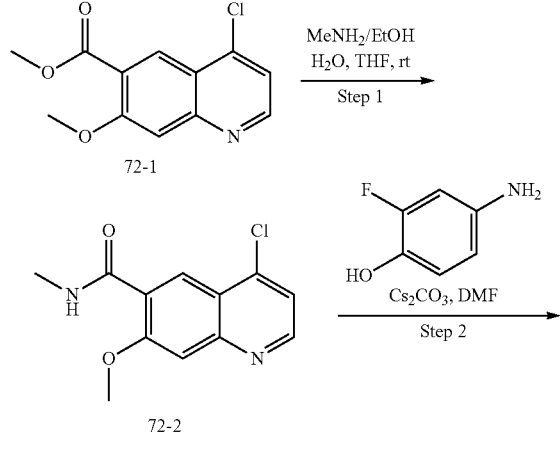

Example 73: 4-((7-(1-(Difluoromethyl)-1H-pyrazol-4-yl)quinolin-4-yl)oxy)aniline (QA1-10)

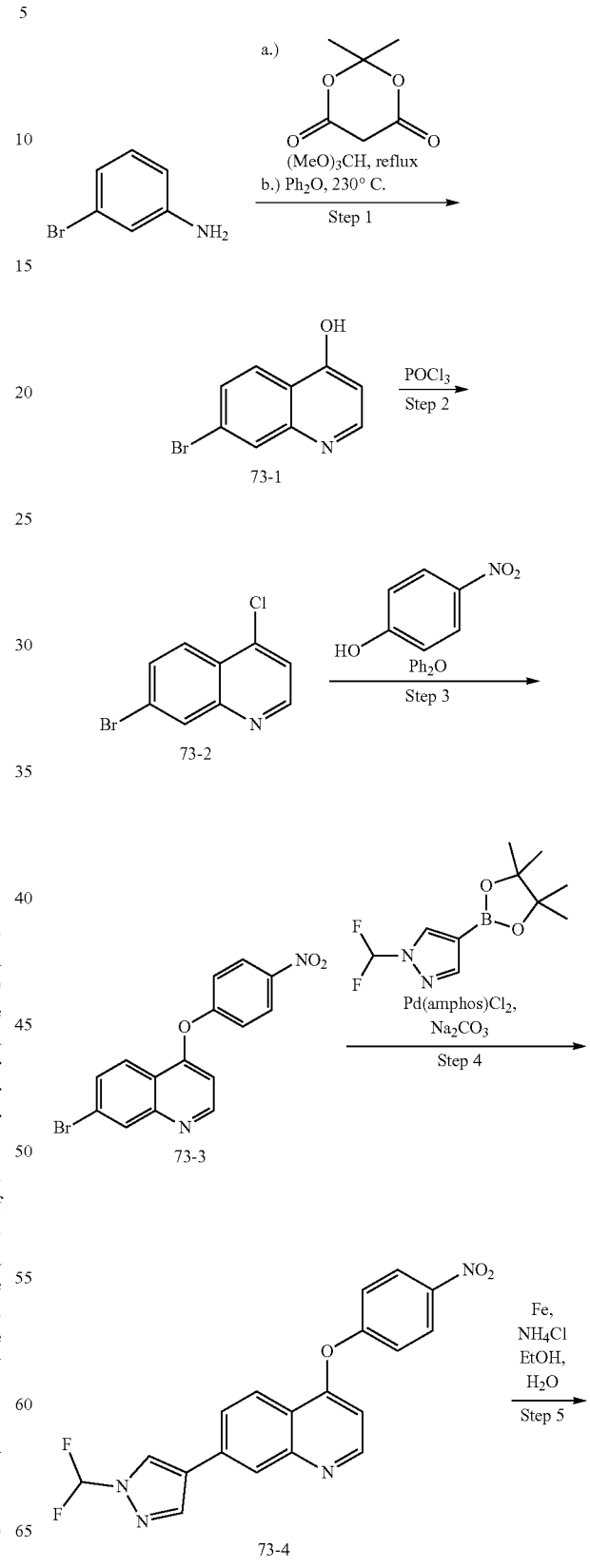

Step 1: 4-Chloro-7-methoxy-N-methylquinoline-6-carboxamide (72-2): Methylamine (8 M, 50 mL, 10 eq) in EtOH was added to a solution of Compound 72-1 (10 g, 40 mmol, 1 eq) in THF (150 mL) at 30° C. The reaction mixture was stirred at 30° C. for 25 h. The mixture was concentrated under vacuum. The residue was slurried with warm water (100 mL) and filtered. The filtered cake was dried under vacuum to give Compound 72-2 (9 g, 90% yield). MS for $C_{12}H_{11}CN_2O_2$, m/z 251.0 (MH+).

Step 2: 4-(4-Amino-2-fluorophenoxy)-7-methoxy-N-methylquinoline-6-carboxamide (QA1-6): To a mixture of Compound 72-2 (2 g, 8 mmol, 1 eq) and 4-amino-2-fluorophenol (1.5 g, 12 mmol, 1.5 eq) in DMF (20 mL) was added $Cs_2CO_3$ (5.2 g, 16 mmol, 2 eq) in one portion at 25° C. The mixture was stirred at 85° C. for 20 hr. The mixture was cooled to 25° C., diluted with water, and filtered. The crude residue was purified by flash silica gel chromatography (0-5% MeOH/DCM) to give Compound QA1-6 (276 mg, 10% yield). MS for $C_{18}H_{16}FN_3O_3$, m/z 342.1 (MH+).

The following compound was made in the same fashion as Compound QA1-6 in Example 72:

4-(4-Aminophenoxy)-7-methoxy-N-methylquinoline-6-carboxamide (QA1-5): The 4-amino-2-fluoro-phenol in step 2 was replaced with 4-aminophenol. MS for $C_{11}H_{17}N_3O_3$, m/z 324 (MH+).

-continued

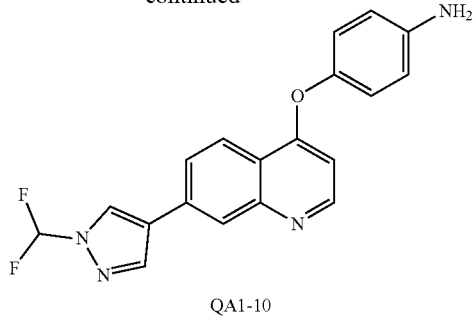

QA1-10

Step 1: 7-Bromoquinolin-4-ol (73-1): A mixture of 2,2-dimethyl-1,3-dioxane-4,6-dione (10 g, 70 mmol, 1.2 eq) in trimethyl orthoformate (97 g, 912 mmol, 100 mL, 16 eq) was stirred at 105° C. for 1.5 h. 3-Bromoaniline (10 g, 58 mmol, 6.3 mL, 1 eq) was then added and the resulting mixture stirred for 1 h. The resulting suspension was filtered and the solid was washed with methanol and dried under vacuum. The recovered solid was added to $Ph_2O$ (90 mL) at 230° C. and the mixture was stirred for 0.5 h. The reaction mixture was poured into petroleum ether after being cooled to room temperature. The resulting precipitate was filtered and washed with petroleum ether to give Compound 73-1 (6.1 g) which was used in subsequent reactions without further purification.

Step 2: 7-Bromo-4-chloroquinoline (73-2): Compound 73-2 was made from Compound 73-1 in the same manner that Compound 61-2 was made from Compound 61-1 in Example 61. MS for $C_9H_5BrClN$, found 243.9 (MH+).

Step 3: 7-Bromo-4-(4-nitrophenoxy)quinoline (73-3): A mixture of Compound 73-2 (1 g, 4 mmol, 1 eq) and 4-nitrophenol (574 mg, 4.1 mmol, 1 eq) in $Ph_2O$ (10 mL) was heated and stirred at 140° C. for 16 h, followed by stirring at 150° C. for another 4 h. The mixture was added to petroleum ether (10 ml), then filtered and concentrated to give Compound 73-3 (1.23 g, 86% yield). MS for $C_{15}H_9BrN_2O_3$, found 346.9 (MH+).

Step 4: 7-(1-(Difluoromethyl)-1H-pyrazol-4-yl)-4-(4-nitrophenoxy)quinoline (73-4): $Na_2CO_3$ (460 mg, 4.3 mmol, 3 eq) and Pd(amphos)$Cl_2$ (105 mg, 0.15 mmol, 0.1 eq) were added to a mixture of Compound 73-3 (500 mg, 1.4 mmol, 1 eq) and 1-(difluoromethyl)-4-(4,4,5, 5-tetramethyl-1,3,2-dioxaborolan-2-yl) pyrazole (435 mg, 1.8 mmol, 1.2 eq) in dioxane (10 mL) and water (2 mL) which was purged with nitrogen. The mixture was stirred at 90° C. under an atmosphere of nitrogen for 16 h. After cooling to room temperature, the mixture was diluted with EtOAc (20 mL) and filtered through a pad of Celite. The filtrate was quenched with water (10 mL) and extracted with EtOAc (3×10 mL). The combined extracts were dried over anhyd $Na_2SO_4$ and concentrated. The resulting residue was purified by flash silica gel chromatography (30-50% petroleum ether: EtOAc) to give Compound 73-4 (374 mg, 65% yield). MS for $C_{19}H_{12}F_2N_4O_3$, found 383.0 (MH+).

Step 5: 4-((7-(1-(Difluoromethyl)-1H-pyrazol-4-yl)quinolin-4-yl)oxy)aniline (QA1-10): Compound QA1-10 was made from Compound 73-4 using step 3 of General Procedure G. MS for $C_{19}H_{14}F_2N_4O$, m/z 352.9 (MH+).

Example 74: 3-Fluoro-4-((6-methoxy-1,7-naphthyridin-4-yl)oxy)aniline (NA3-1)

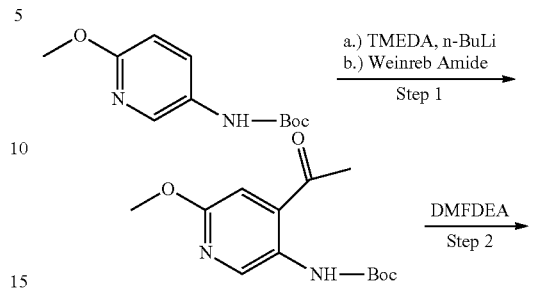

74-1

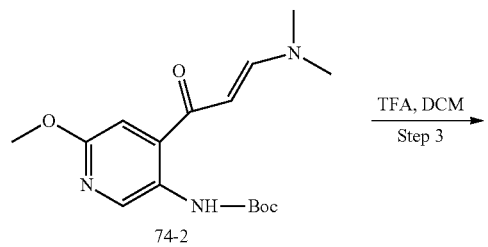

74-2

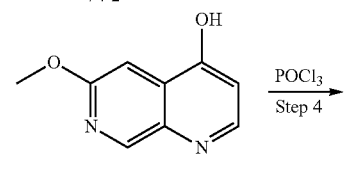

74-3

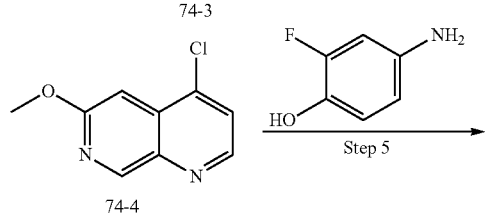

74-4

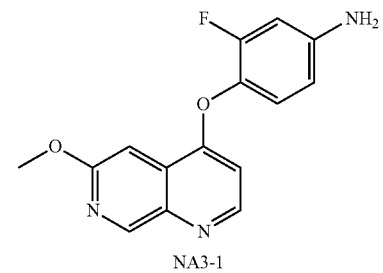

NA3-1

Step 1: tert-Butyl (4-acetyl-6-methoxypyridin-3-yl)carbamate (74-1): tert-Butyl (6-methoxypyridin-3-yl)carbamate (2.5 g, 11 mmol) was added to an oven dried round bottom flask equipped with a magnetic stir bar under nitrogen. Anhyd $Et_2O$ (50 mL) was added to the flask under nitrogen, followed by tetramethylethylenediamine (TMEDA) (5.0 mL, 3 eq). The homogenous mixture was cooled to −78° C. and stirred for 15 min under nitrogen. N-Butyl lithium (10 mL, 2.5 M in hexanes) was added to the mixture dropwise. After addition was complete, the mixture was warmed to −20° C. and stirred at that temperature for 2 h, after which the reaction mixture was cooled back down to −78° C. and Weinreb amide was added to the mixture. The resulting mixture was allowed to warm up to −20° C. and stirred under nitrogen for 2 h. The mixture was quenched at low temperature with water. EtOAc was used to extract the aqueous layer. The organic extracts were dried over anhyd $Na_2SO_4$ and concentrated under reduced pressure. The resulting residue was absorbed into silica gel and purified by flash chromatography (EtOAc/hexanes) to give Compound 74-1 (745 mg, 25% yield). $^1$H NMR (400 MHz, $CDCl_3$) δ 9.61 (bs, 1H), 9.20 (s, 1H), 7.10 (s, 1H), 3.97 (s, 3H), 2.64 (s, 3H), 1.54 (s, 9H).

Step 2: tert-Butyl (E)-(4-(3-(dimethylamino)acryloyl)-6-methoxypyridin-3-yl)carbamate (74-2): To a solution of Compound 74-1 (745 mg, 2.8 mmol) in toluene was added N,N-dimethylformamide diethyl acetal (DMF-DEA) (1.5 mL, 2.0 eq) and the reaction mixture was heated at 80° C. Upon completion of reaction, the solution was concentrated under reduced pressure to remove toluene. EtOAc was added to the residue and the mixture was absorbed into silica gel and purified by flash chromatography (EtOAc/hexanes) to give Compound 74-2 (800 mg, 89% yield). $^1$H NMR (400 MHz, $CDCl_3$) δ 9.50 (bs, 1H), 9.03 (s, 1H), 7.79 (d, 1H), 6.95 (s, 1H), 5.56 (d, 1H), 3.97 (s, 3H), 3.21 (s, 3H), 2.96 (s, 3H), 1.51 (s, 9H); MS for $C_{16}H_{23}N_3O_4$, found 322 (MH+).

Step 3: 6-Methoxy-1,7-naphthyridin-4-ol (74-3): Compound 74-2 (800 mg, 2.5 mmol) was dissolved in DCM (12.5 mL) and trifluoroacetic acid (TFA) (3.8 mL, 20 eq) was added dropwise. The resulting mixture was stirred at room temperature for 1 h. Upon completion of reaction, the reaction mixture was concentrated under reduced pressure to remove TFA. The residual solid was suspended in EtOAc and aq saturated $NaHCO_3$ solution was added dropwise until solid dissolved into the organic layer. The phases were separated, solid NaCl was added to the aqueous phase and the resulting mixture was extracted with DCM. The EtOAc and DCM layers were combined, dried over anhyd $Na_2SO_4$ and concentrated under reduced pressure to give crude Compound 74-3 (435 mg, 99% yield) which was used for the next step without further purification. $^1$H NMR (400 MHz, DMSO-$d_6$) δ 8.76 (s, 1H), 7.97 (d, 1H), 7.24 (s, 1H), 6.02 (d, 1H), 3.91 (s, 3H); MS for $C_9H_8N_2O_2$, found 177 (MH+).

Step 4: 4-Chloro-6-methoxy-1,7-naphthyridine (74-4): Compound 74-4 was made from Compound 74-3 in the same manner that Compound 61-2 was made from Compound 61-1 in Example 61. MS for $C_9H_7ClN_2O$, found 195 (MH+).

Step 5: 3-Fluoro-4-((6-methoxy-1,7-naphthyridin-4-yl)oxy)aniline (NA3-1): Compound 74-4 (353 mg, 1.8 mmol) was dissolved in anhyd DMF (9 mL) in a 20 mL microwave tube. $Cs_2CO_3$ (1.77 g, 3 eq) was added to the mixture followed by 4-amino-2-fluoro-phenol (461 mg, 2 eq). The mixture was degassed with nitrogen for 5 min, capped heated to 85° C. under microwave irradiation for 15 min. The resulting mixture was diluted with DCM and filtered. The mother liquor was washed with water and concentrated under reduced pressure. The resulting residue was diluted with DCM, washed with water, dried over anhyd $Na_2SO_4$, absorbed onto silica gel and purified by flash column chromatography (0-5% MeOH in DCM) to give Compound NA3-1 (402 mg, 78% yield). $^1$H NMR (400 MHz, DMSO-$d_6$) δ 9.15 (s, 1H), 8.62 (d, 1H), 7.39 (s, 1H), 7.10 (t, 1H), 6.66 (d, 1H), 6.56 (d, 1H), 6.48 (d, 1H), 5.54 (s, 2H), 4.01 (s, 3H). MS for $C_{15}H_{12}FN_3O_2$, found 286 (MH+).

Example 75: 4-((6-Chloro-1,7-naphthyridin-4-yl)oxy)-3-fluoroaniline (NA3-2)

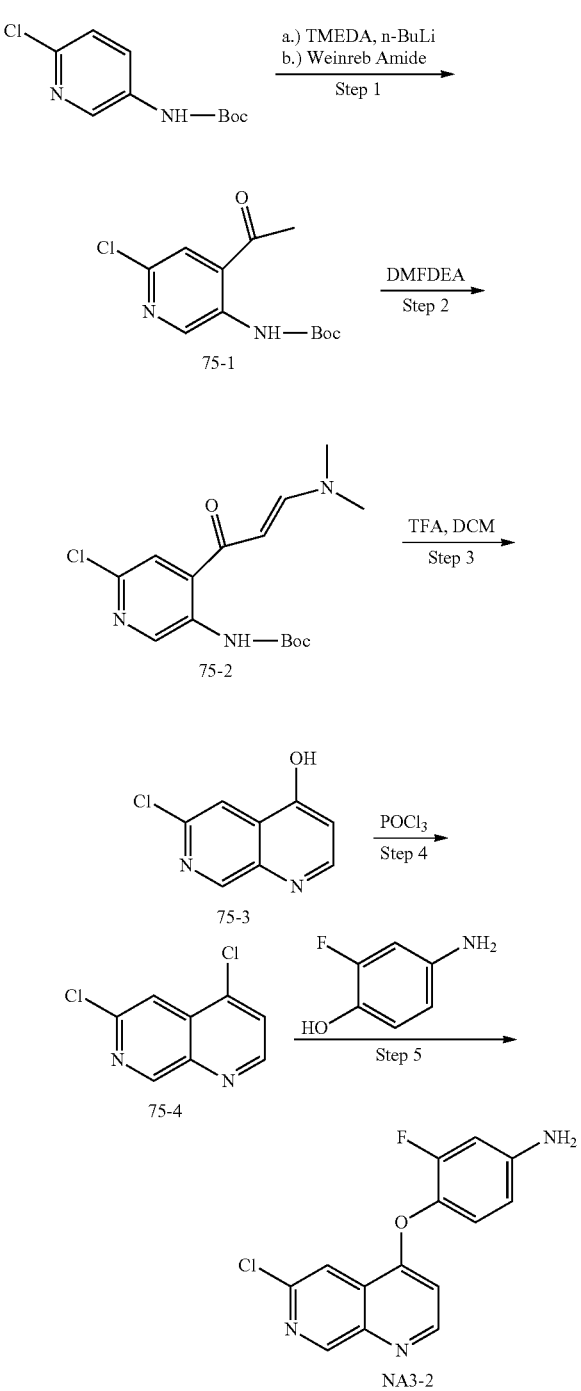

Steps 1-5: 4-((6-Chloro-1,7-naphthyridin-4-yl)oxy)-3-fluoroaniline (NA3-2): Starting with tert-butyl (6-chloropyridin-3-yl)carbamate instead of tert-butyl (6-methoxypyridin-3-yl)carbamate, Compound NA3-2 was made using the same 5 step sequence used to synthesize Compound NA3-1 in Example 74. $^1$H NMR (400 MHz, DMSO-$d_6$) δ 9.29 (s, 1H), 8.85 (d, 1H), 8.25 (s, 1H), 7.13 (t, 1H), 6.85 (d, 1H), 6.57 (d, 1H), 6.48 (d, 1H), 5.71 (s, 2H).

Example 76: 4-(4-Aminophenoxy)-N-methyl-1,7-naphthyridine-6-carboxamide (NA3-4)

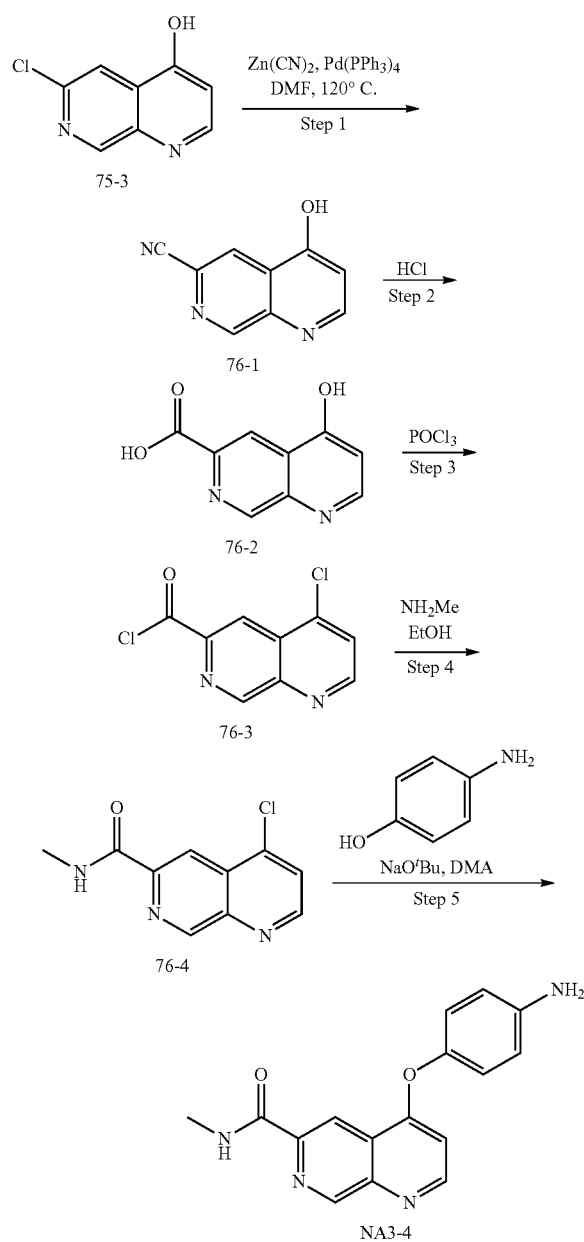

give crude Compound 76-2 (1.1 g, quantitative yield). MS for $C_9H_6N_2O_3$, found 190.8 (MH+).

Step 3: 4-Chloro-1,7-naphthyridine-6-carbonyl chloride (76-3): A solution of Compound 76-2 (300 mg, 1.6 mmol, 1 eq) in $POCl_3$ (6 mL) was stirred at 100° C. for 2 h. The reaction mixture was concentrated under reduced pressure to give crude Compound 76-3 (350 mg, quantitative yield).

Step 4: 4-Chloro-N-methyl-1,7-naphthyridine-6-carboxamide (76-4): A solution of Compound 76-3 (350 mg, 1.5 mmol, 1 eq) in THF (6 mL) was stirred at 0° C. for 0.5 h. To the mixture was added methylamine (47.9 mg, 1.5 mmol, 1 eq) and the resulting mixture was stirred at 25° C. for 12 h. The reaction mixture was concentrated under reduced pressure and the resulting residue was purified by flash silica gel chromatography (0-70% EtOAc/Petroleum ether) to give Compound 76-4 (46 mg, 13% yield). MS for $C_{10}H_8ClN_3O$, found 221.9 (MH+).

Step 5: 4-(4-Aminophenoxy)-N-methyl-1,7-naphthyridine-6-carboxamide (NA3-4): To a solution of Compound 76-4 (140 mg, 0.64 mmol, 1 eq) and 4-aminophenol (75.8 mg, 0.69 mmol, 1.1 eq) in DMA (2 mL) was added $NaO^tBu$ (91 mg, 0.95 mmol, 1.5 eq). The mixture was stirred at 100° C. for 12 h. The mixture was adjusted to pH 5 with aq 1 M HCl, diluted with water (50 mL) and extracted with EtOAc (150 mL). The organic extracts were washed with aq saturated NaCl (50 mL), dried over anhyd $Na_2SO_4$ and concentrated under reduced pressure. The resulting residue was purified by flash silica gel chromatography (0-5% MeOH/DCM) to give Compound NA3-4 (180 mg, 97% yield). MS for $C_{16}H_{14}N_4O_2$, found 295.1 (MH+).

Example 77: 4-(4-Aminophenoxy)-N-methyl-1,7-naphthyridin-8-amine (NA3-3)

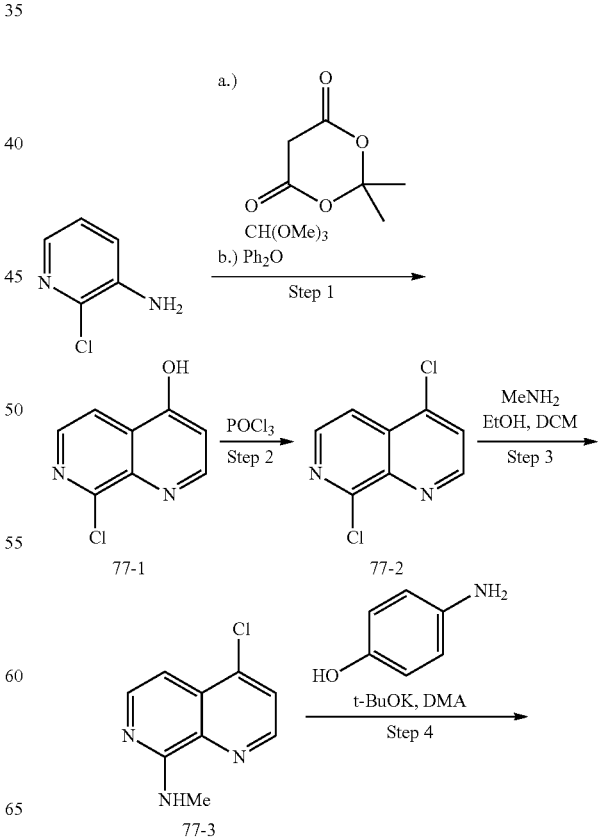

Step 1: 4-Hydroxy-1,7-naphthyridine-6-carbonitrile (76-1): To a solution of Compound 75-3 (1 g, 5.5 mmol, 1 eq) and zinc cyanide (390 mg, 3.3 mmol, 0.6 eq) in DMF (15 mL) was added Pd $(PPh_3)_4$ (1.3 g, 1.1 mmol, 0.2 eq). The mixture was stirred at 120° C. under nitrogen for 10 h. The mixture was diluted with water (50 mL) and filtered. The filtrate was concentrated, and the resulting residue was purified by silica gel column chromatography (0-10% MeOH in DCM) to give Compound 76-1 (800 mg, 85% yield). MS for $C_9H_5N_3O$, found 171.9 (MH+).

Step 2: 4-Hydroxy-1,7-naphthyridine-6-carboxylic acid (76-2): A solution of Compound 76-1 (1 g, 5.8 mmol, 1 eq) in aq HCl (15 mL) was stirred at 100° C. for 12 h. The reaction mixture was concentrated under reduced pressure to -continued

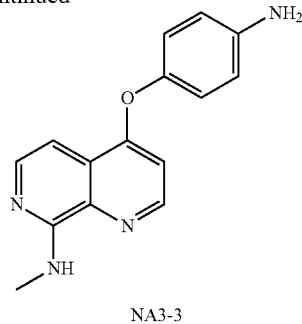

NA3-3

-continued

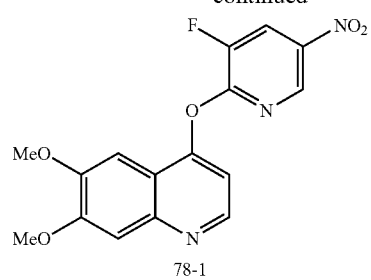

78-1

Step 1: 8-Chloro-1,7-naphthyridin-4-ol (77-1): A mixture of 2,2-dimethyl-1,3-dioxane-4,6-dione (6.7 g, 46.7 mmol, 1 eq) in triethoxymethane (60 mL, 361 mmol, 7.7 eq) was stirred at 105° C. for 1 h. 2-Chloropyridin-3-amine (6 g, 46.7 mmol, 1 eq) was added and the resulting mixture was stirred at 105° C. for 0.5 h. The mixture was concentrated, diluted with petroleum ether (100 mL), filtered, washed with petroleum ether (50 mL) and concentrated. A portion of the resulting solid (4 g) was mixed with Ph$_2$O (40 mL) and then stirred at 170° C. for 1 h. After cooling to 30° C., the mixture was diluted with petroleum ether (200 mL) and filtered. The filtered cake was washed with petroleum ether (80 mL) and dried to give Compound 77-1 (2.4 g, 94% yield) which was used in subsequent reactions without further purification.

Step 2: 4,8-Dichloro-1,7-naphthyridine (77-2): Compound 77-2 was made from Compound 77-1 in the same manner that Compound 61-2 was made from Compound 61-1 in Step 2 of Example 61. MS for $C_8H_4Cl_2N_2$, found 198.9 (MH+).

Step 3: 4-Chloro-N-methyl-1,7-naphthyridin-8-amine (77-3): To a mixture of Compound 77-2 (82 mg, 0.41 mmol, 1 eq) in EtOH (1 mL) and DCM (3 mL) was added 33% MeNH$_2$ in EtOH (465 mg, 4.9 mmol, 12 eq). The mixture was stirred at 25° C. for 72 h. The mixture was concentrated and purified by flash silica gel chromatography (0~100% EtOAc/Petroleum ether) to give Compound 77-3 (63 mg, 79% yield). MS for $C_9H_8ClN_3$, found 193.8 (MH+).

Step 4: 4-(4-Aminophenoxy)-N-methyl-1,7-naphthyridin-8-amine (NA3-3): To a mixture of Compound 77-3 (63 mg, 0.32 mmol, 1 eq) and 4-aminophenol (107 mg, 0.98 mmol, 3 eq) in DMA (2 mL) was added t-BuOK (128 mg, 1.1 mmol, 3.5 eq) at 25° C. The mixture was stirred at 100° C. for 12 h. The mixture was diluted with water (20 mL) and extracted with EtOAc (2×10 mL). The combined organic layers were washed with aq saturated NaCl (10 mL), dried over anhyd Na$_2$SO$_4$ and concentrated. The resulting residue was purified by flash silica gel chromatography (0-30% EtOAc/petroleum ether gradient) to give Compound NA3-3 (84 mg, 97% yield). MS for $C_{15}H_{14}N_4O$, found 266.9 (MH+).

Example 78: 6-((6,7-Dimethoxyquinolin-4-yl)oxy)-5-fluoropyridin-3-amine (QA1-8)

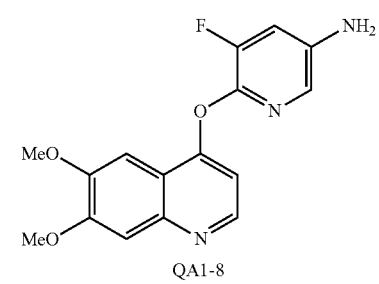

QA1-8

Step 1: 4-((3-Fluoro-5-nitropyridin-2-yl)oxy)-6,7-dimethoxyquinoline (78-1): A mixture of 6,7-dimethoxy-1,5-naphthyridin-4-ol (1.05 g, 5 mmol), 2-chloro-3-fluoro-5-nitropyridine (0.91 g, 5.1 mmol) and Cs$_2$CO$_3$ (3.0, 9.1 mmol) in ACN (20 mL) was stirred at room temperature overnight. The resulting reaction mixture was diluted with EtOAc (100 mL) and filtered. The filtrate was concentrated, and the resulting residue purified by silica gel chromatography (0-100% EtOAc in hexane) to give Compound 78-1 (1.02 g, 59% yield). MS for $C_{16}H_{12}FN_3O_5$: m/z 346 (MH+).

Step 2: 6-((6,7-Dimethoxyquinolin-4-yl)oxy)-5-fluoropyridin-3-amine (QA1-8): Compound 78-1 (702 mg, 2.03 mmol) was mixed with Fe (600 mg, 10.7 mmol), NH$_4$Cl (1.1 g, 20.6 mmol), water (20 mL), and MeOH (100 mL). The mixture was stirred at 85° C. for 60 min, cooled to room temperature and filtered through Celite. The filtrate was concentrated, and the residue partitioned between water and EtOAc. The phases were separated, and the aqueous phase was extracted with EtOAc (2×). The combined organic extracts were dried over anhyd Na$_2$SO$_4$ and evaporated to give Compound QA1-8 (620 mg, 97% yield). MS for $C_{16}H_{14}FN_3O_3$: m/z 316 (MH+).

Example 79: 4-((6,7-Dimethoxyquinazolin-4-yl)oxy)-3-fluoroaniline (QA2-1)

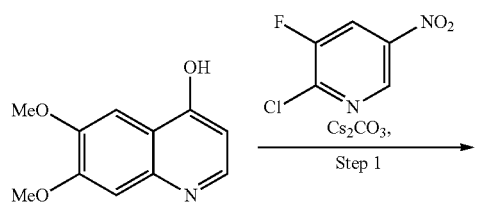

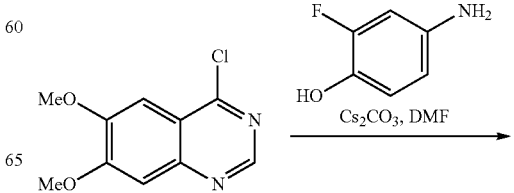

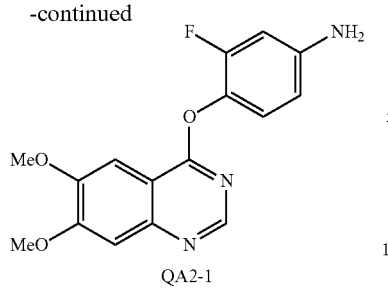

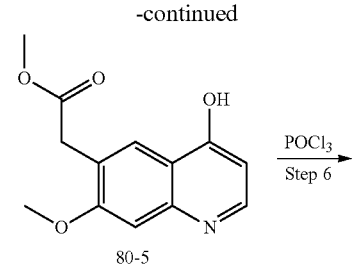

4-((6,7-Dimethoxyquinazolin-4-yl)oxy)-3-fluoroaniline (QA2-1): A mixture of 4-chloro-6,7-dimethoxyquinazoline (225 mg, 1 mmol), 4-amino-2-fluorophenol (150 mg, 1.09 mmol) and $Cs_2CO_3$ (500 mg, 1.52 mmol) in DMF (2 mL) was stirred at 80° C. for 20 min and then cooled to room temperature. Water was added and the resulting suspension was filtered. The collected solid was washed with water and dried to give crude Compound QA2-1 (336 mg). MS for $C_{16}H_{14}FN_3O_3$: m/z 316 (MH+).

Example 80: 2-(4-(4-Amino-2-fluorophenoxy)-7-methoxyquinolin-6-yl)-N-methylacetamide (QA1-9)

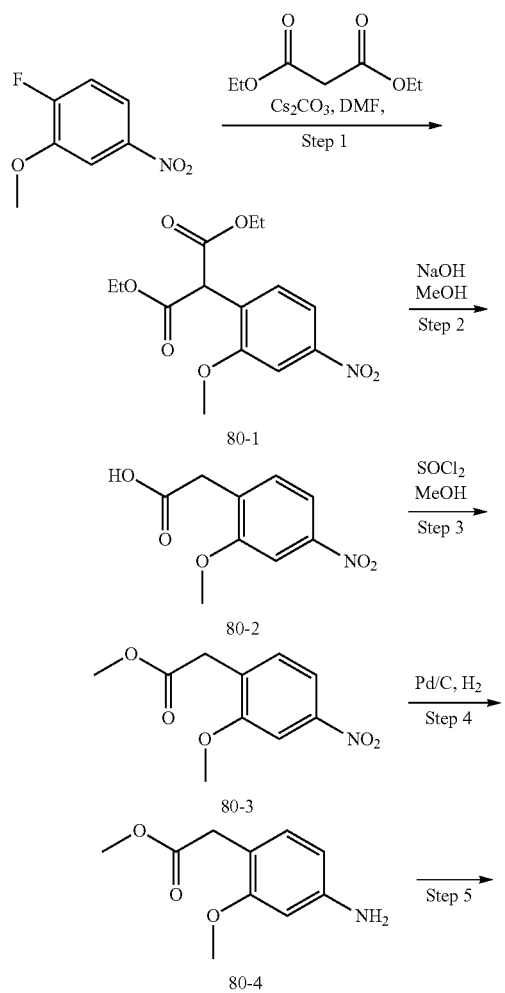

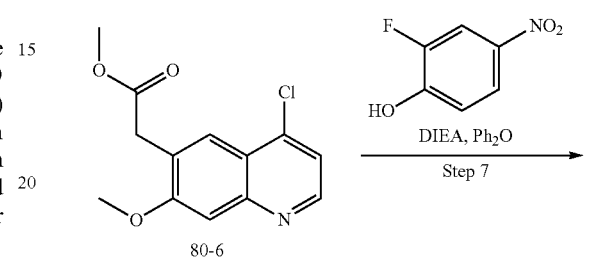

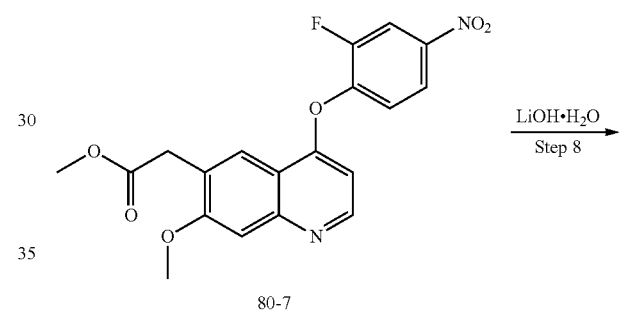

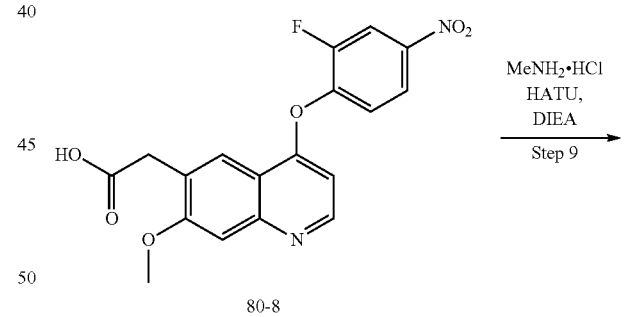

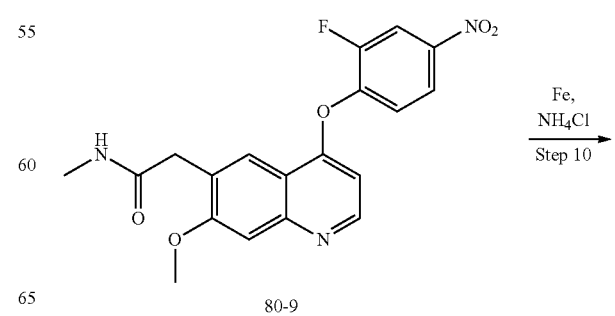

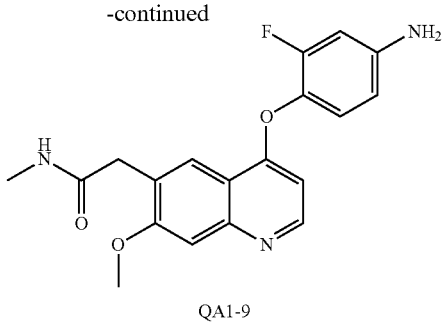

QA1-9

Step 1: Diethyl 2-(2-methoxy-4-nitrophenyl)malonate (80-1): Compound 80-1 was made from 1-fluoro-2-methoxy-4-nitrobenzene using the same method that Compound 71-1 was made from 2-chloro-3-methoxy-5-nitropyridine in Step 1 of Example 71. $^1$H NMR (400 MHz, CDCl$_3$) δ 7.87 (dd, 1H), 7.75 (d, 1H), 7.55 (d, 1H), 5.16 (s, 1H), 4.35-4.15 (m, 4H), 3.95 (s, 3H), 1.29 (t, 6H).

Step 2: 2-(2-Methoxy-4-nitrophenyl)acetic acid (80-2): NaOH (1.93 g, 48 mmol, 3 eq) was added to a solution of Compound 80-1 (5 g, 16 mmol, 1 eq) in MeOH (40 mL). The reaction mixture was stirred at 50° C. for 16 h. The mixture was concentrated under vacuum. To the resulting residue was added water (10 mL) and aq saturated citric acid (30 mL). The resulting solid was filtered, washed with water (20 mL) and dried in the air to give Compound 80-2 (2.67 g, 78% yield). $^1$H NMR (400 MHz, CDCl$_3$) δ 7.83 (dd, 1H), 7.73 (d, 1H), 7.35 (d, 1H), 3.93 (s, 3H), 3.75 (s, 2H).

Step 3: Methyl 2-(2-methoxy-4-nitrophenyl)acetate (80-3): Compound 80-2 (2.6 g, 12.3 mmol, 1 eq) was dissolved in MeOH (30 mL). Thionyl chloride (5.86 g, 49.2 mmol, 4 eq) was added dropwise at 0° C. After addition was complete, the reaction mixture was stirred at 25° C. for 1 h. The solvent was concentrated in vacuum and the mixture was extracted with EtOAc (3×20 mL). The combined EtOAc extracts were dried over anhyd Na$_2$SO$_4$ and concentrated under vacuum to give Compound 80-3 (2.49 g, 90% yield). $^1$H NMR (400 MHz, CDCl$_3$) δ 7.80 (br d, 1H), 7.70 (s, 1H), 7.33 (d, 1H), 3.91 (s, 3H), 3.70 (s, 2H), 3.695 (s, 3H).

Step 4: Methyl 2-(4-amino-2-methoxyphenyl)acetate (80-4): 10% Pd/C (700 mg, 4.2 mmol, 0.1 eq) was added to a mixture of Compound 80-3 (9.57 g, 42.5 mmol, 1 eq) in EtOAc (150 mL) under an atmosphere of hydrogen (15 psi). The mixture was stirred at 25° C. for 4 h. The solution was filtered through Celite and washed with EtOAc (20 mL). The filtrate was concentrated in vacuo to give Compound 80-4 (8.27 g, 100% yield). $^1$H NMR (400 MHz, CDCl$_3$) δ 6.87-6.81 (m, 1H), 6.18-6.11 (m, 2H), 3.68-3.62 (m, 3H), 3.58 (s, 3H), 3.43 (s, 2H).

Step 5: Methyl 2-(4-hydroxy-7-methoxyquinolin-6-yl)acetate (80-5): Compound 80-5 was made from Compound 80-4 using the same method that Compound 77-1 was made from 2-chloropyridin-3-amine in Step 1 of Example 77. $^1$H NMR (400 MHz, CDCl$_3$) δ 7.91 (s, 1H), 7.82 (br d, 1H), 6.93 (s, 1H), 5.96 (d, 1H), 3.85 (s, 3H), 3.71 (s, 2H), 3.60 (s, 3H).

Step 6: Methyl 2-(4-chloro-7-methoxyquinolin-6-yl)acetate (80-6): Compound 80-6 was made from Compound 80-5 in the same manner that Compound 61-2 was made from Compound 61-1 in Step 2 of Example 61. MS for C$_{13}$H$_{12}$CNO$_3$: m/z 265.9 (MH+).

Step 7: Methyl 2-(4-(2-fluoro-4-nitrophenoxy)-7-methoxyquinolin-6-yl)acetate (80-7): To a solution of Compound 80-6 (1 g, 3.8 mmol, 1 eq) and 2-fluoro-4-nitrophenol (769 mg, 4.9 mmol, 1.3 eq) in Ph$_2$O (10 mL) was added DIEA (730 mg, 5.6 mmol, 1.5 eq) at 180° C. for 2 h. The reaction mixture was cooled to 25° C., filtered and washed with EtOAc (40 mL). The combined organic layers were concentrated under reduced pressure. The resulting residue was purified by silica gel column chromatography (0-50% EtOAc in petroleum) to give Compound 80-7 (800 mg, 55% yield). MS for C$_{19}$H$_{15}$FN$_2$O$_6$: m/z 387.0 (MH+).

Step 8: 2-(4-(2-Fluoro-4-nitrophenoxy)-7-methoxyquinolin-6-yl)acetic acid (80-8): To a mixture of Compound 80-7 (750 mg, 1.9 mmol, 1 eq) in THF (10 mL) and water (3 mL) was added LiOH·H$_2$O (326 mg, 7.8 mmol, 4 eq) slowly. The mixture was stirred at 25° C. for 2 h. The mixture was concentrated under vacuum to remove the organic solvent. The aqueous layer was acidified with aq 2 M HCl to pH 4-5. The resulting precipitate was filtered, and the filtered cake was washed with water (2×30 mL). The collected solid was dissolved in EtOAc (10 mL), dried over anhyd Na$_2$SO$_4$ and concentrated under vacuum to give Compound 80-8 (600 mg, 83% yield). MS for C$_{18}$H$_{13}$FN$_2$O$_6$: m/z 373.0 (MH+).

Step 9: 2-(4-(2-Fluoro-4-nitrophenoxy)-7-methoxyquinolin-6-yl)-N-methylacetamide (80-9): To a mixture of Compound 80-8 (570 mg, 1.5 mmol, 1 eq) and methylamine hydrochloride (207 mg, 3.0 mmol, 2 eq) in DMF (5 mL) was added HATU (699 mg, 1.8 mmol, 1.2 eq) and DIEA (594. mg, 4.6 mmol, 3 eq). The resulting solution was stirred at 25° C. for 15 h. The reaction mixture was diluted with EtOAc (50 mL), washed with a 1:1 mixture of water and aq saturated NaCl (4×100 mL). The organic layer was dried over anhyd Na$_2$SO$_4$ and concentrated under reduced pressure to give crude Compound 80-9 (680 mg). MS for C$_{19}$H$_{16}$FN$_3$O$_5$: m/z 386.0 (MH+).

Step 10: 2-(4-(4-Amino-2-fluorophenoxy)-7-methoxyquinolin-6-yl)-N-methylacetamide (QA1-9): Compound QA1-9 was made Compound 80-9 using the same method that Compound QA1-8 was made from Compound 78-1 in Step 2 of Example 78. MS for C$_{19}$H$_{18}$FN$_3$O$_3$: m/z 356.2 (MH+).

Example 81: N-[4-[(6,7-Dimethoxy-1,5-naphthyridin-4-yl)oxy]-3-fluorophenyl]-6-(fluoromethyl)-5-(4-fluorophenyl)-1-methyl-4-oxopyridine-3-carboxamide (73)

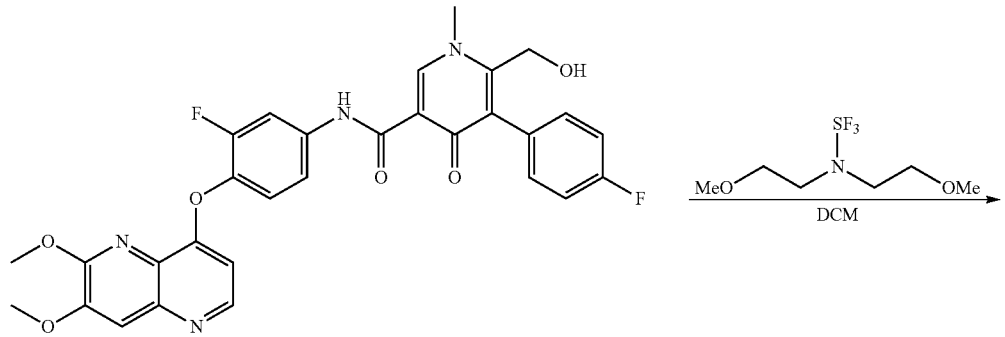

N-[4-[(6,7-Dimethoxy-1,5-naphthyridin-4-yl)oxy]-3-fluorophenyl]-6-(fluoromethyl)-5-(4-fluorophenyl)-1-methyl-4-oxopyridine-3-carboxamide (73): To a stirring mixture of Compound 72 (39.7 mg, 0.069 mmol, 1 eq) and DCM (1.0 mL) was added deoxo-fluor (50 mg, 0.2 mmol, 3 eq) at ambient temperature. After 1 h, the reaction was quenched by the addition of water (3 mL) and a few drops of aq NaHCO$_3$. The mixture was extracted with DCM (4×Veq). The combined extracts were dried over anhyd Na$_2$SO$_4$, adsorbed onto Celite and purified by silica gel chromatography (0% to 10% MeOH in DCM) to give Compound 73 (33 mg, 83% yield). $^1$H NMR (400 MHz, DMSO-d$_6$) δ 12.87 (s, 1H), 8.89 (s, 1H), 8.56 (d, 1H), 8.05-7.98 (m, 1H), 7.66 (s, 1H), 7.45 (d, 1H), 7.38-7.26 (m, 5H), 6.83 (d, 1H), 5.31 (d, 2H), 4.03 (s, 3H), 3.98 (s, 3H), 3.95 (s, 3H); MS for C$_{30}$H$_{23}$F$_3$N$_4$O$_5$: m/z 577.2 (MH+).

The following compounds were made using the same method used to convert Compound 72 to Compound 73 in Example 81:

N-[4-[(6,7-Dimethoxy-1,5-naphthyridin-4-yl)oxy]-3-fluorophenyl]-6-(fluoromethyl)-5-(4-fluoro-2-methylphenyl)-1-methyl-4-oxopyridine-3-carboxamide (556): Made in one step from Compound 282. MS for C$_{31}$H$_{25}$F$_3$N$_4$O$_5$: m/z 591.2 (MH+).

N-[3-Fluoro-4-[[7-methoxy-6-(2-methoxyethoxy)-1,5-naphthyridin-4-yl]oxy]phenyl]-6-(fluoromethyl)-5-(4-fluorophenyl)-1-methyl-4-oxopyridine-3-carboxamide (557): Made in one step from Compound 228. MS for C$_{32}$H$_{27}$F$_3$N$_4$O$_6$: m/z 621.2 (MH+).

N-[4-[(6,7-Dimethoxy-1,5-naphthyridin-4-yl)oxy]phenyl]-1-ethyl-6-(fluoromethyl)-5-(4-fluorophenyl)-4-oxopyridine-3-carboxamide (558): Made in one step from Compound 272. MS for C$_{31}$H$_{26}$F$_2$N$_4$O$_5$: m/z 573.2 (MH+).

1-Ethyl-N-[3-fluoro-4-[(7-methoxy-1,5-naphthyridin-4-yl)oxy]phenyl]-6-(fluoromethyl)-5-(4-fluorophenyl)-4-oxopyridine-3-carboxamide (559): Made in one step from Compound 273. MS for C$_{30}$H$_{23}$F$_3$N$_4$O$_4$: m/z 561.2 (MH+).

N-[4-[(6,7-Dimethoxy-1,5-naphthyridin-4-yl)oxy]phenyl]-6-(fluoromethyl)-5-(4-fluorophenyl)-1-methyl-4-oxopyridine-3-carboxamide (560): Made in one step from Compound 221. MS for C$_{30}$H$_{24}$F$_2$N$_4$O$_5$: m/z 559.2 (MH+).

N-[3-Fluoro-4-[(6-methoxy-1,5-naphthyridin-4-yl)oxy]phenyl]-6-(fluoromethyl)-5-(4-fluorophenyl)-1-methyl-4-oxopyridine-3-carboxamide (561): Made in one step from Compound 224. MS for C$_{29}$H$_{21}$F$_3$N$_4$O$_4$: m/z 547.2 (MH+).

N-[4-[(6,7-Dimethoxy-1,5-naphthyridin-4-yl)oxy]-3-fluorophenyl]-1-ethyl-6-(fluoromethyl)-5-(4-fluorophenyl)-4-oxopyridine-3-carboxamide (562): Made in one step from Compound 271. MS for C$_{31}$H$_{25}$F$_3$N$_4$O$_5$: m/z 591.2 (MH+).

Example 82: N-[4-[(6,7-Dimethoxy-1,5-naphthyridin-4-yl)oxy]-3-fluorophenyl]-5-(4-fluorophenyl)-1-methyl-6-(methylamino)-4-oxopyridine-3-carboxamide (76)

Example 83: 6-Cyano-N-[4-[(6,7-dimethoxy-1,5-naphthyridin-4-yl)oxy]-3-fluorophenyl]-5-(4-fluorophenyl)-1-methyl-4-oxopyridine-3-carboxamide (77)

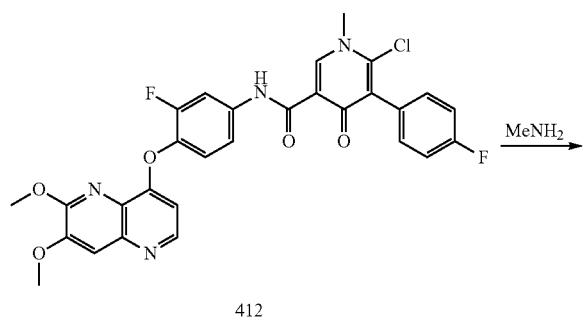

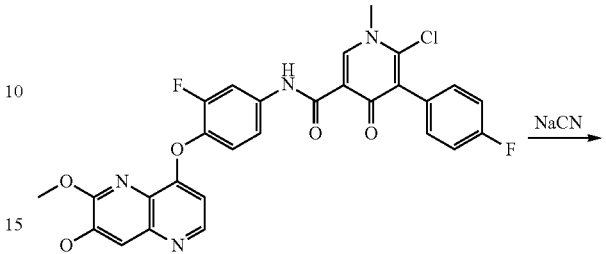

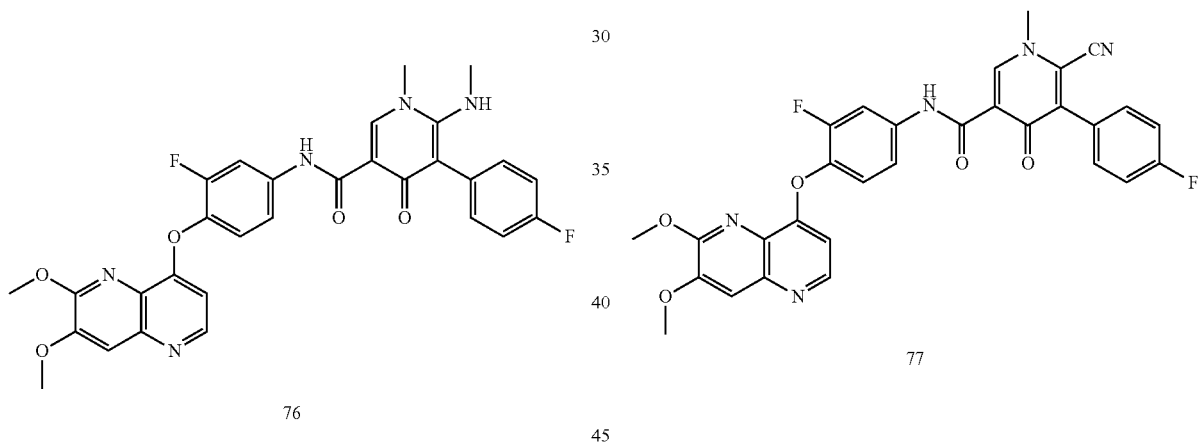

N-[4-[(6,7-Dimethoxy-1,5-naphthyridin-4-yl)oxy]-3-fluorophenyl]-5-(4-fluorophenyl)-1-methyl-6-(methylamino)-4-oxopyridine-3-carboxamide (76): A mixture of Compound 412 (10 mg, 0.018 mmol) and 8 M MeNH$_2$ in MeOH (0.3 mL) in DMF (0.5 mL) was heated at 70° C. Upon completion of the reaction as monitored by LC-MS, the reaction mixture was purified by prep HPLC to give Compound 76 (4 mg, 40% yield). MS for C$_{30}$H$_{25}$F$_2$N$_5$O$_5$: m/z 574 (MH+).

The following compound was made using the same method used to convert Compound 412 to Compound 76 in Example 82:

N-[3-Fluoro-4-[(7-methoxy-1,5-naphthyridin-4-yl)oxy]phenyl]-5-(4-fluorophenyl)-1-methyl-6-(methylamino)-4-oxopyridine-3-carboxamide (585): Made in one step from Compound 411. MS for C$_{29}$H$_{23}$F$_2$N$_5$O$_4$: m/z 544 (MH+).

6-Cyano-N-[4-[(6,7-dimethoxy-1,5-naphthyridin-4-yl)oxy]-3-fluorophenyl]-5-(4-fluorophenyl)-1-methyl-4-oxopyridine-3-carboxamide (77): A mixture of Compound 412 (10 mg, 0.018 mmol), TEA (72 mg, 0.72 mmol), and NaCN (50 mg, 1 mmol) in DMF (0.5 mL) was stirred at 70° C. for 2 h and quenched with water. The precipitate was collected by filtration and purified by prep HPLC to give Compound 77 (7 mg, 70% yield). $^1$H NMR (400 MHz, DMSO-d$_6$) δ 12.5 (s, 1H), 8.99 (s, 1H), 8.56 (d, 1H), 8.01 (dd, 1H), 7.66 (s, 1H), 7.62-7.54 (m, 1H), 7.48 (dd, 1H), 7.44-7.30 (m, 4H), 6.85 (d, 1H), 4.09 (s, 3H), 3.98 (s, 3H), 3.94 (s, 3H). MS for C$_{30}$H$_{21}$F$_2$N$_5$O$_5$: m/z 570 (MH+).

The following compound was made using the same method used to convert Compound 412 to Compound 77 in Example 83:

6-Cyano-N-[3-fluoro-4-[(7-methoxy-1,5-naphthyridin-4-yl)oxy]phenyl]-5-(4-fluorophenyl)-1-methyl-4-oxopyridine-3-carboxamide (586): Made in one step from Compound 411. MS for C$_{29}$H$_{19}$F$_2$N$_5$O$_4$: m/z 540 (MH+).

701

Example 84: N-[4-[(6,7-Dimethoxy-1,5-naphthyridin-4-yl)oxy]-3-fluorophenyl]-5-(4-fluorophenyl)-6-methoxy-1-methyl-4-oxopyridine-3-carboxamide (78)

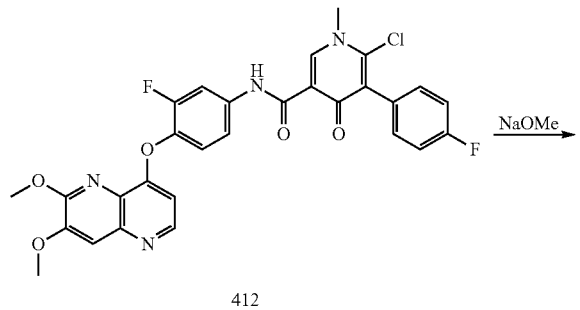

412

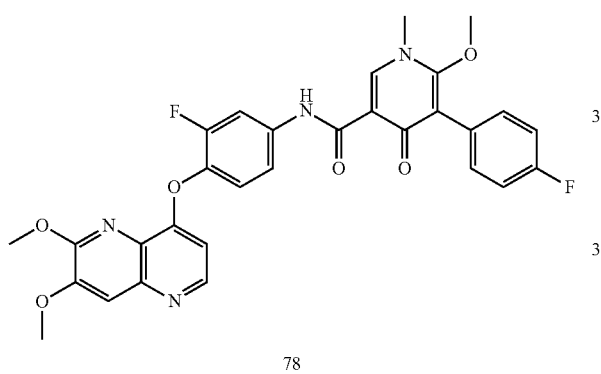

78

N-[4-[(6,7-Dimethoxy-1,5-naphthyridin-4-yl)oxy]-3-fluorophenyl]-5-(4-fluorophenyl)-6-methoxy-1-methyl-4-oxopyridine-3-carboxamide (78): A mixture of Compound 412 (25 mg, 0.043 mmol) and NaOMe (15 mg, 0.28 mmol) in DMF (1.0 mL) was stirred at room temperature until the reaction was complete. The resulting mixture was quenched with aq saturated NaHCO₃. The resulting solid was filtered, washed with water and dried under vacuum to give Compound 78 (18 mg, 72% yield). $^1$H NMR (400 MHz, DMSO-d$_6$) δ 13.1 (s, 1H), 8.71 (s, 1H), 8.56 (d, 1H), 8.02 (d, 1H), 7.66 (s, 1H), 7.50-7.38 (m, 3H), 7.38-7.25 (m, 3H), 6.83 (d, 1H), 3.98 (s, 3H), 3.95 (s, 3H), 3.80 (s, 3H), 3.50 (s, 3H). MS for $C_{30}H_{24}F_2N_4O_5$: m/z 575 (MH+).

The following compound was made using the same method used to convert Compound 412 to Compound 78 in Example 84:

N-[3-Fluoro-4-[(7-methoxy-1,5-naphthyridin-4-yl)oxy]phenyl]-5-(4-fluorophenyl)-6-methoxy-1-methyl-4-oxopyridine-3-carboxamide (587): Made in one step from Compound 411. $^1$H NMR (400 MHz, DMSO-d$_6$) δ 13.1 (s, 1H), 8.76 (d, 1H), 8.72 (s, 1H), 8.71 (d, 1H), 8.06 (dd, 1H), 7.81 (d, 1H), 7.52-7.37 (m, 4H), 7.30 (t, 2H), 6.76 (d, 1H), 4.01 (s, 3H), 3.81 (s, 3H), 3.50 (s, 3H); MS for $C_{29}H_{22}F_2N_4O_5$: m/z 545 (MH).

702

Example 85: 5-Cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide (87)

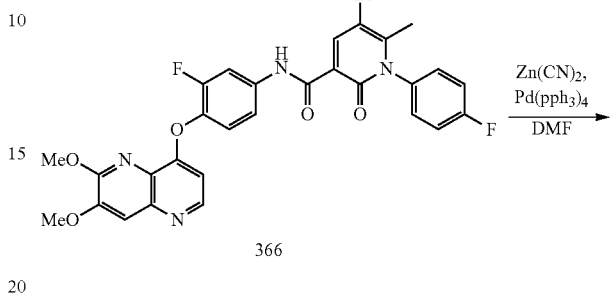

366

87

5-Cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide (87): A mixture of Compound 366 (80 mg, 0.13 mmol, 1 eq), Pd(PPh₃)₄ (15 mg, 0.013 mmol, 0.1 eq) and Zn(CN)₂ (48 mg, 0.41 mmol, 3.2 eq) in DMF (2 mL) was stirred at 140° C. under microwave irradiation and under an atmosphere of nitrogen for 0.5 h. The reaction was allowed to cool to room temperature. Aq saturated FeSO₄ solution was added and the mixture was extracted with EtOAc (3×50 mL). The combined organic extracts were washed with water, aq saturated NaCl, dried over anhyd Na₂SO₄ and concentrated. The resulting residue was purified by silica gel column chromatography (petroleum ether/EtOAc=50~100%) and triturated with MTBE (2×10 mL) to give Compound 87 (34.1 mg, 45% yield). MS for $C_{30}H_{21}F_2N_5O_5$: m/z 570.1 (MH+).

Example 86: N-[3-Fluoro-4-[(7-hydroxy-1,5-naphthyridin-4-yl)oxy]phenyl]-1-(4-fluorophenyl)-6-methyl-2-oxopyridine-3-carboxamide (551)

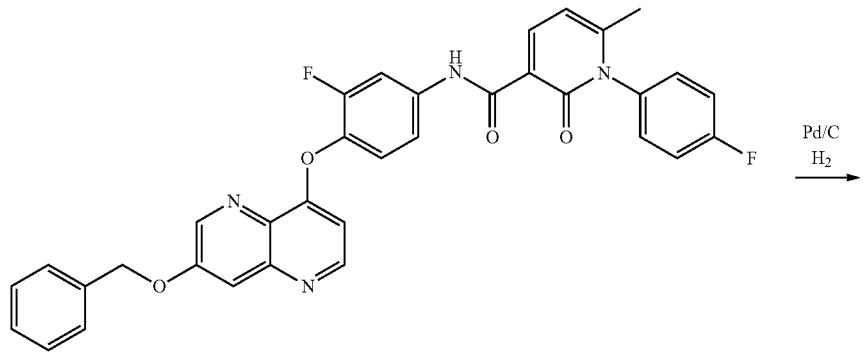

275

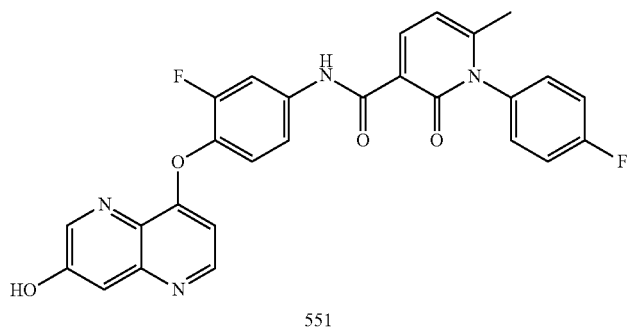

551

N-[3-Fluoro-4-[(7-hydroxy-1,5-naphthyridin-4-yl)oxy]phenyl]-1-(4-fluorophenyl)-6-methyl-2-oxopyridine-3-carboxamide (551): A stirring mixture Compound 275 (25 mg, 0.042 mmol, 1 eq), THF (2.1 mL), DCM (0.3 mL) and 10% Pd/C (16 mg, 0.015 mmol, 0.36 eq) was placed under an atmosphere of hydrogen (1 atm). After 16 h the reaction was filtered through Celite and purified by silica gel chromatography (0% to 5% MeOH in EtOAc) followed by further purification by prep HPLC (10% to 100% ACN in water (+FA)) to give Compound 551 (13 mg, 62% yield). $^1$H NMR (400 MHz, DMSO-$d_6$) δ12.08 (s, 1H), 11.2-10.6 (bs, 1H) 8.65 (d, 1H), 8.63 (d, 1H), 8.52 (d, 1H), 8.05 (d, 1H), 7.59-7.34 (m, 7H), 6.73 (d, 1H), 6.64 (d, 1H), 2.10 (s, 3H); MS for $C_{27}H_{18}F_2N_4O_4$: m/z 501 (MH+).

The following compound was made using the same method used to convert Compound 275 to Compound 551 in Example 86:

N-[3-Fluoro-4-[(7-hydroxy-1,5-naphthyridin-4-yl)oxy]phenyl]-5-(4-fluorophenyl)-4-hydroxy-2,6-dimethylpyridine-3-carboxamide (554): Made in one step from Compound 277. MS for $C_{28}H_{20}F_2N_4O_4$: m/z 515.2 (MH+).

Example 87: N-[3-Fluoro-4-[[7-(2-methoxyethoxy)-1,5-naphthyridin-4-yl]oxy]phenyl]-1-(4-fluorophenyl)-6-methyl-2-oxopyridine-3-carboxamide (552)

551

N-[3-Fluoro-4-[[7-(2-methoxyethoxy)-1,5-naphthyridin-4-yl]oxy]phenyl]-1-(4-fluorophenyl)-6-methyl-2-oxopyridine-3-carboxamide (552): To a stirring mixture of Compound 551 (6 mg, 0.012 mmol, 1 eq), 2-methoxyethanol (12 mg, 0.16 mmol, 13 eq), triphenylphosphine (16 mg, 0.061 mmol, 5 eq) and DCM (0.40 mL) was added diisopropyl azodicarboxylate (20 mg, 0.10 mmol, 8 eq). The mixture was stirred for 1 h at ambient temperature and then purified by silica gel chromatography (0% to 5% MeOH in DCM) followed by further purification by prep HPLC (10% to 100% ACN in water (+FA)) to give Compound 552 (2.1 mg, 31% yield). $^1$H NMR (400 MHz, CD$_3$OD) δ 12.12 (s, 1H), 8.84-8.62 (m, 2H), 8.55 (d, 1H), 7.97 (d, 1H), 7.75 (s, 1H), 7.45-7.25 (m, 6H), 6.73 (d, 1H), 6.66 (d, 1H), 4.37 (t, 2H), 3.87 (t, 2H), 3.47 (s, 3H), 2.14 (s, 3H); MS for C$_{30}$H$_{24}$F$_2$N$_4$O$_5$: m/z 559.2 (MH+).

The following compound was made using the same method used to convert Compound 551 to Compound 552 in Example 87:

N-[3-Fluoro-4-[[7-(2-methoxyethoxy)-1,5-naphthyridin-4-yl]oxy]phenyl]-5-(4-fluorophenyl)-4-hydroxy-2,6-dimethylpyridine-3-carboxamide (555): Made in two steps from Compound 277. MS for C$_{30}$H$_{26}$F$_2$N$_4$O$_5$: m/z 573.2 (MH+).

Example 88: 5-[[4-[(6,7-Dimethoxy-1,5-naphthyridin-4-yl)oxy]-3-fluorophenyl]carbamoyl]-3-(4-fluorophenyl)-1-methyl-4-oxopyridine-2-carboxylic acid (553)

5-[[4-[(6,7-Dimethoxy-1,5-naphthyridin-4-yl)oxy]-3-fluorophenyl]carbamoyl]-3-(4-fluorophenyl)-1-methyl-4-oxopyridine-2-carboxylic acid (553): A mixture of Compound 72 (43 mg, 0.075 mmol, 1 eq), DCM (1.0 mL), DMF (0.60 mL) and Dess-Martin periodinane (90 mg, 0.21 mmol, 2.8 eq) was stirred at ambient temperature. After 3 days the DCM was removed and the reaction was purified by prep HPLC (10% to 100% ACN in water (+FA)) to give Compound 553 (15 mg, 35% yield). $^1$H NMR (400 MHz, DMSO-d$_6$) δ 13.19 (s, 1H), 12.75 (s, 1H), 8.68 (s, 1H), 8.55 (d, 1H), 8.14 (s, 1H), 8.02 (d, 1H), 7.66 (s, 1H), 7.47-7.29 (m, 3H), 7.19 (t, 2H), 6.83 (d, 1H), 3.98 (s, 3H), 3.96 (s, 3H), 3.84 (s, 3H); MS for C$_{30}$H$_{22}$F$_2$N$_4$O$_7$: m/z 589.2 (MH+).

Example 89: 5-N-[4-[(6,7-Dimethoxy-1,5-naphthyridin-4-yl)oxy]-3-fluorophenyl]-3-(4-fluorophenyl)-2-N,1-dimethyl-4-oxopyridine-2,5-dicarboxamide (563)

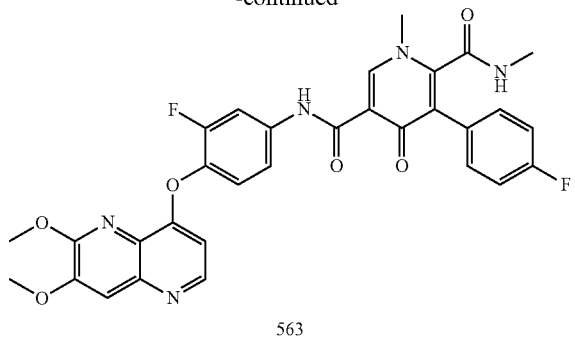

563

5-N-[4-[(6,7-Dimethoxy-1,5-naphthyridin-4-yl)oxy]-3-fluorophenyl]-3-(4-fluorophenyl)-2-N,1-dimethyl-4-oxopyridine-2,5-dicarboxamide (563): Compound 563 was made from Compound 553 and methylamine using standard HATU coupling techniques such as that exemplified in Step 1 of Example 1 for coupling Compound NA-1 to Compound PA2-2. MS for $C_{31}H_{25}F_2N_5O_6$: m/z 602.2 (MH+).

Example 90: N-[4-[(6,7-Dimethoxy-1,5-naphthyridin-4-yl)oxy]-3-fluorophenyl]-9-(4-fluorophenyl)-8-oxo-3,4-dihydro-1H-pyrido[2,1-c][1,4]oxazine-7-carboxamide (564)

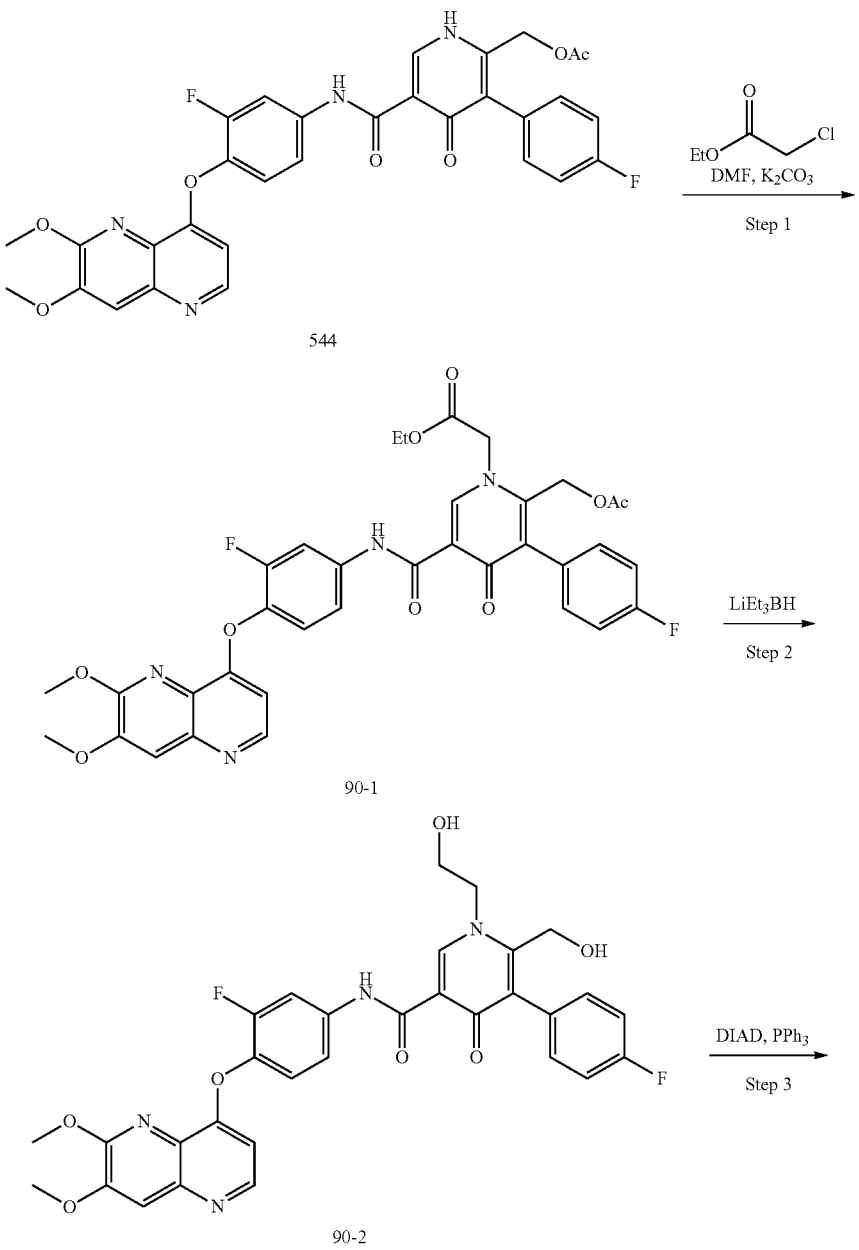

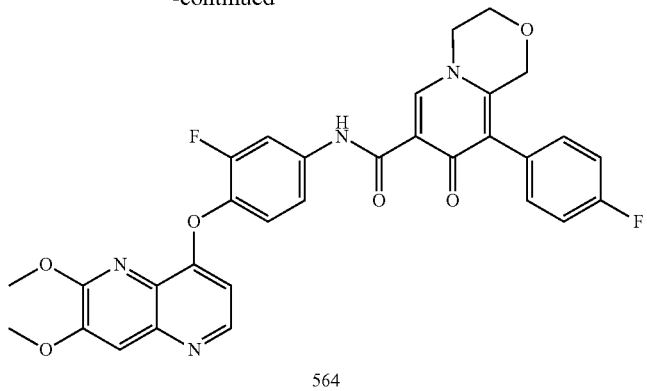

564

Step 1: Ethyl 2-(2-(acetoxymethyl)-5-((4-((6,7-dimethoxy-1,5-naphthyridin-4-yl)oxy)-3-fluorophenyl)carbamoyl)-3-(4-fluorophenyl)-4-oxopyridin-1(4H)-yl)acetate (90-1): A mixture of Compound 544 (139 mg, 0.23 mmol, 1 eq), DMF (0.5 mL), ethyl 2-chloroacetate (150 mg, 1.2 mmol, 5.3 eq) and potassium carbonate (0.11 g, 1.1 mmol, 4.8 eq) was stirred at ambient temperature overnight. The reaction mixture was then heated to 65° C. for 18 h. The crude reaction mixture was purified by silica gel chromatography (0 to 1% MeOH in DCM) to give Compound 90-1 (110 mg, 0.14 mmol, 62% yield). MS for $C_{35}H_{30}F_2N_4O_9$: m/z 689 (MH+).

Step 2: N-(4-((6,7-Dimethoxy-1,5-naphthyridin-4-yl)oxy)-3-fluorophenyl)-5-(4-fluorophenyl)-1-(2-hydroxyethyl)-6-(hydroxymethyl)-4-oxo-1,4-dihydropyridine-3-carboxamide (90-2): To a stirring mixture of Compound 90-1 (59 mg, 0.086 mmol, 1 eq) in THF (1.1 mL) was added a 1 M solution of lithium triethylborohydride (0.446 g, 0.505 mmol, 5.9 eq) and the resulting mixture was stirred for 2 h. The reaction mixture was then poured onto ice and acidified with dilute aq HCl to pH 3. The resulting aqueous mixture was extracted with DCM (4×Veq). The combined organic extracts were concentrated to give crude Compound 90-2 (52 mg) which was used in the subsequent step without further purification.

Step 3: N-[4-[(6,7-Dimethoxy-1,5-naphthyridin-4-yl)oxy]-3-fluorophenyl]-9-(4-fluorophenyl)-8-oxo-3,4-dihydro-1H-pyrido[2,1-c][1,4]oxazine-7-carboxamide (564): To a solution of Compound 90-2 (52 mg, 0.086 mmol, 1 eq), DCM (4.0 mL) and triphenylphosphine (50 mg, 0.19 mmol, 2.2 eq) was added DIAD (60 mg, 0.30 mmol, 3.5 eq). After 1 h the mixture was purified by silica gel chromatography (0% to 2% MeOH in DCM) followed by further purification by prep HPLC (10% to 60% ACN in water+FAC) to give Compound 564 (5 mg, 0.0085 mmol, 10% yield over 2 steps from Compound 90-1). H NMR (400 MHz, DMSO-$d_6$) δ 13.02 (s, 1H), 8.63 (s, 1H), 8.47 (d, 1H), 7.93 (dd, 1H), 7.58 (s, 1H), 7.40-7.33 (m, 1H), 7.24 (dd, 5H), 6.75 (d, 1H), 4.42 (s, 2H), 4.26 (t, 2H), 3.99 (t, 2H), 3.90 (s, 3H), 3.87 (s, 3H); MS for $C_{31}H_{24}F_2N_4O_6$: m/z 587 (MH+).

Example 91: 2-Amino-N-[4-[(6,7-dimethoxy-1,5-naphthyridin-4-yl)oxy]-3-fluorophenyl]-1-(4-fluorophenyl)-6-oxopyrimidine-5-carboxamide (565)

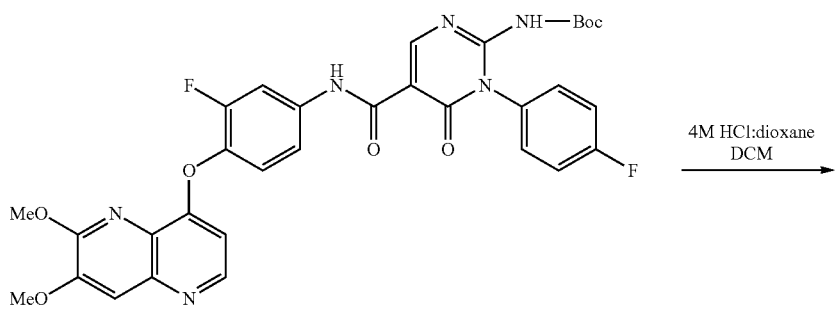

344

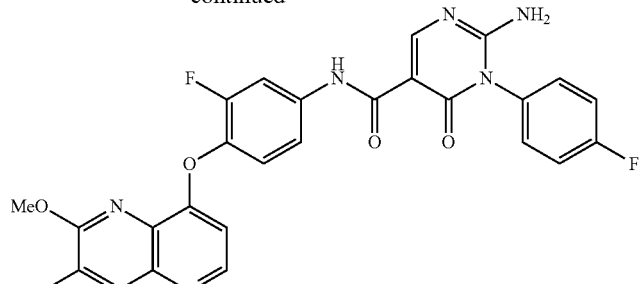

565

2-Amino-N-[4-[(6,7-dimethoxy-1,5-naphthyridin-4-yl)oxy]-3-fluorophenyl]-1-(4-fluorophenyl)-6-oxopyrimidine-5-carboxamide (565): A 20-mL scintillation vial bearing Compound 344 (11 mg, 0.017 mmol) was charged with a Teflon stir bar and fitted with a rubber septa. An atmosphere of nitrogen was established, and the material was dissolved in dry DCM and cooled to 0° C. A 4 M solution of HCl in dioxane (1 mL, 4 mmol, 235 eq) was slowly added to the vial and the reaction was allowed to warm to room temperature and stirred for 6 h. The reaction was then diluted with toluene and reduced to dryness. The resulting solid purified by prep HPLC to give Compound 565 (3.4 mg, 37% yield). $^1$H NMR (DMSO-d$_6$) δ: 11.11 (s, 1H), 8.58 (s, 1H), 8.47 (d, 2H), 8.36 (s, 1H), 7.90 (dd, 1H), 7.57 (s, 1H), 7.43 (dd, 2H), 7.40-7.28 (m, 3H), 7.22 (t, 1H), 6.73 (d, 1H), 3.88 (d, 6H); MS for $C_{27}H_{20}F_2N_6O_5$, found 547 (MH+).

The following compound was made using standard techniques for the removal of Boc protecting groups from amines such as that exemplified by the conversion of Compound 344 to Compound 565 in Example 91:

1-(Azetidin-3-yl)-N-[4-[(6,7-dimethoxy-1,5-naphthyridin-4-yl)oxy]-3-fluorophenyl]-5-(4-fluorophenyl)-4-oxopyridine-3-carboxamide (576): Made in one step from Compound 114. MS for $C_{31}H_{25}F_2N_5O_5$: m/z 586 (MH+).

Example 92: N-[3-Fluoro-4-[(7-methoxy-1,5-naphthyridin-4-yl)oxy]phenyl]-5-(4-fluorophenyl)-6-methyl-4-oxo-1-propan-2-ylpyridazine-3-carboxamide (566) and N-[3-Fluoro-4-[(7-methoxy-1,5-naphthyridin-4-yl)oxy]phenyl]-5-(4-fluorophenyl)-6-methyl-4-propan-2-yloxypyridazine-3-carboxamide (567)

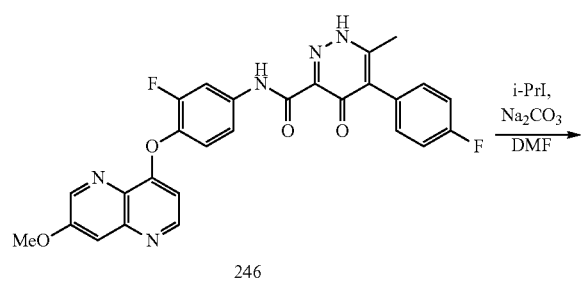

246

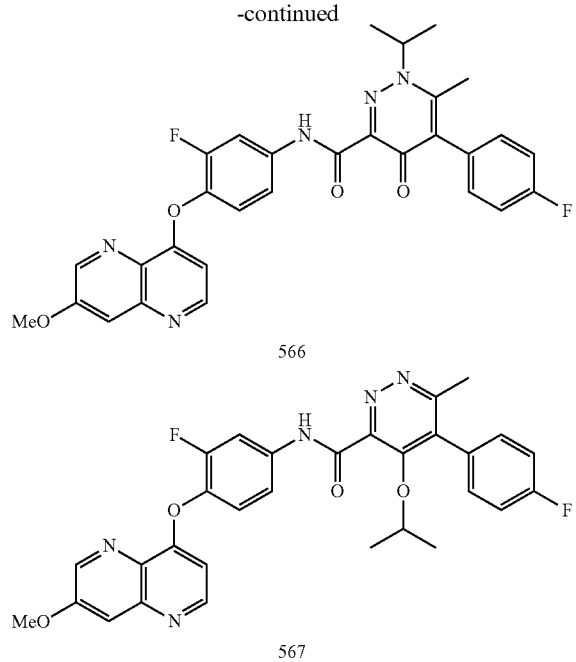

566

567

N-[3-Fluoro-4-[(7-methoxy-1,5-naphthyridin-4-yl)oxy]phenyl]-5-(4-fluorophenyl)-6-methyl-4-oxo-1-propan-2-ylpyridazine-3-carboxamide (566) and N-[3-Fluoro-4-[(7-methoxy-1,5-naphthyridin-4-yl)oxy]phenyl]-5-(4-fluorophenyl)-6-methyl-4-propan-2-yloxypyridazine-3-carboxamide (567): To a mixture of Compound 246 (0.2 g, 0.39 mmol, 1 eq) and NaHCO$_3$ (97.79 mg, 1.2 mmol, 0.045 mL, 3 eq) in DMF (3 mL) was added 2-iodopropane (132 mg, 0.78 mmol, 2 eq) and the resulting mixture was stirred at 20° C. for 15 h. Na$_2$CO$_3$ (123 mg, 1.2 mmol, 3 eq) was added and stirring continued at room temperature for an additional 15 h, followed by stirring at 60° C. for 15 h. The reaction mixture was added to water (80 mL) and stirred for 15 min. The resulting solid was filtered and washed with water (2×5 mL) and dissolved in DCM (50 mL). The resulting DCM solution was dried over anhyd Na$_2$SO$_4$ and concentrated under reduced pressure. The resulting residue was purified by silica gel column chromatography (DCM:MeOH=1:0-20:1) twice followed by further purification by prep TLC (DCM:EtOAc:MeOH=10:10:1, then EtOAc three times) to give Compound 566 (52.3 mg, 0.09 mmol, 24% yield) and Compound 567 (57.2 mg, 26% yield). Compound 566: $^1$H NMR (CDCl$_3$) δ: 12.90 (s, 1H), 8.79 (d, 1H), 8.67 (d, 1H), 8.07 (dd, 1H), 7.66 (d, 1H), 7.44 (br d, 1H), 7.27-7.19 (m, 5H), 6.63 (d, 1H), 4.83 (quin, 1H), 4.01 (s, 3H), 2.43 (s, 3H), 1.67 (d, 6H); MS for $C_{30}H_{25}F_2N_5O_4$: m/z 558.2 (MH+). Compound 567: $^1$H NMR (CDCl$_3$) δ:13.69 (br s, 1H), 8.79 (d, 1H), 8.66 (d, 1H), 7.97 (dd, 1H), 7.66 (d, 1H), 7.44 (br d, 1H), 7.37-7.27 (m, 3H), 7.24-7.17 (m, 2H), 6.60 (d, 1H), 6.31 (br s, 1H), 4.01 (s, 3H), 2.39 (s, 3H), 1.66 (d, 6H); MS for $C_{30}H_{25}F_2N_5O_4$: m/z 558.1 (MH+).

The following compounds were made using the same method used to make Compounds 566 and 567 from Compound 246 in Example 92:

N-[4-[(6,7-Dimethoxy-1,5-naphthyridin-4-yl)oxy]-3-fluorophenyl]-1-ethyl-5-(4-fluorophenyl)-6-methyl-4-oxopyridazine-3-carboxamide (568) and N-[4-[(6,7-Dimethoxy-1,5-naphthyridin-4-yl)oxy]-3-fluorophenyl]-4-ethoxy-5-(4-fluorophenyl)-6-methylpyridazine-3-carboxamide (569): Made in one step from Compound 88. Compound 568: $^1$H NMR (CDCl$_3$) δ: 12.77 (s, 1H), 8.46 (d, 1H), 7.93 (dd, 1H), 7.45 (s, 1H), 7.31 (br d, 1H), 7.18-7.13 (m, 4H), 7.12-7.06 (m, 1H), 6.70 (d, 1H), 4.42 (q, 2H), 4.02 (s, 3H), 3.95 (s, 3H), 2.34 (s, 3H), 1.54 (t, 3H); MS for $C_{30}H_{25}F_2N_5O_5$, m/z 574.2 (MH+). Compound 569: $^1$H NMR (CDCl$_3$) δ:14.00 (s, 1H), 8.46 (d, 1H), 7.86 (dd, 1H), 7.45 (s, 1H), 7.32-7.23 (m, 3H), 7.18-7.08 (m, 3H), 6.69 (d, 1H), 5.17 (q, 2H), 4.01 (s, 3H), 3.95 (s, 3H), 2.29 (s, 3H), 1.66 (t, 3H); MS for $C_{30}H_{25}F_2N_5O_5$, m/z 574.1 (MH+).

N-[4-(6,7-Dimethoxyquinolin-4-yl)oxy-3-fluorophenyl]-5-(4-fluorophenyl)-4-methoxy-6-methylpyridazine-3-carboxamide (571): Made in one step from Compound 546. $^1$H NMR (CDCl$_3$) δ: 14.09 (s, 1H), 8.51 (d, 1H), 7.97 (dd, 1H), 7.59 (s, 1H), 7.47-7.40 (m, 2H), 7.37-7.33 (m, 2H), 7.26-7.20 (m, 3H), 6.45 (d, 1H), 4.82 (s, 3H), 4.07 (d, 6H), 2.37 (s, 3H); MS for $C_{30}H_{24}F_2N_4O_5$: m/z 559.2 (MH+).

N-[4-(6,7-Dimethoxyquinolin-4-yl)oxy-3-fluorophenyl]-4-ethoxy-5-(4-fluorophenyl)-6-methylpyridazine-3-carboxamide (572) and N-[4-(6,7-Dimethoxyquinolin-4-yl)oxy-3-fluorophenyl]-1-ethyl-5-(4-fluorophenyl)-6-methyl-4-oxopyridazine-3-carboxamide (573): Made in one step from Compound 546. Compound 572: $^1$H NMR (CDCl$_3$) δ:14.15 (s, 1H), 8.50 (d, 1H), 7.98 (dd, 1H), 7.59 (s, 1H), 7.48-7.41 (m, 2H), 7.35 (dd, 2H), 7.25-7.20 (m, 3H), 6.45 (d, 1H), 5.25 (q, 2H), 4.07 (d, 6H), 2.38 (s, 3H), 1.75 (t, 3H); MS for $C_{31}H_{26}F_2N_4O_5$, m/z 573.1 (MH+). Compound 573: $^1$H NMR (CDCl$_3$) δ: 12.71 (s, 1H), 8.48 (d, 1H), 8.03 (dd, 1H), 7.55-7.29 (m, 8H), 6.49 (d, 1H), 4.40 (q, 2H), 3.95 (s, 6H), 2.37 (s, 3H), 1.46 (t, 3H); MS for $C_{31}H_{26}F_2N_4O_5$, m/z 573.1 (MH+).

N-[4-(6,7-Dimethoxyquinolin-4-yl)oxy-3-fluorophenyl]-5-(4-fluorophenyl)-6-methyl-4-propan-2-yloxypyridazine-3-carboxamide (574) and N-[4-(6,7-Dimethoxyquinolin-4-yl)oxy-3-fluorophenyl]-5-(4-fluorophenyl)-6-methyl-4-oxo-1-propan-2-ylpyridazine-3-carboxamide (575): Made in one step from Compound 546. Compound 574: $^1$H NMR (CDCl$_3$) δ: 13.64 (br s, 1H), 8.50 (d, 1H), 7.97 (dd, 1H), 7.57 (s, 1H), 7.48-7.38 (m, 2H), 7.32-7.27 (m, 2H), 7.25-7.15 (m, 3H), 6.41 (d, 1H), 6.30-6.20 (m, 1H), 4.07-4.04 (m, 3H), 4.03 (s, 3H), 2.39 (s, 3H), 1.65 (d, 6H); MS for $C_{32}H_{28}F_2N_4O_5$: m/z 587.1 (MH+). Compound 575: $^1$H NMR (CDCl$_3$) δ:12.72 (s, 1H), 8.49 (d, 1H), 8.06 (dd, 1H), 7.55-7.30 (m, 8H), 6.50 (d, 1H), 5.01-4.92 (m, 1H), 3.99-3.93 (m, 6H), 2.40 (s, 3H), 1.49 (d, 6H); MS for $C_{32}H_{28}F_2N_4O_5$: m/z 587.1 (MH+).

Example 93: N-[3-Fluoro-4-[[7-methoxy-6-[2-(methylamino)-2-oxoethyl]-1,5-naphthyridin-4-yl]oxy]phenyl]-5-(4-fluorophenyl)-4-hydroxy-6-methylpyridine-3-carboxamide (570)

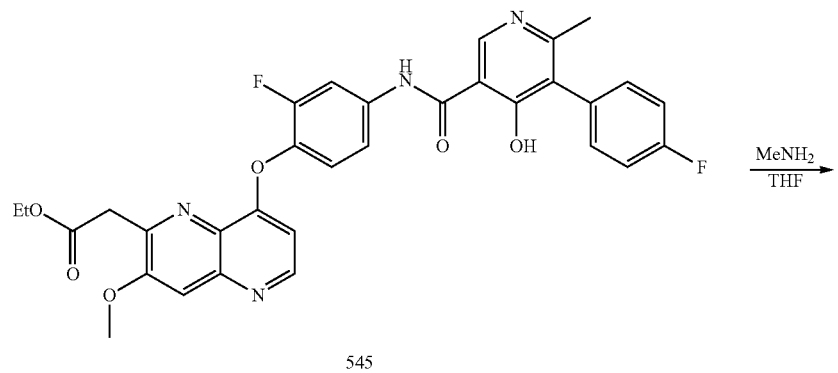

545

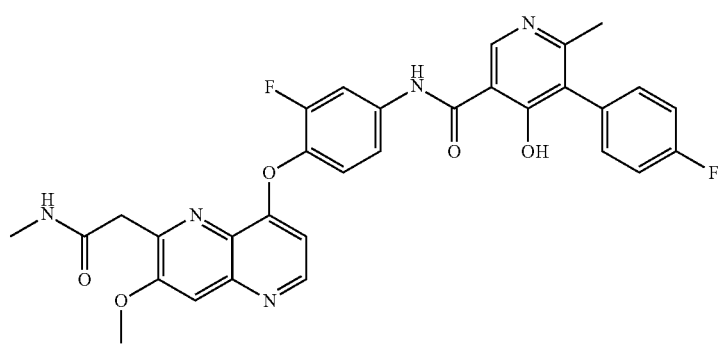

570

N-[3-Fluoro-4-[[7-methoxy-6-[2-(methylamino)-2-oxoethyl]-1,5-naphthyridin-4-yl]oxy]phenyl]-5-(4-fluorophenyl)-4-hydroxy-6-methylpyridine-3-carboxamide (570): To a mixture of Compound 545 (200 mg, 0.33 mmol, 1 eq) in THF (0.5 mL) was added 30% methylamine in EtOH (690 mg, 6.7 mmol, 20 eq). The mixture was stirred at 66° C. for 15 h. The reaction mixture was concentrated under reduced pressure. 1 N HCl (100 mL) was added to the resulting residue and the mixture was stirred for 5 min. The pH was then adjusted to 7 with aq saturated NaHCO$_3$ and the resulting mixture was extracted with EtOAc (3×100 mL). The combined organic extracts were dried over anhyd Na$_2$SO$_4$ and concentrated. The resulting residue was purified by prep HPLC (water (0.05% HCl)-ACN) to give Compound 570 (19 mg, 19% yield). MS for $C_{31}H_{25}F_2N_5O_5$: m/z 586.0 (MH+).

Example 94: 8-[2-Fluoro-4-[[5-(4-fluorophenyl)-4-hydroxy-6-methylpyridine-3-carbonyl]amino]phenoxy]-1,5-naphthyridine-3-carboxamide (577)

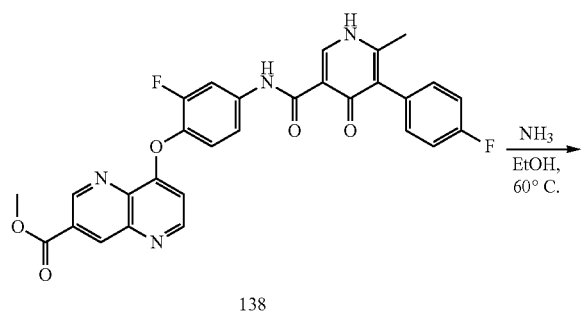

138

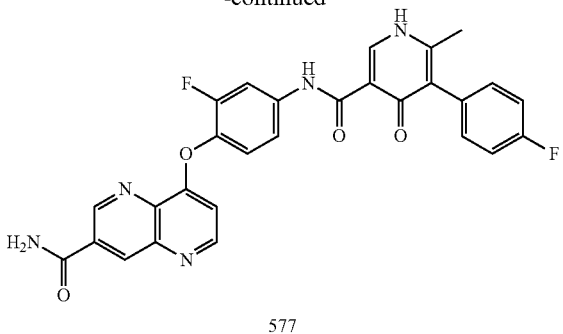

577

8-[2-Fluoro-4-[[5-(4-fluorophenyl)-4-hydroxy-6-methylpyridine-3-carbonyl]amino]phenoxy]-1,5-naphthyridine-3-carboxamide (577): Compound 138 (20 mg, 0.037 mmol) was mixed with 7M NH$_3$ in MeOH (1 mL) and EtOH (3 mL). The resulting mixture was stirred at 60° C. for 2 days. All volatiles were removed and resulting residue was purified by silica gel column chromatography (5% MeOH in EtOAc) to give Compound 577 (12 mg, 62% yield). $^1$H NMR (400 MHz, DMSO-d$_6$) δ 13.33 (s, 1H), 12.61 (s, 1H), 9.37 (d, 1H), 8.87 (d, 1H), 8.84 (d, 1H), 8.54 (s, 1H), 8.47 (s, 1H), 8.05 (dd, 1H), 7.83 (s, 1H), 7.50-7.35 (m, 2H), 7.35-7.12 (m, 4H), 6.96 (d, 1H), 2.15 (s, 3H). MS for $C_{28}H_{19}F_2N_5O_4$: m/z 528 (MH+).

The following compound was made in the same way that Compound 138 was converted to Compound 577 in Example 94:

8-[2-Fluoro-4-[[5-(4-fluorophenyl)-4-hydroxy-6-methylpyridine-3-carbonyl]amino]phenoxy]-N-methyl-1,5-naphthyridine-3-carboxamide (578): Made in one step from Compound 138. $^1$H NMR (400 MHz, DMSO-d$_6$) δ 13.42 (s, 1H), 12.68 (br. s, 1H), 9.38 (d, 1H), 8.99 (d, 1H), 8.87 (d, 1H), 8.83 (d, 1H), 8.57 (s, 1H), 8.17-7.99 (m, 1H), 7.57-7.35 (m, 2H), 7.35-7.16 (m, 4H), 6.98 (d, 1H), 2.90 (d, 3H), 2.18 (s, 3H); MS for $C_{29}H_{21}F_2N_5O_4$: m/z 542 (MH+).

Example 95: N-[3-Fluoro-4-[[6-(methanesulfonamido)-7-methoxy-1,5-naphthyridin-4-yl]oxy]phenyl]-5-(4-fluorophenyl)-6-methyl-4-oxo-1-propan-2-ylpyridine-3-carboxamide (581)

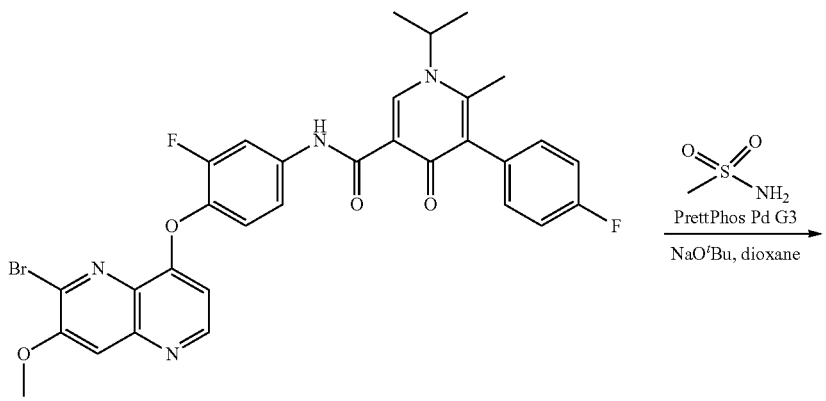

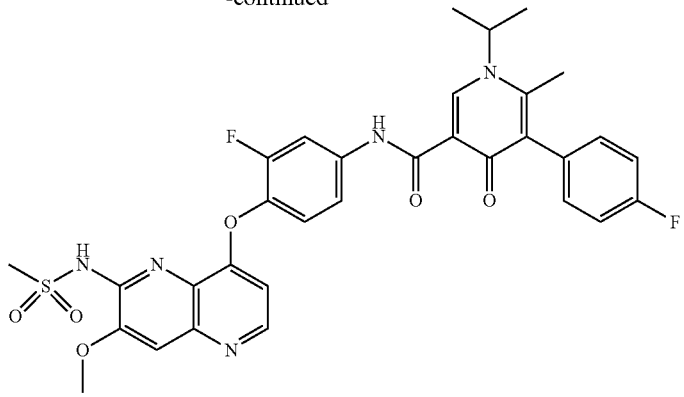

581

N-[3-Fluoro-4-[[6-(methanesulfonamido)-7-methoxy-1,5-naphthyridin-4-yl]oxy]phenyl]-5-(4-fluorophenyl)-6-methyl-4-oxo-1-propan-2-ylpyridine-3-carboxamide (581): A mixture of Compound 143 (26 mg, 0.041 mmol), methanesulfonamide (10 eq), NaO$^t$Bu (50 mg, 0.52 mmol) and BrettPhos Pd G3 catalyst (25 mg, 0.027 mmol) in dioxane (1.5 mL) was stirred at 90° C. overnight. The resulting mixture purified by silica gel chromatography to give Compound 581. $^1$H NMR (400 MHz, DMSO-d$_6$) δ 13.13 (s, 1H), 10.81 (br. s, 1H), 8.72 (s, 1H), 8.54 (d, 1H), 8.03 (dd, 1H), 7.67 (s, 1H), 7.42 (dd, 1H), 7.35-7.15 (m, 5H), 6.79 (d, 1H), 4.79 (p, 1H), 4.00 (s, 3H), 3.40 (s, 3H), 2.30 (s, 3H), 1.52 (d, 6H). MS for $C_{32}H_{29}F_2N_5O_6S$: m/z 650 (MH+).

The following compounds were made in the same way that Compound 143 was converted to Compound 581 in Example 95:

N-[4-[(6-Amino-7-methoxy-1,5-naphthyridin-4-yl)oxy]-3-fluorophenyl]-5-(4-fluorophenyl)-6-methyl-4-oxo-1-propan-2-ylpyridine-3-carboxamide (579): Made in one step from Compound 143 and ammonia. $^1$H NMR (400 MHz, DMSO-d$_6$) δ 13.13 (s, 1H), 8.71 (s, 1H), 8.28 (d, 1H), 8.02 (dd, 1H), 7.49-7.35 (m, 2H), 7.35-7.17 (m, 4H), 6.80 (s, 2H), 6.65 (s, 1H), 6.55 (d, 1H), 4.79 (p, 1H), 3.98 (s, 3H), 2.30 (s, 3H), 1.52 (d, 6H); MS for $C_{31}H_{27}F_2N_5O_4$: m/z 572 (MH+).

N-[3-Fluoro-4-[(6-hydroxy-7-methoxy-1,5-naphthyridin-4-yl)oxy]phenyl]-5-(4-fluorophenyl)-6-methyl-4-oxo-1-propan-2-ylpyridine-3-carboxamide (580): Compound 580 was recovered as a by-product from the reaction that produced Compound 579. MS for $C_{31}H_{26}F_2N_4O_5$: m/z 573 (MH+).

N-[3-Fluoro-4-[[7-methoxy-6-(methylamino)-1,5-naphthyridin-4-yl]oxy]phenyl]-5-(4-fluorophenyl)-6-methyl-4-oxo-1-propan-2-ylpyridine-3-carboxamide (582): Made in one step from Compound 143 and methylamine. MS for $C_{32}H_{29}F_2N_5O_4$: m/z 586 (MH+).

N-[4-[[6-(Dimethylamino)-7-methoxy-1,5-naphthyridin-4-yl]oxy]-3-fluorophenyl]-5-(4-fluorophenyl)-6-methyl-4-oxo-1-propan-2-ylpyridine-3-carboxamide (583): Made in one step from Compound 143 and dimethylamine. MS for $C_{33}H_{31}F_2N_5O_4$: m/z 600 (MH+).

N-[3-Fluoro-4-[[6-(methanesulfonamido)-7-methoxy-1,5-naphthyridin-4-yl]oxy]phenyl]-5-(4-fluorophenyl)-4-hydroxy-6-methylpyridine-3-carboxamide (584): Made in one step from Compound 142 and methanesulfonamide. MS for $C_{29}H_{23}F_2N_5O_6S$: m/z 608 (MH+).

Example 96: N-[4-[(6-Ethyl-7-methoxy-1,5-naphthyridin-4-yl)oxy]-3-fluorophenyl]-5-(4-fluorophenyl)-6-methyl-4-oxo-1-propan-2-ylpyridine-3-carboxamide (588)

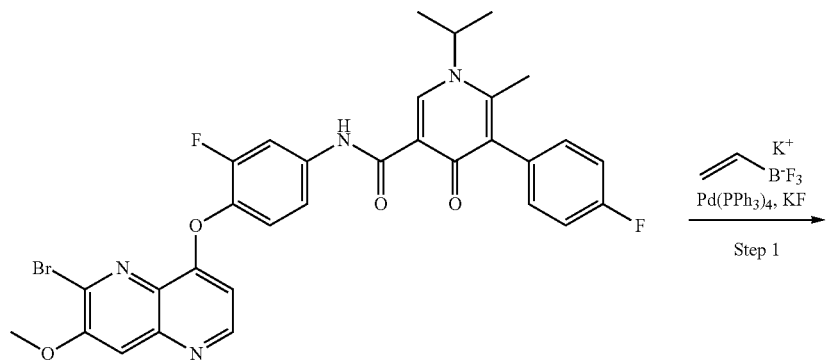

143

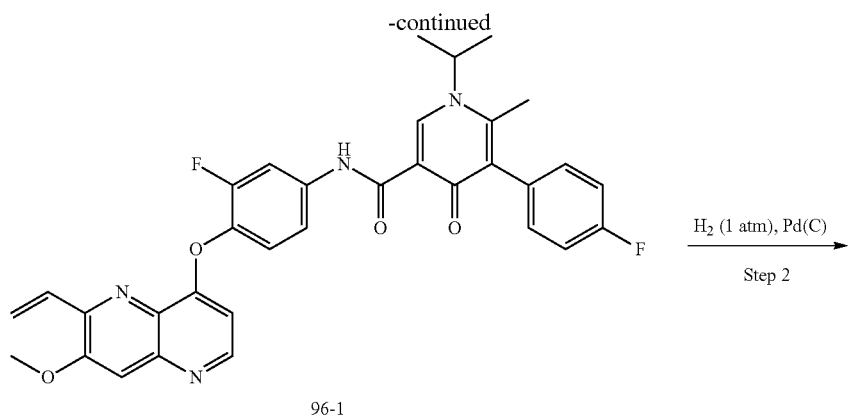

96-1

H₂ (1 atm), Pd(C)
Step 2

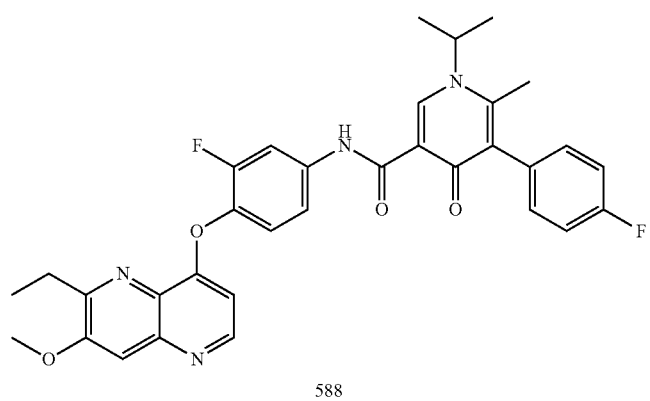

588

Step 1: N-(3-Fluoro-4-((7-methoxy-6-vinyl-1,5-naphthyridin-4-yl)oxy)phenyl)-5-(4-fluorophenyl)-1-isopropyl-6-methyl-4-oxo-1,4-dihydropyridine-3-carboxamide (96-1): A mixture of Compound 143 (45 mg, 0.071 mmol), Pd(PPh₃)₂Cl₂ (20 mg, 0.028 mmol), potassium vinyltriflouroborate (30 mg, 0.22 mmol) and KF (50 mg, 0.86 mmol) in dioxane/water (2/1 mL) was stirred at 80° C. for 1 h, after which the reaction mixture was allowed to cool to room temperature. The mixture was partitioned between EtOAc and water, the phases were separated, and the aqueous phase was further extracted with EtOAc (2×). The combined organic phases were dried over anhyd Na₂SO₄ and evaporated to dryness to give crude Compound 96-1 which was used without further purification. MS for C₃₃H₂₈F₂N₄O₄: m/z 583 (MH+).

Step 2: N-[4-[(6-Ethyl-7-methoxy-1,5-naphthyridin-4-yl)oxy]-3-fluorophenyl]-5-(4-fluorophenyl)-6-methyl-4-oxo-1-propan-2-ylpyridine-3-carboxamide (588): Crude Compound 96-1 was mixed with 10% Pd/C (53% wet, 15 mg) in EtOAc (4 mL) and the resulting suspension was degassed under vacuum for 2 min, purged with hydrogen gas and then stirred under an atmosphere of hydrogen at room temperature overnight. The reaction mixture was filtered, the filtrate concentrated, and the resulting residue purified by prep HPLC to give Compound 588 (16 mg, 39% yield). ¹H NMR (400 MHz, DMSO-d₆) δ 13.08 (s, 1H), 8.64 (s, 1H), 8.57 (d, 1H), 7.97 (dd, 1H), 7.63 (s, 1H), 7.38 (d, 1H), 7.36-7.30 (m, 1H), 7.30-7.18 (m, 4H), 6.68 (d, 1H), 4.72 (m, 1H), 3.94 (s, 3H), 2.88 (q, 2H), 2.22 (s, 3H), 1.45 (s, 3H), 1.44 (s, 3H), 1.17 (t, 3H). MS for C₃₃H₃₀F₂N₄O₄: m/z 585 (MH+).

The following compound was made using the same two step process to convert Compound 143 to Compound 588 in two steps Example 96:

N-[4-[(6-Ethyl-7-methoxy-1,5-naphthyridin-4-yl)oxy]-3-fluorophenyl]-5-(4-fluorophenyl)-4-hydroxy-6-methylpyridine-3-carboxamide (589): Made in 2 steps from Compound 142. MS for C₃₀H₂₄F₂N₄O₄: m/z 543 (MH+).

Example 97: N-[3-Fluoro-4-[(6-methoxy-7-propan-2-yl-1,5-naphthyridin-4-yl)oxy]phenyl]-5-(4-fluorophenyl)-4-hydroxy-6-methylpyridine-3-carboxamide (590)

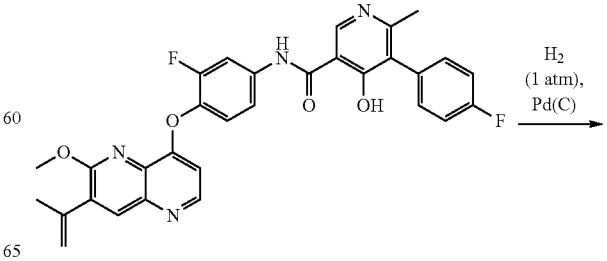

452

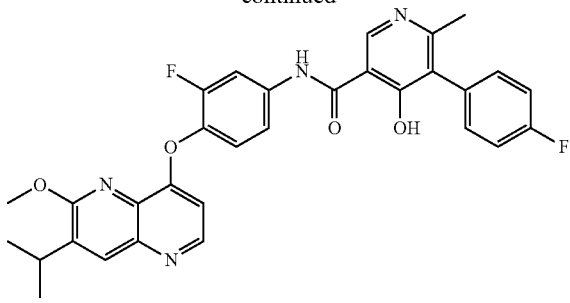

590

N-[3-Fluoro-4-[(6-methoxy-7-propan-2-yl-1,5-naphthyridin-4-yl)oxy]phenyl]-5-(4 fluorophenyl)-4-hydroxy-6-methylpyridine-3-carboxamide (590): Compound 590 was made from Compound 452 using standard hydrogenation conditions (10% Pd/C under 1 atmosphere of hydrogen) very similar to those employed in Step 2 of Example 96 to convert Compound 96-1 to Compound 588. $^1$H NMR (400 MHz, DMSO-d$_6$) δ 13.3 (s, 1H), 12.6 (s, 1H), 8.58 (d, 1H), 8.56 (s, 1H), 8.09 (s, 1H), 8.02 (d, 1H), 7.42 (d, 1H), 7.30 (m, 5H), 6.93 (d, 1H), 3.96 (s, 3H), 3.18 (m, 1H), 2.18 (s, 3H), 1.30 (d, 6H). MS for $C_{31}H_{26}F_2N_4O_4$: m/z 557 (MH+).

The following compounds were made using the hydrogenation conditions used to convert Compound 452 to Compound 590 in Example 97:

N-[3-Fluoro-4-[(6-methoxy-7-propan-2-yl-1,5-naphthyridin-4-yl)oxy]phenyl]-5-(4-fluoro-2-methylphenyl)-4-hydroxy-6-methylpyridine-3-carboxamide (591): Made in one step from Compound 449. $^1$H NMR (400 MHz, DMSO-d$_6$) δ 13.3 (s, 1H), 12.5 (s, 1H), 8.57 (m, 2H), 8.08 (s, 1H), 8.02 (d, 1H), 7.40 (d, 1H), 7.32 (m, 1H), 7.16 (d, 1H), 7.07 (m, 2H), 6.92 (d, 1H), 3.96 (s, 3H), 3.18 (m, 1H), 2.06 (s, 3H), 2.05 (s, 3H), 1.30 (d, 6H); MS for $C_{32}H_{28}F_2N_4O_4$: m/z 571 (MH+).

N-[3-Fluoro-4-[(6-methoxy-7-propan-2-yl-1,5-naphthyridin-4-yl)oxy]phenyl]-5-(4-fluorophenyl)-4-hydroxy-2,6-dimethylpyridine-3-carboxamide (592): Made in one step from Compound 453. $^1$H NMR (400 MHz, DMSO-d$_6$) δ 13.5 (s, 1H), 11.9 (s, 1H), 8.59 (d, 1H), 8.08 (s, 1H), 8.00 (d, 1H), 7.36 (m, 1H), 7.27 (m, 5H), 6.90 (d, 1H), 3.97 (s, 3H), 3.18 (m, 1H), 2.75 (s, 3H), 2.14 (s, 3H), 1.30 (d, 6H); MS for $C_{32}H_{28}F_2N_4O_4$: m/z 571 (MH+).

5-(4-Fluoro-2-methylphenyl)-N-[3-fluoro-4-[(7-propan-2-yl-1,5-naphthyridin-4-yl)oxy]phenyl]-4-hydroxy-6-methylpyridine-3-carboxamide (593): Made in one step from Compound 450. MS for $C_{31}H_{26}F_2N_4O_3$: m/z 541 (MH+).

5-(4-Fluorophenyl)-4-hydroxy-6-methyl-N-[4-[(7-propan-2-yl-1,5-naphthyridin-4-yl)oxy]phenyl]pyridine-3-carboxamide (594): Made in one step from Compound 454. MS for $C_{30}H_{25}FN_4O_3$: m/z 509 (MH+).

5-(4-Fluorophenyl)-N-[3-fluoro-4-[(7-propan-2-yl-1,5-naphthyridin-4-yl)oxy]phenyl]-4-hydroxy-2,6-dimethylpyridine-3-carboxamide (595): Made in one step from Compound 451. MS for $C_{31}H_{26}F_2N_4O_3$: m/z 541 (MH+).

5-(4-Fluorophenyl)-N-[3-fluoro-4-[(7-propan-2-yl-1,5-naphthyridin-4-yl)oxy]phenyl]-4-hydroxy-6-methylpyridine-3-carboxamide (596): Made in one step from Compound 456. MS for $C_{30}H_{24}F_2N_4O_3$: m/z 527 (MH+).

5-(4-Fluoro-2-methylphenyl)-4-hydroxy-6-methyl-N-[4-[(7-propan-2-yl-1,5-naphthyridin-4-yl)oxy]phenyl]pyridine-3-carboxamide (597): Made in one step from Compound 448. MS for $C_{31}H_{27}FN_4O_3$: m/z 523 (MH+).

5-(4-Fluorophenyl)-4-hydroxy-2,6-dimethyl-N-[4-[(7-propan-2-yl-1,5-naphthyridin-4-yl)oxy]phenyl]pyridine-3-carboxamide (598): Made in one step from Compound 455. $^1$H NMR (400 MHz, DMSO-d$_6$) δ 13.2 (s, 1H), 11.9 (s, 1H), 8.96 (s, 1H), 8.74 (d, 1H), 8.21 (s, 1H), 7.79 (d, 2H), 7.25 (m, 6H), 6.81 (d, 1H), 3.18 (m, 1H), 2.76 (s, 3H), 2.15 (s, 3H), 1.38 (d, 6H); MS for $C_{31}H_{27}FN_4O_3$: m/z 523 (MH+).

Example 98: N-[3-Fluoro-4-[[7-(1-hydroxypropan-2-yl)-1,5-naphthyridin-4-yl]oxy]phenyl]-1-(4-fluorophenyl)-4,6-dimethyl-2-oxopyridine-3-carboxamide (599)

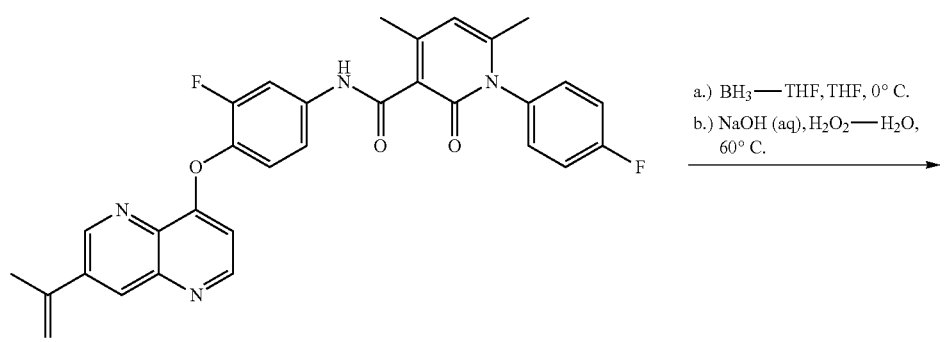

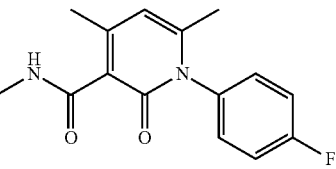

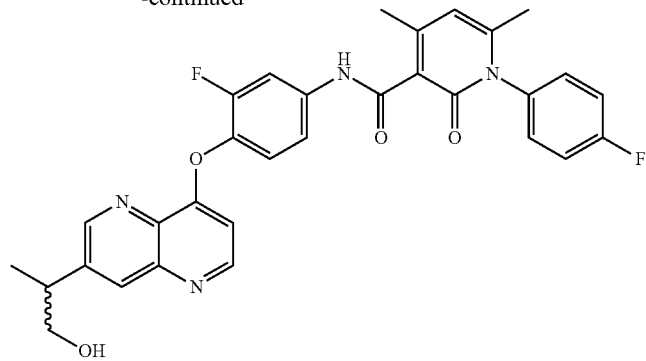

599

N-[3-Fluoro-4-[[7-(1-hydroxypropan-2-yl)-1,5-naphthyridin-4-yl]oxy]phenyl]-1-(4-fluorophenyl)-4,6-dimethyl-2-oxopyridine-3-carboxamide (599): Borane-THF complex (BH₃-THF, 2M, 0.30 mL, 0.60 mmol) was added to a stirring solution of Compound 457 (50 mg, 0.09 mmol) in THF (2 mL) at 0° C. under a nitrogen atmosphere and the resulting mixture was allowed to warm to room temperature and stirred for 24 h. The resulting mixture was then cooled to 0° C. and aq 1 M NaOH (0.6 mL, 0.60 mmol) and aq 30% hydrogen peroxide (1.8 mL, 0.60 mmol) were sequentially added and the resulting solution was stirred at 60° C. for 1 h. The reaction mixture was diluted in water (10 mL) and extracted with EtOAc (3×6 mL). The combined organic extracts were dried over anhyd MgSO₄, concentrated, redissolved in DMF, filtered and purified by prep HPLC (0-100% ACN in water (0.1% formic acid) to give Compound 599 (10 mg, 19% yield). ¹H NMR (400 MHz, DMSO-d₆) δ 11.2 (s, 1H), 8.92 (d, 1H), 8.74 (d, 1H), 8.22 (s, 1H), 7.98 (dd, 1H), 7.49 (dd, 1H), 7.40 (m, 1H), m, 4H), 6.84 (dd, 1H), 6.39 (s, 1H), 4.10 (q, 1H), 3.65 (q, 1H), 3.16 (d, 3H), 2.38 (s, 3H), 1.98 (s, 3H), 1.34 (d, 2H). MS for C₃₁H₂₆F₂N₄O₄: m/z 557 (MH+).

Example 99: N-[4-[(7-Amino-6-methoxy-1,5-naphthyridin-4-yl)oxy]-3-fluorophenyl]-5-(4-fluorophenyl)-4-hydroxy-2,6-dimethylpyridine-3-carboxamide (600)

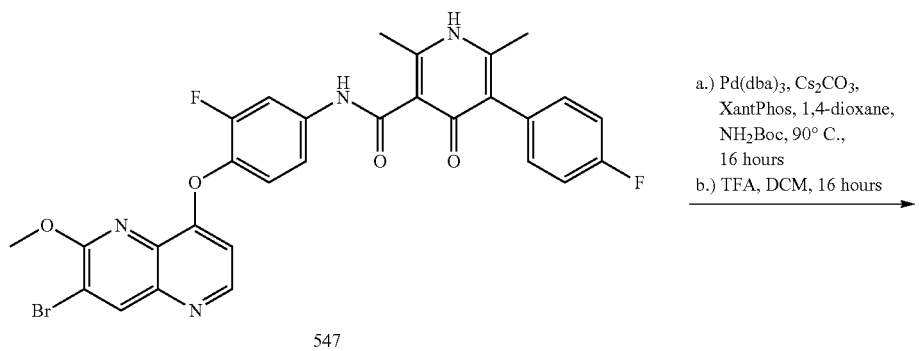

547 a.) Pd(dba)₃, Cs₂CO₃, XantPhos, 1,4-dioxane, NH₂Boc, 90° C., 16 hours
b.) TFA, DCM, 16 hours

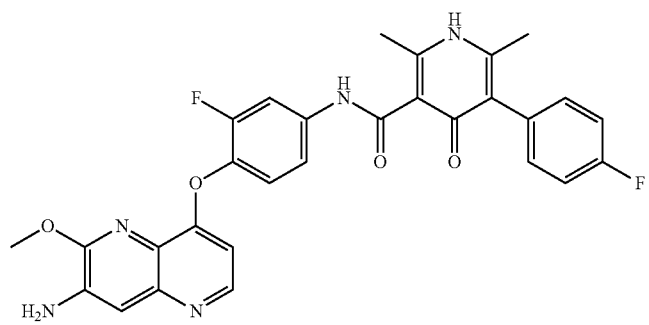

600

N-[4-[(7-Amino-6-methoxy-1,5-naphthyridin-4-yl)oxy]-3-fluorophenyl]-5-(4-fluorophenyl)-4-hydroxy-2,6-dimethylpyridine-3-carboxamide (600): Cesium carbonate (70 mg, 0.21 mmol) was added to a mixture of Compound 547 (50 mg, 0.08 mmol), tert-butyl carbamate (15 mg, 0.13 mmol), XantPhos (10 mg, 0.02 mmol) and Pd(dba)₃ (16 mg, 0.02 mmol) in 1,4-dioxane (2 mL) and the reaction mixture was stirred at 90° C. for 16 h. The reaction mixture was cooled to room temperature, water (10 mL) was added and the resulting slurry was filtered. The filter cake was redissolved in DMF, filtered and the filtrate was purified by prep HPLC (0-100% ACN in water (0.1% formic acid) to give the Boc protected precursor to Compound 600. This Boc protected intermediate was dissolved in DCM (6 mL) and TFA (0.1 mL, 1.3 mmol, 16 eq) and the resulting mixture was stirred at room temperature vigorously for 20 h, concentrated, redissolved in DMF and purified by prep HPLC (0-100% ACN in water (0.1% formic acid) to give Compound 600 (2 mg, 4.5% yield). MS for $C_{29}H_{23}F_2N_5O_4$: m/z 544 (MH+).

Example 100: N-[4-[(6,7-Dimethoxy-1,5-naphthyridin-4-yl)oxy]-3-fluorophenyl]-5-(4-fluorophenyl)-6-methylpyridazine-3-carboxamide (601)

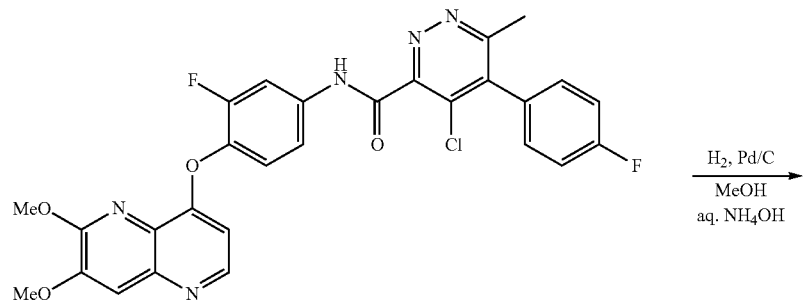

488

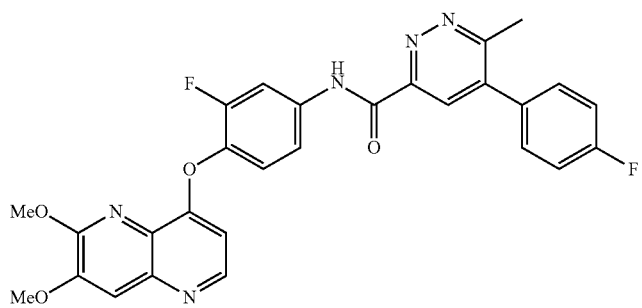

601

N-[4-[(6,7-Dimethoxy-1,5-naphthyridin-4-yl)oxy]-3-fluorophenyl]-5-(4-fluorophenyl)-6-methylpyridazine-3-carboxamide (601): To a 25 mL round bottom flask equipped with a magnetic stir bar and a rubber septum was added 10% Pd/C (67% water w/w) (20 mg) and the reaction was purged with nitrogen gas. A solution of Compound 488 (25 mg, 0.04 mmol) in MeOH (2 mL) and was then added and the atmosphere was purged with hydrogen gas. The reaction was allowed to proceed at room temperature under 1 atm of hydrogen for 16 h. Ammonium hydroxide (0.2 mL) (30% aqueous solution) was added and a fresh hydrogen balloon attached, purging the solvent with hydrogen gas and stirring at room temperature for an additional 6 h. The reaction was filtered through Celite, concentrated and purified by prep HPLC to give Compound 601 (7.6 mg, 32% yield). $^1$H NMR (400 MHz, DMSO-d$_6$) δ 11.37 (s, 1H), 8.49 (d, 1H), 8.09 (dd, 1H), 8.01 (s, 1H), 7.91-7.80 (m, 1H), 7.69-7.56 (m, 3H), 7.34 (td, 3H), 6.77 (d, 1H), 3.90 (s, 3H), 3.89 (s, 3H), 2.68 (s, 3H); MS for $C_{28}H_{20}F_2N_5O_4$: m/z 530.2 (MH+).

Example 101: N-[4-[(6,7-Dimethoxy-1,5-naphthyridin-4-yl)oxy]-3-fluorophenyl]-5-(4-fluorophenyl)-6-methyl-4-methylsulfanylpyridazine-3-carboxamide (602)

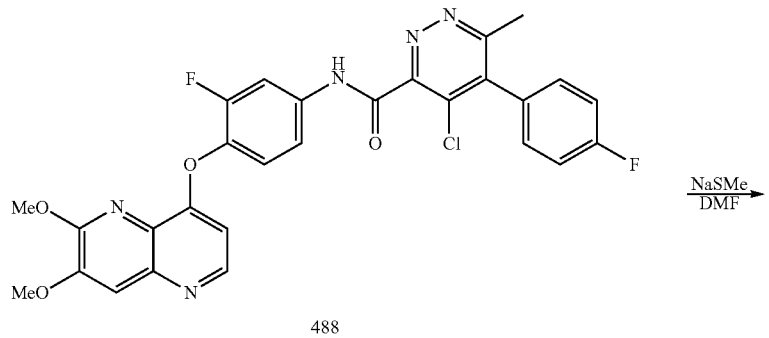

488

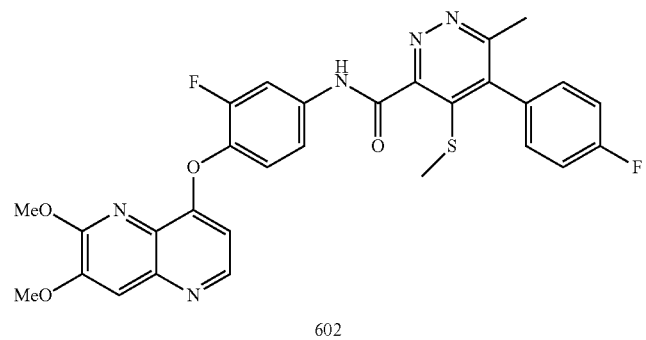

602

N-[4-[(6,7-Dimethoxy-1,5-naphthyridin-4-yl)oxy]-3-fluorophenyl]-5-(4-fluorophenyl)-6-methyl-4-methylsulfanylpyridazine-3-carboxamide (602): To a 4 mL vial equipped with a magnetic stir bar and a pressure relief septum was added Compound 488 (25 mg, 0.044 mmol) in DMF (0.5 mL). Sodium thiomethoxide (11 mg, 0.16 mmol, 3.5 eq) was added in a single portion and the reaction was allowed to proceed at room temperature for 2 h. The reaction was diluted with water (3 mL), and a fine white precipitate was formed. The suspension was transferred to a separatory funnel and extracted with DCM. The organic extracts were concentrated to dryness under reduced pressure, dissolved in hot ACN (3 mL), filtered and purified by prep HPLC to give Compound 602 (9.1 mg, 36% yield). $^1$H NMR (400 MHz, DMSO-$d_6$) δ 11.18 (s, 1H), 8.49 (d, 1H), 7.91 (dd, 1H), 7.59 (s, 1H), 7.53 (d, 1H), 7.37 (dtd, 6H), 6.79 (d, 1H), 3.90 (s, 3H), 3.88 (s, 3H), 2.35 (s, 3H), 2.01 (s, 2H); MS for $C_{29}H_{23}N_5O_4S$: m/z 576.2 (MH+).

Example 102: N-[4-[(6,7-Dimethoxy-1,5-naphthyridin-4-yl)oxy]-3-fluorophenyl]-5-(4-fluorophenyl)-6-methyl-4-(methylamino)pyridazine-3-carboxamide (603)

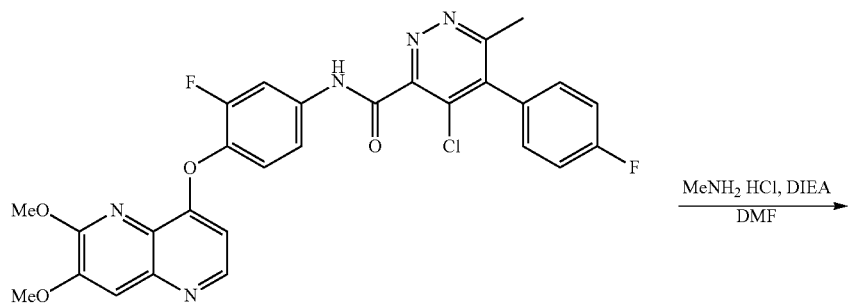

488

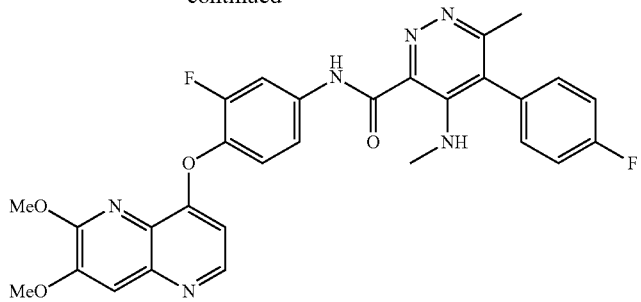

603

N-[4-[(6,7-Dimethoxy-1,5-naphthyridin-4-yl)oxy]-3-fluorophenyl]-5-(4-fluorophenyl)-6-methyl-4-(methylamino)pyridazine-3-carboxamide (603): To a 4 mL vial equipped with a magnetic stir bar and a pressure relief septum was added Compound 488 (25 mg, 0.044 mmol) and methylamine hydrochloride (50 mg, 0.74 mmol, 17 eq) in DMF (1 mL). DIEA (0.2 mL, 1 mmol, 30 eq) was added in a single portion and the reaction was heated to 60° C. overnight. The reaction mixture was diluted with water (3 mL) and stirred vigorously. The resulting white precipitate was filtered to yield a white powder which was subsequently purified by prep HPLC to give Compound 603 (2.5 mg, 10% yield). $^1$H NMR (400 MHz, DMSO-$d_6$) δ 11.21 (s, 1H), 8.49 (d, 1H), 8.41 (s, 1H), 8.04-7.96 (m, 1H), 7.73 (d, 1H), 7.59 (s, 1H), 7.41-7.21 (m, 5H), 6.77 (d, 1H), 3.91 (s, 3H), 3.88 (s, 3H), 2.21 (d, 3H), 2.14 (s, 3H); MS for $C_{29}H_{24}F_2N_6O_4$: m/z 559.2 (MH+).

Example 103: N-[4-[[7-[1-(Difluoromethyl)pyrazol-4-yl]-6-methoxy-1,5-naphthyridin-4-yl]oxy]-3-fluorophenyl]-5-(4-fluorophenyl)-4-hydroxy-6-methylpyridine-3-carboxamide (607)

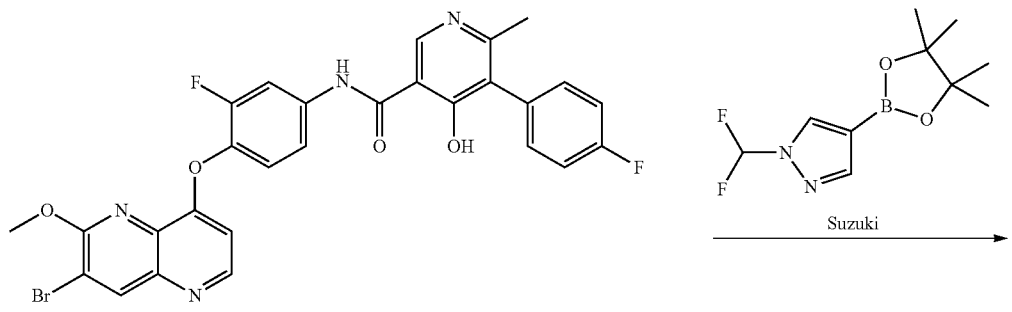

130

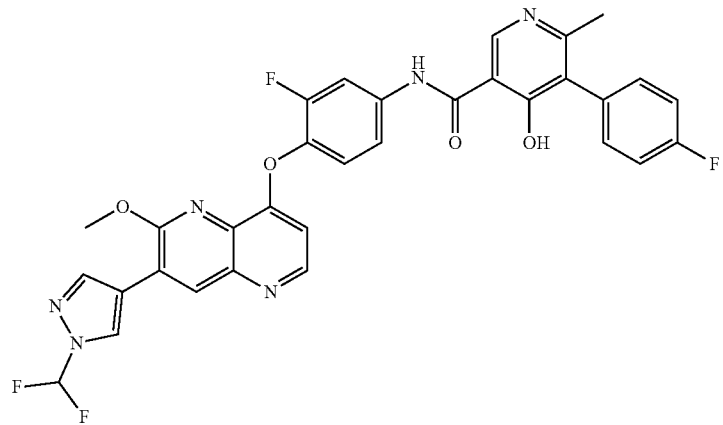

607

N-[4-[[7-[1-(Difluoromethyl)pyrazol-4-yl]-6-methoxy-1,5-naphthyridin-4-yl]oxy]-3-fluorophenyl]-5-(4-fluorophenyl)-4-hydroxy-6-methylpyridine-3-carboxamide (607):

Compound 607 was made from Compound 130 using standard Suzuki conditions very similar to those employed in Step 4 of Example 73 to convert Compound 73-3 to Compound 73-4. MS for $C_{32}H_{22}F_4N_6O_4$: m/z 631.2 (MH+).

The following compounds were made using the standard Suzuki conditions used to convert Compound 130 to Compound 607 in Example 103:

N-[3-Fluoro-4-[(6-methoxy-7-pyridin-3-yl-1,5-naphthyridin-4-yl)oxy]phenyl]-5-(4-fluorophenyl)-4-hydroxy-6-methylpyridine-3-carboxamide hydrochloride (604): Made in one step from Compound 130. MS for $C_{33}H_{23}F_2N_5O_4$: m/z 592.2 (MH+).

N-[3-Fluoro-4-[(6-methoxy-7-pyridin-3-yl-1,5-naphthyridin-4-yl)oxy]phenyl]-5-(4-fluorophenyl)-4-oxo-1-propan-2-ylpyridine-3-carboxamide hydrochloride (605): Made in one step from Compound 131. MS for $C_{35}H_{27}F_2N_5O_4$: m/z 620.2 (MH+).

N-[3-Fluoro-4-[(6-methoxy-7-pyridin-3-yl-1,5-naphthyridin-4-yl)oxy]phenyl]-5-(4-fluorophenyl)-6-methyl-4-oxo-1-propan-2-ylpyridine-3-carboxamide hydrochloride (606): Made in one step from Compound 132. MS for $C_{36}H_{29}F_2N_5O_4$: m/z 634.2 (MH+).

N-[4-[[7-[1-(Difluoromethyl)pyrazol-4-yl]-6-methoxy-1,5-naphthyridin-4-yl]oxy]-3-fluorophenyl]-5-(4-fluorophenyl)-4-oxo-1-propan-2-ylpyridine-3-carboxamide (608): Made in one step from Compound 131. MS for $C_{34}H_{26}F_4N_6O_4$: m/z 659.2 (MH+).

N-[4-[[7-[1-(Difluoromethyl)pyrazol-4-yl]-6-methoxy-1,5-naphthyridin-4-yl]oxy]-3-fluorophenyl]-5-(4-fluorophenyl)-6-methyl-4-oxo-1-propan-2-ylpyridine-3-carboxamide (609): Made in one step from Compound 132 MS for $C_{35}H_{28}F_4N_6O_4$: m/z 673.2 (MH+).

N-[4-[[7-[1-(Difluoromethyl)pyrazol-4-yl]-1,5-naphthyridin-4-yl]oxy]-3-fluorophenyl]-5-(4-fluorophenyl)-4-hydroxy-6-methylpyridine-3-carboxamide hydrochloride (610): Made in one step from Compound 133. MS for $C_{30}H_{21}F_4N_6O_3$: m/z 601.2 (MH+).

N-[4-[[7-[1-(Difluoromethyl)pyrazol-4-yl]-1,5-naphthyridin-4-yl]oxy]phenyl]-5-(4-fluorophenyl)-4-hydroxy-6-methylpyridine-3-carboxamide (611): Made in one step from Compound 149. MS for $C_{31}H_{21}F_3N_6O_3$: m/z 583.2 (MH+).

N-[4-[[7-[1-(Difluoromethyl)pyrazol-4-yl]-6-methyl-1,5-naphthyridin-4-yl]oxy]phenyl]-5-(4-fluorophenyl)-6-methyl-4-oxo-1-propan-2-ylpyridine-3-carboxamide hydrochloride (612): Made in one step from Compound 548. $^1$H NMR (400 MHz, CD$_3$OD) δ 8.89 (s, 1H), 8.83 (d, 1H), 8.63 (s, 1H), 8.43 (s, 1H), 8.21 (s, 1H), 7.93 (d, 2H), 7.65 (t, 1H), 7.38 (d, 2H), 7.33-7.19 (m, 4H), 7.08 (d, 1H), 4.97-4.90 (m, 1H), 2.96 (d, 3H), 2.38 (s, 3H), 1.63 (d, 6H); MS for $C_{35}H_{29}F_3N_6O_3$: m/z 639.2 (MH+).

5-(4-Fluorophenyl)-6-methyl-N-[4-[(6-methyl-7-pyridin-3-yl-1,5-naphthyridin-4-yl)oxy]phenyl]-4-oxo-1-propan-2-ylpyridine-3-carboxamide hydrochloride (613): Made in one step from Compound 548. MS for $C_{36}H_{30}FN_5O_3$: m/z 600.2 (MH+).

N-[4-[[7-[1-(Difluoromethyl)pyrazol-4-yl]-6-methyl-1,5-naphthyridin-4-yl]oxy]-3-fluorophenyl]-5-(4-fluorophenyl)-6-methyl-4-oxo-1-propan-2-ylpyridine-3-carboxamide hydrochloride (614): Made in one step from Compound 153. MS for $C_{35}H_{28}F_4N_6O_3$: m/z 657.2 (MH+).

N-[4-[[7-[1-(Difluoromethyl)pyrazol-4-yl]-6-methyl-1,5-naphthyridin-4-yl]oxy]-3-fluorophenyl]-5-(4-fluorophenyl)-4-hydroxy-6-methylpyridine-3-carboxamide hydrochloride (615): Made in one step from Compound 549. MS for $C_{32}H_{22}F_4N_6O_3$: n/z 615.2 (MH+).

5-(4-Fluorophenyl)-4-hydroxy-6-methyl-N-[4-[(6-methyl-7-pyridin-3-yl-1,5-naphthyridin-4-yl)oxy]phenyl]pyridine-3-carboxamide hydrochloride (616): Made in one step from Compound 550. MS for $C_{33}H_{24}FN_5O_3$: m/z 558.2 (MH+).

N-[4-[[7-[1-(Difluoromethyl)pyrazol-4-yl]-6-methyl-1,5-naphthyridin-4-yl]oxy]phenyl]-5-(4-fluorophenyl)-4-hydroxy-6-methylpyridine-3-carboxamide hydrochloride (617): Made in one step from Compound 550. MS for $C_{32}H_{23}F_3N_6O_3$: m/z 597.2 (MH+).

N-[3-Fluoro-4-[(6-methyl-7-pyridin-3-yl-1,5-naphthyridin-4-yl)oxy]phenyl]-5-(4-fluorophenyl)-4-hydroxy-6-methylpyridine-3-carboxamide hydrochloride (618): Made in one step from Compound 549. MS for $C_{33}H_{23}F_2N_5O_3$: m/z 576.2 (MH+).

N-[3-Fluoro-4-[(6-methyl-7-pyridin-3-yl-1,5-naphthyridin-4-yl)oxy]phenyl]-5-(4-fluorophenyl)-6-methyl-4-oxo-1-propan-2-ylpyridine-3-carboxamide (620): Made in one step from Compound 153. MS for $C_{36}H_{29}F_2N_5O_3$: m/z 618.2 (MH+).

Example 104: N-[4-[(6,7-Dimethoxy-1,5-naphthyridin-4-yl)oxy]-3-fluorophenyl]-1-(2-fluoroethyl)-5-(4-fluorophenyl)-6-methyl-4-oxopyridine-3-carboxamide (622)

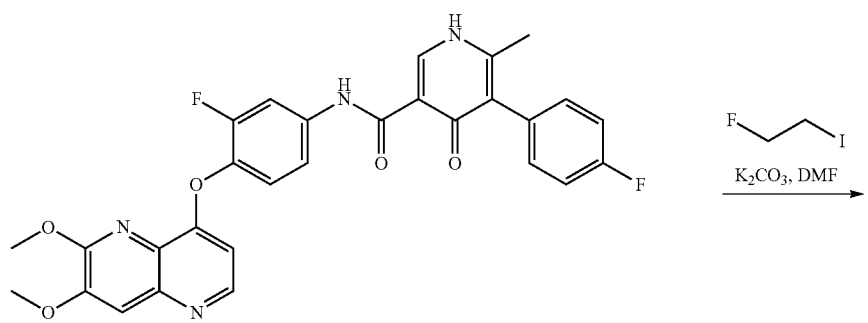

-continued

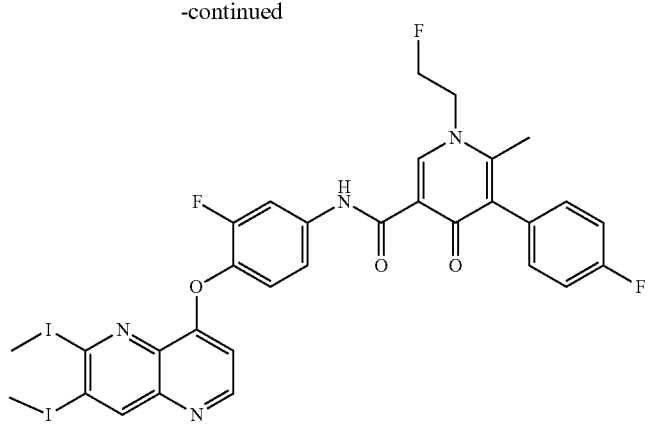

622

N-[4-[(6,7-Dimethoxy-1,5-naphthyridin-4-yl)oxy]-3-fluorophenyl]-1-(2-fluoroethyl)-5-(4-fluorophenyl)-6-methyl-4-oxopyridine-3-carboxamide (622): To a solution of Compound 28 (50 mg, 0.092 mmol) in DMF (0.5 mL) was added 1-fluoro-2-iodo-ethane (0.92 mmol, 10 eq) and $K_2CO_3$ (0.55 mmol, 6 eq). The reaction mixture was heated to 85° C. overnight. Water was added and the resulting mixture was extracted with DCM (3×). The combined organic extracts were concentrated, and the resulting residue was purified using flash silica gel chromatography (0-100% EtOAc/Hexanes and 0-20% MeOH/EtOAc) to give Compound 622 (34.4 mg, 57% yield). $^1$H NMR (400 MHz, DMSO-$d_6$) δ 13.06 (s, 1H), 8.75 (s, 1H), 8.55 (d, 1H), 8.01 (dd, 1H), 7.65 (s, 1H), 7.47-7.39 (m, 1H), 7.39-7.27 (m, 4H), 7.27 (s, 1H), 6.82 (dd, 1H), 4.96-4.56 (m, 4H), 3.96 (d, 6H), 2.24 (s, 3H). MS for $C_{31}H_{25}F_3N_4O_5$: m/z 591 (MH+).

The following compounds were made using the method used to convert Compound 28 to Compound 622 in Example 103:

N-[4-[(6,7-Dimethoxy-1,5-naphthyridin-4-yl)oxy]-3-fluorophenyl]-5-(4-fluorophenyl)-1-(2-hydroxyethyl)-6-methyl-4-oxopyridine-3-carboxamide (619): Made in two steps from Compound 28. MS for $C_{31}H_{26}F_2N_4O_6$: m/z 589.2 (MH+).

N-[3-Fluoro-4-[(7-methoxy-1,5-naphthyridin-4-yl)oxy]phenyl]-5-(4-fluorophenyl)-1-(2-hydroxyethyl)-6-methyl-4-oxopyridine-3-carboxamide (621): Made in two steps from Compound 64. $^1$H NMR (400 MHz, CD$_3$OD) δ 13.05 (s, 1H), 8.80 (s, 1H), 8.77-8.63 (m, 2H), 8.20-7.92 (m, 1H), 7.77 (d, 1H), 7.42 (dt, 2H), 7.35-7.17 (m, 4H), 6.79 (d, 1H), 4.38 (d, 2H), 4.08 (s, 3H), 3.96 (t, 2H), 2.35 (s, 3H); MS for $C_{30}H_{24}F_2N_4O_5$: m/z 559.2 (MH+).

1-(2,2-Difluoroethyl)-N-[4-[(6,7-dimethoxy-1,5-naphthyridin-4-yl)oxy]-3-fluorophenyl]-5-(4-fluorophenyl)-6-methyl-4-oxopyridine-3-carboxamide (623): Made in one step from Compound 28. MS for $C_{31}H_{24}F_4N_4O_5$: m/z 609 (MH+).

1-(2-Fluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide (624): Made in one step from Compound 64. MS for $C_{30}H_{23}F_3N_4O_4$: m/z 561 (MH+).

1-(2,2-Difluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide (625): Made in one step from Compound 64. MS for $C_{30}H_{22}F_4N_4O_4$: m/z 579 (MH+).

1-(Difluoromethyl)-N-[3-fluoro-4-[(7-methoxy-1,5-naphthyridin-4-yl)oxy]phenyl]-5-(4-fluorophenyl)-6-methyl-4-oxopyridine-3-carboxamide (626): Made in one step from Compound 64. $^1$H NMR (400 MHz, DMSO-$d_6$) δ 12.47 (s, 1H), 8.95 (s, 1H), 8.78-8.68 (m, 2H), 8.29-7.87 (m, 2H), 7.80 (d, 1H), 7.53 (d, 1H), 7.43 (t, 1H), 7.32 (d, 4H), 6.76 (dd, 1H), 4.01 (s, 3H), 2.35-2.31 (m, 3H); MS for $C_{29}H_{20}F_4N_4O_4$: m/z 565 (MH+).

5-(4-Fluorophenyl)-1-(2-hydroxyethyl)-N-[4-[(7-methoxy-1,5-naphthyridin-4-yl)oxy]phenyl]-6-methyl-4-oxopyridine-3-carboxamide (627): Made in two steps from Compound 147. MS for $C_{30}H_{25}FN_4O_5$: m/z 541 (MH+).

N-[4-[(6,7-Dimethoxy-1,5-naphthyridin-4-yl)oxy]phenyl]-5-(4-fluorophenyl)-1-(2-hydroxyethyl)-6-methyl-4-oxopyridine-3-carboxamide (628): Made in two steps from Compound 119. $^1$H NMR (400 MHz, DMSO-$d_6$) δ 12.97 (s, 1H), 8.68 (s, 1H), 8.54 (d, 1H), 7.77 (d, 2H), 7.64 (s, 1H), 7.33-7.15 (m, 6H), 6.80 (d, 1H), 4.30 (s, 2H), 3.95 (d, 7H), 3.76 (t, 2H), 2.25 (s, 3H); MS for $C_{31}H_{27}FN_4O_6$: m/z 571 (MH+).

1-(2,2-Difluoroethyl)-5-(4-fluorophenyl)-N-[4-[(7-methoxy-1,5-naphthyridin-4-yl)oxy]phenyl]-6-methyl-4-oxopyridine-3-carboxamide (629): Made in one step from Compound 147. $^1$H NMR (400 MHz, DMSO-$d_6$) δ 12.79 (s, 1H), 8.77 (s, 1H), 8.75-8.67 (m, 2H), 7.86-7.76 (m, 3H), 7.34-7.21 (m, 6H), 6.74 (d, 1H), 6.55 (t, 1H), 4.93-4.82 (m, 2H), 4.00 (s, 3H), 2.25 (s, 3H); MS for $C_{30}H_{23}F_3N_4O_4$: m/z 561 (MH+).

1-(2,2-Difluoroethyl)-N-[4-[(6,7-dimethoxy-1,5-naphthyridin-4-yl)oxy]phenyl]-5-(4-fluorophenyl)-6-methyl-4-oxopyridine-3-carboxamide (630): Made in one step from Compound 119. MS for $C_{31}H_{25}F_3N_4O_5$: m/z 591 (MH+).

N-[4-[(6,7-Dimethoxy-1,5-naphthyridin-4-yl)oxy]phenyl]-1-(2-fluoroethyl)-5-(4-fluorophenyl)-6-methyl-4-oxopyridine-3-carboxamide (631): Made in one step from Compound 119. MS for $C_{31}H_{26}F_2N_4O_5$: m/z 573 (MH+).

1-(2-Fluoroethyl)-5-(4-fluorophenyl)-N-[4-[(7-methoxy-1,5-naphthyridin-4-yl)oxy]phenyl]-6-methyl-4-oxopyridine-3-carboxamide (632): Made in one step from Compound 147. MS for $C_{30}H_{24}F_2N_4O_4$: m/z 543 (MH+).

1-(Difluoromethyl)-N-[4-[(6,7-dimethoxy-1,5-naphthyridin-4-yl)oxy]phenyl]-5-(4-fluorophenyl)-6-methyl-4-oxopyridine-3-carboxamide (633): Made in one step from Compound 119. $^1$H NMR (400 MHz, CD$_3$OD) δ 12.14 (s, 1H), 8.85 (s, 1H), 8.40 (d, 1H), 7.90 (s, 1H), 7.81-7.71 (m, 2H), 7.15-7.05 (m, 6H), 6.97 (m, 1H), 6.77 (d, 1H), 4.09 (s, 3H), 4.02 (s, 3H), 2.32 (s, 3H); MS for $C_{30}H_{23}F_3N_4O_5$: m/z 577 (MH+).

The following compounds in Table 4 were also made, using the same or similar techniques to those described in the preceding examples or using procedures reported in the literature or otherwise typically familiar to those skilled in the art.

TABLE 4

| Cpd # | Molecular Formula | Observed MS (MH+) |
|---|---|---|
| 647 | C30 H23 Cl F2 N4 O5 | 593 |
| 648 | C31 H26 F2 N4 O6 | 589.1 |
| 649 | C31 H27 F2 N5 O5 | 588.2 |
| 650 | C30 H25 F2 N5 O6 | 590.2 |
| 651 | C29 H22 F2 N4 O5 | 545.2 |
| 652 | C30 H24 F2 N4 O6 | 575.2 |
| 653 | C28 H21 F2 N5 O5 | 546.1 |
| 654 | C31 H24 F2 N4 O6 | 587.1 |
| 655 | C29 H23 F2 N5 O5 | 559.9 |
| 656 | C30 H22 F2 N4 O5 | 557.1 |
| 657 | C29 H23 F2 N5 O5 | 559.9 |
| 658 | C30 H22 F2 N4 O4 | 541.1 |
| 659 | C31 H25 F N4 O6 | 569.1 |
| 660 | C31 H25 F N4 O6 | 569.1 |
| 661 | C30 H22 F2 N4 O5 | 557 |
| 662 | C31 H24 F2 N4 O5 | 571.4 |
| 663 | C32 H28 F2 N4 O6 | 603.2 |
| 664 | C29 H21 F3 N4 O5 | 563 |
| 665 | C29 H22 F2 N4 O5 | 545 |
| 666 | C31 H25 F3 N4 O5 | 591.1 |
| 667 | C32 H28 F2 N4 O5 | 587 |
| 668 | C30 H22 F4 N4 O5 | 595 |
| 669 | C29 H21 F3 N4 O4 | 547 |
| 670 | C29 H22 F2 N4 O5 | 545 |
| 671 | C30 H25 F N4 O5 | 541 |
| 672 | C32 H29 F N4 O6 | 585 |
| 673 | C31 H27 F N4 O5 | 555 |
| 674 | C32 H29 F N4 O5 | 569 |
| 675 | C30 H24 F2 N4 O5 | 559 |
| 676 | C32 H28 F2 N4 O6 | 603 |
| 677 | C31 H26 F2 N4 O5 | 573 |
| 678 | C32 H28 F2 N4 O5 | 587 |
| 679 | C30 H24 F2 N4 O5 | 559.1 |
| 680 | C30 H25 F N4 O5 | 541.1 |
| 681 | C31 H27 F N4 O5 | 555.2 |
| 682 | C30 H25 F N4 O4 | 525.1 |
| 683 | C32 H28 F2 N4 O5 | 587.2 |
| 684 | C28 H21 F2 N5 O5 | 546.1 |
| 685 | C31 H24 F2 N4 O4 | 555.2 |
| 686 | C30 H24 F2 N4 O5 | 559 |
| 687 | C29 H21 F3 N4 O4 | 547 |
| 688 | C30 H24 F2 N4 O5 | 559 |
| 689 | C30 H24 F2 N4 O4 | 543 |
| 690 | C32 H29 F N4 O4 | 553 |
| 691 | C30 H24 F2 N4 O5 | 559 |
| 692 | C31 H27 F N4 O5 | 555 |
| 693 | C30 H24 F2 N4 O5 | 559 |
| 694 | C30 H25 F N4 O6 S | 589 |
| 695 | C31 H27 F N4 O6 | 571 |
| 696 | C30 H25 F N4 O6 | 557 |
| 697 | C29 H23 F N4 O6 S | 575 |
| 698 | C29 H22 F2 N4 O5 | 545 |
| 699 | C30 H25 F N4 O5 | 541 |
| 700 | C29 H22 F2 N4 O5 | 545 |
| 701 | C29 H22 F2 N4 O4 | 529 |
| 702 | C31 H24 F4 N4 O5 | 609.1 |
| 703 | C31 H26 F2 N4 O6 | 589.1 |
| 704 | C31 H27 F N4 O6 | 571.1 |
| 705 | C31 H27 F N4 O4 | 539 |
| 706 | C28 H19 F3 N4 O4 | 533 |
| 707 | C29 H22 F2 N4 O5 | 545 |
| 708 | C30 H23 F3 N4 O5 | 577 |
| 709 | C31 H26 F2 N4 O6 | 589 |
| 710 | C31 H26 F2 N4 O5 | 573 |
| 711 | C33 H31 F N4 O5 | 583 |
| 712 | C32 H29 F N4 O6 | 585 |
| 713 | C32 H29 F N4 O7 | 601 |
| 714 | C28 H21 F2 N5 O4 | 530.1 |
| 715 | C30 H24 F2 N4 O6 | 575 |
| 716 | C29 H22 F2 N4 O5 | 545 |
| 717 | C29 H23 F N4 O5 | 527 |

TABLE 4-continued

| Cpd # | Molecular Formula | Observed MS (MH+) |
|---|---|---|
| 718 | C30 H25 F N4 O6 | 557 |
| 719 | C29 H22 F2 N4 O4 | 529.1 |
| 720 | C32 H26 F2 N4 O6 | 601.2 |
| 721 | C29 H21 F4 N5 O5 | 596.1 |
| 722 | C32 H27 F3 N4 O5 | 605 |
| 723 | C31 H24 F4 N4 O4 | 593 |
| 724 | C32 H29 F N4 O5 | 569.2 |
| 725 | C33 H31 F N4 O6 | 599.2 |
| 726 | C31 H23 F3 N4 O4 | 573.1 |
| 727 | C31 H23 F5 N4 O5 | 627.1 |
| 728 | C32 H26 F2 N4 O5 | 585.1 |
| 729 | C30 H22 F4 N4 O5 | 595.1 |
| 730 | C32 H26 F4 N4 O5 | 623 |
| 731 | C31 H25 F3 N4 O4 | 575 |
| 732 | C29 H24 F N5 O5 | 542 |
| 733 | C28 H22 F N5 O4 | 512 |
| 734 | C28 H21 F2 N5 O4 | 530 |
| 735 | C30 H24 Cl F N4 O4 | 559 |
| 736 | C30 H23 Cl F2 N4 O4 | 577 |
| 737 | C30 H22 Cl F3 N4 O4 | 595 |
| 738 | C29 H23 F2 N5 O5 | 560.1 |
| 739 | C32 H26 F2 N4 O6 | 601.2 |
| 740 | C34 H30 F2 N4 O6 | 629.2 |
| 741 | C34 H31 F N4 O6 | 611.2 |
| 742 | C33 H28 F2 N4 O5 | 599.2 |
| 743 | C31 H26 F2 N4 O6 | 589 |
| 744 | C31 H26 F2 N4 O5 | 573 |
| 745 | C31 H26 F2 N4 O6 | 589 |
| 746 | C31 H26 F2 N4 O5 | 573 |
| 747 | C30 H24 Br F N4 O5 | 621 |
| 748 | C28 H20 F2 N4 O4 | 515.1 |
| 749 | C29 H22 F2 N4 O4 | 529.1 |
| 750 | C30 H25 F2 N5 O5 | 574.2 |
| 751 | C30 H23 F3 N4 O4 | 561.1 |
| 752 | C33 H27 F3 N4 O4 | 601.2 |
| 753 | C31 H25 F N4 O7 | 585.1 |
| 754 | C31 H24 F2 N4 O7 | 603.1 |
| 755 | C31 H27 F N4 O5 | 555.2 |
| 756 | C32 H27 F3 N4 O5 | 605.1 |
| 757 | C33 H29 F N4 O7 | 613.2 |
| 758 | C32 H26 F2 N4 O6 | 601.2 |
| 759 | C31 H24 F2 N4 O6 | 587.1 |
| 760 | C32 H28 F2 N4 O6 | 603 |
| 761 | C32 H28 F2 N4 O7 | 619 |
| 762 | C31 H27 F N4 O6 | 571 |
| 763 | C31 H27 F N4 O5 | 555 |
| 764 | C28 H21 F2 N5 O4 | 530.2 |
| 765 | C32 H28 F2 N4 O7 | 619.2 |
| 766 | C32 H26 F2 N4 O6 | 601.1 |
| 767 | C30 H23 F3 N4 O4 | 561.1 |
| 768 | C30 H22 F4 N4 O4 | 579.1 |
| 769 | C31 H25 F3 N4 O5 | 591 |
| 770 | C30 H23 Cl F2 N4 O4 | 577.1 |
| 771 | C31 H26 F2 N4 O4 | 557 |
| 772 | C32 H27 F3 N4 O5 | 605 |
| 773 | C30 H25 F2 N5 O5 | 574 |
| 774 | C32 H28 F2 N4 O5 | 587 |
| 775 | C32 H26 F2 N4 O6 | 601.1 |
| 776 | C30 H24 F3 N5 O5 | 592 |
| 777 | C30 H22 F4 N4 O5 | 595 |
| 778 | C31 H24 F4 N4 O6 | 625 |
| 779 | C29 H20 F4 N4 O4 | 565 |
| 780 | C33 H31 F N4 O6 | 599 |
| 781 | C32 H29 F N4 O5 | 569 |
| 782 | C33 H28 F2 N4 O6 | 615.1 |
| 783 | C31 H24 F2 N4 O5 | 571.1 |
| 784 | C32 H26 F2 N4 O5 | 585.1 |
| 785 | C32 H28 F2 N4 O6 | 603.1 |
| 786 | C32 H26 F4 N4 O5 | 623.2 |
| 787 | C31 H26 F2 N4 O6 | 589.1 |
| 788 | C31 H25 F3 N4 O5 | 591.1 |
| 789 | C31 H24 F4 N4 O5 | 609.1 |
| 790 | C30 H21 F5 N4 O4 | 597.1 |
| 791 | C32 H29 F N4 O5 | 569 |
| 792 | C30 H24 F2 N4 O6 | 575 |
| 793 | C29 H22 F2 N4 O5 | 545 |

TABLE 4-continued

| Cpd # | Molecular Formula | Observed MS (MH+) |
|---|---|---|
| 794 | C30 H24 F2 N4 O5 | 559 |
| 795 | C29 H22 F2 N4 O4 | 529 |
| 796 | C29 H21 F3 N4 O5 | 563 |
| 797 | C28 H19 F3 N4 O4 | 533 |
| 798 | C31 H26 F2 N4 O4 | 557 |
| 799 | C31 H25 F3 N4 O4 | 575 |
| 800 | C32 H28 F2 N4 O5 | 587 |
| 801 | C32 H27 F3 N4 O5 | 605 |
| 802 | C32 H25 F5 N4 O5 | 641.1 |
| 803 | C29 H23 F2 N5 O4 | 544 |
| 804 | C30 H25 F2 N5 O4 | 558 |
| 805 | C32 H27 F3 N4 O6 | 621 |
| 806 | C32 H27 F3 N4 O5 | 605 |
| 807 | C30 H22 F4 N4 O4 | 579 |
| 808 | C31 H24 F2 N4 O6 | 587.1 |
| 809 | C30 H22 F2 N4 O5 | 557.1 |
| 810 | C32 H26 F4 N4 O6 | 639 |
| 811 | C31 H24 F4 N4 O5 | 609 |
| 812 | C32 H26 F4 N4 O5 | 623 |
| 813 | C31 H25 F3 N4 O4 | 575 |
| 814 | C31 H24 F4 N4 O4 | 593 |
| 815 | C31 H24 F4 N4 O5 | 609 |
| 816 | C31 H23 F5 N4 O5 | 627 |
| 817 | C30 H21 F5 N4 O4 | 597 |
| 818 | C31 H26 F2 N4 O5 | 573 |
| 819 | C31 H26 F2 N4 O4 | 557 |
| 820 | C30 H23 F3 N4 O4 | 561 |
| 821 | C32 H28 F2 N4 O5 | 587 |
| 822 | C31 H25 F3 N4 O5 | 591 |
| 823 | C31 H25 F3 N4 O5 | 591 |
| 824 | C30 H23 F3 N4 O4 | 561 |

The following compounds from Table 1 were made following the method detailed in Example 1, with appropriately substituted boronic acids or esters being used in Step 2: Compounds 670, 686-701, 705-713, and 792-797.

The following compounds were made following the method detailed in Example 2 and using different combinations of the intermediate anilines and carboxylic acids described within: Compounds 656, 659, 667, 671-678, 681-683, 703-704, 719, 724-725, 732-734, 741-742, 748-749, 757-758 and 780-781.

The following compounds were made by N and/or O-alkylation methods similar to either Example 92 or Example 13 followed by amide coupling as in Example 2: Compounds 663, 685, and 728.

The following compounds were made by installing an acetyl group in a manner similar to Example 28 followed by amide coupling as in Example 2: Compounds 654, 720 and 739.

The following compounds from were made in a manner similar to Example 29 followed by amide coupling as in Example 2: Compounds 679 and 680.

The following compounds from were made in a manner similar to Example 29: Compounds 660-661 and 765-766. Alternatively, a similar sequence of reactions can be performed on an intermediate such as Compound 5-3 to form the corresponding bicyclic carboxylic acid intermediate which can then be coupled to aniline intermediates as in Example 2.

The following compounds were made by N and/or O-alkylation methods similar to Example 92: Compounds 655, 657, 721, 750, 773 and 776.

The following compounds were made by N-alkylation methods similar to Example 104: Compounds 666, 668-669, 702, 722-723, 727, 729-731, 756, 786, 788-790, 798-802, 805-807 and 810-817.

The following compounds were made by N-alkylation methods similar to General Procedure F1 followed by amide coupling as in Example 2: Compounds 771-772, 774 and 791.

The following compounds were made by a modification of General Procedure C2 where an intermediate such as Compound C3-B is N-alkylated (such as by General Procedure F1) prior to the bromination and Suzuki steps. The resulting intermediates were then coupled to anilines via Example 2: Compounds 818-824.

The following compounds were by the method of Example 2 where the corresponding anilines were made by General Procedure G using the appropriately substituted fluoronitrophenols (Compound 15) in Step 2: Compounds 743-746, 751, 762-763, 767-770 and 777-779.

Compound 647 was made by the method of Example 2. The carboxylic acid intermediate used in the amide coupling was made by the following scheme.

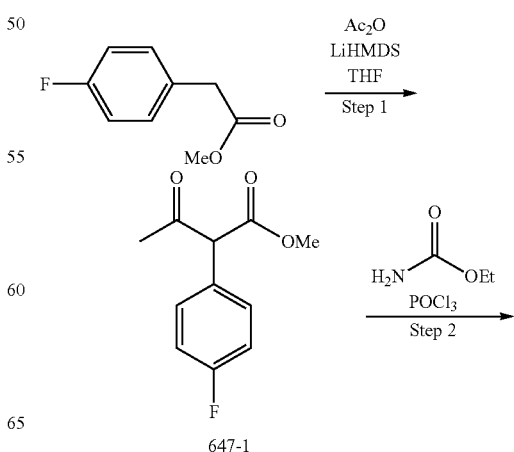

647-1

-continued
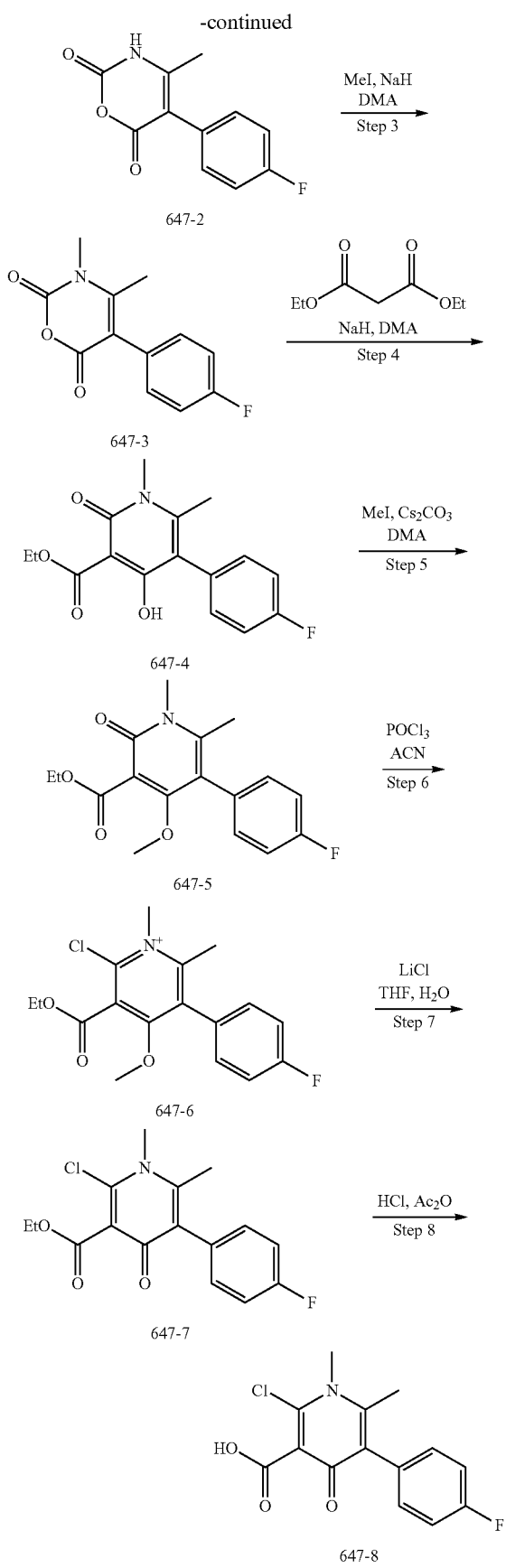
Compound 648 was made from Compound 647 using the same method employed in Example 84.
Compound 649 was made from Compound 647 using the same method employed in Example 82.
Compound 650 was made by the method of General Procedure J using Compound I3-2 and Intermediate 650-8. Intermediate 650-8 made by the following scheme.
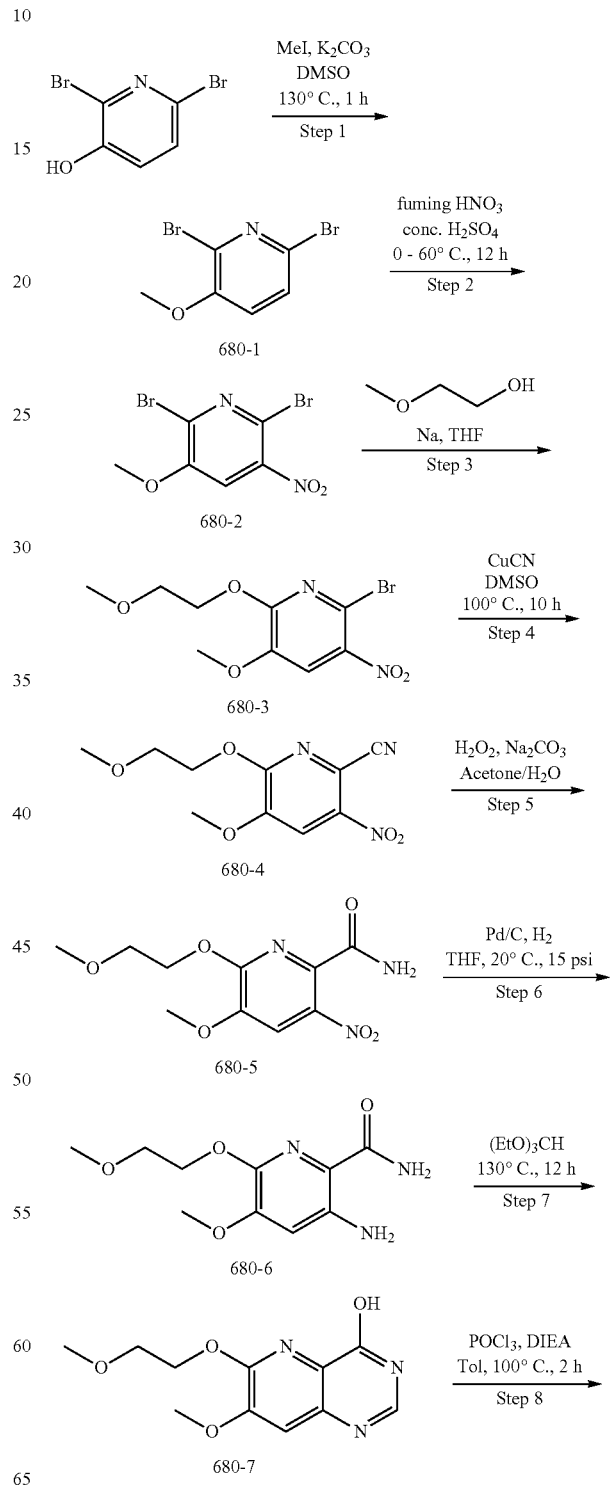

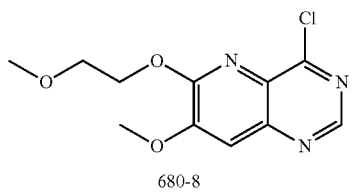
680-8

Compounds 651 and 652 were made by De-methylation using BBr₃ of Compound PA5-11, followed by protection of the resulting alcohol with TBS-C₁, coupling to the desired aniline by the method of Example 2 and subsequent deprotection of the TBS group.

Compound 653 was made by the method of Example 2. The carboxylic acid intermediate used in the amide coupling was made by the following scheme. Compound 738 was made in a similar fashion.

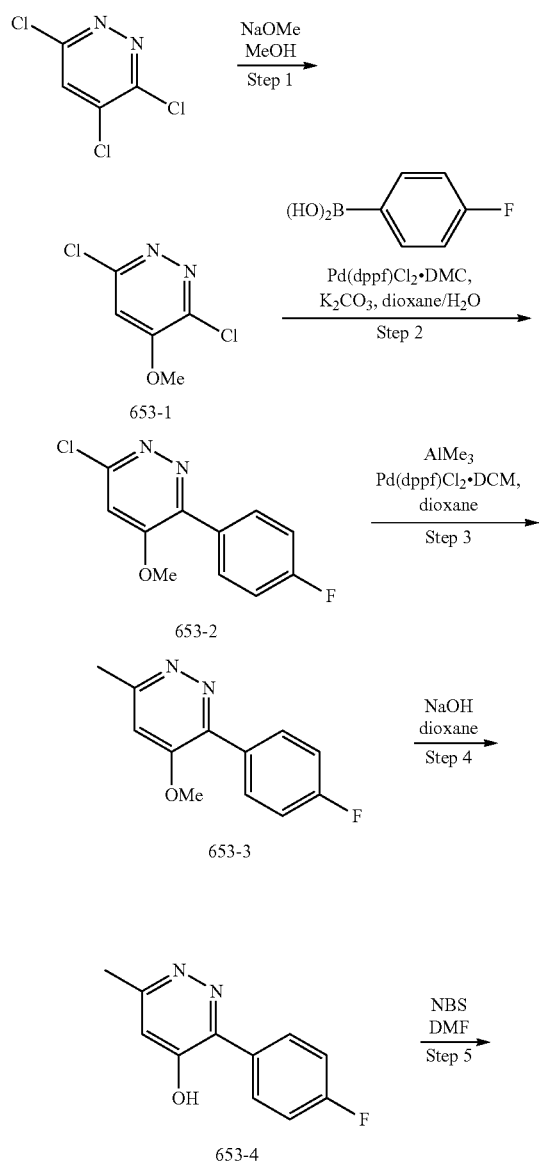

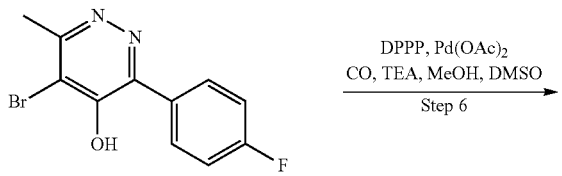
653-5

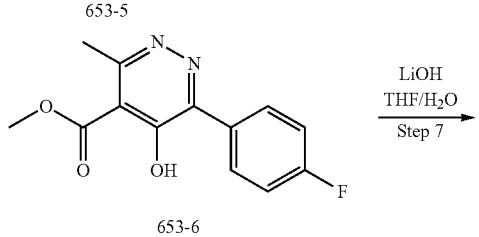
653-6

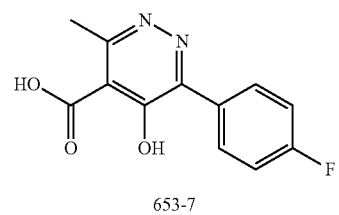
653-7

Compound 658 was made by the method of Example 2. The carboxylic acid intermediate used in the amide coupling was made by the following scheme. Compound 662 was made in a similar fashion.

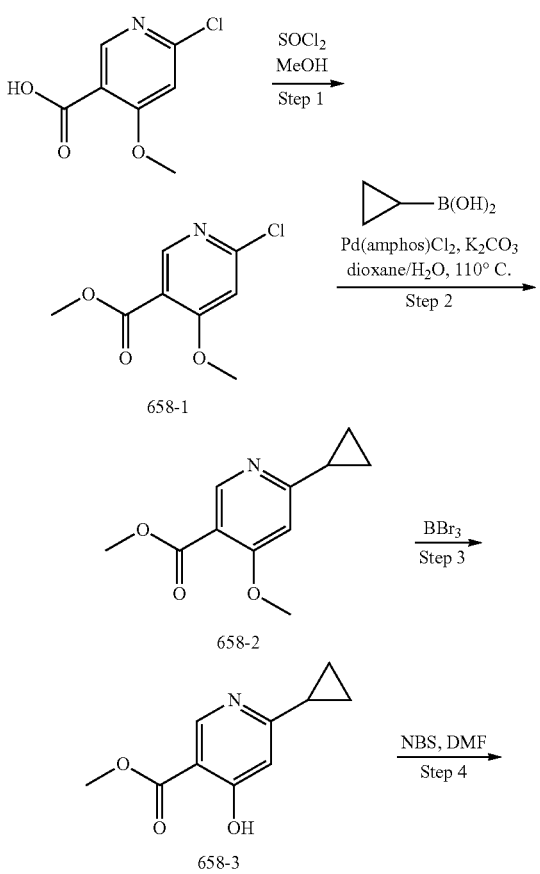

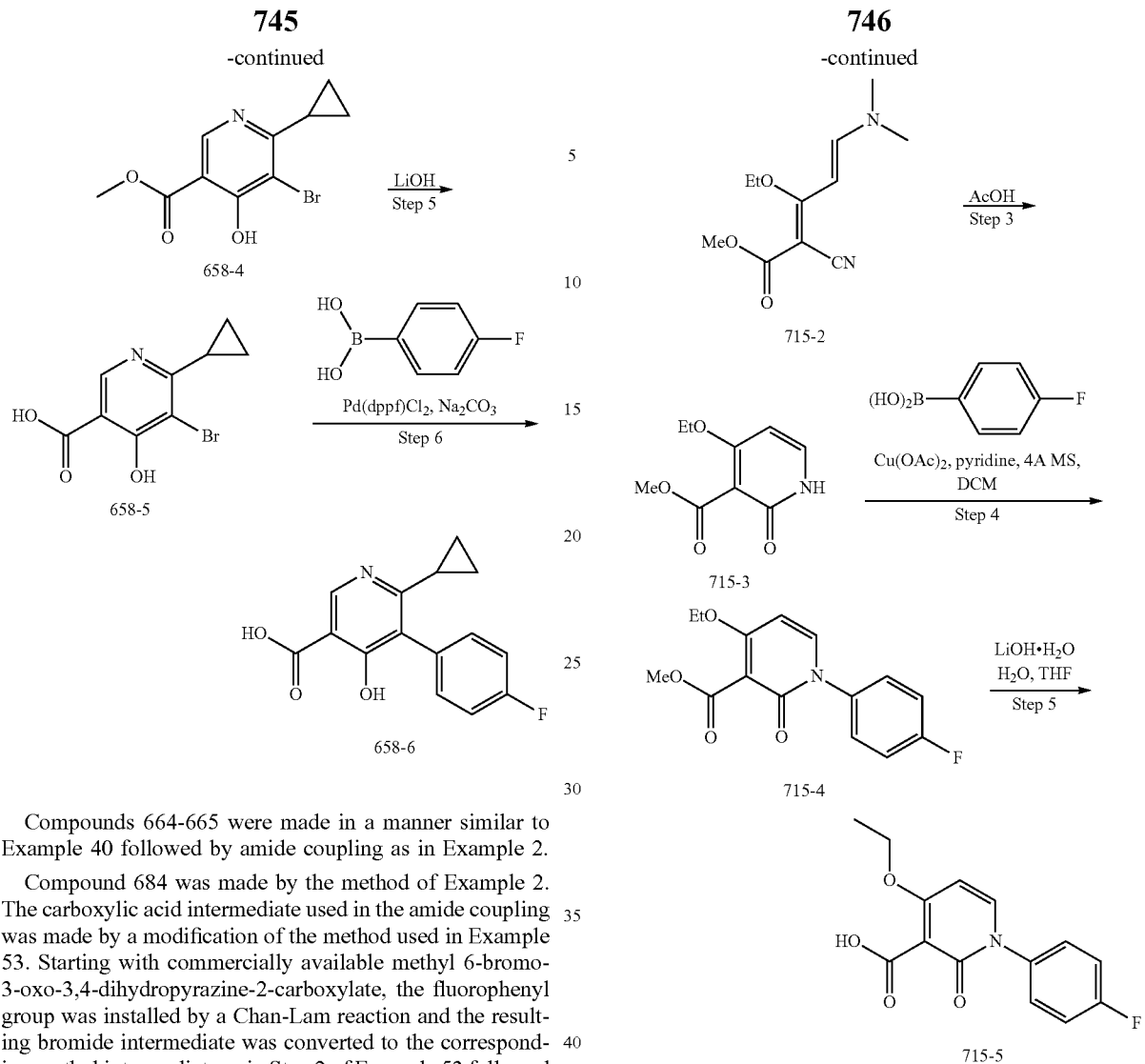

Compounds 664-665 were made in a manner similar to Example 40 followed by amide coupling as in Example 2.

Compound 684 was made by the method of Example 2. The carboxylic acid intermediate used in the amide coupling was made by a modification of the method used in Example 53. Starting with commercially available methyl 6-bromo-3-oxo-3,4-dihydropyrazine-2-carboxylate, the fluorophenyl group was installed by a Chan-Lam reaction and the resulting bromide intermediate was converted to the corresponding methyl intermediate as in Step 2 of Example 53 followed by ester hydrolysis to give the desired carboxylic acid intermediate.

Compound 714 was made by General Procedure I followed by General Procedure J.

Compound 715 was made by the method of Example 2. The carboxylic acid intermediate used in the amide coupling was made by the following scheme. Compounds 716-718 were made in a similar fashion.

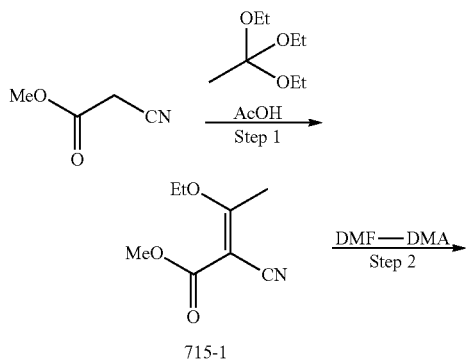

Compound 726 was made by the following scheme. Compound 752 was made in a similar fashion.

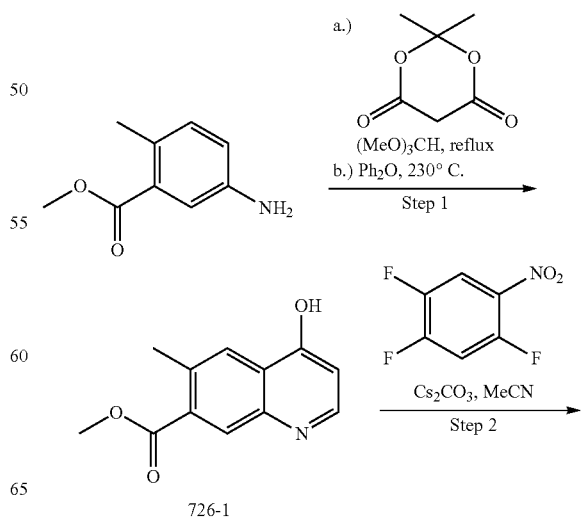

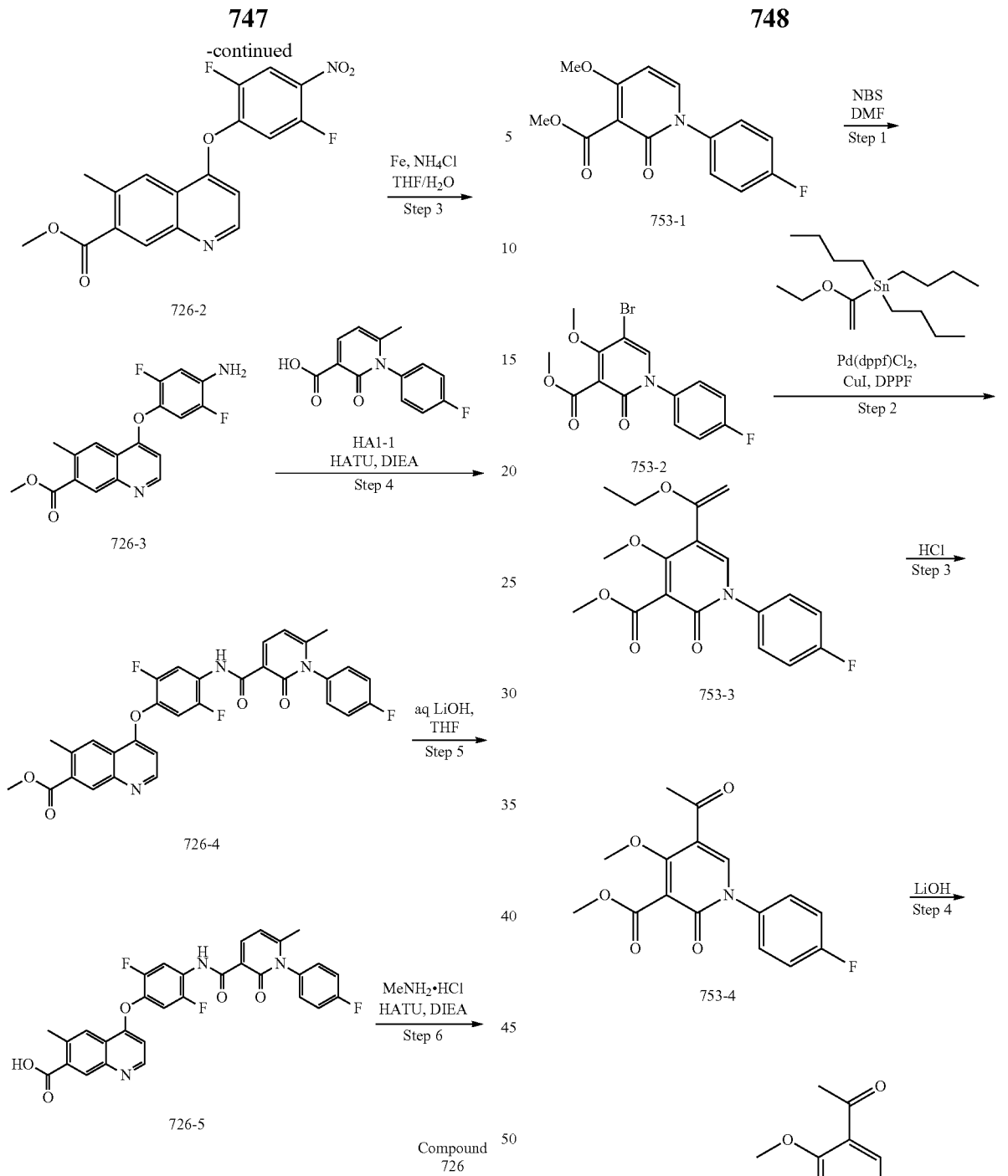

Compounds 735-737 were made by the method of Example 2. The aniline used for these compounds was made by the method of General Procedure G starting from commercially available 6-chloro-5-methoxypyridin-3-amine.

Compound 747 was made in a manner similar to Example 31 followed by amide coupling as in Example 2.

Compound 753 was made by the method of Example 2. The carboxylic acid intermediate used in the amide coupling was made by the following scheme. Intermediate 753-1 was made in the same fashion as intermediate 715-4. The rest of the scheme is very similar to the synthesis of Compound HA1-3 in Example 28. Compound 754 was made in a similar fashion.

Compound 755 was made in a manner similar to Example 32 followed by amide coupling as in Example 2.

Compound 759 was made from the double bond reduction of Compound 491.

Compound 760 was made by the method of Example 2. The aniline intermediate used in the amide coupling was made by the following scheme. Compound 761 was made in a similar fashion.

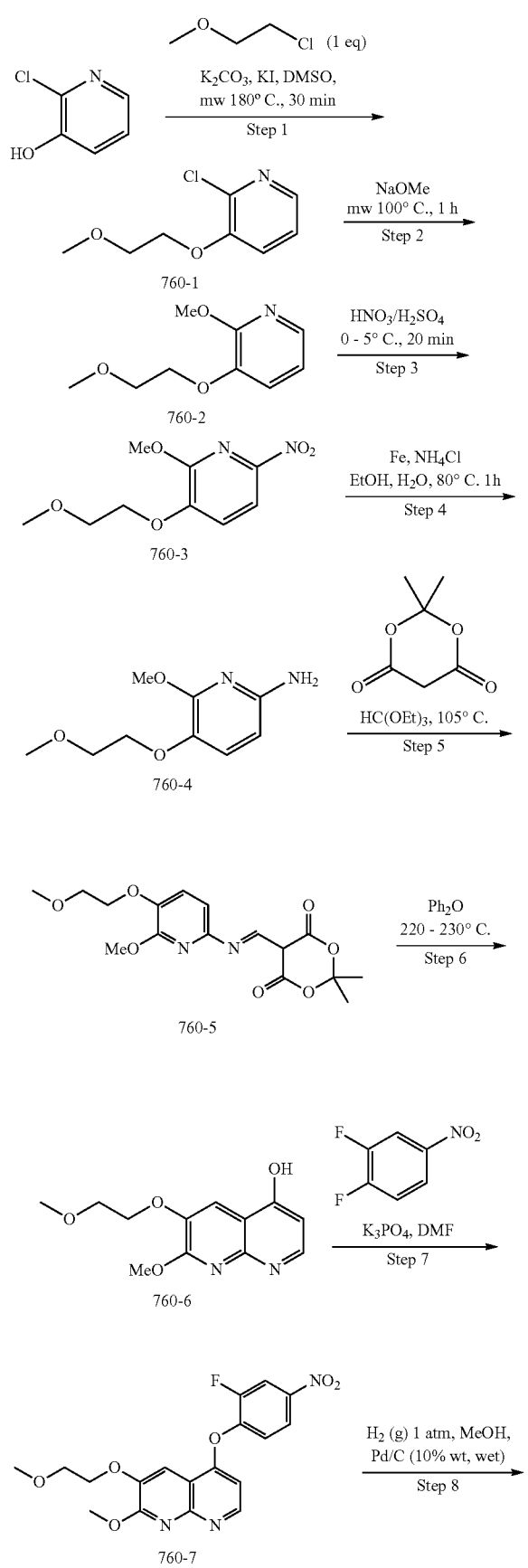

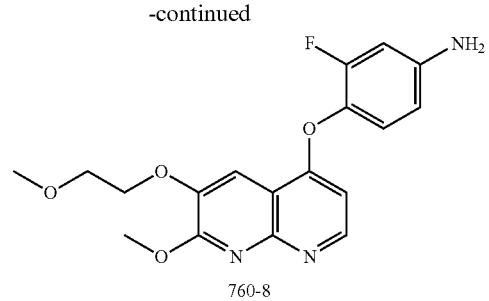

Compound 764 was made by a modification of the method of Example 1 in which Compound NA1-1 was coupled to commercially available 5-methylpyrazine-2-carboxylic acid followed by bromination and then Suzuki reaction.

Compound 775 was made by the method of Example 2. The carboxylic acid intermediate used in the amide coupling was made by the following scheme. Compounds 782-784 and 808-809 were made in a similar fashion.

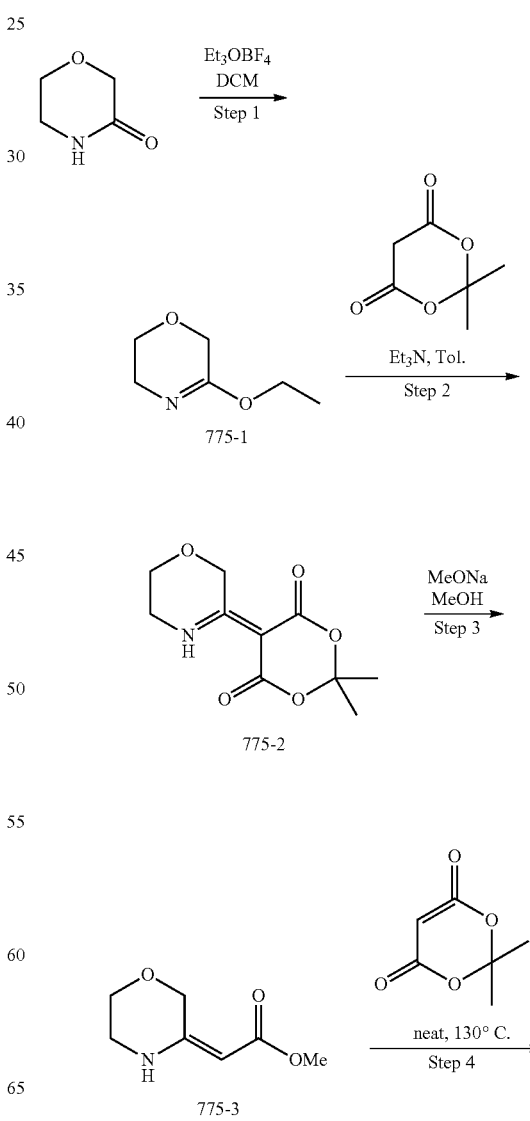

751
-continued

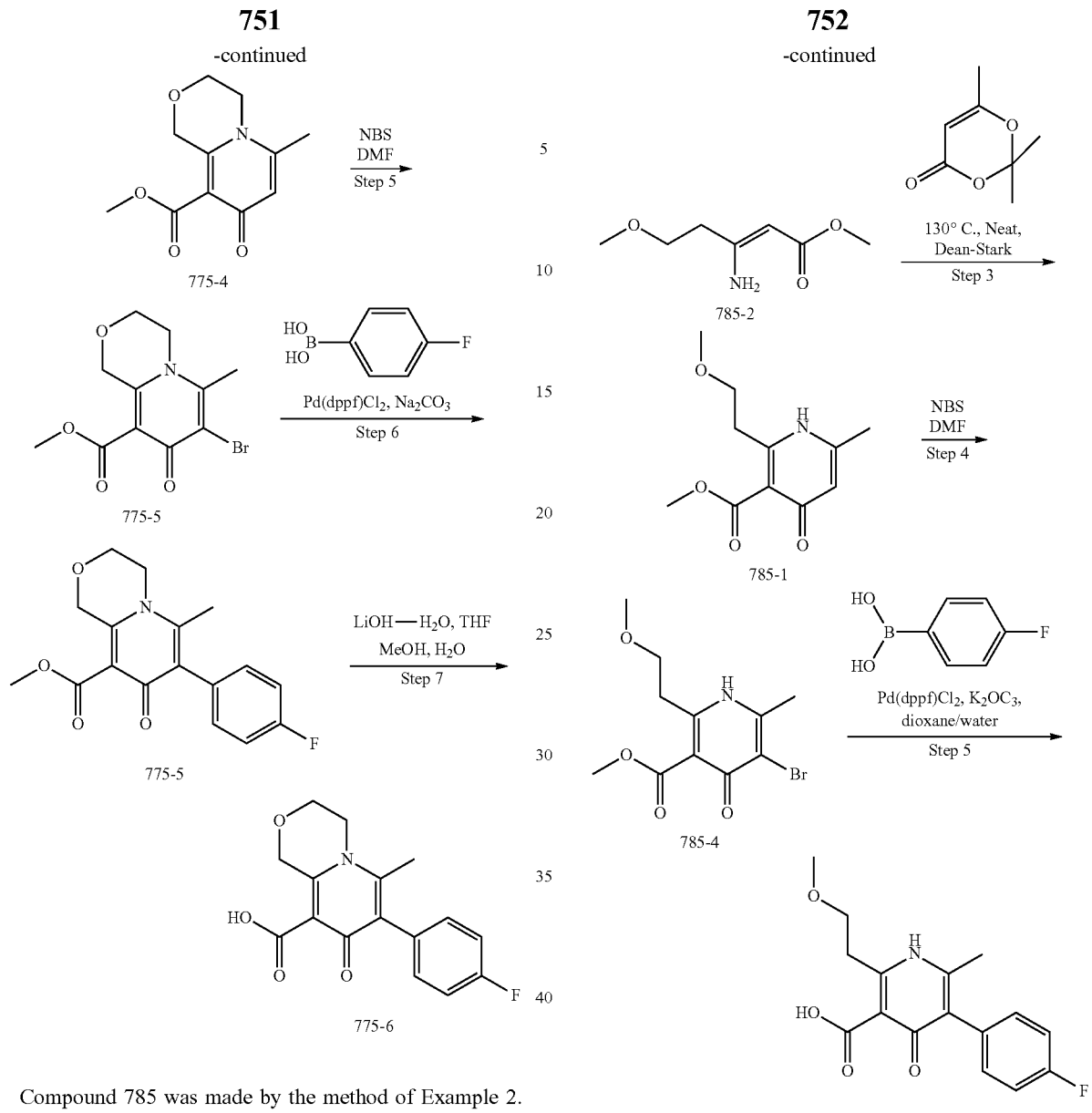

Compound 785 was made by the method of Example 2. The carboxylic acid intermediate used in the amide coupling was made by the following scheme.

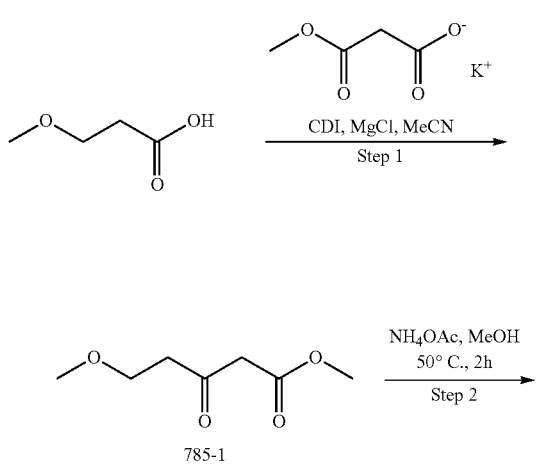

752
-continued

Compound 787 was made by reduction of the carbonyl of the acetyl group of Compound 86 to the corresponding alcohol.

Compounds 803-804 were made in a manner similar to Example 99.

Kinase Assays

Kinase activity and compound inhibition were investigated using the $^{33}$P-Phosphoryl transfer radiometric kinase assay, performed using the KinaseProfiler™ service of Eurofins Pharma Discovery Services UK Limited. Dose-response experiments were performed using nine compound concentrations in a 96-well microtiter plate. For each assay, all compounds were prepared to a 50× final assay concentration (50 μM) in 100% DMSO, then diluted in a half-log series, with the final top concentration at 1 μM. This working stock of the compound was added to the assay well as the first component in the reaction, followed by the remaining components as detailed in the following assay protocols below.

The positive control wells (100% kinase activity) contain all components of the reaction including 2% DMSO (control for solvent effects), except the compound of interest. Blank wells contain all components of the reaction, with the reference inhibitor, staurosporine. This reference compound was used to abolish kinase activity and generated the 0% kinase activity base-line. $IC_{50}$ values were calculated by nonlinear regression analysis using the sigmoidal dose-response (variable slope) curve fit on XLFit version 5.3 (ID Business Solutions).

Kinase activity and compound inhibition were also investigated using the HTRF® KinEase assay (Cisbio Cat #62TKOPEB) per manufacturer's instructions. In short, compounds were delivered in 300 nL volumes at 10 different concentrations in DMSO (3% final) to empty 384-well assay plates (Corning cat #3824). A mixture of enzyme, 1 M biotynlated peptide substrate, and buffer in 10 µL volume was added. The assay was started upon the addition of ATP (at Km). The 10 µL reaction was incubated at room temperature. The reaction was stopped upon the addition of detection buffer containing streptavidin-XL665 (5 L) and TK antibody-Eu3+(5 L). After a 60 min incubation at room temperature, the fluorescence at 665 nm and 620 nm was read on an Envision microplate reader (Perkin Elmer).

Kinase activity normalized to DMSO (100% activity) and reference compound at 1 M and (0% activity) was calculated using the fluorescence ratio 620/665×10,000. $IC_{50}$ values were calculated by nonlinear regression analysis using a 4-parameter logistic curve fit in ActivityBase XE (IDBS).

Example A: Human AXL Kinase Assay

Example A-1: Human Axl (residues H473-A894 with Q764R, 161 nM) was incubated with 8 mM MOPS pH 7.0, 0.2 mM EDTA, 250 M KKSRGDYMTMQIG (SEQ ID NO:1), 10 mM magnesium acetate and 10 µM [$\gamma$-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example A-2: Human AXL (residues 464-885; CarnaBio, 1 ng/well) was also incubated with enzymatic buffer (Cisbio) supplemented with 5 mM $MgCl_2$, 1 mM DTT, and Supplemental Enzymatic Buffer (SEB; Cisbio). The mixture was added to the pre-plated compounds. The reaction was initiated upon addition of ATP at Km (1.0 µM). The reaction was incubated at room temperature for 50 min and stopped upon the addition of SA-XL665 and TK-antibody both diluted in EDTA-containing kinase detection buffer (Cisbio). The kinase activity was calculated as stated above and the $IC_{50}$ values were reported.

Example B: Human KDR Kinase Assay

Example B-1: Human KDR (residues K790-V1356, 55 nM) was incubated with 8 mM MOPS pH 7.0, 0.2 mM EDTA, 0.33 mg/mL myelin basic protein, 10 mM magnesium acetate, and 10 µM [$\gamma$-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example B-2: Human KDR (residues 790-1356; CarnaBio, 0.1 ng/well) was also incubated with enzymatic buffer (Cisbio) supplemented with 5 mM $MgCl_2$, 1 mM $MnCl_2$, and 1 mM DTT. The mixture was added to the pre-plated compounds. The reaction was initiated upon addition of ATP at Km (4.0 µM). The reaction was incubated at room temperature for 40 min and stopped upon the addition of SA-XL665 and TK-antibody both diluted in EDTA-containing kinase detection buffer (Cisbio). The kinase activity was calculated as stated above and the $IC_{50}$ values were reported.

Example C: Human Mer Kinase Assay

Example C-1: Human Mer (residues R557-E882 with H628Q and R794A, 0.7 nM) was incubated with 8 mM MOPS pH 7.0, 0.2 mM EDTA, 30 mM NaCl, 250 µM GGMEDIYFEFMGGKKK (SEQ ID NO:2), 10 mM magnesium acetate, and 10 µM [$\gamma$-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example C-2: Human MER (residues 528-999; CarnaBio, 1 ng/well) was also incubated with enzymatic buffer (Cisbio) supplemented with 5 mM $MgCl_2$ and 1 mM DTT. The mixture was added to the pre-plated compounds. The reaction was initiated upon addition of ATP at Km (40 µM). The reaction was incubated at room temperature for 60 min and stopped upon the addition of SA-XL665 and TK-antibody both diluted in EDTA-containing kinase detection buffer (Cisbio). The kinase activity was calculated as stated above and the $IC_{50}$ values were reported.

Example D: Human Met Kinase Assay

Example D-1: Human Met (residues R974-S1390 with A1209G and V1290L, 3.4 nM) was incubated with 8 mM MOPS pH 7.0, 0.2 mM EDTA, 250 M KKKGQEEEYVFIE (SEQ ID NO:3), 1 mM sodium orthovanadate, 5 mM sodium-6-glycerophosphate, 10 mM magnesium acetate, and 10 µM [$\gamma$-$^{33}$P-ATP]. The reaction was initiated by the addition of the Mg/ATP mix. After incubation for 40 minutes at room temperature, the reaction was stopped by the addition of phosphoric acid to a concentration of 0.5%. A reaction aliquot of 10 µL was then spotted onto a P30 filtermat and washed four times for 4 minutes in 0.425% phosphoric acid and once in methanol prior to drying and scintillation counting. Incorporated $^{33}$P was measured using the Wallac Microbeta scintillation counter (Perkin Elmer).

Example D-2: Human MET (residues 956-1390; CarnaBio, 0.1 ng/well) was also incubated with enzymatic buffer (Cisbio) supplemented with 5 mM $MgCl_2$, 1 mM DTT and 1 mM $MnCl_2$. The mixture was added to the pre-plated compounds. The reaction was initiated upon addition of ATP at Km (3.0 µM). The reaction was incubated at room temperature for 40 min and stopped upon the addition of SA-XL665 and TK-antibody both diluted in EDTA-containing kinase detection buffer (Cisbio). The kinase activity was calculated as stated above and the $IC_{50}$ values were reported.

Example E: AXL Autophosphorylation ELISA in A-172 Cells

A-172 glioblastoma cells (ATCC #CRL-1620) were seeded at $2.5 \times 10^5$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). A-172 cells were incubated at 37° C., 5% $CO_2$ for 24 h and then starved for 24 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 1 g/mL recombinant human Gas6 (R&D Systems #885-GSB-500) for 15 min, washed with cold PBS, and immediately lysed with 150 µL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 µL/well added into the human phospho-AXL DuoSet IC ELISA (R&D Systems #DYC2228-2). Assay was performed according to manufacturer's instructions and sample phospho-AXL concentrations were extrapolated using human phospho-AXL control (R&D Systems #841645) as a standard. Positive control wells (100% activity) contained Gas6-stimulated, DMSO-treated cell lysates. Negative control wells (0% activity) contained Gas6-stimulated, reference inhibitor-treated cell lysates. $IC_{50}$ values were calculated by nonlinear regression analysis using a 4-parameter logistic curve fit in ActivityBase XE (IDBS).

Example F: Met Autophosphorylation ELISA in PC-3 Cells

PC-3 prostate cancer cells (ATCC #CRL-1435) were seeded at $4 \times 10^4$ cells/well onto 24-well plates (Greiner #662165), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). PC-3 cells were incubated at 37° C., 5% $CO_2$ for 24 h and then starved for 3 h in serum-free medium. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human HGF (R&D Systems #294-HG-250) for 10 min, washed with cold PBS, and immediately lysed with 130 L of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 100 µL/well added into the PathScan phospho-Met (panTyr) Sandwich ELISA (Cell Signaling Technology #7333). Assay was performed according to manufacturer's instructions. Positive control wells (100% activity) contained HGF-stimulated, DMSO-treated cell lysates. Negative control wells (0% activity) contained HGF-stimulated, reference inhibitor-treated cell lysates. $IC_{50}$ values were calculated by nonlinear regression analysis using a 4-parameter logistic curve fit in ActivityBase XE (IDBS).

Example G: KDR Autophosphorylation ELISA in HUVEC Cells

Human umbilical vein endothelial cells or HUVEC (Lonza #C2519A) were seeded at $2 \times 10^4$ cells/well onto 96-well plates (Corning #3904), in EGM-2 growth medium (Lonza #CC-3162) containing 1% Penicillin Streptomycin (Thermo Fisher #15140-122). HUVEC cells were incubated at 37° C., 5% $CO_2$ for 24 h and then starved for 24 h in serum-free EBM-2 basal medium (Lonza #CC-3156) containing 1% Penicillin Streptomycin. Test compounds were serially diluted to produce an 8-point dose curve in fresh serum-free medium to a final concentration of 0.3% DMSO (vehicle) and added to the cells and incubated for 1 h. Cells were then stimulated with 100 ng/mL recombinant human VEGF165 (R&D Systems #293-VE-500) for 5 min, washed with cold PBS, and immediately lysed with 130 L of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were collected and 100 µL/well added into the human phospho-KDR DuoSet IC ELISA (R&D Systems #DYC1766-2). Assay was performed according to manufacturer's instructions and sample phospho-KDR concentrations were extrapolated using human phospho-KDR control (R&D Systems #841421) as a standard. Positive control wells (100% activity) contained VEGF165-stimulated, DMSO-treated cell lysates. Negative control wells (0% activity) contained non-stimulated cell lysates. $IC_{50}$ values were calculated by nonlinear regression analysis using a 4-parameter logistic curve fit in ActivityBase XE (IDBS).

Example H: Mer Autophosphorylation ELISA in Transient Transfected 293A Cells 293A cells (Thermo Fisher #R70507) were seeded at $1.5 \times 10^6$ cells/well onto 100 mm dish (Greiner #664169), in DMEM (Thermo Fisher #11995-040) containing 10% FBS (Thermo Fisher #26140-079), 1% MEM NEAA (Thermo Fisher #11140-050), 1% GlutaMax (Thermo Fisher #35050-061), and 1% Penicillin Streptomycin (Thermo Fisher #15140-122). 293A cells were incubated at 37° C., 5% $CO_2$ for 24 h and then transfected with 6 g MERTK DNA (Genecopoeia #EX-Z8208-M02) using TransIT LT1 transfection reagent (Mirus-Bio #MIR2305). After 24 h incubation, the transfected 293A cells were seeded at $1 \times 10^5$ cells/well onto 96-well plates (Corning #3904) in DMEM growth medium overnight. Test compounds were serially diluted to produce an 8-point dose curve in fresh serum-free medium to a final concentration of 0.3% DMSO (vehicle) and added to the cells and incubated for 1 h. Cells were then immediately lysed with 150 µL of cold 1× lysis buffer [20 mM Tris, 137 mM sodium chloride, 2 mM EDTA, 10% glycerol, 1% NP-40 alternative, 1 mM activated sodium orthovanadate, 1 mM PefaBloc SC (Sigma-Aldrich #11429868001), protease/phosphatase inhibitor tablet (Thermo Fisher #A32959)]. Lysates were clarified by centrifugation and 50 L/well added in to the human phospho-Mer DuoSet IC ELISA (R&D Systems #DYC2579-2). Assay was performed according to manufacturer's instructions and sample phospho-Mer concentrations were extrapolated using human phospho-Mer control (R&D Systems #841793) as a standard. Positive control wells (100% activity) contained DMSO-treated cell lysates. Negative control wells (0% activity) contained reference inhibitor-treated cell lysates. $IC_{50}$ values were calculated by nonlinear regression analysis using a 4-parameter logistic curve fit in Activity-Base XE (JDBS).

Results of Examples A-H are summarized in Table 5 and Table 6. A, B, and C of Tables 5 and 6 have the following meanings: $A=IC_{50}\leq100$ nM; $B=100<IC_{50}\leq300$ nM; $C=IC_{50}>300$ nM. "NT" refers to "Not Tested." The data for compounds 21-27, 41-47, 99, and 104 in Table 5 were obtained using the protocols set forth in Examples A-1, B-1, C-1 and D-1. The data for other compounds in Table 5 were obtained using the protocols set forth in Examples A-2, B-2, C-2, and D-2.

TABLE 5

Biological Activities of Selected Compounds

| Compound No. | Axl $IC_{50}$ (nM) | Mer $IC_{50}$ (nM) | c-Met $IC_{50}$ (nM) | KDR $IC_{50}$ (nM) |
|---|---|---|---|---|
| 21 | A | A | A | A |
| 22 | A | A | A | A |
| 23 | A | B | A | A |
| 24 | A | A | A | A |
| 25 | A | A | A | A |
| 26 | A | A | A | A |
| 27 | A | A | A | A |
| 28 | A | A | A | A |
| 29 | A | A | A | A |
| 30 | A | A | A | A |
| 31 | A | A | A | A |
| 32 | A | A | A | B |
| 33 | A | A | A | A |
| 34 | A | A | B | A |
| 35 | A | A | A | A |
| 36 | A | A | A | A |
| 37 | A | A | A | B |
| 38 | A | A | A | B |
| 39 | A | A | A | A |
| 40 | A | A | A | C |
| 41 | A | A | A | A |
| 42 | A | A | A | A |
| 43 | A | A | A | A |
| 44 | A | A | A | A |
| 45 | A | A | A | A |
| 46 | A | A | A | A |
| 47 | A | A | A | A |
| 48 | A | A | A | C |
| 49 | A | NT | A | NT |
| 50 | A | NT | A | NT |
| 51 | A | NT | A | NT |
| 52 | NT | NT | A | NT |
| 53 | A | A | A | C |
| 58 | A | A | A | A |
| 59 | A | A | A | B |
| 60 | A | A | A | C |
| 61 | A | A | A | C |
| 62 | A | A | A | C |
| 63 | A | A | A | A |
| 64 | A | A | A | A |
| 65 | A | A | A | A |
| 66 | A | A | A | A |
| 67 | A | A | A | A |
| 68 | A | A | A | A |
| 69 | A | A | A | A |
| 70 | A | A | A | B |
| 71 | A | A | A | A |
| 72 | A | A | A | B |
| 73 | A | A | A | B |
| 74 | A | A | A | A |
| 75 | A | A | A | B |
| 76 | A | A | A | A |
| 77 | A | A | A | C |
| 78 | A | A | A | A |
| 79 | A | A | B | C |
| 80 | A | A | A | A |
| 81 | A | A | A | A |
| 82 | A | A | A | B |
| 83 | A | A | A | A |
| 84 | A | A | A | B |
| 85 | A | A | B | C |
| 86 | A | A | A | C |
| 87 | A | A | A | C |
| 88 | A | A | A | A |
| 89 | A | A | A | A |
| 90 | A | A | A | A |
| 91 | A | A | A | B |
| 92 | A | A | A | B |
| 93 | A | A | A | A |
| 94 | A | A | A | C |
| 95 | A | A | A | B |
| 96 | A | A | A | A |
| 97 | A | A | A | A |
| 98 | A | A | A | A |
| 99 | A | A | A | A |
| 100 | A | A | A | A |
| 101 | A | A | A | A |
| 102 | A | A | A | A |
| 103 | A | A | A | C |
| 104 | C | C | C | C |
| 105 | A | A | A | B |
| 106 | A | A | A | C |
| 107 | A | A | A | C |
| 108 | A | A | A | A |
| 109 | A | A | A | A |
| 110 | A | A | A | NT |
| 111 | A | A | A | C |
| 112 | A | A | A | C |
| 113 | A | A | B | C |
| 114 | NT | NT | A | NT |
| 115 | A | A | A | A |
| 116 | A | A | A | A |
| 117 | A | A | A | A |
| 118 | A | A | A | A |
| 119 | A | A | A | A |
| 120 | A | A | A | A |
| 121 | A | A | A | C |
| 122 | A | A | A | A |
| 123 | A | A | A | C |
| 124 | A | A | A | C |
| 125 | A | A | A | C |
| 126 | A | A | A | A |
| 127 | A | A | A | A |
| 128 | A | A | A | B |
| 129 | A | A | A | A |
| 130 | A | A | A | A |
| 131 | A | A | A | C |
| 132 | A | A | A | B |
| 133 | A | NT | A | NT |
| 134 | A | NT | A | NT |
| 135 | A | A | A | NT |
| 136 | A | A | A | NT |
| 137 | A | NT | A | NT |
| 138 | A | B | A | C |
| 139 | A | A | A | C |
| 140 | A | A | A | C |
| 141 | A | A | A | C |
| 142 | A | A | A | A |
| 143 | A | A | A | C |
| 144 | A | A | A | A |
| 145 | A | NT | A | NT |
| 146 | A | A | A | A |
| 147 | A | A | A | NT |
| 148 | A | A | A | C |
| 149 | A | A | A | B |
| 150 | A | A | A | C |
| 151 | A | A | A | C |
| 152 | A | C | C | C |
| 153 | A | A | A | C |

TABLE 5-continued

Biological Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 154 | A | A | A | A |
| 155 | A | A | A | C |
| 156 | A | A | A | C |
| 157 | A | A | A | C |
| 158 | A | NT | A | NT |
| 159 | A | NT | A | NT |
| 160 | A | A | A | A |
| 161 | A | A | A | A |
| 162 | A | B | A | C |
| 163 | A | A | A | C |
| 164 | A | A | A | C |
| 165 | A | A | A | C |
| 166 | A | A | A | C |
| 167 | A | A | A | B |
| 168 | A | A | A | B |
| 169 | A | A | A | C |
| 170 | A | A | A | C |
| 171 | A | A | A | A |
| 172 | A | A | A | B |
| 173 | A | A | A | A |
| 174 | A | A | A | A |
| 175 | A | A | A | B |
| 176 | A | A | A | C |
| 177 | A | A | A | A |
| 178 | A | A | A | A |
| 179 | A | A | A | A |
| 180 | A | A | A | A |
| 181 | A | A | A | C |
| 182 | A | A | A | B |
| 183 | A | A | A | C |
| 184 | A | A | A | A |
| 185 | A | A | A | A |
| 186 | A | A | A | A |
| 187 | A | A | A | C |
| 188 | A | A | A | A |
| 189 | A | A | A | B |
| 190 | A | A | A | A |
| 191 | A | A | A | A |
| 192 | A | A | A | A |
| 193 | A | A | A | B |
| 194 | A | A | A | B |
| 195 | A | A | B | C |
| 196 | A | A | A | B |
| 197 | A | A | A | A |
| 198 | A | A | A | B |
| 199 | A | A | A | A |
| 200 | A | A | A | C |
| 201 | A | A | A | B |
| 202 | A | A | B | B |
| 203 | A | A | B | A |
| 204 | A | A | B | B |
| 205 | A | A | A | C |
| 206 | A | A | B | C |
| 216 | A | A | A | A |
| 217 | A | A | A | B |
| 218 | A | A | A | B |
| 219 | A | A | A | A |
| 220 | A | A | A | A |
| 221 | A | A | A | B |
| 222 | A | A | A | C |
| 223 | A | A | A | C |
| 224 | A | A | A | C |
| 225 | A | A | A | A |
| 226 | A | A | A | B |
| 227 | A | A | A | A |
| 228 | A | A | A | B |
| 229 | A | A | A | A |
| 230 | A | A | A | C |
| 231 | A | A | A | B |
| 232 | A | A | A | C |
| 233 | A | A | B | A |
| 234 | A | A | C | C |
| 235 | A | A | A | A |
| 236 | A | A | A | A |
| 237 | A | A | A | A |
| 238 | A | A | A | C |
| 239 | A | A | A | C |
| 240 | A | A | A | C |
| 241 | A | A | B | C |
| 242 | A | A | A | A |
| 243 | A | A | C | C |
| 245 | A | A | A | B |
| 246 | A | A | A | A |
| 247 | A | A | A | A |
| 248 | A | A | A | C |
| 249A | A | A | A | C |
| 249B | A | A | A | C |
| 249C | A | A | A | C |
| 250 | A | A | A | C |
| 251 | A | A | A | C |
| 252 | A | A | A | B |
| 254 | A | A | A | A |
| 255 | A | A | B | C |
| 256 | A | A | A | B |
| 257 | A | A | A | A |
| 258 | A | A | A | A |
| 259 | A | A | B | B |
| 260 | A | A | A | C |
| 261 | A | A | A | C |
| 262 | A | A | A | A |
| 263 | A | A | A | C |
| 264 | A | A | A | C |
| 265 | A | A | A | C |
| 266 | A | A | A | C |
| 267 | C | C | NT | C |
| 268 | A | A | A | C |
| 269 | A | A | A | C |
| 270 | A | A | A | C |
| 271 | A | A | A | A |
| 272 | A | A | A | B |
| 273 | A | A | A | C |
| 274 | A | A | A | C |
| 275 | A | A | B | B |
| 276 | A | A | B | C |
| 277 | A | A | A | B |
| 278 | A | A | A | A |
| 279 | A | A | A | A |
| 280 | A | A | A | A |
| 281 | A | A | A | A |
| 282 | A | A | A | C |
| 283 | A | A | A | C |
| 284 | A | A | A | C |
| 285 | A | A | A | C |
| 286 | A | A | A | A |
| 287 | A | A | B | A |
| 288 | A | A | A | A |
| 289 | A | A | A | A |
| 290 | A | A | B | A |
| 291 | A | A | A | C |
| 292 | A | A | A | C |
| 293 | A | A | A | A |
| 294 | A | A | A | A |
| 295 | A | A | A | A |
| 296 | A | A | B | B |
| 297 | A | A | A | A |
| 298 | A | A | B | A |
| 299 | A | A | A | A |
| 300 | A | A | B | B |
| 301 | A | A | A | A |
| 302 | A | A | NT | C |
| 303 | A | B | NT | C |
| 304 | A | A | NT | C |
| 305 | A | A | NT | C |
| 306 | A | A | NT | C |
| 307 | A | A | NT | C |
| 308 | A | A | NT | C |
| 309 | A | A | NT | C |
| 310 | A | B | NT | C |
| 339 | A | B | B | C |
| 340 | A | A | A | A |

TABLE 5-continued

Biological Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 341 | A | A | A | C |
| 342 | A | A | A | B |
| 343 | A | A | A | B |
| 344 | A | A | B | B |
| 345 | A | A | A | B |
| 346 | A | A | A | B |
| 347 | A | A | A | B |
| 348 | A | A | A | B |
| 349 | A | A | A | A |
| 350 | A | A | A | B |
| 351 | A | A | A | C |
| 352 | A | A | A | B |
| 353 | A | A | A | C |
| 354 | A | A | A | B |
| 355 | A | A | A | A |
| 356 | A | A | B | C |
| 357 | A | A | NT | A |
| 364 | A | A | A | A |
| 365 | A | B | C | C |
| 366 | A | A | B | B |
| 367 | A | A | B | C |
| 368 | A | A | A | B |
| 369 | A | A | C | B |
| 370 | A | A | A | A |
| 371 | A | A | NT | A |
| 372 | A | A | NT | A |
| 373 | A | A | A | C |
| 374 | A | A | A | C |
| 375 | A | A | A | C |
| 376 | A | A | NT | A |
| 377 | A | A | B | A |
| 378 | A | A | A | C |
| 379 | A | A | A | A |
| 380 | A | A | A | C |
| 381 | A | A | A | C |
| 382 | A | A | A | C |
| 383 | A | A | A | C |
| 384 | A | A | A | B |
| 385 | A | A | NT | C |
| 386 | A | A | A | A |
| 388 | A | A | A | A |
| 389 | A | A | C | C |
| 390 | A | A | A | C |
| 391 | A | A | A | B |
| 392 | A | A | A | C |
| 393 | A | A | A | A |
| 394 | A | A | A | C |
| 399 | NT | A | A | C |
| 400 | A | A | A | C |
| 401 | A | A | A | C |
| 402 | A | A | A | C |
| 403 | A | A | B | C |
| 404 | A | A | A | NT |
| 405 | A | A | A | NT |
| 406 | A | A | A | C |
| 407 | A | A | A | B |
| 408 | A | A | A | A |
| 409 | A | A | A | A |
| 410 | A | A | A | C |
| 411 | A | A | A | C |
| 412 | A | A | A | A |
| 413 | A | A | A | A |
| 414 | A | A | A | C |
| 415 | A | A | A | B |
| 416 | A | A | A | C |
| 417 | A | B | A | C |
| 418 | A | A | A | B |
| 419 | A | A | A | C |
| 420 | A | A | B | B |
| 421 | A | A | B | C |
| 422 | A | A | B | A |
| 423 | A | A | B | C |
| 424 | A | A | A | A |
| 425 | A | A | A | A |
| 426 | A | A | A | B |
| 427 | A | A | B | C |
| 428 | A | A | A | B |
| 429 | A | A | A | C |
| 430 | A | A | A | C |
| 431 | A | A | A | A |
| 432 | A | A | A | A |
| 433 | A | A | A | C |
| 434 | A | A | A | C |
| 435 | A | A | A | C |
| 436 | A | A | A | B |
| 437 | A | A | A | A |
| 438 | A | A | A | A |
| 439 | A | A | B | C |
| 440 | A | A | A | C |
| 441 | A | A | B | C |
| 442 | A | A | A | A |
| 443 | A | A | A | A |
| 444 | A | C | C | C |
| 448 | A | A | A | B |
| 449 | A | A | C | C |
| 450 | A | A | A | B |
| 451 | A | A | A | A |
| 452 | A | A | C | B |
| 453 | A | A | C | B |
| 454 | A | A | A | A |
| 455 | A | A | A | A |
| 456 | A | A | A | A |
| 457 | A | A | A | A |
| 458 | A | A | B | B |
| 459 | A | A | B | B |
| 460 | A | A | B | C |
| 479 | A | A | A | A |
| 480 | A | B | B | B |
| 481 | A | A | A | B |
| 482 | A | A | A | A |
| 483 | A | B | C | C |
| 494 | A | A | A | B |
| 503 | A | A | A | A |
| 504 | A | A | A | A |
| 505 | A | B | A | C |
| 506 | A | A | A | C |
| 507 | A | B | A | C |
| 508 | A | A | A | C |
| 509 | A | A | A | A |
| 510 | A | A | A | B |
| 511 | A | A | A | B |
| 512 | A | A | A | A |
| 513 | A | A | A | A |
| 514 | A | A | A | A |
| 515 | A | A | A | A |
| 516 | A | A | A | C |
| 517 | A | A | A | A |
| 518 | A | A | A | A |
| 519 | A | A | B | C |
| 520 | A | A | A | C |
| 521 | A | A | A | C |
| 522 | A | B | B | C |
| 523 | A | A | A | C |
| 524 | A | A | B | B |
| 525 | A | A | B | C |
| 526 | A | A | B | C |
| 527 | A | A | NT | B |
| 528 | A | A | NT | B |
| 529 | A | B | NT | C |
| 530 | A | B | B | C |
| 539 | NT | A | B | B |
| 540 | A | NT | A | NT |
| 541 | A | A | A | A |
| 542 | A | A | A | B |
| 543 | A | A | B | C |
| 544 | A | A | A | A |
| 551 | A | A | A | B |
| 552 | A | A | A | A |
| 553 | A | A | A | C |
| 554 | A | A | A | A |

TABLE 5-continued

Biological Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 555 | A | A | A | A |
| 556 | A | A | B | C |
| 557 | A | A | A | B |
| 558 | A | A | B | C |
| 559 | A | A | A | C |
| 560 | A | A | A | C |
| 561 | A | A | B | C |
| 562 | A | A | B | C |
| 563 | A | A | NT | C |
| 565 | A | A | A | A |
| 566 | A | A | NT | C |
| 567 | A | A | NT | A |
| 568 | A | A | A | A |
| 569 | A | A | NT | A |
| 576 | NT | NT | A | NT |
| 577 | A | A | A | A |
| 578 | A | A | A | B |
| 579 | A | A | A | C |
| 580 | A | A | A | C |
| 581 | A | A | A | A |
| 582 | A | A | A | A |
| 583 | A | A | A | C |
| 584 | A | A | A | A |
| 585 | A | A | A | C |
| 586 | A | A | A | C |
| 587 | A | A | A | C |
| 588 | A | A | A | C |
| 589 | A | A | A | A |
| 590 | A | A | C | C |
| 591 | A | B | C | C |
| 592 | A | A | C | C |
| 593 | A | B | B | C |
| 594 | A | A | A | C |
| 595 | A | A | B | B |
| 596 | A | A | A | C |
| 597 | A | C | B | C |
| 598 | A | A | A | B |
| 604 | A | NT | A | NT |
| 605 | A | A | A | NT |
| 606 | A | A | A | NT |
| 607 | A | NT | A | NT |
| 608 | A | NT | A | NT |
| 609 | A | A | A | NT |
| 610 | A | A | A | B |
| 611 | A | A | A | A |
| 612 | A | A | A | C |
| 613 | A | A | A | C |
| 614 | A | A | A | C |
| 615 | A | A | A | A |
| 616 | A | A | A | C |
| 617 | A | A | A | B |
| 618 | A | A | A | B |
| 619 | A | A | A | C |
| 620 | A | A | A | C |
| 621 | A | A | A | C |
| 636 | A | A | A | A |
| 637 | A | A | A | C |
| 639 | A | A | A | C |
| 640 | A | A | A | C |
| 641 | A | A | B | C |
| 642 | NT | A | A | A |
| 643 | A | A | A | A |
| 644 | A | A | A | B |
| 645 | A | A | A | A |

TABLE 6

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 21 | A | A | A | A |
| 22 | A | A | A | B |
| 23 | A | A | B | C |
| 24 | A | A | A | B |
| 25 | A | A | A | B |
| 26 | A | A | A | A |
| 27 | A | A | A | A |
| 28 | A | A | A | A |
| 29 | A | A | A | B |
| 30 | A | A | A | C |
| 31 | A | A | B | C |
| 32 | A | A | A | C |
| 33 | A | A | A | A |
| 35 | A | A | A | A |
| 36 | A | A | A | B |
| 37 | A | A | A | B |
| 38 | A | A | B | A |
| 39 | A | A | A | A |
| 40 | A | A | A | A |
| 41 | A | A | A | B |
| 42 | A | A | A | A |
| 43 | A | A | A | A |
| 44 | A | A | A | B |
| 45 | A | A | A | A |
| 46 | A | A | A | B |
| 47 | A | A | A | C |
| 48 | A | A | A | C |
| 49 | A | A | A | C |
| 50 | A | A | A | B |
| 51 | A | A | A | C |
| 52 | A | A | A | C |
| 53 | A | A | A | C |
| 54 | A | A | A | C |
| 55 | A | A | A | C |
| 56 | A | A | A | C |
| 57 | A | A | A | C |
| 58 | A | A | A | A |
| 59 | A | A | A | C |
| 60 | A | A | A | C |
| 61 | A | A | A | C |
| 62 | A | A | A | C |
| 63 | A | A | A | A |
| 64 | A | A | A | A |
| 65 | A | A | A | A |
| 66 | A | A | A | A |
| 67 | A | A | A | A |
| 68 | A | A | A | A |
| 69 | A | A | A | A |
| 70 | A | A | A | A |
| 71 | A | A | A | A |
| 72 | A | A | A | B |
| 73 | A | A | A | A |
| 74 | A | A | A | B |
| 75 | A | A | A | A |
| 76 | A | A | A | A |
| 77 | A | A | A | C |
| 78 | A | A | A | B |
| 79 | A | A | B | NT |
| 80 | A | A | A | A |
| 81 | A | A | A | A |
| 82 | A | A | A | B |
| 83 | A | A | A | A |
| 84 | A | A | A | A |
| 85 | A | A | A | A |
| 86 | A | A | A | B |
| 87 | A | A | A | C |
| 88 | A | A | A | A |
| 89 | A | A | A | A |
| 90 | A | A | A | A |
| 91 | A | A | A | B |
| 92 | A | A | A | A |
| 93 | A | A | A | A |
| 94 | A | A | A | C |
| 95 | A | A | A | C |
| 96 | A | A | A | A |

TABLE 6-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 97 | A | A | A | A |
| 98 | A | A | A | A |
| 99 | A | A | A | A |
| 100 | A | A | A | A |
| 101 | A | A | A | A |
| 102 | A | A | A | A |
| 104 | A | A | A | A |
| 105 | A | A | A | A |
| 106 | A | A | A | B |
| 107 | A | A | B | B |
| 108 | A | A | B | A |
| 109 | A | A | A | A |
| 110 | A | A | A | C |
| 111 | A | A | B | C |
| 112 | A | A | A | C |
| 113 | A | A | A | C |
| 115 | A | A | A | C |
| 116 | A | A | A | A |
| 117 | A | A | A | A |
| 118 | A | A | A | A |
| 119 | A | A | A | A |
| 120 | A | A | A | A |
| 121 | A | A | A | C |
| 122 | A | A | A | B |
| 123 | A | A | A | C |
| 124 | A | A | A | NT |
| 125 | A | A | A | C |
| 126 | A | A | A | A |
| 127 | A | A | A | A |
| 128 | A | A | A | A |
| 129 | A | A | B | A |
| 130 | A | A | A | A |
| 131 | A | A | A | C |
| 132 | A | A | B | B |
| 133 | A | B | B | B |
| 134 | A | B | C | A |
| 135 | A | A | A | A |
| 136 | A | A | A | A |
| 137 | A | A | A | B |
| 138 | A | B | C | B |
| 139 | A | A | B | C |
| 140 | A | A | A | C |
| 141 | A | A | A | NT |
| 142 | A | A | A | A |
| 143 | A | A | A | B |
| 144 | A | A | A | A |
| 145 | A | A | A | NT |
| 146 | A | A | A | A |
| 147 | A | A | A | A |
| 148 | A | A | A | C |
| 149 | A | A | A | NT |
| 151 | A | A | A | A |
| 153 | A | A | A | C |
| 154 | A | A | A | A |
| 155 | A | A | B | C |
| 156 | A | A | A | C |
| 157 | A | A | A | B |
| 158 | A | A | A | A |
| 159 | A | A | B | C |
| 160 | A | NT | A | A |
| 162 | A | A | B | C |
| 163 | A | A | A | C |
| 164 | A | A | A | C |
| 165 | A | A | NT | NT |
| 166 | A | A | A | C |
| 167 | A | A | A | A |
| 168 | A | A | A | B |
| 169 | NT | A | A | C |
| 170 | A | A | A | C |
| 171 | A | A | A | A |
| 172 | A | A | A | A |
| 173 | A | A | A | A |
| 174 | A | A | A | A |
| 175 | A | A | A | A |
| 176 | A | A | A | A |
| 177 | A | A | A | A |
| 178 | A | A | A | A |
| 179 | A | A | A | A |
| 180 | A | A | A | A |
| 181 | A | A | A | C |
| 182 | A | A | A | A |
| 183 | A | A | B | C |
| 184 | A | A | A | A |
| 185 | A | A | A | A |
| 186 | A | A | A | A |
| 187 | A | A | A | C |
| 188 | A | A | A | A |
| 189 | A | A | A | A |
| 190 | A | A | A | A |
| 191 | A | A | A | A |
| 192 | A | A | A | A |
| 193 | A | A | A | A |
| 194 | A | A | A | A |
| 195 | A | A | A | A |
| 196 | A | A | A | A |
| 197 | NT | A | A | A |
| 198 | A | A | A | A |
| 199 | A | A | A | A |
| 200 | A | A | A | A |
| 201 | A | A | A | A |
| 202 | A | A | A | A |
| 203 | A | A | A | A |
| 204 | A | A | A | A |
| 205 | A | A | A | A |
| 206 | A | A | A | A |
| 207 | A | A | A | A |
| 208 | A | A | A | A |
| 209 | A | A | A | NT |
| 210 | A | A | A | NT |
| 211 | A | A | A | NT |
| 212 | A | A | A | NT |
| 213 | A | A | A | NT |
| 214 | A | A | A | NT |
| 216 | A | A | A | A |
| 217 | A | A | A | A |
| 218 | A | A | A | A |
| 219 | A | A | A | A |
| 220 | A | A | A | A |
| 221 | A | A | A | B |
| 222 | A | A | A | C |
| 223 | A | A | A | C |
| 224 | A | A | B | C |
| 225 | A | A | A | A |
| 226 | A | A | A | A |
| 227 | A | A | A | A |
| 228 | A | A | A | C |
| 229 | A | A | A | A |
| 230 | A | A | B | B |
| 231 | A | A | A | A |
| 232 | A | A | A | B |
| 233 | A | A | B | A |
| 234 | A | A | A | B |
| 235 | A | A | A | A |
| 236 | A | A | A | A |
| 237 | A | A | A | A |
| 238 | A | A | A | NT |
| 239 | A | A | B | C |
| 240 | A | A | A | C |
| 241 | A | A | A | C |
| 242 | A | A | A | A |
| 243 | A | A | A | C |
| 244 | A | A | A | C |
| 245 | A | A | A | A |
| 246 | A | A | A | A |
| 247 | A | A | A | A |
| 248 | A | A | A | C |
| 249A | A | A | A | B |
| 249B | A | A | A | A |
| 249C | A | A | A | A |
| 250 | A | A | A | C |

TABLE 6-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 251 | A | A | A | C |
| 252 | A | A | A | A |
| 253 | A | A | A | A |
| 254 | A | A | A | A |
| 255 | NT | A | B | NT |
| 256 | A | A | B | C |
| 257 | A | A | A | A |
| 258 | A | A | A | B |
| 259 | A | A | A | B |
| 260 | A | A | B | C |
| 261 | A | A | A | C |
| 262 | A | A | A | A |
| 263 | A | A | A | C |
| 264 | A | A | A | C |
| 265 | A | A | A | B |
| 266 | A | A | A | C |
| 267 | A | NT | A | C |
| 268 | A | A | A | C |
| 269 | A | A | A | C |
| 270 | A | A | B | C |
| 271 | A | A | A | B |
| 272 | A | A | A | C |
| 273 | A | A | A | C |
| 274 | A | A | A | C |
| 275 | A | A | A | A |
| 276 | A | A | B | A |
| 277 | A | A | A | A |
| 278 | A | A | A | A |
| 279 | A | A | A | A |
| 280 | A | A | A | A |
| 281 | A | A | A | A |
| 282 | A | A | A | A |
| 283 | A | A | A | B |
| 284 | A | A | A | C |
| 285 | A | A | A | C |
| 286 | A | A | A | A |
| 287 | A | A | A | A |
| 288 | A | A | A | A |
| 289 | A | A | A | A |
| 290 | A | A | A | A |
| 291 | A | A | A | A |
| 292 | A | A | A | A |
| 293 | A | A | A | A |
| 294 | A | A | A | A |
| 295 | A | A | A | A |
| 296 | A | A | A | A |
| 297 | A | A | A | A |
| 298 | A | A | A | A |
| 299 | A | A | A | A |
| 300 | A | A | A | A |
| 301 | A | A | A | A |
| 302 | A | A | A | B |
| 303 | C | A | A | C |
| 304 | B | A | A | B |
| 305 | A | A | A | B |
| 306 | A | A | A | B |
| 307 | A | A | A | C |
| 308 | A | A | A | A |
| 309 | A | A | A | C |
| 310 | A | A | A | C |
| 311 | A | A | A | A |
| 312 | A | A | A | B |
| 313 | A | A | A | A |
| 314 | A | A | A | A |
| 315 | A | A | A | A |
| 316 | A | A | A | A |
| 317 | A | A | A | A |
| 318 | A | A | A | C |
| 319 | A | A | A | C |
| 320 | A | A | A | C |
| 321 | A | A | A | B |
| 322 | A | A | A | B |
| 323 | A | A | A | B |
| 324 | A | A | A | A |
| 325 | A | A | A | A |
| 326 | A | A | A | B |
| 327 | A | A | A | A |
| 328 | A | A | A | C |
| 329 | A | A | A | B |
| 330 | A | A | A | C |
| 331 | A | A | A | C |
| 332 | A | A | A | A |
| 333 | A | A | A | B |
| 334 | B | A | A | A |
| 335 | A | A | A | C |
| 336 | A | A | A | NT |
| 337 | A | A | A | NT |
| 338 | A | A | A | NT |
| 340 | A | A | A | A |
| 341 | A | A | A | C |
| 342 | A | A | A | A |
| 343 | A | A | A | A |
| 345 | A | A | A | A |
| 346 | A | A | A | A |
| 347 | A | A | A | A |
| 348 | A | A | A | A |
| 349 | A | A | A | A |
| 350 | A | A | A | A |
| 351 | A | A | A | A |
| 352 | A | A | A | A |
| 353 | A | A | A | A |
| 354 | A | A | A | A |
| 355 | A | A | A | A |
| 356 | A | A | A | C |
| 357 | A | A | A | NT |
| 358 | A | A | A | A |
| 359 | A | A | A | C |
| 360 | A | A | B | C |
| 361 | A | A | A | A |
| 362 | A | A | A | A |
| 363 | A | A | A | A |
| 364 | A | A | A | A |
| 366 | A | A | A | NT |
| 367 | A | A | A | B |
| 368 | A | A | A | A |
| 369 | A | A | A | A |
| 370 | A | A | A | A |
| 371 | A | A | A | A |
| 372 | A | A | A | A |
| 373 | A | A | A | C |
| 374 | A | A | A | C |
| 375 | A | A | A | C |
| 376 | A | A | A | A |
| 377 | A | A | A | A |
| 378 | A | A | A | C |
| 379 | A | A | A | A |
| 380 | A | A | A | C |
| 381 | A | A | A | C |
| 382 | A | A | A | C |
| 383 | A | A | A | C |
| 384 | A | A | A | A |
| 385 | A | A | A | C |
| 386 | A | A | A | A |
| 387 | A | A | A | A |
| 388 | A | A | A | A |
| 389 | A | A | A | C |
| 390 | A | A | A | A |
| 391 | A | A | A | C |
| 392 | A | A | A | C |
| 393 | A | A | A | A |
| 394 | A | A | A | C |
| 395 | A | A | A | A |
| 396 | A | A | A | A |
| 398 | A | A | A | NT |
| 399 | A | A | A | C |
| 400 | A | A | A | C |
| 401 | A | A | A | C |
| 402 | A | A | A | C |
| 403 | A | A | A | B |
| 404 | A | A | A | A |

TABLE 6-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 405 | A | A | A | C |
| 406 | A | A | A | A |
| 407 | A | A | A | C |
| 408 | A | A | A | A |
| 409 | A | A | A | A |
| 410 | A | B | B | C |
| 411 | A | A | A | C |
| 412 | A | A | A | A |
| 413 | A | A | A | A |
| 414 | A | A | A | A |
| 415 | A | A | A | A |
| 416 | NT | A | A | A |
| 417 | A | B | A | B |
| 418 | A | A | A | A |
| 419 | A | A | A | A |
| 420 | A | A | A | A |
| 421 | A | A | A | A |
| 422 | A | A | A | A |
| 423 | A | A | A | A |
| 424 | A | A | A | A |
| 425 | A | A | A | A |
| 426 | A | A | A | A |
| 427 | A | A | A | A |
| 428 | A | A | A | A |
| 429 | B | A | A | C |
| 430 | A | A | A | C |
| 431 | A | A | A | A |
| 432 | A | A | A | A |
| 433 | A | A | A | C |
| 434 | A | A | A | C |
| 435 | A | A | A | C |
| 436 | A | A | A | A |
| 437 | A | A | A | A |
| 438 | A | A | A | A |
| 439 | A | A | A | C |
| 440 | A | A | A | C |
| 441 | A | A | A | C |
| 442 | A | A | A | A |
| 443 | C | A | B | C |
| 445 | A | A | A | A |
| 446 | A | A | A | A |
| 448 | A | A | A | A |
| 450 | A | A | A | A |
| 451 | A | A | A | A |
| 454 | A | A | A | A |
| 455 | A | A | A | A |
| 456 | A | A | A | A |
| 457 | A | A | A | A |
| 458 | A | A | A | A |
| 459 | A | A | A | A |
| 460 | A | A | A | A |
| 461 | A | A | A | A |
| 462 | A | A | A | A |
| 463 | A | A | A | A |
| 464 | A | A | A | A |
| 465 | A | A | A | B |
| 466 | A | A | A | A |
| 467 | A | A | A | A |
| 468 | A | A | A | A |
| 469 | A | A | A | A |
| 470 | A | A | A | A |
| 471 | A | A | A | A |
| 472 | A | A | A | A |
| 473 | A | A | C | C |
| 474 | A | A | A | A |
| 475 | A | A | A | A |
| 476 | A | A | A | A |
| 477 | A | A | A | C |
| 478 | A | A | A | A |
| 479 | A | A | A | A |
| 480 | A | A | A | A |
| 481 | A | A | A | A |
| 482 | A | A | A | A |
| 483 | A | A | A | C |
| 484 | A | A | A | A |
| 485 | A | A | A | A |
| 486 | A | A | A | A |
| 487 | A | A | A | A |
| 488 | B | A | C | C |
| 489 | A | A | A | A |
| 490 | B | A | A | A |
| 491 | A | A | A | C |
| 492 | B | A | A | NT |
| 493 | A | A | A | NT |
| 494 | A | A | A | A |
| 496 | A | A | A | A |
| 497 | A | A | A | C |
| 498 | A | A | A | C |
| 499 | A | A | A | B |
| 500 | A | A | A | B |
| 501 | A | A | A | A |
| 502 | A | A | A | A |
| 503 | A | A | A | A |
| 504 | A | A | A | A |
| 505 | A | B | A | A |
| 506 | A | A | A | A |
| 507 | A | B | NT | A |
| 508 | A | A | A | C |
| 509 | A | A | A | A |
| 510 | A | A | A | A |
| 511 | A | A | A | B |
| 512 | A | A | A | A |
| 513 | A | A | A | A |
| 514 | A | A | A | A |
| 515 | A | A | A | A |
| 516 | A | A | A | B |
| 517 | A | A | A | A |
| 518 | A | A | A | A |
| 519 | A | A | A | A |
| 520 | A | A | A | A |
| 521 | A | C | B | C |
| 522 | A | C | A | C |
| 523 | A | A | A | C |
| 524 | A | A | A | B |
| 525 | A | A | A | A |
| 526 | A | A | A | A |
| 527 | A | A | A | A |
| 528 | A | A | A | A |
| 529 | A | A | A | A |
| 530 | A | A | A | A |
| 531 | A | A | A | A |
| 532 | A | A | A | C |
| 533 | A | A | A | A |
| 534 | A | A | A | A |
| 535 | A | A | A | C |
| 536 | C | C | C | C |
| 537 | A | A | A | A |
| 538 | A | A | A | A |
| 539 | A | A | A | C |
| 540 | A | A | B | A |
| 541 | A | A | A | A |
| 542 | A | A | A | A |
| 543 | A | A | A | B |
| 544 | A | A | A | A |
| 551 | A | A | A | A |
| 552 | A | A | A | A |
| 553 | A | B | A | C |
| 554 | A | A | A | A |
| 555 | A | A | A | A |
| 556 | A | A | A | A |
| 557 | A | A | A | B |
| 558 | A | A | A | B |
| 559 | NT | A | A | C |
| 560 | A | A | A | B |
| 561 | A | A | A | C |
| 562 | A | A | A | B |
| 563 | A | A | A | C |
| 564 | A | A | A | B |
| 565 | A | A | A | A |
| 566 | A | A | A | C |

TABLE 6-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 567 | A | A | A | A |
| 568 | A | A | A | A |
| 569 | A | A | A | A |
| 570 | A | A | A | A |
| 571 | A | A | A | A |
| 572 | A | A | A | A |
| 573 | A | A | A | A |
| 574 | A | A | A | A |
| 575 | A | A | A | A |
| 576 | A | A | A | C |
| 577 | A | B | A | A |
| 578 | B | C | C | C |
| 579 | A | A | A | C |
| 580 | A | A | A | C |
| 581 | A | A | B | C |
| 582 | A | A | A | B |
| 584 | A | B | A | A |
| 585 | A | A | A | C |
| 586 | A | A | B | C |
| 587 | A | A | A | C |
| 588 | A | A | A | C |
| 589 | A | A | A | A |
| 593 | A | A | A | A |
| 594 | A | A | A | A |
| 595 | A | A | A | A |
| 596 | A | A | A | A |
| 597 | B | NT | NT | B |
| 598 | A | A | A | A |
| 599 | A | A | A | NT |
| 601 | C | A | C | C |
| 602 | B | A | B | NT |
| 604 | A | A | A | A |
| 605 | A | A | A | B |
| 606 | A | A | A | B |
| 607 | A | A | A | A |
| 608 | A | A | A | A |
| 609 | A | A | A | A |
| 610 | A | A | A | A |
| 611 | A | A | A | A |
| 612 | A | A | B | C |
| 613 | A | A | A | C |
| 614 | A | A | B | C |
| 615 | NT | A | A | A |
| 616 | NT | B | C | A |
| 617 | NT | A | A | A |
| 618 | NT | A | B | A |
| 619 | A | A | A | A |
| 620 | A | A | B | C |
| 621 | A | B | NT | B |
| 622 | A | A | A | NT |
| 623 | A | A | A | NT |
| 624 | A | A | A | NT |
| 625 | A | A | A | NT |
| 626 | A | A | A | NT |
| 635 | A | A | A | A |
| 636 | A | A | A | C |
| 637 | A | A | A | C |
| 638 | A | A | A | A |
| 639 | A | A | A | A |
| 640 | A | A | A | C |
| 641 | A | A | A | A |
| 642 | A | A | A | A |
| 643 | A | A | A | A |
| 644 | A | A | A | A |
| 645 | A | A | A | A |
| 646 | A | A | A | A |
| 647 | A | A | A | C |
| 648 | A | A | A | B |
| 649 | B | A | A | C |
| 650 | A | A | A | A |
| 651 | A | A | A | A |
| 652 | A | A | A | A |
| 653 | A | A | A | A |
| 654 | A | A | A | A |
| 655 | A | A | A | A |
| 656 | A | A | A | C |
| 657 | A | A | A | A |
| 658 | A | A | A | C |
| 659 | A | A | A | C |
| 660 | A | A | A | B |
| 661 | A | A | A | C |
| 662 | A | A | A | B |
| 663 | A | A | A | C |
| 664 | A | A | A | A |
| 665 | A | A | A | B |
| 666 | A | A | A | B |
| 667 | A | A | A | C |
| 668 | A | A | A | A |
| 669 | A | A | A | C |
| 670 | A | A | A | A |
| 671 | A | A | A | A |
| 672 | A | A | A | A |
| 673 | A | A | A | A |
| 674 | A | A | A | A |
| 675 | A | A | A | A |
| 676 | A | A | A | A |
| 677 | A | A | A | A |
| 678 | A | A | A | A |
| 679 | A | A | A | A |
| 680 | A | A | A | A |
| 681 | A | A | A | A |
| 682 | A | A | A | A |
| 683 | A | A | A | A |
| 684 | A | A | A | C |
| 685 | A | A | A | C |
| 686 | A | A | A | A |
| 687 | A | A | A | A |
| 688 | A | A | A | A |
| 689 | A | A | A | A |
| 690 | C | B | C | C |
| 691 | B | A | A | A |
| 692 | B | A | A | A |
| 693 | C | A | B | A |
| 694 | C | A | B | C |
| 695 | C | A | A | A |
| 696 | C | A | B | A |
| 697 | C | A | B | C |
| 698 | C | A | C | A |
| 699 | C | A | B | A |
| 700 | C | A | A | A |
| 701 | A | A | A | A |
| 702 | A | A | A | B |
| 703 | A | A | A | A |
| 704 | A | A | A | A |
| 705 | NT | A | A | C |
| 706 | NT | A | A | A |
| 707 | NT | A | A | A |
| 708 | NT | A | A | A |
| 709 | NT | A | A | A |
| 710 | NT | A | A | A |
| 711 | NT | A | A | A |
| 712 | NT | A | A | A |
| 713 | NT | A | A | NT |
| 714 | NT | A | A | NT |
| 715 | NT | A | A | A |
| 716 | NT | A | A | C |
| 717 | NT | A | A | C |
| 718 | NT | A | A | B |
| 719 | NT | A | A | A |
| 720 | NT | A | A | C |
| 721 | A | A | A | B |
| 722 | A | A | A | C |
| 723 | A | A | A | C |
| 724 | A | A | A | A |
| 725 | A | A | A | A |
| 726 | A | A | A | A |
| 727 | NT | A | A | B |
| 728 | A | A | A | B |
| 729 | NT | A | A | A |
| 730 | A | A | A | B |

TABLE 6-continued

Cellular Activities of Selected Compounds

| Compound No. | Axl IC$_{50}$ (nM) | Mer IC$_{50}$ (nM) | c-Met IC$_{50}$ (nM) | KDR IC$_{50}$ (nM) |
|---|---|---|---|---|
| 731 | A | A | A | C |
| 732 | A | A | A | C |
| 733 | C | A | A | C |
| 734 | B | A | A | C |
| 735 | A | A | A | A |
| 736 | A | A | A | A |
| 737 | A | A | A | A |
| 738 | A | A | A | A |
| 739 | A | A | A | C |
| 740 | A | A | A | A |
| 741 | A | A | A | B |
| 742 | A | A | A | C |
| 743 | A | A | A | C |
| 744 | A | A | A | C |
| 745 | A | A | A | C |
| 746 | A | A | A | C |
| 747 | A | A | A | B |
| 748 | A | A | A | C |
| 749 | A | A | A | C |
| 750 | A | A | A | B |
| 751 | A | A | A | A |
| 752 | A | A | A | A |
| 753 | A | A | A | C |
| 754 | A | A | A | C |
| 755 | NT | A | A | B |
| 756 | NT | A | A | A |
| 757 | A | A | A | C |
| 758 | A | A | A | C |
| 759 | A | A | A | A |
| 760 | A | A | A | C |
| 761 | NT | A | A | C |
| 762 | A | A | A | A |
| 763 | A | A | A | A |
| 764 | NT | A | A | C |
| 765 | A | A | A | C |
| 766 | A | A | A | C |
| 767 | A | A | A | A |
| 768 | NT | A | A | A |
| 769 | A | A | A | B |
| 770 | A | A | A | A |
| 771 | A | A | A | C |
| 772 | A | A | A | B |
| 773 | NT | A | A | A |
| 774 | A | A | A | B |
| 775 | NT | A | A | A |
| 776 | NT | A | A | C |
| 777 | NT | A | A | A |
| 778 | NT | A | A | A |
| 779 | NT | A | A | A |
| 780 | NT | A | A | B |
| 781 | NT | A | A | C |
| 782 | A | A | A | C |
| 783 | A | A | A | C |
| 784 | A | A | A | C |
| 785 | A | A | A | A |
| 786 | NT | A | A | A |
| 787 | NT | A | A | C |
| 788 | NT | A | A | B |
| 789 | NT | A | A | C |
| 790 | NT | A | A | C |
| 791 | NT | A | A | C |
| 792 | A | A | A | A |
| 793 | A | A | A | A |
| 794 | A | A | A | A |
| 795 | A | A | A | A |
| 796 | A | A | A | A |
| 797 | A | A | A | A |
| 798 | A | A | A | NT |
| 799 | A | A | A | NT |
| 800 | A | A | A | NT |
| 801 | A | A | A | NT |
| 802 | NT | A | A | NT |
| 803 | A | A | A | NT |
| 804 | A | A | A | NT |
| 805 | A | A | A | NT |
| 806 | A | A | A | NT |
| 807 | A | A | B | NT |
| 808 | A | A | A | C |
| 809 | A | A | A | C |
| 810 | A | A | A | A |
| 811 | A | A | A | A |
| 812 | A | A | A | C |
| 813 | A | A | A | B |
| 814 | A | A | A | C |
| 815 | A | A | A | B |
| 816 | A | A | A | C |
| 817 | NT | A | A | C |
| 818 | NT | A | A | C |
| 819 | NT | A | A | C |
| 820 | NT | A | A | C |
| 821 | A | A | A | B |
| 822 | NT | A | A | C |
| 823 | NT | A | A | C |
| 824 | NT | A | A | C |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A compound of formula (I'):

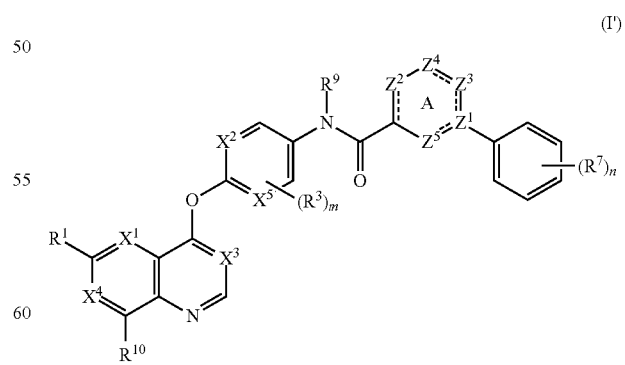

or a pharmaceutically acceptable salt, tautomer or stereoisomer thereof, wherein:
$X^1$ is N;
$X^2$ is N, $CR^3$, or CH;

$X^3$ is N or CH;
$X^4$ is N or $CR^2$;
$X^5$ is N, $CR^3$, or CH;
ring A is

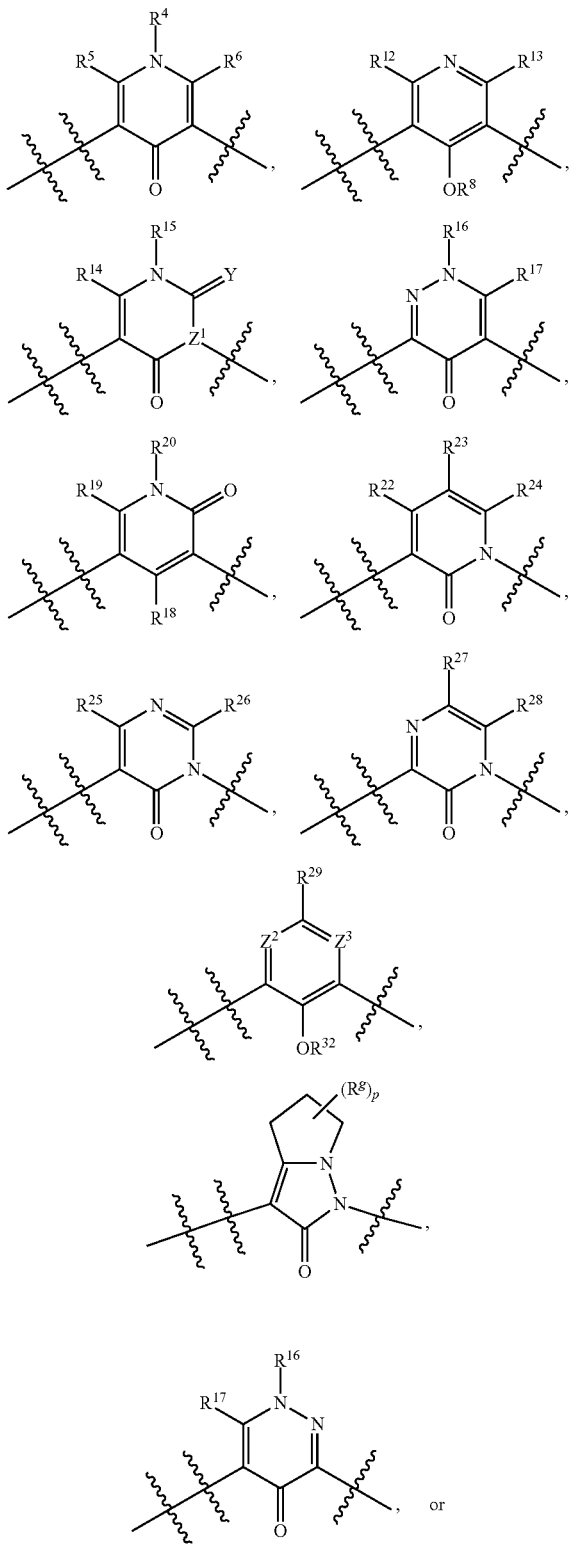

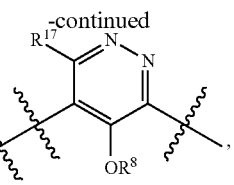

wherein the single wavy line indicates the point of attachment to the phenyl ring and the double wavy line indicates the point of attachment to the carbonyl of the amide linkage;
Y is O or S;
when ring A is

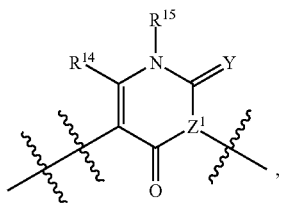

$Z^1$ is N or CH;
when ring A is

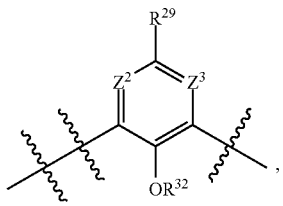

$Z^2$ is N or $CR^{45}$; and $Z^3$ is N or $CR^{42}$;
$R^1$ and $R^2$ and $R^{10}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, $NR^aC(=NR^a)R^a$, $NR^aC(O)OR^a$, $NR^aC(O)NR^aR^a$, $C(=NR^a)R^a$, $C(=NOH)R^a$, $C(=NOH)NR^a$, $C(=NCN)NR^aR^a$, $NR^aC(=NCN)NR^aR^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, and (4-14 membered heterocycloalkyl)-$C_{1-4}$ alkylene of $R^1$, $R^2$, and $R^{10}$ are each optionally substituted with 1, 2, 3, 4, or 5 independently selected $R^b$ substituents;
each $R^3$ is independently selected from halo, OH, CN, —C(O)OH, —C(O)NH($C_{1-6}$ alkyl), —S(O)$_2$($C_{1-6}$ alkyl), —S(O)$_2$NH($C_{1-6}$ alkyl), $C_1$-$C_6$ alkyl, $C_1$-$C_6$ alkoxy, $C_1$-$C_6$ haloalkoxy, $NH_2$, —NH($C_1$-$C_6$ alkyl), —N($C_1$-$C_6$ alkyl)$_2$, and $C_3$-$C_6$ cycloalkyl, wherein the $C_1$-$C_6$ alkyl, $C_1$-$C_6$ alkoxy, —NH($C_1$-$C_6$alkyl), —N($C_1$-$C_6$ alkyl)$_2$, and $C_3$-$C_6$ cycloalkyl of $R^3$ are each optionally substituted with 1, 2, or 3 independently selected $R^g$ substituents;

each $R^7$ is independently selected from halo, OH, C(O) $OR^a$, $C(O)NR^aR^a$, CN, $NH_2$, —NH($C_1$-$C_6$ alkyl), —N($C_1$-$C_6$ alkyl)$_2$, $C_1$-$C_6$ alkyl, $C_1$-$C_6$ alkoxy, $C_1$-$C_6$ haloalkyl, $C_1$-$C_6$ haloalkoxy, $C(O)NR^aR^a$, $NR^aC(O)$ $R^a$, $NR^aC(O)NR^aR^a$, $S(O)_2R^a$, $NR^aS(O)_2R^a$, $NR^aS(O)_2NR^aR^a$, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4 to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene-, wherein the $C_1$-$C_6$ alkyl, $C_3$-$C_6$ cycloalkyl, 4- to 6-membered heterocycloalkyl, phenyl, 5- or 6-membered heteroaryl, $C_3$-$C_6$ cycloalkyl-$C_1$-$C_4$ alkylene-, (4 to 6-membered heterocycloalkyl)-$C_1$-$C_4$ alkylene-, phenyl-$C_1$-$C_2$ alkylene, and (5- or 6-membered heteroaryl)-$C_1$-$C_4$ alkylene of $R^7$ are each optionally substituted with 1, 2, or 3 independently selected $R^f$ substituents;

$R^9$ is H or $C_{1-6}$ alkyl optionally substituted with 1, 2, or 3 independently selected $R^g$ substituents;

$R^{18}$ is H, halo, CN, $C_{1-6}$ alkyl, $NH_2$, —$NHC_{1-4}$alkyl, —N($C_{1-4}$ alkyl)$_2$, or —S—$C_{1-6}$ alkyl;

$R^4$, $R^{15}$, $R^{16}$ and $R^{20}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, (4-14 membered heterocycloalkyl)-$C_{1-4}$ alkylene-, CN, $NO_2$, $OR^a$, $SR^a$, $NHOR^a$, $C(O)R^a$, $C(O)NR^aR^a$, $C(O)OR^a$, $C(O)NR^aS(O)_2R^a$, $OC(O)R^a$, $OC(O)NR^aR^a$, $NHR^a$, $NR^aR^a$, $NR^aC(O)R^a$, N=C $(NR^aR^a)_2$, $NR^aC(=NR^a)R^a$, $NR^aC(O)OR^a$, $NR^aC(O)NR^aR^a$, $C(=NR^a)R^a$, $C(=NOH)R^a$, $C(=NOH) NR^a$, $C(=NCN)NR^aR^a$, $NR^aC(=NCN)NR^aR^a$, $C(=NR^a)NR^aR^a$, $NR^aC(=NR^a) NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, $S(O)_2NR^aC(O)R^a$, $P(O)R^aR^a$, $P(O)(OR^a)(OR^a)$, $B(OH)_2$, $B(OR^a)_2$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkylene-, $C_{3-14}$ cycloalkyl-$C_{1-4}$ alkylene-, (5-14 membered heteroaryl)-$C_{1-4}$ alkylene-, and (4-14 membered heterocycloalkyl)-$C_{1-4}$ alkylene of $R^4$, $R^{15}$, $R^{16}$ and $R^{20}$ are each optionally substituted with 1, 2, 3, 4, or 5 independently selected $R^b$ substituents;

$R^5$, $R^{14}$, $R^{19}$, $R^{25}$, $R^{27}$, $R^{28}$, and $R^{45}$ are each independently H, $C_{1-6}$ alkyl optionally substituted with 1 or 2 independently selected $R^g$ substituents, CN, $C_{1-4}$ haloalkyl, $C_{1-4}$ haloalkoxy, OH, —$C(O)OC_{1-4}$alkyl, —$C(O)NC_{1-4}$alkyl, $NH_2$, —$NHC_{1-4}$alkyl, or —N($C_{1-4}$ alkyl) 2;

$R^{22}$ is H, $C_{2-6}$ alkyl optionally substituted with 1 or 2 independently selected $R^g$ substituents, CN, $C_{1-4}$ haloalkyl, $C_{1-4}$ haloalkoxy, OH, —$C(O)OC_{1-4}$alkyl, —$C(O)NC_{1-4}$alkyl, $NH_2$, —$NHC_{1-4}$alkyl, or —N($C_{1-4}$ alkyl)$_2$;

$R^6$, $R^{17}$, $R^{23}$, $R^{24}$, $R^{26}$, $R^{29}$ and $R^{42}$ are each independently H, $C_{1-6}$ alkyl optionally substituted with 1 or 2 independently selected $R^g$ substituents, CN, $C_{1-4}$ haloalkyl, $C_{1-4}$ haloalkoxy, OH, —$C(O)OC_{1-4}$alkyl, —$C(O)NC_{1-4}$alkyl, $NH_2$, —$NHC_{1-4}$alkyl, or —N($C_{1-4}$ alkyl)$_2$;

or $R^4$ and $R^5$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^4$ and $R^6$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{14}$ and $R^{15}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{16}$ and $R^{17}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{19}$ and $R^{20}$ taken together with the atoms to which they are attached form 4- to 7-membered fused heterocycloalkyl or 5- to 6-membered fused heteroaryl, wherein the 4- to 7-membered fused heterocycloalkyl and 5- to 6-membered fused heteroaryl are each optionally substituted with 1 or 2 independently selected $R^g$ substituents;

or $R^{22}$ and $R^{23}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents;

or $R^{23}$ and $R^{24}$ taken together with the atoms to which they are attached form fused $C_{3-7}$ cycloalkyl, fused phenyl, or fused heteroaryl, wherein the fused $C_{3-7}$ cycloalkyl, fused phenyl, and fused heteroaryl are each optionally substituted with 1 or 2 independently selected $R^g$ substituents;

or $R^{27}$ and $R^{28}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents;

or $R^{29}$ and $R^{45}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents;

or $R^{42}$ and $R^{29}$ taken together with the atoms to which they are attached form fused $C_{3-7}$ cycloalkyl or fused phenyl, wherein the fused $C_{3-7}$ cycloalkyl and fused phenyl are each optionally substituted with 1 or 2 independently selected $R^g$ substituents;

$R^8$ and $R^{32}$ are each independently H, $C_{1-6}$ alkyl, or a hydroxy protecting group;

$R^{12}$ is H or $C_{1-6}$ alkyl optionally substituted with 1 or 2 independently selected $R^g$ substituents; and $R^{13}$ is H or $C_{1-6}$ alkyl optionally substituted with 1 or 2 independently selected $R^g$ substituents;

each $R^a$ is independently selected from the group consisting of H, CN, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene-, wherein the $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-14 membered heteroaryl, 4-14 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-14 membered heteroaryl)-$C_1$-$C_4$ alkylene-, and (4-14 membered heterocycloalkyl)-$C_1$-$C_4$ alkylene of $R^a$ are each optionally substituted with 1, 2, 3, 4, or 5 independently selected $R^d$ substituents;

or any two $R^a$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^b$ is independently selected from the group consisting of halo, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^c$, $C(=NCN)NR^cR^c$, $NR^cC(=NCN)$ $NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)$ $R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, $Si(R^c)_3$, $P(O)$ $R^cR^c$, $P(O)(OR^c)(OR^c)$, $B(OH)_2$, $B(OR^c)_2$, and $S(O)_2$ $NR^cR^c$, wherein the $C_1$-$C_6$ alkyl, $C_1$-$C_6$ haloalkyl, $C_1$-$C_6$ haloalkoxy, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene of $R^b$ are each further optionally substituted with 1, 2, or 3 independently selected $R^d$ substituents;

each $R^c$ is independently selected from the group consisting of H, $C_1$-$C_6$ alkyl, $C_1$-$C_6$ haloalkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene-, wherein the $C_1$-$C_6$ alkyl, $C_2$-$C_6$ alkenyl, $C_2$-$C_6$ alkynyl, $C_6$-$C_{10}$ aryl, $C_3$-$C_{10}$ cycloalkyl, 5-10 membered heteroaryl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene of $R^e$ are each optionally substituted with 1, 2, 3, 4, or 5 independently selected $R^f$ substituents;

or any two $R^c$ substituents together with the nitrogen atom to which they are attached form 4-, 5-, 6-, 7-, 8-, 9-, or 10-membered heterocycloalkyl, each of which is optionally substituted with 1, 2, or 3 independently selected $R^f$ substituents;

each $R^d$ is independently selected from the group consisting of $C_1$-$C_6$ alkyl, $C_1$-$C_6$ haloalkyl, halo, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, (4-10 membered heterocycloalkyl)-$C_1$-$C_4$ alkylene-, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein the $C_1$-$C_6$ alkyl, $C_1$-$C_6$ haloalkyl, $C_6$-$C_{10}$ aryl, 5-10 membered heteroaryl, $C_3$-$C_{10}$ cycloalkyl, 4-10 membered heterocycloalkyl, $C_6$-$C_{10}$ aryl-$C_1$-$C_4$ alkylene-, $C_3$-$C_{10}$ cycloalkyl-$C_1$-$C_4$ alkylene-, (5-10 membered heteroaryl)-$C_1$-$C_4$ alkylene-, and (4-10 membered heterocycloalkyl)-$C_1$-$C_4$ alkylene of $R^d$ are each optionally substituted with 1, 2, or 3 independently selected $R^f$ substituents;

each $R^e$ is independently selected from the group consisting of H, $C_1$-$C_6$ alkyl, $C_3$-$C_6$ cycloalkyl, $C_3$-$C_6$ cycloalkyl-$C_1$-$C_4$ alkylene-, $C_6$-$C_{10}$ aryl, $C_6$-$C_{10}$ aryl-$C_1$-$C_4$ alkylene-, 5- or 6-membered heteroaryl, (5- or 6-membered heteroaryl)-$C_1$-$C_4$ alkylene-, 4-7-membered heterocycloalkyl, (4-7-membered heterocycloalkyl)-$C_1$-$C_4$ alkylene-, $C_1$-$C_6$ haloalkyl, $C_1$-$C_6$ haloalkoxy, $C_2$-$C_4$ alkenyl, and $C_2$-$C_4$ alkynyl, wherein the $C_1$-$C_6$ alkyl, $C_3$-$C_6$ cycloalkyl, $C_6$-$C_{10}$ aryl, 5 or 6-membered heteroaryl, 4-7-membered heterocycloalkyl, $C_6$-$C_{10}$ aryl-$C_1$-$C_4$ alkylene-, (5- or 6-membered heteroaryl)-$C_1$-$C_4$ alkylene-, (4-7-membered heterocycloalkyl)-$C_1$-$C_4$ alkylene-, $C_2$-$C_4$ alkenyl, and $C_2$-$C_4$ alkynyl of $R^e$ are each optionally substituted with 1, 2, or 3 $R^f$ substituents;

or any two $R^e$ substituents together with the nitrogen atom to which they are attached form a 4-, 5-, 6-, 7-, 8-, 9-, or 10-membered heterocycloalkyl, each of which is optionally substituted with 1, 2, or 3 independently selected $R^f$ substituents;

each $R^f$ is independently selected from the group consisting of halo, OH, CN, C(O)OH, $NH_2$, —$NH(C_1$-$C_6$ alkyl), —$N(C_1$-$C_6$ alkyl)$_2$, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl, wherein the $C_1$-$C_6$ alkyl, phenyl, $C_3$-$C_6$ cycloalkyl, 4-6 membered heterocycloalkyl, and 5-6 membered heteroaryl of $R^f$ are each optionally substituted with 1, 2, or 3 substituents selected from halo, OH, CN, —COOH, —$NH_2$, $C_1$-$C_4$ alkyl, $C_1$-$C_4$ alkoxy, $C_1$-$C_4$ haloalkyl, $C_1$-$C_4$ haloalkoxy, phenyl, $C_3$-$C_{10}$ cycloalkyl, 5-6 membered heteroaryl, and 4-6 membered heterocycloalkyl;

each $R^g$ is independently selected from the group consisting of halo, OH, CN, C(O)OH, —C(O)O—$C_1$-$C_4$ alkyl, —OC(O)$C_1$-$C_4$ alkyl, $NH_2$, $NH(C_1$-$C_6$ alkyl), —$N(C_1$-$C_6$ alkyl) 2, $C_1$-$C_6$ alkyl, $C_1$-$C_6$ alkoxy, $C_1$-$C_6$ alkylthio, $C_1$-$C_6$ haloalkyl, $C_1$-$C_6$ haloalkoxy, phenyl, 5-6 membered heteroaryl, 4-6 membered heterocycloalkyl, and $C_3$-$C_6$ cycloalkyl;

the ring nitrogen atom in formula (I') is optionally oxidized;

the subscript m is 0, 1, or 2;

the subscript n is 0, 1, 2, 3, 4, or 5; and the subscript p is 0, 1, or 2.

2. The compound of claim 1 having formula (I):

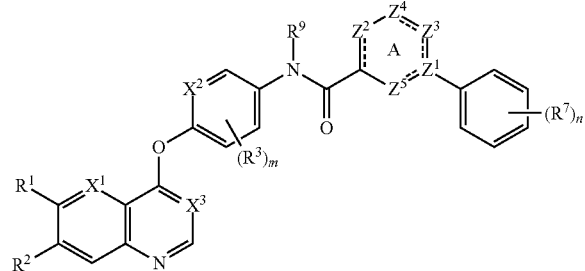

(I)

or a pharmaceutically acceptable salt or stereoisomer thereof, wherein:

$R^{18}$ is H, halo, CN, or $C_{1-6}$ alkyl when ring A is:

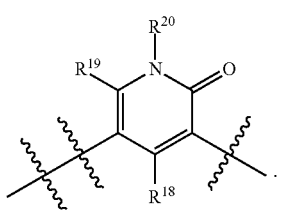

3. The compound of claim 1, having formula (Ia):

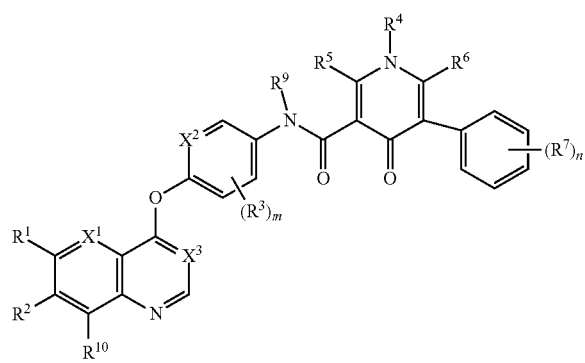

(Ia)

or pharmaceutically acceptable salt or stereoisomer thereof.

4. The compound of claim 1, having formula (Ib):

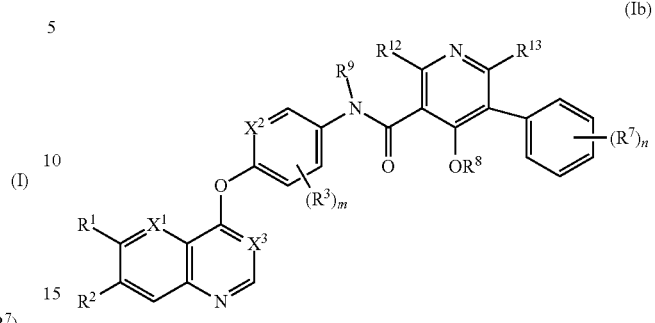

(Ib)

or pharmaceutically acceptable salt or stereoisomer thereof.

5. The compound of claim 1, having formula (Ic), (Id), (Ie), (If), (Ig), (Ih), (Ij), (Ik), (Im), (In), (Io), (Ip), (Iq), (Ir), (Is), (It), (Iu), (Iv), (Iw), (Iy), or (Iaa):

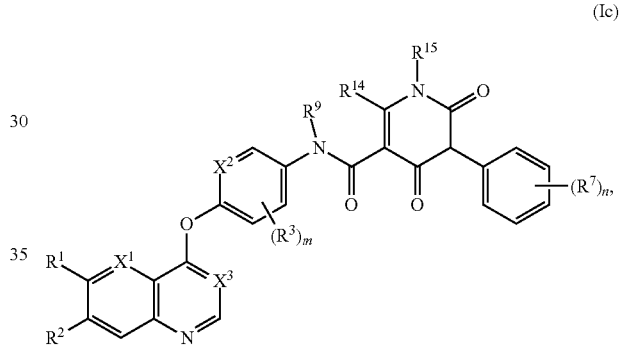

(Ic)

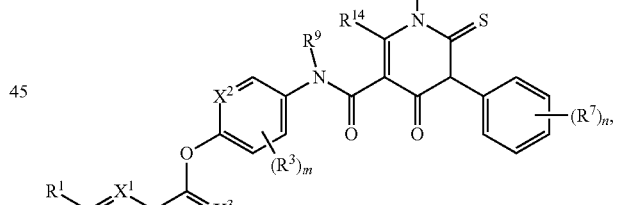

(Id)

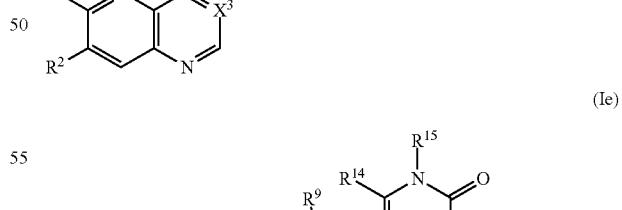

(Ie)

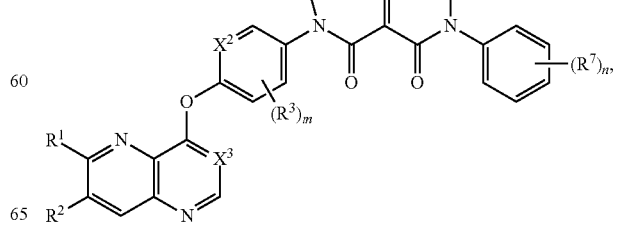

(If)
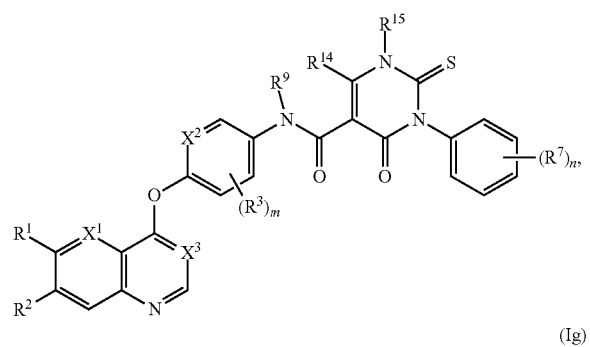
(Ig)
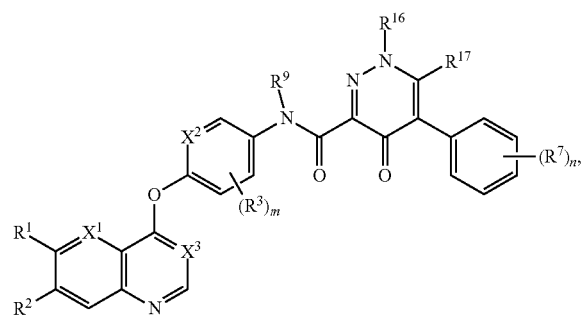
(Ih)
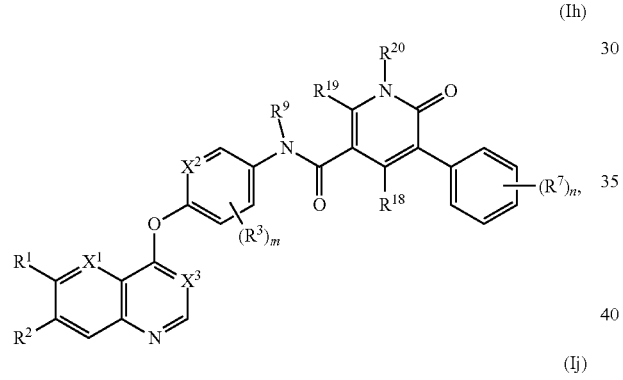
(Ij)
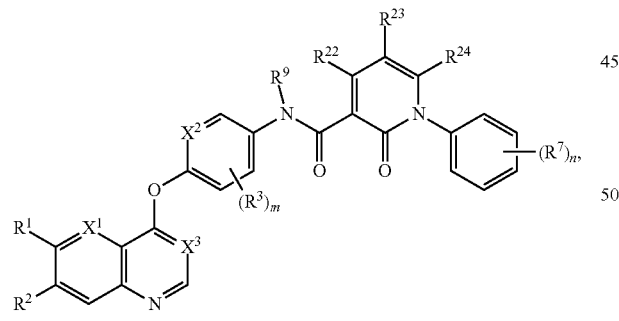
(Ik)
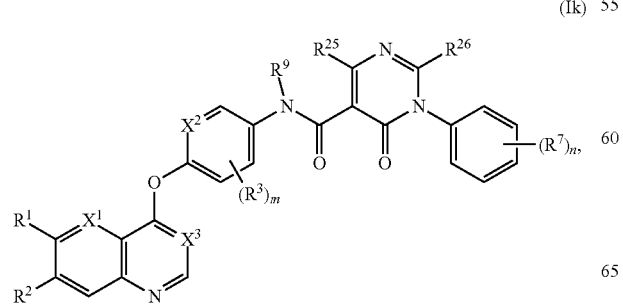
(Im)
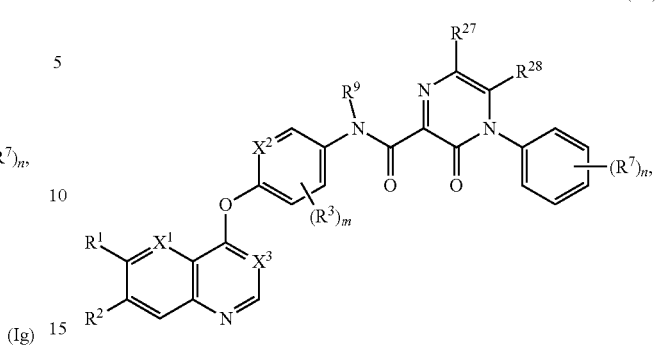
(In)
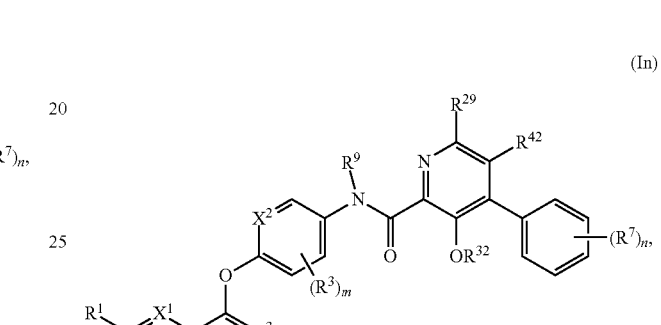
(Io)
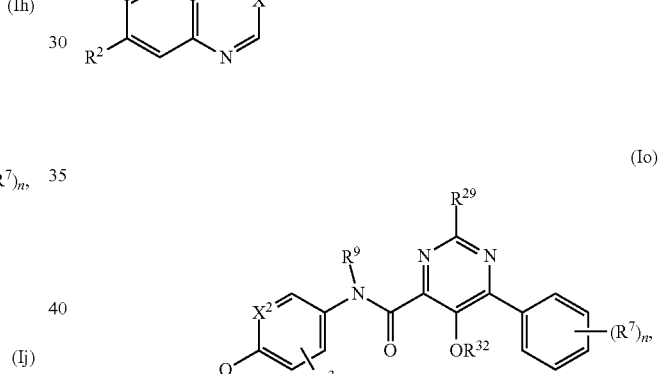
(Ip)
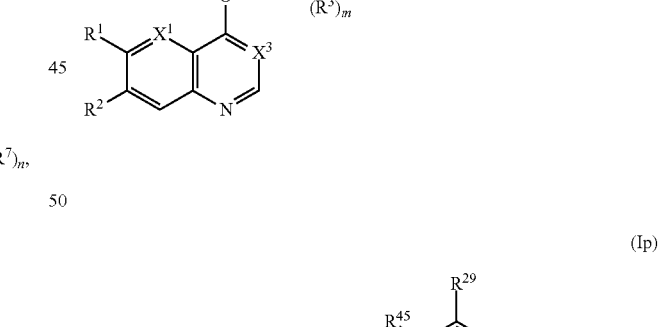

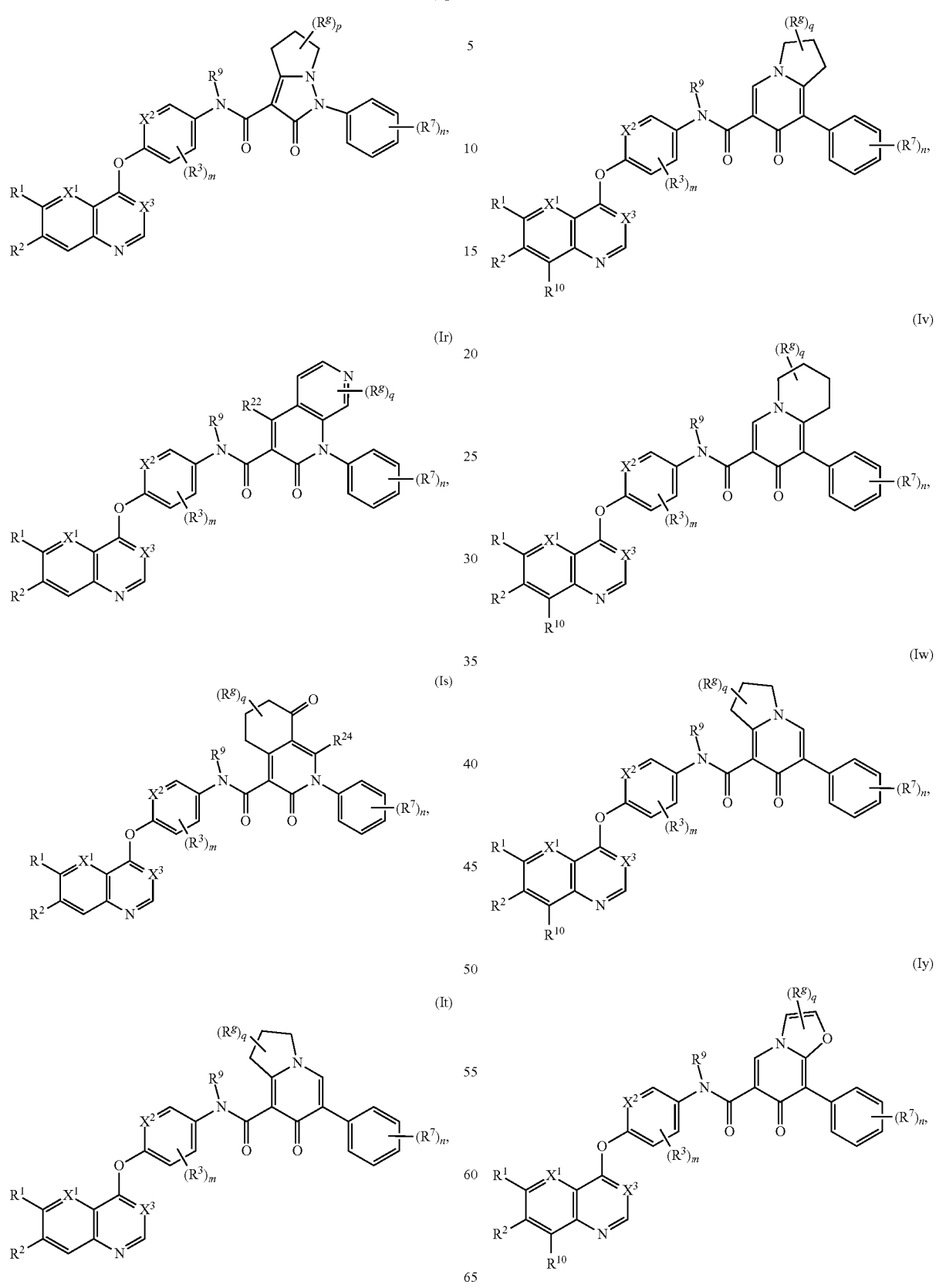

-continued (Iaa)

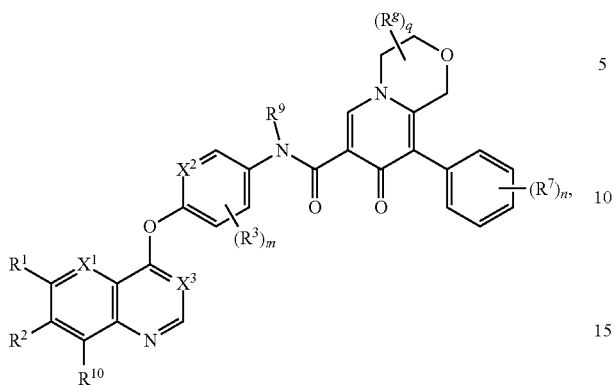

or a pharmaceutically acceptable salt or stereoisomer thereof, wherein each subscript q is independently 0, 1, or 2.

6. The compound of claim 1, having formula (Ia-1):

(Ia-1)

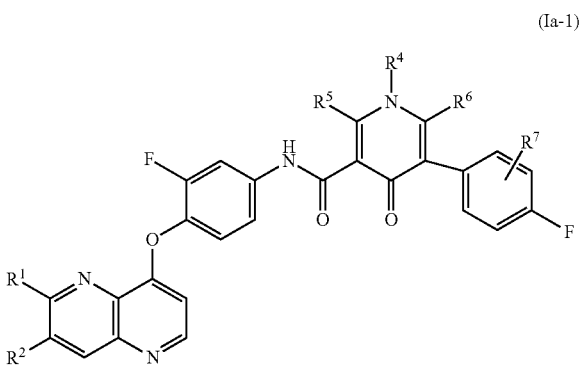

or a pharmaceutically acceptable salt or stereoisomer thereof.

7. The compound of claim 1, having formula (III-1):

(III-1)

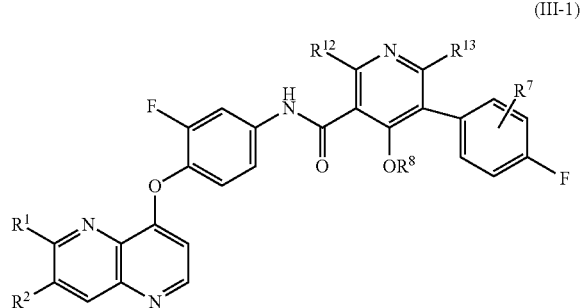

or a pharmaceutically acceptable salt or stereoisomer thereof.

8. The compound of claim 1, having formula (IV-1):

(IV-1)

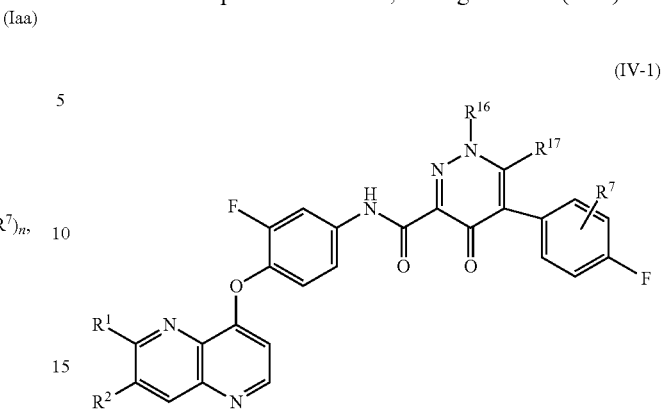

or a pharmaceutically acceptable salt or stereoisomer thereof.

9. The compound of claim 8, or a pharmaceutically acceptable salt or stereoisomer thereof, wherein $R^{16}$ is H, $C_{1-6}$ alkyl, or $C_{1-6}$ haloalkyl; and $R^{17}$ is H or $C_{1-6}$ alkyl.

10. The compound of claim 1, or a pharmaceutically acceptable salt or stereoisomer thereof, wherein $R^1$ is H, $C_{1-6}$ alkyl, $C_{1-6}$ alkoxy, halo, $NH_2$, —NH($C_{1-6}$ alkyl), —N($C_{1-6}$ alkyl)$_2$, $C_{1-6}$ alkyl-NHC(O)—, or $C_{1-6}$ alkyl-S(O)$_2$NH—.

11. The compound of claim 1, or a pharmaceutically acceptable salt or stereoisomer thereof, wherein $R^2$ is H, $C_{1-6}$ alkyl, $C_{1-6}$ alkoxy, halo, OH, $NH_2$, —NH($C_{1-6}$ alkyl), —N($C_{1-6}$ alkyl)$_2$, —$C_{1-6}$ alkyl-NHC(O)—, $CF_3$, $C_{1-6}$ alkyl-OC(O)—, pyridyl, $C_{1-6}$alkyl-S(O)$_2$NH— or 1H-pyrazol-4-yl optionally substituted with $R^b$.

12. The compound of claim 1, or a pharmaceutically salt or stereoisomer thereof, wherein $R^3$ is halo.

13. The compound of claim 1, or a pharmaceutically acceptable salt or stereoisomer thereof, wherein $R^7$ is halo, $C_{1-6}$ alkyl, or $C_{1-6}$ alkoxy.

14. The compound of claim 1, or a pharmaceutically acceptable salt or stereoisomer thereof, wherein $R^9$ is H.

15. The compound of claim 1, or a pharmaceutically acceptable salt or stereoisomer thereof, wherein $R^4$, $R^{15}$, $R^{16}$, and $R^{20}$ are each independently selected from H, $C_{1-6}$ alkyl, $C_{1-6}$ alkoxy, OH, $NH_2$, —$NHC_{1-6}$ alkyl, —N($C_{1-6}$ alkyl)$_2$, $C_{3-6}$ cycloalkyl, $C_{1-6}$ haloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N($C_{1-6}$ alkyl)($C_{1-6}$ alkyl)]$_2$, wherein the $C_{1-6}$ alkyl, $C_{1-6}$ alkoxy, —$NHC_{1-6}$ alkyl, —N($C_{1-6}$ alkyl)$_2$, $C_{3-6}$ cycloalkyl, $C_{3-6}$ cycloalkyl-$C_{1-4}$ alkylene-, 4-6 membered heterocycloalkyl, (4-6 membered heterocycloalkyl)-$C_{1-4}$ alkylene-, 5-6 membered heteroaryl, (5-6 membered heteroaryl)-$C_{1-4}$ alkylene-, and N═C[N($C_{1-6}$ alkyl)($C_{1-6}$ alkyl)]$_2$ of $R^4$, $R^{15}$, $R^{16}$, and $R^{20}$ are each optionally substituted with 1 or 2 independently selected $R^b$ substituents.

16. The compound of claim 1, or a pharmaceutically acceptable salt or stereoisomer thereof, wherein $R^{23}$, $R^{27}$ and $R^{29}$ are each independently selected from H, methyl, isopropyl, t-butyl, ethyl, OH, $NH_2$, methylamino, dimethylamino, 2,2,2-trifluoroethyl, 2-morpholinoethyl, 2-hydroxyethyl, 2-(imidazol-1-yl) ethyl, and 2-hydroxy-1,1-dimethylethyl, wherein each of methyl, isopropyl, t-butyl, and ethyl is optionally substituted with 1 or 2 independently selected $R^g$ substituents.

17. The compound of claim 1, or a pharmaceutically acceptable salt or stereoisomer thereof, wherein $R^{45}$, $R^{42}$, $R^5$, $R^6$, and $R^{17}$ are each independently selected from H, OH, halo, CN, $C_{1-6}$ alkyl, and $C_{1-4}$ halo alkyl, wherein each $C_{1-6}$ alkyl of $R^{45}$, $R^{42}$, $R^5$, $R^6$, and $R^{17}$ is optionally substituted with 1 or 2 independently selected $R^g$ substituents.

18. The compound of claim 1, or a pharmaceutically acceptable salt or stereoisomer thereof, wherein $R^{45}$, $R^{42}$, $R^5$ and $R^6$ are each independently selected from H, methyl, CN 2-fluoroethyl, isopropyl, OH, t-butyl, ethyl, hydroxymethyl, and methoxymethyl.

19. The compound of claim 1, or a pharmaceutically acceptable salt or stereoisomer thereof, wherein $R^8$ and $R^{32}$ are each independently H or $C_{1-6}$ alkyl.

20. The compound of claim 1, or a pharmaceutically acceptable salt or stereoisomer thereof, wherein $X^3$ is CH.

21. The compound of claim 1, having the following formula

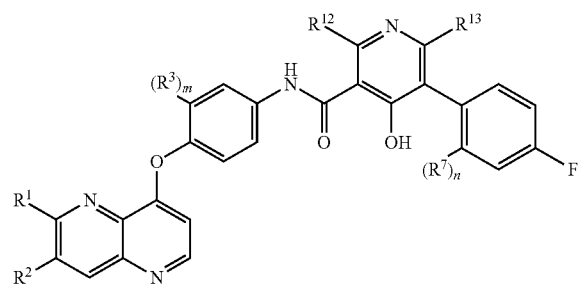

or a pharmaceutically acceptable salt, tautomer or stereoisomer thereof, wherein:
- $R^1$ is H, halo, $C_{1-6}$ alkyl, $C_{1-6}$ alkoxy, $C_{1-6}$ alkyl-C(O)—, $NH_2C(O)$—, or $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ are each optionally substituted with $C_{1-6}$ alkoxy or OH;
- $R^2$ is $C_{1-6}$ alkoxy;
- $R^3$ is halo;
- $R^{12}$ is H or $C_{1-6}$ alkyl optionally substituted with $C_{1-6}$ alkoxy or OH;
- $R^{13}$ is H or $C_{1-6}$ alkyl optionally substituted with $C_{1-6}$ alkoxy or OH;
- $R^7$ is $C_{1-6}$ alkyl;
- subscript m is 0 or 1; and
- subscript n is 0 or 1.

22. The compound of claim 1, having the following formula:

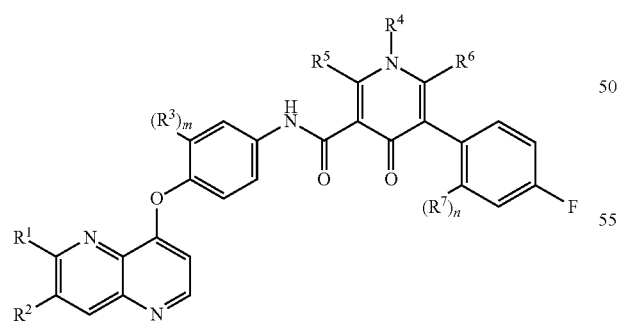

or a pharmaceutically acceptable salt, tautomer or stereoisomer thereof, wherein:
- $R^1$ is H, $C_{1-6}$ alkyl, $C_{1-6}$ alkoxy, $C_{1-6}$ alkyl-C(O)—, $NH_2C(O)$—, or $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ are each optionally substituted with $C_{1-6}$ alkoxy or OH;
- $R^2$ is $C_{1-6}$ alkoxy;
- $R^3$ is halo;
- $R^4$ is H, $C_{1-6}$ haloalkyl, or $C_{1-6}$ alkyl optionally substituted with $C_{1-6}$ alkoxy or OH;
- $R^5$ is H or $C_{1-6}$ alkyl optionally substituted with $C_{1-6}$ alkoxy or OH;
- $R^6$ is H or $C_{1-6}$ alkyl optionally substituted with $C_{1-6}$ alkoxy or OH;
- $R^7$ is $C_{1-6}$ alkyl;
- subscript m is 0 or 1; and
- subscript n is 0 or 1.

23. The compound of claim 1, having the following formula:

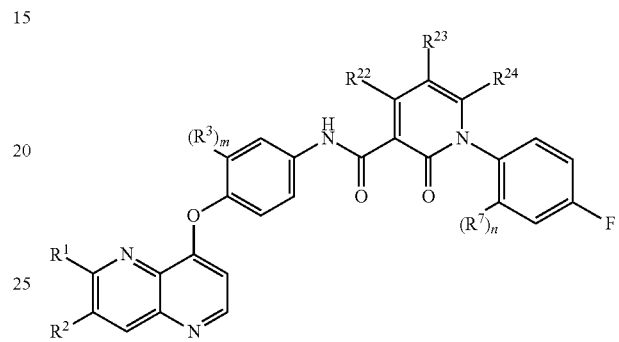

or a pharmaceutically acceptable salt, tautomer or stereoisomer thereof, wherein:
- $R^1$ is $C_{1-6}$ alkyl, $C_{1-6}$ alkoxy, $C_{1-6}$ alkyl-C(O)—, $NH_2C(O)$—, or $C_{1-6}$ alkyl-NHC(O)—, wherein the $C_{1-6}$ alkyl, $C_{1-6}$ alkyl-C(O)— and $C_{1-6}$ alkyl-NHC(O)— of $R^1$ is optionally substituted with $C_{1-6}$ alkoxy or OH;
- $R^2$ is $C_{1-6}$ alkoxy;
- $R^3$ is halo;
- $R^{22}$ is H or $C_{2-6}$ alkyl optionally substituted with $C_{1-6}$ alkoxy or OH;
- $R^{23}$ is H, $C_{1-6}$ alkyl or $C_{1-6}$ alkyl-C(O)—, wherein the $C_{1-6}$ alkyl and $C_{1-6}$ alkyl-C(O)— of $R^{23}$ are each optionally substituted with $C_{1-6}$ alkoxy or OH;
- $R^{24}$ is H or $C_{1-6}$ alkyl optionally substituted with $C_{1-6}$ alkoxy or OH;
- $R^7$ is $C_{1-6}$ alkyl;
- subscript m is 0 or 1; and
- subscript n is 0 or 1.

24. The compound of claim 1, having formula (V):

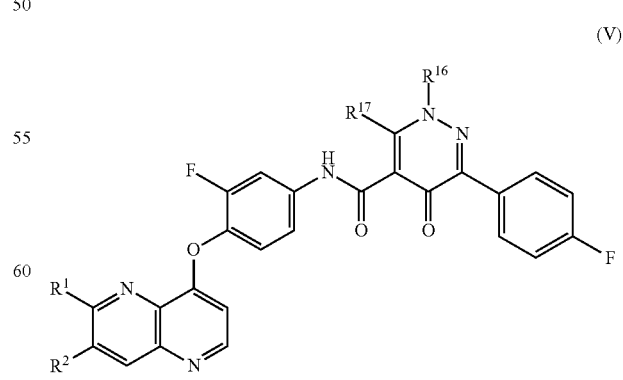

(V)

or a pharmaceutically acceptable salt or stereoisomer thereof, wherein:

R[1] is H, halo, $C_{1-6}$ alkyl, $C_{1-6}$ alkoxy, $C_{1-6}$ alkyl-C(O)—, $NH_2C(O)$—, or $C_{1-6}$ alkyl-NHC(O)—, wherein the $C_{1-6}$ alkyl, $C_{1-6}$ alkyl-C(O)— and $C_{1-6}$ alkyl-NHC(O)— of R[1] are each optionally substituted with $C_{1-6}$ alkoxy or OH;

R[2] is $C_{1-6}$ alkoxy;

R[16] is H, $C_{1-6}$ alkyl, or $C_{1-6}$ haloalkyl; and

R[17] is H or $C_{1-6}$ alkyl.

25. A pharmaceutical composition comprising a compound of claim 1, or a pharmaceutically acceptable salt or stereoisomer thereof, and a pharmaceutically acceptable carrier or excipient.

26. A compound selected from:

N-[4-[(6,7-dimethoxy-1,5-naphthyridin-4-yl) oxy]-3-fluorophenyl]-5-(4-fluorophenyl)-6-methyl-4-oxo-1-propan-2-ylpyridine-3-carboxamide;

N-[4-(6,7-dimethoxyquinolin-4-yl) oxy-3-fluorophenyl]-5-(4-fluorophenyl)-6-methyl-4-oxo-1-propan-2-ylpyridine-3-carboxamide;

5-(3,4-dichlorophenyl)-N-[4-(6,7-dimethoxyquinolin-4-yl) oxy-3-fluorophenyl]-6-methyl-4-oxo-1-propan-2-ylpyridine-3-carboxamide;

5-(3-chloro-4-fluorophenyl)-N-[4-[(6,7-dimethoxy-1,5-naphthyridin-4-yl) oxy]-3-fluorophenyl]-6-methyl-4-oxo-1-propan-2-ylpyridine-3-carboxamide;

5-(3,4-dichlorophenyl)-N-[4-[(6,7-dimethoxy-1,5-naphthyridin-4-yl) oxy]-3-fluorophenyl]-6-methyl-4-oxo-1-propan-2-ylpyridine-3-carboxamide;

1-cyclopentyl-N-[4-[(6,7-dimethoxy-1,5-naphthyridin-4-yl) oxy]-3-fluorophenyl]-5-(4-fluorophenyl)-6-methyl-4-oxopyridine-3-carboxamide;

5-(3-chloro-4-fluorophenyl)-1-cyclopentyl-N-[4-[(6,7-dimethoxy-1,5-naphthyridin-4-yl) oxy]-3-fluorophenyl]-6-methyl-4-oxopyridine-3-carboxamide;

N-[4-[(6,7-dimethoxy-1,5-naphthyridin-4-yl) oxy]-3-fluorophenyl]-5-(4-fluorophenyl)-4-hydroxy-6-methylpyridine-3-carboxamide;

N-[4-[(6,7-dimethoxy-1,5-naphthyridin-4-yl) oxy]-3-fluorophenyl]-6-methyl-4-oxo-5-phenyl-1-propan-2-ylpyridine-3-carboxamide;

N-[4-[(6,7-dimethoxy-1,5-naphthyridin-4-yl) oxy]-3-fluorophenyl]-5-(3-fluorophenyl)-6-methyl-4-oxo-1-propan-2-ylpyridine-3-carboxamide;

N-[4-[(6,7-dimethoxy-1,5-naphthyridin-4-yl) oxy]-3-fluorophenyl]-5-(4-methoxyphenyl)-6-methyl-4-oxo-1-propan-2-ylpyridine-3-carboxamide;

N-[4-[(6,7-dimethoxy-1,5-naphthyridin-4-yl) oxy]-3-fluorophenyl]-5-(4-fluoro-2-methylphenyl)-6-methyl-4-oxo-1-propan-2-ylpyridine-3-carboxamide;

N-[4-[(6,7-dimethoxy-1,5-naphthyridin-4-yl) oxy]-3-fluorophenyl]-1-methyl-4-oxo-5-phenylpyridine-3-carboxamide;

N-[4-[(6,7-dimethoxy-1,5-naphthyridin-4-yl) oxy]-3-fluorophenyl]-5-(4-methoxyphenyl)-1-methyl-4-oxopyridine-3-carboxamide;

N-[4-[(6,7-dimethoxy-1,5-naphthyridin-4-yl) oxy]-3-fluorophenyl]-5-(3-fluorophenyl)-1-methyl-4-oxopyridine-3-carboxamide;

N-[4-[(6,7-dimethoxy-1,5-naphthyridin-4-yl) oxy]-3-fluorophenyl]-1,6-dimethyl-4-oxo-5-phenylpyridine-3-carboxamide;

N-[4-[(6,7-dimethoxy-1,5-naphthyridin-4-yl) oxy]-3-fluorophenyl]-5-(3-fluorophenyl)-1,6-dimethyl-4-oxopyridine-3-carboxamide;

5-(4-chlorophenyl)-N-[4-[(6,7-dimethoxy-1,5-naphthyridin-4-yl) oxy]-3-fluorophenyl]-1-methyl-4-oxopyridine-3-carboxamide;

N-[4-[(6,7-dimethoxy-1,5-naphthyridin-4-yl) oxy]phenyl]-1-methyl-4-oxo-5-phenylpyridine-3-carboxamide;

N-[3-fluoro-4-[(7-methoxy-1,5-naphthyridin-4-yl) oxy]phenyl]-1-methyl-4-oxo-5-phenylpyridine-3-carboxamide;

1-cyclopropyl-N-[4-[(6,7-dimethoxy-1,5-naphthyridin-4-yl) oxy]-3-fluorophenyl]-5-(4-fluorophenyl)-4-oxopyridine-3-carboxamide;

N-[4-[(6,7-dimethoxy-1,5-naphthyridin-4-yl) oxy]-3-fluorophenyl]-5-(4-fluorophenyl)-4-hydroxypyridine-3-carboxamide;

N-[4-(6,7-dimethoxyquinolin-4-yl) oxy-3-fluorophenyl]-5-(4-fluorophenyl)-4-oxo-1-propan-2-ylpyridine-3-carboxamide;

N-[4-[(6,7-dimethoxy-1,5-naphthyridin-4-yl) oxy]-3-fluorophenyl]-5-(4-fluorophenyl)-4-oxo-1-propan-2-ylpyridine-3-carboxamide;

N-[4-[(6,7-dimethoxy-1,5-naphthyridin-4-yl) oxy]-3-fluorophenyl]-5-(4-fluorophenyl)-1-methyl-4-oxopyridine-3-carboxamide;

1-cyclopentyl-N-[4-[(6,7-dimethoxy-1,5-naphthyridin-4-yl) oxy]-3-fluorophenyl]-5-(4-fluorophenyl)-4-oxopyridine-3-carboxamide;

N-[4-[(6,7-dimethoxy-1,5-naphthyridin-4-yl) oxy]-3-fluorophenyl]-5-(4-fluorophenyl)-1-(oxetan-3-yl)-4-oxopyridine-3-carboxamide;

1-tert-butyl-N-[4-[(6,7-dimethoxy-1,5-naphthyridin-4-yl) oxy]-3-fluorophenyl]-5-(4-fluorophenyl)-4-oxopyridine-3-carboxamide;

N-[4-[(6,7-dimethoxy-1,5-naphthyridin-4-yl) oxy]-3-fluorophenyl]-5-(4-fluorophenyl)-4-oxo-1-(2,2,2-trifluoroethyl) pyridine-3-carboxamide;

1-cyclobutyl-N-[4-[(6,7-dimethoxy-1,5-naphthyridin-4-yl) oxy]-3-fluorophenyl]-5-(4-fluorophenyl)-4-oxopyridine-3-carboxamide;

N-[4-[(6,7-dimethoxy-1,5-naphthyridin-4-yl) oxy]-3-fluorophenyl]-5-(4-fluorophenyl)-1-(1-methylpyrazol-4-yl)-4-oxopyridine-3-carboxamide;

N-[4-[(6,7-dimethoxy-1,5-naphthyridin-4-yl) oxy]-3-fluorophenyl]-5-(4-fluorophenyl)-1-(1-methylazetidin-3-yl)-4-oxopyridine-3-carboxamide;

N-[4-[(6,7-dimethoxy-1,5-naphthyridin-4-yl) oxy]-3-fluorophenyl]-5-(4-fluorophenyl)-1-(1-methylpyrazol-3-yl)-4-oxopyridine-3-carboxamide;

N-[4-[(6,7-dimethoxy-1,5-naphthyridin-4-yl) oxy]-3-fluorophenyl]-5-(4-fluorophenyl)-1-(3-methyloxetan-3-yl)-4-oxopyridine-3-carboxamide;

N-[4-(6,7-dimethoxyquinolin-4-yl) oxy-3-fluorophenyl]-5-(4-fluorophenyl)-1-(3-methyloxetan-3-yl)-4-oxopyridine-3-carboxamide;

N-[4-[(6,7-dimethoxy-1,5-naphthyridin-4-yl) oxy]-3-fluorophenyl]-5-(4-fluorophenyl)-1-(1-hydroxy-2-methylpropan-2-yl)-4-oxopyridine-3-carboxamide;

N-[4-(6,7-dimethoxyquinolin-4-yl) oxy-3-fluorophenyl]-5-(4-fluorophenyl)-1-(1-hydroxy-2-methylpropan-2-yl)-4-oxopyridine-3-carboxamide;

N-[4-[(6,7-dimethoxy-1,5-naphthyridin-4-yl) oxy]-3-fluorophenyl]-5-(4-fluorophenyl)-1,6-dimethyl-4-oxopyridine-3-carboxamide;

N-[4-[(6,7-dimethoxy-1,5-naphthyridin-4-yl) oxy]-3-fluorophenyl]-5-(4-fluorophenyl)-4-oxo-1-[1-(trifluoromethyl)cyclopropyl]pyridine-3-carboxamide;

1-[1-(difluoromethyl) pyrazol-4-yl]-N-[4-[(6,7-dimethoxy-1,5-naphthyridin-4-yl) oxy]-3-fluorophenyl]-5-(4-fluorophenyl)-4-oxopyridine-3-carboxamide;

N-[4-[(6,7-dimethoxy-1,5-naphthyridin-4-yl) oxy]-3-fluorophenyl]-5-(4-fluorophenyl)-4-oxo-1-(1H-pyrazol-3-yl)pyridine-3-carboxamide;

N-[4-[(6,7-dimethoxy-1,5-naphthyridin-4-yl) oxy]-3-fluorophenyl]-5-(4-fluorophenyl)-4-oxo-1-(1H-pyrazol-4-yl)pyridine-3-carboxamide;

N-[4-[(6,7-dimethoxy-1,5-naphthyridin-4-yl) oxy]-3-fluorophenyl]-1-ethyl-5-(4-fluorophenyl)-6-methyl-4-oxopyridine-3-carboxamide;

N-[3-fluoro-4-[(7-methoxy-1,5-naphthyridin-4-yl) oxy]phenyl]-5-(4-fluorophenyl)-4-hydroxy-6-methylpyridine-3-carboxamide;

N-[4-[(6,7-dimethoxy-1,5-naphthyridin-4-yl) oxy]phenyl]-5-(4-fluorophenyl)-1,6-dimethyl-4-oxopyridine-3-carboxamide;

N-[3-fluoro-4-[(7-methoxy-1,5-naphthyridin-4-yl) oxy]phenyl]-5-(4-fluorophenyl)-4-hydroxy-2,6-dimethylpyridine-3-carboxamide;

N-[3-fluoro-4-[(6-methoxy-1,5-naphthyridin-4-yl) oxy]phenyl]-5-(4-fluorophenyl)-4-hydroxy-2,6-dimethylpyridine-3-carboxamide;

N-[3-fluoro-4-[[7-methoxy-6-(2-methoxyethoxy)-1,5-naphthyridin-4-yl]oxy]phenyl]-5-(4-fluorophenyl)-4-hydroxy-6-methylpyridine-3-carboxamide;

N-[4-[(6,7-dimethoxy-1,5-naphthyridin-4-yl) oxy]-3-fluorophenyl]-5-(4-fluoro-2-methylphenyl)-4-hydroxy-6-methylpyridine-3-carboxamide;

N-[3-fluoro-4-[(6-methoxy-1,5-naphthyridin-4-yl) oxy]phenyl]-5-(4-fluoro-2-methylphenyl)-4-hydroxy-2,6-dimethylpyridine-3-carboxamide;

N-[4-[(6,7-dimethoxy-1,5-naphthyridin-4-yl) oxy]-3-fluorophenyl]-5-(4-fluorophenyl)-4-hydroxy-6-(hydroxymethyl)pyridine-3-carboxamide;

N-[4-[(6,7-dimethoxy-1,5-naphthyridin-4-yl) oxy]-3-fluorophenyl]-5-(4-fluorophenyl)-6-(hydroxymethyl)-1-methyl-4-oxopyridine-3-carboxamide;

N-[4-[(6,7-dimethoxy-1,5-naphthyridin-4-yl) oxy]-3-fluorophenyl]-6-(fluoromethyl)-5-(4-fluorophenyl)-1-methyl-4-oxopyridine-3-carboxamide;

N-[4-[(6,7-dimethoxy-1,5-naphthyridin-4-yl) oxy]-3-fluorophenyl]-5-(4-fluorophenyl)-6-methyl-4-oxo-1-(2,2,2-trifluoroethyl) pyridine-3-carboxamide;

N-[4-[(6,7-dimethoxy-1,5-naphthyridin-4-yl) oxy]-3-fluorophenyl]-5-(4-fluoro-2-methylphenyl)-1,6-dimethyl-4-oxopyridine-3-carboxamide;

N-[4-[(6,7-dimethoxy-1,5-naphthyridin-4-yl) oxy]-3-fluorophenyl]-5-(4-fluorophenyl)-1-methyl-6-(methylamino)-4-oxopyridine-3-carboxamide;

6-cyano-N-[4-[(6,7-dimethoxy-1,5-naphthyridin-4-yl) oxy]-3-fluorophenyl]-5-(4-fluorophenyl)-1-methyl-4-oxopyridine-3-carboxamide;

N-[4-[(6,7-dimethoxy-1,5-naphthyridin-4-yl) oxy]-3-fluorophenyl]-5-(4-fluorophenyl)-6-methoxy-1-methyl-4-oxopyridine-3-carboxamide;

N-[4-[(6,7-dimethoxy-1,5-naphthyridin-4-yl) oxy]-3-fluorophenyl]-5-(4-fluorophenyl)-4-hydroxy-6-(trifluoromethyl)pyridine-3-carboxamide;

N-[3-fluoro-4-[(7-methoxy-1,5-naphthyridin-4-yl) oxy]phenyl]-5-(4-fluorophenyl)-4-hydroxy-2-methylpyridine-3-carboxamide;

N-[4-[(6,7-dimethoxy-1,5-naphthyridin-4-yl) oxy]-3-fluorophenyl]-5-(4-fluorophenyl)-1,2-dimethyl-4-oxopyridine-3-carboxamide;

N-[4-[(6,7-dimethoxy-1,5-naphthyridin-4-yl) oxy]-3-fluorophenyl]-1-ethyl-5-(4-fluorophenyl)-2-methyl-4-oxopyridine-3-carboxamide;

N-[3-fluoro-4-[(7-methoxy-1,5-naphthyridin-4-yl) oxy]phenyl]-1-(4-fluorophenyl)-6-methyl-2-oxopyridine-3-carboxamide;

N-[3-fluoro-4-[(6-methoxy-1,5-naphthyridin-4-yl) oxy]phenyl]-1-(4-fluorophenyl)-6-methyl-2-oxopyridine-3-carboxamide;

N-[3-fluoro-4-[(6-methoxy-1,5-naphthyridin-4-yl) oxy]phenyl]-1-(4-fluoro-2-methylphenyl)-6-methyl-2-oxopyridine-3-carboxamide;

5-acetyl-N-[4-[(6,7-dimethoxy-1,5-naphthyridin-4-yl) oxy]-3-fluorophenyl]-1-(4-fluorophenyl)-6-methyl-2-oxopyridine-3-carboxamide;

5-cyano-N-[4-[(6,7-dimethoxy-1,5-naphthyridin-4-yl) oxy]-3-fluorophenyl]-1-(4-fluorophenyl)-6-methyl-2-oxopyridine-3-carboxamide;

N-[4-[(6,7-dimethoxy-1,5-naphthyridin-4-yl) oxy]-3-fluorophenyl]-5-(4-fluorophenyl)-6-methyl-4-oxo-1H-pyridazine-3-carboxamide;

N-[3-fluoro-4-[(6-methoxy-1,5-naphthyridin-4-yl) oxy]phenyl]-5-(4-fluorophenyl)-6-methyl-4-oxo-1H-pyridazine-3-carboxamide;

N-[4-[(6,7-dimethoxy-1,5-naphthyridin-4-yl) oxy]-3-fluorophenyl]-5-(4-fluoro-2-methylphenyl)-6-methyl-4-oxo-1H-pyridazine-3-carboxamide;

N-[4-[(6,7-dimethoxy-1,5-naphthyridin-4-yl) oxy]phenyl]-5-(4-fluorophenyl)-1,6-dimethyl-4-oxopyridazine-3-carboxamide;

N-[4-[(6,7-dimethoxy-1,5-naphthyridin-4-yl) oxy]-3-fluorophenyl]-5-(4-fluorophenyl)-1,6-dimethyl-4-oxopyridazine-3-carboxamide;

N-[4-[(6,7-dimethoxy-1,5-naphthyridin-4-yl) oxy]-3-fluorophenyl]-4-(4-fluorophenyl)-5-methyl-3-oxopyrazine-2-carboxamide;

N-[3-fluoro-4-[(7-methoxy-1,5-naphthyridin-4-yl) oxy]phenyl]-4-(4-fluorophenyl)-5-methyl-3-oxopyrazine-2-carboxamide;

N-[4-[(6,7-dimethoxy-1,5-naphthyridin-4-yl) oxy]-3-fluorophenyl]-4-(4-fluorophenyl)-5,6-dimethyl-3-oxopyrazine-2-carboxamide;

N-[4-[(6,7-dimethoxy-1,5-naphthyridin-4-yl) oxy]-3-fluorophenyl]-6-(4-fluorophenyl)-5-hydroxypyrimidine-4-carboxamide;

N-[4-[(6,7-dimethoxy-1,5-naphthyridin-4-yl) oxy]-3-fluorophenyl]-1-(4-fluorophenyl)-2-methyl-6-oxopyrimidine-5-carboxamide;

N-[4-[(6,7-dimethoxy-1,5-naphthyridin-4-yl) oxy]-3-fluorophenyl]-1-(4-fluorophenyl)-4-methyl-6-oxopyrimidine-5-carboxamide;

N-[4-[(6,7-dimethoxy-1,5-naphthyridin-4-yl) oxy]-3-fluorophenyl]-1-(4-fluorophenyl)-2-(methylamino)-6-oxopyrimidine-5-carboxamide;

N-[4-[(6,7-dimethoxy-1,5-naphthyridin-4-yl) oxy]-3-fluorophenyl]-2-(dimethylamino)-1-(4-fluorophenyl)-6-oxopyrimidine-5-carboxamide;

N-[4-[(6,7-dimethoxy-1,5-naphthyridin-4-yl) oxy]-3-fluorophenyl]-1-(4-fluorophenyl)-2,4-dimethyl-6-oxopyrimidine-5-carboxamide;

N-[4-[(6,7-dimethoxy-1,5-naphthyridin-4-yl) oxy]-3-fluorophenyl]-3-(4-fluorophenyl)-2,4-dioxo-1H-pyrimidine-5-carboxamide;

N-[3-fluoro-4-[(6-methoxy-1,5-naphthyridin-4-yl) oxy]phenyl]-3-(4-fluorophenyl)-2,4-dioxo-1H-pyrimidine-5-carboxamide; and N-[4-[(6,7-dimethoxy-1,5-naphthyridin-4-yl) oxy]-3-fluorophenyl]-3-(4-fluorophenyl)-4-oxo-2-sulfanylidene-1H-pyrimidine-5-carboxamide;

or a pharmaceutically acceptable salt or stereoisomer thereof.

27. A compound or a pharmaceutically acceptable salt or stereoisomer thereof, the compound selected from Compounds 21-824:

| Cpd # | Structure | IUPAC Name |
|---|---|---|
| 21 | 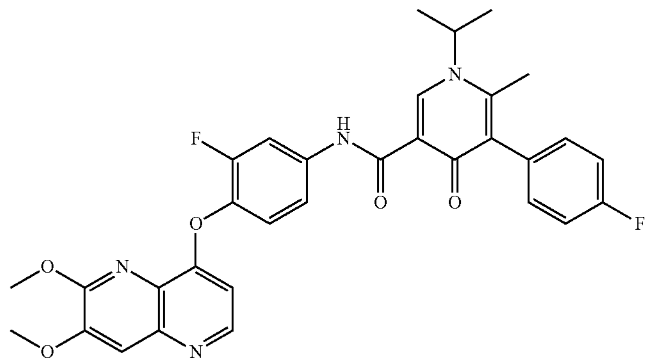 [SMILES: COc1cc2nccc(Oc3ccc(NC(=O)c4cn(C(C)C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-4-oxo-1-propan-2-ylpyridine-3-carboxamide |
| 22 | 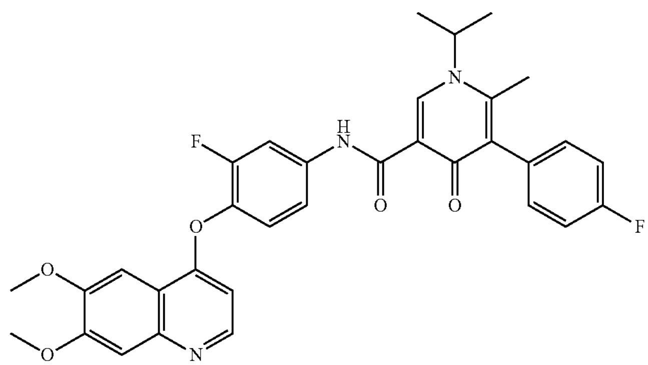 [SMILES: COc1cc2nccc(Oc3ccc(NC(=O)c4cn(C(C)C)c(C)c(-c5ccc(F)cc5)c4=O)cc3F)c2cc1OC] | N-[4-(6,7-dimethoxyquinolin-4-yl)oxy-3-fluorophenyl]-5-(4-fluorophenyl)-6-methyl-4-oxo-1-propan-2-ylpyridine-3-carboxamide |
| 23 | 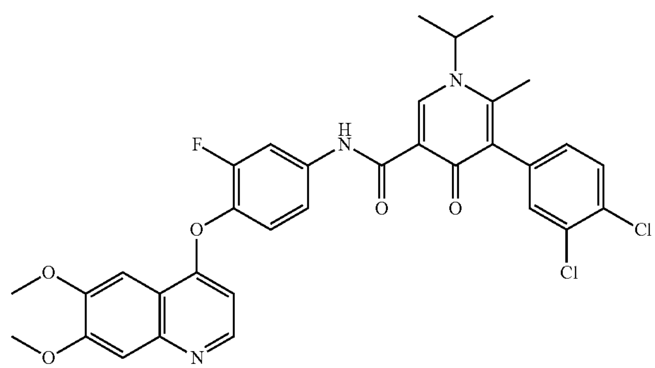 [SMILES: COc1cc2nccc(Oc3ccc(NC(=O)c4cn(C(C)C)c(C)c(-c5ccc(Cl)c(Cl)c5)c4=O)cc3F)c2cc1OC] | 5-(3,4-dichlorophenyl)-N-[4-(6,7-dimethoxyquinolin-4-yl)oxy-3-fluorophenyl]-6-methyl-4-oxo-1-propan-2-ylpyridine-3-carboxamide |
| 24 | 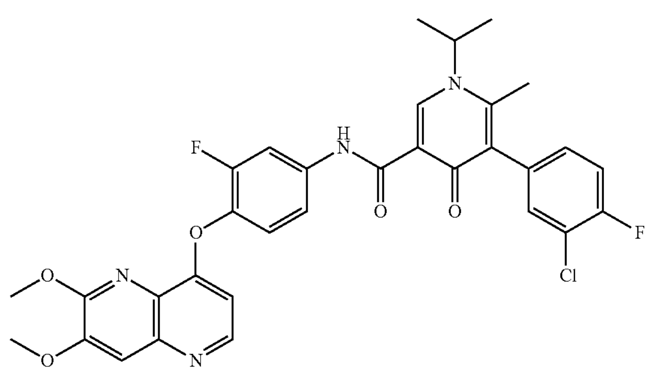 [SMILES: COc1cc2nccc(Oc3ccc(NC(=O)c4cn(C(C)C)c(C)c(-c5ccc(F)c(Cl)c5)c4=O)cc3F)c2nc1OC] | 5-(3-chloro-4-fluorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide |

-continued

| Cpd # | Structure | IUPAC Name |
|---|---|---|
| 25 | 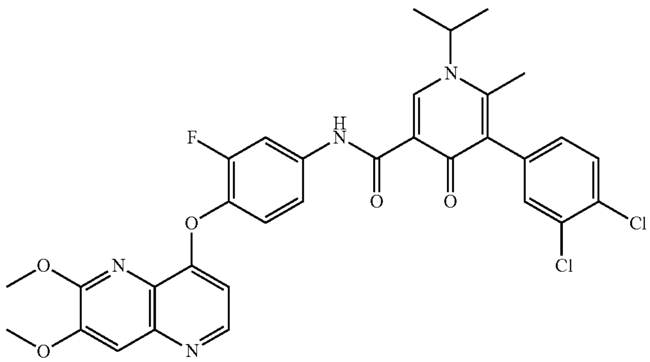 [SMILES: COc1cc2nccc(Oc3ccc(NC(=O)c4cn(C(C)C)c(C)c(-c5ccc(Cl)c(Cl)c5)c4=O)cc3F)c2nc1OC] | 5-(3,4-dichlorophenyl)-N-[4-[(6,7-dimethoxy-1,5-naphthyridin-4-yl)oxy]-3-fluorophenyl]-6-methyl-4-oxo-1-propan-2-ylpyridine-3-carboxamide |
| 26 | 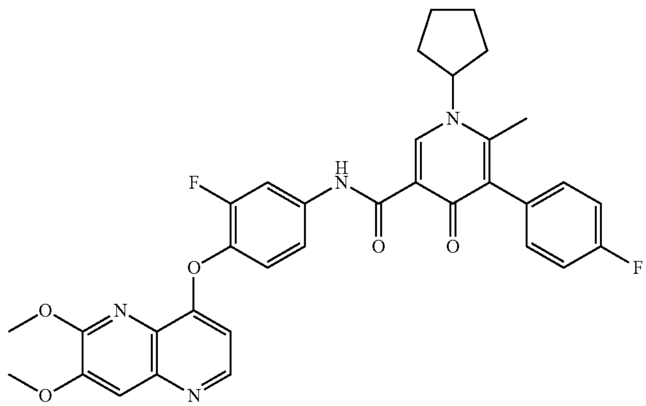 [SMILES: COc1cc2nccc(Oc3ccc(NC(=O)c4cn(C5CCCC5)c(C)c(-c5ccc(F)cc5)c4=O)cc3F)c2nc1OC] | 1-cyclopentyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 27 | 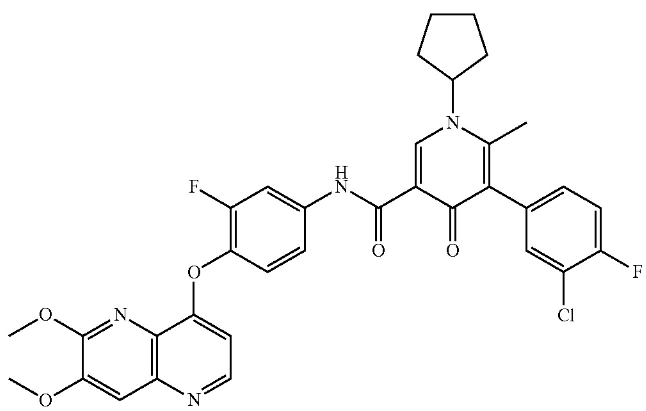 [SMILES: COc1cc2nccc(Oc3ccc(NC(=O)c4cn(C5CCCC5)c(C)c(-c5ccc(F)c(Cl)c5)c4=O)cc3F)c2nc1OC] | 5-(3-chloro-4-fluorophenyl)-1-cyclopentyl-N-[4-[(6,7-dimethoxy-1,5-naphthyridin-4-yl)oxy]-3-fluorophenyl]-6-methyl-4-oxopyridine-3-carboxamide |
| 28 | 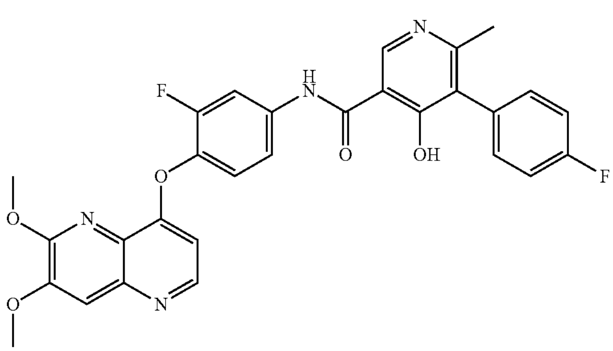 [SMILES: COc1cc2nccc(Oc3ccc(NC(=O)c4cnc(C)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-methylpyridine-3-carboxamide |

| Cpd # | Structure | IUPAC Name |
|---|---|---|
| 29 | 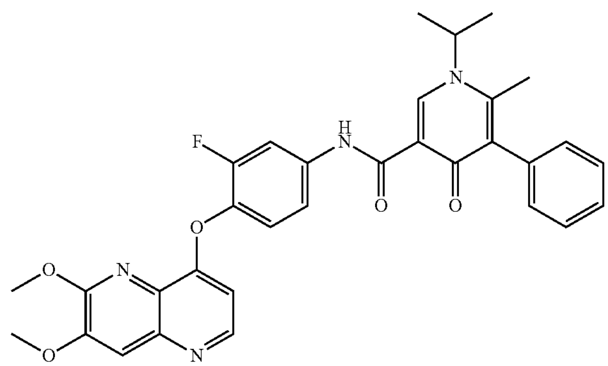 [SMILES: COc1cc2nccc(Oc3ccc(NC(=O)c4cn(C(C)C)c(C)c(-c5ccccc5)c4=O)cc3F)c2nc1OC] | N-[4-[(6,7-dimethoxy-1,5-naphthyridin-4-yl)oxy]-3-fluorophenyl]-6-methyl-4-oxo-5-phenyl-1-propan-2-ylpyridine-3-carboxamide |
| 30 | 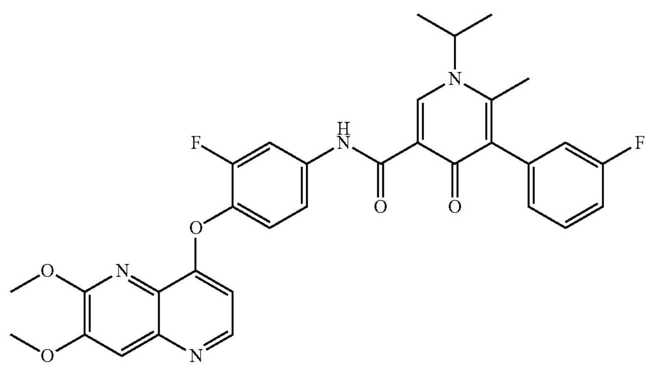 [SMILES: COc1cc2nccc(Oc3ccc(NC(=O)c4cn(C(C)C)c(C)c(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-6-methyl-4-oxo-1-propan-2-ylpyridine-3-carboxamide |
| 31 | 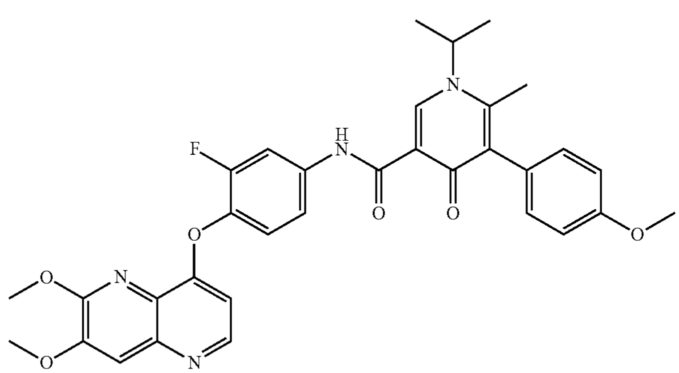 | N-[4-[(6, 7-dimethoxy-1,5-naphthyridin-4-yl)oxy]-3-fluorophenyl]-5-(4-methoxyphenyl)-6-methyl-4-oxo-1-propan-2-ylpyridine-3-carboxamide |
| 32 | 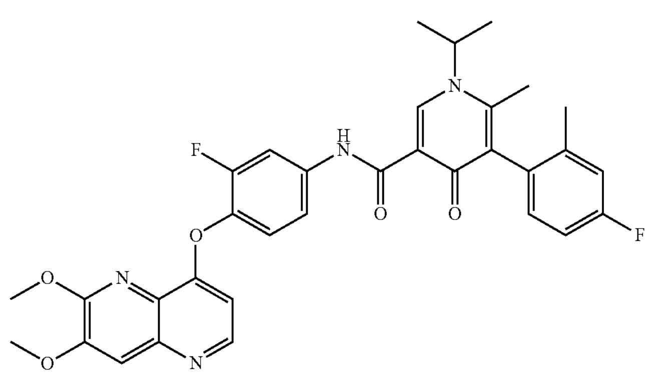 [SMILES: COc1cc2nccc(Oc3ccc(NC(=O)c4cn(C(C)C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-6-methyl-4-oxo-1-propan-2-ylpyridine-3-carboxamide |

-continued

| Cpd # | Structure | IUPAC Name |
|---|---|---|
| 33 | 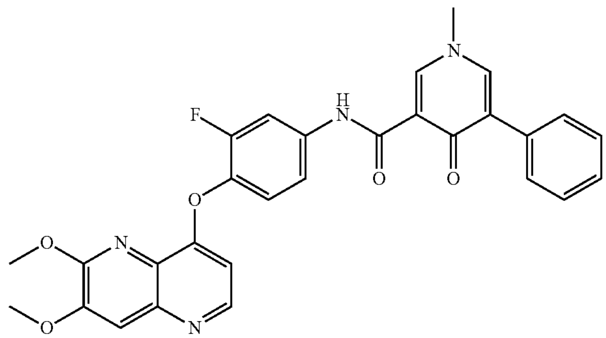 [SMILES: COc1cc2nccc(Oc3ccc(NC(=O)c4cn(C)cc(-c5ccccc5)c4=O)cc3F)c2nc1OC] | N-[4-[(6,7-dimethoxy-1,5-naphthyridin-4-yl)oxy]-3-fluorophenyl]-1-methyl-4-oxo-5-phenylpyridine-3-carboxamide |
| 34 | 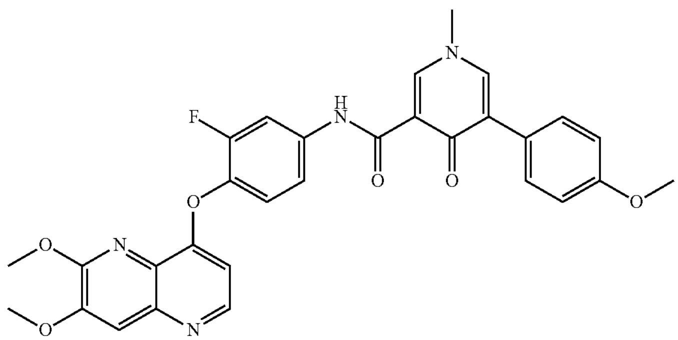 | N-[4-[(6,7-dimethoxy-1,5-naphthyridin-4-yl)oxy]-3-fluorophenyl]-5-(4-methoxyphenyl)-1-methyl-4-oxopyridine-3-carboxamide |
| 35 | 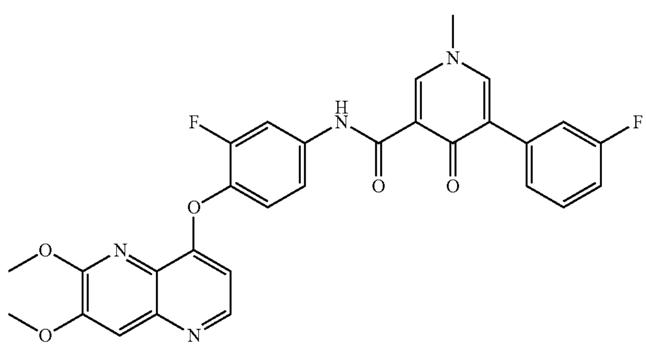 [SMILES: COc1cc2nccc(Oc3ccc(NC(=O)c4cn(C)cc(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-1-methyl-4-oxopyridine-3-carboxamide |
| 36 | 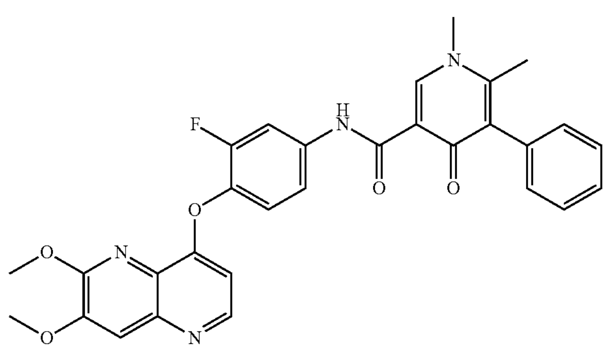 [SMILES: COc1cc2nccc(Oc3ccc(NC(=O)c4cn(C)c(C)c(-c5ccccc5)c4=O)cc3F)c2nc1OC] | N-[4-[(6,7-dimethoxy-1,5-naphthyridin-4-yl)oxy]-3-fluorophenyl]-1,6-dimethyl-4-oxo-5-phenylpyridine-3-carboxamide |

-continued

| Cpd # | Structure | IUPAC Name |
|---|---|---|
| 37 | 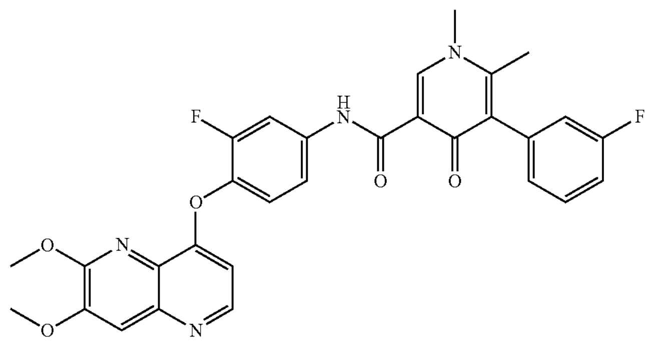 [SMILES: COc1cc2nccc(Oc3ccc(NC(=O)c4cn(C)c(C)c(-c5cccc(F)c5)c4=O)cc3F)c2nc1OC] | N-[4-[(6,7-dimethoxy-1,5-naphthyridin-4-yl)oxy]-3-fluorophenyl]-5-(3-fluorophenyl)-1,6-dimethyl-4-oxopyridine-3-carboxamide |
| 38 | 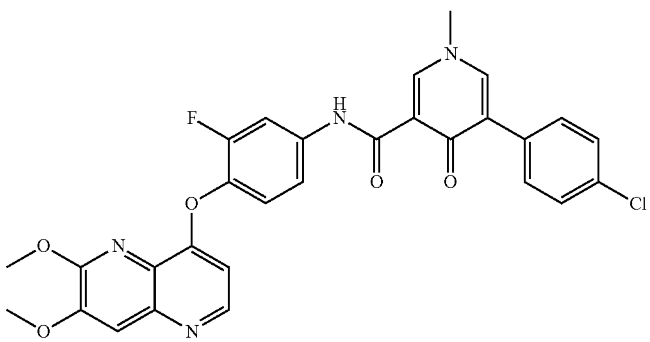 [SMILES: COc1cc2nccc(Oc3ccc(NC(=O)c4cn(C)cc(-c5ccc(Cl)cc5)c4=O)cc3F)c2nc1OC] | 5-(4-chlorophenyl)-N-[4-[(6,7-dimethoxy-1,5-naphthyridin-4-yl)oxy]-3-fluorophenyl]-1-methyl-4-oxopyridine-3-carboxamide |
| 39 | 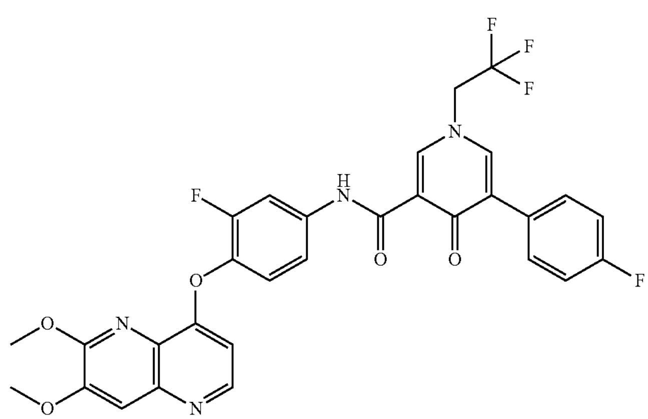 [SMILES: COc1cc2nccc(Oc3ccc(NC(=O)c4cn(CC(F)(F)F)cc(-c5ccc(F)cc5)c4=O)cc3F)c2nc1OC] | N-[4-[(6,7-dimethoxy-1,5-naphthyridin-4-yl)oxy]phenyl]-1-methyl-4-oxo-5-phenylpyridine-3-carboxamide |
| 40 | 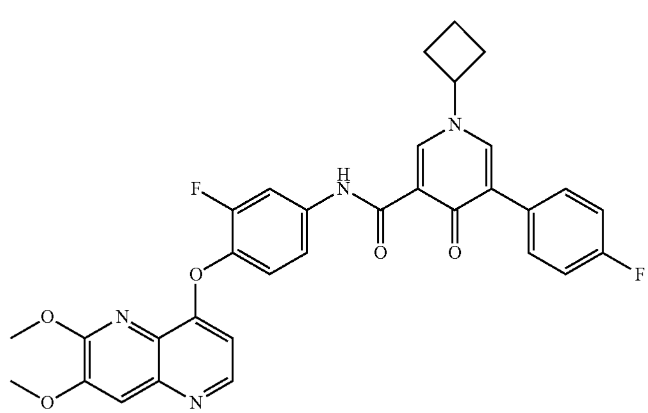 [SMILES: COc1cc2nccc(Oc3ccc(NC(=O)c4cn(C5CCC5)cc(-c5ccc(F)cc5)c4=O)cc3F)c2nc1OC] | N-[3-fluoro-4-[(7-methoxy-1,5-naphthyridin-4-yl)oxy]phenyl]-1-methyl-4-oxo-5-phenylpyridine-3-carboxamide |

-continued

| Cpd # | Structure | IUPAC Name |
|---|---|---|
| 41 | 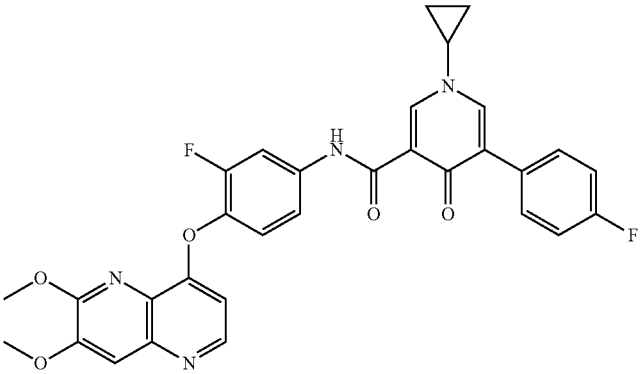 [SMILES: COc1cc2nccc(Oc3ccc(NC(=O)c4cn(C5CC5)cc(-c5ccc(F)cc5)c4=O)cc3F)c2nc1OC] | 1-cyclopropyl-N-[4-[(6,7-dimethoxy-1,5-naphthyridin-4-yl)oxy]-3-fluorophenyl]-5-(4-fluorophenyl)-4-oxopyridine-3-carboxamide |
| 42 | 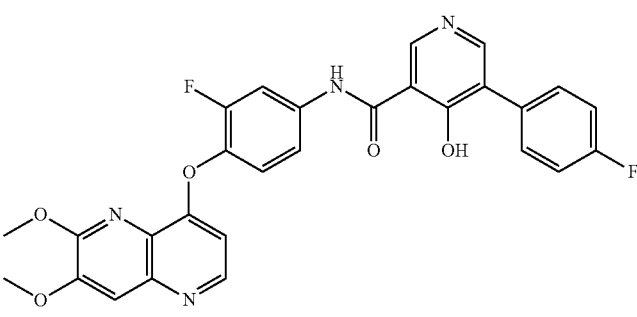 [SMILES: COc1cc2nccc(Oc3ccc(NC(=O)c4cncc(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxypyridine-3-carboxamide |
| 43 | 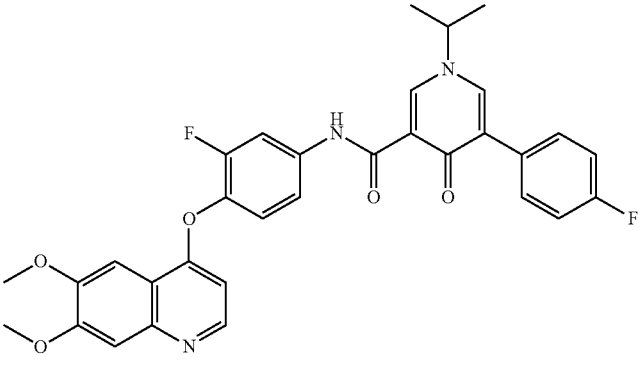 [SMILES: COc1cc2nccc(Oc3ccc(NC(=O)c4cn(C(C)C)cc(-c5ccc(F)cc5)c4=O)cc3F)c2cc1OC] | N-[4-(6,7-dimethoxyquinolin-4-yl)oxy-3-fluorophenyl]-5-(4-fluorophenyl)-4-oxo-1-propan-2-ylpyridine-3-carboxamide |
| 44 | 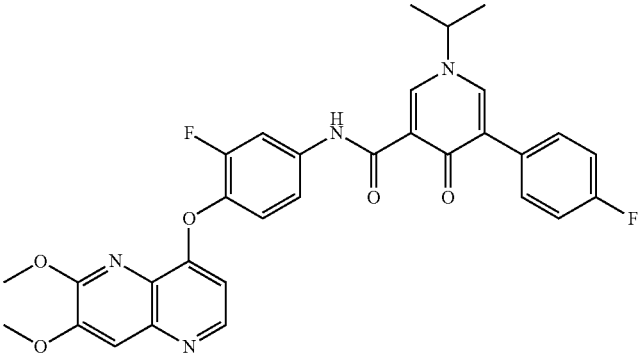 [SMILES: COc1cc2nccc(Oc3ccc(NC(=O)c4cn(C(C)C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-propan-2-ylpyridine-3-carboxamide |

-continued

| Cpd # | Structure | IUPAC Name |
|---|---|---|
| 45 | 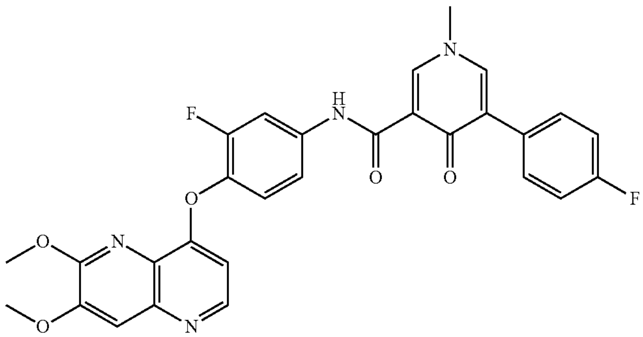 [SMILES: COc1cc2nccc(Oc3ccc(NC(=O)c4cn(C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 46 | 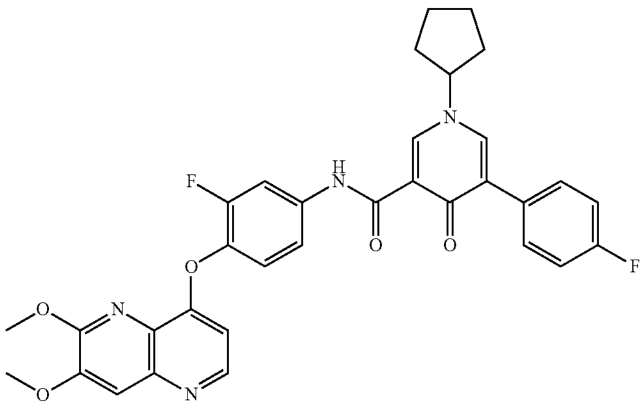 [SMILES: COc1cc2nccc(Oc3ccc(NC(=O)c4cn(C5CCCC5)cc(-c5ccc(F)cc5)c4=O)cc3F)c2nc1OC] | 1-cyclopentyl-N-[4-[(6,7-dimethoxy-1,5-naphthyridin-4-yl)oxy]-3-fluorophenyl]-5-(4-fluorophenyl)-4-oxopyridine-3-carboxamide |
| 47 | 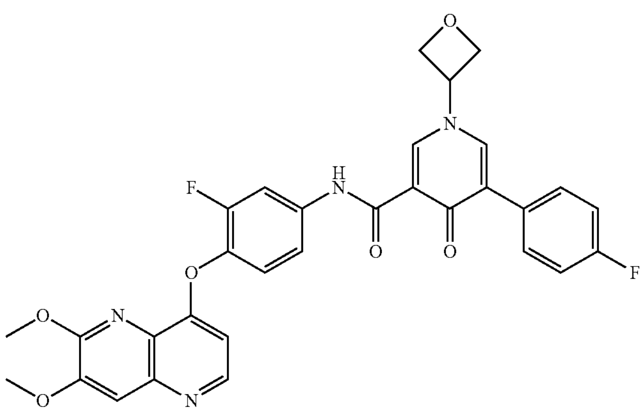 [SMILES: COc1cc2nccc(Oc3ccc(NC(=O)c4cn(C5COC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(oxetan-3-yl)-4-oxopyridine-3-carboxamide |
| 48 | 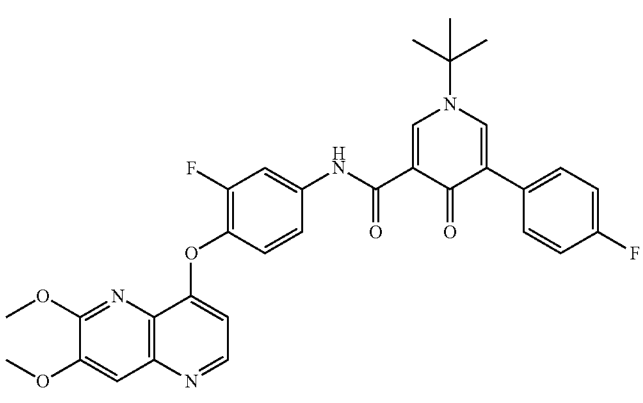 [SMILES: COc1cc2nccc(Oc3ccc(NC(=O)c4cn(C(C)(C)C)cc(-c5ccc(F)cc5)c4=O)cc3F)c2nc1OC] | 1-tert-butyl-N-[4-[(6,7-dimethoxy-1,5-naphthyridin-4-yl)oxy]-3-fluorophenyl]-5-(4-fluorophenyl)-4-oxopyridine-3-carboxamide |

| Cpd # | Structure | IUPAC Name |
|---|---|---|
| 49 | 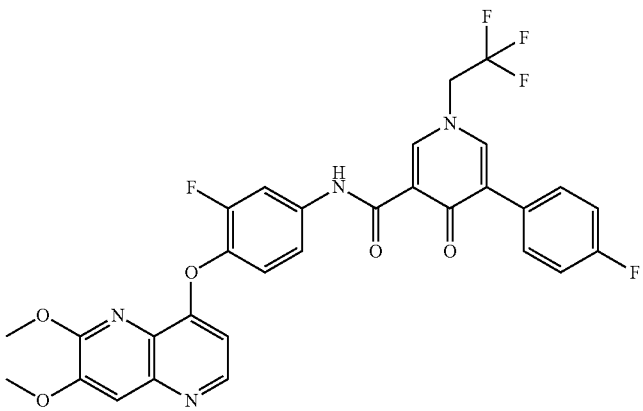 [SMILES: COc1cc2nccc(Oc3ccc(NC(=O)c4cn(CC(F)(F)F)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(2,2,2-trifluoroethyl)pyridine-3-carboxamide |
| 50 | 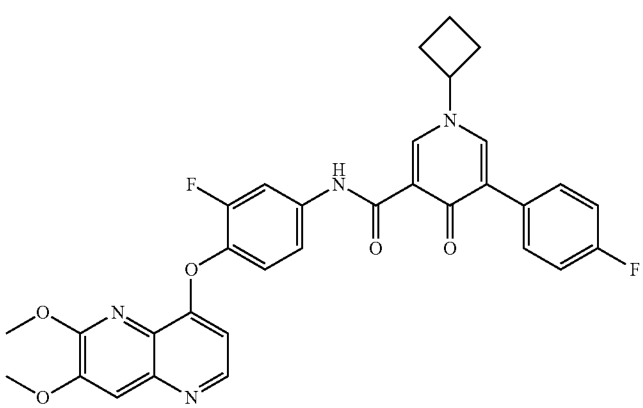 [SMILES: COc1cc2nccc(Oc3ccc(NC(=O)c4cn(C5CCC5)cc(-c5ccc(F)cc5)c4=O)cc3F)c2nc1OC] | 1-cyclobutyl-N-[4-[(6,7-dimethoxy-1,5-naphthyridin-4-yl)oxy]-3-fluorophenyl]-5-(4-fluorophenyl)-4-oxopyridine-3-carboxamide |
| 51 | 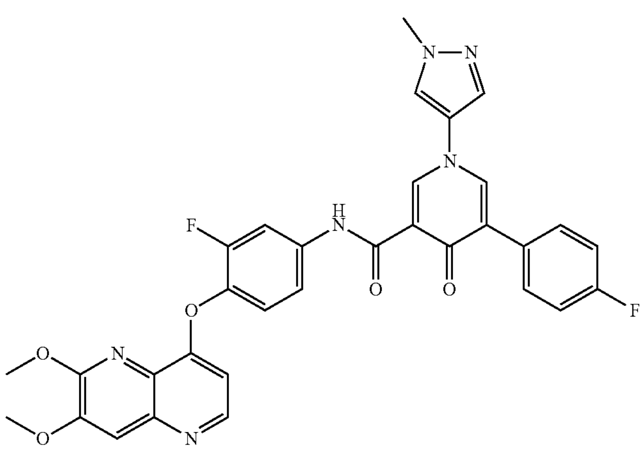 [SMILES: COc1cc2nccc(Oc3ccc(NC(=O)c4cn(-c5cnn(C)c5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-methylpyrazol-4-yl)-4-oxopyridine-3-carboxamide |

| Cpd # | Structure | IUPAC Name |
|---|---|---|
| 52 | 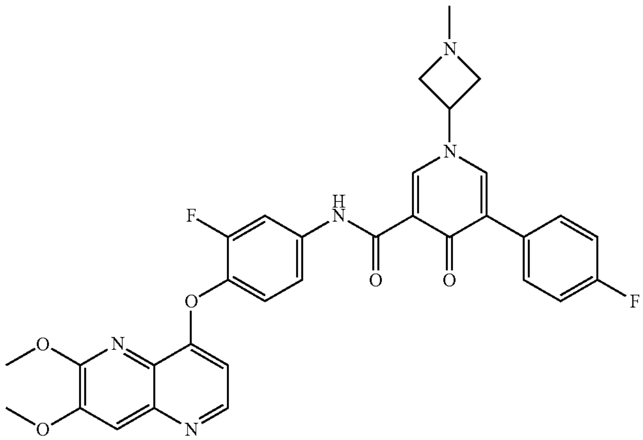 [SMILES: COc1cc2nccc(Oc3ccc(NC(=O)c4cn(C5CN(C)C5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-methylazetidin-3-yl)-4-oxopyridine-3-carboxamide |
| 53 | 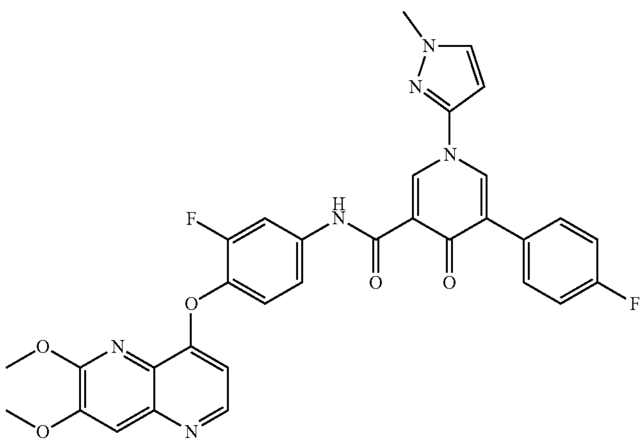 | N-[4-[(6,7-dimethoxy-1,5-naphthyridin-4-yl)oxy]-3-fluorophenyl]-5-(4-fluorophenyl)-1-(1-methylpyrazol-3-yl)-4-oxopyridine-3-carboxamide |
| 54 | 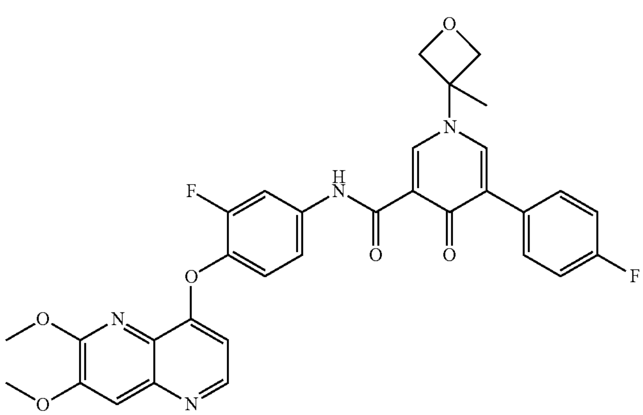 [SMILES: COc1cc2nccc(Oc3ccc(NC(=O)c4cn(C5(C)COC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(3-methyloxetan-3-yl)-4-oxopyridine-3-carboxamide |

-continued

| Cpd # | Structure | IUPAC Name |
|---|---|---|
| 55 | 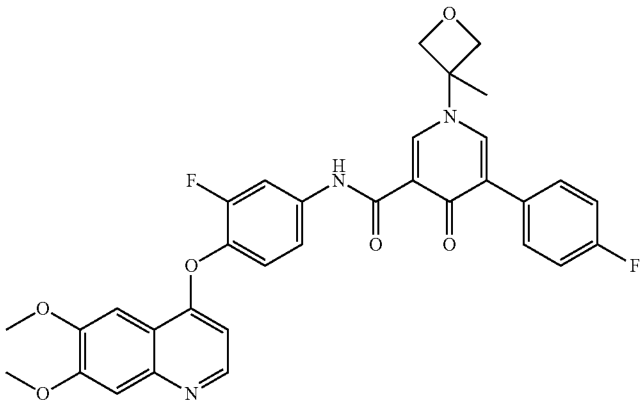 [SMILES: COc1cc2nccc(Oc3ccc(NC(=O)c4cn(C5(C)COC5)cc(-c5ccc(F)cc5)c4=O)cc3F)c2cc1OC] | N-[4-(6,7-dimethoxyquinolin-4-yl)oxy-3-fluorophenyl]-5-(4-fluorophenyl)-1-(3-methyloxetan-3-yl)-4-oxopyridine-3-carboxamide |
| 56 | 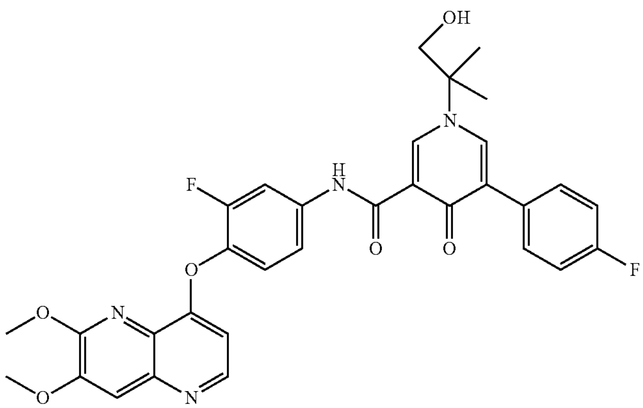 [SMILES: COc1cc2nccc(Oc3ccc(NC(=O)c4cn(C(C)(C)CO)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(1-hydroxy-2-methylpropan-2-yl)-4-oxopyridine-3-carboxamide |
| 57 | 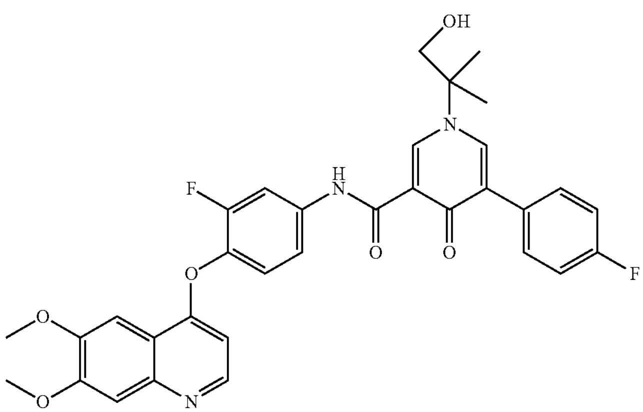 [SMILES: COc1cc2nccc(Oc3ccc(NC(=O)c4cn(C(C)(C)CO)cc(-c5ccc(F)cc5)c4=O)cc3F)c2cc1OC] | N-[4-(6,7-dimethoxyquinolin-4-yl)oxy-3-fluorophenyl]-5-(4-fluorophenyl)-1-(1-hydroxy-2-methylpropan-2-yl)-4-oxopyridine-3-carboxamide |
| 58 | 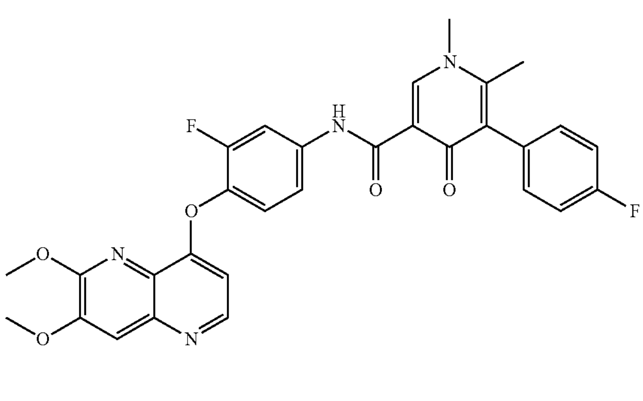 | N-[4-[(6,7-dimethoxy-1,5-naphthyridin-4-yl)oxy]-3-fluorophenyl]-5-(4-fluorophenyl)-1,6-dimethyl-4-oxopyridine-3-carboxamide |

| Cpd # | Structure | IUPAC Name |
|---|---|---|
| 59 | 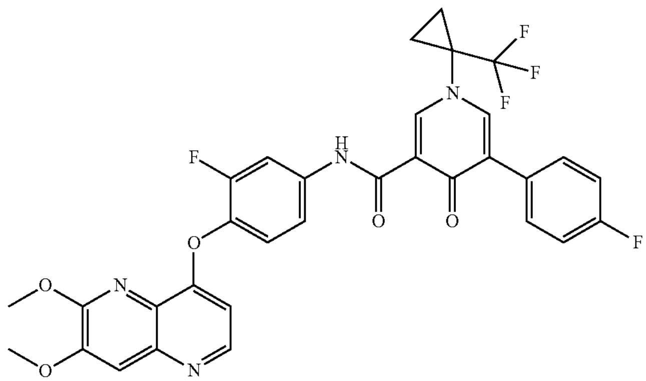 [SMILES: COc1cc2nccc(Oc3ccc(NC(=O)c4cn(C5(C(F)(F)F)CC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-[1-(trifluoromethyl)cyclopropyl]pyridine-3-carboxamide |
| 60 | 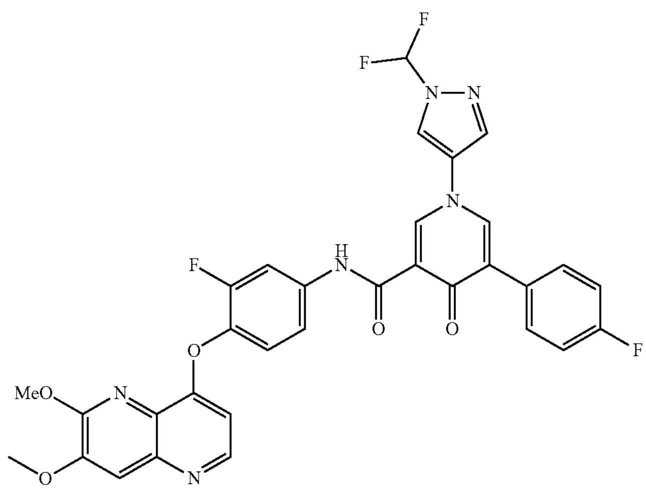 [SMILES: COc1cc2nccc(Oc3ccc(NC(=O)c4cn(-c5cnn(C(F)F)c5)cc(-c5ccc(F)cc5)c4=O)cc3F)c2nc1OC] | 1-[1-(difluoromethyl)pyrazol-4-yl]-N-[4-[(6,7-dimethoxy-1,5-naphthyridin-4-yl)oxy]-3-fluorophenyl]-5-(4-fluorophenyl)-4-oxopyridine-3-carboxamide |
| 61 | 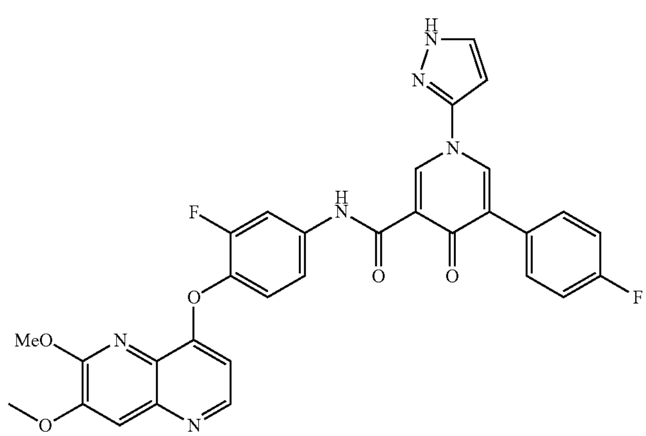 [SMILES: COc1cc2nccc(Oc3ccc(NC(=O)c4cn(-c5cc[nH]n5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(1H-pyrazol-3-yl)pyridine-3-carboxamide |

-continued

| Cpd # | Structure | IUPAC Name |
|---|---|---|
| 62 | 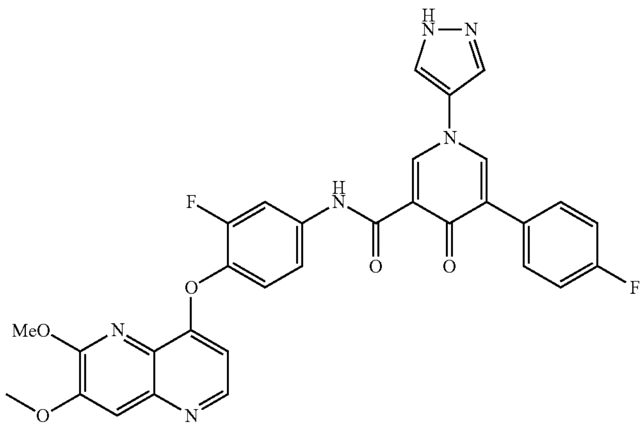 [SMILES: COc1cc2nccc(Oc3ccc(NC(=O)c4cn(-c5cn[nH]c5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-(1H-pyrazol-4-yl)pyridine-3-carboxamide |
| 63 | 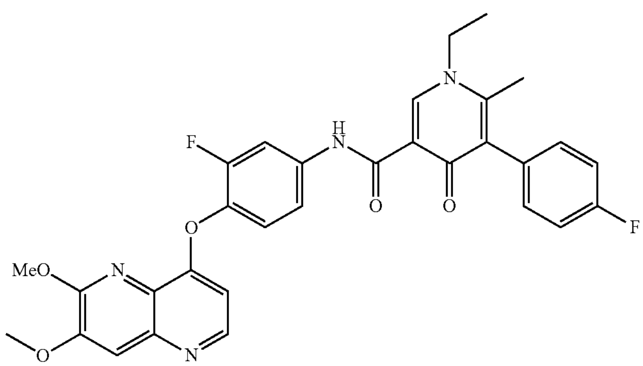 [SMILES: CCn1cc(C(=O)Nc2ccc(Oc3ccnc4cc(OC)c(OC)nc34)c(F)c2)c(=O)c(-c2ccc(F)cc2)c1C] | N-[4-[(6,7-dimethoxy-1,5-naphthyridin-4-yl)oxy]-3-fluorophenyl]-1-ethyl-5-(4-fluorophenyl)-6-methyl-4-oxopyridine-3-carboxamide |
| 64 | 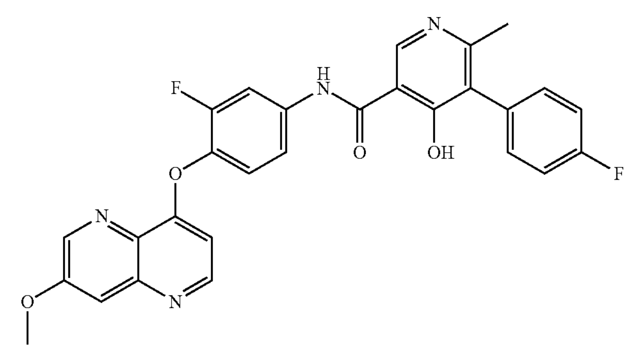 [SMILES: COc1cnc2c(Oc3ccc(NC(=O)c4cnc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-methylpyridine-3-carboxamide |
| 65 | 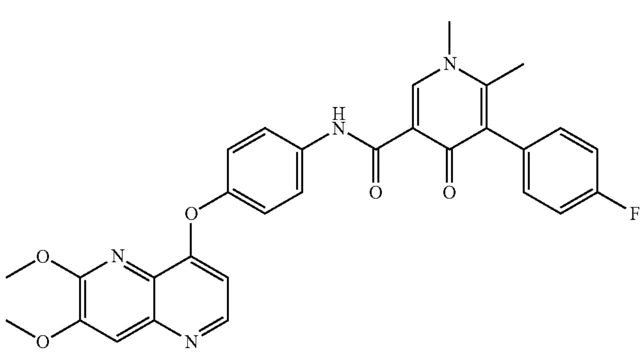 | N-[4-[(6,7-dimethoxy-1,5-naphthyridin-4-yl)oxy]phenyl]-5-(4-fluorophenyl)-1,6-dimethyl-4-oxopyridine-3-carboxamide |

-continued

| Cpd # | Structure | IUPAC Name |
|---|---|---|
| 66 | 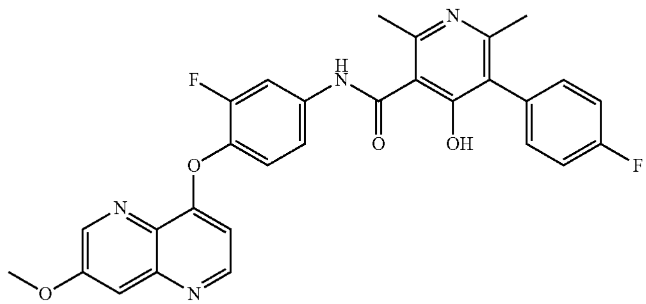 [SMILES: COc1cnc2c(Oc3ccc(NC(=O)c4c(C)nc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2,6-dimethylpyridine-3-carboxamide |
| 67 | 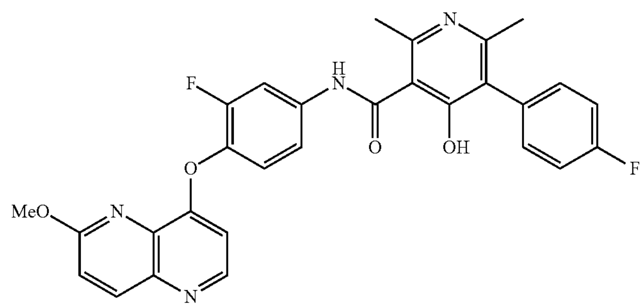 [SMILES: COc1ccc2nccc(Oc3ccc(NC(=O)c4c(C)nc(C)c(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-2,6-dimethylpyridine-3-carboxamide |
| 68 | 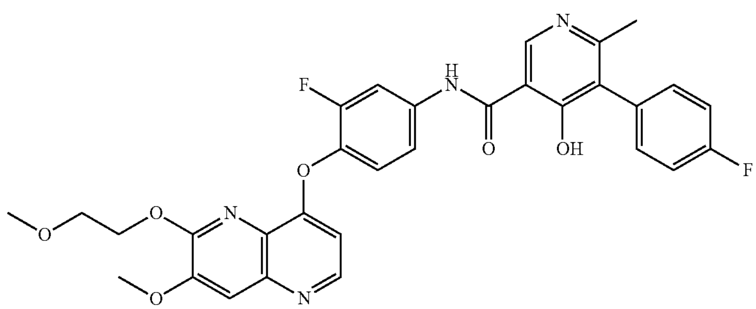 [SMILES: COCCOc1nc2c(Oc3ccc(NC(=O)c4cnc(C)c(-c5ccc(F)cc5)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-6-methylpyridine-3-carboxamide |
| 69 | 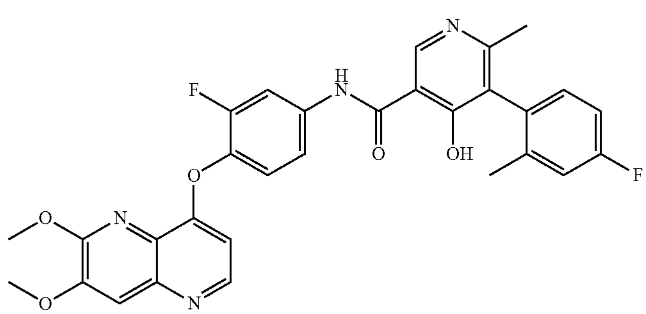 [SMILES: COc1cc2nccc(Oc3ccc(NC(=O)c4cnc(C)c(-c5ccc(F)cc5C)c4O)cc3F)c2nc1OC] | N-[4-[(6,7-dimethoxy-1,5-naphthyridin-4-yl)oxy]-3-fluorophenyl]-5-(4-fluoro-2-methylphenyl)-4-hydroxy-6-methylpyridine-3-carboxamide |
| 70 | 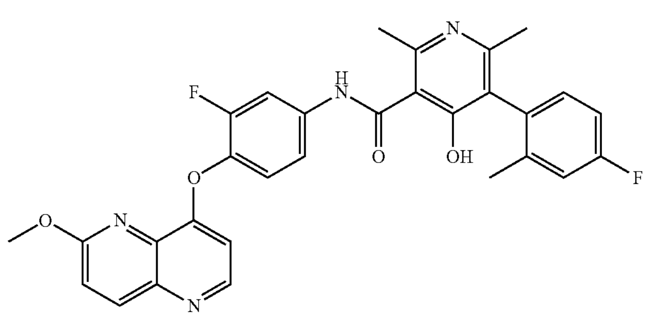 [SMILES: COc1ccc2nccc(Oc3ccc(NC(=O)c4c(C)nc(C)c(-c5ccc(F)cc5C)c4O)cc3F)c2n1] | N-[3-fluoro-4-[(6-methoxy-1,5-naphthyridin-4-yl)oxy]phenyl]-5-(4-fluoro-2-methylphenyl)-4-hydroxy-2,6-dimethylpyridine-3-carboxamide |

| Cpd # | Structure | IUPAC Name |
|---|---|---|
| 71 | 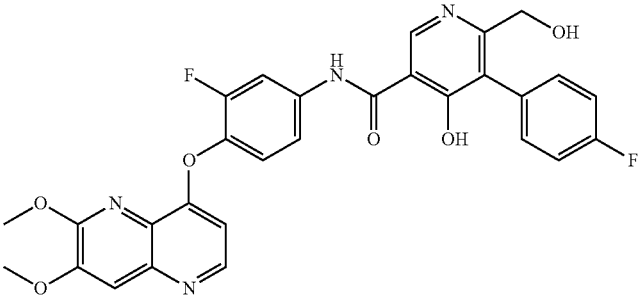 [SMILES: COc1cc2nccc(Oc3ccc(NC(=O)c4cnc(CO)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-(hydroxymethyl)pyridine-3-carboxamide |
| 72 | 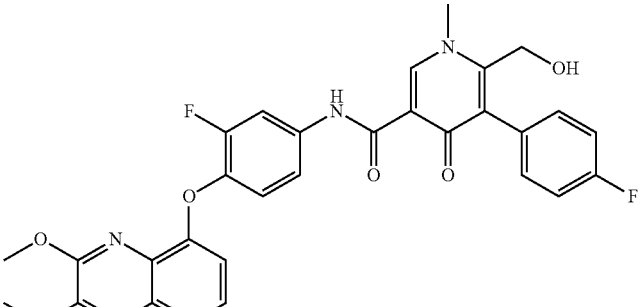 | N-[4-[(6,7-dimethoxy-1,5-naphthyridin-4-yl)oxy]-3-fluorophenyl]-5-(4-fluorophenyl)-6-(hydroxymethyl)-1-methyl-4-oxopyridine-3-carboxamide |
| 73 | 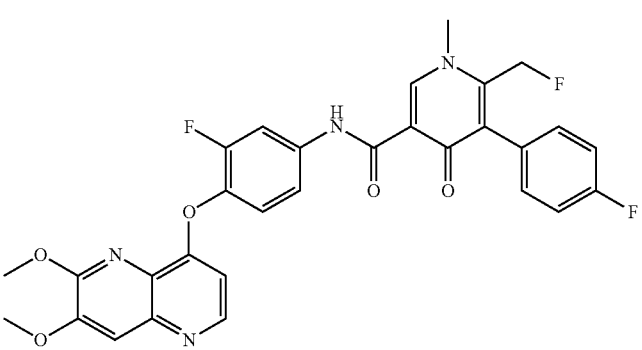 [SMILES: COc1cc2nccc(Oc3ccc(NC(=O)c4cn(C)c(CF)c(-c5ccc(F)cc5)c4=O)cc3F)c2nc1OC] | N-[4-[(6,7-dimethoxy-1,5-naphthyridin-4-yl)oxy]-3-fluorophenyl]-6-(fluoromethyl)-5-(4-fluorophenyl)-1-methyl-4-oxopyridine-3-carboxamide |
| 74 | 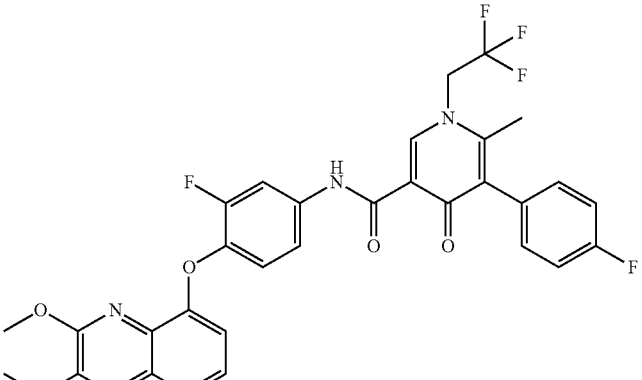 | N-[4-[(6,7-dimethoxy-1,5-naphthyridin-4-yl)oxy]-3-fluorophenyl]-5-(4-fluorophenyl)-6-methyl-4-oxo-1-(2,2,2-trifluoroethyl)pyridine-3-carboxamide |

-continued

| Cpd # | Structure | IUPAC Name |
|---|---|---|
| 75 | 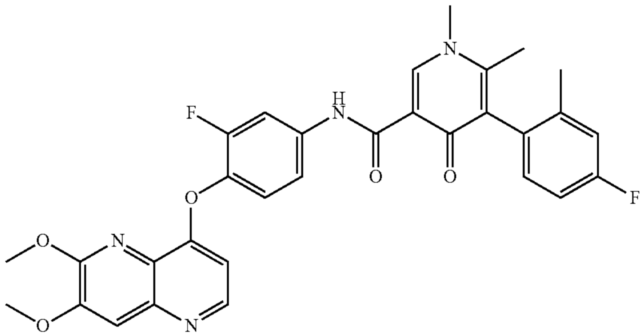 [SMILES: COc1cc2nccc(Oc3ccc(NC(=O)c4cn(C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1,6-dimethyl-4-oxopyridine-3-carboxamide |
| 76 | 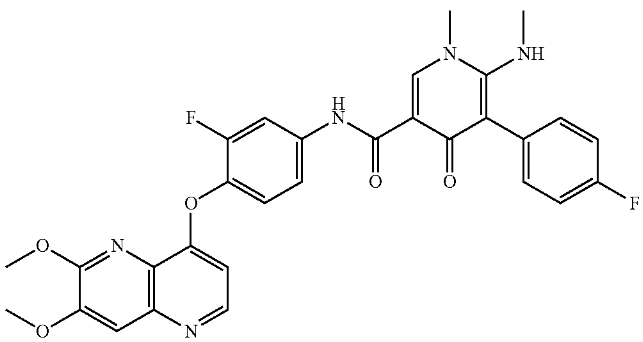 [SMILES: CNc1c(-c2ccc(F)cc2)c(=O)c(C(=O)Nc2ccc(Oc3ccnc4cc(OC)c(OC)nc34)c(F)c2)cn1C] | N-[4-[(6,7-dimethoxy-1,5-naphthyridin-4-yl)oxy]-3-fluorophenyl]-5-(4-fluorophenyl)-1-methyl-6-(methylamino)-4-oxopyridine-3-carboxamide |
| 77 | 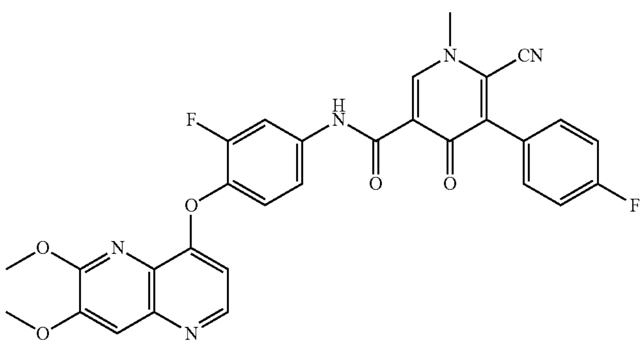 [SMILES: COc1cc2nccc(Oc3ccc(NC(=O)c4cn(C)c(C#N)c(-c5ccc(F)cc5)c4=O)cc3F)c2nc1OC] | 6-cyano-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 78 | 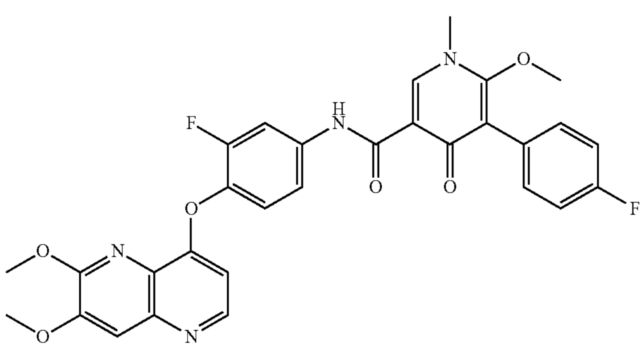 [SMILES: COc1cc2nccc(Oc3ccc(NC(=O)c4cn(C)c(OC)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methoxy-1-methyl-4-oxopyridine-3-carboxamide |

| Cpd # | Structure | IUPAC Name |
|---|---|---|
| 79 | 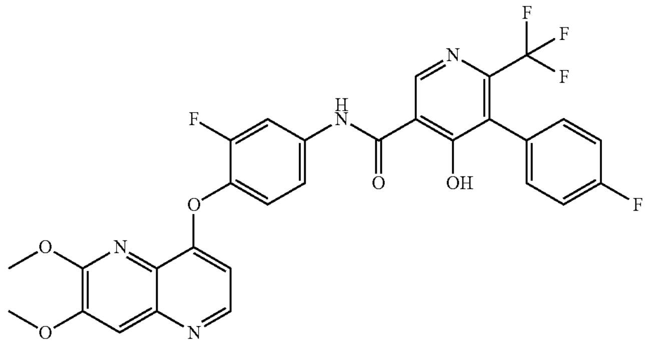 [SMILES: COc1cc2nccc(Oc3ccc(NC(=O)c4cnc(C(F)(F)F)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-(trifluoromethyl)pyridine-3-carboxamide |
| 80 | 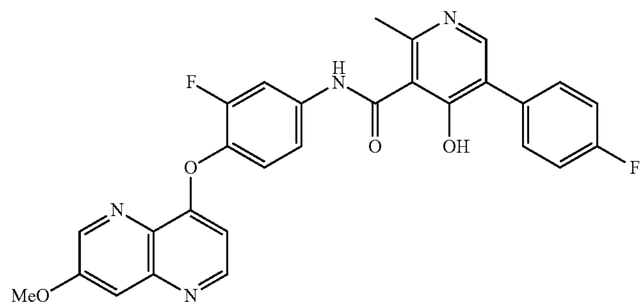 [SMILES: COc1cnc2c(Oc3ccc(NC(=O)c4c(C)ncc(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2-methylpyridine-3-carboxamide |
| 81 | 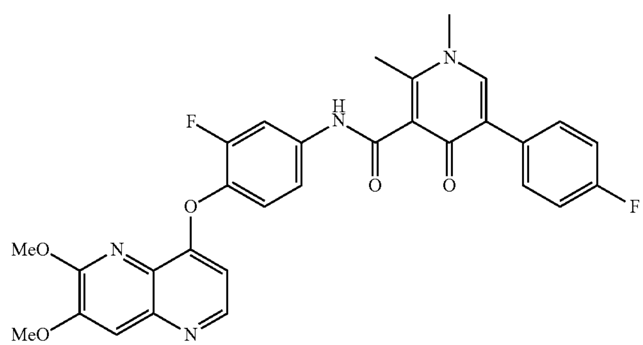 [SMILES: COc1cc2nccc(Oc3ccc(NC(=O)c4c(C)n(C)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,2-dimethyl-4-oxopyridine-3-carboxamide |
| 82 | 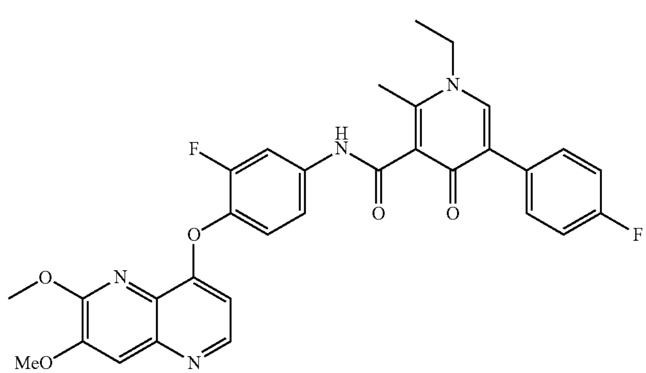 [SMILES: CCn1cc(-c2ccc(F)cc2)c(=O)c(C(=O)Nc2ccc(Oc3ccnc4cc(OC)c(OC)nc34)c(F)c2)c1C] | N-[4-[(6,7-dimethoxy-1,5-naphthyridin-4-yl)oxy]-3-fluorophenyl]-1-ethyl-5-(4-fluorophenyl)-2-methyl-4-oxopyridine-3-carboxamide |

-continued

| Cpd # | Structure | IUPAC Name |
|---|---|---|
| 83 | 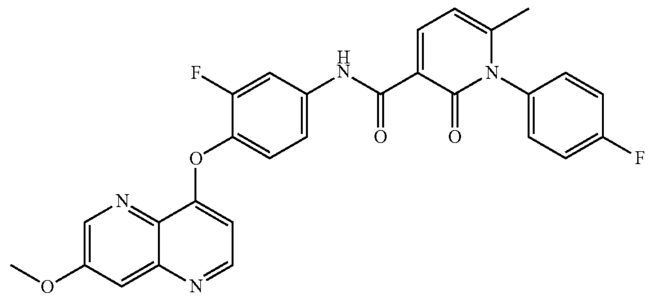 [SMILES: COc1cnc2c(Oc3ccc(NC(=O)c4ccc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-6-methyl-2-oxopyridine-3-carboxamide |
| 84 | 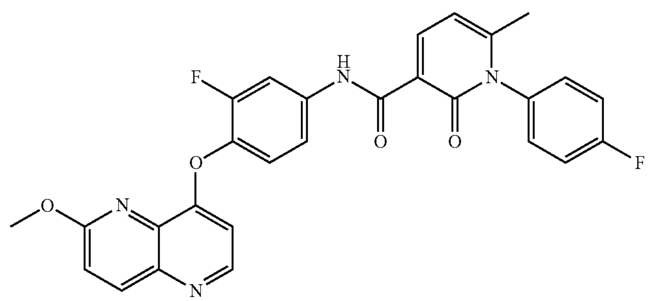 | N-[3-fluoro-4-[(6-methoxy-1,5-naphthyridin-4-yl)oxy]phenyl]-1-(4-fluorophenyl)-6-methyl-2-oxopyridine-3-carboxamide |
| 85 | 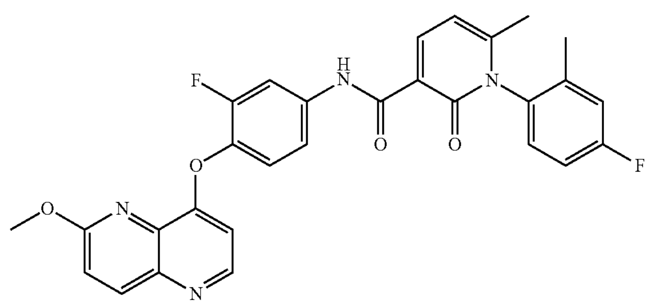 | N-[3-fluoro-4-[(6-methoxy-1,5-naphthyridin-4-yl)oxy]phenyl]-1-(4-fluoro-2-methylphenyl)-6-methyl-2-oxopyridine-3-carboxamide |
| 86 | 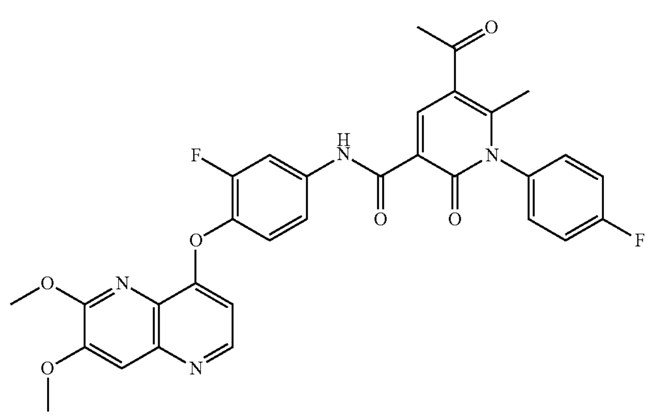 [SMILES: COc1cc2nccc(Oc3ccc(NC(=O)c4cc(C(C)=O)c(C)n(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-6-methyl-2-oxopyridine-3-carboxamide |

| Cpd # | Structure | IUPAC Name |
|---|---|---|
| 87 | 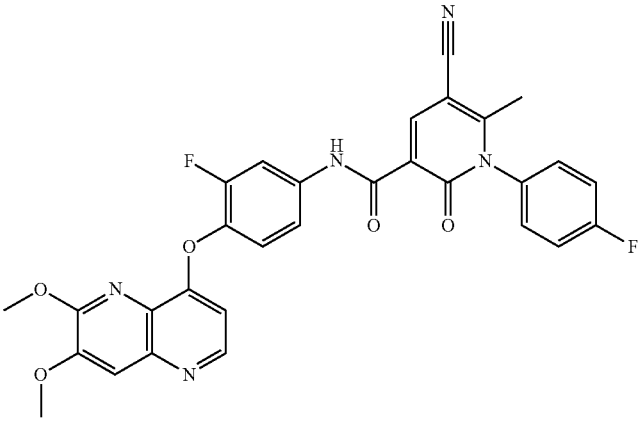 [SMILES: COc1cc2nccc(Oc3ccc(NC(=O)c4cc(C#N)c(C)n(-c5ccc(F)cc5)c4=O)cc3F)c2nc1OC] | 5-cyano-N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 88 | 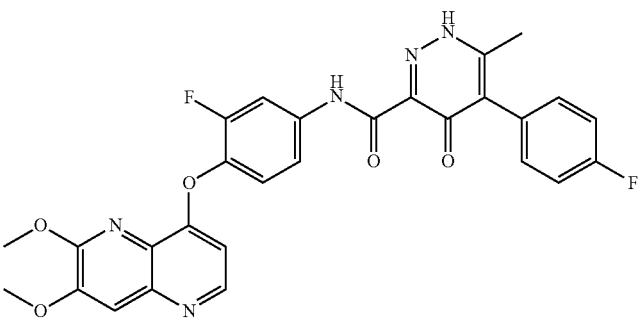 [SMILES: COc1cc2nccc(Oc3ccc(NC(=O)c4n[nH]c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-4-oxo-1H-pyridazine-3-carboxamide |
| 89 | 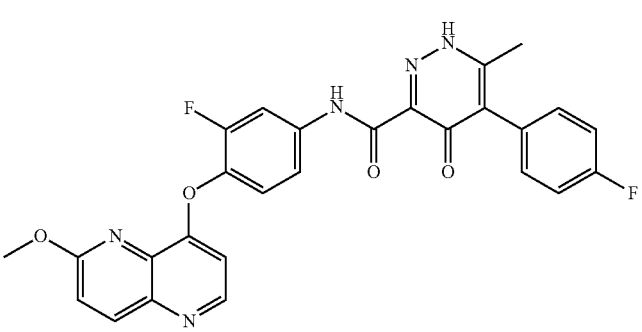 [SMILES: COc1ccc2nccc(Oc3ccc(NC(=O)c4n[nH]c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-6-methyl-4-oxo-1H-pyridazine-3-carboxamide |
| 90 | 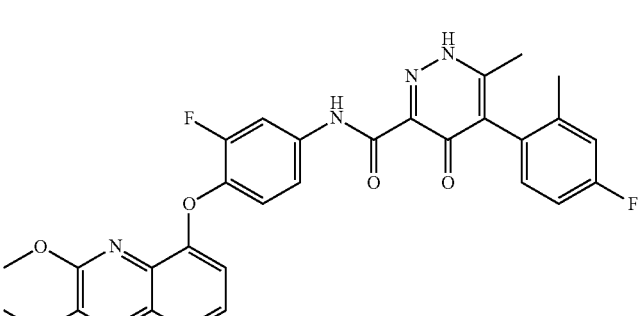 | N-[4-[(6,7-dimethoxy-1,5-naphthyridin-4-yl)oxy]-3-fluorophenyl]-5-(4-fluoro-2-methylphenyl)-6-methyl-4-oxo-1H-pyridazine-3-carboxamide |

| Cpd # | Structure | IUPAC Name |
|---|---|---|
| 91 | 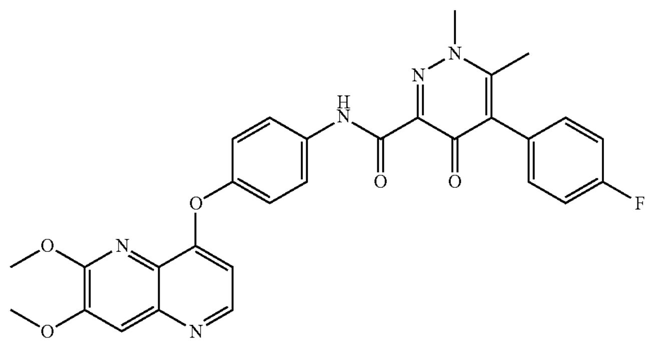 [SMILES: COc1cc2nccc(Oc3ccc(NC(=O)c4nn(C)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,6-dimethyl-4-oxopyridazine-3-carboxamide |
| 92 | 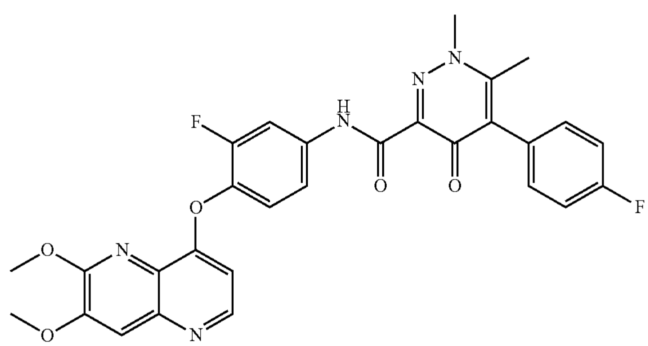 [SMILES: COc1cc2nccc(Oc3ccc(NC(=O)c4nn(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,6-dimethyl-4-oxopyridazine-3-carboxamide |
| 93 | 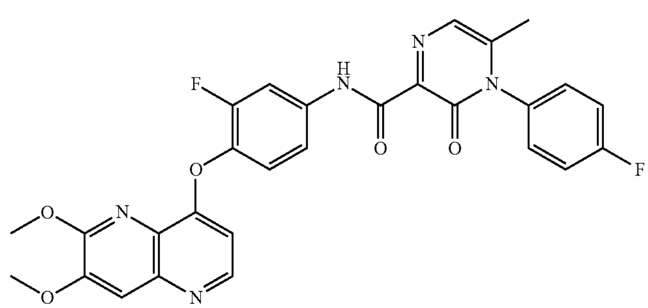 [SMILES: COc1cc2nccc(Oc3ccc(NC(=O)c4ncc(C)n(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-5-methyl-3-oxopyrazine-2-carboxamide |
| 94 | 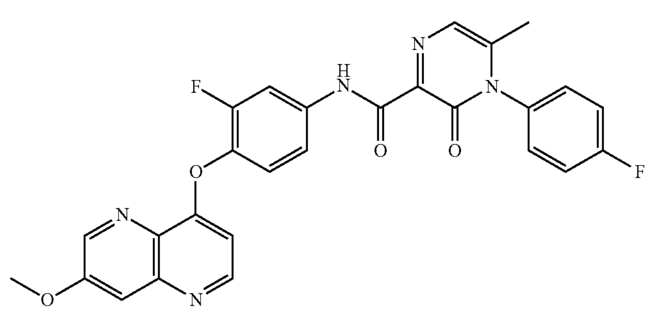 [SMILES: COc1cnc2c(Oc3ccc(NC(=O)c4ncc(C)n(-c5ccc(F)cc5)c4=O)cc3F)ccnc2c1] | N-[3-fluoro-4-[(7-methoxy-1,5-naphthyridin-4-yl)oxy]phenyl]-4-(4-fluorophenyl)-5-methyl-3-oxopyrazine-2-carboxamide |

-continued

| Cpd # | Structure | IUPAC Name |
|---|---|---|
| 95 | 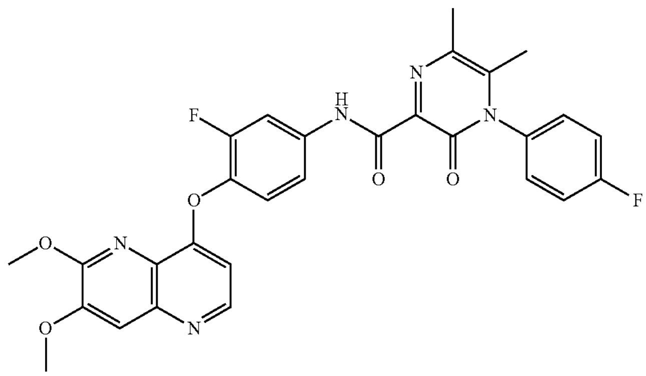 [SMILES: COc1cc2nccc(Oc3ccc(NC(=O)c4nc(C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-5,6-dimethyl-3-oxopyrazine-2-carboxamide |
| 96 | 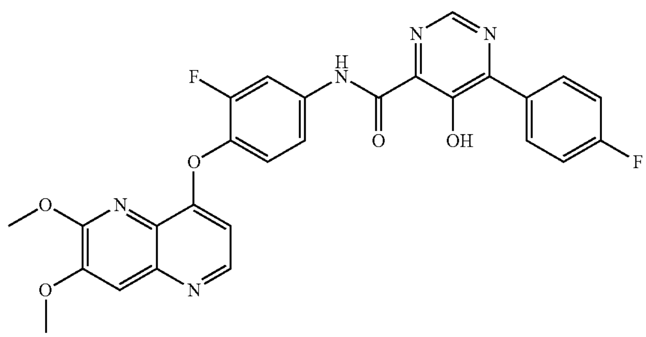 [SMILES: COc1cc2nccc(Oc3ccc(NC(=O)c4ncnc(-c5ccc(F)cc5)c4O)cc3F)c2nc1OC] | N-[4-[(6,7-dimethoxy-1,5-naphthyridin-4-yl)oxy]-3-fluorophenyl]-6-(4-fluorophenyl)-5-hydroxypyrimidine-4-carboxamide |
| 97 | 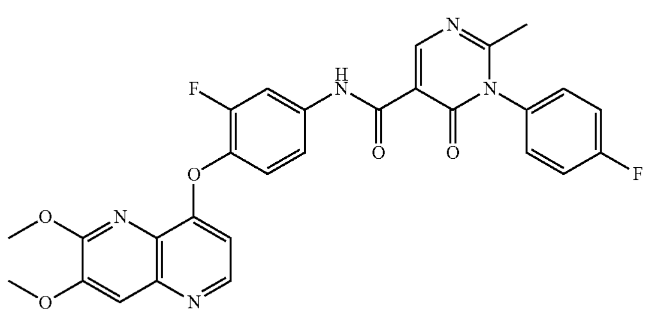 [SMILES: COc1cc2nccc(Oc3ccc(NC(=O)c4cnc(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-2-methyl-6-oxopyrimidine-5-carboxamide |
| 98 | 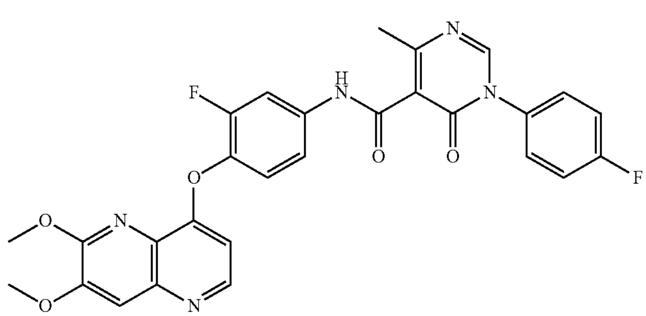 [SMILES: COc1cc2nccc(Oc3ccc(NC(=O)c4c(C)ncn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4-methyl-6-oxopyrimidine-5-carboxamide |

| Cpd # | Structure | IUPAC Name |
|---|---|---|
| 99 | 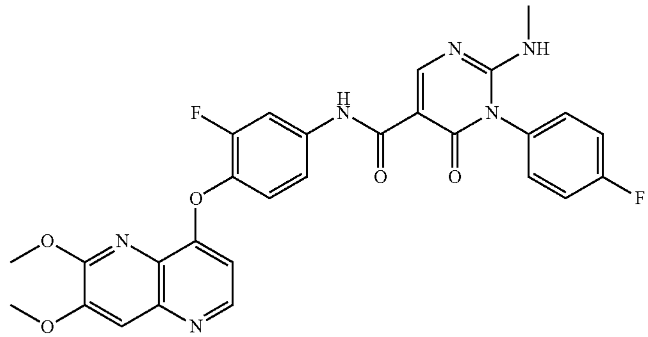 [SMILES: CNc1ncc(C(=O)Nc2ccc(Oc3ccnc4cc(OC)c(OC)nc34)c(F)c2)c(=O)n1-c1ccc(F)cc1] | N-[4-[(6,7-dimethoxy-1,5-naphthyridin-4-yl)oxy]-3-fluorophenyl]-1-(4-fluorophenyl)-2-(methylamino)-6-oxopyrimidine-5-carboxamide |
| 100 | 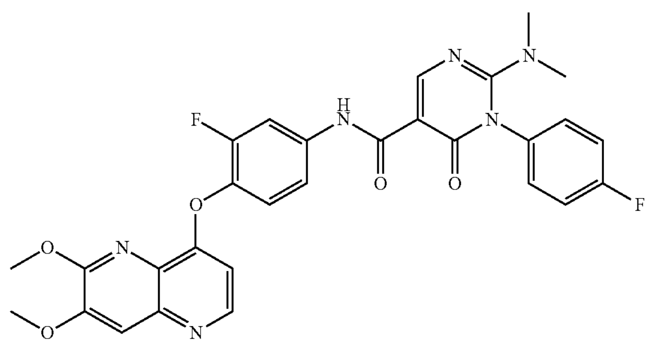 [SMILES: COc1cc2nccc(Oc3ccc(NC(=O)c4cnc(N(C)C)n(-c5ccc(F)cc5)c4=O)cc3F)c2nc1OC] | N-[4-[(6,7-dimethoxy-1,5-naphthyridin-4-yl)oxy]-3-fluorophenyl]-2-(dimethylamino)-1-(4-fluorophenyl)-6-oxopyrimidine-5-carboxamide |
| 101 | 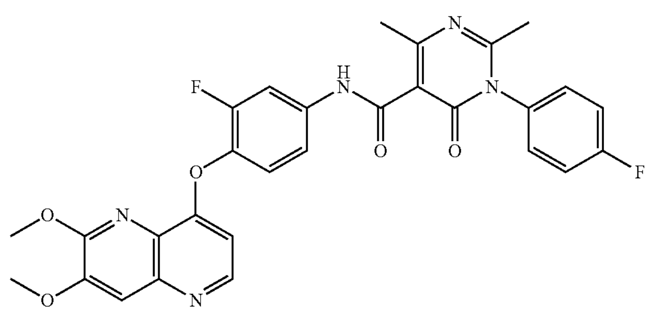 [SMILES: COc1cc2nccc(Oc3ccc(NC(=O)c4c(C)nc(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-2,4-dimethyl-6-oxopyrimidine-5-carboxamide |
| 102 | 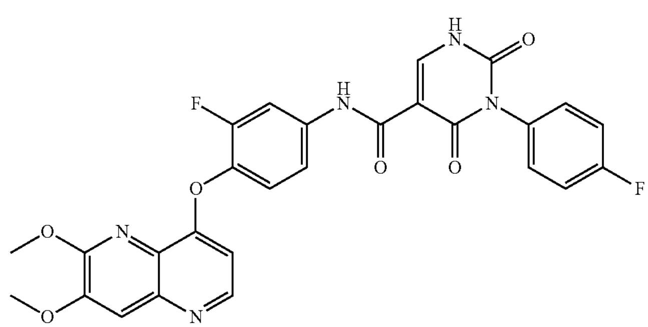 [SMILES: COc1cc2nccc(Oc3ccc(NC(=O)c4c[nH]c(=O)n(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-2,4-dioxo-1H-pyrimidine-5-carboxamide |

| Cpd # | Structure | IUPAC Name |
|---|---|---|
| 103 | 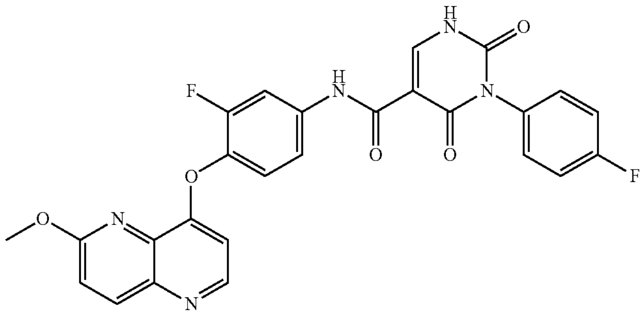 [SMILES: COc1ccc2nccc(Oc3ccc(NC(=O)c4c[nH]c(=O)n(-c5ccc(F)cc5)c4=O)cc3F)c2n1] | N-[3-fluoro-4-[(6-methoxy-1,5-naphthyridin-4-yl)oxy]phenyl]-3-(4-fluorophenyl)-2,4-dioxo-1H-pyrimidine-5-carboxamide |
| 104 | 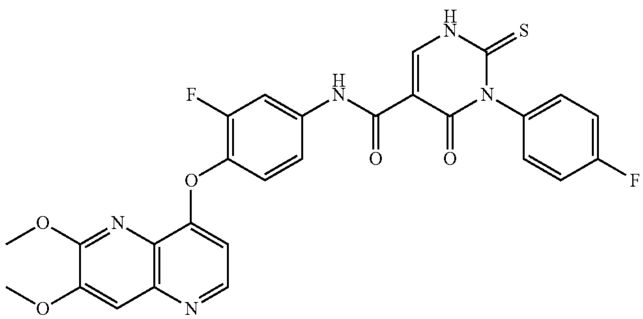 [SMILES: COc1cc2nccc(Oc3ccc(NC(=O)c4c[nH]c(=S)n(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-4-oxo-2-sulfanylidene-1H-pyrimidine-5-carboxamide |
| 105 | 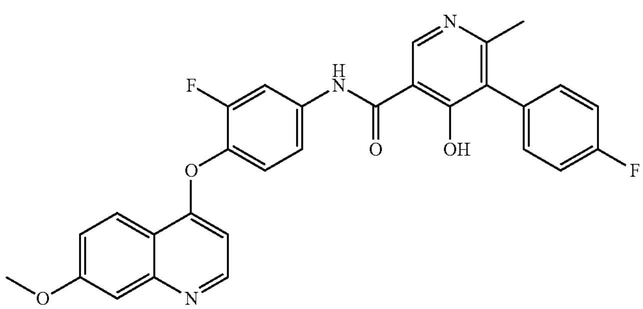 [SMILES: COc1ccc2c(Oc3ccc(NC(=O)c4cnc(C)c(-c5ccc(F)cc5)c4O)cc3F)ccnc2c1] | N-[3-fluoro-4-(7-methoxyquinolin-4-yl)oxyphenyl]-5-(4-fluorophenyl)-4-hydroxy-6-methylpyridine-3-carboxamide |
| 106 | 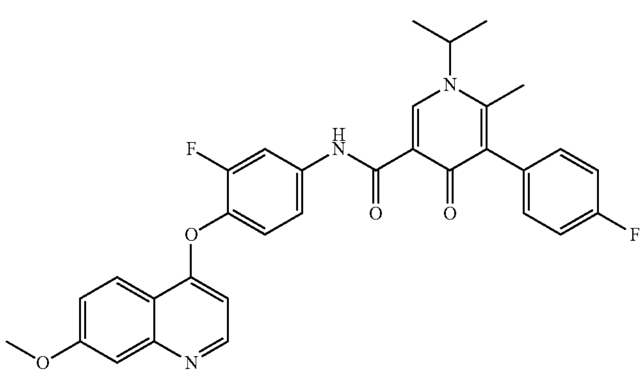 [SMILES: COc1ccc2c(Oc3ccc(NC(=O)c4cn(C(C)C)c(C)c(-c5ccc(F)cc5)c4=O)cc3F)ccnc2c1] | N-[3-fluoro-4-(7-methoxyquinolin-4-yl)oxyphenyl]-5-(4-fluorophenyl)-6-methyl-4-oxo-1-propan-2-ylpyridine-3-carboxamide |

-continued

| Cpd # | Structure | IUPAC Name |
|---|---|---|
| 107 | 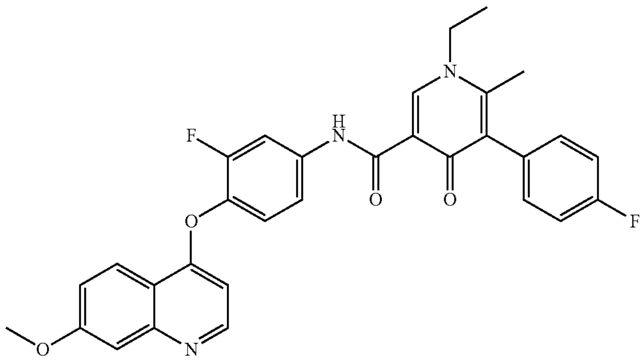 [SMILES: CCn1cc(C(=O)Nc2ccc(Oc3ccnc4cc(OC)ccc34)c(F)c2)c(=O)c(-c2ccc(F)cc2)c1C] | 1-ethyl-N-[3-fluoro-4-(7-methoxyquinolin-4-yl)oxyphenyl]-5-(4-fluorophenyl)-6-methyl-4-oxopyridine-3-carboxamide |
| 108 | 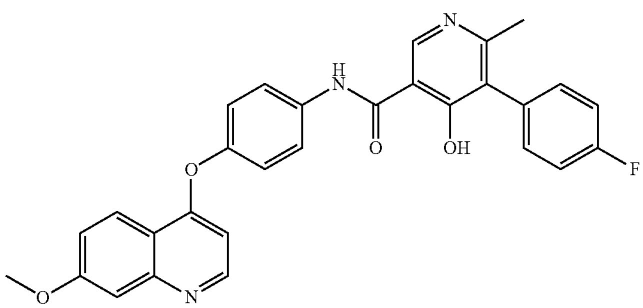 [SMILES: COc1ccc2c(Oc3ccc(NC(=O)c4cnc(C)c(-c5ccc(F)cc5)c4O)cc3)ccnc2c1] | 5-(4-fluorophenyl)-4-hydroxy-N-[4-(7-methoxyquinolin-4-yl)oxyphenyl]-6-methylpyridine-3-carboxamide |
| 109 | 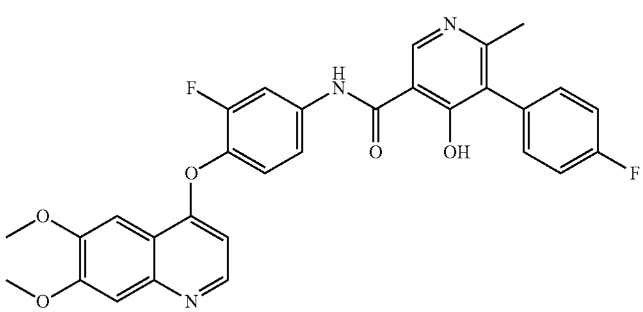 [SMILES: COc1cc2nccc(Oc3ccc(NC(=O)c4cnc(C)c(-c5ccc(F)cc5)c4O)cc3F)c2cc1OC] | N-[4-(6,7-dimethoxyquinolin-4-yl)oxy-3-fluorophenyl]-5-(4-fluorophenyl)-4-hydroxy-6-methylpyridine-3-carboxamide |
| 110 | 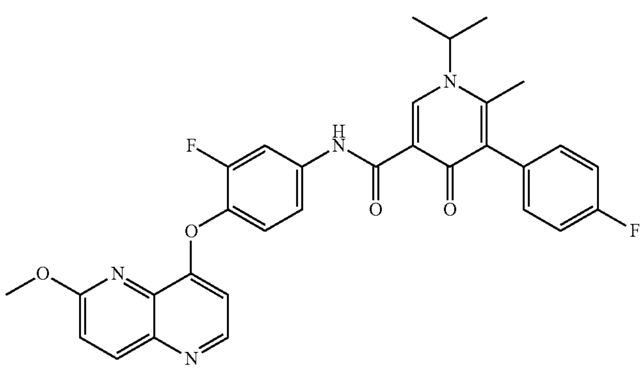 [SMILES: COc1ccc2nccc(Oc3ccc(NC(=O)c4cn(C(C)C)c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-6-methyl-4-oxo-1-propan-2-ylpyridine-3-carboxamide |

-continued

| Cpd # | Structure | IUPAC Name |
|---|---|---|
| 111 | 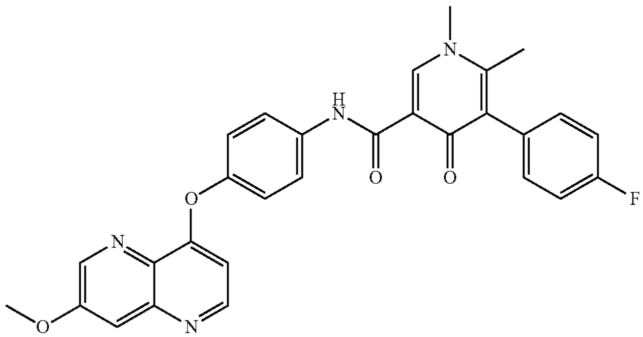 [SMILES: COc1cnc2c(Oc3ccc(NC(=O)c4cn(C)c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-1,6-dimethyl-4-oxopyridine-3-carboxamide |
| 112 | 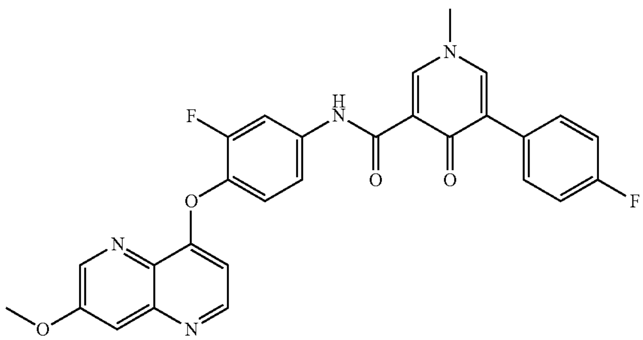 [SMILES: COc1cnc2c(Oc3ccc(NC(=O)c4cn(C)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-methyl-4-oxopyridine-3-carboxamide |
| 113 | 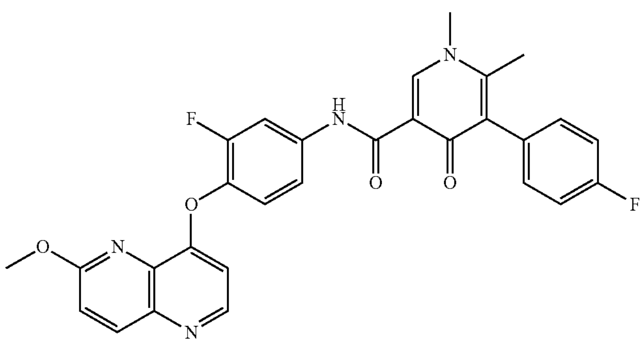 [SMILES: COc1ccc2nccc(Oc3ccc(NC(=O)c4cn(C)c(C)c(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-1,6-dimethyl-4-oxopyridine-3-carboxamide |
| 114 | 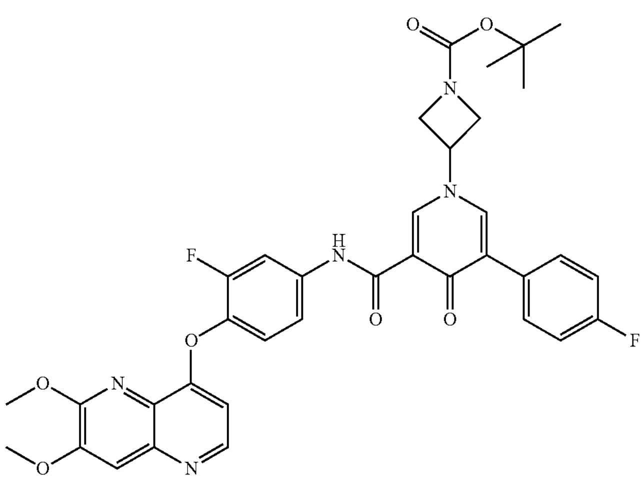 [SMILES: COc1cc2nccc(Oc3ccc(NC(=O)c4cn(C5CN(C(=O)OC(C)(C)C)C5)cc(-c5ccc(F)cc5)c4=O)cc3F)c2nc1OC] | tert-butyl 3-[3-[[4-[(6,7-dimethoxy-1,5-naphthyridin-4-yl)oxy]-3-fluorophenyl]carbamoyl]-5-(4-fluorophenyl)-4-oxopyridin-1-yl]azetidine-1-carboxylate |

| Cpd # | Structure | IUPAC Name |
|---|---|---|
| 115 | 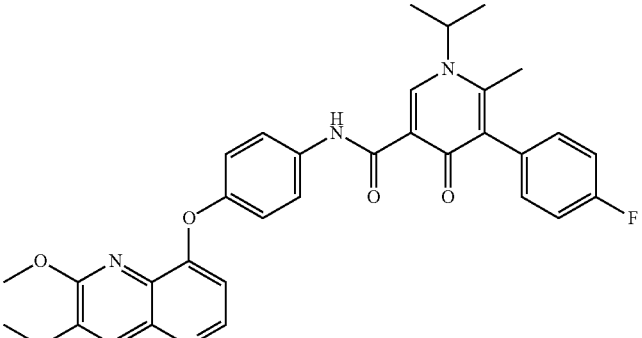 | N-[4-[(6,7-dimethoxy-1,5-naphthyridin-4-yl)oxy]phenyl]-5-(4-fluorophenyl)-6-methyl-4-oxo-1-propan-2-ylpyridine-3-carboxamide |
| 116 | 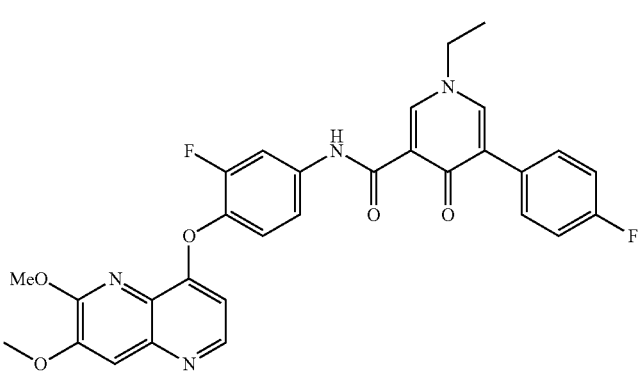 [SMILES: CCn1cc(C(=O)Nc2ccc(Oc3ccnc4cc(OC)c(OC)nc34)c(F)c2)c(=O)c(-c2ccc(F)cc2)c1] | N-[4-[(6,7-dimethoxy-1,5-naphthyridin-4-yl)oxy]-3-fluorophenyl]-1-ethyl-5-(4-fluorophenyl)-4-oxopyridine-3-carboxamide |
| 117 | 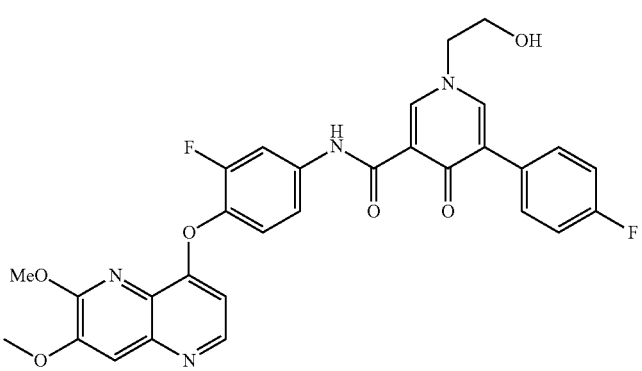 [SMILES: COc1cc2nccc(Oc3ccc(NC(=O)c4cn(CCO)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-hydroxyethyl)-4-oxopyridine-3-carboxamide |
| 118 | 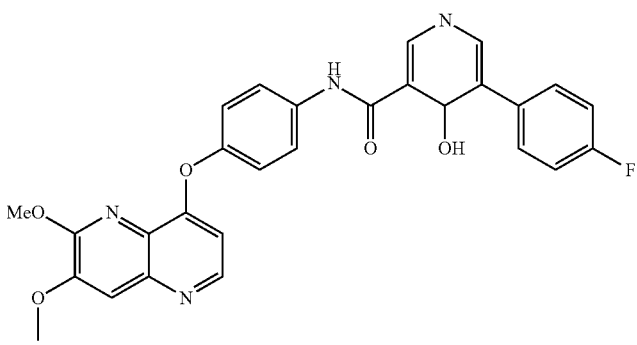 [SMILES: COc1cc2nccc(Oc3ccc(NC(=O)C4=CNC=C(c5ccc(F)cc5)C4O)cc3)c2nc1OC] | N-[4-[(6,7-dimethoxy-1,5-naphthyridin-4-yl)oxy]phenyl]-5-(4-fluorophenyl)-4-hydroxypyridine-3-carboxamide |

| Cpd # | Structure | IUPAC Name |
|---|---|---|
| 119 | 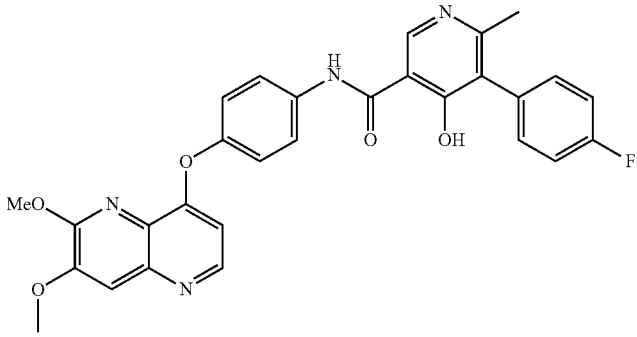 [SMILES: COc1cc2nccc(Oc3ccc(NC(=O)c4cnc(C)c(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxy-6-methylpyridine-3-carboxamide |
| 120 | 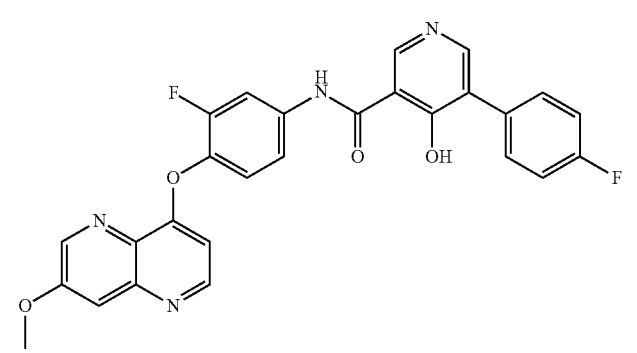 [SMILES: COc1cnc2c(Oc3ccc(NC(=O)c4cncc(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxypyridine-3-carboxamide |
| 121 | 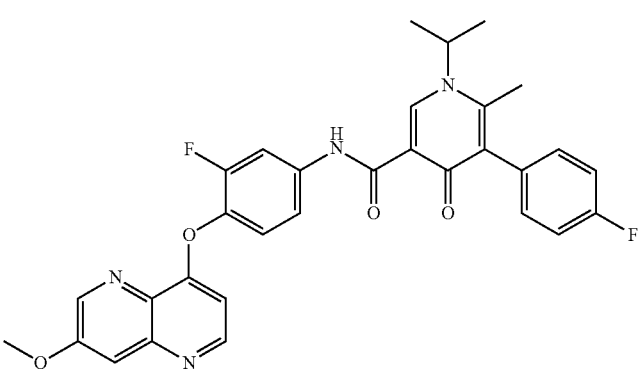 [SMILES: COc1cnc2c(Oc3ccc(NC(=O)c4cn(C(C)C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1-propan-2-ylpyridine-3-carboxamide |
| 122 | 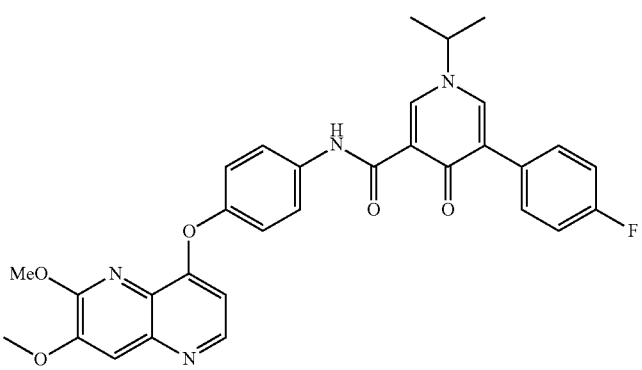 [SMILES: COc1cc2nccc(Oc3ccc(NC(=O)c4cn(C(C)C)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-4-oxo-1-propan-2-ylpyridine-3-carboxamide |

-continued

| Cpd # | Structure | IUPAC Name |
|---|---|---|
| 123 | 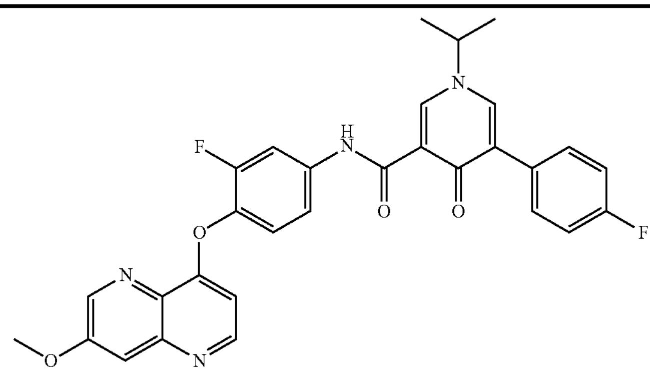 | N-[3-fluoro-4-[(7-methoxy-1,5-naphthyridin-4-yl)oxy]phenyl]-5-(4-fluorophenyl)-4-oxo-1-propan-2-ylpyridine-3-carboxamide |
| 124 | 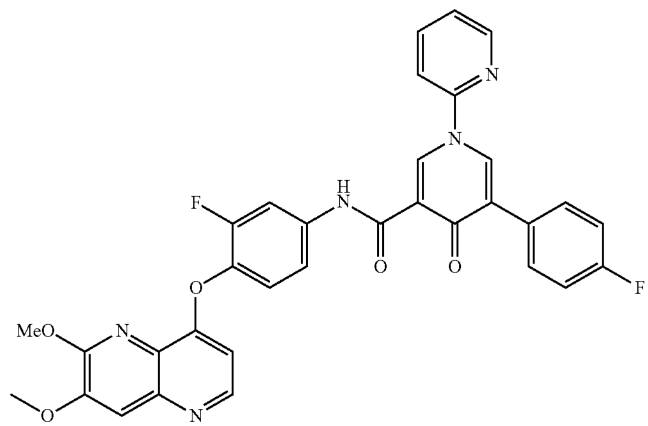 [SMILES: COc1cc2nccc(Oc3ccc(NC(=O)c4cn(-c5ccccn5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-pyridin-2-ylpyridine-3-carboxamide |
| 125 | 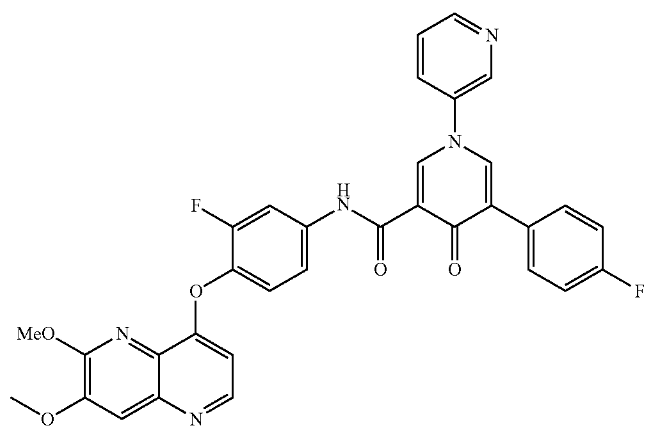 [SMILES: COc1cc2nccc(Oc3ccc(NC(=O)c4cn(-c5cccnc5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-4-oxo-1-pyridin-3-ylpyridine-3-carboxamide |
| 126 | 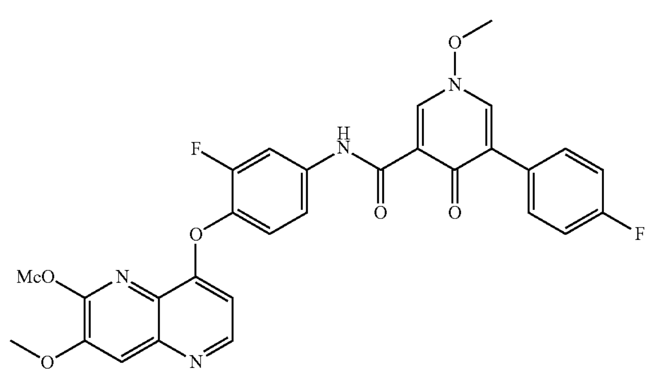 | N-[4-[(6,7-dimethoxy-1,5-naphthyridin-4-yl)oxy]-3-fluorophenyl]-5-(4-fluorophenyl)-1-methoxy-4-oxopyridine-3-carboxamide |

-continued

| Cpd # | Structure | IUPAC Name |
|---|---|---|
| 127 | 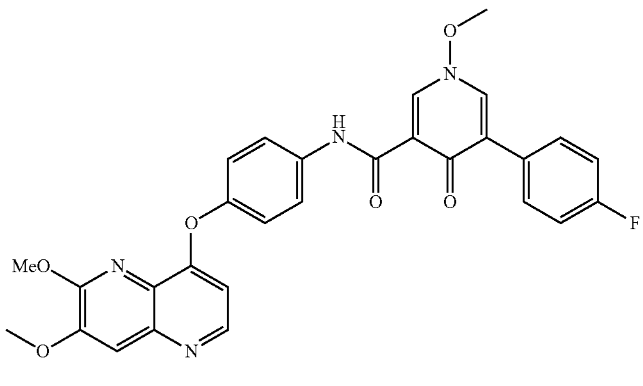 [SMILES: COc1cc2nccc(Oc3ccc(NC(=O)c4cn(OC)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1-methoxy-4-oxopyridine-3-carboxamide |
| 128 | 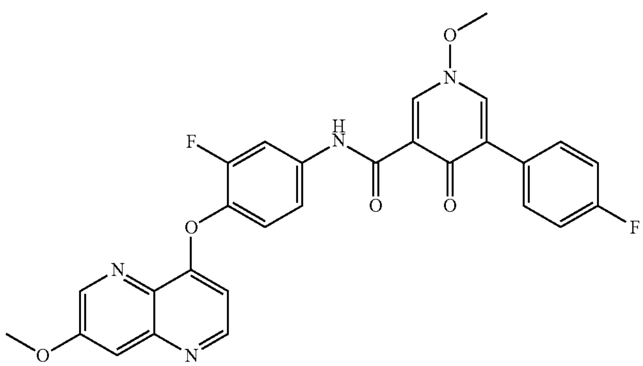 [SMILES: COc1cnc2c(Oc3ccc(NC(=O)c4cn(OC)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-methoxy-4-oxopyridine-3-carboxamide |
| 129 | 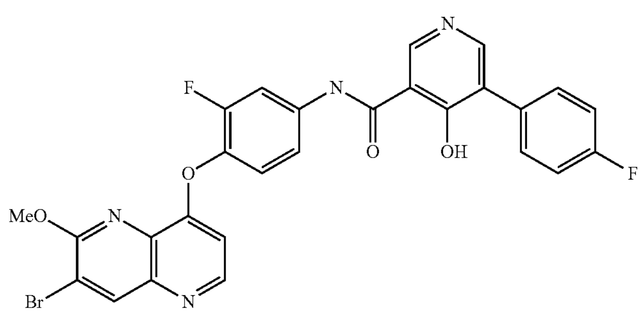 | N-[4-[(7-bromo-6-methoxy-1,5-naphthyridin-4-yl)oxy]-3-fluorophenyl]-5-(4-fluorophenyl)-4-hydroxypyridine-3-carboxamide |
| 130 | 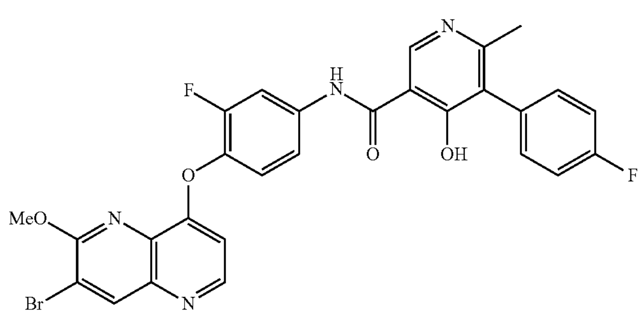 [SMILES: COc1nc2c(Oc3ccc(NC(=O)c4cnc(C)c(-c5ccc(F)cc5)c4O)cc3F)ccnc2cc1Br] | N-[4-[(7-bromo-6-methoxy-1,5-naphthyridin-4-yl)oxy]-3-fluorophenyl]-5-(4-fluorophenyl)-4-hydroxy-6-methylpyridine-3-carboxamide |

| Cpd # | Structure | IUPAC Name |
|---|---|---|
| 131 | 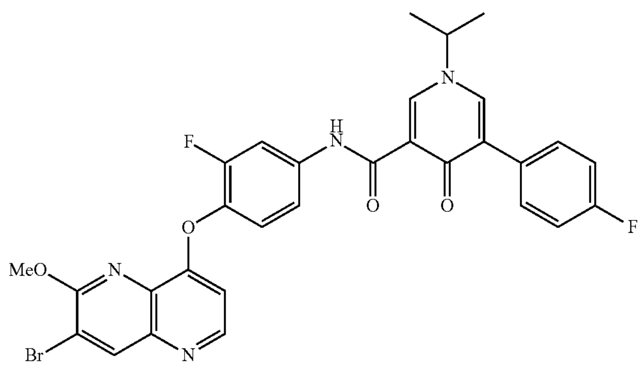 [SMILES: COc1nc2c(Oc3ccc(NC(=O)c4cn(C(C)C)cc(-c5ccc(F)cc5)c4=O)cc3F)ccnc2cc1Br] | N-[4-[(7-bromo-6-methoxy-1,5-naphthyridin-4-yl)oxy]-3-fluorophenyl]-5-(4-fluorophenyl)-4-oxo-1-propan-2-ylpyridine-3-carboxamide |
| 132 | 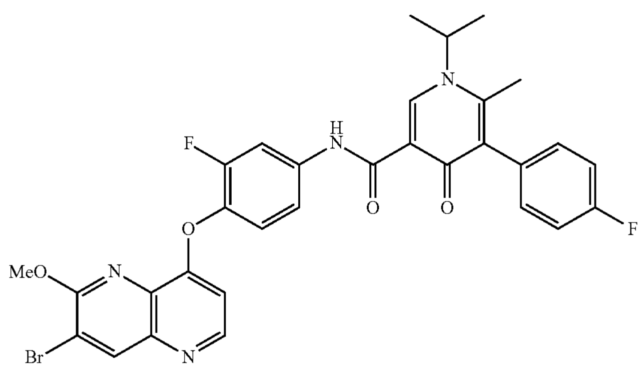 [SMILES: COc1nc2c(Oc3ccc(NC(=O)c4cn(C(C)C)c(C)c(-c5ccc(F)cc5)c4=O)cc3F)ccnc2cc1Br] | N-[4-[(7-bromo-6-methoxy-1,5-naphthyridin-4-yl)oxy]-3-fluorophenyl]-5-(4-fluorophenyl)-6-methyl-4-oxo-1-propan-2-ylpyridine-3-carboxamide |
| 133 | 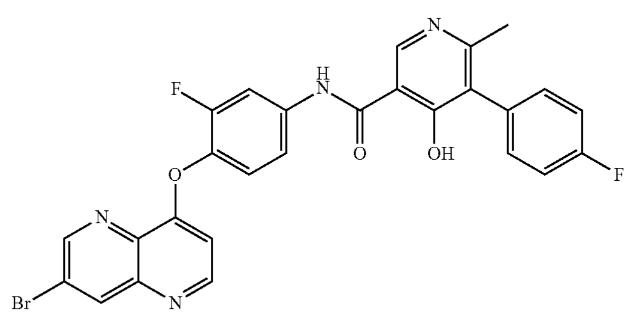 [SMILES: Cc1ncc(C(=O)Nc2ccc(Oc3ccnc4cc(Br)cnc34)c(F)c2)c(O)c1-c1ccc(F)cc1] | N-[4-[(7-bromo-1,5-naphthyridin-4-yl)oxy]-3-fluorophenyl]-5-(4-fluorophenyl)-4-hydroxy-6-methylpyridine-3-carboxamide |
| 134 | 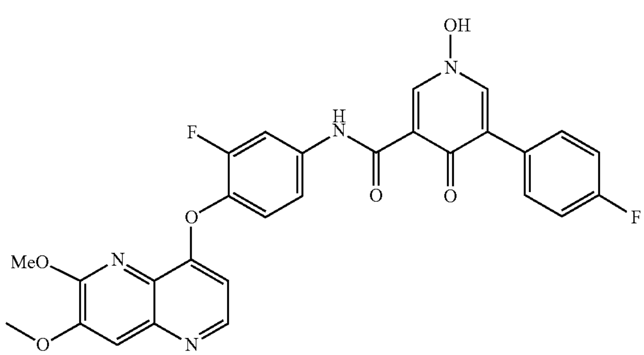 [SMILES: COc1cc2nccc(Oc3ccc(NC(=O)c4cn(O)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-hydroxy-4-oxopyridine-3-carboxamide |

| Cpd # | Structure | IUPAC Name |
|---|---|---|
| 135 | 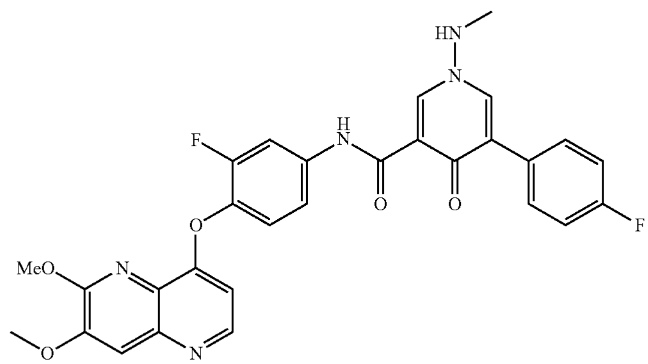 [SMILES: CNn1cc(C(=O)Nc2ccc(Oc3ccnc4cc(OC)c(OC)nc34)c(F)c2)c(=O)c(-c2ccc(F)cc2)c1] | N-[4-[(6,7-dimethoxy-1,5-naphthyridin-4-yl)oxy]-3-fluorophenyl]-5-(4-fluorophenyl)-1-(methylamino)-4-oxopyridine-3-carboxamide |
| 136 | 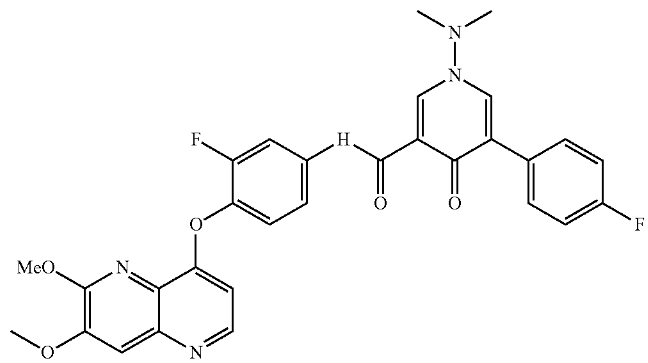 | N-[4-[(6,7-dimethoxy-1,5-naphthyridin-4-yl)oxy]-3-fluorophenyl]-1-(dimethylamino)-5-(4-fluorophenyl)-4-oxopyridine-3-carboxamide |
| 137 | 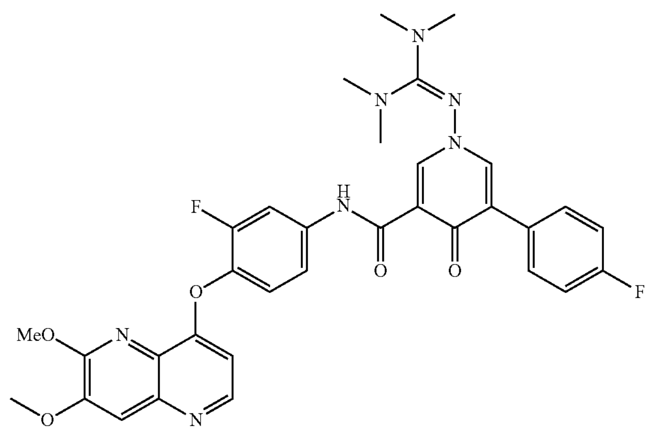 [SMILES: COc1cc2nccc(Oc3ccc(NC(=O)c4cn(N=C(N(C)C)N(C)C)cc(-c5ccc(F)cc5)c4=O)cc3F)c2nc1OC] | 1-[bis(dimethylamino)methylideneamino]-N-[4-[(6,7-dimethoxy-1,5-naphthyridin-4-yl)oxy]-3-fluorophenyl]-5-(4-fluorophenyl)-4-oxopyridine-3-carboxamide |
| 138 | 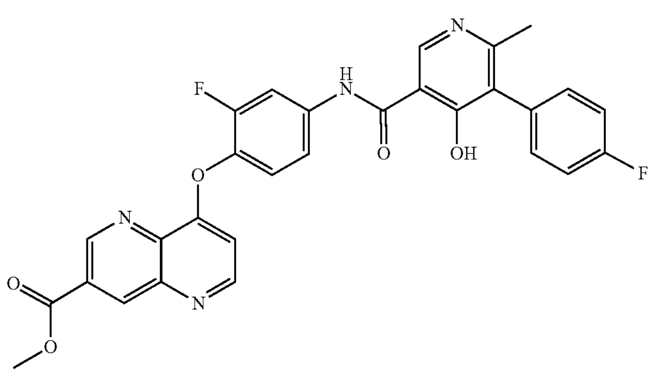 [SMILES: COC(=O)c1cnc2c(Oc3ccc(NC(=O)c4cnc(C)c(-c5ccc(F)cc5)c4O)cc3F)ccnc2c1] | methyl 8-[2-fluoro-4-[[5-(4-fluorophenyl)-4-hydroxy-6-methylpyridine-3-carbonyl]amino]phenoxy]-1,5-naphthyridine-3-carboxylate |

-continued

| Cpd # | Structure | IUPAC Name |
|---|---|---|
| 139 | 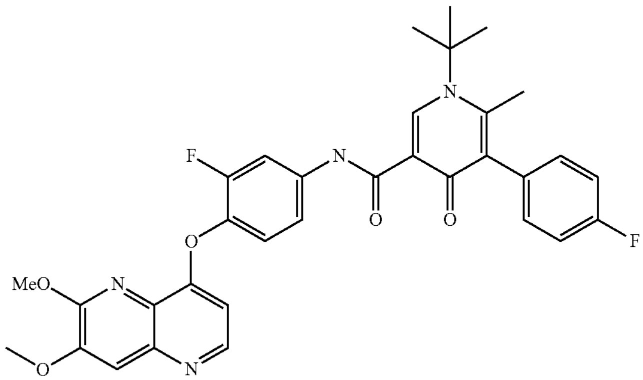 | 1-tert-butyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 140 | 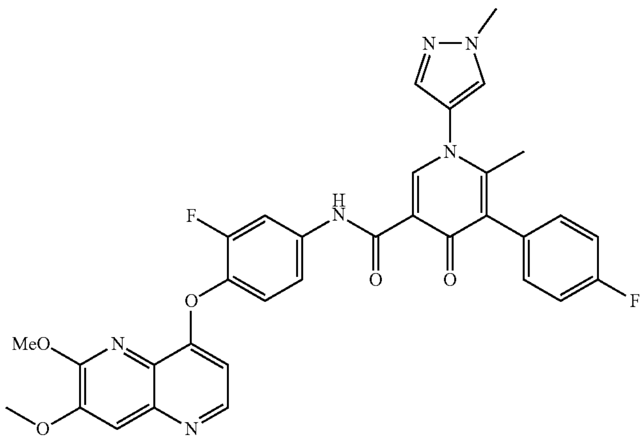 [SMILES: COc1cc2nccc(Oc3ccc(NC(=O)c4cn(-c5cnn(C)c5)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-6-methyl-1-(1-methylpyrazol-4-yl)-4-oxopyridine-3-carboxamide |
| 141 | 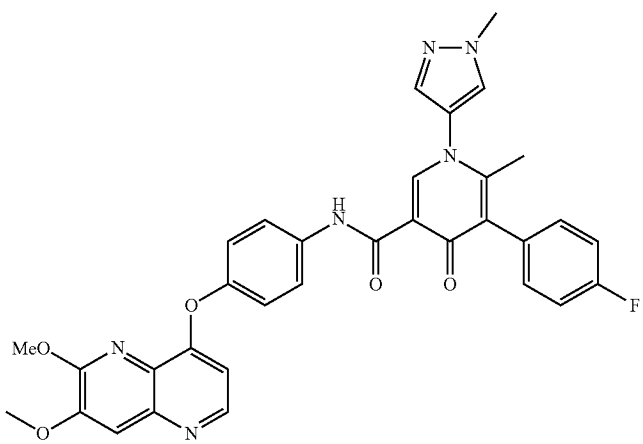 [SMILES: COc1cc2nccc(Oc3ccc(NC(=O)c4cn(-c5cnn(C)c5)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-methyl-1-(1-methylpyrazol-4-yl)-4-oxopyridine-3-carboxamide |
| 142 | 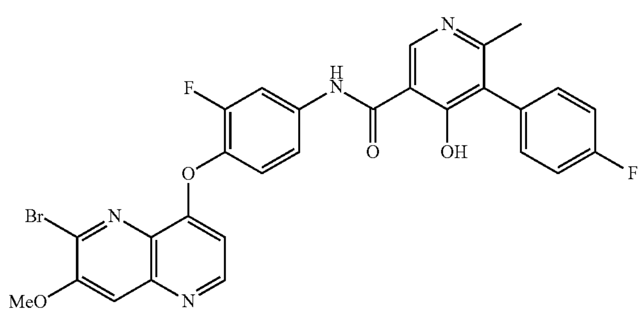 [SMILES: COc1cc2nccc(Oc3ccc(NC(=O)c4cnc(C)c(-c5ccc(F)cc5)c4O)cc3F)c2nc1Br] | N-[4-[(6-bromo-7-methoxy-1,5-naphthyridin-4-yl)oxy]-3-fluorophenyl]-5-(4-fluorophenyl)-4-hydroxy-6-methylpyridine-3-carboxamide |

| Cpd # | Structure | IUPAC Name |
|---|---|---|
| 143 | 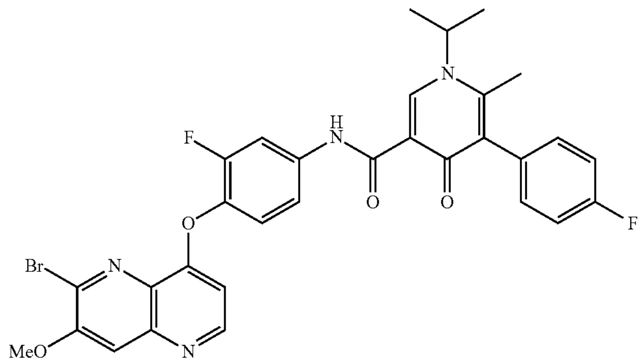 | N-[4-[(6-bromo-7-methoxy-1,5-naphthyridin-4-yl)oxy]-3-fluorophenyl]-5-(4-fluorophenyl)-6-methyl-4-oxo-1-propan-2-ylpyridine-3-carboxamide |
| 144 | 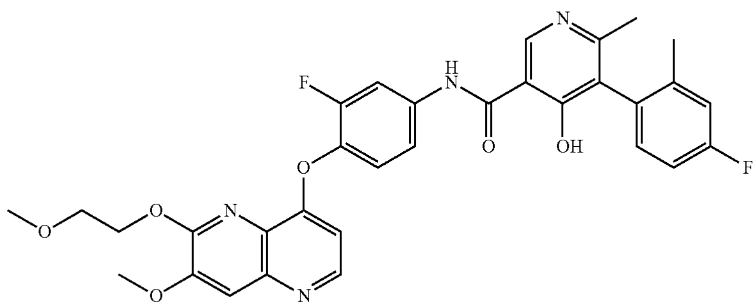 [SMILES: COCCOc1nc2c(Oc3ccc(NC(=O)c4cnc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-4-hydroxy-6-methylpyridine-3-carboxamide |
| 145 | 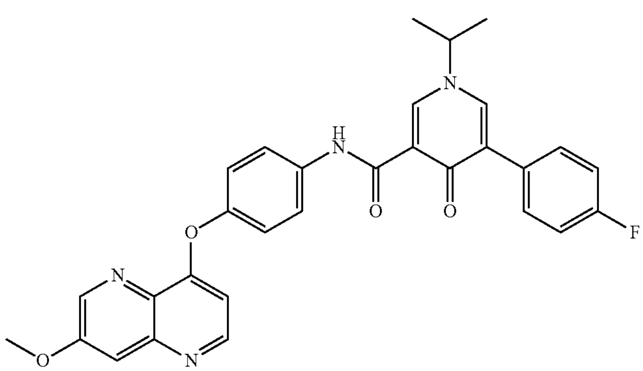 [SMILES: COc1cnc2c(Oc3ccc(NC(=O)c4cn(C(C)C)cc(-c5ccc(F)cc5)c4=O)cc3)ccnc2c1] | 5-(4-fluorophenyl)-N-[4-[(7-methoxy-1,5-naphthyridin-4-yl)oxy]phenyl]-4-oxo-1-propan-2-ylpyridine-3-carboxamide |
| 146 | 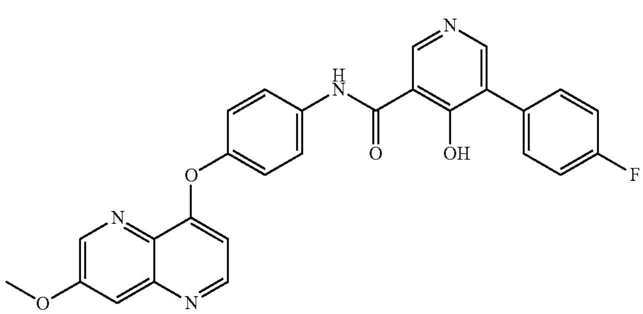 [SMILES: COc1cnc2c(Oc3ccc(NC(=O)c4cncc(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]pyridine-3-carboxamide |

| Cpd # | Structure | IUPAC Name |
|---|---|---|
| 147 | 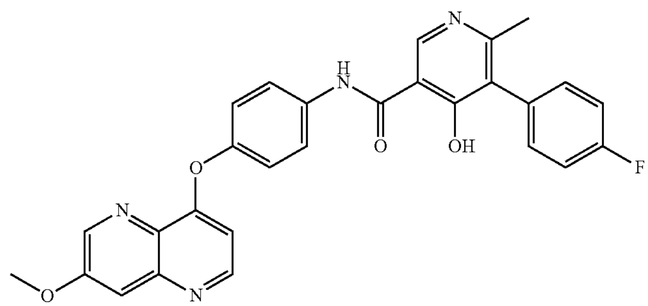 [SMILES: COc1cnc2c(Oc3ccc(NC(=O)c4cnc(C)c(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-6-methylpyridine-3-carboxamide |
| 148 | 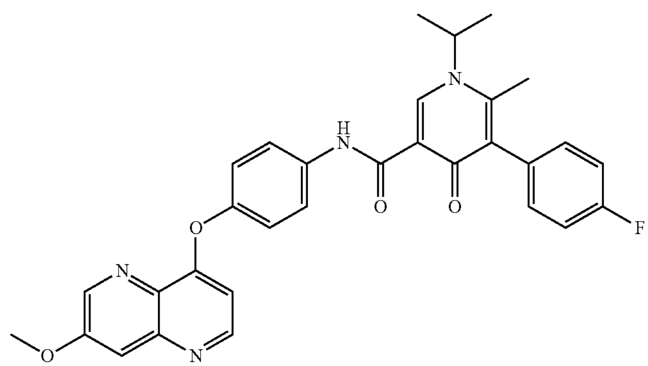 [SMILES: COc1cnc2c(Oc3ccc(NC(=O)c4cn(C(C)C)c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-6-methyl-4-oxo-1-propan-2-ylpyridine-3-carboxamide |
| 149 | 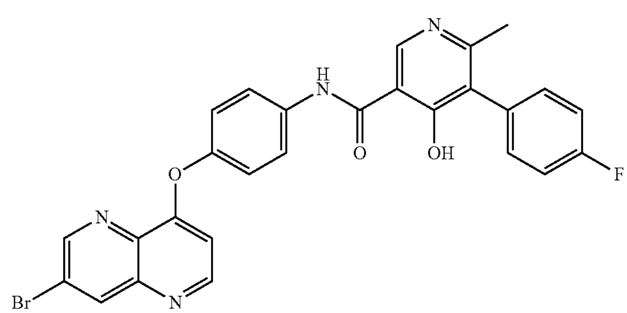 [SMILES: Cc1ncc(C(=O)Nc2ccc(Oc3ccnc4cc(Br)cnc34)cc2)c(O)c1-c1ccc(F)cc1] | N-[4-[(7-bromo-1,5-naphthyridin-4-yl)oxy]phenyl]-5-(4-fluorophenyl)-4-hydroxy-6-methylpyridine-3-carboxamide |
| 150 | 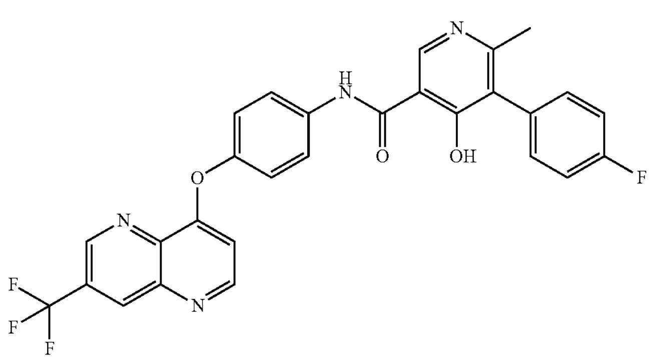 [SMILES: Cc1ncc(C(=O)Nc2ccc(Oc3ccnc4cc(C(F)(F)F)cnc34)cc2)c(O)c1-c1ccc(F)cc1] | 5-(4-fluorophenyl)-4-hydroxy-6-methyl-N-[4-[[7-(trifluoromethyl)-1,5-naphthyridin-4-yl]oxy]phenyl]pyridine-3-carboxamide |

| Cpd # | Structure | IUPAC Name |
|---|---|---|
| 151 | 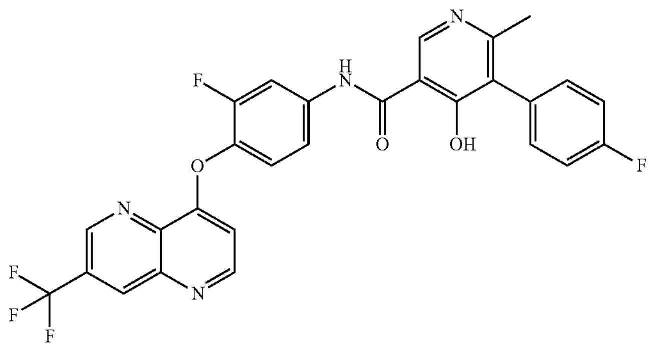 [SMILES: Cc1ncc(C(=O)Nc2ccc(Oc3ccnc4cc(C(F)(F)F)cnc34)c(F)c2)c(O)c1-c1ccc(F)cc1] | 5-(4-fluorophenyl)-N-[3-fluoro-4-[[7-(trifluoromethyl)-1,5-naphthyridin-4-yl]oxy]phenyl]-4-hydroxy-6-methylpyridine-3-carboxamide |
| 152 | 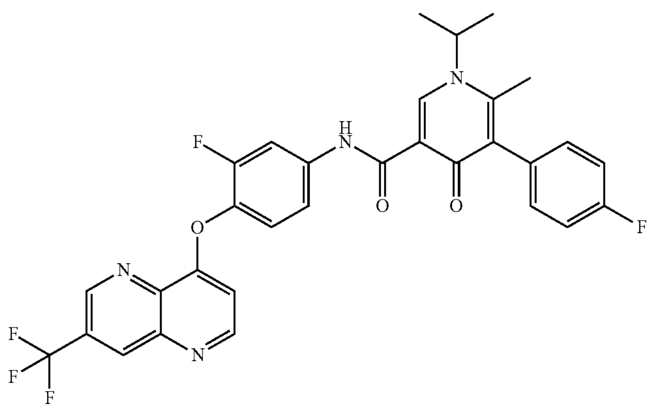 [SMILES: Cc1c(-c2ccc(F)cc2)c(=O)c(C(=O)Nc2ccc(Oc3ccnc4cc(C(F)(F)F)cnc34)c(F)c2)cn1C(C)C] | 5-(4-fluorophenyl)-N-[3-fluoro-4-[[7-(trifluoromethyl)-1,5-naphthyridin-4-yl]oxy]phenyl]-6-methyl-4-oxo-1-propan-2-ylpyridine-3-carboxamide |
| 153 | 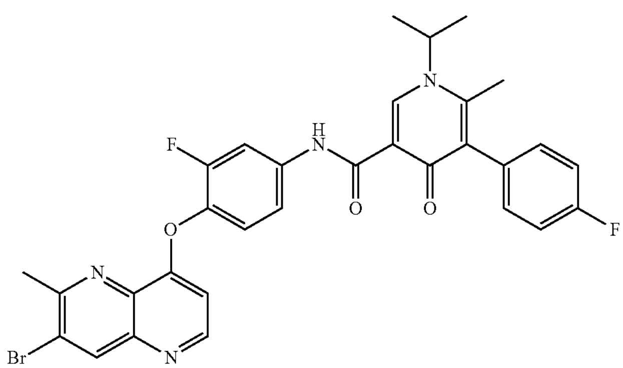 [SMILES: Cc1nc2c(Oc3ccc(NC(=O)c4cn(C(C)C)c(C)c(-c5ccc(F)cc5)c4=O)cc3F)ccnc2cc1Br] | N-[4-[(7-bromo-6-methyl-1,5-naphthyridin-4-yl)oxy]-3-fluorophenyl]-5-(4-fluorophenyl)-6-methyl-4-oxo-1-propan-2-ylpyridine-3-carboxamide |
| 154 | 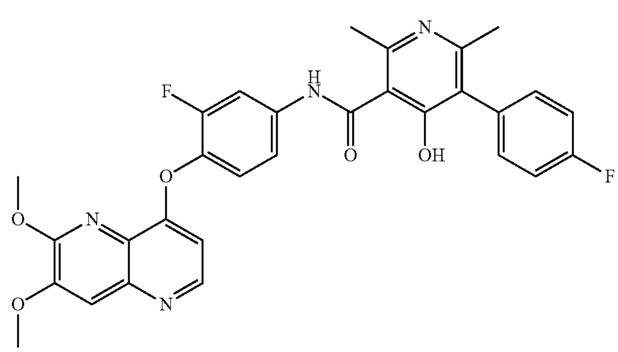 [SMILES: COc1cc2nccc(Oc3ccc(NC(=O)c4c(C)nc(C)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-2,6-dimethylpyridine-3-carboxamide |

-continued

| Cpd # | Structure | IUPAC Name |
|---|---|---|
| 155 | 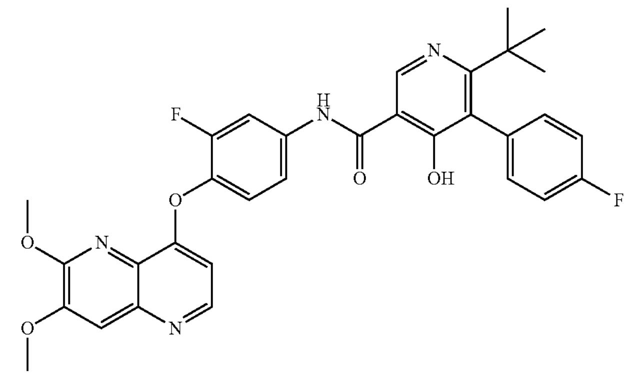 [SMILES: COc1cc2nccc(Oc3ccc(NC(=O)c4cnc(C(C)(C)C)c(-c5ccc(F)cc5)c4O)cc3F)c2nc1OC] | 6-tert-butyl-N-[4-[(6,7-dimethoxy-1,5-naphthyridin-4-yl)oxy]-3-fluorophenyl]-5-(4-fluorophenyl)-4-hydroxypyridine-3-carboxamide |
| 156 | 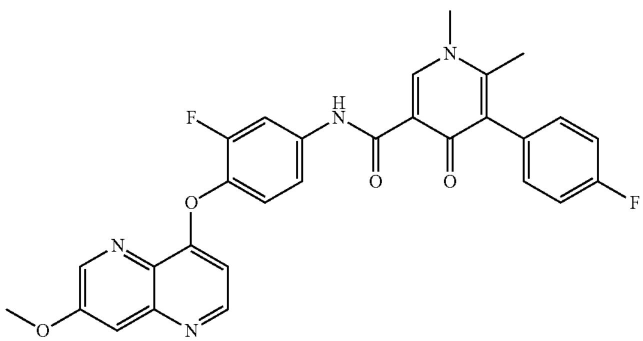 [SMILES: COc1cnc2c(Oc3ccc(NC(=O)c4cn(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,6-dimethyl-4-oxopyridine-3-carboxamide |
| 157 | 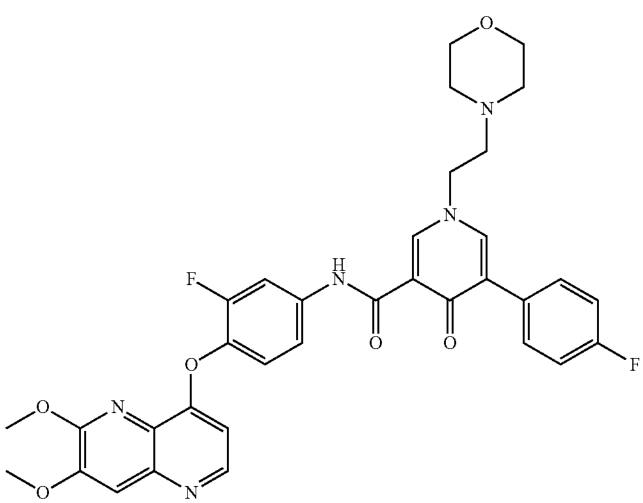 [SMILES: COc1cc2nccc(Oc3ccc(NC(=O)c4cn(CCN5CCOCC5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-morpholin-4-ylethyl)-4-oxopyridine-3-carboxamide |
| 158 | 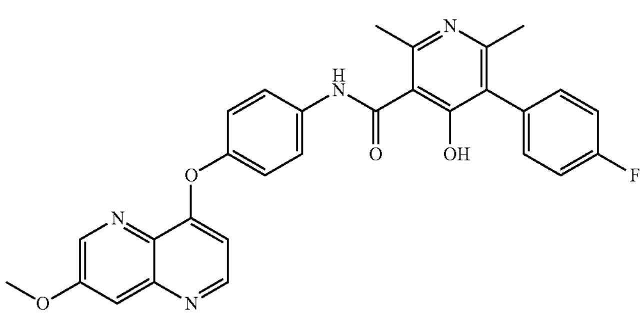 [SMILES: COc1cnc2c(Oc3ccc(NC(=O)c4c(C)nc(C)c(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-2,6-dimethylpyridine-3-carboxamide |

| Cpd # | Structure | IUPAC Name |
|---|---|---|
| 159 | 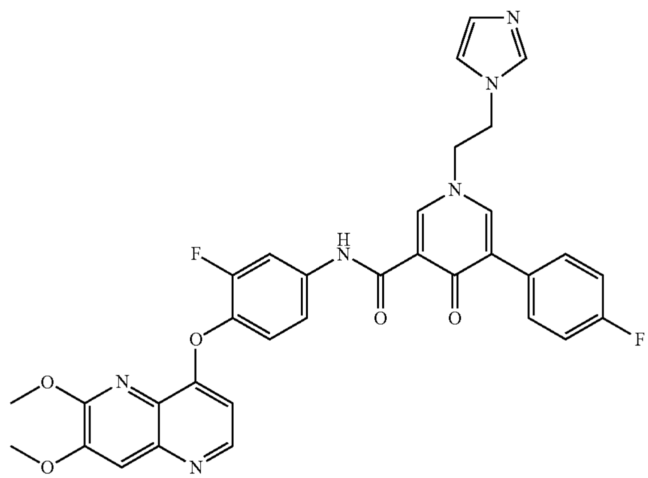 [SMILES: COc1cc2nccc(Oc3ccc(NC(=O)c4cn(CCn5ccnc5)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1-(2-imidazol-1-ylethyl)-4-oxopyridine-3-carboxamide |
| 160 | 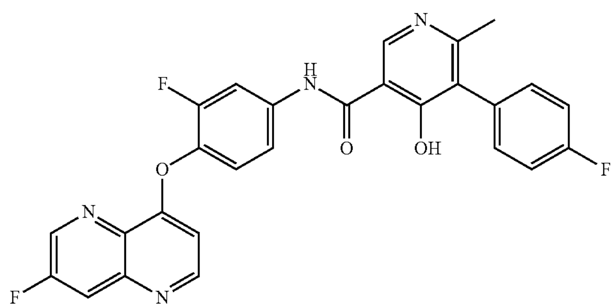 [SMILES: Cc1ncc(C(=O)Nc2ccc(Oc3ccnc4cc(F)cnc34)c(F)c2)c(O)c1-c1ccc(F)cc1] | N-[3-fluoro-4-[(7-fluoro-1,5-naphthyridin-4-yl)oxy]phenyl]-5-(4-fluorophenyl)-4-hydroxy-6-methylpyridine-3-carboxamide |
| 161 | 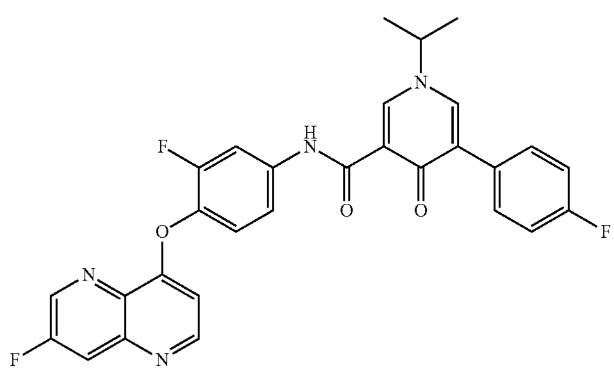 [SMILES: CC(C)n1cc(C(=O)Nc2ccc(Oc3ccnc4cc(F)cnc34)c(F)c2)c(=O)c(-c2ccc(F)cc2)c1] | N-[3-fluoro-4-[(7-fluoro-1,5-naphthyridin-4-yl)oxy]phenyl]-5-(4-fluorophenyl)-4-oxo-1-propan-2-ylpyridine-3-carboxamide |
| 162 | 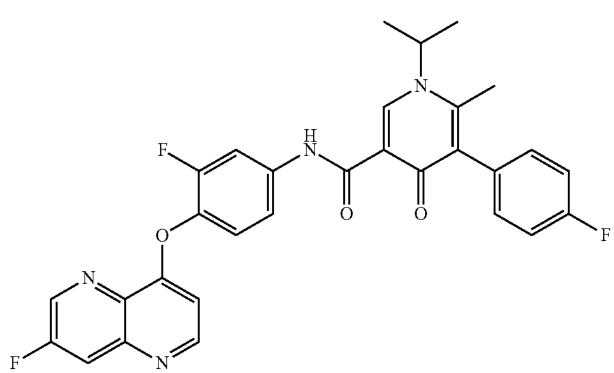 [SMILES: Cc1c(-c2ccc(F)cc2)c(=O)c(C(=O)Nc2ccc(Oc3ccnc4cc(F)cnc34)c(F)c2)cn1C(C)C] | N-[3-fluoro-4-[(7-fluoro-1,5-naphthyridin-4-yl)oxy]phenyl]-5-(4-fluorophenyl)-6-methyl-4-oxo-1-propan-2-ylpyridine-3-carboxamide |

| Cpd # | Structure | IUPAC Name |
|---|---|---|
| 163 | 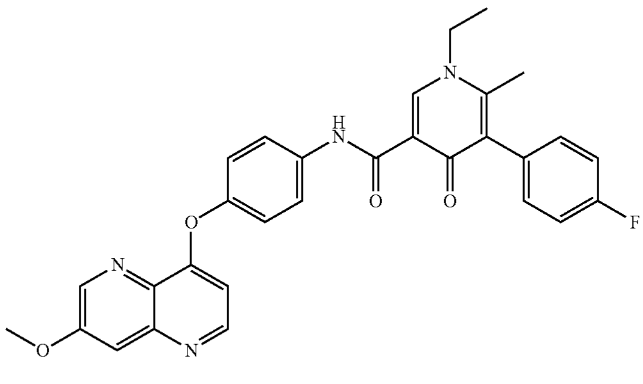 [SMILES: CCn1cc(C(=O)Nc2ccc(Oc3ccnc4cc(OC)cnc34)cc2)c(=O)c(-c2ccc(F)cc2)c1C] | 1-ethyl-5-(4-fluorophenyl)-N-[4-[(7-methoxy-1,5-naphthyridin-4-yl)oxy]phenyl]-6-methyl-4-oxopyridine-3-carboxamide |
| 164 | 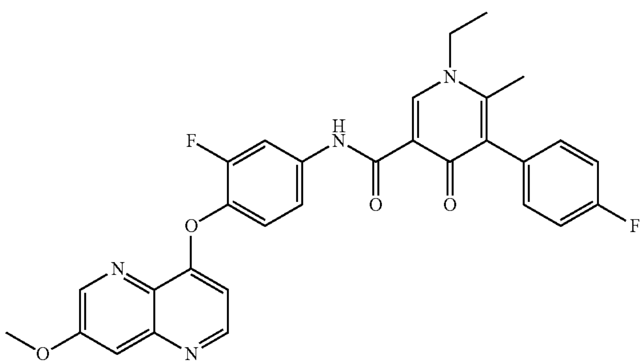 [SMILES: CCn1cc(C(=O)Nc2ccc(Oc3ccnc4cc(OC)cnc34)c(F)c2)c(=O)c(-c2ccc(F)cc2)c1C] | 1-ethyl-N-[3-fluoro-4-[(7-methoxy-1,5-naphthyridin-4-yl)oxy]phenyl]-5-(4-fluorophenyl)-6-methyl-4-oxopyridine-3-carboxamide |
| 165 | 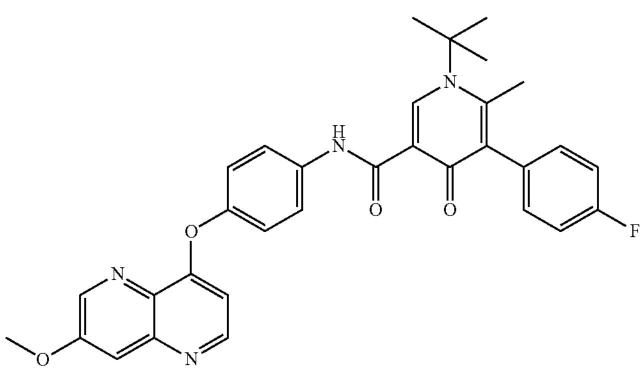 [SMILES: COc1cnc2c(Oc3ccc(NC(=O)c4cn(C(C)(C)C)c(C)c(-c5ccc(F)cc5)c4=O)cc3)ccnc2c1] | 1-tert-butyl-5-(4-fluorophenyl)-N-[4-[(7-methoxy-1,5-naphthyridin-4-yl)oxy]phenyl]-6-methyl-4-oxopyridine-3-carboxamide |
| 166 | 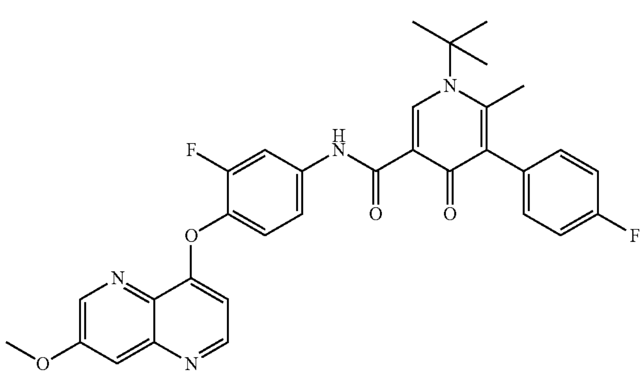 [SMILES: COc1cnc2c(Oc3ccc(NC(=O)c4cn(C(C)(C)C)c(C)c(-c5ccc(F)cc5)c4=O)cc3F)ccnc2c1] | 1-tert-butyl-N-[3-fluoro-4-[(7-methoxy-1,5-naphthyridin-4-yl)oxy]phenyl]-5-(4-fluorophenyl)-6-methyl-4-oxopyridine-3-carboxamide |

| Cpd # | Structure | IUPAC Name |
|---|---|---|
| 167 | 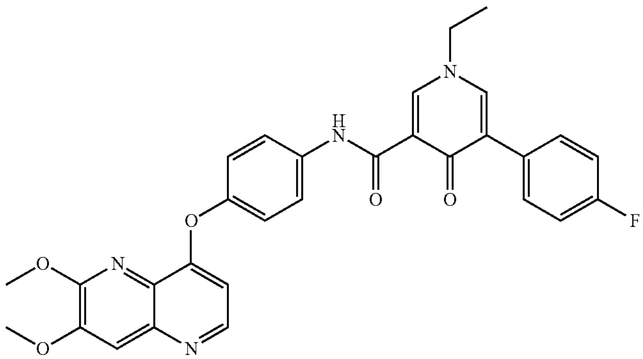 [SMILES: CCn1cc(C(=O)Nc2ccc(Oc3ccnc4cc(OC)c(OC)nc34)cc2)c(=O)c(-c2ccc(F)cc2)c1] | N-[4-[(6,7-dimethoxy-1,5-naphthyridin-4-yl)oxy]phenyl]-1-ethyl-5-(4-fluorophenyl)-4-oxopyridine-3-carboxamide |
| 168 | 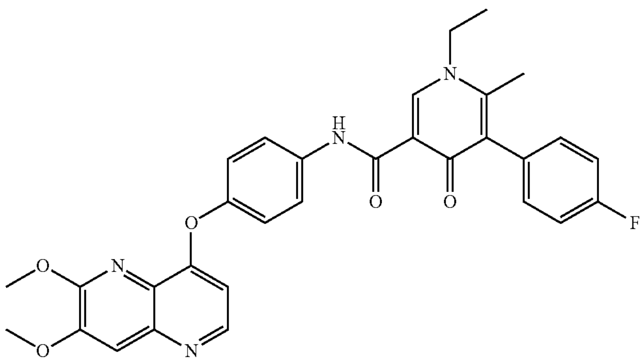 [SMILES: CCn1cc(C(=O)Nc2ccc(Oc3ccnc4cc(OC)c(OC)nc34)cc2)c(=O)c(-c2ccc(F)cc2)c1C] | N-[4-[(6,7-dimethoxy-1,5-naphthyridin-4-yl)oxy]phenyl]-1-ethyl-5-(4-fluorophenyl)-6-methyl-4-oxopyridine-3-carboxamide |
| 169 | 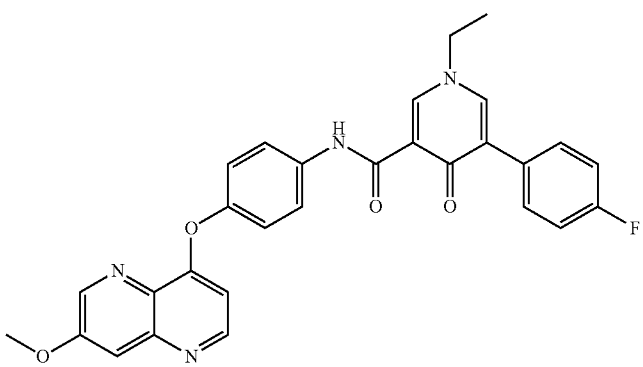 [SMILES: CCn1cc(C(=O)Nc2ccc(Oc3ccnc4cc(OC)cnc34)cc2)c(=O)c(-c2ccc(F)cc2)c1] | 1-ethyl-5-(4-fluorophenyl)-N-[4-[(7-methoxy-1,5-naphthyridin-4-yl)oxy]phenyl]-4-oxopyridine-3-carboxamide |
| 170 | 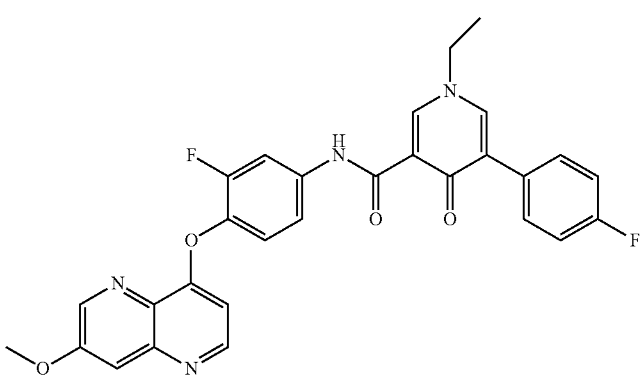 | 1-ethyl-N-[3-fluoro-4-[(7-methoxy-1,5-naphthyridin-4-yl)oxy]phenyl]-5-(4-fluorophenyl)-4-oxopyridine-3-carboxamide |

| Cpd # | Structure | IUPAC Name |
|---|---|---|
| 171 | 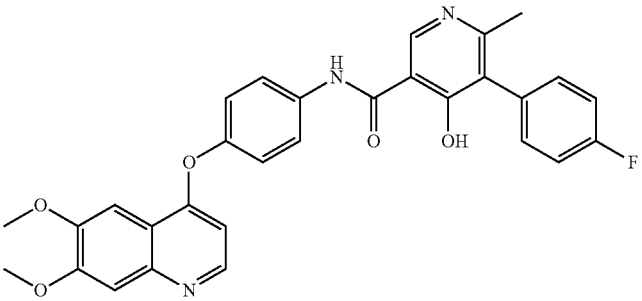 [SMILES: COc1cc2nccc(Oc3ccc(NC(=O)c4cnc(C)c(-c5ccc(F)cc5)c4O)cc3)c2cc1OC] | N-[4-(6, 7-dimethoxyquinolin-4-yl)oxyphenyl]-5-(4-fluorophenyl)-4-hydroxy-6-methylpyridine-3-carboxamide |
| 172 | 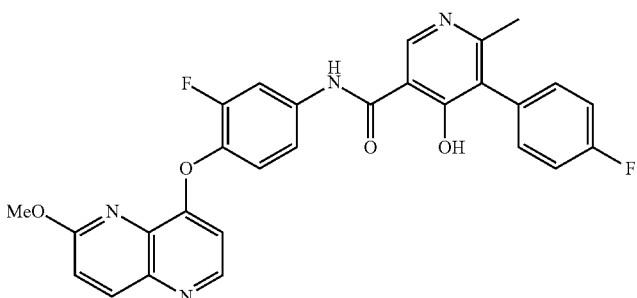 | N-[3-fluoro-4-[(6-methoxy-1,5-naphthyridin-4-yl)oxy]phenyl]-5-(4-fluorophenyl)-4-hydroxy-6-methylpyridine-3-carboxamide |
| 173 | 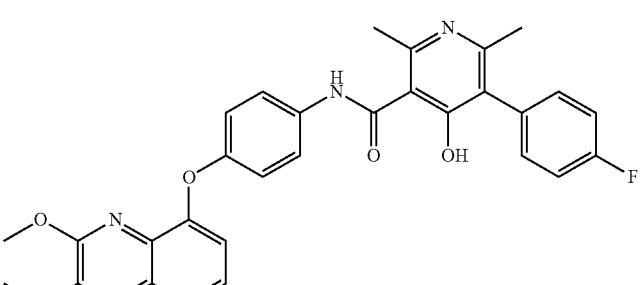 | N-[4-[(6,7-dimethoxy-1,5-naphthyridin-4-yl)oxy]phenyl]-5-(4-fluorophenyl)-4-hydroxy-2,6-dimethylpyridine-3-carboxamide |
| 174 | 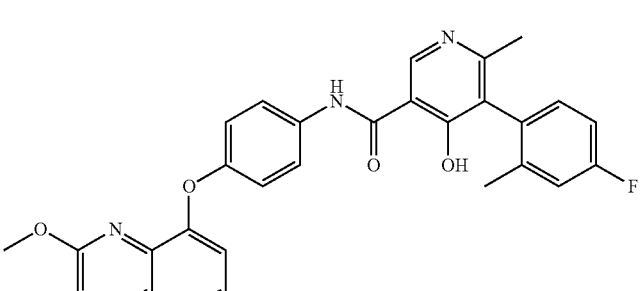 | N-[4-[(6,7-dimethoxy-1,5-naphthyridin-4-yl)oxy]phenyl]-5-(4-fluoro-2-methylphenyl)-4-hydroxy-6-methylpyridine-3-carboxamide |
| 175 | 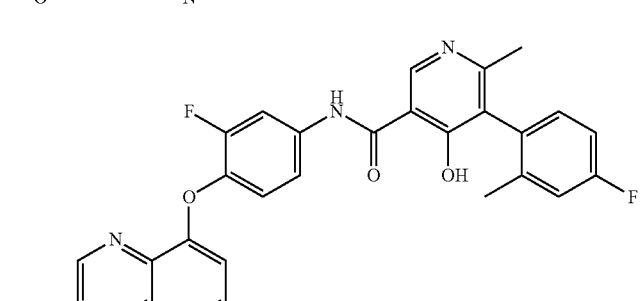 | N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |

| Cpd # | Structure | IUPAC Name |
|---|---|---|
| 176 | 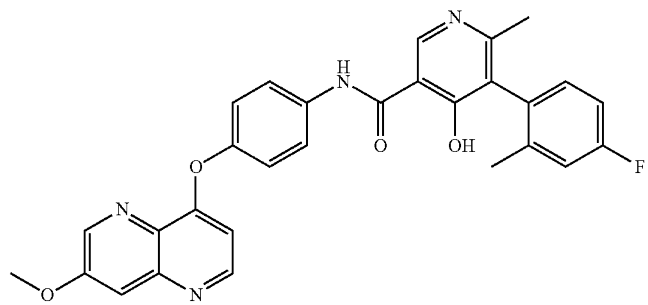 [SMILES: COc1cnc2c(Oc3ccc(NC(=O)c4cnc(C)c(-c5ccc(F)cc5C)c4O)cc3)ccnc2c1] | 5-(4-fluoro-2-methylphenyl)-4-hydroxy-N-[4-[(7-methoxy-1,5-naphthyridin-4-yl)oxy]phenyl]-6-methylpyridine-3-carboxamide |
| 177 | 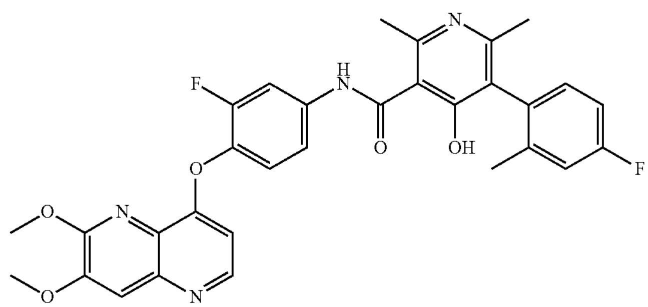 [SMILES: COc1cc2nccc(Oc3ccc(NC(=O)c4c(C)nc(C)c(-c5ccc(F)cc5C)c4O)cc3F)c2nc1OC] | N-[4-[(6,7-dimethoxy-1,5-naphthyridin-4-yl)oxy]-3-fluorophenyl]-5-(4-fluoro-2-methylphenyl)-4-hydroxy-2,6-dimethylpyridine-3-carboxamide |
| 178 | 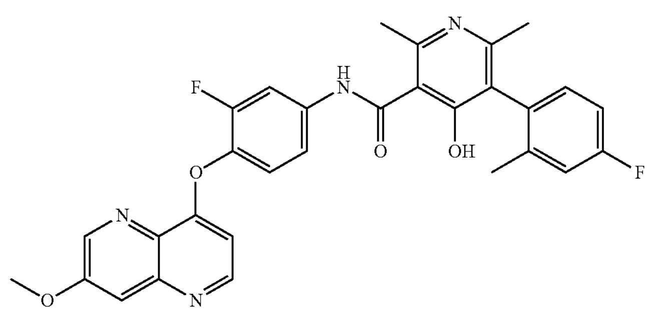 [SMILES: COc1cnc2c(Oc3ccc(NC(=O)c4c(C)nc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 179 | 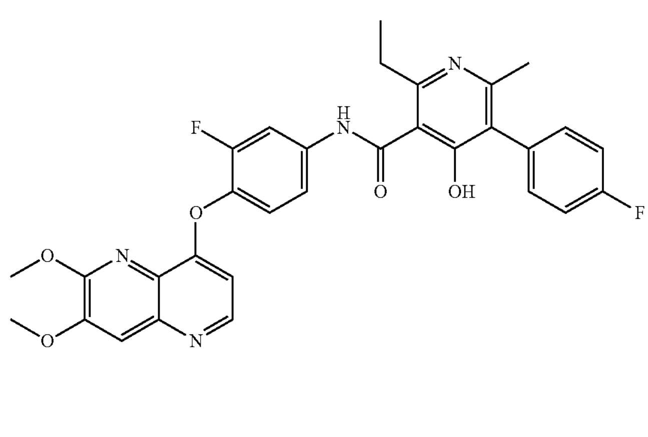 [SMILES: CCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-ethyl-5-(4-fluorophenyl)-4-hydroxy-6-methylpyridine-3-carboxamide |

| Cpd # | Structure | IUPAC Name |
|---|---|---|
| 180 | 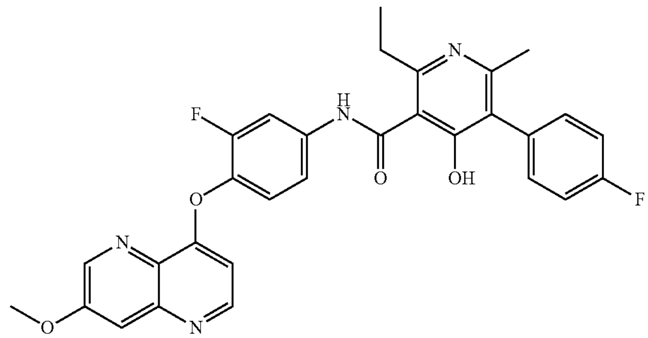 [SMILES: CCc1nc(C)c(-c2ccc(F)cc2)c(O)c1C(=O)Nc1ccc(Oc2ccnc3cc(OC)cnc23)c(F)c1] | 2-ethyl-N-[3-fluoro-4-[(7-methoxy-1,5-naphthyridin-4-yl)oxy]phenyl]-5-(4-fluorophenyl)-4-hydroxy-6-methylpyridine-3-carboxamide |
| 181 | 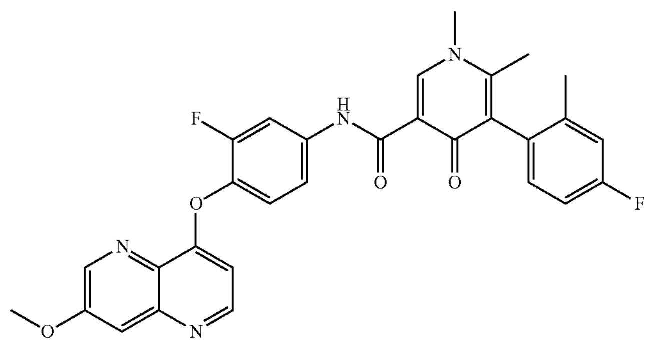 [SMILES: COc1cnc2c(Oc3ccc(NC(=O)c4cn(C)c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-1,6-dimethyl-4-oxopyridine-3-carboxamide |
| 182 | 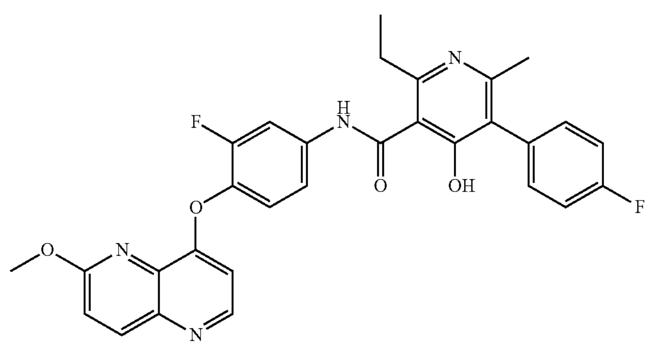 [SMILES: CCc1nc(C)c(-c2ccc(F)cc2)c(O)c1C(=O)Nc1ccc(Oc2ccnc3ccc(OC)nc23)c(F)c1] | 2-ethyl-N-[3-fluoro-4-[(6-methoxy-1,5-naphthyridin-4-yl)oxy]phenyl]-5-(4-fluorophenyl)-4-hydroxy-6-methylpyridine-3-carboxamide |
| 183 | 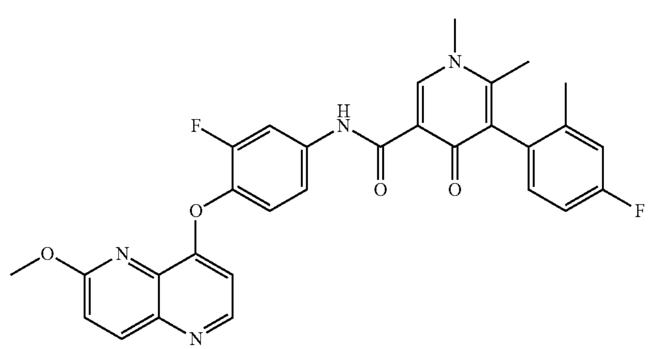 [SMILES: COc1ccc2nccc(Oc3ccc(NC(=O)c4cn(C)c(C)c(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-1,6-dimethyl-4-oxopyridine-3-carboxamide |

| Cpd # | Structure | IUPAC Name |
|---|---|---|
| 184 | 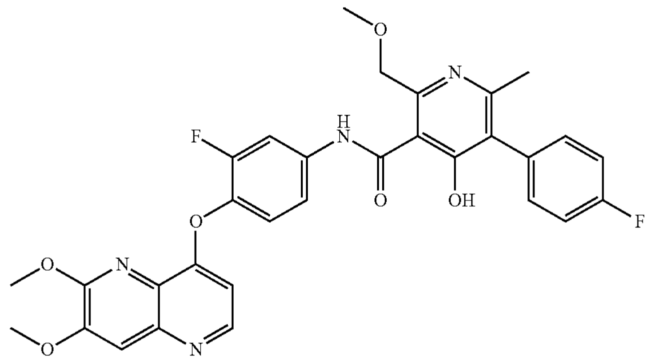 [SMILES: COCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-hydroxy-2-(methoxymethyl)-6-methylpyridine-3-carboxamide |
| 185 | 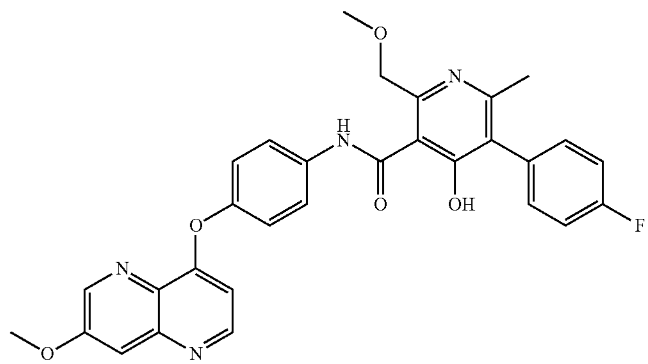 [SMILES: COCc1nc(C)c(-c2ccc(F)cc2)c(O)c1C(=O)Nc1ccc(Oc2ccnc3cc(OC)cnc23)cc1] | 5-(4-fluorophenyl)-4-hydroxy-2-(methoxymethyl)-N-[4-[(7-methoxy-1,5-naphthyridin-4-yl)oxy]phenyl]-6-methylpyridine-3-carboxamide |
| 186 | 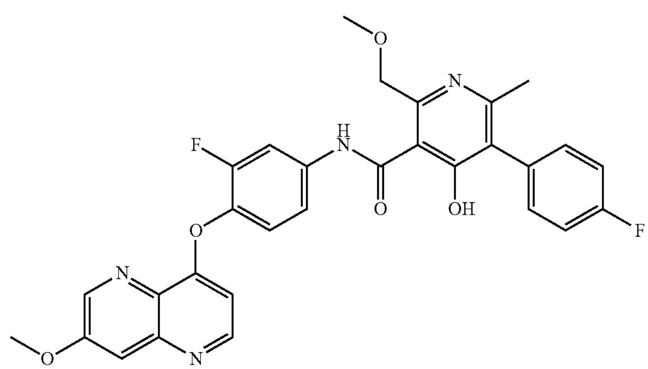 [SMILES: COCc1nc(C)c(-c2ccc(F)cc2)c(O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-5-(4-fluorophenyl)-4-hydroxy-2-(methoxymethyl)-6-methylpyridine-3-carboxamide |
| 187 | 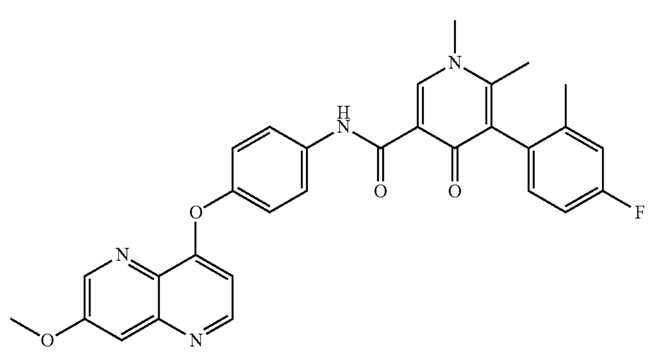 [SMILES: COc1cnc2c(Oc3ccc(NC(=O)c4cn(C)c(C)c(-c5ccc(F)cc5C)c4=O)cc3)ccnc2c1] | 5-(4-fluoro-2-methylphenyl)-N-[4-[(7-methoxy-1,5-naphthyridin-4-yl)oxy]phenyl]-1,6-dimethyl-4-oxopyridine-3-carboxamide |

| Cpd # | Structure | IUPAC Name |
|---|---|---|
| 188 | 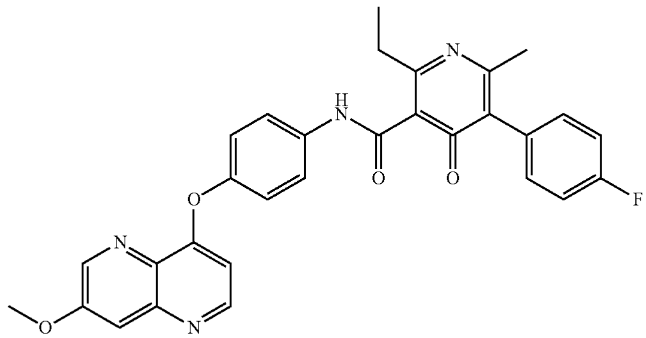 | 2-ethyl-5-(4-fluorophenyl)-4-hydroxy-N-[4-[(7-methoxy-1,5-naphthyridin-4-yl)oxy]phenyl]-6-methylpyridine-3-carboxamide |
| 189 | 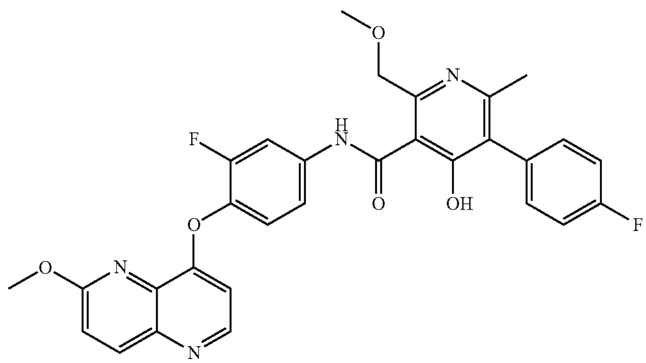 [SMILES: COCc1nc(C)c(-c2ccc(F)cc2)c(O)c1C(=O)Nc1ccc(Oc2ccnc3ccc(OC)nc23)c(F)c1] | N-[3-fluoro-4-[(6-methoxy-1,5-naphthyridin-4-yl)oxy]phenyl]-5-(4-fluorophenyl)-4-hydroxy-2-(methoxymethyl)-6-methylpyridine-3-carboxamide |
| 190 | 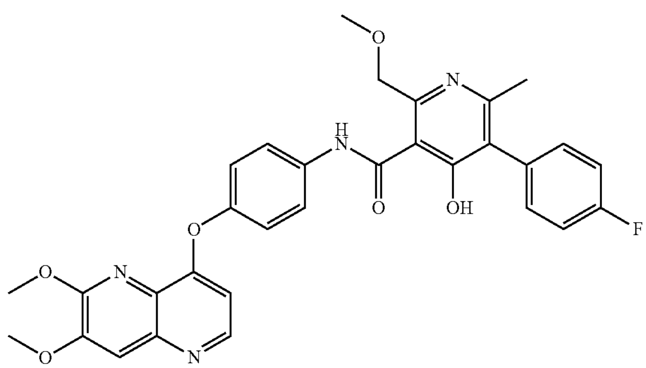 [SMILES: COCc1nc(C)c(-c2ccc(F)cc2)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-5-(4-fluorophenyl)-4-hydroxy-2-(methoxymethyl)-6-methylpyridine-3-carboxamide |
| 191 | 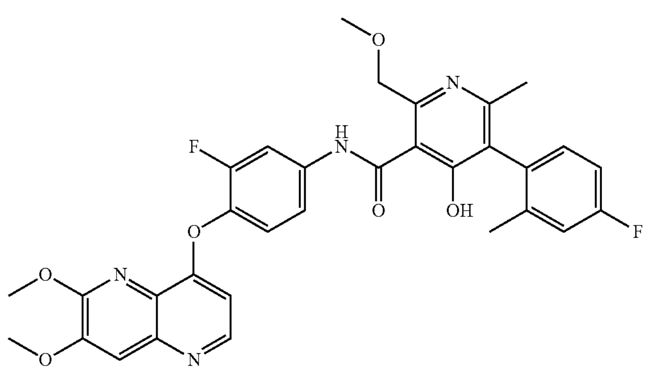 [SMILES: COCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluoro-2-methylphenyl)-4-hydroxy-2-(methoxymethyl)-6-methylpyridine-3-carboxamide |

| Cpd # | Structure | IUPAC Name |
|---|---|---|
| 192 | 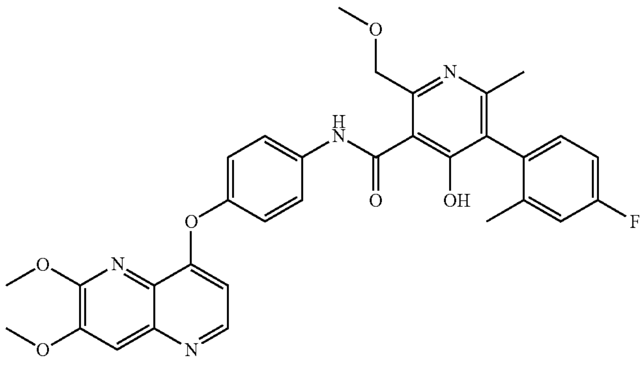 [SMILES: COCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-5-(4-fluoro-2-methylphenyl)-4-hydroxy-2-(methoxymethyl)-6-methylpyridine-3-carboxamide |
| 193 | 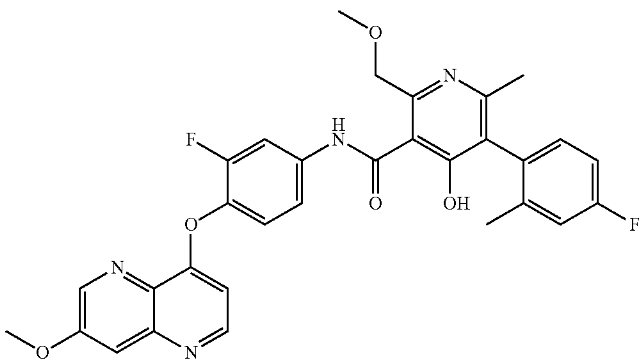 [SMILES: COCc1nc(C)c(-c2ccc(F)cc2C)c(O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-5-(4-fluoro-2-methylphenyl)-4-hydroxy-2-(methoxymethyl)-6-methylpyridine-3-carboxamide |
| 194 | 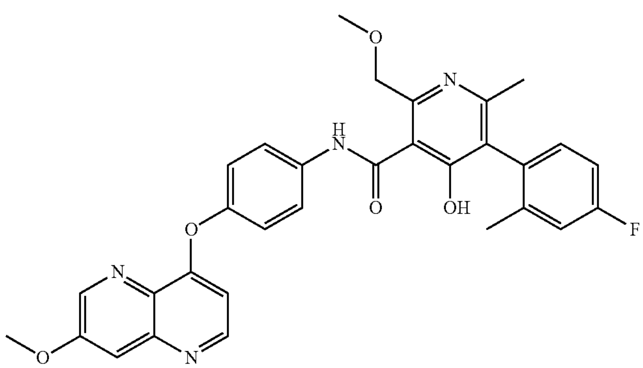 [SMILES: COCc1nc(C)c(-c2ccc(F)cc2C)c(O)c1C(=O)Nc1ccc(Oc2ccnc3cc(OC)cnc23)cc1] | 5-(4-fluoro-2-methylphenyl)-4-hydroxy-2-(methoxymethyl)-N-[4-[(7-methoxy-1,5-naphthyridin-4-yl)oxy]phenyl]-6-methylpyridine-3-carboxamide |
| 195 | 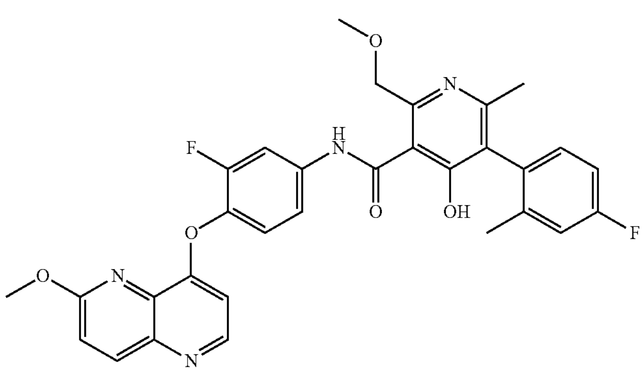 [SMILES: COCc1nc(C)c(-c2ccc(F)cc2C)c(O)c1C(=O)Nc1ccc(Oc2ccnc3ccc(OC)nc23)c(F)c1] | N-[3-fluoro-4-[(6-methoxy-1,5-naphthyridin-4-yl)oxy]phenyl]-5-(4-fluoro-2-methylphenyl)-4-hydroxy-2-(methoxymethyl)-6-methylpyridine-3-carboxamide |

| Cpd # | Structure | IUPAC Name |
|---|---|---|
| 196 | 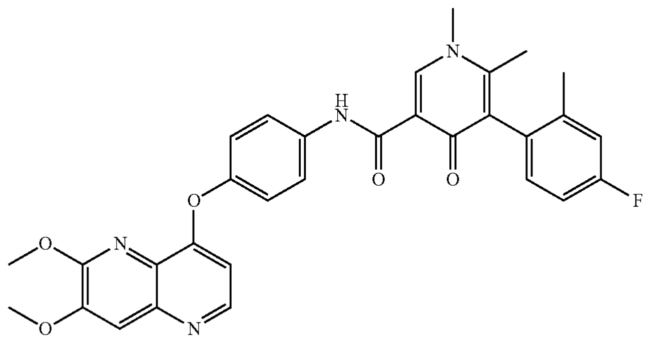 [SMILES: COc1cc2nccc(Oc3ccc(NC(=O)c4cn(C)c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-1,6-dimethyl-4-oxopyridine-3-carboxamide |
| 197 | 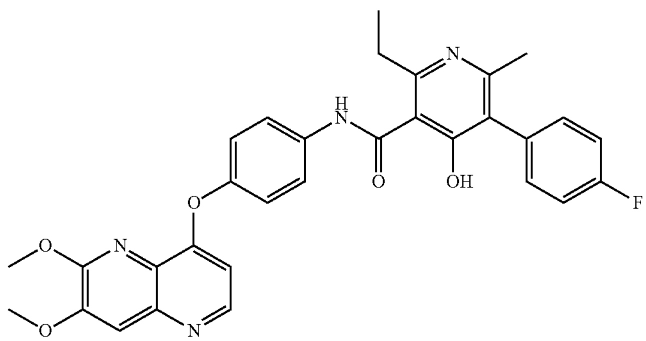 [SMILES: CCc1nc(C)c(-c2ccc(F)cc2)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-ethyl-5-(4-fluorophenyl)-4-hydroxy-6-methylpyridine-3-carboxamide |
| 198 | 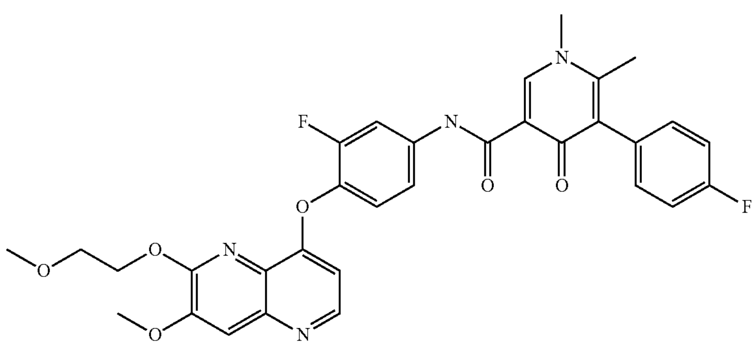 [SMILES: COCCOc1nc2c(Oc3ccc(NC(=O)c4cn(C)c(C)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-1,6-dimethyl-4-oxopyridine-3-carboxamide |
| 199 | 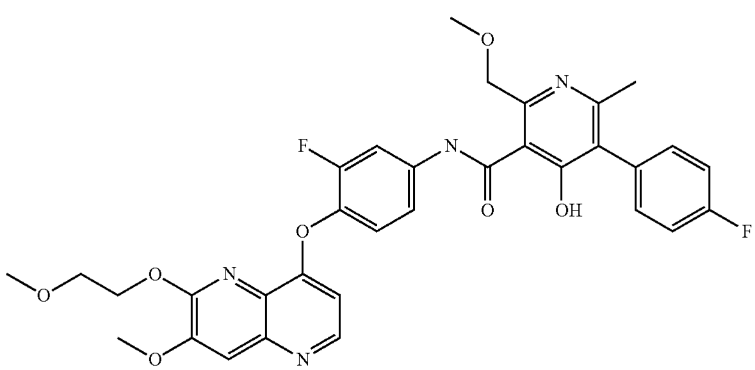 [SMILES: COCCOc1nc2c(Oc3ccc(NC(=O)c4c(COC)nc(C)c(-c5ccc(F)cc5)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide |

| Cpd # | Structure | IUPAC Name |
|---|---|---|
| 200 | 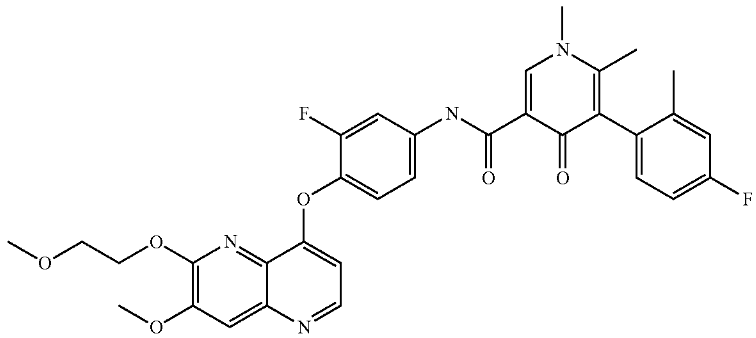 [SMILES: COCCOc1nc2c(Oc3ccc(NC(=O)c4cn(C)c(C)c(-c5ccc(F)cc5C)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-1,6-dimethyl-4-oxopyridine-3-carboxamide |
| 201 | 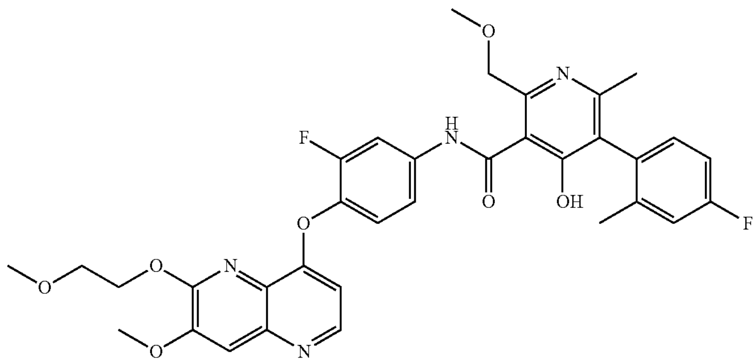 [SMILES: COCCOc1nc2c(Oc3ccc(NC(=O)c4c(COC)nc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxyphenyl]-5-(4-fluoro-2-methylphenyl)-4-hydroxy-2-(methoxymethyl)-6-methylpyridine-3-carboxamide |
| 202 | 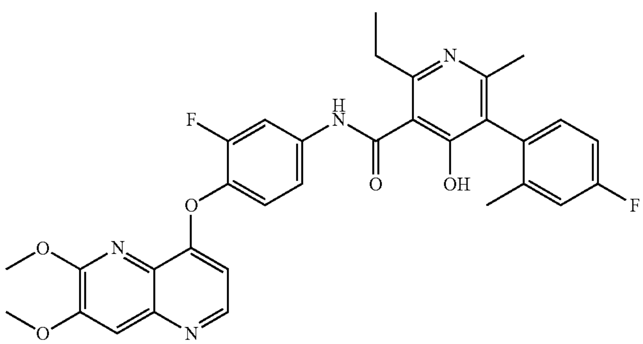 [SMILES: CCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-ethyl-5-(4-fluoro-2-methylphenyl)-4-hydroxy-6-methylpyridine-3-carboxamide |
| 203 | 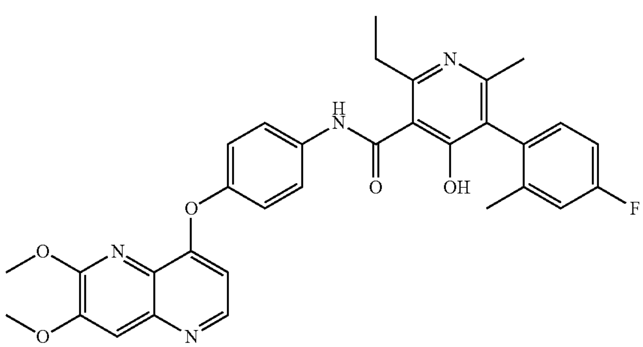 [SMILES: CCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-ethyl-5-(4-fluoro-2-methylphenyl)-4-hydroxy-6-methylpyridine-3-carboxamide |

| Cpd # | Structure | IUPAC Name |
|---|---|---|
| 204 | 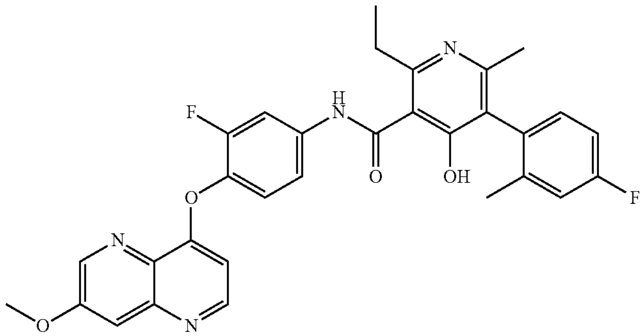 [SMILES: CCc1nc(C)c(-c2ccc(F)cc2C)c(O)c1C(=O)Nc1ccc(Oc2ccnc3cc(OC)cnc23)c(F)c1] | 2-ethyl-N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |
| 205 | 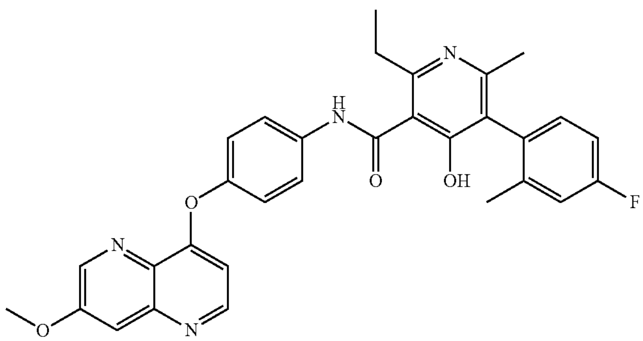 [SMILES: CCc1nc(C)c(-c2ccc(F)cc2C)c(O)c1C(=O)Nc1ccc(Oc2ccnc3cc(OC)cnc23)cc1] | 2-ethyl-5-(4-fluoro-2-methylphenyl)-4-hydroxy-N-[4-[(7-methoxy-1,5-naphthyridin-4-yl)oxy]phenyl]-6-methylpyridine-3-carboxamide |
| 206 | 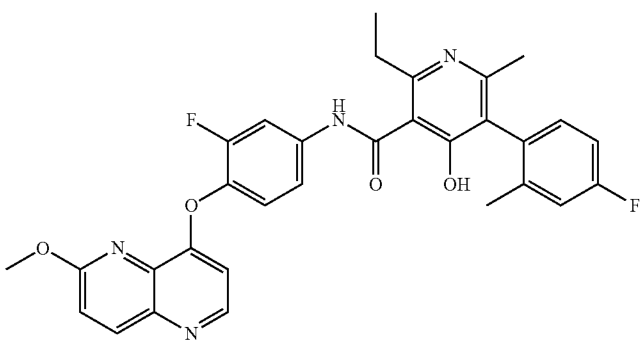 [SMILES: CCc1nc(C)c(-c2ccc(F)cc2C)c(O)c1C(=O)Nc1ccc(Oc2ccnc3ccc(OC)nc23)c(F)c1] | 2-ethyl-N-[3-fluoro-4-[(6-methoxy-1,5-naphthyridin-4-yl)oxy]phenyl]-5-(4-fluoro-2-methylphenyl)-4-hydroxy-6-methylpyridine-3-carboxamide |
| 207 | 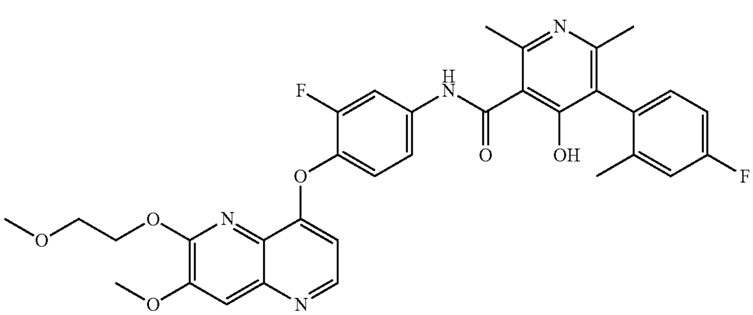 [SMILES: COCCOc1nc2c(Oc3ccc(NC(=O)c4c(C)nc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-4-hydroxy-2,6-dimethylpyridine-3-carboxamide |

| Cpd # | Structure | IUPAC Name |
|---|---|---|
| 208 | 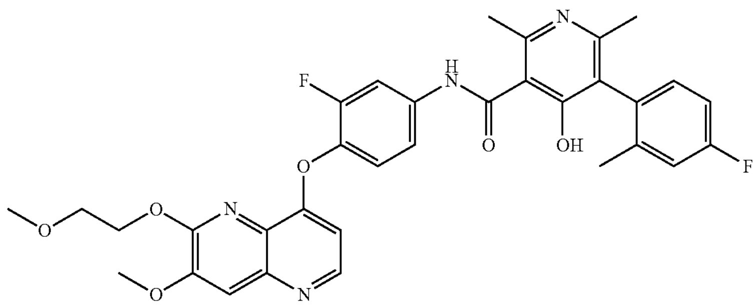 [SMILES: COCCOc1nc2c(Oc3ccc(NC(=O)c4c(C)nc(C)c(-c5ccc(F)cc5C)c4O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-4-hydroxy-2,6-dimethylpyridine-3-carboxamide |
| 209 | 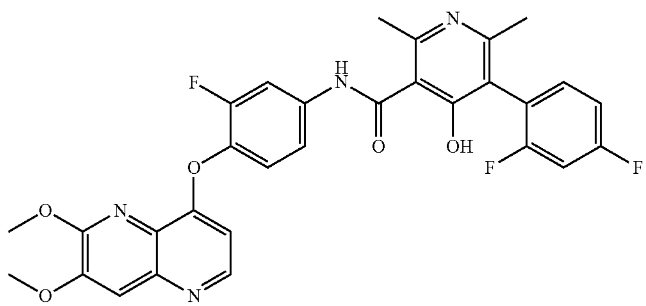 [SMILES: COc1cc2nccc(Oc3ccc(NC(=O)c4c(C)nc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-3-fluorophenyl]-4-hydroxy-2,6-dimethylpyridine-3-carboxamide |
| 210 | 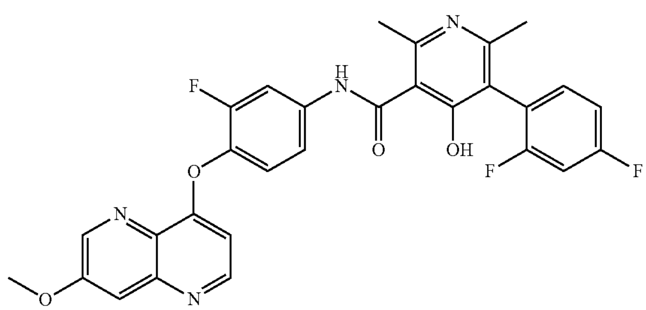 [SMILES: COc1cnc2c(Oc3ccc(NC(=O)c4c(C)nc(C)c(-c5ccc(F)cc5F)c4O)cc3F)ccnc2c1] | 5-(2,4-difluorophenyl)-N-[3-fluoro-4-[(7-methoxy-1,5-naphthyridin-4-yl)oxy]phenyl]-4-hydroxy-2,6-dimethylpyridine-3-carboxamide |
| 211 | 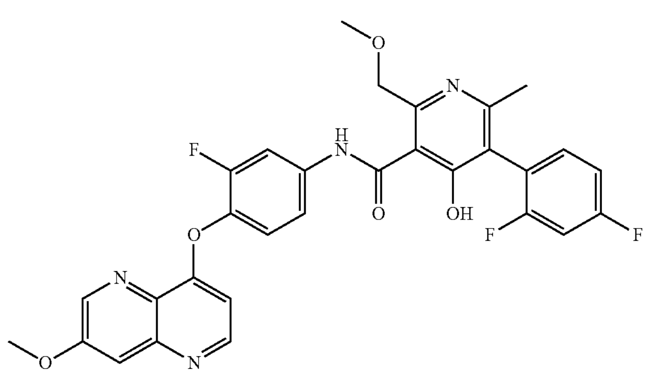 | 5-(2,4-difluorophenyl)-N-[3-fluoro-4-[(7-methoxy-1,5-naphthyridin-4-yl)oxy]phenyl]-4-hydroxy-2-(methoxymethyl)-6-methylpyridine-3-carboxamide |

| Cpd # | Structure | IUPAC Name |
|---|---|---|
| 212 | 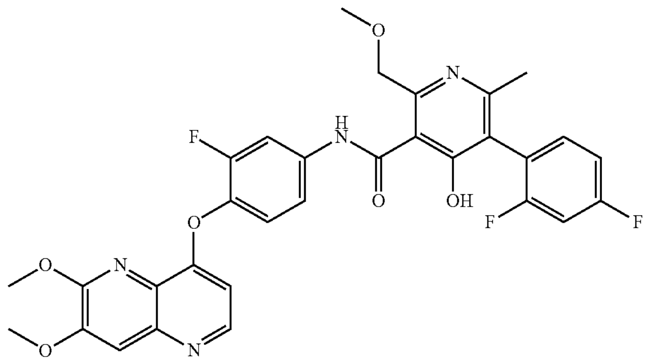 [SMILES: COCc1nc(C)c(-c2ccc(F)cc2F)c(O)c1C(=O)Nc1ccc(Oc2ccnc3cc(OC)c(OC)nc23)c(F)c1] | 5-(2,4-difluorophenyl)-N-[4-[(6,7-dimethoxy-1,5-naphthyridin-4-yl)oxy]-3-fluorophenyl]-4-hydroxy-2-(methoxymethyl)-6-methylpyridine-3-carboxamide |
| 213 | 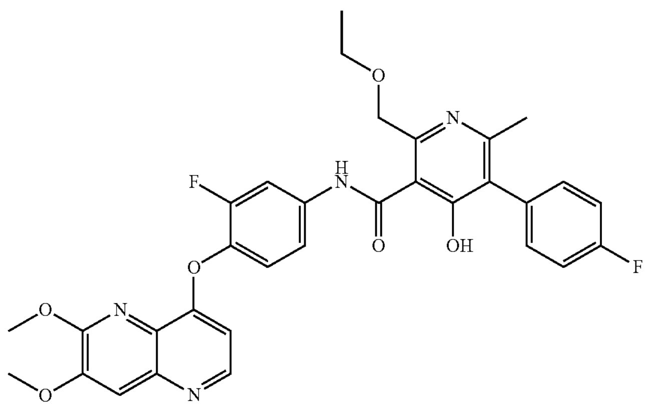 [SMILES: CCOCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(ethoxymethyl)-5-(4-fluorophenyl)-4-hydroxy-6-methylpyridine-3-carboxamide |
| 214 | 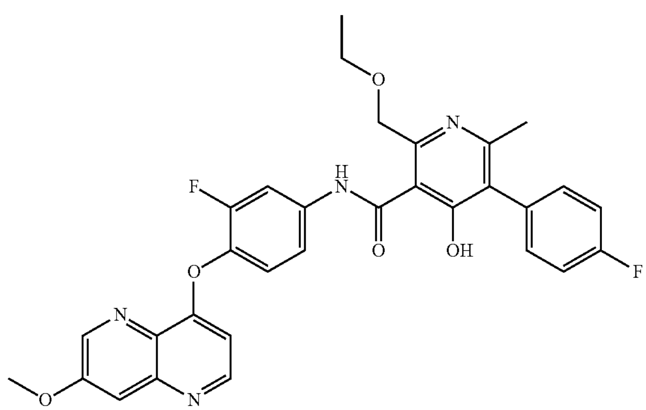 [SMILES: CCOCc1nc(C)c(-c2ccc(F)cc2)c(O)c1C(=O)Nc1ccc(Oc2ccnc3cc(OC)cnc23)c(F)c1] | 2-(ethoxymethyl)-N-[3-fluoro-4-[(7-methoxy-1,5-naphthyridin-4-yl)oxy]phenyl]-5-(4-fluorophenyl)-4-hydroxy-6-methylpyridine-3-carboxamide |
| 215 | 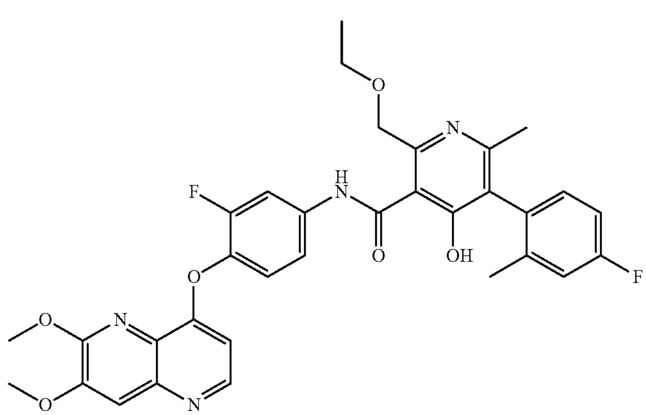 [SMILES: CCOCc1nc(C)c(-c2ccc(F)cc2C)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(ethoxymethyl)-5-(4-fluoro-2-methylphenyl)-4-hydroxy-6-methylpyridine-3-carboxamide |

-continued

| Cpd # | Structure | IUPAC Name |
|---|---|---|
| 216 | 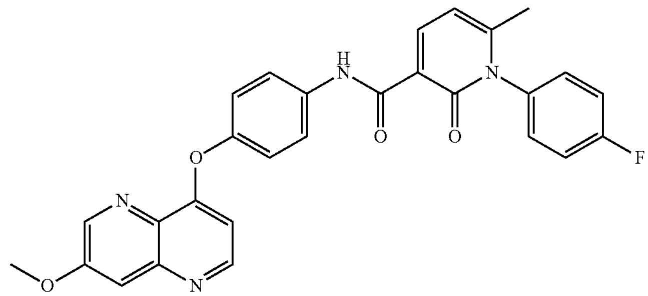 [SMILES: COc1cnc2c(Oc3ccc(NC(=O)c4ccc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-6-methyl-2-oxopyridine-3-carboxamide |
| 217 | 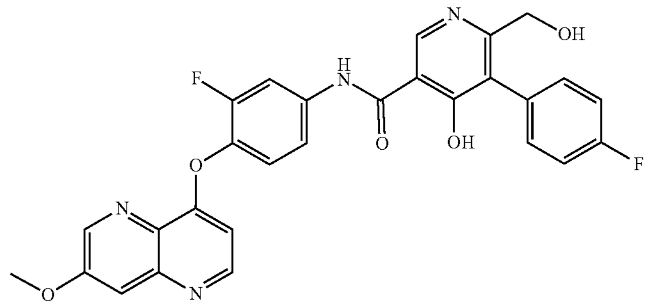 [SMILES: COc1cnc2c(Oc3ccc(NC(=O)c4cnc(CO)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-(hydroxymethyl)pyridine-3-carboxamide |
| 218 | 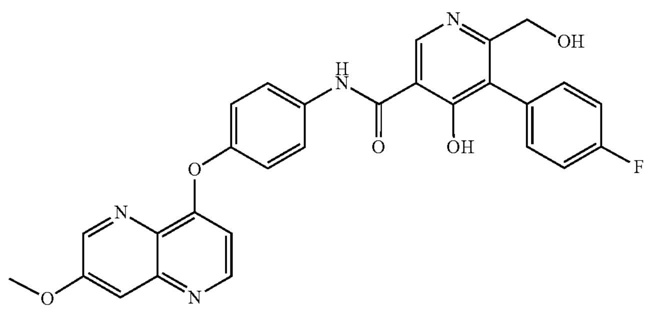 [SMILES: COc1cnc2c(Oc3ccc(NC(=O)c4cnc(CO)c(-c5ccc(F)cc5)c4O)cc3)ccnc2c1] | 5-(4-fluorophenyl)-4-hydroxy-6-(hydroxymethyl)-N-[4-[(7-methoxy-1,5-naphthyridin-4-yl)oxy]phenyl]pyridine-3-carboxamide |
| 219 | 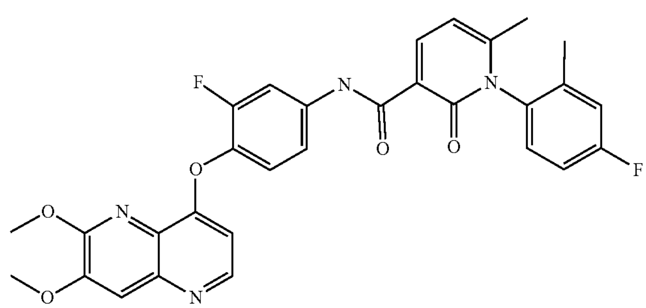 | N-[4-[(6,7-dimethoxy-1,5-naphthyridin-4-yl)oxy]-3-fluorophenyl]-1-(4-fluoro-2-methylphenyl)-6-methyl-2-oxopyridine-3-carboxamide |
| 220 | 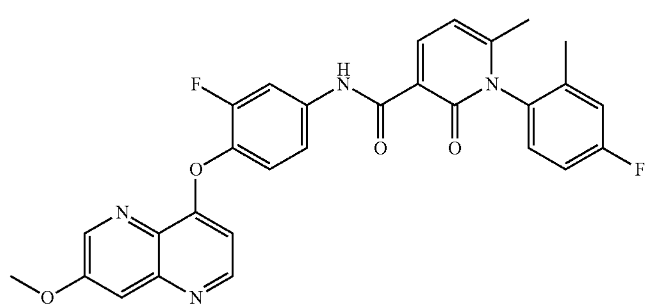 [SMILES: COc1cnc2c(Oc3ccc(NC(=O)c4ccc(C)n(-c5ccc(F)cc5C)c4=O)cc3F)ccnc2c1] | N-[3-fluoro-4-[(7-methoxy-1,5-naphthyridin-4-yl)oxy]phenyl]-1-(4-fluoro-2-methylphenyl)-6-methyl-2-oxopyridine-3-carboxamide |

| Cpd # | Structure | IUPAC Name |
|---|---|---|
| 221 | 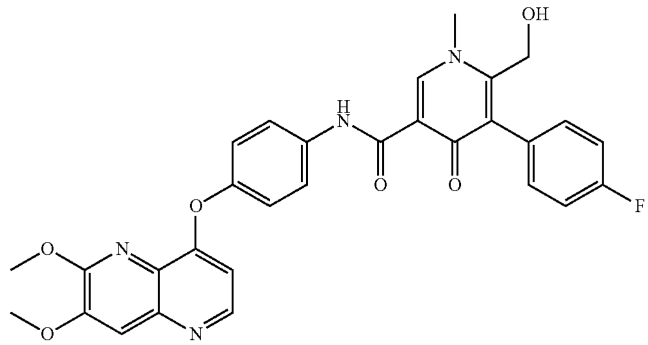 [SMILES: COc1cc2nccc(Oc3ccc(NC(=O)c4cn(C)c(CO)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-(hydroxymethyl)-1-methyl-4-oxopyridine-3-carboxamide |
| 222 | 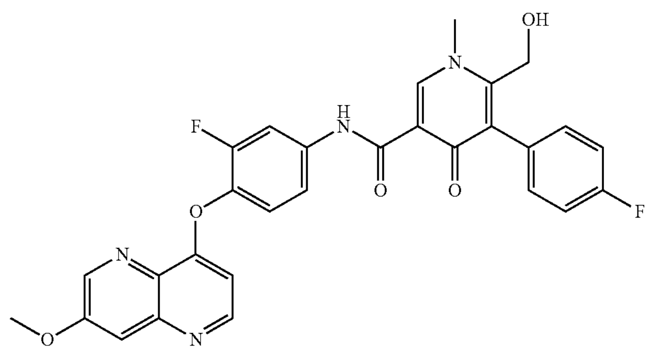 [SMILES: COc1cnc2c(Oc3ccc(NC(=O)c4cn(C)c(CO)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-(hydroxymethyl)-1-methyl-4-oxopyridine-3-carboxamide |
| 223 | 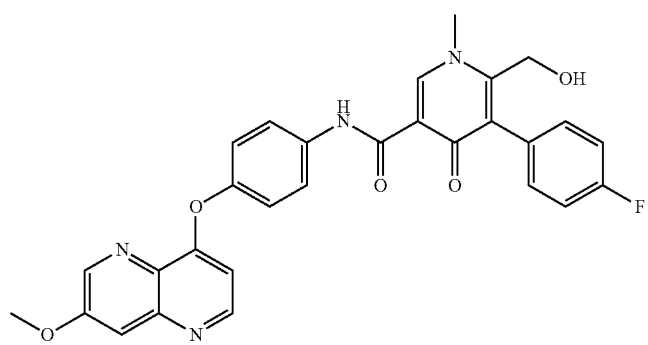 [SMILES: COc1cnc2c(Oc3ccc(NC(=O)c4cn(C)c(CO)c(-c5ccc(F)cc5)c4=O)cc3)ccnc2c1] | 5-(4-fluorophenyl)-6-(hydroxymethyl)-N-[4-[(7-methoxy-1,5-naphthyridin-4-yl)oxy]phenyl]-1-methyl-4-oxopyridine-3-carboxamide |
| 224 | 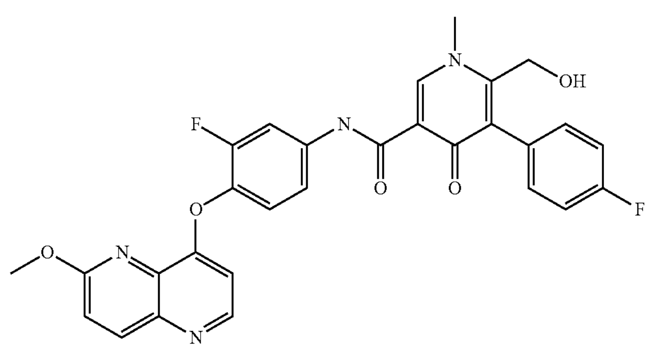 | N-[3-fluoro-4-[(6-methoxy-1,5-naphthyridin-4-yl)oxy]phenyl]-5-(4-fluorophenyl)-6-(hydroxymethyl)-1-methyl-4-oxopyridine-3-carboxamide |

-continued

| Cpd # | Structure | IUPAC Name |
|---|---|---|
| 225 | 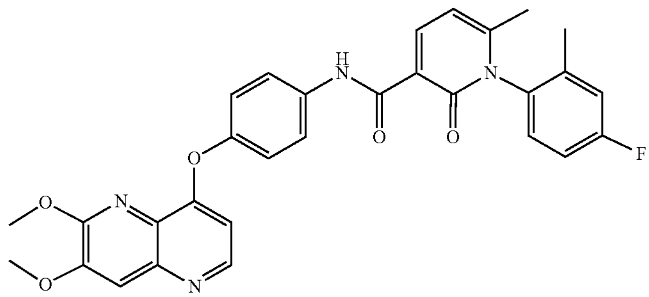 [SMILES: COc1cc2nccc(Oc3ccc(NC(=O)c4ccc(C)n(-c5ccc(F)cc5C)c4=O)cc3)c2nc1OC] | N-[4-[(6,7-dimethoxy-1,5-naphthyridin-4-yl)oxy]phenyl]-1-(4-fluoro-2-methylphenyl)-6-methyl-2-oxopyridine-3-carboxamide |
| 226 | 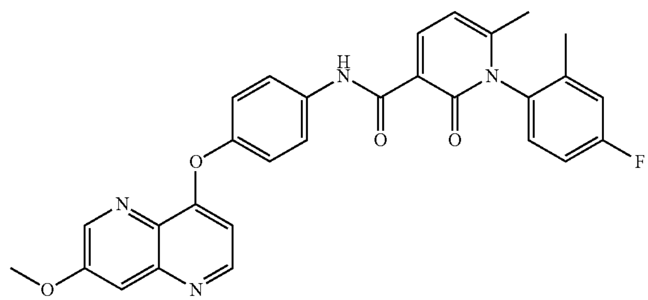 [SMILES: COc1cnc2c(Oc3ccc(NC(=O)c4ccc(C)n(-c5ccc(F)cc5C)c4=O)cc3)ccnc2c1] | 1-(4-fluoro-2-methylphenyl)-N-[4-[(7-methoxy-1,5-naphthyridin-4-yl)oxy]phenyl]-6-methyl-2-oxopyridine-3-carboxamide |
| 227 | 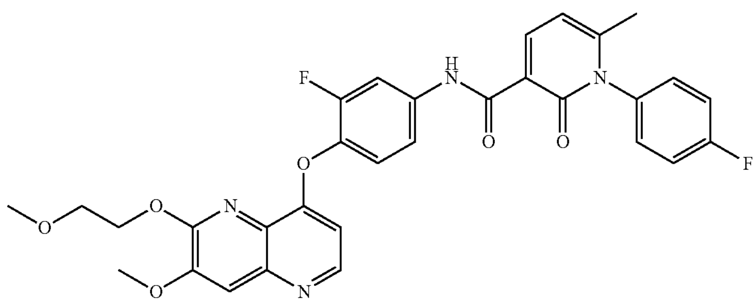 [SMILES: COCCOc1nc2c(Oc3ccc(NC(=O)c4ccc(C)n(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-1-(4-fluorophenyl)-6-methyl-2-oxopyridine-3-carboxamide |
| 228 | 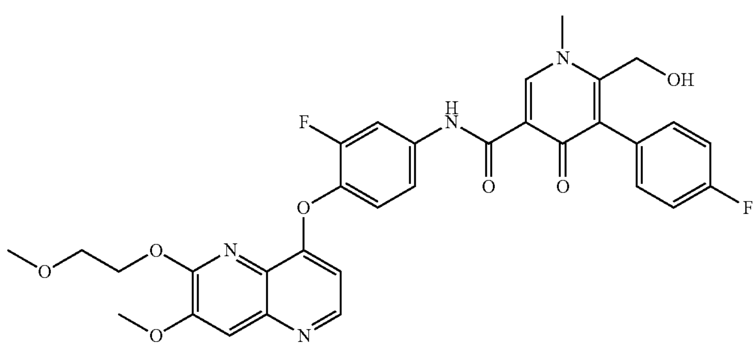 [SMILES: COCCOc1nc2c(Oc3ccc(NC(=O)c4cn(C)c(CO)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluorophenyl)-6-(hydroxymethyl)-1-methyl-4-oxopyridine-3-carboxamide |
| 229 | 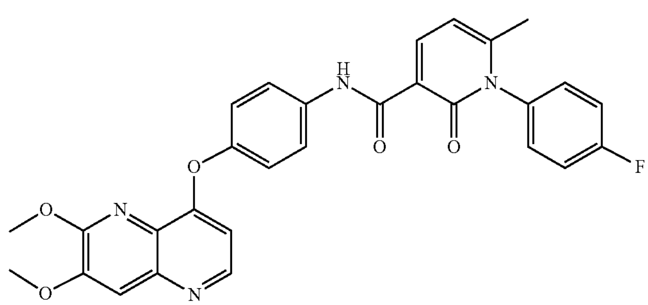 [SMILES: COc1cc2nccc(Oc3ccc(NC(=O)c4ccc(C)n(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-6-methyl-2-oxopyridine-3-carboxamide |

-continued

| Cpd # | Structure | IUPAC Name |
|---|---|---|
| 230 | 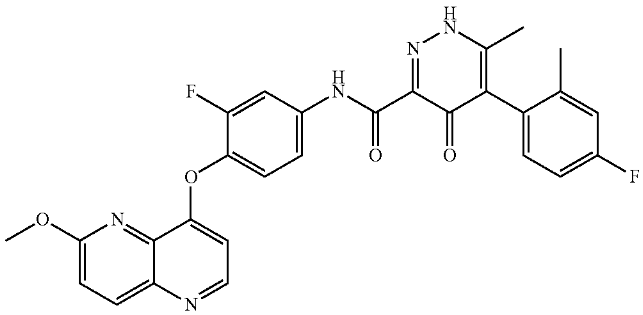 [SMILES: COc1ccc2nccc(Oc3ccc(NC(=O)c4n[nH]c(C)c(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-6-methyl-4-oxo-1H-pyridazine-3-carboxamide |
| 231 | 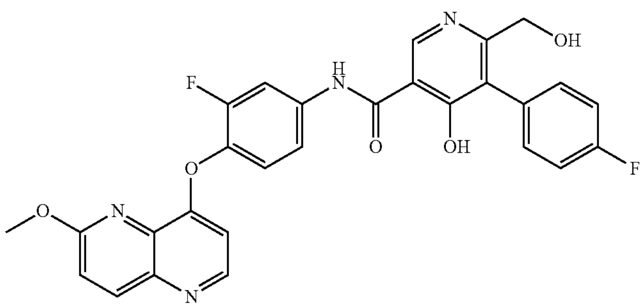 [SMILES: COc1ccc2nccc(Oc3ccc(NC(=O)c4cnc(CO)c(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-6-(hydroxymethyl)pyridine-3-carboxamide |
| 232 | 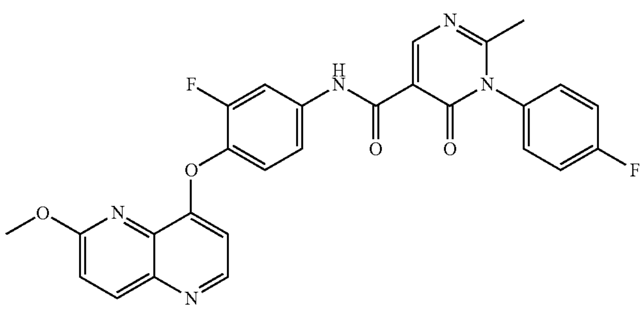 [SMILES: COc1ccc2nccc(Oc3ccc(NC(=O)c4cnc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-2-methyl-6-oxopyrimidine-5-carboxamide |
| 233 | 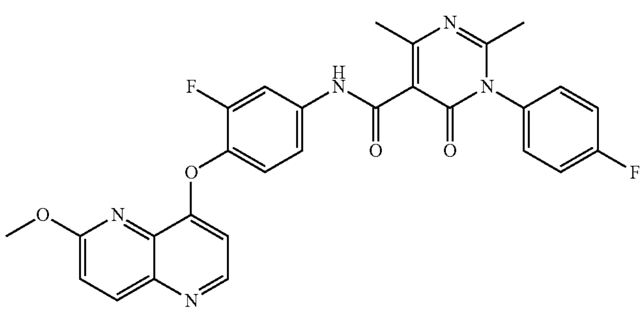 [SMILES: COc1ccc2nccc(Oc3ccc(NC(=O)c4c(C)nc(C)n(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-2,4-dimethyl-6-oxopyrimidine-5-carboxamide |
| 234 | 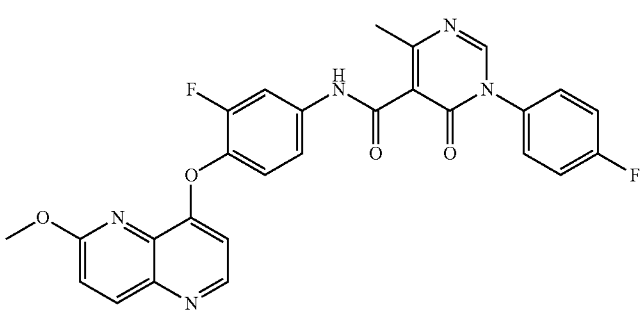 [SMILES: COc1ccc2nccc(Oc3ccc(NC(=O)c4c(C)ncn(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-4-methyl-6-oxopyrimidine-5-carboxamide |

-continued

| Cpd # | Structure | IUPAC Name |
|---|---|---|
| 235 | 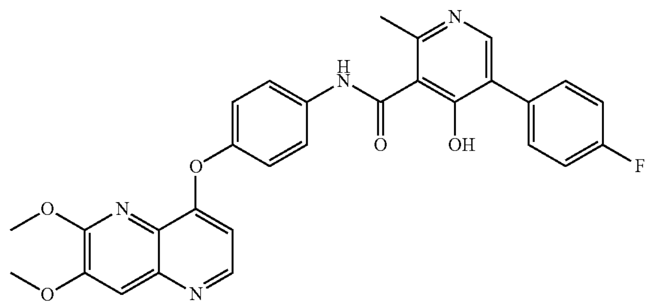 [SMILES: COc1cc2nccc(Oc3ccc(NC(=O)c4c(C)ncc(-c5ccc(F)cc5)c4O)cc3)c2nc1OC] | N-[4-[(6,7-dimethoxy-1,5-naphthyridin-4-yl)oxy]phenyl]-5-(4-fluorophenyl)-4-hydroxy-2-methylpyridine-3-carboxamide |
| 236 | 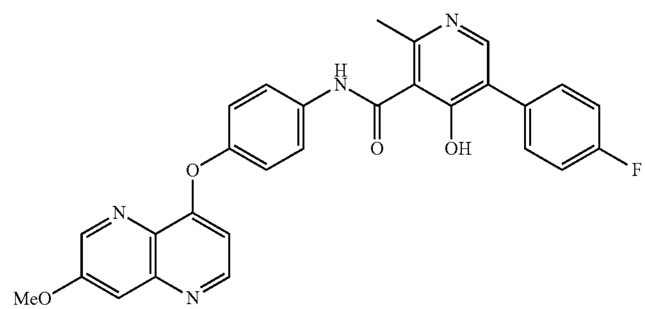 [SMILES: COc1cnc2c(Oc3ccc(NC(=O)c4c(C)ncc(-c5ccc(F)cc5)c4O)cc3)ccnc2c1] | 5-(4-fluorophenyl)-4-hydroxy-N-[4-[(7-methoxy-1,5-naphthyridin-4-yl)oxy]phenyl]-2-methylpyridine-3-carboxamide |
| 237 | 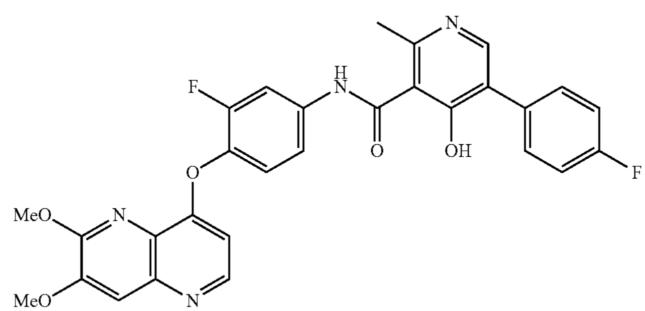 [SMILES: COc1cc2nccc(Oc3ccc(NC(=O)c4c(C)ncc(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-2-methylpyridine-3-carboxamide |
| 238 | 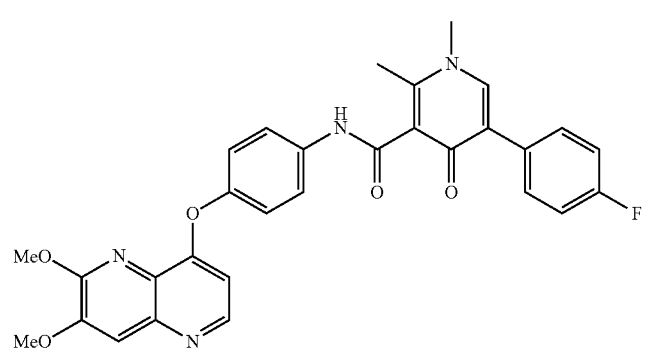 [SMILES: COc1cc2nccc(Oc3ccc(NC(=O)c4c(C)n(C)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,2-dimethyl-4-oxopyridine-3-carboxamide |

-continued

| Cpd # | Structure | IUPAC Name |
|---|---|---|
| 239 | 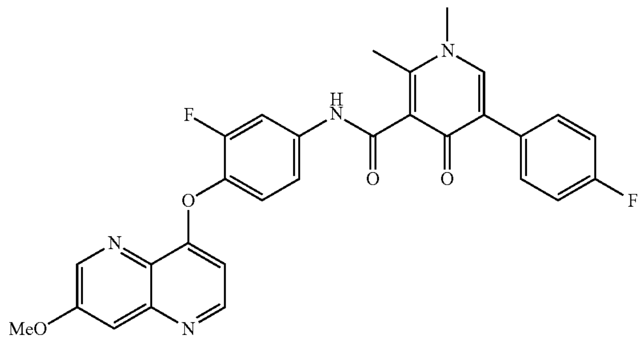 [SMILES: COc1cnc2c(Oc3ccc(NC(=O)c4c(C)n(C)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,2-dimethyl-4-oxopyridine-3-carboxamide |
| 240 | 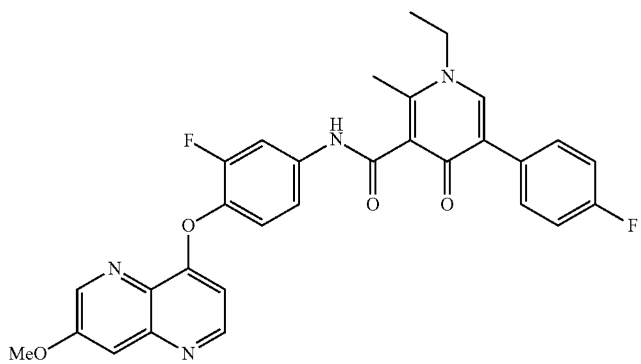 [SMILES: CCn1cc(-c2ccc(F)cc2)c(=O)c(C(=O)Nc2ccc(Oc3ccnc4cc(OC)cnc34)c(F)c2)c1C] | 1-ethyl-N-[3-fluoro-4-[(7-methoxy-1,5-naphthyridin-4-yl)oxy]phenyl]-5-(4-fluorophenyl)-2-methyl-4-oxopyridine-3-carboxamide |
| 241 | 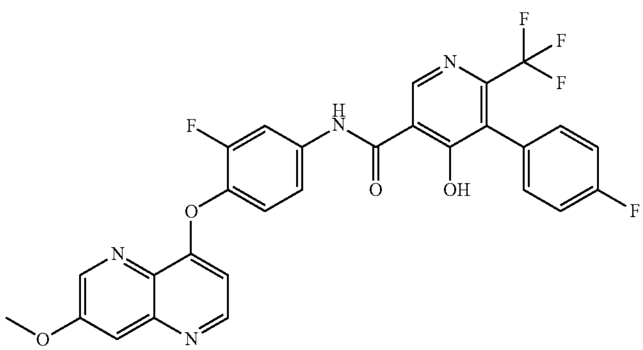 [SMILES: COc1cnc2c(Oc3ccc(NC(=O)c4cnc(C(F)(F)F)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-6-(trifluoromethyl)pyridine-3-carboxamide |
| 242 | 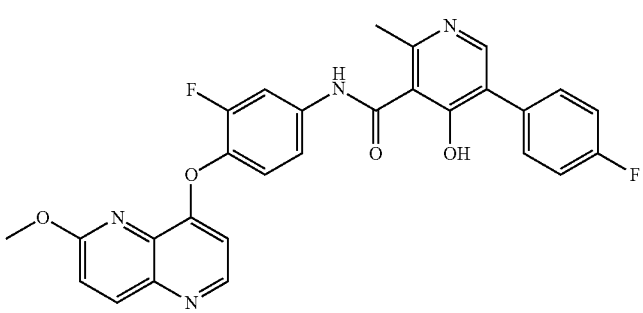 [SMILES: COc1ccc2nccc(Oc3ccc(NC(=O)c4c(C)ncc(-c5ccc(F)cc5)c4O)cc3F)c2n1] | N-[3-fluoro-4-[(6-methoxy-1,5-naphthyridin-4-yl)oxy]phenyl]-5-(4-fluorophenyl)-4-hydroxy-2-methylpyridine-3-carboxamide |

-continued

| Cpd # | Structure | IUPAC Name |
|---|---|---|
| 243 | 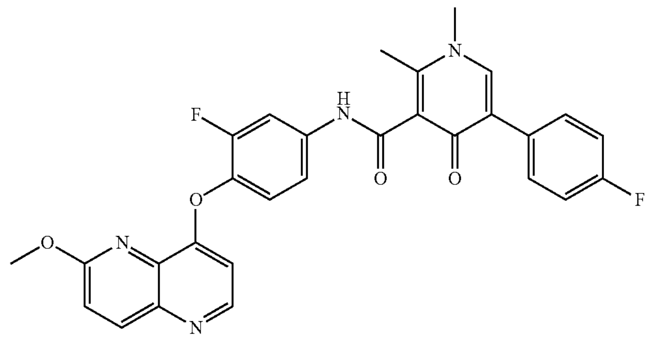 [SMILES: COc1ccc2nccc(Oc3ccc(NC(=O)c4c(C)n(C)cc(-c5ccc(F)cc5)c4=O)cc3F)c2n1] | N-[3-fluoro-4-[(6-methoxy-1,5-naphthyridin-4-yl)oxy]phenyl]-5-(4-fluorophenyl)-1,2-dimethyl-4-oxopyridine-3-carboxamide |
| 244 | 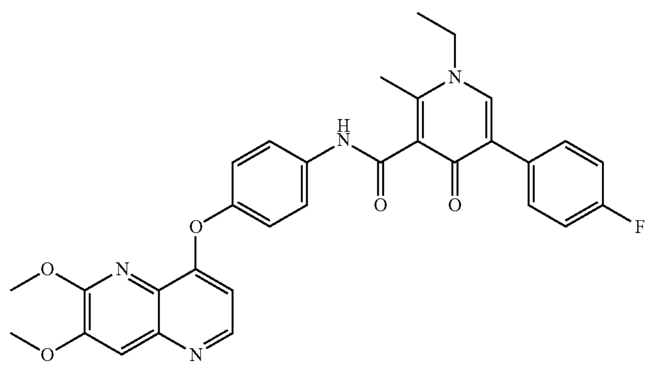 [SMILES: CCn1cc(-c2ccc(F)cc2)c(=O)c(C(=O)Nc2ccc(Oc3ccnc4cc(OC)c(OC)nc34)cc2)c1C] | N-[4-[(6,7-dimethoxy-1,5-naphthyridin-4-yl)oxy]phenyl]-1-ethyl-5-(4-fluorophenyl)-2-methyl-4-oxopyridine-3-carboxamide |
| 245 | 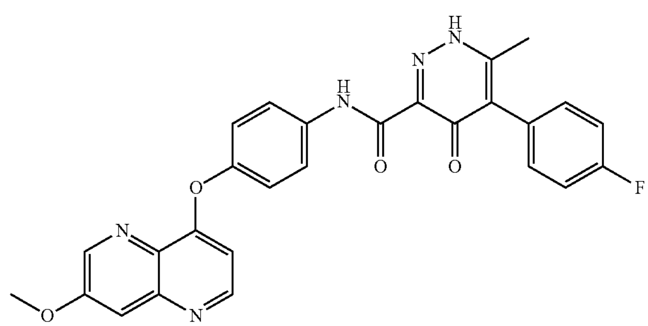 [SMILES: COc1cnc2c(Oc3ccc(NC(=O)c4n[nH]c(C)c(-c5ccc(F)cc5)c4=O)cc3)ccnc2c1] | 5-(4-fluorophenyl)-N-[4-[(7-methoxy-1,5-naphthyridin-4-yl)oxy]phenyl]-6-methyl-4-oxo-1H-pyridazine-3-carboxamide |
| 246 | 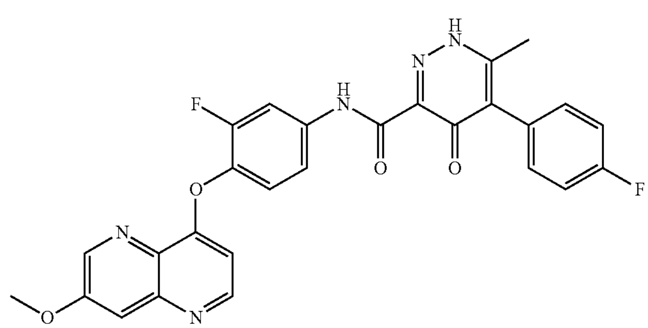 [SMILES: COc1cnc2c(Oc3ccc(NC(=O)c4n[nH]c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1H-pyridazine-3-carboxamide |

| Cpd # | Structure | IUPAC Name |
|---|---|---|
| 247 | 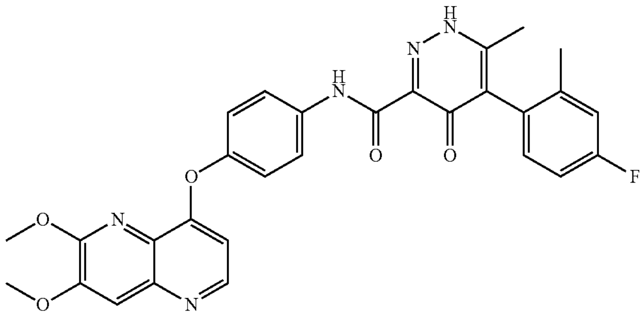 | N-[4-[(6,7-dimethoxy-1,5-naphthyridin-4-yl)oxy]phenyl]-5-(4-fluoro-2-methylphenyl)-6-methyl-4-oxo-1H-pyridazine-3-carboxamide |
| 248 | 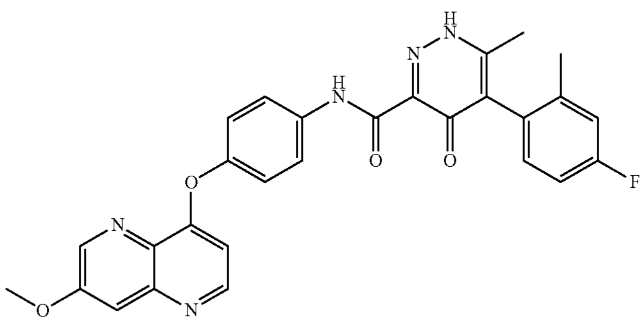 [SMILES: COc1cnc2c(Oc3ccc(NC(=O)c4n[nH]c(C)c(-c5ccc(F)cc5C)c4=O)cc3)ccnc2c1] | 5-(4-fluoro-2-methylphenyl)-N-[4-[(7-methoxy-1,5-naphthyridin-4-yl)oxy]phenyl]-6-methyl-4-oxo-1H-pyridazine-3-carboxamide |
| 249A | 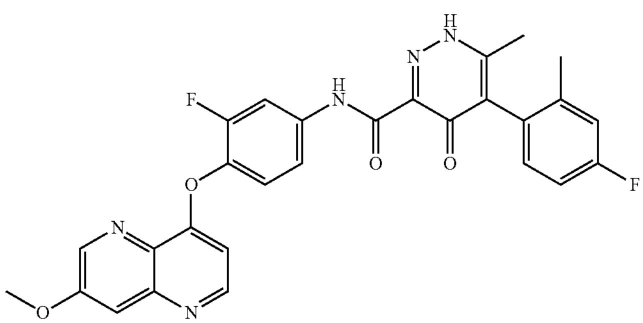 [SMILES: COc1cnc2c(Oc3ccc(NC(=O)c4n[nH]c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-6-methyl-4-oxo-1H-pyridazine-3-carboxamide |
| 249B | 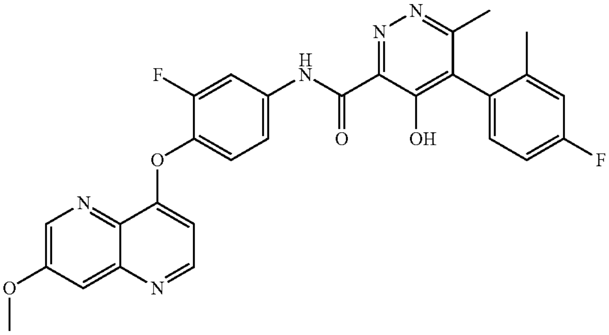 [SMILES: COc1cnc2c(Oc3ccc(NC(=O)c4nnc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropoisomer 1 |

| Cpd # | Structure | IUPAC Name |
|---|---|---|
| 249C | 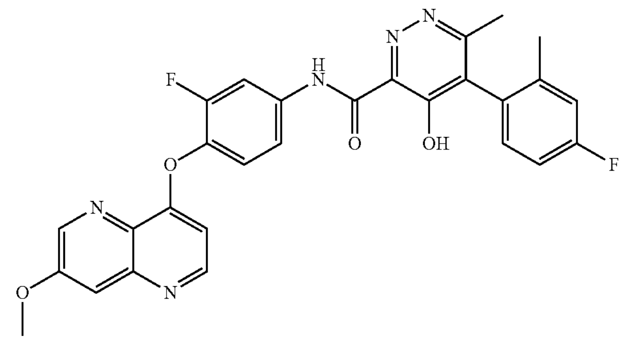 [SMILES: COc1cnc2c(Oc3ccc(NC(=O)c4nnc(C)c(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-6-methylpyridazine-3-carboxamide, atropisomer 2 |
| 250 | 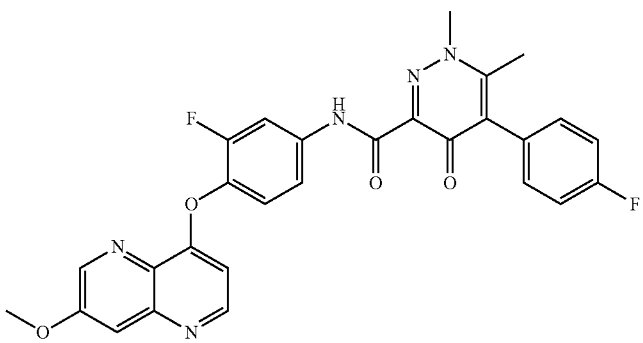 [SMILES: COc1cnc2c(Oc3ccc(NC(=O)c4nn(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,6-dimethyl-4-oxopyridazine-3-carboxamide |
| 251 | 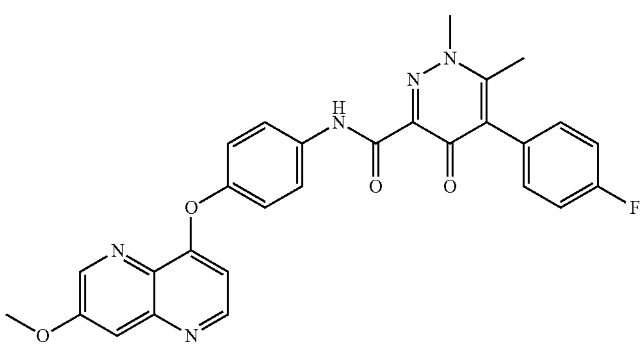 | 5-(4-fluorophenyl)-N-[4-[(7-methoxy-1,5-naphthyridin-4-yl)oxy]phenyl]-1,6-dimethyl-4-oxopyridazine-3-carboxamide |
| 252 | 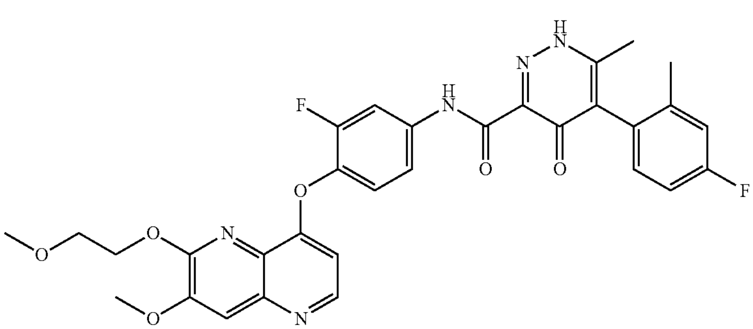 [SMILES: COCCOc1nc2c(Oc3ccc(NC(=O)c4n[nH]c(C)c(-c5ccc(F)cc5C)c4=O)cc3F)ccnc2cc1OC] | N-[3-fluoro-4-[[7-methoxy-6-(2-methoxyethoxy)-1,5-naphthyridin-4-yl]oxy]phenyl]-5-(4-fluoro-2-methylphenyl)-6-methyl-4-oxo-1H-pyridazine-3-carboxamide |

| Cpd # | Structure | IUPAC Name |
|---|---|---|
| 253 | 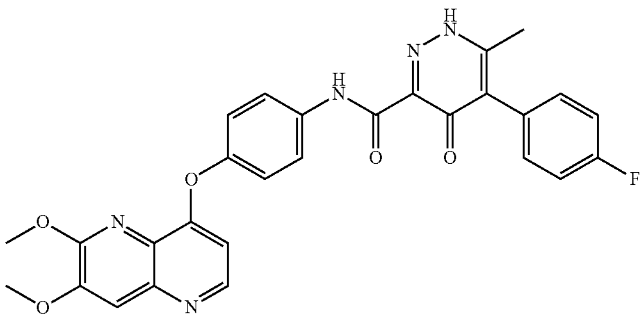 [SMILES: COc1cc2nccc(Oc3ccc(NC(=O)c4n[nH]c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-6-methyl-4-oxo-1H-pyridazine-3-carboxamide |
| 254 | 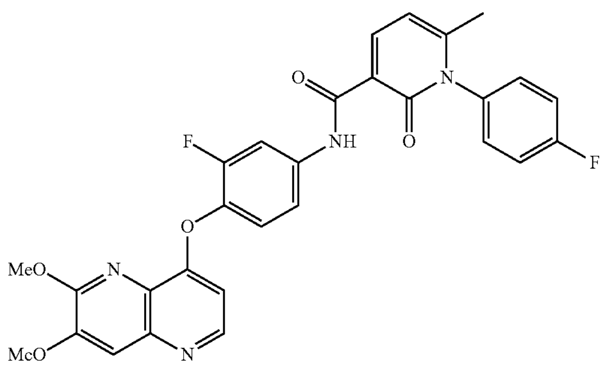 | N-[4-[(6,7-dimethoxy-1,5-naphthyridin-4-yl)oxy]-3-fluorophenyl]-1-(4-fluorophenyl)-6-methyl-2-oxopyridine-3-carboxamide |
| 255 | 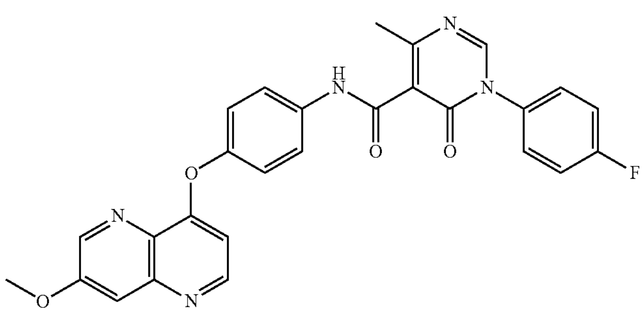 [SMILES: COc1cnc2c(Oc3ccc(NC(=O)c4c(C)ncn(-c5ccc(F)cc5)c4=O)cc3)ccnc2c1] | 1-(4-fluorophenyl)-N-[4-[(7-methoxy-1,5-naphthyridin-4-yl)oxy]phenyl]-4-methyl-6-oxopyrimidine-5-carboxamide |
| 256 | 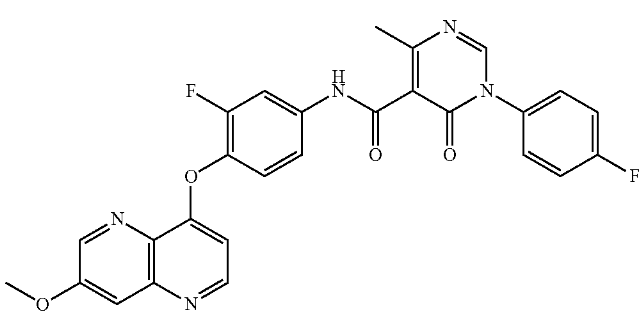 [SMILES: COc1cnc2c(Oc3ccc(NC(=O)c4c(C)ncn(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4-methyl-6-oxopyrimidine-5-carboxamide |

| Cpd # | Structure | IUPAC Name |
|---|---|---|
| 257 | 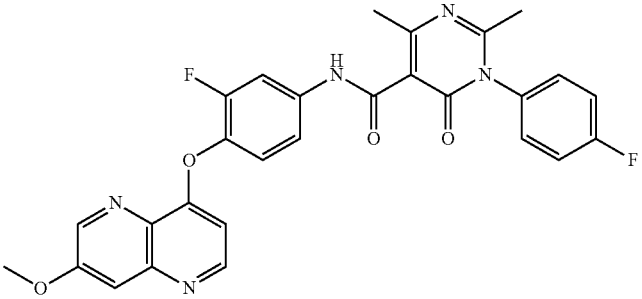 [SMILES: COc1cnc2c(Oc3ccc(NC(=O)c4c(C)nc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-2,4-dimethyl-6-oxopyrimidine-5-carboxamide |
| 258 | 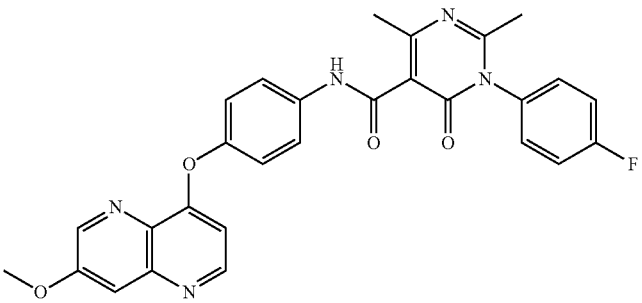 [SMILES: COc1cnc2c(Oc3ccc(NC(=O)c4c(C)nc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-2,4-dimethyl-6-oxopyrimidine-5-carboxamide |
| 259 | 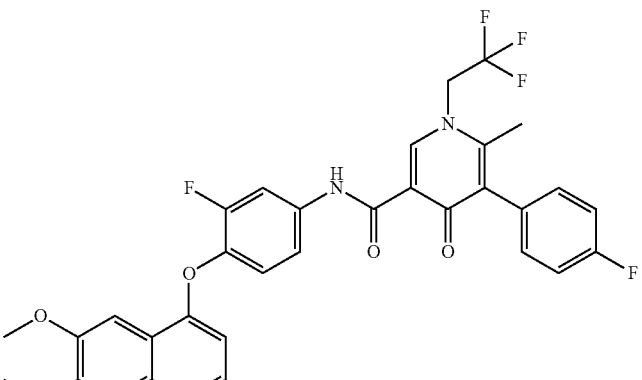 | N-[4-(6,7-dimethoxyquinolin-4-yl)oxy-3-fluorophenyl]-5-(4-fluorophenyl)-6-methyl-4-oxo-1-(2,2,2-trifluoroethyl)pyridine-3-carboxamide |
| 260 | 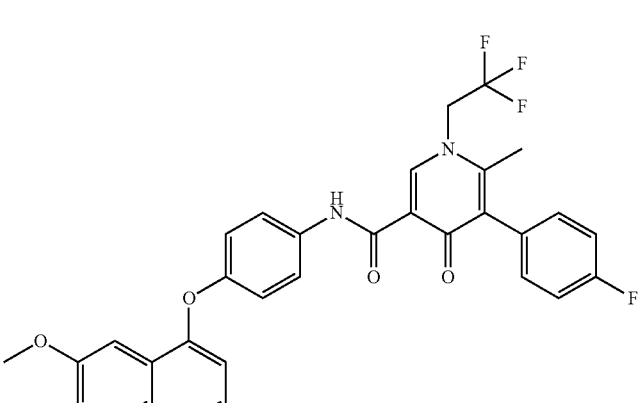 | N-[4-(6,7-dimethoxyquinolin-4-yl)oxyphenyl]-5-(4-fluorophenyl)-6-methyl-4-oxo-1-(2,2,2-trifluoroethyl)pyridine-3-carboxamide |

-continued

| Cpd # | Structure | IUPAC Name |
|---|---|---|
| 261 | 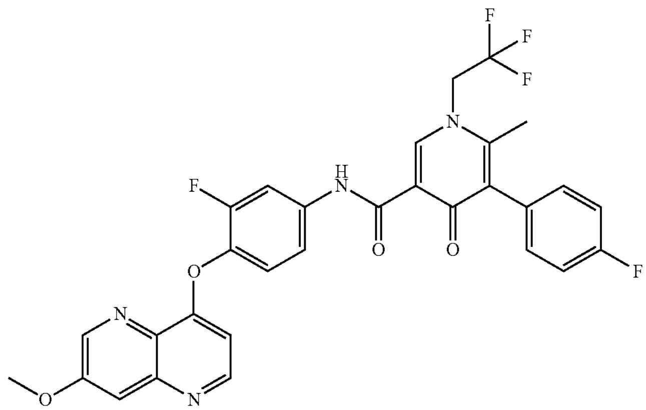 [SMILES: COc1cnc2c(Oc3ccc(NC(=O)c4cn(CC(F)(F)F)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1-(2,2,2-trifluoroethyl)pyridine-3-carboxamide |
| 262 | 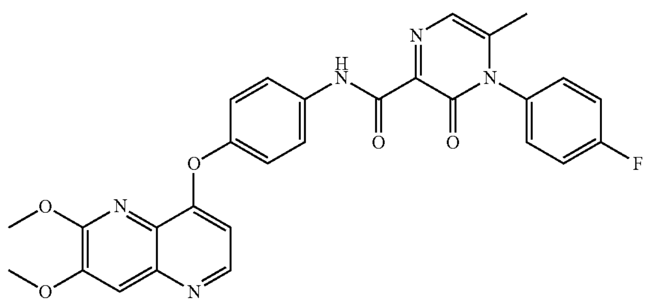 [SMILES: COc1cc2nccc(Oc3ccc(NC(=O)c4ncc(C)n(-c5ccc(F)cc5)c4=O)cc3)c2nc1OC] | N-[4-[(6,7-dimethoxy-1,5-naphthyridin-4-yl)oxy]phenyl]-4-(4-fluorophenyl)-5-methyl-3-oxopyrazine-2-carboxamide |
| 263 | 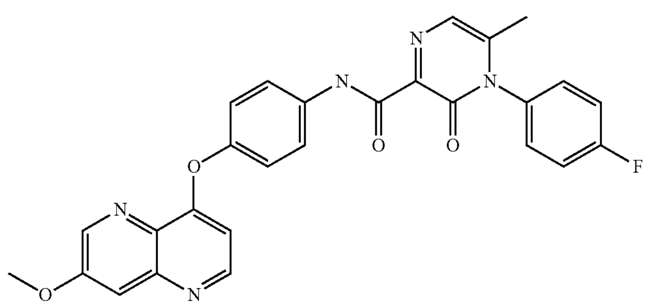 | 4-(4-fluorophenyl)-N-[4-[(7-methoxy-1,5-naphthyridin-4-yl)oxy]phenyl]-5-methyl-3-oxopyrazine-2-carboxamide |
| 264 | 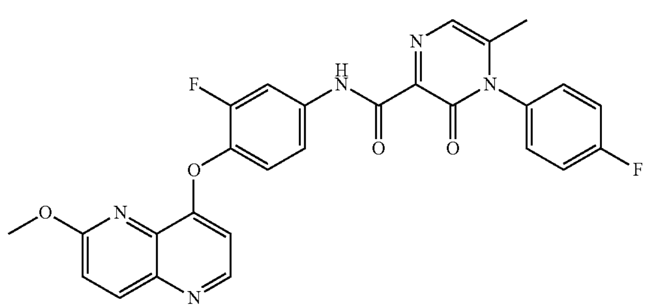 [SMILES: COc1ccc2nccc(Oc3ccc(NC(=O)c4ncc(C)n(-c5ccc(F)cc5)c4=O)cc3F)c2n1] | N-[3-fluoro-4-[(6-methoxy-1,5-naphthyridin-4-yl)oxy]phenyl]-4-(4-fluorophenyl)-5-methyl-3-oxopyrazine-2-carboxamide |

| Cpd # | Structure | IUPAC Name |
|---|---|---|
| 265 | 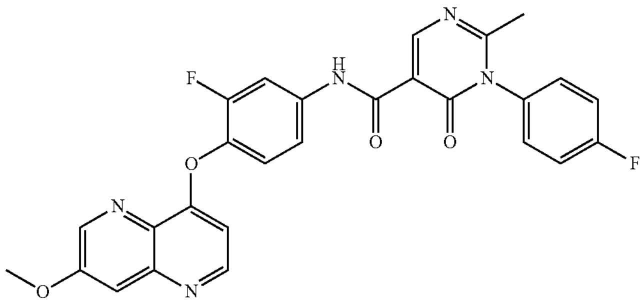 [SMILES: COc1cnc2c(Oc3ccc(NC(=O)c4cnc(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-2-methyl-6-oxopyrimidine-5-carboxamide |
| 266 | 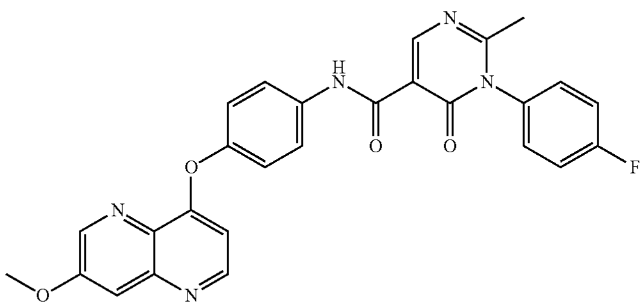 [SMILES: COc1cnc2c(Oc3ccc(NC(=O)c4cnc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-2-methyl-6-oxopyrimidine-5-carboxamide |
| 267 | 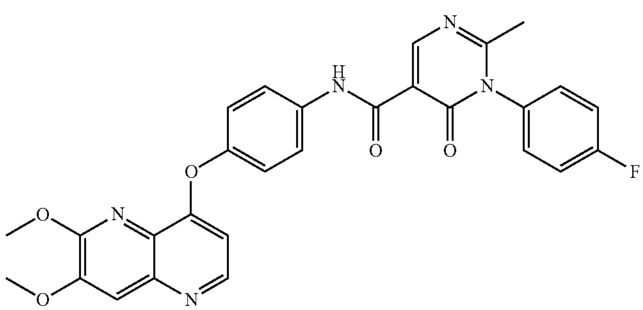 [SMILES: COc1cc2nccc(Oc3ccc(NC(=O)c4cnc(C)n(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-2-methyl-6-oxopyrimidine-5-carboxamide |
| 268 | 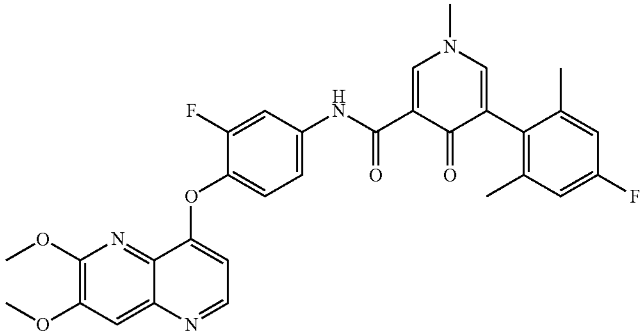 [SMILES: COc1cc2nccc(Oc3ccc(NC(=O)c4cn(C)cc(-c5c(C)cc(F)cc5C)c4=O)cc3F)c2nc1OC] | N-[4-[(6,7-dimethoxy-1,5-naphthyridin-4-yl)oxy]-3-fluorophenyl]-5-(4-fluoro-2,6-dimethylphenyl)-1-methyl-4-oxopyridine-3-carboxamide |

| Cpd # | Structure | IUPAC Name |
|---|---|---|
| 269 | 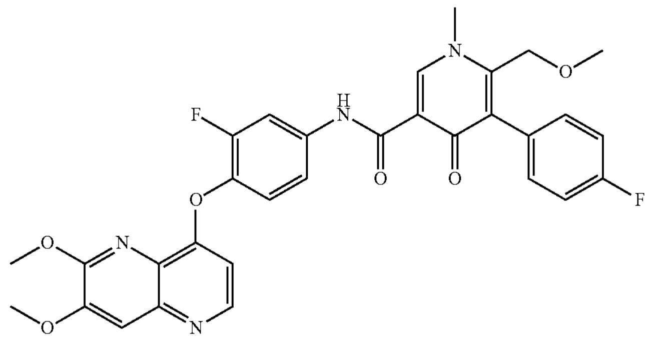 [SMILES: COCc1c(-c2ccc(F)cc2)c(=O)c(C(=O)Nc2ccc(Oc3ccnc4cc(OC)c(OC)nc34)c(F)c2)cn1C] | N-[4-[(6,7-dimethoxy-1,5-naphthyridin-4-yl)oxy]-3-fluorophenyl]-5-(4-fluorophenyl)-6-(methoxymethyl)-1-methyl-4-oxopyridine-3-carboxamide |
| 270 | 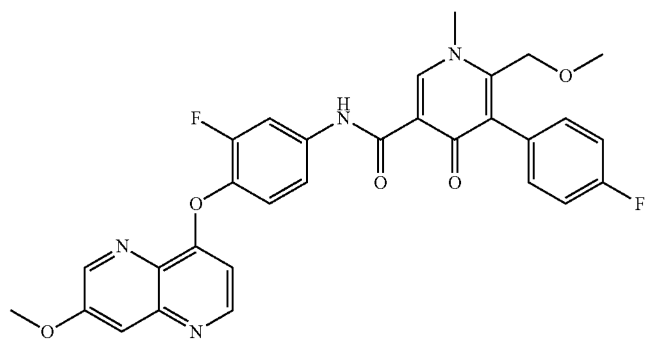 [SMILES: COCc1c(-c2ccc(F)cc2)c(=O)c(C(=O)Nc2ccc(Oc3ccnc4cc(OC)cnc34)c(F)c2)cn1C] | N-[3-fluoro-4-[(7-methoxy-1,5-naphthyridin-4-yl)oxy]phenyl]-5-(4-fluorophenyl)-6-(methoxymethyl)-1-methyl-4-oxopyridine-3-carboxamide |
| 271 | 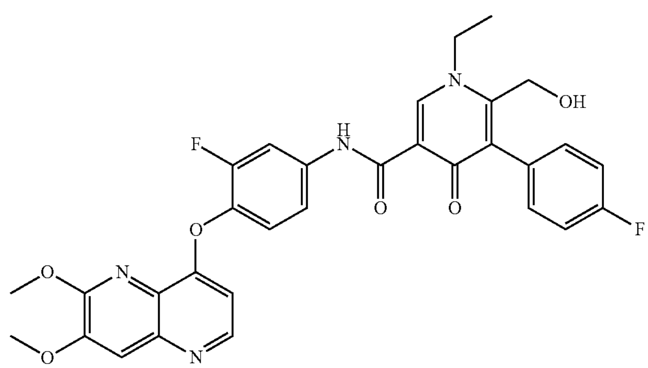 [SMILES: CCn1cc(C(=O)Nc2ccc(Oc3ccnc4cc(OC)c(OC)nc34)c(F)c2)c(=O)c(-c2ccc(F)cc2)c1CO] | N-[4-[(6,7-dimethoxy-1,5-naphthyridin-4-yl)oxy]-3-fluorophenyl]-1-ethyl-5-(4-fluorophenyl)-6-(hydroxymethyl)-4-oxopyridine-3-carboxamide |
| 272 | 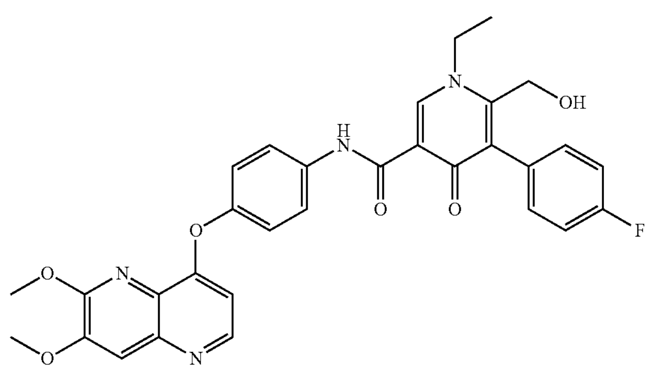 [SMILES: CCn1cc(C(=O)Nc2ccc(Oc3ccnc4cc(OC)c(OC)nc34)cc2)c(=O)c(-c2ccc(F)cc2)c1CO] | N-[4-[(6,7-dimethoxy-1,5-naphthyridin-4-yl)oxy]phenyl]-1-ethyl-5-(4-fluorophenyl)-6-(hydroxymethyl)-4-oxopyridine-3-carboxamide |

-continued

| Cpd # | Structure | IUPAC Name |
|---|---|---|
| 273 | 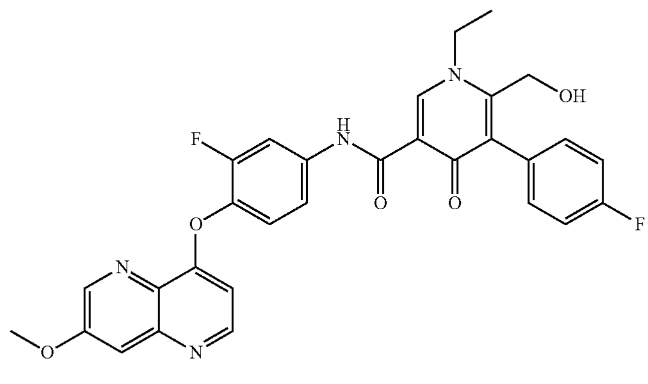 [SMILES: CCn1cc(C(=O)Nc2ccc(Oc3ccnc4cc(OC)cnc34)c(F)c2)c(=O)c(-c2ccc(F)cc2)c1CO] | 1-ethyl-N-[3-fluoro-4-[(7-methoxy-1,5-naphthyridin-4-yl)oxy]phenyl]-5-(4-fluorophenyl)-6-(hydroxymethyl)-4-oxopyridine-3-carboxamide |
| 274 | 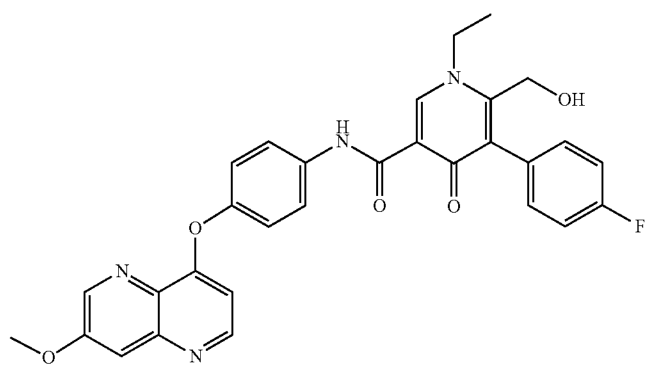 [SMILES: CCn1cc(C(=O)Nc2ccc(Oc3ccnc4cc(OC)cnc34)cc2)c(=O)c(-c2ccc(F)cc2)c1CO] | 1-ethyl-5-(4-fluorophenyl)-6-(hydroxymethyl)-N-[4-[(7-methoxy-1,5-naphthyridin-4-yl)oxy]phenyl]-4-oxopyridine-3-carboxamide |
| 275 | 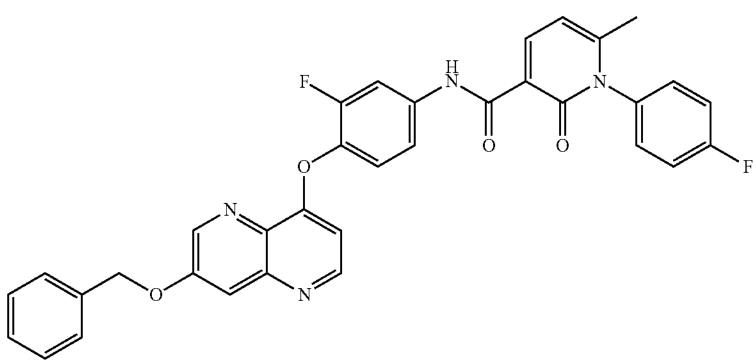 [SMILES: Cc1ccc(C(=O)Nc2ccc(Oc3ccnc4cc(OCc5ccccc5)cnc34)c(F)c2)c(=O)n1-c1ccc(F)cc1] | 1-(4-fluorophenyl)-N-[3-fluoro-4-[(7-phenylmethoxy-1,5-naphthyridin-4-yl)oxy]phenyl]-6-methyl-2-oxopyridine-3-carboxamide |
| 276 | 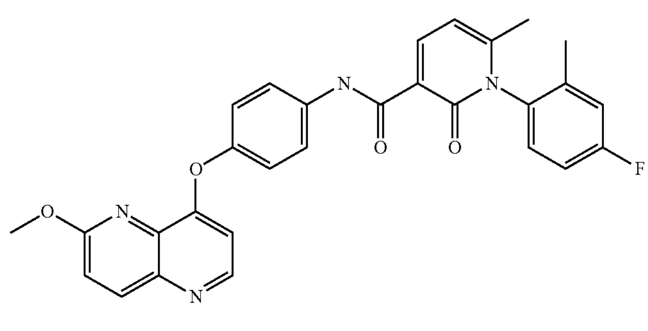 | 1-(4-fluoro-2-methylphenyl)-N-[4-[(6-methoxy-1,5-naphthyridin-4-yl)oxyphenyl]-6-methyl-2-oxopyridine-3-carboxamide |

| Cpd # | Structure | IUPAC Name |
|---|---|---|
| 277 | 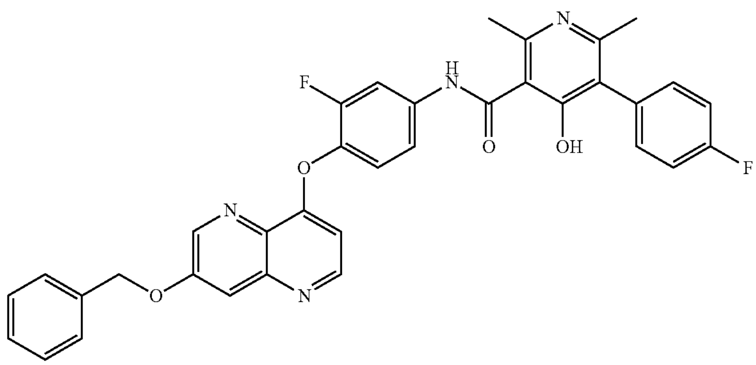 [SMILES: Cc1nc(C)c(-c2ccc(F)cc2)c(O)c1C(=O)Nc1ccc(Oc2ccnc3cc(OCc4ccccc4)cnc23)c(F)c1] | 5-(4-fluorophenyl)-N-[3-fluoro-4-[(7-phenylmethoxy-1,5-naphthyridin-4-yl)oxy]phenyl]-4-hydroxy-2,6-dimethylpyridine-3-carboxamide |
| 278 | 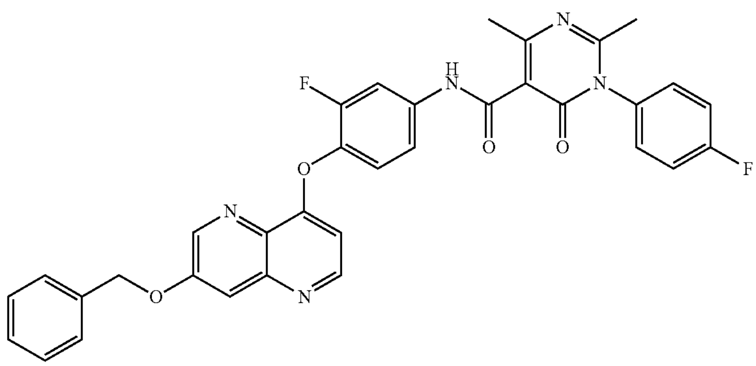 [SMILES: Cc1nc(C)n(-c2ccc(F)cc2)c(=O)c1C(=O)Nc1ccc(Oc2ccnc3cc(OCc4ccccc4)cnc23)c(F)c1] | 1-(4-fluorophenyl)-N-[3-fluoro-4-[(7-phenylmethoxy-1,5-naphthyridin-4-yl)oxy]phenyl]-2,4-dimethyl-6-oxopyrimidine-5-carboxamide |
| 279 | 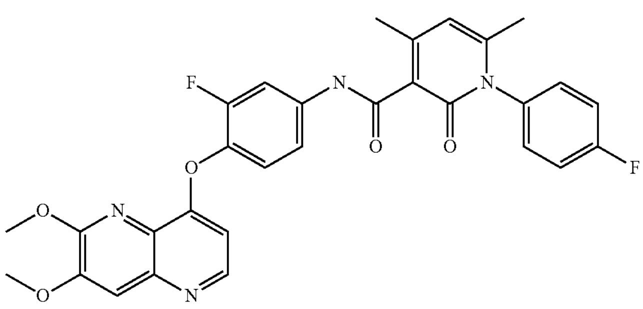 | N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 280 | 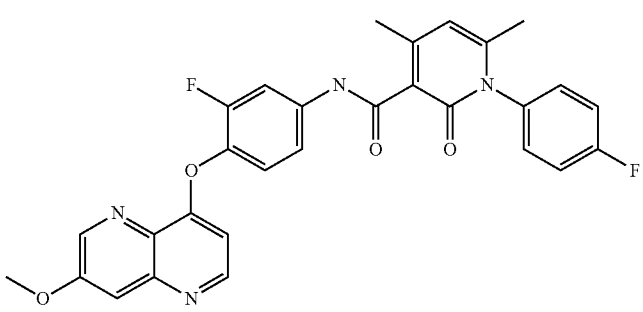 | N-[3-fluoro-4-[(7-methoxy-1,5-naphthyridin-4-yl)oxy]phenyl]-1-(4-fluorophenyl)-4,6-dimethyl-2-oxopyridine-3-carboxamide |

-continued

| Cpd # | Structure | IUPAC Name |
|---|---|---|
| 281 | 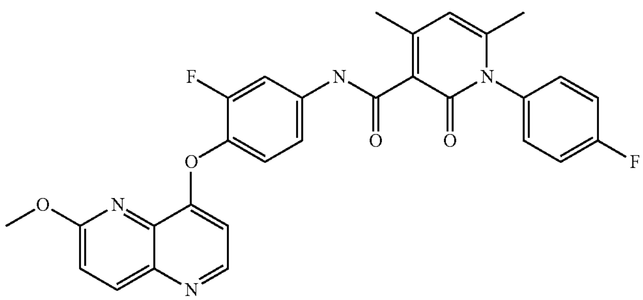 | N-[3-fluoro-4-[(6-methoxy-1,5-naphthyridin-4-yl)oxy]phenyl]-1-(4-fluorophenyl)-4,6-dimethyl-2-oxopyridine-3-carboxamide |
| 282 | 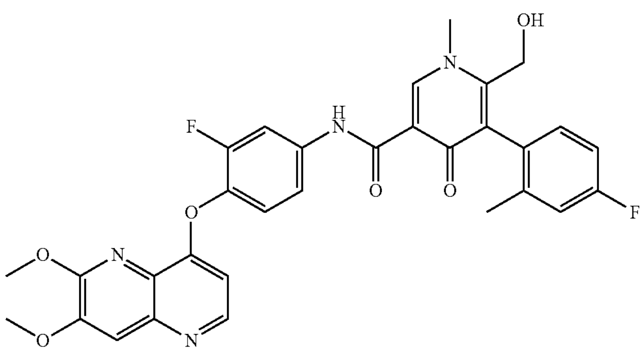 [SMILES: COc1cc2nccc(Oc3ccc(NC(=O)c4cn(C)c(CO)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-6-(hydroxymethyl)-1-methyl-4-oxopyridine-3-carboxamide |
| 283 | 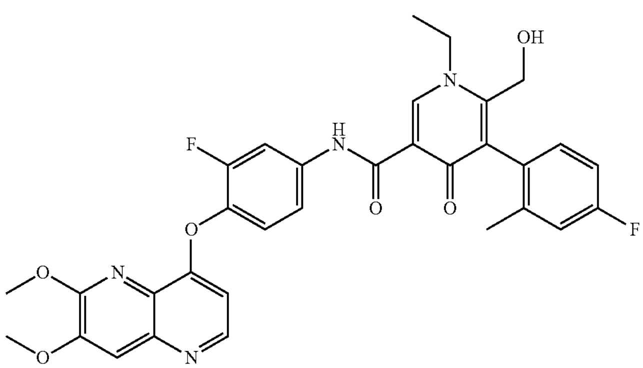 [SMILES: CCn1cc(C(=O)Nc2ccc(Oc3ccnc4cc(OC)c(OC)nc34)c(F)c2)c(=O)c(-c2ccc(F)cc2C)c1CO] | N-[4-[(6,7-dimethoxy-1,5-naphthyridin-4-yl)oxy]-3-fluorophenyl]-1-ethyl-5-(4-fluoro-2-methylphenyl)-6-(hydroxymethyl)-4-oxopyridine-3-carboxamide |
| 284 | 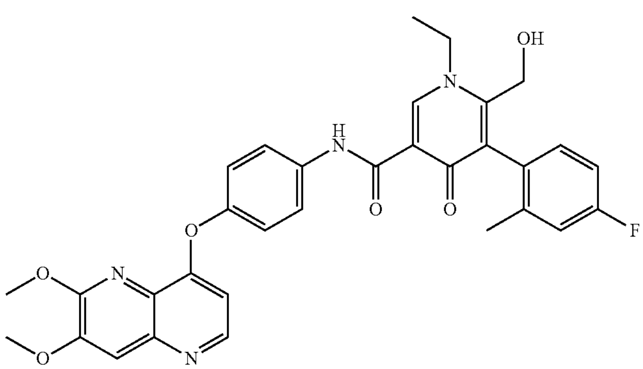 [SMILES: CCn1cc(C(=O)Nc2ccc(Oc3ccnc4cc(OC)c(OC)nc34)cc2)c(=O)c(-c2ccc(F)cc2C)c1CO] | N-[4-[(6,7-dimethoxy-1,5-naphthyridin-4-yl)oxy]phenyl]-1-ethyl-5-(4-fluoro-2-methylphenyl)-6-(hydroxymethyl)-4-oxopyridine-3-carboxamide |

| Cpd # | Structure | IUPAC Name |
|---|---|---|
| 285 | 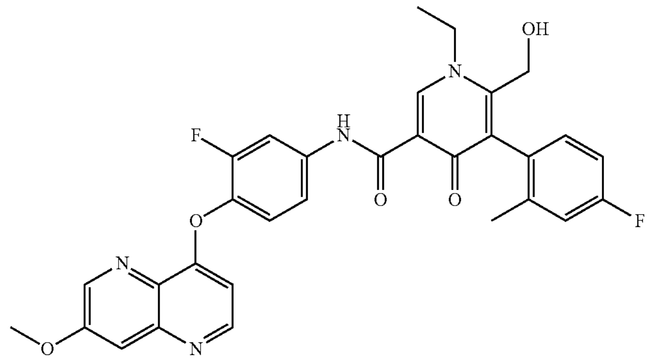 [SMILES: CCn1cc(C(=O)Nc2ccc(Oc3ccnc4cc(OC)cnc34)c(F)c2)c(=O)c(-c2ccc(F)cc2C)c1CO] | 1-ethyl-N-[3-fluoro-4-[(7-methoxy-1,5-naphthyridin-4-yl)oxy]phenyl]-5-(4-fluoro-2-methylphenyl)-6-(hydroxymethyl)-4-oxopyridine-3-carboxamide |
| 286 | 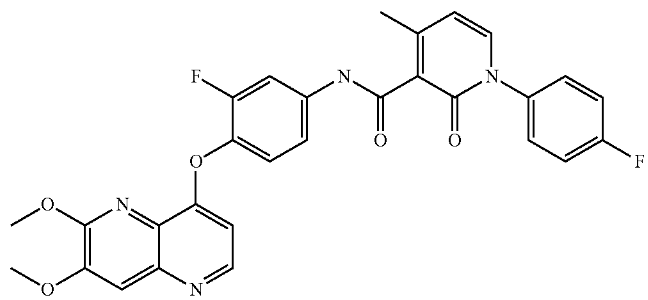 | N-[4-[(6,7-dimethoxy-1,5-naphthyridin-4-yl)oxy]-3-fluorophenyl]-1-(4-fluorophenyl)-4-methyl-2-oxopyridine-3-carboxamide |
| 287 | 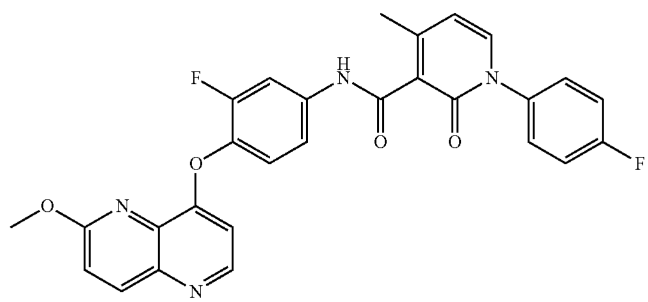 [SMILES: COc1ccc2nccc(Oc3ccc(NC(=O)c4c(C)ccn(-c5ccc(F)cc5)c4=O)cc3F)c2n1] | N-[3-fluoro-4-[(6-methoxy-1,5-naphthyridin-4-yl)oxy]phenyl]-1-(4-fluorophenyl)-4-methyl-2-oxopyridine-3-carboxamide |
| 288 | 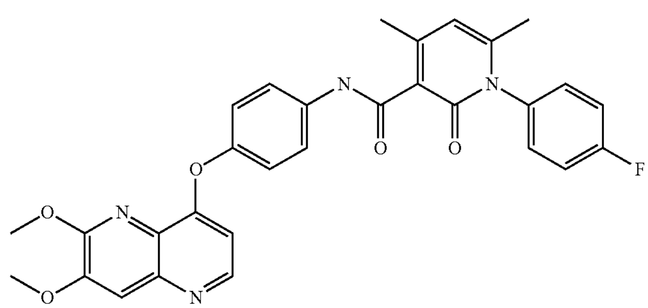 | N-[4-[(6,7-dimethoxy-1,5-naphthyridin-4-yl)oxy]phenyl]-1-(4-fluorophenyl)-4,6-dimethyl-2-oxopyridine-3-carboxamide |
| 289 | 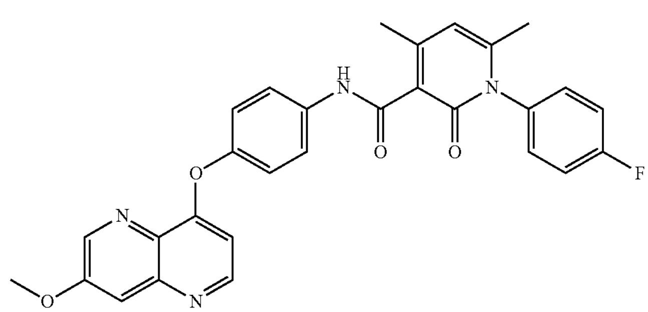 [SMILES: COc1cnc2c(Oc3ccc(NC(=O)c4c(C)cc(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-4,6-dimethyl-2-oxopyridine-3-carboxamide |

-continued

| Cpd # | Structure | IUPAC Name |
|---|---|---|
| 290 | 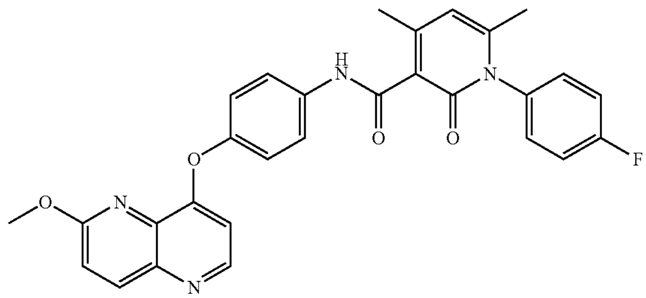 [SMILES: COc1ccc2nccc(Oc3ccc(NC(=O)c4c(C)cc(C)n(-c5ccc(F)cc5)c4=O)cc3)c2n1] | 1-(4-fluorophenyl)-N-[4-[(6-methoxy-1,5-naphthyridin-4-yl)oxy]phenyl]-4,6-dimethyl-2-oxopyridine-3-carboxamide |
| 291 | 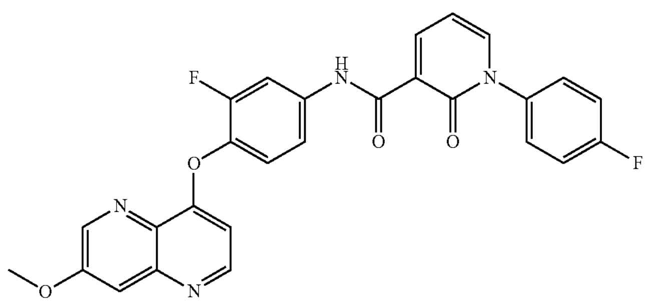 | N-[3-fluoro-4-[(7-methoxy-1,5-naphthyridin-4-yl)oxy]phenyl]-1-(4-fluorophenyl)-2-oxopyridine-3-carboxamide |
| 292 | 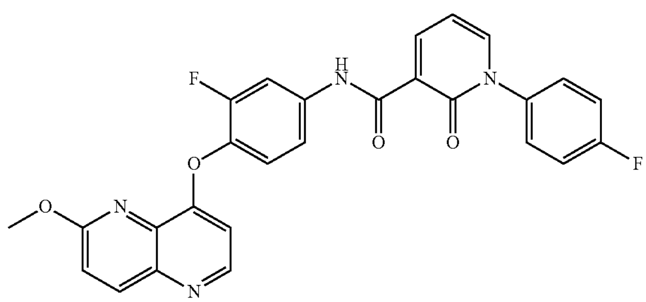 | N-[3-fluoro-4-[(6-methoxy-1,5-naphthyridin-4-yl)oxy]phenyl]-1-(4-fluorophenyl)-2-oxopyridine-3-carboxamide |
| 293 | 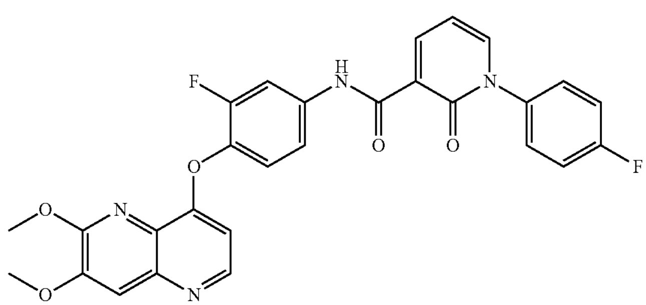 [SMILES: COc1cc2nccc(Oc3ccc(NC(=O)c4cccn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-2-oxopyridine-3-carboxamide |
| 294 | 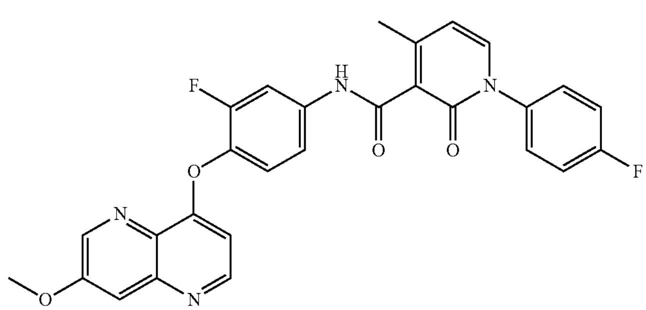 [SMILES: COc1cnc2c(Oc3ccc(NC(=O)c4c(C)ccn(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4-methyl-2-oxopyridine-3-carboxamide |

| Cpd # | Structure | IUPAC Name |
|---|---|---|
| 295 | 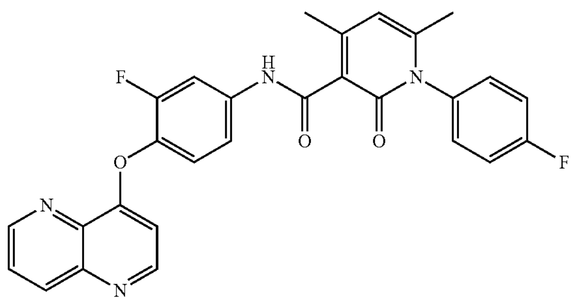 [SMILES: Cc1cc(C)n(-c2ccc(F)cc2)c(=O)c1C(=O)Nc1ccc(Oc2ccnc3cccnc23)c(F)c1] | N-[3-fluoro-4-(1,5-naphthyridin-4-yloxy)phenyl]-1-(4-fluorophenyl)-4,6-dimethyl-2-oxopyridine-3-carboxamide |
| 296 | 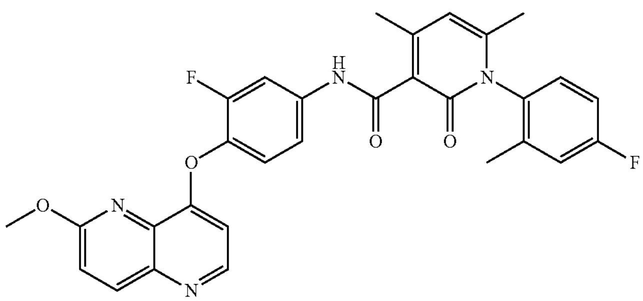 [SMILES: COc1ccc2nccc(Oc3ccc(NC(=O)c4c(C)cc(C)n(-c5ccc(F)cc5C)c4=O)cc3F)c2n1] | N-[3-fluoro-4-[(6-methoxy-1,5-naphthyridin-4-yl)oxy]phenyl]-1-(4-fluoro-2-methylphenyl)-4,6-dimethyl-2-oxopyridine-3-carboxamide |
| 297 | 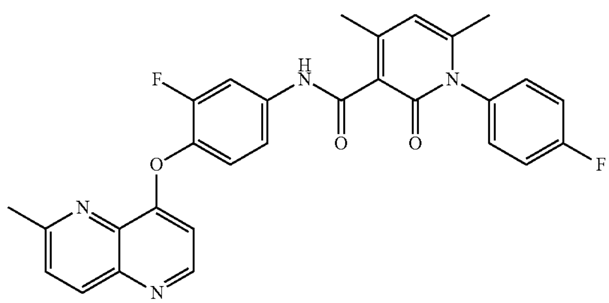 [SMILES: Cc1ccc2nccc(Oc3ccc(NC(=O)c4c(C)cc(C)n(-c5ccc(F)cc5)c4=O)cc3F)c2n1] | N-[3-fluoro-4-[(6-methyl-1,5-naphthyridin-4-yl)oxy]phenyl]-1-(4-fluorophenyl)-4,6-dimethyl-2-oxopyridine-3-carboxamide |
| 298 | 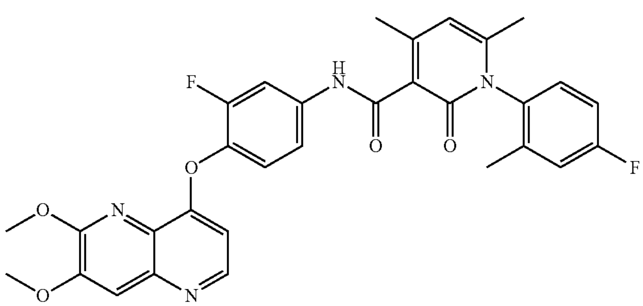 [SMILES: COc1cc2nccc(Oc3ccc(NC(=O)c4c(C)cc(C)n(-c5ccc(F)cc5C)c4=O)cc3F)c2nc1OC] | N-[4-[(6,7-dimethoxy-1,5-naphthyridin-4-yl)oxy]-3-fluorophenyl]-1-(4-fluoro-2-methylphenyl)-4,6-dimethyl-2-oxopyridine-3-carboxamide |
| 299 | 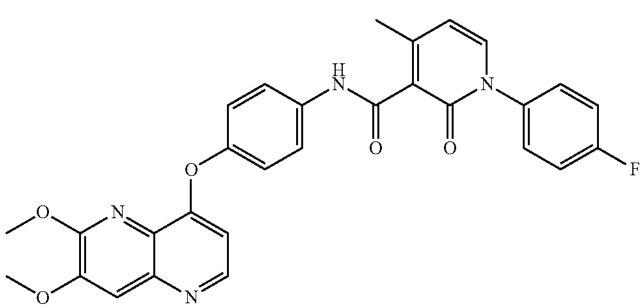 [SMILES: COc1cc2nccc(Oc3ccc(NC(=O)c4c(C)ccn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-4-methyl-2-oxopyridine-3-carboxamide |

| Cpd # | Structure | IUPAC Name |
|---|---|---|
| 300 | 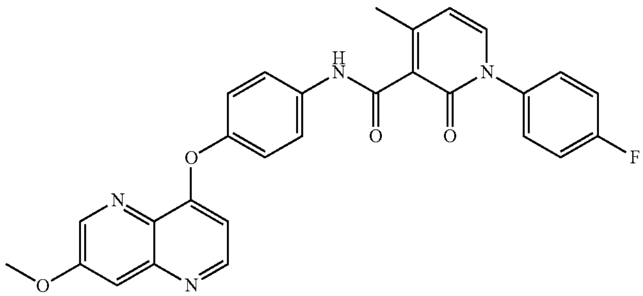 [SMILES: COc1cnc2c(Oc3ccc(NC(=O)c4c(C)ccn(-c5ccc(F)cc5)c4=O)cc3)ccnc2c1] | 1-(4-fluorophenyl)-N-[4-[(7-methoxy-1,5-naphthyridin-4-yl)oxy]phenyl]-4-methyl-2-oxopyridine-3-carboxamide |
| 301 | 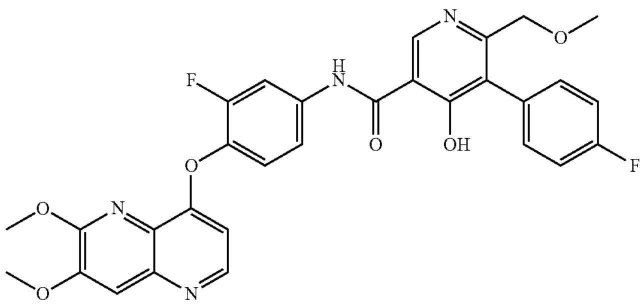 [SMILES: COCc1ncc(C(=O)Nc2ccc(Oc3ccnc4cc(OC)c(OC)nc34)c(F)c2)c(O)c1-c1ccc(F)cc1] | N-[4-[(6,7-dimethoxy-1,5-naphthyridin-4-yl)oxy]-3-fluorophenyl]-5-(4-fluorophenyl)-4-hydroxy-6-(methoxymethyl)pyridine-3-carboxamide |
| 302 | 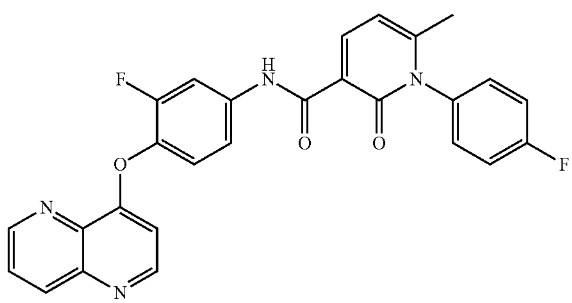 | N-[3-fluoro-4-(1,5-naphthyridin-4-yloxy)phenyl]-1-(4-fluorophenyl)-6-methyl-2-oxopyridine-3-carboxamide |
| 303 | 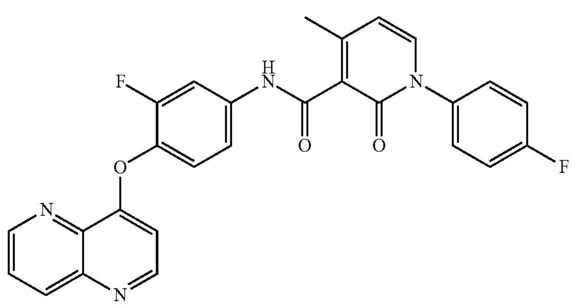 [SMILES: Cc1ccn(-c2ccc(F)cc2)c(=O)c1C(=O)Nc1ccc(Oc2ccnc3cccnc23)c(F)c1] | N-[3-fluoro-4-(1,5-naphthyridin-4-yloxy)phenyl]-1-(4-fluorophenyl)-4-methyl-2-oxopyridine-3-carboxamide |
| 304 | 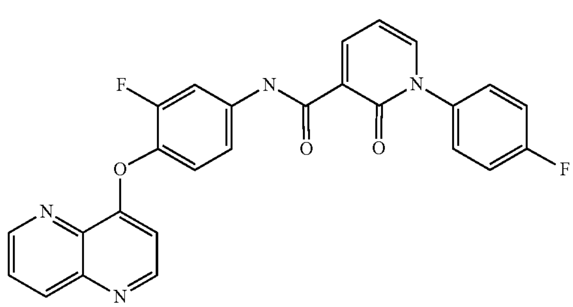 | N-[3-fluoro-4-(1,5-naphthyridin-4-yloxy)phenyl]-1-(4-fluorophenyl)-2-oxopyridine-3-carboxamide |

-continued

| Cpd # | Structure | IUPAC Name |
|---|---|---|
| 305 | 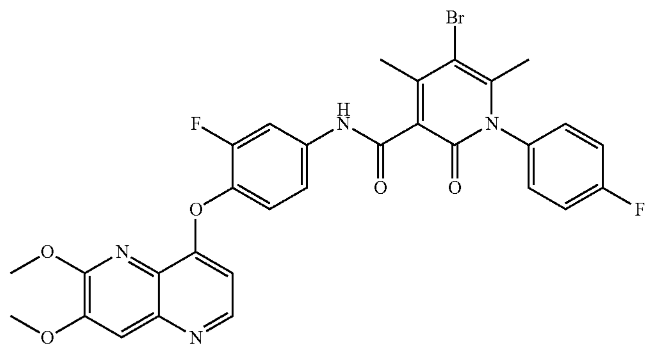 | 5-bromo-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 306 | 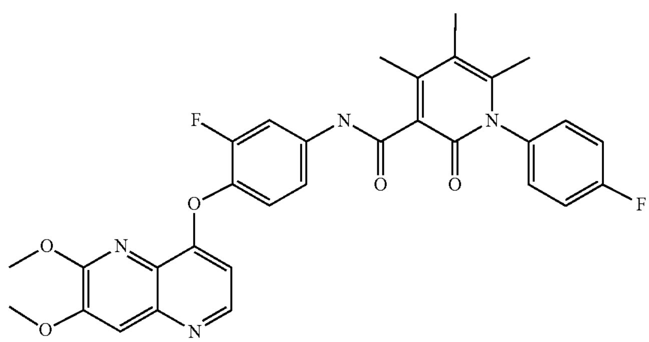 | N-[4-[(6,7-dimethoxy-1,5-naphthyridin-4-yl)oxy]-3-fluorophenyl]-1-(4-fluorophenyl)-4,5,6-trimethyl-2-oxopyridine-3-carboxamide |
| 307 | 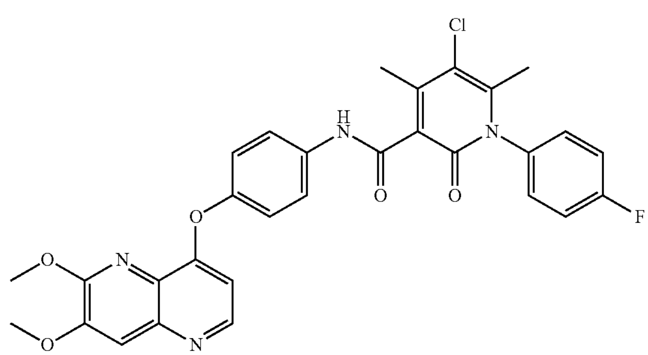 [SMILES: COc1cc2nccc(Oc3ccc(NC(=O)c4c(C)c(Cl)c(C)n(-c5ccc(F)cc5)c4=O)cc3)c2nc1OC] | 5-chloro-N-[4-[(6,7-dimethoxy-1,5-naphthyridin-4-yl)oxy]phenyl]-1-(4-fluorophenyl)-4,6-dimethyl-2-oxopyridine-3-carboxamide |
| 308 | 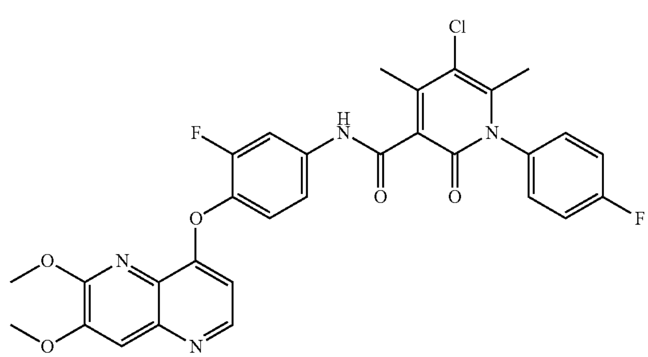 [SMILES: COc1cc2nccc(Oc3ccc(NC(=O)c4c(C)c(Cl)c(C)n(-c5ccc(F)cc5)c4=O)cc3F)c2nc1OC] | 5-chloro-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |

| Cpd # | Structure | IUPAC Name |
|---|---|---|
| 309 | 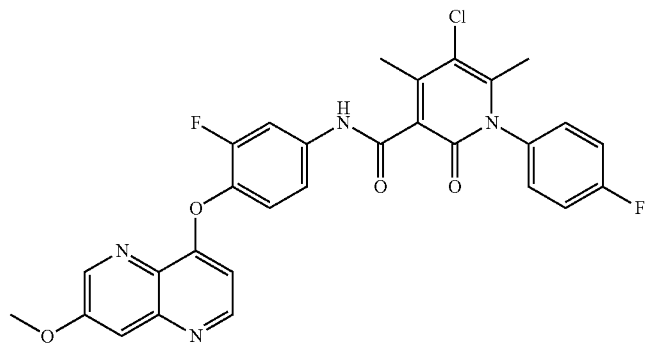 | 5-chloro-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 310 | 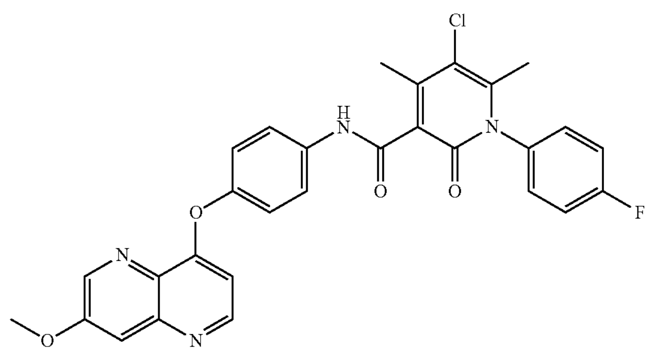 [SMILES: COc1cnc2c(Oc3ccc(NC(=O)c4c(C)c(Cl)c(C)n(-c5ccc(F)cc5)c4=O)cc3)ccnc2c1] | 5-chloro-1-(4-fluorophenyl)-N-[4-[(7-methoxy-1,5-naphthyridin-4-yl)oxy]phenyl]-4,6-dimethyl-2-oxopyridine-3-carboxamide |
| 311 | 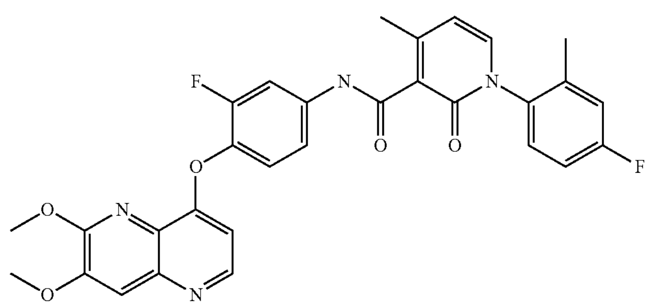 | N-[4-[(6,7-dimethoxy-1,5-naphthyridin-4-yl)oxy]-3-fluorophenyl]-1-(4-fluoro-2-methylphenyl)-4-methyl-2-oxopyridine-3-carboxamide |
| 312 | 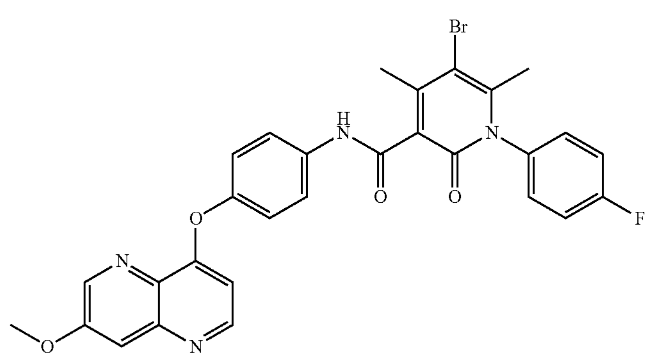 [SMILES: COc1cnc2c(Oc3ccc(NC(=O)c4c(C)c(Br)c(C)n(-c5ccc(F)cc5)c4=O)cc3)ccnc2c1] | 5-bromo-1-(4-fluorophenyl)-N-[4-[(7-methoxy-1,5-naphthyridin-4-yl)oxy]phenyl]-4,6-dimethyl-2-oxopyridine-3-carboxamide |

-continued

| Cpd # | Structure | IUPAC Name |
|---|---|---|
| 313 | 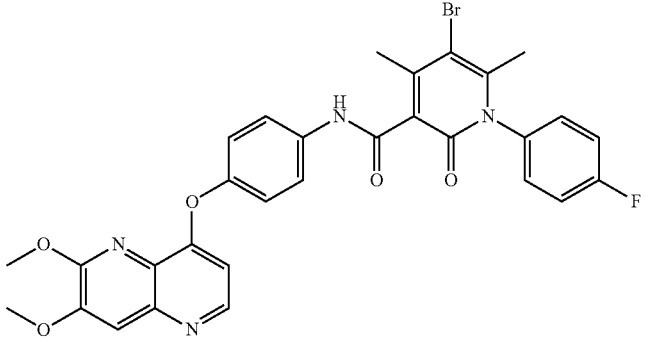 | 5-bromo-N-[4-[(6,7-dimethoxy-1,5-naphthyridin-4-yl)oxy]phenyl]-1-(4-fluorophenyl)-4,6-dimethyl-2-oxopyridine-3-carboxamide |
| 314 | 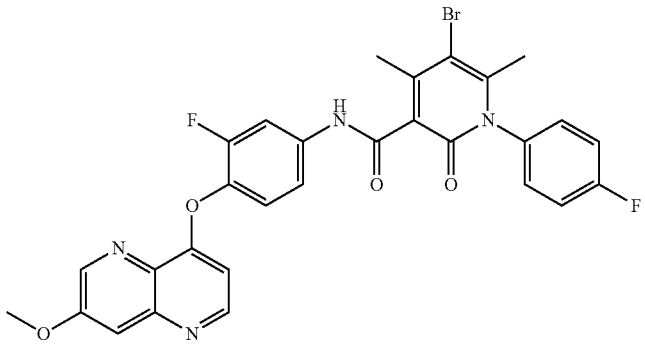 | 5-bromo-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 315 | 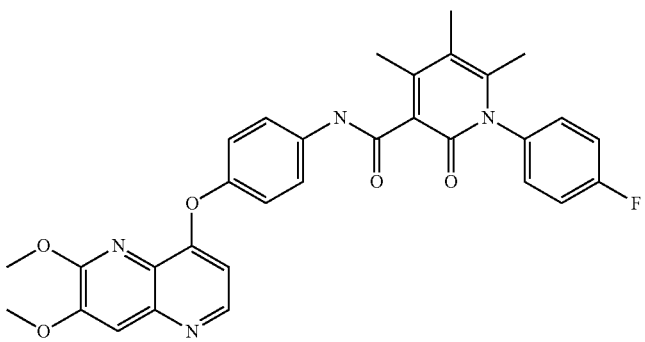 | N-[4-[(6, 7-dimethoxy-1,5-naphthyridin-4-yl)oxy]phenyl]-1-(4-fluorophenyl)-4,5,6-trimethyl-2-oxopyridine-3-carboxamide |
| 316 | 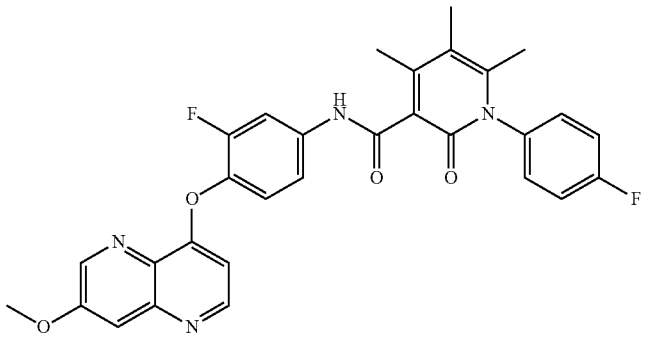 [SMILES: COc1cnc2c(Oc3ccc(NC(=O)c4c(C)c(C)c(C)n(-c5ccc(F)cc5)c4=O)cc3F)ccnc2c1] | N-[3-fluoro-4-[(7-methoxy-1,5-naphthyridin-4-yl)oxy]phenyl]-1-(4-fluorophenyl)-4,5,6-trimethyl-2-oxopyridine-3-carboxamide |

| Cpd # | Structure | IUPAC Name |
|---|---|---|
| 317 | 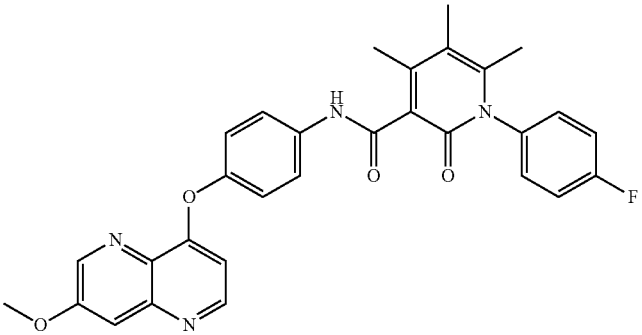 [SMILES: COc1cnc2c(Oc3ccc(NC(=O)c4c(C)c(C)c(C)n(-c5ccc(F)cc5)c4=O)cc3)ccnc2c1] | 1-(4-fluorophenyl)-N-[4-[(7-methoxy-1,5-naphthyridin-4-yl)oxy]phenyl]-4,5,6-trimethyl-2-oxopyridine-3-carboxamide |
| 318 | 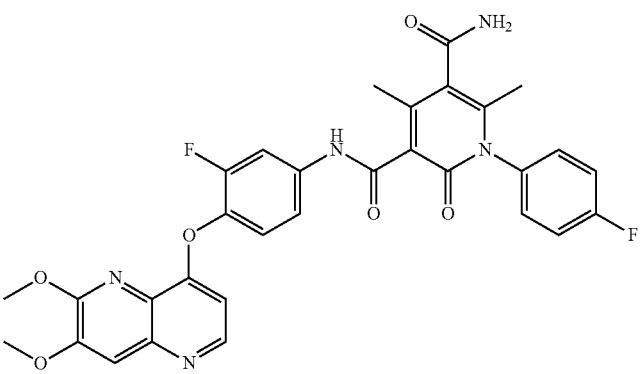 [SMILES: COc1cc2nccc(Oc3ccc(NC(=O)c4c(C)c(C(N)=O)c(C)n(-c5ccc(F)cc5)c4=O)cc3F)c2nc1OC] | 5-N-[4-[(6,7-dimethoxy-1,5-naphthyridin-4-yl)oxy]-3-fluorophenyl]-1-(4-fluorophenyl)-2,4-dimethyl-6-oxopyridine-3,5-dicarboxamide |
| 319 | 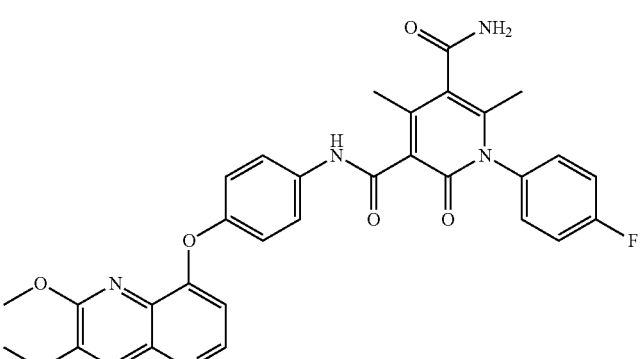 | 5-N-[4-[(6,7-dimethoxy-1,5-naphthyridin-4-yl)oxy]phenyl]-1-(4-fluorophenyl)-2,4-dimethyl-6-oxopyridine-3,5-dicarboxamide |
| 320 | 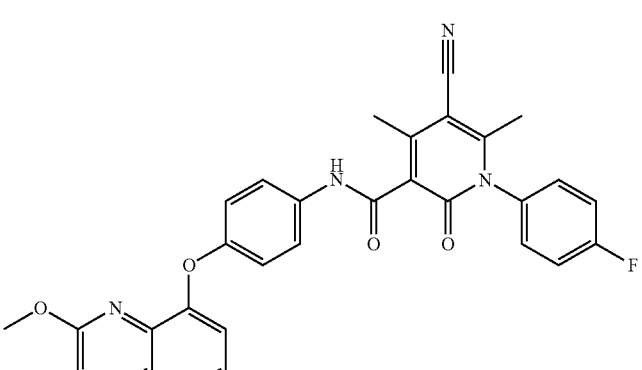 | 5-cyano-N-[4-[(6,7-dimethoxy-1,5-naphthyridin-4-yl)oxy]phenyl]-1-(4-fluorophenyl)-4,6-dimethyl-2-oxopyridine-3-carboxamide |

| Cpd # | Structure | IUPAC Name |
|---|---|---|
| 321 | 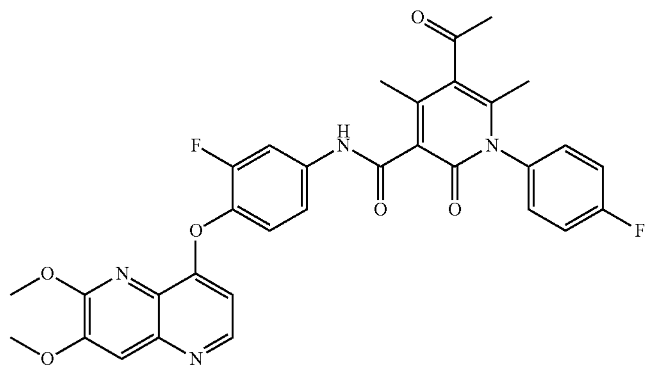 [SMILES: COc1cc2nccc(Oc3ccc(NC(=O)c4c(C)c(C(C)=O)c(C)n(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4,6-dimethyl-2-oxopyridine-3-carboxamide |
| 322 | 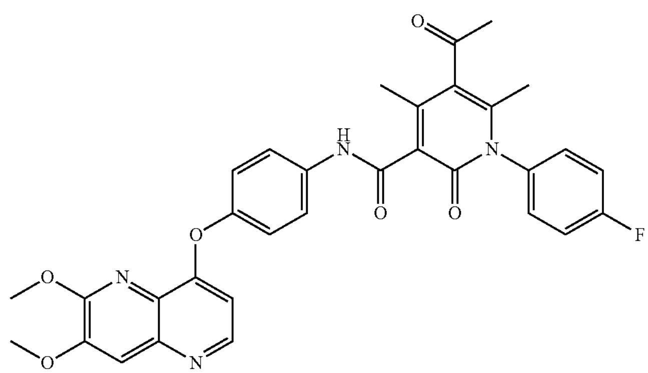 [SMILES: COc1cc2nccc(Oc3ccc(NC(=O)c4c(C)c(C(C)=O)c(C)n(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-4,6-dimethyl-2-oxopyridine-3-carboxamide |
| 323 | 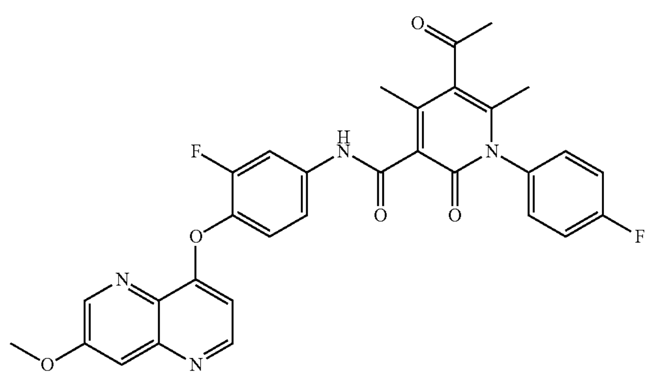 [SMILES: COc1cnc2c(Oc3ccc(NC(=O)c4c(C)c(C(C)=O)c(C)n(-c5ccc(F)cc5)c4=O)cc3F)ccnc2c1] | 5-acetyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 324 | 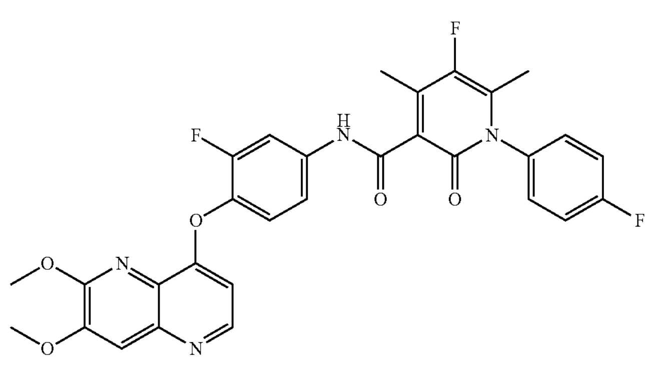 | N-[4-[(6,7-dimethoxy-1,5-naphthyridin-4-yl)oxy]-3-fluorophenyl]-5-fluoro-1-(4-fluorophenyl)-4,6-dimethyl-2-oxopyridine-3-carboxamide |

| Cpd # | Structure | IUPAC Name |
|---|---|---|
| 325 | 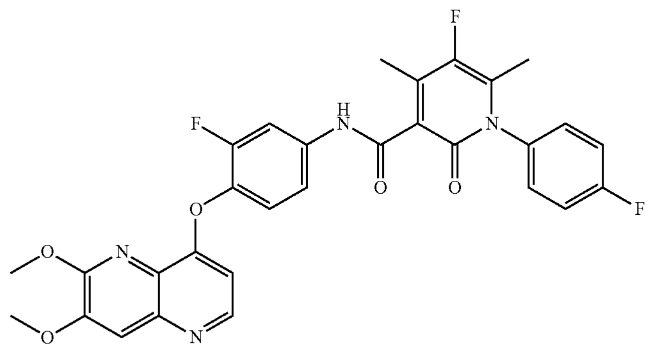 | N-[4-[(6,7-dimethoxy-1,5-naphthyridin-4-yl)oxy]phenyl]-5-fluoro-1-(4-fluorophenyl)-4,6-dimethyl-2-oxopyridine-3-carboxamide |
| 326 | 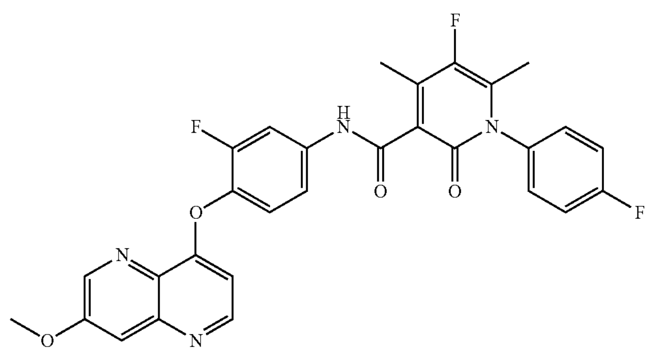 [SMILES: COc1cnc2c(Oc3ccc(NC(=O)c4c(C)c(F)c(C)n(-c5ccc(F)cc5)c4=O)cc3F)ccnc2c1] | 5-fluoro-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 327 | 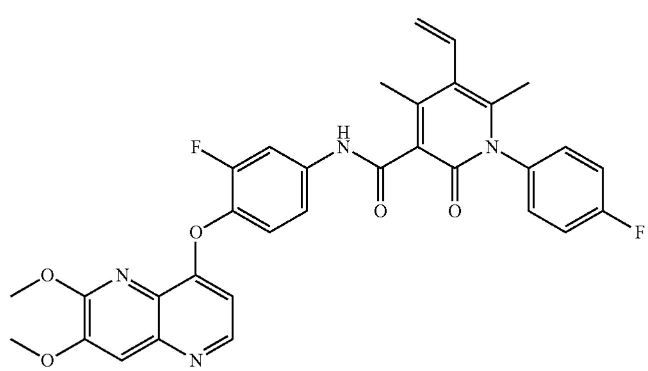 [SMILES: C=Cc1c(C)c(C(=O)Nc2ccc(Oc3ccnc4cc(OC)c(OC)nc34)c(F)c2)c(=O)n(-c2ccc(F)cc2)c1C] | N-[4-[(6,7-dimethoxy-1,5-naphthyridin-4-yl)oxy]-3-fluorophenyl]-5-ethenyl-1-(4-fluorophenyl)-4,6-dimethyl-2-oxopyridine-3-carboxamide |
| 328 | 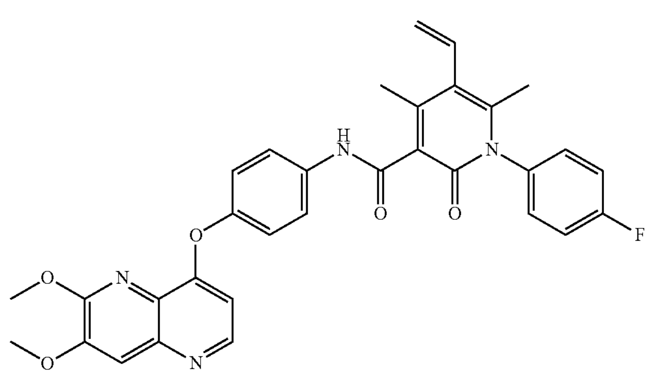 [SMILES: C=Cc1c(C)c(C(=O)Nc2ccc(Oc3ccnc4cc(OC)c(OC)nc34)cc2)c(=O)n(-c2ccc(F)cc2)c1C] | N-[4-[(6,7-dimethoxy-1,5-naphthyridin-4-yl)oxy]phenyl]-5-ethenyl-1-(4-fluorophenyl)-4,6-dimethyl-2-oxopyridine-3-carboxamide |

| Cpd # | Structure | IUPAC Name |
|---|---|---|
| 329 | 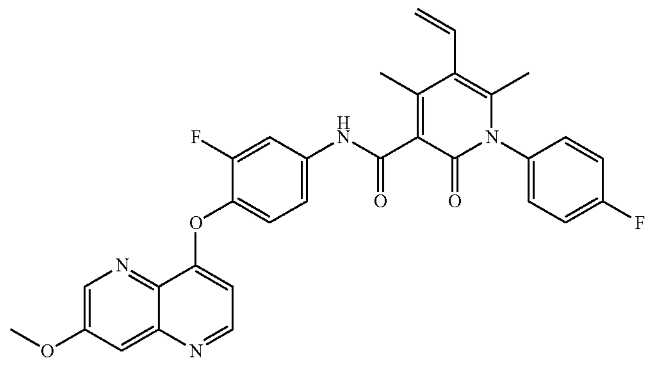 [SMILES: C=Cc1c(C)c(C(=O)Nc2ccc(Oc3ccnc4cc(OC)cnc34)c(F)c2)c(=O)n(-c2ccc(F)cc2)c1C] | 5-ethenyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 330 | 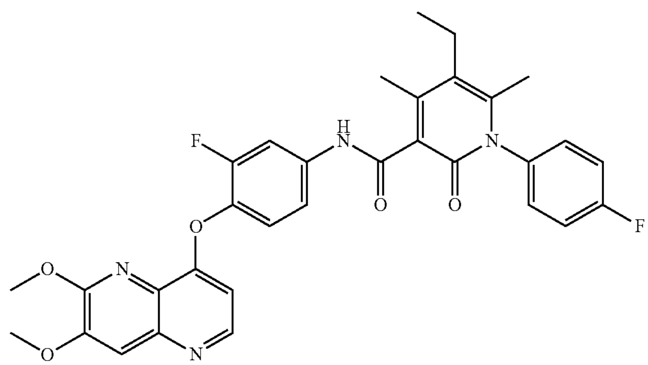 [SMILES: CCc1c(C)c(C(=O)Nc2ccc(Oc3ccnc4cc(OC)c(OC)nc34)c(F)c2)c(=O)n(-c2ccc(F)cc2)c1C] | N-[4-[(6,7-dimethoxy-1,5-naphthyridin-4-yl)oxy]-3-fluorophenyl]-5-ethyl-1-(4-fluorophenyl)-4,6-dimethyl-2-oxopyridine-3-carboxamide |
| 331 | 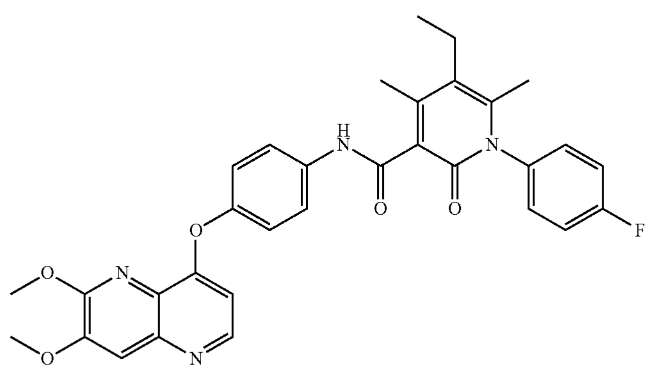 [SMILES: CCc1c(C)c(C(=O)Nc2ccc(Oc3ccnc4cc(OC)c(OC)nc34)cc2)c(=O)n(-c2ccc(F)cc2)c1C] | N-[4-[(6,7-dimethoxy-1,5-naphthyridin-4-yl)oxy]phenyl]-5-ethyl-1-(4-fluorophenyl)-4,6-dimethyl-2-oxopyridine-3-carboxamide |
| 332 | 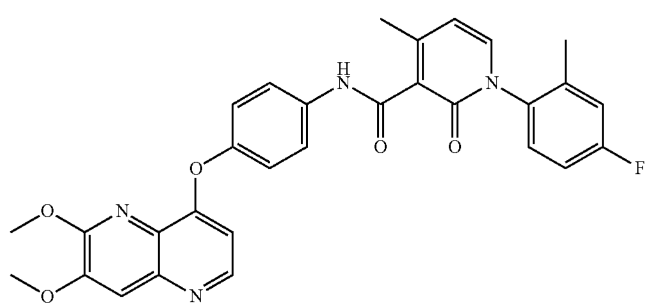 [SMILES: COc1cc2nccc(Oc3ccc(NC(=O)c4c(C)ccn(-c5ccc(F)cc5C)c4=O)cc3)c2nc1OC] | N-[4-[(6,7-dimethoxy-1,5-naphthyridin-4-yl)oxy]phenyl]-1-(4-fluoro-2-methylphenyl)-4-methyl-2-oxopyridine-3-carboxamide |

| Cpd # | Structure | IUPAC Name |
|---|---|---|
| 333 | 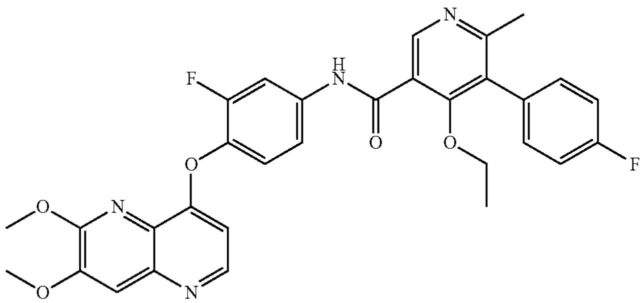 [SMILES: CCOc1c(C(=O)Nc2ccc(Oc3ccnc4cc(OC)c(OC)nc34)c(F)c2)cnc(C)c1-c1ccc(F)cc1] | N-[4-[(6,7-dimethoxy-1,5-naphthyridin-4-yl)oxy]-3-fluorophenyl]-4-ethoxy-5-(4-fluorophenyl)-6-methylpyridine-3-carboxamide |
| 334 | 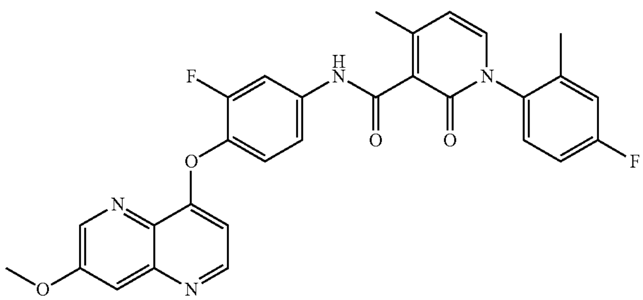 [SMILES: COc1cnc2c(Oc3ccc(NC(=O)c4c(C)ccn(-c5ccc(F)cc5C)c4=O)cc3F)ccnc2c1] | N-[3-fluoro-4-[(7-methoxy-1,5-naphthyridin-4-yl)oxy]phenyl]-1-(4-fluoro-2-methylphenyl)-4-methyl-2-oxopyridine-3-carboxamide |
| 335 | 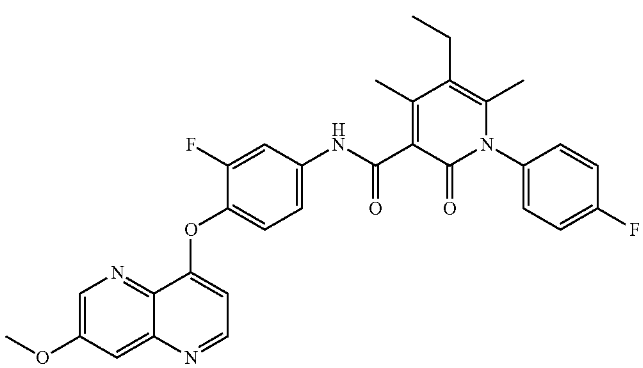 [SMILES: CCc1c(C)c(C(=O)Nc2ccc(Oc3ccnc4cc(OC)cnc34)c(F)c2)c(=O)n(-c2ccc(F)cc2)c1C] | 5-ethyl-N-[3-fluoro-4-[(7-methoxy-1,5-naphthyridin-4-yl)oxy]phenyl]-1-(4-fluorophenyl)-4,6-dimethyl-2-oxopyridine-3-carboxamide |
| 336 | 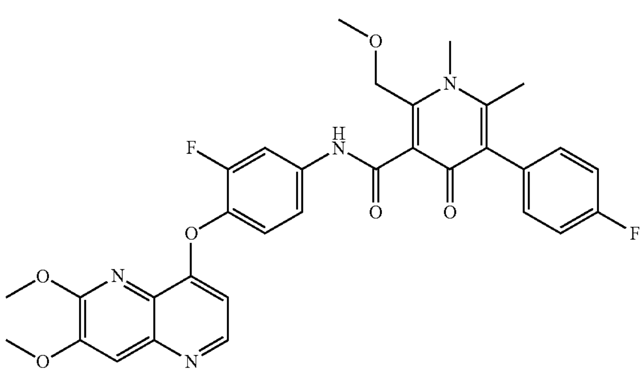 [SMILES: COCc1c(C(=O)Nc2ccc(Oc3ccnc4cc(OC)c(OC)nc34)c(F)c2)c(=O)c(-c2ccc(F)cc2)c(C)n1C] | N-[4-[(6,7-dimethoxy-1,5-naphthyridin-4-yl)oxy]-3-fluorophenyl]-5-(4-fluorophenyl)-2-(methoxymethyl)-1,6-dimethyl-4-oxopyridine-3-carboxamide |

| Cpd # | Structure | IUPAC Name |
|---|---|---|
| 337 | 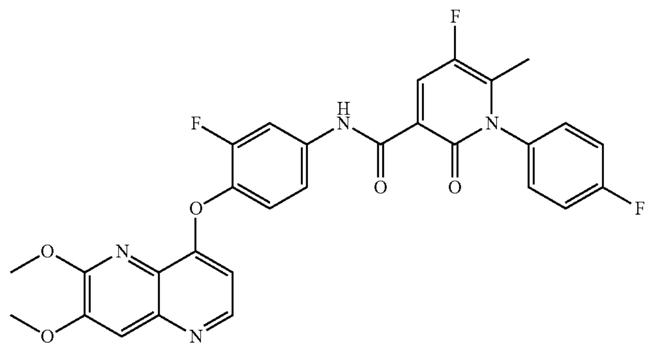 [SMILES: COc1cc2nccc(Oc3ccc(NC(=O)c4cc(F)c(C)n(-c5ccc(F)cc5)c4=O)cc3F)c2nc1OC] | N-[4-[(6,7-dimethoxy-1,5-naphthyridin-4-yl)oxy]-3-fluorophenyl]-5-fluoro-1-(4-fluorophenyl)-6-methyl-2-oxopyridine-3-carboxamide |
| 338 | 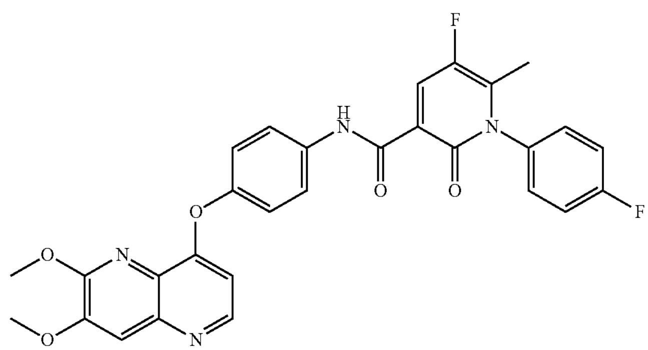 [SMILES: COc1cc2nccc(Oc3ccc(NC(=O)c4cc(F)c(C)n(-c5ccc(F)cc5)c4=O)cc3)c2nc1OC] | N-[4-[(6,7-dimethoxy-1,5-naphthyridin-4-yl)oxy]phenyl]-5-fluoro-1-(4-fluorophenyl)-6-methyl-2-oxopyridine-3-carboxamide |
| 339 | 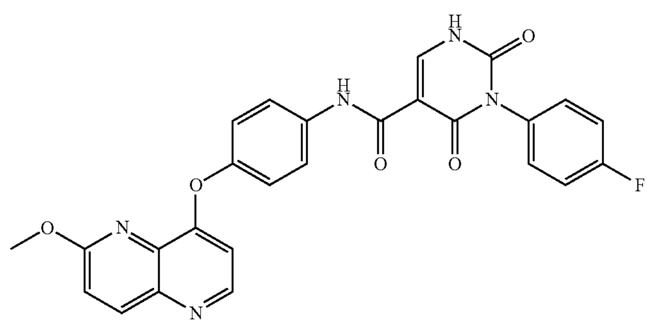 [SMILES: COc1ccc2nccc(Oc3ccc(NC(=O)c4c[nH]c(=O)n(-c5ccc(F)cc5)c4=O)cc3)c2n1] | 3-(4-fluorophenyl)-N-[4-[(6-methoxy-1,5-naphthyridin-4-yl)oxy]phenyl]-2,4-dioxo-1H-pyrimidine-5-carboxamide |
| 340 | 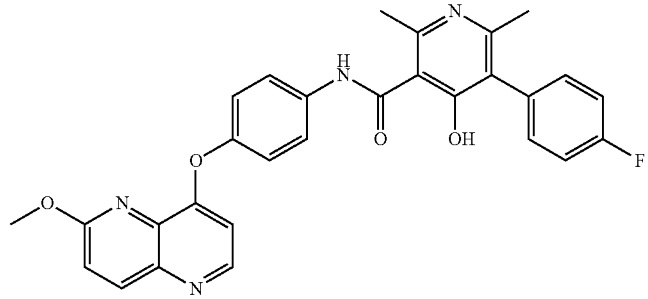 [SMILES: COc1ccc2nccc(Oc3ccc(NC(=O)c4c(C)nc(C)c(-c5ccc(F)cc5)c4O)cc3)c2n1] | 5-(4-fluorophenyl)-4-hydroxy-N-[4-[(6-methoxy-1,5-naphthyridin-4-yl)oxy]phenyl]-2,6-dimethylpyridine-3-carboxamide |

| Cpd # | Structure | IUPAC Name |
|---|---|---|
| 341 | 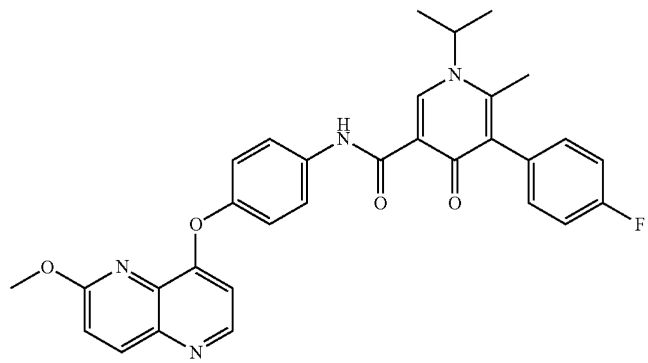 [SMILES: COc1ccc2nccc(Oc3ccc(NC(=O)c4cn(C(C)C)c(C)c(-c5ccc(F)cc5)c4=O)cc3)c2n1] | 5-(4-fluorophenyl)-N-[4-[(6-methoxy-1,5-naphthyridin-4-yl)oxy]phenyl]-6-methyl-4-oxo-1-propan-2-ylpyridine-3-carboxamide |
| 342 | 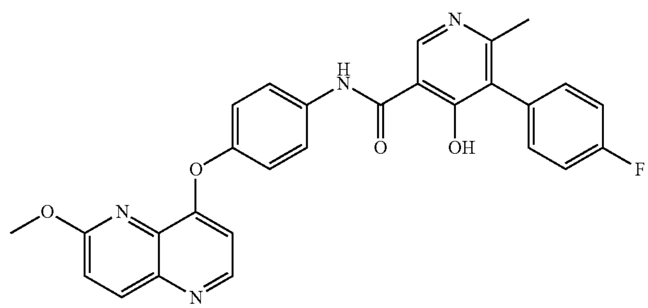 [SMILES: COc1ccc2nccc(Oc3ccc(NC(=O)c4cnc(C)c(-c5ccc(F)cc5)c4O)cc3)c2n1] | 5-(4-fluorophenyl)-4-hydroxy-N-[4-[(6-methoxy-1,5-naphthyridin-4-yl)oxy]phenyl]-6-methylpyridine-3-carboxamide |
| 343 | 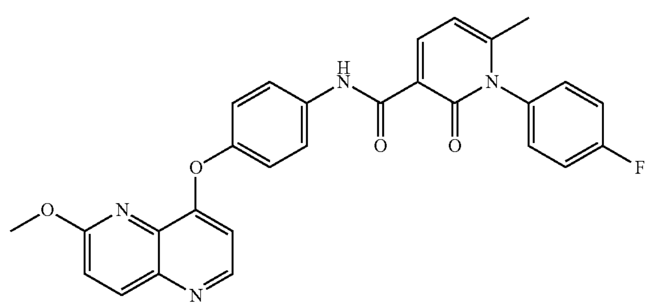 | 1-(4-fluorophenyl)-N-[4-[(6-methoxy-1,5-naphthyridin-4-yl)oxy]phenyl]-6-methyl-2-oxopyridine-3-carboxamide |
| 344 | 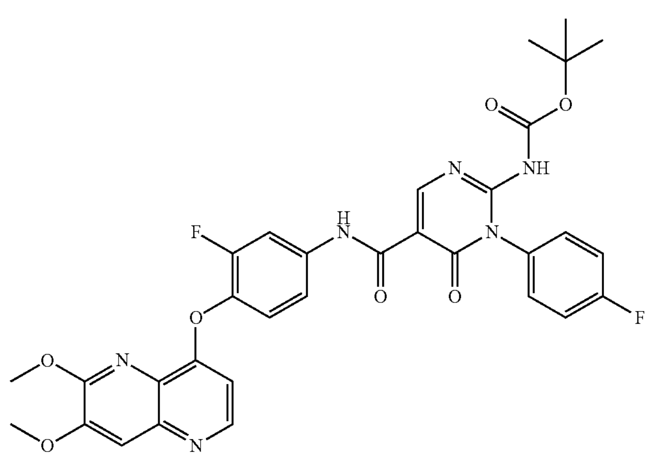 [SMILES: COc1cc2nccc(Oc3ccc(NC(=O)c4cnc(NC(=O)OC(C)(C)C)n(-c5ccc(F)cc5)c4=O)cc3F)c2nc1OC] | tert-butyl N-[5-[[4-[(6,7-dimethoxy-1,5-naphthyridin-4-yl)oxy]-3-fluorophenyl]carbamoyl]-1-(4-fluorophenyl)-6-oxopyrimidin-2-yl]carbamate |

-continued

| Cpd # | Structure | IUPAC Name |
|---|---|---|
| 345 | 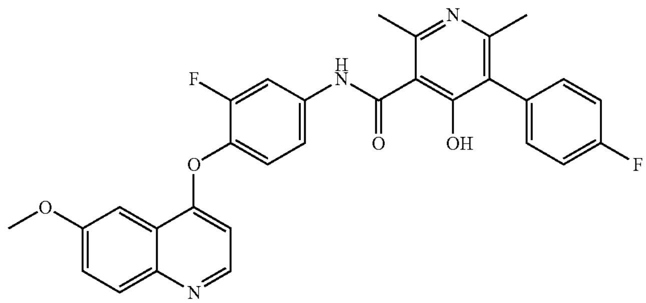 [SMILES: COc1ccc2nccc(Oc3ccc(NC(=O)c4c(C)nc(C)c(-c5ccc(F)cc5)c4O)cc3F)c2c1] | N-[3-fluoro-4-(6-methoxyquinolin-4-yl)oxyphenyl]-5-(4-fluorophenyl)-4-hydroxy-2,6-dimethylpyridine-3-carboxamide |
| 346 | 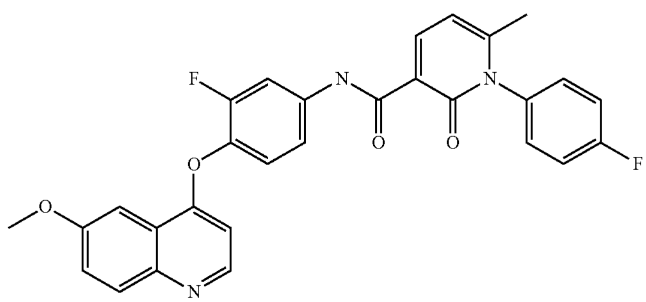 | N-[3-fluoro-4-(6-methoxyquinolin-4-yl)oxyphenyl]-1-(4-fluorophenyl)-6-methyl-2-oxopyridine-3-carboxamide |
| 347 | 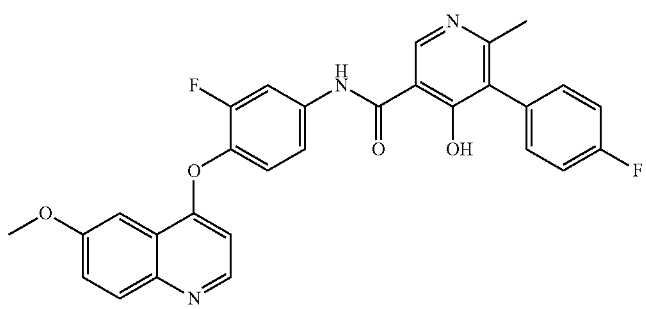 | N-[3-fluoro-4-(6-methoxyquinolin-4-yl)oxyphenyl]-5-(4-fluorophenyl)-4-hydroxy-6-methylpyridine-3-carboxamide |
| 348 | 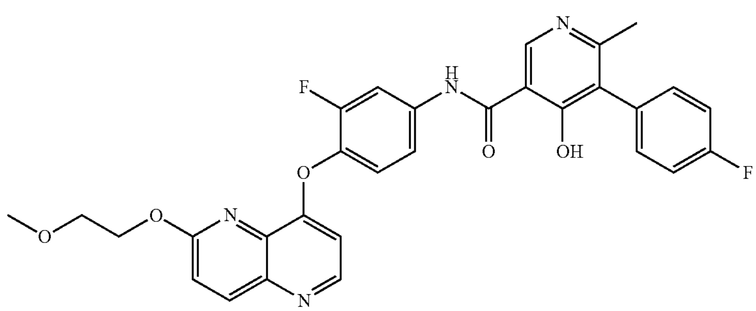 [SMILES: COCCOc1ccc2nccc(Oc3ccc(NC(=O)c4cnc(C)c(-c5ccc(F)cc5)c4O)cc3F)c2n1] | N-[3-fluoro-4-[[6-(2-methoxyethoxy)-1,5-naphthyridin-4-yl]oxy]phenyl]-5-(4-fluorophenyl)-4-hydroxy-6-methylpyridine-3-carboxamide |
| 349 | 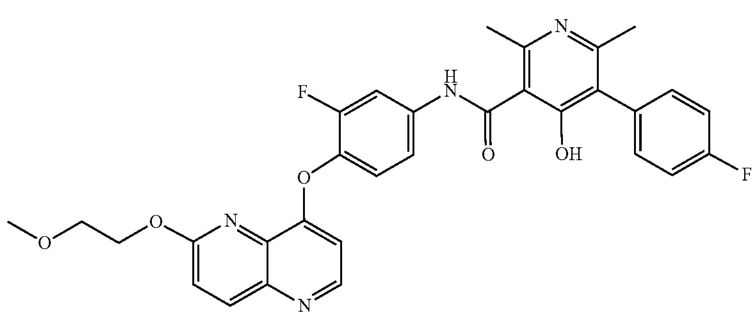 [SMILES: COCCOc1ccc2nccc(Oc3ccc(NC(=O)c4c(C)nc(C)c(-c5ccc(F)cc5)c4O)cc3F)c2n1] | N-[3-fluoro-4-[[6-(2-methoxyethoxy)-1,5-naphthyridin-4-yl]oxy]phenyl]-5-(4-fluorophenyl)-4-hydroxy-2,6-dimethylpyridine-3-carboxamide |

-continued

| Cpd # | Structure | IUPAC Name |
|---|---|---|
| 350 | 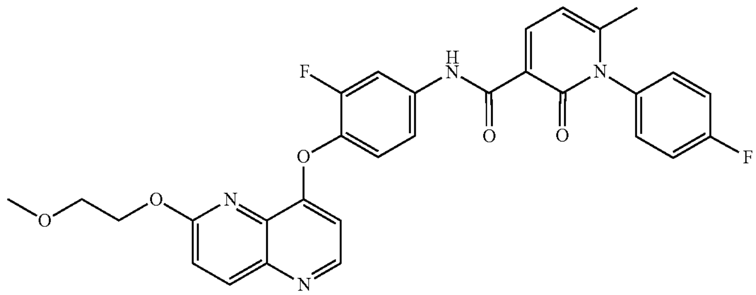 [SMILES: COCCOc1ccc2nccc(Oc3ccc(NC(=O)c4ccc(C)n(-c5ccc(F)cc5)c4=O)cc3F)c2n1] | N-[3-fluoro-4-[[6-(2-methoxyethoxy)-1,5-naphthyridin-4-yl]oxy]phenyl]-1-(4-fluorophenyl)-6-methyl-2-oxopyridine-3-carboxamide |
| 351 | 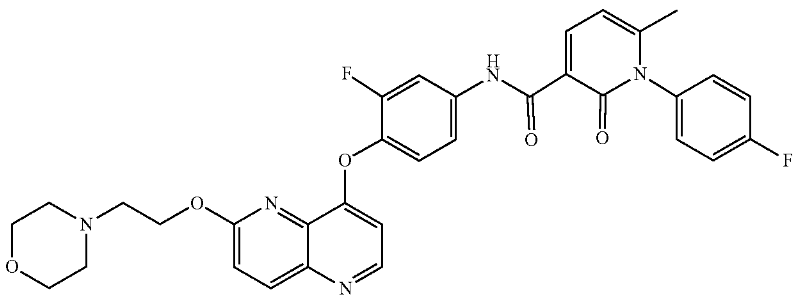 [SMILES: Cc1ccc(C(=O)Nc2ccc(Oc3ccnc4ccc(OCCN5CCOCC5)nc34)c(F)c2)c(=O)n1-c1ccc(F)cc1] | N-[3-fluoro-4-[[6-(2-morpholin-4-ylethoxy)-1,5-naphthyridin-4-yl]oxy]phenyl]-1-(4-fluorophenyl)-6-methyl-2-oxopyridine-3-carboxamide |
| 352 | 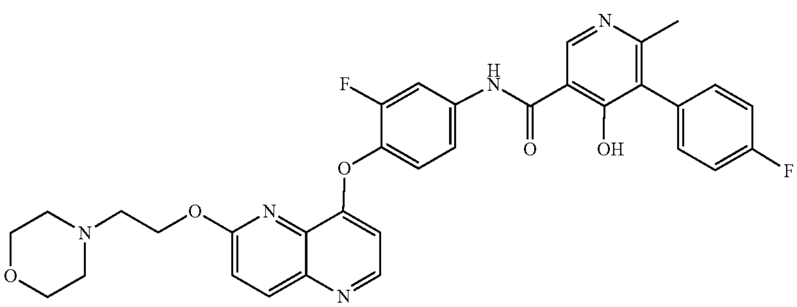 [SMILES: Cc1ncc(C(=O)Nc2ccc(Oc3ccnc4ccc(OCCN5CCOCC5)nc34)c(F)c2)c(O)c1-c1ccc(F)cc1] | N-[3-fluoro-4-[[6-(2-morpholin-4-ylethoxy)-1,5-naphthyridin-4-yl]oxy]phenyl]-5-(4-fluorophenyl)-4-hydroxy-6-methylpyridine-3-carboxamide |
| 353 | 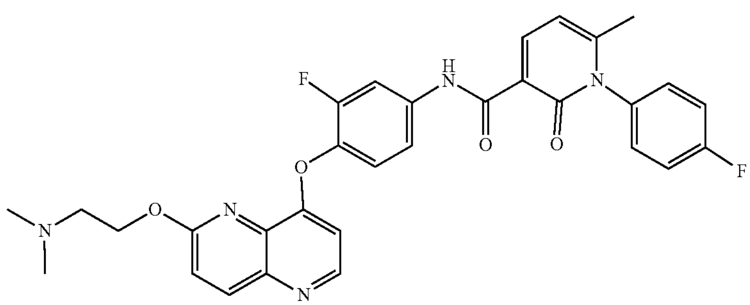 [SMILES: Cc1ccc(C(=O)Nc2ccc(Oc3ccnc4ccc(OCCN(C)C)nc34)c(F)c2)c(=O)n1-c1ccc(F)cc1] | N-[4-[[6-[2-(dimethylamino)ethoxy]-1,5-naphthyridin-4-yl]oxy]-3-fluorophenyl]-1-(4-fluorophenyl)-6-methyl-2-oxopyridine-3-carboxamide |
| 354 | 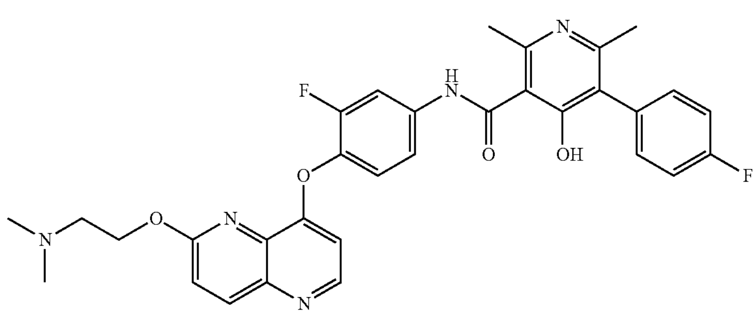 [SMILES: Cc1nc(C)c(-c2ccc(F)cc2)c(O)c1C(=O)Nc1ccc(Oc2ccnc3ccc(OCCN(C)C)nc23)c(F)c1] | N-[4-[[6-[2-(dimethylamino)ethoxy]-1,5-naphthyridin-4-yl]oxy]-3-fluorophenyl]-5-(4-fluorophenyl)-4-hydroxy-2,6-dimethylpyridine-3-carboxamide |

| Cpd # | Structure | IUPAC Name |
|---|---|---|
| 355 | 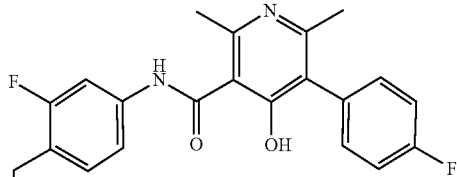 | N-[3-fluoro-4-[[6-(2-morpholin-4-ylethoxy)-1,5-naphthyridin-4-yl]oxy]phenyl]-5-(4-fluorophenyl)-4-hydroxy-2,6-dimethylpyridine-3-carboxamide |
| 356 | 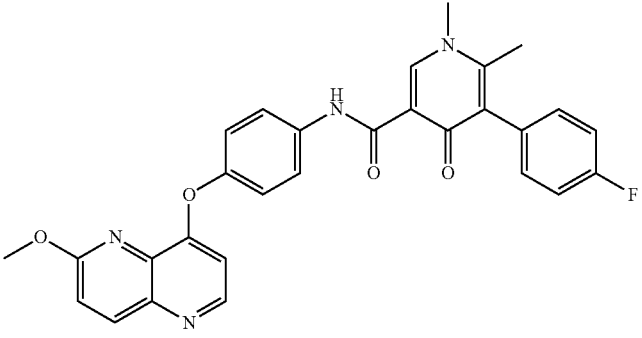 [SMILES: COc1ccc2nccc(Oc3ccc(NC(=O)c4cn(C)c(C)c(-c5ccc(F)cc5)c4=O)cc3)c2n1] | 5-(4-fluorophenyl)-N-[4-[(6-methoxy-1,5-naphthyridin-4-yl)oxy]phenyl]-1,6-dimethyl-4-oxopyridine-3-carboxamide |
| 357 | 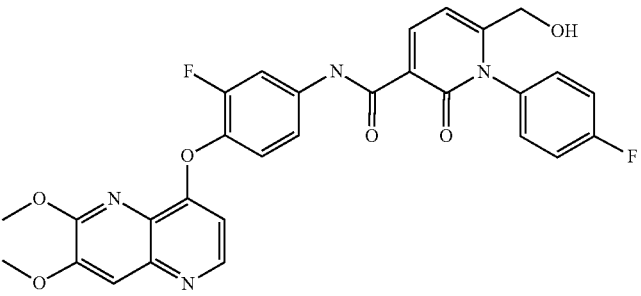 | N-[4-[(6,7-dimethoxy-1,5-naphthyridin-4-yl)oxy]-3-fluorophenyl]-1-(4-fluorophenyl)-6-(hydroxymethyl)-2-oxopyridine-3-carboxamide |
| 358 | 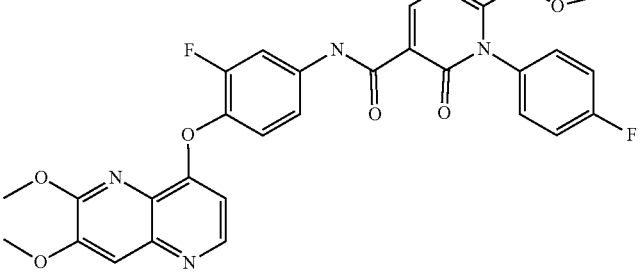 | N-[4-[(6,7-dimethoxy-1,5-naphthyridin-4-yl)oxy]-3-fluorophenyl]-1-(4-fluorophenyl)-6-(methoxymethyl)-2-oxopyridine-3-carboxamide |

| Cpd # | Structure | IUPAC Name |
|---|---|---|
| 359 | 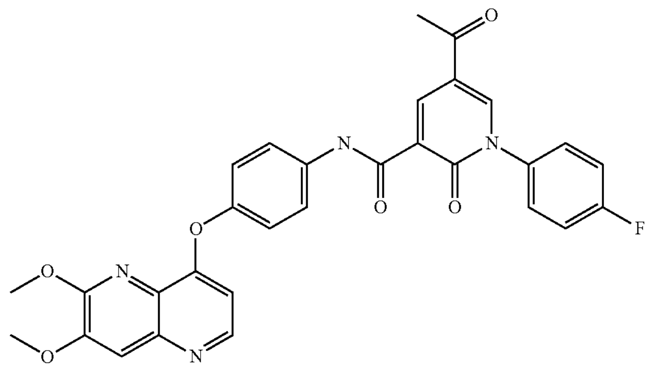 | 5-acetyl-N-[4-[(6,7-dimethoxy-1,5-naphthyridin-4-yl)oxy]phenyl]-1-(4-fluorophenyl)-2-oxopyridine-3-carboxamide |
| 360 | 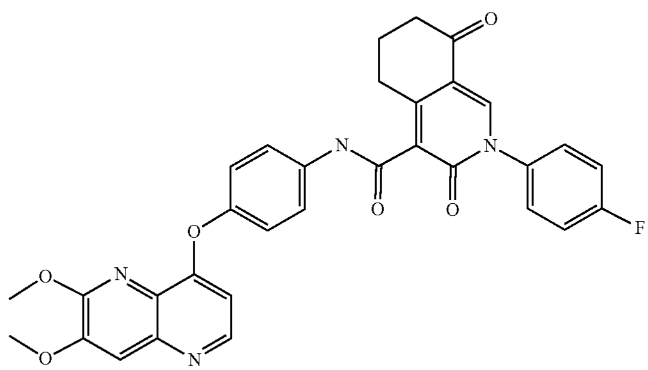 | N-[4-[(6,7-dimethoxy-1,5-naphthyridin-4-yl)oxy]phenyl]-2-(4-fluorophenyl)-3,8-dioxo-6,7-dihydro-5H-isoquinoline-4-carboxamide |
| 361 | 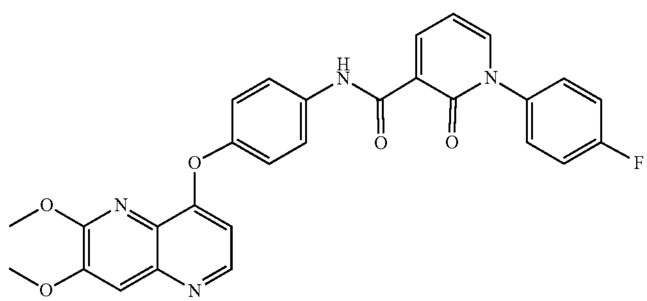 [SMILES: COc1cc2nccc(Oc3ccc(NC(=O)c4cccn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-2-oxopyridine-3-carboxamide |
| 362 | 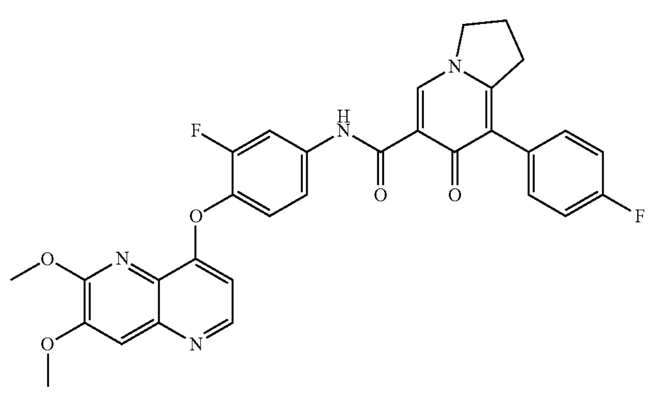 [SMILES: COc1cc2nccc(Oc3ccc(NC(=O)c4cn5c(c(-c6ccc(F)cc6)c4=O)CCC5)cc3F)c2nc1OC] | N-[4-[(6,7-dimethoxy-1,5-naphthyridin-4-yl)oxy]-3-fluorophenyl]-8-(4-fluorophenyl)-7-oxo-2,3-dihydro-1H-indolizine-6-carboxamide |

| Cpd # | Structure | IUPAC Name |
|---|---|---|
| 363 | 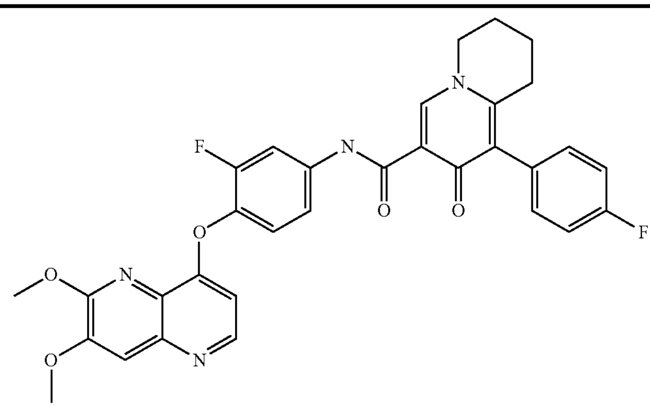 | N-[4-[(6,7-dimethoxy-1,5-naphthyridin-4-yl)oxy]-3-fluorophenyl]-1-(4-fluorophenyl)-2-oxo-6,7,8,9-tetrahydroquinolizine-3-carboxamide |
| 364 | 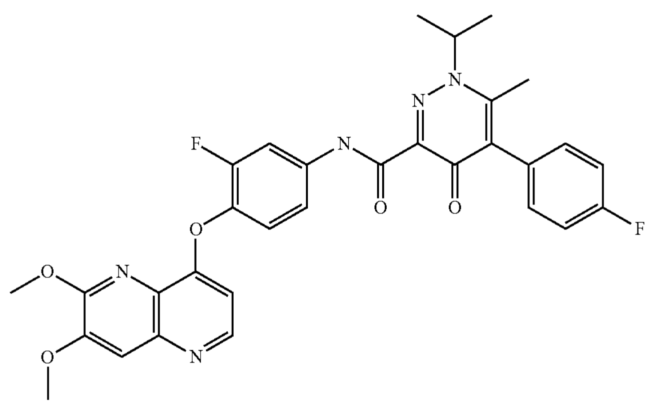 | N-[4-[(6,7-dimethoxy-1,5-naphthyridin-4-yl)oxy]-3-fluorophenyl]-5-(4-fluorophenyl)-6-methyl-4-oxo-1-propan-2-ylpyridazine-3-carboxamide |
| 365 | 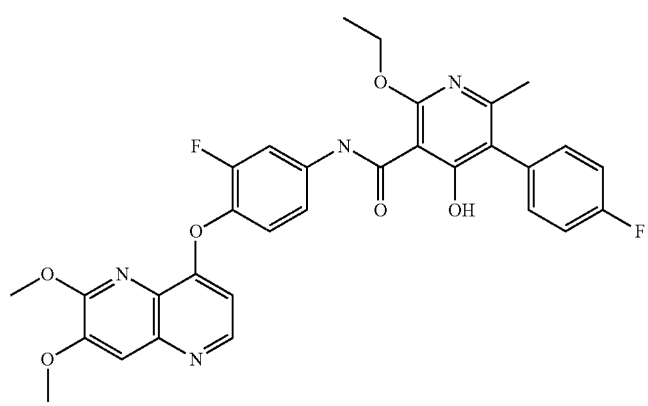 | N-[4-[(6,7-dimethoxy-1,5-naphthyridin-4-yl)oxy]-3-fluorophenyl]-2-ethoxy-5-(4-fluorophenyl)-4-hydroxy-6-methylpyridine-3-carboxamide |
| 366 | 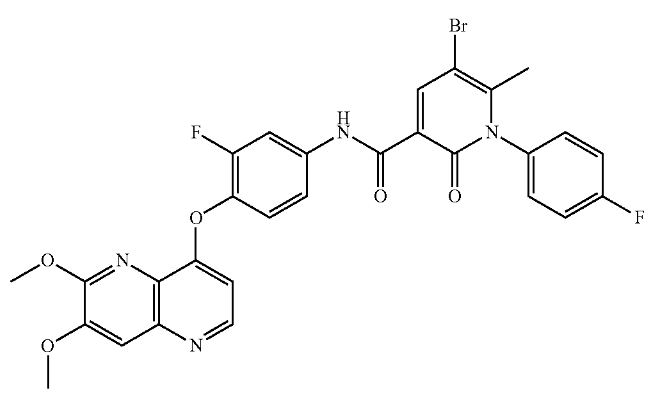 [SMILES: COc1cc2nccc(Oc3ccc(NC(=O)c4cc(Br)c(C)n(-c5ccc(F)cc5)c4=O)cc3F)c2nc1OC] | 5-bromo-N-[4-[(6,7-dimethoxy-1,5-naphthyridin-4-yl)oxy]-3-fluorophenyl]-1-(4-fluorophenyl)-6-methyl-2-oxopyridine-3-carboxamide |

-continued

| Cpd # | Structure | IUPAC Name |
|---|---|---|
| 367 | 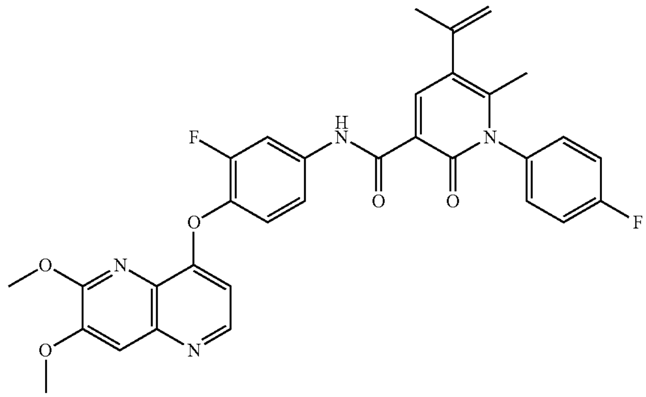 [SMILES: C=C(C)c1cc(C(=O)Nc2ccc(Oc3ccnc4cc(OC)c(OC)nc34)c(F)c2)c(=O)n(-c2ccc(F)cc2)c1C] | N-[4-[(6,7-dimethoxy-1,5-naphthyridin-4-yl)oxy]-3-fluorophenyl]-1-(4-fluorophenyl)-6-methyl-2-oxo-5-prop-1-en-2-ylpyridine-3-carboxamide |
| 368 | 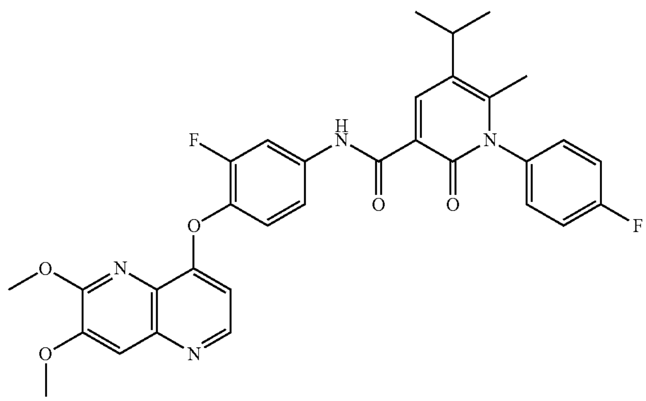 [SMILES: COc1cc2nccc(Oc3ccc(NC(=O)c4cc(C(C)C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-6-methyl-2-oxo-5-propan-2-ylpyridine-3-carboxamide |
| 369 | 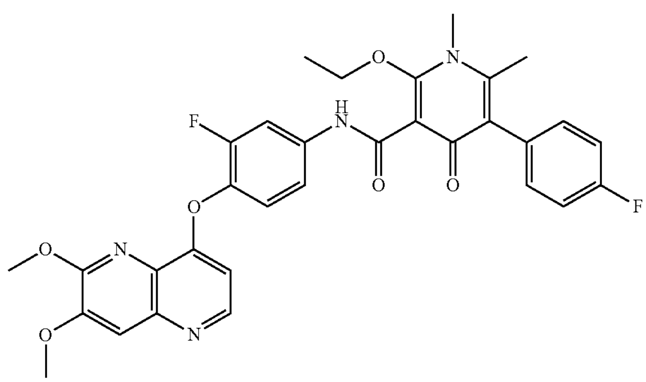 [SMILES: CCOc1c(C(=O)Nc2ccc(Oc3ccnc4cc(OC)c(OC)nc34)c(F)c2)c(=O)c(-c2ccc(F)cc2)c(C)n1C] | N-[4-[(6,7-dimethoxy-1,5-naphthyridin-4-yl)oxy]-3-fluorophenyl]-2-ethoxy-5-(4-fluorophenyl)-1,6-dimethyl-4-oxopyridine-3-carboxamide |
| 370 | 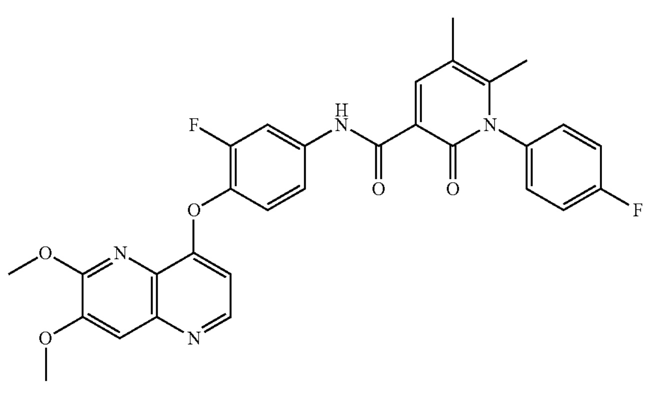 [SMILES: COc1cc2nccc(Oc3ccc(NC(=O)c4cc(C)c(C)n(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-5,6-dimethyl-2-oxopyridine-3-carboxamide |

| Cpd # | Structure | IUPAC Name |
|---|---|---|
| 371 | 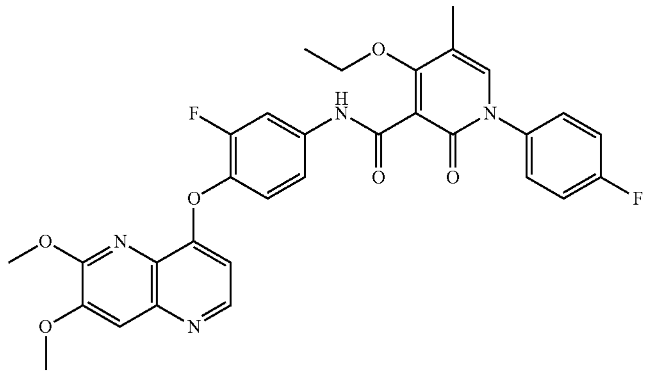 [SMILES: CCOc1c(C)cn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-1-(4-fluorophenyl)-5-methyl-2-oxopyridine-3-carboxamide |
| 372 | 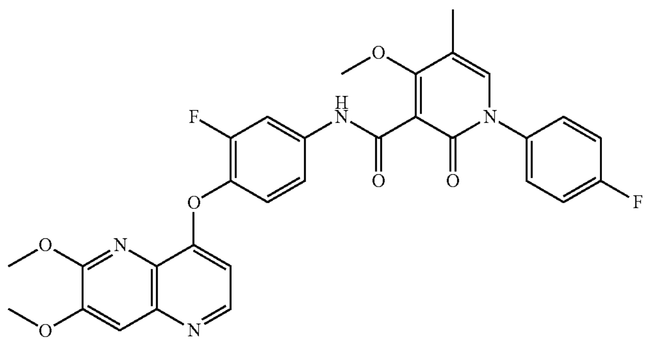 [SMILES: COc1cc2nccc(Oc3ccc(NC(=O)c4c(OC)c(C)cn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4-methoxy-5-methyl-2-oxopyridine-3-carboxamide |
| 373 | 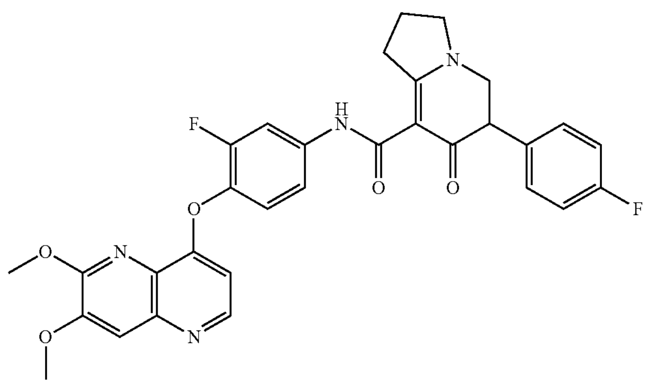 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide |
| 374 | 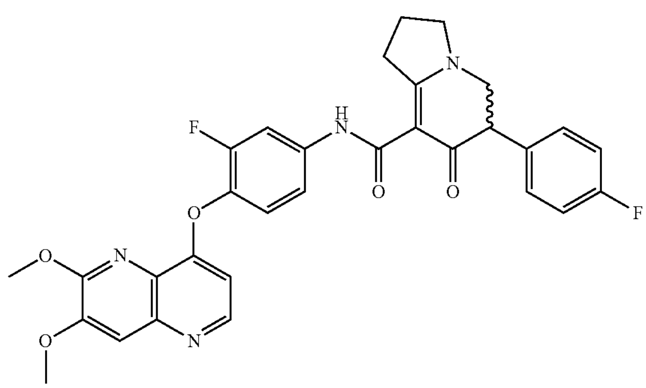 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 1 |

-continued

| Cpd # | Structure | IUPAC Name |
|---|---|---|
| 375 | 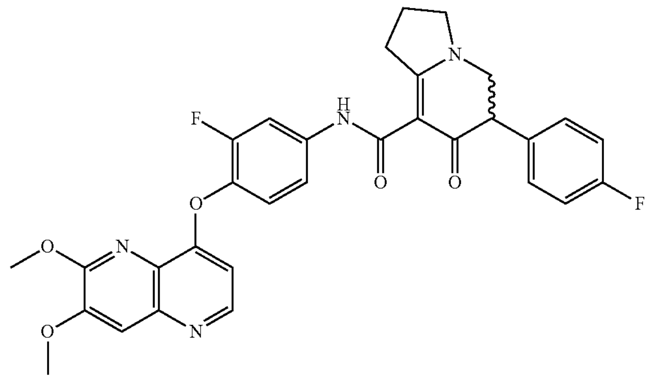 [SMILES: COc1cc2nccc(Oc3ccc(NC(=O)C4=C5CCCN5CC(c5ccc(F)cc5)C4=O)cc3F)c2nc1OC] | N-[4-[(6,7-dimethoxy-1,5-naphthyridin-4-yl)oxy]-3-fluorophenyl]-6-(4-fluorophenyl)-7-oxo-2,3,5,6-tetrahydro-1H-indolizine-8-carboxamide, enantiomer 2 |
| 376 | 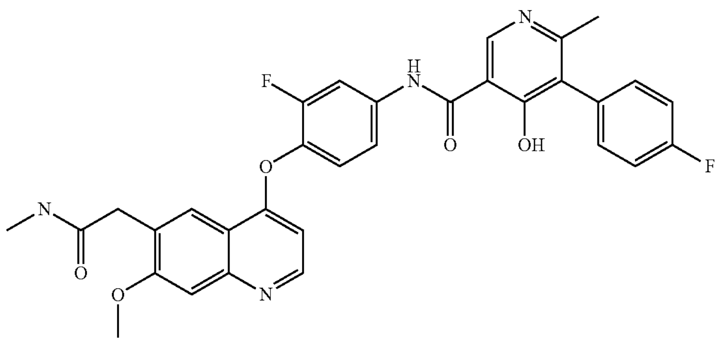 | N-[3-fluoro-4-[7-methoxy-6-[2-(methylamino)-2-oxoethyl]quinolin-4-yl]oxyphenyl]-5-(4-fluorophenyl)-4-hydroxy-6-methylpyridine-3-carboxamide |
| 377 | 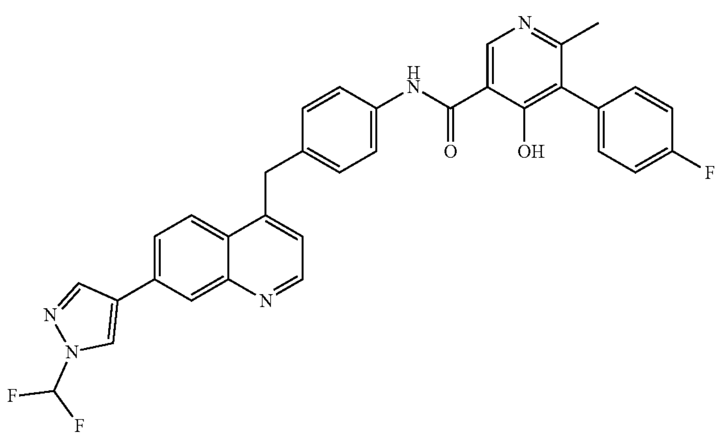 [SMILES: Cc1ncc(C(=O)Nc2ccc(Cc3ccnc4cc(-c5cnn(C(F)F)c5)ccc34)cc2)c(O)c1-c1ccc(F)cc1] | N-[4-[7-[1-(difluoromethyl)pyrazol-4-yl]quinolin-4-yl]oxyphenyl]-5-(4-fluorophenyl)-4-hydroxy-6-methylpyridine-3-carboxamide |
| 378 | 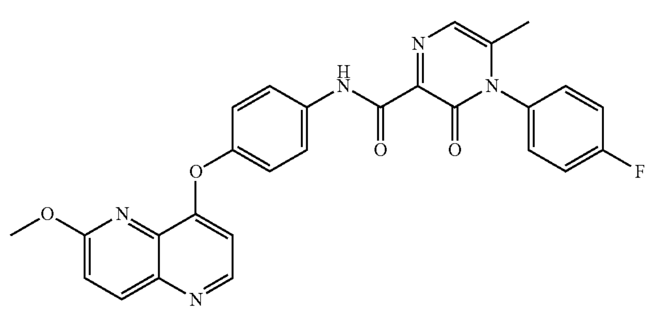 [SMILES: COc1ccc2nccc(Oc3ccc(NC(=O)c4ncc(C)n(-c5ccc(F)cc5)c4=O)cc3)c2n1] | 4-(4-fluorophenyl)-N-[4-[(6-methoxy-1,5-naphthyridin-4-yl)oxy]phenyl]-5-methyl-3-oxopyrazine-2-carboxamide |

-continued

| Cpd # | Structure | IUPAC Name |
|---|---|---|
| 379 | 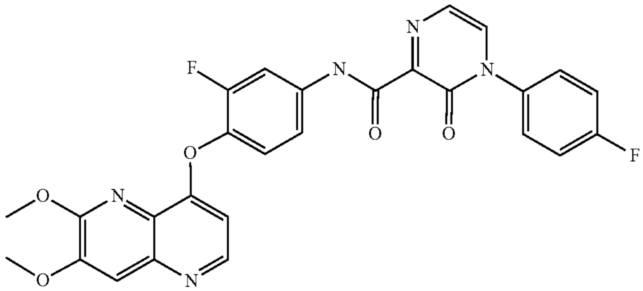 | N-[4-[(6,7-dimethoxy-1,5-naphthyridin-4-yl)oxy]-3-fluorophenyl]-4-(4-fluorophenyl)-3-oxopyrazine-2-carboxamide |
| 380 | 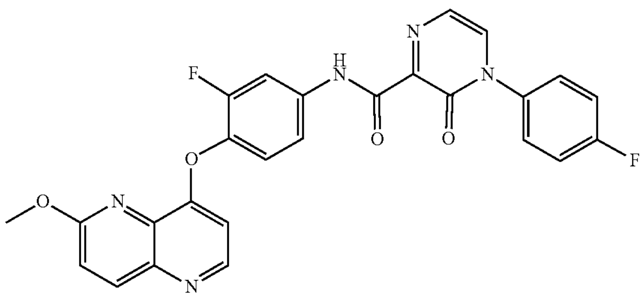 [SMILES: COc1ccc2nccc(Oc3ccc(NC(=O)c4nccn(-c5ccc(F)cc5)c4=O)cc3F)c2n1] | N-[3-fluoro-4-[(6-methoxy-1,5-naphthyridin-4-yl)oxy]phenyl]-4-(4-fluorophenyl)-3-oxopyrazine-2-carboxamide |
| 381 | 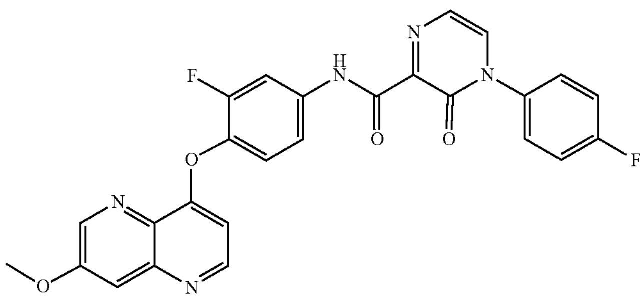 [SMILES: COc1cnc2c(Oc3ccc(NC(=O)c4nccn(-c5ccc(F)cc5)c4=O)cc3F)ccnc2c1] | N-[3-fluoro-4-[(7-methoxy-1,5-naphthyridin-4-yl)oxy]phenyl]-4-(4-fluorophenyl)-3-oxopyrazine-2-carboxamide |
| 382 | 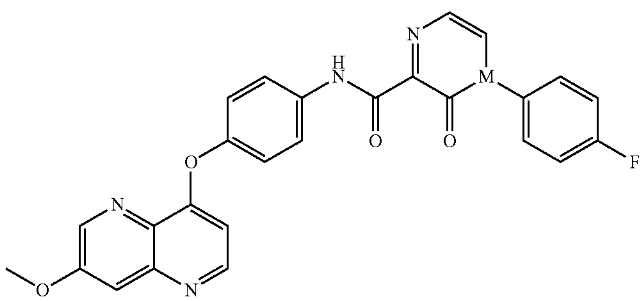 | 4-(4-fluorophenyl)-N-[4-[(7-methoxy-1,5-naphthyridin-4-yl)oxy]phenyl]-3-oxopyrazine-2-carboxamide |
| 383 | 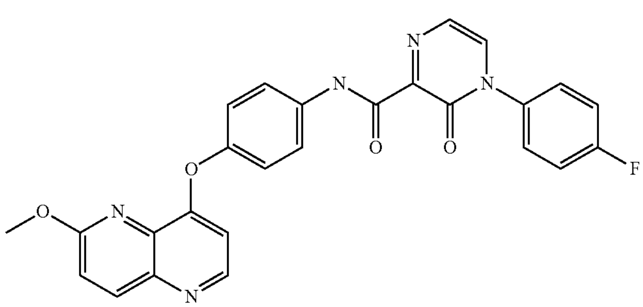 | 4-(4-fluorophenyl)-N-[4-[(6-methoxy-1,5-naphthyridin-4-yl)oxy]phenyl]-3-oxopyrazine-2-carboxamide |

| Cpd # | Structure | IUPAC Name |
|---|---|---|
| 384 | 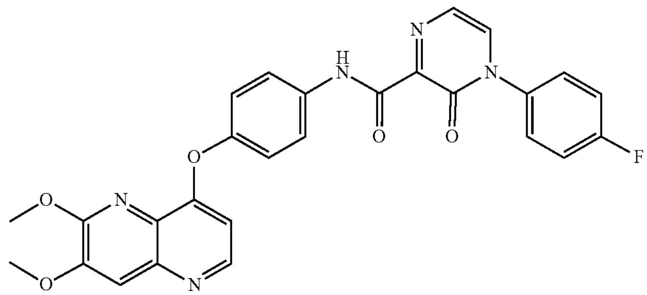 | N-[4-[(6,7-dimethoxy-1,5-naphthyridin-4-yl)oxy]phenyl]-4-(4-fluorophenyl)-3-oxopyrazine-2-carboxamide |
| 385 | 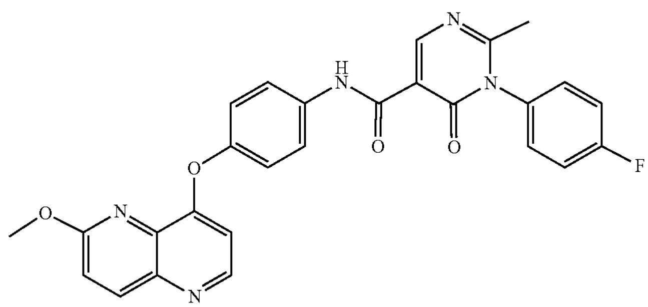 [SMILES: COc1ccc2nccc(Oc3ccc(NC(=O)c4cnc(C)n(-c5ccc(F)cc5)c4=O)cc3)c2n1] | 1-(4-fluorophenyl)-N-[4-[(6-methoxy-1,5-naphthyridin-4-yl)oxy]phenyl]-2-methyl-6-oxopyrimidine-5-carboxamide |
| 386 | 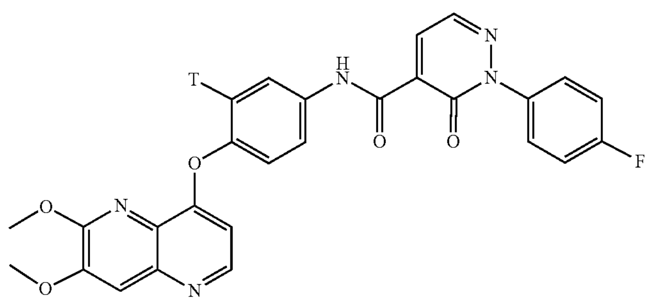 | N-[4-[(6,7-dimethoxy-1,5-naphthyridin-4-yl)oxy]-3-fluorophenyl]-2-(4-fluorophenyl)-3-oxopyridazine-4-carboxamide |
| 387 | 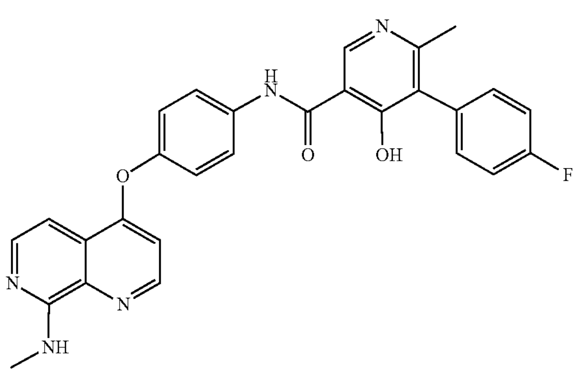 [SMILES: CNc1nccc2c(Oc3ccc(NC(=O)c4cnc(C)c(-c5ccc(F)cc5)c4O)cc3)ccnc12] | 5-(4-fluorophenyl)-4-hydroxy-6-methyl-N-[4-[[8-(methylamino)-1,7-naphthyridin-4-yl]oxy]phenyl]pyridine-3-carboxamide |

| Cpd # | Structure | IUPAC Name |
|---|---|---|
| 388 | 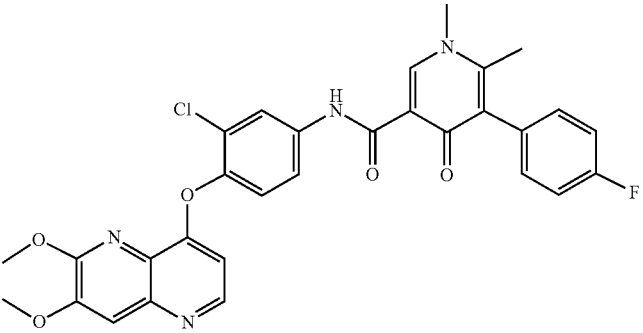 [SMILES: COc1cc2nccc(Oc3ccc(NC(=O)c4cn(C)c(C)c(-c5ccc(F)cc5)c4=O)cc3Cl)c2nc1OC] | N-[3-chloro-4-[(6,7-dimethoxy-1,5-naphthyridin-4-yl)oxy]phenyl]-5-(4-fluorophenyl)-1,6-dimethyl-4-oxopyridine-3-carboxamide |
| 389 | 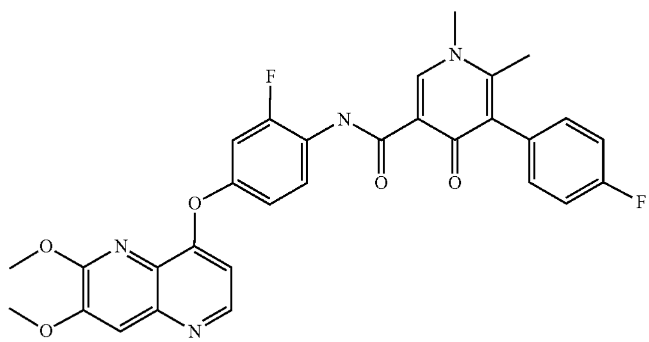 | N-[4-[(6,7-dimethoxy-1,5-naphthyridin-4-yl)oxy]-2-fluorophenyl]-5-(4-fluorophenyl)-1,6-dimethyl-4-oxopyridine-3-carboxamide |
| 390 | 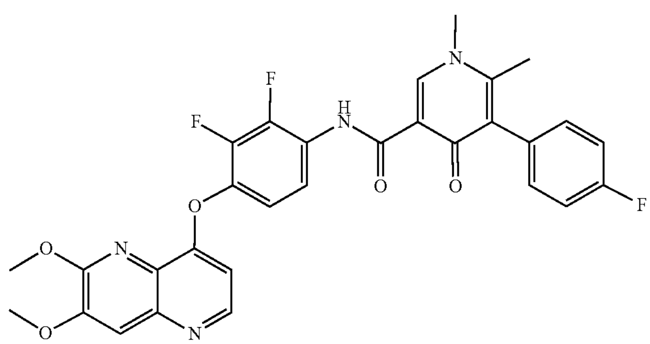 [SMILES: COc1cc2nccc(Oc3ccc(NC(=O)c4cn(C)c(C)c(-c5ccc(F)cc5)c4=O)c(F)c3F)c2nc1OC] | N-[4-[(6,7-dimethoxy-1,5-naphthyridin-4-yl)oxy]-2,3-difluorophenyl]-5-(4-fluorophenyl)-1,6-dimethyl-4-oxopyridine-3-carboxamide |
| 391 | 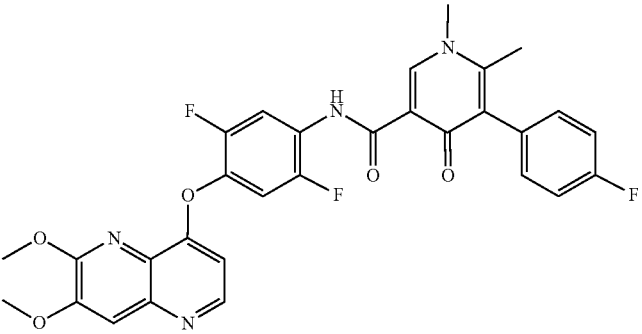 [SMILES: COc1cc2nccc(Oc3cc(F)c(NC(=O)c4cn(C)c(C)c(-c5ccc(F)cc5)c4=O)cc3F)c2nc1OC] | N-[4-[(6,7-dimethoxy-1,5-naphthyridin-4-yl)oxy]-2,5-difluorophenyl]-5-(4-fluorophenyl)-1,6-dimethyl-4-oxopyridine-3-carboxamide |

| Cpd # | Structure | IUPAC Name |
|---|---|---|
| 392 | 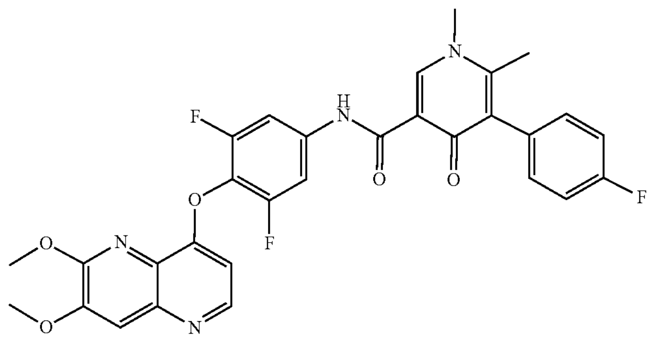 [SMILES: COc1cc2nccc(Oc3c(F)cc(NC(=O)c4cn(C)c(C)c(-c5ccc(F)cc5)c4=O)cc3F)c2nc1OC] | N-[4-[(6,7-dimethoxy-1,5-naphthyridin-4-yl)oxy]-3,5-difluorophenyl]-5-(4-fluorophenyl)-1,6-dimethyl-4-oxopyridine-3-carboxamide |
| 393 | 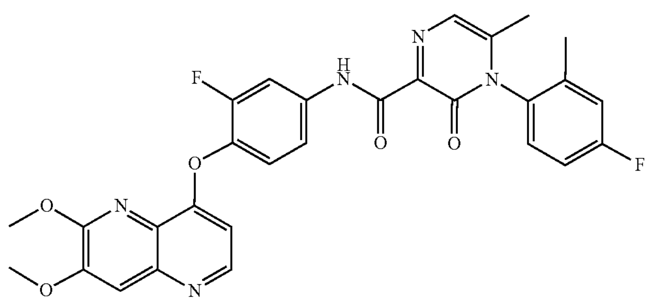 [SMILES: COc1cc2nccc(Oc3ccc(NC(=O)c4ncc(C)n(-c5ccc(F)cc5C)c4=O)cc3F)c2nc1OC] | N-[4-[(6,7-dimethoxy-1,5-naphthyridin-4-yl)oxy]-3-fluorophenyl]-4-(4-fluoro-2-methylphenyl)-5-methyl-3-oxopyrazine-2-carboxamide |
| 394 | 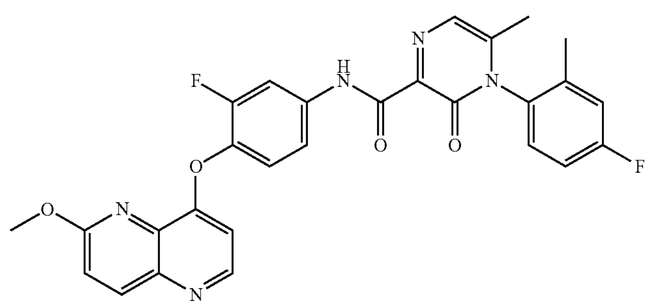 | N-[3-fluoro-4-[(6-methoxy-1,5-naphthyridin-4-yl)oxy]phenyl]-4-(4-fluoro-2-methylphenyl)-5-methyl-3-oxopyrazine-2-carboxamide |
| 395 | 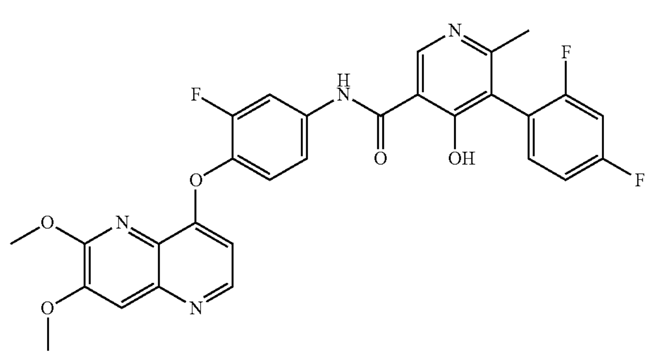 [SMILES: COc1cc2nccc(Oc3ccc(NC(=O)c4cnc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-3-fluorophenyl]-4-hydroxy-6-methylpyridine-3-carboxamide |

-continued

| Cpd # | Structure | IUPAC Name |
|---|---|---|
| 396 | 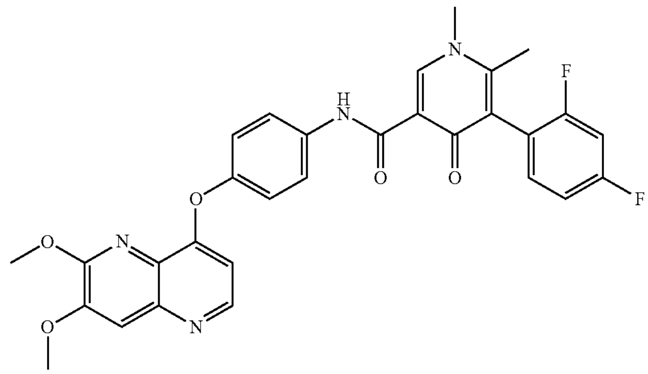 [SMILES: COc1cc2nccc(Oc3ccc(NC(=O)c4cn(C)c(C)c(-c5ccc(F)cc5F)c4=O)cc3)c2nc1OC] | 5-(2,4-difluorophenyl)-N-[4-[(6,7-dimethoxy-1,5-naphthyridin-4-yl)oxy]phenyl]-1,6-dimethyl-4-oxopyridine-3-carboxamide |
| 397 | 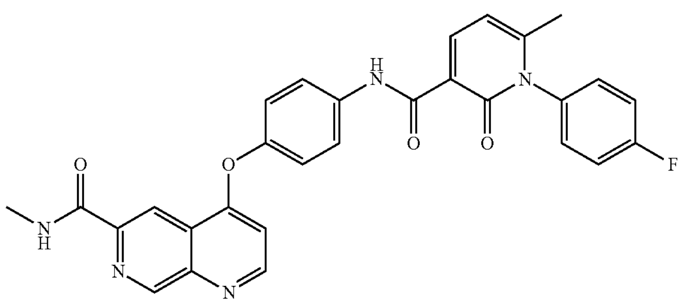 [SMILES: CNC(=O)c1cc2c(Oc3ccc(NC(=O)c4ccc(C)n(-c5ccc(F)cc5)c4=O)cc3)ccnc2cn1] | 4-[4-[1-(4-fluorophenyl)-6-methyl-2-oxopyridine-3-carbonyl]amino]phenoxy]-N-methyl-1,7-naphthyridine-6-carboxamide |
| 398 | 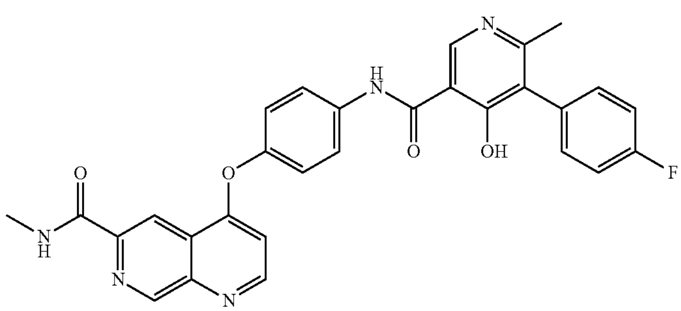 [SMILES: CNC(=O)c1cc2c(Oc3ccc(NC(=O)c4cnc(C)c(-c5ccc(F)cc5)c4O)cc3)ccnc2cn1] | 4-[4-[[5-(4-fluorophenyl)-4-hydroxy-6-methylpyridine-3-carbonyl]amino]phenoxy]-N-methyl-1,7-naphthyridine-6-carboxamide |
| 399 | 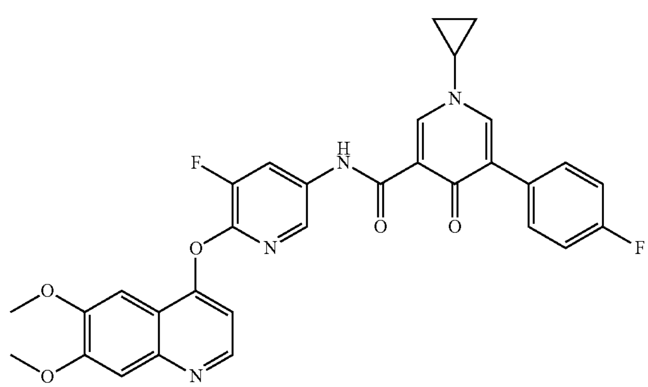 [SMILES: COc1cc2nccc(Oc3ncc(NC(=O)c4cn(C5CC5)cc(-c5ccc(F)cc5)c4=O)cc3F)c2cc1OC] | 1-cyclopropyl-N-[6-(6,7-dimethoxyquinolin-4-yl)oxy-5-fluoropyridin-3-yl]-5-(4-fluorophenyl)-4-oxopyridine-3-carboxamide |

| Cpd # | Structure | IUPAC Name |
|---|---|---|
| 400 | 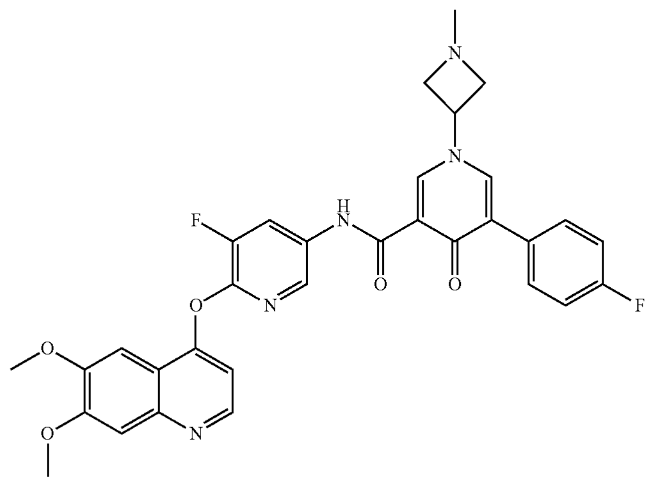 [SMILES: COc1cc2nccc(Oc3ncc(NC(=O)c4cn(C5CN(C)C5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylazetidin-3-yl)-4-oxopyridine-3-carboxamide |
| 401 | 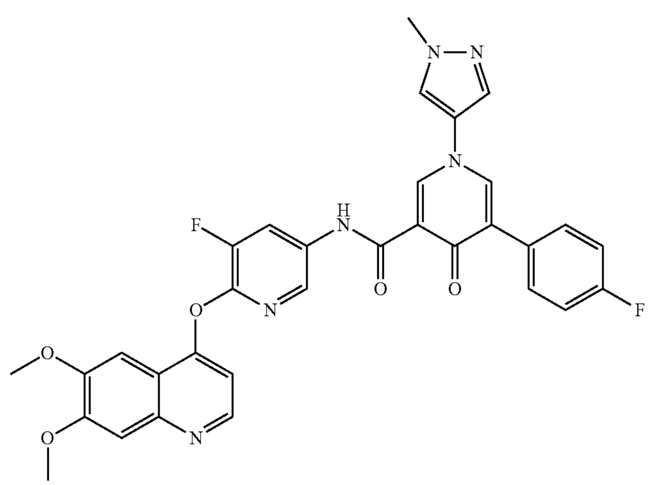 [SMILES: COc1cc2nccc(Oc3ncc(NC(=O)c4cn(-c5cnn(C)c5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylpyrazol-4-yl)-4-oxopyridine-3-carboxamide |
| 402 | 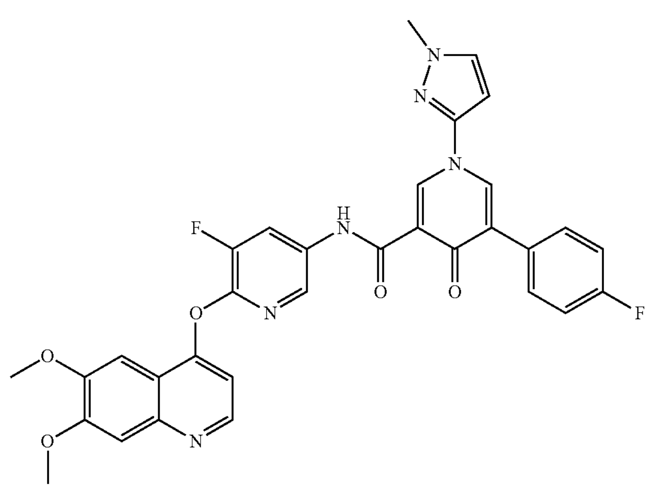 [SMILES: COc1cc2nccc(Oc3ncc(NC(=O)c4cn(-c5ccn(C)n5)cc(-c5ccc(F)cc5)c4=O)cc3F)c2cc1OC] | N-[6-(6,7-dimethoxyquinolin-4-yl)oxy-5-fluoropyridin-3-yl]-5-(4-fluorophenyl)-1-(1-methylpyrazol-3-yl)-4-oxopyridine-3-carboxamide |

| Cpd # | Structure | IUPAC Name |
|---|---|---|
| 403 | 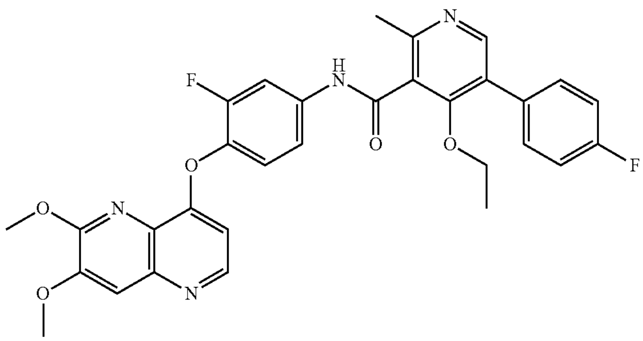 [SMILES: CCOc1c(-c2ccc(F)cc2)cnc(C)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-5-(4-fluorophenyl)-2-methylpyridine-3-carboxamide |
| 404 | 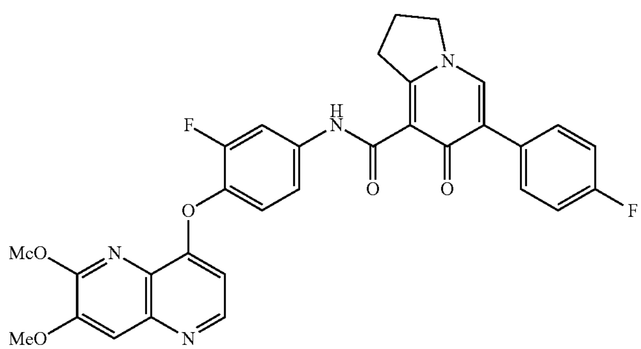 | N-[4-[(6,7-dimethoxy-1,5-naphthyridin-4-yl)oxy]-3-fluorophenyl]-6-(4-fluorophenyl)-7-oxo-2,3-dihydro-1H-indolizine-8-carboxamide |
| 405 | 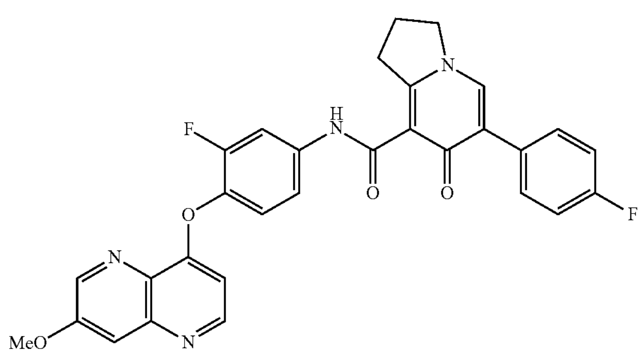 [SMILES: COc1cnc2c(Oc3ccc(NC(=O)c4c5n(cc(-c6ccc(F)cc6)c4=O)CCC5)cc3F)ccnc2c1] | N-[3-fluoro-4-[(7-methoxy-1,5-naphthyridin-4-yl)oxy]phenyl]-6-(4-fluorophenyl)-7-oxo-2,3-dihydro-1H-indolizine-8-carboxamide |
| 406 | 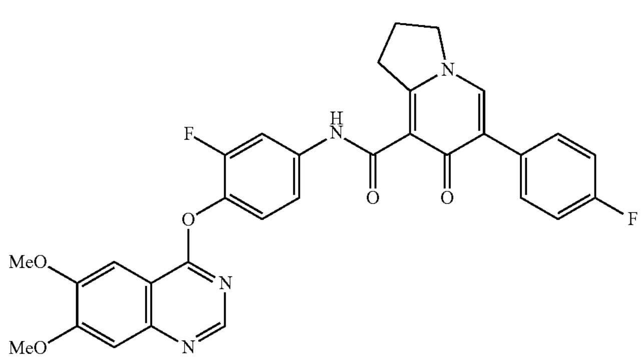 | N-[4-(6,7-dimethoxyquinazolin-4-yl)oxy-3-fluorophenyl]-6-(4-fluorophenyl)-7-oxo-2,3-dihydro-1H-indolizine-8-carboxamide |

| Cpd # | Structure | IUPAC Name |
|---|---|---|
| 407 | 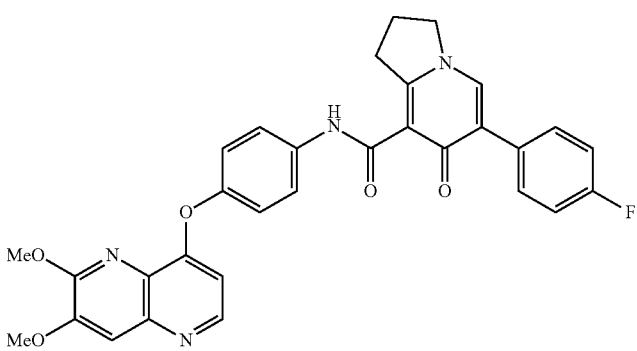 [SMILES: COc1cc2nccc(Oc3ccc(NC(=O)c4c5n(cc(-c6ccc(F)cc6)c4=O)CCC5)cc3)c2nc1OC] | N-[4-[(6,7-dimethoxy-1,5-naphthyridin-4-yl)oxy]phenyl]-6-(4-fluorophenyl)-7-oxo-2,3-dihydro-1H-indolizine-8-carboxamide |
| 408 | 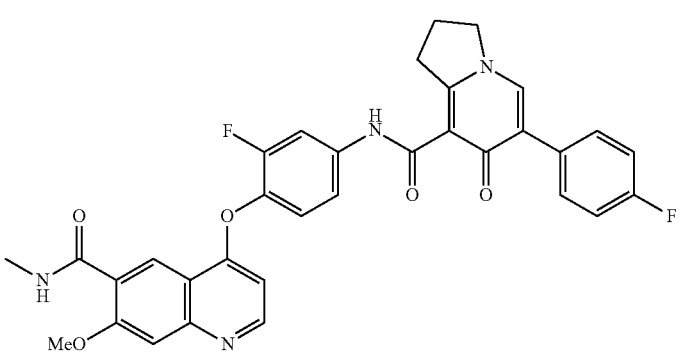 [SMILES: CNC(=O)c1cc2c(Oc3ccc(NC(=O)c4c5n(cc(-c6ccc(F)cc6)c4=O)CCC5)cc3F)ccnc2cc1OC] | 4-[2-fluoro-4-[[6-(4-fluorophenyl)-7-oxo-2,3-dihydro-1H-indolizine-8-carbonyl]amino]phenoxy]-7-methoxy-N-methylquinoline-6-carboxamide |
| 409 | 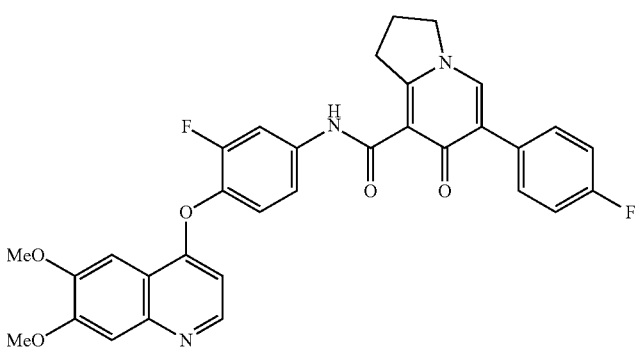 [SMILES: COc1cc2nccc(Oc3ccc(NC(=O)c4c5n(cc(-c6ccc(F)cc6)c4=O)CCC5)cc3F)c2cc1OC] | N-[4-(6,7-dimethoxyquinolin-4-yl)oxy-3-fluorophenyl]-6-(4-fluorophenyl)-7-oxo-2,3-dihydro-1H-indolizine-8-carboxamide |
| 410 | 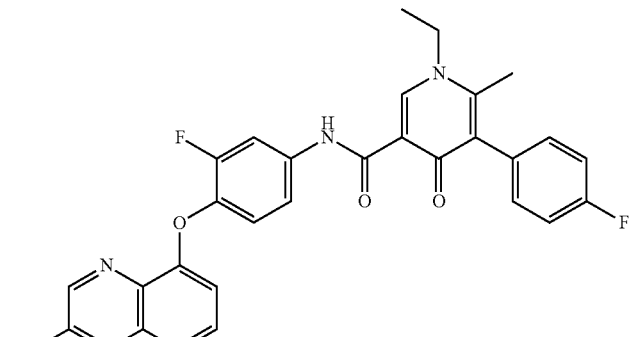 | 1-ethyl-N-[3-fluoro-4-[(7-hydroxy-1,5-naphthyridin-4-yl)oxy]phenyl]-5-(4-fluorophenyl)-6-methyl-4-oxopyridine-3-carboxamide |

| Cpd # | Structure | IUPAC Name |
|---|---|---|
| 411 | 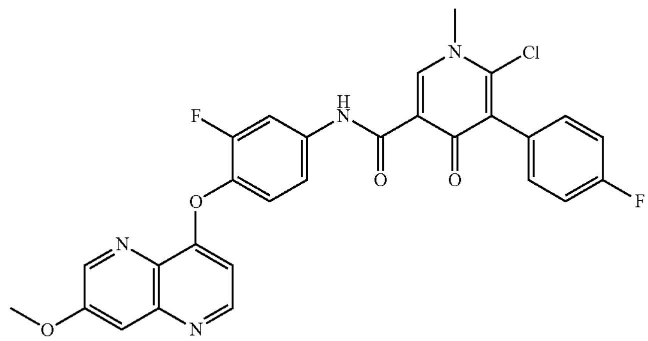 [SMILES: COc1cnc2c(Oc3ccc(NC(=O)c4cn(C)c(Cl)c(-c5ccc(F)cc5)c4=O)cc3F)ccnc2c1] | 6-chloro-N-[3-fluoro-4-[(7-methoxy-1,5-naphthyridin-4-yl)oxy]phenyl]-5-(4-fluorophenyl)-1-methyl-4-oxopyridine-3-carboxamide |
| 412 | 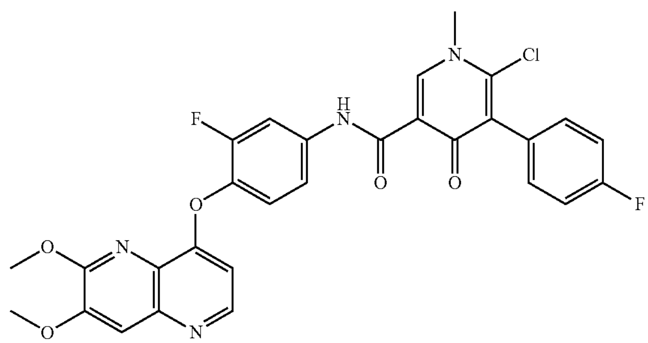 | 6-chloro-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 413 | 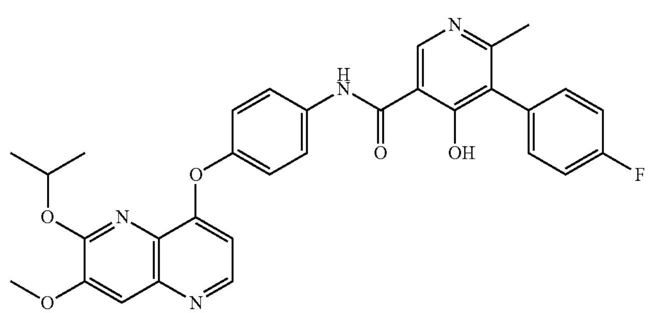 [SMILES: COc1cc2nccc(Oc3ccc(NC(=O)c4cnc(C)c(-c5ccc(F)cc5)c4O)cc3)c2nc1OC(C)C] | 5-(4-fluorophenyl)-4-hydroxy-N-[4-[(7-methoxy-6-propan-2-yloxy-1,5-naphthyridin-4-yl)oxy]phenyl]-6-methylpyridine-3-carboxamide |
| 414 | 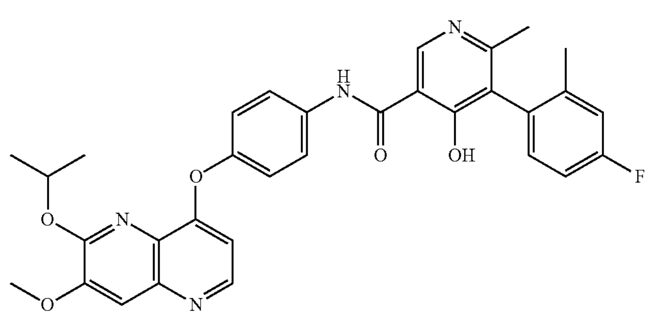 [SMILES: COc1cc2nccc(Oc3ccc(NC(=O)c4cnc(C)c(-c5ccc(F)cc5C)c4O)cc3)c2nc1OC(C)C] | 5-(4-fluoro-2-methylphenyl)-4-hydroxy-N-[4-[(7-methoxy-6-propan-2-yloxy-1,5-naphthyridin-4-yl)oxy]phenyl]-6-methylpyridine-3-carboxamide |

-continued

| Cpd # | Structure | IUPAC Name |
|---|---|---|
| 415 | 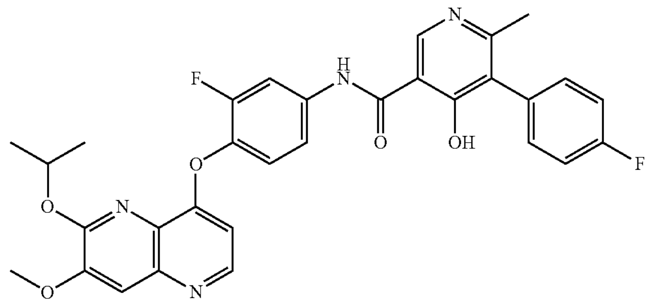 [SMILES: COc1cc2nccc(Oc3ccc(NC(=O)c4cnc(C)c(-c5ccc(F)cc5)c4O)cc3F)c2nc1OC(C)C] | N-[3-fluoro-4-[(7-methoxy-6-propan-2-yloxy-1,5-naphthyridin-4-yl)oxy]phenyl]-5-(4-fluorophenyl)-4-hydroxy-6-methylpyridine-3-carboxamide |
| 416 | 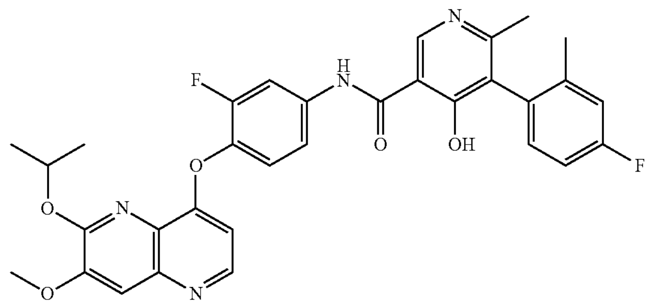 | N-[3-fluoro-4-[(7-methoxy-6-propan-2-yloxy-1,5-naphthyridin-4-yl)oxy]phenyl]-5-(4-fluoro-2-methylphenyl)-4-hydroxy-6-methylpyridine-3-carboxamide |
| 417 | 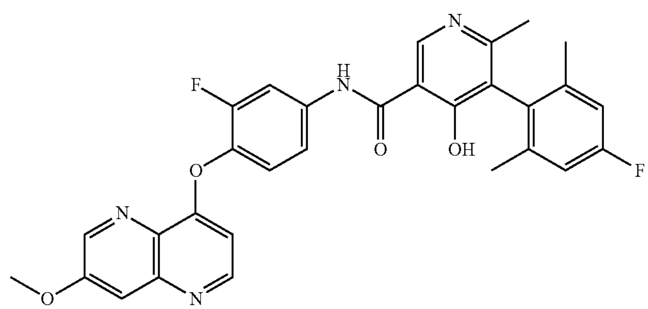 [SMILES: COc1cnc2c(Oc3ccc(NC(=O)c4cnc(C)c(-c5c(C)cc(F)cc5C)c4O)cc3F)ccnc2c1] | 5-(4-fluoro-2,6-dimethylphenyl)-N-[3-fluoro-4-[(7-methoxy-1,5-naphthyridin-4-yl)oxy]phenyl]-4-hydroxy-6-methylpyridine-3-carboxamide |
| 418 | 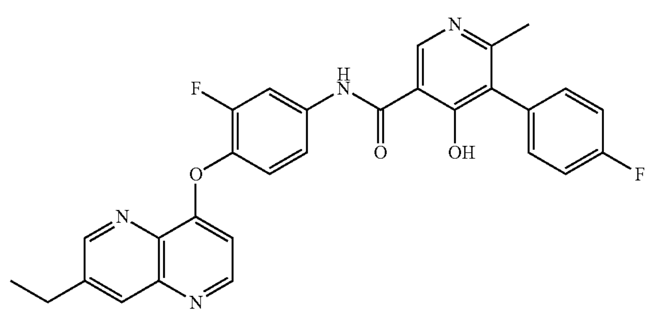 | N-[4-[(7-ethyl-1,5-naphthyridin-4-yl)oxy]-3-fluorophenyl]-5-(4-fluorophenyl)-4-hydroxy-6-methylpyridine-3-carboxamide |
| 419 | 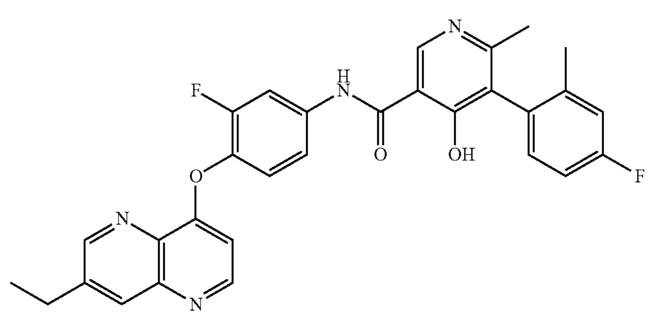 [SMILES: CCc1cnc2c(Oc3ccc(NC(=O)c4cnc(C)c(-c5ccc(F)cc5C)c4O)cc3F)ccnc2c1] | N-[4-[(7-ethyl-1,5-naphthyridin-4-yl)oxy]-3-fluorophenyl]-5-(4-fluoro-2-methylphenyl)-4-hydroxy-6-methylpyridine-3-carboxamide |

| Cpd # | Structure | IUPAC Name |
|---|---|---|
| 420 | 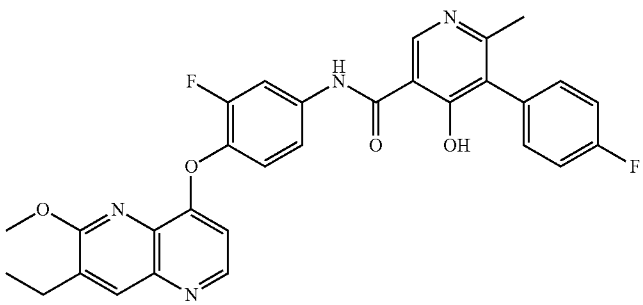 [SMILES: CCc1cc2nccc(Oc3ccc(NC(=O)c4cnc(C)c(-c5ccc(F)cc5)c4O)cc3F)c2nc1OC] | N-[4-[(7-ethyl-6-methoxy-1,5-naphthyridin-4-yl)oxy]-3-fluorophenyl]-5-(4-fluorophenyl)-4-hydroxy-6-methylpyridine-3-carboxamide |
| 421 | 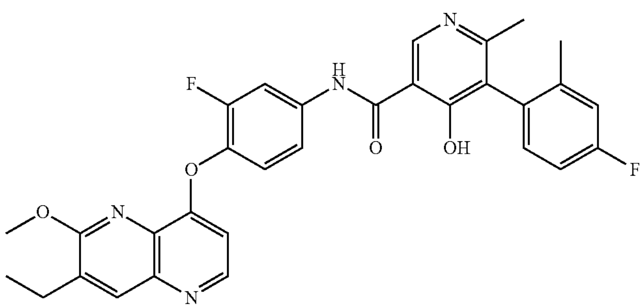 [SMILES: CCc1cc2nccc(Oc3ccc(NC(=O)c4cnc(C)c(-c5ccc(F)cc5C)c4O)cc3F)c2nc1OC] | N-[4-[(7-ethyl-6-methoxy-1,5-naphthyridin-4-yl)oxy]-3-fluorophenyl]-5-(4-fluoro-2-methylphenyl)-4-hydroxy-6-methylpyridine-3-carboxamide |
| 422 | 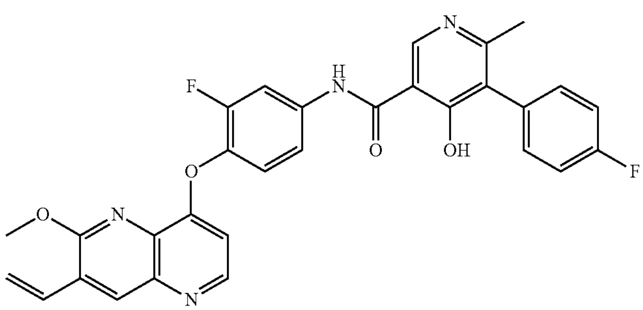 [SMILES: C=Cc1cc2nccc(Oc3ccc(NC(=O)c4cnc(C)c(-c5ccc(F)cc5)c4O)cc3F)c2nc1OC] | N-[4-[(7-ethenyl-6-methoxy-1,5-naphthyridin-4-yl)oxy]-3-fluorophenyl]-5-(4-fluorophenyl)-4-hydroxy-6-methylpyridine-3-carboxamide |
| 423 | 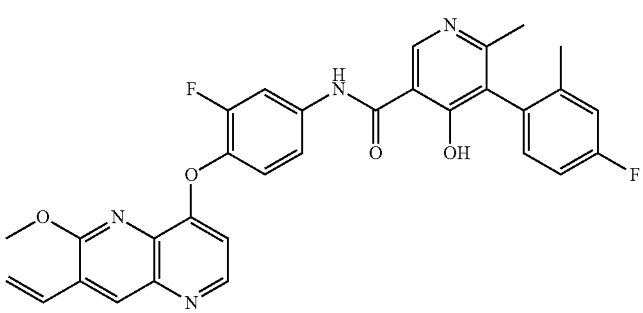 [SMILES: C=Cc1cc2nccc(Oc3ccc(NC(=O)c4cnc(C)c(-c5ccc(F)cc5C)c4O)cc3F)c2nc1OC] | N-[4-[(7-ethenyl-6-methoxy-1,5-naphthyridin-4-yl)oxy]-3-fluorophenyl]-5-(4-fluoro-2-methylphenyl)-4-hydroxy-6-methylpyridine-3-carboxamide |
| 424 | 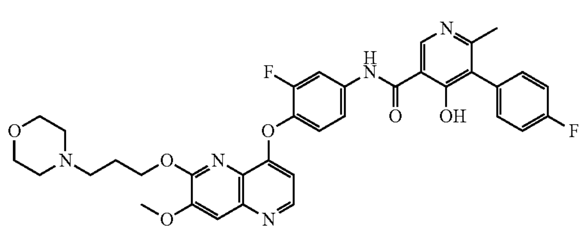 [SMILES: COc1cc2nccc(Oc3ccc(NC(=O)c4cnc(C)c(-c5ccc(F)cc5)c4O)cc3F)c2nc1OCCCN1CCOCC1] | N-[3-fluoro-4-[[7-methoxy-6-(3-morpholin-4-ylpropoxy)-1,5-naphthyridin-4-yl]oxy]phenyl]-5-(4-fluorophenyl)-4-hydroxy-6-methylpyridine-3-carboxamide |

| Cpd # | Structure | IUPAC Name |
|---|---|---|
| 425 | 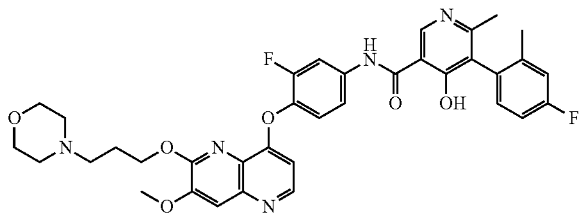 [SMILES: COc1cc2nccc(Oc3ccc(NC(=O)c4cnc(C)c(-c5ccc(F)cc5C)c4O)cc3F)c2nc1OCCCN1CCOCC1] | N-[3-fluoro-4-[[7-methoxy-6-(3-morpholin-4-ylpropoxy)-1,5-naphthyridin-4-yl]oxy]phenyl]-5-(4-fluoro-2-methylphenyl)-4-hydroxy-6-methylpyridine-3-carboxamide |
| 426 | 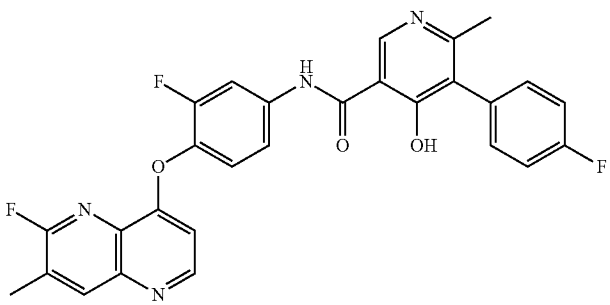 | N-[3-fluoro-4-[(6-fluoro-7-methyl-1,5-naphthyridin-4-yl)oxy]phenyl]-5-(4-fluorophenyl)-4-hydroxy-6-methylpyridine-3-carboxamide |
| 427 | 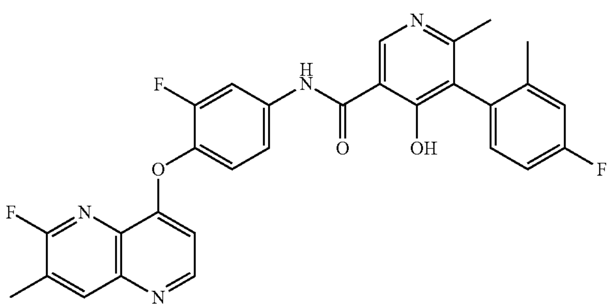 [SMILES: Cc1cc(F)ccc1-c1c(C)ncc(C(=O)Nc2ccc(Oc3ccnc4cc(C)c(F)nc34)c(F)c2)c1O] | N-[3-fluoro-4-[(6-fluoro-7-methyl-1,5-naphthyridin-4-yl)oxy]phenyl]-5-(4-fluoro-2-methylphenyl)-4-hydroxy-6-methylpyridine-3-carboxamide |
| 428 | 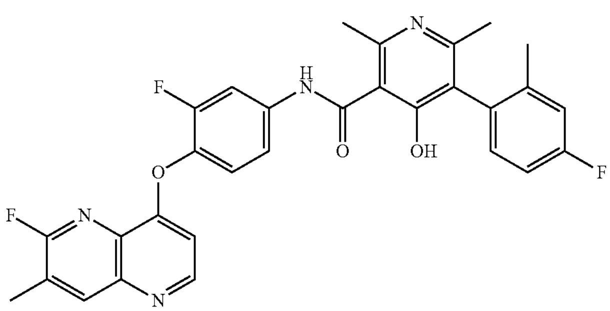 [SMILES: Cc1cc(F)ccc1-c1c(C)nc(C)c(C(=O)Nc2ccc(Oc3ccnc4cc(C)c(F)nc34)c(F)c2)c1O] | N-[3-fluoro-4-[(6-fluoro-7-methyl-1,5-naphthyridin-4-yl)oxy]phenyl]-5-(4-fluoro-2-methylphenyl)-4-hydroxy-2,6-dimethylpyridine-3-carboxamide |
| 429 | 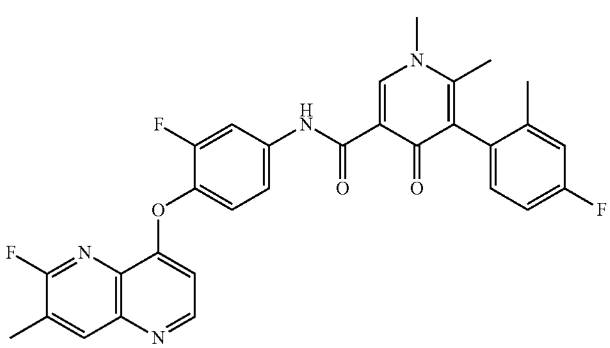 [SMILES: Cc1cc(F)ccc1-c1c(C)n(C)cc(C(=O)Nc2ccc(Oc3ccnc4cc(C)c(F)nc34)c(F)c2)c1=O] | N-[3-fluoro-4-[(6-fluoro-7-methyl-1,5-naphthyridin-4-yl)oxy]phenyl]-5-(4-fluoro-2-methylphenyl)-1,6-dimethyl-4-oxopyridine-3-carboxamide |

| Cpd # | Structure | IUPAC Name |
|---|---|---|
| 430 | 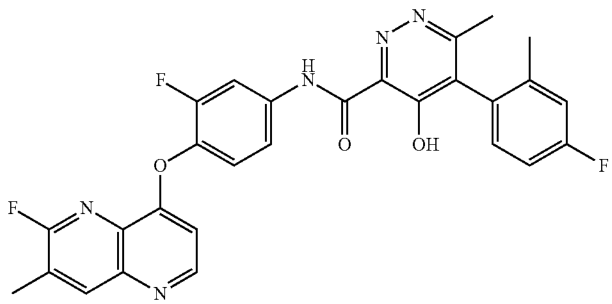 | N-[3-fluoro-4-[(6-fluoro-7-methyl-1,5-naphthyridin-4-yl)oxy]phenyl]-5-(4-fluoro-2-methylphenyl)-4-hydroxy-6-methylpyridazine-3-carboxamide |
| 431 | 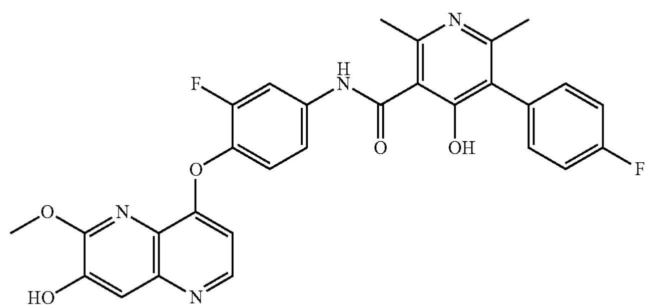 [SMILES: COc1nc2c(Oc3ccc(NC(=O)c4c(C)nc(C)c(-c5ccc(F)cc5)c4O)cc3F)ccnc2cc1O] | N-[3-fluoro-4-[(7-hydroxy-6-methoxy-1,5-naphthyridin-4-yl)oxy]phenyl]-5-(4-fluorophenyl)-4-hydroxy-2,6-dimethylpyridine-3-carboxamide |
| 432 | 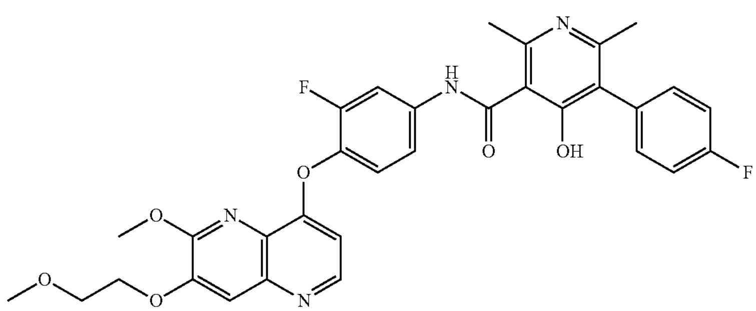 [SMILES: COCCOc1cc2nccc(Oc3ccc(NC(=O)c4c(C)nc(C)c(-c5ccc(F)cc5)c4O)cc3F)c2nc1OC] | N-[3-fluoro-4-[[6-methoxy-7-(2-methoxyethoxy)-1,5-naphthyridin-4-yl]oxy]phenyl]-5-(4-fluorophenyl)-4-hydroxy-2,6-dimethylpyridine-3-carboxamide |
| 433 | 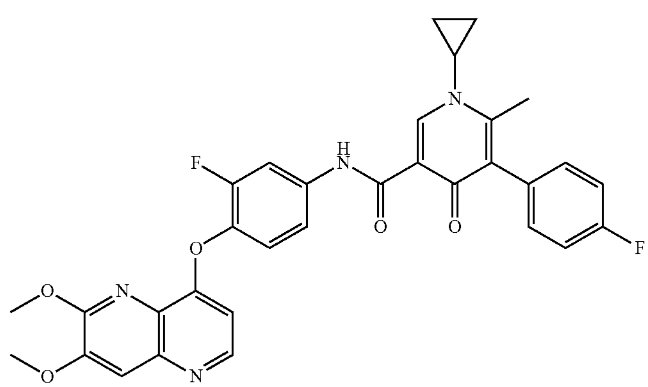 [SMILES: COc1cc2nccc(Oc3ccc(NC(=O)c4cn(C5CC5)c(C)c(-c5ccc(F)cc5)c4=O)cc3F)c2nc1OC] | 1-cyclopropyl-N-[4-[(6,7-dimethoxy-1,5-naphthyridin-4-yl)oxy]-3-fluorophenyl]-5-(4-fluorophenyl)-6-methyl-4-oxopyridine-3-carboxamide |

| Cpd # | Structure | IUPAC Name |
|---|---|---|
| 434 | 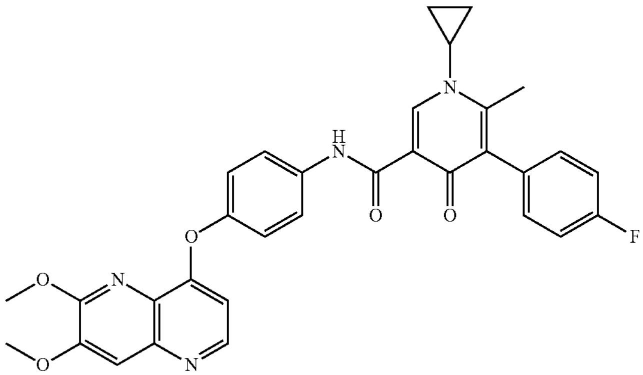 [SMILES: COc1cc2nccc(Oc3ccc(NC(=O)c4cn(C5CC5)c(C)c(-c5ccc(F)cc5)c4=O)cc3)c2nc1OC] | 1-cyclopropyl-N-[4-[(6,7-dimethoxy-1,5-naphthyridin-4-yl)oxy]phenyl]-5-(4-fluorophenyl)-6-methyl-4-oxopyridine-3-carboxamide |
| 435 | 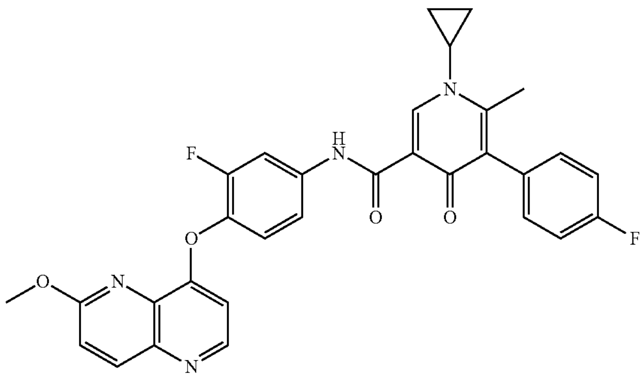 [SMILES: COc1ccc2nccc(Oc3ccc(NC(=O)c4cn(C5CC5)c(C)c(-c5ccc(F)cc5)c4=O)cc3F)c2n1] | 1-cyclopropyl-N-[3-fluoro-4-[(6-methoxy-1,5-naphthyridin-4-yl)oxy]phenyl]-5-(4-fluorophenyl)-6-methyl-4-oxopyridine-3-carboxamide |
| 436 | 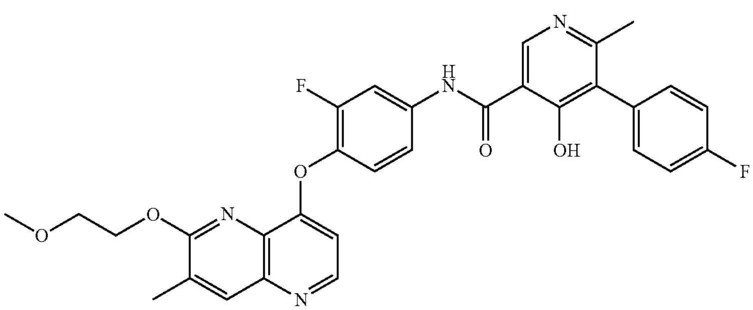 [SMILES: COCCOc1nc2c(Oc3ccc(NC(=O)c4cnc(C)c(-c5ccc(F)cc5)c4O)cc3F)ccnc2cc1C] | N-[3-fluoro-4-[[6-(2-methoxyethoxy)-7-methyl-1,5-naphthyridin-4-yl]oxy]phenyl]-5-(4-fluorophenyl)-4-hydroxy-6-methylpyridine-3-carboxamide |
| 437 | 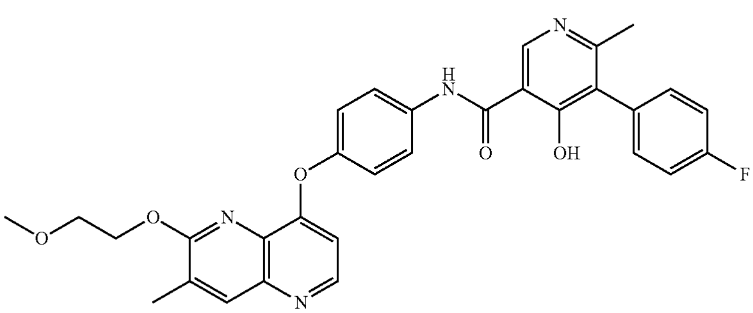 [SMILES: COCCOc1nc2c(Oc3ccc(NC(=O)c4cnc(C)c(-c5ccc(F)cc5)c4O)cc3)ccnc2cc1C] | 5-(4-fluorophenyl)-4-hydroxy-N-[4-[[6-(2-methoxyethoxy)-7-methyl-1,5-naphthyridin-4-yl]oxy]phenyl]-6-methylpyridine-3-carboxamide |
| 438 | 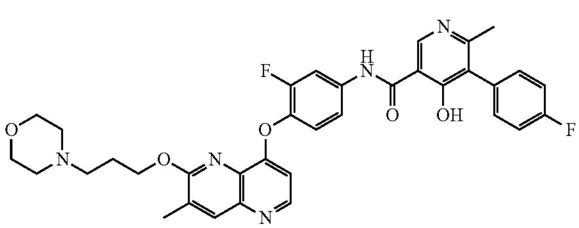 [SMILES: Cc1cc2nccc(Oc3ccc(NC(=O)c4cnc(C)c(-c5ccc(F)cc5)c4O)cc3F)c2nc1OCCCN1CCOCC1] | N-[3-fluoro-4-[7-methyl-6-(3-morpholin-4-ylpropoxy)-1,5-naphthyridin-4-yl]oxy]phenyl]-5-(4-fluorophenyl)-4-hydroxy-6-methylpyridine-3-carboxamide |

-continued

| Cpd # | Structure | IUPAC Name |
|---|---|---|
| 439 | 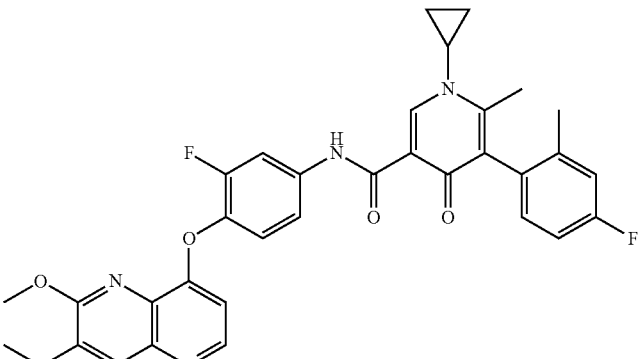 | 1-cyclopropyl-N-[4-[(6,7-dimethoxy-1,5-naphthyridin-4-yl)oxy]-3-fluorophenyl]-5-(4-fluoro-2-methylphenyl)-6-methyl-4-oxopyridine-3-carboxamide |
| 440 | 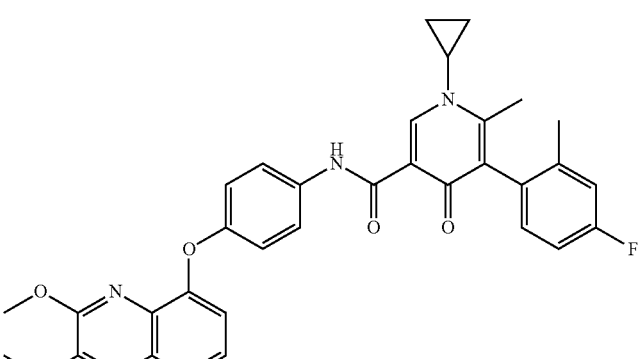 | 1-cyclopropyl-N-[4-[(6,7-dimethoxy-1,5-naphthyridin-4-yl)oxy]phenyl]-5-(4-fluoro-2-methylphenyl)-6-methyl-4-oxopyridine-3-carboxamide |
| 441 | 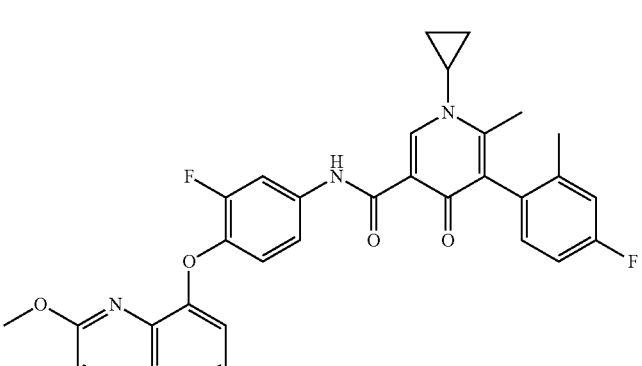 | 1-cyclopropyl-N-[3-fluoro-4-[(6-methoxy-1,5-naphthyridin-4-yl)oxy]phenyl]-5-(4-fluoro-2-methylphenyl)-6-methyl-4-oxopyridine-3-carboxamide |
| 442 | 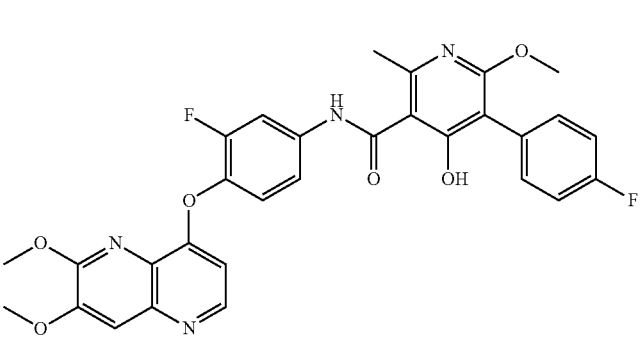 [SMILES: COc1cc2nccc(Oc3ccc(NC(=O)c4c(C)nc(OC)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-6-methoxy-2-methylpyridine-3-carboxamide |

| Cpd # | Structure | IUPAC Name |
|---|---|---|
| 443 | 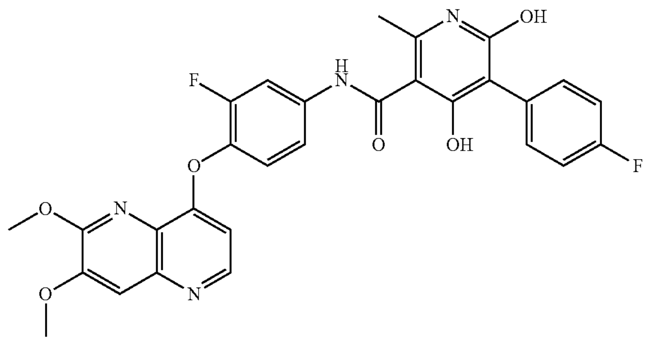 [SMILES: COc1cc2nccc(Oc3ccc(NC(=O)c4c(C)nc(O)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4,6-dihydroxy-2-methylpyridine-3-carboxamide |
| 444 | 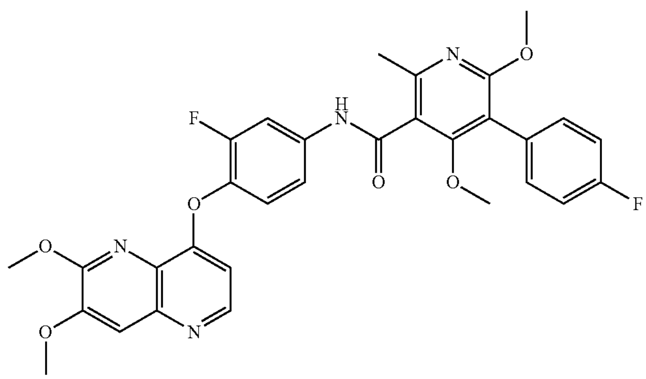 [SMILES: COc1cc2nccc(Oc3ccc(NC(=O)c4c(C)nc(OC)c(-c5ccc(F)cc5)c4OC)cc3F)c2nc1OC] | N-[4-[(6,7-dimethoxy-1,5-naphthyridin-4-yl)oxy]-3-fluorophenyl]-5-(4-fluorophenyl)-4,6-dimethoxy-2-methylpyridine-3-carboxamide |
| 445 | 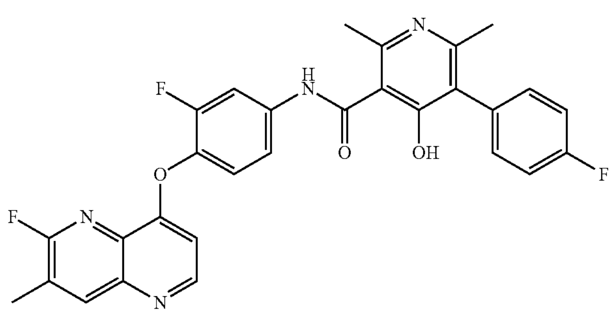 [SMILES: Cc1cc2nccc(Oc3ccc(NC(=O)c4c(C)nc(C)c(-c5ccc(F)cc5)c4O)cc3F)c2nc1F] | N-[3-fluoro-4-[(6-fluoro-7-methyl-1,5-naphthyridin-4-yl)oxy]phenyl]-5-(4-fluorophenyl)-4-hydroxy-2,6-dimethylpyridine-3-carboxamide |
| 446 | 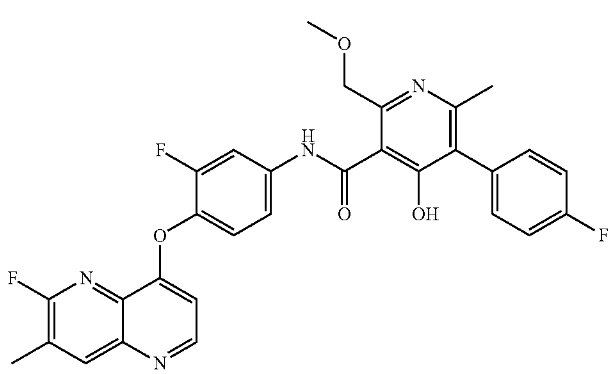 [SMILES: COCc1nc(C)c(-c2ccc(F)cc2)c(O)c1C(=O)Nc1ccc(Oc2ccnc3cc(C)c(F)nc23)c(F)c1] | N-[3-fluoro-4-[(6-fluoro-7-methyl-1,5-naphthyridin-4-yl)oxy]phenyl]-5-(4-fluorophenyl)-4-hydroxy-2-(methoxymethyl)-6-methylpyridine-3-carboxamide |

-continued

| Cpd # | Structure | IUPAC Name |
|---|---|---|
| 447 | 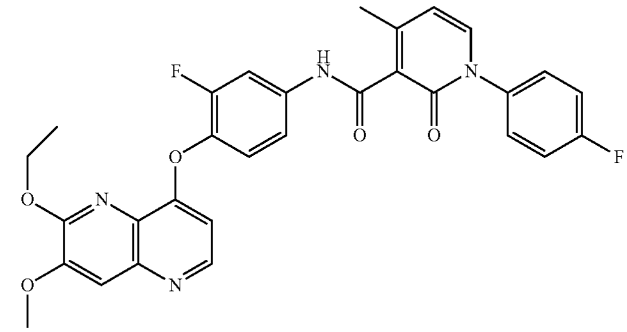 [SMILES: CCOc1nc2c(Oc3ccc(NC(=O)c4c(C)ccn(-c5ccc(F)cc5)c4=O)cc3F)ccnc2cc1OC] | N-[4-[(6-ethoxy-7-methoxy-1,5-naphthyridin-4-yl)oxy]-3-fluorophenyl]-1-(4-fluorophenyl)-4-methyl-2-oxopyridine-3-carboxamide |
| 448 | 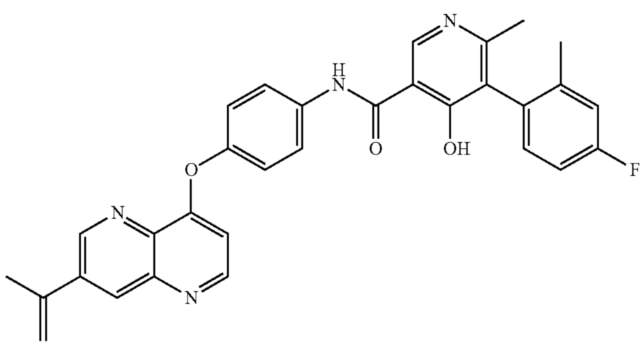 [SMILES: C=C(C)c1cnc2c(Oc3ccc(NC(=O)c4cnc(C)c(-c5ccc(F)cc5C)c4O)cc3)ccnc2c1] | 5-(4-fluoro-2-methylphenyl)-4-hydroxy-6-methyl-N-[4-[(7-prop-1-en-2-yl-1,5-naphthyridin-4-yl)oxy]phenyl]pyridine-3-carboxamide |
| 449 | 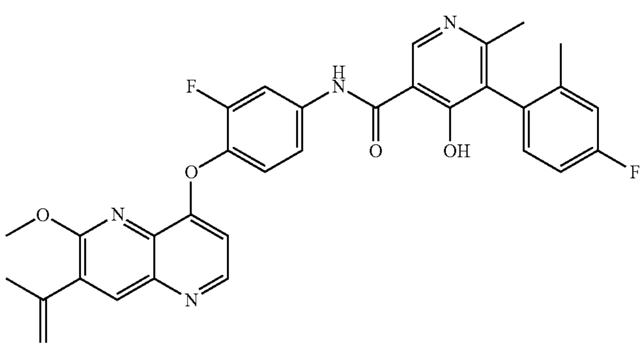 | N-[3-fluoro-4-[(6-methoxy-7-prop-1-en-2-yl-1,5-naphthyridin-4-yl)oxy]phenyl]-5-(4-fluoro-2-methylphenyl)-4-hydroxy-6-methylpyridine-3-carboxamide |
| 450 | 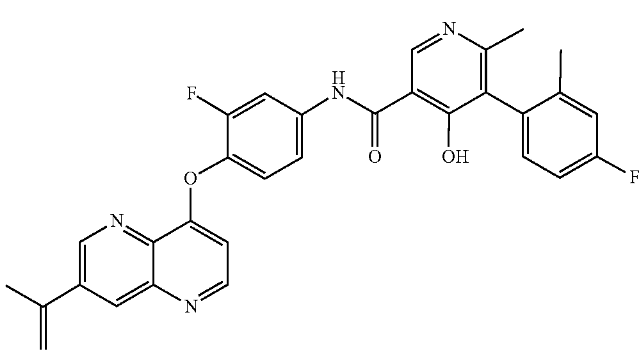 [SMILES: C=C(C)c1cnc2c(Oc3ccc(NC(=O)c4cnc(C)c(-c5ccc(F)cc5C)c4O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-4-hydroxy-6-methylpyridine-3-carboxamide |

| Cpd # | Structure | IUPAC Name |
|---|---|---|
| 451 | 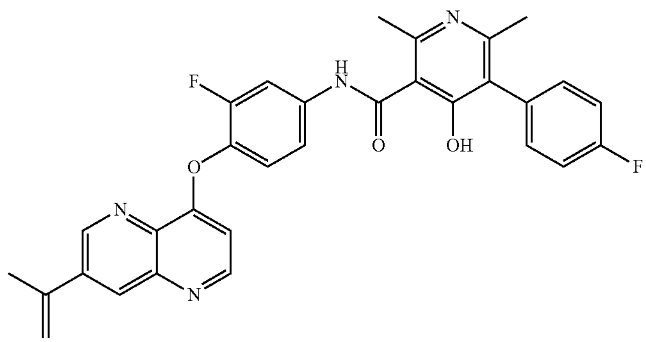 [SMILES: C=C(C)c1cnc2c(Oc3ccc(NC(=O)c4c(C)nc(C)c(-c5ccc(F)cc5)c4O)cc3F)ccnc2c1] | 5-(4-fluorophenyl)-N-[3-fluoro-4-[(7-prop-1-en-2-yl-1,5-naphthyridin-4-yl)oxy]phenyl]-4-hydroxy-2,6-dimethylpyridine-3-carboxamide |
| 452 | 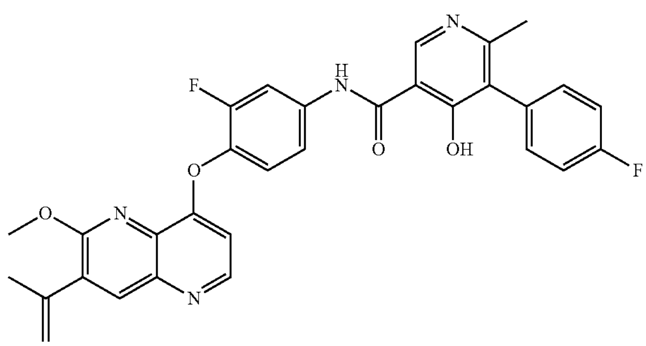 [SMILES: C=C(C)c1cc2nccc(Oc3ccc(NC(=O)c4cnc(C)c(-c5ccc(F)cc5)c4O)cc3F)c2nc1OC] | N-[3-fluoro-4-[(6-methoxy-7-prop-1-en-2-yl-1,5-naphthyridin-4-yl)oxy]phenyl]-5-(4-fluorophenyl)-4-hydroxy-6-methylpyridine-3-carboxamide |
| 453 | 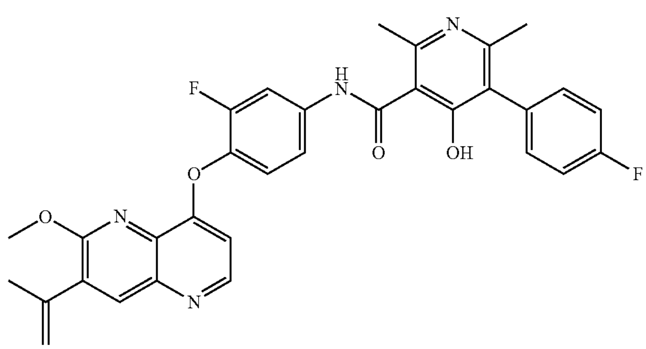 | N-[3-fluoro-4-[(6-methoxy-7-prop-1-en-2-yl-1,5-naphthyridin-4-yl)oxy]phenyl]-5-(4-fluorophenyl)-4-hydroxy-2,6-dimethylpyridine-3-carboxamide |
| 454 | 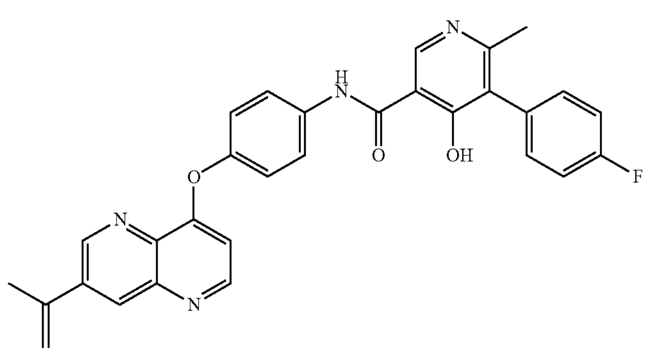 [SMILES: C=C(C)c1cnc2c(Oc3ccc(NC(=O)c4cnc(C)c(-c5ccc(F)cc5)c4O)cc3)ccnc2c1] | 5-(4-fluorophenyl)-4-hydroxy-6-methyl-N-[4-[(7-prop-1-en-2-yl-1,5-naphthyridin-4-yl)oxy]phenyl]pyridine-3-carboxamide |

| Cpd # | Structure | IUPAC Name |
|---|---|---|
| 455 | 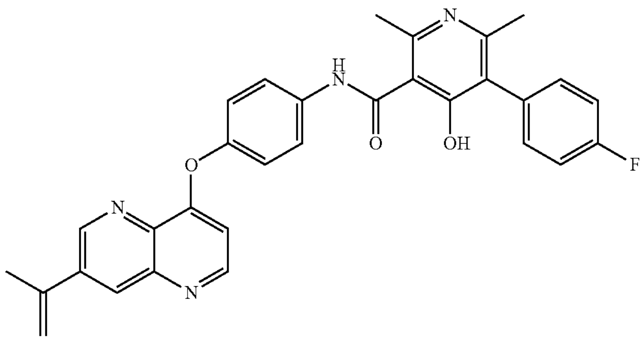 [SMILES: C=C(C)c1cnc2c(Oc3ccc(NC(=O)c4c(C)nc(C)c(-c5ccc(F)cc5)c4O)cc3)ccnc2c1] | 5-(4-fluorophenyl)-4-hydroxy-2,6-dimethyl-N-[4-[(7-prop-1-en-2-yl-1,5-naphthyridin-4-yl)oxy]phenyl]pyridine-3-carboxamide |
| 456 | 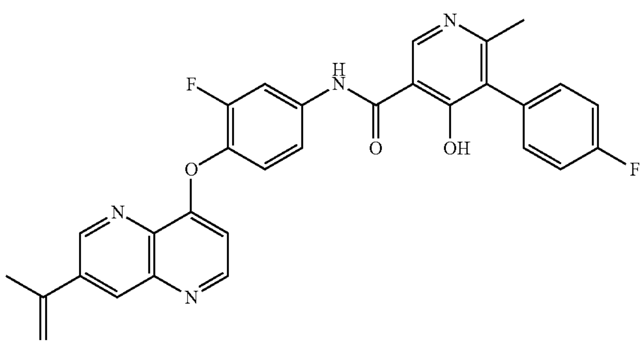 [SMILES: C=C(C)c1cnc2c(Oc3ccc(NC(=O)c4cnc(C)c(-c5ccc(F)cc5)c4O)cc3F)ccnc2c1] | 5-(4-fluorophenyl)-N-[3-fluoro-4-[(7-prop-1-en-2-yl-1,5-naphthyridin-4-yl)oxy]phenyl]-4-hydroxy-6-methylpyridine-3-carboxamide |
| 457 | 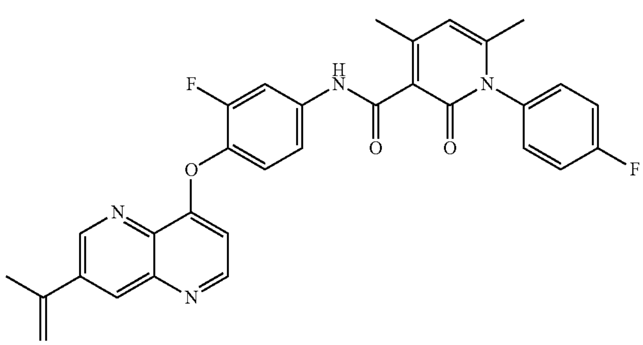 | 1-(4-fluorophenyl)-N-[3-fluoro-4-[(7-prop-1-en-2-yl-1,5-naphthyridin-4-yl)oxy]phenyl]-4,6-dimethyl-2-oxopyridine-3-carboxamide |
| 458 | 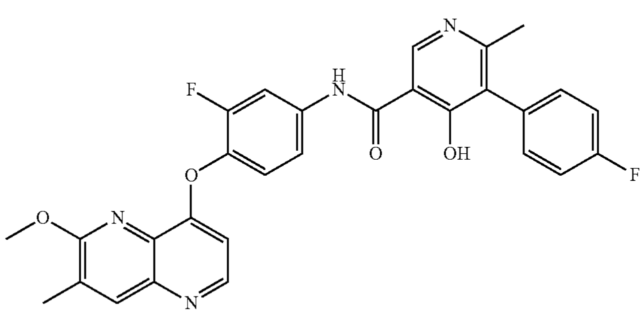 | N-[3-fluoro-4-[(6-methoxy-7-methyl-1,5-naphthyridin-4-yl)oxy]phenyl]-5-(4-fluorophenyl)-4-hydroxy-6-methylpyridine-3-carboxamide |

| Cpd # | Structure | IUPAC Name |
|---|---|---|
| 459 | 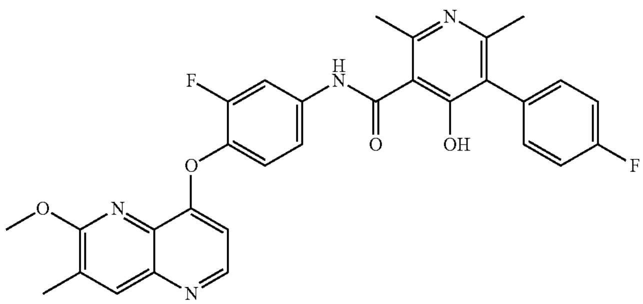 [SMILES: COc1nc2c(Oc3ccc(NC(=O)c4c(C)nc(C)c(-c5ccc(F)cc5)c4O)cc3F)ccnc2cc1C] | N-[3-fluoro-4-[(6-methoxy-7-methyl-1,5-naphthyridin-4-yl)oxy]phenyl]-5-(4-fluorophenyl)-4-hydroxy-2,6-dimethylpyridine-3-carboxamide |
| 460 | 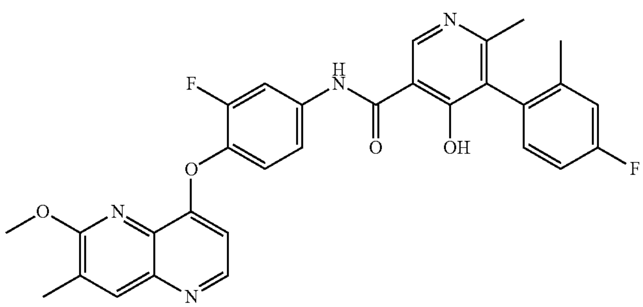 [SMILES: COc1nc2c(Oc3ccc(NC(=O)c4cnc(C)c(-c5ccc(F)cc5C)c4O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-4-hydroxy-6-methylpyridine-3-carboxamide |
| 461 | 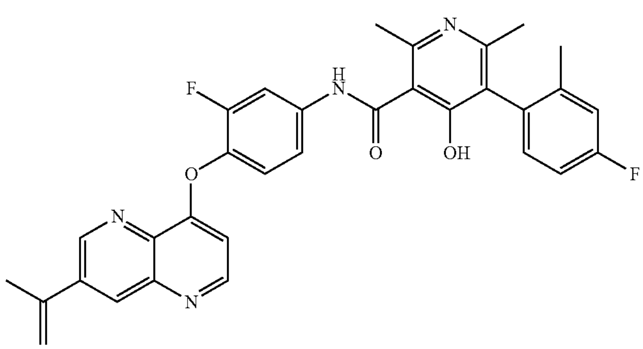 | 5-(4-fluoro-2-methylphenyl)-N-[3-fluoro-4-[(7-prop-1-en-2-yl-1,5-naphthyridin-4-yl)oxy]phenyl]-4-hydroxy-2,6-dimethylpyridine-3-carboxamide |
| 462 | 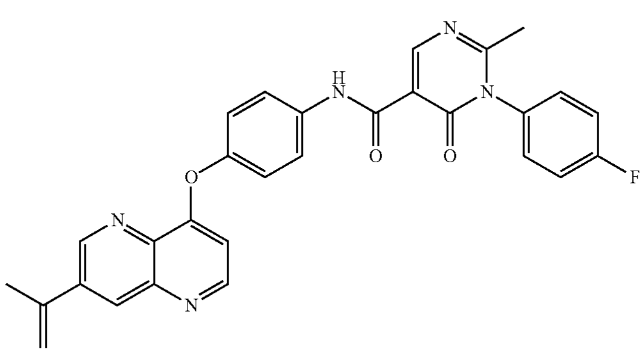 | 1-(4-fluorophenyl)-2-methyl-6-oxo-N-[4-[(7-prop-1-en-2-yl-1,5-naphthyridin-4-yl)oxy]phenyl]pyrimidine-5-carboxamide |

| Cpd # | Structure | IUPAC Name |
|---|---|---|
| 463 | 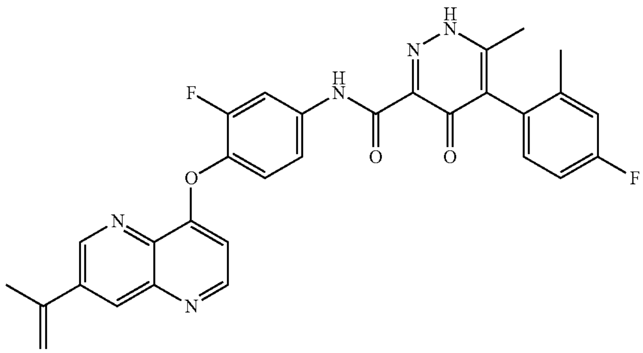 [SMILES: C=C(C)c1cnc2c(Oc3ccc(NC(=O)c4n[nH]c(C)c(-c5ccc(F)cc5C)c4=O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-6-methyl-4-oxo-1H-pyridazine-3-carboxamide |
| 464 | 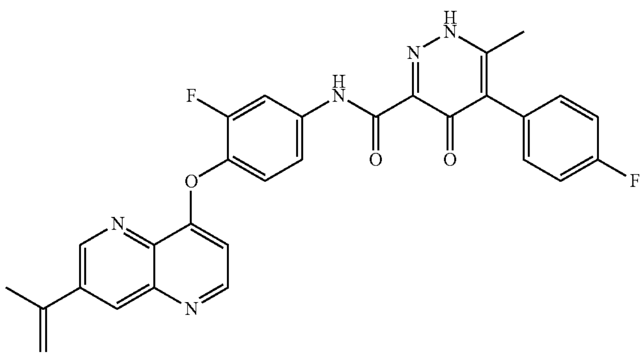 [SMILES: C=C(C)c1cnc2c(Oc3ccc(NC(=O)c4n[nH]c(C)c(-c5ccc(F)cc5)c4=O)cc3F)ccnc2c1] | 5-(4-fluorophenyl)-N-[3-fluoro-4-[(7-prop-1-en-2-yl-1,5-naphthyridin-4-yl)oxy]phenyl]-6-methyl-4-oxo-1H-pyridazine-3-carboxamide |
| 465 | 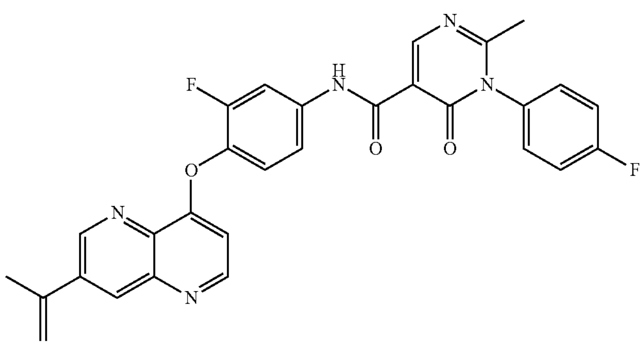 [SMILES: C=C(C)c1cnc2c(Oc3ccc(NC(=O)c4cnc(C)n(-c5ccc(F)cc5)c4=O)cc3F)ccnc2c1] | 1-(4-fluorophenyl)-N-[3-fluoro-4-[(7-prop-1-en-2-yl-1,5-naphthyridin-4-yl)oxy]phenyl]-2-methyl-6-oxopyrimidine-5-carboxamide |
| 466 | 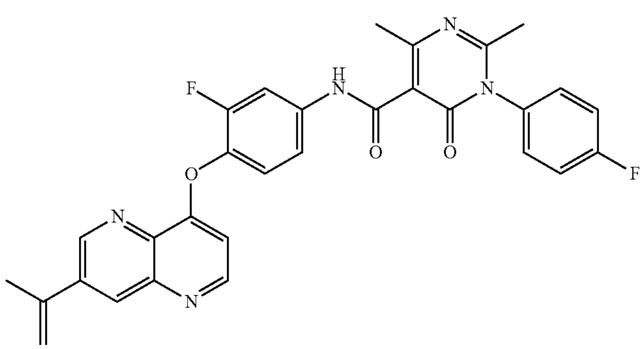 [SMILES: C=C(C)c1cnc2c(Oc3ccc(NC(=O)c4c(C)nc(C)n(-c5ccc(F)cc5)c4=O)cc3F)ccnc2c1] | 1-(4-fluorophenyl)-N-[3-fluoro-4-[(7-prop-1-en-2-yl-1,5-naphthyridin-4-yl)oxy]phenyl]-2,4-dimethyl-6-oxopyrimidine-5-carboxamide |

| Cpd # | Structure | IUPAC Name |
|---|---|---|
| 467 | 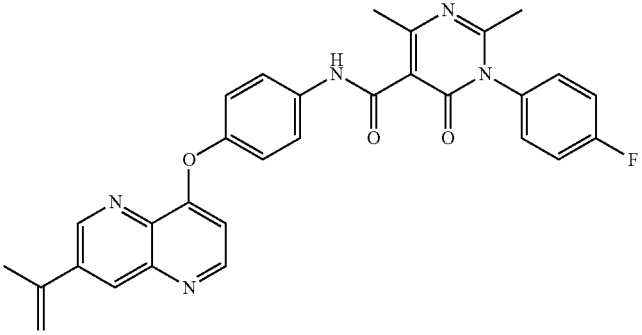 [SMILES: C=C(C)c1cnc2c(Oc3ccc(NC(=O)c4c(C)nc(C)n(-c5ccc(F)cc5)c4=O)cc3)ccnc2c1] | 1-(4-fluorophenyl)-2,4-dimethyl-6-oxo-N-[4-[(7-prop-1-en-2-yl-1,5-naphthyridin-4-yl)oxy]phenyl]pyrimidine-5-carboxamide |
| 468 | 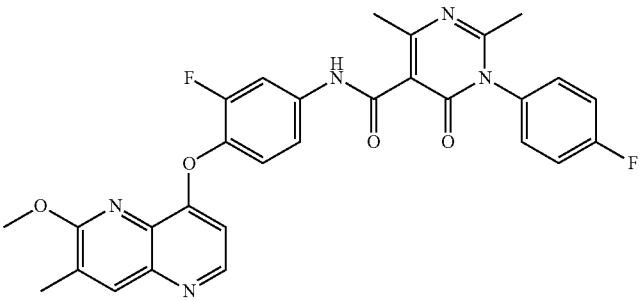 [SMILES: COc1nc2c(Oc3ccc(NC(=O)c4c(C)nc(C)n(-c5ccc(F)cc5)c4=O)cc3F)ccnc2cc1C] | N-[3-fluoro-4-[(6-methoxy-7-methyl-1,5-naphthyridin-4-yl)oxy]phenyl]-1-(4-fluorophenyl)-2,4-dimethyl-6-oxopyrimidine-5-carboxamide |
| 469 | 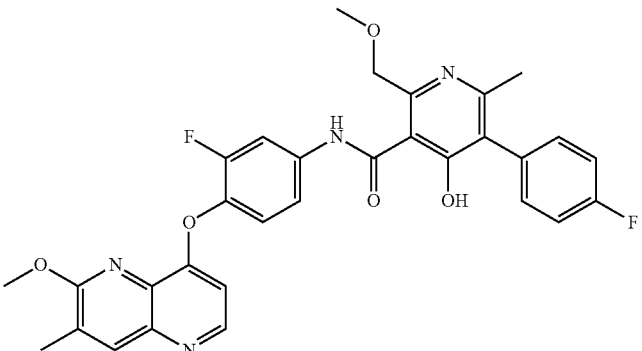 | N-[3-fluoro-4-[(6-methoxy-7-methyl-1,5-naphthyridin-4-yl)oxy]phenyl]-5-(4-fluorophenyl)-4-hydroxy-2-(methoxymethyl)-6-methylpyridine-3-carboxamide |
| 470 | 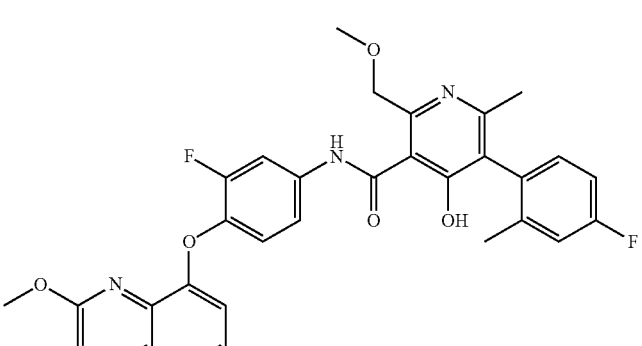 | N-[3-fluoro-4-[(6-methoxy-7-methyl-1,5-naphthyridin-4-yl)oxy]phenyl]-5-(4-fluoro-2-methylphenyl)-4-hydroxy-2-(methoxymethyl)-6-methylpyridine-3-carboxamide |

| Cpd # | Structure | IUPAC Name |
|---|---|---|
| 471 | 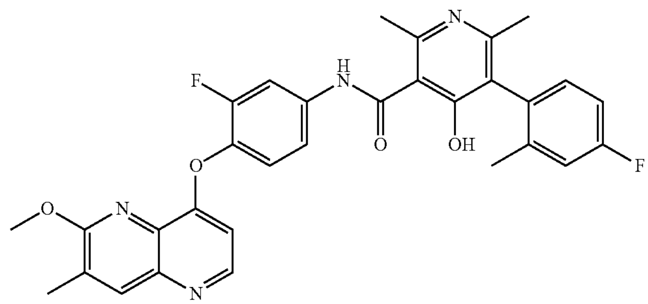 [SMILES: COc1nc2c(Oc3ccc(NC(=O)c4c(C)nc(C)c(-c5ccc(F)cc5C)c4O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-4-hydroxy-2,6-dimethylpyridine-3-carboxamide |
| 472 | 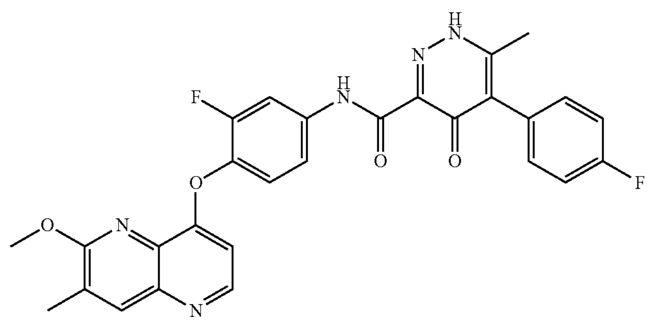 [SMILES: COc1nc2c(Oc3ccc(NC(=O)c4n[nH]c(C)c(-c5ccc(F)cc5)c4=O)cc3F)ccnc2cc1C] | N-[3-fluoro-4-[(6-methoxy-7-methyl-1,5-naphthyridin-4-yl)oxy]phenyl]-5-(4-fluorophenyl)-6-methyl-4-oxo-1H-pyridazine-3-carboxamide |
| 473 | 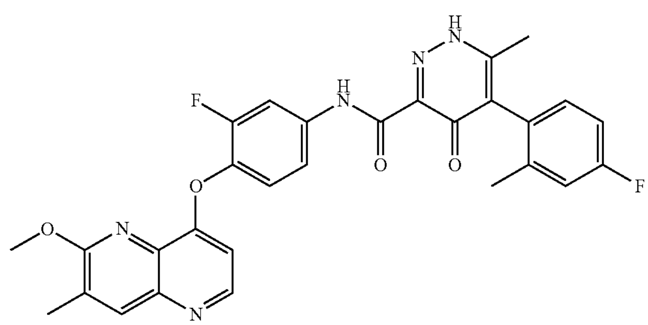 [SMILES: COc1nc2c(Oc3ccc(NC(=O)c4n[nH]c(C)c(-c5ccc(F)cc5C)c4=O)cc3F)ccnc2cc1C] | N-[3-fluoro-4-[(6-methoxy-7-methyl-1,5-naphthyridin-4-yl)oxy]phenyl]-5-(4-fluoro-2-methylphenyl)-6-methyl-4-oxo-1H-pyridazine-3-carboxamide |
| 474 | 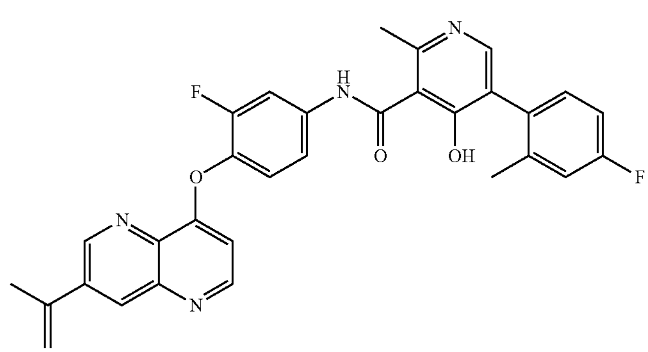 [SMILES: C=C(C)c1cnc2c(Oc3ccc(NC(=O)c4c(C)ncc(-c5ccc(F)cc5C)c4O)cc3F)ccnc2c1] | 5-(4-fluoro-2-methylphenyl)-N-[3-fluoro-4-[(7-prop-1-en-2-yl-1,5-naphthyridin-4-yl)oxy]phenyl]-4-hydroxy-2-methylpyridine-3-carboxamide |

-continued

| Cpd # | Structure | IUPAC Name |
|---|---|---|
| 475 | 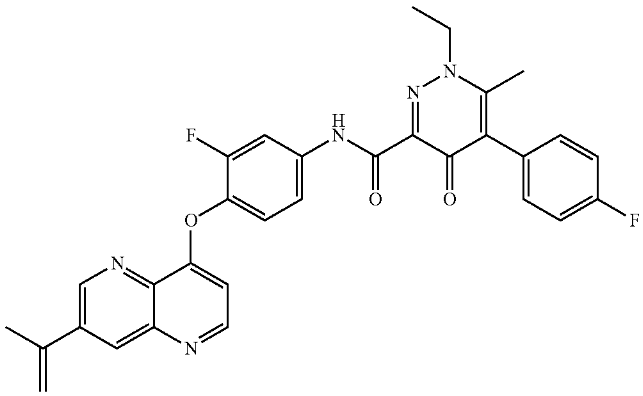 [SMILES: C=C(C)c1cnc2c(Oc3ccc(NC(=O)c4nn(CC)c(C)c(-c5ccc(F)cc5)c4=O)cc3F)ccnc2c1] | 1-ethyl-5-(4-fluorophenyl)-N-[3-fluoro-4-[(7-prop-1-en-2-yl-1,5-naphthyridin-4-yl)oxy]phenyl]-6-methyl-4-oxopyridazine-3-carboxamide |
| 476 | 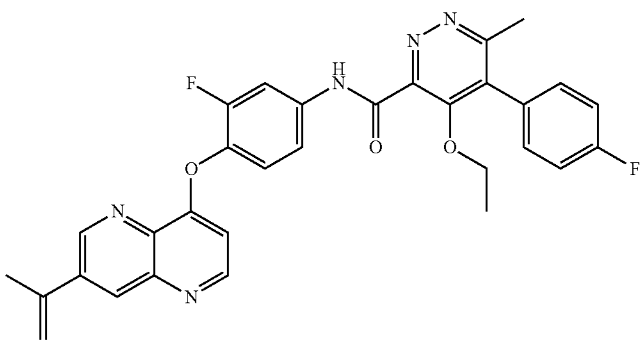 [SMILES: C=C(C)c1cnc2c(Oc3ccc(NC(=O)c4nnc(C)c(-c5ccc(F)cc5)c4OCC)cc3F)ccnc2c1] | 4-ethoxy-5-(4-fluorophenyl)-N-[3-fluoro-4-[(7-prop-1-en-2-yl-1,5-naphthyridin-4-yl)oxy]phenyl]-6-methylpyridazine-3-carboxamide |
| 477 | 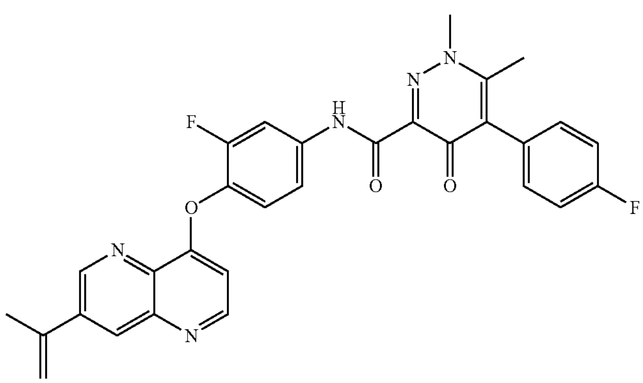 [SMILES: C=C(C)c1cnc2c(Oc3ccc(NC(=O)c4nn(C)c(C)c(-c5ccc(F)cc5)c4=O)cc3F)ccnc2c1] | 5-(4-fluorophenyl)-N-[3-fluoro-4-[(7-prop-1-en-2-yl-1,5-naphthyridin-4-yl)oxy]phenyl]-1,6-dimethyl-4-oxopyridazine-3-carboxamide |
| 478 | 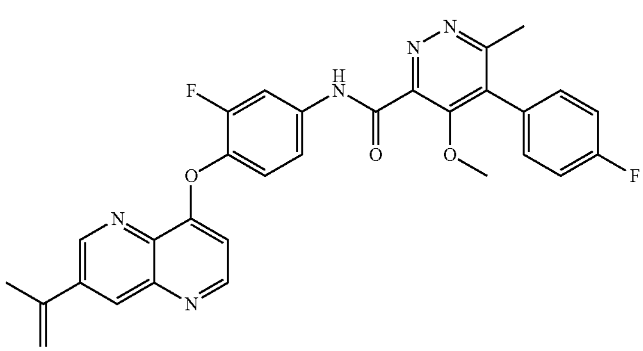 [SMILES: C=C(C)c1cnc2c(Oc3ccc(NC(=O)c4nnc(C)c(-c5ccc(F)cc5)c4OC)cc3F)ccnc2c1] | 5-(4-fluorophenyl)-N-[3-fluoro-4-[(7-prop-1-en-2-yl-1,5-naphthyridin-4-yl)oxy]phenyl]-4-methoxy-6-methylpyridazine-3-carboxamide |

| Cpd # | Structure | IUPAC Name |
|---|---|---|
| 479 | 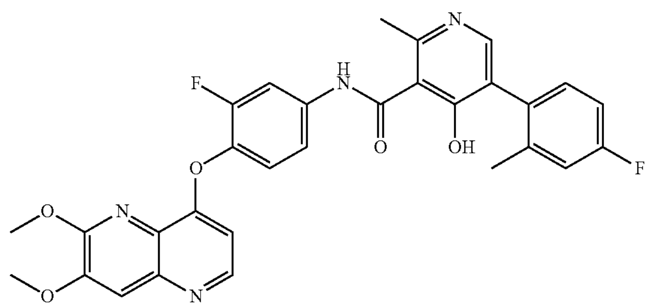 [SMILES: COc1cc2nccc(Oc3ccc(NC(=O)c4c(C)ncc(-c5ccc(F)cc5C)c4O)cc3F)c2nc1OC] | N-[4-[(6,7-dimethoxy-1,5-naphthyridin-4-yl)oxy]-3-fluorophenyl]-5-(4-fluoro-2-methylphenyl)-4-hydroxy-2-methylpyridine-3-carboxamide |
| 480 | 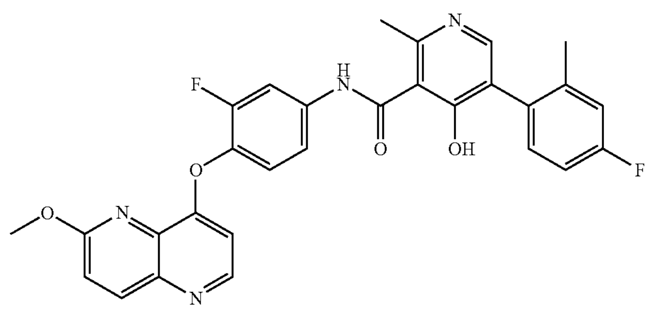 [SMILES: COc1ccc2nccc(Oc3ccc(NC(=O)c4c(C)ncc(-c5ccc(F)cc5C)c4O)cc3F)c2n1] | N-[3-fluoro-4-[(6-methoxy-1,5-naphthyridin-4-yl)oxy]phenyl]-5-(4-fluoro-2-methylphenyl)-4-hydroxy-2-methylpyridine-3-carboxamide |
| 481 | 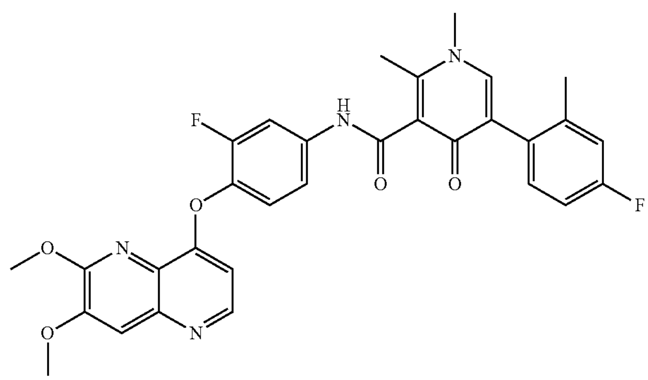 [SMILES: COc1cc2nccc(Oc3ccc(NC(=O)c4c(C)n(C)cc(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1,2-dimethyl-4-oxopyridine-3-carboxamide |
| 482 | 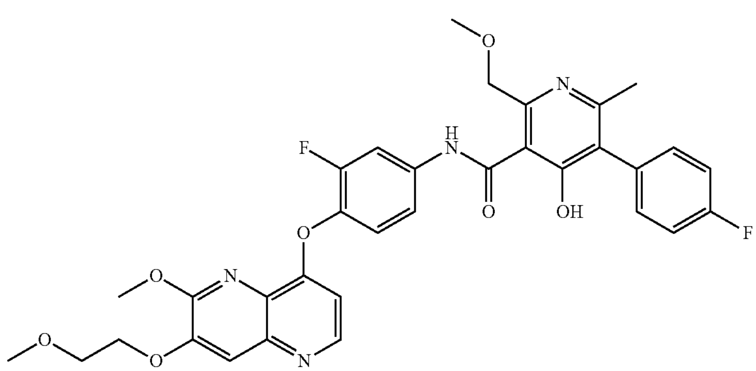 [SMILES: COCCOc1cc2nccc(Oc3ccc(NC(=O)c4c(COC)nc(C)c(-c5ccc(F)cc5)c4O)cc3F)c2nc1OC] | N-[3-fluoro-4-[6-methoxy-7-(2-methoxyethoxy)-1,5-naphthyridin-4-yl]oxy]phenyl]-5-(4-fluorophenyl)-4-hydroxy-2-(methoxymethyl)-6-methylpyridine-3-carboxamide |

-continued

| Cpd # | Structure | IUPAC Name |
|---|---|---|
| 483 | 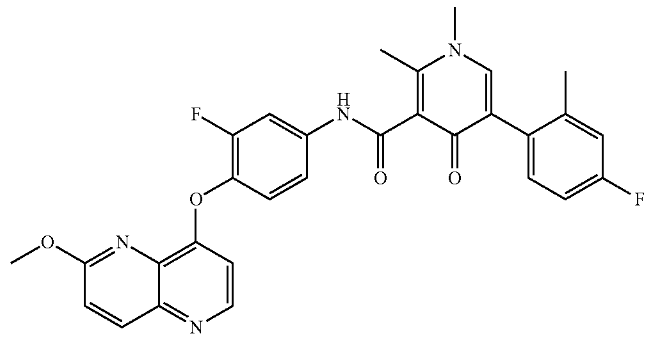 [SMILES: COc1ccc2nccc(Oc3ccc(NC(=O)c4c(C)n(C)cc(-c5ccc(F)cc5C)c4=O)cc3F)c2n1] | N-[3-fluoro-4-[(6-methoxy-1,5-naphthyridin-4-yl)oxy]phenyl]-5-(4-fluoro-2-methylphenyl)-1,2-dimethyl-4-oxopyridine-3-carboxamide |
| 484 | 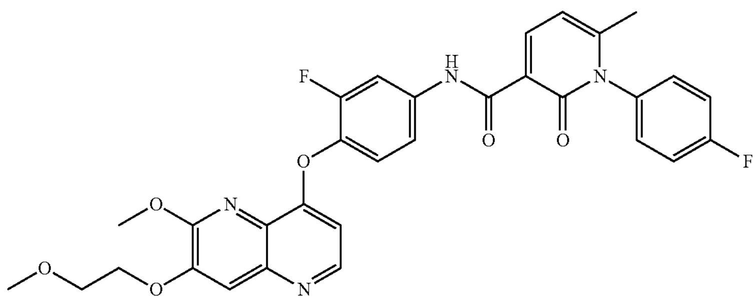 [SMILES: COCCOc1cc2nccc(Oc3ccc(NC(=O)c4ccc(C)n(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-1-(4-fluorophenyl)-6-methyl-2-oxopyridine-3-carboxamide |
| 485 | 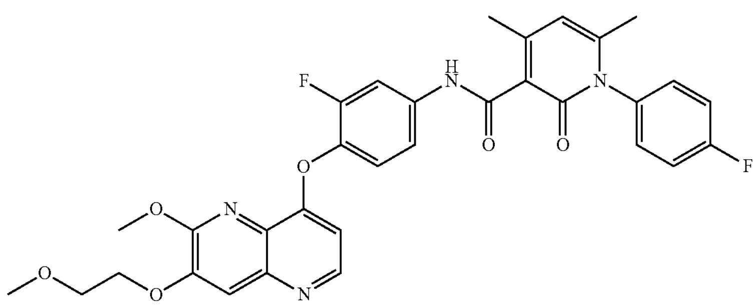 [SMILES: COCCOc1cc2nccc(Oc3ccc(NC(=O)c4c(C)cc(C)n(-c5ccc(F)cc5)c4=O)cc3F)c2nc1OC] | N-[3-fluoro-4-[6-methoxy-7-(2-methoxyethoxy)-1,5-naphthyridin-4-yl]oxy]phenyl]-1-(4-fluorophenyl)-4,6-dimethyl-2-oxopyridine-3-carboxamide |
| 486 | 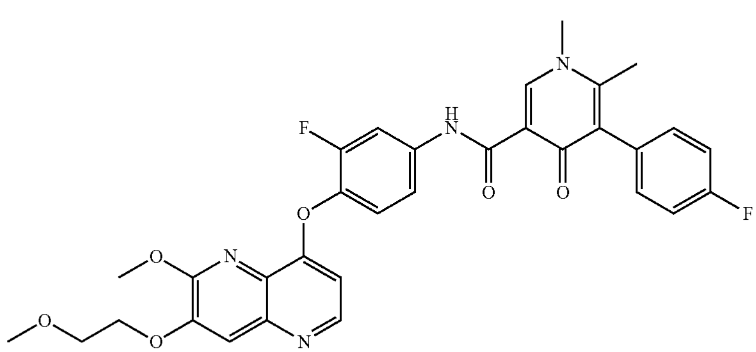 [SMILES: COCCOc1cc2nccc(Oc3ccc(NC(=O)c4cn(C)c(C)c(-c5ccc(F)cc5)c4=O)cc3F)c2nc1OC] | N-[3-fluoro-4-[6-methoxy-7-(2-methoxyethoxy)-1,5-naphthyridin-4-yl]oxy]phenyl]-5-(4-fluorophenyl)-1,6-dimethyl-4-oxopyridine-3-carboxamide |

-continued

| Cpd # | Structure | IUPAC Name |
|---|---|---|
| 487 | 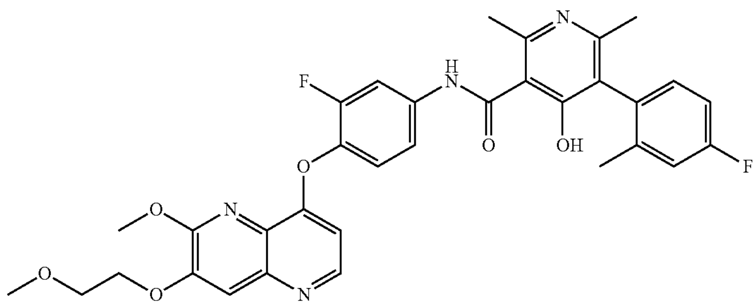 [SMILES: COCCOc1cc2nccc(Oc3ccc(NC(=O)c4c(C)nc(C)c(-c5ccc(F)cc5C)c4O)cc3F)c2nc1OC] | N-[3-fluoro-4-[[6-methoxy-7-(2-methoxyethoxy)-1,5-naphthyridin-4-yl]oxy]phenyl]-5-(4-fluoro-2-methylphenyl)-4-hydroxy-2,6-dimethylpyridine-3-carboxamide |
| 488 | 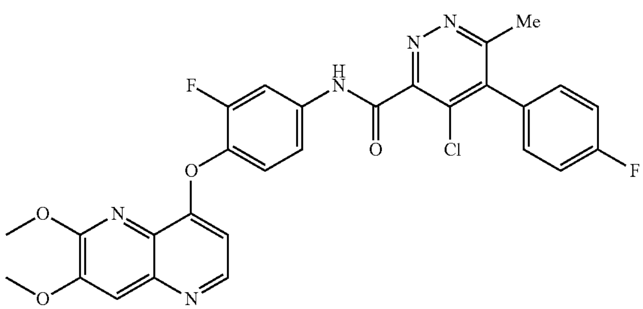 [SMILES: COc1cc2nccc(Oc3ccc(NC(=O)c4nnc(C)c(-c5ccc(F)cc5)c4Cl)cc3F)c2nc1OC] | 4-chloro-N-[4-[(6,7-dimethoxy-1,5-naphthyridin-4-yl)oxy]-3-fluorophenyl]-5-(4-fluorophenyl)-6-methylpyridazine-3-carboxamide |
| 489 | 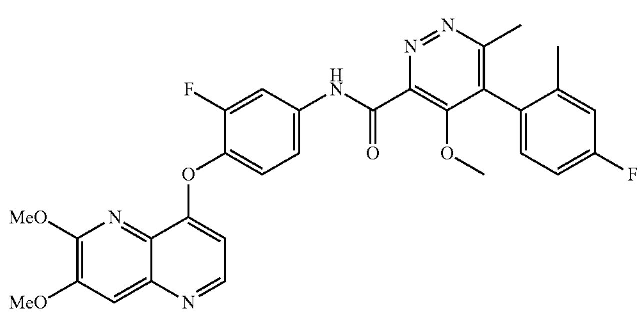 [SMILES: COc1cc2nccc(Oc3ccc(NC(=O)c4nnc(C)c(-c5ccc(F)cc5C)c4OC)cc3F)c2nc1OC] | N-[4-[(6,7-dimethoxy-1,5-naphthyridin-4-yl)oxy]-3-fluorophenyl]-5-(4-fluoro-2-methylphenyl)-4-methoxy-6-methylpyridazine-3-carboxamide |
| 491 | 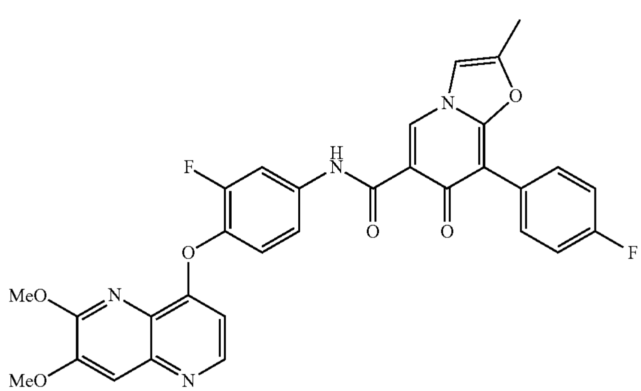 [SMILES: COc1cc2nccc(Oc3ccc(NC(=O)c4cn5cc(C)oc5c(-c5ccc(F)cc5)c4=O)cc3F)c2nc1OC] | N-[4-[(6,7-dimethoxy-1,5-naphthyridin-4-yl)oxy]-3-fluorophenyl]-8-(4-fluorophenyl)-2-methyl-7-oxo-[1,3]oxazolo[3,2-a]pyridine-6-carboxamide |

-continued

| Cpd # | Structure | IUPAC Name |
|---|---|---|
| 493 | 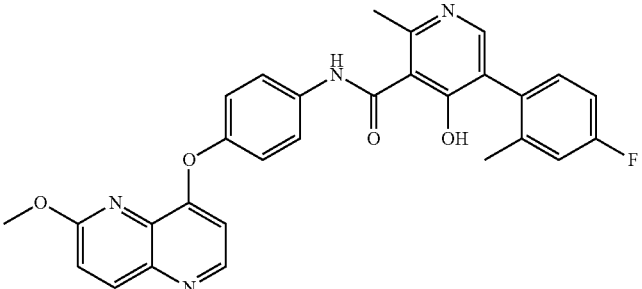 | 5-(4-fluoro-2-methylphenyl)-4-hydroxy-N-[4-[(6-methoxy-1,5-naphthyridin-4-yl)oxy]phenyl]-2-methylpyridine-3-carboxamide |
| 494 | 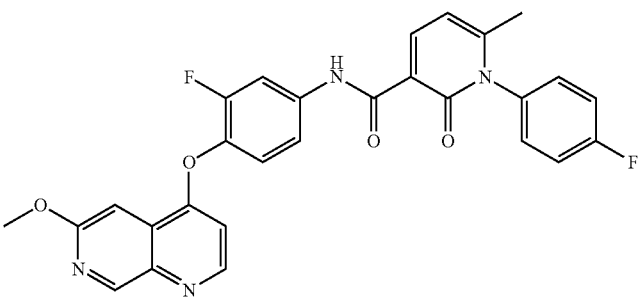 [SMILES: COc1cc2c(Oc3ccc(NC(=O)c4ccc(C)n(-c5ccc(F)cc5)c4=O)cc3F)ccnc2cn1] | N-[3-fluoro-4-[(6-methoxy-1,7-naphthyridin-4-yl)oxy]phenyl]-1-(4-fluorophenyl)-6-methyl-2-oxopyridine-3-carboxamide |
| 496 | 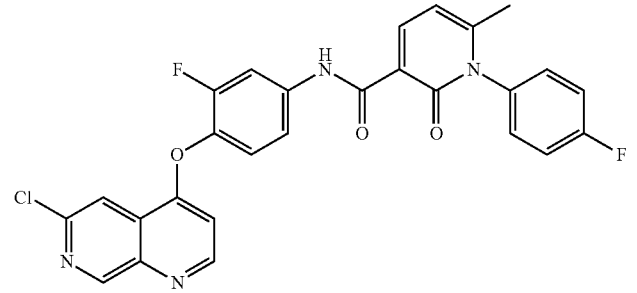 [SMILES: Cc1ccc(C(=O)Nc2ccc(Oc3ccnc4cnc(Cl)cc34)c(F)c2)c(=O)n1-c1ccc(F)cc1] | N-[4-[(6-chloro-1,7-naphthyridin-4-yl)oxy]-3-fluorophenyl]-1-(4-fluorophenyl)-6-methyl-2-oxopyridine-3-carboxamide |
| 497 | 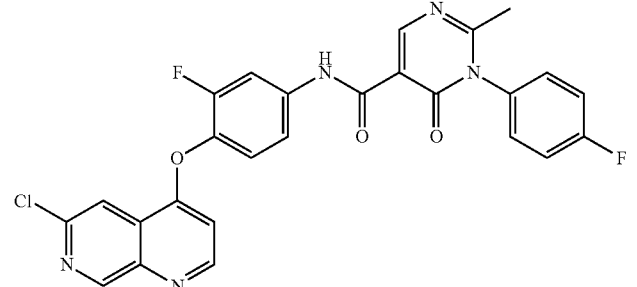 | N-[4-[(6-chloro-1,7-naphthyridin-4-yl)oxy]-3-fluorophenyl]-1-(4-fluorophenyl)-2-methyl-6-oxopyrimidine-5-carboxamide |
| 498 | 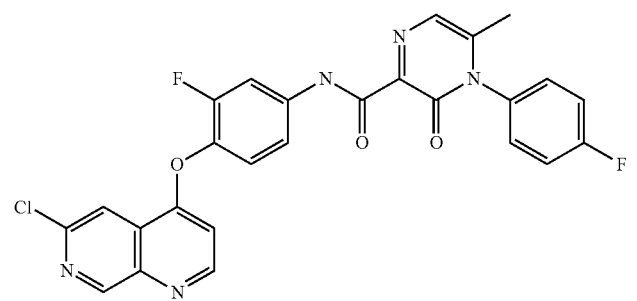 | N-[4-[(6-chloro-1,7-naphthyridin-4-yl)oxy]-3-fluorophenyl]-4-(4-fluorophenyl)-5-methyl-3-oxopyrazine-2-carboxamide |

-continued

| Cpd # | Structure | IUPAC Name |
|---|---|---|
| 499 | 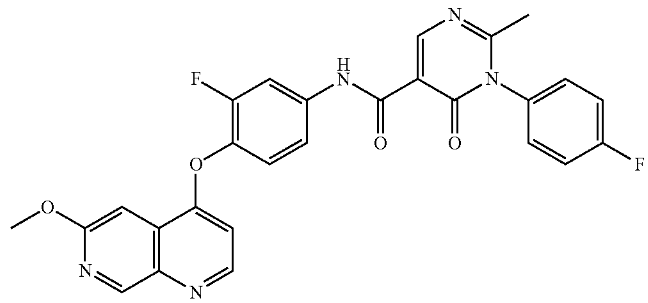 [SMILES: COc1cc2c(Oc3ccc(NC(=O)c4cnc(C)n(-c5ccc(F)cc5)c4=O)cc3F)ccnc2cn1] | N-[3-fluoro-4-[(6-methoxy-1,7-naphthyridin-4-yl)oxy]phenyl]-1-(4-fluorophenyl)-2-methyl-6-oxopyrimidine-5-carboxamide |
| 500 | 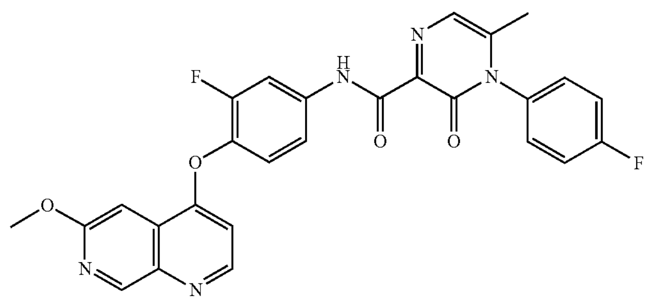 [SMILES: COc1cc2c(Oc3ccc(NC(=O)c4ncc(C)n(-c5ccc(F)cc5)c4=O)cc3F)ccnc2cn1] | N-[3-fluoro-4-[(6-methoxy-1,7-naphthyridin-4-yl)oxy]phenyl]-4-(4-fluorophenyl)-5-methyl-3-oxopyrazine-2-carboxamide |
| 501 | 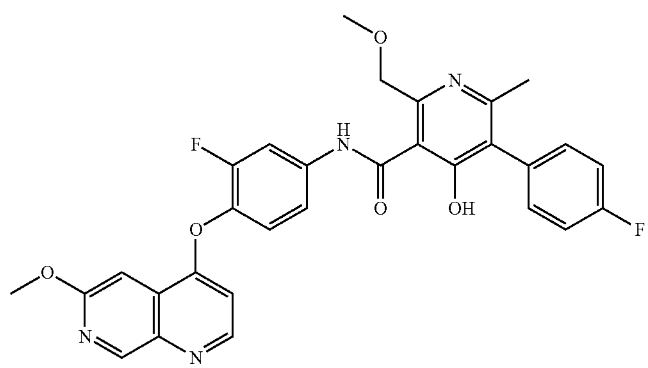 [SMILES: COCc1nc(C)c(-c2ccc(F)cc2)c(O)c1C(=O)Nc1ccc(Oc2ccnc3cnc(OC)cc23)c(F)c1] | N-[3-fluoro-4-[(6-methoxy-1,7-naphthyridin-4-yl)oxy]phenyl]-5-(4-fluorophenyl)-4-hydroxy-2-(methoxymethyl)-6-methylpyridine-3-carboxamide |
| 502 | 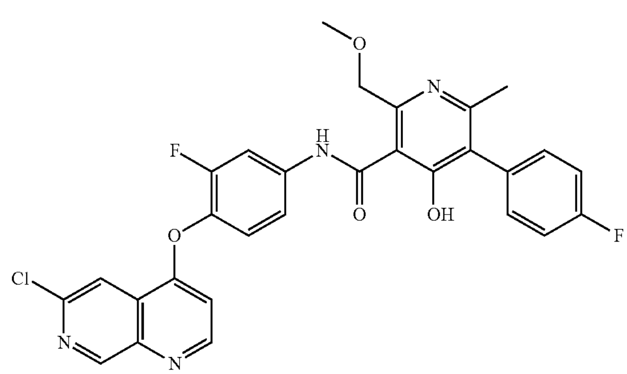 [SMILES: COCc1nc(C)c(-c2ccc(F)cc2)c(O)c1C(=O)Nc1ccc(Oc2ccnc3cnc(Cl)cc23)c(F)c1] | N-[4-[(6-chloro-1,7-naphthyridin-4-yl)oxy]-3-fluorophenyl]-5-(4-fluorophenyl)-4-hydroxy-2-(methoxymethyl)-6-methylpyridine-3-carboxamide |

| Cpd # | Structure | IUPAC Name |
|---|---|---|
| 503 | 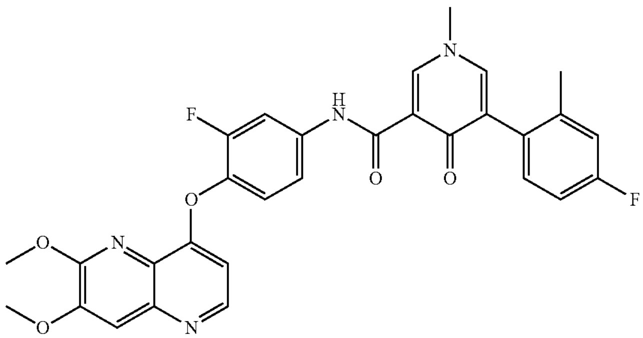 [SMILES: COc1cc2nccc(Oc3ccc(NC(=O)c4cn(C)cc(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1-methyl-4-oxopyridine-3-carboxamide |
| 504 | 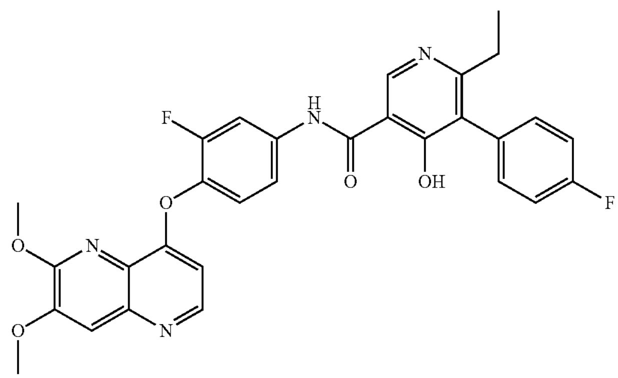 [SMILES: CCc1ncc(C(=O)Nc2ccc(Oc3ccnc4cc(OC)c(OC)nc34)c(F)c2)c(O)c1-c1ccc(F)cc1] | N-[4-[(6,7-dimethoxy-1,5-naphthyridin-4-yl)oxy]-3-fluorophenyl]-6-ethyl-5-(4-fluorophenyl)-4-hydroxypyridine-3-carboxamide |
| 505 | 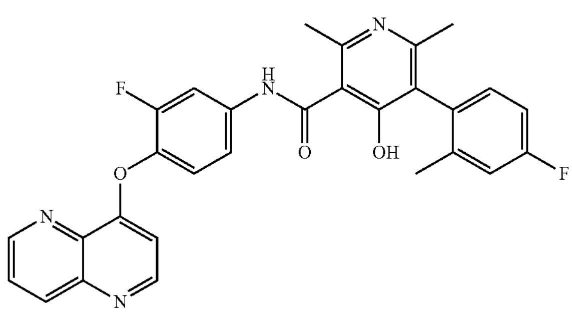 [SMILES: Cc1cc(F)ccc1-c1c(C)nc(C)c(C(=O)Nc2ccc(Oc3ccnc4cccnc34)c(F)c2)c1O] | 5-(4-fluoro-2-methylphenyl)-N-[3-fluoro-4-(1,5-naphthyridin-4-yloxy)phenyl]-4-hydroxy-2,6-dimethylpyridine-3-carboxamide |
| 506 | 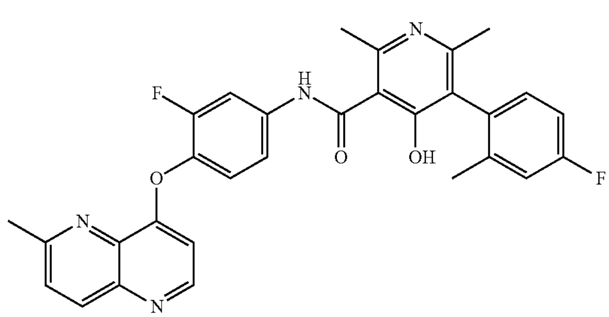 [SMILES: Cc1ccc2nccc(Oc3ccc(NC(=O)c4c(C)nc(C)c(-c5ccc(F)cc5C)c4O)cc3F)c2n1] | N-[3-fluoro-4-[(6-methyl-1,5-naphthyridin-4-yl)oxy]phenyl]-5-(4-fluoro-2-methylphenyl)-4-hydroxy-2,6-dimethylpyridine-3-carboxamide |

| Cpd # | Structure | IUPAC Name |
|---|---|---|
| 507 | 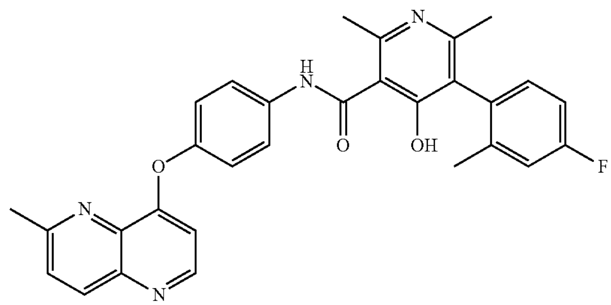 [SMILES: Cc1ccc2nccc(Oc3ccc(NC(=O)c4c(C)nc(C)c(-c5ccc(F)cc5C)c4O)cc3)c2n1] | 5-(4-fluoro-2-methylphenyl)-4-hydroxy-2,6-dimethyl-N-[4-[(6-methyl-1,5-naphthyridin-4-yl)oxy]phenyl]pyridine-3-carboxamide |
| 508 | 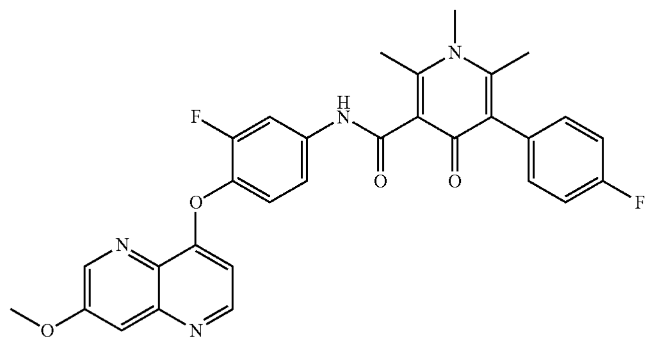 [SMILES: COc1cnc2c(Oc3ccc(NC(=O)c4c(C)n(C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1,2,6-trimethyl-4-oxopyridine-3-carboxamide |
| 509 | 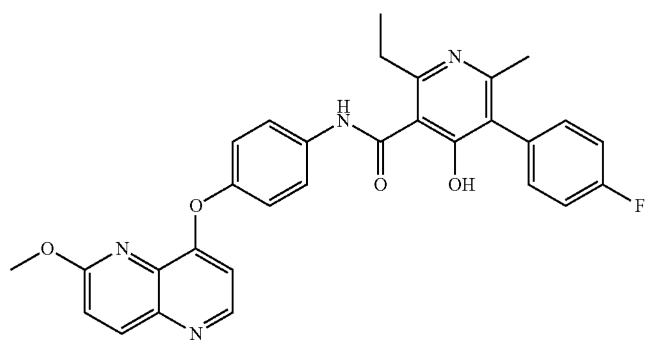 [SMILES: CCc1nc(C)c(-c2ccc(F)cc2)c(O)c1C(=O)Nc1ccc(Oc2ccnc3ccc(OC)nc23)cc1] | 2-ethyl-5-(4-fluorophenyl)-4-hydroxy-N-[4-[(6-methoxy-1,5-naphthyridin-4-yl)oxy]phenyl]-6-methylpyridine-3-carboxamide |
| 510 | 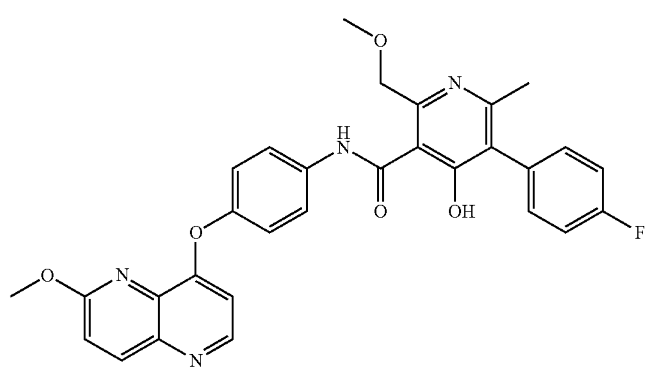 [SMILES: COCc1nc(C)c(-c2ccc(F)cc2)c(O)c1C(=O)Nc1ccc(Oc2ccnc3ccc(OC)nc23)cc1] | 5-(4-fluorophenyl)-4-hydroxy-2-(methoxymethyl)-N-[4-[(6-methoxy-1,5-naphthyridin-4-yl)oxy]phenyl]-6-methylpyridine-3-carboxamide |

-continued

| Cpd # | Structure | IUPAC Name |
|---|---|---|
| 511 | 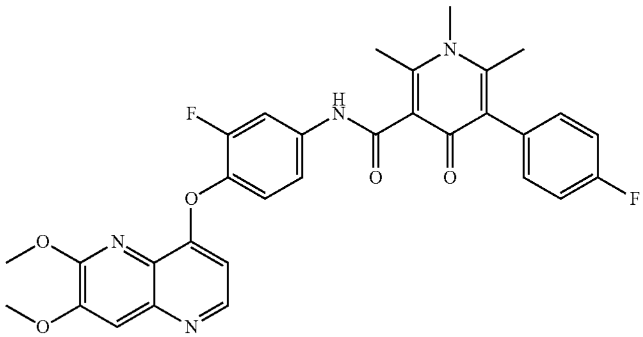 [SMILES: COc1cc2nccc(Oc3ccc(NC(=O)c4c(C)n(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-1,2,6-trimethyl-4-oxopyridine-3-carboxamide |
| 512 | 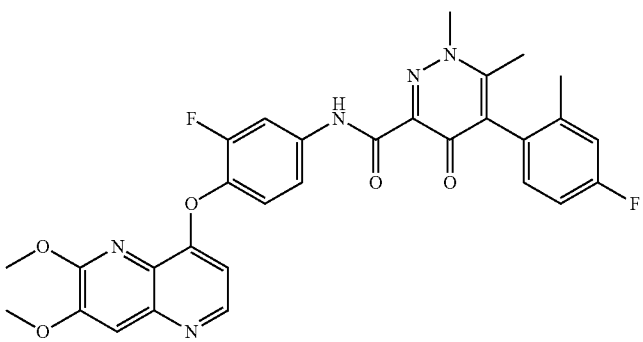 | N-[4-[(6,7-dimethoxy-1,5-naphthyridin-4-yl)oxy]-3-fluorophenyl]-5-(4-fluoro-2-methylphenyl)-1,6-dimethyl-4-oxopyridazine-3-carboxamide |
| 513 | 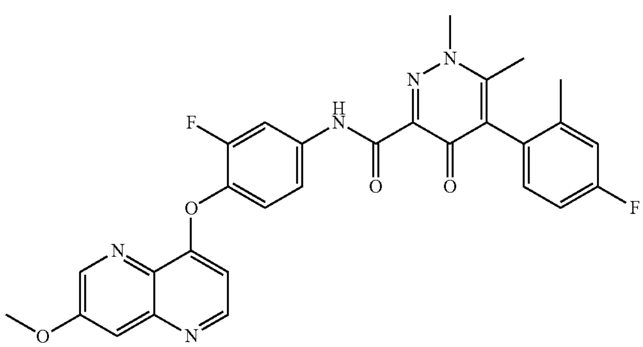 | N-[3-fluoro-4-[(7-methoxy-1,5-naphthyridin-4-yl)oxy]phenyl]-5-(4-fluoro-2-methylphenyl)-1,6-dimethyl-4-oxopyridazine-3-carboxamide |
| 514 | 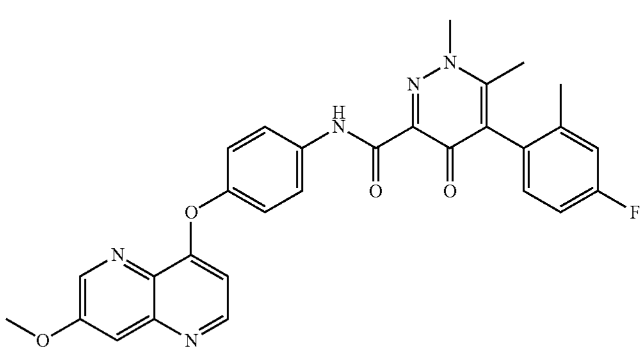 | 5-(4-fluoro-2-methylphenyl)-N-[4-[(7-methoxy-1,5-naphthyridin-4-yl)oxy]phenyl]-1,6-dimethyl-4-oxopyridazine-3-carboxamide |

| Cpd # | Structure | IUPAC Name |
|---|---|---|
| 515 | 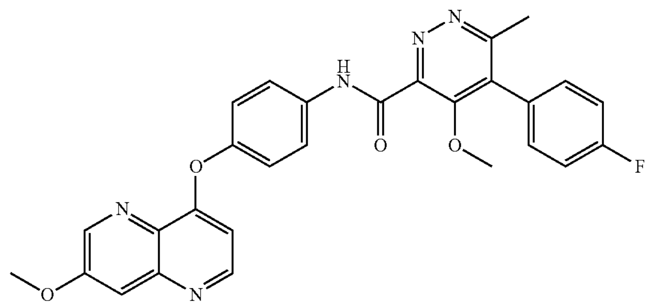 [SMILES: COc1cnc2c(Oc3ccc(NC(=O)c4nnc(C)c(-c5ccc(F)cc5)c4OC)cc3)ccnc2c1] | 5-(4-fluorophenyl)-4-methoxy-N-[4-[(7-methoxy-1,5-naphthyridin-4-yl)oxy]phenyl]-6-methylpyridazine-3-carboxamide |
| 516 | 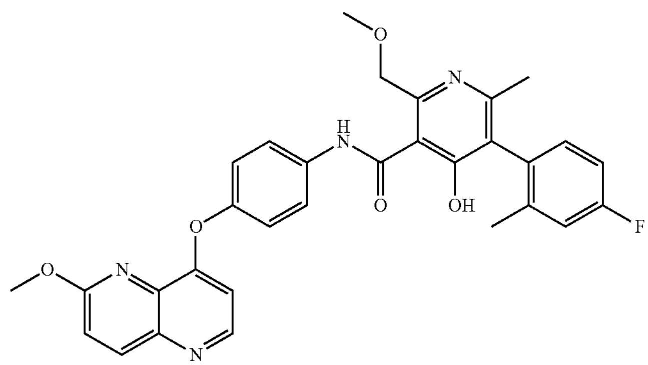 [SMILES: COCc1nc(C)c(-c2ccc(F)cc2C)c(O)c1C(=O)Nc1ccc(Oc2ccnc3ccc(OC)nc23)cc1] | 5-(4-fluoro-2-methylphenyl)-4-hydroxy-2-(methoxymethyl)-N-[4-[(6-methoxy-1,5-naphthyridin-4-yl)oxy]phenyl]-6-methylpyridine-3-carboxamide |
| 517 | 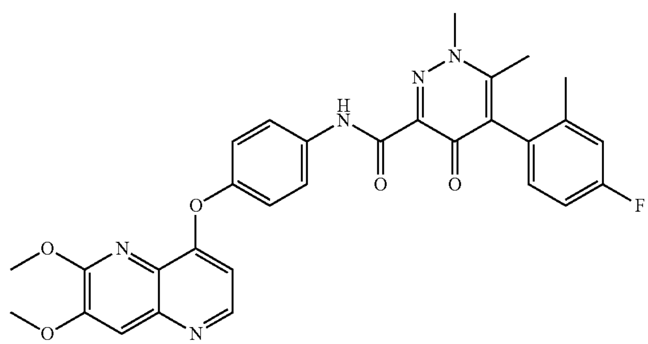 [SMILES: COc1cc2nccc(Oc3ccc(NC(=O)c4nn(C)c(C)c(-c5ccc(F)cc5C)c4=O)cc3)c2nc1OC] | N-[4-[(6,7-dimethoxy-1,5-naphthyridin-4-yl)oxy]phenyl]-5-(4-fluoro-2-methylphenyl)-1,6-dimethyl-4-oxopyridazine-3-carboxamide |
| 518 | 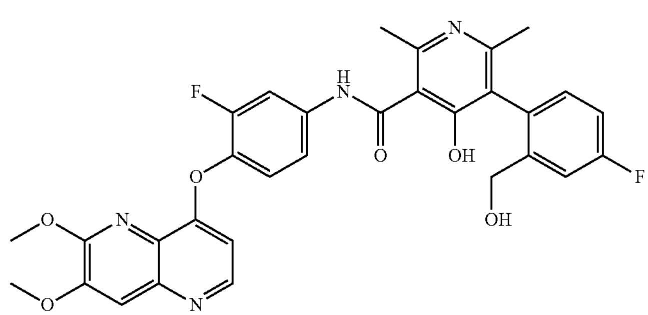 [SMILES: COc1cc2nccc(Oc3ccc(NC(=O)c4c(C)nc(C)c(-c5ccc(F)cc5CO)c4O)cc3F)c2nc1OC] | N-[4-[(6,7-dimethoxy-1,5-naphthyridin-4-yl)oxy]-3-fluorophenyl]-5-[4-fluoro-2-(hydroxymethyl)phenyl]-4-hydroxy-2,6-dimethylpyridine-3-carboxamide |

| Cpd # | Structure | IUPAC Name |
|---|---|---|
| 519 | 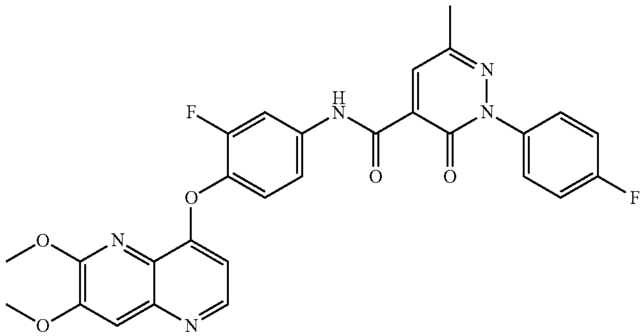 [SMILES: COc1cc2nccc(Oc3ccc(NC(=O)c4cc(C)nn(-c5ccc(F)cc5)c4=O)cc3F)c2nc1OC] | N-[4-[(6,7-dimethoxy-1,5-naphthyridin-4-yl)oxy]-3-fluorophenyl]-2-(4-fluorophenyl)-6-methyl-3-oxopyridazine-4-carboxamide |
| 520 | 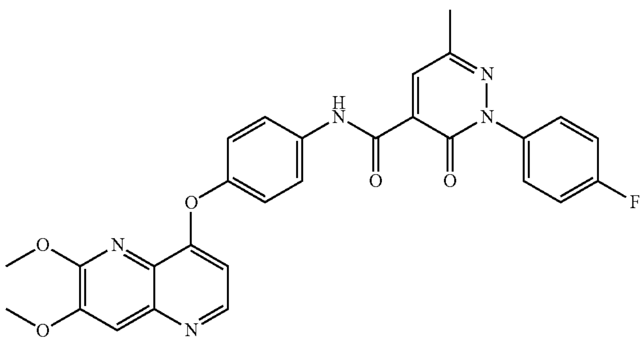 [SMILES: COc1cc2nccc(Oc3ccc(NC(=O)c4cc(C)nn(-c5ccc(F)cc5)c4=O)cc3)c2nc1OC] | N-[4-[(6,7-dimethoxy-1,5-naphthyridin-4-yl)oxy]phenyl]-2-(4-fluorophenyl)-6-methyl-3-oxopyridazine-4-carboxamide |
| 521 | 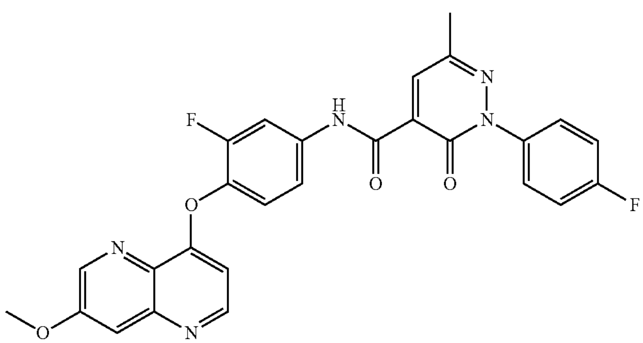 [SMILES: COc1cnc2c(Oc3ccc(NC(=O)c4cc(C)nn(-c5ccc(F)cc5)c4=O)cc3F)ccnc2c1] | N-[3-fluoro-4-[(7-methoxy-1,5-naphthyridin-4-yl)oxy]phenyl]-2-(4-fluorophenyl)-6-methyl-3-oxopyridazine-4-carboxamide |
| 522 | 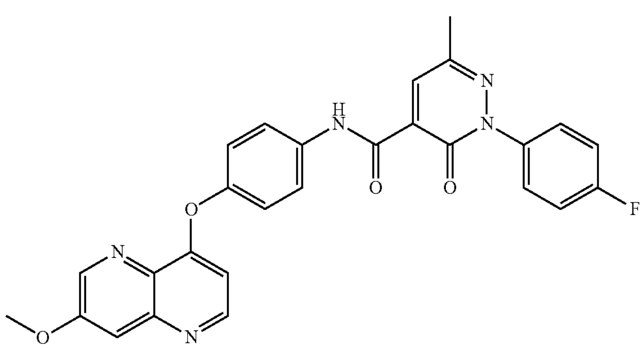 [SMILES: COc1cnc2c(Oc3ccc(NC(=O)c4cc(C)nn(-c5ccc(F)cc5)c4=O)cc3)ccnc2c1] | 2-(4-fluorophenyl)-N-[4-[(7-methoxy-1,5-naphthyridin-4-yl)oxy]phenyl]-6-methyl-3-oxopyridazine-4-carboxamide |

| Cpd # | Structure | IUPAC Name |
|---|---|---|
| 523 | 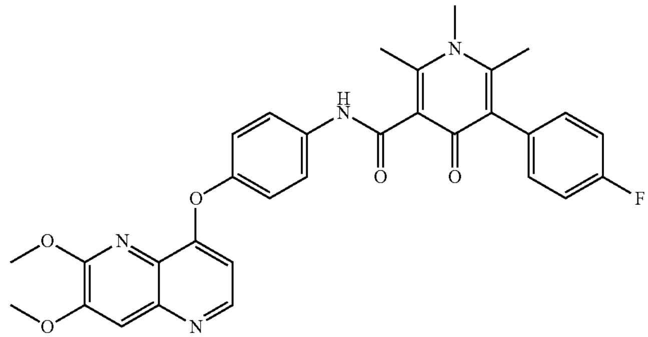 [SMILES: COc1cc2nccc(Oc3ccc(NC(=O)c4c(C)n(C)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1,2,6-trimethyl-4-oxopyridine-3-carboxamide |
| 524 | 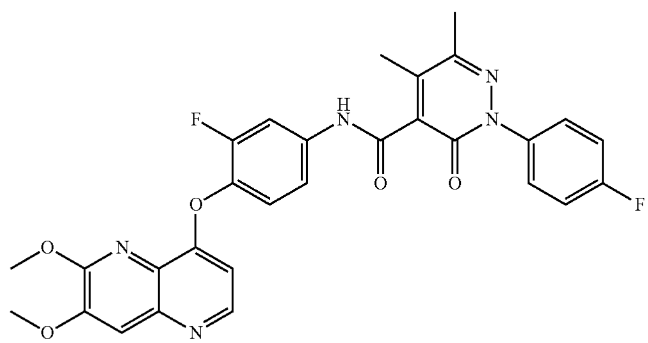 [SMILES: COc1cc2nccc(Oc3ccc(NC(=O)c4c(C)c(C)nn(-c5ccc(F)cc5)c4=O)cc3F)c2nc1OC] | N-[4-[(6,7-dimethoxy-1,5-naphthyridin-4-yl)oxy]-3-fluorophenyl]-2-(4-fluorophenyl)-5,6-dimethyl-3-oxopyridazine-4-carboxamide |
| 525 | 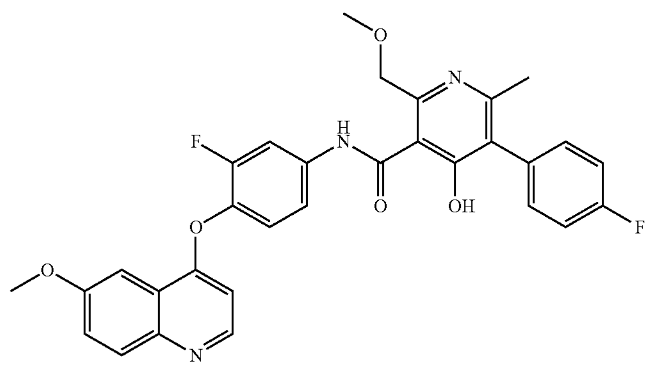 [SMILES: COCc1nc(C)c(-c2ccc(F)cc2)c(O)c1C(=O)Nc1ccc(Oc2ccnc3ccc(OC)cc23)c(F)c1] | N-[3-fluoro-4-(6-methoxyquinolin-4-yl)oxyphenyl]-5-(4-fluorophenyl)-4-hydroxy-2-(methoxymethyl)-6-methylpyridine-3-carboxamide |
| 526 | 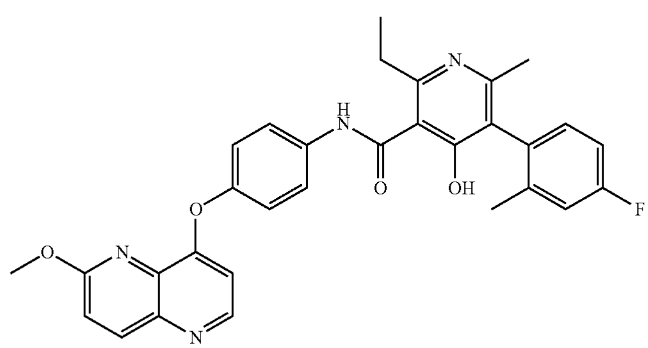 [SMILES: CCc1nc(C)c(-c2ccc(F)cc2C)c(O)c1C(=O)Nc1ccc(Oc2ccnc3ccc(OC)nc23)cc1] | 2-ethyl-5-(4-fluoro-2-methylphenyl)-4-hydroxy-N-[4-[(6-methoxy-1,5-naphthyridin-4-yl)oxy]phenyl]-6-methylpyridine-3-carboxamide |

-continued

| Cpd # | Structure | IUPAC Name |
|---|---|---|
| 527 | 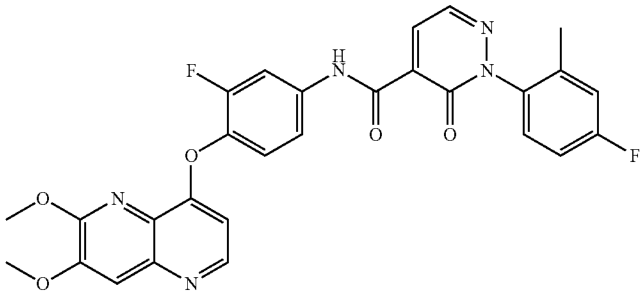 [SMILES: COc1cc2nccc(Oc3ccc(NC(=O)c4ccnn(-c5ccc(F)cc5C)c4=O)cc3F)c2nc1OC] | N-[4-[(6,7-dimethoxy-1,5-naphthyridin-4-yl)oxy]-3-fluorophenyl]-2-(4-fluoro-2-methylphenyl)-3-oxopyridazine-4-carboxamide |
| 528 | 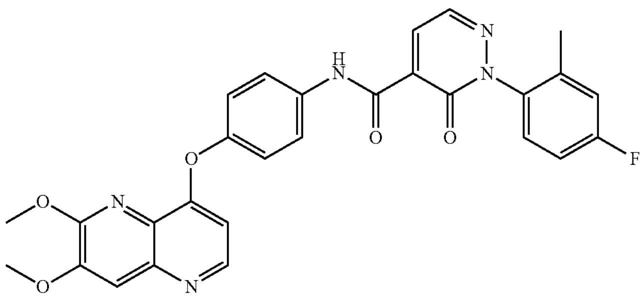 [SMILES: COc1cc2nccc(Oc3ccc(NC(=O)c4ccnn(-c5ccc(F)cc5C)c4=O)cc3)c2nc1OC] | N-[4-[(6,7-dimethoxy-1,5-naphthyridin-4-yl)oxy]phenyl]-2-(4-fluoro-2-methylphenyl)-3-oxopyridazine-4-carboxamide |
| 529 | 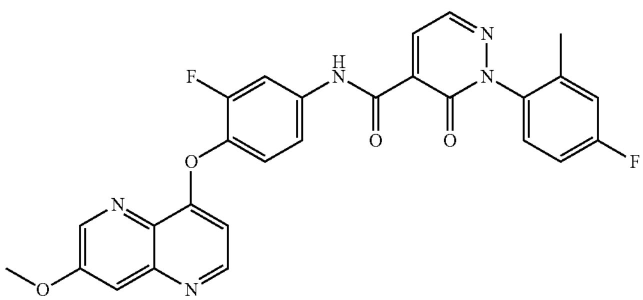 [SMILES: COc1cnc2c(Oc3ccc(NC(=O)c4ccnn(-c5ccc(F)cc5C)c4=O)cc3F)ccnc2c1] | N-[3-fluoro-4-[(7-methoxy-1,5-naphthyridin-4-yl)oxy]phenyl]-2-(4-fluoro-2-methylphenyl)-3-oxopyridazine-4-carboxamide |
| 530 | 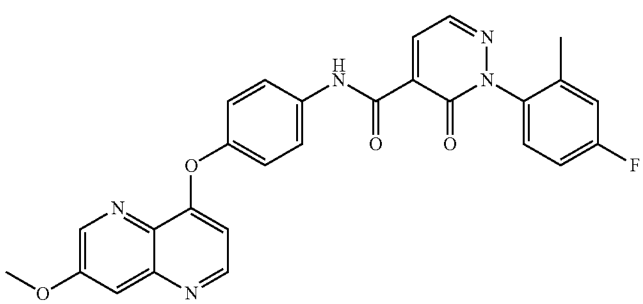 [SMILES: COc1cnc2c(Oc3ccc(NC(=O)c4ccnn(-c5ccc(F)cc5C)c4=O)cc3)ccnc2c1] | 2-(4-fluoro-2-methylphenyl)-N-[4-[(7-methoxy-1,5-naphthyridin-4-yl)oxy]phenyl]-3-oxopyridazine-4-carboxamide |
| 531 | 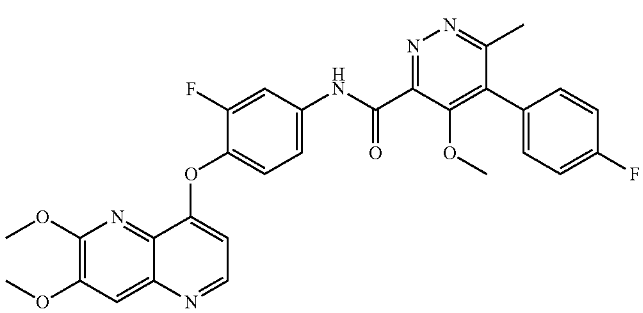 [SMILES: COc1cc2nccc(Oc3ccc(NC(=O)c4nnc(C)c(-c5ccc(F)cc5)c4OC)cc3F)c2nc1OC] | N-[4-[(6,7-dimethoxy-1,5-naphthyridin-4-yl)oxy]-3-fluorophenyl]-5-(4-fluorophenyl)-4-methoxy-6-methylpyridazine-3-carboxamide |

| Cpd # | Structure | IUPAC Name |
|---|---|---|
| 532 | 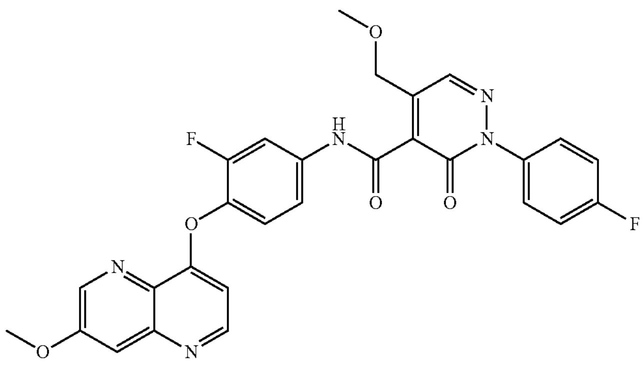 [SMILES: COCc1cnn(-c2ccc(F)cc2)c(=O)c1C(=O)Nc1ccc(Oc2ccnc3cc(OC)cnc23)c(F)c1] | N-[3-fluoro-4-[(7-methoxy-1,5-naphthyridin-4-yl)oxy]phenyl]-2-(4-fluorophenyl)-5-(methoxymethyl)-3-oxopyridazine-4-carboxamide |
| 533 | 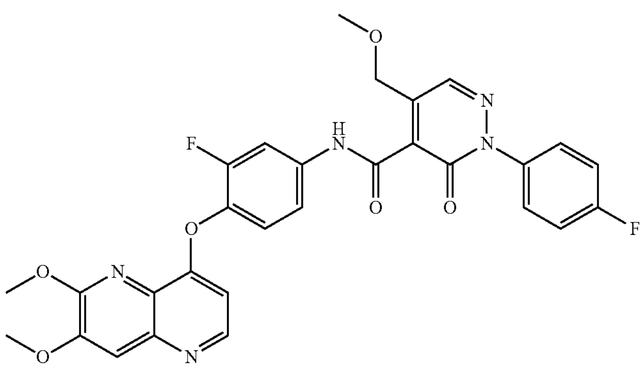 [SMILES: COCc1cnn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-2-(4-fluorophenyl)-5-(methoxymethyl)-3-oxopyridazine-4-carboxamide |
| 534 | 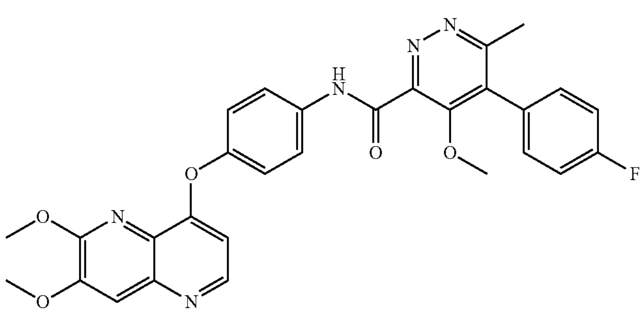 [SMILES: COc1cc2nccc(Oc3ccc(NC(=O)c4nnc(C)c(-c5ccc(F)cc5)c4OC)cc3)c2nc1OC] | N-[4-[(6,7-dimethoxy-1,5-naphthyridin-4-yl)oxy]phenyl]-5-(4-fluorophenyl)-4-methoxy-6-methylpyridazine-3-carboxamide |
| 537 | 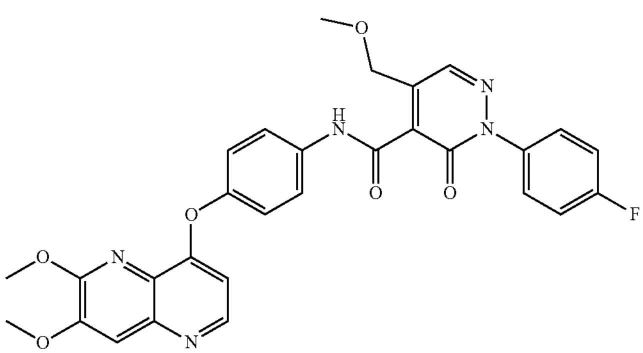 [SMILES: COCc1cnn(-c2ccc(F)cc2)c(=O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-(4-fluorophenyl)-5-(methoxymethyl)-3-oxopyridazine-4-carboxamide |

-continued

| Cpd # | Structure | IUPAC Name |
|---|---|---|
| 538 | 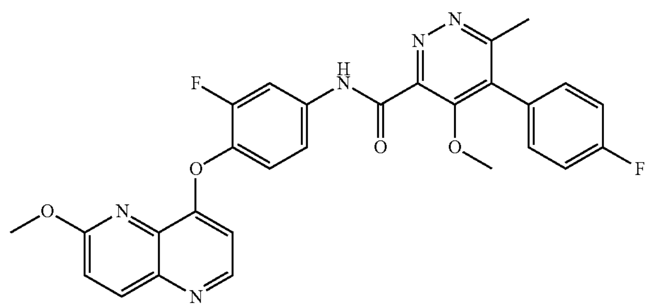 [SMILES: COc1ccc2nccc(Oc3ccc(NC(=O)c4nnc(C)c(-c5ccc(F)cc5)c4OC)cc3F)c2n1] | N-[3-fluoro-4-[(6-methoxy-1,5-naphthyridin-4-yl)oxy]phenyl]-5-(4-fluorophenyl)-4-methoxy-6-methylpyridazine-3-carboxamide |
| 539 | 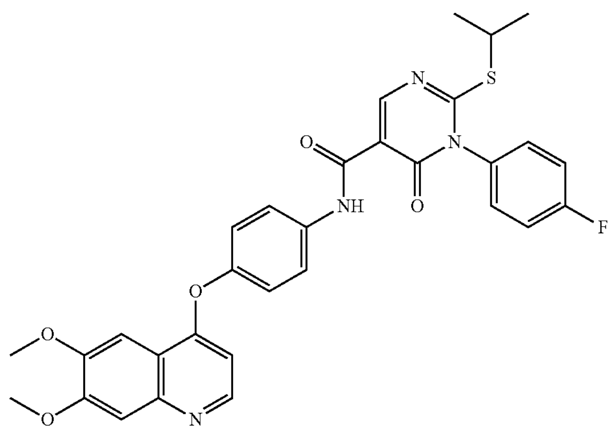 [SMILES: COc1cc2nccc(Oc3ccc(NC(=O)c4cnc(SC(C)C)n(-c5ccc(F)cc5)c4=O)cc3)c2cc1OC] | N-[4-(6, 7-dimethoxyquinolin-4-yl)oxyphenyl]-1-(4-fluorophenyl)-6-oxo-2-propan-2-ylsulfanylpyrimidine-5-carboxamide |
| 540 | 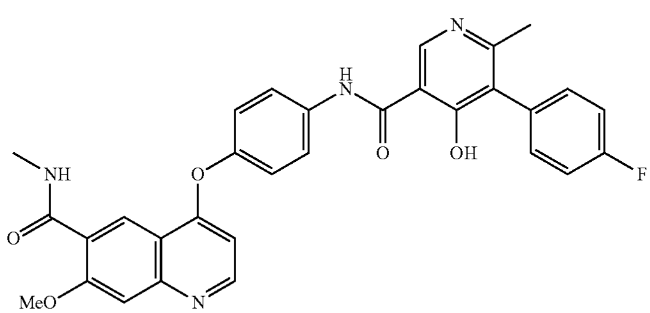 [SMILES: CNC(=O)c1cc2c(Oc3ccc(NC(=O)c4cnc(C)c(-c5ccc(F)cc5)c4O)cc3)ccnc2cc1OC] | 4-[4-[[5-(4-fluorophenyl)-4-hydroxy-6-methylpyridine-3-carbonyl]amino]phenoxy]-7-methoxy-N-methylquinoline-6-carboxamide |
| 541 | 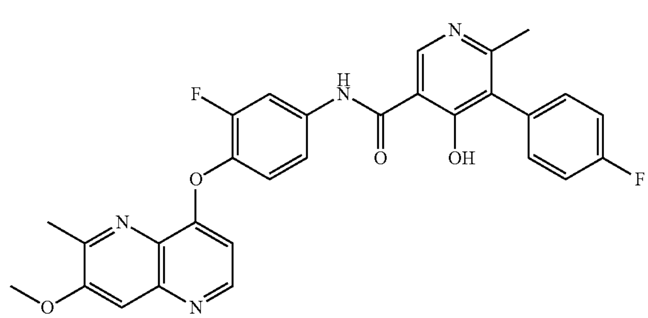 [SMILES: COc1cc2nccc(Oc3ccc(NC(=O)c4cnc(C)c(-c5ccc(F)cc5)c4O)cc3F)c2nc1C] | N-[3-fluoro-4-[(7-methoxy-6-methyl-1,5-naphthyridin-4-yl)oxy]phenyl]-5-(4-fluorophenyl)-4-hydroxy-6-methylpyridine-3-carboxamide |

| Cpd # | Structure | IUPAC Name |
|---|---|---|
| 542 | 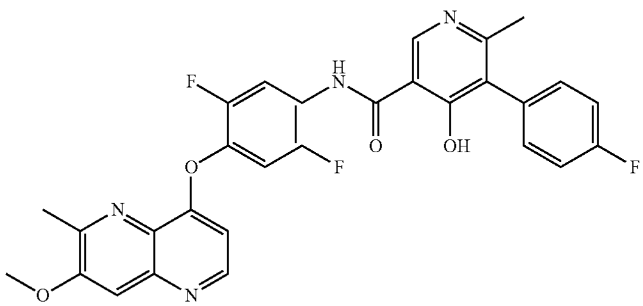 | N-[2,5-difluoro-4-[(7-methoxy-6-methyl-1,5-naphthyridin-4-yl)oxy]phenyl]-5-(4-fluorophenyl)-4-hydroxy-6-methylpyridine-3-carboxamide |
| 543 | 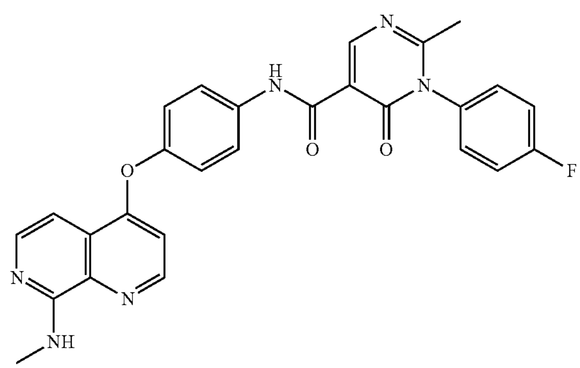 [SMILES: CNc1nccc2c(Oc3ccc(NC(=O)c4cnc(C)n(-c5ccc(F)cc5)c4=O)cc3)ccnc12] | 1-(4-fluorophenyl)-2-methyl-N-[4-[[8-(methylamino)-1,7-naphthyridin-4-yl]oxy]phenyl]-6-oxopyrimidine-5-carboxamide |
| 544 | 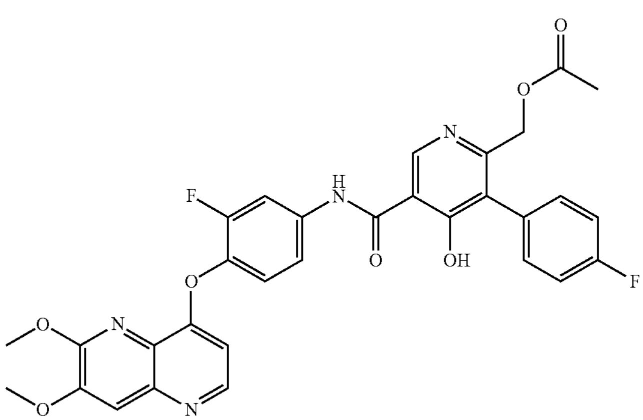 [SMILES: COc1cc2nccc(Oc3ccc(NC(=O)c4cnc(COC(C)=O)c(-c5ccc(F)cc5)c4O)cc3F)c2nc1OC] | [5-[[4-[(6,7-dimethoxy-1,5-naphthyridin-4-yl)oxy]-3-fluorophenyl]carbamoyl]-3-(4-fluorophenyl)-4-hydroxypyridin-2-yl]methyl acetate |
| 551 | 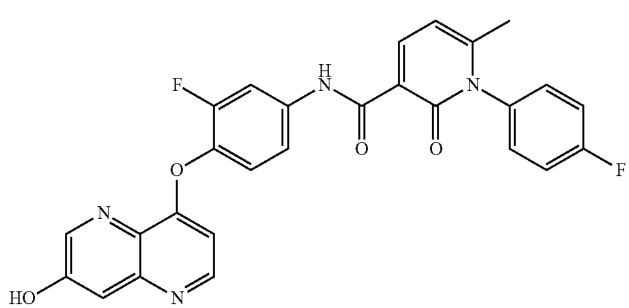 [SMILES: Cc1ccc(C(=O)Nc2ccc(Oc3ccnc4cc(O)cnc34)c(F)c2)c(=O)n1-c1ccc(F)cc1] | N-[3-fluoro-4-[(7-hydroxy-1,5-naphthyridin-4-yl)oxy]phenyl]-1-(4-fluorophenyl)-6-methyl-2-oxopyridine-3-carboxamide |

-continued

| Cpd # | Structure | IUPAC Name |
|---|---|---|
| 552 | 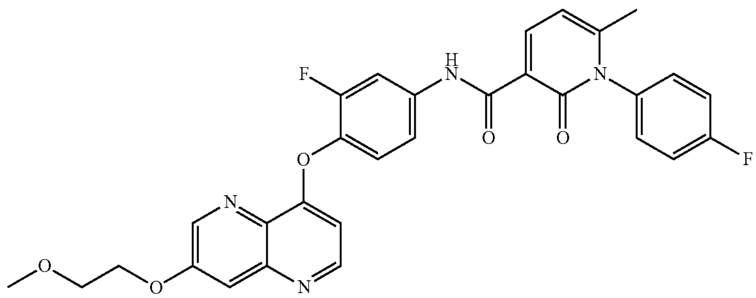 [SMILES: COCCOc1cnc2c(Oc3ccc(NC(=O)c4ccc(C)n(-c5ccc(F)cc5)c4=O)cc3F)ccnc2c1] | N-[3-fluoro-4-[[7-(2-methoxyethoxy)-1,5-naphthyridin-4-yl]oxy]phenyl]-1-(4-fluorophenyl)-6-methyl-2-oxopyridine-3-carboxamide |
| 553 | 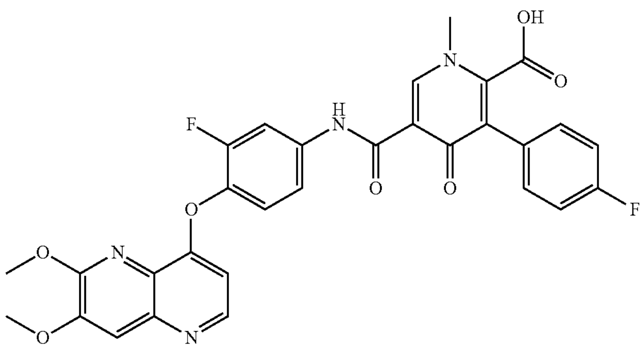 [SMILES: COc1cc2nccc(Oc3ccc(NC(=O)c4cn(C)c(C(=O)O)c(-c5ccc(F)cc5)c4=O)cc3F)c2nc1OC] | 5-[[4-[(6,7-dimethoxy-1,5-naphthyridin-4-yl)oxy]-3-fluorophenyl]carbamoyl]-3-(4-fluorophenyl)-1-methyl-4-oxopyridine-2-carboxylic acid |
| 554 | 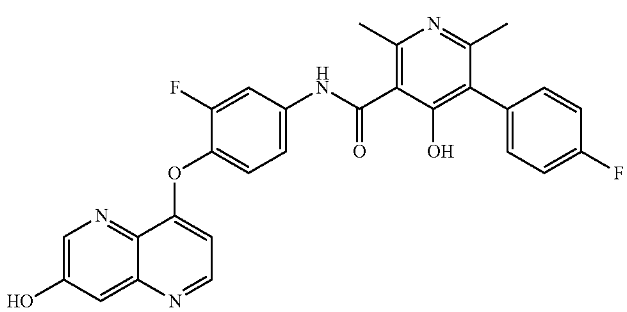 [SMILES: Cc1nc(C)c(-c2ccc(F)cc2)c(O)c1C(=O)Nc1ccc(Oc2ccnc3cc(O)cnc23)c(F)c1] | N-[3-fluoro-4-[(7-hydroxy-1,5-naphthyridin-4-yl)oxy]phenyl]-5-(4-fluorophenyl)-4-hydroxy-2,6-dimethylpyridine-3-carboxamide |
| 555 | 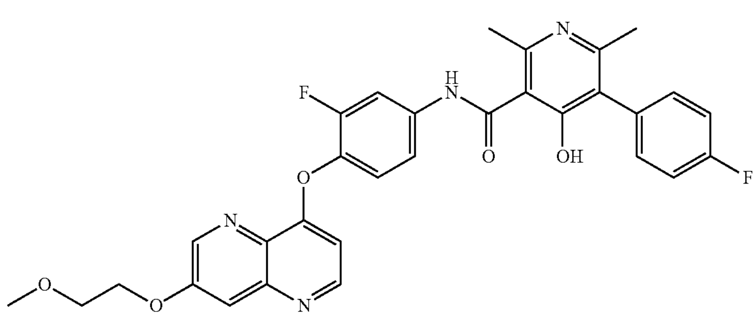 [SMILES: COCCOc1cnc2c(Oc3ccc(NC(=O)c4c(C)nc(C)c(-c5ccc(F)cc5)c4O)cc3F)ccnc2c1] | N-[3-fluoro-4-[[7-(2-methoxyethoxy)-1,5-naphthyridin-4-yl]oxy]phenyl]-5-(4-fluorophenyl)-4-hydroxy-2,6-dimethylpyridine-3-carboxamide |

-continued

| Cpd # | Structure | IUPAC Name |
|---|---|---|
| 556 | 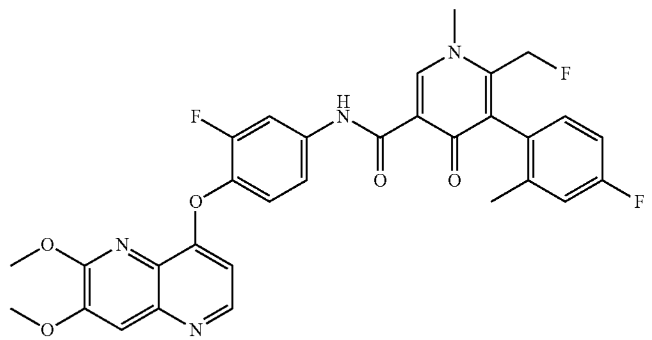 [SMILES: COc1cc2nccc(Oc3ccc(NC(=O)c4cn(C)c(CF)c(-c5ccc(F)cc5C)c4=O)cc3F)c2nc1OC] | N-[4-[(6,7-dimethoxy-1,5-naphthyridin-4-yl)oxy]-3-fluorophenyl]-6-(fluoromethyl)-5-(4-fluoro-2-methylphenyl)-1-methyl-4-oxopyridine-3-carboxamide |
| 557 | 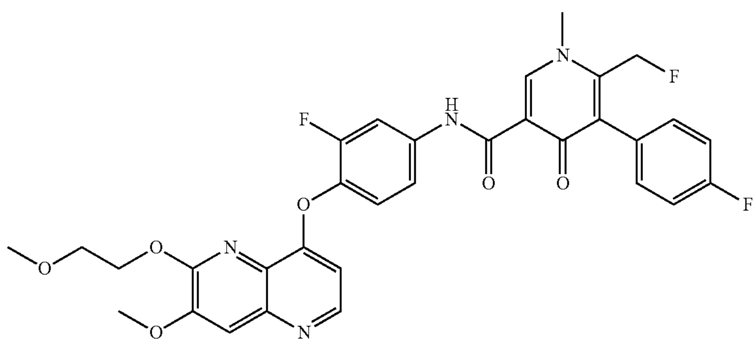 [SMILES: COCCOc1nc2c(Oc3ccc(NC(=O)c4cn(C)c(CF)c(-c5ccc(F)cc5)c4=O)cc3F)ccnc2cc1OC] | N-[3-fluoro-4-[[7-methoxy-6-(2-methoxyethoxy)-1,5-naphthyridin-4-yl]oxy]phenyl]-6-(fluoromethyl)-5-(4-fluorophenyl)-1-methyl-4-oxopyridine-3-carboxamide |
| 558 | 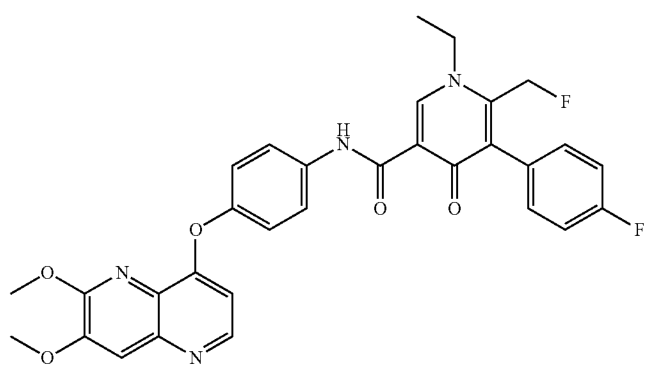 [SMILES: CCn1cc(C(=O)Nc2ccc(Oc3ccnc4cc(OC)c(OC)nc34)cc2)c(=O)c(-c2ccc(F)cc2)c1CF] | N-[4-[(6,7-dimethoxy-1,5-naphthyridin-4-yl)oxy]phenyl]-1-ethyl-6-(fluoromethyl)-5-(4-fluorophenyl)-4-oxopyridine-3-carboxamide |
| 559 | 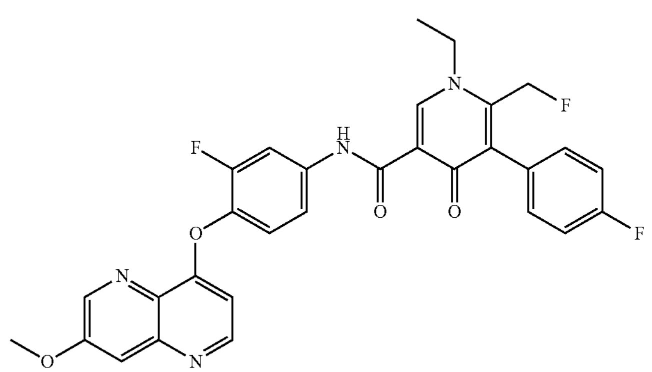 [SMILES: CCn1cc(C(=O)Nc2ccc(Oc3ccnc4cc(OC)cnc34)c(F)c2)c(=O)c(-c2ccc(F)cc2)c1CF] | 1-ethyl-N-[3-fluoro-4-[(7-methoxy-1,5-naphthyridin-4-yl)oxy]phenyl]-6-(fluoromethyl)-5-(4-fluorophenyl)-4-oxopyridine-3-carboxamide |

-continued

| Cpd # | Structure | IUPAC Name |
|---|---|---|
| 560 | 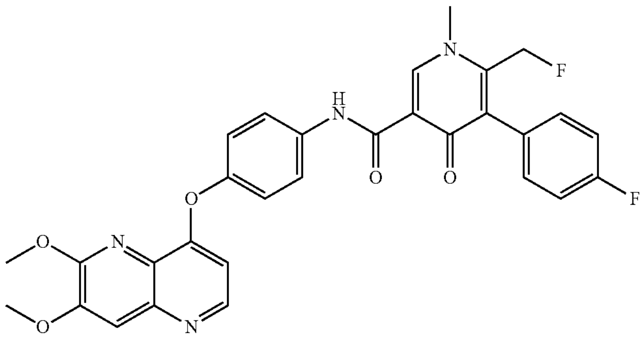 [SMILES: COc1cc2nccc(Oc3ccc(NC(=O)c4cn(C)c(CF)c(-c5ccc(F)cc5)c4=O)cc3)c2nc1OC] | N-[4-[(6,7-dimethoxy-1,5-naphthyridin-4-yl)oxy]phenyl]-6-(fluoromethyl)-5-(4-fluorophenyl)-1-methyl-4-oxopyridine-3-carboxamide |
| 561 | 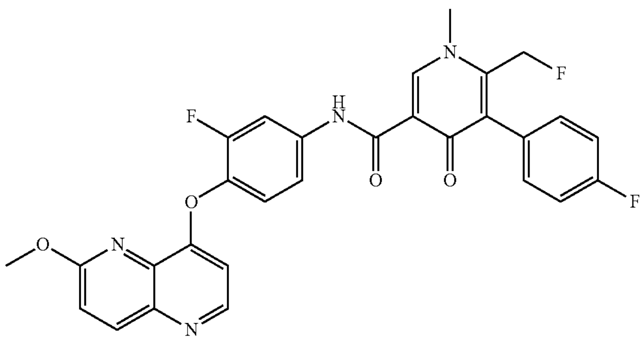 [SMILES: COc1ccc2nccc(Oc3ccc(NC(=O)c4cn(C)c(CF)c(-c5ccc(F)cc5)c4=O)cc3F)c2n1] | N-[3-fluoro-4-[(6-methoxy-1,5-naphthyridin-4-yl)oxy]phenyl]-6-(fluoromethyl)-5-(4-fluorophenyl)-1-methyl-4-oxopyridine-3-carboxamide |
| 562 | 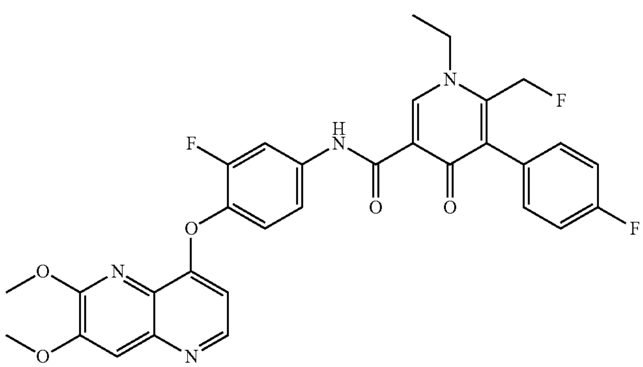 [SMILES: CCn1cc(C(=O)Nc2ccc(Oc3ccnc4cc(OC)c(OC)nc34)c(F)c2)c(=O)c(-c2ccc(F)cc2)c1CF] | N-[4-[(6,7-dimethoxy-1,5-naphthyridin-4-yl)oxy]-3-fluorophenyl]-1-ethyl-6-(fluoromethyl)-5-(4-fluorophenyl)-4-oxopyridine-3-carboxamide |
| 563 | 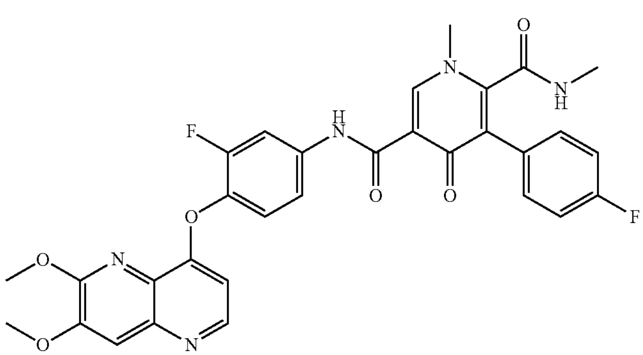 [SMILES: CNC(=O)c1c(-c2ccc(F)cc2)c(=O)c(C(=O)Nc2ccc(Oc3ccnc4cc(OC)c(OC)nc34)c(F)c2)cn1C] | 5-N-[4-[(6,7-dimethoxy-1,5-naphthyridin-4-yl)oxy]-3-fluorophenyl]-3-(4-fluorophenyl)-2-N,1-dimethyl-4-oxopyridine-2,5-dicarboxamide |

-continued

| Cpd # | Structure | IUPAC Name |
|---|---|---|
| 564 | 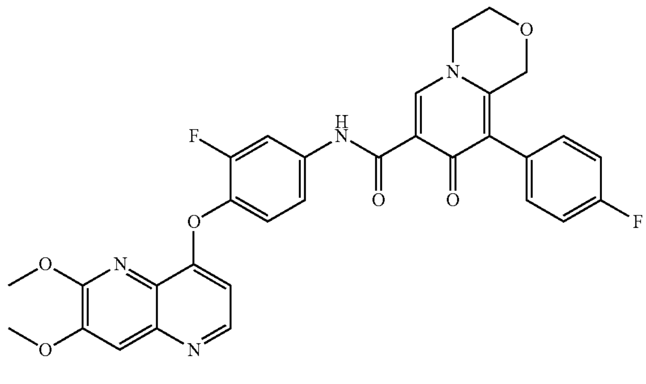 [SMILES: COc1cc2nccc(Oc3ccc(NC(=O)c4cn5c(c(-c6ccc(F)cc6)c4=O)COCC5)cc3F)c2nc1OC] | N-[4-[(6,7-dimethoxy-1,5-naphthyridin-4-yl)oxy]-3-fluorophenyl]-9-(4-fluorophenyl)-8-oxo-3,4-dihydro-1H-pyrido[2,1-c][1,4]oxazine-7-carboxamide |
| 565 | 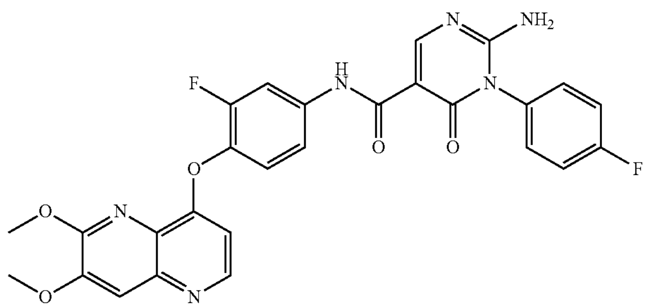 [SMILES: COc1cc2nccc(Oc3ccc(NC(=O)c4cnc(N)n(-c5ccc(F)cc5)c4=O)cc3F)c2nc1OC] | 2-amino-N-[4-[(6,7-dimethoxy-1,5-naphthyridin-4-yl)oxy]-3-fluorophenyl]-1-(4-fluorophenyl)-6-oxopyrimidine-5-carboxamide |
| 566 | 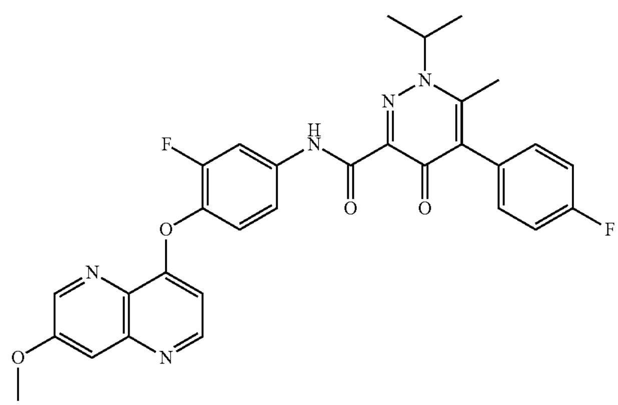 [SMILES: COc1cnc2c(Oc3ccc(NC(=O)c4nn(C(C)C)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methyl-4-oxo-1-propan-2-ylpyridazine-3-carboxamide |
| 567 | 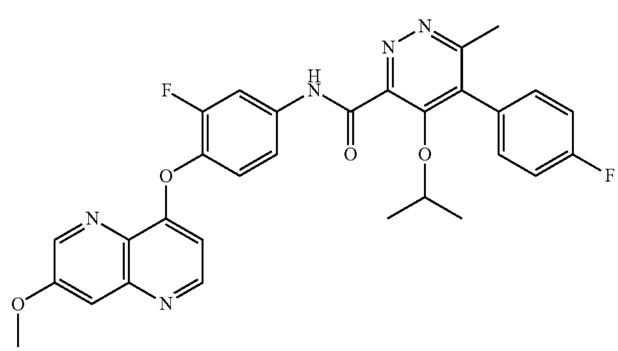 [SMILES: COc1cnc2c(Oc3ccc(NC(=O)c4nnc(C)c(-c5ccc(F)cc5)c4OC(C)C)cc3F)ccnc2c1] | N-[3-fluoro-4-[(7-methoxy-1,5-naphthyridin-4-yl)oxy]phenyl]-5-(4-fluorophenyl)-6-methyl-4-propan-2-yloxypyridazine-3-carboxamide |

-continued

| Cpd # | Structure | IUPAC Name |
|---|---|---|
| 568 | 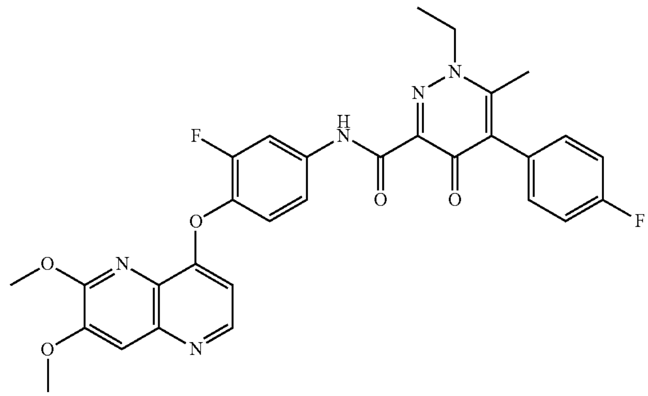 [SMILES: CCn1nc(C(=O)Nc2ccc(Oc3ccnc4cc(OC)c(OC)nc34)c(F)c2)c(=O)c(-c2ccc(F)cc2)c1C] | N-[4-[(6,7-dimethoxy-1,5-naphthyridin-4-yl)oxy]-3-fluorophenyl]-1-ethyl-5-(4-fluorophenyl)-6-methyl-4-oxopyridazine-3-carboxamide |
| 569 | 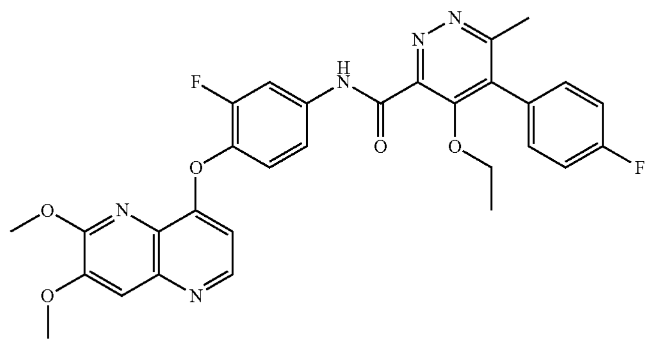 [SMILES: CCOc1c(C(=O)Nc2ccc(Oc3ccnc4cc(OC)c(OC)nc34)c(F)c2)nnc(C)c1-c1ccc(F)cc1] | N-[4-[(6,7-dimethoxy-1,5-naphthyridin-4-yl)oxy]-3-fluorophenyl]-4-ethoxy-5-(4-fluorophenyl)-6-methylpyridazine-3-carboxamide |
| 570 | 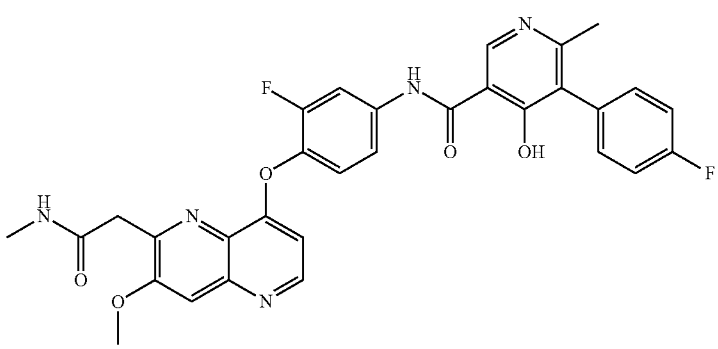 [SMILES: CNC(=O)Cc1nc2c(Oc3ccc(NC(=O)c4cnc(C)c(-c5ccc(F)cc5)c4O)cc3F)ccnc2cc1OC] | N-[3-fluoro-4-[[7-methoxy-6-[2-(methylamino)-2-oxoethyl]-1,5-naphthyridin-4-yl]oxy]phenyl]-5-(4-fluorophenyl)-4-hydroxy-6-methylpyridine-3-carboxamide |
| 571 | 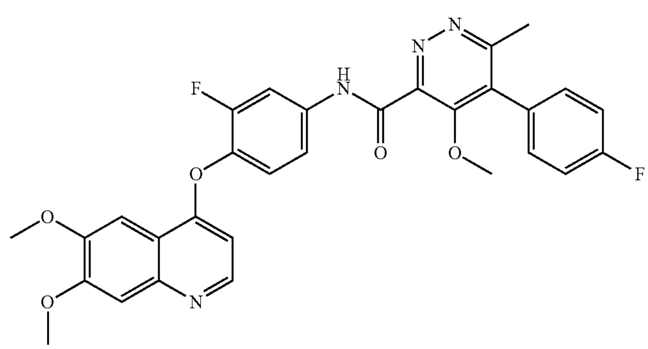 [SMILES: COc1cc2nccc(Oc3ccc(NC(=O)c4nnc(C)c(-c5ccc(F)cc5)c4OC)cc3F)c2cc1OC] | N-[4-(6,7-dimethoxyquinolin-4-yl)oxy-3-fluorophenyl]-5-(4-fluorophenyl)-4-methoxy-6-methylpyridazine-3-carboxamide |

| Cpd # | Structure | IUPAC Name |
|---|---|---|
| 572 | 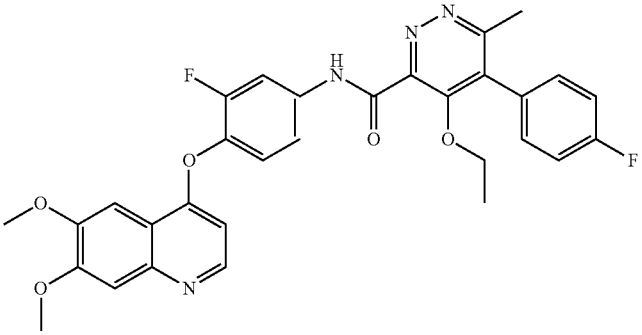 | N-[4-(6,7-dimethoxyquinolin-4-yl)oxy-3-fluorophenyl]-4-ethoxy-5-(4-fluorophenyl)-6-methylpyridazine-3-carboxamide |
| 573 | 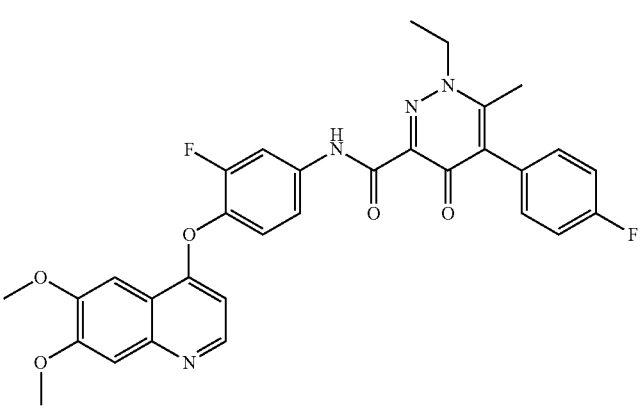 [SMILES: CCn1nc(C(=O)Nc2ccc(Oc3ccnc4cc(OC)c(OC)cc34)c(F)c2)c(=O)c(-c2ccc(F)cc2)c1C] | N-[4-(6,7-dimethoxyquinolin-4-yl)oxy-3-fluorophenyl]-1-ethyl-5-(4-fluorophenyl)-6-methyl-4-oxopyridazine-3-carboxamide |
| 574 | 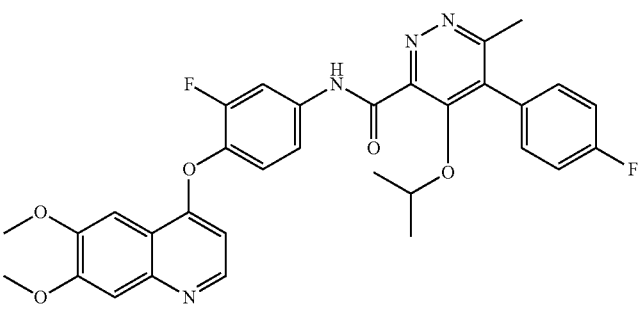 [SMILES: COc1cc2nccc(Oc3ccc(NC(=O)c4nnc(C)c(-c5ccc(F)cc5)c4OC(C)C)cc3F)c2cc1OC] | N-[4-(6,7-dimethoxyquinolin-4-yl)oxy-3-fluorophenyl]-5-(4-fluorophenyl)-6-methyl-4-propan-2-yloxypyridazine-3-carboxamide |
| 575 | 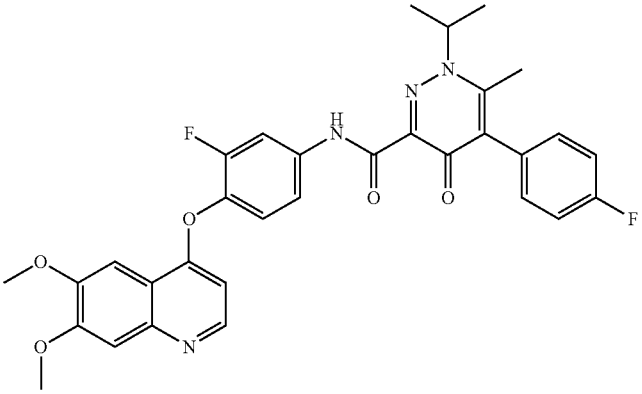 [SMILES: COc1cc2nccc(Oc3ccc(NC(=O)c4nn(C(C)C)c(C)c(-c5ccc(F)cc5)c4=O)cc3F)c2cc1OC] | N-[4-(6,7-dimethoxyquinolin-4-yl)oxy-3-fluorophenyl]-5-(4-fluorophenyl)-6-methyl-4-oxo-1-propan-2-ylpyridazine-3-carboxamide |

| Cpd # | Structure | IUPAC Name |
|---|---|---|
| 576 | 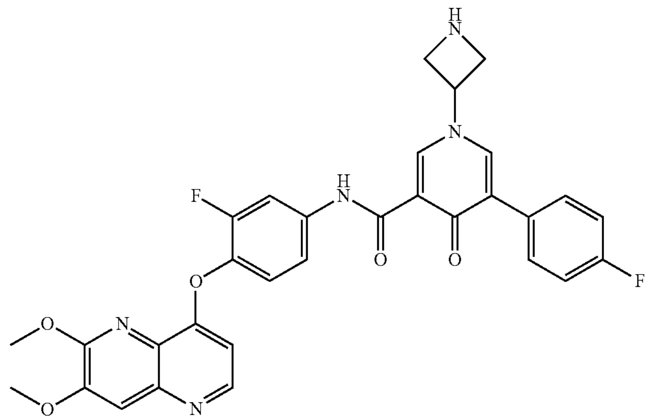 [SMILES: COc1cc2nccc(Oc3ccc(NC(=O)c4cn(C5CNC5)cc(-c5ccc(F)cc5)c4=O)cc3F)c2nc1OC] | 1-(azetidin-3-yl)-N-[4-[(6,7-dimethoxy-1,5-naphthyridin-4-yl)oxy]-3-fluorophenyl]-5-(4-fluorophenyl)-4-oxopyridine-3-carboxamide |
| 577 | 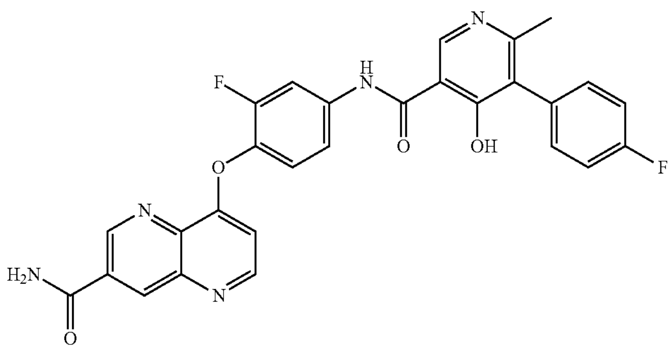 [SMILES: Cc1ncc(C(=O)Nc2ccc(Oc3ccnc4cc(C(N)=O)cnc34)c(F)c2)c(O)c1-c1ccc(F)cc1] | 8-[2-fluoro-4-[[5-(4-fluorophenyl)-4-hydroxy-6-methylpyridine-3-carbonyl]amino]phenoxy]-1,5-naphthyridine-3-carboxamide |
| 578 | 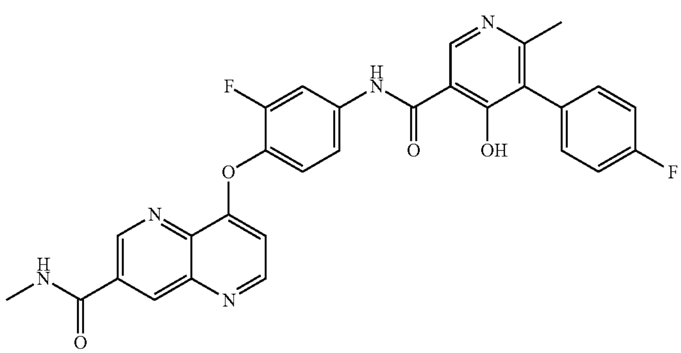 [SMILES: CNC(=O)c1cnc2c(Oc3ccc(NC(=O)c4cnc(C)c(-c5ccc(F)cc5)c4O)cc3F)ccnc2c1] | 8-[2-fluoro-4-[5-(4-fluorophenyl)-4-hydroxy-6-methylpyridine-3-carbonyl]amino]phenoxy]-N-methyl-1,5-naphthyridine-3-carboxamide |
| 579 | 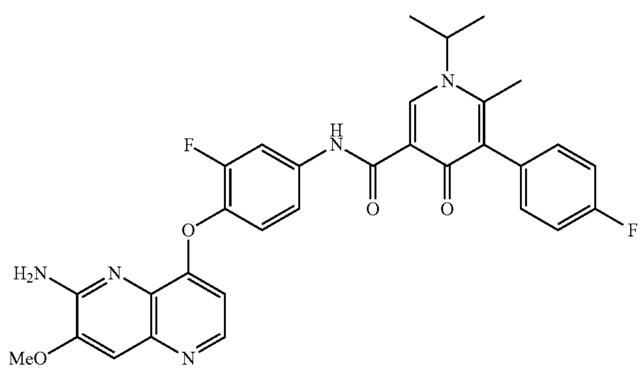 [SMILES: COc1cc2nccc(Oc3ccc(NC(=O)c4cn(C(C)C)c(C)c(-c5ccc(F)cc5)c4=O)cc3F)c2nc1N] | N-[4-[(6-amino-7-methoxy-1,5-naphthyridin-4-yl)oxy]-3-fluorophenyl]-5-(4-fluorophenyl)-6-methyl-4-oxo-1-propan-2-ylpyridine-3-carboxamide |

-continued

| Cpd # | Structure | IUPAC Name |
|---|---|---|
| 580 | 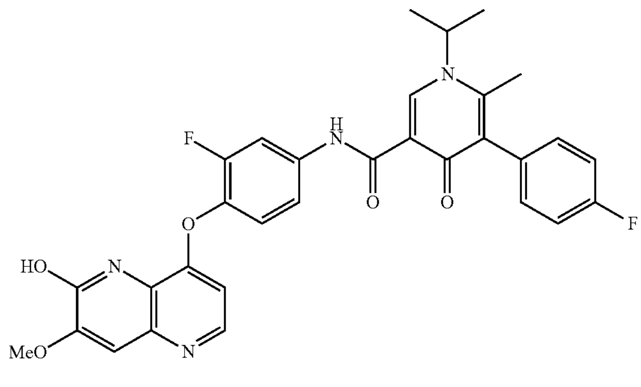 | N-[3-fluoro-4-[(6-hydroxy-7-methoxy-1,5-naphthyridin-4-yl)oxy]phenyl]-5-(4-fluorophenyl)-6-methyl-4-oxo-1-propan-2-ylpyridine-3-carboxamide |
| 581 | 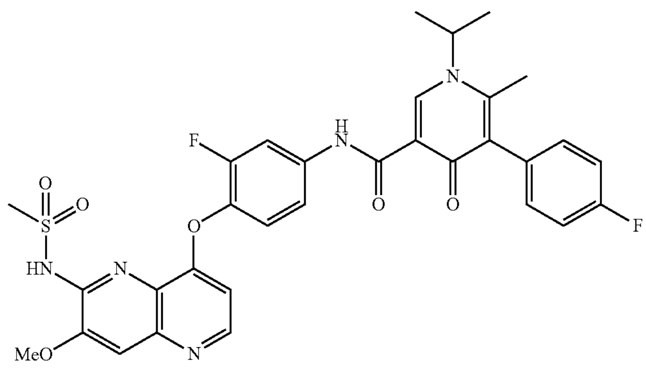 [SMILES: COc1cc2nccc(Oc3ccc(NC(=O)c4cn(C(C)C)c(C)c(-c5ccc(F)cc5)c4=O)cc3F)c2nc1NS(C)(=O)=O] | N-[3-fluoro-4-[[6-(methanesulfonamido)-7-methoxy-1,5-naphthyridin-4-yl]oxy]phenyl]-5-(4-fluorophenyl)-6-methyl-4-oxo-1-propan-2-ylpyridine-3-carboxamide |
| 582 | 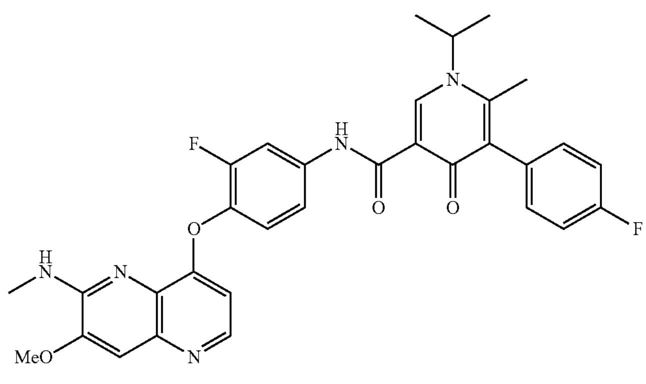 [SMILES: CNc1nc2c(Oc3ccc(NC(=O)c4cn(C(C)C)c(C)c(-c5ccc(F)cc5)c4=O)cc3F)ccnc2cc1OC] | N-[3-fluoro-4-[[7-methoxy-6-(methylamino)-1,5-naphthyridin-4-yl]oxy]phenyl]-5-(4-fluorophenyl)-6-methyl-4-oxo-1-propan-2-ylpyridine-3-carboxamide |
| 583 | 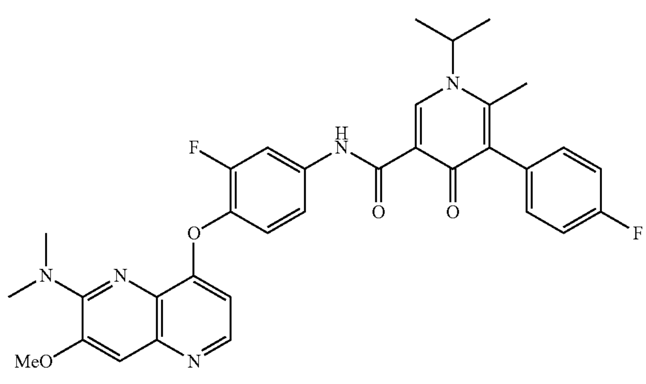 [SMILES: COc1cc2nccc(Oc3ccc(NC(=O)c4cn(C(C)C)c(C)c(-c5ccc(F)cc5)c4=O)cc3F)c2nc1N(C)C] | N-[4-[[6-(dimethylamino)-7-methoxy-1,5-naphthyridin-4-yl]oxy]-3-fluorophenyl]-5-(4-fluorophenyl)-6-methyl-4-oxo-1-propan-2-ylpyridine-3-carboxamide |

| Cpd # | Structure | IUPAC Name |
|---|---|---|
| 584 | 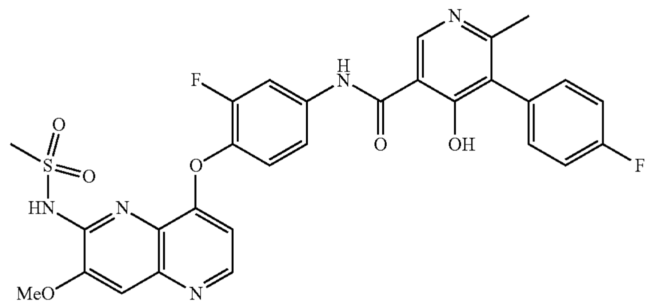 [SMILES: COc1cc2nccc(Oc3ccc(NC(=O)c4cnc(C)c(-c5ccc(F)cc5)c4O)cc3F)c2nc1NS(C)(=O)=O] | N-[3-fluoro-4-[[6-(methanesulfonamido)-7-methoxy-1,5-naphthyridin-4-yl]oxy]phenyl]-5-(4-fluorophenyl)-4-hydroxy-6-methylpyridine-3-carboxamide |
| 585 | 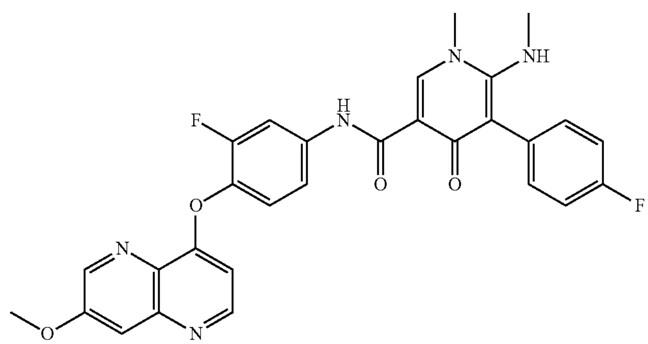 [SMILES: CNc1c(-c2ccc(F)cc2)c(=O)c(C(=O)Nc2ccc(Oc3ccnc4cc(OC)cnc34)c(F)c2)cn1C] | N-[3-fluoro-4-[(7-methoxy-1,5-naphthyridin-4-yl)oxy]phenyl]-5-(4-fluorophenyl)-1-methyl-6-(methylamino)-4-oxopyridine-3-carboxamide |
| 586 | 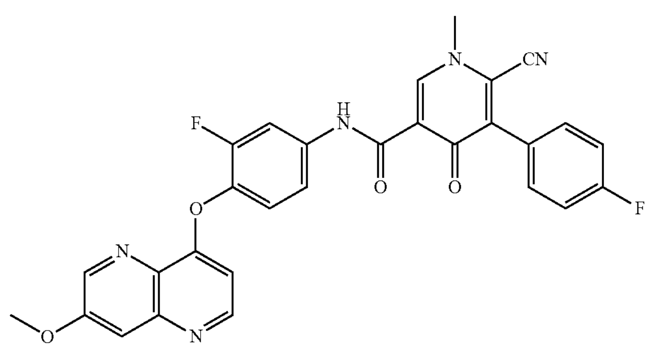 [SMILES: COc1cnc2c(Oc3ccc(NC(=O)c4cn(C)c(C#N)c(-c5ccc(F)cc5)c4=O)cc3F)ccnc2c1] | 6-cyano-N-[3-fluoro-4-[(7-methoxy-1,5-naphthyridin-4-yl)oxy]phenyl]-5-(4-fluorophenyl)-1-methyl-4-oxopyridine-3-carboxamide |
| 587 | 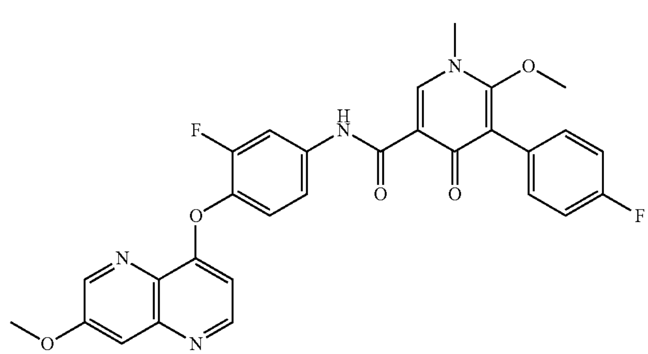 [SMILES: COc1cnc2c(Oc3ccc(NC(=O)c4cn(C)c(OC)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-6-methoxy-1-methyl-4-oxopyridine-3-carboxamide |

| Cpd # | Structure | IUPAC Name |
|---|---|---|
| 588 | 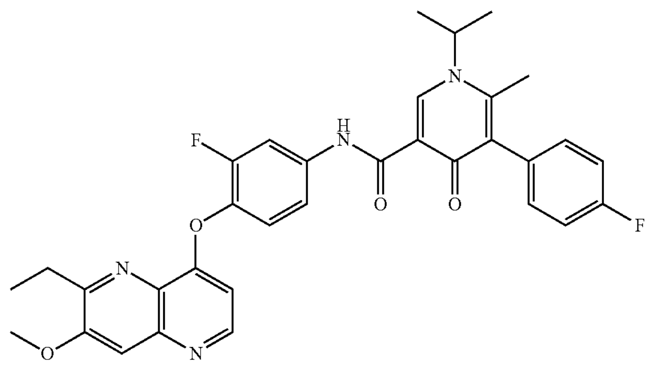 [SMILES: CCc1nc2c(Oc3ccc(NC(=O)c4cn(C(C)C)c(C)c(-c5ccc(F)cc5)c4=O)cc3F)ccnc2cc1OC] | N-[4-[(6-ethyl-7-methoxy-1,5-naphthyridin-4-yl)oxy]-3-fluorophenyl]-5-(4-fluorophenyl)-6-methyl-4-oxo-1-propan-2-ylpyridine-3-carboxamide |
| 589 | 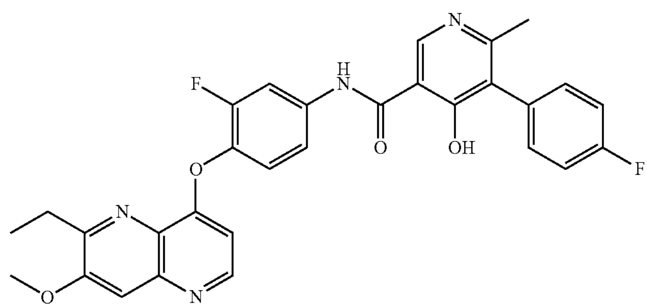 [SMILES: CCc1nc2c(Oc3ccc(NC(=O)c4cnc(C)c(-c5ccc(F)cc5)c4O)cc3F)ccnc2cc1OC] | N-[4-[(6-ethyl-7-methoxy-1,5-naphthyridin-4-yl)oxy]-3-fluorophenyl]-5-(4-fluorophenyl)-4-hydroxy-6-methylpyridine-3-carboxamide |
| 590 | 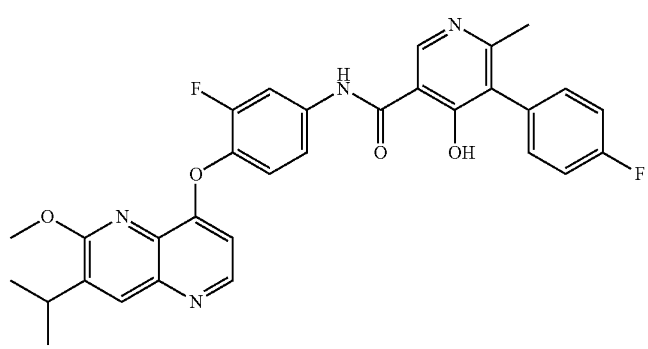 [SMILES: COc1nc2c(Oc3ccc(NC(=O)c4cnc(C)c(-c5ccc(F)cc5)c4O)cc3F)ccnc2cc1C(C)C] | N-[3-fluoro-4-[(6-methoxy-7-propan-2-yl-1,5-naphthyridin-4-yl)oxy]phenyl]-5-(4-fluorophenyl)-4-hydroxy-6-methylpyridine-3-carboxamide |
| 591 | 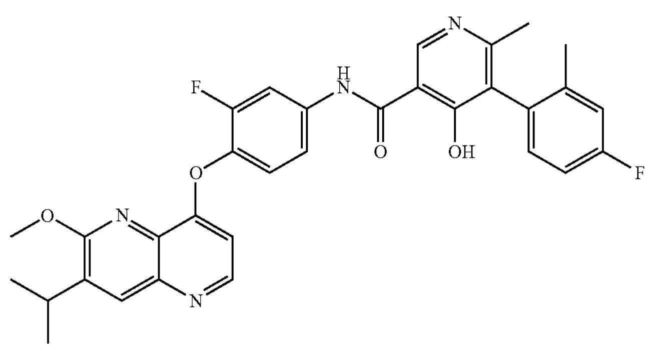 [SMILES: COc1nc2c(Oc3ccc(NC(=O)c4cnc(C)c(-c5ccc(F)cc5C)c4O)cc3F)ccnc2cc1C(C)C] | N-[3-fluoro-4-[(6-methoxy-7-propan-2-yl-1,5-naphthyridin-4-yl)oxy]phenyl]-5-(4-fluoro-2-methylphenyl)-4-hydroxy-6-methylpyridine-3-carboxamide |

-continued

| Cpd # | Structure | IUPAC Name |
|---|---|---|
| 592 | 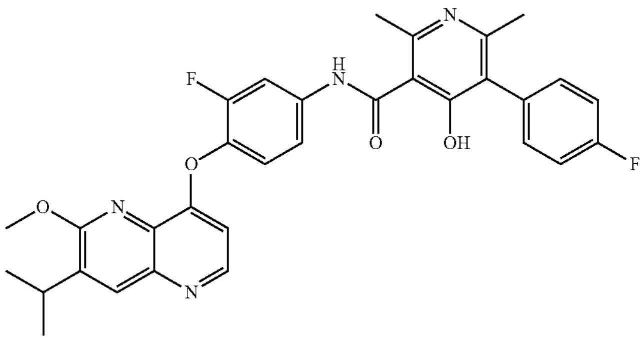 [SMILES: COc1nc2c(Oc3ccc(NC(=O)c4c(C)nc(C)c(-c5ccc(F)cc5)c4O)cc3F)ccnc2cc1C(C)C] | N-[3-fluoro-4-[(6-methoxy-7-propan-2-yl-1,5-naphthyridin-4-yl)oxy]phenyl]-5-(4-fluorophenyl)-4-hydroxy-2,6-dimethylpyridine-3-carboxamide |
| 593 | 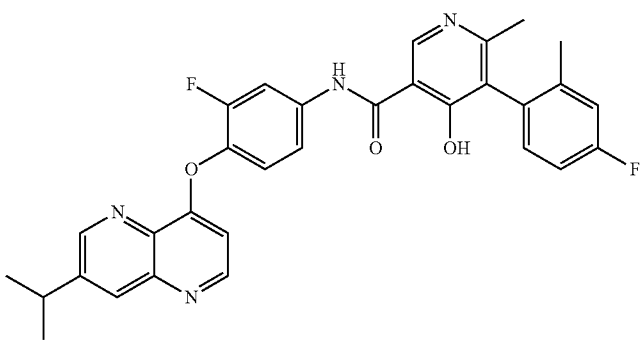 [SMILES: Cc1cc(F)ccc1-c1c(C)ncc(C(=O)Nc2ccc(Oc3ccnc4cc(C(C)C)cnc34)c(F)c2)c1O] | 5-(4-fluoro-2-methylphenyl)-N-[3-fluoro-4-[(7-propan-2-yl-1,5-naphthyridin-4-yl)oxy]phenyl]-4-hydroxy-6-methylpyridine-3-carboxamide |
| 594 | 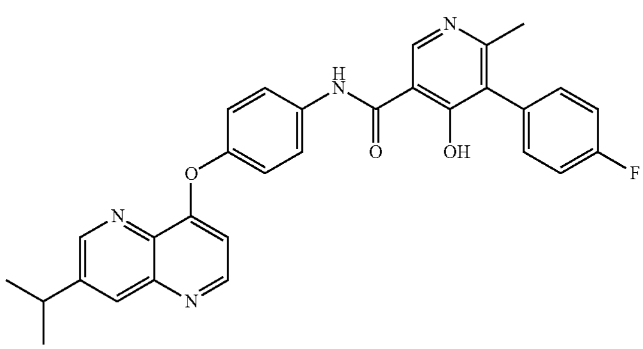 [SMILES: Cc1ncc(C(=O)Nc2ccc(Oc3ccnc4cc(C(C)C)cnc34)cc2)c(O)c1-c1ccc(F)cc1] | 5-(4-fluorophenyl)-4-hydroxy-6-methyl-N-[4-[(7-propan-2-yl-1,5-naphthyridin-4-yl)oxy]phenyl]pyridine-3-carboxamide |
| 595 | 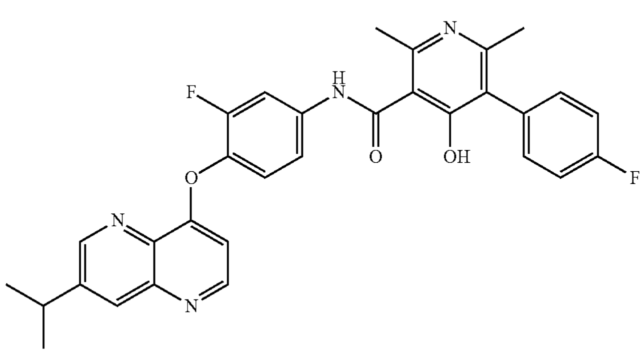 [SMILES: Cc1nc(C)c(-c2ccc(F)cc2)c(O)c1C(=O)Nc1ccc(Oc2ccnc3cc(C(C)C)cnc23)c(F)c1] | 5-(4-fluorophenyl)-N-[3-fluoro-4-[(7-propan-2-yl-1,5-naphthyridin-4-yl)oxy]phenyl]-4-hydroxy-2,6-dimethylpyridine-3-carboxamide |

| Cpd # | Structure | IUPAC Name |
|---|---|---|
| 596 | 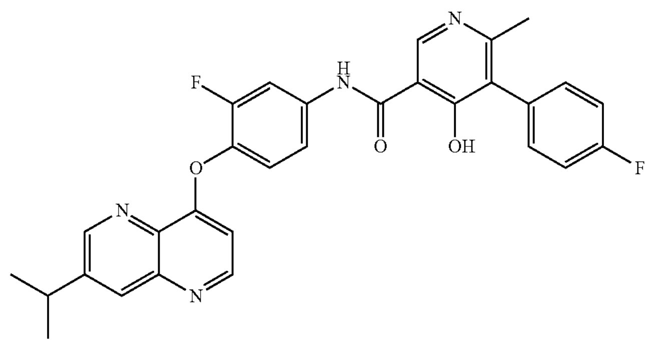 [SMILES: Cc1ncc(C(=O)Nc2ccc(Oc3ccnc4cc(C(C)C)cnc34)c(F)c2)c(O)c1-c1ccc(F)cc1] | 5-(4-fluorophenyl)-N-[3-fluoro-4-[(7-propan-2-yl-1,5-naphthyridin-4-yl)oxy]phenyl]-4-hydroxy-6-methylpyridine-3-carboxamide |
| 597 | 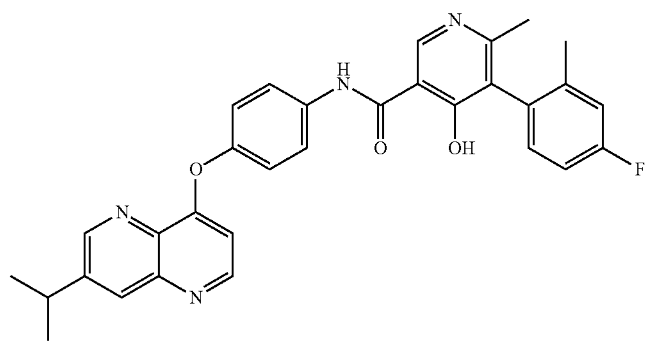 [SMILES: Cc1cc(F)ccc1-c1c(C)ncc(C(=O)Nc2ccc(Oc3ccnc4cc(C(C)C)cnc34)cc2)c1O] | 5-(4-fluoro-2-methylphenyl)-4-hydroxy-6-methyl-N-[4-[(7-propan-2-yl-1,5-naphthyridin-4-yl)oxy]phenyl]pyridine-3-carboxamide |
| 598 | 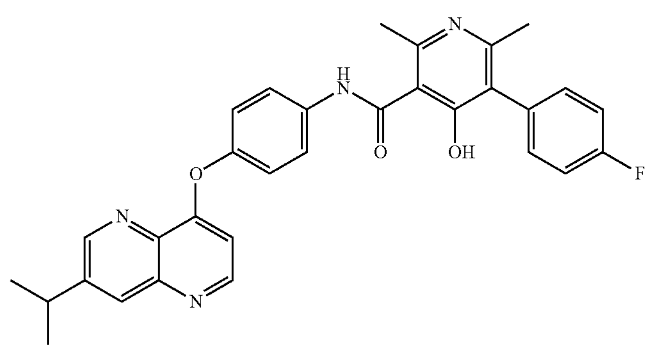 [SMILES: Cc1nc(C)c(-c2ccc(F)cc2)c(O)c1C(=O)Nc1ccc(Oc2ccnc3cc(C(C)C)cnc23)cc1] | 5-(4-fluorophenyl)-4-hydroxy-2,6-dimethyl-N-[4-[(7-propan-2-yl-1,5-naphthyridin-4-yl)oxy]phenyl]pyridine-3-carboxamide |
| 599 | 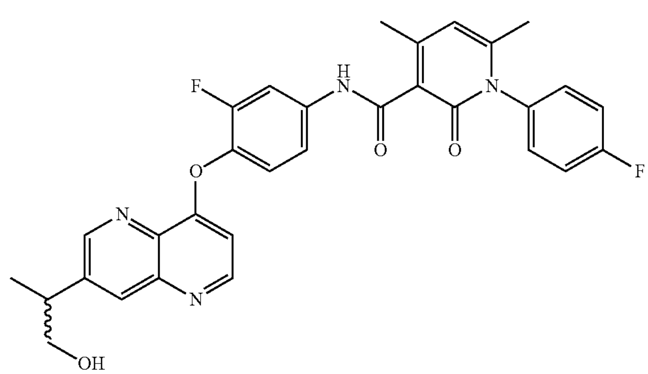 [SMILES: Cc1cc(C)n(-c2ccc(F)cc2)c(=O)c1C(=O)Nc1ccc(Oc2ccnc3cc(C(C)CO)cnc23)c(F)c1] | N-[3-fluoro-4-[[7-(1-hydroxypropan-2-yl)-1,5-naphthyridin-4-yl]oxy]phenyl]-1-(4-fluorophenyl)-4,6-dimethyl-2-oxopyridine-3-carboxamide |

-continued

| Cpd # | Structure | IUPAC Name |
|---|---|---|
| 600 | 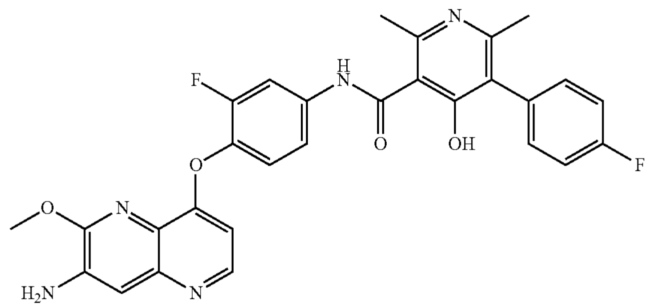 [SMILES: COc1nc2c(Oc3ccc(NC(=O)c4c(C)nc(C)c(-c5ccc(F)cc5)c4O)cc3F)ccnc2cc1N] | N-[4-[(7-amino-6-methoxy-1,5-naphthyridin-4-yl)oxy]-3-fluorophenyl]-5-(4-fluorophenyl)-4-hydroxy-2,6-dimethylpyridine-3-carboxamide |
| 601 | 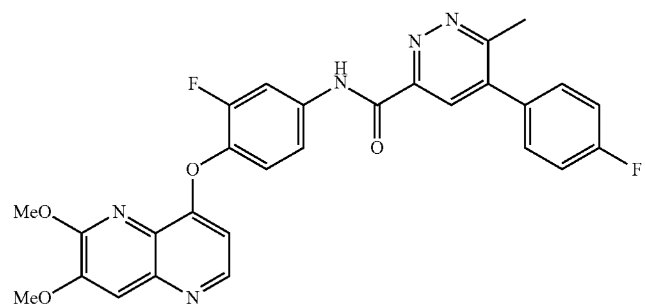 [SMILES: COc1cc2nccc(Oc3ccc(NC(=O)c4cc(-c5ccc(F)cc5)c(C)nn4)cc3F)c2nc1OC] | N-[4-[(6,7-dimethoxy-1,5-naphthyridin-4-yl)oxy]-3-fluorophenyl]-5-(4-fluorophenyl)-6-methylpyridazine-3-carboxamide |
| 602 | 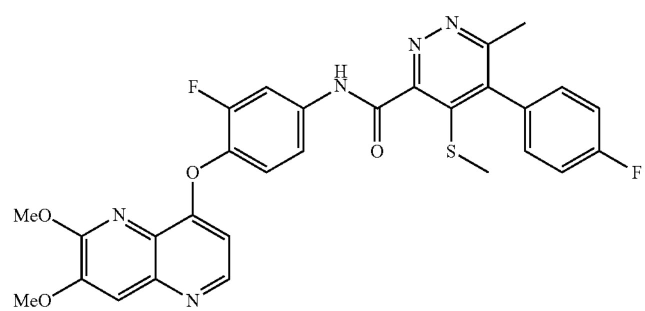 [SMILES: COc1cc2nccc(Oc3ccc(NC(=O)c4nnc(C)c(-c5ccc(F)cc5)c4SC)cc3F)c2nc1OC] | N-[4-[(6,7-dimethoxy-1,5-naphthyridin-4-yl)oxy]-3-fluorophenyl]-5-(4-fluorophenyl)-6-methyl-4-methylsulfanylpyridazine-3-carboxamide |
| 603 | 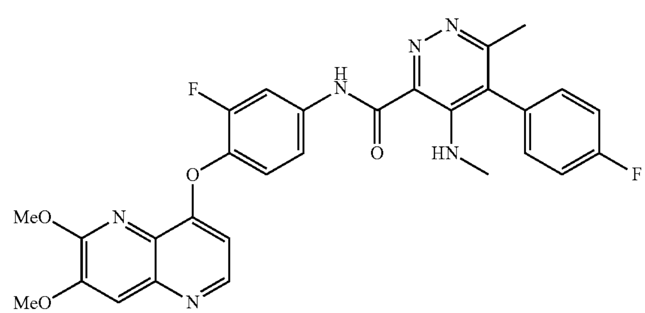 [SMILES: CNc1c(C(=O)Nc2ccc(Oc3ccnc4cc(OC)c(OC)nc34)c(F)c2)nnc(C)c1-c1ccc(F)cc1] | N-[4-[(6,7-dimethoxy-1,5-naphthyridin-4-yl)oxy]-3-fluorophenyl]-5-(4-fluorophenyl)-6-methyl-4-(methylamino)pyridazine-3-carboxamide |

-continued

| Cpd # | Structure | IUPAC Name |
|---|---|---|
| 604 | 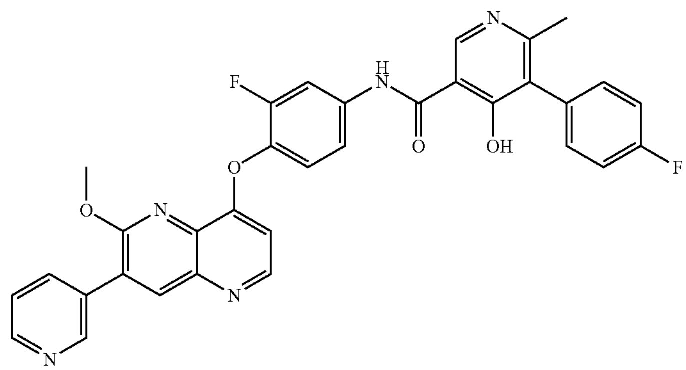 [SMILES: COc1nc2c(Oc3ccc(NC(=O)c4cnc(C)c(-c5ccc(F)cc5)c4O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-4-hydroxy-6-methylpyridine-3-carboxamide |
| 605 | 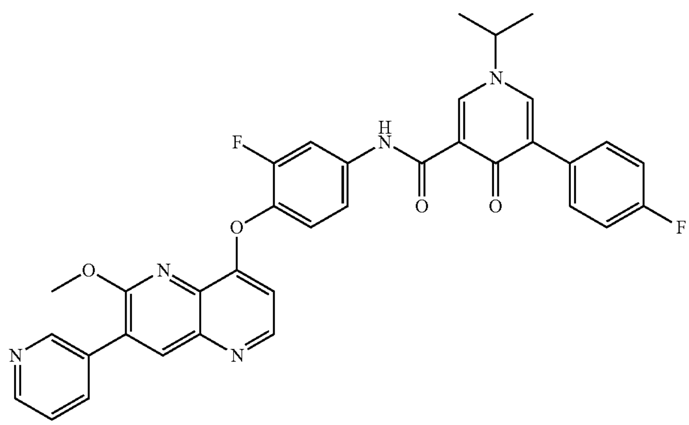 [SMILES: COc1nc2c(Oc3ccc(NC(=O)c4cn(C(C)C)cc(-c5ccc(F)cc5)c4=O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-4-oxo-1-propan-2-ylpyridine-3-carboxamide |
| 606 | 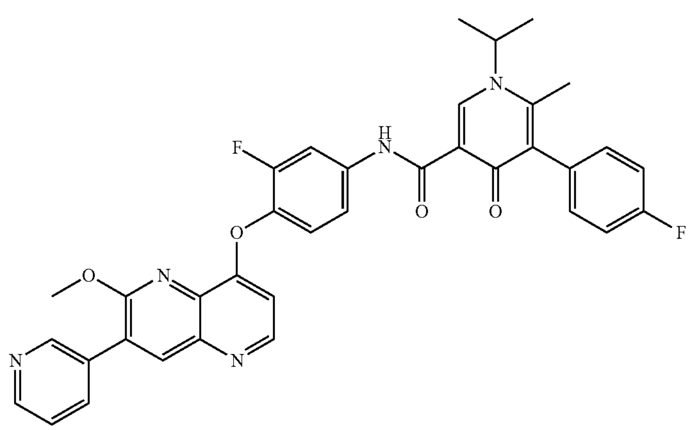 [SMILES: COc1nc2c(Oc3ccc(NC(=O)c4cn(C(C)C)c(C)c(-c5ccc(F)cc5)c4=O)cc3F)ccnc2cc1-c1cccnc1] | N-[3-fluoro-4-[(6-methoxy-7-pyridin-3-yl-1,5-naphthyridin-4-yl)oxy]phenyl]-5-(4-fluorophenyl)-6-methyl-4-oxo-1-propan-2-ylpyridine-3-carboxamide |
| 607 | 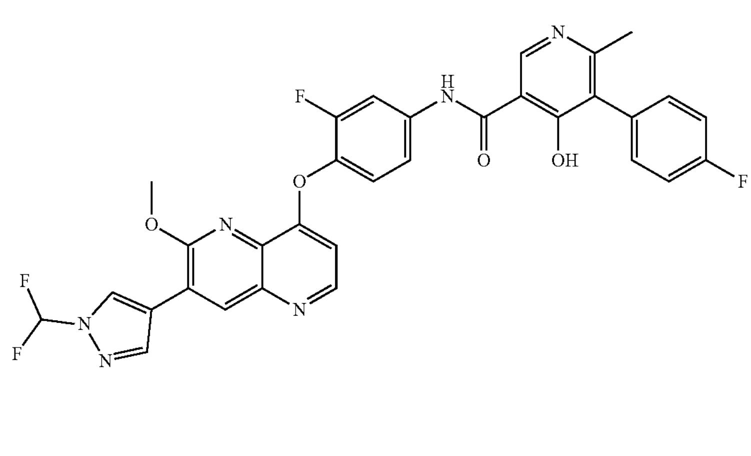 [SMILES: COc1nc2c(Oc3ccc(NC(=O)c4cnc(C)c(-c5ccc(F)cc5)c4O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-4-hydroxy-6-methylpyridine-3-carboxamide |

-continued

| Cpd # | Structure | IUPAC Name |
|---|---|---|
| 608 | 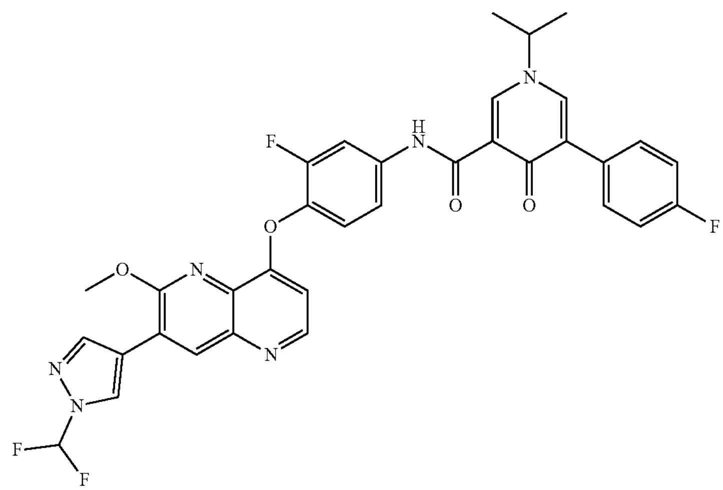 [SMILES: COc1nc2c(Oc3ccc(NC(=O)c4cn(C(C)C)cc(-c5ccc(F)cc5)c4=O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-4-oxo-1-propan-2-ylpyridine-3-carboxamide |
| 609 | 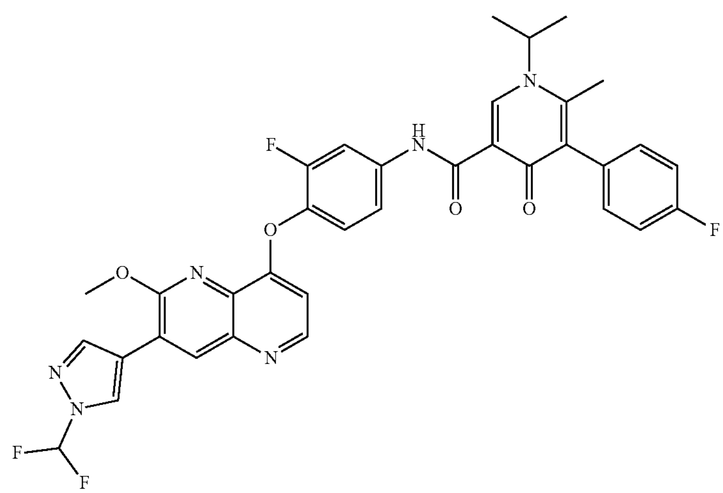 [SMILES: COc1nc2c(Oc3ccc(NC(=O)c4cn(C(C)C)c(C)c(-c5ccc(F)cc5)c4=O)cc3F)ccnc2cc1-c1cnn(C(F)F)c1] | N-[4-[[7-[1-(difluoromethyl)pyrazol-4-yl]-6-methoxy-1,5-naphthyridin-4-yl]oxy]-3-fluorophenyl]-5-(4-fluorophenyl)-6-methyl-4-oxo-1-propan-2-ylpyridine-3-carboxamide |
| 610 | 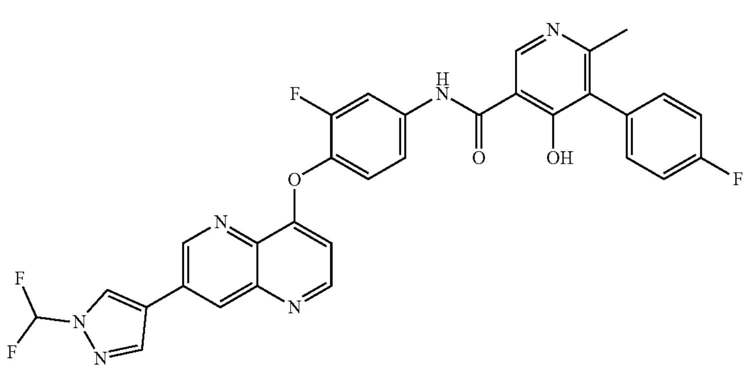 [SMILES: Cc1ncc(C(=O)Nc2ccc(Oc3ccnc4cc(-c5cnn(C(F)F)c5)cnc34)c(F)c2)c(O)c1-c1ccc(F)cc1] | N-[4-[[7-[1-(difluoromethyl)pyrazol-4-yl]-1,5-naphthyridin-4-yl]oxy]-3-fluorophenyl]-5-(4-fluorophenyl)-4-hydroxy-6-methylpyridine-3-carboxamide |

| Cpd # | Structure | IUPAC Name |
|---|---|---|
| 611 | 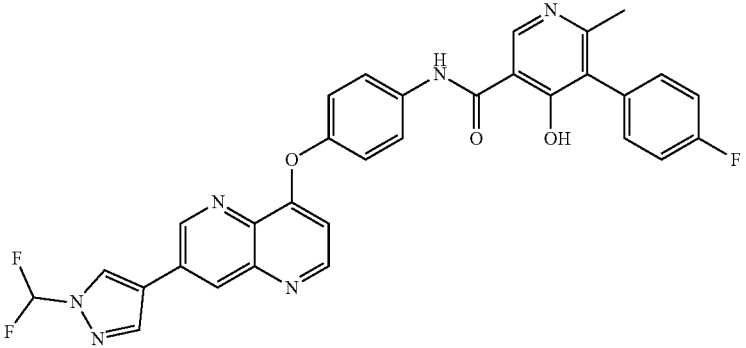 | N-[4-[[7-[1-(difluoromethyl)pyrazol-4-yl]-1,5-naphthyridin-4-yl]oxy]phenyl]-5-(4-fluorophenyl)-4-hydroxy-6-methylpyridine-3-carboxamide |
| 612 | 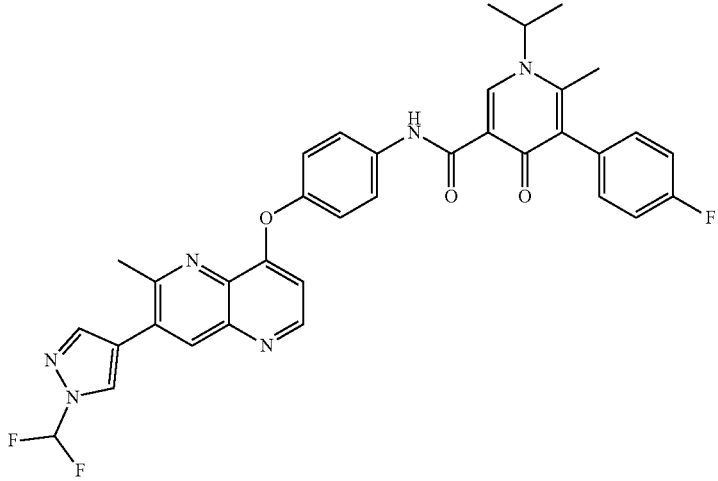 [SMILES: Cc1nc2c(Oc3ccc(NC(=O)c4cn(C(C)C)c(C)c(-c5ccc(F)cc5)c4=O)cc3)ccnc2cc1-c1cnn(C(F)F)c1] | N-[4-[7-[1-(difluoromethyl)pyrazol-4-yl]-6-methyl-1,5-naphthyridin-4-yl]oxy]phenyl]-5-(4-fluorophenyl)-6-methyl-4-oxo-1-propan-2-ylpyridine-3-carboxamide |
| 613 | 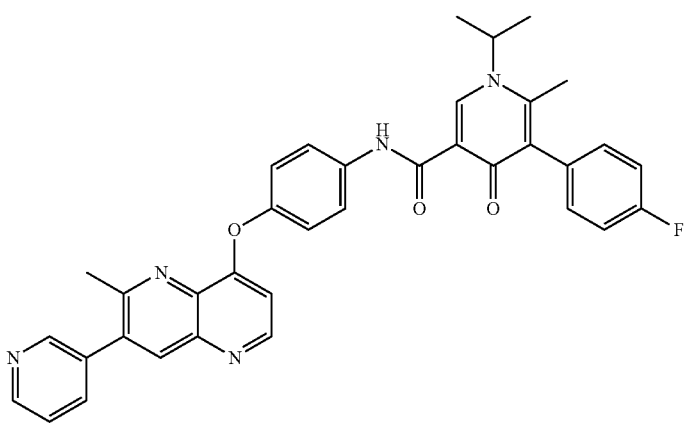 [SMILES: Cc1nc2c(Oc3ccc(NC(=O)c4cn(C(C)C)c(C)c(-c5ccc(F)cc5)c4=O)cc3)ccnc2cc1-c1cccnc1] | 5-(4-fluorophenyl)-6-methyl-N-[4-[(6-methyl-7-pyridin-3-yl-1,5-naphthyridin-4-yl)oxy]phenyl]-4-oxo-1-propan-2-ylpyridine-3-carboxamide |

-continued

| Cpd # | Structure | IUPAC Name |
|---|---|---|
| 614 | 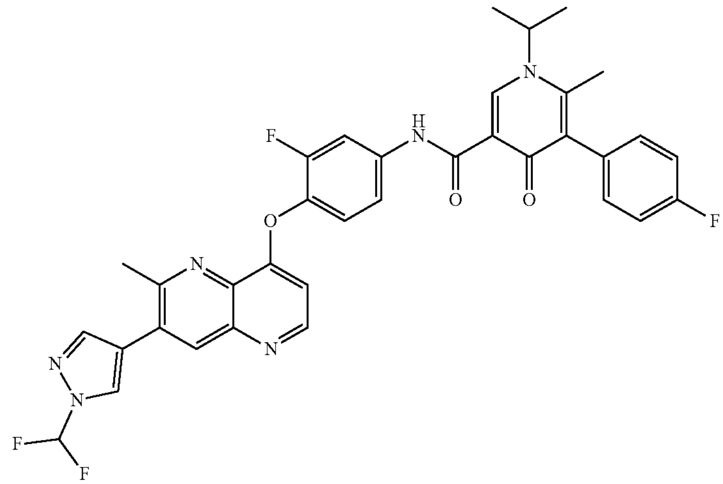 [SMILES: Cc1nc2c(Oc3ccc(NC(=O)c4cn(C(C)C)c(C)c(-c5ccc(F)cc5)c4=O)cc3F)ccnc2cc1-c1cnn(C(F)F)c1] | N-[4-[7-[1-(difluoromethyl)pyrazol-4-yl]-6-methyl-1,5-naphthyridin-4-yl]oxy]-3-fluorophenyl]-5-(4-fluorophenyl)-6-methyl-4-oxo-1-propan-2-ylpyridine-3-carboxamide |
| 615 | 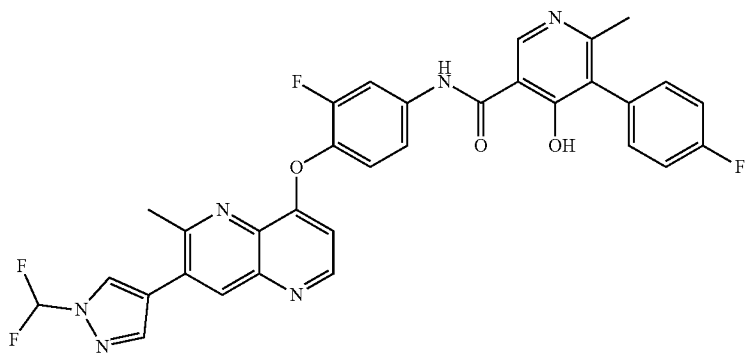 [SMILES: Cc1nc2c(Oc3ccc(NC(=O)c4cnc(C)c(-c5ccc(F)cc5)c4O)cc3F)ccnc2cc1-c1cnn(C(F)F)c1] | N-[4-[[7-[1-(difluoromethyl)pyrazol-4-yl]-6-methyl-1,5-naphthyridin-4-yl]oxy]-3-fluorophenyl]-5-(4-fluorophenyl)-4-hydroxy-6-methylpyridine-3-carboxamide |
| 616 | 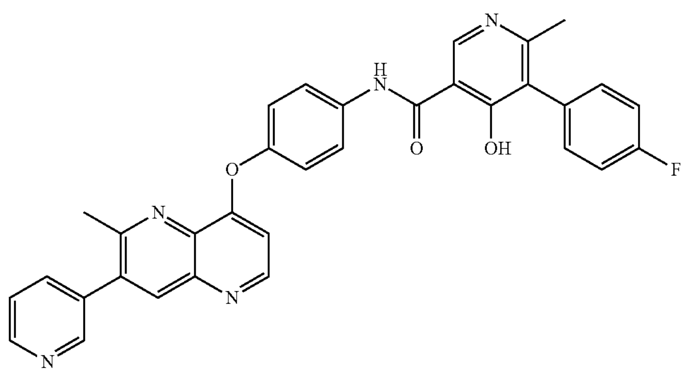 [SMILES: Cc1nc2c(Oc3ccc(NC(=O)c4cnc(C)c(-c5ccc(F)cc5)c4O)cc3)ccnc2cc1-c1cccnc1] | 5-(4-fluorophenyl)-4-hydroxy-6-methyl-N-[4-[(6-methyl-7-pyridin-3-yl-1,5-naphthyridin-4-yl)oxy]phenyl]pyridine-3-carboxamide |
| 617 | 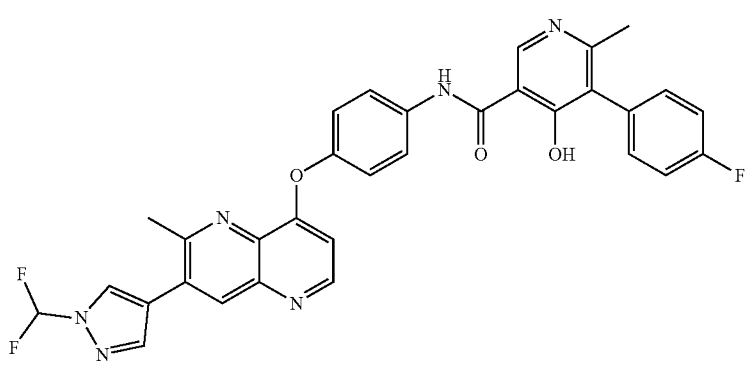 [SMILES: Cc1nc2c(Oc3ccc(NC(=O)c4cnc(C)c(-c5ccc(F)cc5)c4O)cc3)ccnc2cc1-c1cnn(C(F)F)c1] | N-[4-[[7-[1-(difluoromethyl)pyrazol-4-yl]-6-methyl-1,5-naphthyridin-4-yl]oxy]phenyl]-5-(4-fluorophenyl)-4-hydroxy-6-methylpyridine-3-carboxamide |

-continued

| Cpd # | Structure | IUPAC Name |
|---|---|---|
| 618 | 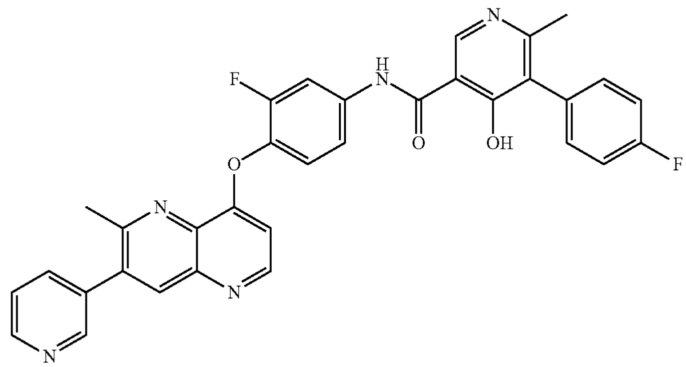 [SMILES: Cc1nc2c(Oc3ccc(NC(=O)c4cnc(C)c(-c5ccc(F)cc5)c4O)cc3F)ccnc2cc1-c1cccnc1] | N-[3-fluoro-4-[(6-methyl-7-pyridin-3-yl-1,5-naphthyridin-4-yl)oxy]phenyl]-5-(4-fluorophenyl)-4-hydroxy-6-methylpyridine-3-carboxamide |
| 619 | 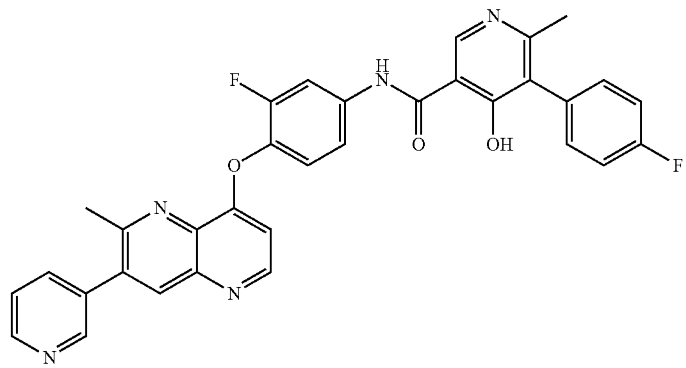 [SMILES: Cc1nc2c(Oc3ccc(NC(=O)c4cnc(C)c(-c5ccc(F)cc5)c4O)cc3F)ccnc2cc1-c1cccnc1] | N-[4-[(6,7-dimethoxy-1,5-naphthyridin-4-yl)oxy]-3-fluorophenyl]-5-(4-fluorophenyl)-1-(2-hydroxyethyl)-6-methyl-4-oxopyridine-3-carboxamide |
| 620 | 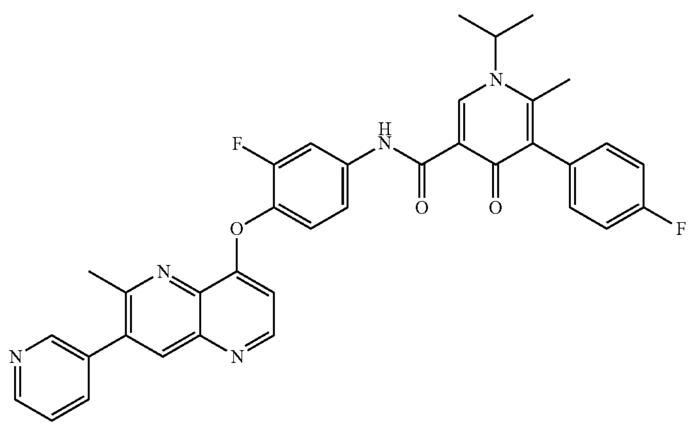 [SMILES: Cc1nc2c(Oc3ccc(NC(=O)c4cn(C(C)C)c(C)c(-c5ccc(F)cc5)c4=O)cc3F)ccnc2cc1-c1cccnc1] | N-[3-fluoro-4-[(6-methyl-7-pyridin-3-yl-1,5-naphthyridin-4-yl)oxy]phenyl]-5-(4-fluorophenyl)-6-methyl-4-oxo-1-propan-2-ylpyridine-3-carboxamide |
| 621 | 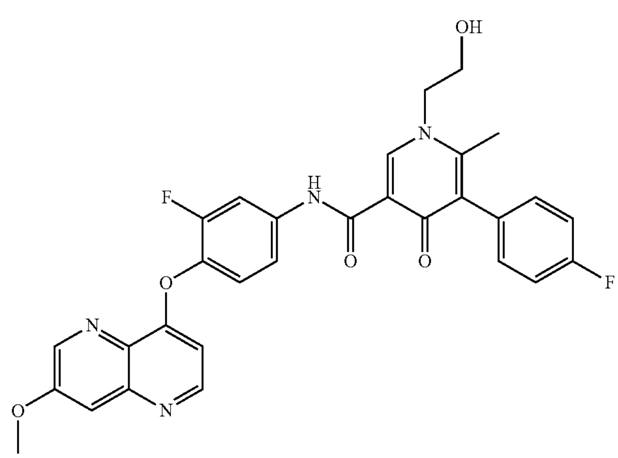 [SMILES: COc1cnc2c(Oc3ccc(NC(=O)c4cn(CCO)c(C)c(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-1-(2-hydroxyethyl)-6-methyl-4-oxopyridine-3-carboxamide |

-continued

| Cpd # | Structure | IUPAC Name |
|---|---|---|
| 622 | 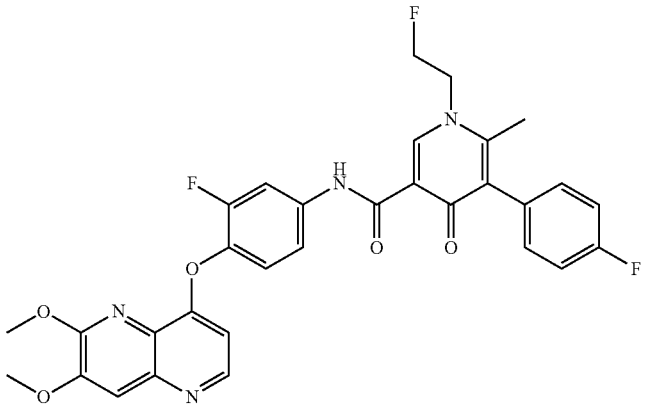 [SMILES: COc1cc2nccc(Oc3ccc(NC(=O)c4cn(CCF)c(C)c(-c5ccc(F)cc5)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluorophenyl)-6-methyl-4-oxopyridine-3-carboxamide |
| 623 | 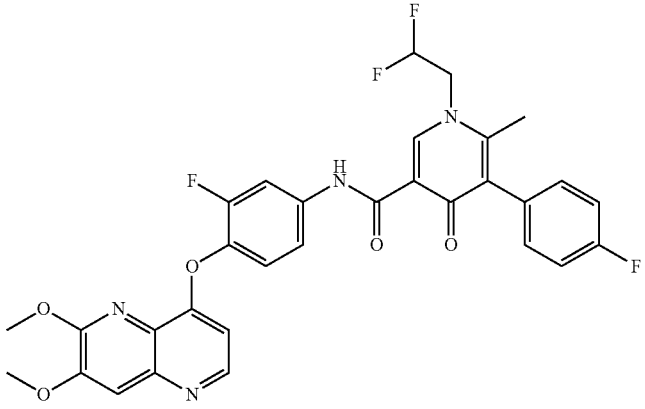 [SMILES: COc1cc2nccc(Oc3ccc(NC(=O)c4cn(CC(F)F)c(C)c(-c5ccc(F)cc5)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 624 | 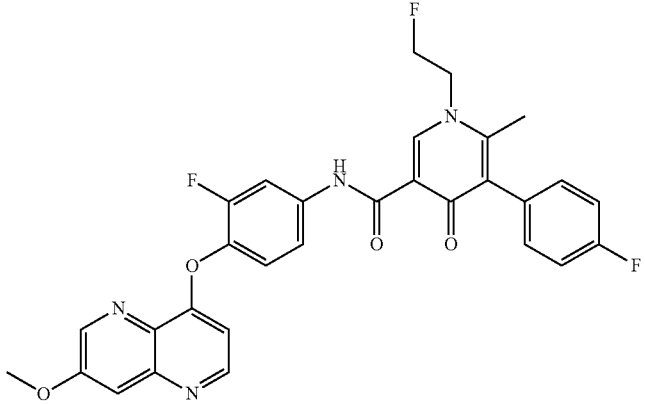 [SMILES: COc1cnc2c(Oc3ccc(NC(=O)c4cn(CCF)c(C)c(-c5ccc(F)cc5)c4=O)cc3F)ccnc2c1] | 1-(2-fluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide |

-continued

| Cpd # | Structure | IUPAC Name |
|---|---|---|
| 625 | 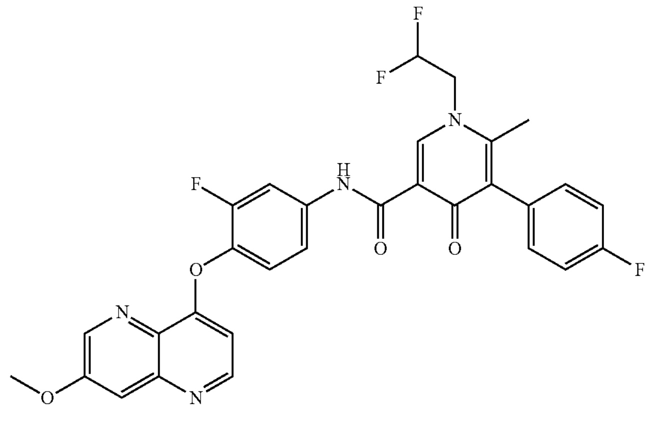 [SMILES: COc1cnc2c(Oc3ccc(NC(=O)c4cn(CC(F)F)c(C)c(-c5ccc(F)cc5)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluorophenyl)-6-methyl-4-oxopyridine-3-carboxamide |
| 626 | 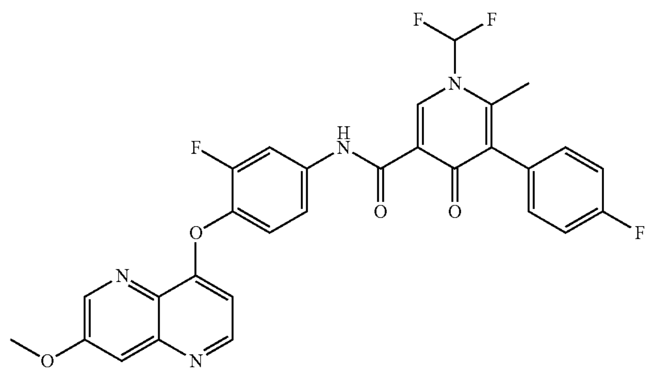 [SMILES: COc1cnc2c(Oc3ccc(NC(=O)c4cn(C(F)F)c(C)c(-c5ccc(F)cc5)c4=O)cc3F)ccnc2c1] | 1-(difluoromethyl)-N-[3-fluoro-4-[(7-methoxy-1,5-naphthyridin-4-yl)oxy]phenyl]-5-(4-fluorophenyl)-6-methyl-4-oxopyridine-3-carboxamide |
| 627 | 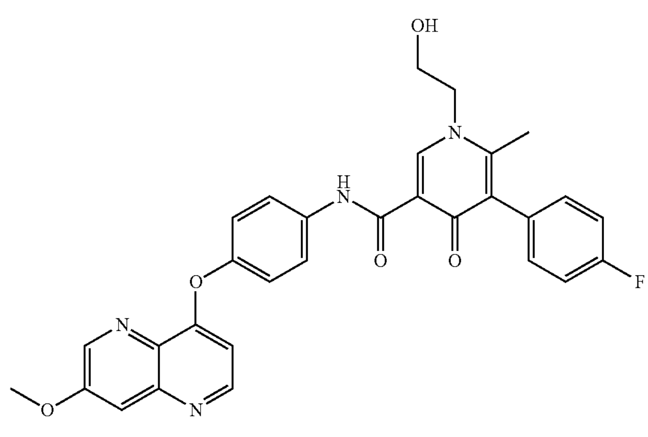 [SMILES: COc1cnc2c(Oc3ccc(NC(=O)c4cn(CCO)c(C)c(-c5ccc(F)cc5)c4=O)cc3)ccnc2c1] | 5-(4-fluorophenyl)-1-(2-hydroxyethyl)-N-[4-[(7-methoxy-1,5-naphthyridin-4-yl)oxy]phenyl]-6-methyl-4-oxopyridine-3-carboxamide |

| Cpd # | Structure | IUPAC Name |
|---|---|---|
| 628 | 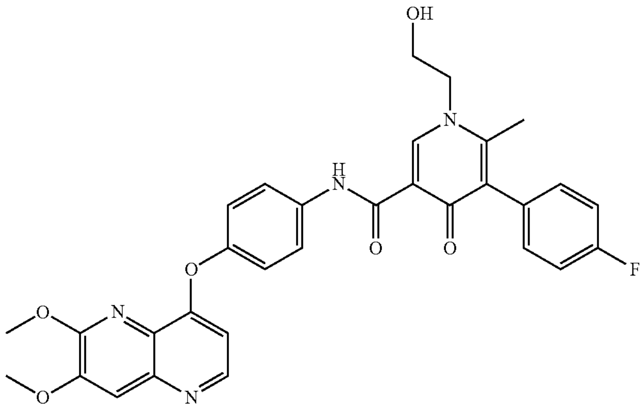 [SMILES: COc1cc2nccc(Oc3ccc(NC(=O)c4cn(CCO)c(C)c(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-1-(2-hydroxyethyl)-6-methyl-4-oxopyridine-3-carboxamide |
| 629 | 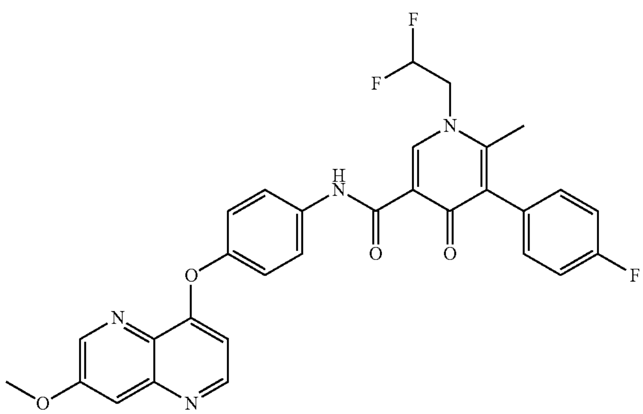 [SMILES: COc1cnc2c(Oc3ccc(NC(=O)c4cn(CC(F)F)c(C)c(-c5ccc(F)cc5)c4=O)cc3)ccnc2c1] | 1-(2,2-difluoroethyl)-5-(4-fluorophenyl)-N-[4-[(7-methoxy-1,5-naphthyridin-4-yl)oxy]phenyl]-6-methyl-4-oxopyridine-3-carboxamide |
| 630 | 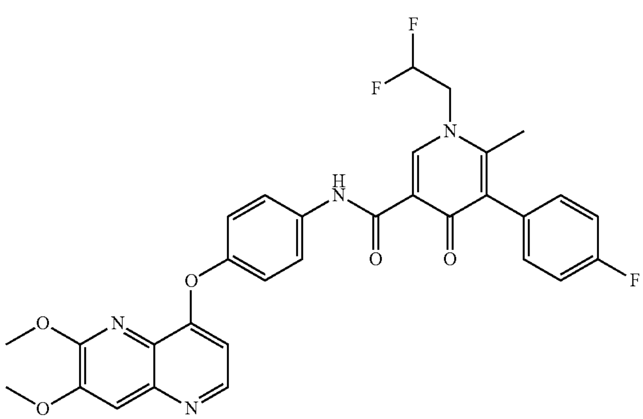 [SMILES: COc1cc2nccc(Oc3ccc(NC(=O)c4cn(CC(F)F)c(C)c(-c5ccc(F)cc5)c4=O)cc3)c2nc1OC] | 1-(2,2-difluoroethyl)-N-[4-[(6,7-dimethoxy-1,5-naphthyridin-4-yl)oxy]phenyl]-5-(4-fluorophenyl)-6-methyl-4-oxopyridine-3-carboxamide |

-continued

| Cpd # | Structure | IUPAC Name |
|---|---|---|
| 631 | 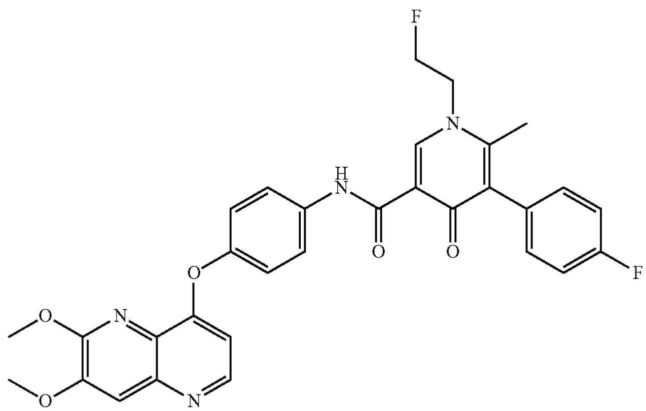 | N-[4-[(6,7-dimethoxy-1,5-naphthyridin-4-yl)oxy]phenyl]-1-(2-fluoroethyl)-5-(4-fluorophenyl)-6-methyl-4-oxopyridine-3-carboxamide |
| 632 | 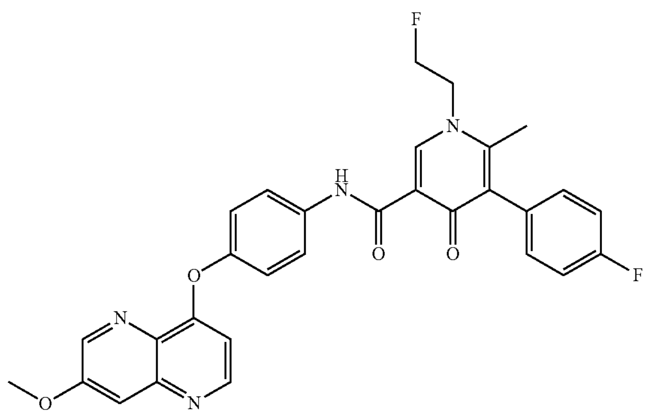 [SMILES: COc1cnc2c(Oc3ccc(NC(=O)c4cn(CCF)c(C)c(-c5ccc(F)cc5)c4=O)cc3)ccnc2c1] | 1-(2-fluoroethyl)-5-(4-fluorophenyl)-N-[4-[(7-methoxy-1,5-naphthyridin-4-yl)oxy]phenyl]-6-methyl-4-oxopyridine-3-carboxamide |
| 633 | 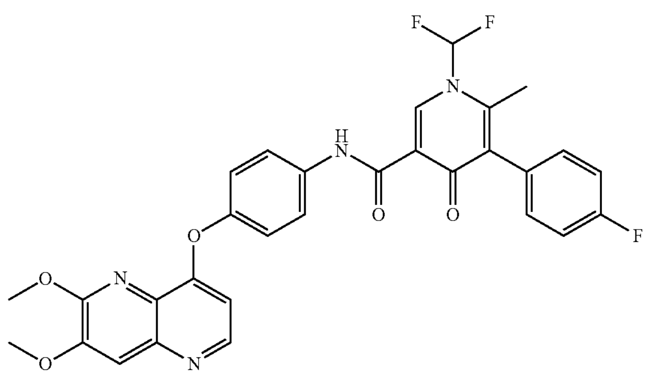 [SMILES: COc1cc2nccc(Oc3ccc(NC(=O)c4cn(C(F)F)c(C)c(-c5ccc(F)cc5)c4=O)cc3)c2nc1OC] | 1-(difluoromethyl)-N-[4-[(6,7-dimethoxy-1,5-naphthyridin-4-yl)oxy]phenyl]-5-(4-fluorophenyl)-6-methyl-4-oxopyridine-3-carboxamide |
| 634 | 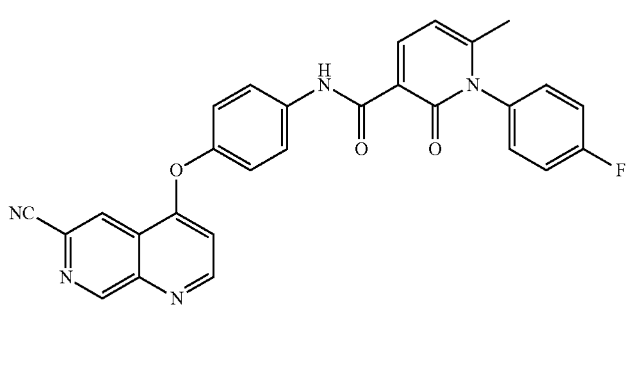 [SMILES: Cc1ccc(C(=O)Nc2ccc(Oc3ccnc4cnc(C#N)cc34)cc2)c(=O)n1-c1ccc(F)cc1] | N-[4-[(6-cyano-1,7-naphthyridin-4-yl)oxy]phenyl]-1-(4-fluorophenyl)-6-methyl-2-oxopyridine-3-carboxamide |

| Cpd # | Structure | IUPAC Name |
|---|---|---|
| 635 | 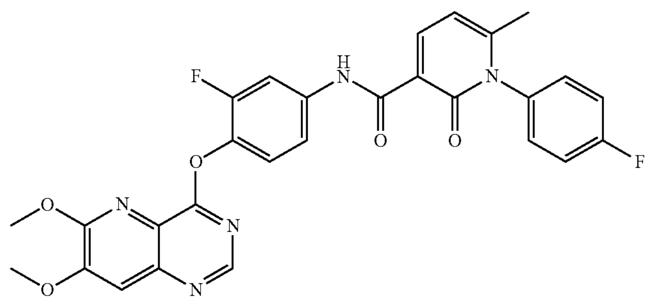 [SMILES: COc1cc2ncnc(Oc3ccc(NC(=O)c4ccc(C)n(-c5ccc(F)cc5)c4=O)cc3F)c2nc1OC] | N-[4-(6,7-dimethoxypyrido[3,2-d]pyrimidin-4-yl)oxy-3-fluorophenyl]-1-(4-fluorophenyl)-6-methyl-2-oxopyridine-3-carboxamide |
| 636 | 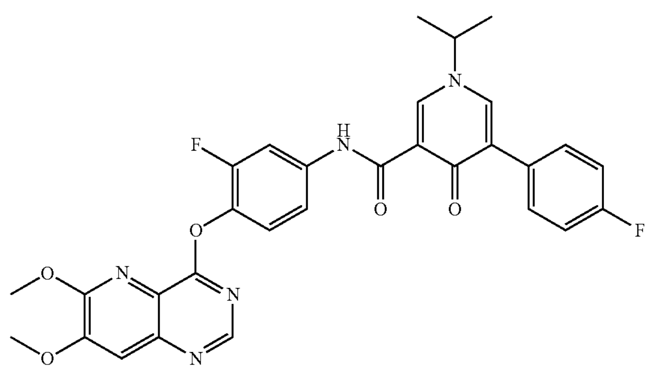 [SMILES: COc1cc2ncnc(Oc3ccc(NC(=O)c4cn(C(C)C)cc(-c5ccc(F)cc5)c4=O)cc3F)c2nc1OC] | N-[4-(6,7-dimethoxypyrido[3,2-d]pyrimidin-4-yl)oxy-3-fluorophenyl]-5-(4-fluorophenyl)-4-oxo-1-propan-2-ylpyridine-3-carboxamide |
| 637 | 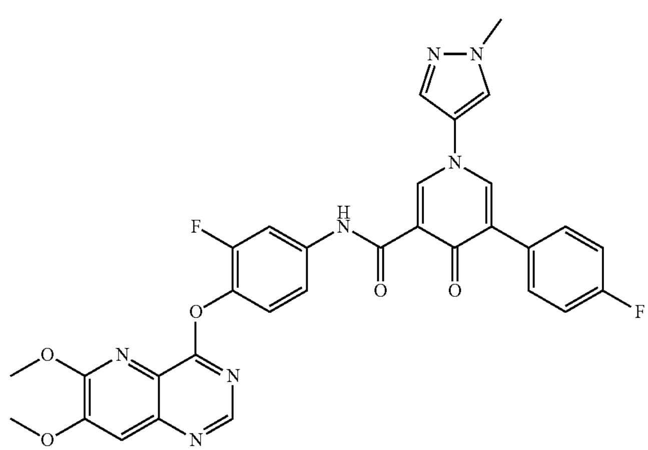 [SMILES: COc1cc2ncnc(Oc3ccc(NC(=O)c4cn(-c5cnn(C)c5)cc(-c5ccc(F)cc5)c4=O)cc3F)c2nc1OC] | N-[4-(6,7-dimethoxypyrido[3,2-d]pyrimidin-4-yl)oxy-3-fluorophenyl]-5-(4-fluorophenyl)-1-(1-methylpyrazol-4-yl)-4-oxopyridine-3-carboxamide |
| 638 | 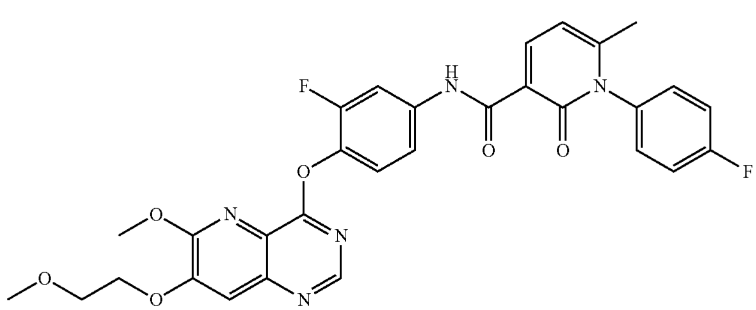 [SMILES: COCCOc1cc2ncnc(Oc3ccc(NC(=O)c4ccc(C)n(-c5ccc(F)cc5)c4=O)cc3F)c2nc1OC] | N-[3-fluoro-4-[6-methoxy-7-(2-methoxyethoxy)pyrido[3,2-d]pyrimidin-4-yl]oxyphenyl]-1-(4-fluorophenyl)-6-methyl-2-oxopyridine-3-carboxamide |

| Cpd # | Structure | IUPAC Name |
|---|---|---|
| 639 | 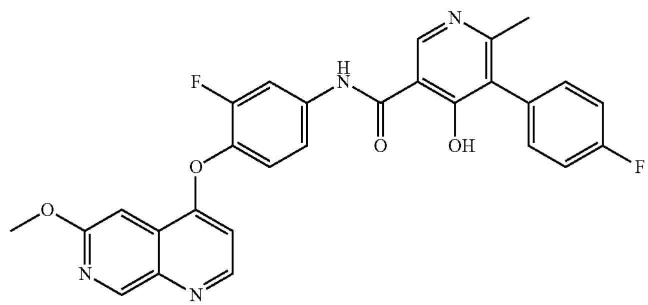 [SMILES: COc1cc2c(Oc3ccc(NC(=O)c4cnc(C)c(-c5ccc(F)cc5)c4O)cc3F)ccnc2cn1] | N-[3-fluoro-4-[(6-methoxy-1,7-naphthyridin-4-yl)oxy]phenyl]-5-(4-fluorophenyl)-4-hydroxy-6-methylpyridine-3-carboxamide |
| 640 | 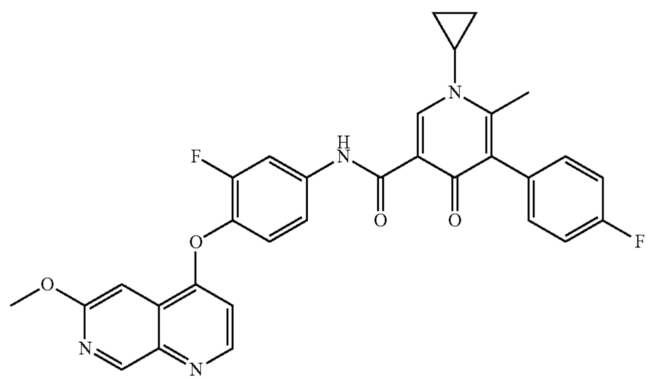 [SMILES: COc1cc2c(Oc3ccc(NC(=O)c4cn(C5CC5)c(C)c(-c5ccc(F)cc5)c4=O)cc3F)ccnc2cn1] | 1-cyclopropyl-N-[3-fluoro-4-[(6-methoxy-1,7-naphthyridin-4-yl)oxy]phenyl]-5-(4-fluorophenyl)-6-methyl-4-oxopyridine-3-carboxamide |
| 641 | 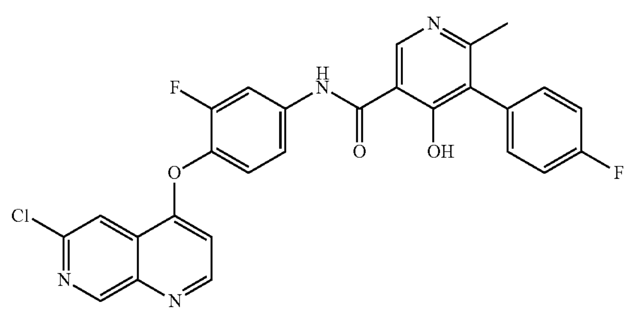 [SMILES: Cc1ncc(C(=O)Nc2ccc(Oc3ccnc4cnc(Cl)cc34)c(F)c2)c(O)c1-c1ccc(F)cc1] | N-[4-[(6-chloro-1,7-naphthyridin-4-yl)oxy]-3-fluorophenyl]-5-(4-fluorophenyl)-4-hydroxy-6-methylpyridine-3-carboxamide |
| 642 | 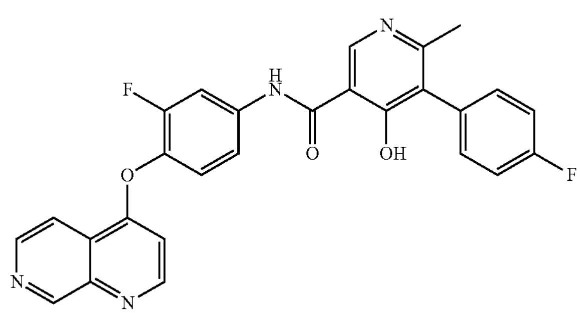 [SMILES: Cc1ncc(C(=O)Nc2ccc(Oc3ccnc4cnccc34)c(F)c2)c(O)c1-c1ccc(F)cc1] | N-[3-fluoro-4-(1,7-naphthyridin-4-yloxy)phenyl]-5-(4-fluorophenyl)-4-hydroxy-6-methylpyridine-3-carboxamide |

| Cpd # | Structure | IUPAC Name |
|---|---|---|
| 643 | 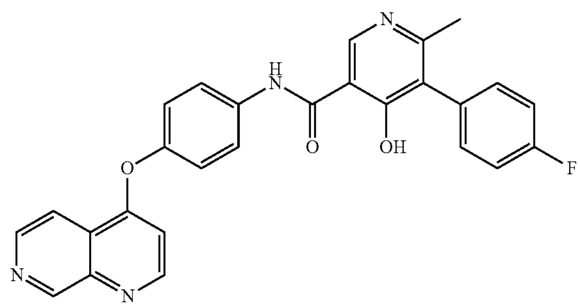 [SMILES: Cc1ncc(C(=O)Nc2ccc(Oc3ccnc4cnccc34)cc2)c(O)c1-c1ccc(F)cc1] | 5-(4-fluorophenyl)-4-hydroxy-6-methyl-N-[4-(1,7-naphthyridin-4-yloxy)phenyl]pyridine-3-carboxamide |
| 644 | 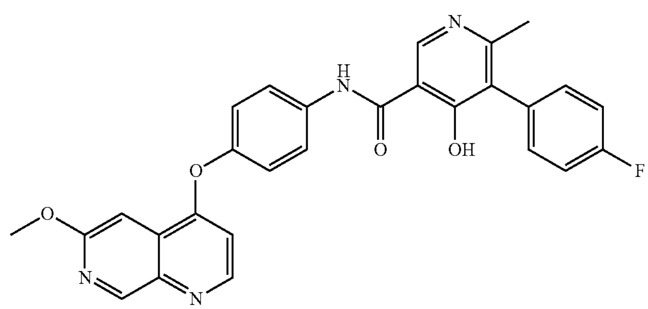 [SMILES: COc1cc2c(Oc3ccc(NC(=O)c4cnc(C)c(-c5ccc(F)cc5)c4O)cc3)ccnc2cn1] | 5-(4-fluorophenyl)-4-hydroxy-N-[4-[(6-methoxy-1,7-naphthyridin-4-yl)oxy]phenyl]-6-methylpyridine-3-carboxamide |
| 645 | 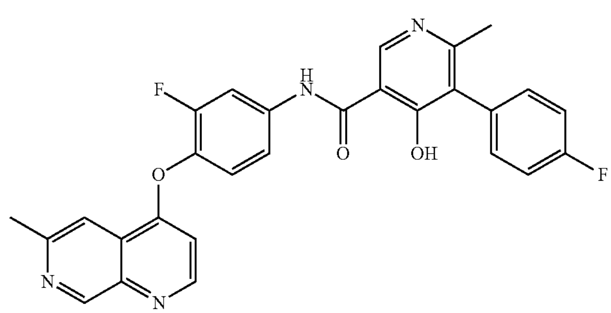 [SMILES: Cc1cc2c(Oc3ccc(NC(=O)c4cnc(C)c(-c5ccc(F)cc5)c4O)cc3F)ccnc2cn1] | N-[3-fluoro-4-[(6-methyl-1,7-naphthyridin-4-yl)oxy]phenyl]-5-(4-fluorophenyl)-4-hydroxy-6-methylpyridine-3-carboxamide |
| 646 | 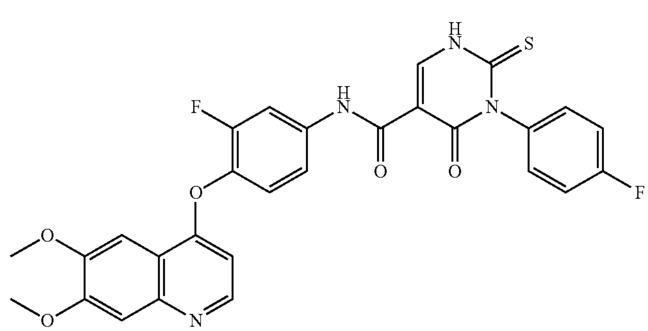 [SMILES: COc1cc2nccc(Oc3ccc(NC(=O)c4c[nH]c(=S)n(-c5ccc(F)cc5)c4=O)cc3F)c2cc1OC] | N-[4-(6,7-dimethoxyquinolin-4-yl)oxy-3-fluorophenyl]-3-(4-fluorophenyl)-4-oxo-2-sulfanylidene-1H-pyrimidine-5-carboxamide |

-continued

| Cpd # | Structure | IUPAC Name |
|---|---|---|
| 647 | 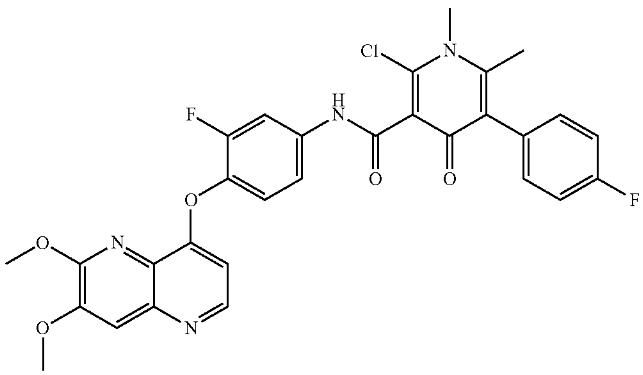 [SMILES: COc1cc2nccc(Oc3ccc(NC(=O)c4c(Cl)n(C)c(C)c(-c5ccc(F)cc5)c4=O)cc3F)c2nc1OC] | 2-chloro-N-[4-[(6,7-dimethoxy-1,5-naphthyridin-4-yl)oxy]-3-fluorophenyl]-5-(4-fluorophenyl)-1,6-dimethyl-4-oxopyridine-3-carboxamide |
| 648 | 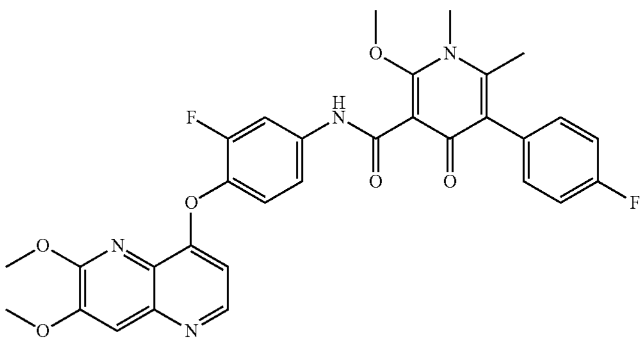 [SMILES: COc1cc2nccc(Oc3ccc(NC(=O)c4c(OC)n(C)c(C)c(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-2-methoxy-1,6-dimethyl-4-oxopyridine-3-carboxamide |
| 649 | 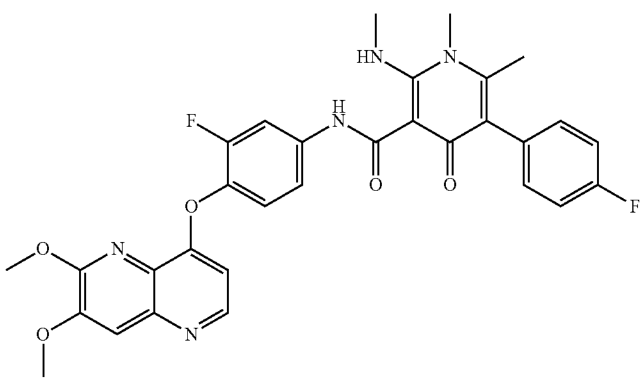 [SMILES: CNc1c(C(=O)Nc2ccc(Oc3ccnc4cc(OC)c(OC)nc34)c(F)c2)c(=O)c(-c2ccc(F)cc2)c(C)n1C] | N-[4-[(6,7-dimethoxy-1,5-naphthyridin-4-yl)oxy]-3-fluorophenyl]-5-(4-fluorophenyl)-1,6-dimethyl-2-(methylamino)-4-oxopyridine-3-carboxamide |
| 650 | 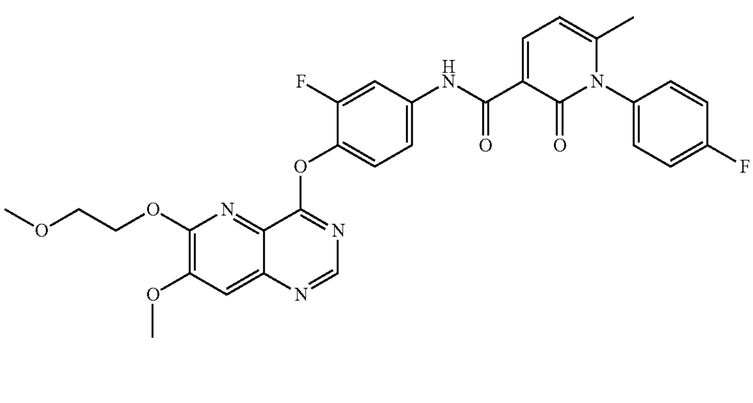 [SMILES: COCCOc1nc2c(Oc3ccc(NC(=O)c4ccc(C)n(-c5ccc(F)cc5)c4=O)cc3F)ncnc2cc1OC] | N-[3-fluoro-4-[7-methoxy-6-(2-methoxyethoxy)pyrido[3,2-d]pyrimidin-4-yl]oxyphenyl]-1-(4-fluorophenyl)-6-methyl-2-oxopyridine-3-carboxamide |

| Cpd # | Structure | IUPAC Name |
|---|---|---|
| 651 | 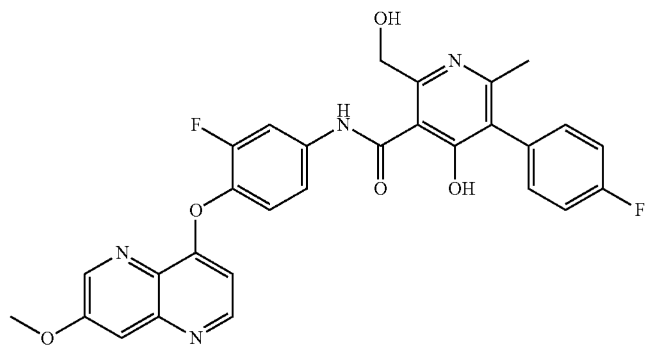 [SMILES: COc1cnc2c(Oc3ccc(NC(=O)c4c(CO)nc(C)c(-c5ccc(F)cc5)c4O)cc3F)ccnc2c1] | N-[3-fluoro-4-[(7-methoxy-1,5-naphthyridin-4-yl)oxy]phenyl]-5-(4-fluorophenyl)-4-hydroxy-2-(hydroxymethyl)-6-methylpyridine-3-carboxamide |
| 652 | 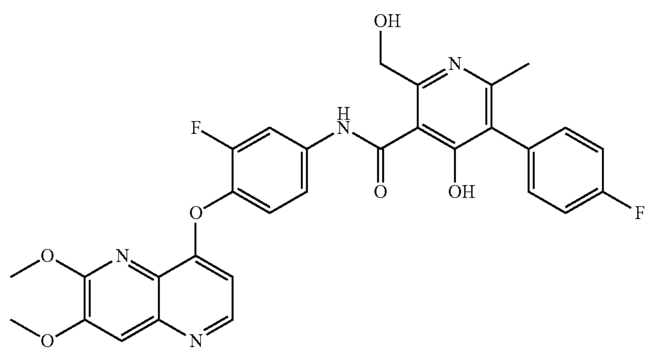 [SMILES: COc1cc2nccc(Oc3ccc(NC(=O)c4c(CO)nc(C)c(-c5ccc(F)cc5)c4O)cc3F)c2nc1OC] | N-[4-[(6,7-dimethoxy-1,5-naphthyridin-4-yl)oxy]-3-fluorophenyl]-5-(4-fluorophenyl)-4-hydroxy-2-(hydroxymethyl)-6-methylpyridine-3-carboxamide |
| 653 | 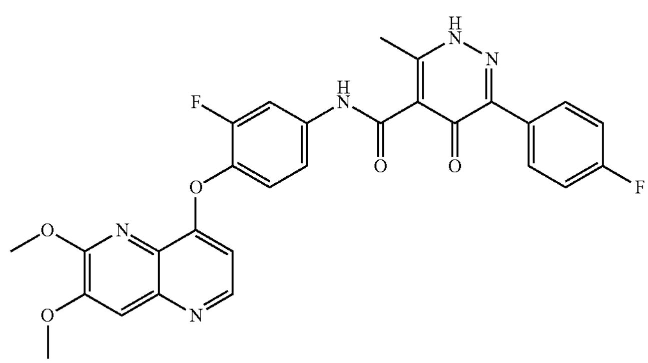 [SMILES: COc1cc2nccc(Oc3ccc(NC(=O)c4c(C)[nH]nc(-c5ccc(F)cc5)c4=O)cc3F)c2nc1OC] | N-[4-[(6,7-dimethoxy-1,5-naphthyridin-4-yl)oxy]-3-fluorophenyl]-3-(4-fluorophenyl)-6-methyl-4-oxo-1H-pyridazine-5-carboxamide |
| 654 | 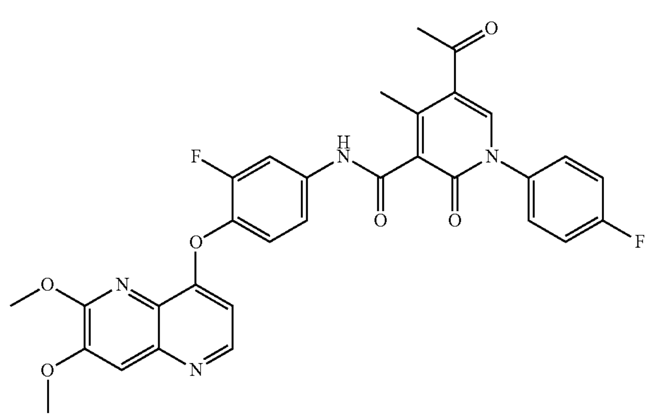 [SMILES: COc1cc2nccc(Oc3ccc(NC(=O)c4c(C)c(C(C)=O)cn(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4-methyl-2-oxopyridine-3-carboxamide |

| Cpd # | Structure | IUPAC Name |
|---|---|---|
| 655 | 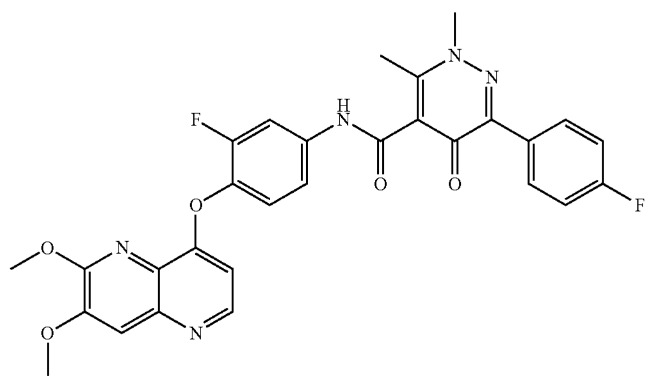 [SMILES: COc1cc2nccc(Oc3ccc(NC(=O)c4c(C)n(C)nc(-c5ccc(F)cc5)c4=O)cc3F)c2nc1OC] | N-[4-[(6,7-dimethoxy-1,5-naphthyridin-4-yl)oxy]-3-fluorophenyl]-6-(4-fluorophenyl)-2,3-dimethyl-5-oxopyridazine-4-carboxamide |
| 656 | 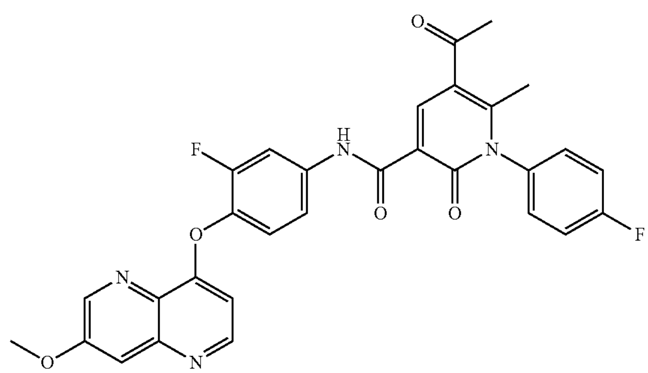 [SMILES: COc1cnc2c(Oc3ccc(NC(=O)c4cc(C(C)=O)c(C)n(-c5ccc(F)cc5)c4=O)cc3F)ccnc2c1] | 5-acetyl-N-[3-fluoro-4-[(7-methoxy-1,5-naphthyridin-4-yl)oxy]phenyl]-1-(4-fluorophenyl)-6-methyl-2-oxopyridine-3-carboxamide |
| 657 | 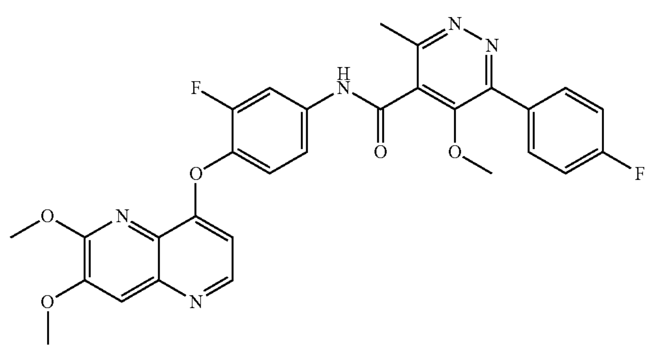 [SMILES: COc1cc2nccc(Oc3ccc(NC(=O)c4c(C)nnc(-c5ccc(F)cc5)c4OC)cc3F)c2nc1OC] | N-[4-[(6,7-dimethoxy-1,5-naphthyridin-4-yl)oxy]-3-fluorophenyl]-6-(4-fluorophenyl)-5-methoxy-3-methylpyridazine-4-carboxamide |
| 658 | 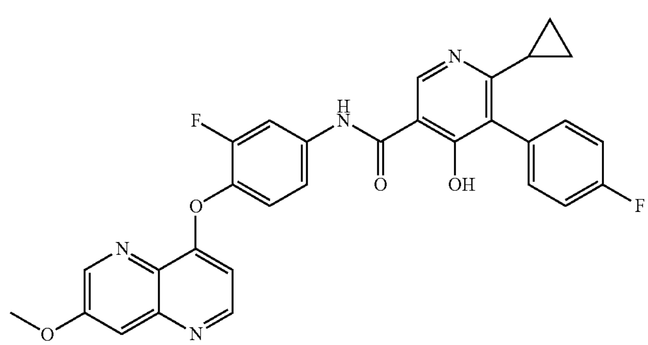 [SMILES: COc1cnc2c(Oc3ccc(NC(=O)c4cnc(C5CC5)c(-c5ccc(F)cc5)c4O)cc3F)ccnc2c1] | 6-cyclopropyl-N-[3-fluoro-4-[(7-methoxy-1,5-naphthyridin-4-yl)oxy]phenyl]-5-(4-fluorophenyl)-4-hydroxypyridine-3-carboxamide |

-continued

| Cpd # | Structure | IUPAC Name |
|---|---|---|
| 659 | 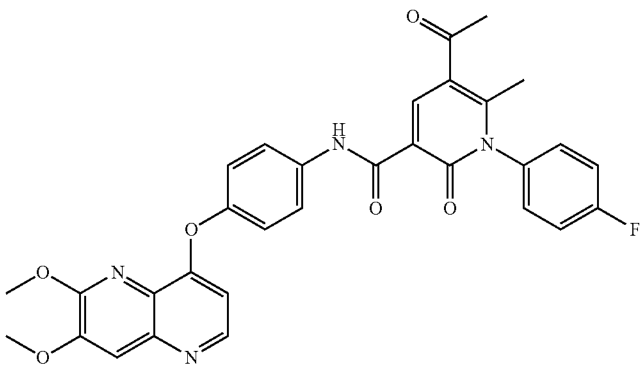 [SMILES: COc1cc2nccc(Oc3ccc(NC(=O)c4cc(C(C)=O)c(C)n(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-6-methyl-2-oxopyridine-3-carboxamide |
| 660 | 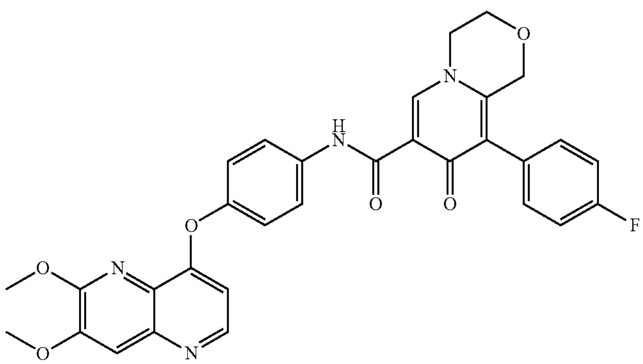 [SMILES: COc1cc2nccc(Oc3ccc(NC(=O)c4cn5c(c(-c6ccc(F)cc6)c4=O)COCC5)cc3)c2nc1OC] | N-[4-[(6,7-dimethoxy-1,5-naphthyridin-4-yl)oxy]phenyl]-9-(4-fluorophenyl)-8-oxo-3,4-dihydro-1H-pyrido[2,1-c][1,4]oxazine-7-carboxamide |
| 661 | 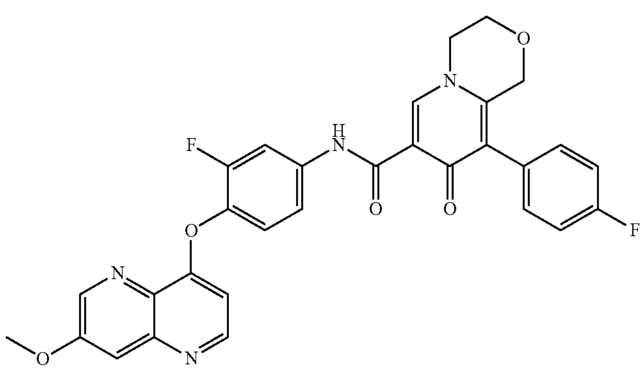 [SMILES: COc1cnc2c(Oc3ccc(NC(=O)c4cn5c(c(-c6ccc(F)cc6)c4=O)COCC5)cc3F)ccnc2c1] | N-[3-fluoro-4-[(7-methoxy-1,5-naphthyridin-4-yl)oxy]phenyl]-9-(4-fluorophenyl)-8-oxo-3,4-dihydro-1H-pyrido[2,1-c][1,4]oxazine-7-carboxamide |
| 662 | 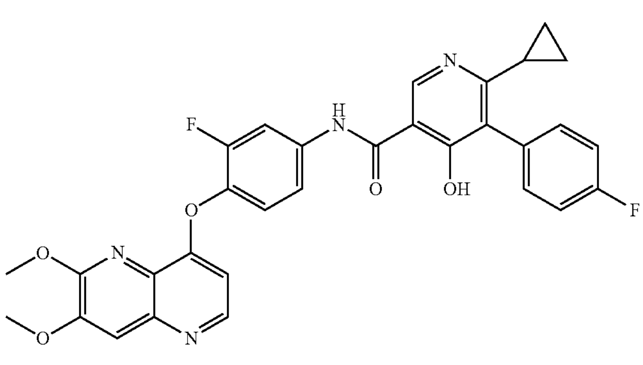 [SMILES: COc1cc2nccc(Oc3ccc(NC(=O)c4cnc(C5CC5)c(-c5ccc(F)cc5)c4O)cc3F)c2nc1OC] | 6-cyclopropyl-N-[4-[(6,7-dimethoxy-1,5-naphthyridin-4-yl)oxy]-3-fluorophenyl]-5-(4-fluorophenyl)-4-hydroxypyridine-3-carboxamide |

| Cpd # | Structure | IUPAC Name |
|---|---|---|
| 663 | 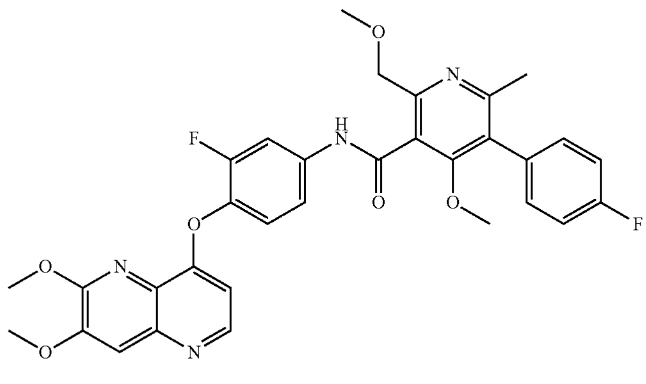 [SMILES: COCc1nc(C)c(-c2ccc(F)cc2)c(OC)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-methoxy-2-(methoxymethyl)-6-methylpyridine-3-carboxamide |
| 664 | 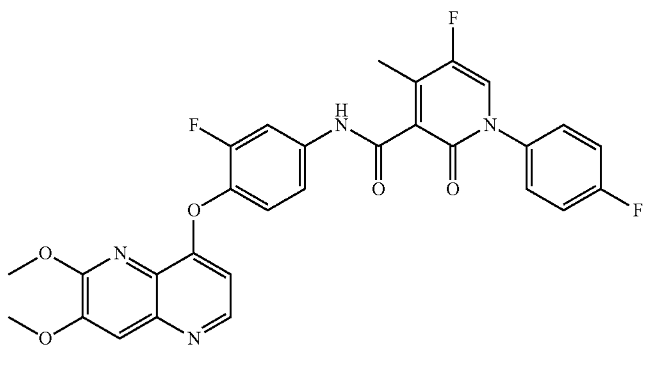 [SMILES: COc1cc2nccc(Oc3ccc(NC(=O)c4c(C)c(F)cn(-c5ccc(F)cc5)c4=O)cc3F)c2nc1OC] | N-[4-[(6,7-dimethoxy-1,5-naphthyridin-4-yl)oxy]-3-fluorophenyl]-5-fluoro-1-(4-fluorophenyl)-4-methyl-2-oxopyridine-3-carboxamide |
| 665 | 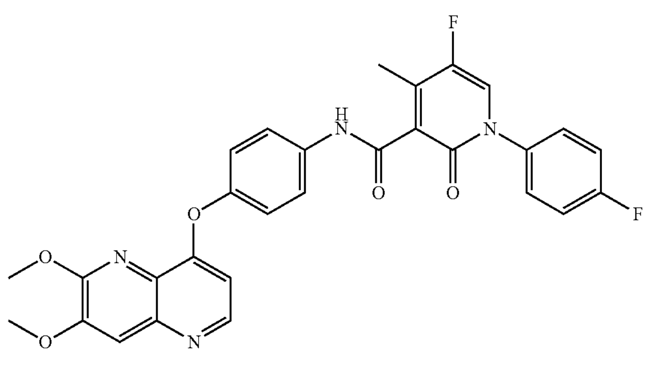 [SMILES: COc1cc2nccc(Oc3ccc(NC(=O)c4c(C)c(F)cn(-c5ccc(F)cc5)c4=O)cc3)c2nc1OC] | N-[4-[(6,7-dimethoxy-1,5-naphthyridin-4-yl)oxy]phenyl]-5-fluoro-1-(4-fluorophenyl)-4-methyl-2-oxopyridine-3-carboxamide |
| 666 | 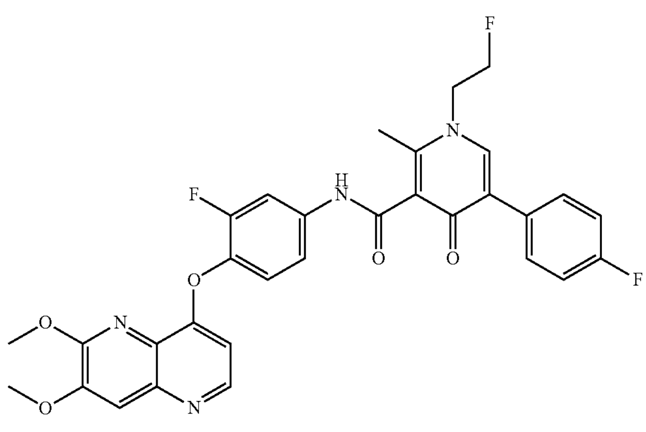 [SMILES: COc1cc2nccc(Oc3ccc(NC(=O)c4c(C)n(CCF)cc(-c5ccc(F)cc5)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluorophenyl)-2-methyl-4-oxopyridine-3-carboxamide |

| Cpd # | Structure | IUPAC Name |
|---|---|---|
| 667 | 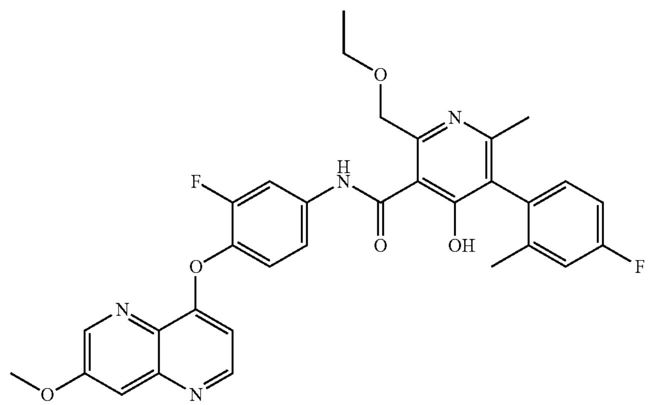 [SMILES: CCOCc1nc(C)c(-c2ccc(F)cc2C)c(O)c1C(=O)Nc1ccc(Oc2ccnc3cc(OC)cnc23)c(F)c1] | 2-(ethoxymethyl)-N-[3-fluoro-4-[(7-methoxy-1,5-naphthyridin-4-yl)oxy]phenyl]-5-(4-fluoro-2-methylphenyl)-4-hydroxy-6-methylpyridine-3-carboxamide |
| 668 | 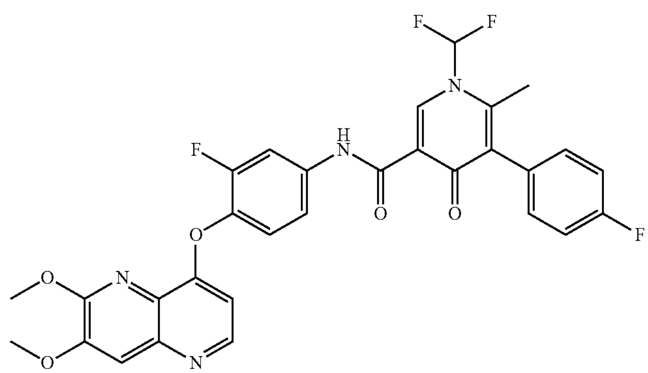 [SMILES: COc1cc2nccc(Oc3ccc(NC(=O)c4cn(C(F)F)c(C)c(-c5ccc(F)cc5)c4=O)cc3F)c2nc1OC] | 1-(difluoromethyl)-N-[4-[(6,7-dimethoxy-1,5-naphthyridin-4-yl)oxy]-3-fluorophenyl]-5-(4-fluorophenyl)-6-methyl-4-oxopyridine-3-carboxamide |
| 669 | 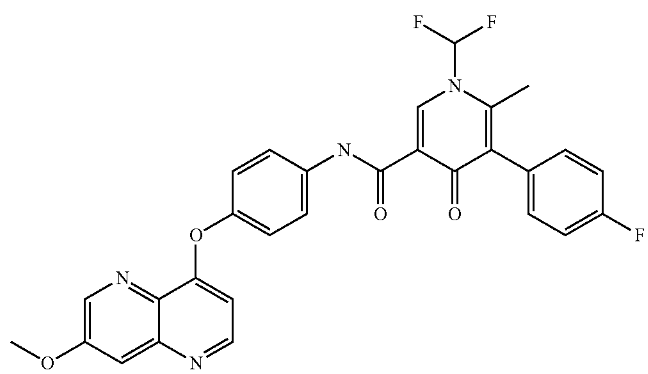 | 1-(difluoromethyl)-5-(4-fluorophenyl)-N-[4-[(7-methoxy-1,5-naphthyridin-4-yl)oxy]phenyl]-6-methyl-4-oxopyridine-3-carboxamide |
| 670 | 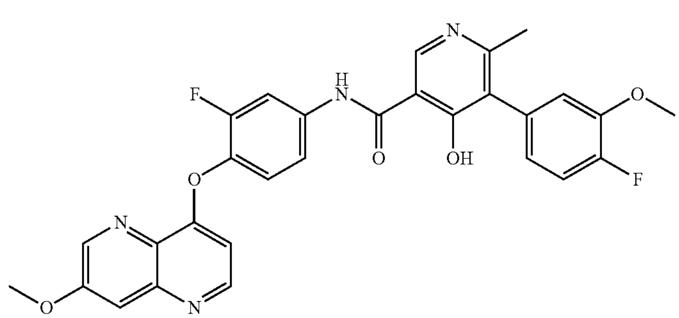 | N-[3-fluoro-4-[(7-methoxy-1,5-naphthyridin-4-yl)oxy]phenyl]-5-(4-fluoro-3-methoxyphenyl)-4-hydroxy-6-methylpyridine-3-carboxamide |

| Cpd # | Structure | IUPAC Name |
|---|---|---|
| 671 | 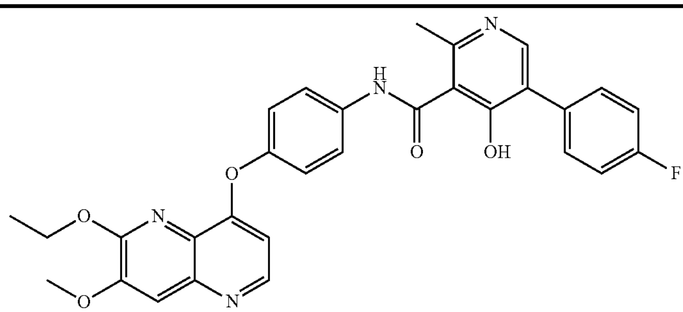 | N-[4-[(6-ethoxy-7-methoxy-1,5-naphthyridin-4-yl)oxy]phenyl]-5-(4-fluorophenyl)-4-hydroxy-2-methylpyridine-3-carboxamide |
| 672 | 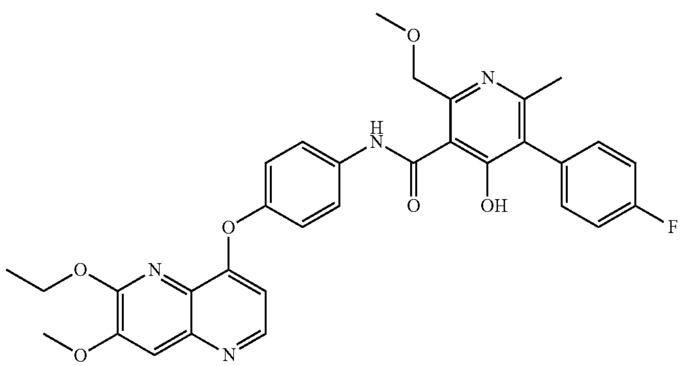 [SMILES: CCOc1nc2c(Oc3ccc(NC(=O)c4c(COC)nc(C)c(-c5ccc(F)cc5)c4O)cc3)ccnc2cc1OC] | N-[4-[(6-ethoxy-7-methoxy-1,5-naphthyridin-4-yl)oxy]phenyl]-5-(4-fluorophenyl)-4-hydroxy-2-(methoxymethyl)-6-methylpyridine-3-carboxamide |
| 673 | 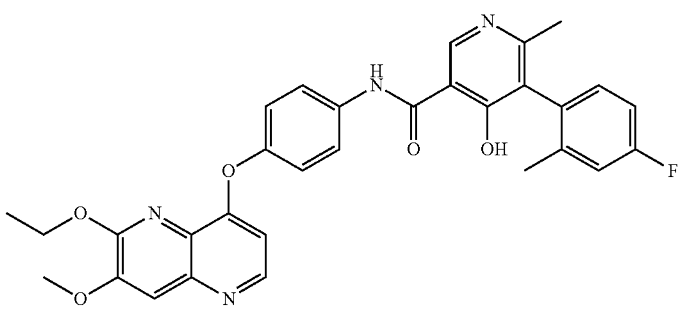 [SMILES: CCOc1nc2c(Oc3ccc(NC(=O)c4cnc(C)c(-c5ccc(F)cc5C)c4O)cc3)ccnc2cc1OC] | N-[4-[(6-ethoxy-7-methoxy-1,5-naphthyridin-4-yl)oxy]phenyl]-5-(4-fluoro-2-methylphenyl)-4-hydroxy-6-methylpyridine-3-carboxamide |
| 674 | 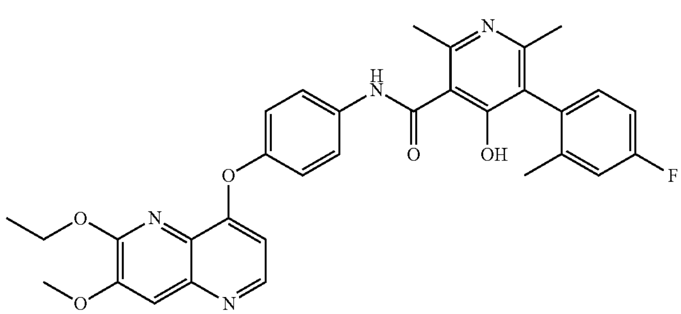 [SMILES: CCOc1nc2c(Oc3ccc(NC(=O)c4c(C)nc(C)c(-c5ccc(F)cc5C)c4O)cc3)ccnc2cc1OC] | N-[4-[(6-ethoxy-7-methoxy-1,5-naphthyridin-4-yl)oxy]phenyl]-5-(4-fluoro-2-methylphenyl)-4-hydroxy-2,6-dimethylpyridine-3-carboxamide |
| 675 | 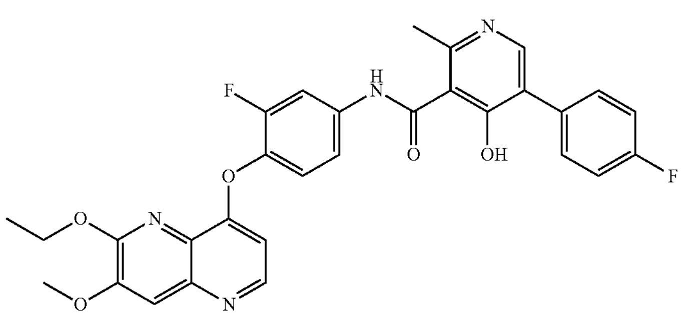 [SMILES: CCOc1nc2c(Oc3ccc(NC(=O)c4c(C)ncc(-c5ccc(F)cc5)c4O)cc3F)ccnc2cc1OC] | N-[4-[(6-ethoxy-7-methoxy-1,5-naphthyridin-4-yl)oxy]-3-fluorophenyl]-5-(4-fluorophenyl)-4-hydroxy-2-methylpyridine-3-carboxamide |

| Cpd # | Structure | IUPAC Name |
|---|---|---|
| 676 | 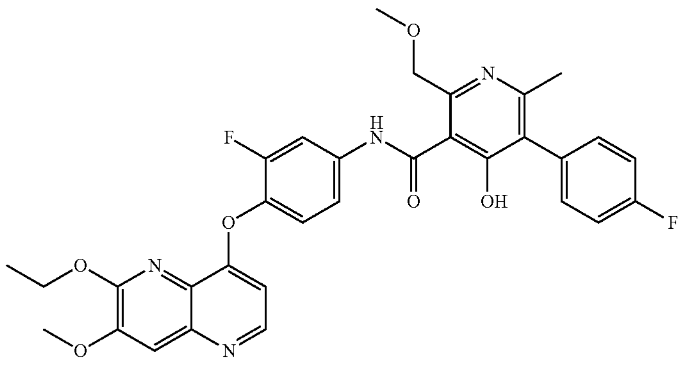 [SMILES: CCOc1nc2c(Oc3ccc(NC(=O)c4c(COC)nc(C)c(-c5ccc(F)cc5)c4O)cc3F)ccnc2cc1OC] | N-[4-[(6-ethoxy-7-methoxy-1,5-naphthyridin-4-yl)oxy]-3-fluorophenyl]-5-(4-fluorophenyl)-4-hydroxy-2-(methoxymethyl)-6-methylpyridine-3-carboxamide |
| 677 | 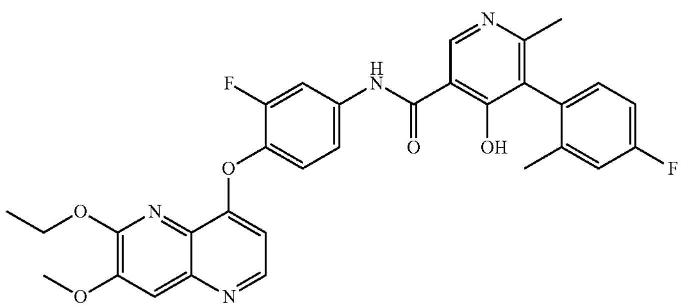 [SMILES: CCOc1nc2c(Oc3ccc(NC(=O)c4cnc(C)c(-c5ccc(F)cc5C)c4O)cc3F)ccnc2cc1OC] | N-[4-[(6-ethoxy-7-methoxy-1,5-naphthyridin-4-yl)oxy]-3-fluorophenyl]-5-(4-fluoro-2-methylphenyl)-4-hydroxy-6-methylpyridine-3-carboxamide |
| 678 | 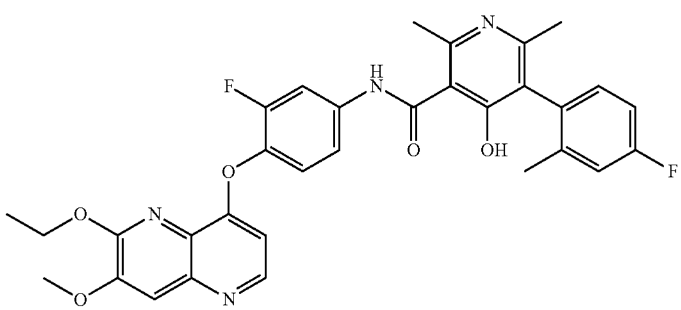 [SMILES: CCOc1nc2c(Oc3ccc(NC(=O)c4c(C)nc(C)c(-c5ccc(F)cc5C)c4O)cc3F)ccnc2cc1OC] | N-[4-[(6-ethoxy-7-methoxy-1,5-naphthyridin-4-yl)oxy]-3-fluorophenyl]-5-(4-fluoro-2-methylphenyl)-4-hydroxy-2,6-dimethylpyridine-3-carboxamide |
| 679 | 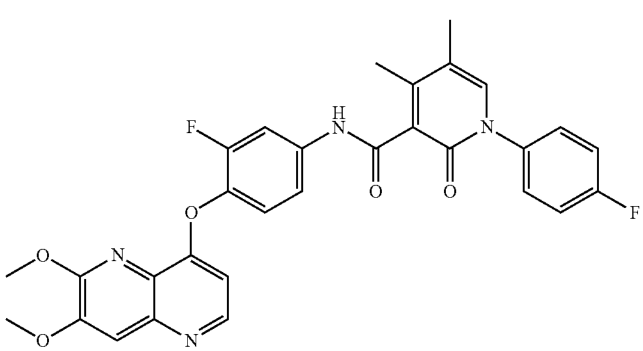 [SMILES: COc1cc2nccc(Oc3ccc(NC(=O)c4c(C)c(C)cn(-c5ccc(F)cc5)c4=O)cc3F)c2nc1OC] | N-[4-[(6,7-dimethoxy-1,5-naphthyridin-4-yl)oxy]-3-fluorophenyl]-1-(4-fluorophenyl)-4,5-dimethyl-2-oxopyridine-3-carboxamide |

-continued

| Cpd # | Structure | IUPAC Name |
|---|---|---|
| 680 | 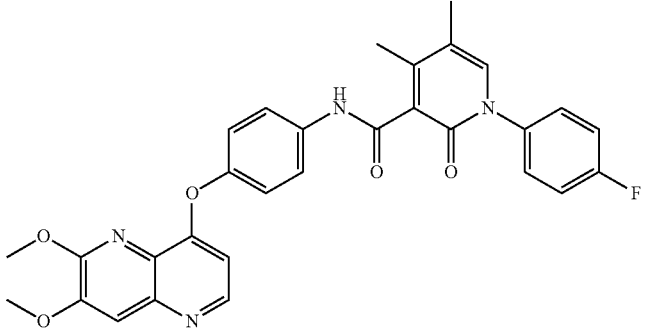 [SMILES: COc1cc2nccc(Oc3ccc(NC(=O)c4c(C)c(C)cn(-c5ccc(F)cc5)c4=O)cc3)c2nc1OC] | N-[4-[(6,7-dimethoxy-1,5-naphthyridin-4-yl)oxy]phenyl]-1-(4-fluorophenyl)-4,5-dimethyl-2-oxopyridine-3-carboxamide |
| 681 | 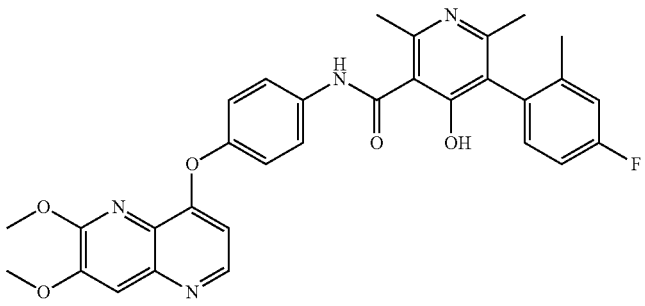 [SMILES: COc1cc2nccc(Oc3ccc(NC(=O)c4c(C)nc(C)c(-c5ccc(F)cc5C)c4O)cc3)c2nc1OC] | N-[4-[(6,7-dimethoxy-1,5-naphthyridin-4-yl)oxy]phenyl]-5-(4-fluoro-2-methylphenyl)-4-hydroxy-2,6-dimethylpyridine-3-carboxamide |
| 682 | 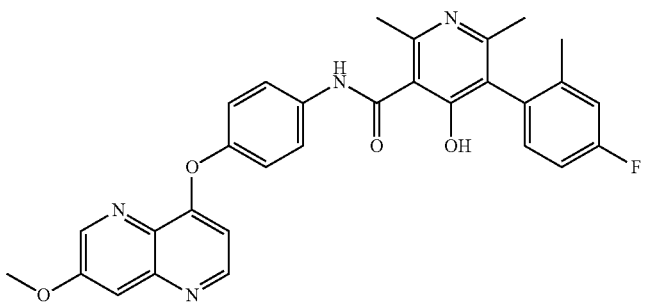 [SMILES: COc1cnc2c(Oc3ccc(NC(=O)c4c(C)nc(C)c(-c5ccc(F)cc5C)c4O)cc3)ccnc2c1] | 5-(4-fluoro-2-methylphenyl)-4-hydroxy-N-[4-[(7-methoxy-1,5-naphthyridin-4-yl)oxy]phenyl]-2,6-dimethylpyridine-3-carboxamide |
| 683 | 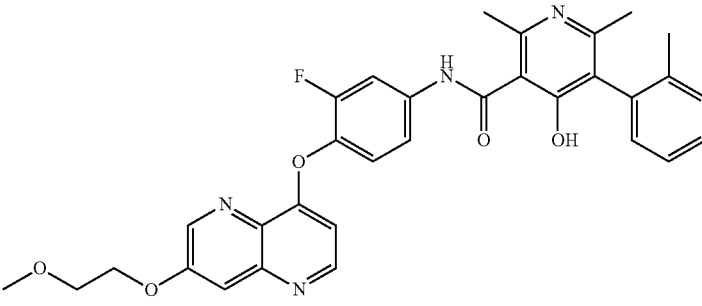 | N-[3-fluoro-4-[[7-(2-methoxyethoxy)-1,5-naphthyridin-4-yl]oxy]phenyl]-5-(4-fluoro-2-methylphenyl)-4-hydroxy-2,6-dimethylpyridine-3-carboxamide |

-continued

| Cpd # | Structure | IUPAC Name |
|---|---|---|
| 684 | 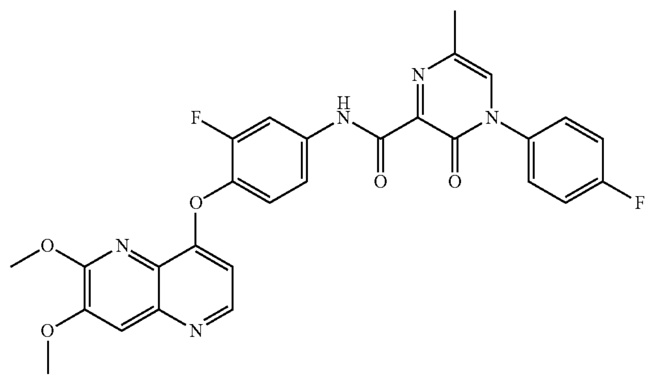 [SMILES: COc1cc2nccc(Oc3ccc(NC(=O)c4nc(C)cn(-c5ccc(F)cc5)c4=O)cc3F)c2nc1OC] | N-[4-[(6,7-dimethoxy-1,5-naphthyridin-4-yl)oxy]-3-fluorophenyl]-4-(4-fluorophenyl)-6-methyl-3-oxopyrazine-2-carboxamide |
| 685 | 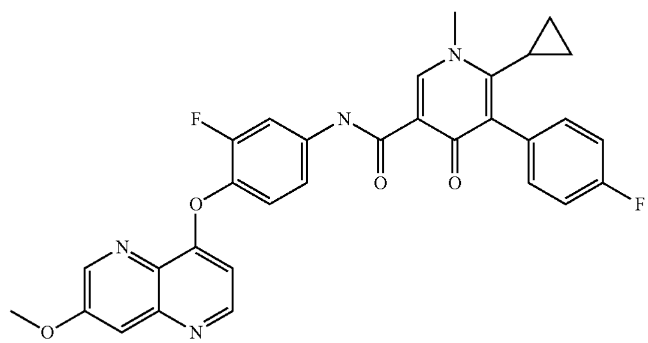 | 6-cyclopropyl-N-[3-fluoro-4-[(7-methoxy-1,5-naphthyridin-4-yl)oxy]phenyl]-5-(4-fluorophenyl)-1-methyl-4-oxopyridine-3-carboxamide |
| 686 | 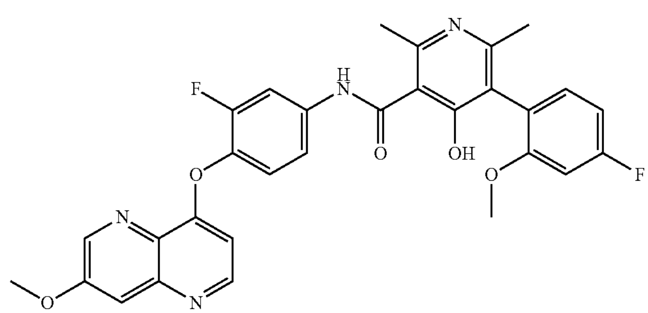 [SMILES: COc1cnc2c(Oc3ccc(NC(=O)c4c(C)nc(C)c(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-2,6-dimethylpyridine-3-carboxamide |
| 687 | 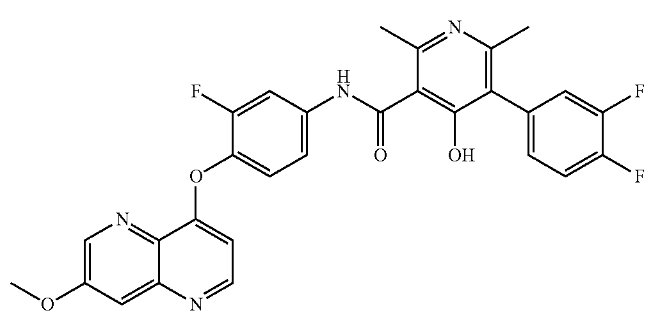 [SMILES: COc1cnc2c(Oc3ccc(NC(=O)c4c(C)nc(C)c(-c5ccc(F)c(F)c5)c4O)cc3F)ccnc2c1] | 5-(3,4-difluorophenyl)-N-[3-fluoro-4-[(7-methoxy-1,5-naphthyridin-4-yl)oxy]phenyl]-4-hydroxy-2,6-dimethylpyridine-3-carboxamide |

| Cpd # | Structure | IUPAC Name |
|---|---|---|
| 688 | 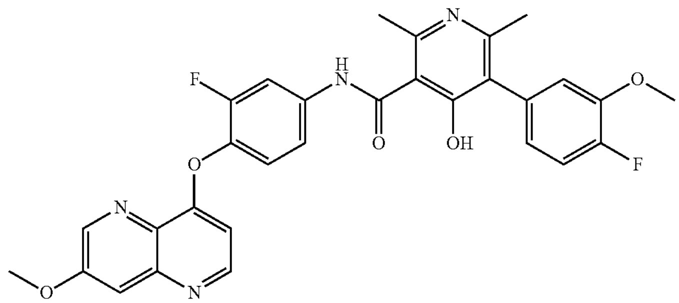 | N-[3-fluoro-4-[(7-methoxy-1,5-naphthyridin-4-yl)oxy]phenyl]-5-(4-fluoro-3-methoxyphenyl)-4-hydroxy-2,6-dimethylpyridine-3-carboxamide |
| 689 | 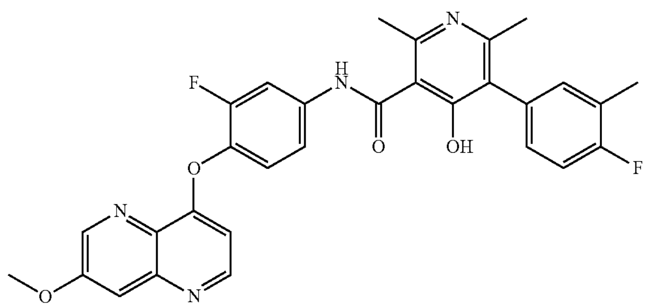 [SMILES: COc1cnc2c(Oc3ccc(NC(=O)c4c(C)nc(C)c(-c5ccc(F)c(C)c5)c4O)cc3F)ccnc2c1] | N-[3-fluoro-4-[(7-methoxy-1,5-naphthyridin-4-yl)oxy]phenyl]-5-(4-fluoro-3-methylphenyl)-4-hydroxy-2,6-dimethylpyridine-3-carboxamide |
| 690 | 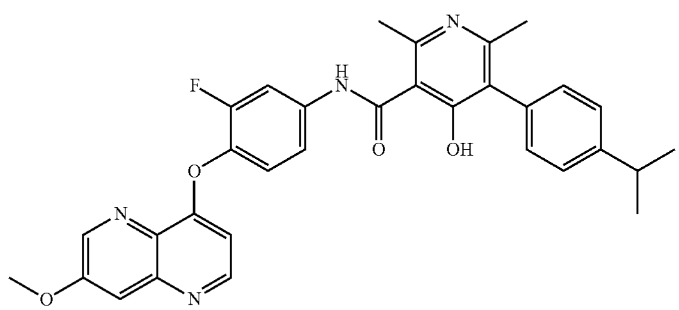 [SMILES: COc1cnc2c(Oc3ccc(NC(=O)c4c(C)nc(C)c(-c5ccc(C(C)C)cc5)c4O)cc3F)ccnc2c1] | N-[3-fluoro-4-[(7-methoxy-1,5-naphthyridin-4-yl)oxy]phenyl]-4-hydroxy-2,6-dimethyl-5-(4-propan-2-ylphenyl)pyridine-3-carboxamide |
| 691 | 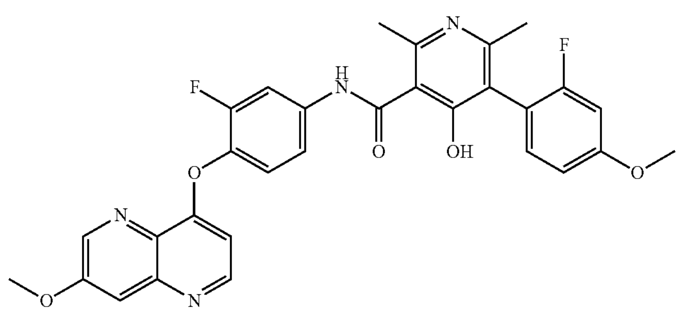 | N-[3-fluoro-4-[(7-methoxy-1,5-naphthyridin-4-yl)oxy]phenyl]-5-(2-fluoro-4-methoxyphenyl)-4-hydroxy-2,6-dimethylpyridine-3-carboxamide |
| 692 | 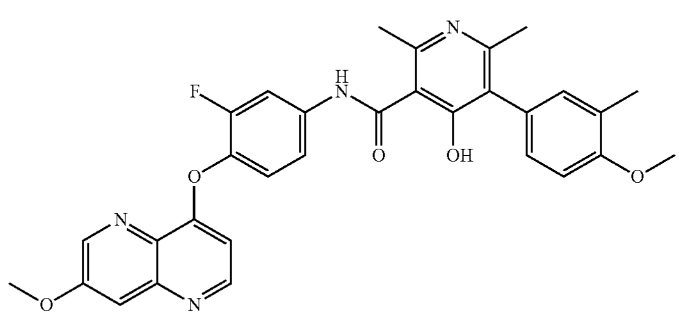 | N-[3-fluoro-4-[(7-methoxy-1,5-naphthyridin-4-yl)oxy]phenyl]-4-hydroxy-5-(4-methoxy-3-methylphenyl)-2,6-dimethylpyridine-3-carboxamide |

| Cpd # | Structure | IUPAC Name |
|---|---|---|
| 693 | 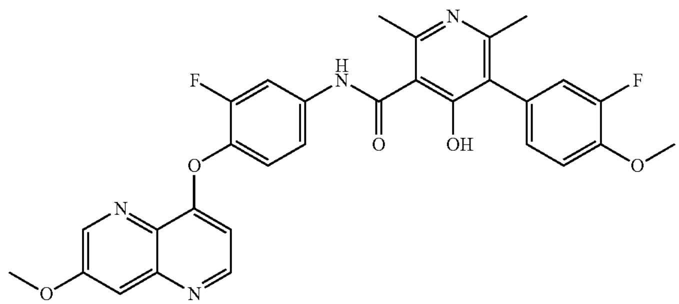 | N-[3-fluoro-4-[(7-methoxy-1,5-naphthyridin-4-yl)oxy]phenyl]-5-(3-fluoro-4-methoxyphenyl)-4-hydroxy-2,6-dimethylpyridine-3-carboxamide |
| 694 | 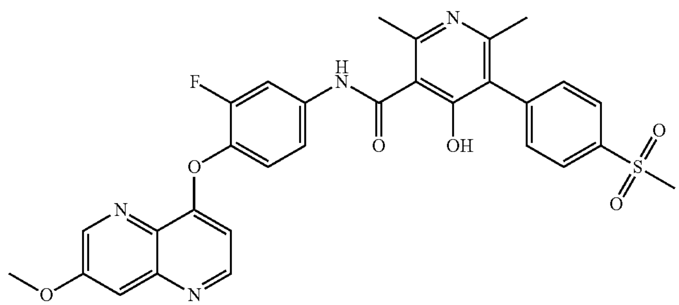 | N-[3-fluoro-4-[(7-methoxy-1,5-naphthyridin-4-yl)oxy]phenyl]-4-hydroxy-2,6-dimethyl-5-(4-methylsulfonylphenyl)pyridine-3-carboxamide |
| 695 | 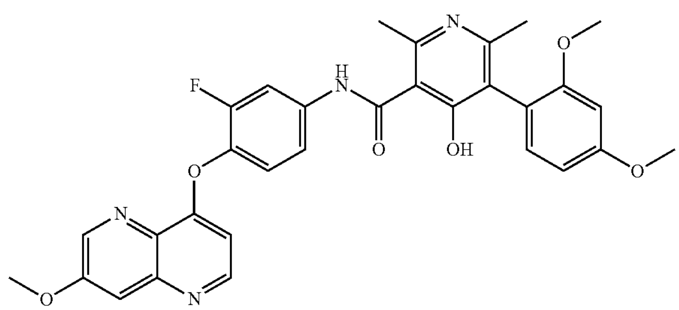 | 5-(2,4-dimethoxyphenyl)-N-[3-fluoro-4-[(7-methoxy-1,5-naphthyridin-4-yl)oxy]phenyl]-4-hydroxy-2,6-dimethylpyridine-3-carboxamide |
| 696 | 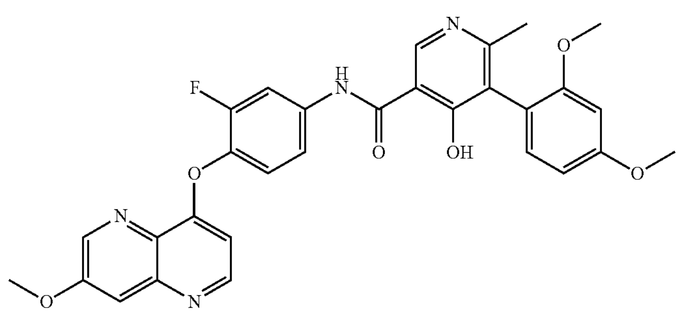 | 5-(2,4-dimethoxyphenyl)-N-[3-fluoro-4-[(7-methoxy-1,5-naphthyridin-4-yl)oxy]phenyl]-4-hydroxy-6-methylpyridine-3-carboxamide |
| 697 | 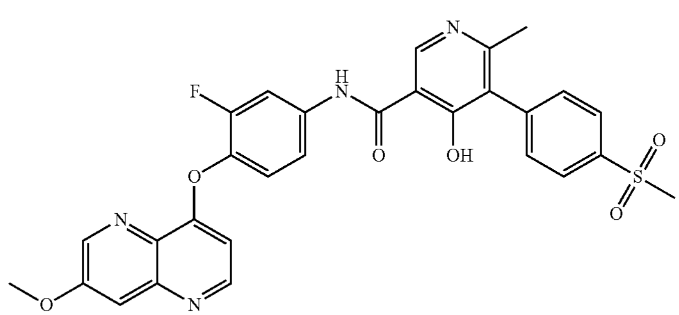 | N-[3-fluoro-4-[(7-methoxy-1,5-naphthyridin-4-yl)oxy]phenyl]-4-hydroxy-6-methyl-5-(4-methylsulfonylphenyl)pyridine-3-carboxamide |

-continued

| Cpd # | Structure | IUPAC Name |
|---|---|---|
| 698 | 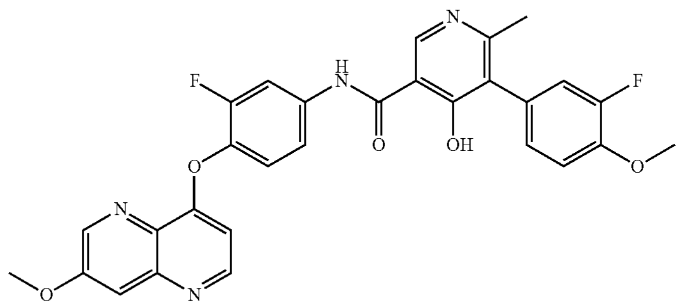 | N-[3-fluoro-4-[(7-methoxy-1,5-naphthyridin-4-yl)oxy]phenyl]-5-(3-fluoro-4-methoxyphenyl)-4-hydroxy-6-methylpyridine-3-carboxamide |
| 699 | 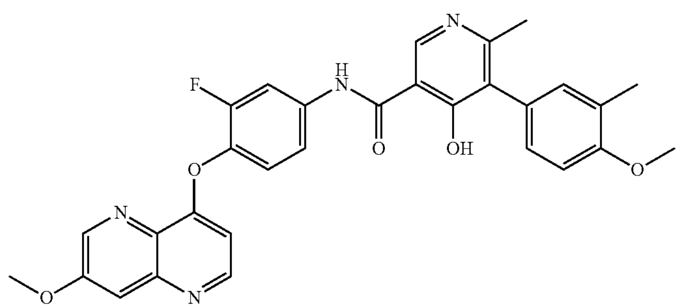 | N-[3-fluoro-4-[(7-methoxy-1,5-naphthyridin-4-yl)oxy]phenyl]-4-hydroxy-5-(4-methoxy-3-methylphenyl)-6-methylpyridine-3-carboxamide |
| 700 | 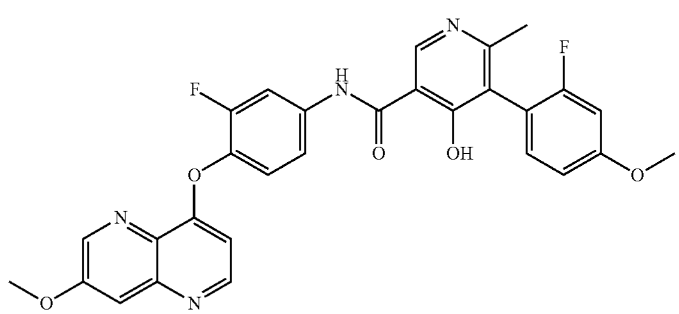 | N-[3-fluoro-4-[(7-methoxy-1,5-naphthyridin-4-yl)oxy]phenyl]-5-(2-fluoro-4-methoxyphenyl)-4-hydroxy-6-methylpyridine-3-carboxamide |
| 701 | 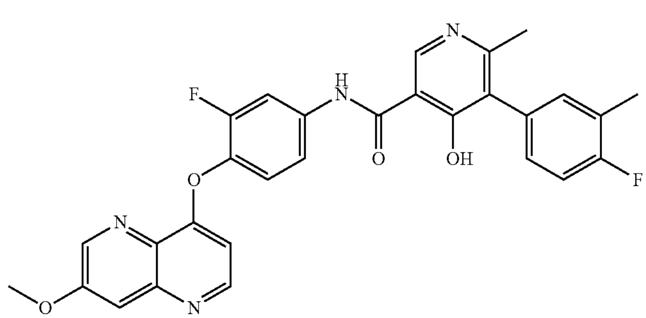 | N-[3-fluoro-4-[(7-methoxy-1,5-naphthyridin-4-yl)oxy]phenyl]-5-(4-fluoro-3-methylphenyl)-4-hydroxy-6-methylpyridine-3-carboxamide |

-continued

| Cpd # | Structure | IUPAC Name |
|---|---|---|
| 702 | 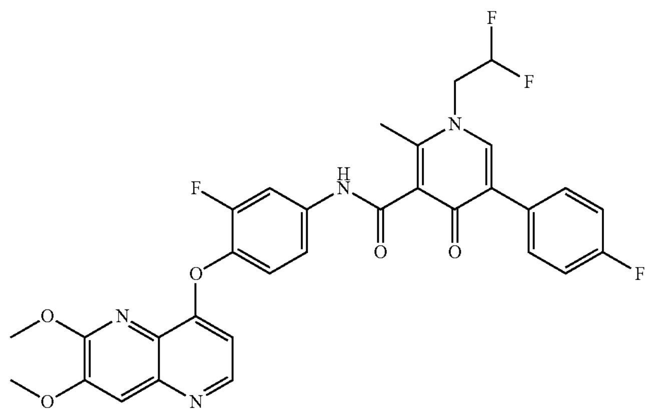 [SMILES: COc1cc2nccc(Oc3ccc(NC(=O)c4c(C)n(CC(F)F)cc(-c5ccc(F)cc5)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluorophenyl)-2-methyl-4-oxopyridine-3-carboxamide |
| 703 | 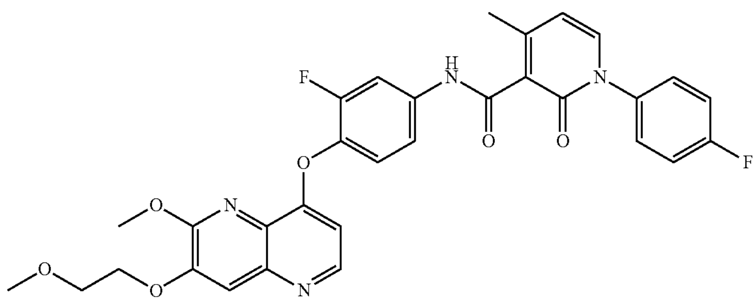 [SMILES: COCCOc1cc2nccc(Oc3ccc(NC(=O)c4c(C)ccn(-c5ccc(F)cc5)c4=O)cc3F)c2nc1OC] | N-[3-fluoro-4-[[6-methoxy-7-(2-methoxyethoxy)-1,5-naphthyridin-4-yl]oxy]phenyl]-1-(4-fluorophenyl)-4-methyl-2-oxopyridine-3-carboxamide |
| 704 | 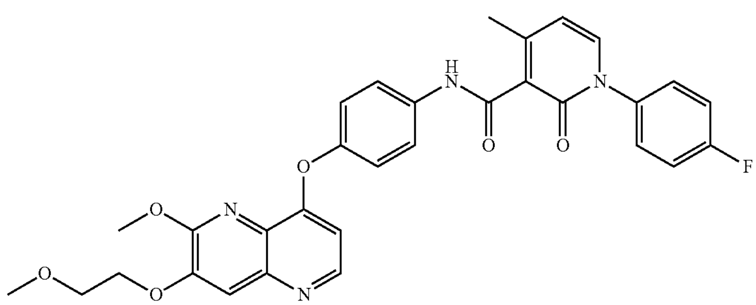 [SMILES: COCCOc1cc2nccc(Oc3ccc(NC(=O)c4c(C)ccn(-c5ccc(F)cc5)c4=O)cc3)c2nc1OC] | 1-(4-fluorophenyl)-N-[4-[[6-methoxy-7-(2-methoxyethoxy)-1,5-naphthyridin-4-yl]oxy]phenyl]-4-methyl-2-oxopyridine-3-carboxamide |
| 705 | 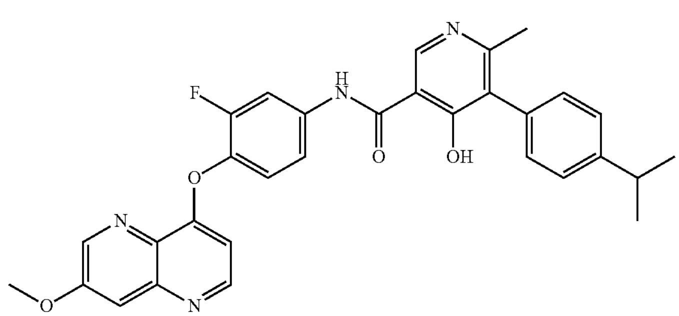 [SMILES: COc1cnc2c(Oc3ccc(NC(=O)c4cnc(C)c(-c5ccc(C(C)C)cc5)c4O)cc3F)ccnc2c1] | N-[3-fluoro-4-[(7-methoxy-1,5-naphthyridin-4-yl)oxy]phenyl]-4-hydroxy-6-methyl-5-(4-propan-2-ylphenyl)pyridine-3-carboxamide |

| Cpd # | Structure | IUPAC Name |
|---|---|---|
| 706 | 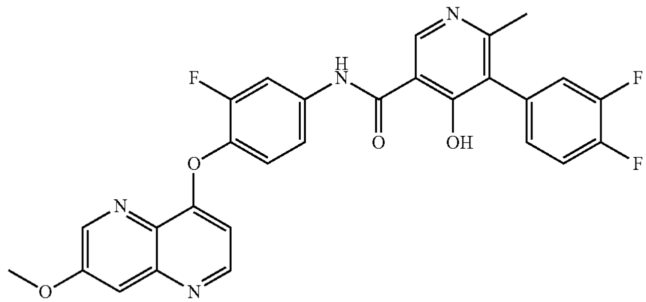 [SMILES: COc1cnc2c(Oc3ccc(NC(=O)c4cnc(C)c(-c5ccc(F)c(F)c5)c4O)cc3F)ccnc2c1] | 5-(3,4-difluorophenyl)-N-[3-fluoro-4-[(7-methoxy-1,5-naphthyridin-4-yl)oxy]phenyl]-4-hydroxy-6-methylpyridine-3-carboxamide |
| 707 | 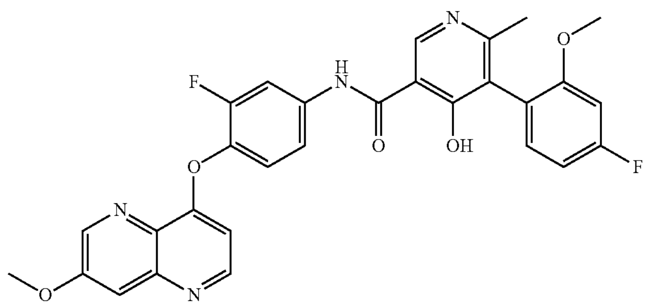 [SMILES: COc1cnc2c(Oc3ccc(NC(=O)c4cnc(C)c(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-6-methylpyridine-3-carboxamide |
| 708 | 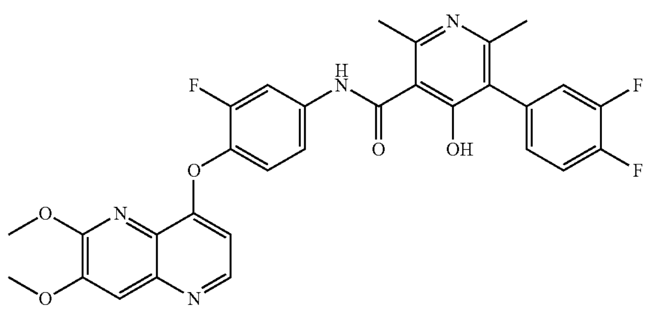 | 5-(3,4-difluorophenyl)-N-[4-[(6,7-dimethoxy-1,5-naphthyridin-4-yl)oxy]-3-fluorophenyl]-4-hydroxy-2,6-dimethylpyridine-3-carboxamide |
| 709 | 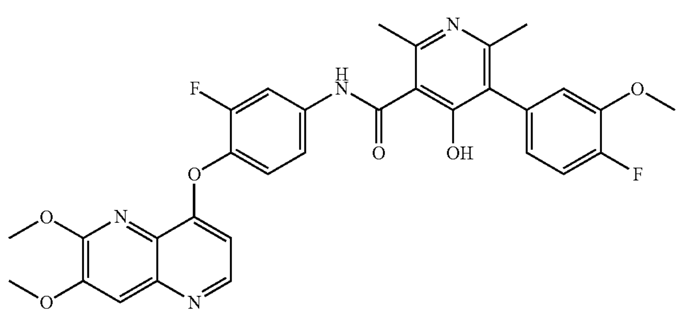 | N-[4-[(6,7-dimethoxy-1,5-naphthyridin-4-yl)oxy]-3-fluorophenyl]-5-(4-fluoro-3-methoxyphenyl)-4-hydroxy-2,6-dimethylpyridine-3-carboxamide |
| 710 | 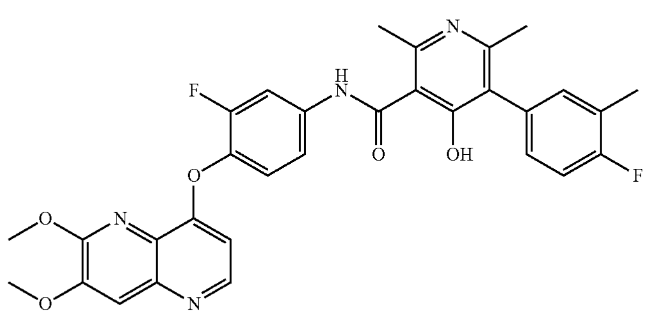 | N-[4-[(6,7-dimethoxy-1,5-naphthyridin-4-yl)oxy]-3-fluorophenyl]-5-(4-fluoro-3-methylphenyl)-4-hydroxy-2,6-dimethylpyridine-3-carboxamide |

-continued

| Cpd # | Structure | IUPAC Name |
|---|---|---|
| 711 | 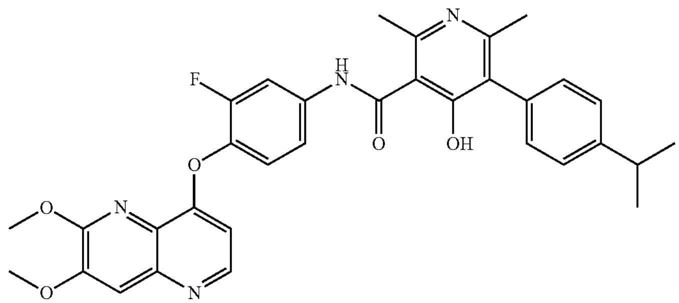 [SMILES: COc1cc2nccc(Oc3ccc(NC(=O)c4c(C)nc(C)c(-c5ccc(C(C)C)cc5)c4O)cc3F)c2nc1OC] | N-[4-[(6,7-dimethoxy-1,5-naphthyridin-4-yl)oxy]-3-fluorophenyl]-4-hydroxy-2,6-dimethyl-5-(4-propan-2-ylphenyl)pyridine-3-carboxamide |
| 712 | 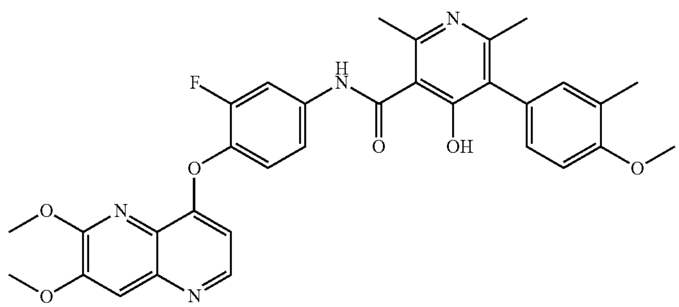 | N-[4-[(6,7-dimethoxy-1,5-naphthyridin-4-yl)oxy]-3-fluorophenyl]-4-hydroxy-5-(4-methoxy-3-methylphenyl)-2,6-dimethylpyridine-3-carboxamide |
| 713 | 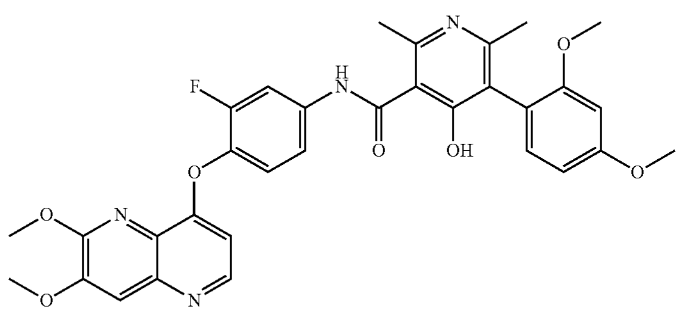 | N-[4-[(6,7-dimethoxy-1,5-naphthyridin-4-yl)oxy]-3-fluorophenyl]-5-(2,4-dimethoxyphenyl)-4-hydroxy-2,6-dimethylpyridine-3-carboxamide |
| 714 | 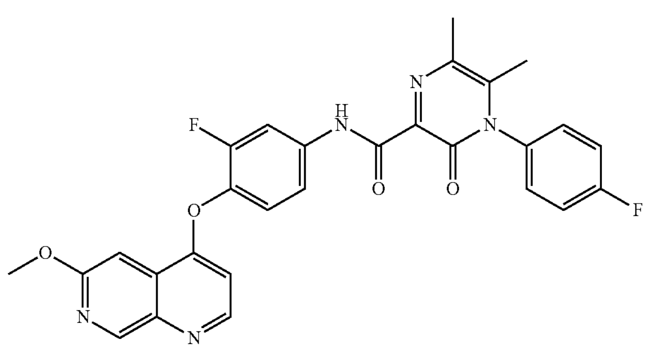 [SMILES: COc1cc2c(Oc3ccc(NC(=O)c4nc(C)c(C)n(-c5ccc(F)cc5)c4=O)cc3F)ccnc2cn1] | N-[3-fluoro-4-[(6-methoxy-1,7-naphthyridin-4-yl)oxy]phenyl]-4-(4-fluorophenyl)-5,6-dimethyl-3-oxopyrazine-2-carboxamide |

-continued

| Cpd # | Structure | IUPAC Name |
|---|---|---|
| 715 | 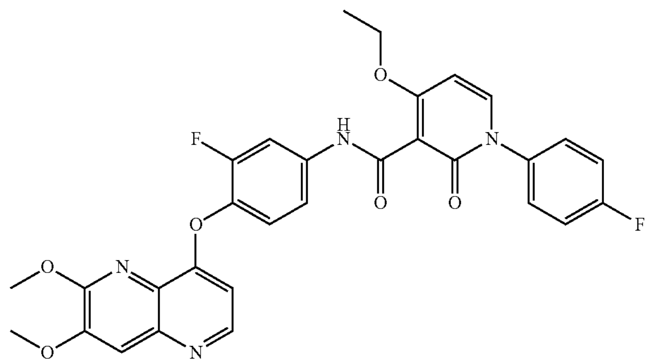 [SMILES: CCOc1ccn(-c2ccc(F)cc2)c(=O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-4-ethoxy-1-(4-fluorophenyl)-2-oxopyridine-3-carboxamide |
| 716 | 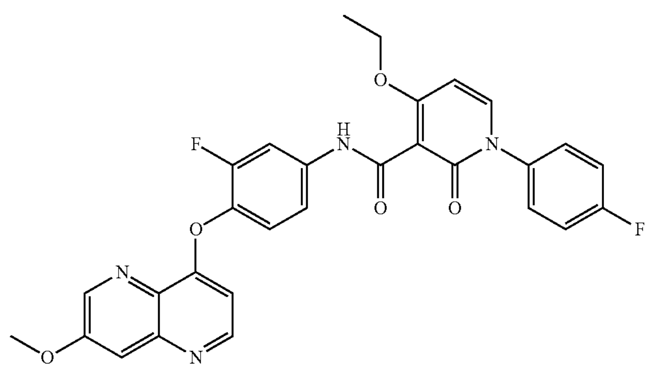 [SMILES: CCOc1ccn(-c2ccc(F)cc2)c(=O)c1C(=O)Nc1ccc(Oc2ccnc3cc(OC)cnc23)c(F)c1] | 4-ethoxy-N-[3-fluoro-4-[(7-methoxy-1,5-naphthyridin-4-yl)oxy]phenyl]-1-(4-fluorophenyl)-2-oxopyridine-3-carboxamide |
| 717 | 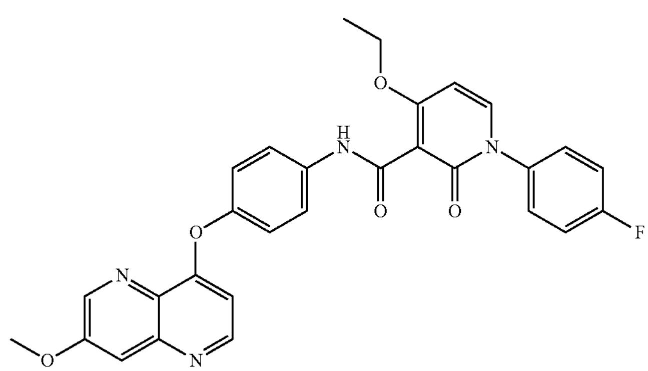 [SMILES: CCOc1ccn(-c2ccc(F)cc2)c(=O)c1C(=O)Nc1ccc(Oc2ccnc3cc(OC)cnc23)cc1] | 4-ethoxy-1-(4-fluorophenyl)-N-[4-[(7-methoxy-1,5-naphthyridin-4-yl)oxy]phenyl]-2-oxopyridine-3-carboxamide |
| 718 | 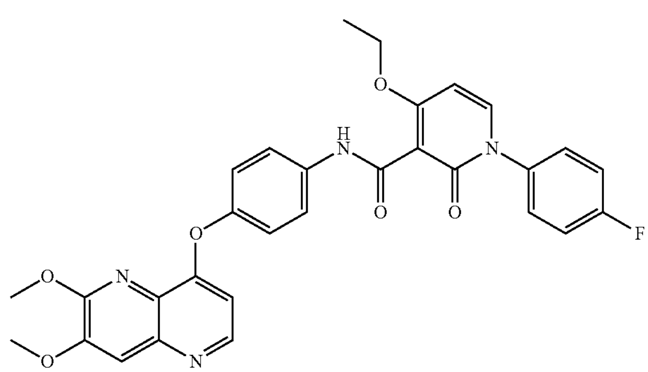 [SMILES: CCOc1ccn(-c2ccc(F)cc2)c(=O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-4-ethoxy-1-(4-fluorophenyl)-2-oxopyridine-3-carboxamide |

| Cpd # | Structure | IUPAC Name |
|---|---|---|
| 719 | 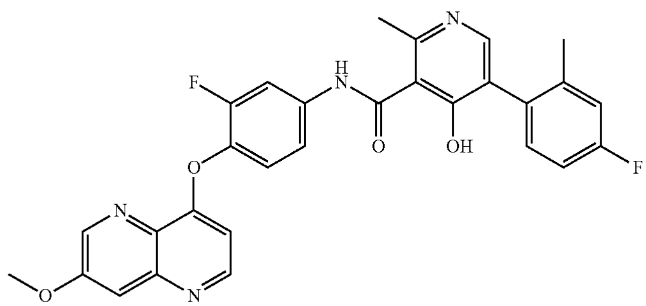 [SMILES: COc1cnc2c(Oc3ccc(NC(=O)c4c(C)ncc(-c5ccc(F)cc5C)c4O)cc3F)ccnc2c1] | N-[3-fluoro-4-[(7-methoxy-1,5-naphthyridin-4-yl)oxy]phenyl]-5-(4-fluoro-2-methylphenyl)-4-hydroxy-2-methylpyridine-3-carboxamide |
| 720 | 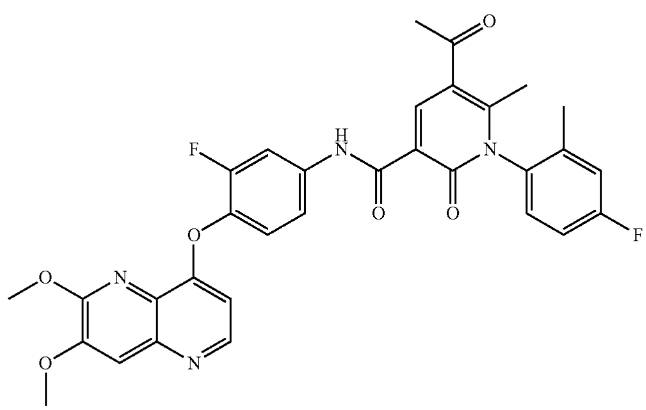 [SMILES: COc1cc2nccc(Oc3ccc(NC(=O)c4cc(C(C)=O)c(C)n(-c5ccc(F)cc5C)c4=O)cc3F)c2nc1OC] | 5-acetyl-N-[4-[(6,7-dimethoxy-1,5-naphthyridin-4-yl)oxy]-3-fluorophenyl]-1-(4-fluoro-2-methylphenyl)-6-methyl-2-oxopyridine-3-carboxamide |
| 721 | 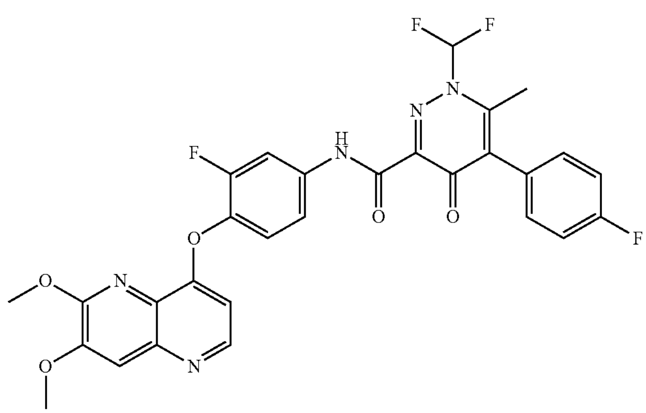 [SMILES: COc1cc2nccc(Oc3ccc(NC(=O)c4nn(C(F)F)c(C)c(-c5ccc(F)cc5)c4=O)cc3F)c2nc1OC] | 1-(difluoromethyl)-N-[4-[(6,7-dimethoxy-1,5-naphthyridin-4-yl)oxy]-3-fluorophenyl]-5-(4-fluorophenyl)-6-methyl-4-oxopyridazine-3-carboxamide |
| 722 | 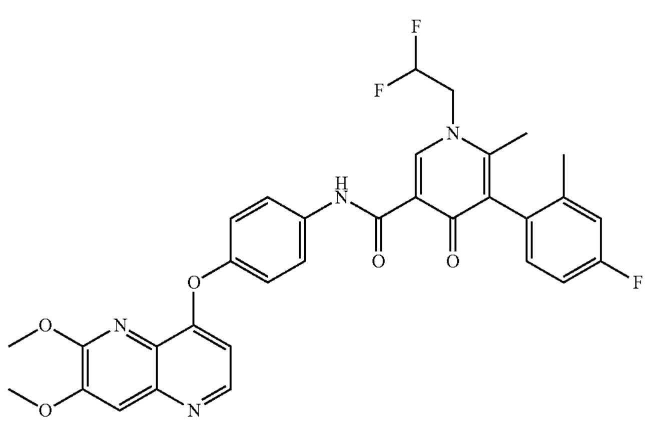 [SMILES: COc1cc2nccc(Oc3ccc(NC(=O)c4cn(CC(F)F)c(C)c(-c5ccc(F)cc5C)c4=O)cc3)c2nc1OC] | 1-(2,2-difluoroethyl)-N-[4-[(6,7-dimethoxy-1,5-naphthyridin-4-yl)oxy]phenyl]-5-(4-fluoro-2-methylphenyl)-6-methyl-4-oxopyridine-3-carboxamide |

| Cpd # | Structure | IUPAC Name |
|---|---|---|
| 723 | 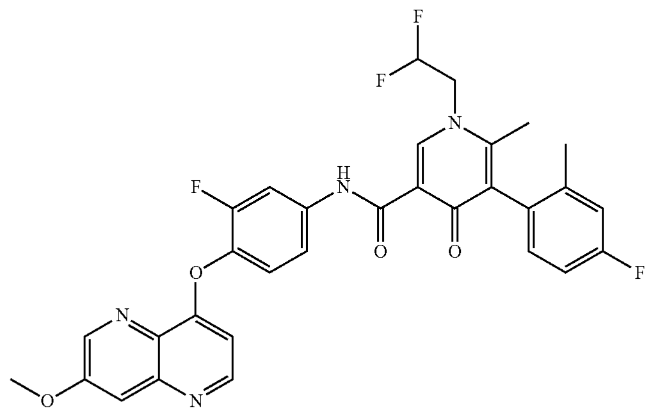 [SMILES: COc1cnc2c(Oc3ccc(NC(=O)c4cn(CC(F)F)c(C)c(-c5ccc(F)cc5C)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluoro-2-methylphenyl)-6-methyl-4-oxopyridine-3-carboxamide |
| 724 | 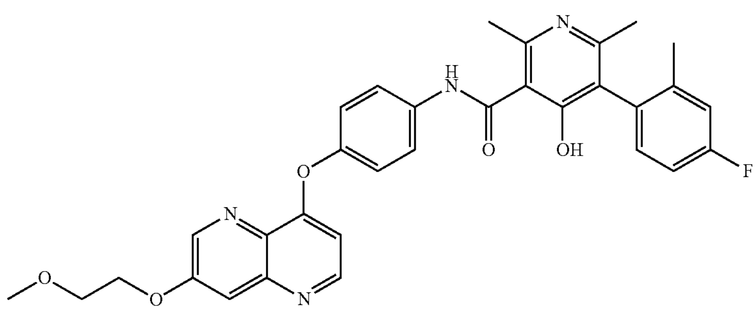 [SMILES: COCCOc1cnc2c(Oc3ccc(NC(=O)c4c(C)nc(C)c(-c5ccc(F)cc5C)c4O)cc3)ccnc2c1] | 5-(4-fluoro-2-methylphenyl)-4-hydroxy-N-[4-[[7-(2-methoxyethoxy)-1,5-naphthyridin-4-yl]oxy]phenyl]-2,6-dimethylpyridine-3-carboxamide |
| 725 | 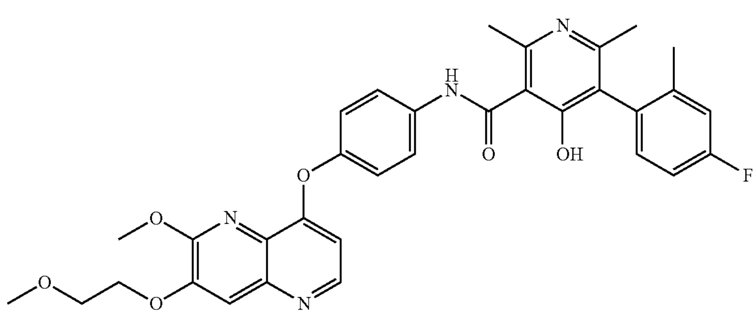 [SMILES: COCCOc1cc2nccc(Oc3ccc(NC(=O)c4c(C)nc(C)c(-c5ccc(F)cc5C)c4O)cc3)c2nc1OC] | 5-(4-fluoro-2-methylphenyl)-4-hydroxy-N-[4-[[6-methoxy-7-(2-methoxyethoxy)-1,5-naphthyridin-4-yl]oxy]phenyl]-2,6-dimethylpyridine-3-carboxamide |
| 726 | 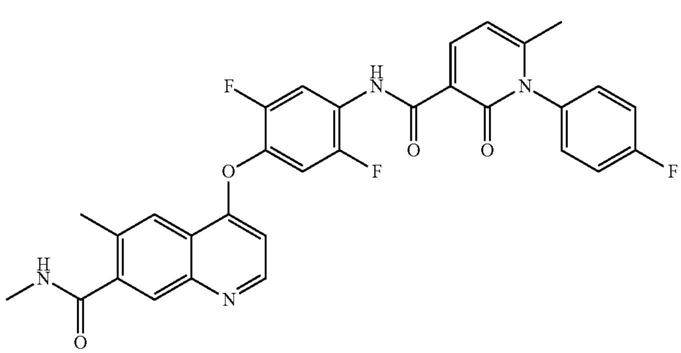 [SMILES: CNC(=O)c1cc2nccc(Oc3cc(F)c(NC(=O)c4ccc(C)n(-c5ccc(F)cc5)c4=O)cc3F)c2cc1C] | 4-[2,5-difluoro-4-[[1-(4-fluorophenyl)-6-methyl-2-oxopyridine-3-carbonyl]amino]phenoxy]-N,6-dimethylquinoline-7-carboxamide |

| Cpd # | Structure | IUPAC Name |
|---|---|---|
| 727 | 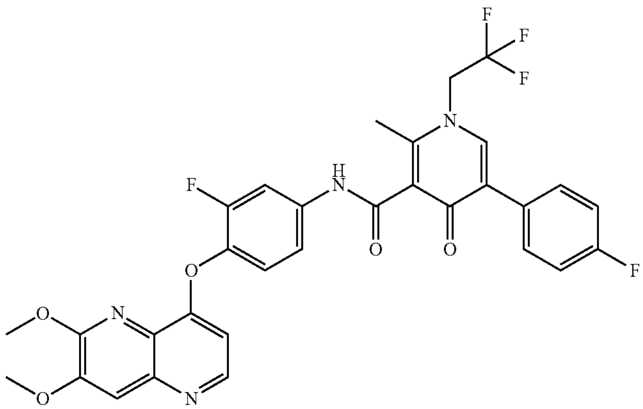 [SMILES: COc1cc2nccc(Oc3ccc(NC(=O)c4c(C)n(CC(F)(F)F)cc(-c5ccc(F)cc5)c4=O)cc3F)c2nc1OC] | N-[4-[(6,7-dimethoxy-1,5-naphthyridin-4-yl)oxy]-3-fluorophenyl]-5-(4-fluorophenyl)-2-methyl-4-oxo-1-(2,2,2-trifluoroethyl)pyridine-3-carboxamide |
| 728 | 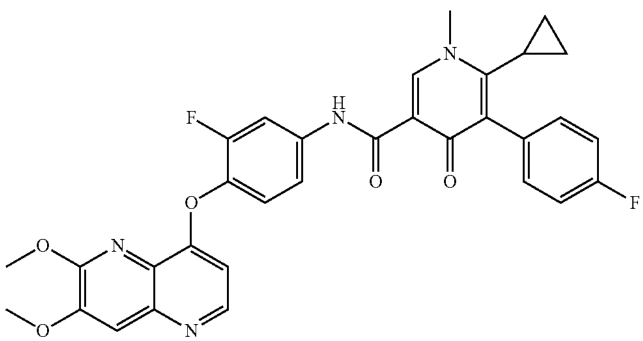 [SMILES: COc1cc2nccc(Oc3ccc(NC(=O)c4cn(C)c(C5CC5)c(-c5ccc(F)cc5)c4=O)cc3F)c2nc1OC] | 6-cyclopropyl-N-[4-[(6,7-dimethoxy-1,5-naphthyridin-4-yl)oxy]-3-fluorophenyl]-5-(4-fluorophenyl)-1-methyl-4-oxopyridine-3-carboxamide |
| 729 | 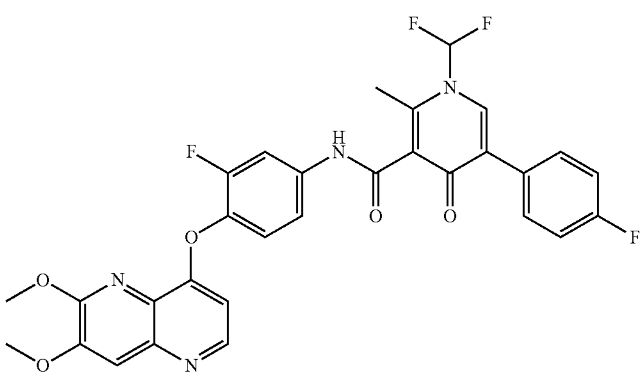 [SMILES: COc1cc2nccc(Oc3ccc(NC(=O)c4c(C)n(C(F)F)cc(-c5ccc(F)cc5)c4=O)cc3F)c2nc1OC] | 1-(difluoromethyl)-N-[4-[(6,7-dimethoxy-1,5-naphthyridin-4-yl)oxy]-3-fluorophenyl]-5-(4-fluorophenyl)-2-methyl-4-oxopyridine-3-carboxamide |
| 730 | 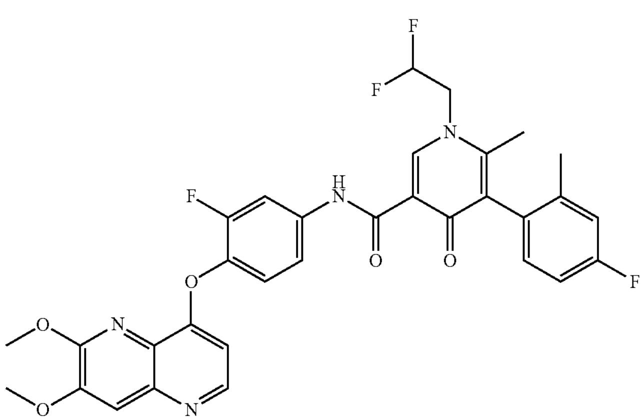 [SMILES: COc1cc2nccc(Oc3ccc(NC(=O)c4cn(CC(F)F)c(C)c(-c5ccc(F)cc5C)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluoro-2-methylphenyl)-6-methyl-4-oxopyridine-3-carboxamide |

| Cpd # | Structure | IUPAC Name |
|---|---|---|
| 731 | 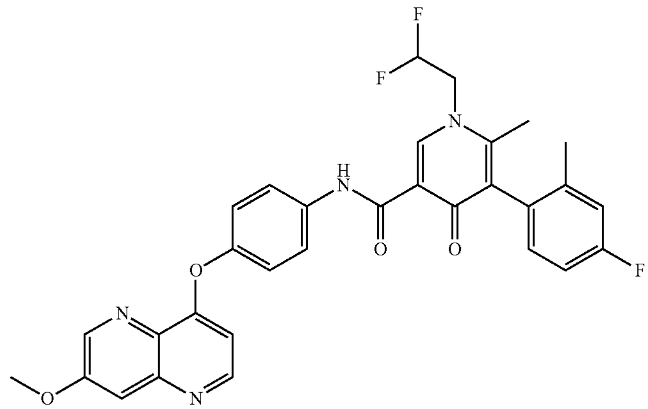 [SMILES: COc1cnc2c(Oc3ccc(NC(=O)c4cn(CC(F)F)c(C)c(-c5ccc(F)cc5C)c4=O)cc3)ccnc2c1] | 1-(2,2-difluoroethyl)-5-(4-fluoro-2-methylphenyl)-N-[4-[(7-methoxy-1,5-naphthyridin-4-yl)oxy]phenyl]-6-methyl-4-oxopyridine-3-carboxamide |
| 732 | 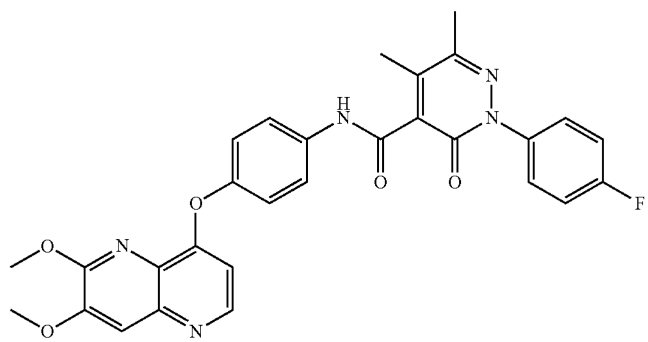 [SMILES: COc1cc2nccc(Oc3ccc(NC(=O)c4c(C)c(C)nn(-c5ccc(F)cc5)c4=O)cc3)c2nc1OC] | N-[4-[(6,7-dimethoxy-1,5-naphthyridin-4-yl)oxy]phenyl]-2-(4-fluorophenyl)-5,6-dimethyl-3-oxopyridazine-4-carboxamide |
| 733 | 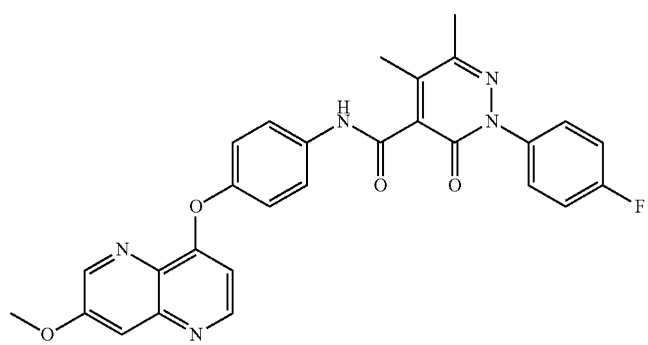 [SMILES: COc1cnc2c(Oc3ccc(NC(=O)c4c(C)c(C)nn(-c5ccc(F)cc5)c4=O)cc3)ccnc2c1] | 2-(4-fluorophenyl)-N-[4-[(7-methoxy-1,5-naphthyridin-4-yl)oxy]phenyl]-5,6-dimethyl-3-oxopyridazine-4-carboxamide |
| 734 | 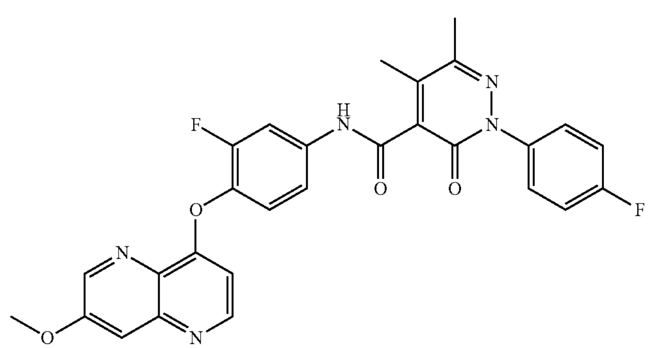 [SMILES: COc1cnc2c(Oc3ccc(NC(=O)c4c(C)c(C)nn(-c5ccc(F)cc5)c4=O)cc3F)ccnc2c1] | N-[3-fluoro-4-[(7-methoxy-1,5-naphthyridin-4-yl)oxy]phenyl]-2-(4-fluorophenyl)-5,6-dimethyl-3-oxopyridazine-4-carboxamide |

| Cpd # | Structure | IUPAC Name |
|---|---|---|
| 735 | 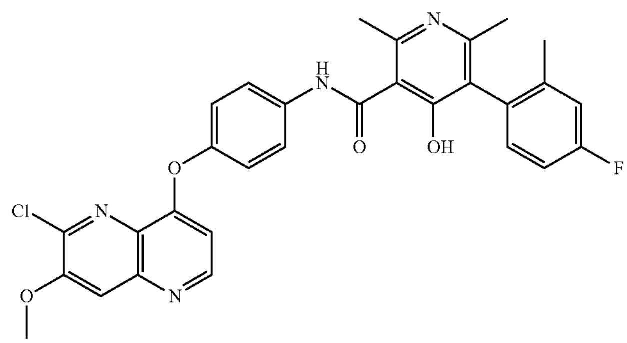 [SMILES: COc1cc2nccc(Oc3ccc(NC(=O)c4c(C)nc(C)c(-c5ccc(F)cc5C)c4O)cc3)c2nc1Cl] | N-[4-[(6-chloro-7-methoxy-1,5-naphthyridin-4-yl)oxy]phenyl]-5-(4-fluoro-2-methylphenyl)-4-hydroxy-2,6-dimethylpyridine-3-carboxamide |
| 736 | 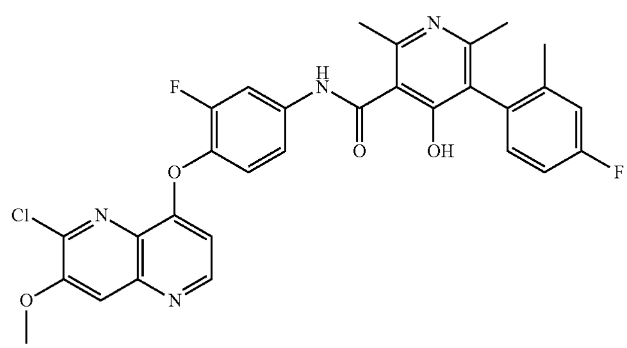 [SMILES: COc1cc2nccc(Oc3ccc(NC(=O)c4c(C)nc(C)c(-c5ccc(F)cc5C)c4O)cc3F)c2nc1Cl] | N-[4-[(6-chloro-7-methoxy-1,5-naphthyridin-4-yl)oxy]-3-fluorophenyl]-5-(4-fluoro-2-methylphenyl)-4-hydroxy-2,6-dimethylpyridine-3-carboxamide |
| 737 | 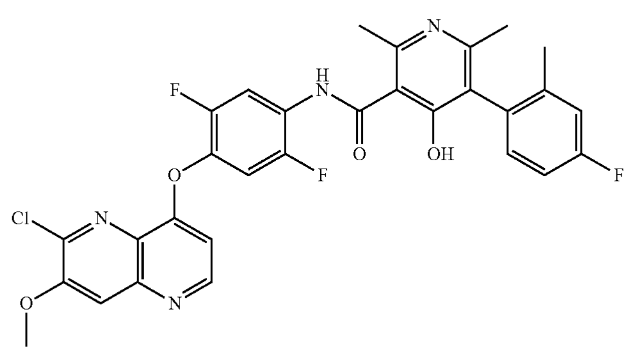 [SMILES: COc1cc2nccc(Oc3cc(F)c(NC(=O)c4c(C)nc(C)c(-c5ccc(F)cc5C)c4O)cc3F)c2nc1Cl] | N-[4-[(6-chloro-7-methoxy-1,5-naphthyridin-4-yl)oxy]-2,5-difluorophenyl]-5-(4-fluoro-2-methylphenyl)-4-hydroxy-2,6-dimethylpyridine-3-carboxamide |
| 738 | 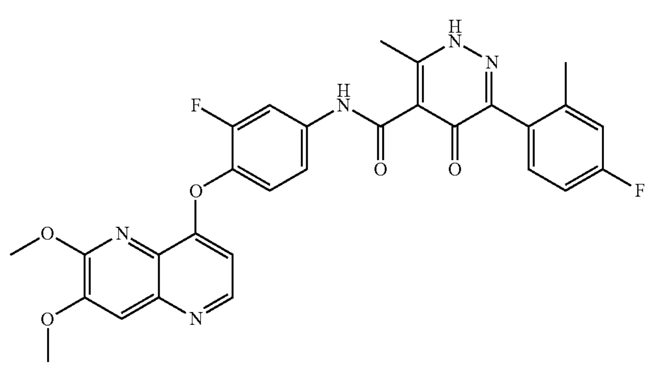 [SMILES: COc1cc2nccc(Oc3ccc(NC(=O)c4c(C)[nH]nc(-c5ccc(F)cc5C)c4=O)cc3F)c2nc1OC] | N-[4-[(6,7-dimethoxy-1,5-naphthyridin-4-yl)oxy]-3-fluorophenyl]-3-(4-fluoro-2-methylphenyl)-6-methyl-4-oxo-1H-pyridazine-5-carboxamide |

| Cpd # | Structure | IUPAC Name |
|---|---|---|
| 739 | 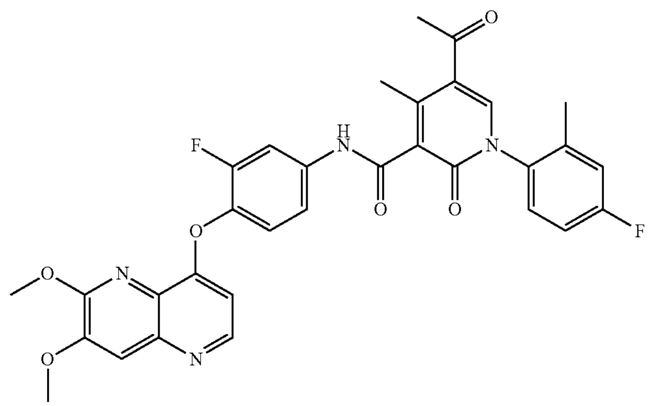 [SMILES: COc1cc2nccc(Oc3ccc(NC(=O)c4c(C)c(C(C)=O)cn(-c5ccc(F)cc5C)c4=O)cc3F)c2nc1OC] | 5-acetyl-N-[4-[(6,7-dimethoxy-1,5-naphthyridin-4-yl)oxy]-3-fluorophenyl]-1-(4-fluoro-2-methylphenyl)-4-methyl-2-oxopyridine-3-carboxamide |
| 740 | 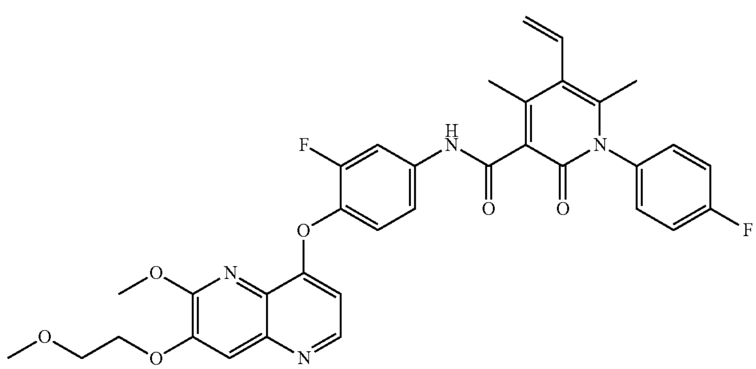 [SMILES: C=Cc1c(C)c(C(=O)Nc2ccc(Oc3ccnc4cc(OCCOC)c(OC)nc34)c(F)c2)c(=O)n(-c2ccc(F)cc2)c1C] | 5-ethenyl-N-[3-fluoro-4-[6-methoxy-7-(2-methoxyethoxy)-1,5-naphthyridin-4-yl]oxy]phenyl]-1-(4-fluorophenyl)-4,6-dimethyl-2-oxopyridine-3-carboxamide |
| 741 | 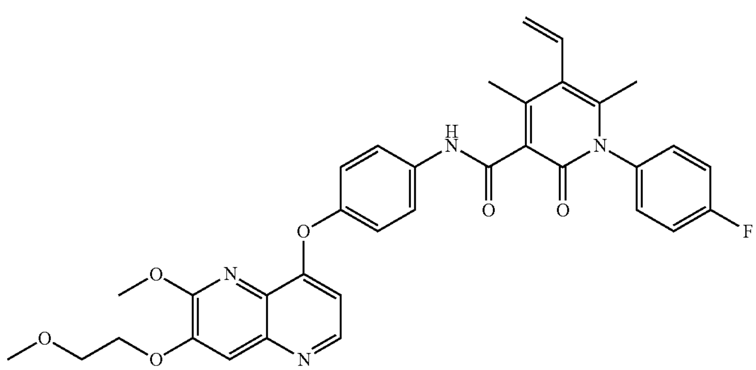 [SMILES: C=Cc1c(C)c(C(=O)Nc2ccc(Oc3ccnc4cc(OCCOC)c(OC)nc34)cc2)c(=O)n(-c2ccc(F)cc2)c1C] | 5-ethenyl-1-(4-fluorophenyl)-N-[4-[[6-methoxy-7-(2-methoxyethoxy)-1,5-naphthyridin-4-yl]oxy]phenyl]-4,6-dimethyl-2-oxopyridine-3-carboxamide |
| 742 | 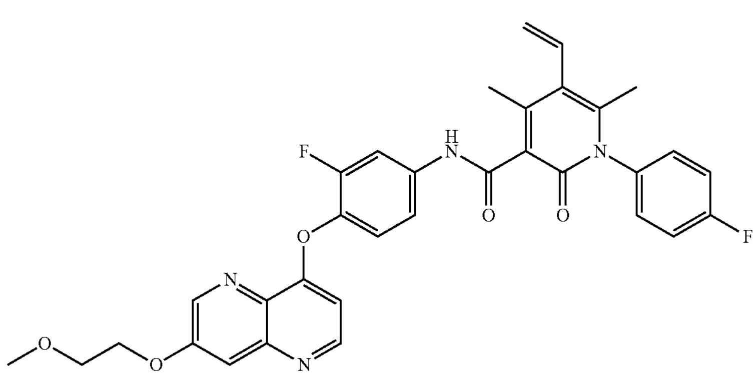 [SMILES: C=Cc1c(C)c(C(=O)Nc2ccc(Oc3ccnc4cc(OCCOC)cnc34)c(F)c2)c(=O)n(-c2ccc(F)cc2)c1C] | 5-ethenyl-N-[3-fluoro-4-[[7-(2-methoxyethoxy)-1,5-naphthyridin-4-yl]oxy]phenyl]-1-(4-fluorophenyl)-4,6-dimethyl-2-oxopyridine-3-carboxamide |

| Cpd # | Structure | IUPAC Name |
|---|---|---|
| 743 | 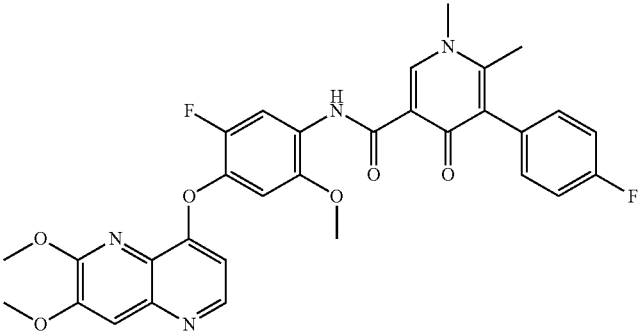 [SMILES: COc1cc(Oc2ccnc3cc(OC)c(OC)nc23)c(F)cc1NC(=O)c1cn(C)c(C)c(-c2ccc(F)cc2)c1=O] | N-[4-[(6,7-dimethoxy-1,5-naphthyridin-4-yl)oxy]-5-fluoro-2-methoxyphenyl]-5-(4-fluorophenyl)-1,6-dimethyl-4-oxopyridine-3-carboxamide |
| 744 | 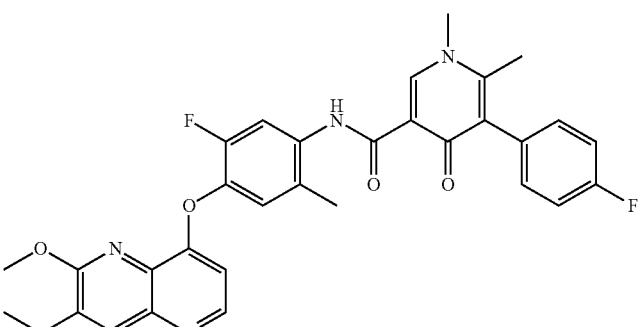 | N-[4-[(6,7-dimethoxy-1,5-naphthyridin-4-yl)oxy]-5-fluoro-2-methylphenyl]-5-(4-fluorophenyl)-1,6-dimethyl-4-oxopyridine-3-carboxamide |
| 745 | 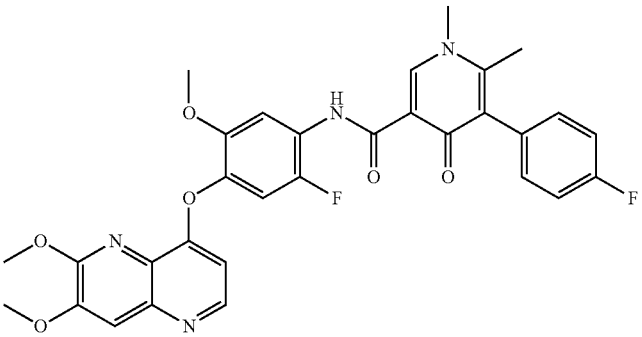 [SMILES: COc1cc(NC(=O)c2cn(C)c(C)c(-c3ccc(F)cc3)c2=O)c(F)cc1Oc1ccnc2cc(OC)c(OC)nc12] | N-[4-[(6,7-dimethoxy-1,5-naphthyridin-4-yl)oxy]-2-fluoro-5-methoxyphenyl]-5-(4-fluorophenyl)-1,6-dimethyl-4-oxopyridine-3-carboxamide |
| 746 | 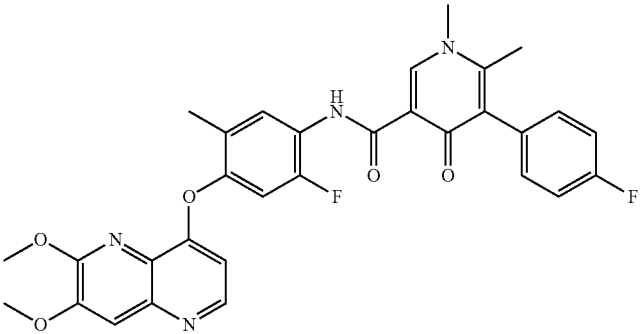 [SMILES: COc1cc2nccc(Oc3cc(F)c(NC(=O)c4cn(C)c(C)c(-c5ccc(F)cc5)c4=O)cc3C)c2nc1OC] | N-[4-[(6,7-dimethoxy-1,5-naphthyridin-4-yl)oxy]-2-fluoro-5-methylphenyl]-5-(4-fluorophenyl)-1,6-dimethyl-4-oxopyridine-3-carboxamide |

-continued

| Cpd # | Structure | IUPAC Name |
|---|---|---|
| 747 | 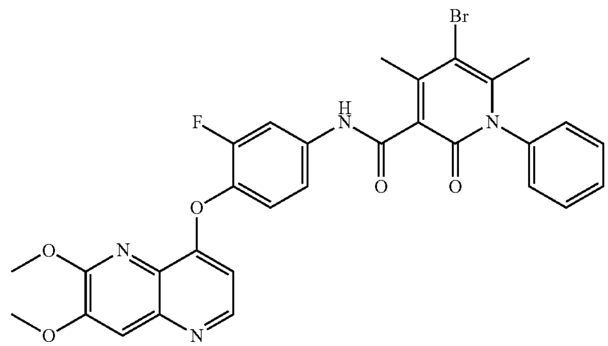 [SMILES: COc1cc2nccc(Oc3ccc(NC(=O)c4c(C)c(Br)c(C)n(-c5ccccc5)c4=O)cc3F)c2nc1OC] | 5-bromo-N-[4-[(6,7-dimethoxy-1,5-naphthyridin-4-yl)oxy]-3-fluorophenyl]-4,6-dimethyl-2-oxo-1-phenylpyridine-3-carboxamide |
| 748 | 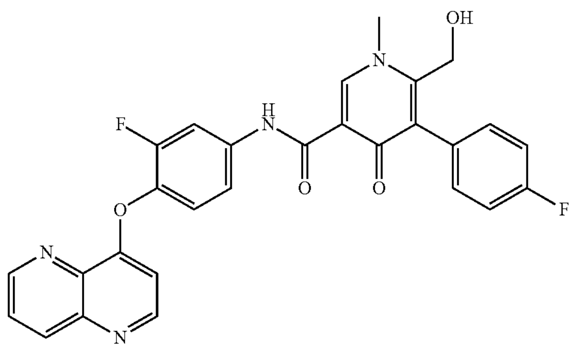 [SMILES: Cn1cc(C(=O)Nc2ccc(Oc3ccnc4cccnc34)c(F)c2)c(=O)c(-c2ccc(F)cc2)c1CO] | N-[3-fluoro-4-(1,5-naphthyridin-4-yloxy)phenyl]-5-(4-fluorophenyl)-6-(hydroxymethyl)-1-methyl-4-oxopyridine-3-carboxamide |
| 749 | 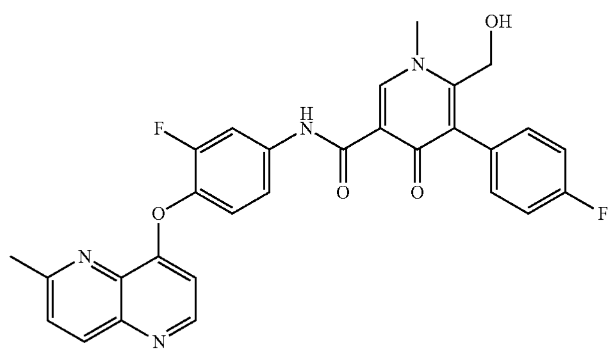 [SMILES: Cc1ccc2nccc(Oc3ccc(NC(=O)c4cn(C)c(CO)c(-c5ccc(F)cc5)c4=O)cc3F)c2n1] | N-[3-fluoro-4-[(6-methyl-1,5-naphthyridin-4-yl)oxy]phenyl]-5-(4-fluorophenyl)-6-(hydroxymethyl)-1-methyl-4-oxopyridine-3-carboxamide |
| 750 | 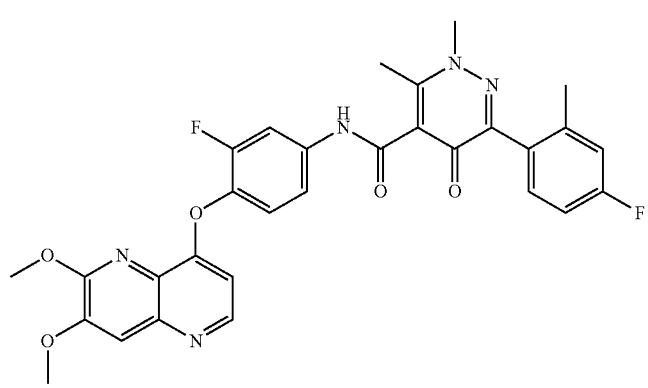 [SMILES: COc1cc2nccc(Oc3ccc(NC(=O)c4c(C)n(C)nc(-c5ccc(F)cc5C)c4=O)cc3F)c2nc1OC] | N-[4-[(6,7-dimethoxy-1,5-naphthyridin-4-yl)oxy]-3-fluorophenyl]-6-(4-fluoro-2-methylphenyl)-2,3-dimethyl-5-oxopyridazine-4-carboxamide |

| Cpd # | Structure | IUPAC Name |
|---|---|---|
| 751 | 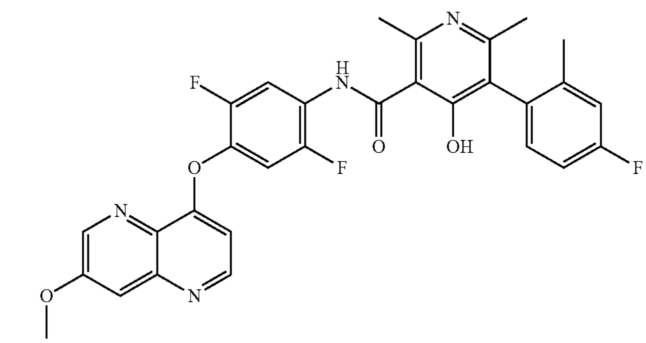 [SMILES: COc1cnc2c(Oc3cc(F)c(NC(=O)c4c(C)nc(C)c(-c5ccc(F)cc5C)c4O)cc3F)ccnc2c1] | N-[2,5-difluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 752 | 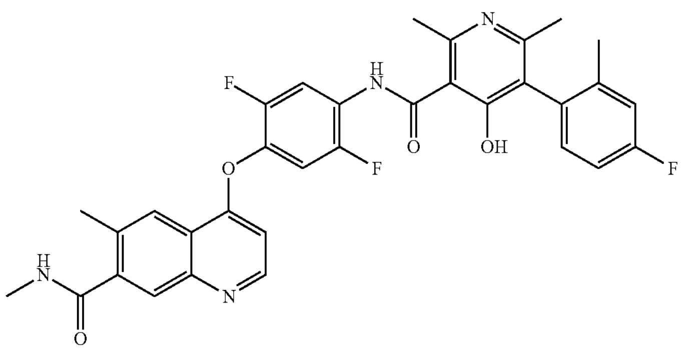 [SMILES: CNC(=O)c1cc2nccc(Oc3cc(F)c(NC(=O)c4c(C)nc(C)c(-c5ccc(F)cc5C)c4O)cc3F)c2cc1C] | 4-[2,5-difluoro-4-[[5-(4-fluoro-2-methylphenyl)-4-hydroxy-2,6-dimethylpyridine-3-carbonyl]amino]phenoxy]-N,6-dimethylquinoline-7-carboxamide |
| 753 | 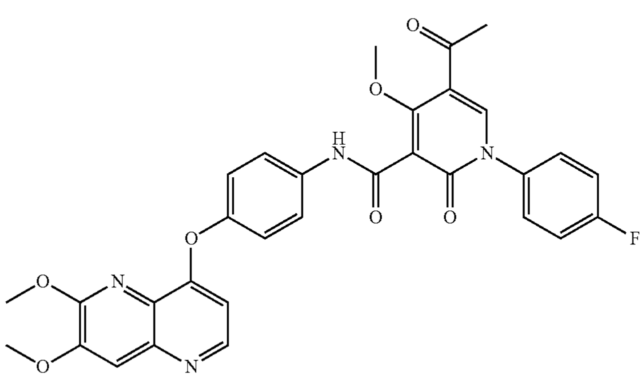 [SMILES: COc1cc2nccc(Oc3ccc(NC(=O)c4c(OC)c(C(C)=O)cn(-c5ccc(F)cc5)c4=O)cc3)c2nc1OC] | 5-acetyl-N-[4-[(6,7-dimethoxy-1,5-naphthyridin-4-yl)oxy]phenyl]-1-(4-fluorophenyl)-4-methoxy-2-oxopyridine-3-carboxamide |
| 754 | 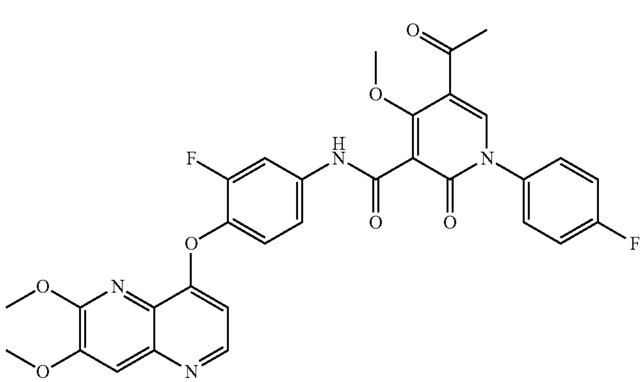 [SMILES: COc1cc2nccc(Oc3ccc(NC(=O)c4c(OC)c(C(C)=O)cn(-c5ccc(F)cc5)c4=O)cc3F)c2nc1OC] | 5-acetyl-N-[4-[(6,7-dimethoxy-1,5-naphthyridin-4-yl)oxy]-3-fluorophenyl]-1-(4-fluorophenyl)-4-methoxy-2-oxopyridine-3-carboxamide |

| Cpd # | Structure | IUPAC Name |
|---|---|---|
| 755 | 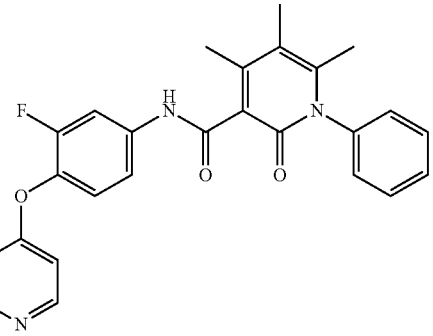 | N-[4-[(6,7-dimethoxy-1,5-naphthyridin-4-yl)oxy]-3-fluorophenyl]-4,5,6-trimethyl-2-oxo-1-phenylpyridine-3-carboxamide |
| 756 | 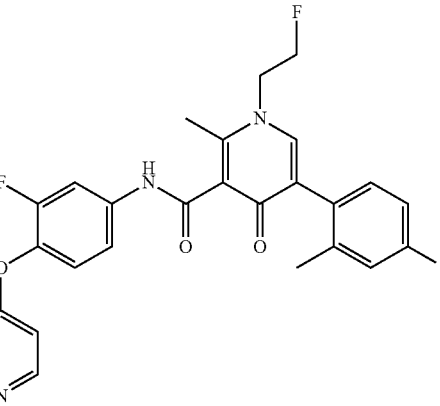 | N-[4-[(6,7-dimethoxy-1,5-naphthyridin-4-yl)oxy]-3-fluorophenyl]-1-(2-fluoroethyl)-5-(4-fluoro-2-methylphenyl)-2-methyl-4-oxopyridine-3-carboxamide |
| 757 | 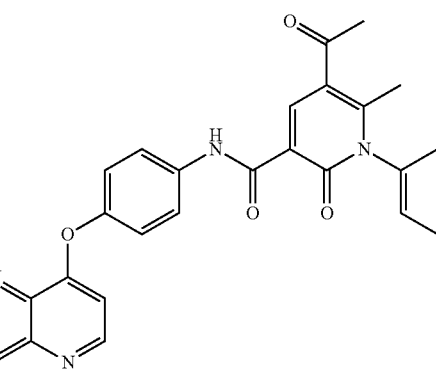 | 5-acetyl-1-(4-fluorophenyl)-N-[4-[6-methoxy-7-(2-methoxyethoxy)-1,5-naphthyridin-4-yl]oxy]phenyl]-6-methyl-2-oxopyridine-3-carboxamide |
| 758 | 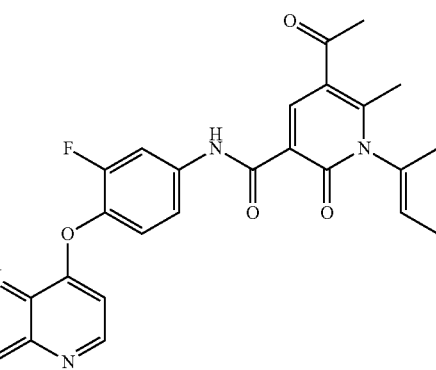 | 5-acetyl-N-[3-fluoro-4-[[7-(2-methoxyethoxy)-1,5-naphthyridin-4-yl]oxy]phenyl]-1-(4-fluorophenyl)-6-methyl-2-oxopyridine-3-carboxamide |

| Cpd # | Structure | IUPAC Name |
|---|---|---|
| 759 | 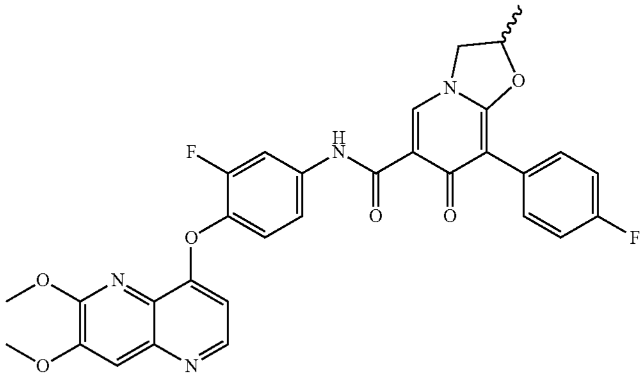 [SMILES: COc1cc2nccc(Oc3ccc(NC(=O)c4cn5c(c(-c6ccc(F)cc6)c4=O)OC(C)C5)cc3F)c2nc1OC] | N-[4-[(6,7-dimethoxy-1,5-naphthyridin-4-yl)oxy]-3-fluorophenyl]-8-(4-fluorophenyl)-2-methyl-7-oxo-2,3-dihydro-[1,3]oxazolo[3,2-a]pyridine-6-carboxamide |
| 760 | 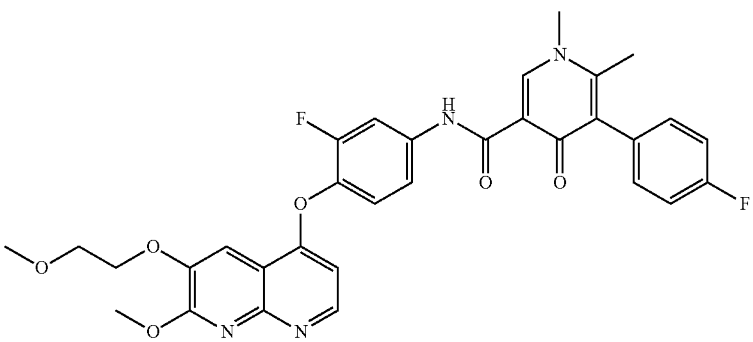 [SMILES: COCCOc1cc2c(Oc3ccc(NC(=O)c4cn(C)c(C)c(-c5ccc(F)cc5)c4=O)cc3F)ccnc2nc1OC] | N-[3-fluoro-4-[[7-methoxy-6-(2-methoxyethoxy)-1,8-naphthyridin-4-yl]oxy]phenyl]-5-(4-fluorophenyl)-1,6-dimethyl-4-oxopyridine-3-carboxamide |
| 761 | 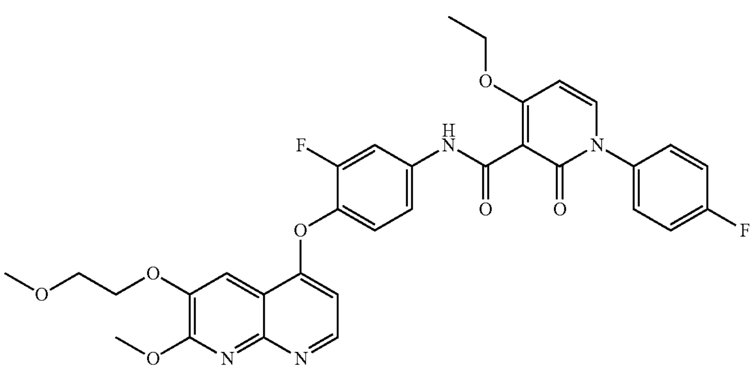 [SMILES: CCOc1ccn(-c2ccc(F)cc2)c(=O)c1C(=O)Nc1ccc(Oc2ccnc3nc(OC)c(OCCOC)cc23)c(F)c1] | 4-ethoxy-N-[3-fluoro-4-[[7-methoxy-6-(2-methoxyethoxy)-1,8-naphthyridin-4-yl]oxy]phenyl]-1-(4-fluorophenyl)-2-oxopyridine-3-carboxamide |
| 762 | 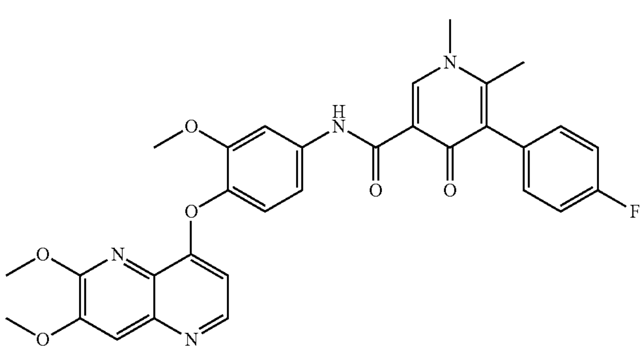 [SMILES: COc1cc(NC(=O)c2cn(C)c(C)c(-c3ccc(F)cc3)c2=O)ccc1Oc1ccnc2cc(OC)c(OC)nc12] | N-[4-[(6,7-dimethoxy-1,5-naphthyridin-4-yl)oxy]-3-methoxyphenyl]-5-(4-fluorophenyl)-1,6-dimethyl-4-oxopyridine-3-carboxamide |

-continued

| Cpd # | Structure | IUPAC Name |
|---|---|---|
| 763 | 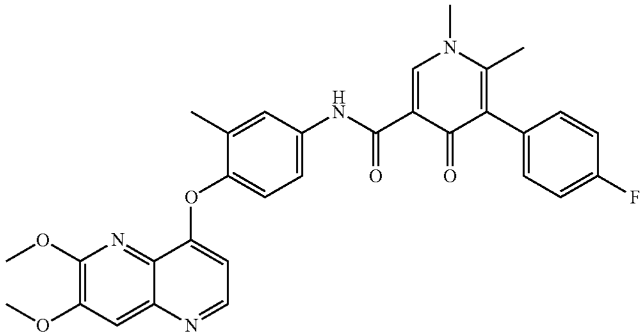 [SMILES: COc1cc2nccc(Oc3ccc(NC(=O)c4cn(C)c(C)c(-c5ccc(F)cc5)c4=O)cc3C)c2nc1OC] | N-[4-[(6,7-dimethoxy-1,5-naphthyridin-4-yl)oxy]-3-methylphenyl]-5-(4-fluorophenyl)-1,6-dimethyl-4-oxopyridine-3-carboxamide |
| 764 | 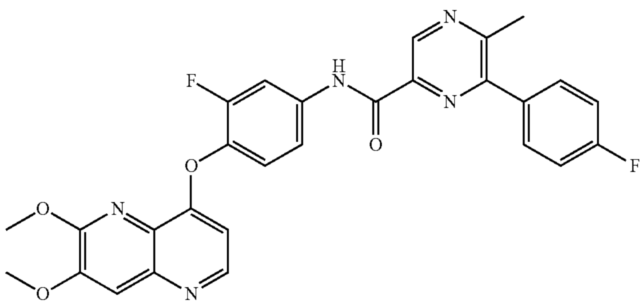 [SMILES: COc1cc2nccc(Oc3ccc(NC(=O)c4cnc(C)c(-c5ccc(F)cc5)n4)cc3F)c2nc1OC] | N-[4-[(6,7-dimethoxy-1,5-naphthyridin-4-yl)oxy]-3-fluorophenyl]-6-(4-fluorophenyl)-5-methylpyrazine-2-carboxamide |
| 765 | 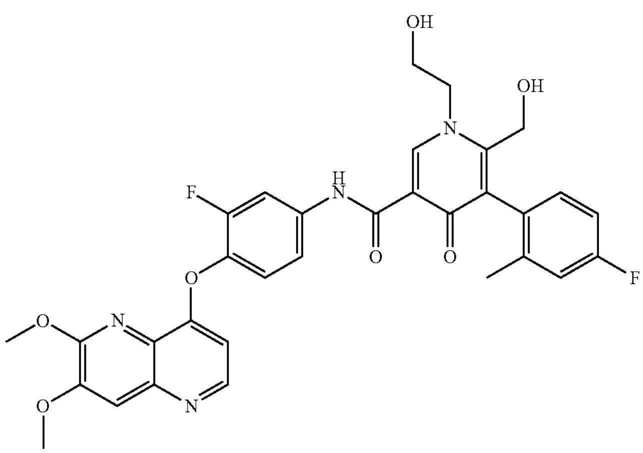 [SMILES: COc1cc2nccc(Oc3ccc(NC(=O)c4cn(CCO)c(CO)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1-(2-hydroxyethyl)-6-(hydroxymethyl)-4-oxopyridine-3-carboxamide |
| 766 | 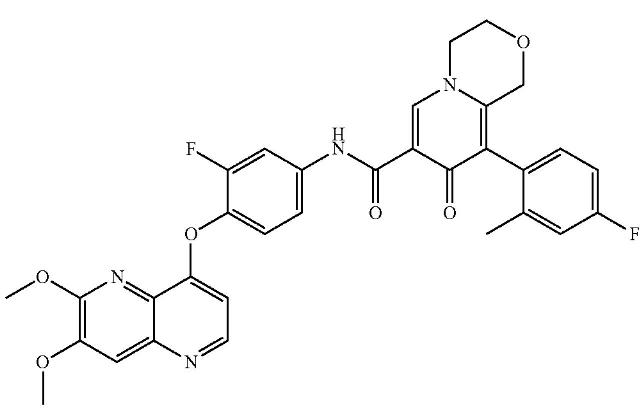 [SMILES: COc1cc2nccc(Oc3ccc(NC(=O)c4cn5c(c(-c6ccc(F)cc6C)c4=O)COCC5)cc3F)c2nc1OC] | N-[4-[(6,7-dimethoxy-1,5-naphthyridin-4-yl)oxy]-3-fluorophenyl]-9-(4-fluoro-2-methylphenyl)-8-oxo-3,4-dihydro-1H-pyrido[2,1-c][1,4]oxazine-7-carboxamide |

| Cpd # | Structure | IUPAC Name |
|---|---|---|
| 767 | 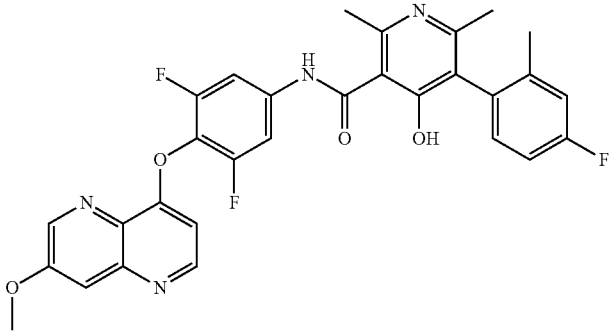 [SMILES: COc1cnc2c(Oc3c(F)cc(NC(=O)c4c(C)nc(C)c(-c5ccc(F)cc5C)c4O)cc3F)ccnc2c1] | N-[3,5-difluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |
| 768 | 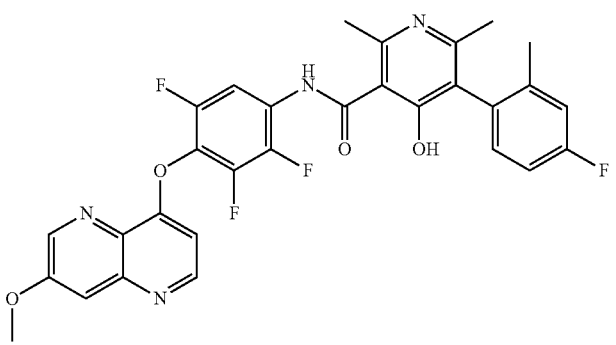 | 5-(4-fluoro-2-methylphenyl)-4-hydroxy-2,6-dimethyl-N-[2,3,5-trifluoro-4-[(7-methoxy-1,5-naphthyridin-4-yl)oxy]phenyl]pyridine-3-carboxamide |
| 769 | 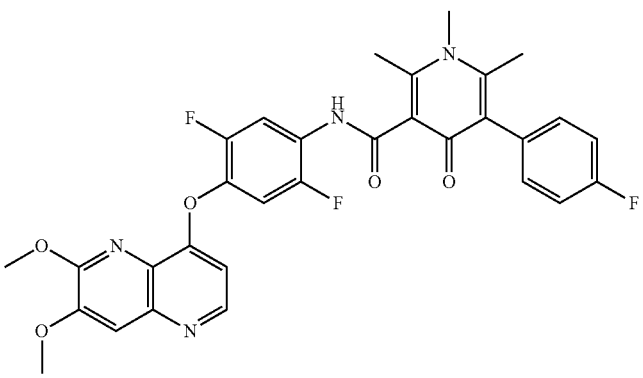 [SMILES: COc1cc2nccc(Oc3cc(F)c(NC(=O)c4c(C)n(C)c(C)c(-c5ccc(F)cc5)c4=O)cc3F)c2nc1OC] | N-[4-[(6,7-dimethoxy-1,5-naphthyridin-4-yl)oxy]-2,5-difluorophenyl]-5-(4-fluorophenyl)-1,2,6-trimethyl-4-oxopyridine-3-carboxamide |
| 770 | 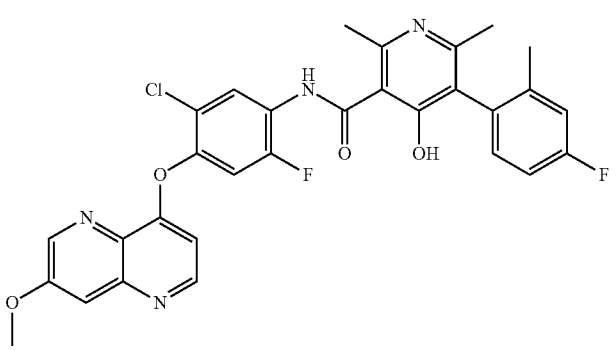 [SMILES: COc1cnc2c(Oc3cc(F)c(NC(=O)c4c(C)nc(C)c(-c5ccc(F)cc5C)c4O)cc3Cl)ccnc2c1] | N-[5-chloro-2-fluoro-4-[(7-methoxy-1,5-naphthyridin-4-yl)oxy]phenyl]-5-(4-fluoro-2-methylphenyl)-4-hydroxy-2,6-dimethylpyridine-3-carboxamide |

-continued

| Cpd # | Structure | IUPAC Name |
|---|---|---|
| 771 | 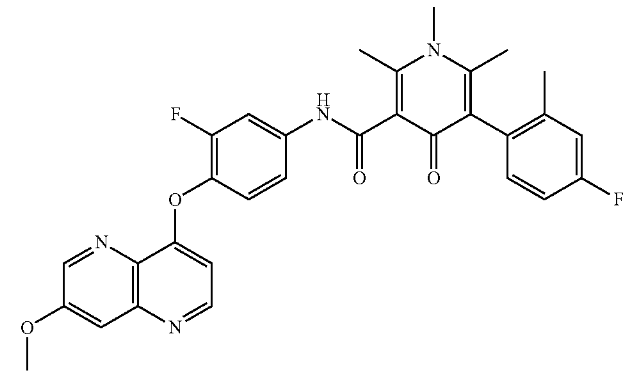 [SMILES: COc1cnc2c(Oc3ccc(NC(=O)c4c(C)n(C)c(C)c(-c5ccc(F)cc5C)c4=O)cc3F)ccnc2c1] | N-[3-fluoro-4-[(7-methoxy-1,5-naphthyridin-4-yl)oxy]phenyl]-5-(4-fluoro-2-methylphenyl)-1,2,6-trimethyl-4-oxopyridine-3-carboxamide |
| 772 | 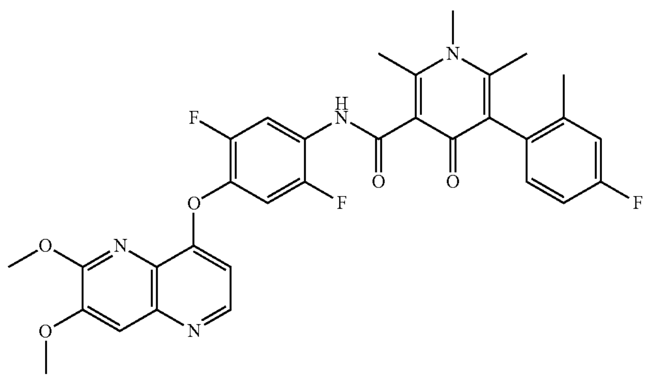 [SMILES: COc1cc2nccc(Oc3cc(F)c(NC(=O)c4c(C)n(C)c(C)c(-c5ccc(F)cc5C)c4=O)cc3F)c2nc1OC] | N-[4-[(6,7-dimethoxy-1,5-naphthyridin-4-yl)oxy]-2,5-difluorophenyl]-5-(4-fluoro-2-methylphenyl)-1,2,6-trimethyl-4-oxopyridine-3-carboxamide |
| 773 | 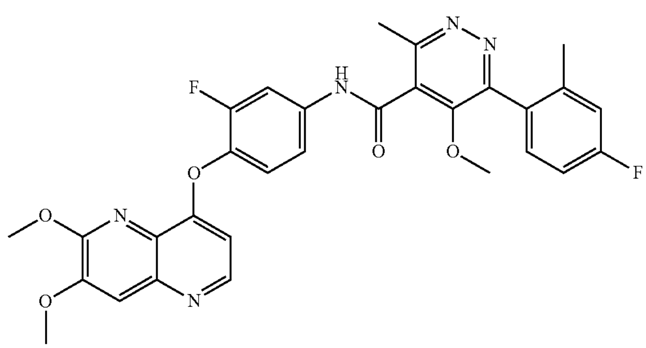 | N-[4-[(6,7-dimethoxy-1,5-naphthyridin-4-yl)oxy]-3-fluorophenyl]-6-(4-fluoro-2-methylphenyl)-5-methoxy-3-methylpyridazine-4-carboxamide |
| 774 | 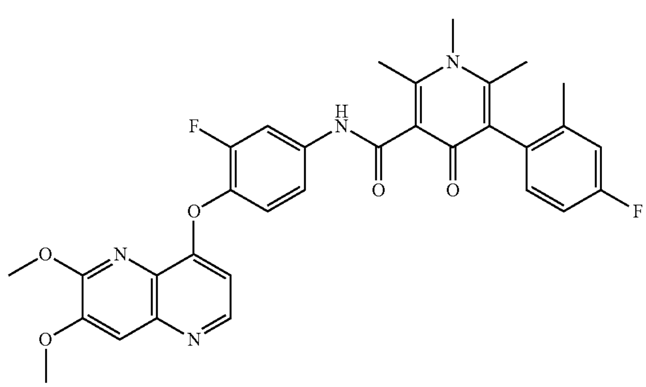 [SMILES: COc1cc2nccc(Oc3ccc(NC(=O)c4c(C)n(C)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-1,2,6-trimethyl-4-oxopyridine-3-carboxamide |

| Cpd # | Structure | IUPAC Name |
|---|---|---|
| 775 | 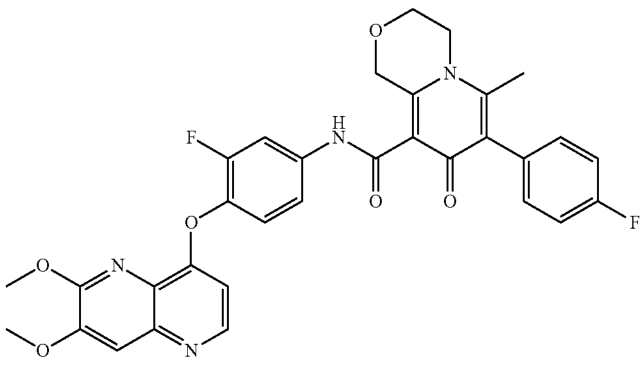 [SMILES: COc1cc2nccc(Oc3ccc(NC(=O)c4c5n(c(C)c(-c6ccc(F)cc6)c4=O)CCOC5)cc3F)c2nc1OC] | N-[4-[(6,7-dimethoxy-1,5-naphthyridin-4-yl)oxy]-3-fluorophenyl]-7-(4-fluorophenyl)-6-methyl-8-oxo-3,4-dihydro-1H-pyrido[2,1-c][1,4]oxazine-9-carboxamide |
| 776 | 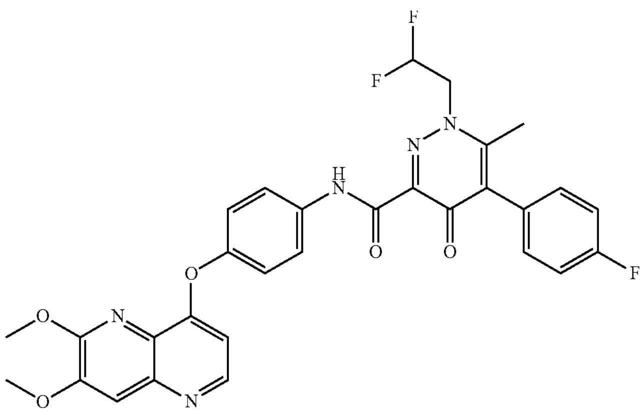 | 1-(2,2-difluoroethyl)-N-[4-[(6,7-dimethoxy-1,5-naphthyridin-4-yl)oxy]phenyl]-5-(4-fluorophenyl)-6-methyl-4-oxopyridazine-3-carboxamide |
| 777 | 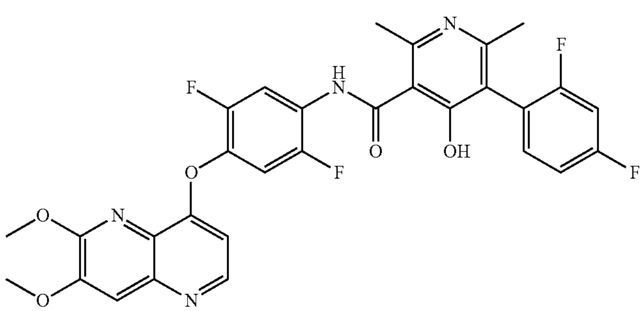 [SMILES: COc1cc2nccc(Oc3cc(F)c(NC(=O)c4c(C)nc(C)c(-c5ccc(F)cc5F)c4O)cc3F)c2nc1OC] | 5-(2,4-difluorophenyl)-N-[4-[(6,7-dimethoxy-1,5-naphthyridin-4-yl)oxy]-2,5-difluorophenyl]-4-hydroxy-2,6-dimethylpyridine-3-carboxamide |
| 778 | 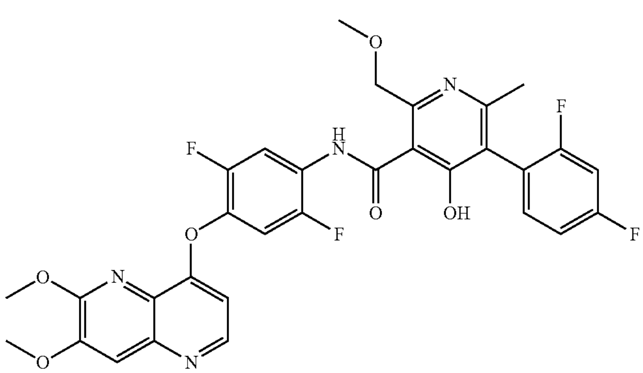 [SMILES: COCc1nc(C)c(-c2ccc(F)cc2F)c(O)c1C(=O)Nc1cc(F)c(Oc2ccnc3cc(OC)c(OC)nc23)cc1F] | 5-(2,4-difluorophenyl)-N-[4-[(6,7-dimethoxy-1,5-naphthyridin-4-yl)oxy]-2,5-difluorophenyl]-4-hydroxy-2-(methoxymethyl)-6-methylpyridine-3-carboxamide |

| Cpd # | Structure | IUPAC Name |
|---|---|---|
| 779 | 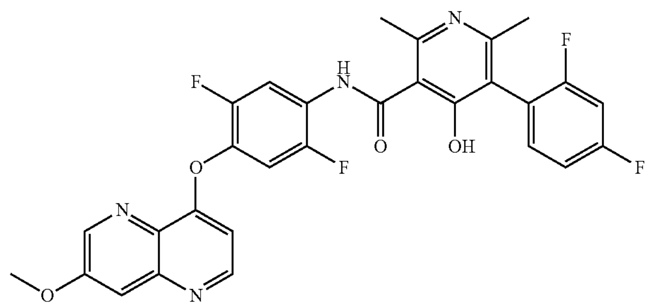 [SMILES: COc1cnc2c(Oc3cc(F)c(NC(=O)c4c(C)nc(C)c(-c5ccc(F)cc5F)c4O)cc3F)ccnc2c1] | N-[2,5-difluoro-4-[(7-methoxy-1,5-naphthyridin-4-yl)oxy]phenyl]-5-(2,4-difluorophenyl)-4-hydroxy-2,6-dimethylpyridine-3-carboxamide |
| 780 | 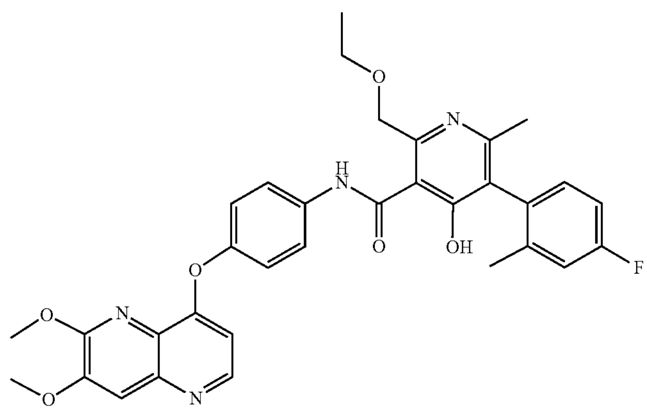 [SMILES: CCOCc1nc(C)c(-c2ccc(F)cc2C)c(O)c1C(=O)Nc1ccc(Oc2ccnc3cc(OC)c(OC)nc23)cc1] | N-[4-[(6,7-dimethoxy-1,5-naphthyridin-4-yl)oxy]phenyl]-2-(ethoxymethyl)-5-(4-fluoro-2-methylphenyl)-4-hydroxy-6-methylpyridine-3-carboxamide |
| 781 | 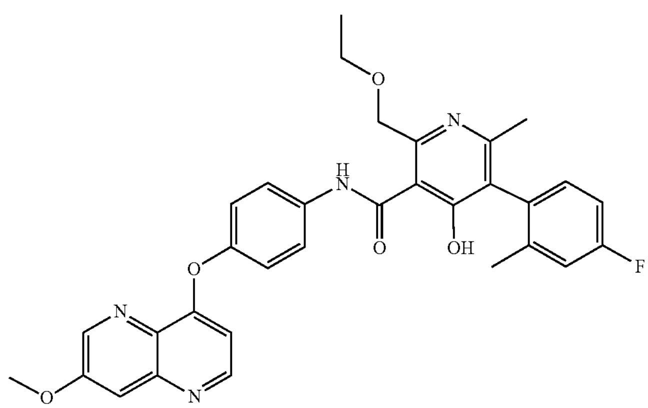 [SMILES: CCOCc1nc(C)c(-c2ccc(F)cc2C)c(O)c1C(=O)Nc1ccc(Oc2ccnc3cc(OC)cnc23)cc1] | 2-(ethoxymethyl)-5-(4-fluoro-2-methylphenyl)-4-hydroxy-N-[4-[(7-methoxy-1,5-naphthyridin-4-yl)oxy]phenyl]-6-methylpyridine-3-carboxamide |
| 782 | 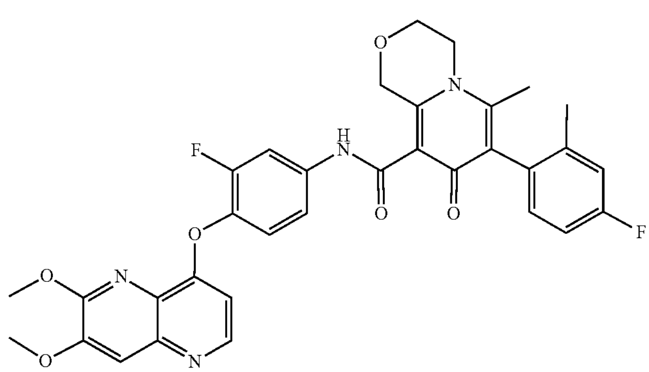 [SMILES: COc1cc2nccc(Oc3ccc(NC(=O)c4c5n(c(C)c(-c6ccc(F)cc6C)c4=O)CCOC5)cc3F)c2nc1OC] | N-[4-[(6,7-dimethoxy-1,5-naphthyridin-4-yl)oxy]-3-fluorophenyl]-7-(4-fluoro-2-methylphenyl)-6-methyl-8-oxo-3,4-dihydro-1H-pyrido[2,1-c][1,4]oxazine-9-carboxamide |

-continued

| Cpd # | Structure | IUPAC Name |
|---|---|---|
| 783 | 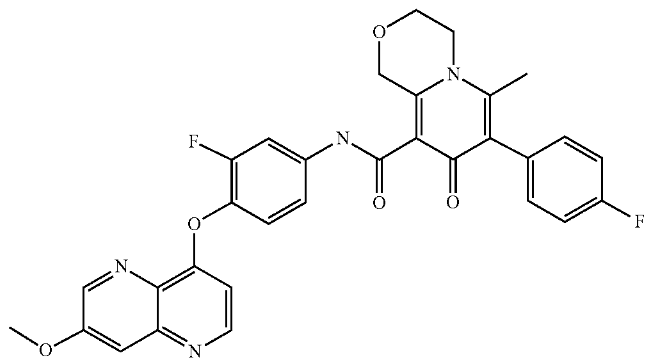 | N-[3-fluoro-4-[(7-methoxy-1,5-naphthyridin-4-yl)oxy]phenyl]-7-(4-fluorophenyl)-6-methyl-8-oxo-3,4-dihydro-1H-pyrido[2,1-c][1,4]oxazine-9-carboxamide |
| 784 | 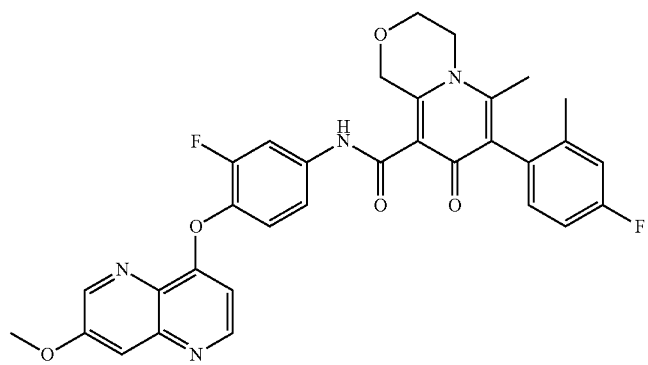 [SMILES: COc1cnc2c(Oc3ccc(NC(=O)c4c5n(c(C)c(-c6ccc(F)cc6C)c4=O)CCOC5)cc3F)ccnc2c1] | N-[3-fluoro-4-[(7-methoxy-1,5-naphthyridin-4-yl)oxy]phenyl]-7-(4-fluoro-2-methylphenyl)-6-methyl-8-oxo-3,4-dihydro-1H-pyrido[2,1-c][1,4]oxazine-9-carboxamide |
| 785 | 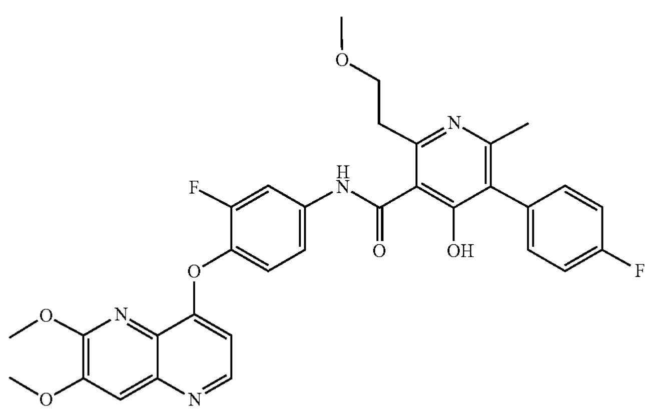 [SMILES: COCCc1nc(C)c(-c2ccc(F)cc2)c(O)c1C(=O)Nc1ccc(Oc2ccnc3cc(OC)c(OC)nc23)c(F)c1] | N-[4-[(6,7-dimethoxy-1,5-naphthyridin-4-yl)oxy]-3-fluorophenyl]-5-(4-fluorophenyl)-4-hydroxy-2-(2-methoxyethyl)-6-methylpyridine-3-carboxamide |
| 786 | 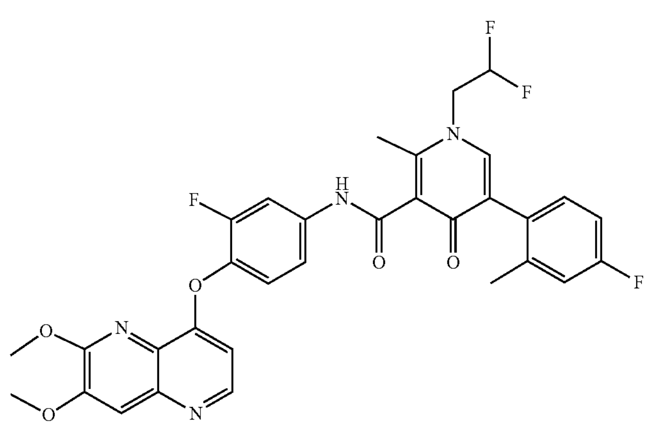 [SMILES: COc1cc2nccc(Oc3ccc(NC(=O)c4c(C)n(CC(F)F)cc(-c5ccc(F)cc5C)c4=O)cc3F)c2nc1OC] | 1-(2,2-difluoroethyl)-N-[4-[(6,7-dimethoxy-1,5-naphthyridin-4-yl)oxy]-3-fluorophenyl]-5-(4-fluoro-2-methylphenyl)-2-methyl-4-oxopyridine-3-carboxamide |

| Cpd # | Structure | IUPAC Name |
|---|---|---|
| 787 | 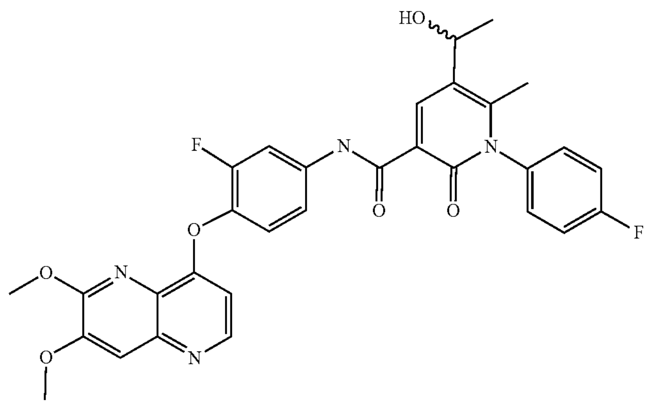 | N-[4-[(6,7-dimethoxy-1,5-naphthyridin-4-yl)oxy]-3-fluorophenyl]-1-(4-fluorophenyl)-5-(1-hydroxyethyl)-6-methyl-2-oxopyridine-3-carboxamide |
| 788 | 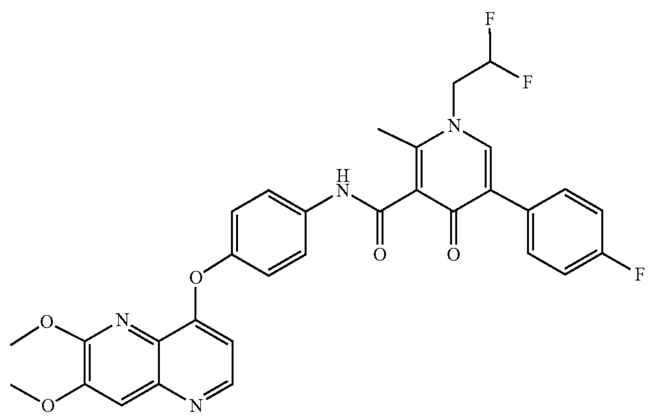 [SMILES: COc1cc2nccc(Oc3ccc(NC(=O)c4c(C)n(CC(F)F)cc(-c5ccc(F)cc5)c4=O)cc3)c2nc1OC] | 1-(2,2-difluoroethyl)-N-[4-[(6,7-dimethoxy-1,5-naphthyridin-4-yl)oxy]phenyl]-5-(4-fluorophenyl)-2-methyl-4-oxopyridine-3-carboxamide |
| 789 | 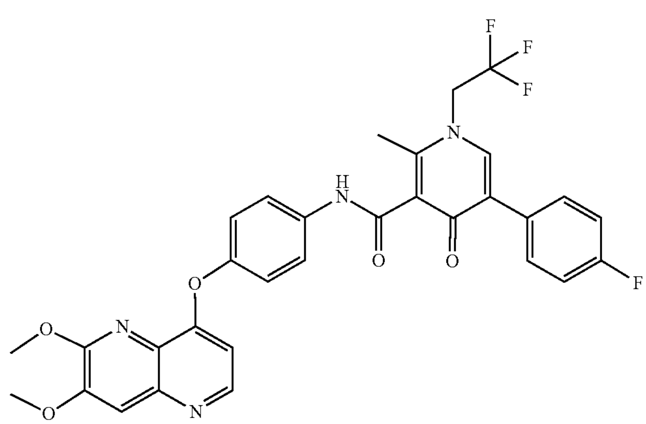 [SMILES: COc1cc2nccc(Oc3ccc(NC(=O)c4c(C)n(CC(F)(F)F)cc(-c5ccc(F)cc5)c4=O)cc3)c2nc1OC] | N-[4-[(6,7-dimethoxy-1,5-naphthyridin-4-yl)oxy]phenyl]-5-(4-fluorophenyl)-2-methyl-4-oxo-1-(2,2,2-trifluoroethyl)pyridine-3-carboxamide |

| Cpd # | Structure | IUPAC Name |
|---|---|---|
| 790 | 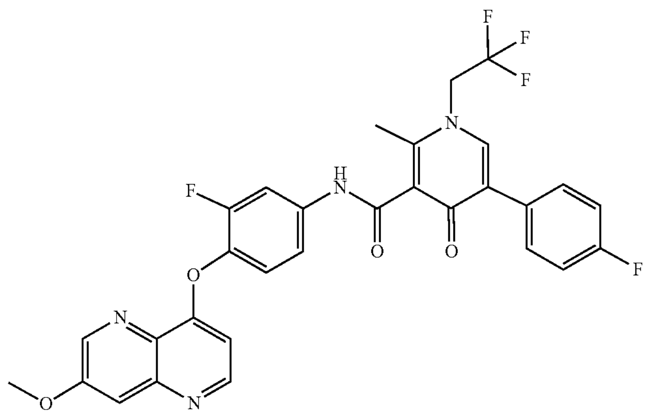 [SMILES: COc1cnc2c(Oc3ccc(NC(=O)c4c(C)n(CC(F)(F)F)cc(-c5ccc(F)cc5)c4=O)cc3F)ccnc2c1] | N-[3-fluoro-4-[(7-methoxy-1,5-naphthyridin-4-yl)oxy]phenyl]-5-(4-fluorophenyl)-2-methyl-4-oxo-1-(2,2,2-trifluoroethyl)pyridine-3-carboxamide |
| 791 | 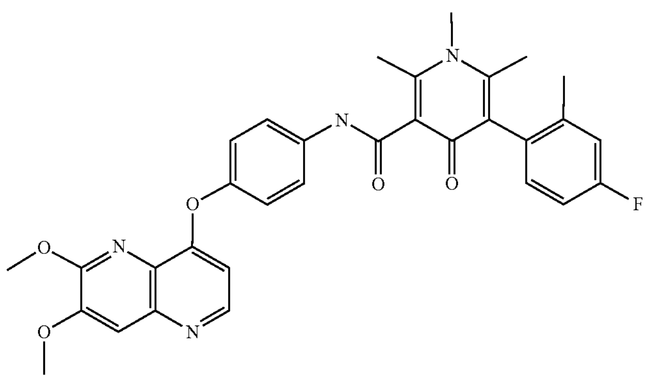 | N-[4-[(6,7-dimethoxy-1,5-naphthyridin-4-yl)oxy]phenyl]-5-(4-fluoro-2-methylphenyl)-1,2,6-trimethyl-4-oxopyridine-3-carboxamide |
| 792 | 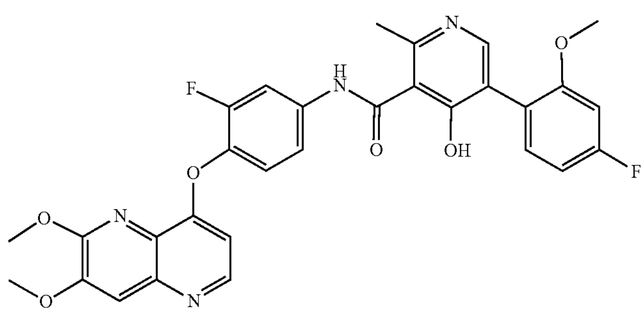 [SMILES: COc1cc(F)ccc1-c1cnc(C)c(C(=O)Nc2ccc(Oc3ccnc4cc(OC)c(OC)nc34)c(F)c2)c1O] | N-[4-[(6,7-dimethoxy-1,5-naphthyridin-4-yl)oxy]-3-fluorophenyl]-5-(4-fluoro-2-methoxyphenyl)-4-hydroxy-2-methylpyridine-3-carboxamide |
| 793 | 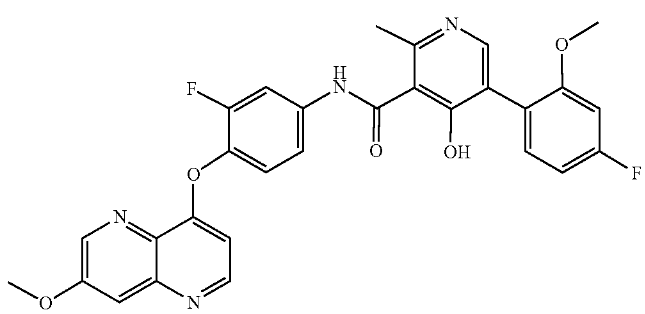 [SMILES: COc1cnc2c(Oc3ccc(NC(=O)c4c(C)ncc(-c5ccc(F)cc5OC)c4O)cc3F)ccnc2c1] | N-[3-fluoro-4-[(7-methoxy-1,5-naphthyridin-4-yl)oxy]phenyl]-5-(4-fluoro-2-methoxyphenyl)-4-hydroxy-2-methylpyridine-3-carboxamide |

-continued

| Cpd # | Structure | IUPAC Name |
|---|---|---|
| 794 | 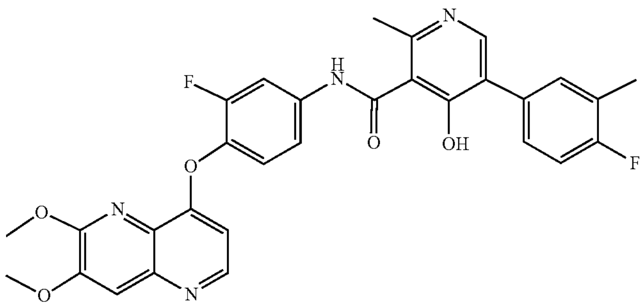 | N-[4-[(6,7-dimethoxy-1,5-naphthyridin-4-yl)oxy]-3-fluorophenyl]-5-(4-fluoro-3-methylphenyl)-4-hydroxy-2-methylpyridine-3-carboxamide |
| 795 | 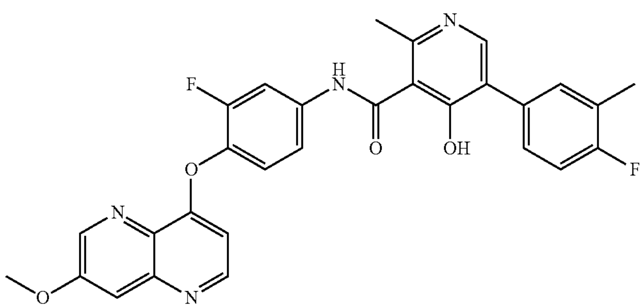 [SMILES: COc1cnc2c(Oc3ccc(NC(=O)c4c(C)ncc(-c5ccc(F)c(C)c5)c4O)cc3F)ccnc2c1] | N-[3-fluoro-4-[(7-methoxy-1,5-naphthyridin-4-yl)oxy]phenyl]-5-(4-fluoro-3-methylphenyl)-4-hydroxy-2-methylpyridine-3-carboxamide |
| 796 | 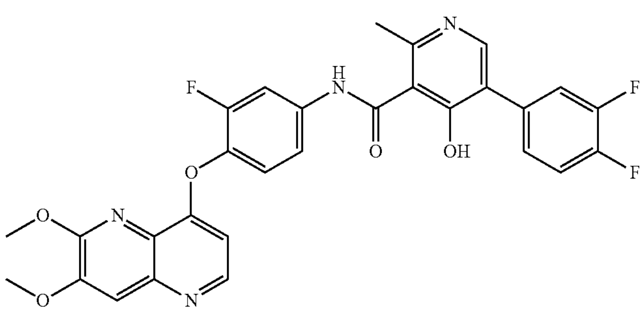 [SMILES: COc1cc2nccc(Oc3ccc(NC(=O)c4c(C)ncc(-c5ccc(F)c(F)c5)c4O)cc3F)c2nc1OC] | 5-(3,4-difluorophenyl)-N-[4-[(6,7-dimethoxy-1,5-naphthyridin-4-yl)oxy]-3-fluorophenyl]-4-hydroxy-2-methylpyridine-3-carboxamide |
| 797 | 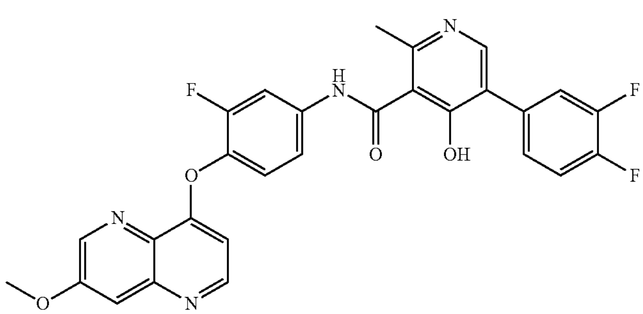 [SMILES: COc1cnc2c(Oc3ccc(NC(=O)c4c(C)ncc(-c5ccc(F)c(F)c5)c4O)cc3F)ccnc2c1] | 5-(3,4-difluorophenyl)-N-[3-fluoro-4-[(7-methoxy-1,5-naphthyridin-4-yl)oxy]phenyl]-4-hydroxy-2-methylpyridine-3-carboxamide |

| Cpd # | Structure | IUPAC Name |
|---|---|---|
| 798 | 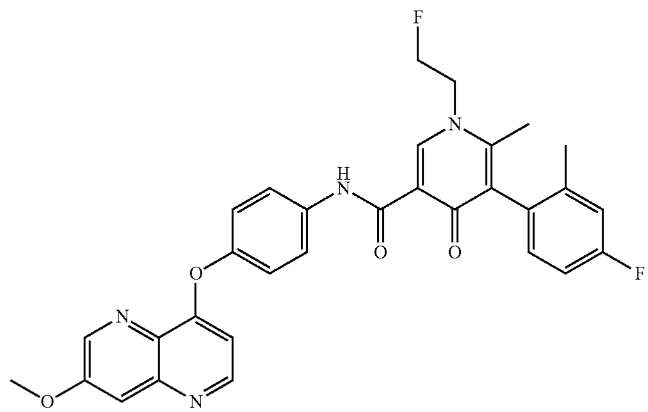 [SMILES: COc1cnc2c(Oc3ccc(NC(=O)c4cn(CCF)c(C)c(-c5ccc(F)cc5C)c4=O)cc3)ccnc2c1] | 1-(2-fluoroethyl)-5-(4-fluoro-2-methylphenyl)-N-[4-[(7-methoxy-1,5-naphthyridin-4-yl)oxy]phenyl]-6-methyl-4-oxopyridine-3-carboxamide |
| 799 | 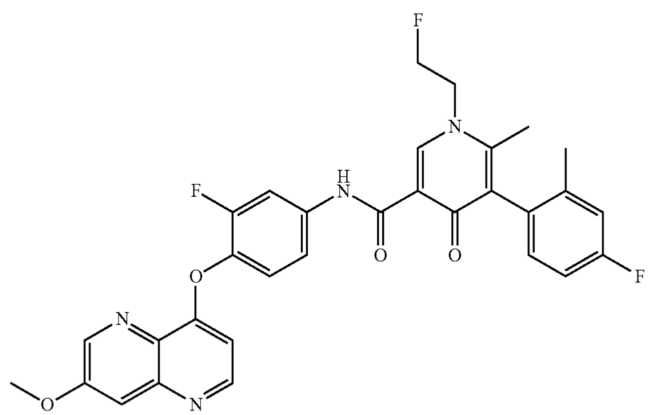 [SMILES: COc1cnc2c(Oc3ccc(NC(=O)c4cn(CCF)c(C)c(-c5ccc(F)cc5C)c4=O)cc3F)ccnc2c1] | 1-(2-fluoroethyl)-N-[3-fluoro-4-[(7-methoxy-1,5-naphthyridin-4-yl)oxy]phenyl]-5-(4-fluoro-2-methylphenyl)-6-methyl-4-oxopyridine-3-carboxamide |
| 800 | 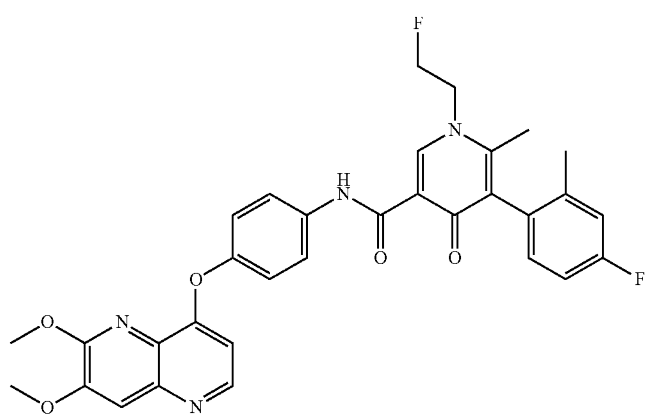 [SMILES: COc1cc2nccc(Oc3ccc(NC(=O)c4cn(CCF)c(C)c(-c5ccc(F)cc5C)c4=O)cc3)c2nc1OC] | N-[4-[(6,7-dimethoxy-1,5-naphthyridin-4-yl)oxy]phenyl]-1-(2-fluoroethyl)-5-(4-fluoro-2-methylphenyl)-6-methyl-4-oxopyridine-3-carboxamide |

-continued

| Cpd # | Structure | IUPAC Name |
|---|---|---|
| 801 | 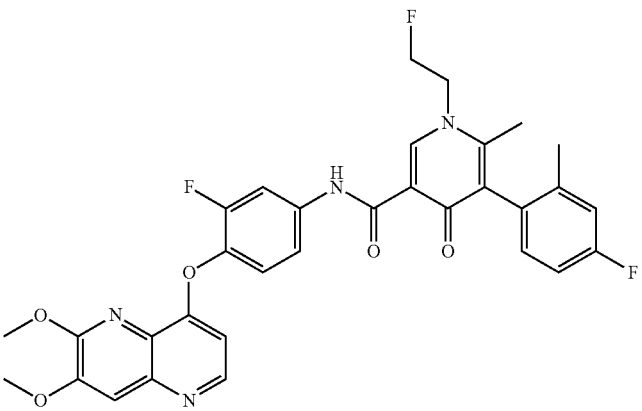 [SMILES: COc1cc2nccc(Oc3ccc(NC(=O)c4cn(CCF)c(C)c(-c5ccc(F)cc5C)c4=O)cc3F)c2nc1OC] | N-[4-[(6,7-dimethoxy-1,5-naphthyridin-4-yl)oxy]-3-fluorophenyl]-1-(2-fluoroethyl)-5-(4-fluoro-2-methylphenyl)-6-methyl-4-oxopyridine-3-carboxamide |
| 802 | 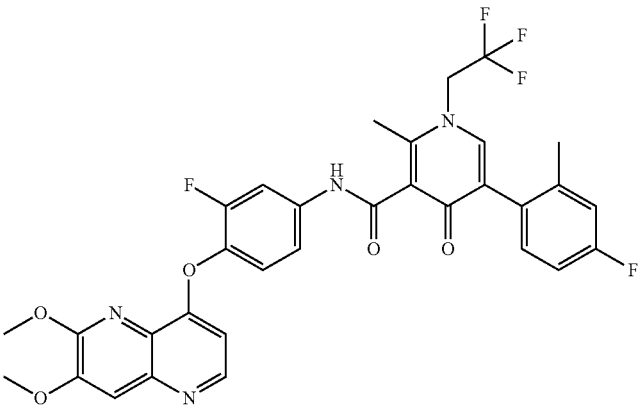 [SMILES: COc1cc2nccc(Oc3ccc(NC(=O)c4c(C)n(CC(F)(F)F)cc(-c5ccc(F)cc5C)c4=O)cc3F)c2nc1OC] | N-[4-[(6,7-dimethoxy-1,5-naphthyridin-4-yl)oxy]-3-fluorophenyl]-5-(4-fluoro-2-methylphenyl)-2-methyl-4-oxo-1-(2,2,2-trifluoroethyl)pyridine-3-carboxamide |
| 803 | 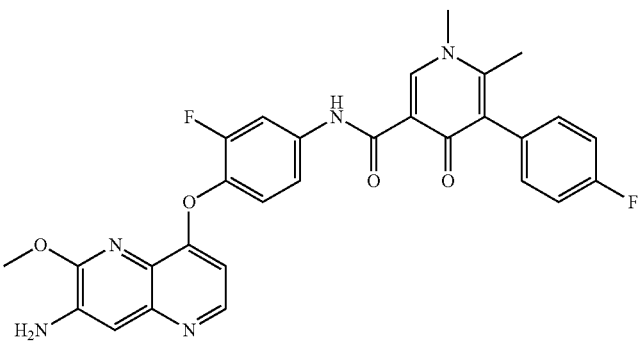 [SMILES: COc1nc2c(Oc3ccc(NC(=O)c4cn(C)c(C)c(-c5ccc(F)cc5)c4=O)cc3F)ccnc2cc1N] | N-[4-[(7-amino-6-methoxy-1,5-naphthyridin-4-yl)oxy]-3-fluorophenyl]-5-(4-fluorophenyl)-1,6-dimethyl-4-oxopyridine-3-carboxamide |
| 804 | 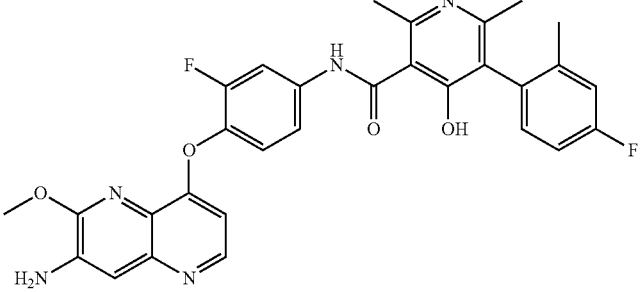 | N-[4-[(7-amino-6-methoxy-1,5-naphthyridin-4-yl)oxy]-3-fluorophenyl]-5-(4-fluoro-2-methylphenyl)-4-hydroxy-2,6-dimethylpyridine-3-carboxamide |

-continued

| Cpd # | Structure | IUPAC Name |
|---|---|---|
| 805 | 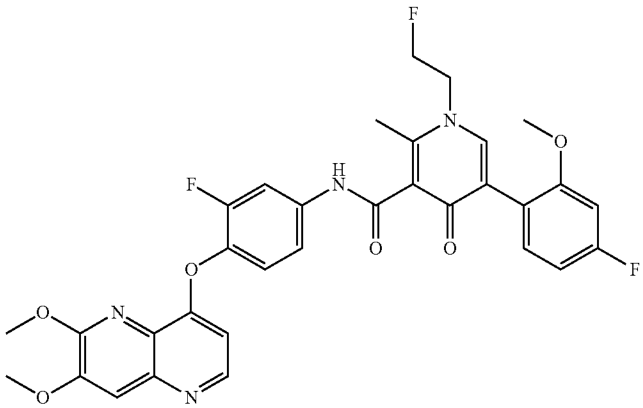 [SMILES: COc1cc(F)ccc1-c1cn(CCF)c(C)c(C(=O)Nc2ccc(Oc3ccnc4cc(OC)c(OC)nc34)c(F)c2)c1=O] | N-[4-[(6,7-dimethoxy-1,5-naphthyridin-4-yl)oxy]-3-fluorophenyl]-1-(2-fluoroethyl)-5-(4-fluoro-2-methoxyphenyl)-2-methyl-4-oxopyridine-3-carboxamide |
| 806 | 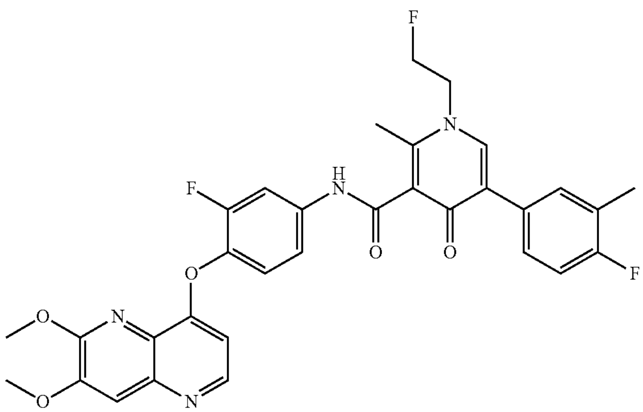 | N-[4-[(6,7-dimethoxy-1,5-naphthyridin-4-yl)oxy]-3-fluorophenyl]-1-(2-fluoroethyl)-5-(4-fluoro-3-methylphenyl)-2-methyl-4-oxopyridine-3-carboxamide |
| 807 | 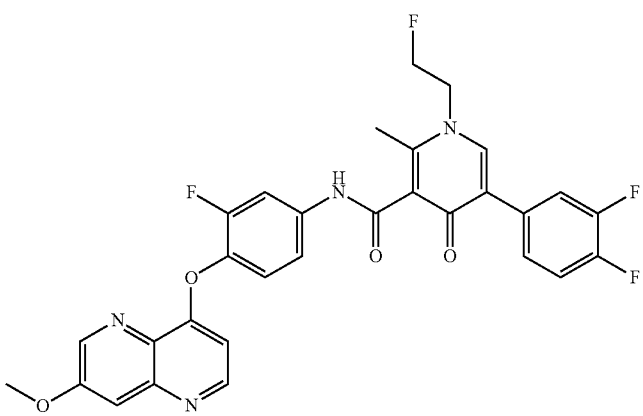 [SMILES: COc1cnc2c(Oc3ccc(NC(=O)c4c(C)n(CCF)cc(-c5ccc(F)c(F)c5)c4=O)cc3F)ccnc2c1] | 5-(3,4-difluorophenyl)-1-(2-fluoroethyl)-N-[3-fluoro-4-[(7-methoxy-1,5-naphthyridin-4-yl)oxy]phenyl]-2-methyl-4-oxopyridine-3-carboxamide |
| 808 | 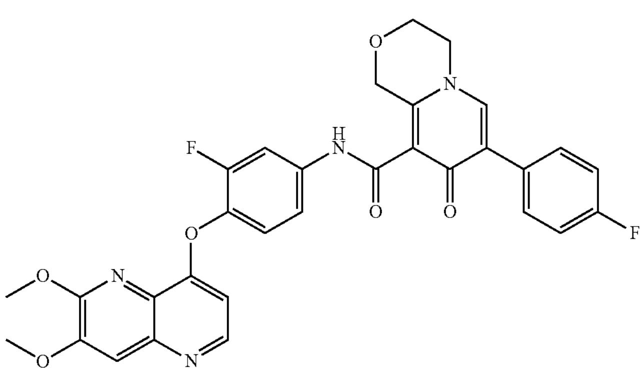 [SMILES: COc1cc2nccc(Oc3ccc(NC(=O)c4c5n(cc(-c6ccc(F)cc6)c4=O)CCOC5)cc3F)c2nc1OC] | N-[4-[(6,7-dimethoxy-1,5-naphthyridin-4-yl)oxy]-3-fluorophenyl]-7-(4-fluorophenyl)-8-oxo-3,4-dihydro-1H-pyrido[2,1-c][1,4]oxazine-9-carboxamide |

-continued

| Cpd # | Structure | IUPAC Name |
|---|---|---|
| 809 | 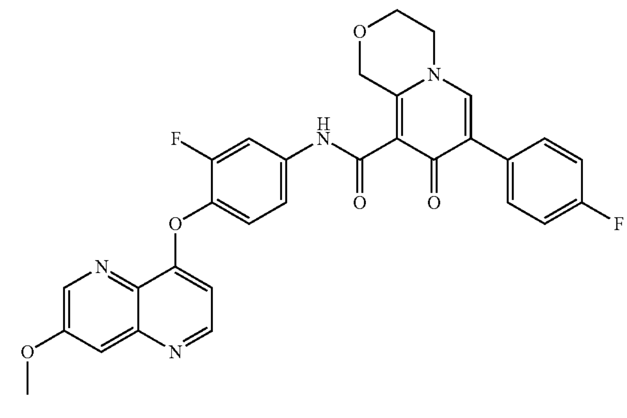 [SMILES: COc1cnc2c(Oc3ccc(NC(=O)c4c5n(cc(-c6ccc(F)cc6)c4=O)CCOC5)cc3F)ccnc2c1] | N-[3-fluoro-4-[(7-methoxy-1,5-naphthyridin-4-yl)oxy]phenyl]-7-(4-fluorophenyl)-8-oxo-3,4-dihydro-1H-pyrido[2,1-c][1,4]oxazine-9-carboxamide |
| 810 | 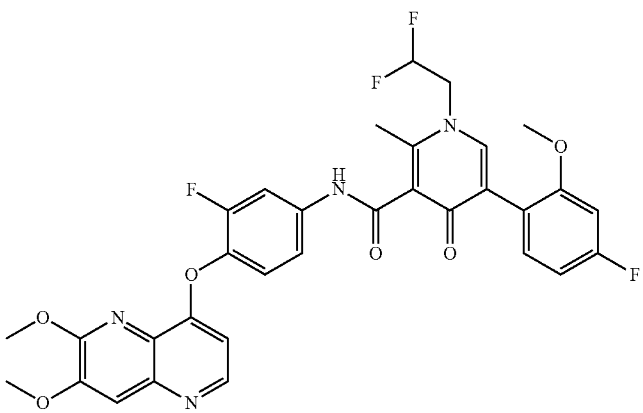 [SMILES: COc1cc(F)ccc1-c1cn(CC(F)F)c(C)c(C(=O)Nc2ccc(Oc3ccnc4cc(OC)c(OC)nc34)c(F)c2)c1=O] | 1-(2,2-difluoroethyl)-N-[4-[(6,7-dimethoxy-1,5-naphthyridin-4-yl)oxy]-3-fluorophenyl]-5-(4-fluoro-2-methoxyphenyl)-2-methyl-4-oxopyridine-3-carboxamide |
| 811 | 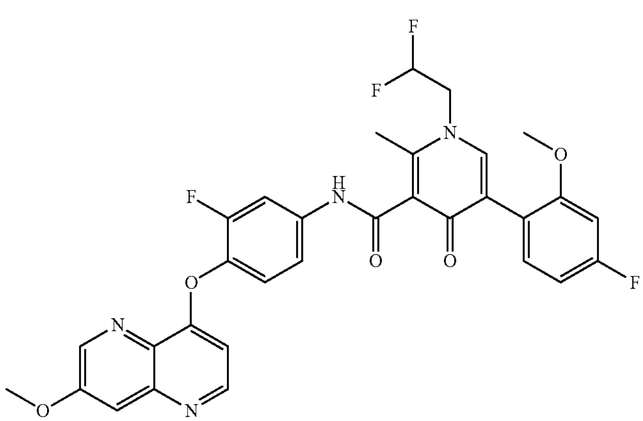 [SMILES: COc1cnc2c(Oc3ccc(NC(=O)c4c(C)n(CC(F)F)cc(-c5ccc(F)cc5OC)c4=O)cc3F)ccnc2c1] | 1-(2,2-difluoroethyl)-N-[3-fluoro-4-[(7-methoxy-1,5-naphthyridin-4-yl)oxy]phenyl]-5-(4-fluoro-2-methoxyphenyl)-2-methyl-4-oxopyridine-3-carboxamide |

-continued

| Cpd # | Structure | IUPAC Name |
|---|---|---|
| 812 | 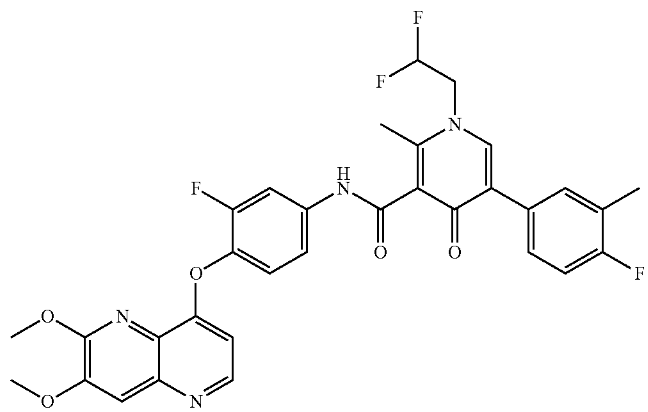 | 1-(2,2-difluoroethyl)-N-[4-[(6,7-dimethoxy-1,5-naphthyridin-4-yl)oxy]-3-fluorophenyl]-5-(4-fluoro-3-methylphenyl)-2-methyl-4-oxopyridine-3-carboxamide |
| 813 | 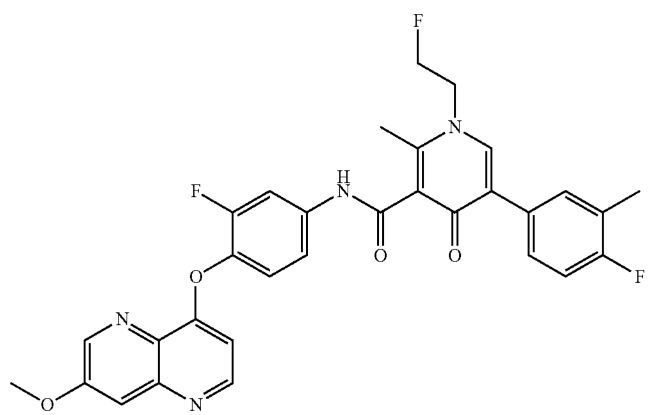 | 1-(2-fluoroethyl)-N-[3-fluoro-4-[(7-methoxy-1,5-naphthyridin-4-yl)oxy]phenyl]-5-(4-fluoro-3-methylphenyl)-2-methyl-4-oxopyridine-3-carboxamide |
| 814 | 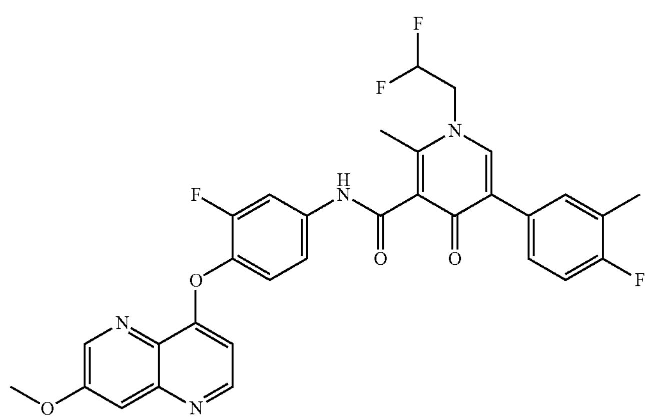 | 1-(2,2-difluoroethyl)-N-[3-fluoro-4-[(7-methoxy-1,5-naphthyridin-4-yl)oxy]phenyl]-5-(4-fluoro-3-methylphenyl)-2-methyl-4-oxopyridine-3-carboxamide |

-continued

| Cpd # | Structure | IUPAC Name |
|---|---|---|
| 815 | 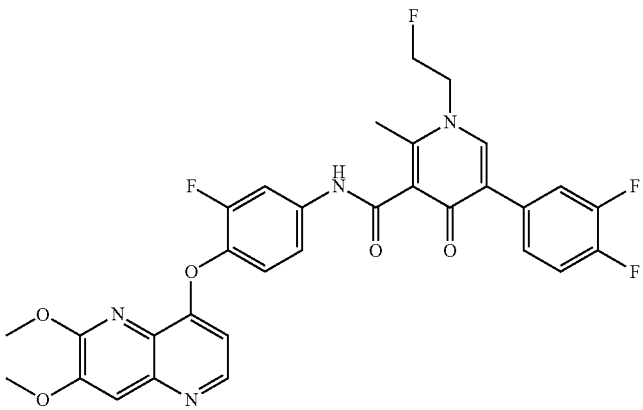 [SMILES: COc1cc2nccc(Oc3ccc(NC(=O)c4c(C)n(CCF)cc(-c5ccc(F)c(F)c5)c4=O)cc3F)c2nc1OC] | 5-(3,4-difluorophenyl)-N-[4-[(6,7-dimethoxy-1,5-naphthyridin-4-yl)oxy]-3-fluorophenyl]-1-(2-fluoroethyl)-2-methyl-4-oxopyridine-3-carboxamide |
| 816 | 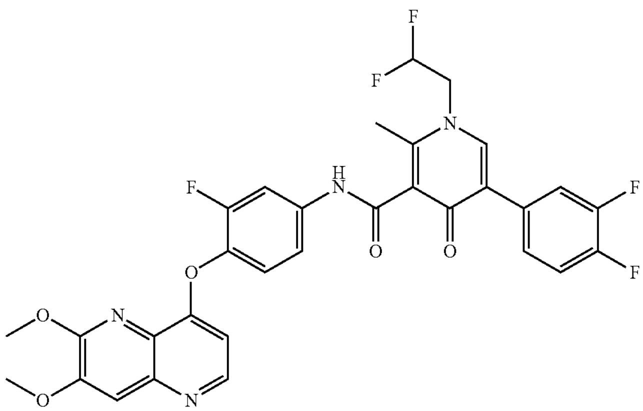 [SMILES: COc1cc2nccc(Oc3ccc(NC(=O)c4c(C)n(CC(F)F)cc(-c5ccc(F)c(F)c5)c4=O)cc3F)c2nc1OC] | 1-(2,2-difluoroethyl)-5-(3,4-difluorophenyl)-N-[4-[(6,7-dimethoxy-1,5-naphthyridin-4-yl)oxy]-3-fluorophenyl]-2-methyl-4-oxopyridine-3-carboxamide |
| 817 | 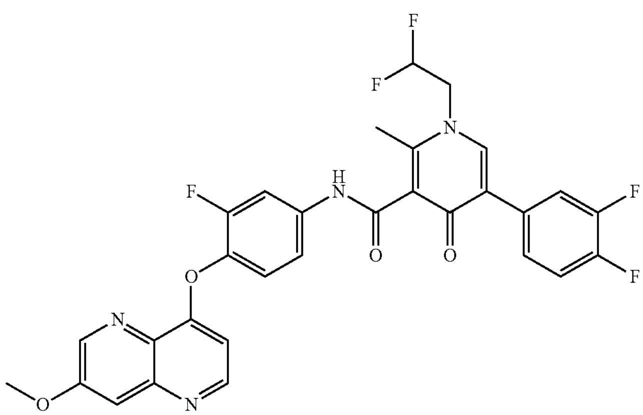 [SMILES: COc1cnc2c(Oc3ccc(NC(=O)c4c(C)n(CC(F)F)cc(-c5ccc(F)c(F)c5)c4=O)cc3F)ccnc2c1] | 1-(2,2-difluoroethyl)-5-(3,4-difluorophenyl)-N-[3-fluoro-4-[(7-methoxy-1,5-naphthyridin-4-yl)oxy]phenyl]-2-methyl-4-oxopyridine-3-carboxamide |
| 818 | 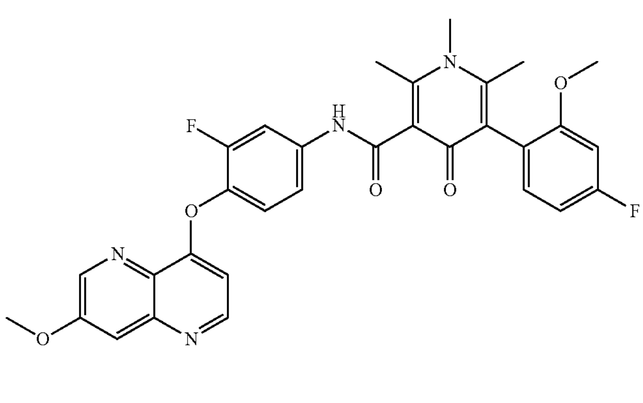 [SMILES: COc1cnc2c(Oc3ccc(NC(=O)c4c(C)n(C)c(C)c(-c5ccc(F)cc5OC)c4=O)cc3F)ccnc2c1] | N-[3-fluoro-4-[(7-methoxy-1,5-naphthyridin-4-yl)oxy]phenyl]-5-(4-fluoro-2-methoxyphenyl)-1,2,6-trimethyl-4-oxopyridine-3-carboxamide |

-continued

| Cpd # | Structure | IUPAC Name |
|---|---|---|
| 819 | 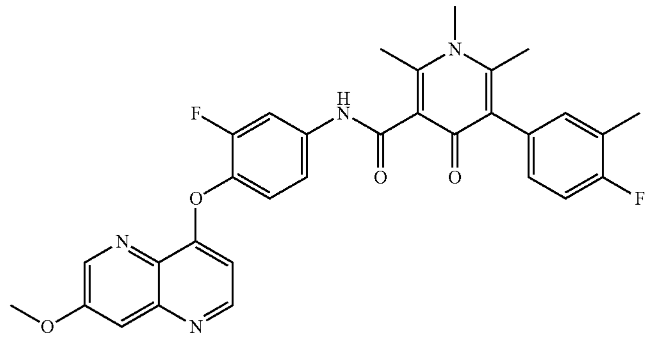 | N-[3-fluoro-4-[(7-methoxy-1,5-naphthyridin-4-yl)oxy]phenyl]-5-(4-fluoro-3-methylphenyl)-1,2,6-trimethyl-4-oxopyridine-3-carboxamide |
| 820 | 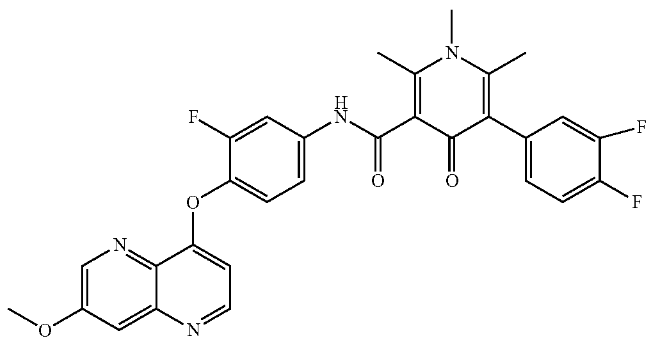 [SMILES: COc1cnc2c(Oc3ccc(NC(=O)c4c(C)n(C)c(C)c(-c5ccc(F)c(F)c5)c4=O)cc3F)ccnc2c1] | 5-(3,4-difluorophenyl)-N-[3-fluoro-4-[(7-methoxy-1,5-naphthyridin-4-yl)oxy]phenyl]-1,2,6-trimethyl-4-oxopyridine-3-carboxamide |
| 821 | 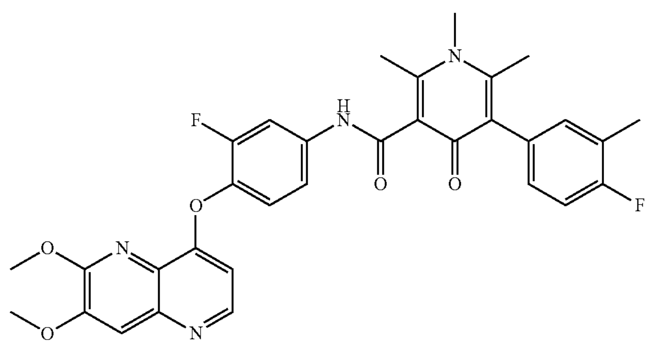 | N-[4-[(6,7-dimethoxy-1,5-naphthyridin-4-yl)oxy]-3-fluorophenyl]-5-(4-fluoro-3-methylphenyl)-1,2,6-trimethyl-4-oxopyridine-3-carboxamide |
| 822 | 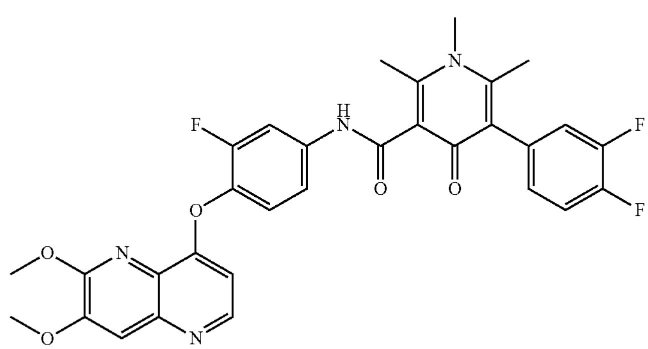 [SMILES: COc1cc2nccc(Oc3ccc(NC(=O)c4c(C)n(C)c(C)c(-c5ccc(F)c(F)c5)c4=O)cc3F)c2nc1OC] | 5-(3,4-difluorophenyl)-N-[4-[(6,7-dimethoxy-1,5-naphthyridin-4-yl)oxy]-3-fluorophenyl]-1,2,6-trimethyl-4-oxopyridine-3-carboxamide |

-continued
| Cpd # | Structure | IUPAC Name |
|---|---|---|
| 823 | 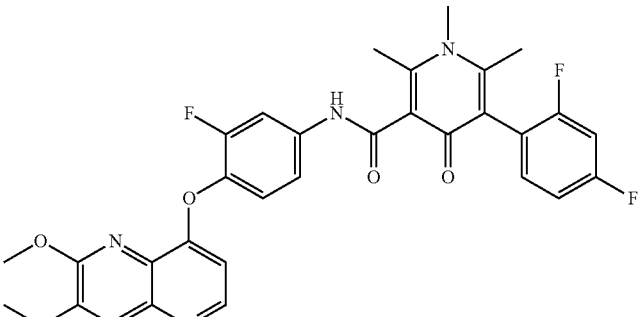 | 5-(2,4-difluorophenyl)-N-[4-[(6,7-dimethoxy-1,5-naphthyridin-4-yl)oxy]-3-fluorophenyl]-1,2,6-trimethyl-4-oxopyridine-3-carboxamide |
| 824 | 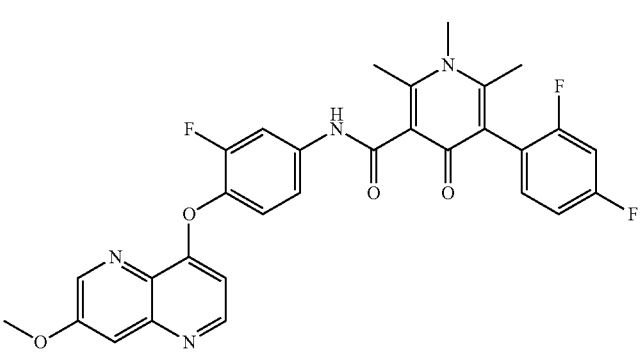 [SMILES: COc1cnc2c(Oc3ccc(NC(=O)c4c(C)n(C)c(C)c(-c5ccc(F)cc5F)c4=O)cc3F)ccnc2c1] | 5-(2,4-difluorophenyl)-N-[3-fluoro-4-[(7-methoxy-1,5-naphthyridin-4-yl)oxy]phenyl]-1,2,6-trimethyl-4-oxopyridine-3-carboxamide |
\* \* \* \* \*